United States Patent
Kirman et al.

(10) Patent No.: US 12,065,445 B2
(45) Date of Patent: Aug. 20, 2024

(54) CDK2 INHIBITORS AND METHODS OF USING THE SAME

(71) Applicant: Cedilla Therapeutics, Inc., Foxboro, MA (US)

(72) Inventors: Louise Clare Kirman, Swampscott, MA (US); Carl Eric Schwartz, Marblehead, MA (US); Wojtek Michowski, Worthington, OH (US); Dale A. Porter, Jr., Cambridge, MA (US); Justin Ripper, Thebarton (AU); John Feutrill, Rosanna (AU); John Paul Sherrill, Melrose, MA (US); Thomas P. Blaisdell, Watertown, MA (US)

(73) Assignee: Cedilla Therapeutics, Inc., Foxboro, MA (US)

( * ) Notice: Subject to any disclaimer, the term of this patent is extended or adjusted under 35 U.S.C. 154(b) by 0 days.

(21) Appl. No.: 17/649,269

(22) Filed: Jan. 28, 2022

(65) Prior Publication Data

US 2023/0109076 A1    Apr. 6, 2023

Related U.S. Application Data

(60) Provisional application No. 63/143,360, filed on Jan. 29, 2021.

(51) Int. Cl.
*C07D 487/10*    (2006.01)
*C07D 519/00*    (2006.01)

(52) U.S. Cl.
CPC ......... *C07D 487/10* (2013.01); *C07D 519/00* (2013.01)

(58) Field of Classification Search
CPC .......................... C07D 487/10; C07D 519/00; A61K 31/4155; A61K 31/4439; A61K 31/454; A61K 31/507; A61K 31/4245; A61K 31/5377; A61K 31/427; A61K 31/422; A61K 31/4178; A61K 31/404; A61K 31/416
USPC ....... 544/124, 133; 546/18, 193, 199, 269.7, 546/275.4; 548/147, 216, 301.1, 357.5, 548/409; 514/232.8, 256.06, 332, 338, 514/365, 397, 406
See application file for complete search history.

(56) References Cited

U.S. PATENT DOCUMENTS

| | | |
|---|---|---|
| 7,351,719 B2 | 4/2008 | Stenkamp et al. |
| 7,435,830 B2 | 10/2008 | Pennell et al. |
| 7,435,831 B2 | 10/2008 | Chen et al. |
| 7,452,911 B2 | 11/2008 | Stenkamp et al. |
| 7,544,695 B2 | 6/2009 | Berk et al. |
| 7,592,373 B2 | 9/2009 | Lehmann-lintz et al. |
| 7,638,526 B2 | 12/2009 | Mckittrick et al. |
| 7,834,026 B2 | 11/2010 | Berk et al. |
| 8,232,288 B2 | 7/2012 | Schunk et al. |
| 8,349,825 B2 | 1/2013 | Mampreian et al. |
| 8,455,475 B2 | 6/2013 | Schunk et al. |
| 8,618,132 B2 | 12/2013 | Stenkamp et al. |
| 8,629,147 B2 | 1/2014 | Anikin et al. |
| 8,686,020 B2 | 4/2014 | Hamblett et al. |
| 8,999,985 B2 | 4/2015 | Gao |
| 9,150,587 B2 | 10/2015 | Chen et al. |
| 9,493,486 B2 | 11/2016 | Hunziker et al. |
| 9,527,856 B2 | 12/2016 | Braje et al. |
| 9,579,314 B2 | 2/2017 | Rancati et al. |
| 9,920,073 B2 | 3/2018 | Cocklin |
| 10,004,728 B2 | 6/2018 | Rancati et al. |
| 10,045,979 B2 | 8/2018 | Long et al. |
| 10,059,690 B2 | 8/2018 | Ciblat et al. |
| 10,106,526 B2 | 10/2018 | Sprott et al. |
| 10,150,769 B2 | 12/2018 | Khan |
| 10,196,369 B2 | 2/2019 | Pinkerton et al. |
| 10,246,464 B2 | 4/2019 | Grembecka et al. |
| 10,259,787 B2 | 4/2019 | Brown et al. |
| 10,266,497 B2 | 4/2019 | Grice et al. |
| 10,323,038 B2 | 6/2019 | Grice et al. |
| 10,463,661 B2 | 11/2019 | Long et al. |
| 10,519,135 B2 | 12/2019 | Sprott et al. |
| 10,633,384 B2 | 4/2020 | Hunziker et al. |
| 10,717,716 B2 | 7/2020 | Lee et al. |

(Continued)

FOREIGN PATENT DOCUMENTS

CN    102952118 A    3/2013
CN    105461693 A    4/2016

(Continued)

OTHER PUBLICATIONS

Asghar et al., "The history and future of targeting cyclin-dependent kinases in cancer therapy", Nat Rev Drug Discov. Feb. 2015;14(2):130-46.

(Continued)

*Primary Examiner* — Jeffrey H Murray
(74) *Attorney, Agent, or Firm* — Morrison & Foerster LLP

(57) ABSTRACT

The present disclosure provides compounds according to Formula I or a pharmaceutically acceptable salt thereof:

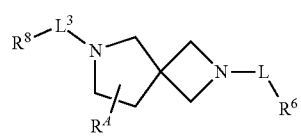

wherein each variable is as defined and described herein, compositions thereof, and methods of using the same for the inhibition of CDK2, and the treatment of CDK2 related diseases and disorders.

38 Claims, No Drawings

(56) References Cited

U.S. PATENT DOCUMENTS

| | | |
|---|---|---|
| 10,759,751 B2 | 9/2020 | Brown et al. |
| 2004/0152742 A1 | 8/2004 | Stenkamp et al. |
| 2004/0209865 A1 | 10/2004 | Stenkamp et al. |
| 2005/0234034 A1 | 10/2005 | Pennell et al. |
| 2005/0267093 A1 | 12/2005 | Lehmann-lintz et al. |
| 2006/0074121 A1 | 4/2006 | Chen et al. |
| 2007/0117824 A1 | 5/2007 | Berk et al. |
| 2007/0249648 A1 | 10/2007 | Bladh et al. |
| 2008/0089858 A1 | 4/2008 | Mckittrick et al. |
| 2008/0207635 A1 | 8/2008 | Anikin et al. |
| 2008/0247964 A1 | 10/2008 | Xu et al. |
| 2009/0069282 A1 | 3/2009 | Stenkamp et al. |
| 2009/0111794 A1 | 4/2009 | Bacani et al. |
| 2009/0156575 A1 | 6/2009 | Borjesson et al. |
| 2009/0209566 A1 | 8/2009 | Berk et al. |
| 2010/0249095 A1 | 9/2010 | Schunk et al. |
| 2011/0009382 A1 | 1/2011 | Schunk et al. |
| 2011/0098268 A1 | 4/2011 | Mampreian et al. |
| 2013/0131041 A1 | 5/2013 | Berk et al. |
| 2013/0224107 A1 | 8/2013 | Gao |
| 2013/0231327 A1 | 9/2013 | Schunk et al. |
| 2015/0099734 A1 | 4/2015 | Hunziker et al. |
| 2015/0344489 A1 | 12/2015 | Braje et al. |
| 2016/0176875 A1 | 6/2016 | Pinkerton et al. |
| 2016/0214998 A1 | 7/2016 | Cocklin |
| 2016/0235734 A1 | 8/2016 | Rancati et al. |
| 2017/0029425 A1 | 2/2017 | Hunziker et al. |
| 2017/0037050 A1 | 2/2017 | Wu et al. |
| 2017/0100394 A1 | 4/2017 | Long et al. |
| 2017/0119753 A1 | 5/2017 | Rancati et al. |
| 2017/0183355 A1 | 6/2017 | Sprott et al. |
| 2017/0247391 A1 | 8/2017 | Grembecka et al. |
| 2018/0105491 A1 | 4/2018 | Brown et al. |
| 2018/0208578 A1 | 7/2018 | Ciblat et al. |
| 2018/0230114 A1 | 8/2018 | Lee et al. |
| 2018/0291023 A1 | 10/2018 | Khan |
| 2018/0319772 A1 | 11/2018 | Sprott et al. |
| 2018/0327416 A1 | 11/2018 | Grice et al. |
| 2018/0338972 A1 | 11/2018 | Long et al. |
| 2018/0339970 A1 | 11/2018 | Grice et al. |
| 2019/0194200 A1 | 6/2019 | Khan |
| 2019/0202783 A1 | 7/2019 | Brown et al. |
| 2019/0218230 A1 | 7/2019 | Angibaud et al. |
| 2019/0330209 A1 | 10/2019 | Khan |
| 2020/0087304 A1 | 3/2020 | Grice et al. |
| 2020/0172573 A1 | 6/2020 | Zhang et al. |
| 2020/0207769 A1 | 7/2020 | Hunziker et al. |
| 2020/0216471 A1 | 7/2020 | Wu et al. |
| 2020/0290963 A1 | 9/2020 | Brown et al. |
| 2020/0407374 A1 | 12/2020 | Mach et al. |
| 2023/0121337 A1 | 4/2023 | Kirman |

FOREIGN PATENT DOCUMENTS

| | | |
|---|---|---|
| CN | 111138358 A | 5/2020 |
| WO | 2004039764 A1 | 5/2004 |
| WO | 2004039780 A1 | 5/2004 |
| WO | 2005040167 A1 | 5/2005 |
| WO | 2005063239 A1 | 7/2005 |
| WO | 2005084667 A1 | 9/2005 |
| WO | 2007027734 A2 | 3/2007 |
| WO | 2007030061 A1 | 3/2007 |
| WO | 2007027734 A3 | 5/2007 |
| WO | 2007056155 A1 | 5/2007 |
| WO | 2007061880 A1 | 5/2007 |
| WO | 2007061978 A1 | 5/2007 |
| WO | 2007140383 A2 | 12/2007 |
| WO | 2007140383 A3 | 1/2008 |
| WO | 2008033456 A1 | 3/2008 |
| WO | 2007133561 A3 | 10/2008 |
| WO | 2010108651 A1 | 9/2010 |
| WO | 2010142402 A1 | 12/2010 |
| WO | 2011092198 A1 | 8/2011 |
| WO | 2012071684 A1 | 6/2012 |
| WO | 2013131010 A2 | 9/2013 |
| WO | 2013131010 A3 | 11/2013 |
| WO | 2013186159 A1 | 12/2013 |
| WO | 2015048567 A1 | 4/2015 |
| WO | 2015051230 A1 | 4/2015 |
| WO | 2015154039 A2 | 10/2015 |
| WO | 2015173392 A1 | 11/2015 |
| WO | 2015179414 A1 | 11/2015 |
| WO | 2015154039 A3 | 12/2015 |
| WO | 2016040330 A1 | 3/2016 |
| WO | 2016128456 A1 | 8/2016 |
| WO | 2015154039 A8 | 10/2016 |
| WO | 2017023133 A2 | 2/2017 |
| WO | 2017023133 A3 | 3/2017 |
| WO | 2017087863 A1 | 5/2017 |
| WO | 2018026798 A1 | 2/2018 |
| WO | 2018069732 A1 | 4/2018 |
| WO | 2018106818 A1 | 6/2018 |
| WO | 2018106820 A1 | 6/2018 |
| WO | 2018153312 A1 | 8/2018 |
| WO | 2018175746 A1 | 9/2018 |
| WO | 2018217805 A1 | 11/2018 |
| WO | 2018217809 A1 | 11/2018 |
| WO | 2019015644 A1 | 1/2019 |
| WO | 2019046330 A1 | 3/2019 |
| WO | 2019060365 A1 | 3/2019 |
| WO | 2019129121 A1 | 7/2019 |
| WO | 2019158051 A1 | 8/2019 |
| WO | 2020069027 A1 | 4/2020 |
| WO | 2020086739 A1 | 4/2020 |
| WO | 2020104494 A1 | 5/2020 |
| WO | 2020112905 A1 | 6/2020 |
| WO | 2020113071 A1 | 6/2020 |
| WO | 2020131627 A1 | 6/2020 |
| WO | 2022165513 A1 | 8/2022 |
| WO | 2022272106 A1 | 12/2022 |
| WO | 2024026479 A2 | 2/2024 |
| WO | 2024026481 A2 | 2/2024 |
| WO | 2024026483 A2 | 2/2024 |
| WO | 2024026484 A2 | 2/2024 |
| WO | 2024026486 A2 | 2/2024 |

OTHER PUBLICATIONS

Du et al., "Critical role of CDK2 for melanoma growth linked to its melanocyte-specific transcriptional regulation by MITF", Cancer Cell. Dec. 2004; 6(6): 565-576.

PubChem Open Chemistry Database, "CID 143728706 Compound Summary: 1-N-cyclopentyl-7a-hydroxy-3-oxo-2-(2-oxoethyl)-4-N-[4-(trifluoromethyl)phenyl]-1,3a,4,5,6,7-hexahydropyrrolo[3,4-c]pyridine-1,4-dicarboxamide," PubChem. Created Dec. 7, 2019: <https://pubchem.ncbi.nlm.nih.gov/compound/143728706>.

PCT International Search Report and Written Opinion from PCT/US2022/034963, dated Sep. 2, 2022.

Alexander et al., "Cyclin E overexpression as a biomarker for combination treatment strategies in inflammatory breast cancer", Oncotarget. Feb. 28, 2017;8(9):14897-14911.

Au-Yeung et al., "Selective Targeting of Cyclin E1-Amplified High-Grade Serous Ovarian Cancer by Cyclin-Dependent Kinase 2 and AKT Inhibition", Clin Cancer Res. Apr. 1, 2017;23(7):1862-1874.

Ayhan et al., "CCNE1 copy-number gain and overexpression identify ovarian clear cell carcinoma with a poor prognosis", Mod Pathol. Feb. 2017;30(2):297-303.

Bukanov, et al., "Long-lasting arrest of murine polycystic kidney disease with CDK inhibitor roscovitine", Nature. Dec. 14, 2006;444(7121):949-52.

Caldon et al., "Cyclin E2 overexpression is associated with endocrine resistance but not insensitivity to CDK2 inhibition in human breast cancer cells", Mol Cancer Ther. Jul. 2012;11(7):1488-99.

Chunder et al., "Cyclin-dependent kinase 2 controls peripheral immune tolerance", J Immunol. Dec. 15, 2012;189(12):5659-66.

Ehedego et al., "Loss of Cyclin E1 attenuates hepatitis and hepatocarcinogenesis in a mouse model of chronic liver injury", Oncogene. Jun. 2018;37(25):3329-3339.

(56) References Cited

OTHER PUBLICATIONS

Elsawaf et al., "Triple-Negative Breast Cancer: Clinical and Histological Correlations, Breast Care (Basel). 2011;6(4):273-278".

Etemadmoghadam et al., "Resistance to CDK2 inhibitors is associated with selection of polyploid cells in CCNE1-amplified ovarian cancer", Clin Cancer Res. Nov. 1, 2013;19(21):5960-71.

Faber, et al., "Review of rationale and progress toward targeting cyclin-dependent kinase 2 (CDK2) for male contraception, Biol Reprod. Aug. 4, 2020;103(2):357-367".

Herrera-Abreu et al., "Early Adaptation and Acquired Resistance to CDK4/6 Inhibition in Estrogen Receptor-Positive Breast Cancer", Cancer Res. Apr. 15, 2016;76(8):2301-13.

International Search Authority, International Search Report and Written Opinion issue in corresponding PCT/US22/70409, Mailing date: Jun. 2, 2022, 12 pages.

Keyomarsi et al., "Cyclin E and survival in patients with breast cancer", N Engl J Med. Nov. 14, 2002;347(20):1566-75.

Liu, et al., "Cyclin E-Mediated Human Proopiomelanocortin Regulation as a Therapeutic Target for Cushing Disease", J Clin Endocrinol Metab. Jul. 2015;100(7):2557-64.

Nakayama et al., Gene amplification CCNE1 is related to poor survival and potential therapeutic target in ovarian cancer, Cancer. Jun. 1, 2010;116(11):2621-34.

Nevzorova, et al., "Cyclin E1 controls proliferation of hepatic stellate cells and is essential for liver fibrogenesis in mice", Hepatology. Sep. 2012;56(3):1140-9.

Noske et al., "Detection of CCNE1/URI (19q12) amplification by in situ hybridisation is common in high grade and type II endometrial cancer, Oncotarget. Feb. 28, 2017;8(9):14794-14805".

Ooi et al., "Gene amplification of CCNE1, CCND1, and CDK6 in gastric cancers detected by multiplex ligation-dependent probe amplification and fluorescence in situ hybridization", Hum Pathol. Mar. 2017;61:58-67.

Ophascharoensuk et al., "The cyclin-dependent kinase inhibitor p27Kip1 safeguards against inflammatory injury", Nat Med. May 1998;4(5):575-80.

PubChem Open Chemistry Database, Compound Summary for SID 382817814, available Apr. 26, 2019 (5 pages).

Scaltriti et al., "Cyclin E amplification/overexpression is a mechanism of trastuzumab resistance in HER2+ breast cancer patients", Proc Natl Acad Sci U S A. Mar. 1, 2011;108(9):3761-6.

Yang et al., "Neuronal cell death is preceded by cell cycle events at all stages of Alzheimer's disease", J Neurosci. Apr. 1, 2003;23(7):2557-63.

U.S. Appl. No. 17/849,321, filed Jun. 24, 2022, for Bothe et al. (Also cited as U.S. Publication No. US 2023-0121337)(U.S. Patent Application is not submitted herewith pursuant to the waiver of 37 C.F.R. § 1.98(a)(2)(iii) issued by the Office on Sep. 21, 2004.).

U.S. Appl. No. 18/274,962, filed Jan. 28, 2022, for Kirman et al. (U.S. Patent Application is not submitted herewith pursuant to the waiver of 37 C.F.R. § 1.98(a)(2)(iii) issued by the Office on Sep. 21, 2004.).

U.S. Appl. No. 18/545,134, filed Dec. 19, 2023, for Kirman et al. (U.S. Patent Application is not submitted herewith pursuant to the waiver of 37 C.F.R. § 1.98(a)(2)(iii) issued by the Office on Sep. 21, 2004.).

CDK2 INHIBITORS AND METHODS OF USING THE SAME

FIELD

The present disclosure relates generally to Cyclin-dependent kinase 2 (CDK2) inhibiting chemical compounds and uses thereof in the inhibition of the activity of CDK2. The disclosure also provides pharmaceutically acceptable compositions comprising compounds disclosed herein and methods of using said compounds and compositions in the treatment of various disorders related to CDK2 activity.

BACKGROUND

Cell cycle dysregulation, including uncontrolled cell growth, impaired cell differentiation and abnormal apoptosis have been shown to be caused by over activity of Cyclin-dependent kinases (CDKs). CDKs are important serine/threonine protein kinases that become active when combined with a specific cyclin partner. There are various subtypes of CDKs, each having a different role during the cell cycle, with varying levels of activity during each of the phases. CDK1, CDK2, CDK4 and CDK6 have been found to be specifically important subtypes, where over activity of one or more of these subtypes may lead to dysregulation of the cell cycle and the development of a variety of cancers. The S phase of the cell cycle is responsible for DNA replication and is the phase where aberrant DNA replication may occur. The CDK2/cyclin E complex is required for the cell cycle transition from the G1 phase to the S phase and the CDK2/cyclin A complex is required for the cell cycle transition from the S phase to the G2 phase. Therefore, selective inhibition of the CDK2/cyclin E and/or CDK2/cyclin A complexes can prevent aberrant DNA replication and can be used to treat certain cancers.

Accordingly, there is a need for the development of compounds capable of inhibiting the activity of CDK2/cyclin complexes, and pharmaceutical compositions thereof, for the prevention, and treatment of CDK2 related diseases or disorders.

SUMMARY

The present disclosure is based at least in part on the identification of compounds that bind and inhibit Cyclin-dependent kinase 2 (CDK2) and/or CDK2/cyclin complexes and methods of using the same to treat diseases associated with CDK2 activity. Disclosed herein is a compound according to Formula I or a pharmaceutically acceptable salt thereof:

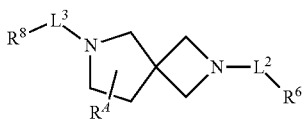

I wherein each variable is as defined and described herein.

Compounds of the present disclosure, and pharmaceutically acceptable compositions thereof, are useful for treating a variety of diseases, disorders or conditions, associated with CDK2 activity. Such diseases, disorders, or conditions include those described herein.

DETAILED DESCRIPTION OF CERTAIN EMBODIMENTS

1. General Description of Compounds of the Disclosure

The present disclosure provides compounds capable of inhibiting Cyclin-dependent kinase 2 (CDK2) and/or CDK2/cyclin complexes.

In some embodiments, provided herein are compounds according to Formula I:

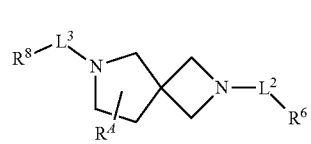

I or a pharmaceutically acceptable salt thereof, wherein:
$R^4$ is

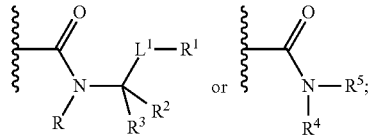

$L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted $C_{1-6}$ aliphatic group, —$C_{1-6}$ alkylene-OR, —$C_{1-3}$ alkylene-O—$C_{1-3}$ alkylene-R, —C(O)OR, or —C(O)NR$_2$; and $R^3$ is hydrogen; or $R^2$ and $R^3$ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur);

$R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); and R is hydrogen; or $R^4$ and $R^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur), or an optionally substituted heteroaryl ring (having 0-3 heteroatoms, in addition to the nitrogen, independently selected from nitrogen, oxygen, and sulfur);

$L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each instance of $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

$L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$;

each instance of $R^9$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not Compound X, wherein Compound X is defined herein.

Overexpression of CDK2 is associated with abnormal regulation of the cell-cycle. The cyclin E/CDK2 complex plays an important role in regulation of the G1/S transition, histone biosynthesis and centrosome duplication. Progressive phosphorylation of retinoblastoma (Rb) by cyclin D/Cdk4/6 and cyclin E/cdk2 releases the G1 transcription factor, E2F, and promotes S-phase entry. Activation of cyclin A/CDK2 during early S-phase promotes phosphorylation of endogenous substrates that permit DNA replication and inactivation of E2F, for S-phase completion. (Asghar et al., Nat. Rev. Drug. Discov. 2015; 14(2): 130-146).

Cyclin E, the regulatory cyclin for CDK2, is frequently overexpressed in cancer. Cyclin E amplification or overexpression has long been associated with poor outcomes in breast cancer. (Keyomarsi et al., Cyclin E and survival in patients with breast cancer. N Engl J Med. (2002) 347:1566-75). Cyclin E2 (CCNE2) overexpression is associated with endocrine resistance in breast cancer cells and CDK2 inhibition has been reported to restore sensitivity to tamoxifen or CDK4 inhibitors in tamoxifen-resistant and CCNE2 overexpressing cells. (Caldon et al., Mol. Cancer Ther. (2012) 11:1488-99; Herrera-Abreu et al., Cancer Res. (2016) 76: 2301-2313). Cyclin E amplification also reportedly contributes to trastuzumab resistance in HER2+ breast cancer. (Scaltriti et al., Proc Natl Acad Sci. (2011) 108: 3761-6). Cyclin E overexpression has also been reported to play a role in basal-like and triple negative breast cancer (TNBC), as well as inflammatory breast cancer. (Elsawaf & Sinn, Breast Care (2011) 6:273-278; Alexander et al., Oncotarget (2017) 8: 14897-14911.)

Amplification or overexpression of cyclin E1 (CCNE1) is also associated with poor outcomes in ovarian, gastric, endometrial and other cancers. (Nakayama et al., Gene amplification CCNE1 is related to poor survival and potential therapeutic target in ovarian cancer, Cancer (2010) 116: 2621-34; Etemadmoghadam et al., Clin Cancer Res (2013) 19: 5960-71; Au-Yeung et al., Clin. Cancer Res. (2017) 23:1862-1874; Ayhan et al., Modern Pathology (2017) 30: 297-303; Ooi et al., Hum Pathol. (2017) 61: 58-67; Noske et al., Oncotarget (2017) 8: 14794-14805).

There remains a need in the art for CDK inhibitors, especially selective CDK2 inhibitors, which may be useful for the treatment of cancer or other proliferative diseases or conditions. In particular, CDK2 inhibitors may be useful in treating CCNE1 or CCNE2 amplified tumors.

2. Compounds and Definitions

Compounds of this present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 101$^{st}$ Ed. Additionally, general principles of organic chemistry are described in "Organic Chemistry", Thomas Sorrell, University Science Books, Sausalito: 2005, and "March's Advanced Organic Chemistry: Reactions Mechanisms and Structure", 8$^{th}$ Ed., Ed.: Smith, M. B., John Wiley & Sons, New York: 2019, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1 to 6 aliphatic carbon atoms. In some embodiments, aliphatic groups contain 1 to 5 aliphatic carbon atoms. In other embodiments, aliphatic groups contain 1 to 4 aliphatic carbon atoms. In still other embodiments, aliphatic groups contain 1 to 3 aliphatic carbon atoms, and in yet other embodiments, aliphatic groups contain 1 to 2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphonates and phosphates), boron, etc. In some embodiments, a bicyclic group has 7-12 ring members and 0-4 heteroatoms independently selected from nitrogen, oxygen, and sulfur. As used herein, the term "bridged bicyclic" refers to any bicyclic ring system, i.e. carbocyclic or heterocyclic, saturated or partially unsaturated, having at least one bridge. As used herein, "bridged bicyclic" rings are to be understood to be a subset of, and falling within the scope of, "bicyclic ring". As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, and sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

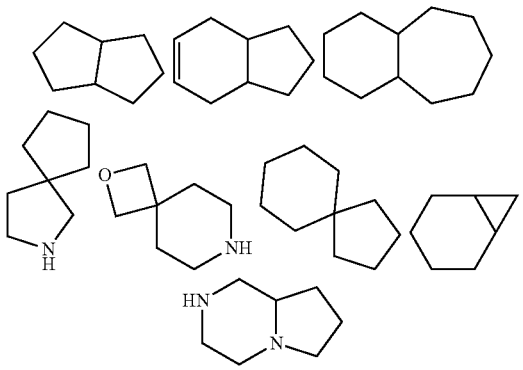

Exemplary bridged bicyclics, contemplated as falling under the scope of a "bicycle" or "bicyclic ring" include:

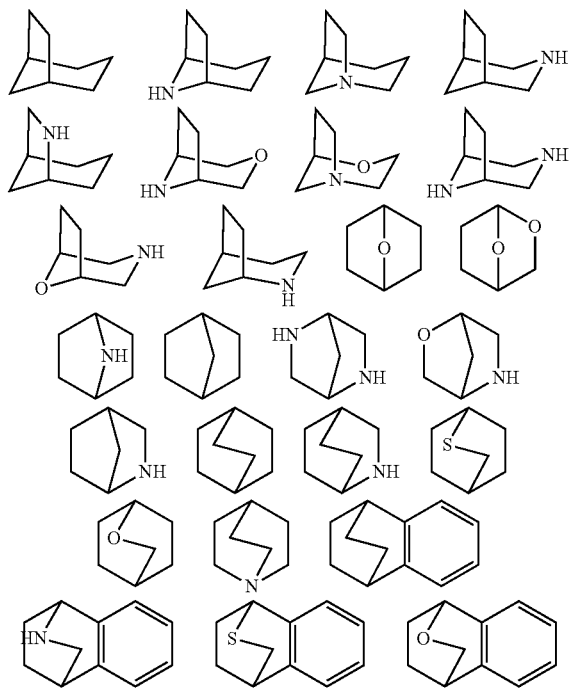

The term "Compound X" refers to 6-(1-benzyl-1H-pyrazole-4-carbonyl)-N-(3-(benzyloxy)-1-(methylamino)-1-oxobutan-2-yl)-2-(2,2-dimethylcyclopropane-1-carbonyl)-2,6-diazaspiro[3.4]octane-8-carboxamide. Compound X may also be depicted as

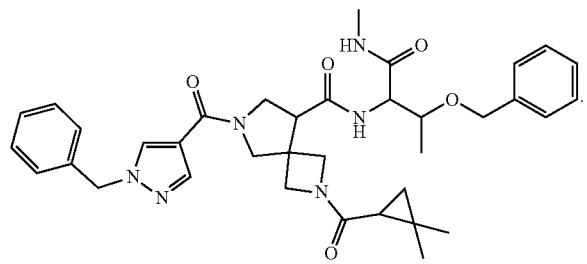 [SMILES: CNC(=O)C(NC(=O)C1CN(C(=O)c2cnn(Cc3ccccc3)c2)CC12CN(C(=O)C1CC1(C)C)C2)C(C)OCc1ccccc1]

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or an oxygen, sulfur, nitrogen, phosphorus, or silicon atom in a heterocyclic ring.

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of 4 to 14 ring members, wherein at least one ring in the system is aromatic and wherein each ring in the system contains three to seven ring members. The term "aryl" may be used interchangeably with the term "aryl ring". In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" in the context of "heteroaryl" particularly includes, but is not limited to, nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. A heteroaryl ring may include one or more oxo (=O) or thioxo (=S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7 to 10-membered bicyclic heterocyclic moiety that is either saturated or partially unsaturated, and having, in addition to carbon atoms, one or more, preferably 1 to 4, heteroatoms, as defined above. When used in reference to a ring atom of a heterocycle, the term "nitrogen" includes a substituted nitrogen. As an example, in a saturated or partially unsaturated ring (having 0 to 3 heteroatoms selected from oxygen, sulfur and nitrogen.

A heterocyclic ring can be attached to a provided compound at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic or bicyclic, bridged bicyclic, or spirocyclic. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the present disclosure may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position. Combinations of substituents envisioned by the present disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-6}$R°; —(CH$_2$)$_{0-6}$OR°; —O(CH$_2$)$_{0-6}$R°, —O—(CH$_2$)$_{0-6}$C(O)OR°; —(CH$_2$)$_{0-6}$CH(OR°)$_2$; —(CH$_2$)$_{0-6}$SR°; —(CH$_2$)$_{0-6}$Ph, which Ph may be substituted with R°; —(CH$_2$)$_{0-6}$O(CH$_2$)$_{0-1}$Ph which Ph may be substituted with R°; —CH=CHPh, which Ph may be substituted with R°; —(CH$_2$)$_{0-6}$O(CH$_2$)$_{0-1}$-pyridyl which pyridyl may be substituted with R°; —NO$_2$; —CN; —N$_3$; —(CH$_2$)$_{0-6}$N(R°)$_2$; —(CH$_2$)$_{0-6}$N(R°)C(O)R°; —N(R°)C(S) R°; —(CH$_2$)$_{0-6}$N(R°)C(O)NR°$_2$; —N(R°)C(S)NR°$_2$; —(CH$_2$)$_{0-6}$N(R°)C(O)OR°; —N(R°)N(R°)C(O)R°; —N(R°)N(R°)C(O)NR°$_2$; —N(R°)N(R°)C(O)OR°; —(CH$_2$)$_{0-6}$C(O)R°; —C(S)R°; —(CH$_2$)$_{0-6}$C(O)OR°; —(CH$_2$)$_{0-6}$C(O)SR°; —(CH$_2$)$_{0-6}$C(O)OSiR°$_3$; —(CH$_2$)$_{0-6}$OC(O)R°; —OC(O)(CH$_2$)$_{0-6}$SR°, —(CH$_2$)$_{0-6}$SC(O)R°; —(CH$_2$)$_{0-6}$C(O)NR°$_2$; —C(S)NR°$_2$; —C(S)SR°; —SC(S)SR°, —(CH$_2$)$_{0-6}$OC(O)NR°$_2$; —C(O)N(OR°)R°; —C(O)C(O)R°; —C(O)CH$_2$C(O)R°; —C(NOR°)R°; —(CH$_2$)$_{0-6}$SSR°; —(CH$_2$)$_{0-6}$S(O)$_2$R°; —(CH$_2$)$_{0-6}$S(O)$_2$OR°; —(CH$_2$)$_{0-6}$OS(O)$_2$R°; —S(O)$_2$NR°$_2$; —(CH$_2$)$_{0-6}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —P(O)(OR°)$_2$; —OP(O)(R°)OR°; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5- to 6-membered heteroaryl ring), or a 3- to 6-membered saturated, partially unsaturated, or aryl ring (having 0 to 4 heteroatoms independently selected from nitrogen, oxygen, and sulfur), or, notwithstanding the definition above, two independent occurrences of R°, taken together with their intervening atom(s), form a 3- to 12-membered saturated, partially unsaturated, or aryl mono- or bicyclic ring (having 0 to 4 heteroatoms independently selected from nitrogen, oxygen, and sulfur), which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5 to 6-membered saturated, partially unsaturated, or aryl ring (having 0 to 4 heteroatoms independently selected from nitrogen, oxygen, and sulfur). Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$)$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5 to 6-membered saturated, partially unsaturated, or aryl ring (having 0 to 4 heteroatoms independently selected from nitrogen, oxygen, and sulfur). Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5 to 6-membered saturated, partially unsaturated, or aryl ring (having 0 to 4 heteroatoms independently selected from nitrogen, oxygen, and sulfur).

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5 to 6-membered saturated, partially unsaturated, or aryl ring (having 0 to 4 heteroatoms independently selected from nitrogen, oxygen, and sulfur).

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, $C_{1-6}$ aliphatic which may be substituted as defined below, unsubstituted —OPh, or an unsubstituted 5 to 6-membered saturated, partially unsaturated, or aryl ring (having 0 to 4 heteroatoms independently selected from nitrogen, oxygen, and sulfur), or, notwithstanding the definition above, two independent occurrences of R†, taken together with their intervening atom(s) form an unsubstituted 3 to 12-membered saturated, partially unsaturated, or aryl mono- or bicyclic ring (having 0 to 4 heteroatoms independently selected from nitrogen, oxygen, and sulfur).

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently $C_{1-4}$ aliphatic, —CH₂Ph, —O(CH₂)₀₋₁Ph, or a 5 to 6-membered saturated, partially unsaturated, or aryl ring (having 0 to 4 heteroatoms independently selected from nitrogen, oxygen, and sulfur).

As used herein, the term "provided compound" or "compound of the present disclosure" refers to any genus, sub-genus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the present disclosure.

As used herein, the term "inhibitor" is defined as a compound that binds to and/or inhibits CDK2 with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM, when measured in an appropriate assay.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this disclosure that, upon administration to a recipient, is capable of providing, either directly or indirectly, a compound of this disclosure or an inhibitorily or degratorily active metabolite or residue thereof.

As used herein, the term "inhibitorily active metabolite or residue thereof" means that a metabolite or residue thereof is also an inhibitor of a CDK2 protein, or a mutant thereof.

3. Description of Exemplary Embodiments

In certain embodiments, the present disclosure provides inhibitors of CDK2 activity.

In some embodiments, the inhibitors of CDK2 include compounds of Formula IA:

IA

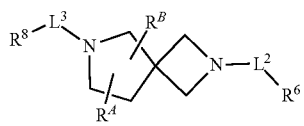

or a pharmaceutically acceptable salt thereof, wherein:
$R^A$ is

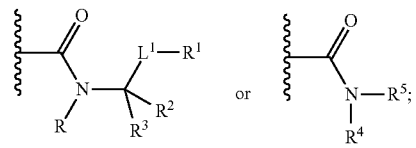

$R^B$ is hydrogen, an optionally substituted $C_{1-6}$ aliphatic group, —OR, —NR$_2$ or a halogen;

$L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted $C_{1-6}$ aliphatic group, —$C_{1-6}$ alkylene-OR, —$C_{1-3}$ alkylene-O—$C_{1-3}$ alkylene-R, —C(O)OR, —C(O)NR$_2$, —S(O)$_2$R, —S(O)$_2$NR$_2$, —S(O)R, —P(O)R$_2$, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); and $R^3$ is hydrogen; or $R^2$ and $R^3$ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur);

$R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); and R is hydrogen; or $R^4$ and $R^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur), or an optionally substituted heteroaryl ring (having 0-3 heteroatoms, in addition to the nitrogen, independently selected from nitrogen, oxygen, and sulfur);

$L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each instance of $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

$L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$;

each instance of $R^9$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted C$_{1-6}$ aliphatic group, an optionally substituted C$_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted C$_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not Compound X, wherein Compound X is defined herein.

In some embodiments, the inhibitors of CDK2 include compounds of Formula I:

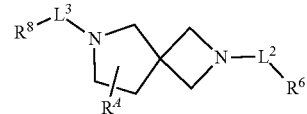

or a pharmaceutically acceptable salt thereof, wherein:

$R^4$ is

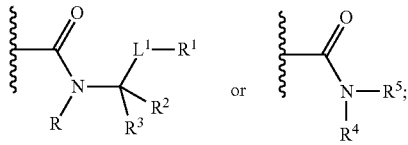

$L^1$ is a covalent bond or a saturated or unsaturated, straight or branched, optionally substituted bivalent C$_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted C$_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted C$_{1-6}$ aliphatic group, —C$_{1-6}$ alkylene-OR, —C$_{1-3}$ alkylene-O—C$_{1-3}$ alkylene-R, —C(O)OR, or —C(O)NR$_2$; and $R^3$ is hydrogen; or $R^2$ and $R^3$ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur);

$R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); and R is hydrogen; or $R^4$ and $R^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur), or an optionally substituted heteroaryl ring (having 0-3 heteroatoms, in addition to the nitrogen, independently selected from nitrogen, oxygen, and sulfur);

$L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^7$;

each instance of $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

$L^3$ is a saturated or unsaturated, straight or branched, optionally substituted bivalent $C_{1-4}$ hydrocarbon chain, wherein 0-2 methylene units of $L^3$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^8$ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of $R^9$;

each instance of $R^9$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not Compound X, wherein Compound X is defined herein.

As defined generally above, $R^A$ is

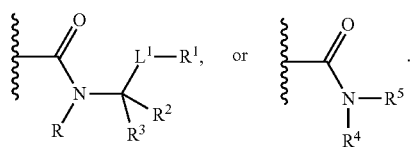

In some embodiments, $R^A$ is

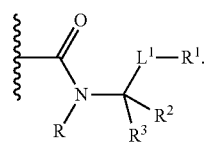

In some embodiments, $R^A$ is

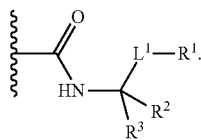

In some embodiments, $R^A$ is

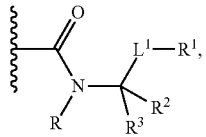

wherein the R group shown is an optionally substituted $C_{1-6}$ aliphatic group. In some embodiments, $R^A$ is

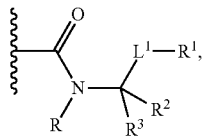

wherein the R group shown is an optionally substituted methyl group. In some embodiments, $R^A$ is

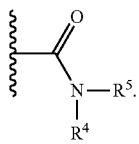

In some embodiments, $R^A$ is selected from those depicted in the compounds of Table 1, below.

As defined generally above, $R^B$ is hydrogen, an optionally substituted $C_{1-6}$ aliphatic group, —OR, —NR$_2$ or a halogen. In some embodiments, $R^B$ is hydrogen. In some embodiments, $R^B$ is an optionally substituted $C_{1-6}$ aliphatic group. In some embodiments, $R^B$ is —OR. In some embodiments, $R^B$ is —NR$_2$. In some embodiments, $R^B$ is a halogen. In some embodiments, $R^B$ is a methyl group. In some embodiments, $R^B$ is a fluoro group. In some embodiments, $R^B$ is selected from those depicted in the compounds of Table 1, below.

As defined generally above, $L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—.

In some embodiments, $L^1$ is a covalent bond. In some embodiments, $L^1$ is a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—.

In some embodiments, $L^1$ is a saturated or unsaturated, straight or branched, optionally substituted bivalent $C_{1-4}$ hydrocarbon chain, wherein 0-2 methylene units of L are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^1$ is a saturated or unsaturated, straight or branched, optionally substituted bivalent $C_{1-4}$ hydrocarbon chain. In some embodiments, $L^1$ is a saturated or unsaturated, straight or branched, optionally substituted bivalent $C_{1-4}$ hydrocarbon chain, wherein 1 or 2 methylene units of $L^1$ are replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^1$ is a saturated, straight or branched, optionally substituted bivalent $C_{1-4}$ hydrocarbon chain. In some embodiments, $L^1$ is a partially unsaturated, straight or branched, optionally substituted bivalent $C_{1-4}$ hydrocarbon chain. In some embodiments, $L^1$ is a saturated, straight, optionally substituted bivalent $C_{1-4}$ hydrocarbon chain, wherein 1-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—. In some embodiments, $L^1$ is an optionally substituted straight or branched $C_{1-4}$ alkylene chain, wherein 1-2 methylene units of $L^1$ are independently replaced by —O—, —NR—, —S—, —C(O)O—, —C(O)—, —S(O)$_2$—, or —NRC(O)—. In some embodiments, $L^1$ is an optionally substituted straight or branched $C_{1-4}$ alkylene chain, wherein 1-2 methylene units of $L^1$ are independently replaced by —O—, —NR—, —C(O)O—, —C(O)—, or —NRC(O)—. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $L^1$ is an optionally substituted straight or branched $C_{1-4}$ alkylene chain, wherein 1-2 methylene units of $L^1$ are independently replaced by —O—. In some embodiments, $L^1$ is an optionally substituted straight or branched $C_{1-4}$ alkylene chain, wherein 1-2 methylene units of $L^1$ are independently replaced by —S—. In some embodiments, $L^1$ is an optionally substituted straight or branched $C_{1-4}$ alkylene chain, wherein 1-2 methylene units of $L^1$ are independently replaced by —S(O)$_2$—. In some embodiments, $L^1$ is an optionally substituted straight or branched $C_{1-4}$ alkylene chain, wherein 1-2 methylene units of $L^1$ are independently replaced by —NR—. In some embodiments, $L^1$ is an optionally substituted straight or branched $C_{1-4}$ alkylene chain, wherein 1-2 methylene units of $L^1$ are independently replaced by —C(O)O—. In some embodiments, $L^1$ is an optionally substituted straight or branched $C_{1-4}$ alkylene chain, wherein 1-2 methylene units of $L^1$ are independently replaced by —NRC(O)—. In some embodiments, $L^1$ is an unsubstituted straight chain $C_{1-4}$ alkynylene. In some embodiments, $L^1$ is selected from those depicted in the compounds of Table 1, below.

In some embodiments, $L^1$ is a covalent bond,

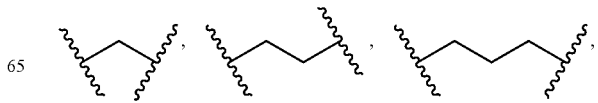

-continued

[structures]

In some embodiments, $L^1$ is

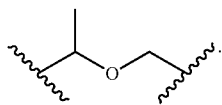 [SMILES: *COC(*)C]

As defined generally above, $R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur).

In some embodiments, $R^1$ is hydrogen. In some embodiments, $R^1$ is an optionally substituted $C_{1-6}$ aliphatic group. In some embodiments, $R^1$ is methyl. In some embodiments, $R^1$ is ethyl. In some embodiments, $R^1$ is isopropyl.

In some embodiments, $R^1$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur). In some embodiments, $R^1$ is an optionally substituted cyclic group selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur). In some embodiments, $R^1$ is an optionally substituted 3-8 membered saturated or partially unsaturated monocyclic carbocyclic ring. In some embodiments, $R^1$ is an optionally substituted phenyl. In some embodiments, $R^1$ is an optionally substituted 8-10 membered bicyclic aromatic carbocyclic ring. In some embodiments, $R^1$ is an optionally substituted 3-8 membered saturated or partially unsaturated monocyclic heterocyclic ring (having 1-2 heteroatoms independently selected from nitrogen, oxygen, and sulfur). In some embodiments, $R^1$ is an optionally substituted 5-6 membered monocyclic heteroaromatic ring (having 1-4 heteroatoms independently selected from nitrogen, oxygen, and sulfur). In some embodiments, $R^1$ is an optionally substituted 8-10 membered bicyclic heteroaromatic ring (having 1-5 heteroatoms independently selected from nitrogen, oxygen, and sulfur). In some embodiments, $R^1$ is an optionally substituted cyclic group selected from phenyl, cyclohexyl, cyclopentyl, cyclobutyl, cyclopropyl, cycloheptyl, oxazolyl, pyridinyl, pyridazinyl, 1,3,4-oxadiazolyl, 1,2,3-triazolyl, pyrazolyl, and tetrahydropyranyl. In some embodiments, $R^1$ is optionally substituted phenyl. In some embodiments, $R^1$ is optionally substituted cyclohexyl. In some embodiments, $R^1$ is selected from those depicted in the compounds of Table 1, below.

In some embodiments, $R^1$ is an optionally substituted 7-12 membered saturated or partially unsaturated bicyclic heterocyclic ring (having 1-4 heteroatoms independently selected from nitrogen, oxygen, and sulfur). In some embodiments, $R^1$ is an optionally substituted a 7-12 membered saturated or partially unsaturated bicyclic carbocyclic ring. In some embodiments, $R^1$ is an optionally substituted 7-12 membered bridge bicyclic carbocyclic ring or an optionally substituted 7-12 membered bridged bicyclic heterocyclic ring (having 1-4 heteroatoms independently selected from nitrogen, oxygen, and sulfur). In some embodiments, $R^1$ is optionally substituted oxabicyclo[2.2.2]octanyl. In some embodiments, $R^1$ is optionally substituted bicyclo[2.2.2]octanyl.

As defined generally above, $R^2$ is hydrogen, an optionally substituted $C_{1-6}$ aliphatic group, —$C_{1-6}$ alkylene-OR, —$C_{1-3}$ alkylene-O—$C_{1-3}$ alkylene-R, —C(O)OR, or —C(O)NR$_2$; and $R^3$ is hydrogen; or $R^2$ and $R^3$ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur).

Alternatively, $R^2$ is hydrogen, an optionally substituted $C_{1-6}$ aliphatic group, —$C_{1-6}$ alkylene-OR, —$C_{1-3}$ alkylene-O—$C_{1-3}$ alkylene-R, —C(O)OR, —C(O)NR$_2$, —S(O)$_2$R, —S(O)$_2$NR$_2$, —S(O)R, —P(O)R$_2$, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); and $R^3$ is hydrogen; or $R^2$ and $R^3$ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur).

In some embodiments, $R^2$ is hydrogen, an optionally substituted $C_{1-6}$ aliphatic group, —$C_{1-6}$ alkylene-OR, —$C_{1-3}$ alkylene-O—$C_{1-3}$ alkylene-R, —C(O)OR, or —C(O)NR$_2$; and $R^3$ is hydrogen. In some embodiments, $R^2$ is hydrogen, methyl, —CH$_2$OR, —CH$_2$OCH$_2$R, —C(O)OR, or —C(O)NR$_2$; and $R^3$ is hydrogen. In some embodiments, $R^2$ is hydrogen. In some embodiments, $R^2$ is an optionally substituted $C_{1-6}$ aliphatic group. In some embodiments, $R^2$ is methyl. In some embodiments, $R^2$ is —$C_{1-6}$ alkylene-OR. In some embodiments, $R^2$ is —CH$_2$OR. In some embodiments, $R^2$ is —CH$_2$OCH$_2$R. In some embodiments, $R^2$ is —C(O)OR. In some embodiments, $R^2$ is —C(O)NR$_2$. In some embodiments, $R^2$ is —C(O)NR$_2$, wherein the two R groups, taken together with the intervening nitrogen atom, form an optionally substituted 4-7 membered saturated, partially unsaturated, or heteroaryl ring (having 0-3 heteroatoms, in addition to the nitrogen, independently selected from nitrogen, oxygen, and sulfur). In some embodiments, $R^2$ is —C(O)NR$_2$, wherein the two R groups, taken together with the intervening nitrogen atom, form an optionally substituted 4-7 membered saturated ring (having 0-3 heteroatoms, in addition to the nitrogen, independently selected from nitrogen, oxygen, and sulfur). In some embodiments, $R^2$ is —C(O)NR$_2$, wherein the two R groups, taken together with the intervening nitrogen atom, form an optionally substituted 4-7 membered saturated ring, selected from a piperidinyl, morpholinyl, piperazinyl, azetidinyl, pyrrolidinyl, azaspiro[3.3]heptanyl, and diazaspiro[3.3]heptanyl.

In some embodiments, $R^2$ is —S(O)$_2$R, —S(O)$_2$NR$_2$, —S(O)R, or —P(O)R$_2$. In some embodiments, $R^2$ is —S(O)$_2$R. In some embodiments, $R^2$ is —S(O)$_2$NR$_2$. In some embodiments, $R^2$ is —S(O)R. In some embodiments, $R^2$ is —P(O)R$_2$. In some embodiments, $R^2$ is —S(O$_2$)CH$_3$. In some embodiments, $R^2$ is —P(O)(CH$_3$)$_2$.

In some embodiments, $R^2$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur). In some embodiments, $R^2$ is an optionally substituted cyclic group selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur). In some embodiments, $R^2$ is an optionally substituted 3-8 membered saturated or partially unsaturated monocyclic carbocyclic ring. In some embodiments, $R^2$ is an optionally substituted phenyl. In some embodiments, $R^2$ is an optionally substituted 8-10 membered bicyclic aromatic carbocyclic ring. In some embodiments, $R^2$ is an optionally substituted 3-8 membered saturated or partially unsaturated monocyclic heterocyclic ring (having 1-2 heteroatoms independently selected from nitrogen, oxygen, and sulfur). In some embodiments, $R^2$ is an optionally substituted 5-6 membered monocyclic heteroaromatic ring (having 1-4 heteroatoms independently selected from nitrogen, oxygen, and sulfur). In some embodiments, $R^2$ is an optionally substituted 8-10 membered bicyclic heteroaromatic ring (having 1-5 heteroatoms independently selected from nitrogen, oxygen, and sulfur). In some embodiments, $R^2$ is a tetrahydrofuranyl. In some embodiments, $R^2$ is a dioxanyl. In some embodiments, $R^2$ is a furanyl. In some embodiments, $R^2$ is an oxadiazolyl. In some embodiments, $R^2$ is an oxazolyl.

In some embodiments, $R^2$ is selected from those depicted in the compounds of Table 1, below.

In some embodiments, $R^3$ is hydrogen and $R^2$ is hydrogen or a substituent in Table $R^2$:

TABLE R²

Exemplary R² substituents

TABLE R²-continued

TABLE R²-continued

Additional exemplary R² substituents

TABLE R²-continued
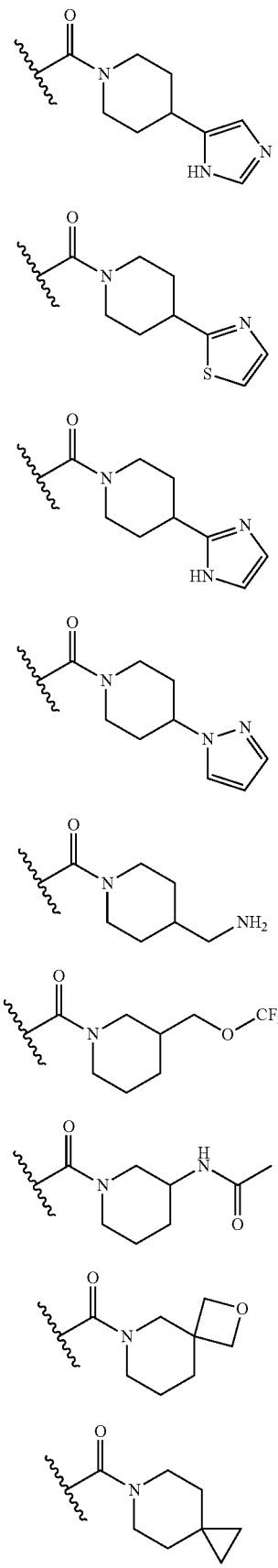
TABLE R²-continued
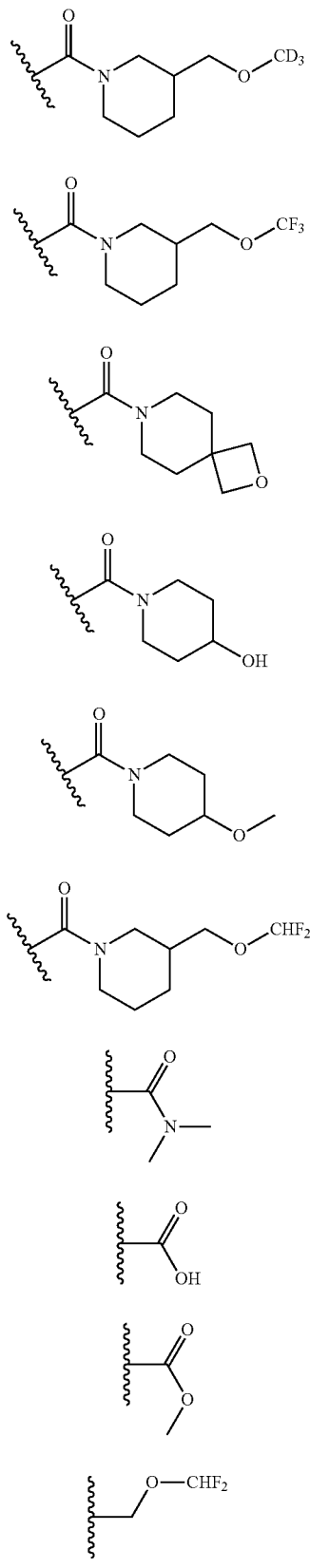

TABLE R²-continued

TABLE R²-continued

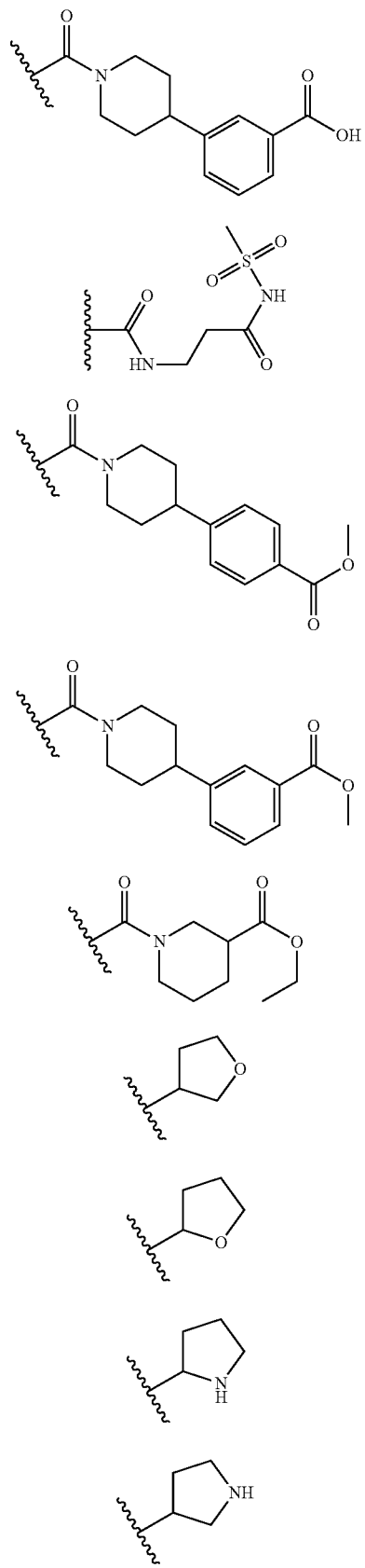

TABLE R²-continued

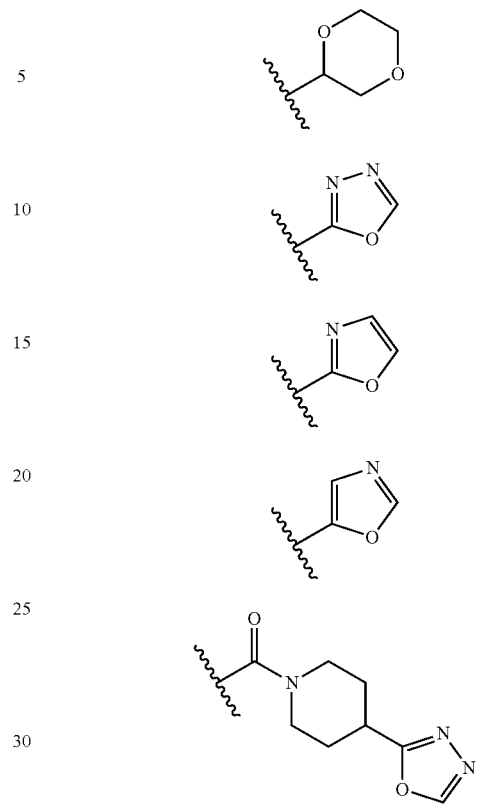

In some embodiments, R³ is hydrogen and R² is hydrogen or a substituent in Table R²-continued:

In some embodiments, R³ is hydrogen and R² is hydrogen or a substituent in Table R² or Table R²-continued.

In some embodiments, R³ is hydrogen and R² is

[structure]

In some embodiments, R² and R³ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur). In some embodiments, R² and R³ together with the intervening carbon atom form an optionally substituted 3-7 membered saturated or partially unsaturated carbocyclic ring. In some embodiments, R² and R³ together with the intervening carbon atom form an optionally substituted 3-7 membered saturated carbocyclic ring. In some embodiments, R² and R³ together with the intervening carbon atom form an optionally substituted 3-7 membered saturated or partially unsaturated heterocyclic ring (having 1-2 heteroatoms independently selected from nitrogen, oxygen, and sulfur). In some embodiments, R² and R³ together with the intervening carbon atom form an optionally substituted 3-7 membered saturated heterocyclic ring (having 1-2 heteroatoms independently selected from nitrogen, oxygen, and sulfur). In some embodiments, R² and R³ together with the intervening carbon atom form an optionally substituted oxetanyl, cyclopropyl, cyclobutyl, cyclopentyl, tetrahydropyranyl, piperidinyl, piperazinyl, morpholinyl, pyrrolidinyl, or 1,4-oxazepanyl. In some embodiments, $R^2$ and $R^3$ form a cyclic group selected from those depicted in the compounds of Table 1, below.

As defined generally above, $R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), and $R^5$ is hydrogen; or $R^4$ and $R^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur), or an optionally substituted heteroaryl ring (having 0-3 heteroatoms, independently selected from nitrogen, oxygen, and sulfur).

In some embodiments, $R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), and $R^5$ is hydrogen. In some embodiments, $R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur). In some embodiments, $R^4$ is an optionally substituted 3-8 membered saturated or partially unsaturated monocyclic carbocyclic ring. In some embodiments, $R^4$ is an optionally substituted 7-12 membered saturated or partially unsaturated bicyclic carbocyclic ring. In some embodiments, $R^4$ is an optionally substituted phenyl. In some embodiments, $R^4$ is an optionally substituted 8-10 membered bicyclic aromatic carbocyclic ring. In some embodiments, $R^4$ is an optionally substituted 3-8 membered saturated or partially unsaturated monocyclic heterocyclic ring (having 1-2 heteroatoms independently selected from nitrogen, oxygen, and sulfur). In some embodiments, $R^4$ is an optionally substituted 5-6 membered monocyclic heteroaromatic ring (having 1-4 heteroatoms independently selected from nitrogen, oxygen, and sulfur). In some embodiments, $R^4$ is an optionally substituted cyclic group selected from phenyl, piperidinyl, tetrahydropyranyl, 1,4-oxazepanyl, oxazolyl, cyclobutyl, cyclopentyl, or pyrrolidinyl. In some embodiments, $R^4$ is selected from those depicted in the compounds of Table 1, below.

In some embodiments, $R^4$ and $R^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur), or an optionally substituted heteroaryl ring (having 0-3 heteroatoms, in addition to the nitrogen, independently selected from nitrogen, oxygen, and sulfur). In some embodiments, $R^4$ and $R^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur). In some embodiments, $R^4$ and $R^5$ together with the intervening nitrogen atom form an optionally substituted heteroaryl ring (having 0-3 heteroatoms, in addition to the nitrogen, independently selected from nitrogen, oxygen, and sulfur). In some embodiments, $R^4$ and $R^5$ together with the intervening nitrogen atom form an optionally substituted cyclic group selected from piperindinyl, piperazinyl, morpholinyl, and pyrrolidinyl. In some embodiments, $R^4$ and $R^5$ together with the intervening nitrogen atom form a substituted cyclic group, wherein the cyclic group is substituted with a group selected from —$C_{1-6}$ alkylene-phenyl, —O—$C_{1-6}$ alkylene-phenyl, —$C_{1-6}$ alkylene-cyclohexyl, and —O—$C_{1-6}$ alkylene-cyclohexyl. In some embodiments, $R^4$ and $R^5$ form a cyclic group selected from those depicted in the compounds of Table 1, below.

In some embodiments, $R^A$ is a substituent of Table A:

TABLE A

Exemplary $R^A$ substituents

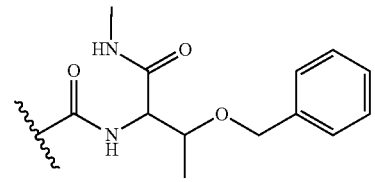 [SMILES: *C(=O)NC(C(=O)NC)C(C)OCc1ccccc1]

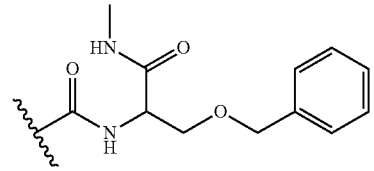 [SMILES: *C(=O)NC(COCc1ccccc1)C(=O)NC]

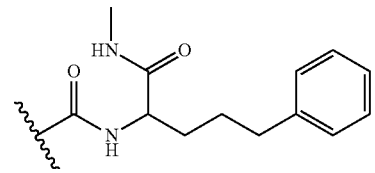 [SMILES: *C(=O)NC(CCCc1ccccc1)C(=O)NC]

TABLE A-continued
Exemplary R⁴ substituents
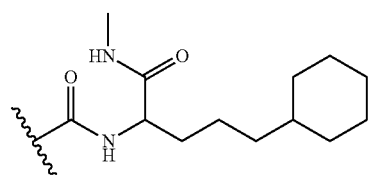 [SMILES: *C(=O)NC(CCCC1CCCCC1)C(=O)NC]
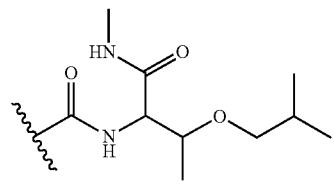 [SMILES: *C(=O)NC(C(=O)NC)C(C)OCC(C)C]
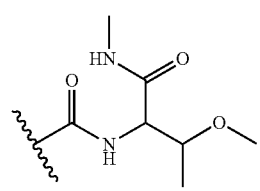 [SMILES: *C(=O)NC(C(=O)NC)C(C)OC]
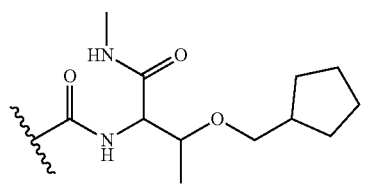 [SMILES: *C(=O)NC(C(=O)NC)C(C)OCC1CCCC1]
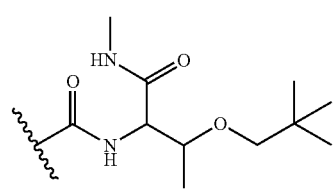 [SMILES: *C(=O)NC(C(=O)NC)C(C)OCC(C)(C)C]
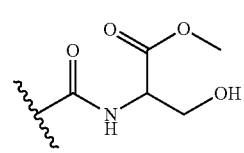 [SMILES: *C(=O)NC(CO)C(=O)OC]
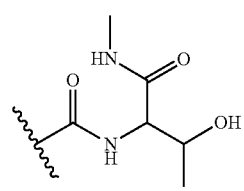 [SMILES: *C(=O)NC(C(=O)NC)C(C)O]
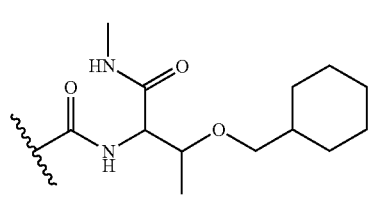 [SMILES: *C(=O)NC(C(=O)NC)C(C)OCC1CCCCC1]
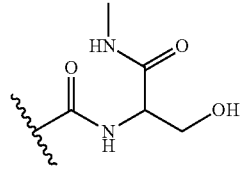 [SMILES: *C(=O)NC(CO)C(=O)NC]
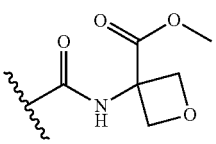 [SMILES: *C(=O)NC1(C(=O)OC)COC1]
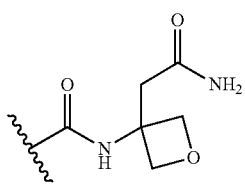 [SMILES: *C(=O)NC1(CC(N)=O)COC1]
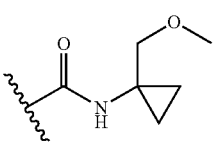 [SMILES: *C(=O)NC1(COC)CC1]
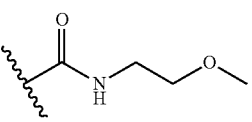 [SMILES: *C(=O)NCCOC]
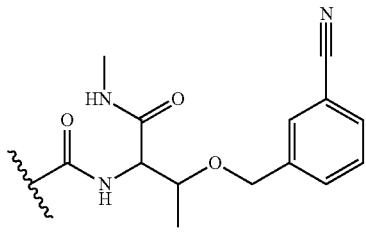 [SMILES: *C(=O)NC(C(=O)NC)C(C)OCc1cccc(C#N)c1]
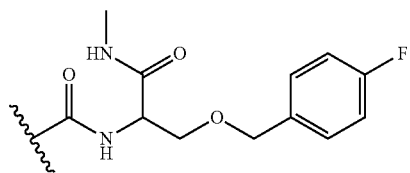 [SMILES: *C(=O)NC(COCc1ccc(F)cc1)C(=O)NC]
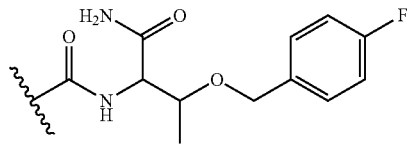 [SMILES: *C(=O)NC(C(N)=O)C(C)OCc1ccc(F)cc1]
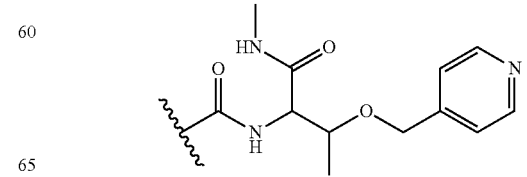

TABLE A-continued
Exemplary R⁴ substituents
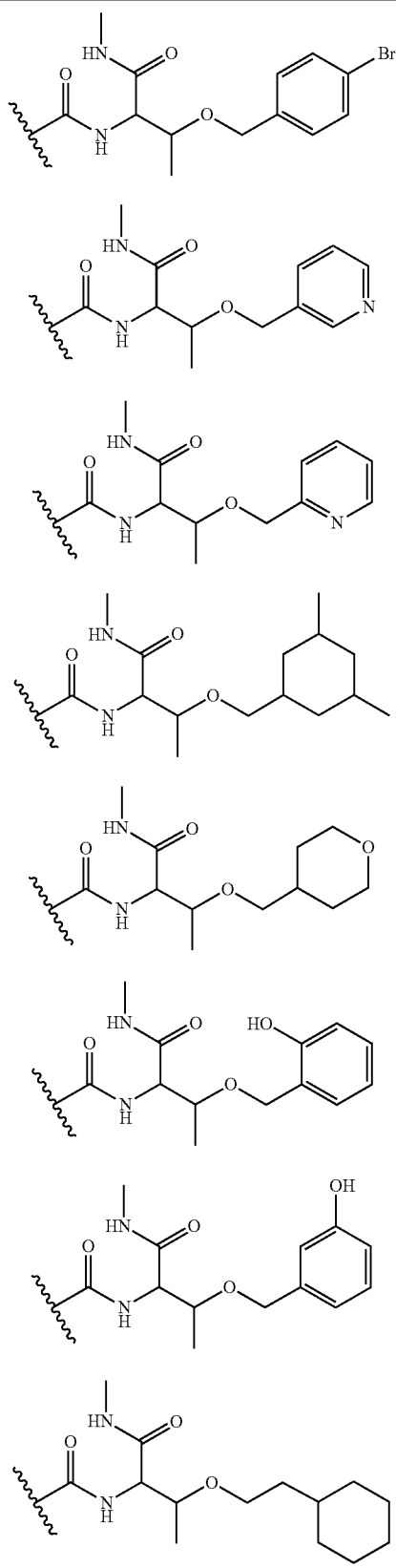
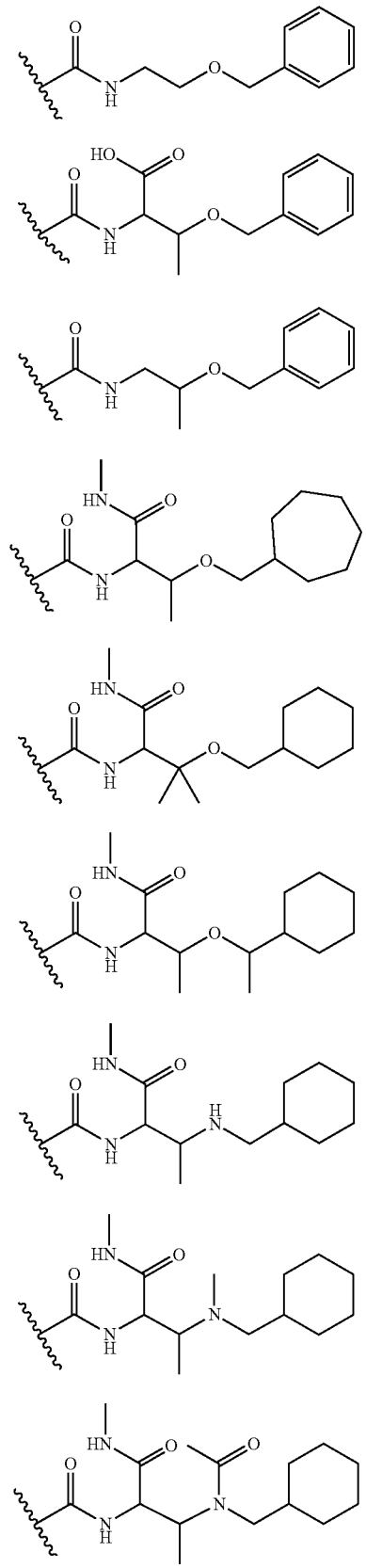

TABLE A-continued
Exemplary $R^A$ substituents
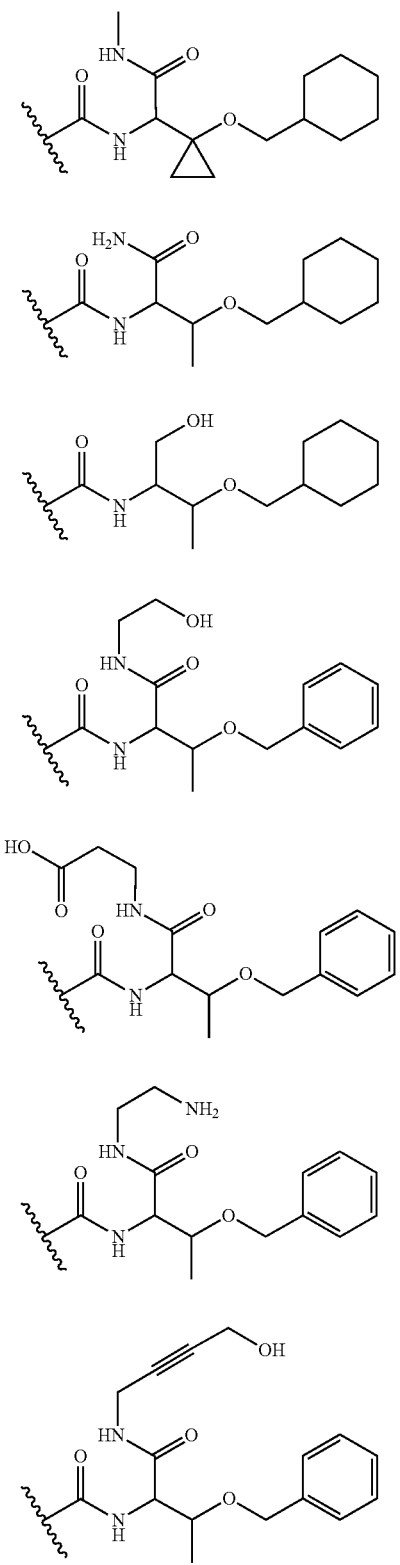
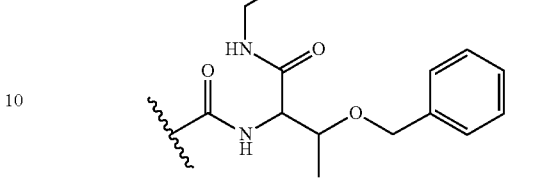
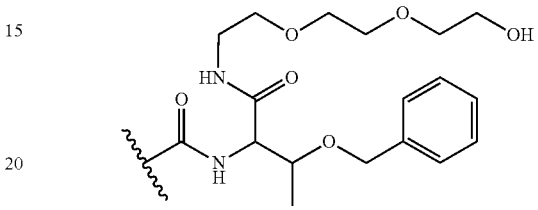
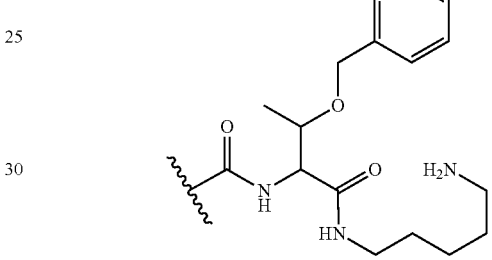
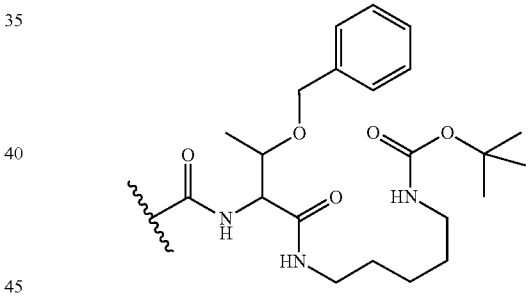
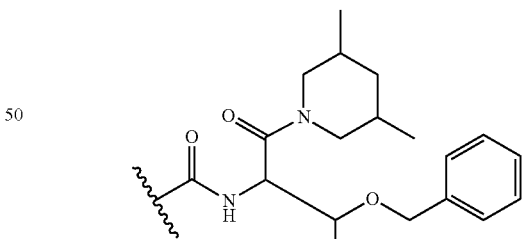
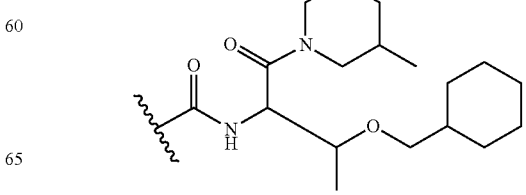

TABLE A-continued
Exemplary R⁴ substituents
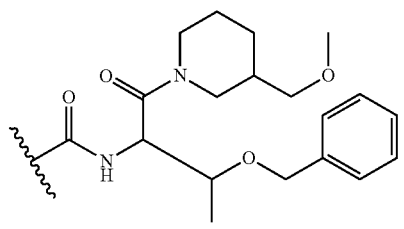 [SMILES: *C(=O)NC(C(=O)N1CCCC(COC)C1)C(C)OCc1ccccc1]
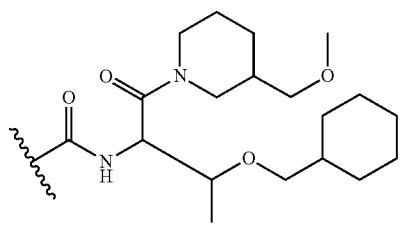 [SMILES: *C(=O)NC(C(=O)N1CCCC(COC)C1)C(C)OCC1CCCCC1]
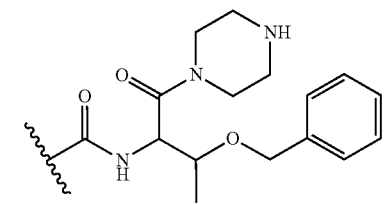 [SMILES: *C(=O)NC(C(=O)N1CCNCC1)C(C)OCc1ccccc1]
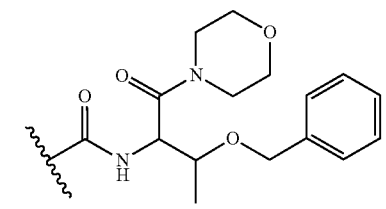 [SMILES: *C(=O)NC(C(=O)N1CCOCC1)C(C)OCc1ccccc1]
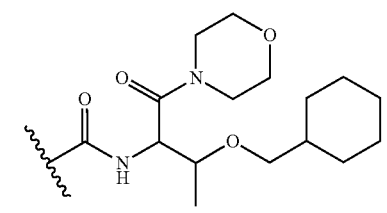 [SMILES: *C(=O)NC(C(=O)N1CCOCC1)C(C)OCC1CCCCC1]
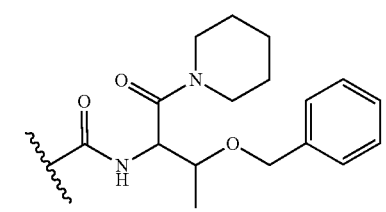 [SMILES: *C(=O)NC(C(=O)N1CCCCC1)C(C)OCc1ccccc1]
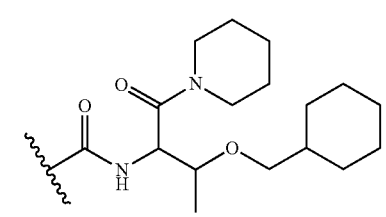 [SMILES: *C(=O)NC(C(=O)N1CCCCC1)C(C)OCC1CCCCC1]
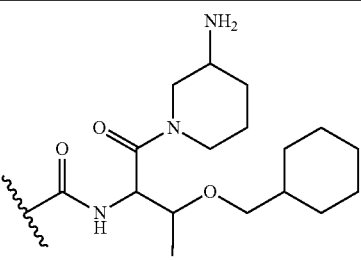
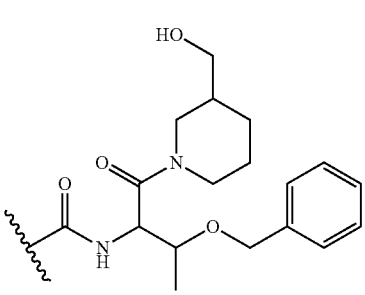 [SMILES: *C(=O)NC(C(=O)N1CCCC(CO)C1)C(C)OCc1ccccc1]
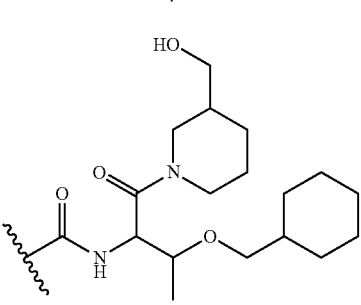
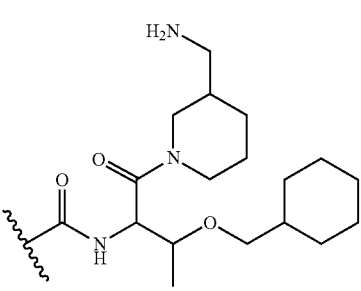 [SMILES: *C(=O)NC(C(=O)N1CCCC(CN)C1)C(C)OCC1CCCCC1]
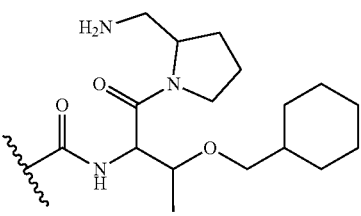 [SMILES: *C(=O)NC(C(=O)N1CCCC1CN)C(C)OCC1CCCCC1]
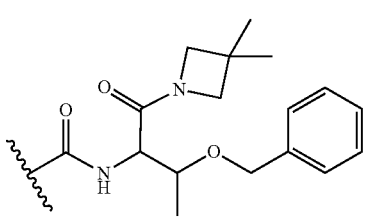 [SMILES: *C(=O)NC(C(=O)N1CC(C)(C)C1)C(C)OCc1ccccc1]

TABLE A-continued
Exemplary R[4] substituents
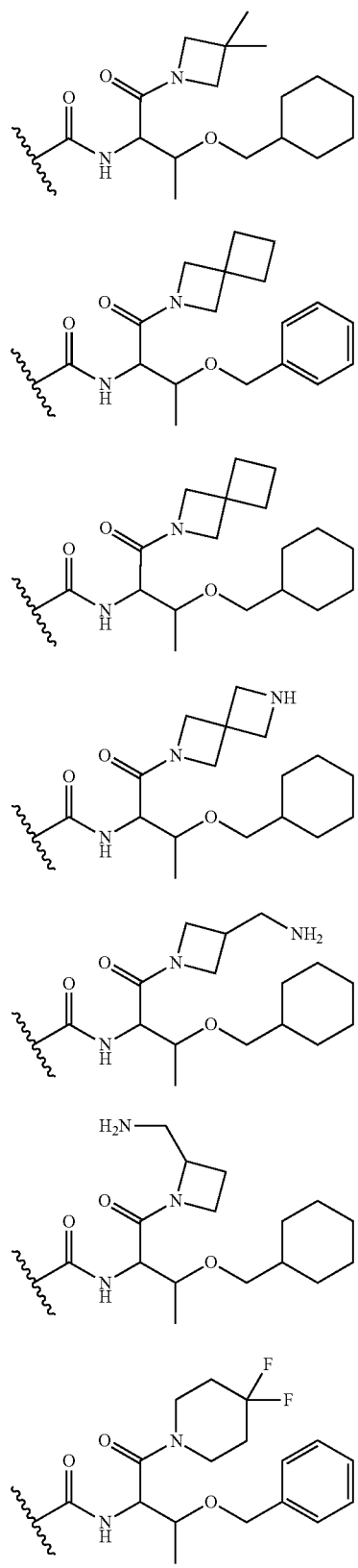
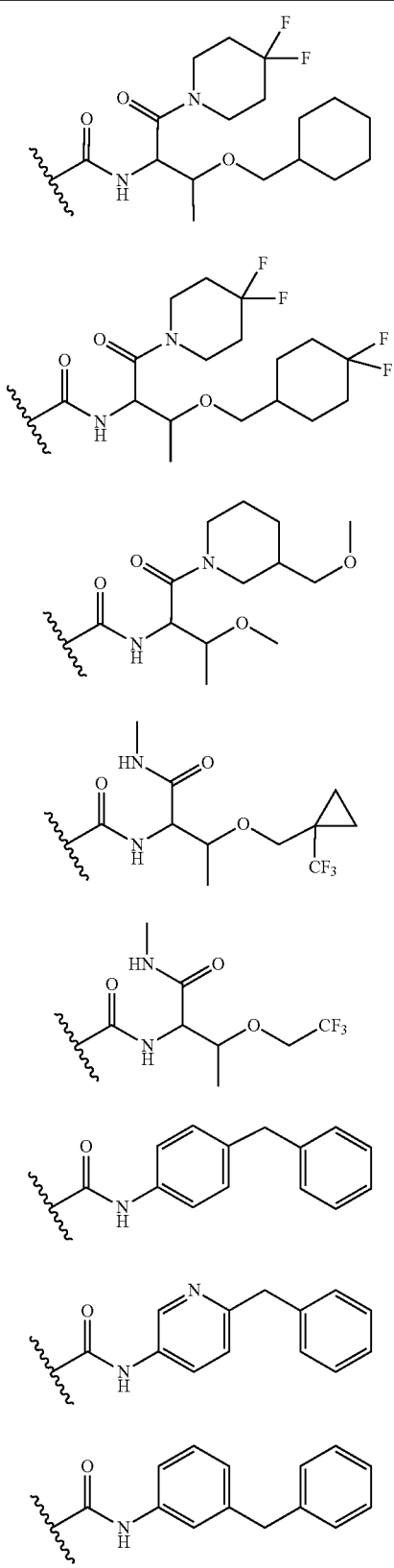

TABLE A-continued

Exemplary R⁴ substituents

TABLE A-continued
Exemplary R^A substituents
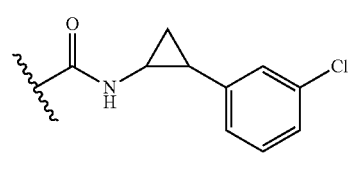 [SMILES: *C(=O)NC1CC1c1cccc(Cl)c1]
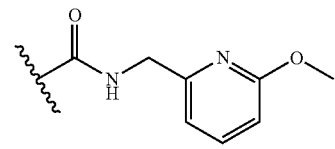 [SMILES: *C(=O)NCc1cccc(OC)n1]
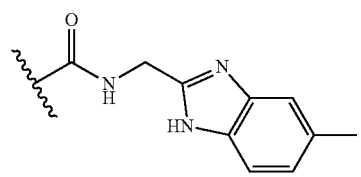 [SMILES: *C(=O)NCc1nc2cc(C)ccc2[nH]1]
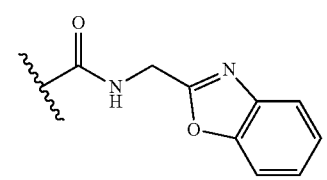 [SMILES: *C(=O)NCc1nc2ccccc2o1]
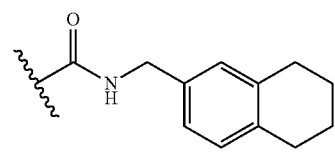 [SMILES: *C(=O)NCc1ccc2c(c1)CCCC2]
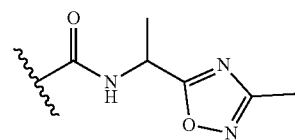 [SMILES: *C(=O)NC(C)c1nc(C)no1]
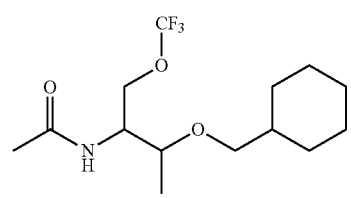 [SMILES: CC(=O)NC(COC(F)(F)F)C(C)OCC1CCCCC1]
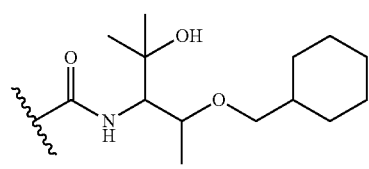 [SMILES: *C(=O)NC(C(C)OCC1CCCCC1)C(C)(C)O]
TABLE A-continued
Exemplary R^A substituents
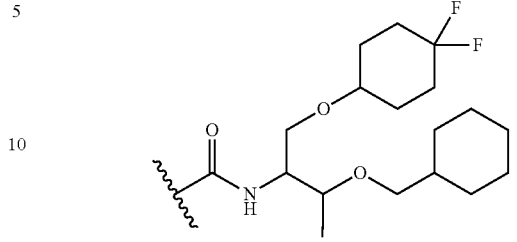
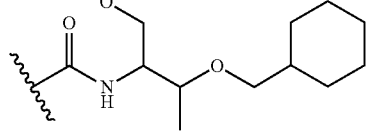
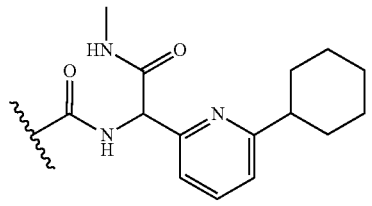 [SMILES: *C(=O)NC(C(=O)NC)c1cccc(C2CCCCC2)n1]
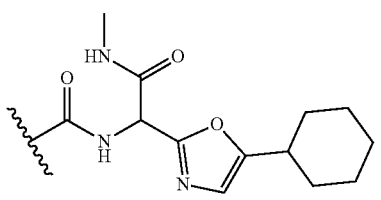 [SMILES: *C(=O)NC(C(=O)NC)c1ncc(C2CCCCC2)o1]
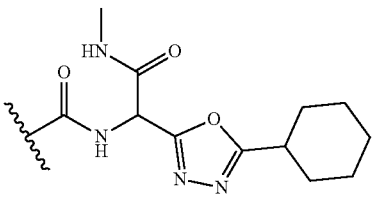 [SMILES: *C(=O)NC(C(=O)NC)c1nnc(C2CCCCC2)o1]
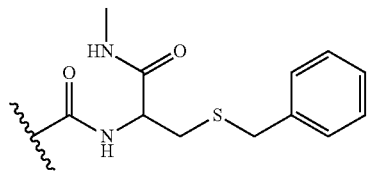 [SMILES: *C(=O)NC(CSCc1ccccc1)C(=O)NC]
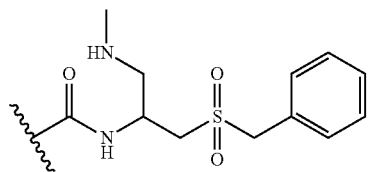 [SMILES: *C(=O)NC(CNC)CS(=O)(=O)Cc1ccccc1]

TABLE A-continued
Exemplary R⁴ substituents
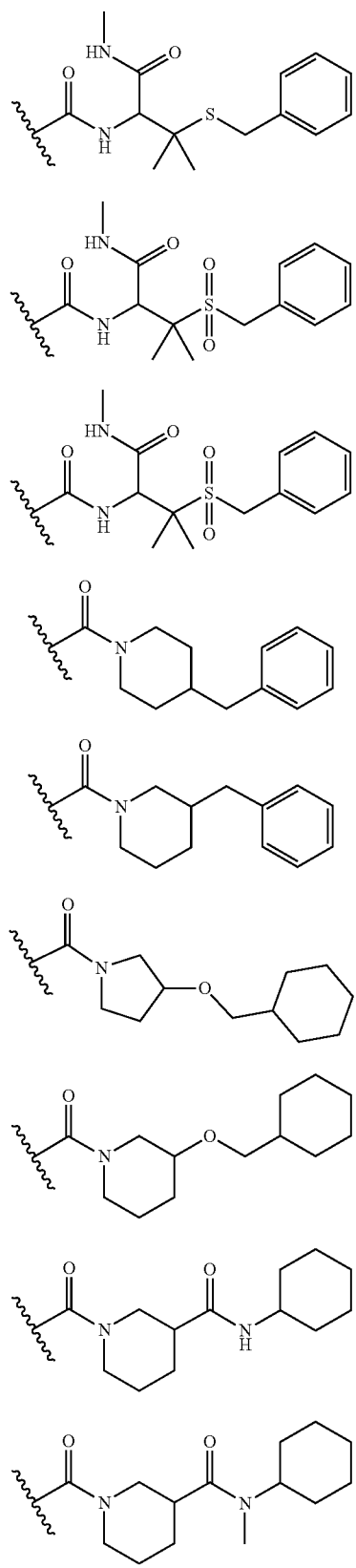
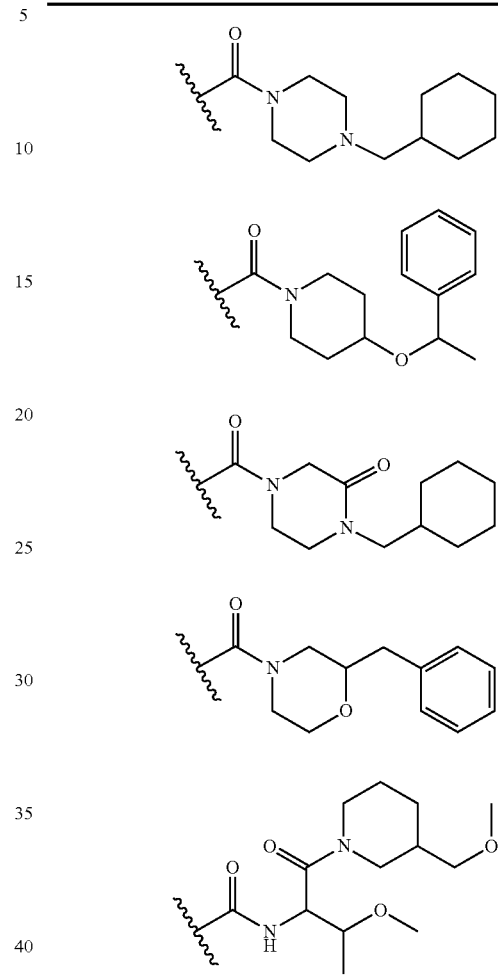
In some embodiments, R⁴ a substituent in Table A-continued:
TABLE A
Additional exemplary R⁴ substituents
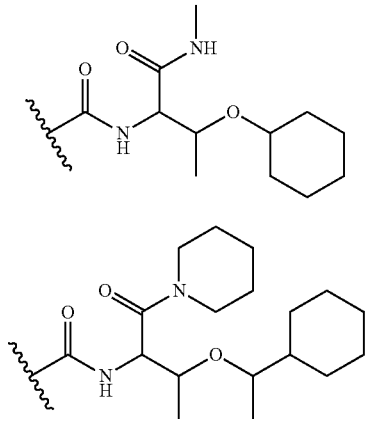

TABLE A-continued
Additional exemplary R⁴ substituents
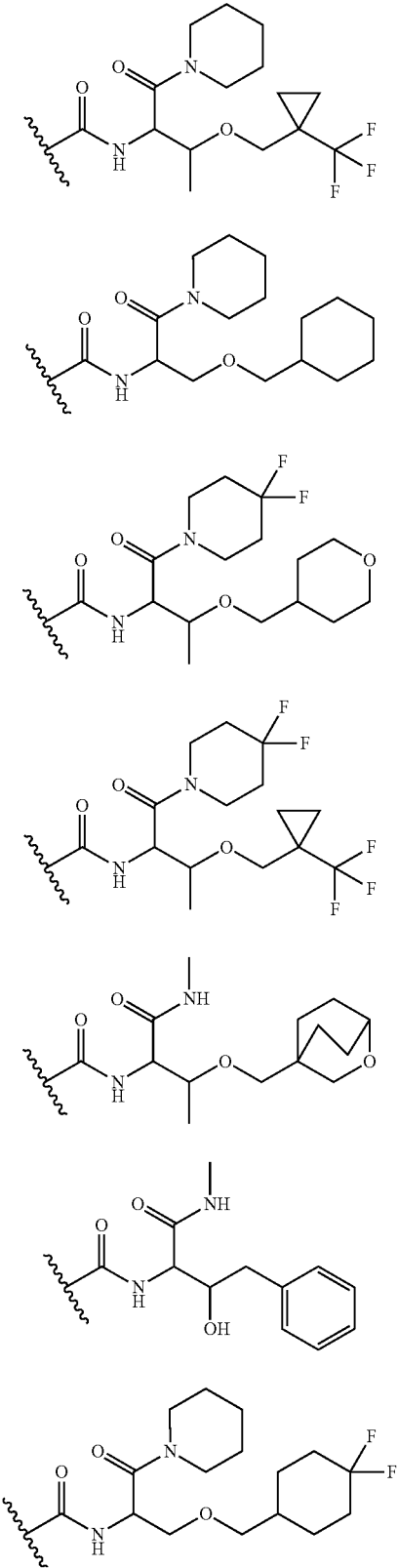
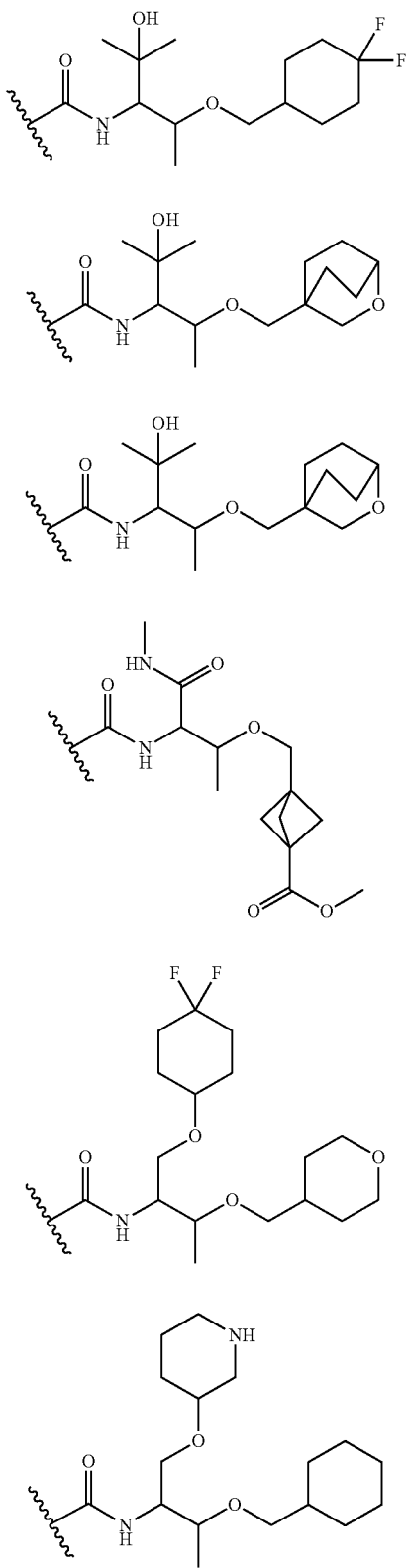

TABLE A-continued
Additional exemplary $R^4$ substituents
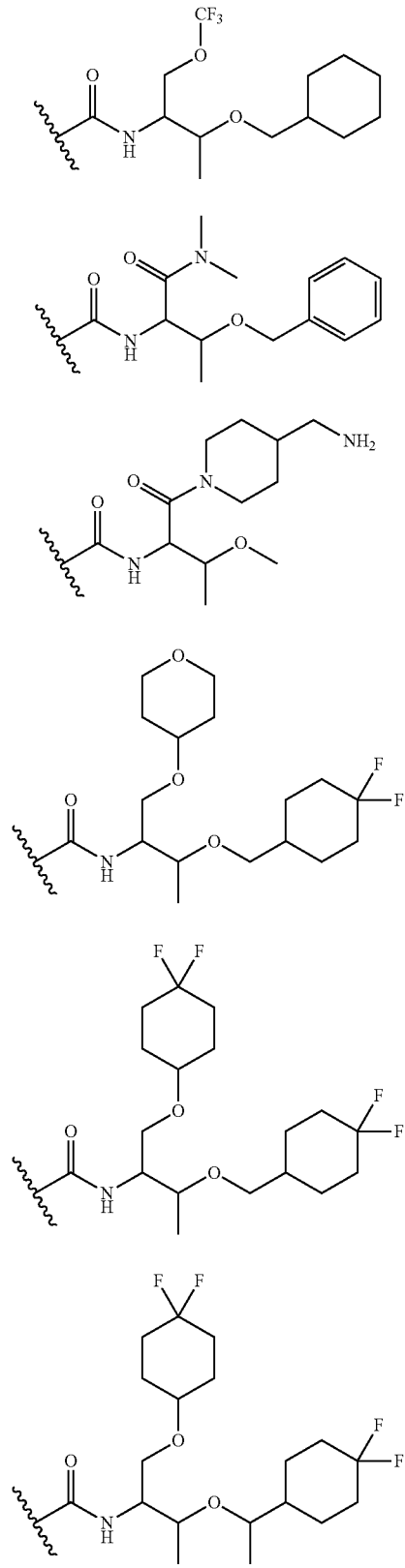
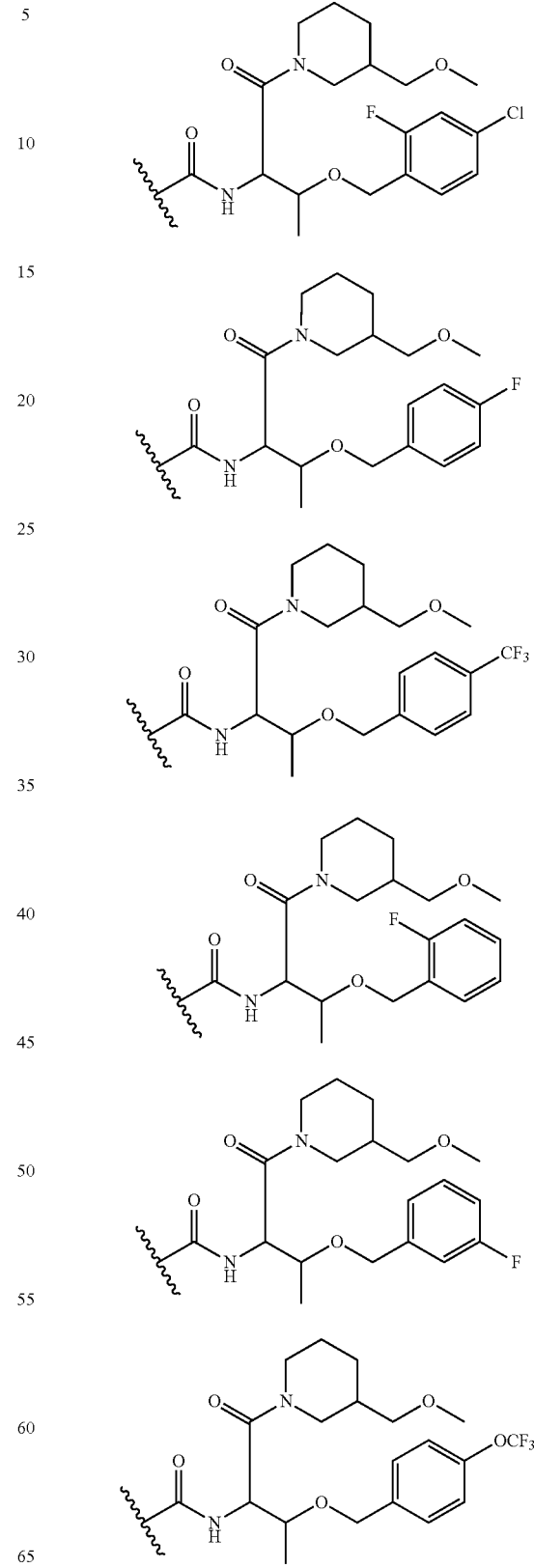

TABLE A-continued
Additional exemplary R<sup>A</sup> substituents
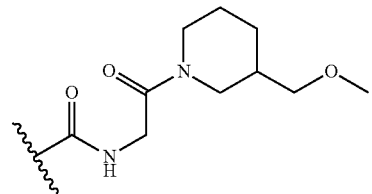 [SMILES: *C(=O)NCC(=O)N1CCCC(COC)C1]
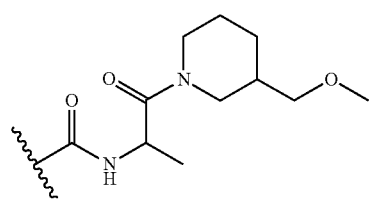 [SMILES: *C(=O)NC(C)C(=O)N1CCCC(COC)C1]
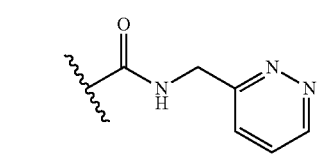 [SMILES: *C(=O)NCc1cccnn1]
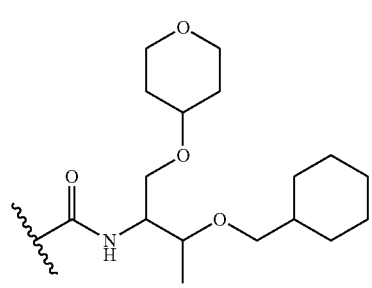 [SMILES: *C(=O)NC(COC1CCOCC1)C(C)OCC1CCCCC1]
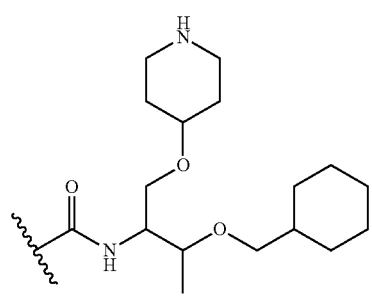 [SMILES: *C(=O)NC(COC1CCNCC1)C(C)OCC1CCCCC1]
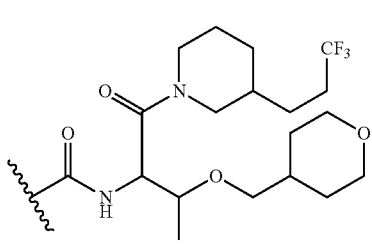 [SMILES: *C(=O)NC(C(=O)N1CCCC(CCC(F)(F)F)C1)C(C)OCC1CCOCC1]
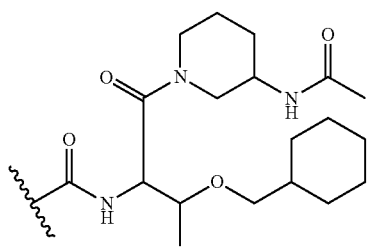 [SMILES: *C(=O)NC(C(=O)N1CCCC(NC(C)=O)C1)C(C)OCC1CCCCC1]
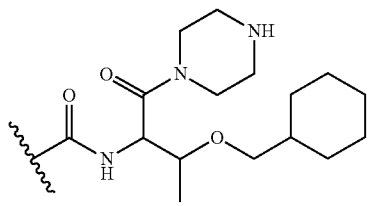 [SMILES: *C(=O)NC(C(=O)N1CCNCC1)C(C)OCC1CCCCC1]
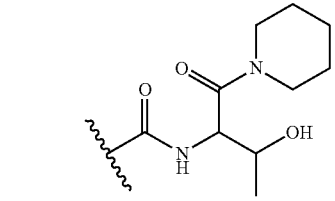 [SMILES: *C(=O)NC(C(=O)N1CCCCC1)C(C)O]
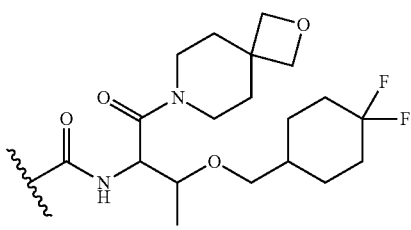 [SMILES: *C(=O)NC(C(=O)N1CCC2(CC1)COC2)C(C)OCC1CCC(F)(F)CC1]
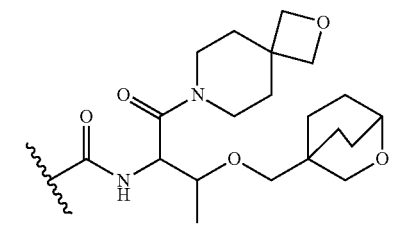 [SMILES: *C(=O)NC(C(=O)N1CCC2(CC1)COC2)C(C)OCC12CCC(CC1)OC2]
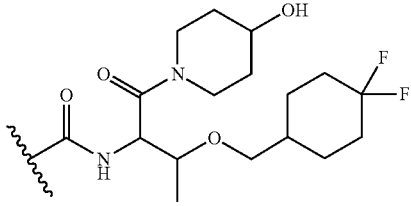 [SMILES: *C(=O)NC(C(=O)N1CCC(O)CC1)C(C)OCC1CCC(F)(F)CC1]
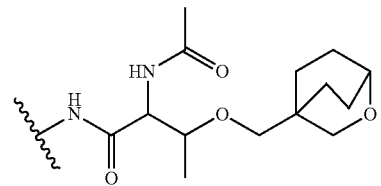 [SMILES: *NC(=O)C(NC(C)=O)C(C)OCC12CCC(CC1)OC2]

TABLE A-continued
Additional exemplary $R^4$ substituents
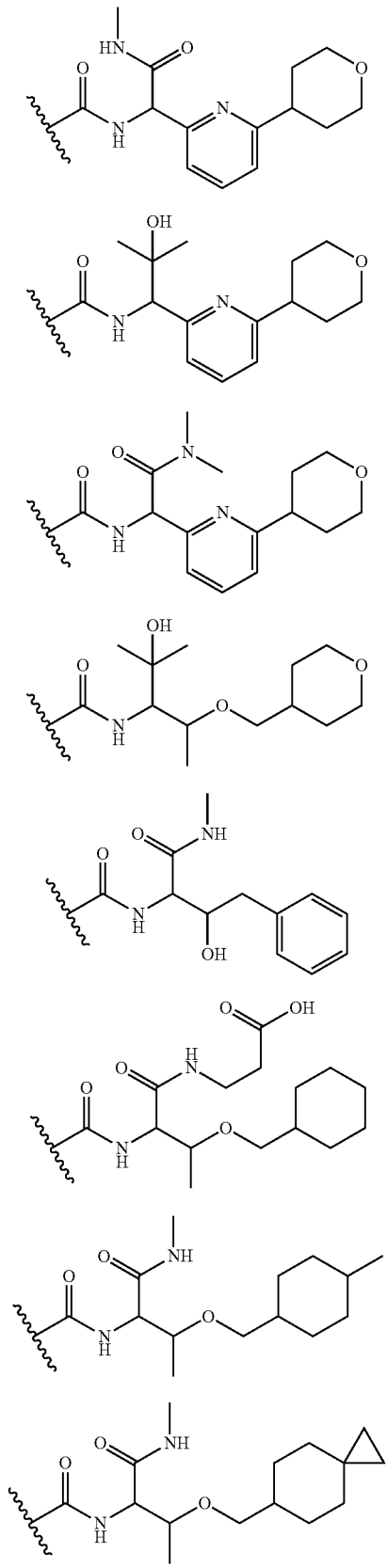
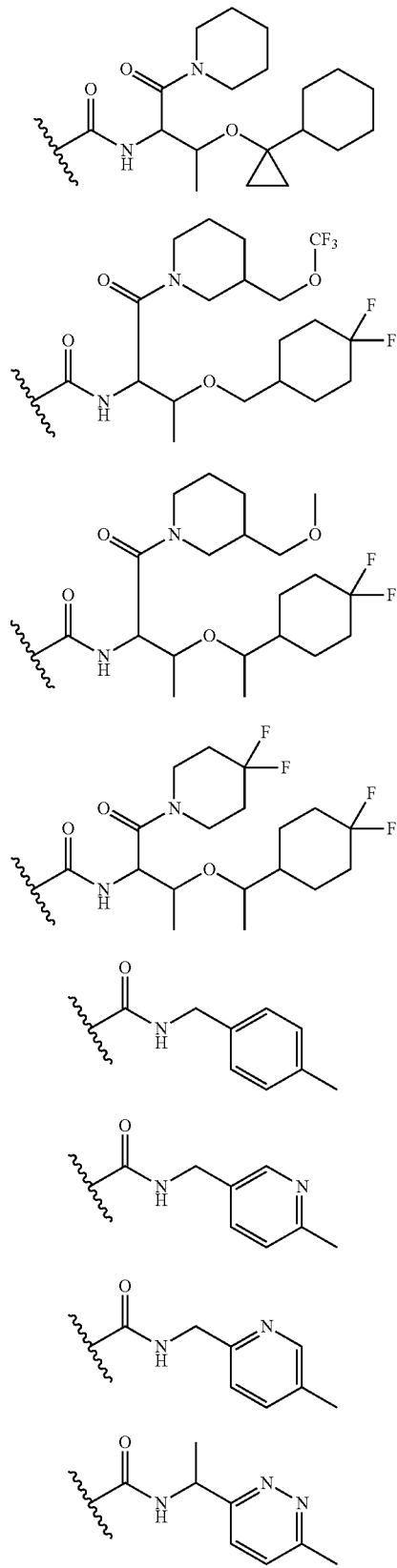

TABLE A-continued
Additional exemplary $R^A$ substituents
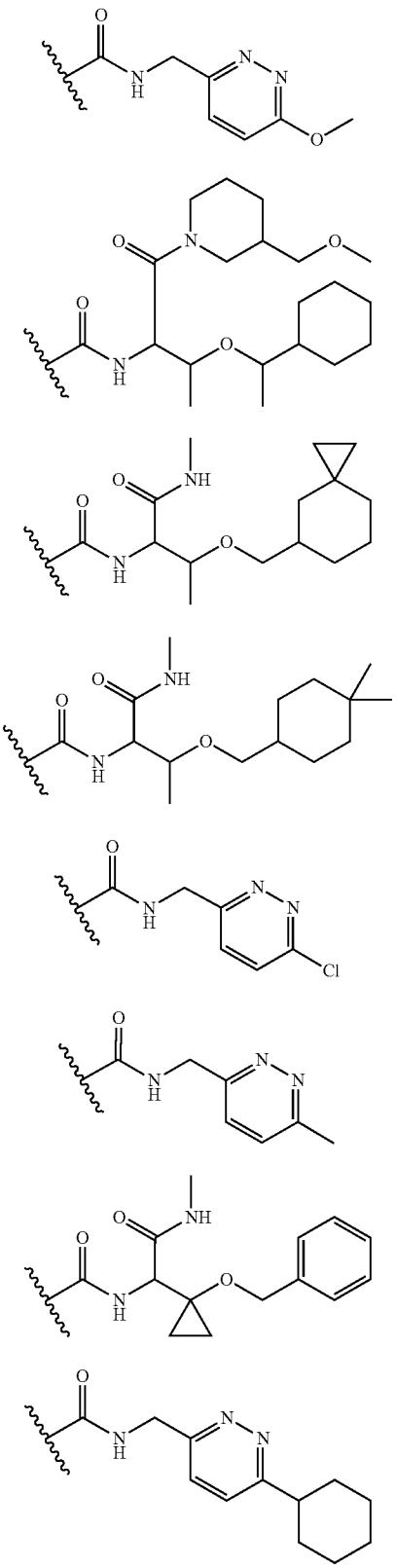
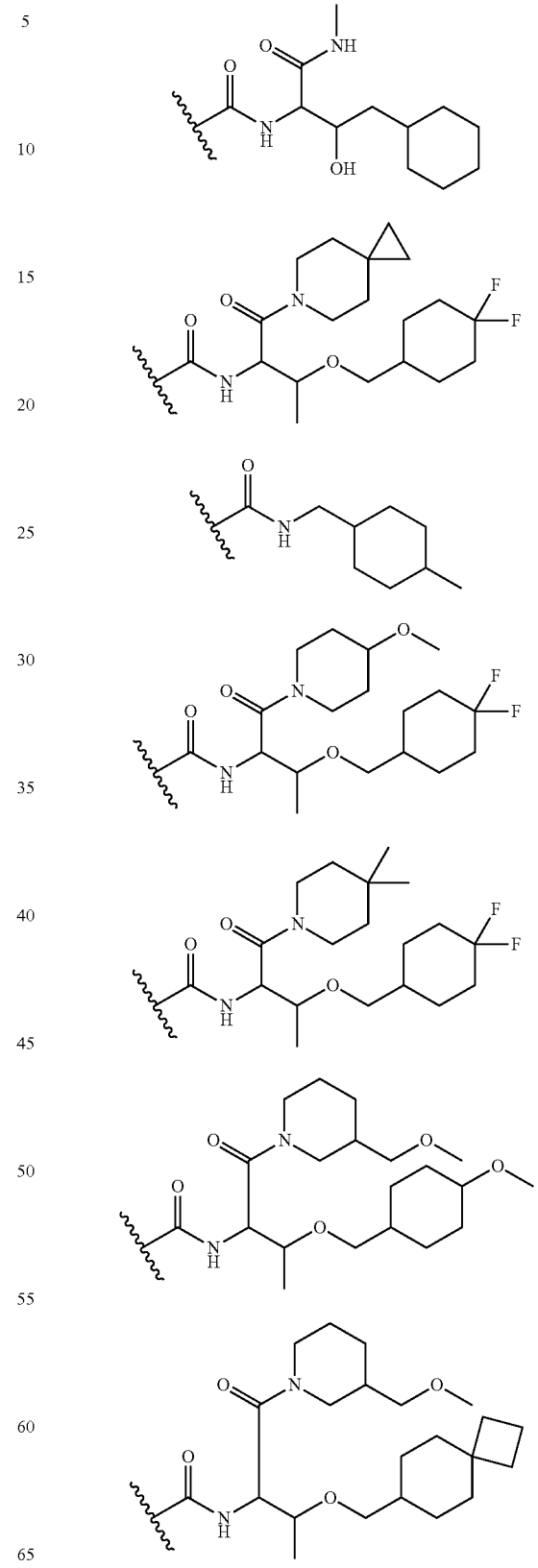

TABLE A-continued
Additional exemplary $R^A$ substituents
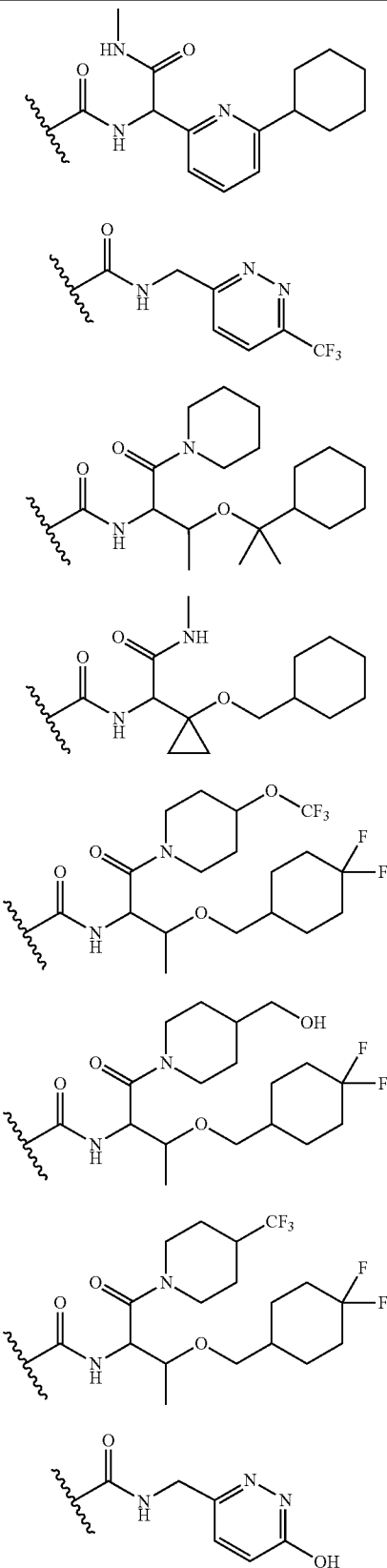
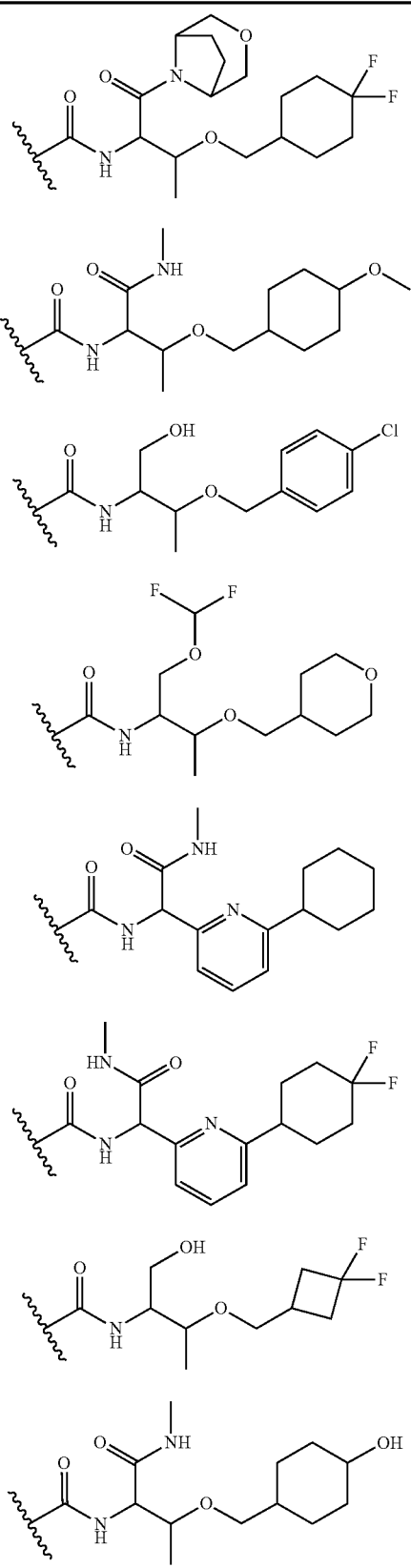

TABLE A-continued

Additional exemplary R^A substituents

TABLE A-continued
Additional exemplary R^A substituents
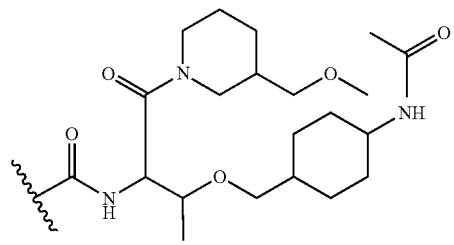
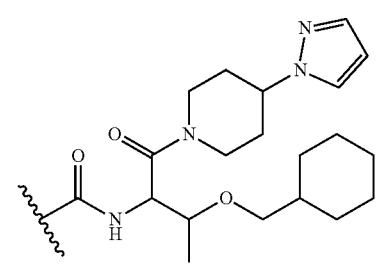 [SMILES: *C(=O)NC(C(=O)N1CCC(n2cccn2)CC1)C(C)OCC1CCCCC1]
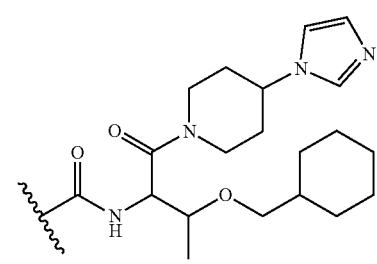 [SMILES: *C(=O)NC(C(=O)N1CCC(n2ccnc2)CC1)C(C)OCC1CCCCC1]
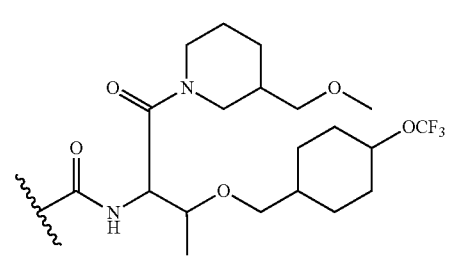 [SMILES: *C(=O)NC(C(=O)N1CCCC(COC)C1)C(C)OCC1CCC(OC(F)(F)F)CC1]
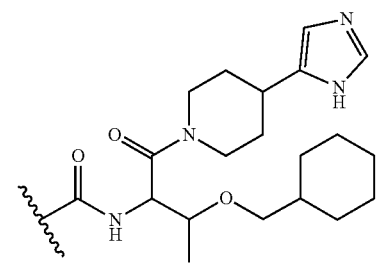 [SMILES: *C(=O)NC(C(=O)N1CCC(c2cnc[nH]2)CC1)C(C)OCC1CCCCC1]
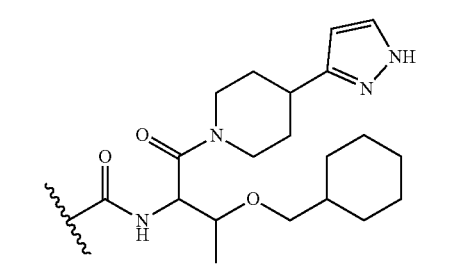 [SMILES: *C(=O)NC(C(=O)N1CCC(c2cc[nH]n2)CC1)C(C)OCC1CCCCC1]
TABLE A-continued
Additional exemplary R^A substituents
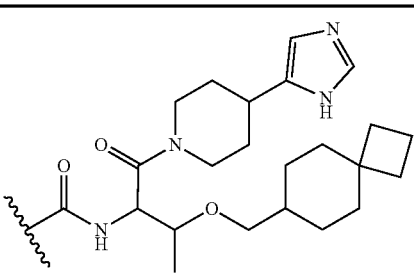
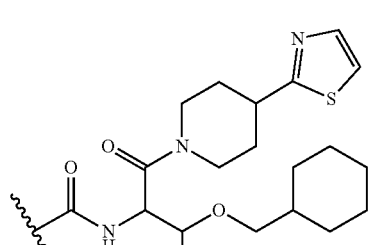
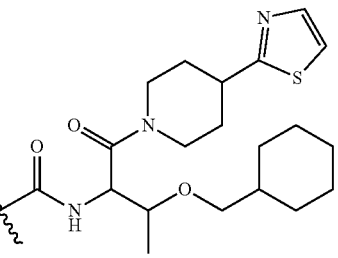
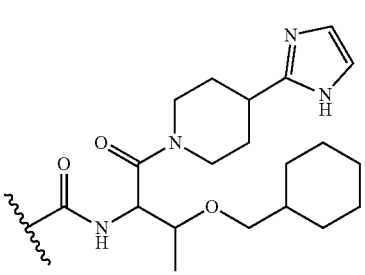 [SMILES: *C(=O)NC(C(=O)N1CCC(c2ncc[nH]2)CC1)C(C)OCC1CCCCC1]
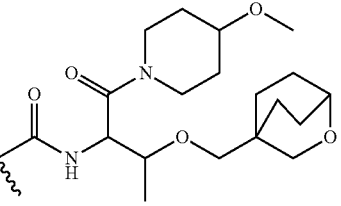
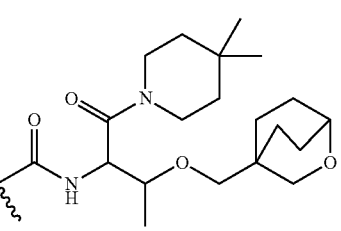
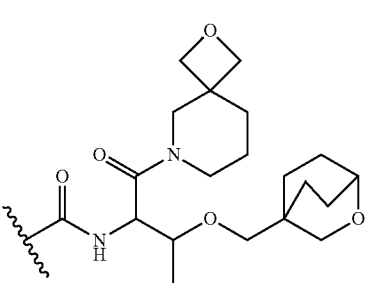 [SMILES: *C(=O)NC(C(=O)N1CCCC2(COC2)C1)C(C)OCC12CCC(CC1)OC2]

TABLE A-continued
Additional exemplary R⁴ substituents
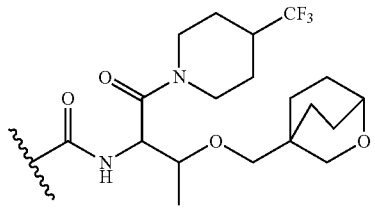 [SMILES: *C(=O)NC(C(=O)N1CCC(C(F)(F)F)CC1)C(C)OCC12CCC(CC1)OC2]
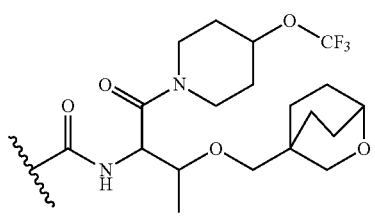 [SMILES: *C(=O)NC(C(=O)N1CCC(OC(F)(F)F)CC1)C(C)OCC12CCC(CC1)OC2]
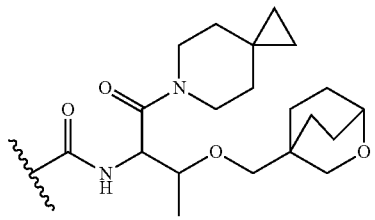 [SMILES: *C(=O)NC(C(=O)N1CCC2(CC1)CC2)C(C)OCC12CCC(CC1)OC2]
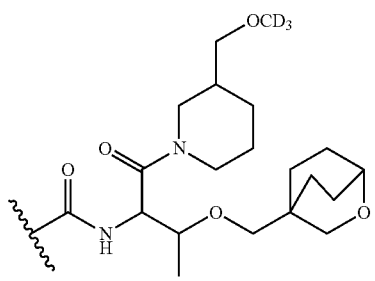
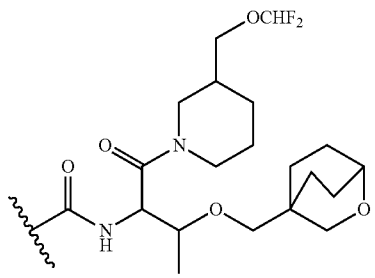
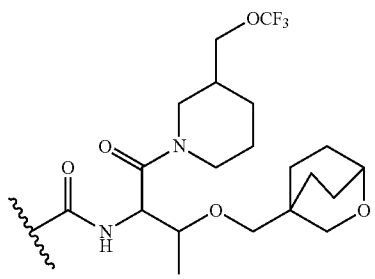 [SMILES: *C(=O)NC(C(=O)N1CCCC(COC(F)(F)F)C1)C(C)OCC12CCC(CC1)OC2]
TABLE A-continued
Additional exemplary R⁴ substituents
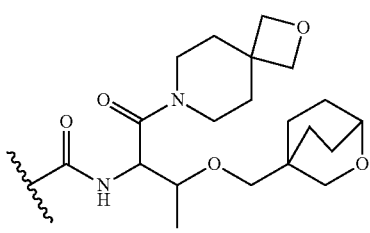 [SMILES: *C(=O)NC(C(=O)N1CCC2(CC1)COC2)C(C)OCC12CCC(CC1)OC2]
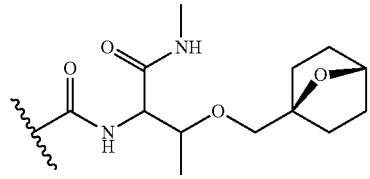 [SMILES: *C(=O)NC(C(=O)NC)C(C)OC[C@]12CC[C@H](CC1)O2]
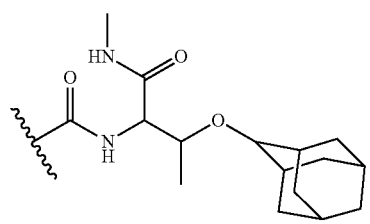 [SMILES: *C(=O)NC(C(=O)NC)C(C)OC1C2CC3CC(C2)CC1C3]
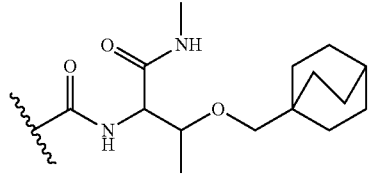 [SMILES: *C(=O)NC(C(=O)NC)C(C)OCC12CCC(CC1)CC2]
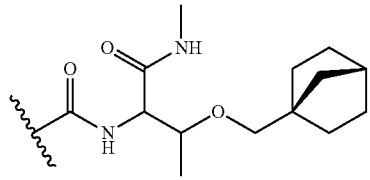 [SMILES: *C(=O)NC(C(=O)NC)C(C)OC[C@]12CC[C@H](CC1)C2]
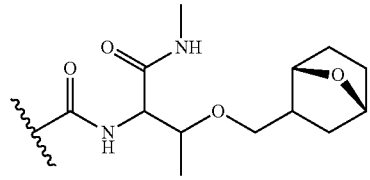 [SMILES: *C(=O)NC(C(=O)NC)C(C)OCC1C[C@H]2CC[C@@H]1O2]
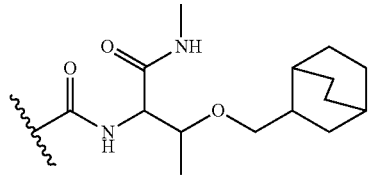 [SMILES: *C(=O)NC(C(=O)NC)C(C)OCC1CC2CCC1CC2]

TABLE A-continued
Additional exemplary R^A substituents
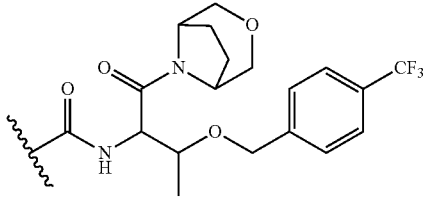 [SMILES: *C(=O)NC(C(=O)N1C2CCC1COC2)C(C)OCc1ccc(C(F)(F)F)cc1]
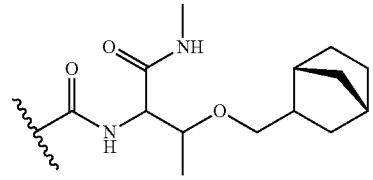 [SMILES: *C(=O)NC(C(=O)NC)C(C)OCC1C[C@H]2CC[C@@H]1C2]
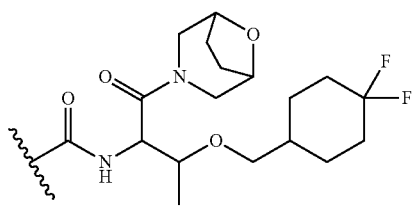 [SMILES: *C(=O)NC(C(=O)N1CC2CCC(C1)O2)C(C)OCC1CCC(F)(F)CC1]
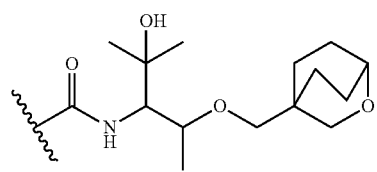 [SMILES: *C(=O)NC(C(C)OCC12CCC(CC1)OC2)C(C)(C)O]
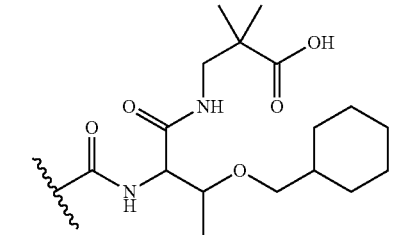 [SMILES: *C(=O)NC(C(=O)NCC(C)(C)C(=O)O)C(C)OCC1CCCCC1]
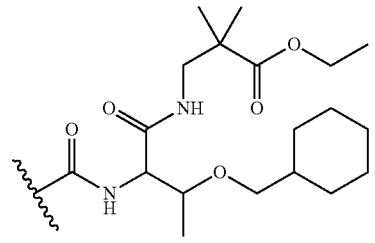 [SMILES: *C(=O)NC(C(=O)NCC(C)(C)C(=O)OCC)C(C)OCC1CCCCC1]
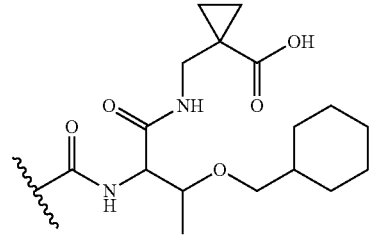 [SMILES: *C(=O)NC(C(=O)NCC1(C(=O)O)CC1)C(C)OCC1CCCCC1]
TABLE A-continued
Additional exemplary R^A substituents
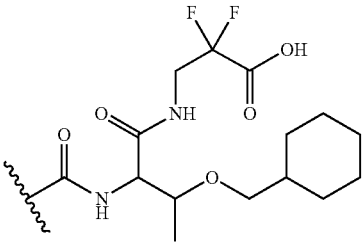 [SMILES: *C(=O)NC(C(=O)NCC(F)(F)C(=O)O)C(C)OCC1CCCCC1]
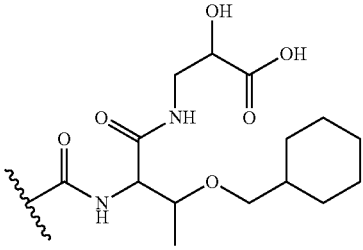 [SMILES: *C(=O)NC(C(=O)NCC(O)C(=O)O)C(C)OCC1CCCCC1]
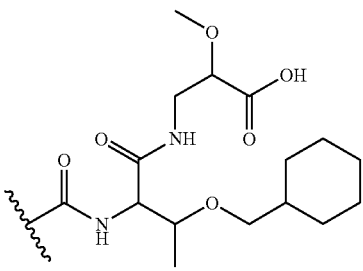 [SMILES: *C(=O)NC(C(=O)NCC(OC)C(=O)O)C(C)OCC1CCCCC1]
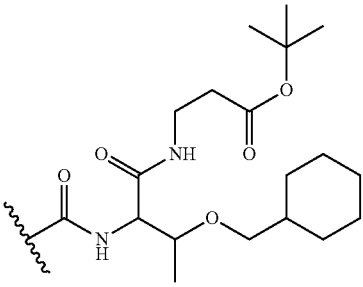 [SMILES: *C(=O)NC(C(=O)NCCC(=O)OC(C)(C)C)C(C)OCC1CCCCC1]
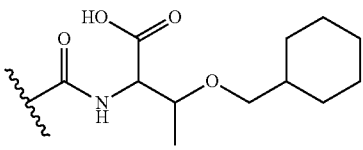 [SMILES: *C(=O)NC(C(=O)O)C(C)OCC1CCCCC1]
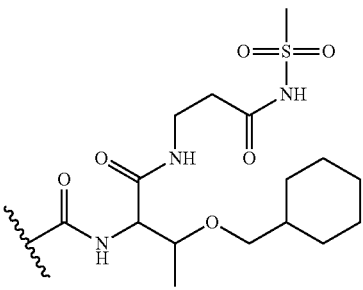 [SMILES: *C(=O)NC(C(=O)NCCC(=O)NS(C)(=O)=O)C(C)OCC1CCCCC1]

TABLE A-continued
Additional exemplary R^A substituents
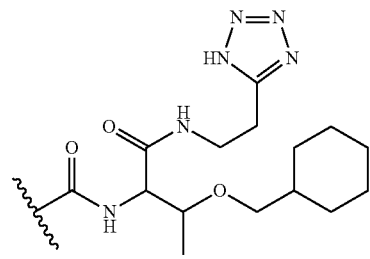 [SMILES: *C(=O)NC(C(=O)NCCc1nnn[nH]1)C(C)OCC1CCCCC1]
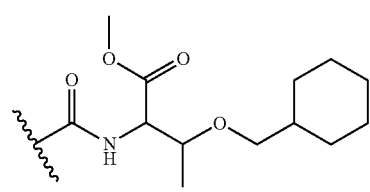 [SMILES: *C(=O)NC(C(=O)OC)C(C)OCC1CCCCC1]
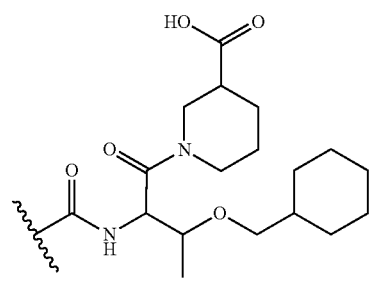 [SMILES: *C(=O)NC(C(=O)N1CCCC(C(=O)O)C1)C(C)OCC1CCCCC1]
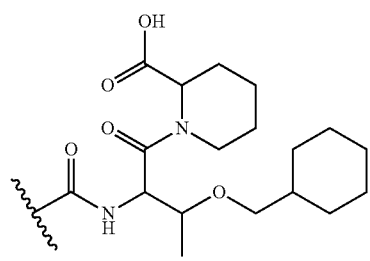 [SMILES: *C(=O)NC(C(=O)N1CCCCC1C(=O)O)C(C)OCC1CCCCC1]
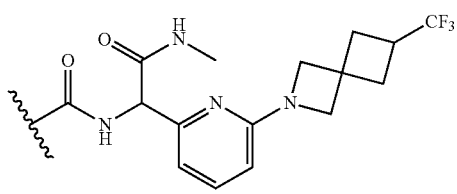 [SMILES: *C(=O)NC(C(=O)NC)c1cccc(N2CC3(CC(C(F)(F)F)C3)C2)n1]
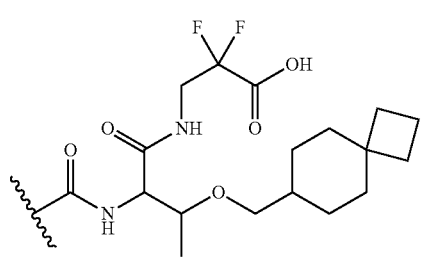 [SMILES: *C(=O)NC(C(=O)NCC(F)(F)C(=O)O)C(C)OCC1CCC2(CCC2)CC1]
TABLE A-continued
Additional exemplary R^A substituents
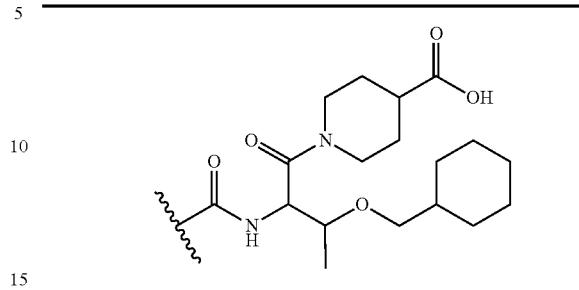
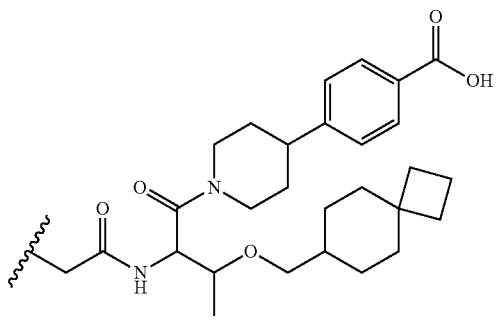 [SMILES: *CC(=O)NC(C(=O)N1CCC(c2ccc(C(=O)O)cc2)CC1)C(C)OCC1CCC2(CCC2)CC1]
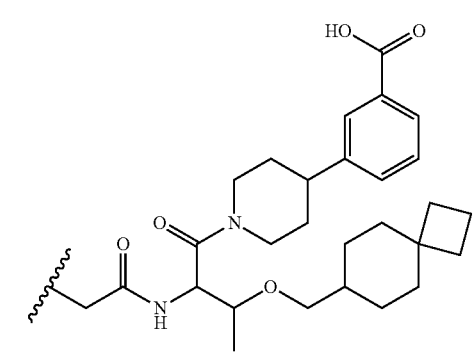 [SMILES: *CC(=O)NC(C(=O)N1CCC(c2cccc(C(=O)O)c2)CC1)C(C)OCC1CCC2(CCC2)CC1]
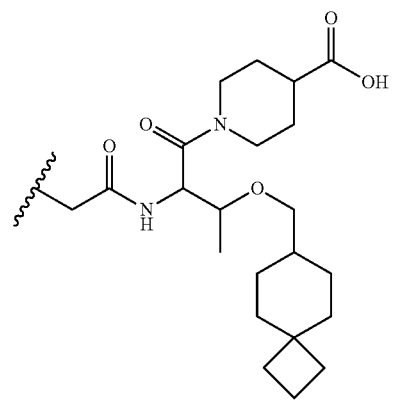 [SMILES: *CC(=O)NC(C(=O)N1CCC(C(=O)O)CC1)C(C)OCC1CCC2(CCC2)CC1]

TABLE A-continued

Additional exemplary R⁴ substituents

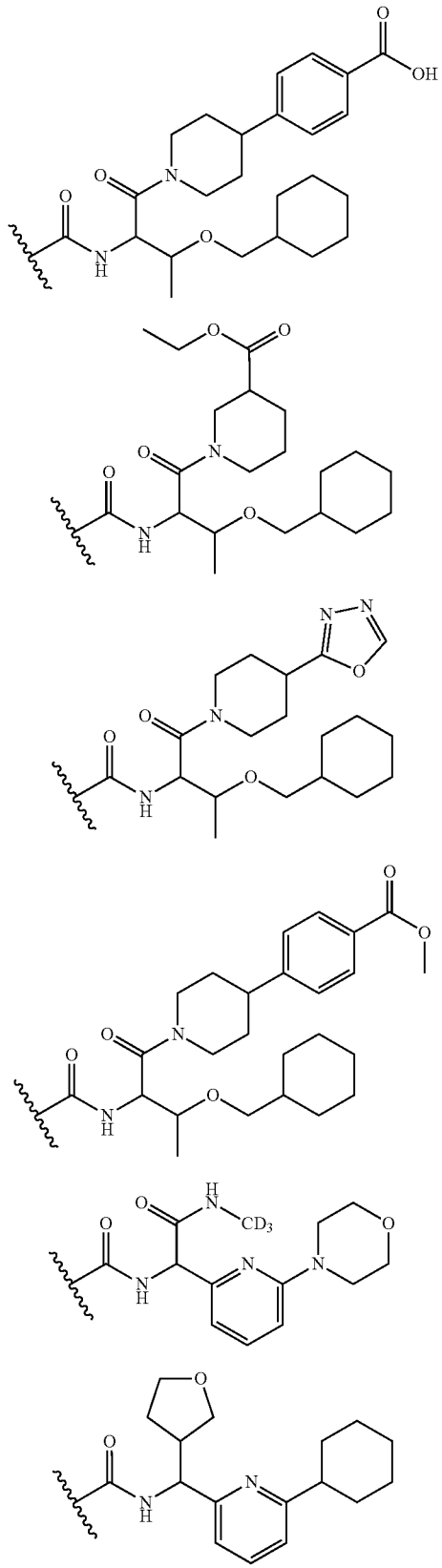

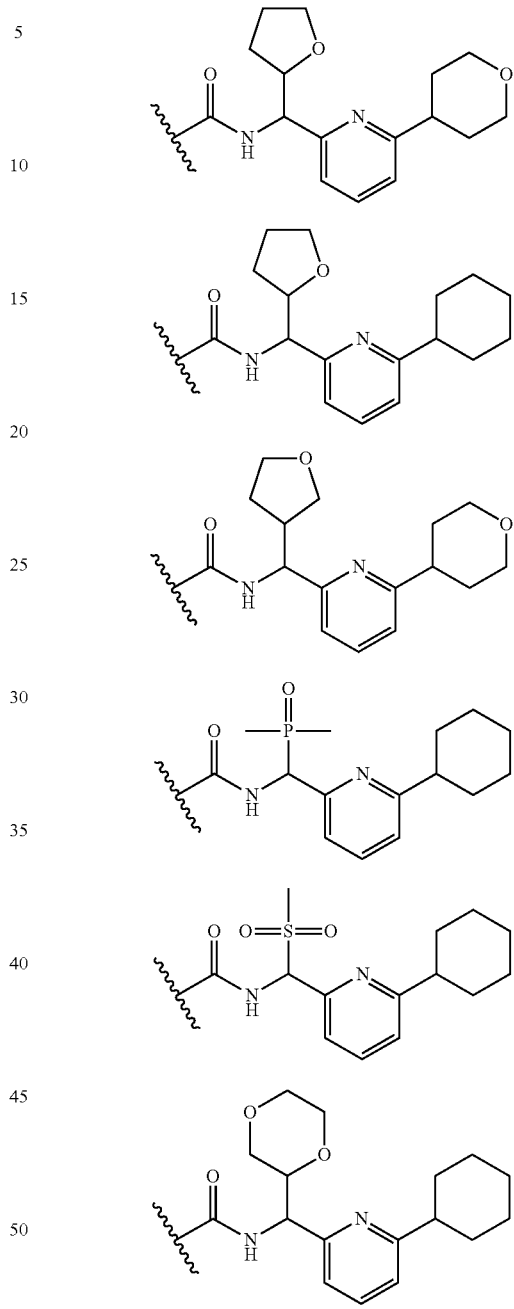

In some embodiments, R³ is hydrogen and R² is hydrogen or a substituent in Table A or Table A-continued.

As defined generally above, $L^2$ is a saturated or unsaturated, straight or branched, optionally substituted bivalent $C_{1-4}$ hydrocarbon chain, wherein 0-2 methylene units of $L^2$ are independently replaced by —O—, —NR—, —S—, —OC(O)—, —C(O)O—, —C(O)—, —S(O)—, —S(O)₂—, —C(S)—, —NRS(O)₂—, —S(O)₂NR—, —NRC(O)—, —C(O)NR—, —OC(O)NR—, —NRC(O)O—, or —NRC(O)NR—.

In some embodiments, $L^2$ is a saturated or unsaturated, straight or branched, optionally substituted bivalent $C_{1-4}$ hydrocarbon chain, wherein 0-2 methylene units of $L^2$ are independently replaced by —C(O)O—, —C(O)—, or —C(O)NR—. In some embodiments, L² is a C₁₋₄ alkylene chain, wherein 1-2 methylene units of L² are independently replaced by —C(O)O—, —C(O)—, or —C(O)NR—. In some embodiments, L² is C₁₋₄ alkylene chain, wherein 1 methylene unit of L² is replaced by —C(O)O—, —C(O)—, or —C(O)NR—. In some embodiments, L² is a saturated optionally substituted bivalent C₁₋₄ hydrocarbon chain. In some embodiments, L² is a saturated bivalent C₁₋₄ hydrocarbon chain, substituted on a single methylene unit by two substituents, which together with the intervening carbon atom form a 3-7 membered carbocyclic ring or heterocyclic ring (having 1-2 heteroatoms independently selected from nitrogen, oxygen, and sulfur). In some embodiments, L² is

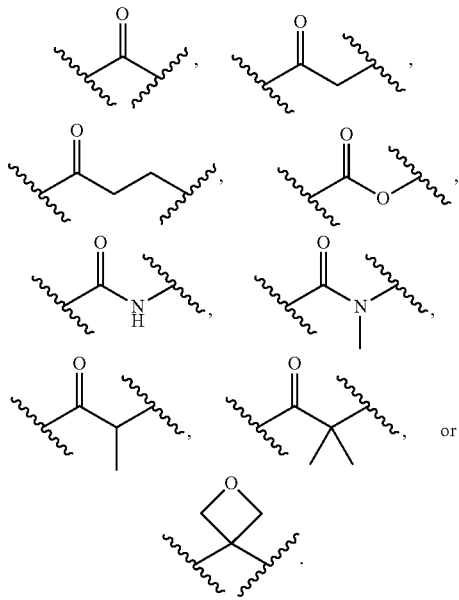

In some embodiments, L² is

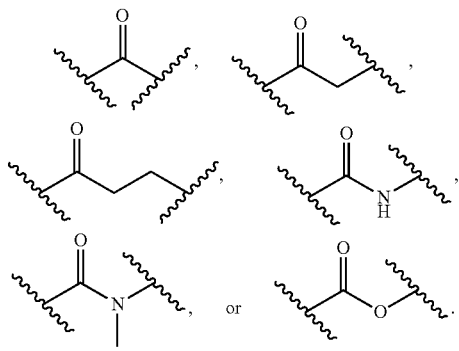

In some embodiments, L² is

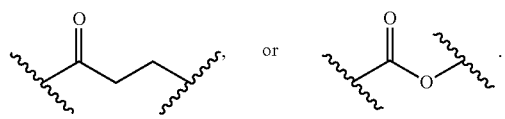 [SMILES: *CCC(*)=O ; *OC(*)=O]

In some embodiments, L² is

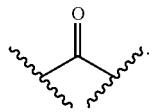

In some embodiments, L² is selected from those depicted in the compounds of Table 1, below.

In some embodiments, L² is a saturated, straight or branched, optionally substituted bivalent C₁₋₄ hydrocarbon chain. In some embodiments, L² is methylene.

In some embodiments, L² is —S(O)₂—.

As defined generally above, R⁶ is an optionally substituted C₁₋₆ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁷.

In some embodiments, R⁶ is an optionally substituted C₁₋₆ aliphatic group. In some embodiments, R⁶ is an optionally substituted methyl, ethyl, isopropyl, or tert-butyl group.

In some embodiments, R⁶ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁷. In some embodiments, R⁶ is a 3-8 membered saturated or partially unsaturated monocyclic carbocyclic ring, optionally substituted with one or more instances of R⁷. In some embodiments, R⁶ is a phenyl group, optionally substituted with one or more instances of R⁷. In some embodiments, R⁶ is a cyclic group selected from cyclopropyl, cyclobutyl, cyclohexyl and phenyl, wherein the cyclic group is optionally substituted with one or more instances of R⁷. In some embodiments, R⁶ is a cyclopropyl group, optionally substituted with one or more instances of R⁷. In some embodiments, R⁶ is selected from those depicted in the compounds of Table 1, below.

In some embodiments, R⁶ is a 3-8 membered saturated or partially unsaturated monocyclic heterocyclic ring (having 1-2 heteroatoms independently selected from nitrogen, oxygen, and sulfur), optionally substituted with one or more instances of R⁷. In some embodiments, R⁶ is tetrahydrofuranyl, optionally substituted with one or more instances of $R^7$. In some embodiments, $R^6$ is tetrahydropyranyl, optionally substituted with one or more instances of $R^7$. In some embodiments, $R^6$ is oxetanyl, optionally substituted with one or more instances of $R^7$.

In some embodiments, $R^6$ is a 5-6 membered monocyclic heteroaromatic ring (having 1-4 heteroatoms independently selected from nitrogen, oxygen, and sulfur), optionally substituted with one or more instances of $R^7$. In some embodiments, $R^6$ is furanyl, optionally substituted with one or more instances of $R^7$. In some embodiments, $R^6$ is pyrazolyl, optionally substituted with one or more instances of $R^7$. In some embodiments, $R^6$ is oxazolyl, optionally substituted with one or more instances of $R^7$.

As defined generally above, each instance of $R^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy. In some embodiments, each instance of $R^7$ is independently halogen, —OR, —CN, an optionally substituted $C_{1-6}$ aliphatic group, an optionally substituted $C_{1-6}$ aliphatic-Cy group, or Cy. In some embodiments, each instance of $R^7$ is independently —F, methyl, ethyl, isopropyl, isobutyl, —CN, optionally substituted phenyl, optionally substituted benzyl, —CF$_3$, —CH$_2$OH, —CH$_2$OCH$_3$, —CH$_2$CH$_2$OCH$_3$, —CH$_2$CH$_2$F, cyclopropyl or —CH$_2$-(cyclopropyl). In some embodiments, each instance of $R^7$ is independently a $C_{1-6}$ aliphatic group.

In some embodiments, -L$^2$-R$^6$ is a substituent of Table B:

TABLE B

| Exemplary L$^2$-R$^6$ substituents |
|---|
| 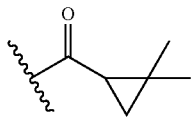 [SMILES: *C(=O)C1CC1(C)C] |
| 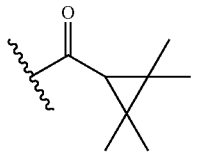 [SMILES: *C(=O)C1C(C)(C)C1(C)C] |
| 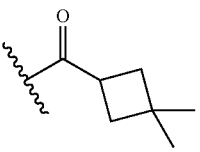 [SMILES: *C(=O)C1CC(C)(C)C1] |
| 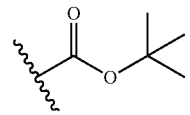 [SMILES: *C(=O)OC(C)(C)C] |
| 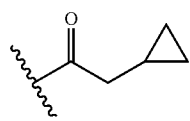 [SMILES: *C(=O)CC1CC1] |

TABLE B-continued

| Exemplary L$^2$-R$^6$ substituents |
|---|
| 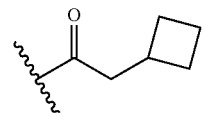 [SMILES: *C(=O)CC1CCC1] |
| 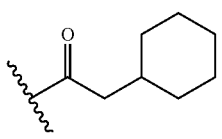 [SMILES: *C(=O)CC1CCCCC1] |
| 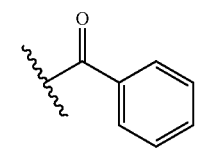 [SMILES: *C(=O)c1ccccc1] |
| 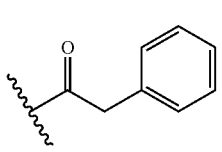 [SMILES: *C(=O)Cc1ccccc1] |
| 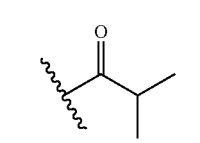 |
| 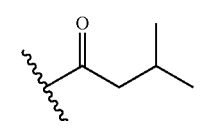 [SMILES: *C(=O)CC(C)C] |
| 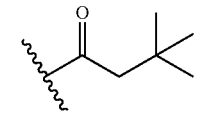 [SMILES: *C(=O)CC(C)(C)C] |
| 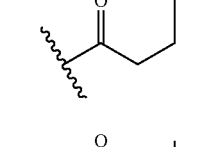 |
| 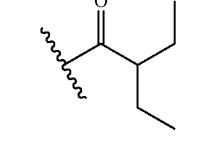 |
| 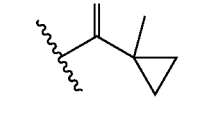 |
| 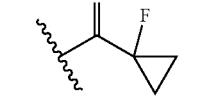 |

TABLE B-continued
Exemplary $L^2$-$R^6$ substituents
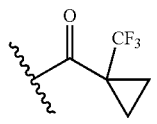 [SMILES: *C(=O)C1(C(F)(F)F)CC1]
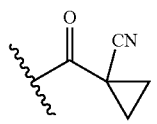 [SMILES: *C(=O)C1(C#N)CC1]
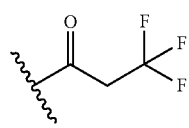
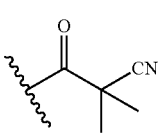
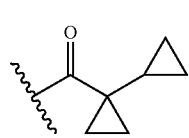 [SMILES: *C(=O)C1(C2CC2)CC1]
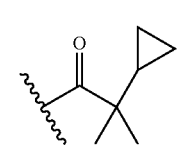 [SMILES: *C(=O)C(C)(C)C1CC1]
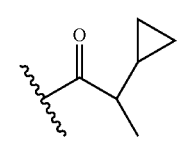
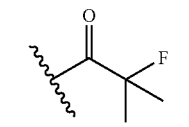 [SMILES: *C(=O)C(C)(C)F]
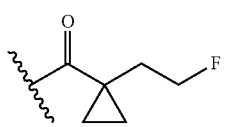 [SMILES: *C(=O)C1(CCF)CC1]
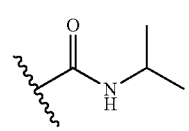 [SMILES: *C(=O)NC(C)C]
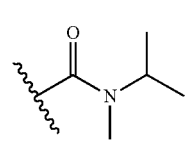 [SMILES: *C(=O)N(C)C(C)C]
TABLE B-continued
Exemplary $L^2$-$R^6$ substituents
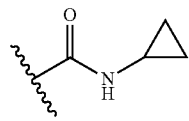 [SMILES: *C(=O)NC1CC1]
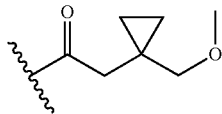 [SMILES: *C(=O)CC1(COC)CC1]
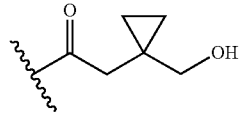 [SMILES: *C(=O)CC1(CO)CC1]
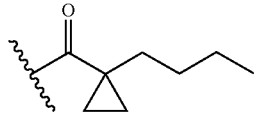 [SMILES: *C(=O)C1(CCCC)CC1]
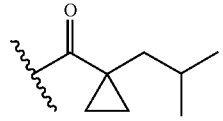 [SMILES: *C(=O)C1(CC(C)C)CC1]
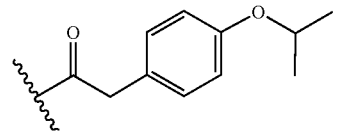 [SMILES: *C(=O)Cc1ccc(OC(C)C)cc1]
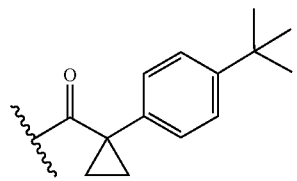 [SMILES: *C(=O)C1(c2ccc(C(C)(C)C)cc2)CC1]
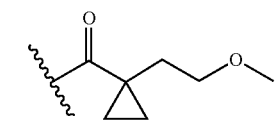 [SMILES: *C(=O)C1(CCOC)CC1]
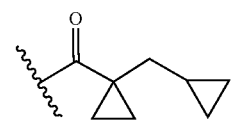 [SMILES: *C(=O)C1(CC2CC2)CC1]
In some embodiments, -$L^2$-$R^6$ is a substituent of Table B-continued:
TABLE B-continued
Additional exemplary -$L^2$-$R^6$ substituents
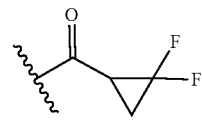 [SMILES: *C(=O)C1CC1(F)F]

TABLE B-continued-continued

Additional exemplary -L²-R⁶ substituents

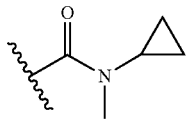
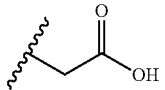 [SMILES: *CC(=O)O]
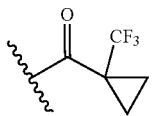 [SMILES: *C(=O)C1(C(F)(F)F)CC1]
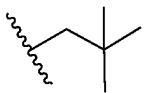 [SMILES: *CC(C)(C)C]
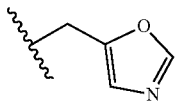 [SMILES: *Cc1cnco1]
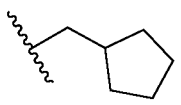 [SMILES: *CC1CCCC1]
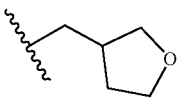 [SMILES: *CC1CCOC1]
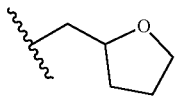 [SMILES: *CC1CCCO1]
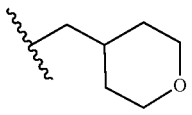 [SMILES: *CC1CCOCC1]
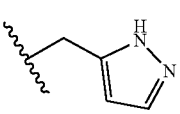 [SMILES: *Cc1ccn[nH]1]
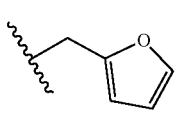 [SMILES: *Cc1ccco1]
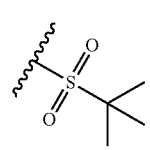

In some embodiments, -L²-R⁶ is a substituent of Table B or Table B-continued.

In some embodiments, -L²-R⁶ is

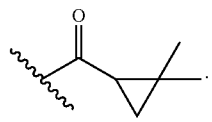

In some embodiments, -L²-R⁶ is

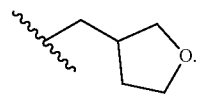 [SMILES: *CC1CCOC1]

In some embodiments, -L²-R⁶ is

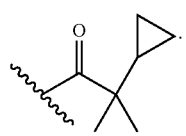 [SMILES: *C(=O)C(C)(C)C1CC1]

As defined generally above, L³ is a saturated or unsaturated, straight or branched, optionally substituted bivalent C$_{1-4}$ hydrocarbon chain, wherein 0-2 methylene units of L³ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—.

In some embodiments, L³ is a saturated or unsaturated, straight or branched, optionally substituted bivalent C$_{1-4}$ hydrocarbon chain, wherein 0-2 methylene units of L³ are independently replaced by —S(O)$_2$—, —C(O)NR—, or —C(O)—. In some embodiments, L³ is a C$_{1-4}$ alkylene chain, wherein 1-2 methylene units of L³ are independently replaced by —S(O)$_2$—, —C(O)NR—, or —C(O)—. In some embodiments, L³ is C$_{1-4}$ alkylene chain, wherein 1 methylene unit of L³ is replaced by —S(O)$_2$—, —C(O)NR—, or —C(O)—. In some embodiments, L³ is a saturated or unsaturated, straight or branched, optionally substituted bivalent C$_{1-4}$ alkylene chain, wherein 0-2 methylene units of L³ are independently replaced by —C(O)O—, or —C(O)—. In some embodiments, L³ is a C$_{1-4}$ alkylene chain, wherein 1-2 methylene units of L³ are independently replaced by —C(O)O—, or —C(O)—. In some embodiments, L³ is C$_{1-4}$ alkylene chain, wherein 1 methylene unit of L³ is replaced by —C(O)O—, or —C(O)—. In some embodiments, L³ is a saturated optionally substituted bivalent C$_{1-4}$ hydrocarbon chain. In some embodiments, L³ is a saturated bivalent C$_{1-4}$ hydrocarbon chain, substituted on a single methylene unit by two substituents, which together with the intervening carbon atom form a 3-7 membered carbocyclic ring or heterocyclic ring (having 1-2 heteroatoms independently selected from nitrogen, oxygen, and sulfur). In some embodiments, L³ is

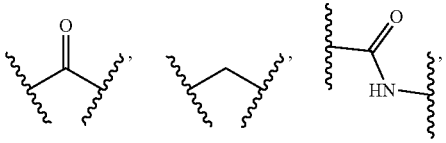

-continued

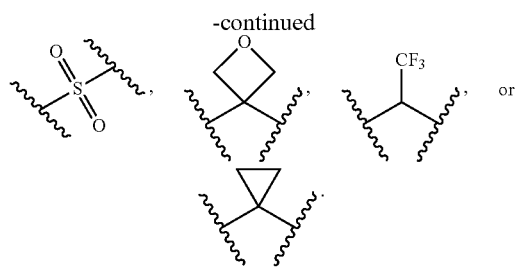

In some embodiments, L³ is

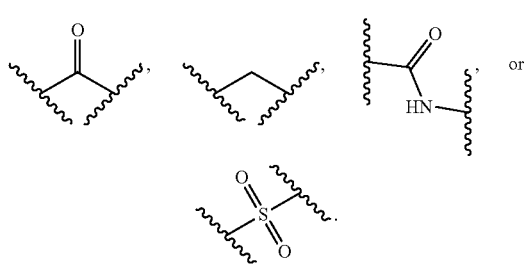

In some embodiments, L³ is

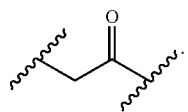

In some embodiments, L³ is

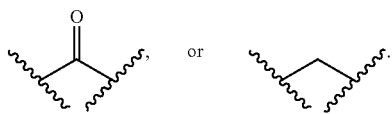

In some embodiments, L³ is selected from those depicted in the compounds of Table 1, below.

As defined generally above, R⁸ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁹.

In some embodiments, R⁸ is a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁹. In some embodiments, R⁸ is a cyclic group selected from a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R⁹. In some embodiments, R⁸ is a 3-8 membered saturated or partially unsaturated monocyclic heterocyclic ring (having 1-2 heteroatoms independently selected from nitrogen, oxygen, and sulfur), optionally substituted with one or more instances of R⁹. In some embodiments, R⁸ is a 5-6 membered monocyclic heteroaromatic ring (having 1-4 heteroatoms independently selected from nitrogen, oxygen, and sulfur), optionally substituted with one or more instances of R⁹. In some embodiments, R⁸ is an 8-10 membered bicyclic heteroaromatic ring (having 1-5 heteroatoms independently selected from nitrogen, oxygen, and sulfur), optionally substituted with one or more instances of R⁹. In some embodiments, R⁸ is a cyclic group selected from pyrazolyl, oxazolyl, thiazolyl, pyrrolidinyl, tetrahydropyranyl, pyridinyl, imidazolyl, indolyl, 1,2,4-triazolyl, 1,2,4-thiadiazolyl, piperidinyl, and indazolyl, wherein the cyclic group is optionally substituted with one or more instances of R⁹. In some embodiments, R⁸ is a pyrazolyl or thiazolyl group, optionally substituted with one or more instances of R⁹. In some embodiments, R⁸ is a pyrazolyl or thiazolyl group. In some embodiments, R⁸ is selected from those depicted in the compounds of Table 1, below.

As defined generally above, each instance of R⁹ is independently halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)C(NR)NR₂, —N(R)S(O)₂NR₂, —N(R)S(O)₂R, an optionally substituted C₁₋₆ aliphatic group, an optionally substituted C₁₋₆ aliphatic-Cy group, or Cy.

In some embodiments, each instance of R⁹ is independently halogen, an optionally substituted C₁₋₆ aliphatic group, an optionally substituted C₁₋₆ aliphatic-Cy group, or Cy. In some embodiments, each instance of R⁹ is independently an optionally substituted C₁₋₆ aliphatic-Cy group, wherein the Cy is an optionally substituted group selected from phenyl, cyclohexyl, pyridinyl, piperidinyl, cyclopropyl, or tetrahydropyranyl. In some embodiments, R⁹ is a benzylic group. In some embodiments, each instance of R⁹ is independently halogen or an optionally substituted C₁₋₆ aliphatic group. In some embodiments, $R^9$ is selected from those depicted in the compounds of Table 1, below.
TABLE C
Exemplary $L^3$-$R^8$ substituents
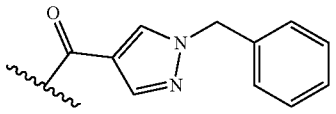 [SMILES: *C(=O)c1cnn(Cc2ccccc2)c1]
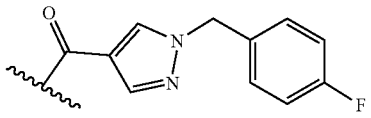 [SMILES: *C(=O)c1cnn(Cc2ccc(F)cc2)c1]
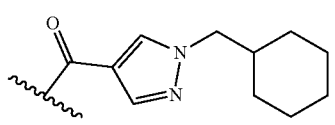 [SMILES: *C(=O)c1cnn(CC2CCCCC2)c1]
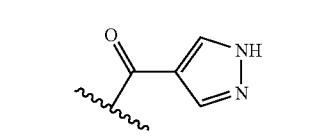 [SMILES: *C(=O)c1cn[nH]c1]
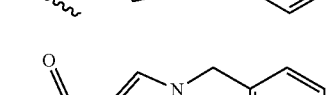
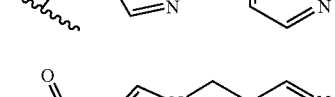
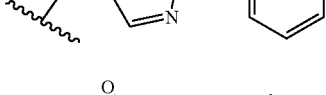
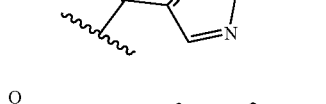
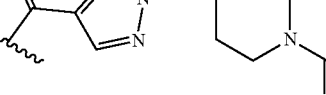
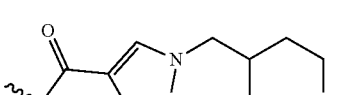
TABLE C-continued
Exemplary $L^3$-$R^8$ substituents
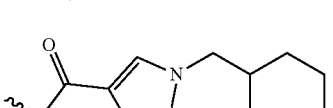
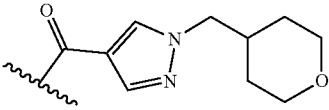
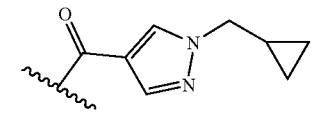 [SMILES: *C(=O)c1cnn(CC2CC2)c1]
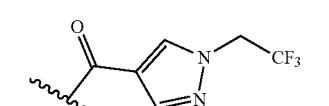
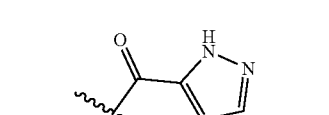
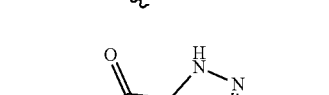
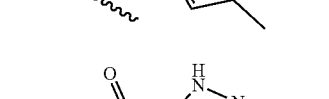
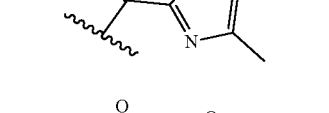
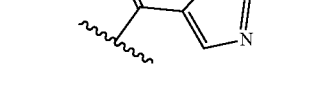
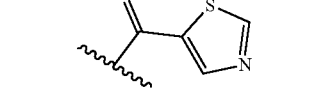
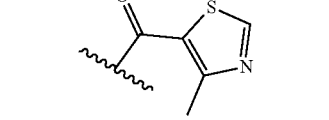

TABLE C-continued
Exemplary $L^3$-$R^8$ substituents
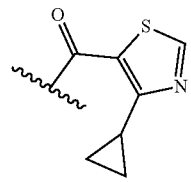 [SMILES: *C(=O)c1scnc1C1CC1]
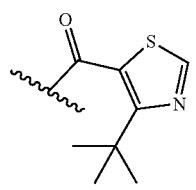 [SMILES: *C(=O)c1scnc1C(C)(C)C]
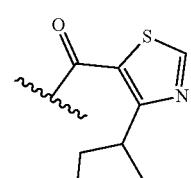
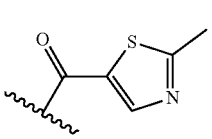 [SMILES: *C(=O)c1cnc(C)s1]
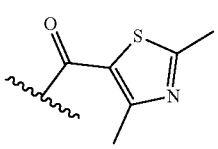 [SMILES: *C(=O)c1sc(C)nc1C]
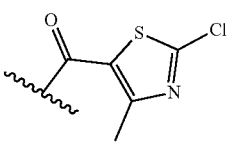 [SMILES: *C(=O)c1sc(Cl)nc1C]
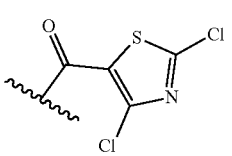 [SMILES: *C(=O)c1sc(Cl)nc1Cl]
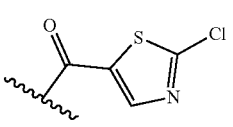 [SMILES: *C(=O)c1cnc(Cl)s1]
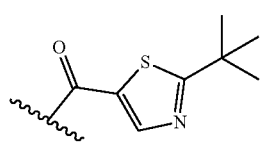 [SMILES: *C(=O)c1cnc(C(C)(C)C)s1]
TABLE C-continued
Exemplary $L^3$-$R^8$ substituents
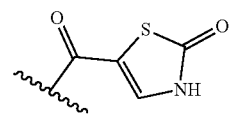 [SMILES: *C(=O)c1c[nH]c(=O)s1]
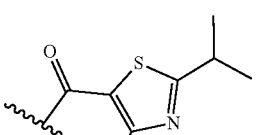
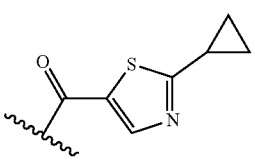 [SMILES: *C(=O)c1cnc(C2CC2)s1]
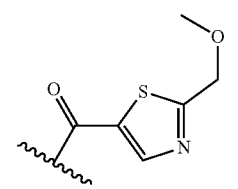 [SMILES: *C(=O)c1cnc(COC)s1]
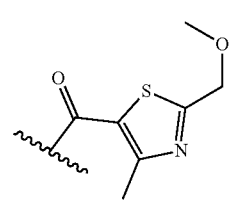 [SMILES: *C(=O)c1sc(COC)nc1C]
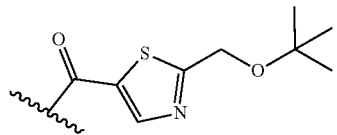 [SMILES: *C(=O)c1cnc(COC(C)(C)C)s1]
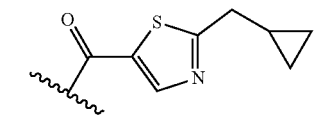 [SMILES: *C(=O)c1cnc(CC2CC2)s1]
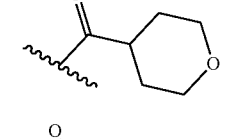
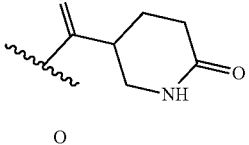
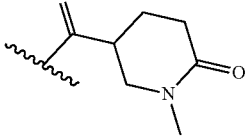

TABLE C-continued
Exemplary L³-R⁸ substituents
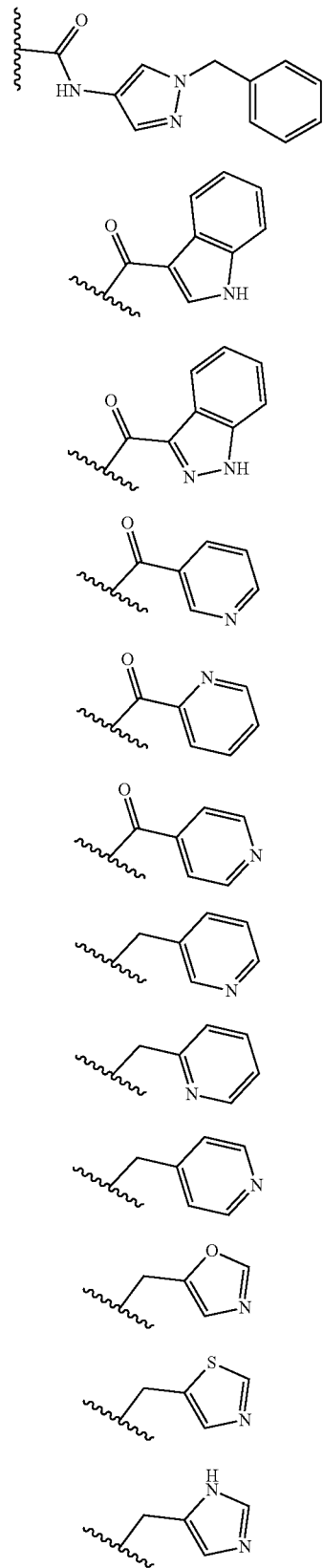
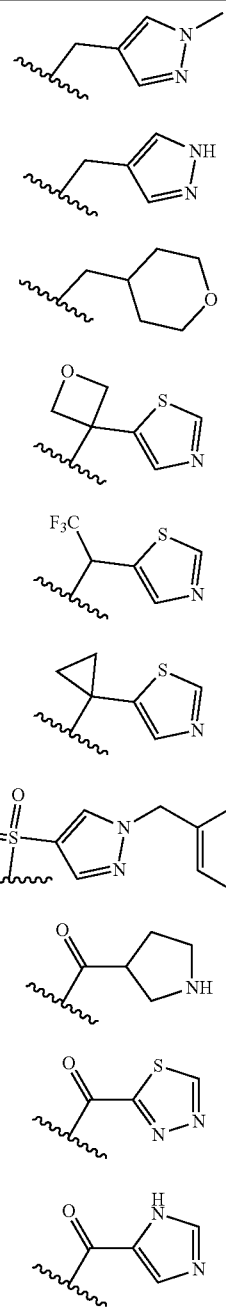
In some embodiments, -L³-R⁸ is a substituent of Table C-continued:
TABLE C-continued
Additional exemplary -L³ -R⁸ substituents

TABLE C-continued-continued

Additional exemplary -L³-R⁸ substituents

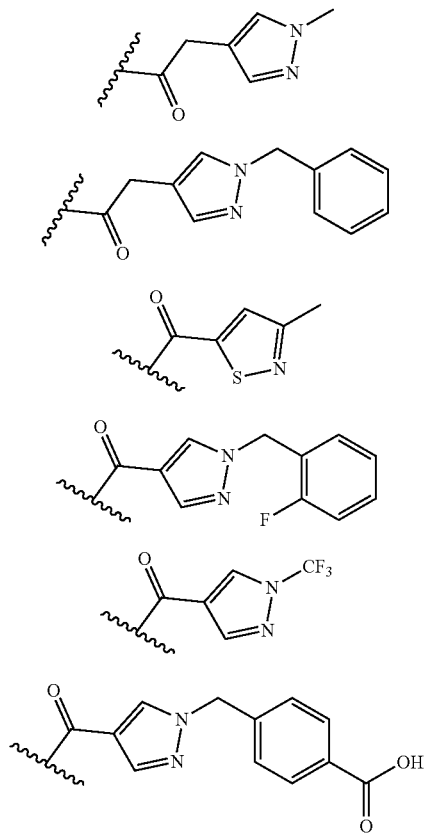

In some embodiments, -L³-R⁸ is a substituent of Table C or Table C-continued.

In some embodiments, -L³-R⁸ is

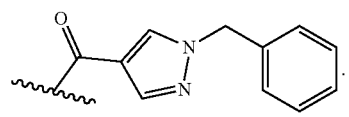 [SMILES: *C(=O)c1cnn(Cc2ccccc2)c1]

In some embodiments, -L³-R⁸ is

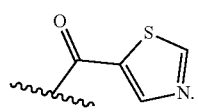

In some embodiments, the compound of Formula IA is a compound of Formula IIA:

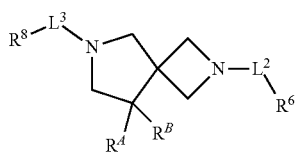

or a pharmaceutically acceptable salt thereof, wherein $R^A$, $R^B$, $L^2$, $R^6$, $L^3$ and $R^8$, and their constituent groups, are each as defined and described herein. In some embodiments, $R^A$, $R^B$, $L^2$, $R^6$, $L^3$ and $R^8$, and their constituent groups, are each as defined and described in Formula IA. In some embodiments, $R^A$ is a substituent from Table A. In some embodiments, -L²-R⁶ is a substituent from Table B. In some embodiments, -L³-R⁸ is a substituent from Table C. In some embodiments, $R^A$ is a substituent from Table A, and -L²-R⁶ is a substituent from Table B. In some embodiments, $R^A$ is a substituent from Table A, and -L³-R⁸ is a substituent from Table C. In some embodiments, -L²-R⁶ is a substituent from Table B, and -L³-R⁸ is a substituent from Table C. And in some embodiments, $R^A$ is a substituent from Table A, -L²-R⁶ is a substituent from Table B, and -L³-R⁸ is a substituent from Table C. In some embodiments, $R^A$ is a substituent from Table A-continued. In some embodiments, -L²-R⁶ is a substituent from Table B-continued. In some embodiments, -L³-R⁸ is a substituent from Table C-continued. In some embodiments, $R^A$ is a substituent from Table A-continued, and -L²-R⁶ is a substituent from Table B-continued. In some embodiments, $R^A$ is a substituent from Table A-continued, and -L³-R⁸ is a substituent from Table C-continued. In some embodiments, -L²-R⁶ is a substituent from Table B-continued, and -L³-R⁸ is a substituent from Table C-continued. And in some embodiments, $R^A$ is a substituent from Table A-continued, -L²-R⁶ is a substituent from Table B-continued, and -L³-R⁸ is a substituent from Table C-continued. In some embodiments, $R^A$ is a substituent from Table A or Table A-continued. In some embodiments, -L²-R⁶ is a substituent from Table B or Table B-continued. In some embodiments, -L³-R is a substituent from Table C or Table C-continued. In some embodiments, $R^A$ is a substituent from Table A or Table A-continued, and -L²-R⁶ is a substituent from Table B or Table B-continued. In some embodiments, $R^A$ is a substituent from Table A or Table A-continued, and -L³-R⁸ is a substituent from Table C or Table C-continued. In some embodiments, -L²-R⁶ is a substituent from Table B or Table B-continued, and -L³-R⁸ is a substituent from Table C or Table C-continued. And in some embodiments, $R^A$ is a substituent from Table A or Table A-continued, -L²-R⁶ is a substituent from Table B or Table B-continued, and -L³-R⁸ is a substituent from Table C or Table C-continued.

In some embodiments, the compound of Formula IA is a compound of Formula IIB:

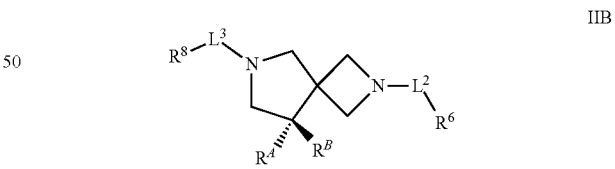

or a pharmaceutically acceptable salt thereof, wherein $R^A$, $R^B$, $L^2$, $R^6$, $L^3$ and $R^8$, and their constituent groups, are each as defined and described herein. In some embodiments, $R^A$, $R^B$, $L^2$, $R^6$, $L^3$ and $R^8$, and their constituent groups, are each as defined and described in Formula IA. In some embodiments, $R^A$ is a substituent from Table A. In some embodiments, -L²-R⁶ is a substituent from Table B. In some embodiments, -L³-R⁸ is a substituent from Table C. In some embodiments, $R^A$ is a substituent from Table A, and -L²-R⁶ is a substituent from Table B. In some embodiments, $R^A$ is a substituent from Table A, and -L³-R⁸ is a substituent from Table C. In some embodiments, -L²-R⁶ is a substituent from Table B, and -L³-R⁸ is a substituent from Table C. And in some embodiments, R⁴ is a substituent from Table A, -L²-R⁶ is a substituent from Table B, and -L³-R⁸ is a substituent from Table C. In some embodiments, R⁴ is a substituent from Table A-continued. In some embodiments, -L²-R⁶ is a substituent from Table B-continued. In some embodiments, -L³-R⁸ is a substituent from Table C-continued. In some embodiments, R⁴ is a substituent from Table A-continued, and -L²-R⁶ is a substituent from Table B-continued. In some embodiments, R⁴ is a substituent from Table A-continued, and -L³-R⁸ is a substituent from Table C-continued. In some embodiments, -L²-R⁶ is a substituent from Table B-continued, and -L³-R⁸ is a substituent from Table C-continued. And in some embodiments, R⁴ is a substituent from Table A-continued, -L²-R⁶ is a substituent from Table B-continued, and -L³-R⁸ is a substituent from Table C-continued. In some embodiments, R⁴ is a substituent from Table A or Table A-continued. In some embodiments, -L²-R⁶ is a substituent from Table B or Table B-continued. In some embodiments, -L³-R is a substituent from Table C or Table C-continued. In some embodiments, R⁴ is a substituent from Table A or Table A-continued, and -L²-R⁶ is a substituent from Table B or Table B-continued. In some embodiments, R⁴ is a substituent from Table A or Table A-continued, and -L³-R⁸ is a substituent from Table C or Table C-continued. In some embodiments, -L²-R⁶ is a substituent from Table B or Table B-continued, and -L³-R⁸ is a substituent from Table C or Table C-continued. And in some embodiments, R⁴ is a substituent from Table A or Table A-continued, -L²-R⁶ is a substituent from Table B or Table B-continued, and -L³-R⁸ is a substituent from Table C or Table C-continued.

In some embodiments, the compound of Formula I or IA is a compound of Formula II.

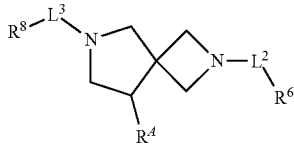

II or a pharmaceutically acceptable salt thereof, wherein R⁴, L², R⁶, L³ and R⁸, and their constituent groups, are each as defined and described herein. In some embodiments, R⁴, L², R⁶, L³ and R⁸, and their constituent groups, are each as defined and described in Formula I. In some embodiments, R⁴ is a substituent from Table A. In some embodiments, -L²-R⁶ is a substituent from Table B. In some embodiments, -L³-R⁸ is a substituent from Table C. In some embodiments, R⁴ is a substituent from Table A, and -L²-R⁶ is a substituent from Table B. In some embodiments, R⁴ is a substituent from Table A, and -L³-R⁸ is a substituent from Table C. In some embodiments, -L²-R⁶ is a substituent from Table B, and -L³-R⁸ is a substituent from Table C. And in some embodiments, R⁴ is a substituent from Table A, -L²-R⁶ is a substituent from Table B, and -L³-R⁸ is a substituent from Table C. In some embodiments, R⁴ is a substituent from Table A-continued. In some embodiments, -L²-R⁶ is a substituent from Table B-continued. In some embodiments, -L³-R⁸ is a substituent from Table C-continued. In some embodiments, R⁴ is a substituent from Table A-continued, and -L²-R⁶ is a substituent from Table B-continued. In some embodiments, R⁴ is a substituent from Table A-continued, and -L³-R⁸ is a substituent from Table C-continued. In some embodiments, -L²-R⁶ is a substituent from Table B-continued, and -L³-R⁸ is a substituent from Table C-continued. And in some embodiments, R⁴ is a substituent from Table A-continued, -L²-R⁶ is a substituent from Table B-continued, and -L³-R⁸ is a substituent from Table C-continued. In some embodiments, R⁴ is a substituent from Table A or Table A-continued. In some embodiments, -L²-R⁶ is a substituent from Table B or Table B-continued. In some embodiments, -L³-R is a substituent from Table C or Table C-continued. In some embodiments, R⁴ is a substituent from Table A or Table A-continued, and -L²-R⁶ is a substituent from Table B or Table B-continued. In some embodiments, R⁴ is a substituent from Table A or Table A-continued, and -L³-R⁸ is a substituent from Table C or Table C-continued. In some embodiments, -L²-R⁶ is a substituent from Table B or Table B-continued, and -L³-R⁸ is a substituent from Table C or Table C-continued. And in some embodiments, R⁴ is a substituent from Table A or Table A-continued, -L²-R⁶ is a substituent from Table B or Table B-continued, and -L³-R⁸ is a substituent from Table C or Table C-continued.

In some embodiments, the compound of Formula I or IA is a compound of Formula IIIa:

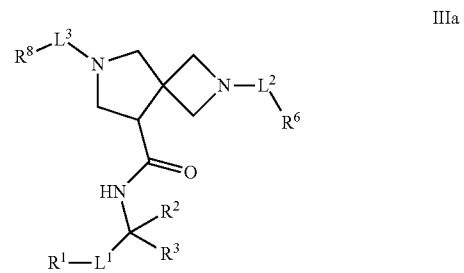

IIIa or a pharmaceutically acceptable salt thereof, wherein L¹, R¹, R², R³, L², R⁶, L³ and R⁸, and their constituent groups, are each as defined and described herein. In some embodiments, R¹ is phenyl. In some embodiments, R¹ is cyclohexyl. In some embodiments, R² is a substituent from Table R². In some embodiments, R² is a substituent from Table R²-continued. In some embodiments, R² is —C(O)NR₂, wherein the two R groups, taken together with the intervening nitrogen atom, form an optionally substituted 4-7 membered saturated ring (having 0-3 heteroatoms, in addition to the nitrogen, independently selected from nitrogen, oxygen, and sulfur), and R³ is hydrogen. In some embodiments, L² is a methylene. In some embodiments, L³ is a methylene. In some embodiments, both L² and L³ are methylene. In some embodiments, L² is a —C(O)—. In some embodiments, L³ is a —C(O)—. In some embodiments, both L² and L³ are —C(O)—. In some embodiments, -L²-R⁶ is a substituent from Table B. In some embodiments, -L²-R⁶ is a substituent from Table B-continued. In some embodiments, -L³-R⁸ is a substituent from Table C. In some embodiments, -L³-R⁸ is a substituent from Table C.

In some embodiments, the compound of Formula I or IA is a compound of Formula IIIb:

IIIb

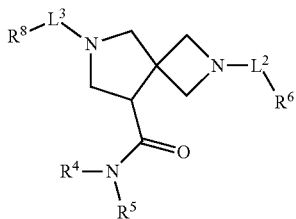

or a pharmaceutically acceptable salt thereof, wherein $R^4$, $R^5$, $L^2$, $R^6$, $L^3$ and $R^8$, and their constituent groups, are each as defined and described herein. In some embodiments, $L^2$ is a methylene. In some embodiments, $L^3$ is a methylene. In some embodiments, both $L^2$ and $L^3$ are methylene. In some embodiments, $L^2$ is a —C(O)—. In some embodiments, $L^3$ is a —C(O)—. In some embodiments, both $L^2$ and $L^3$ are —C(O)—. In some embodiments, -$L^2$-$R^6$ is a substituent from Table B. In some embodiments, -$L^2$-$R^6$ is a substituent from Table B-continued. In some embodiments, -$L^3$-$R^8$ is a substituent from Table C. In some embodiments, -$L^3$-$R^8$ is a substituent from Table C.

In some embodiments, the compound of Formula I or IA is a compound of Formula IVa:

IVa

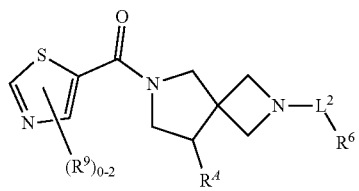

or a pharmaceutically acceptable salt thereof, wherein $R^A$, $L^2$, $R^6$, and $R^8$, and their constituent groups, are each as defined and described herein. In some embodiments, $R^A$ is a substituent from Table A. In some embodiments, $R^A$ is a substituent from Table A-continued. In some embodiments, -$L^2$-$R^6$ is a substituent from Table B. In some embodiments, -$L^2$-$R^6$ is a substituent from Table B-continued. In some embodiments, the compound of Formula I is a compound of Formula IVb:

IVb

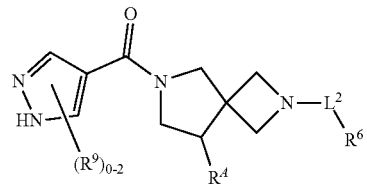

or a pharmaceutically acceptable salt thereof, wherein $R^A$, $L^2$, $R^6$, and $R^9$, and their constituent groups, are each as defined and described herein. In some embodiments, the thiazolyl group is not substituted with $R^9$. In some embodiments, $R^A$ is a substituent from Table A. In some embodiments, $R^A$ is a substituent from Table A-continued. In some embodiments, -$L^2$-$R^6$ is a substituent from Table B. In some embodiments, -$L^2$-$R^6$ is a substituent from Table B-continued.

In some embodiments, the compound of Formula I or IA is a compound of Formula IVc:

IVc

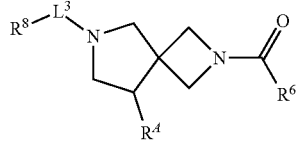

or a pharmaceutically acceptable salt thereof, wherein $R^A$, $L^2$, $R^6$, and $R^9$, and their constituent groups, are each as defined and described herein. In some embodiments, the pyrazolyl group is not substituted with $R^9$. In some embodiments, the pyrazolyl group is substituted with one instance of $R^9$, which is a benzyl group. In some embodiments, $R^A$ is a substituent from Table A. In some embodiments, $R^A$ is a substituent from Table A-continued. In some embodiments, -$L^2$-$R^6$ is a substituent from Table B. In some embodiments, -$L^2$-$R^6$ is a substituent from Table B-continued.

In some embodiments, the compound of Formula I or IA is a compound of Formula Va:

Va

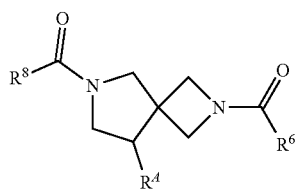

or a pharmaceutically acceptable salt thereof, wherein $R^A$, $R^6$, $L^3$ and $R^8$, and their constituent groups, are each as defined and described herein. In some embodiments, $R^6$ is an optionally substituted cyclopropyl group. In some embodiments, $R^A$ is a substituent from Table A. In some embodiments, $R^A$ is a substituent from Table A-continued. In some embodiments, -$L^3$-$R^8$ is a substituent from Table C. In some embodiments, -$L^3$-$R^8$ is a substituent from Table C-continued.

In some embodiments, the compound of Formula I or IA is a compound of Formula Vb:

Vb or a pharmaceutically acceptable salt thereof, wherein $R^A$, $R^6$, and $R^8$, and their constituent groups, are each as defined and described herein. In some embodiments, $R^6$ is an optionally substituted cyclopropyl group.

In some embodiments, $R^A$ is a substituent from Table A. In some embodiments, $R^A$ is a substituent from Table A-continued.

In some embodiments, the compound of Formula I or IA is a compound of Formula VIa:

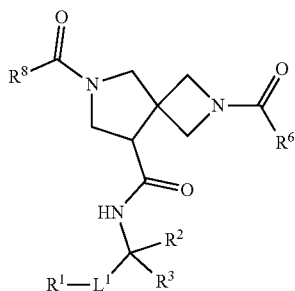

VIa or a pharmaceutically acceptable salt thereof, wherein L, $R^1$, $R^2$, $R^3$, $R^6$, and $R^8$, and their constituent groups, are each as defined and described herein. In some embodiments, $R^1$ is phenyl. In some embodiments, $R^1$ is cyclohexyl. In some embodiments, $R^2$ is a substituent from Table $R^2$ or Table $R^2$-continued. In some embodiments, $R^2$ is —C(O)NR$_2$, wherein the two R groups, taken together with the intervening nitrogen atom, form an optionally substituted 4-7 membered saturated ring (having 0-3 heteroatoms, in addition to the nitrogen, independently selected from nitrogen, oxygen, and sulfur), and $R^3$ is hydrogen. In some embodiments, $R^6$ is an optionally substituted cyclopropyl group.

In some embodiments, the compound of Formula I or IA is a compound of Formula VIb:

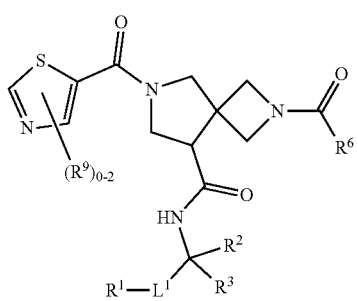

VIb or a pharmaceutically acceptable salt thereof, wherein $L^1$, $R^1$, $R^2$, $R^3$, $R^6$, and $R^9$, and their constituent groups, are each as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^2$ is a substituent from Table $R^2$ or Table $R^2$-continued. In some embodiments, $R^2$ is —C(O)NR$_2$, wherein the two R groups, taken together with the intervening nitrogen atom, form an optionally substituted 4-7 membered saturated ring (having 0-3 heteroatoms, in addition to the nitrogen, independently selected from nitrogen, oxygen, and sulfur), and $R^3$ is hydrogen. In some embodiments, $R^6$ is an optionally substituted cyclopropyl group. In some embodiments, the thiazolyl group is not substituted with $R^7$.

In some embodiments, the compound of Formula I or IA is a compound of Formula VIc:

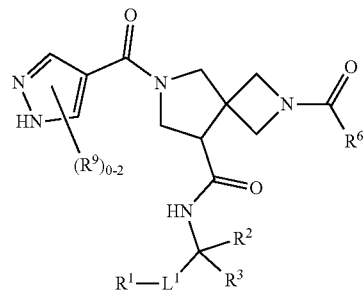

VIc or a pharmaceutically acceptable salt thereof, wherein $L^1$, $R^1$, $R^2$, $R^3$, $R^6$, and $R^9$, and their constituent groups, are each as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^2$ is a substituent from Table $R^2$ or Table $R^2$-continued. In some embodiments, $R^2$ is —C(O)NR$_2$, wherein the two R groups, taken together with the intervening nitrogen atom, form an optionally substituted 4-7 membered saturated ring (having 0-3 heteroatoms, in addition to the nitrogen, independently selected from nitrogen, oxygen, and sulfur), and $R^3$ is hydrogen. In some embodiments, $R^6$ is an optionally substituted cyclopropyl group. In some embodiments, the pyrazolyl group is not substituted with $R^9$. In some embodiments, the pyrazolyl group is substituted with one instance of $R^9$, which is a benzyl group.

In some embodiments, the compound of Formula I or IA is a compound of Formula VId:

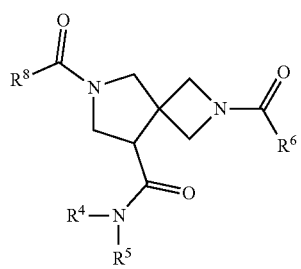

VId or a pharmaceutically acceptable salt thereof, wherein $R^4$, $R^5$, $R^6$, and $R^8$, and their constituent groups, are each as defined and described herein. In some embodiments, $R^6$ is an optionally substituted cyclopropyl group.

In some embodiments, the compound of Formula I or IA is a compound of Formula VIe:

VIe

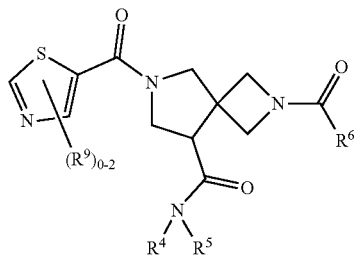

or a pharmaceutically acceptable salt thereof, wherein $R^4$, $R^5$, $R^6$, and $R^9$, and their constituent groups, are each as defined and described herein. In some embodiments, $R^6$ is an optionally substituted cyclopropyl group. In some embodiments, the thiazolyl group is not substituted with $R^9$.

In some embodiments, the compound of Formula I or IA is a compound of Formula VIf:

VIf

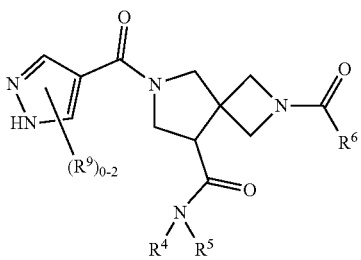

or a pharmaceutically acceptable salt thereof, wherein $R^4$, $R^5$, $R^6$, and $R^9$, and their constituent groups, are each as defined and described herein. In some embodiments, $R^6$ is an optionally substituted cyclopropyl group. In some embodiments, the pyrazolyl group is not substituted with $R^9$. In some embodiments, the pyrazolyl group is substituted with one instance of $R^9$, which is a benzyl group.

In some embodiments, the compound of Formula I or IA is a compound of Formula VIIa:

VIIa

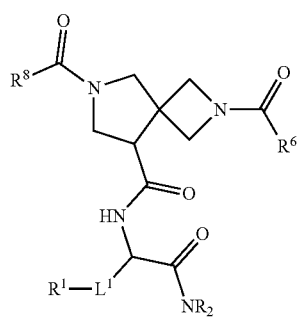

or a pharmaceutically acceptable salt thereof, wherein $L^1$, $R^1$, $R^2$, $R^6$, and $R^8$, and their constituent groups, are each as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^6$ is an optionally substituted cyclopropyl group.

In some embodiments, the compound of Formula I or IA is a compound of Formula VIIb:

VIIb

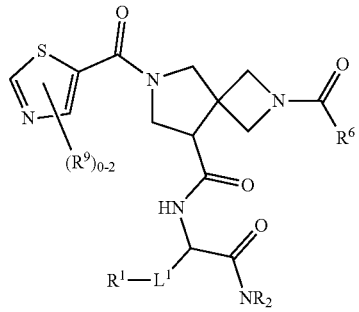

or a pharmaceutically acceptable salt thereof, wherein $L^1$, $R^1$, $R^2$, $R^6$, and $R^9$, and their constituent groups, are each as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^6$ is an optionally substituted cyclopropyl group. In some embodiments, the thiazolyl group is not substituted with $R^9$.

In some embodiments, the compound of Formula I or IA is a compound of Formula VIIc:

VIIc

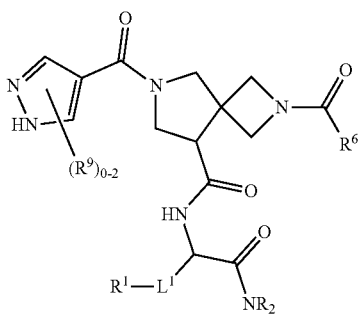

or a pharmaceutically acceptable salt thereof, wherein $L^1$, $R^1$, $R^2$, $R^6$, and $R^9$, and their constituent groups, are each as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^6$ is an optionally substituted cyclopropyl group. In some embodiments, the pyrazolyl group is not substituted with $R^9$. In some embodiments, the pyrazolyl group is substituted with one instance of $R^9$, which is a benzyl group.

In some embodiments, the compound of Formula I or IA is a compound of Formula VIIIa:

VIIIa

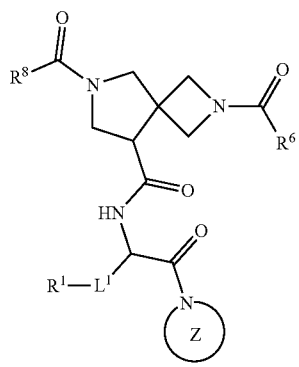

In some embodiments, the compound of Formula I or IA is a compound of Formula VIIIc:

VIIIc

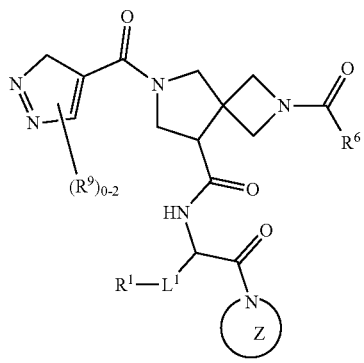

or a pharmaceutically acceptable salt thereof, wherein $L^1$, $R^1$, $R^6$, and $R^8$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^6$ is an optionally substituted cyclopropyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula VIIIb:

VIIIb

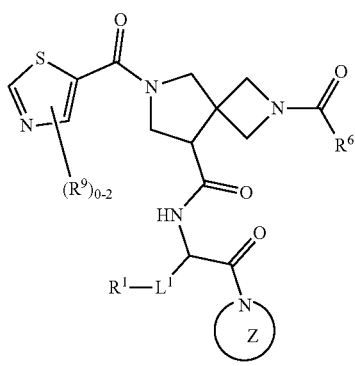

or a pharmaceutically acceptable salt thereof, wherein $L^1$, $R^1$, and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, $L^1$ is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^6$ is an optionally substituted cyclopropyl group. In some embodiments, the thiazolyl group is not substituted with $R^9$. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

or a pharmaceutically acceptable salt thereof, wherein $L^1$, $R^1$, $R^6$, and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, L is an optionally substituted straight or branched $C_{1-4}$ alkylene chain, wherein 1-2 methylene units of $L^1$ are independently replaced by —O—, —NR—, —C(O)O—, or —NRC(O)—. In some embodiments, $R^6$ is an optionally substituted cyclopropyl group. In some embodiments, the pyrazolyl group is not substituted with $R^9$. In some embodiments, the pyrazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXa:

IXa

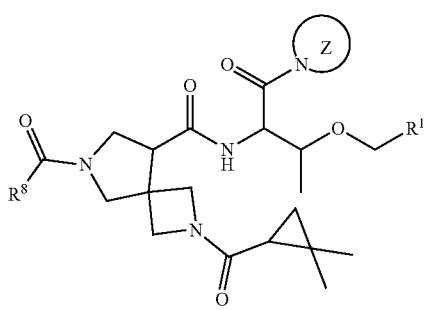

or a pharmaceutically acceptable salt thereof, wherein $R^1$ and $R^8$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXa*:

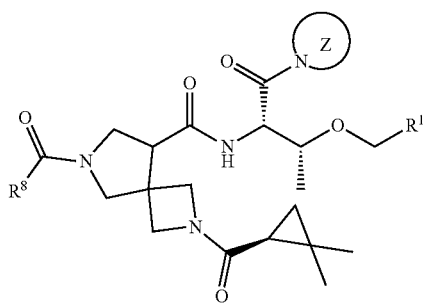

IXa* or a pharmaceutically acceptable salt thereof, wherein $R^1$ and $R^8$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXa**:

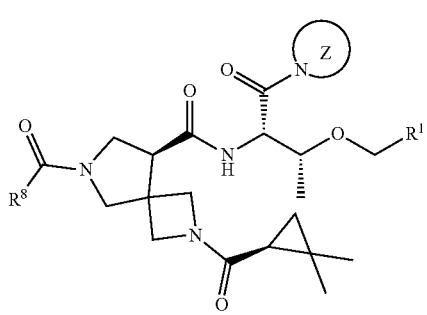

IXa** or a pharmaceutically acceptable salt thereof, wherein $R^1$ and $R^8$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXb:

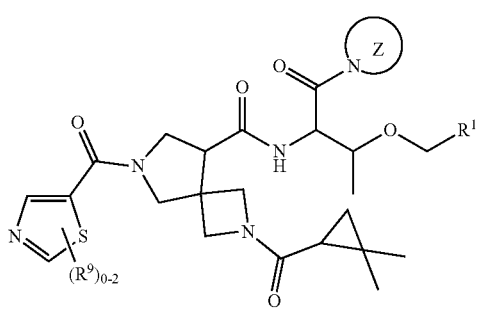

IXb or a pharmaceutically acceptable salt thereof, wherein $R^1$ and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, the thiazolyl group is not substituted with $R^9$. In some embodiments, the thiazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXb*:

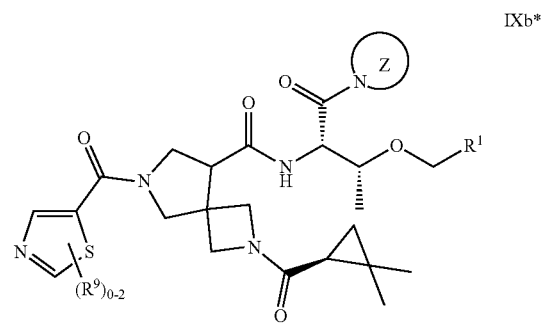

IXb* or a pharmaceutically acceptable salt thereof, wherein $R^1$ and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, the thiazolyl group is not substituted with $R^9$. In some embodiments, the thiazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXb**:

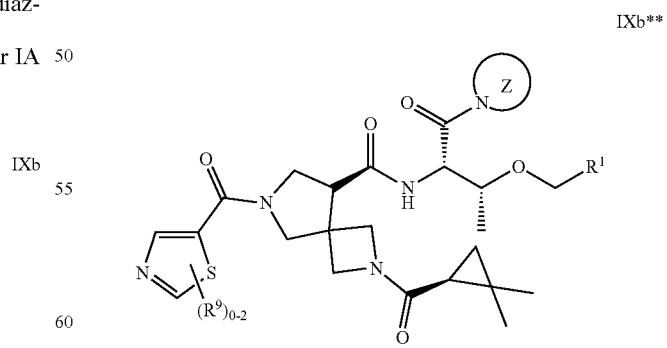

IXb** or a pharmaceutically acceptable salt thereof, wherein $R^1$ and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, the thiazolyl group is not substituted with $R^9$. In some embodiments, the thiazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXc:

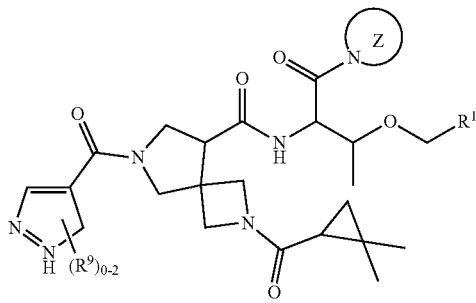

IXc or a pharmaceutically acceptable salt thereof, wherein $R^1$ and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, the pyrazolyl group is not substituted with $R^9$. In some embodiments, the pyrazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXc*:

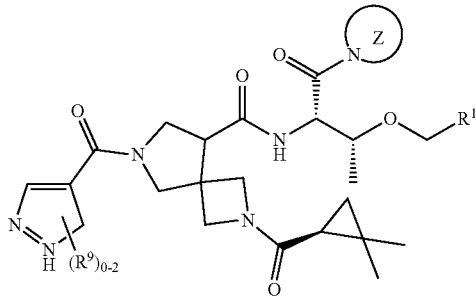

IXc* or a pharmaceutically acceptable salt thereof, wherein $R^1$ and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, the pyrazolyl group is not substituted with $R^9$. In some embodiments, the pyrazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula IXc**:

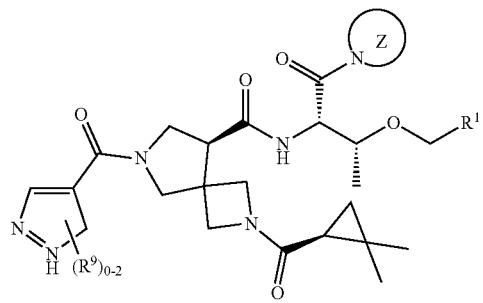

IXc** or a pharmaceutically acceptable salt thereof, wherein $R^1$ and $R^9$, and their constituent groups, are each as defined and described herein, and cyclic moiety Z is an optionally substituted cyclic group formed from two R groups, as defined and described herein. In some embodiments, $R^1$ is phenyl. In some embodiments, $R^1$ is cyclohexyl. In some embodiments, the pyrazolyl group is not substituted with $R^9$. In some embodiments, the pyrazolyl group is substituted with one instance of $R^9$, which is a benzyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula I or IA is a compound of Formula Xa:

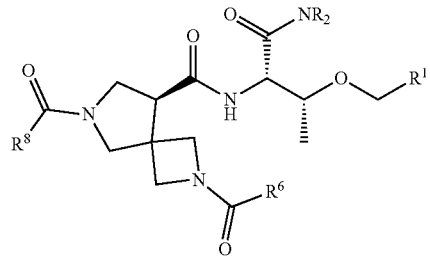

Xa or a pharmaceutically acceptable salt thereof, wherein $R^1$, $R^6$, and $R^8$, and their constituent groups, are each as defined and described herein. In some embodiments, $R^1$ is phenyl. In some embodiments, $R^1$ is cyclohexyl. In some embodiments, $R^6$ is an optionally substituted cyclopropyl group.

In some embodiments, the compound of Formula I or IA is a compound of Formula Xb:

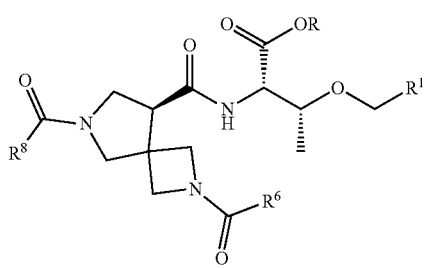

Xb or a pharmaceutically acceptable salt thereof, wherein $R^1$, $R^6$, and $R^8$, and their constituent groups, are each as defined and described herein. In some embodiments, $R^1$ is phenyl. In some embodiments, $R^1$ is cyclohexyl. In some embodiments, $R^6$ is an optionally substituted cyclopropyl group.

In some embodiments, the compound of Formula I or IA is a compound of Formula Xc:

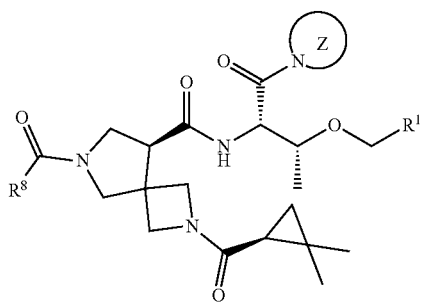

Xc or a pharmaceutically acceptable salt thereof, wherein Z, $R^1$, $R^6$, and $R^8$, and their constituent groups, are each as defined and described herein. In some embodiments, $R^1$ is phenyl. In some embodiments, $R^1$ is cyclohexyl. In some embodiments, $R^6$ is an optionally substituted cyclopropyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, the compound of Formula IA is a compound of Formula XIa:

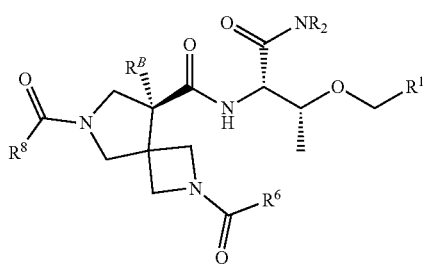

XIa or a pharmaceutically acceptable salt thereof, wherein $R^B$, $R^1$, $R^6$, and $R^8$, and their constituent groups, are each as defined and described herein. In some embodiments, $R^1$ is phenyl. In some embodiments, $R^1$ is cyclohexyl. In some embodiments, $R^6$ is an optionally substituted cyclopropyl group.

In some embodiments, the compound of Formula IA is a compound of Formula XIb:

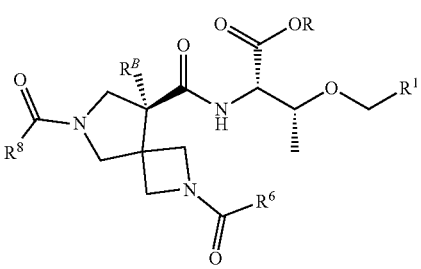

XIb or a pharmaceutically acceptable salt thereof, wherein $R^B$, $R^1$, $R^6$, and R, and their constituent groups, are each as defined and described herein. In some embodiments, $R^1$ is phenyl. In some embodiments, $R^1$ is cyclohexyl. In some embodiments, $R^6$ is an optionally substituted cyclopropyl group.

In some embodiments, the compound of Formula IA is a compound of Formula XIc:

XIc or a pharmaceutically acceptable salt thereof, wherein Z, $R^B$, $R^1$, $R^6$, and $R^8$, and their constituent groups, are each as defined and described herein. In some embodiments, $R^1$ is phenyl. In some embodiments, $R^1$ is cyclohexyl. In some embodiments, $R^6$ is an optionally substituted cyclopropyl group. In some embodiments, Z is an optionally substituted cyclic group selected from piperidinyl, morpholinyl, piperazinyl, azetindinyl, pyrrolidinyl, azaspiro[3.3]heptanyl, and diazaspiro[3.3]heptanyl.

In some embodiments, at least one hydrogen atom of the compound is a deuterium atom. In some embodiments, at least one $C_1$-$C_6$ aliphatic group of the compound is substituted with at least one deuterium atom. In some embodiments, at least one $C_1$-$C_6$ alkyl group of the compound is substituted with at least one deuterium atom. In some embodiments, at least one $C_1$-$C_6$ alkylene group of the compound is substituted with at least one deuterium atom. In some embodiments, at least one bivalent $C_{1-6}$ hydrocarbon chain group of the compound is substituted with at least one deuterium atom. In some embodiments, $R^B$ is —$CD_3$. In some embodiments, $R^2$ is substituted with one or more deuterium atoms. In some embodiments, $R^1$ is substituted with one or more deuterium atoms.

Exemplary compounds of the present disclosure are set forth in Table 1, below.

TABLE 1

| Exemplary Compounds | |
| --- | --- |
| Cmpd # | Structure |
| I-1 | |
| I-2 | |
| I-3 (A) | |
| (B) | |

TABLE 1-continued
Exemplary Compounds
| Cmpd # | Structure |
|---|---|
| I-4 | 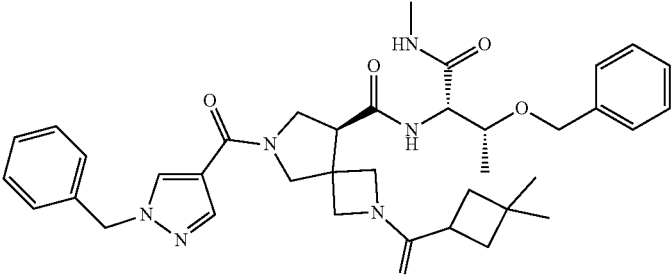<br>(A)<br>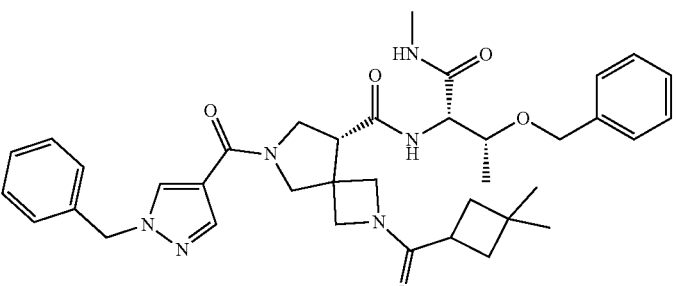<br>(B) |
| I-5 | 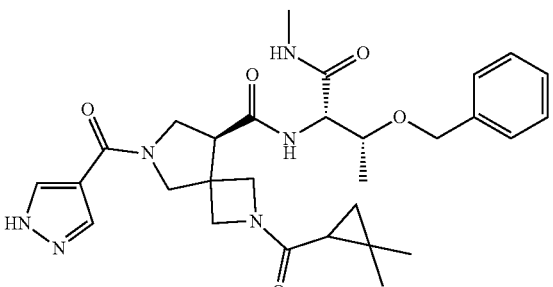<br>(A)<br>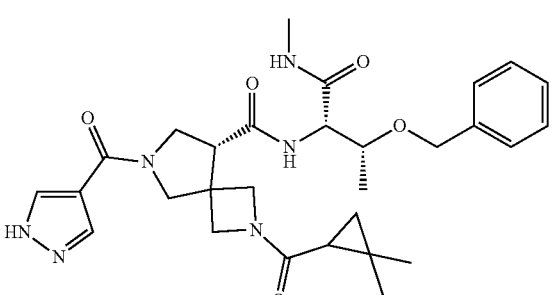<br>(B) |

TABLE 1-continued
Exemplary Compounds
| Cmpd # | Structure |
|---|---|
| I-6 | 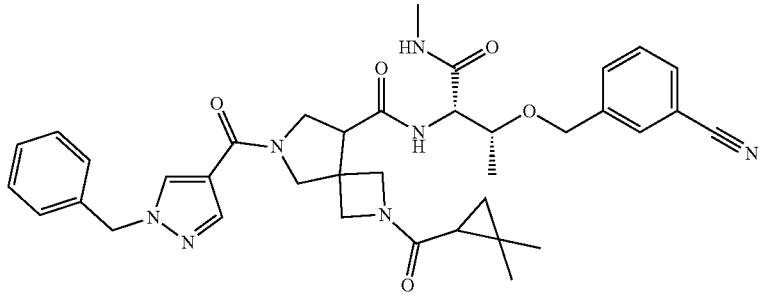 [SMILES: CNC(=O)[C@@H](NC(=O)C1CN(C(=O)c2cnn(Cc3ccccc3)c2)CC12CN(C(=O)C1CC1(C)C)C2)[C@@H](C)OCc1cccc(C#N)c1] |
| I-7 | 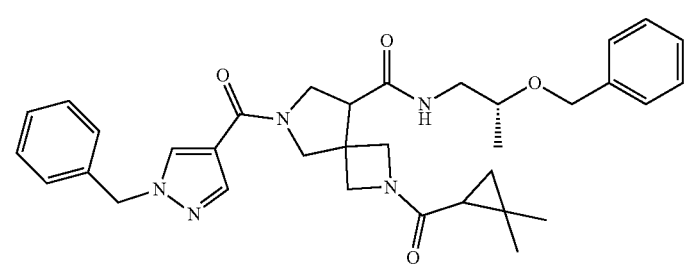 [SMILES: C[C@H](CNC(=O)C1CN(C(=O)c2cnn(Cc3ccccc3)c2)CC12CN(C(=O)C1CC1(C)C)C2)OCc1ccccc1] |
| I-8 | 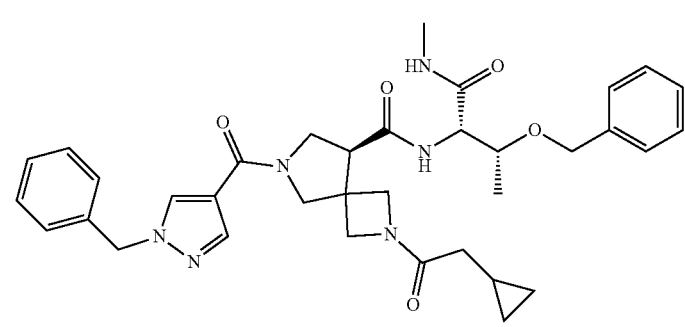 [SMILES: CNC(=O)[C@@H](NC(=O)[C@@H]1CN(C(=O)c2cnn(Cc3ccccc3)c2)CC12CN(C(=O)CC1CC1)C2)[C@@H](C)OCc1ccccc1]<br>(A)<br>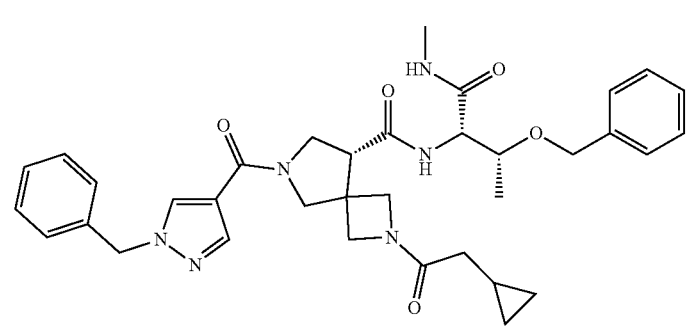 [SMILES: CNC(=O)[C@@H](NC(=O)[C@H]1CN(C(=O)c2cnn(Cc3ccccc3)c2)CC12CN(C(=O)CC1CC1)C2)[C@@H](C)OCc1ccccc1]<br>(B) |
| I-9 | 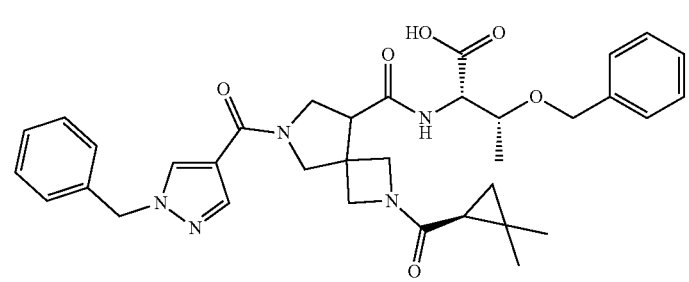 [SMILES: C[C@@H](OCc1ccccc1)[C@H](NC(=O)C1CN(C(=O)c2cnn(Cc3ccccc3)c2)CC12CN(C(=O)[C@H]1CC1(C)C)C2)C(=O)O] |

TABLE 1-continued

Exemplary Compounds

| Cmpd # | Structure |
|---|---|
| I-10 | 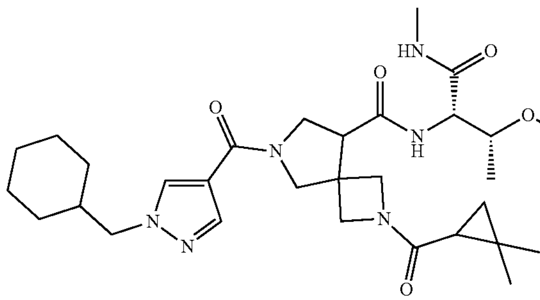 |
| I-11 | 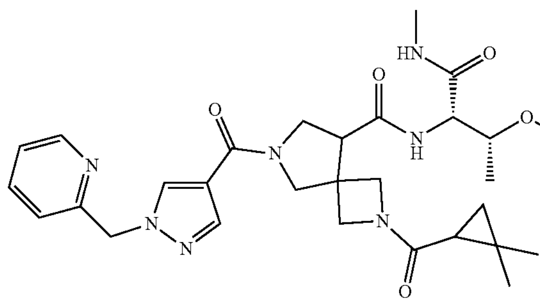 |
| I-12 | Mixture<br>(A) |

TABLE 1-continued
Exemplary Compounds
| Cmpd # | Structure |
|---|---|
| I-13 | 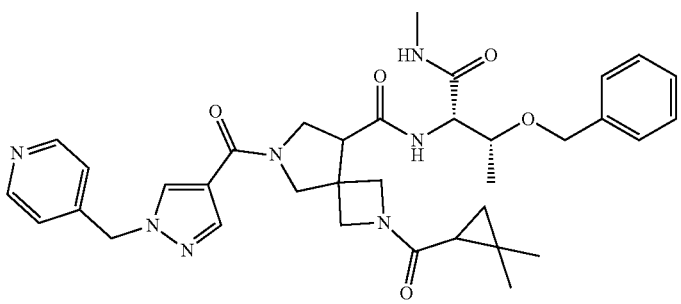 [SMILES: CNC(=O)[C@@H](NC(=O)C1CN(C(=O)c2cnn(Cc3ccncc3)c2)CC12CN(C(=O)C1CC1(C)C)C2)[C@@H](C)OCc1ccccc1] |
| I-14 | 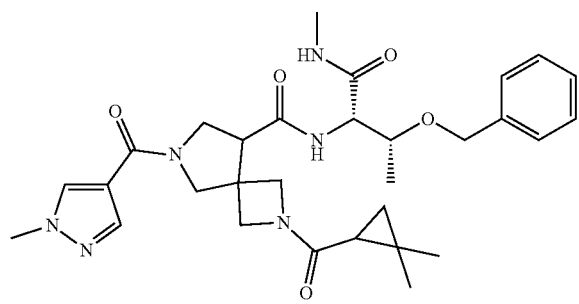 [SMILES: CNC(=O)[C@@H](NC(=O)C1CN(C(=O)c2cnn(C)c2)CC12CN(C(=O)C1CC1(C)C)C2)[C@@H](C)OCc1ccccc1] |
| I-15 | 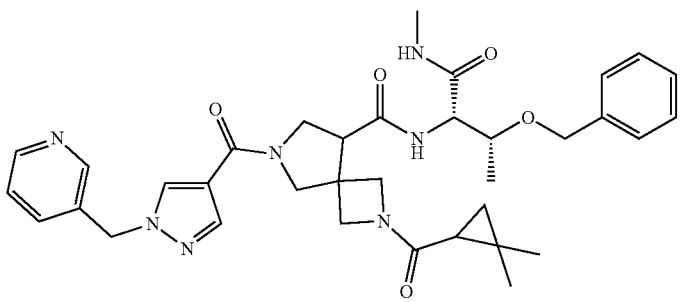 [SMILES: CNC(=O)[C@@H](NC(=O)C1CN(C(=O)c2cnn(Cc3cccnc3)c2)CC12CN(C(=O)C1CC1(C)C)C2)[C@@H](C)OCc1ccccc1] |
| I-16 | 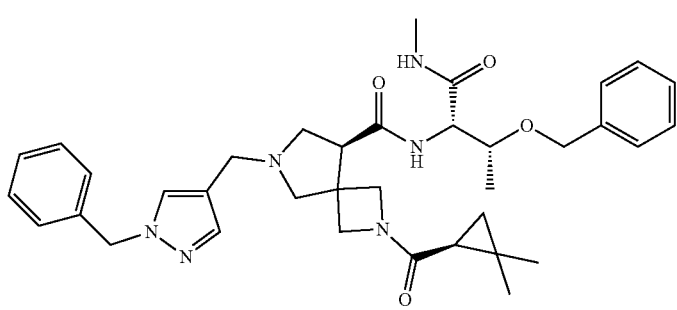 [SMILES: CNC(=O)[C@@H](NC(=O)[C@@H]1CN(Cc2cnn(Cc3ccccc3)c2)CC12CN(C(=O)[C@H]1CC1(C)C)C2)[C@@H](C)OCc1ccccc1] |

TABLE 1-continued
Exemplary Compounds
| Cmpd # | Structure |
|---|---|
| | 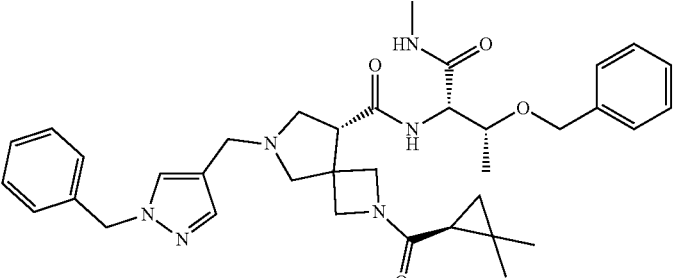<br>(B) |
| I-17 | 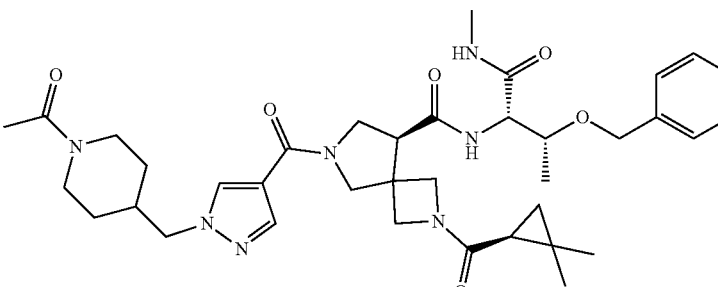<br>(A) |
| | 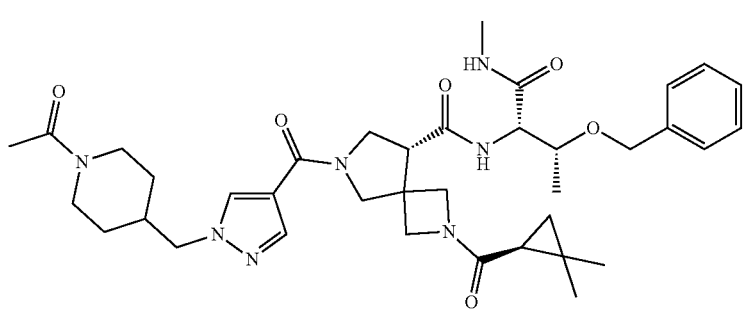 [SMILES: CNC(=O)[C@@H](NC(=O)[C@H]1CN(C(=O)c2cnn(CC3CCN(C(C)=O)CC3)c2)CC12CN(C(=O)[C@H]1CC1(C)C)C2)[C@@H](C)OCc1ccccc1]<br>(B) |
| I-18 | 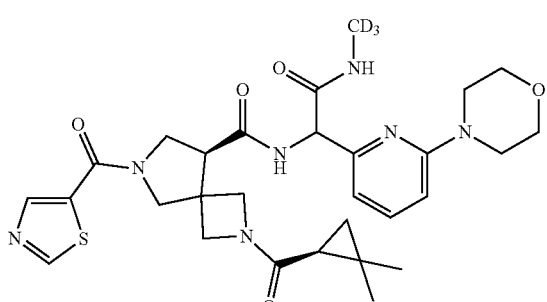 |

TABLE 1-continued

Exemplary Compounds

| Cmpd # | Structure |
|---|---|
| I-19 | (A) |
| | (B) |
| I-20 | 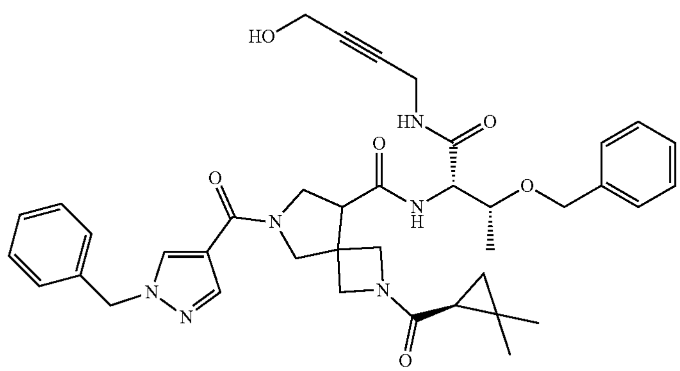 |
| I-21 | 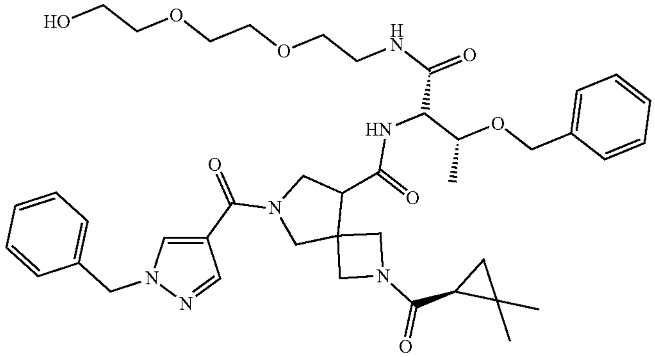 |

TABLE 1-continued
Exemplary Compounds
| Cmpd # | Structure |
|---|---|
| I-22 | 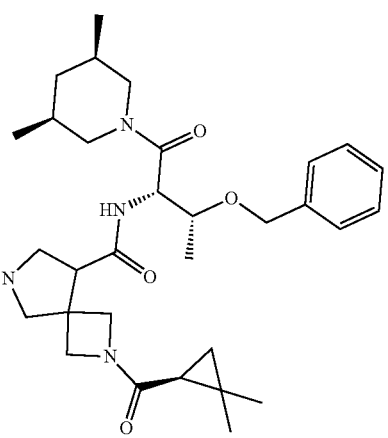 |
| I-23 | 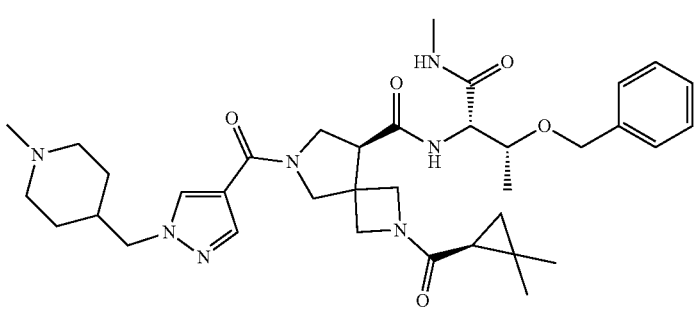 [SMILES: CNC(=O)[C@@H](NC(=O)[C@@H]1CN(C(=O)c2cnn(CC3CCN(C)CC3)c2)CC12CN(C(=O)[C@H]1CC1(C)C)C2)[C@@H](C)OCc1ccccc1]<br>(A)<br>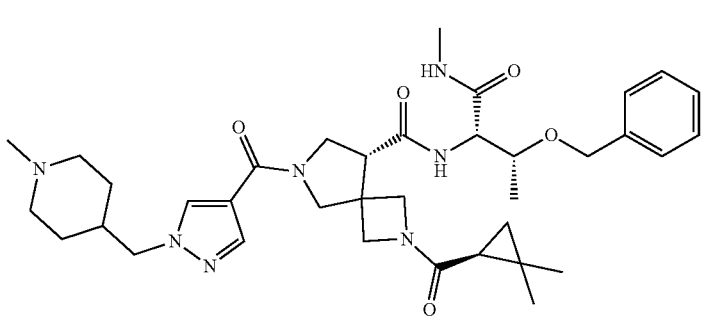 [SMILES: CNC(=O)[C@@H](NC(=O)[C@H]1CN(C(=O)c2cnn(CC3CCN(C)CC3)c2)CC12CN(C(=O)[C@H]1CC1(C)C)C2)[C@@H](C)OCc1ccccc1]<br>(B) |
| I-24 | 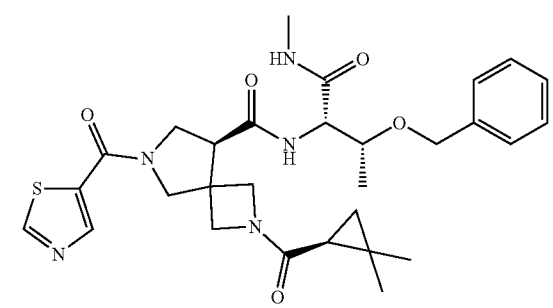 [SMILES: CNC(=O)[C@@H](NC(=O)[C@@H]1CN(C(=O)c2cncs2)CC12CN(C(=O)[C@H]1CC1(C)C)C2)[C@@H](C)OCc1ccccc1]<br>(A) |

TABLE 1-continued
Exemplary Compounds
| Cmpd # | Structure |
|---|---|
| | 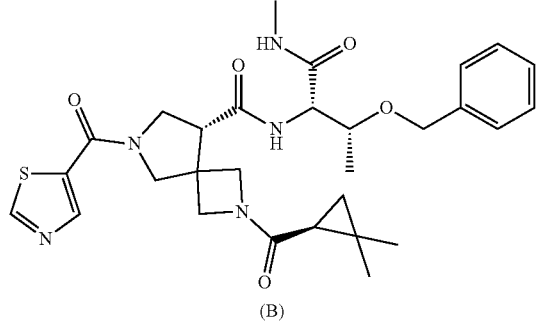<br>(B) |
| I-25 | 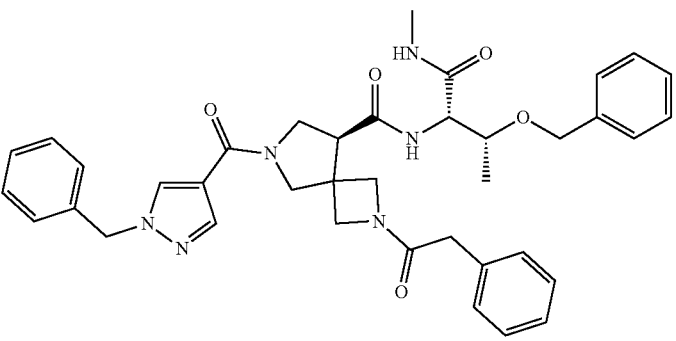 [SMILES: CNC(=O)[C@@H](NC(=O)[C@@H]1CN(C(=O)c2cnn(Cc3ccccc3)c2)CC12CN(C(=O)Cc1ccccc1)C2)[C@@H](C)OCc1ccccc1]<br>(A) |
| | 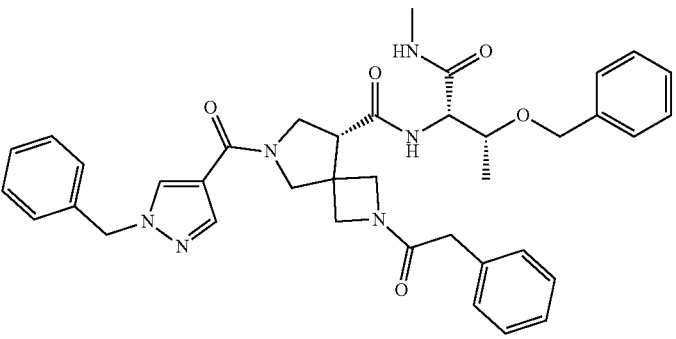 [SMILES: CNC(=O)[C@@H](NC(=O)[C@H]1CN(C(=O)c2cnn(Cc3ccccc3)c2)CC12CN(C(=O)Cc1ccccc1)C2)[C@@H](C)OCc1ccccc1]<br>(B) |
| I-26 | 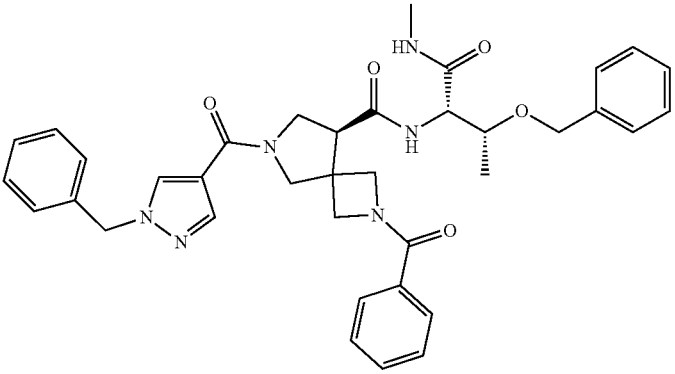 [SMILES: CNC(=O)[C@@H](NC(=O)[C@@H]1CN(C(=O)c2cnn(Cc3ccccc3)c2)CC12CN(C(=O)c1ccccc1)C2)[C@@H](C)OCc1ccccc1]<br>(A) |

TABLE 1-continued
Exemplary Compounds
| Cmpd # | Structure |
|---|---|
| | (B) 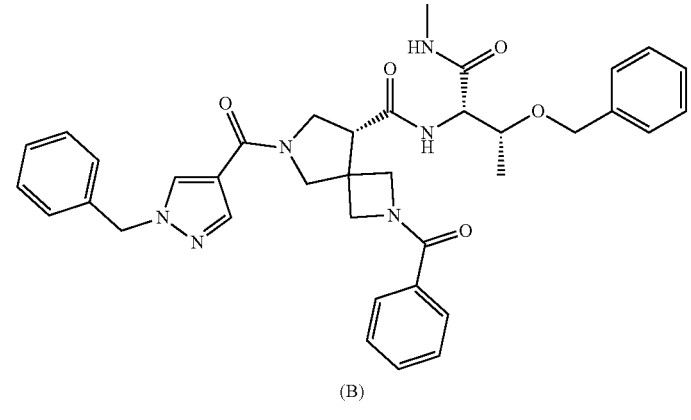 |
| I-27 | (A) 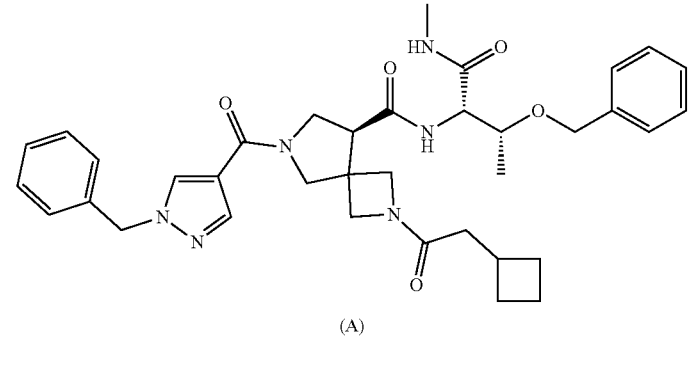 |
| | (B) 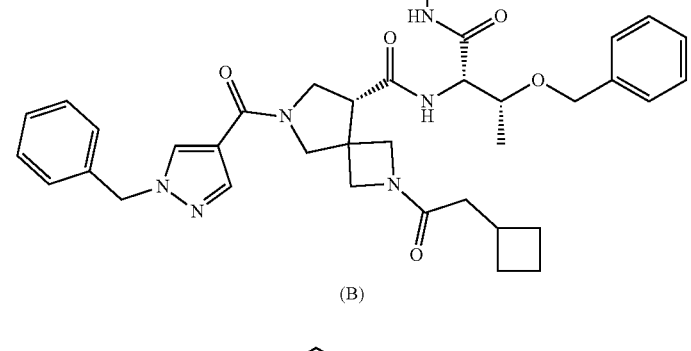 |
| I-28 | 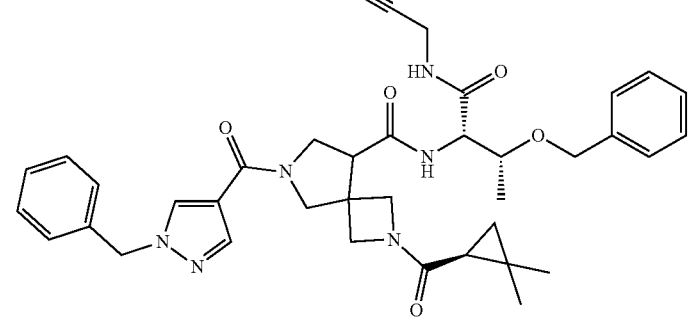 |

TABLE 1-continued
Exemplary Compounds
| Cmpd # | Structure |
| --- | --- |
| I-29 | 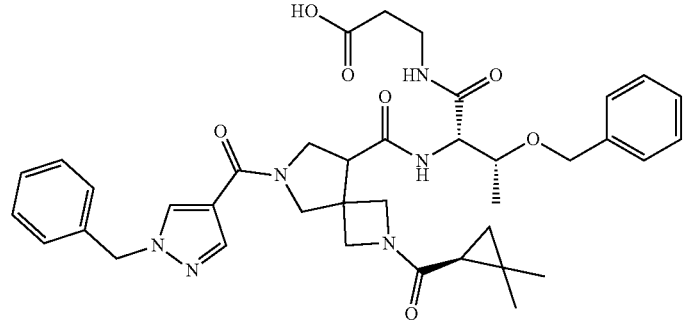 [SMILES: C[C@@H](OCc1ccccc1)[C@H](NC(=O)C1CN(C(=O)c2cnn(Cc3ccccc3)c2)CC12CN(C(=O)[C@H]1CC1(C)C)C2)C(=O)NCCC(=O)O] |
| I-30 | 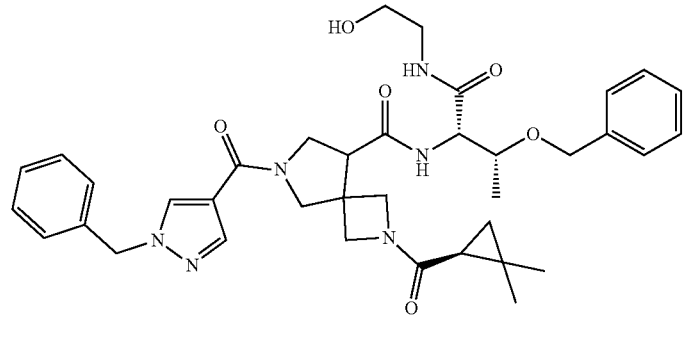 [SMILES: C[C@@H](OCc1ccccc1)[C@H](NC(=O)C1CN(C(=O)c2cnn(Cc3ccccc3)c2)CC12CN(C(=O)[C@H]1CC1(C)C)C2)C(=O)NCCO] |
| I-31 | 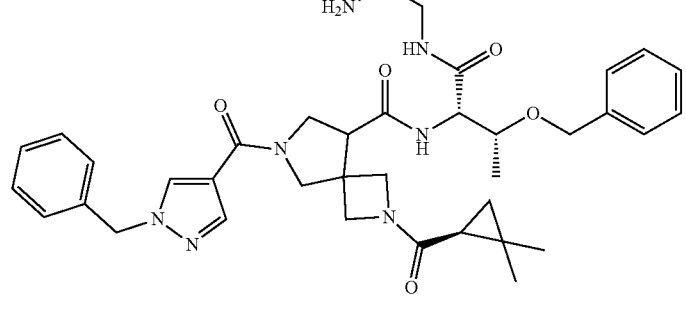 |
| I-32 | 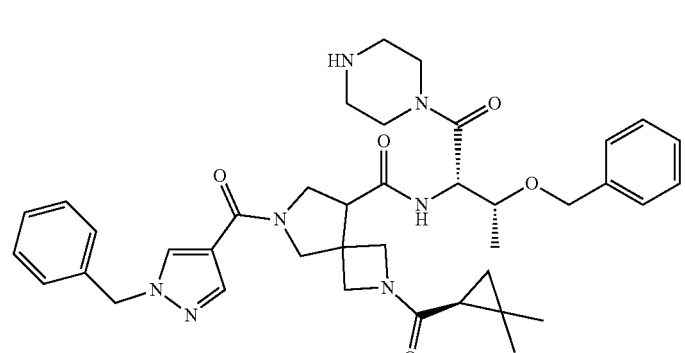 |

TABLE 1-continued

Exemplary Compounds

| Cmpd # | Structure |
|---|---|
| I-33 | (A) |
|  | (B) |
| I-34 | (A) |
|  | (B) |

TABLE 1-continued
Exemplary Compounds
| Cmpd # | Structure |
|---|---|
| I-35 | 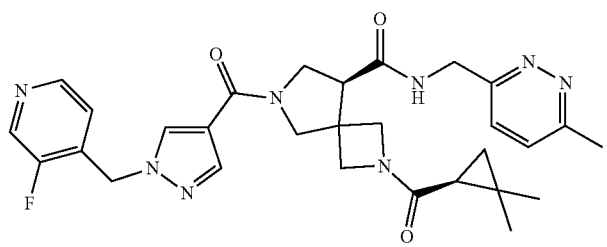 [SMILES: Cc1ccc(CNC(=O)[C@@H]2CN(C(=O)c3cnn(Cc4ccncc4F)c3)CC23CN(C(=O)[C@H]2CC2(C)C)C3)nn1] |
| I-36 | 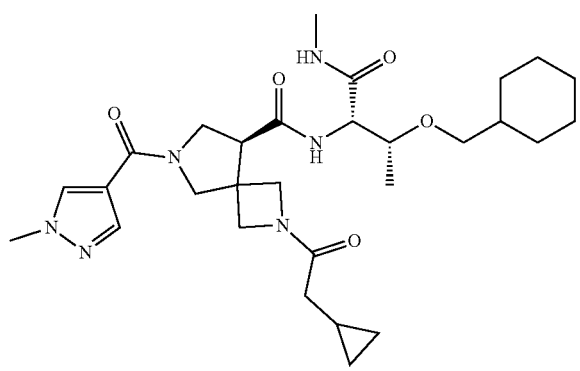 [SMILES: CNC(=O)[C@@H](NC(=O)[C@@H]1CN(C(=O)c2cnn(C)c2)CC12CN(C(=O)CC1CC1)C2)[C@@H](C)OCC1CCCCC1] (A) |
| | 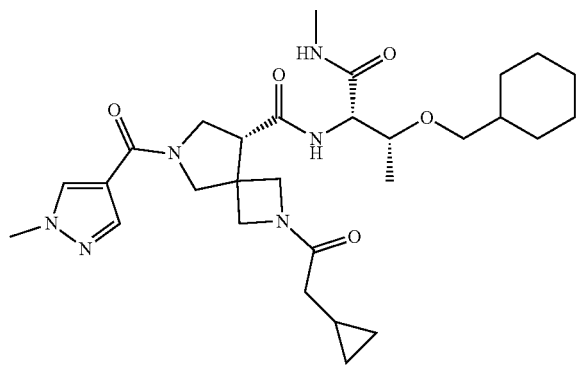 [SMILES: CNC(=O)[C@@H](NC(=O)[C@H]1CN(C(=O)c2cnn(C)c2)CC12CN(C(=O)CC1CC1)C2)[C@@H](C)OCC1CCCCC1] (B) |
| I-37 | 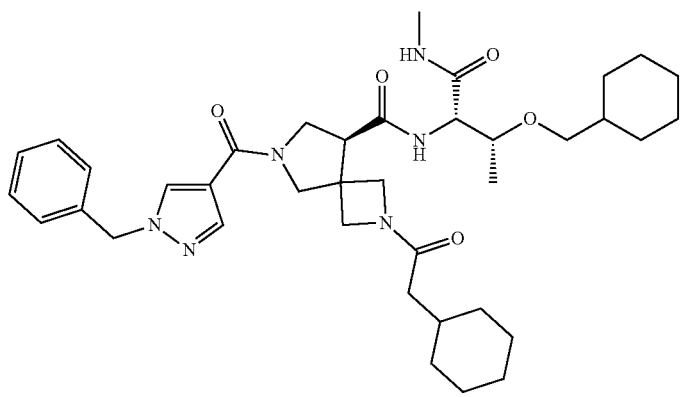 [SMILES: CNC(=O)[C@@H](NC(=O)[C@@H]1CN(C(=O)c2cnn(Cc3ccccc3)c2)CC12CN(C(=O)CC1CCCCC1)C2)[C@@H](C)OCC1CCCCC1] (A) |

TABLE 1-continued
Exemplary Compounds
| Cmpd # | Structure |
|---|---|
| | 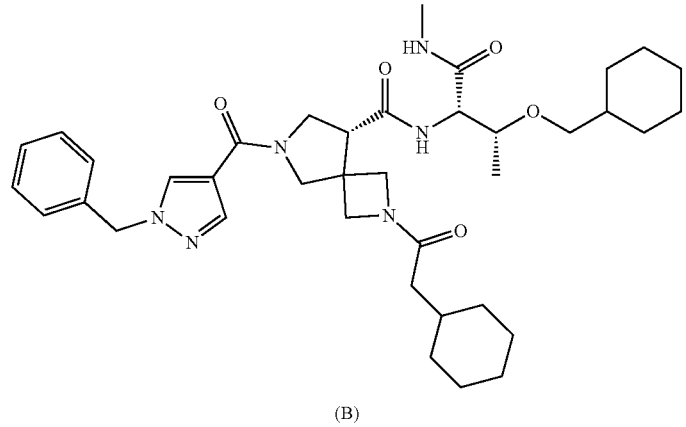<br>(B) |
| I-38 | 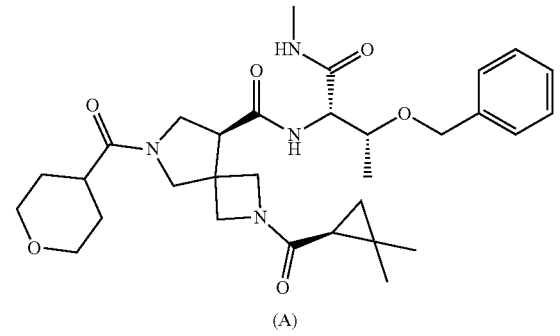<br>(A) |
| | 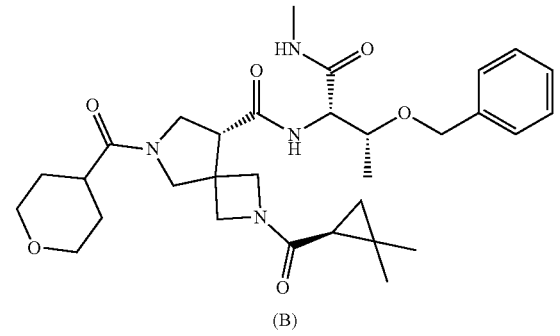<br>(B) |
| I-39 | 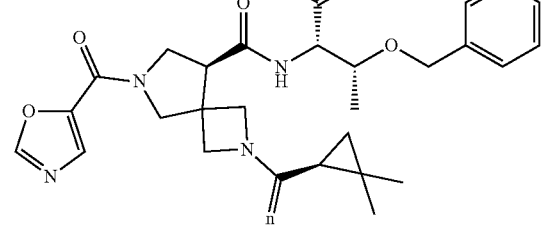<br>(A) |

TABLE 1-continued
Exemplary Compounds
| Cmpd # | Structure |
|---|---|
|  | 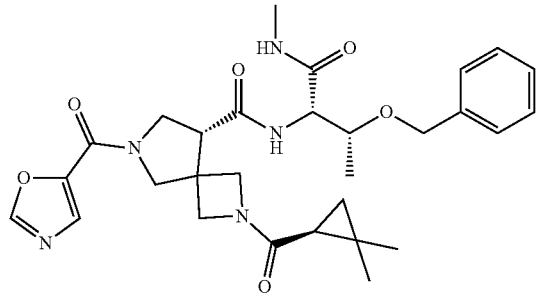(B) |
| I-40 | 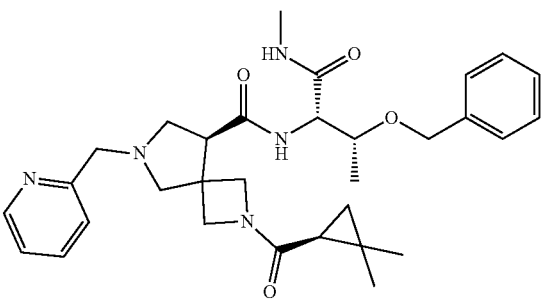(A) |
|  | 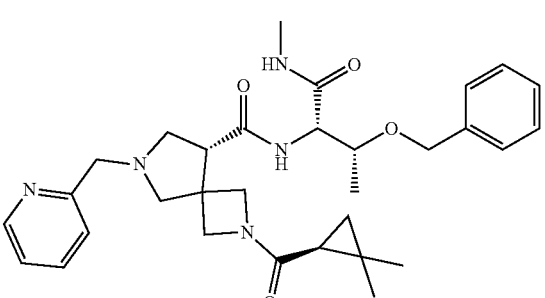(B) |
| I-41 | 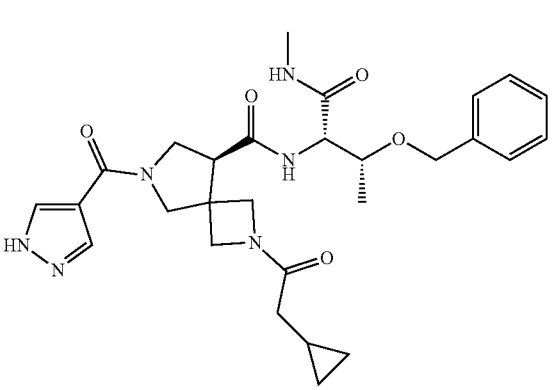(A) |

TABLE 1-continued
Exemplary Compounds
| Cmpd # | Structure |
|---|---|
|  | 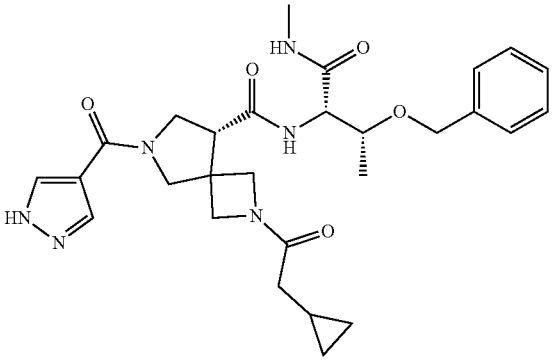 [SMILES: CNC(=O)[C@@H](NC(=O)[C@H]1CN(C(=O)c2cn[nH]c2)CC12CN(C(=O)CC1CC1)C2)[C@@H](C)OCc1ccccc1]<br>(B) |
| I-42 | 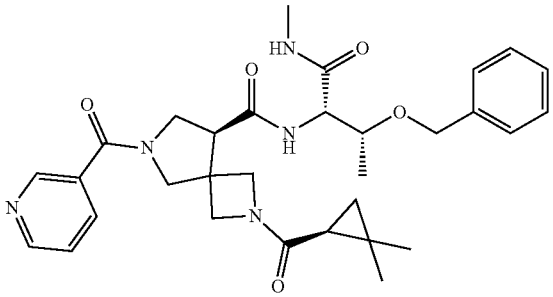 [SMILES: CNC(=O)[C@@H](NC(=O)[C@@H]1CN(C(=O)c2cccnc2)CC12CN(C(=O)[C@H]1CC1(C)C)C2)[C@@H](C)OCc1ccccc1]<br>(A) |
|  | 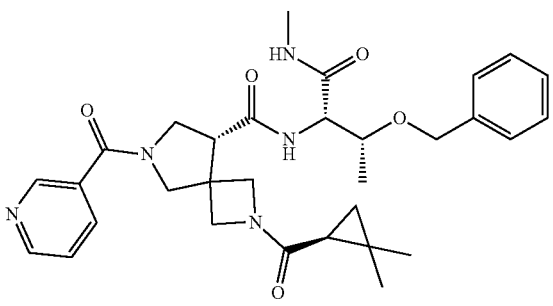 [SMILES: CNC(=O)[C@@H](NC(=O)[C@H]1CN(C(=O)c2cccnc2)CC12CN(C(=O)[C@H]1CC1(C)C)C2)[C@@H](C)OCc1ccccc1]<br>(B) |
| I-43 | 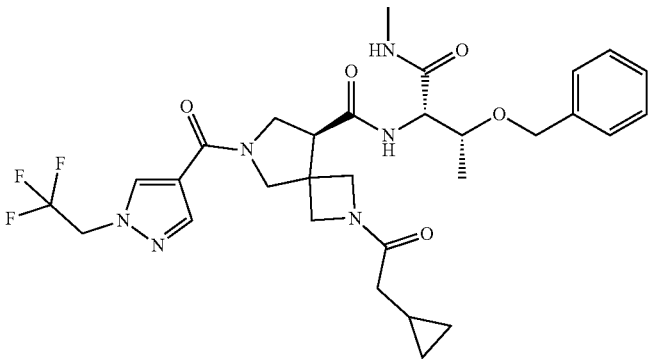 [SMILES: CNC(=O)[C@@H](NC(=O)[C@@H]1CN(C(=O)c2cnn(CC(F)(F)F)c2)CC12CN(C(=O)CC1CC1)C2)[C@@H](C)OCc1ccccc1]<br>(A) |

TABLE 1-continued

Exemplary Compounds

| Cmpd # | Structure |
|---|---|
| | (B) |
| I-44 | (A) |
| | (B) |
| I-45 | (A) |

TABLE 1-continued
Exemplary Compounds
| Cmpd # | Structure |
|---|---|
| | 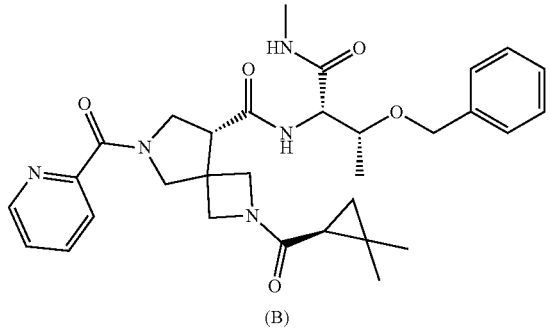<br>(B) |
| I-46 | 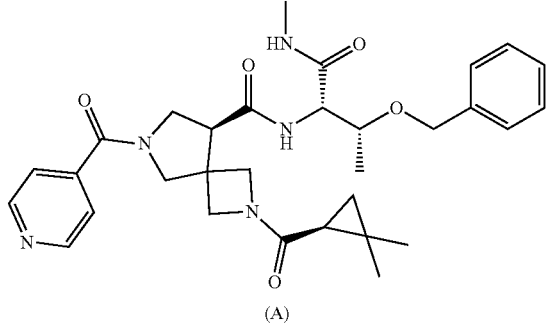<br>(A) |
| | 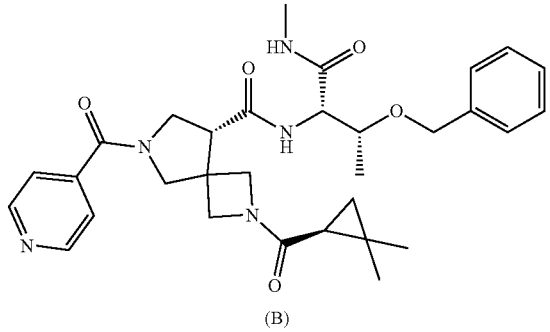<br>(B) |
| I-47 | 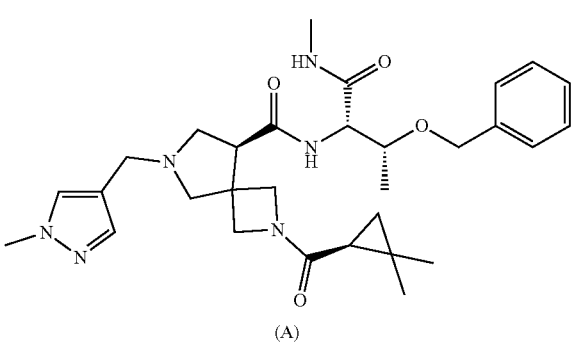<br>(A) |

TABLE 1-continued
Exemplary Compounds
| Cmpd # | Structure |
|---|---|
| | (B) 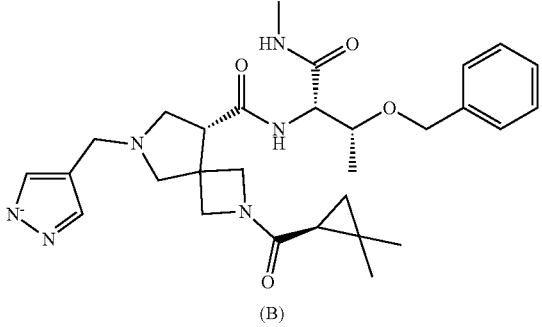 |
| I-48 | (A) 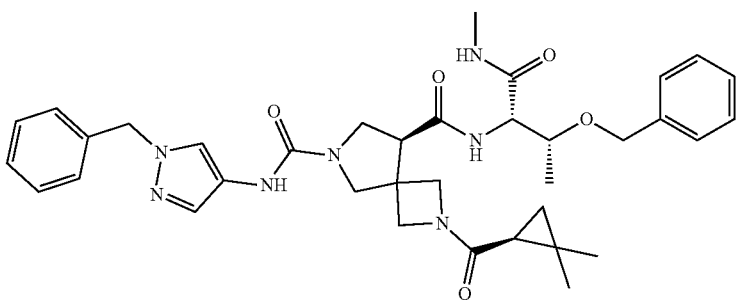 |
| | (B) 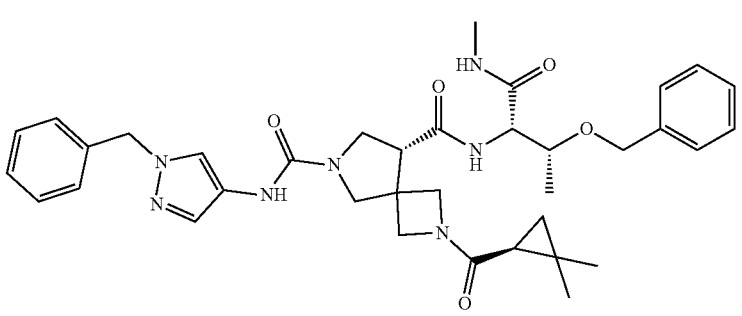 |
| I-49 | (A) 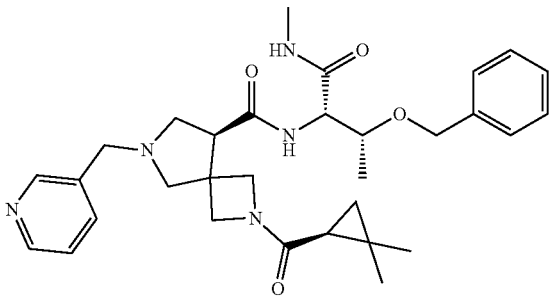 |

TABLE 1-continued

Exemplary Compounds

| Cmpd # | Structure |
|---|---|
| | (B) |
| I-50 | (A) |
| | (B) |
| I-51 | (A) |

TABLE 1-continued
Exemplary Compounds
| Cmpd # | Structure |
|---|---|
| | (B) 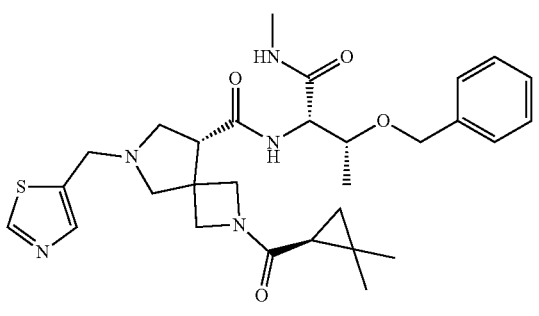 |
| I-52 | 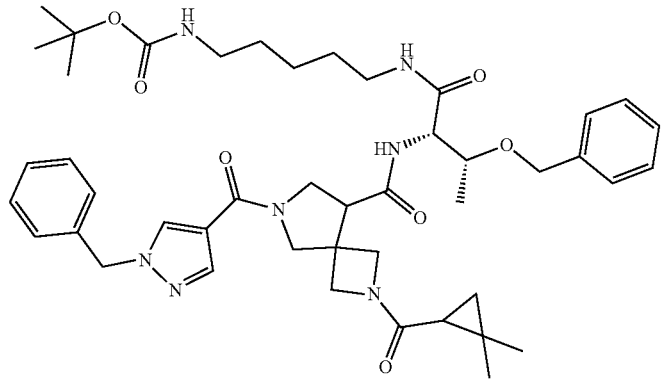 |
| I-53 | (A) 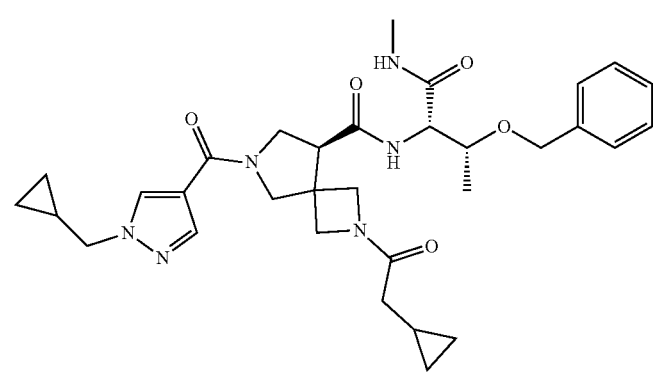 |
| | (B) 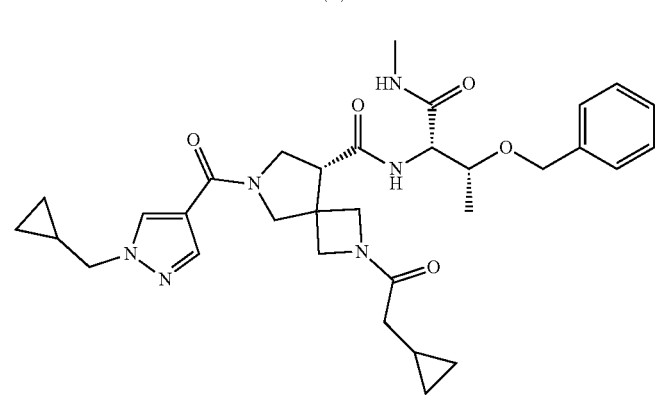 |

TABLE 1-continued
Exemplary Compounds
| Cmpd # | Structure |
|---|---|
| I-54 | 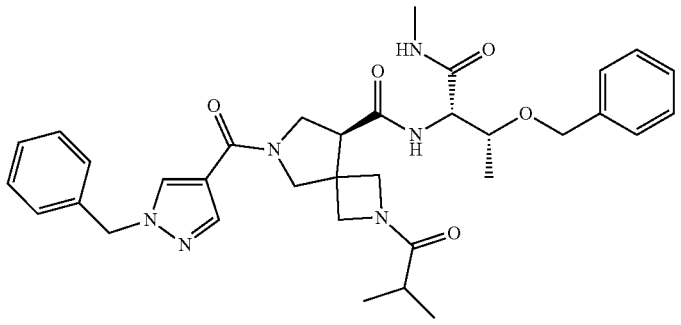 [SMILES: CNC(=O)[C@@H](NC(=O)[C@@H]1CN(C(=O)c2cnn(Cc3ccccc3)c2)CC12CN(C(=O)C(C)C)C2)[C@@H](C)OCc1ccccc1]<br>(A)<br>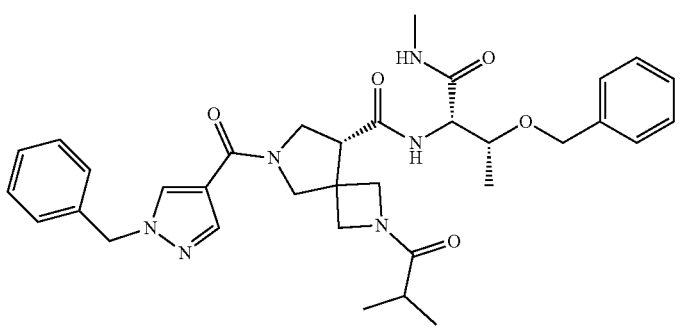 [SMILES: CNC(=O)[C@@H](NC(=O)[C@H]1CN(C(=O)c2cnn(Cc3ccccc3)c2)CC12CN(C(=O)C(C)C)C2)[C@@H](C)OCc1ccccc1]<br>(B) |
| I-55 | 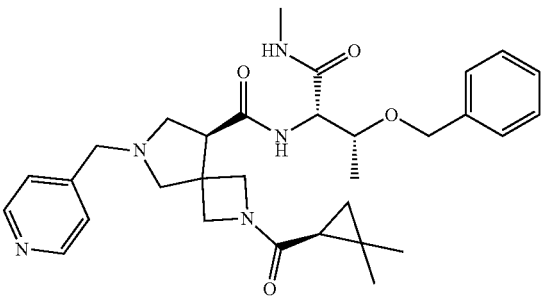 [SMILES: CNC(=O)[C@@H](NC(=O)[C@@H]1CN(Cc2ccncc2)CC12CN(C(=O)[C@H]1CC1(C)C)C2)[C@@H](C)OCc1ccccc1]<br>(A)<br>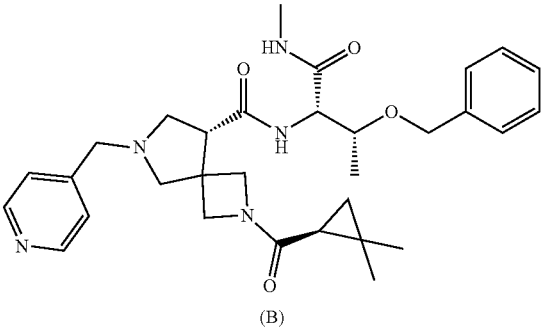<br>(B) |

TABLE 1-continued
Exemplary Compounds
| Cmpd # | Structure |
|---|---|
| I-56 | 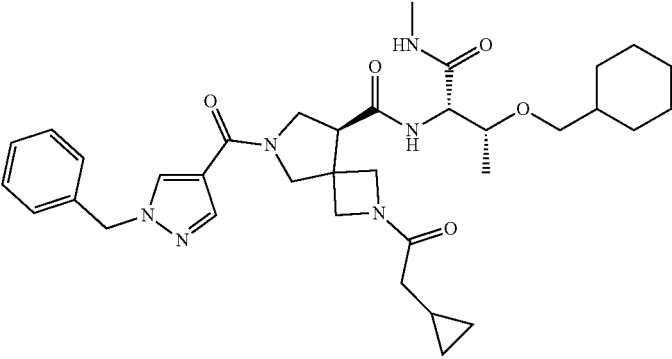 [SMILES: CNC(=O)[C@@H](NC(=O)[C@@H]1CN(C(=O)c2cnn(Cc3ccccc3)c2)CC12CN(C(=O)CC1CC1)C2)[C@@H](C)OCC1CCCCC1]<br>(A)<br>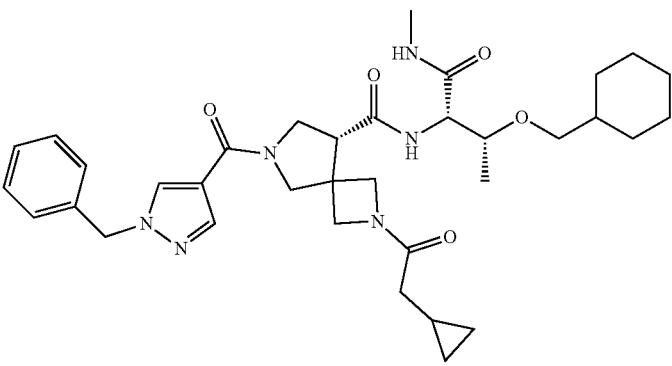 [SMILES: CNC(=O)[C@@H](NC(=O)[C@H]1CN(C(=O)c2cnn(Cc3ccccc3)c2)CC12CN(C(=O)CC1CC1)C2)[C@@H](C)OCC1CCCCC1]<br>(B) |
| I-57 | 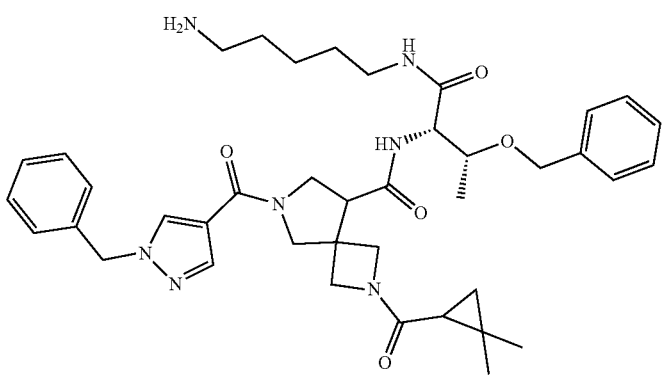 [SMILES: C[C@@H](OCc1ccccc1)[C@H](NC(=O)C1CN(C(=O)c2cnn(Cc3ccccc3)c2)CC12CN(C(=O)C1CC1(C)C)C2)C(=O)NCCCCCN] |
| I-58 | 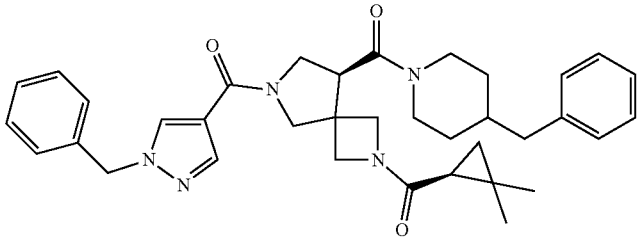 [SMILES: CC1(C)C[C@@H]1C(=O)N1CC2(CN(C(=O)c3cnn(Cc4ccccc4)c3)C[C@H]2C(=O)N2CCC(Cc3ccccc3)CC2)C1]<br>(A) |

TABLE 1-continued
Exemplary Compounds
| Cmpd # | Structure |
|---|---|
| | 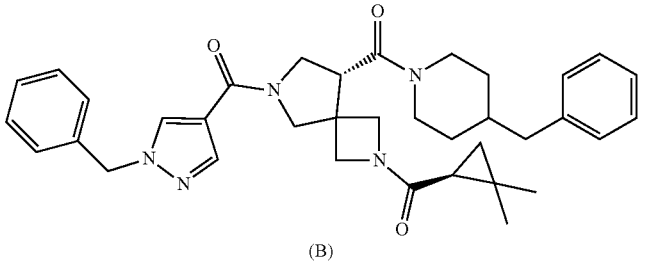 <br> (B) |
| I-59 | 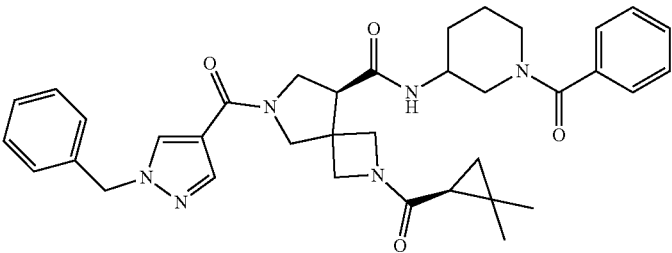 [SMILES: CC1(C)C[C@@H]1C(=O)N1CC2(CN(C(=O)c3cnn(Cc4ccccc4)c3)C[C@H]2C(=O)NC2CCCN(C(=O)c3ccccc3)C2)C1] <br> (A) |
| | 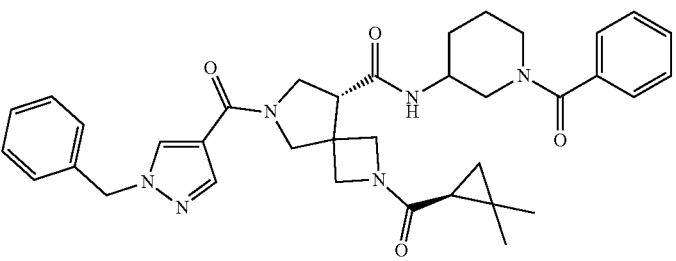 [SMILES: CC1(C)C[C@@H]1C(=O)N1CC2(CN(C(=O)c3cnn(Cc4ccccc4)c3)C[C@@H]2C(=O)NC2CCCN(C(=O)c3ccccc3)C2)C1] <br> (B) |
| I-60 | 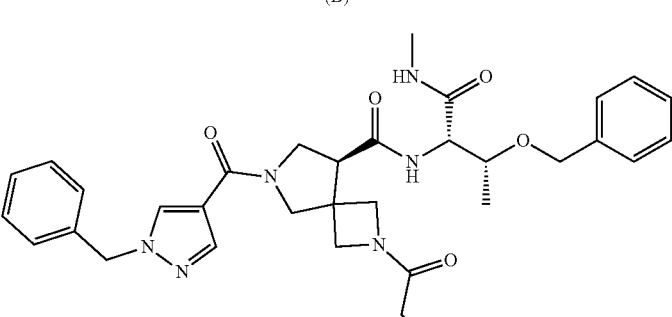 <br> (A) |
| | 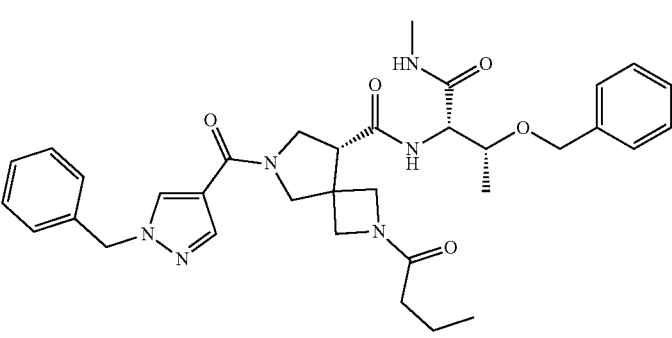 [SMILES: CCCC(=O)N1CC2(C1)CN(C(=O)c1cnn(Cc3ccccc3)c1)C[C@@H]2C(=O)N[C@H](C(=O)NC)[C@@H](C)OCc1ccccc1] <br> (B) |

TABLE 1-continued
Exemplary Compounds
| Cmpd # | Structure |
|---|---|
| I-61 | 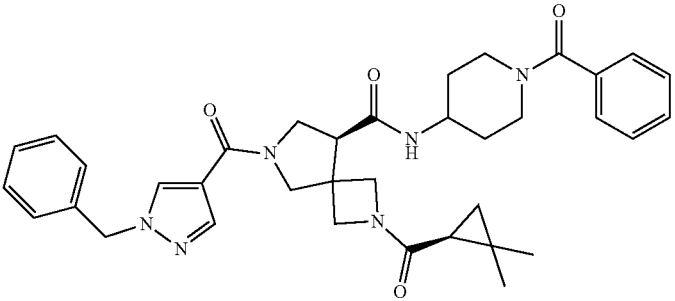 [SMILES: CC1(C)C[C@@H]1C(=O)N1CC2(CN(C(=O)c3cnn(Cc4ccccc4)c3)C[C@H]2C(=O)NC2CCN(C(=O)c3ccccc3)CC2)C1]<br>(A)<br>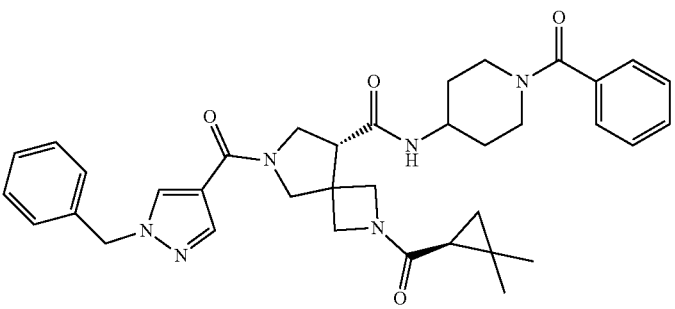 [SMILES: CC1(C)C[C@@H]1C(=O)N1CC2(CN(C(=O)c3cnn(Cc4ccccc4)c3)C[C@@H]2C(=O)NC2CCN(C(=O)c3ccccc3)CC2)C1]<br>(B) |
| I-62 | 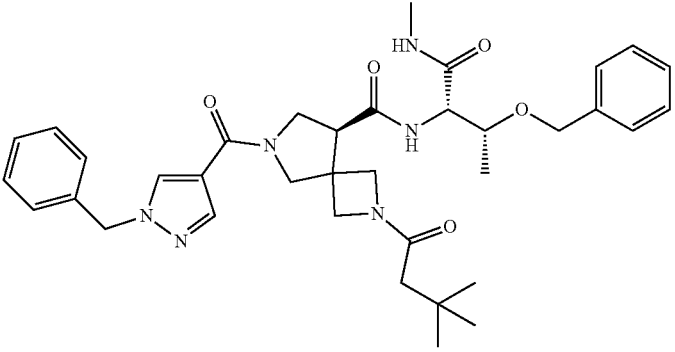 [SMILES: CNC(=O)[C@@H](NC(=O)[C@@H]1CN(C(=O)c2cnn(Cc3ccccc3)c2)CC12CN(C(=O)CC(C)(C)C)C2)[C@@H](C)OCc1ccccc1]<br>(A)<br>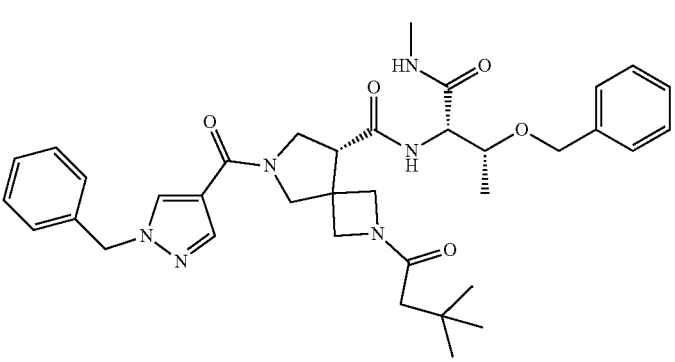 [SMILES: CNC(=O)[C@@H](NC(=O)[C@H]1CN(C(=O)c2cnn(Cc3ccccc3)c2)CC12CN(C(=O)CC(C)(C)C)C2)[C@@H](C)OCc1ccccc1]<br>(B) |

TABLE 1-continued
Exemplary Compounds
| Cmpd # | Structure |
|---|---|
| I-63 | 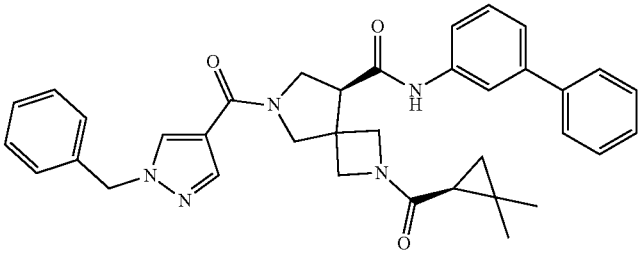 [SMILES: CC1(C)C[C@@H]1C(=O)N1CC2(CN(C(=O)c3cnn(Cc4ccccc4)c3)C[C@H]2C(=O)Nc2cccc(-c3ccccc3)c2)C1]<br>(A)<br>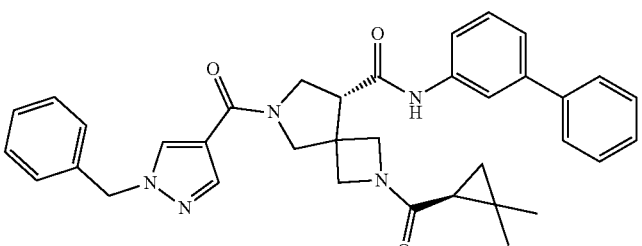<br>(B) |
| I-64 | 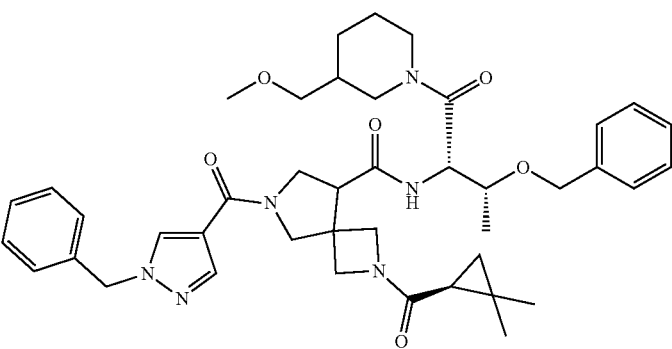 [SMILES: COCC1CCCN(C(=O)[C@@H](NC(=O)C2CN(C(=O)c3cnn(Cc4ccccc4)c3)CC23CN(C(=O)[C@H]2CC2(C)C)C3)[C@@H](C)OCc2ccccc2)C1] |
| I-65 | 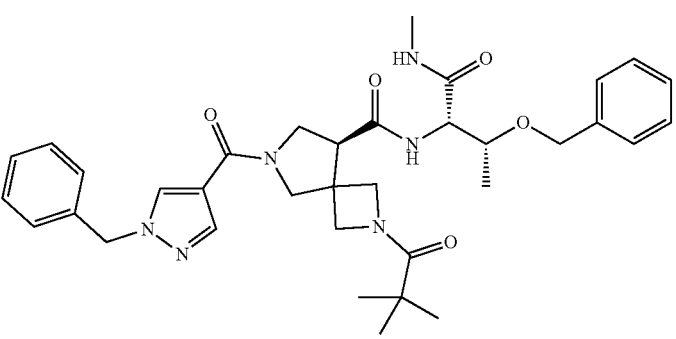 [SMILES: CNC(=O)[C@@H](NC(=O)[C@@H]1CN(C(=O)c2cnn(Cc3ccccc3)c2)CC12CN(C(=O)C(C)(C)C)C2)[C@@H](C)OCc1ccccc1]<br>(A) |

TABLE 1-continued

Exemplary Compounds

| Cmpd # | Structure |
|---|---|
| | (B) |
| I-66 | (A) |
| | (B) |
| I-67 | (A) |

TABLE 1-continued
Exemplary Compounds
| Cmpd # | Structure |
|---|---|
| | 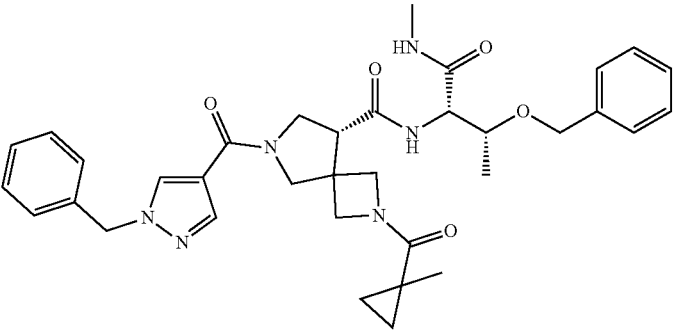 [SMILES: CNC(=O)[C@@H](NC(=O)[C@H]1CN(C(=O)c2cnn(Cc3ccccc3)c2)CC12CN(C(=O)C1(C)CC1)C2)[C@@H](C)OCc1ccccc1]<br>(B) |
| I-68 | 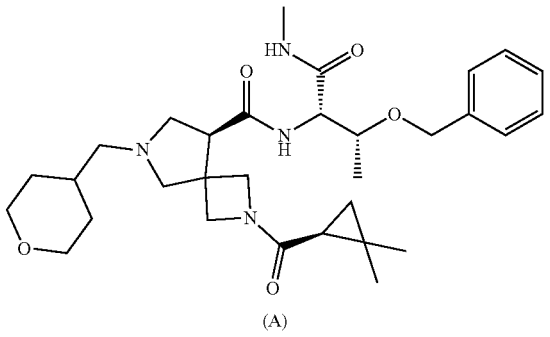<br>(A) |
| | 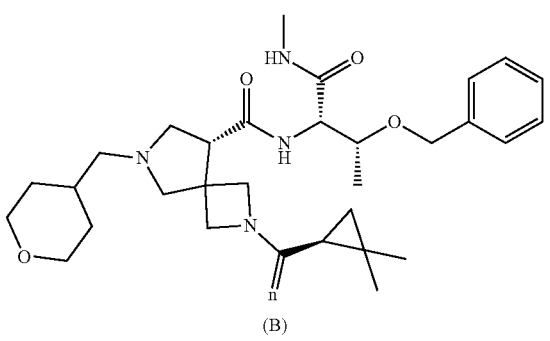<br>(B) |
| I-69 | 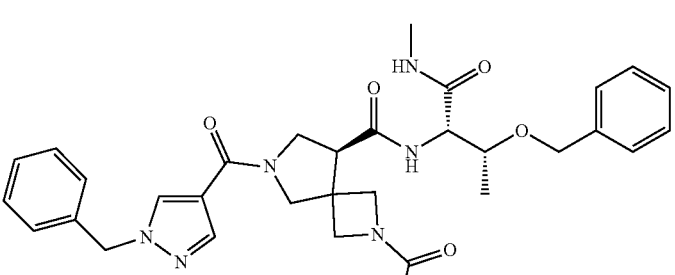<br>(A) |

TABLE 1-continued
Exemplary Compounds
| Cmpd # | Structure |
|---|---|
|  | 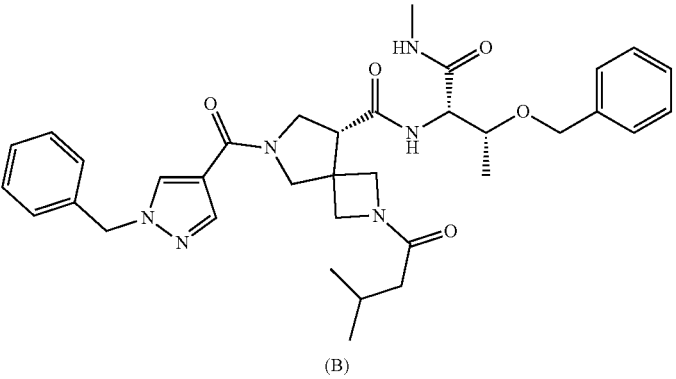 (B) |
| I-70 | 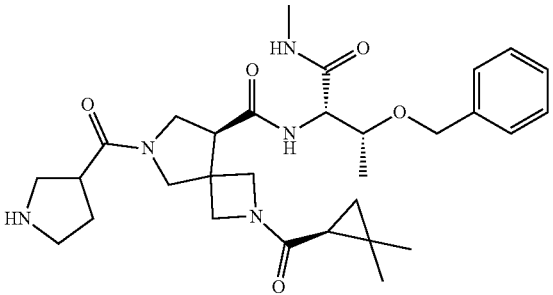 (A) |
|  | 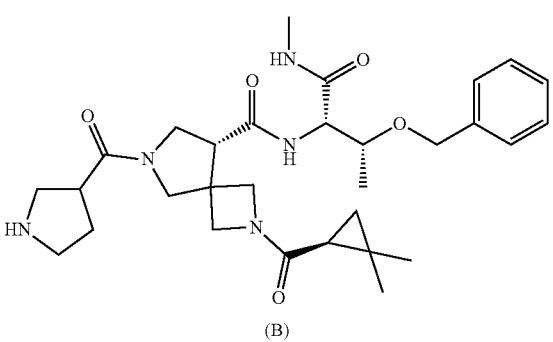 (B) |
| I-71 | 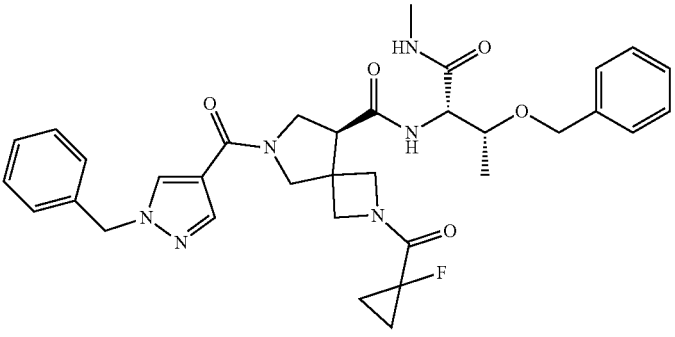 (A) |

TABLE 1-continued
Exemplary Compounds
| Cmpd # | Structure |
|---|---|
| | (B) 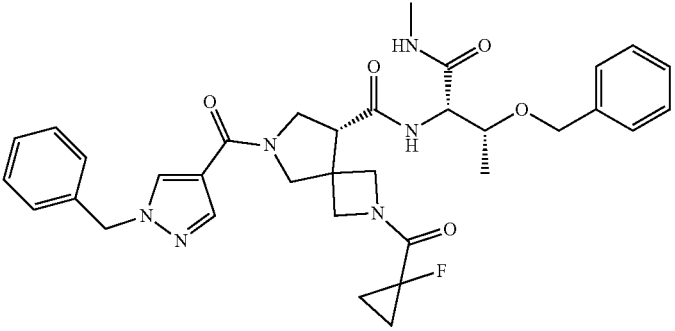 |
| I-72 | (A) 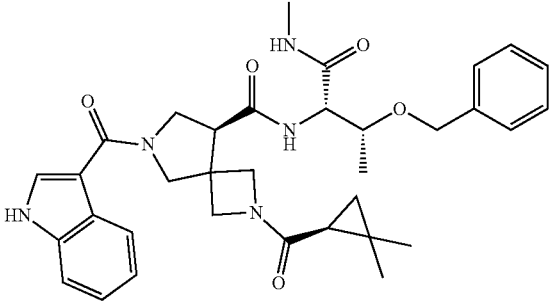 |
| | (B) 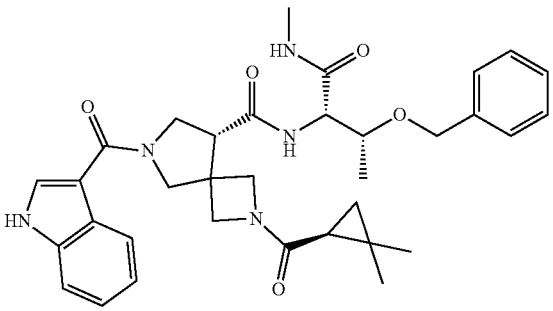 |
| I-73 | (A) 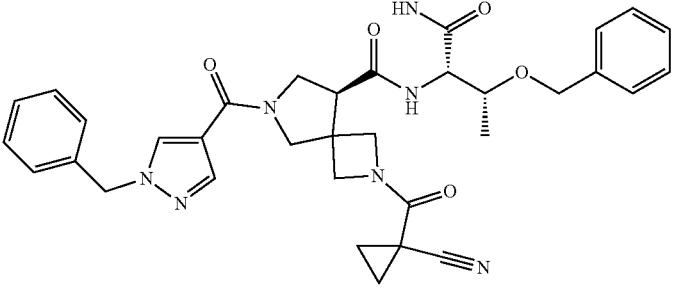 |

TABLE 1-continued
Exemplary Compounds
| Cmpd # | Structure |
|---|---|
| | 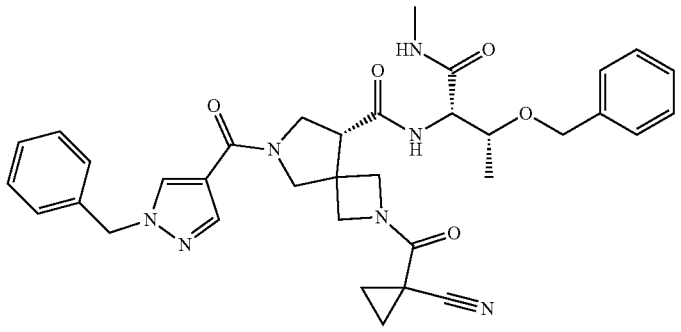 [SMILES: CNC(=O)[C@@H](NC(=O)[C@H]1CN(C(=O)c2cnn(Cc3ccccc3)c2)CC12CN(C(=O)C1(C#N)CC1)C2)[C@@H](C)OCc1ccccc1]<br>(B) |
| I-74 | 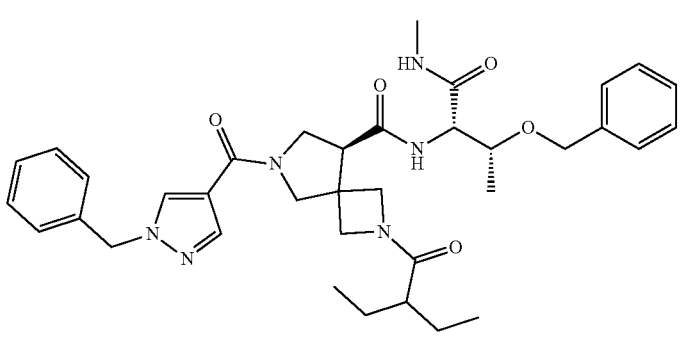 [SMILES: CCC(CC)C(=O)N1CC2(CN(C(=O)c3cnn(Cc4ccccc4)c3)C[C@H]2C(=O)N[C@H](C(=O)NC)[C@@H](C)OCc2ccccc2)C1]<br>(A) |
| | 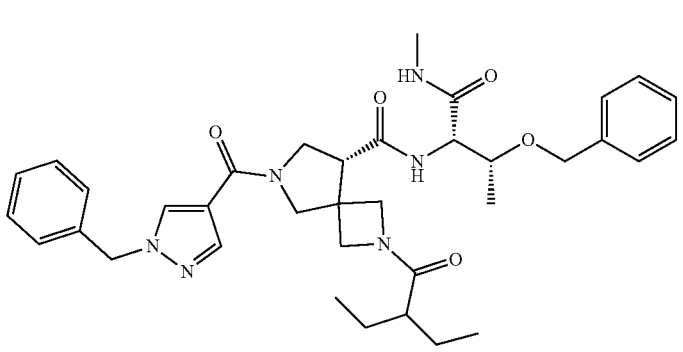 [SMILES: CCC(CC)C(=O)N1CC2(CN(C(=O)c3cnn(Cc4ccccc4)c3)C[C@@H]2C(=O)N[C@H](C(=O)NC)[C@@H](C)OCc2ccccc2)C1]<br>(B) |
| I-75 | 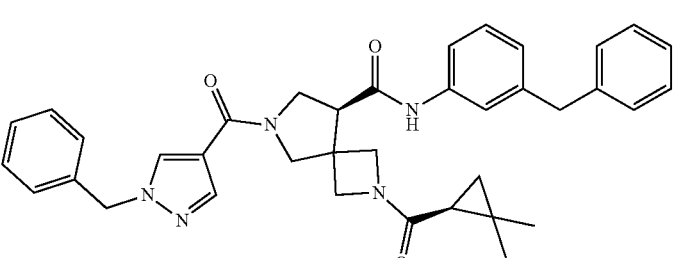<br>(A) |

TABLE 1-continued

Exemplary Compounds

| Cmpd # | Structure |
|---|---|
|  | (B) |
| I-76 | (A) |
|  | (B) |
| I-77 | (A) |
|  | (B) |

TABLE 1-continued
Exemplary Compounds
| Cmpd # | Structure |
|---|---|
| I-78 | (B) 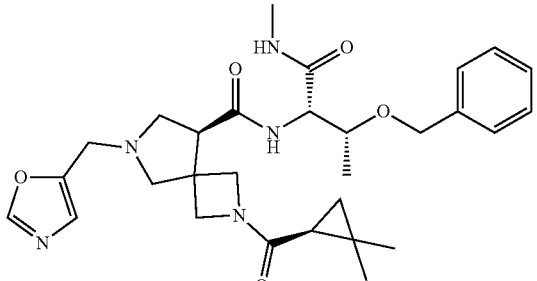 (A) 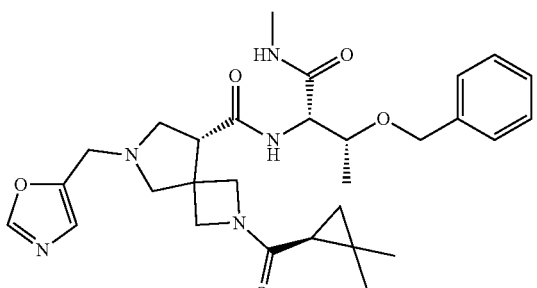 (B) |
| I-79 | 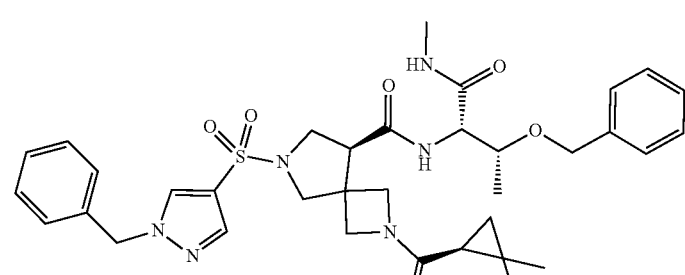 (A) 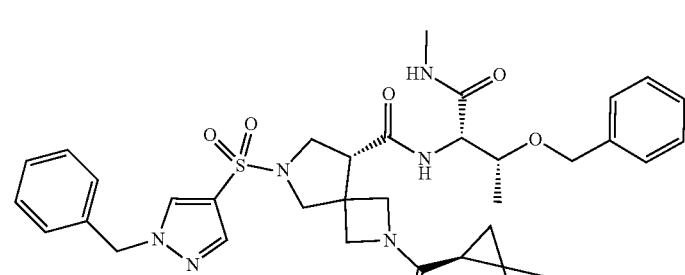 (B) |

TABLE 1-continued
Exemplary Compounds
| Cmpd # | Structure |
|---|---|
| I-80 | 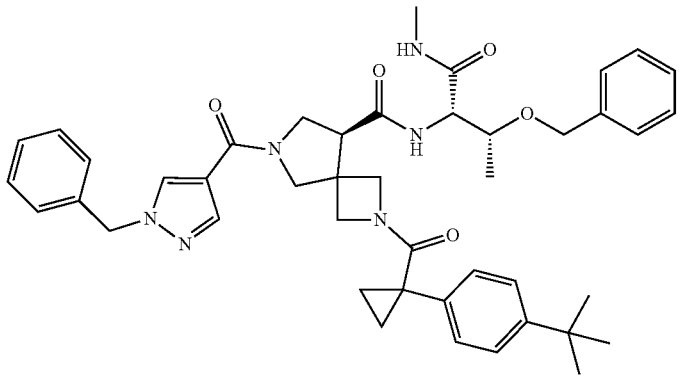 (A) 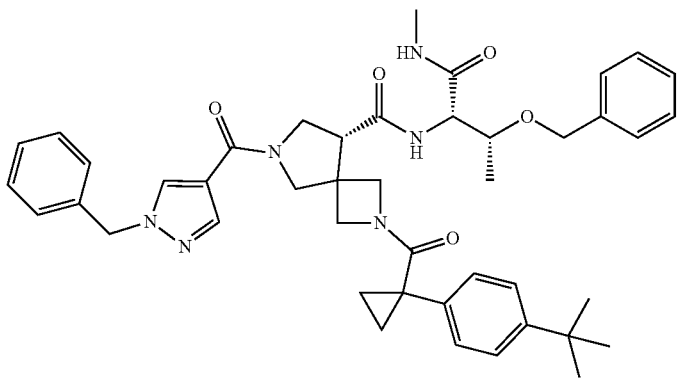 (B) |
| I-81 | 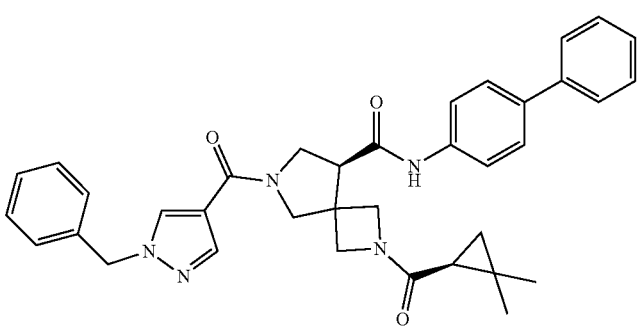 (A) 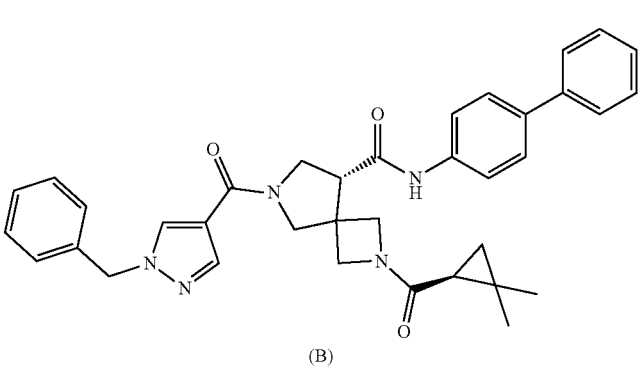 (B) |

TABLE 1-continued
Exemplary Compounds
| Cmpd # | Structure |
|---|---|
| I-82 | 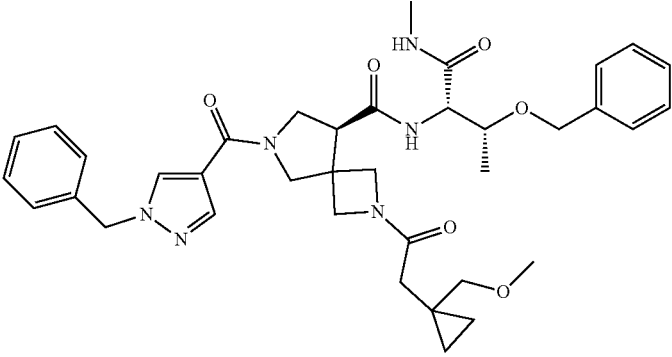 [SMILES: CNC(=O)[C@@H](NC(=O)[C@@H]1CN(C(=O)c2cnn(Cc3ccccc3)c2)CC12CN(C(=O)CC1(COC)CC1)C2)[C@@H](C)OCc1ccccc1]<br>(A)<br>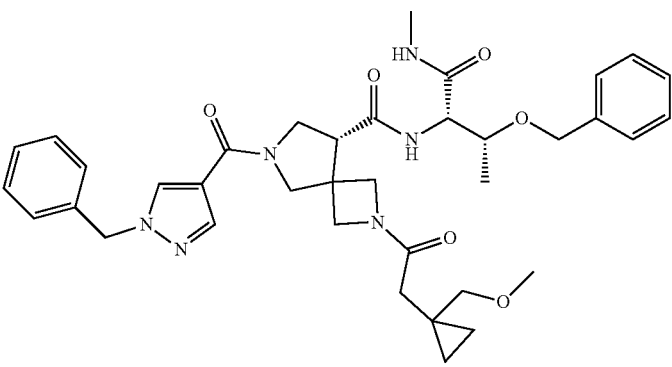 [SMILES: CNC(=O)[C@@H](NC(=O)[C@H]1CN(C(=O)c2cnn(Cc3ccccc3)c2)CC12CN(C(=O)CC1(COC)CC1)C2)[C@@H](C)OCc1ccccc1]<br>(B) |
| I-83 | 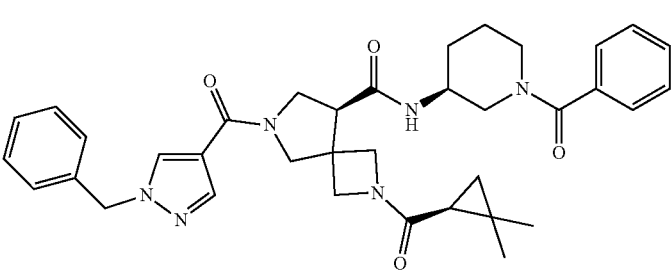 [SMILES: CC1(C)C[C@@H]1C(=O)N1CC2(CN(C(=O)c3cnn(Cc4ccccc4)c3)C[C@H]2C(=O)N[C@H]2CCCN(C(=O)c3ccccc3)C2)C1]<br>(A)<br>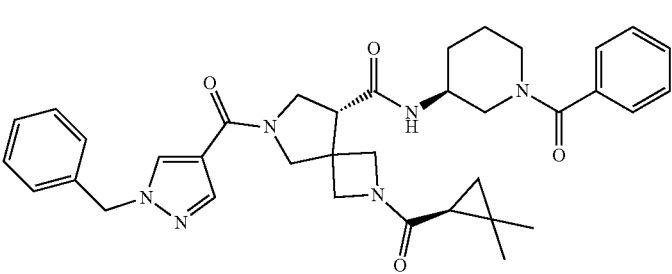 [SMILES: CC1(C)C[C@@H]1C(=O)N1CC2(CN(C(=O)c3cnn(Cc4ccccc4)c3)C[C@@H]2C(=O)N[C@H]2CCCN(C(=O)c3ccccc3)C2)C1]<br>(B) |

TABLE 1-continued
Exemplary Compounds
| Cmpd # | Structure |
|---|---|
| I-84 | 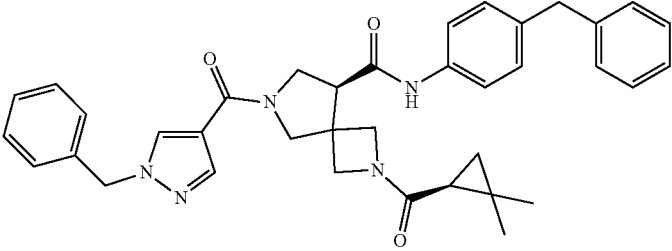 [SMILES: CC1(C)C[C@@H]1C(=O)N1CC2(CN(C(=O)c3cnn(Cc4ccccc4)c3)C[C@H]2C(=O)Nc2ccc(Cc3ccccc3)cc2)C1]<br>(A)<br>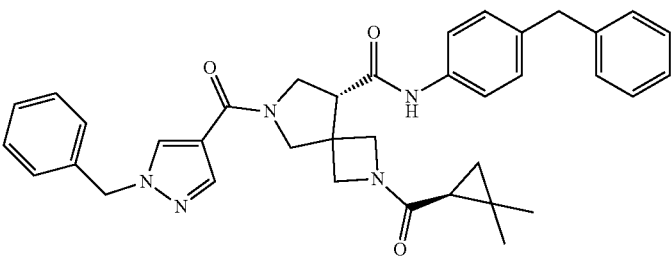 [SMILES: CC1(C)C[C@@H]1C(=O)N1CC2(CN(C(=O)c3cnn(Cc4ccccc4)c3)C[C@@H]2C(=O)Nc2ccc(Cc3ccccc3)cc2)C1]<br>(B) |
| I-85 | 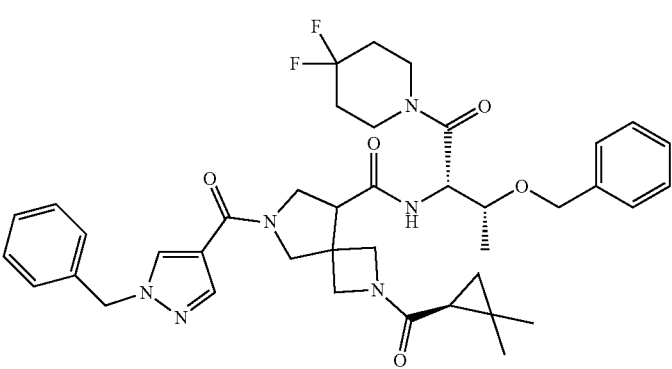 [SMILES: C[C@@H](OCc1ccccc1)[C@H](NC(=O)C1CN(C(=O)c2cnn(Cc3ccccc3)c2)CC12CN(C(=O)[C@H]1CC1(C)C)C2)C(=O)N1CCC(F)(F)CC1] |
| I-86 | 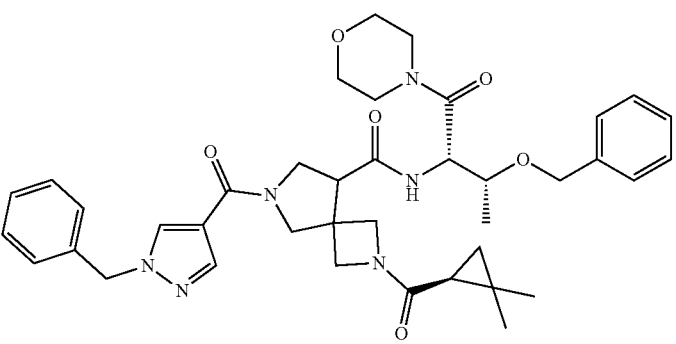 [SMILES: C[C@@H](OCc1ccccc1)[C@H](NC(=O)C1CN(C(=O)c2cnn(Cc3ccccc3)c2)CC12CN(C(=O)[C@H]1CC1(C)C)C2)C(=O)N1CCOCC1] |

TABLE 1-continued

Exemplary Compounds

| Cmpd # | Structure |
|---|---|
| I-87 | (A) |
| | (B) |
| I-88 | Mixture |
| | (A) |

TABLE 1-continued
Exemplary Compounds
| Cmpd # | Structure |
|---|---|
|  | 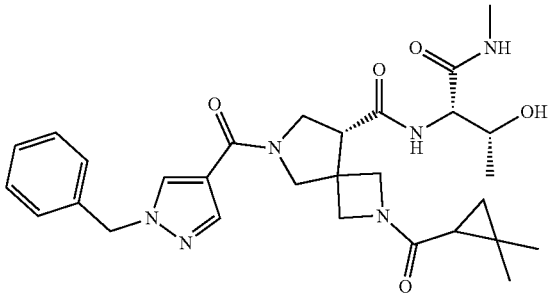 (B) |
| I-89 | 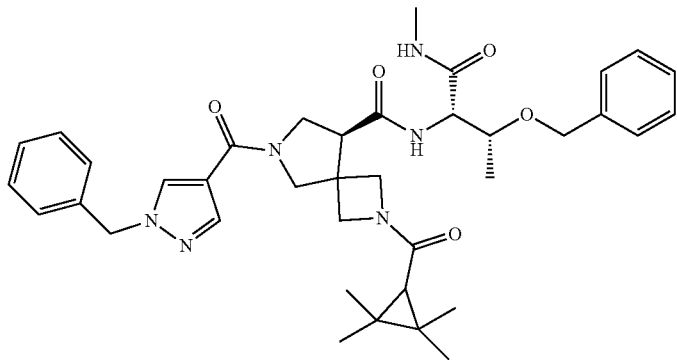 (A) |
|  | 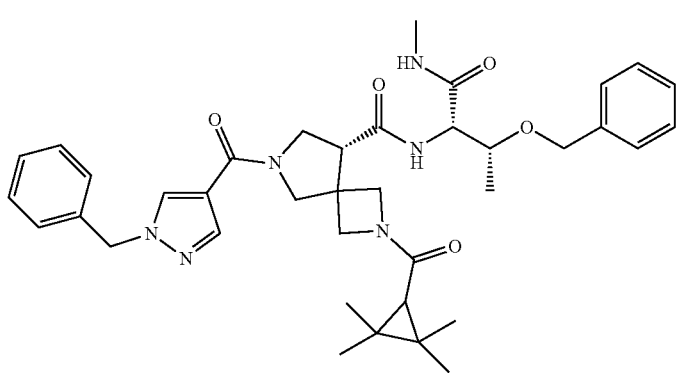 (B) |
| I-90 | 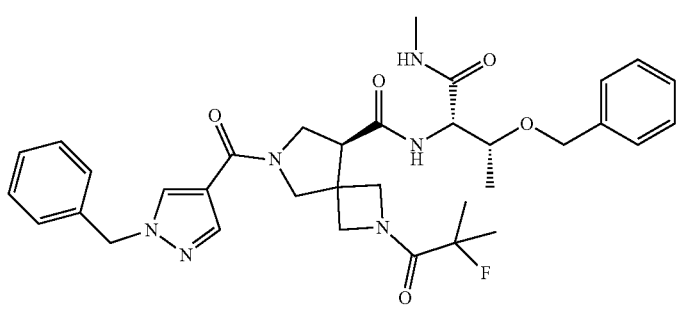 (A) |

TABLE 1-continued
Exemplary Compounds
| Cmpd # | Structure |
|---|---|
| | (B) 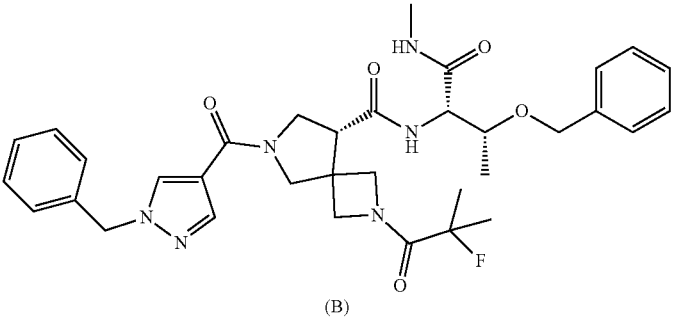 |
| I-91 | (A) 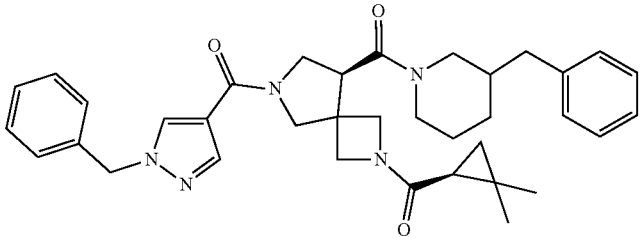 |
| | (B) 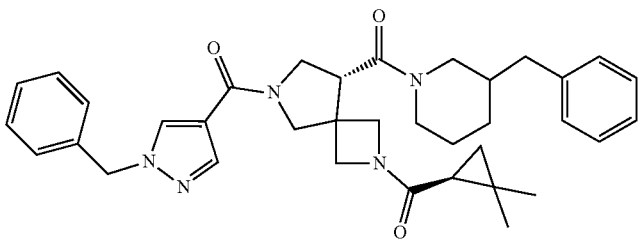 |
| I-92 | (A) 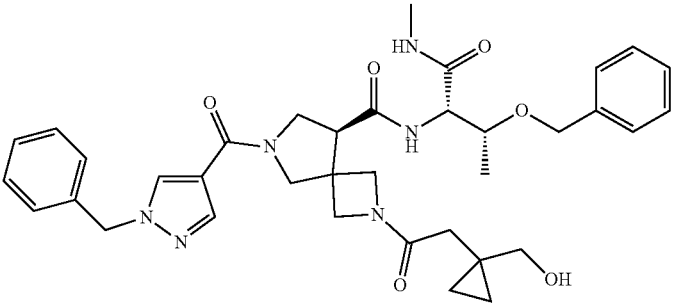 |
| | (B) 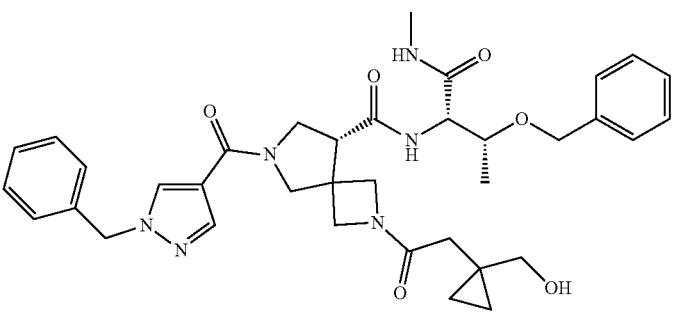 |

TABLE 1-continued

Exemplary Compounds

| Cmpd # | Structure |
|---|---|
| I-93 | 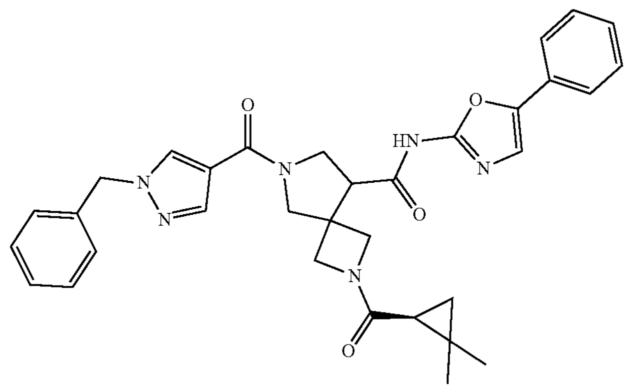 |
| I-94 | (A) <br> (B) |
| I-95 | (A) |

TABLE 1-continued
Exemplary Compounds
| Cmpd # | Structure |
|---|---|
| | (B) |
| I-96 | (A) |
| | (B) |
| I-97 | 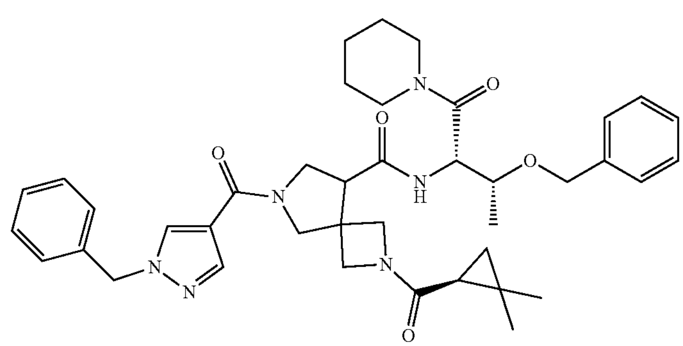 |
| I-98 | 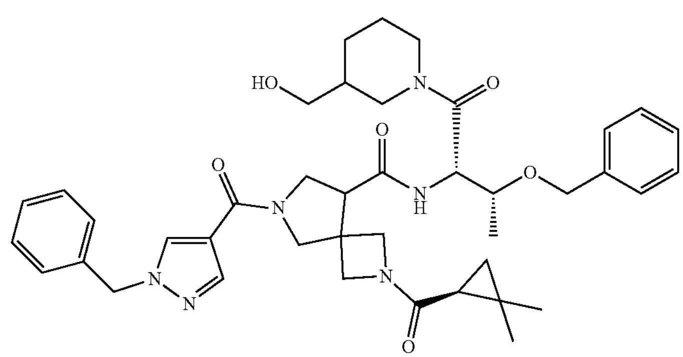 |
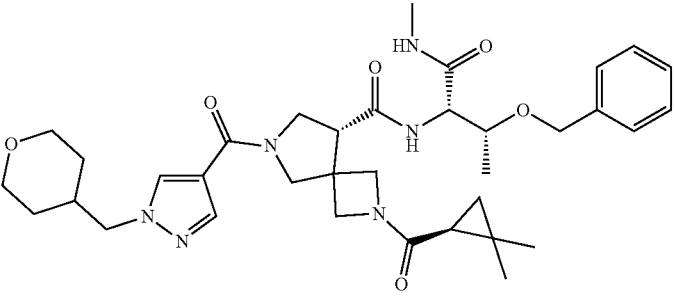 [SMILES: CNC(=O)[C@@H](NC(=O)[C@H]1CN(C(=O)c2cnn(CC3CCOCC3)c2)CC12CN(C(=O)[C@H]1CC1(C)C)C2)[C@@H](C)OCc1ccccc1]
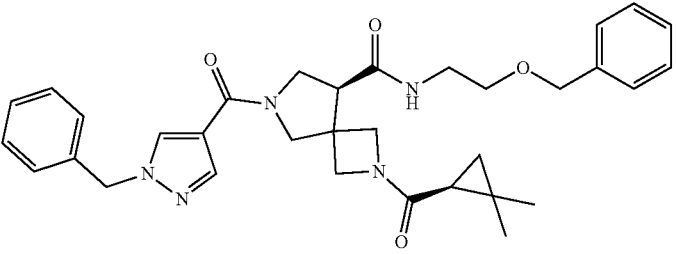 [SMILES: CC1(C)C[C@@H]1C(=O)N1CC2(CN(C(=O)c3cnn(Cc4ccccc4)c3)C[C@H]2C(=O)NCCOCc2ccccc2)C1]
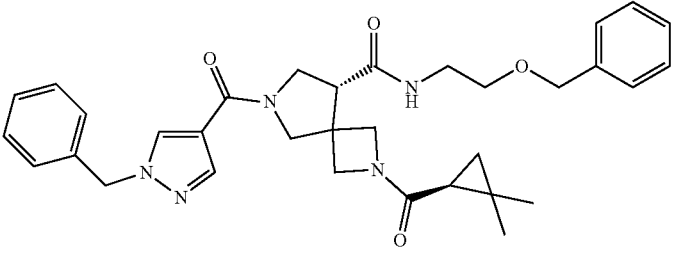 [SMILES: CC1(C)C[C@@H]1C(=O)N1CC2(CN(C(=O)c3cnn(Cc4ccccc4)c3)C[C@@H]2C(=O)NCCOCc2ccccc2)C1]
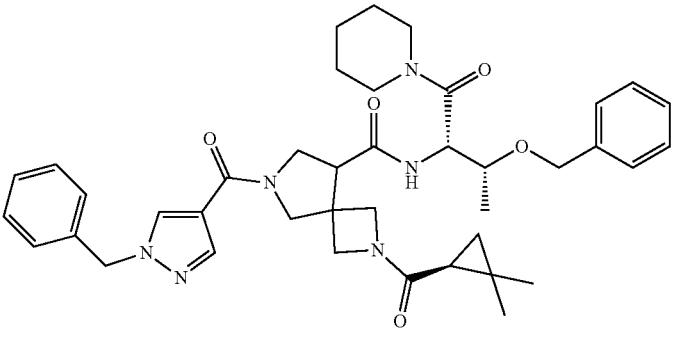 [SMILES: C[C@@H](OCc1ccccc1)[C@H](NC(=O)C1CN(C(=O)c2cnn(Cc3ccccc3)c2)CC12CN(C(=O)[C@H]1CC1(C)C)C2)C(=O)N1CCCCC1]
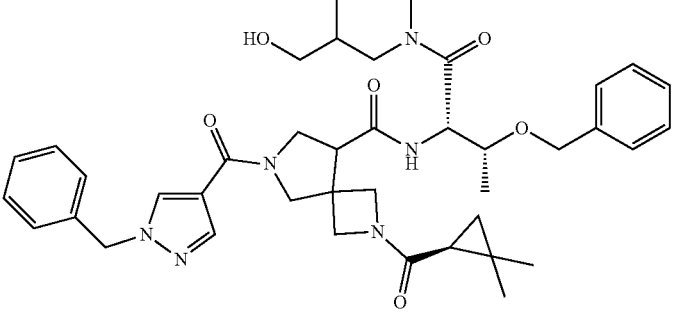

TABLE 1-continued
Exemplary Compounds
| Cmpd # | Structure |
|---|---|
| I-99 | 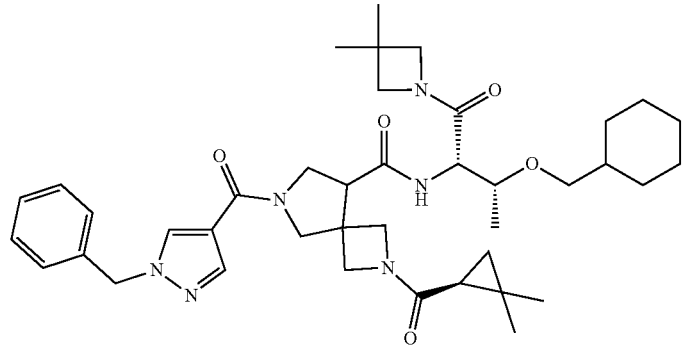 [SMILES: C[C@@H](OCC1CCCCC1)[C@H](NC(=O)C1CN(C(=O)c2cnn(Cc3ccccc3)c2)CC12CN(C(=O)[C@H]1CC1(C)C)C2)C(=O)N1CC(C)(C)C1] |
| I-100 | 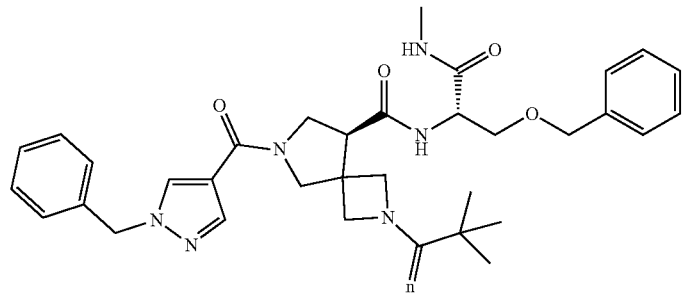<br>(A)<br>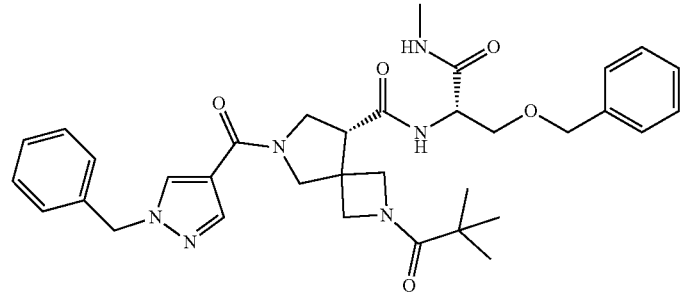 [SMILES: CNC(=O)[C@H](COCc1ccccc1)NC(=O)[C@H]1CN(C(=O)c2cnn(Cc3ccccc3)c2)CC12CN(C(=O)C(C)(C)C)C2]<br>(B) |
| I-101 | 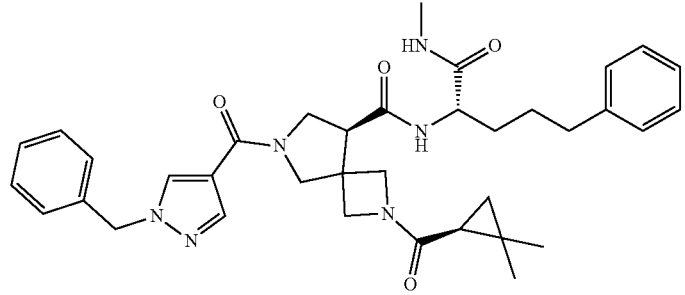 [SMILES: CNC(=O)[C@H](CCCc1ccccc1)NC(=O)[C@@H]1CN(C(=O)c2cnn(Cc3ccccc3)c2)CC12CN(C(=O)[C@H]1CC1(C)C)C2]<br>(A) |

TABLE 1-continued
Exemplary Compounds
| Cmpd # | Structure |
|---|---|
| | 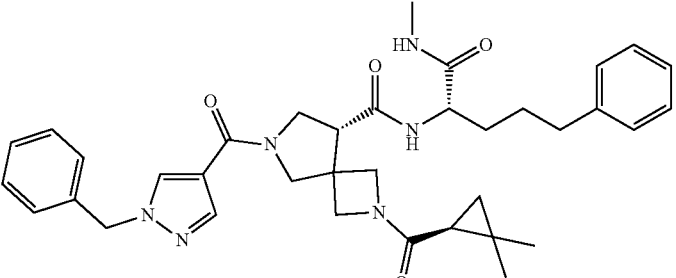<br>(B) |
| I-102 | 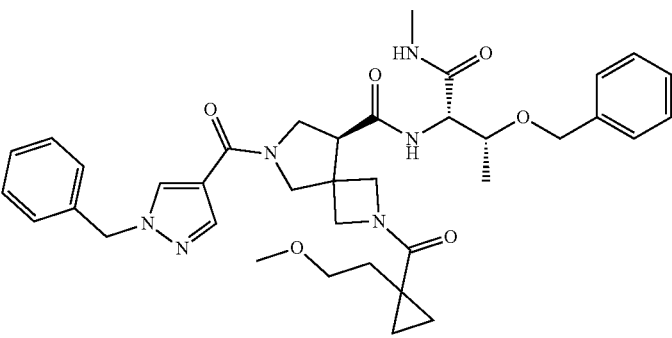 [SMILES: CNC(=O)[C@@H](NC(=O)[C@@H]1CN(C(=O)c2cnn(Cc3ccccc3)c2)CC12CN(C(=O)C1(CCOC)CC1)C2)[C@@H](C)OCc1ccccc1]<br>(A) |
| | 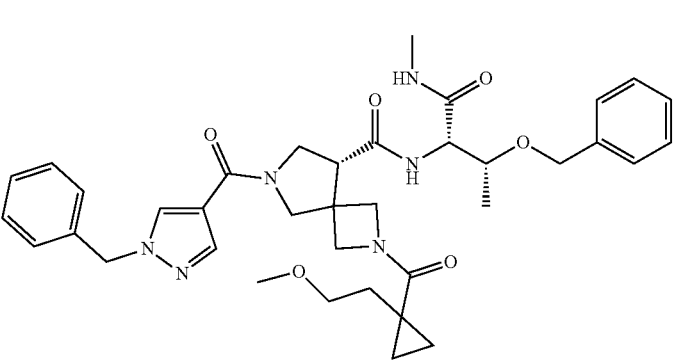 [SMILES: CNC(=O)[C@@H](NC(=O)[C@H]1CN(C(=O)c2cnn(Cc3ccccc3)c2)CC12CN(C(=O)C1(CCOC)CC1)C2)[C@@H](C)OCc1ccccc1]<br>(B) |
| I-103 | 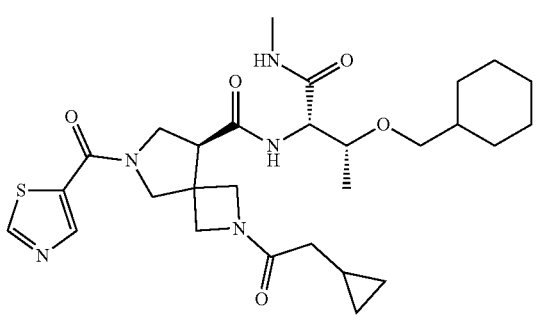 [SMILES: CNC(=O)[C@@H](NC(=O)[C@@H]1CN(C(=O)c2cncs2)CC12CN(C(=O)CC1CC1)C2)[C@@H](C)OCC1CCCCC1]<br>(A) |

TABLE 1-continued
Exemplary Compounds
| Cmpd # | Structure |
| --- | --- |
| | 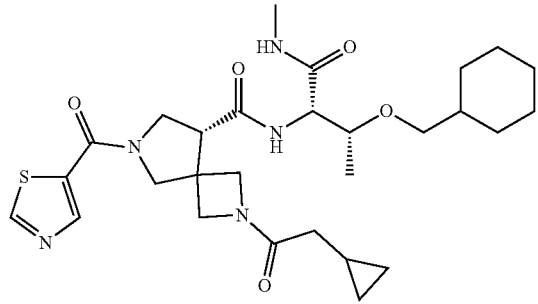 (B) |
| I-104 | 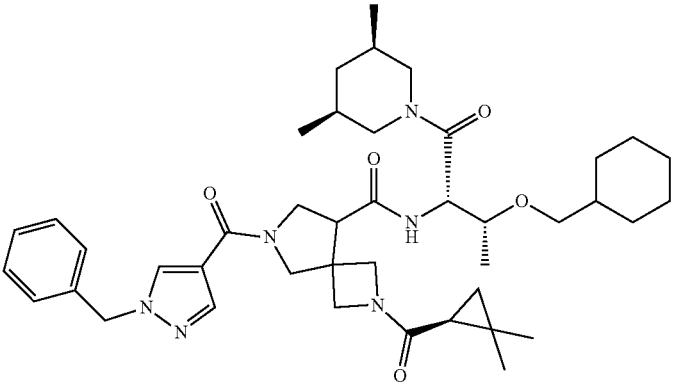 |
| I-105 | 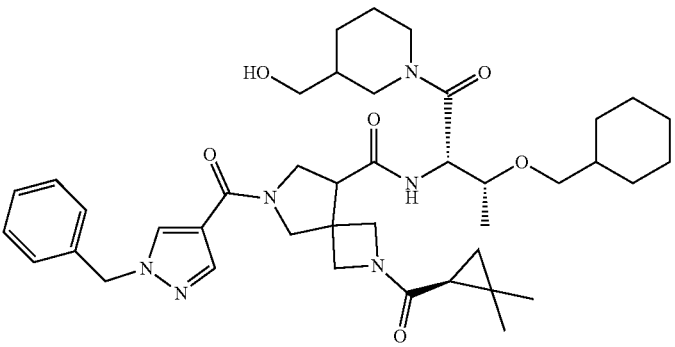 |
| I-106 | 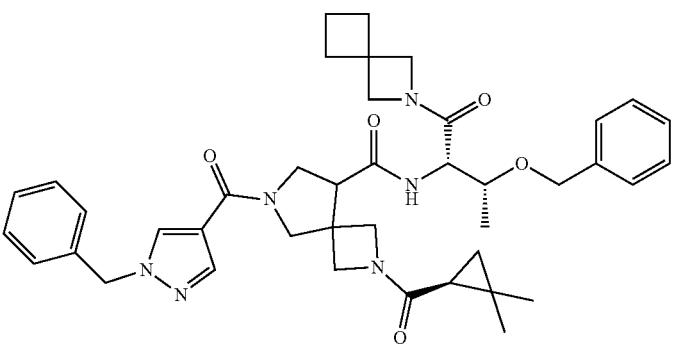 |

TABLE 1-continued

Exemplary Compounds

| Cmpd # | Structure |
|---|---|
| I-107 | 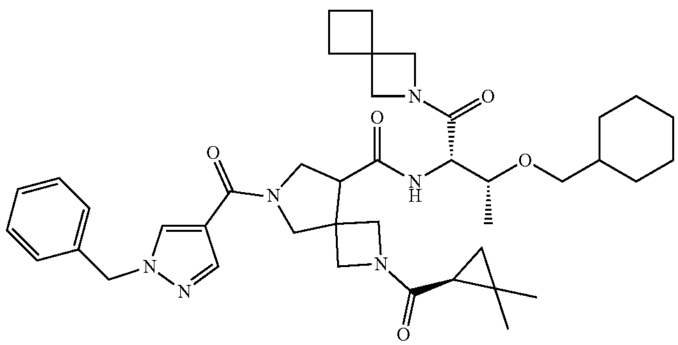 [SMILES: C[C@@H](OCC1CCCCC1)[C@H](NC(=O)C1CN(C(=O)c2cnn(Cc3ccccc3)c2)CC12CN(C(=O)[C@H]1CC1(C)C)C2)C(=O)N1CC2(CCC2)C1] |
| I-108 | (A) |
| | (B) |
| I-109 | (A) |

TABLE 1-continued

Exemplary Compounds

| Cmpd # | Structure |
|---|---|
|  | (B) |
| I-110 | (A) |
|  | (B) |
| I-111 | 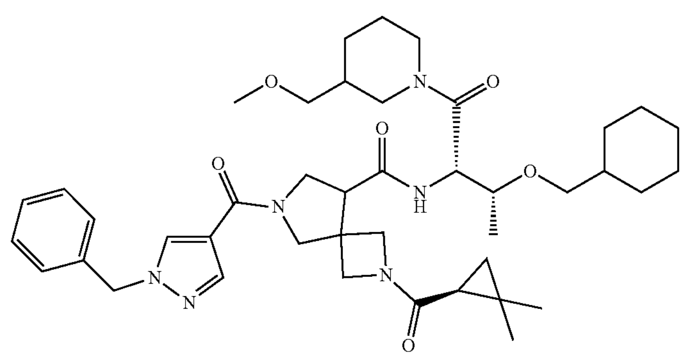 |

TABLE 1-continued
Exemplary Compounds
| Cmpd # | Structure |
|---|---|
| I-112 | 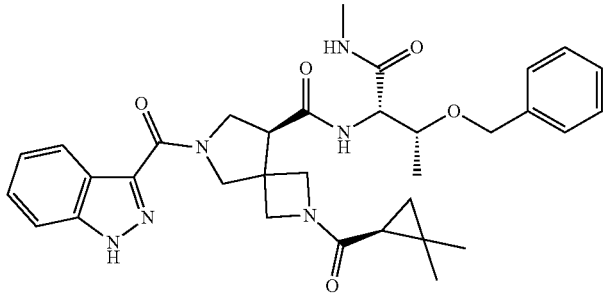 [SMILES: CNC(=O)[C@@H](NC(=O)[C@@H]1CN(C(=O)c2n[nH]c3ccccc23)CC12CN(C(=O)[C@H]1CC1(C)C)C2)[C@@H](C)OCc1ccccc1]<br>(A)<br>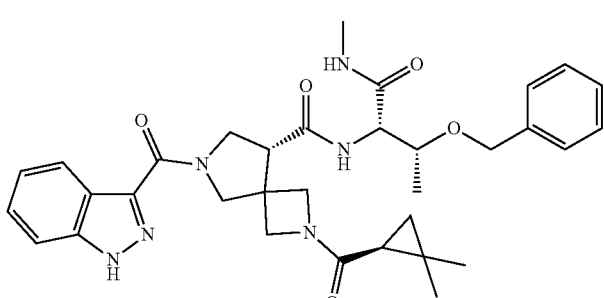<br>(B) |
| I-113 | 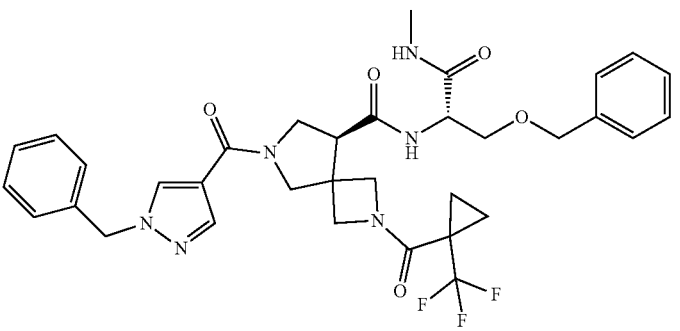 [SMILES: CNC(=O)[C@H](COCc1ccccc1)NC(=O)[C@@H]1CN(C(=O)c2cnn(Cc3ccccc3)c2)CC12CN(C(=O)C1(C(F)(F)F)CC1)C2]<br>(A)<br>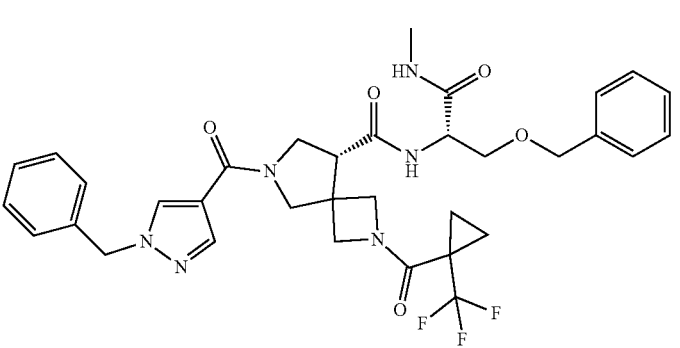 [SMILES: CNC(=O)[C@H](COCc1ccccc1)NC(=O)[C@H]1CN(C(=O)c2cnn(Cc3ccccc3)c2)CC12CN(C(=O)C1(C(F)(F)F)CC1)C2]<br>(B) |

TABLE 1-continued
Exemplary Compounds
| Cmpd # | Structure |
|---|---|
| I-114 | 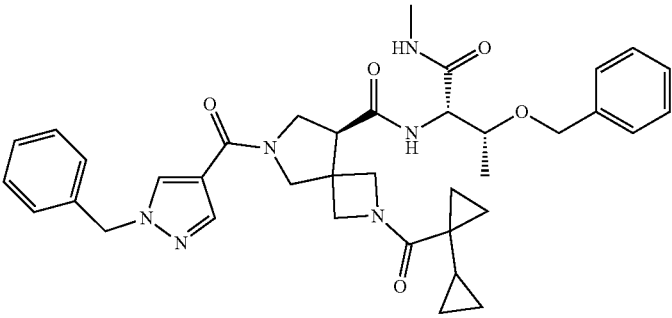 (A) 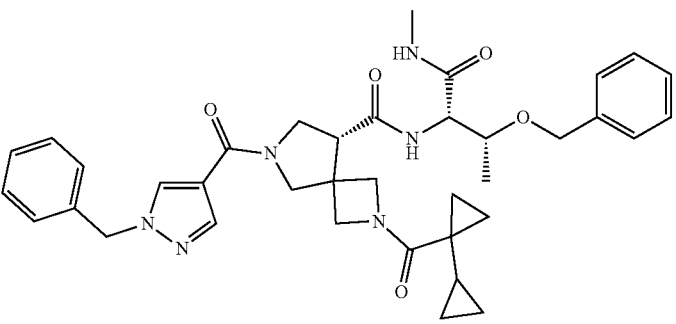 (B) |
| I-115 | 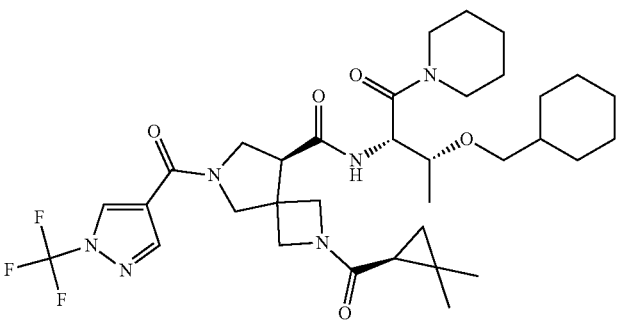 |
| I-116 | 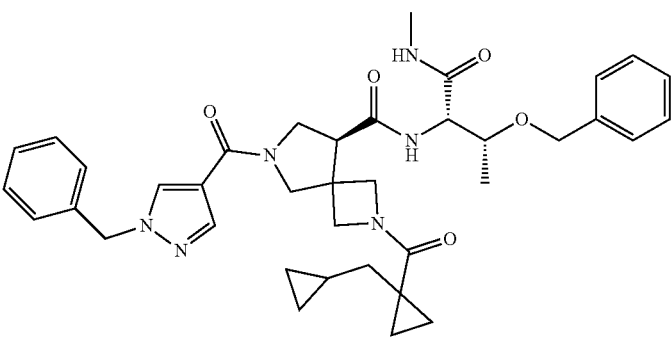 (A) |

TABLE 1-continued
Exemplary Compounds
| Cmpd # | Structure |
|---|---|
| | 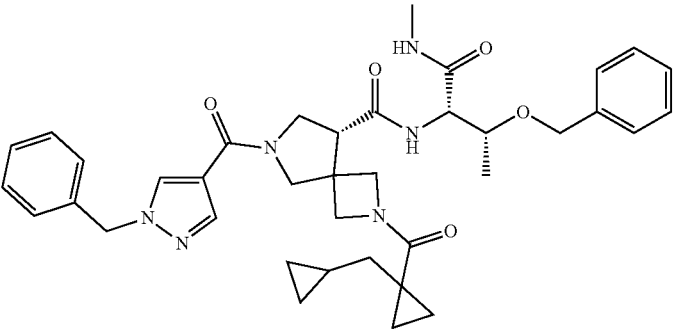 [SMILES: CNC(=O)[C@@H](NC(=O)[C@H]1CN(C(=O)c2cnn(Cc3ccccc3)c2)CC12CN(C(=O)C1(CC3CC3)CC1)C2)[C@@H](C)OCc1ccccc1]<br>(B) |
| I-117 | 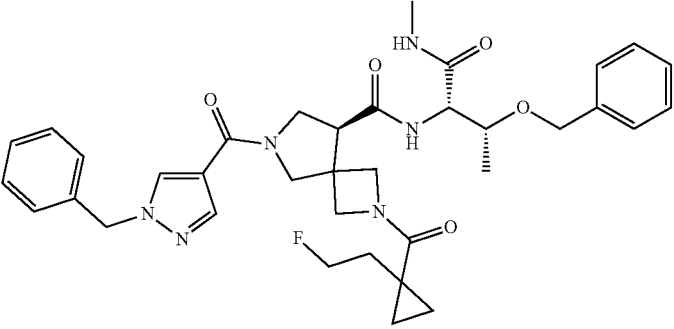 [SMILES: CNC(=O)[C@@H](NC(=O)[C@@H]1CN(C(=O)c2cnn(Cc3ccccc3)c2)CC12CN(C(=O)C1(CCF)CC1)C2)[C@@H](C)OCc1ccccc1]<br>(A) |
| | 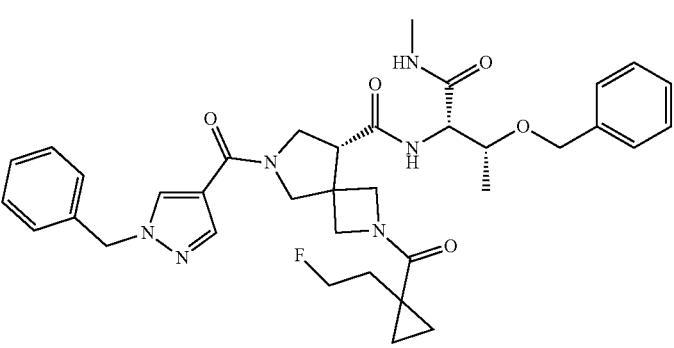 [SMILES: CNC(=O)[C@@H](NC(=O)[C@H]1CN(C(=O)c2cnn(Cc3ccccc3)c2)CC12CN(C(=O)C1(CCF)CC1)C2)[C@@H](C)OCc1ccccc1]<br>(B) |
| I-118 | 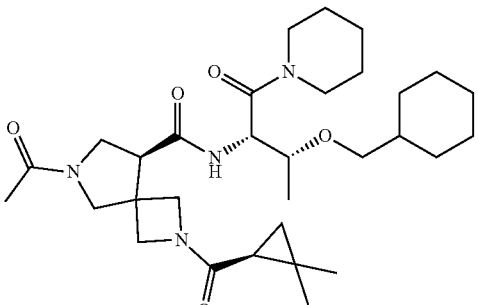 |

TABLE 1-continued
Exemplary Compounds
| Cmpd # | Structure |
|---|---|
| I-119 | (A) <br> (B) |
| I-120 | (A) <br> (B) |
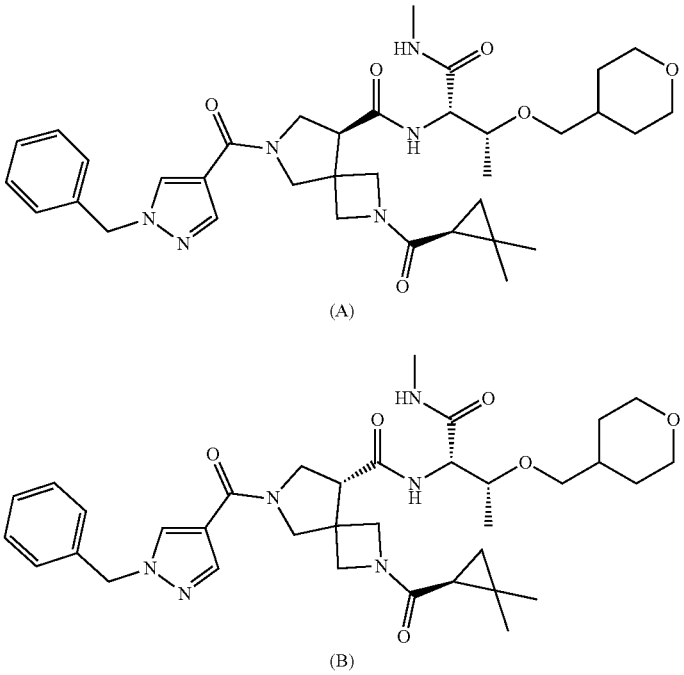

TABLE 1-continued

Exemplary Compounds

| Cmpd # | Structure |
|---|---|
| I-121 | (A) |
| | (B) |
| I-122 | (A) |
| | (B) |
| I-123 | (A) |

TABLE 1-continued
Exemplary Compounds
| Cmpd # | Structure |
|---|---|
| | 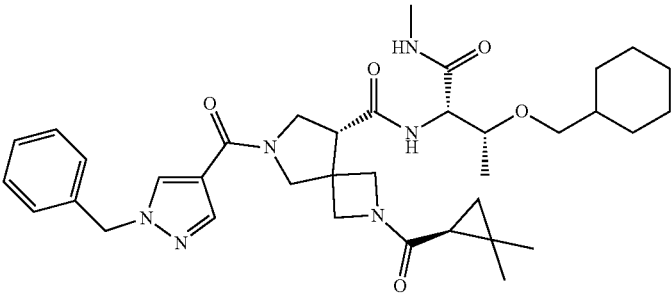 [SMILES: CNC(=O)[C@@H](NC(=O)[C@H]1CN(C(=O)c2cnn(Cc3ccccc3)c2)CC12CN(C(=O)[C@H]1CC1(C)C)C2)[C@@H](C)OCC1CCCCC1]<br>(B) |
| I-124 | 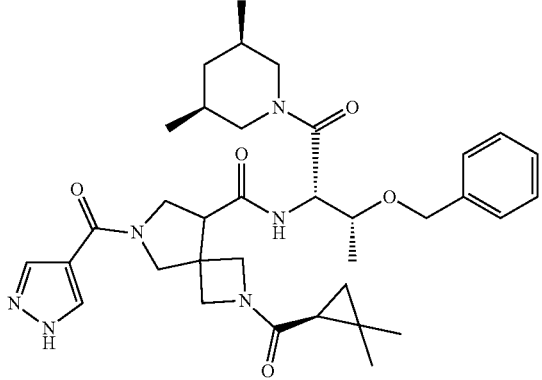 [SMILES: C[C@@H]1C[C@H](C)CN(C(=O)[C@@H](NC(=O)C2CN(C(=O)c3cn[nH]c3)CC23CN(C(=O)[C@H]2CC2(C)C)C3)[C@@H](C)OCc2ccccc2)C1] |
| I-125 | 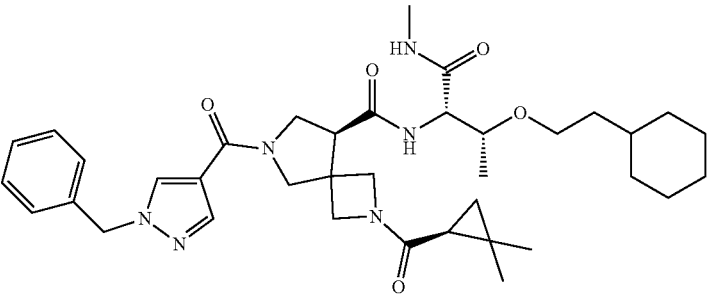 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCCC1CCCCC1]<br>(A)<br>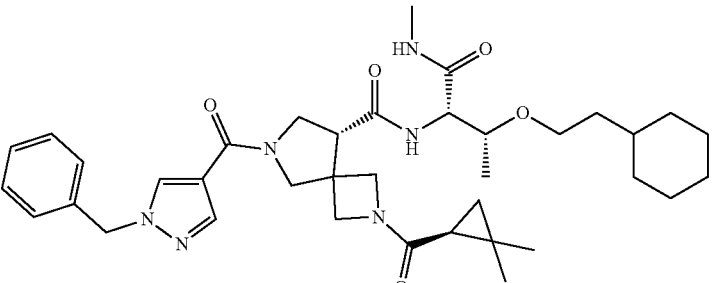<br>(B) |

TABLE 1-continued
| Cmpd # | Structure |
|---|---|
| I-126 | 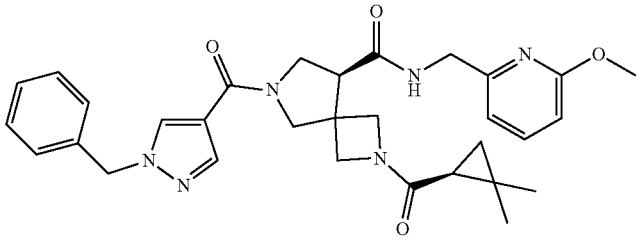 [SMILES: COc1cccc(CNC(=O)[C@@H]2CN(C(=O)c3cnn(Cc4ccccc4)c3)CC23CN(C(=O)[C@H]2CC2(C)C)C3)n1]<br>(A)<br>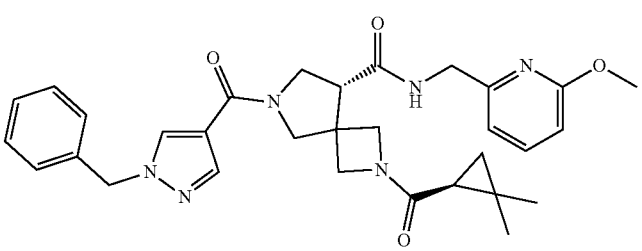 [SMILES: COc1cccc(CNC(=O)[C@H]2CN(C(=O)c3cnn(Cc4ccccc4)c3)CC23CN(C(=O)[C@H]2CC2(C)C)C3)n1]<br>(B) |
| I-127 | 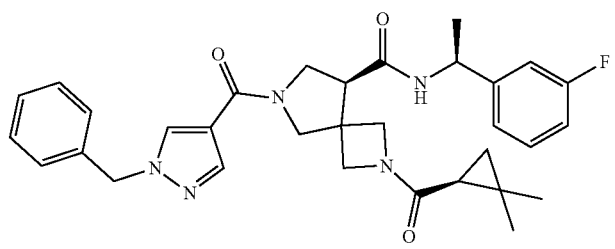 [SMILES: C[C@H](NC(=O)[C@@H]1CN(C(=O)c2cnn(Cc3ccccc3)c2)CC12CN(C(=O)[C@H]1CC1(C)C)C2)c1cccc(F)c1]<br>(A)<br>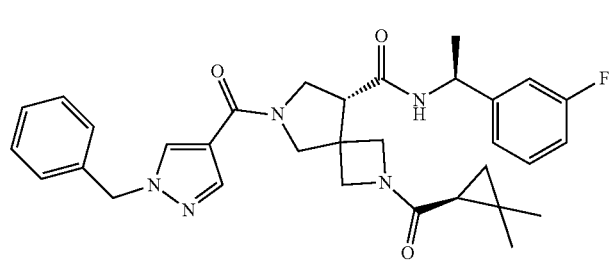 [SMILES: C[C@H](NC(=O)[C@H]1CN(C(=O)c2cnn(Cc3ccccc3)c2)CC12CN(C(=O)[C@H]1CC1(C)C)C2)c1cccc(F)c1]<br>(B) |
| I-128 | 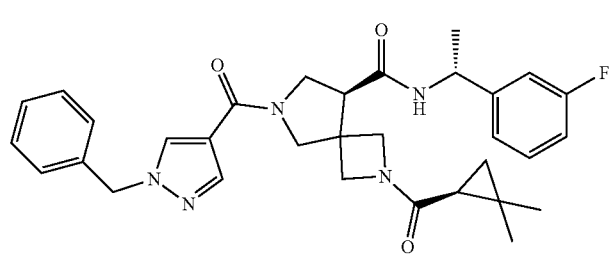 [SMILES: C[C@@H](NC(=O)[C@@H]1CN(C(=O)c2cnn(Cc3ccccc3)c2)CC12CN(C(=O)[C@H]1CC1(C)C)C2)c1cccc(F)c1]<br>(A) |

217 218
TABLE 1-continued
Exemplary Compounds
| Cmpd # | Structure |
|---|---|
| | 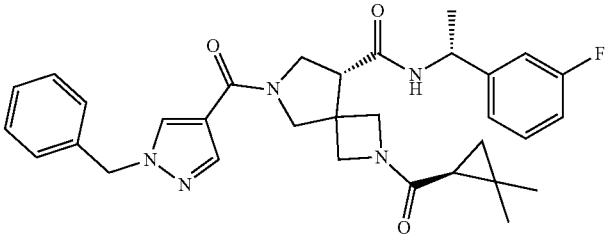 [SMILES: C[C@@H](NC(=O)[C@H]1CN(C(=O)c2cnn(Cc3ccccc3)c2)CC12CN(C(=O)[C@H]1CC1(C)C)C2)c1cccc(F)c1]<br>(B) |
| I-129 | 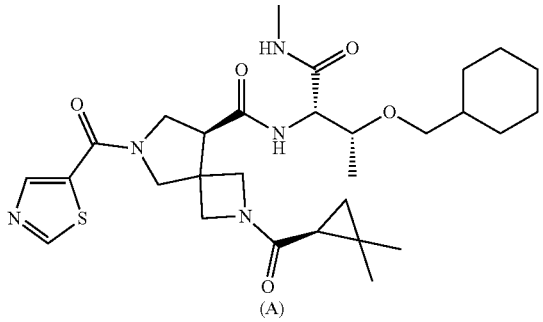<br>(A) |
| | 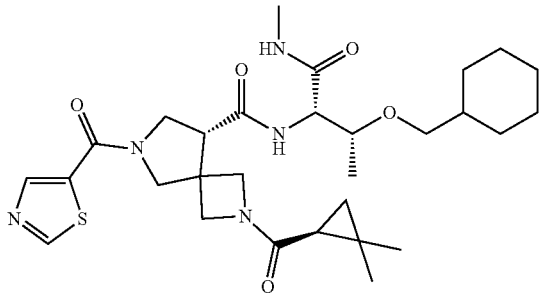 [SMILES: CNC(=O)[C@@H](NC(=O)[C@H]1CN(C(=O)c2cncs2)CC12CN(C(=O)[C@H]1CC1(C)C)C2)[C@@H](C)OCC1CCCCC1]<br>(B) |
| I-130 | 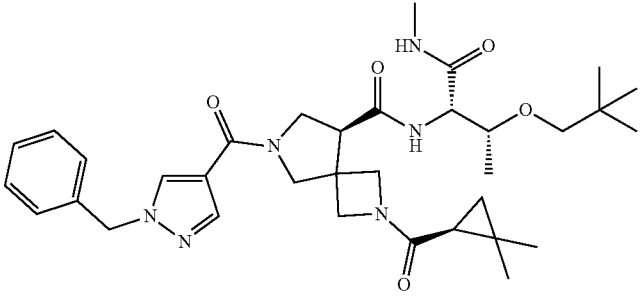 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC(C)(C)C]<br>(A) |
| | 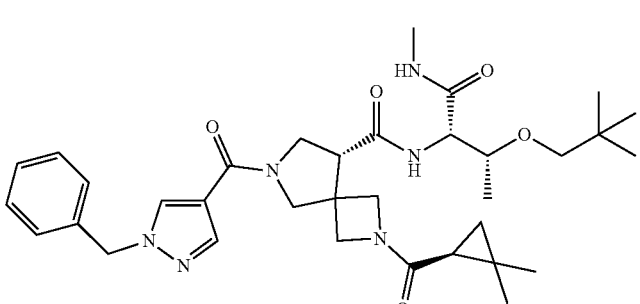<br>(B) |

TABLE 1-continued

Exemplary Compounds

| Cmpd # | Structure |
|---|---|
| I-131 | (A) |
|  | (B) |
| I-132 | 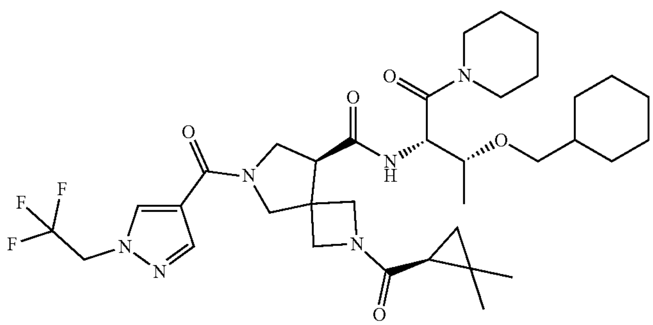 |
| I-133 | (A) |
|  | (B) |

TABLE 1-continued
Exemplary Compounds
| Cmpd # | Structure |
|---|---|
| I-134 | 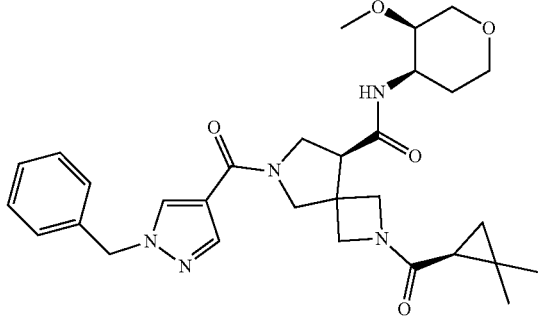 [SMILES: CO[C@H]1COCC[C@H]1NC(=O)[C@@H]1CN(C(=O)c2cnn(Cc3ccccc3)c2)CC12CN(C(=O)[C@H]1CC1(C)C)C2]<br>(A)<br>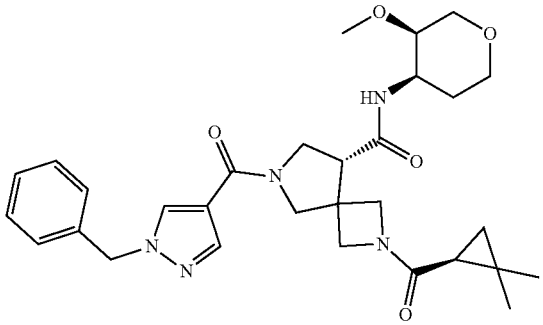 [SMILES: CO[C@H]1COCC[C@H]1NC(=O)[C@H]1CN(C(=O)c2cnn(Cc3ccccc3)c2)CC12CN(C(=O)[C@H]1CC1(C)C)C2]<br>(B) |
| I-135 | 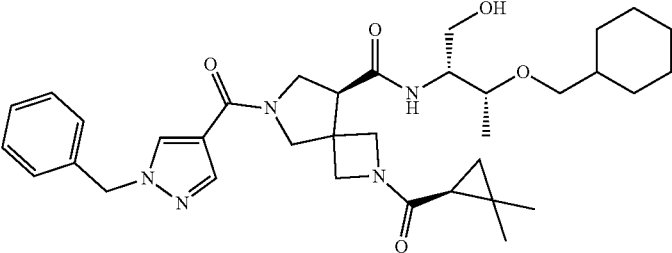 [SMILES: C[C@@H](OCC1CCCCC1)[C@@H](CO)NC(=O)[C@@H]1CN(C(=O)c2cnn(Cc3ccccc3)c2)CC12CN(C(=O)[C@H]1CC1(C)C)C2]<br>(A)<br>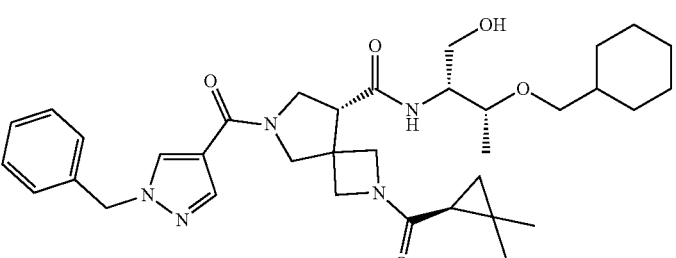<br>(B) |

| Cmpd # | Structure |
|---|---|
| I-136 | 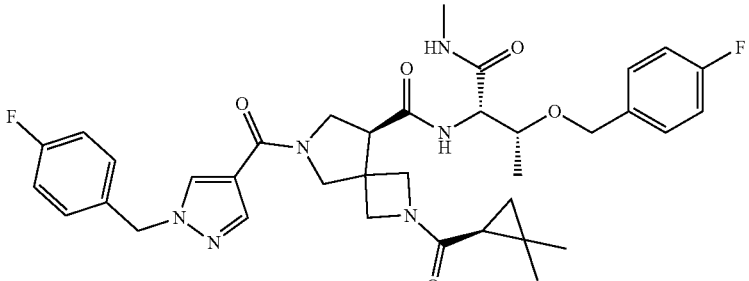 (A)<br>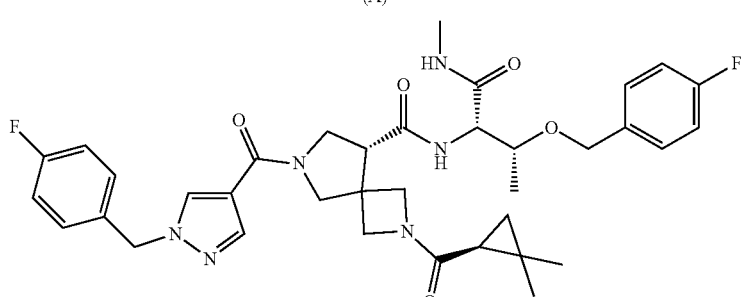 (B) |
| I-137 | 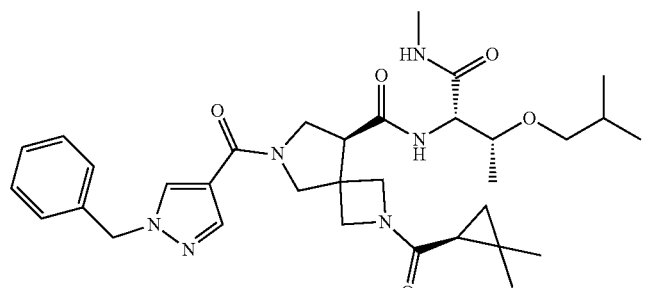 (A) |
| I- | 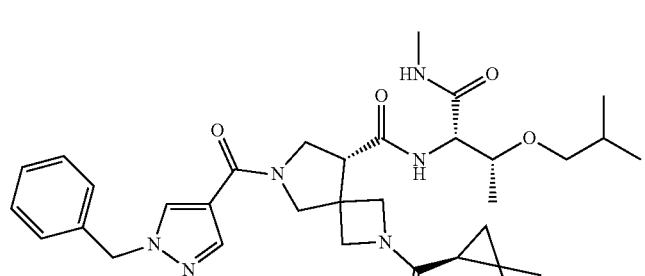 (B) |

TABLE 1-continued

Exemplary Compounds

| Cmpd # | Structure |
|---|---|
| I-138 | 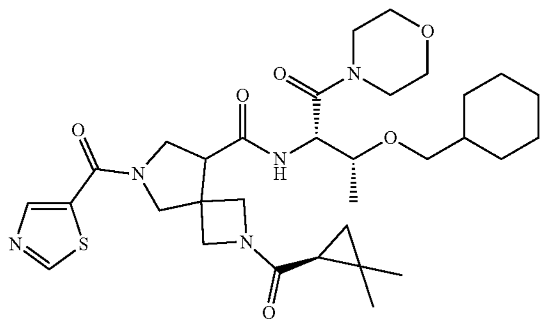 [SMILES: C[C@@H](OCC1CCCCC1)[C@H](NC(=O)C1CN(C(=O)c2cncs2)CC12CN(C(=O)[C@H]1CC1(C)C)C2)C(=O)N1CCOCC1] |
| I-139 | 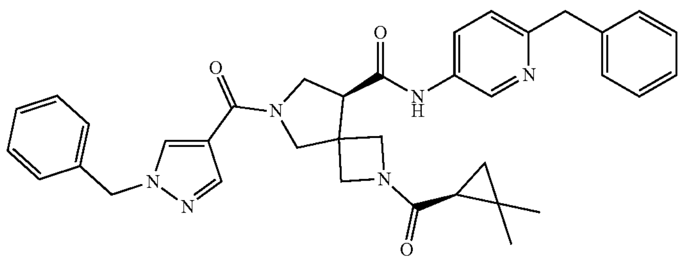 [SMILES: CC1(C)C[C@@H]1C(=O)N1CC2(CN(C(=O)c3cnn(Cc4ccccc4)c3)C[C@H]2C(=O)Nc2ccc(Cc3ccccc3)nc2)C1] |
| I-140 | (A) (B) |
| I-141 | (A) |

TABLE 1-continued
Exemplary Compounds
| Cmpd # | Structure |
|---|---|
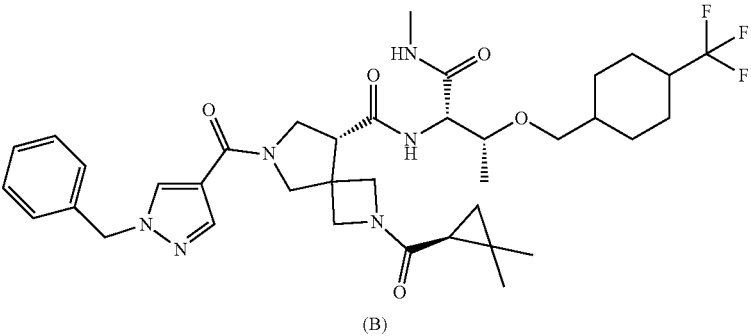
(B)
I-142
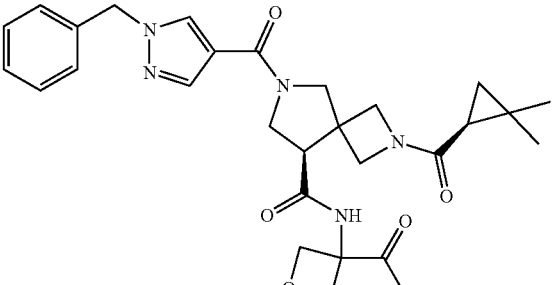
(A)
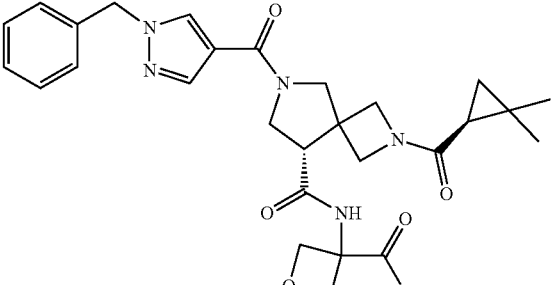
(B)
I-143
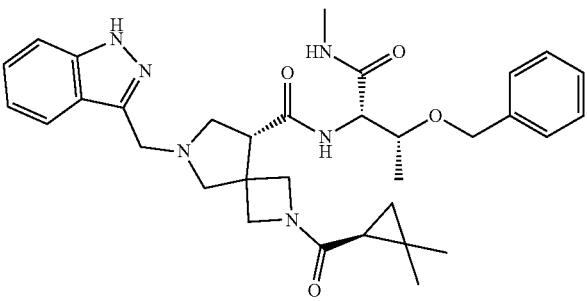

TABLE 1-continued
Exemplary Compounds
| Cmpd # | Structure |
|---|---|
| I-144 | 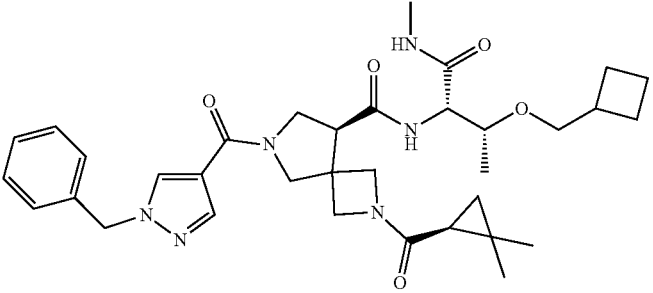 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC1CCC1]<br>(A)<br>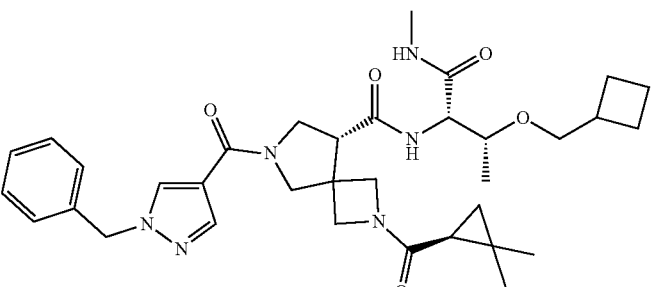<br>(B) |
| I-145 | 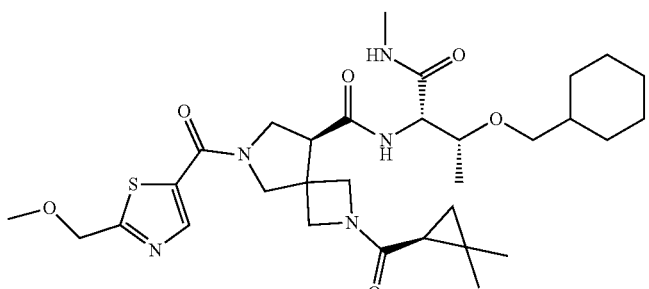<br>(A)<br>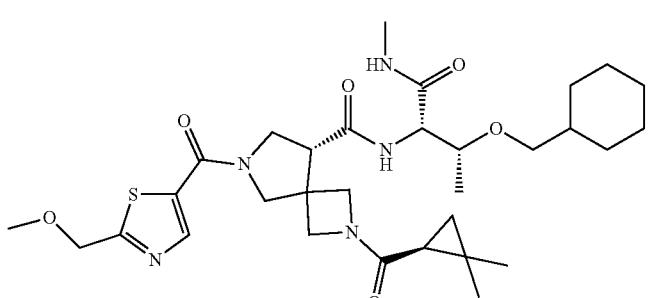<br>(B) |

TABLE 1-continued

Exemplary Compounds

| Cmpd # | Structure |
|---|---|
| I-146 | 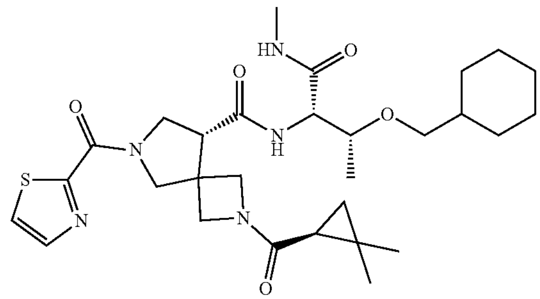 [SMILES: CNC(=O)[C@@H](NC(=O)[C@H]1CN(C(=O)c2nccs2)CC12CN(C(=O)[C@H]1CC1(C)C)C2)[C@@H](C)OCC1CCCCC1] |
| I-147 | 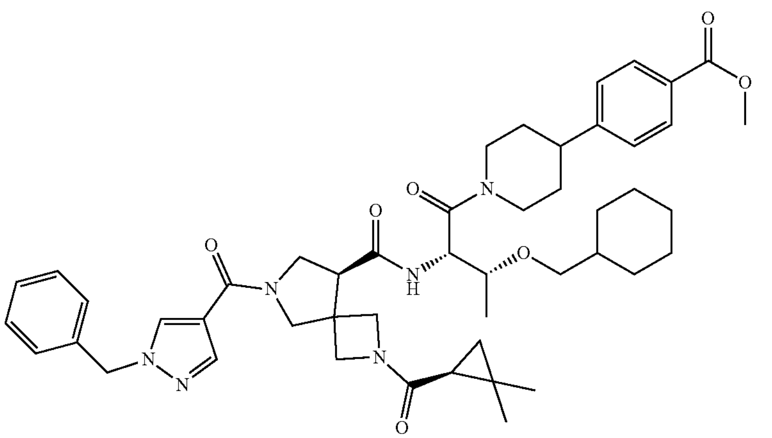 [SMILES: COC(=O)c1ccc(C2CCN(C(=O)[C@@H](NC(=O)[C@@H]3CN(C(=O)c4cnn(Cc5ccccc5)c4)CC34CN(C(=O)[C@H]3CC3(C)C)C4)[C@@H](C)OCC3CCCCC3)CC2)cc1] |
| I-148 | (A) |
| | (B) |

TABLE 1-continued
Exemplary Compounds
| Cmpd # | Structure |
|---|---|
| I-149 | 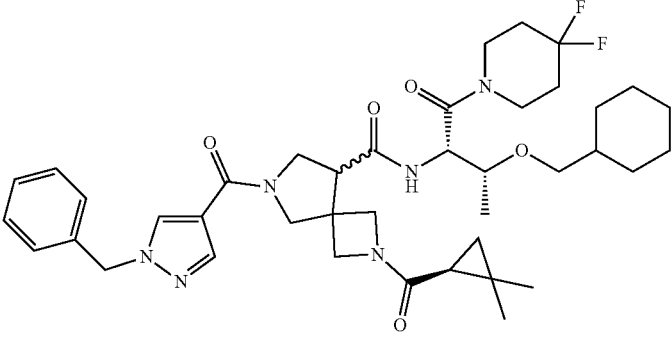 [SMILES: C[C@@H](OCC1CCCCC1)[C@H](NC(=O)C1CN(C(=O)c2cnn(Cc3ccccc3)c2)CC12CN(C(=O)[C@H]1CC1(C)C)C2)C(=O)N1CCC(F)(F)CC1]<br>Mixture<br>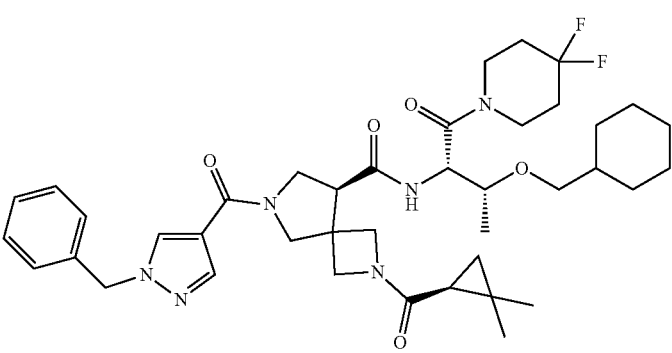 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(F)(F)CC1]<br>(A)<br>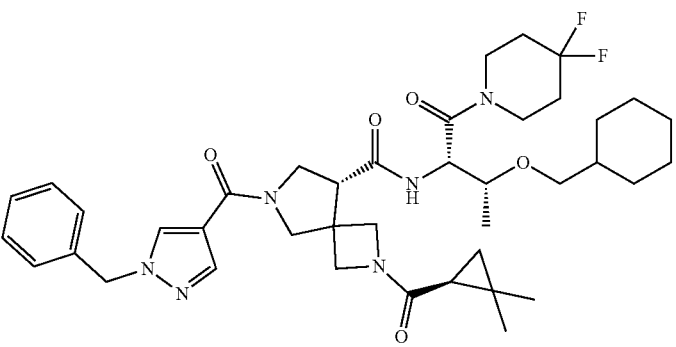 [SMILES: C[C@@H](OCC1CCCCC1)[C@H](NC(=O)[C@H]1CN(C(=O)c2cnn(Cc3ccccc3)c2)CC12CN(C(=O)[C@H]1CC1(C)C)C2)C(=O)N1CCC(F)(F)CC1]<br>(B) |
| I-150 | 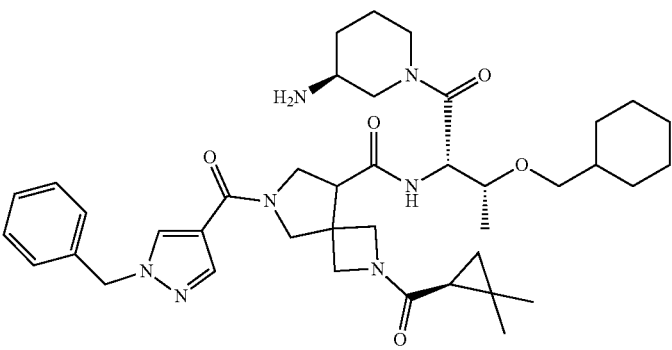 [SMILES: C[C@@H](OCC1CCCCC1)[C@H](NC(=O)C1CN(C(=O)c2cnn(Cc3ccccc3)c2)CC12CN(C(=O)[C@H]1CC1(C)C)C2)C(=O)N1CCC[C@H](N)C1]<br>Mixture |

TABLE 1-continued
Exemplary Compounds
| Cmpd # | Structure |
|---|---|
| | 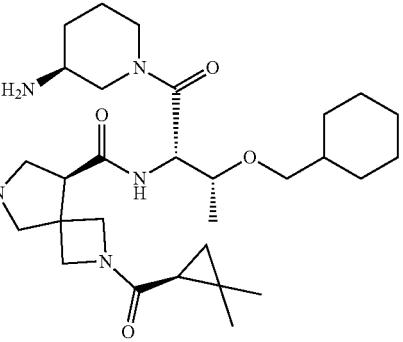<br>(A)<br>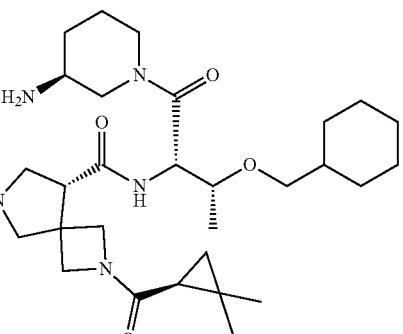<br>(B) |
| I-151 | 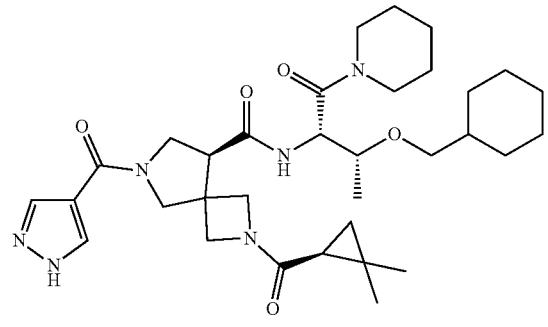 [SMILES: C[C@@H](OCC1CCCCC1)[C@H](NC(=O)[C@@H]1CN(C(=O)c2cn[nH]c2)CC12CN(C(=O)[C@H]1CC1(C)C)C2)C(=O)N1CCCCC1]<br>(A)<br>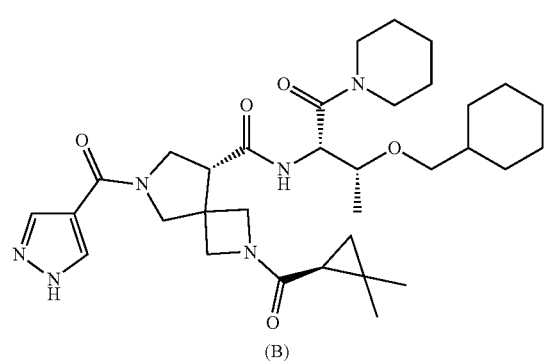<br>(B) |

TABLE 1-continued
Exemplary Compounds
| Cmpd # | Structure |
|---|---|
| I-152 | 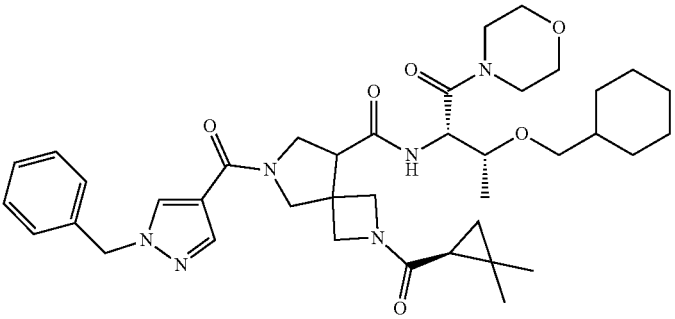 [SMILES: C[C@@H](OCC1CCCCC1)[C@H](NC(=O)[C@H]1CN(C(=O)c2cnn(Cc3ccccc3)c2)CC12CN(C(=O)[C@H]1CC1(C)C)C2)C(=O)N1CCOCC1]<br>Mixture<br><br>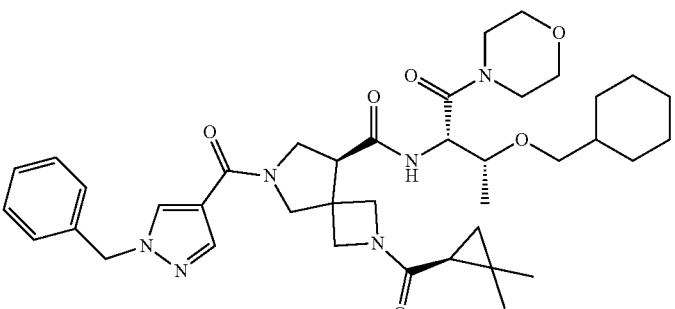<br>(A)<br><br>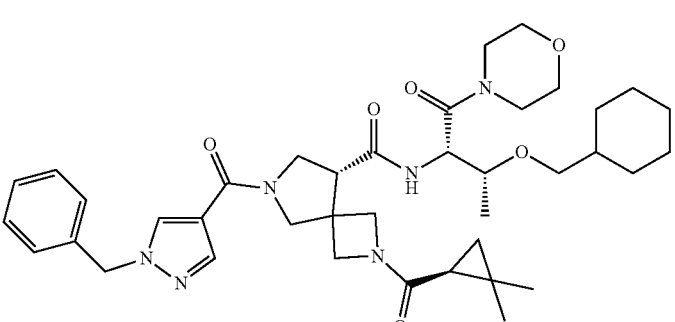<br>(B) |
| I-153 | 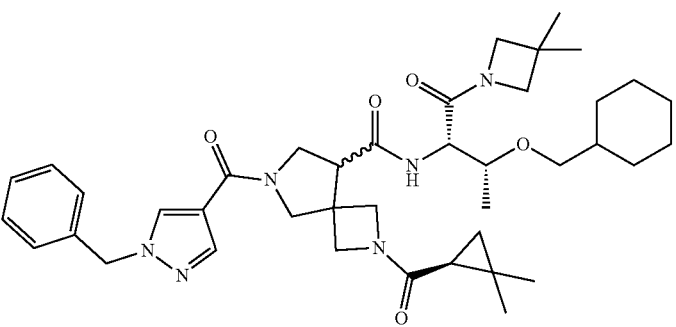<br>Mixture |

TABLE 1-continued
Exemplary Compounds
| Cmpd # | Structure |
| --- | --- |
|  | 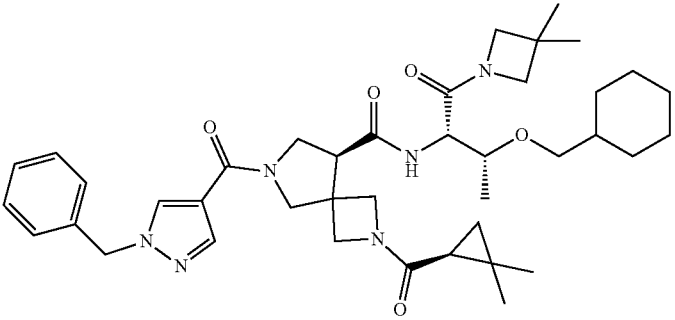 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CC(C)(C)C1]<br>(A)<br>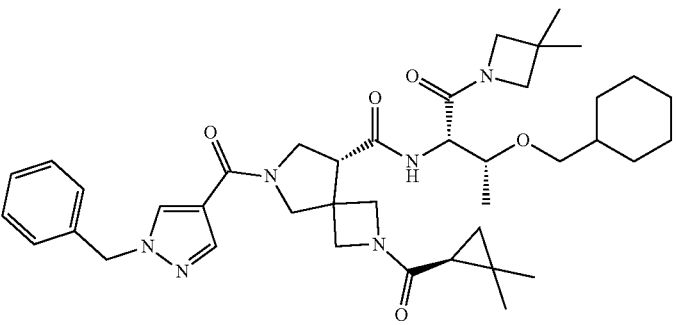 [SMILES: C[C@@H](OCC1CCCCC1)[C@H](NC(=O)[C@H]1CN(C(=O)c2cnn(Cc3ccccc3)c2)CC12CN(C(=O)[C@H]1CC1(C)C)C2)C(=O)N1CC(C)(C)C1]<br>(B) |
| I-154 | 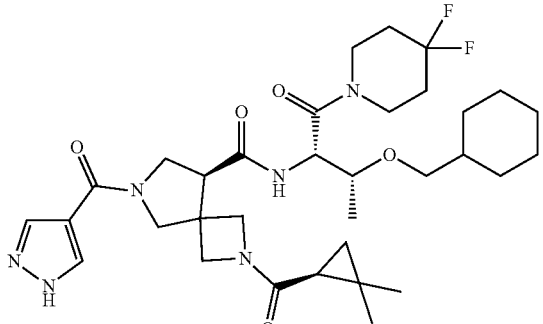<br>(A)<br>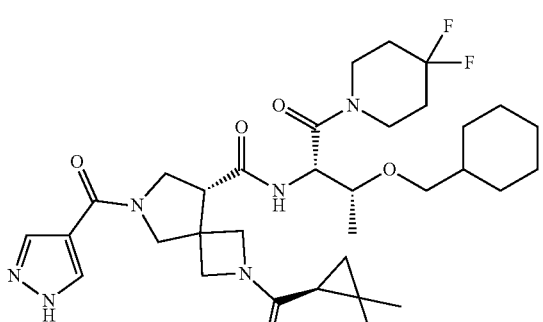<br>(B) |

TABLE 1-continued

Exemplary Compounds

| Cmpd # | Structure |
| --- | --- |
| I-155 | (A) |
|  | (B) |
| I-156 | (A) |
|  | (B) |

US 12,065,445 B2
243                                                                                              244
TABLE 1-continued
Exemplary Compounds
| Cmpd # | Structure |
|---|---|
| I-157 | 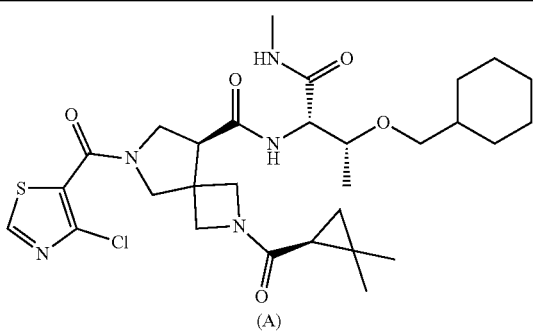<br>(A)<br>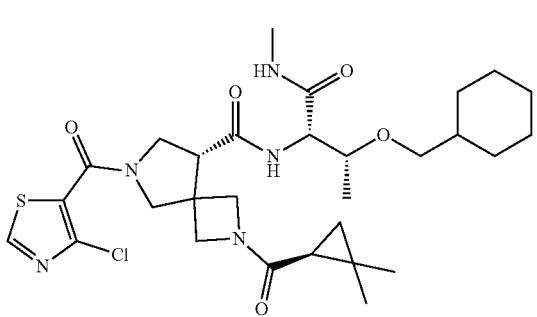 [SMILES: CNC(=O)[C@@H](NC(=O)[C@H]1CN(C(=O)c2scnc2Cl)CC12CN(C(=O)[C@H]1CC1(C)C)C2)[C@@H](C)OCC1CCCCC1]<br>(B) |
| I-158 | 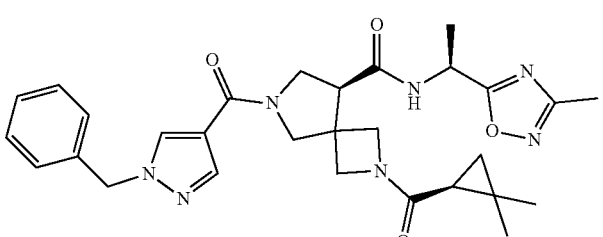<br>(A)<br>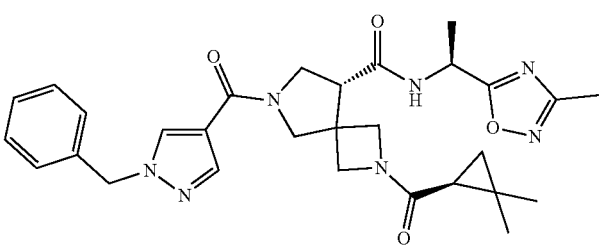 [SMILES: Cc1noc([C@H](C)NC(=O)[C@H]2CN(C(=O)c3cnn(Cc4ccccc4)c3)CC23CN(C(=O)[C@H]2CC2(C)C)C3)n1]<br>(B) |
| I-159 | 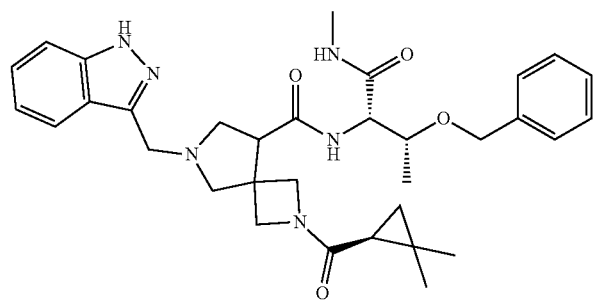 |

TABLE 1-continued
Exemplary Compounds
| Cmpd # | Structure |
|---|---|
| I-160 | 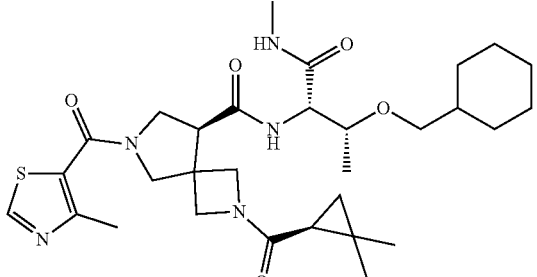<br>(A)<br>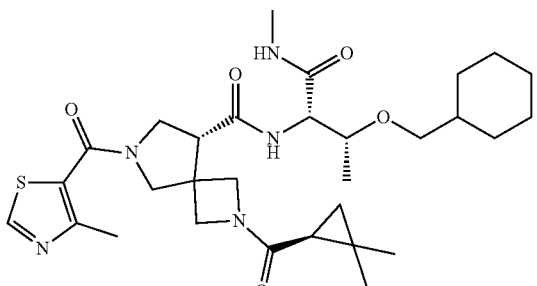<br>(B) |
| I-161 | 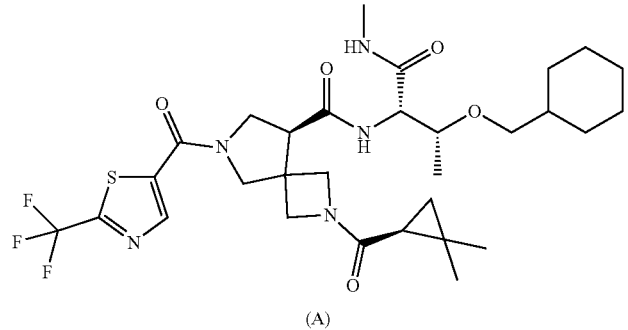<br>(A)<br>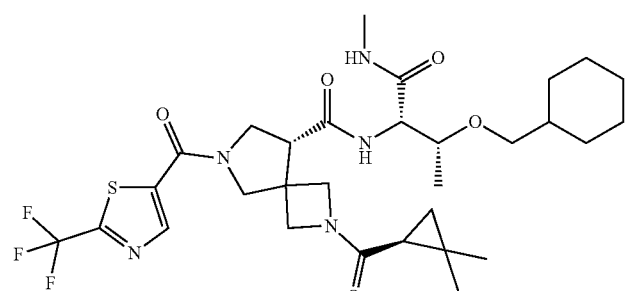<br>(B) |

TABLE 1-continued
Exemplary Compounds
| Cmpd # | Structure |
|---|---|
| I-162 | 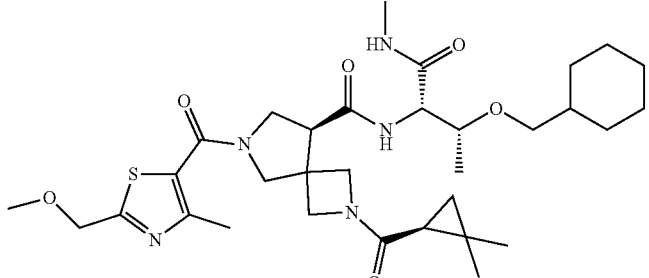<br>(A)<br>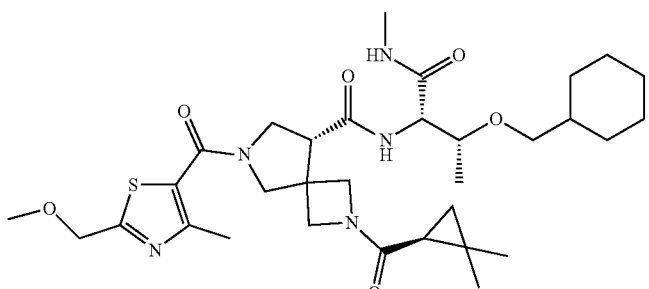<br>(B) |
| I-163 | 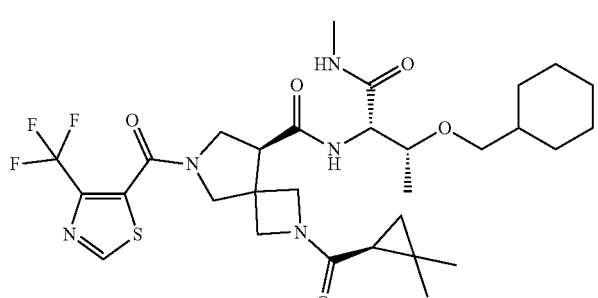<br>(A)<br>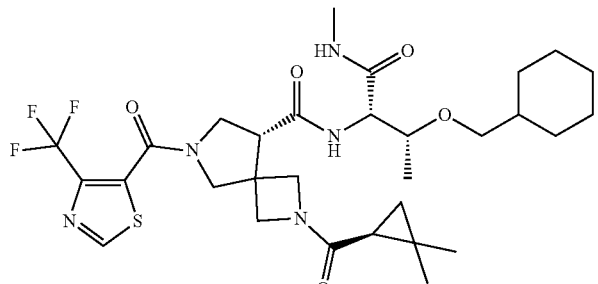<br>(B) |

TABLE 1-continued

Exemplary Compounds

| Cmpd # | Structure |
|---|---|
| I-164 | (A) |
| | (B) |
| I-165 | 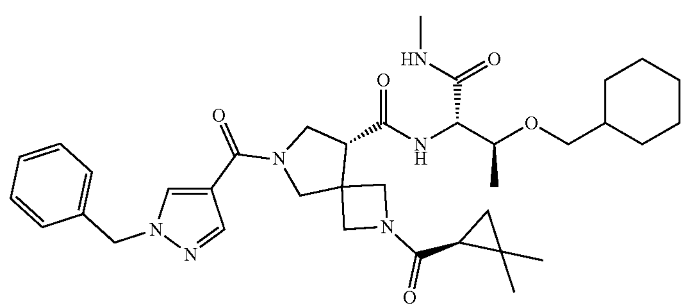 |
| I-166 | (A) |

TABLE 1-continued
Exemplary Compounds
| Cmpd # | Structure |
|---|---|
| | (B) |
| I-167 | 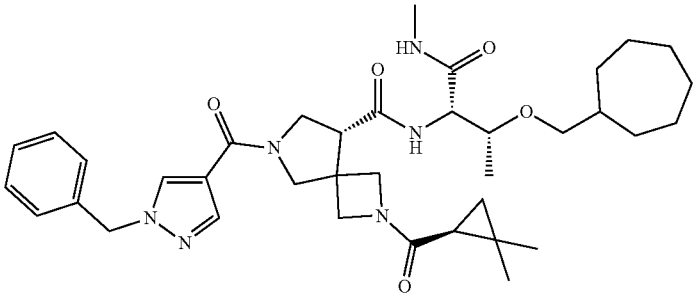 |
| I-168 | 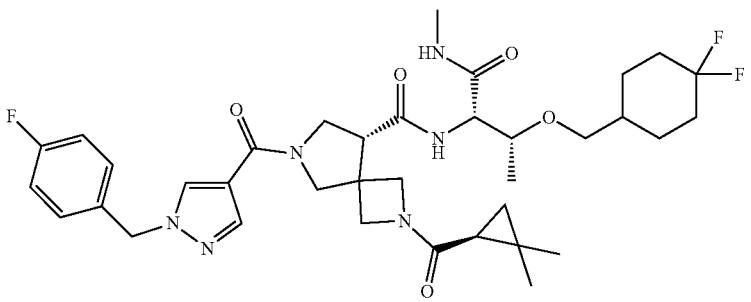 |
| I-169 | 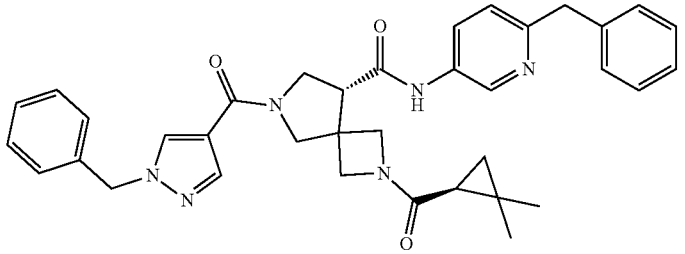 |
| I-170 | 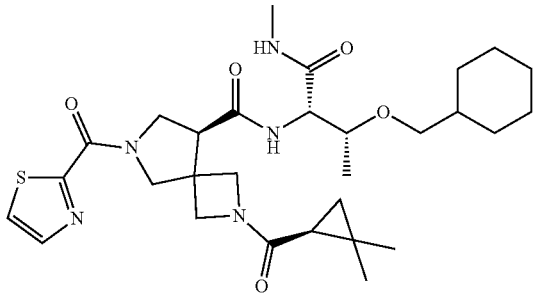 |

TABLE 1-continued

Exemplary Compounds

| Cmpd # | Structure |
|---|---|
| I-171 | (A) |
| | (B) |
| I-172 | 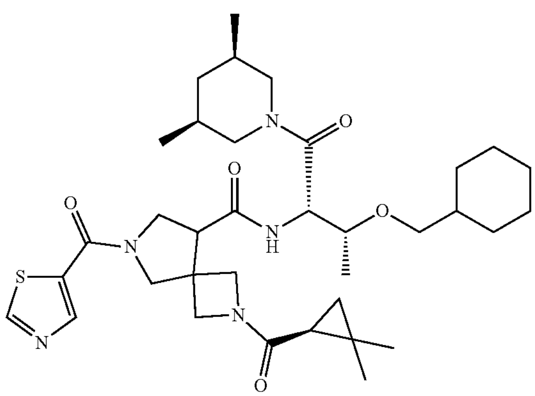 |
| I-173 | Mixture |

TABLE 1-continued
Exemplary Compounds
| Cmpd # | Structure |
|---|---|
|  | 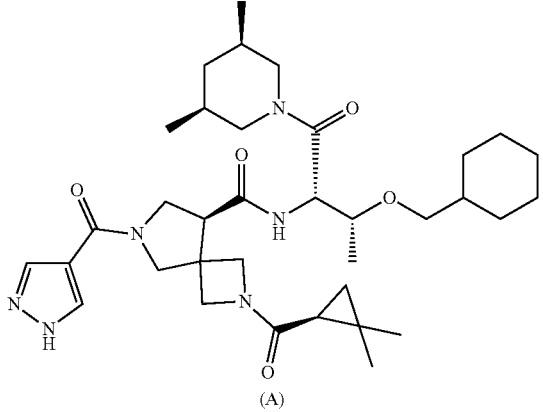<br>(A)<br>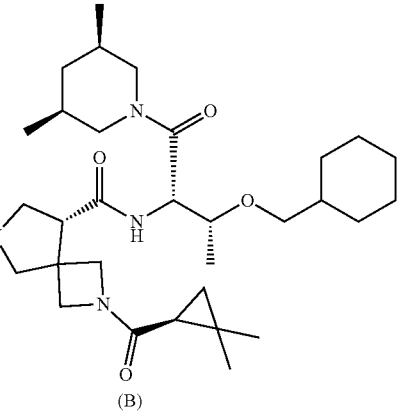<br>(B) |
| I-174 | 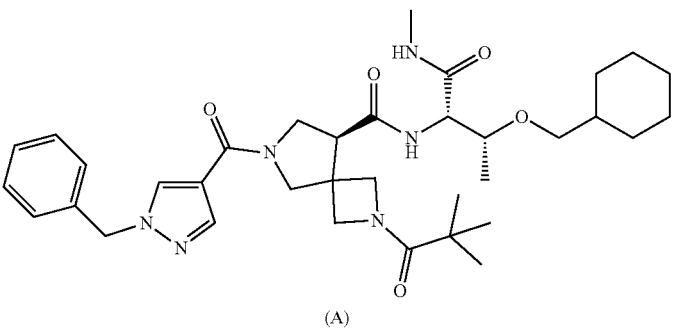<br>(A)<br>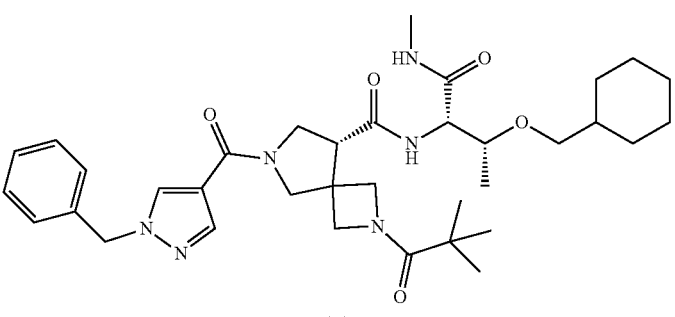 [SMILES: CNC(=O)[C@@H](NC(=O)[C@H]1CN(C(=O)c2cnn(Cc3ccccc3)c2)CC12CN(C(=O)C(C)(C)C)C2)[C@@H](C)OCC1CCCCC1]<br>(B) |

TABLE 1-continued

Exemplary Compounds

| Cmpd # | Structure |
|---|---|
| I-175 | (A) |
| | (B) |
| I-176 | (A) |
| | (B) |
| I-177 | (A) |

TABLE 1-continued

Exemplary Compounds

| Cmpd # | Structure |
| --- | --- |
| I-178 | (B) / (A) / (B) |
| I-179 | 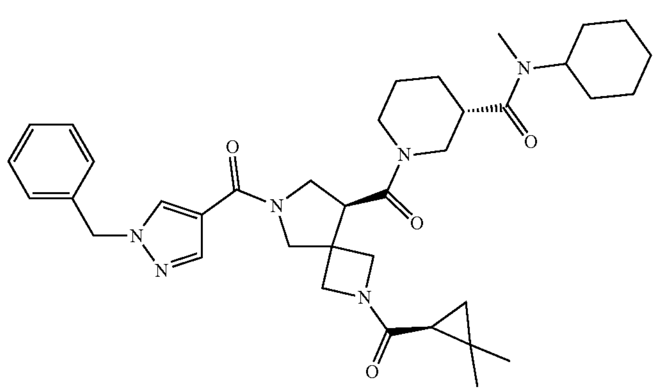 |

TABLE 1-continued

Exemplary Compounds

| Cmpd # | Structure |
| --- | --- |
| I-180 | 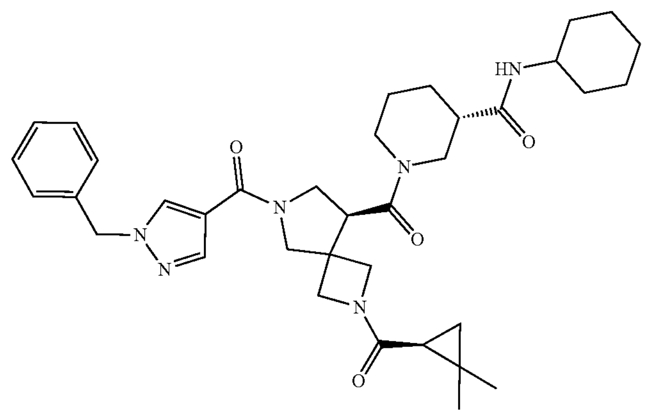 [SMILES: CC1(C)C[C@@H]1C(=O)N1CC2(CN(C(=O)c3cnn(Cc4ccccc4)c3)C[C@H]2C(=O)N2CCC[C@H](C(=O)NC3CCCCC3)C2)C1] |
| I-181 | 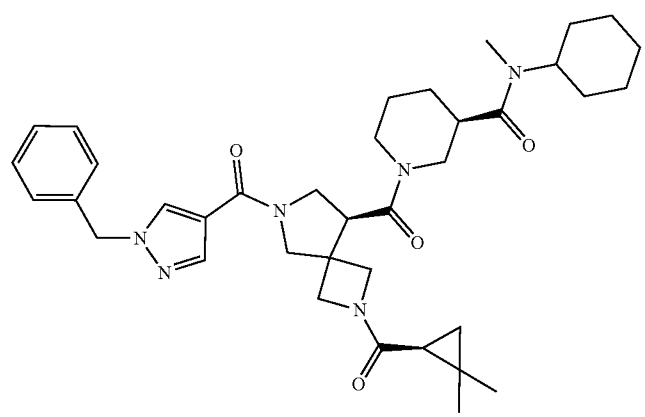 [SMILES: CN(C(=O)[C@@H]1CCCN(C(=O)[C@@H]2CN(C(=O)c3cnn(Cc4ccccc4)c3)CC23CN(C(=O)[C@H]2CC2(C)C)C3)C1)C1CCCCC1] |
| I-182 | 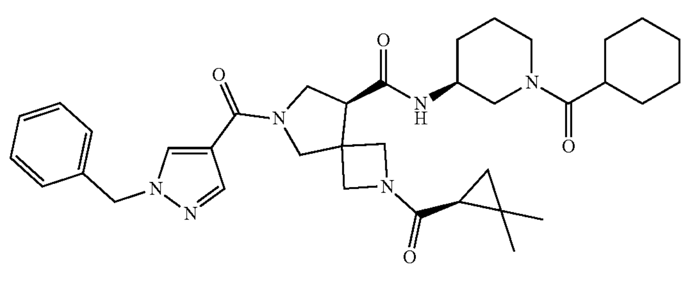 [SMILES: CC1(C)C[C@@H]1C(=O)N1CC2(CN(C(=O)c3cnn(Cc4ccccc4)c3)C[C@H]2C(=O)N[C@H]2CCCN(C(=O)C3CCCCC3)C2)C1] |
| I-183 | 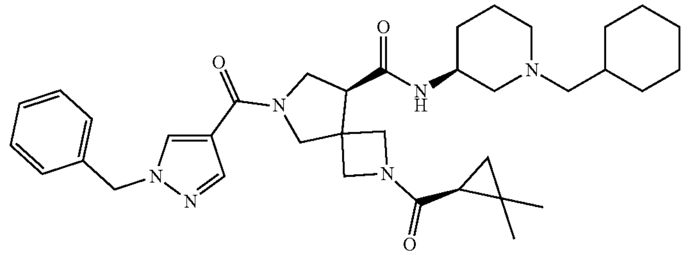 [SMILES: CC1(C)C[C@@H]1C(=O)N1CC2(CN(C(=O)c3cnn(Cc4ccccc4)c3)C[C@H]2C(=O)N[C@H]2CCCN(CC3CCCCC3)C2)C1] |

TABLE 1-continued

Exemplary Compounds

| Cmpd # | Structure |
|---|---|
| I-184 | 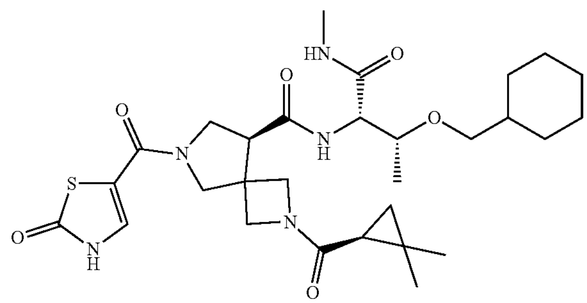 [SMILES: CNC(=O)[C@@H](NC(=O)[C@@H]1CN(C(=O)c2c[nH]c(=O)s2)CC12CN(C(=O)[C@H]1CC1(C)C)C2)[C@@H](C)OCC1CCCCC1] |
| I-185 | (A) |
| | (B) |
| I-186 | (A) |

TABLE 1-continued
Exemplary Compounds
| Cmpd # | Structure |
|---|---|
| | 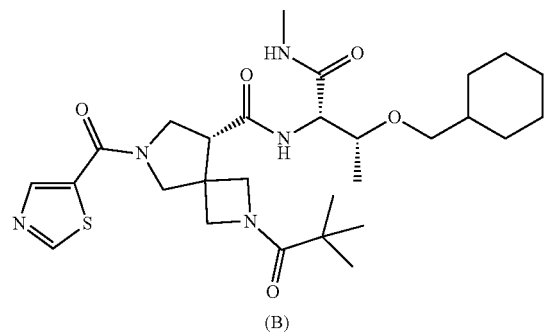<br>(B) |
| I-187 | 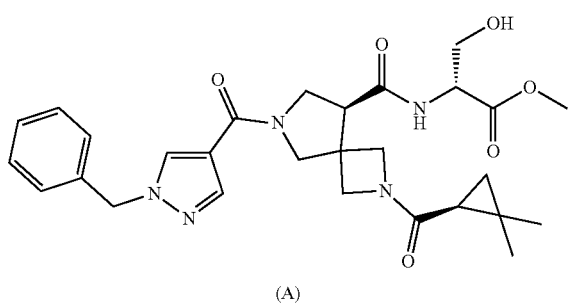<br>(A) |
| | 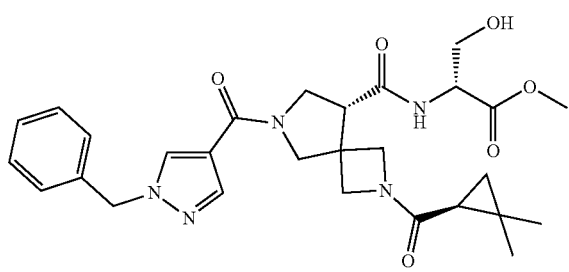 [SMILES: COC(=O)[C@@H](CO)NC(=O)[C@H]1CN(C(=O)c2cnn(Cc3ccccc3)c2)CC12CN(C(=O)[C@H]1CC1(C)C)C2]<br>(B) |
| I-188 | 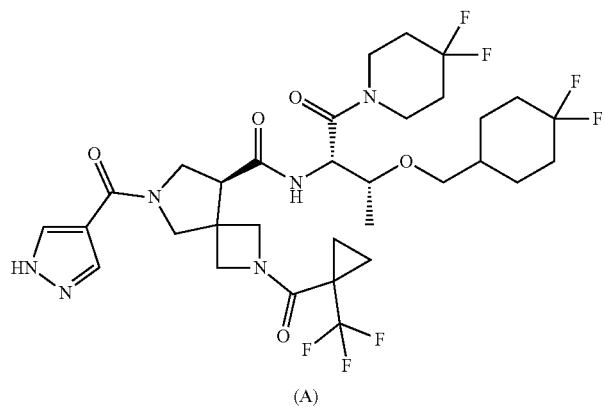<br>(A) |

TABLE 1-continued
Exemplary Compounds
| Cmpd # | Structure |
|---|---|
| | 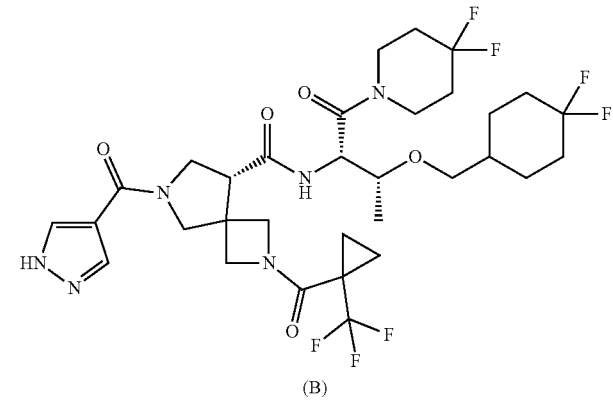 (B) |
| I-189 | 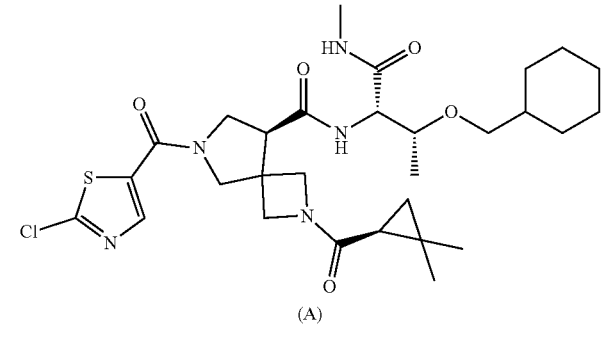 (A) |
| | 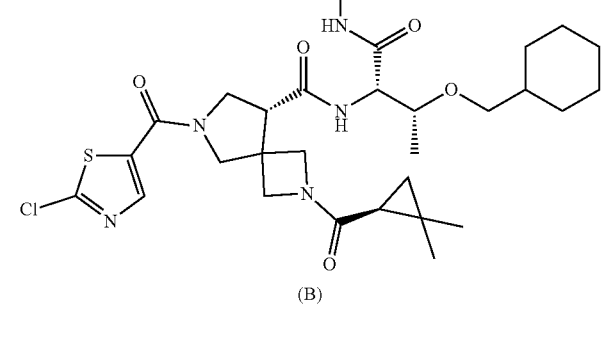 (B) |
| I-190 | 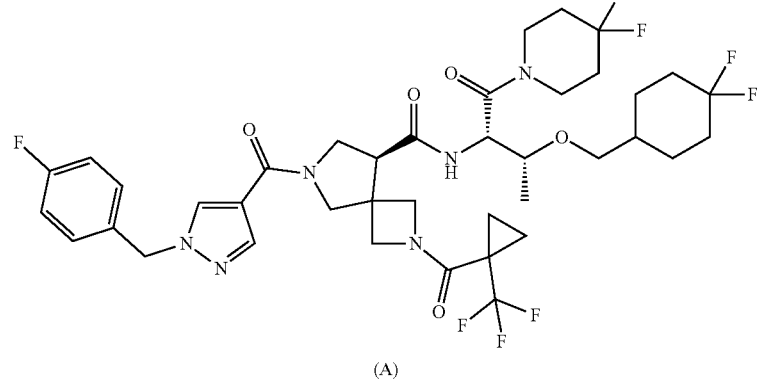 (A) |

US 12,065,445 B2
TABLE 1-continued
Exemplary Compounds
| Cmpd # | Structure |
|---|---|
| | 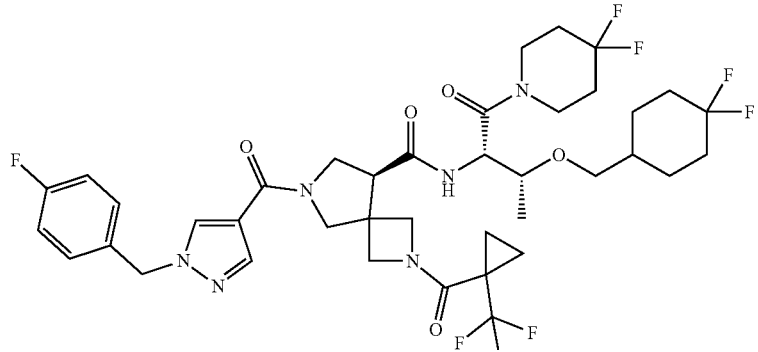(B) |
| I-191 | 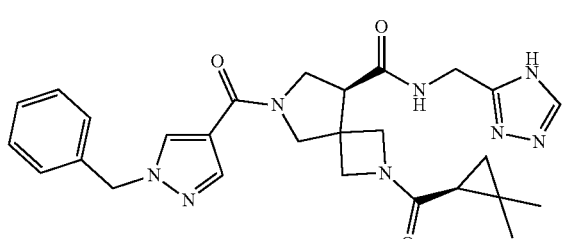(A) |
| | 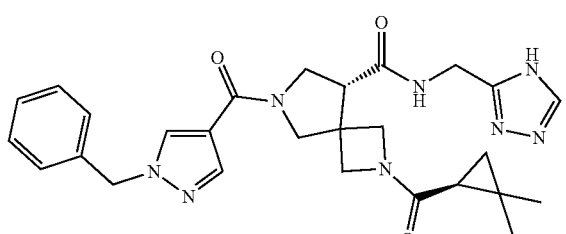(B) |
| I-192 | 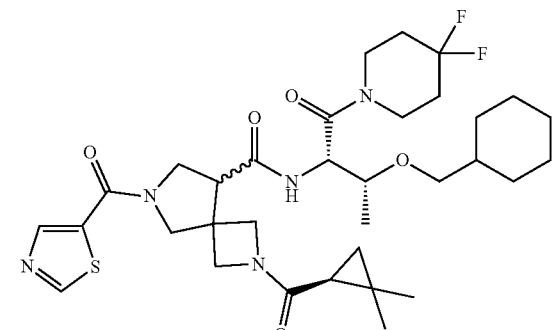Mixture |

TABLE 1-continued
Exemplary Compounds
| Cmpd # | Structure |
|---|---|
|  | 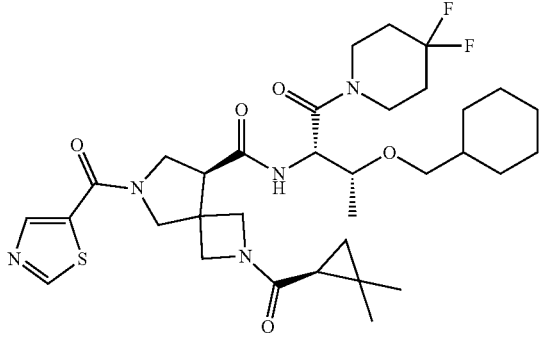 [SMILES: C[C@@H](OCC1CCCCC1)[C@H](NC(=O)[C@@H]1CN(C(=O)c2cncs2)CC12CN(C(=O)[C@H]1CC1(C)C)C2)C(=O)N1CCC(F)(F)CC1]<br>(A)<br>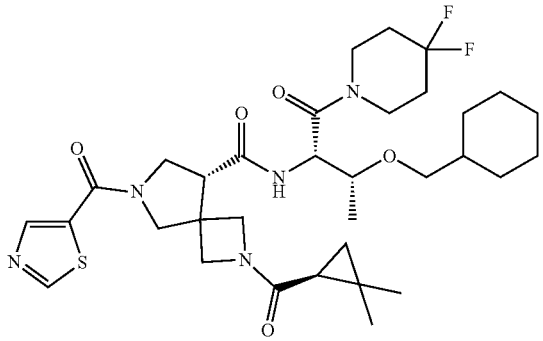 [SMILES: C[C@@H](OCC1CCCCC1)[C@H](NC(=O)[C@H]1CN(C(=O)c2cncs2)CC12CN(C(=O)[C@H]1CC1(C)C)C2)C(=O)N1CCC(F)(F)CC1]<br>(B) |
| I-193 | 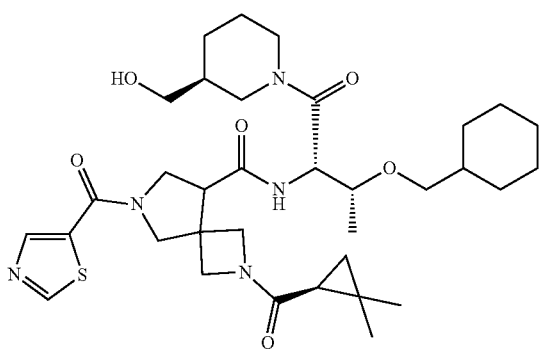 [SMILES: C[C@@H](OCC1CCCCC1)[C@H](NC(=O)C1CN(C(=O)c2cncs2)CC12CN(C(=O)[C@H]1CC1(C)C)C2)C(=O)N1CCC[C@H](CO)C1] |
| I-194 | 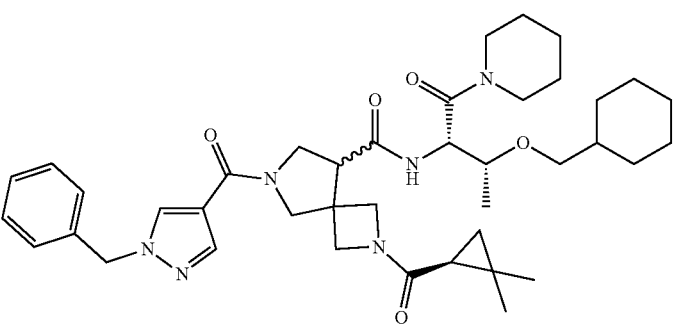 [SMILES: C[C@@H](OCC1CCCCC1)[C@H](NC(=O)[C@H]1CN(C(=O)c2cnn(Cc3ccccc3)c2)CC12CN(C(=O)[C@H]1CC1(C)C)C2)C(=O)N1CCCCC1]<br>Mixture |

TABLE 1-continued

Exemplary Compounds

| Cmpd # | Structure |
|---|---|
| | (A) |
| | (B) |
| I-195 | 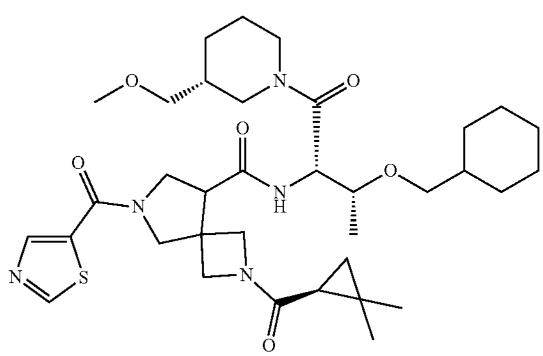 |
| I-196 | Mixture |

TABLE 1-continued
Exemplary Compounds
| Cmpd # | Structure |
|---|---|
| | 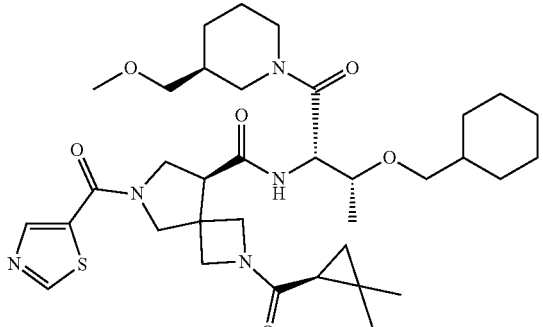<br>(A)<br><br>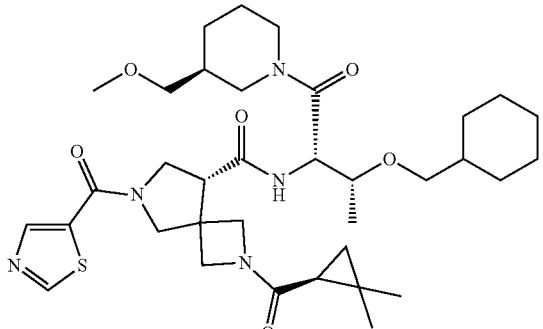<br>(B) |
| I-197 | 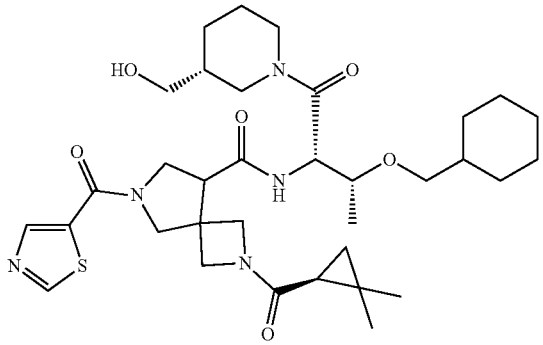 |
| I-198 | 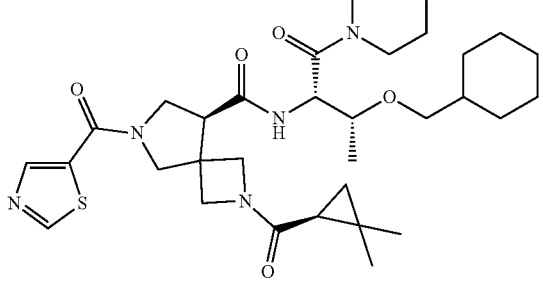 |

TABLE 1-continued

Exemplary Compounds

| Cmpd # | Structure |
| --- | --- |
| I-199 | 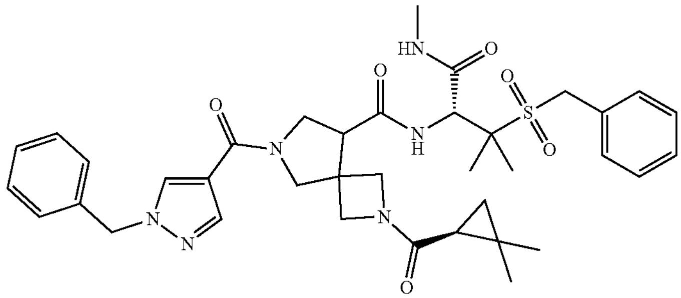 [SMILES: CNC(=O)[C@@H](NC(=O)C1CN(C(=O)c2cnn(Cc3ccccc3)c2)CC12CN(C(=O)[C@H]1CC1(C)C)C2)C(C)(C)S(=O)(=O)Cc1ccccc1] |
| I-200 | 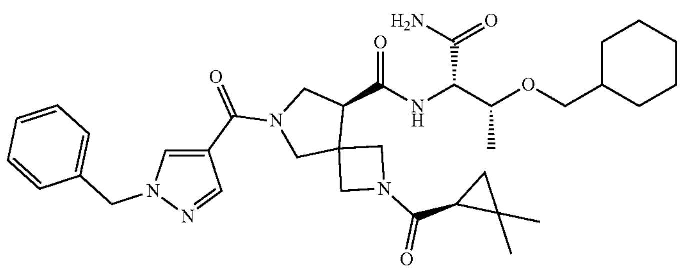 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(N)=O] |
| I-201 | (A) |
| | (B) |
| I-202 | 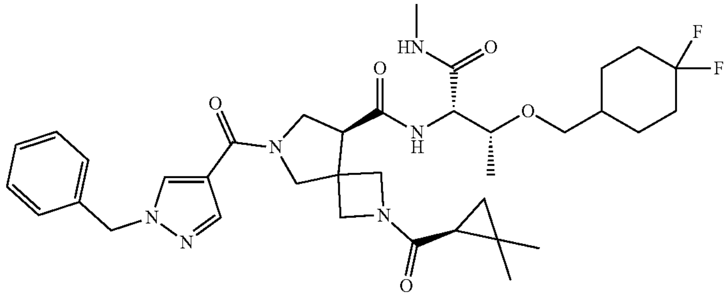 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC1CCC(F)(F)CC1] |

TABLE 1-continued

Exemplary Compounds

| Cmpd # | Structure |
| --- | --- |
| I-203 | 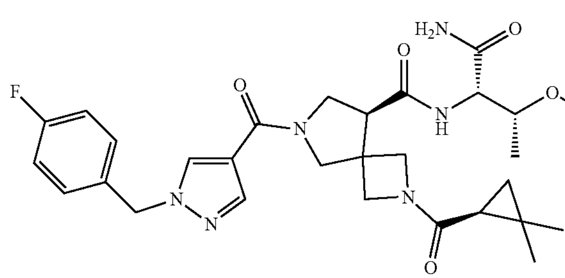 |
| I-204 | 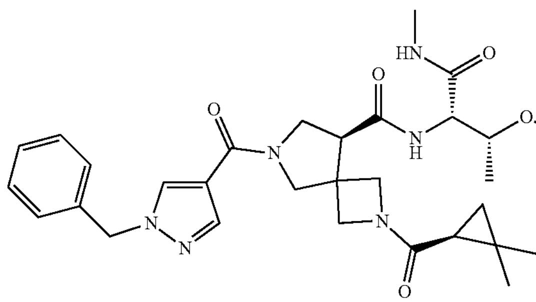 |
| I-205 | (A) |
| | (B) |
| I-206 | 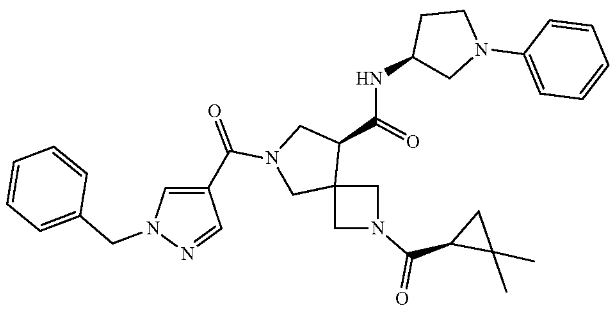 [SMILES: CC1(C)C[C@@H]1C(=O)N1CC2(CN(C(=O)c3cnn(Cc4ccccc4)c3)C[C@H]2C(=O)N[C@H]2CCN(c3ccccc3)C2)C1] |

TABLE 1-continued

Exemplary Compounds

| Cmpd # | Structure |
|---|---|
| I-207 | 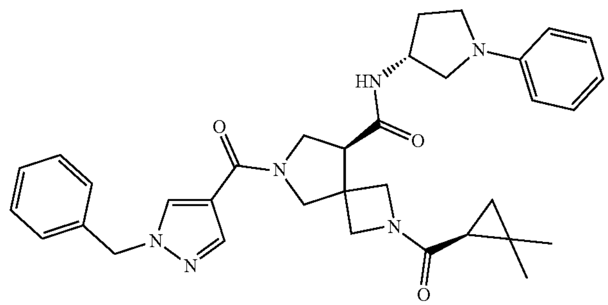 [SMILES: CC1(C)C[C@@H]1C(=O)N1CC2(CN(C(=O)c3cnn(Cc4ccccc4)c3)C[C@H]2C(=O)N[C@@H]2CCN(c3ccccc3)C2)C1] |
| I-208 | (A) |
| | (B) |
| I-209 | (A) |
| | (B) |

TABLE 1-continued

Exemplary Compounds

| Cmpd # | Structure |
|---|---|
| I-210 | 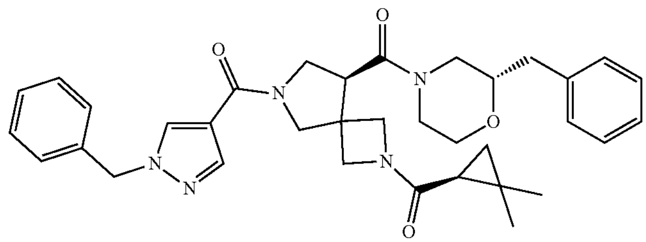 [SMILES: CC1(C)C[C@@H]1C(=O)N1CC2(CN(C(=O)c3cnn(Cc4ccccc4)c3)C[C@H]2C(=O)N2CCO[C@@H](Cc3ccccc3)C2)C1] |
| I-211 | 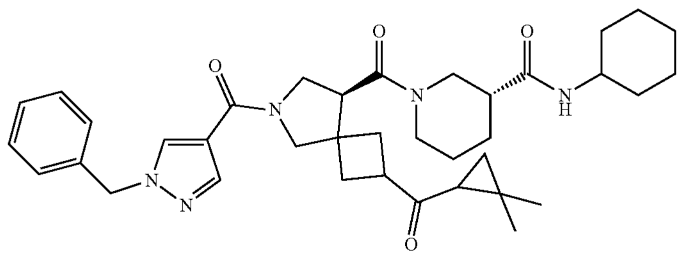 [SMILES: CC1(C)CC1C(=O)C1CC2(C1)CN(C(=O)c1cnn(Cc3ccccc3)c1)C[C@H]2C(=O)N1CCC[C@@H](C(=O)NC2CCCCC2)C1] |
| I-212 | 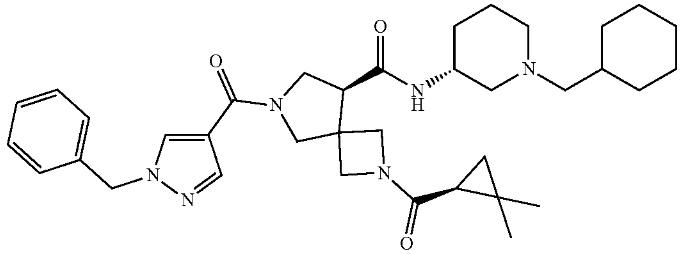 [SMILES: CC1(C)C[C@@H]1C(=O)N1CC2(CN(C(=O)c3cnn(Cc4ccccc4)c3)C[C@H]2C(=O)N[C@@H]2CCCN(CC3CCCCC3)C2)C1] |
| I-213 | (A) |
| | (B) |

TABLE 1-continued

Exemplary Compounds

| Cmpd # | Structure |
|---|---|
| I-214 | 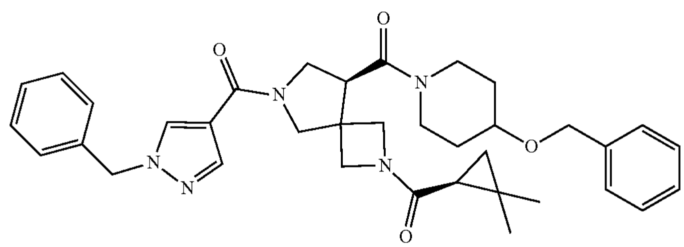 [SMILES: CC1(C)C[C@@H]1C(=O)N1CC2(CN(C(=O)c3cnn(Cc4ccccc4)c3)C[C@H]2C(=O)N2CCC(OCc3ccccc3)CC2)C1] |
| I-215 | 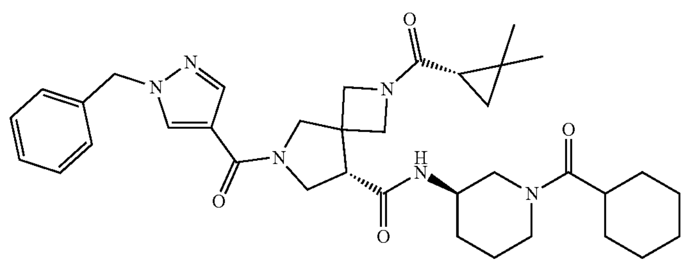 [SMILES: CC1(C)C[C@@H]1C(=O)N1CC2(CN(C(=O)c3cnn(Cc4ccccc4)c3)C[C@H]2C(=O)N[C@@H]2CCCN(C(=O)C3CCCCC3)C2)C1] |
| I-216 | 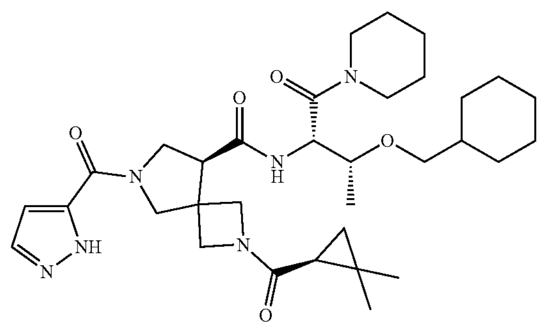 [SMILES: C[C@@H](OCC1CCCCC1)[C@H](NC(=O)[C@@H]1CN(C(=O)c2ccn[nH]2)CC12CN(C(=O)[C@H]1CC1(C)C)C2)C(=O)N1CCCCC1] |
| I-217 | 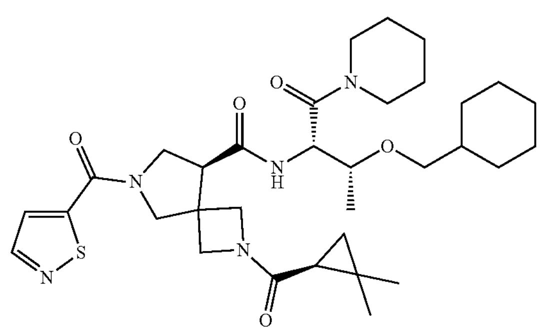 [SMILES: C[C@@H](OCC1CCCCC1)[C@H](NC(=O)[C@@H]1CN(C(=O)c2ccns2)CC12CN(C(=O)[C@H]1CC1(C)C)C2)C(=O)N1CCCCC1] |
| I-218 | 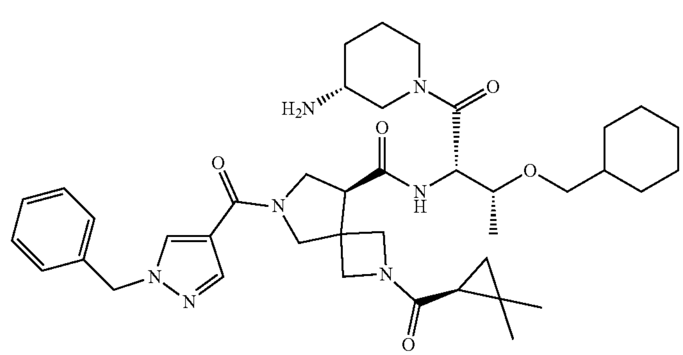 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC[C@@H](N)C1] |

TABLE 1-continued
Exemplary Compounds
| Cmpd # | Structure |
|---|---|
| I-219 | 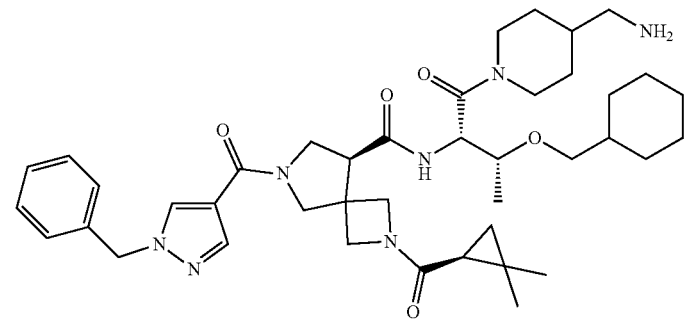 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(CN)CC1] |
| I-220 | 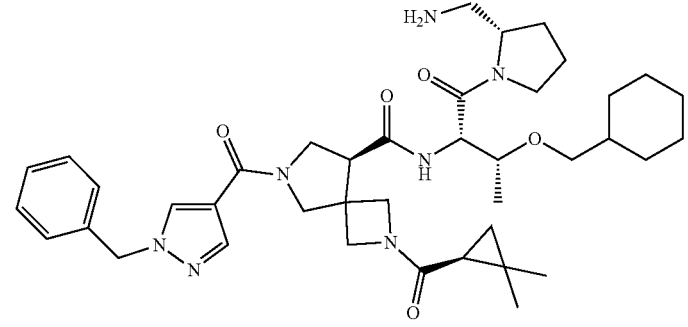 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC[C@H]1CN] |
| I-221 | 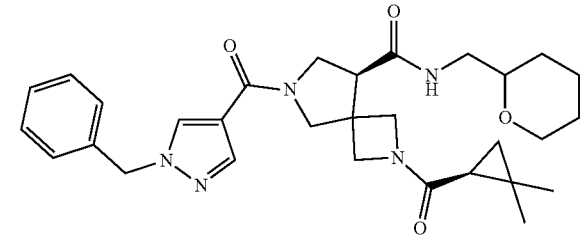 [SMILES: CC1(C)C[C@@H]1C(=O)N1CC2(CN(C(=O)c3cnn(Cc4ccccc4)c3)C[C@H]2C(=O)NCC2CCCCO2)C1] |
| I-223 | 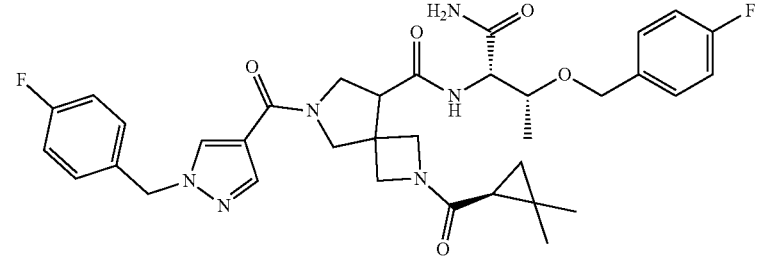 [SMILES: C[C@@H](OCc1ccc(F)cc1)[C@H](NC(=O)C1CN(C(=O)c2cnn(Cc3ccc(F)cc3)c2)CC12CN(C(=O)[C@H]1CC1(C)C)C2)C(N)=O] |
| | 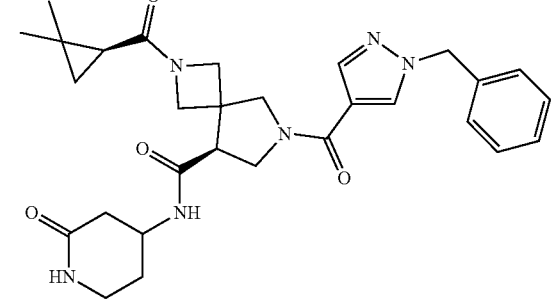 |

TABLE 1-continued
Exemplary Compounds
| Cmpd # | Structure |
|---|---|
| I-224 | 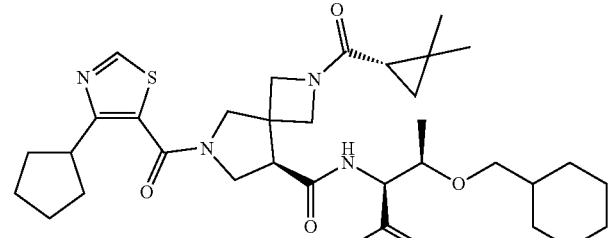 (A)<br>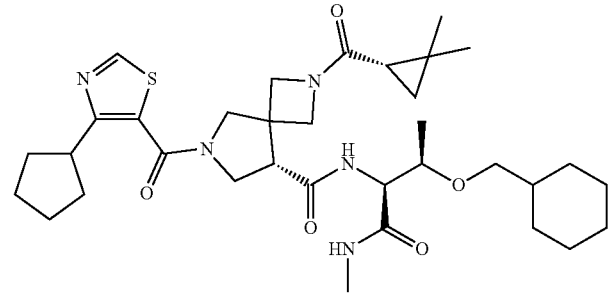 (B) |
| I-225 | 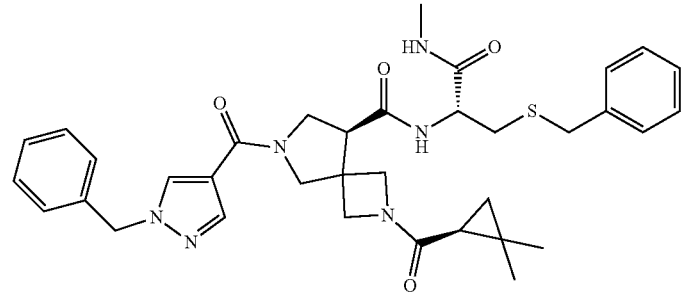 [SMILES: CNC(=O)[C@H](CSCc1ccccc1)NC(=O)[C@@H]1CN(C(=O)c2cnn(Cc3ccccc3)c2)CC12CN(C(=O)[C@H]1CC1(C)C)C2] |
| I-226 | 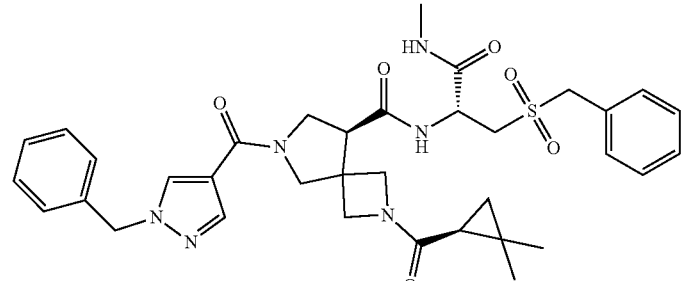 |

TABLE 1-continued
Exemplary Compounds
| Cmpd # | Structure |
|---|---|
| I-227 | 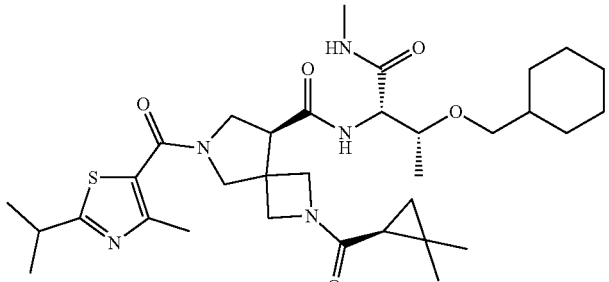 (A)<br>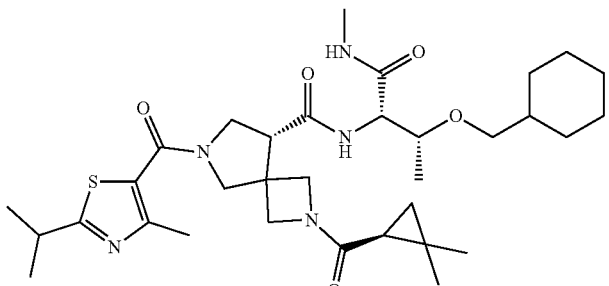 (B) |
| I-228 | 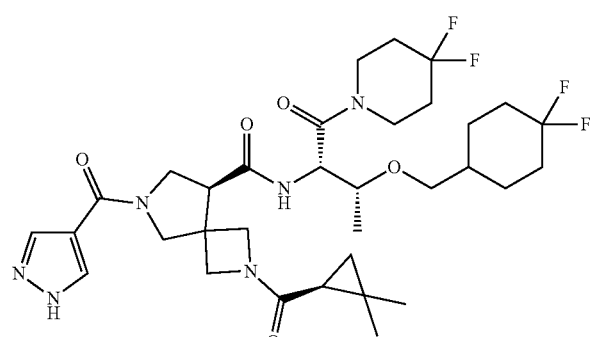 (A)<br>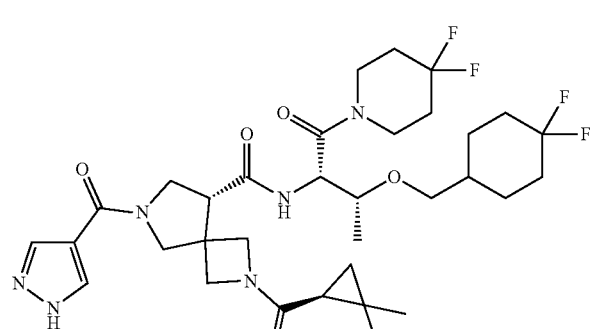 (B) |

TABLE 1-continued

Exemplary Compounds

| Cmpd # | Structure |
|---|---|
| I-229 | (A) |
|  | (B) |
| I-230 | 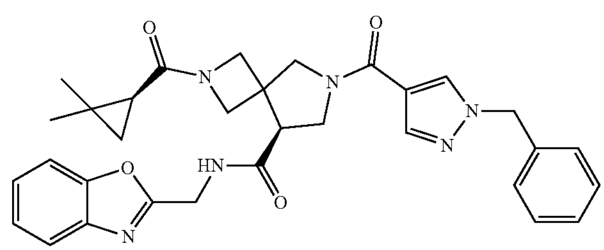 |
| I-231 | (A) |

US 12,065,445 B2
295                                                                          296
TABLE 1-continued
Exemplary Compounds
| Cmpd # | Structure |
|---|---|
|  | 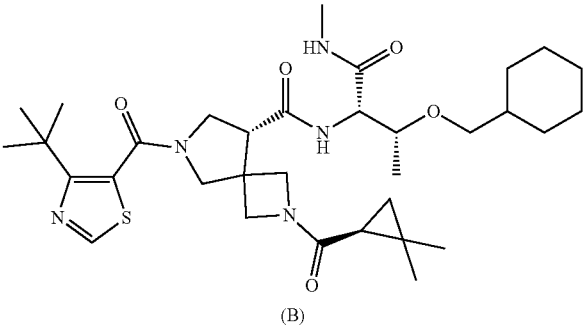<br>(B) |
| I-232 | 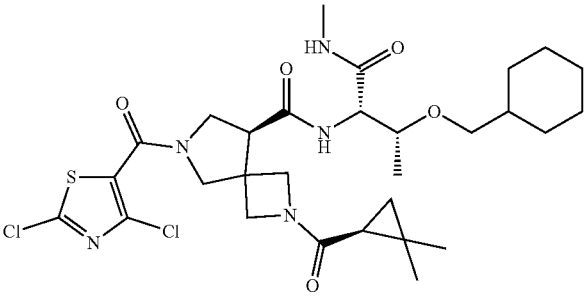<br>(A) |
|  | 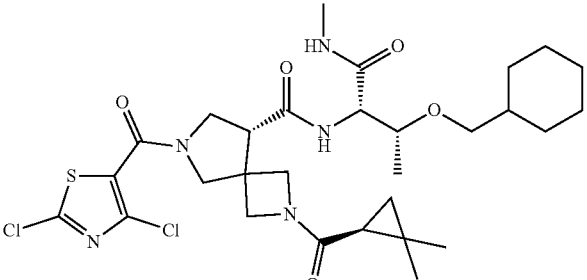<br>(B) |
| I-233 | 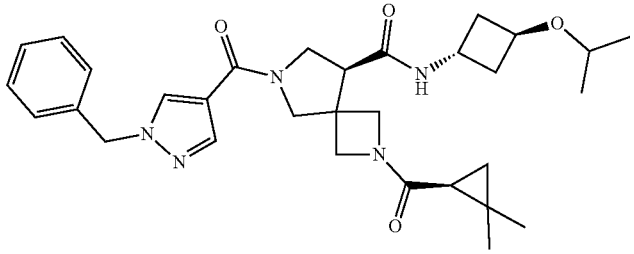 [SMILES: CC(C)O[C@H]1C[C@H](NC(=O)[C@@H]2CN(C(=O)c3cnn(Cc4ccccc4)c3)CC23CN(C(=O)[C@H]2CC2(C)C)C3)C1] |
| I-234 | 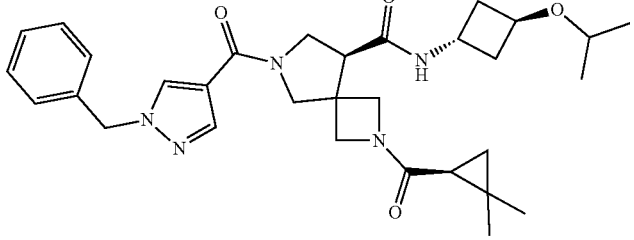 |

TABLE 1-continued
Exemplary Compounds
| Cmpd # | Structure |
|---|---|
| I-235 | 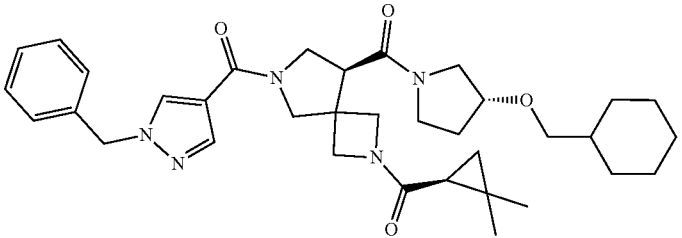 [SMILES: CC1(C)C[C@@H]1C(=O)N1CC2(CN(C(=O)c3cnn(Cc4ccccc4)c3)C[C@H]2C(=O)N2CC[C@@H](OCC3CCCCC3)C2)C1] |
| I-236 | 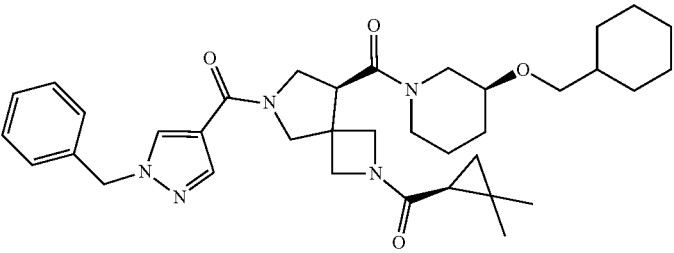 [SMILES: CC1(C)C[C@@H]1C(=O)N1CC2(CN(C(=O)c3cnn(Cc4ccccc4)c3)C[C@H]2C(=O)N2CCC[C@H](OCC3CCCCC3)C2)C1] |
| I-237 | 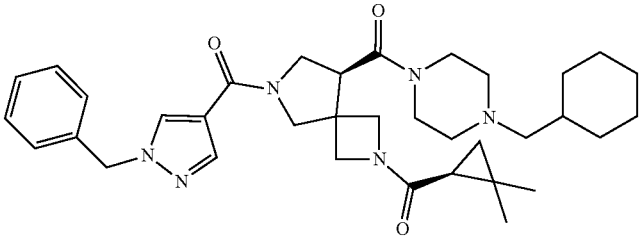 [SMILES: CC1(C)C[C@@H]1C(=O)N1CC2(CN(C(=O)c3cnn(Cc4ccccc4)c3)C[C@H]2C(=O)N2CCN(CC3CCCCC3)CC2)C1] |
| I-238 | 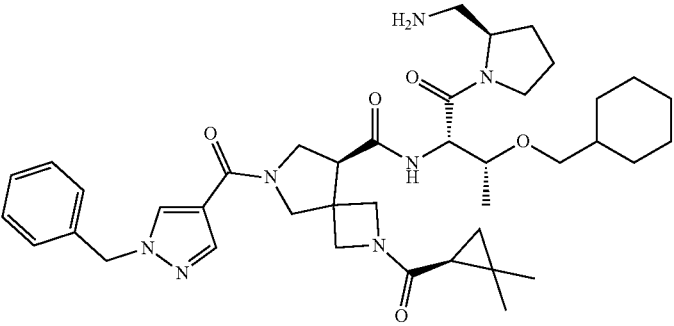 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC[C@@H]1CN] |
| I-239 | 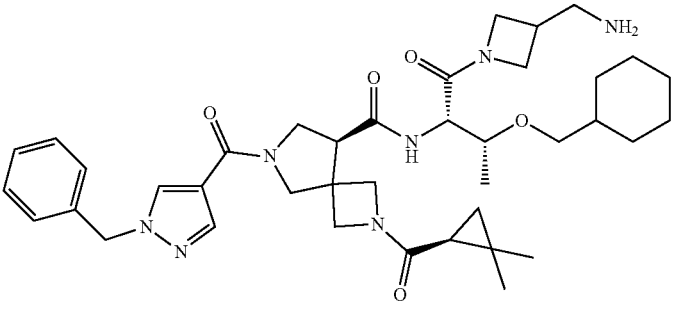 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CC(CN)C1] |

TABLE 1-continued

Exemplary Compounds

| Cmpd # | Structure |
|---|---|
| I-240 | 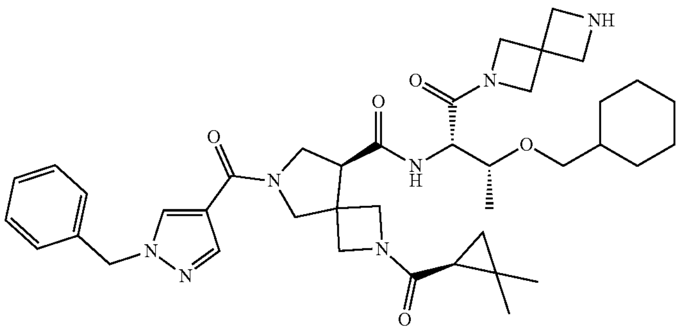 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CC2(CNC2)C1] |
| I-241 | 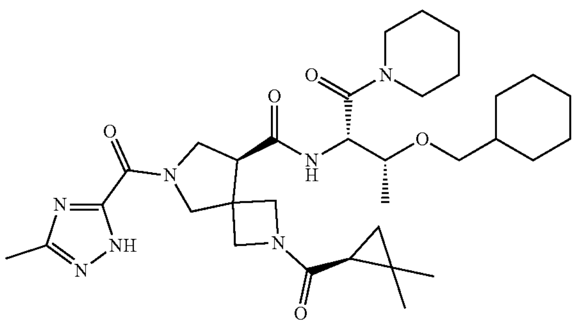 [SMILES: Cc1n[nH]c(C(=O)N2C[C@@H](C(=O)N[C@H](C(=O)N3CCCCC3)[C@@H](C)OCC3CCCCC3)C3(C2)CN(C(=O)[C@H]2CC2(C)C)C3)n1] |
| I-242 | 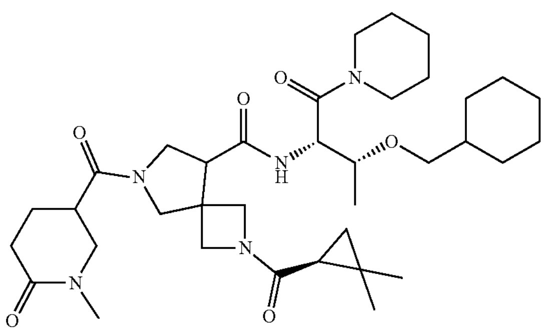 [SMILES: C[C@@H](OCC1CCCCC1)[C@H](NC(=O)C1CN(C(=O)C2CCC(=O)N(C)C2)CC12CN(C(=O)[C@H]1CC1(C)C)C2)C(=O)N1CCCCC1] |
| I-243 | 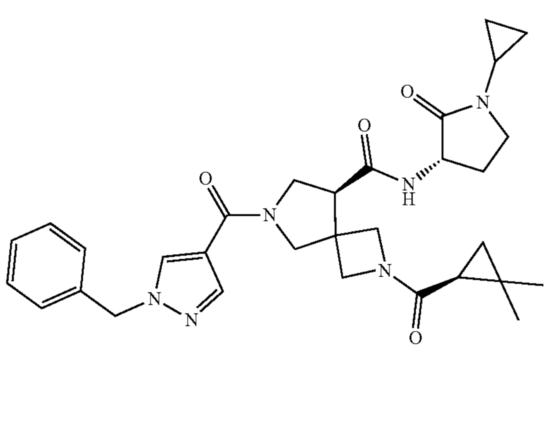 [SMILES: CC1(C)C[C@@H]1C(=O)N1CC2(CN(C(=O)c3cnn(Cc4ccccc4)c3)C[C@H]2C(=O)N[C@H]2CCN(C3CC3)C2=O)C1] |

TABLE 1-continued

Exemplary Compounds

| Cmpd # | Structure |
|--------|-----------|
| I-244 | 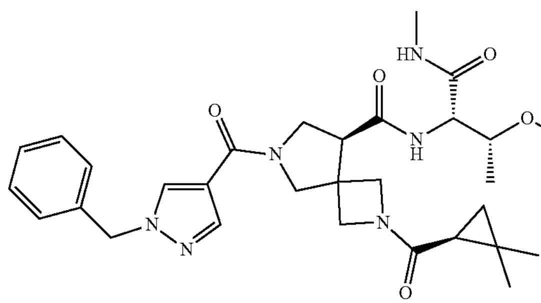 |
| I-245 | 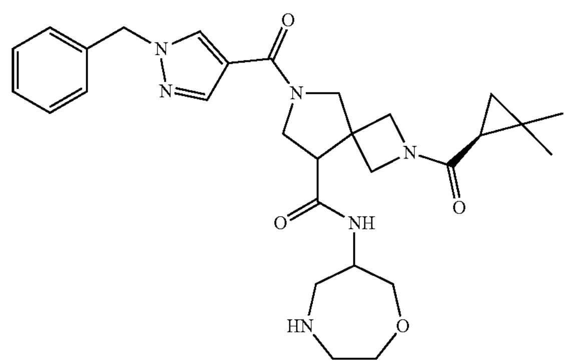 [SMILES: CC1(C)C[C@@H]1C(=O)N1CC2(CN(C(=O)c3cnn(Cc4ccccc4)c3)CC2C(=O)NC2CNCCOC2)C1] |
| I-246 | 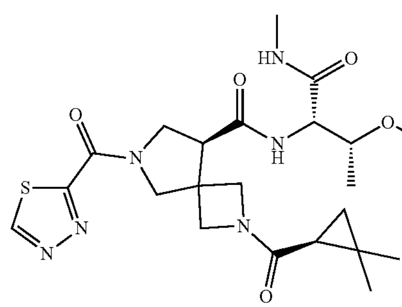 |
| I-247 | 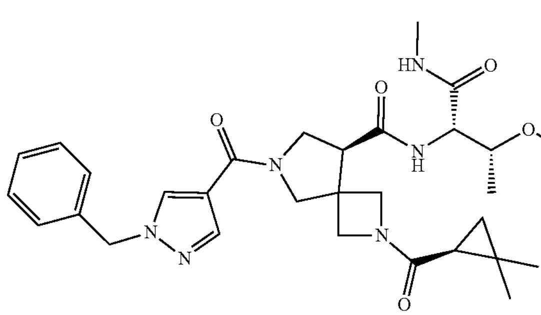 |

TABLE 1-continued

Exemplary Compounds

| Cmpd # | Structure |
|---|---|
| I-248 | 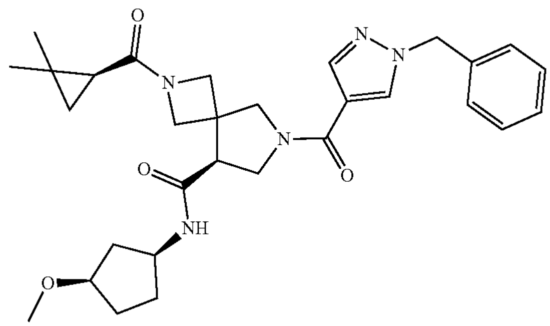 [SMILES: CO[C@@H]1CC[C@H](NC(=O)[C@@H]2CN(C(=O)c3cnn(Cc4ccccc4)c3)CC23CN(C(=O)[C@H]2CC2(C)C)C3)C1] |
| I-249 | 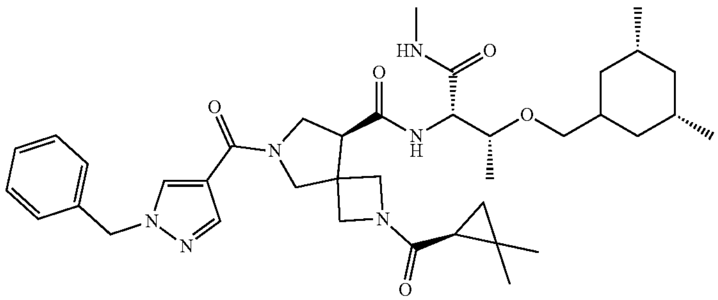 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC1C[C@@H](C)C[C@@H](C)C1] |
| I-250 | 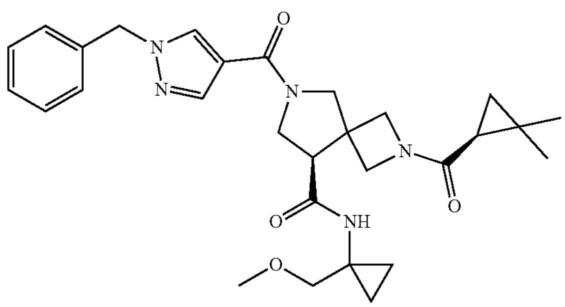 [SMILES: COCC1(NC(=O)[C@H]2CN(C(=O)c3cnn(Cc4ccccc4)c3)CC23CN(C(=O)[C@H]2CC2(C)C)C3)CC1] |
| I-251 | 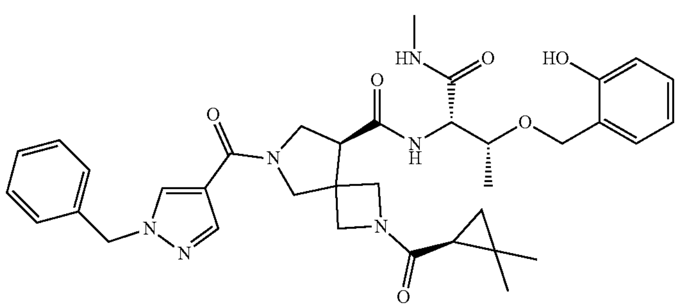 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCc1ccccc1O] |
| I-252 | 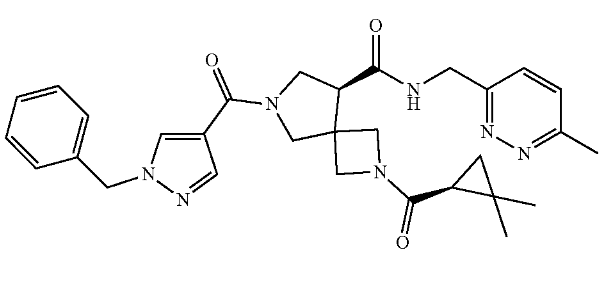 [SMILES: Cc1ccc(CNC(=O)[C@@H]2CN(C(=O)c3cnn(Cc4ccccc4)c3)CC23CN(C(=O)[C@H]2CC2(C)C)C3)nn1] |

TABLE 1-continued

Exemplary Compounds

| Cmpd # | Structure |
|---|---|
| I-253 | 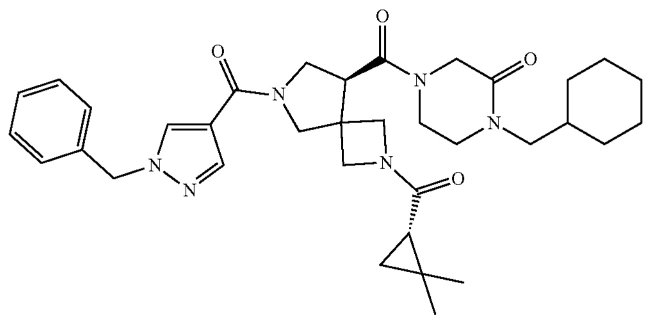 [SMILES: CC1(C)C[C@@H]1C(=O)N1CC2(CN(C(=O)c3cnn(Cc4ccccc4)c3)C[C@H]2C(=O)N2CCN(CC3CCCCC3)C(=O)C2)C1] |
| I-254 | 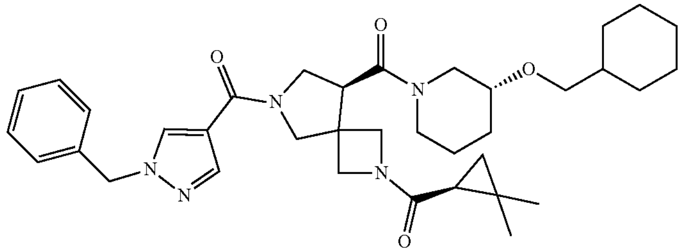 [SMILES: CC1(C)C[C@@H]1C(=O)N1CC2(CN(C(=O)c3cnn(Cc4ccccc4)c3)C[C@H]2C(=O)N2CCC[C@@H](OCC3CCCCC3)C2)C1] |
| I-255 | 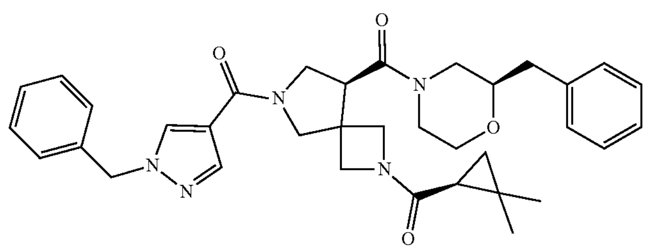 [SMILES: CC1(C)C[C@@H]1C(=O)N1CC2(CN(C(=O)c3cnn(Cc4ccccc4)c3)C[C@H]2C(=O)N2CCO[C@H](Cc3ccccc3)C2)C1] |
| I-256 | 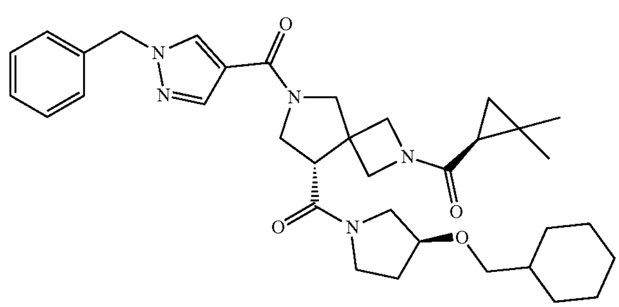 [SMILES: CC1(C)C[C@@H]1C(=O)N1CC2(CN(C(=O)c3cnn(Cc4ccccc4)c3)C[C@H]2C(=O)N2CC[C@H](OCC3CCCCC3)C2)C1] |
| I-257 | 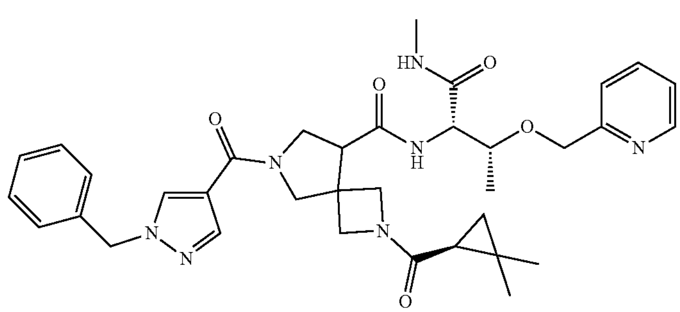 [SMILES: CNC(=O)[C@@H](NC(=O)C1CN(C(=O)c2cnn(Cc3ccccc3)c2)CC12CN(C(=O)[C@H]1CC1(C)C)C2)[C@@H](C)OCc1ccccn1] |

TABLE 1-continued

Exemplary Compounds

| Cmpd # | Structure |
|---|---|
| I-258 | 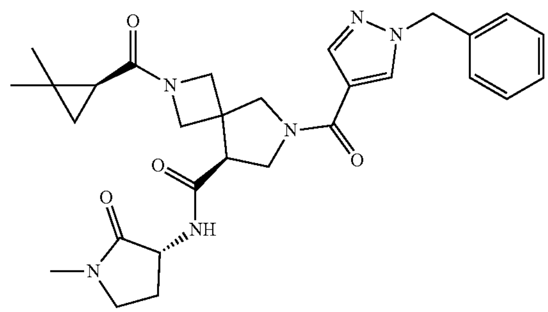 [SMILES: CN1CC[C@@H](NC(=O)[C@@H]2CN(C(=O)c3cnn(Cc4ccccc4)c3)CC23CN(C(=O)[C@H]2CC2(C)C)C3)C1=O] |
| I-259 | 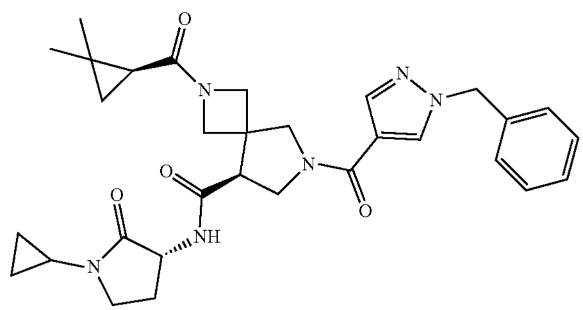 [SMILES: CC1(C)C[C@@H]1C(=O)N1CC2(CN(C(=O)c3cnn(Cc4ccccc4)c3)C[C@H]2C(=O)N[C@@H]2CCN(C3CC3)C2=O)C1] |
| I-260 | 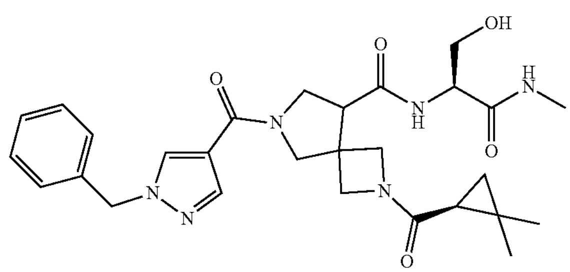 [SMILES: CNC(=O)[C@H](CO)NC(=O)C1CN(C(=O)c2cnn(Cc3ccccc3)c2)CC12CN(C(=O)[C@H]1CC1(C)C)C2] |
| I-261 | 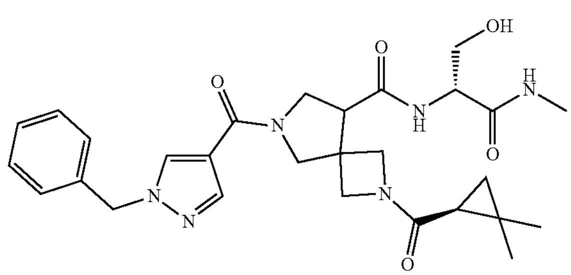 [SMILES: CNC(=O)[C@@H](CO)NC(=O)C1CN(C(=O)c2cnn(Cc3ccccc3)c2)CC12CN(C(=O)[C@H]1CC1(C)C)C2] |
| I-262 | 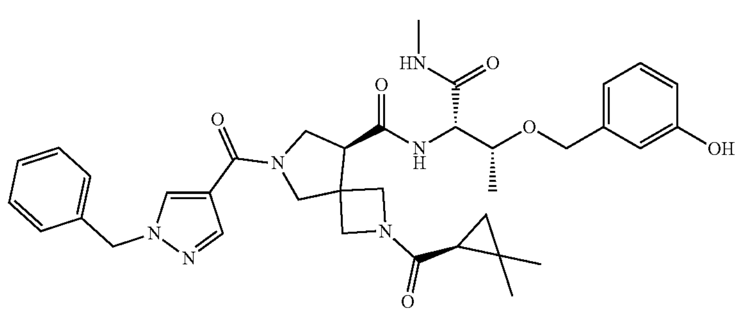 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCc1cccc(O)c1] |

TABLE 1-continued
Exemplary Compounds
| Cmpd # | Structure |
|---|---|
| I-263 | 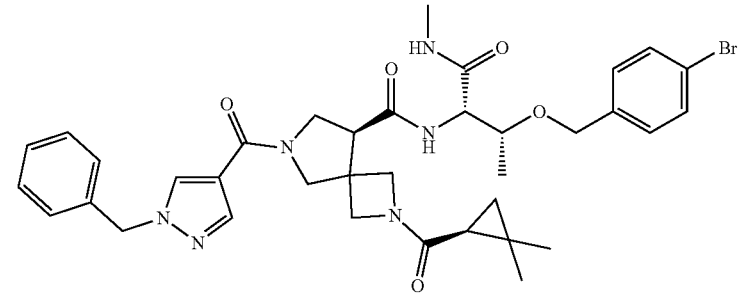 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCc1ccc(Br)cc1] |
| I-264 | 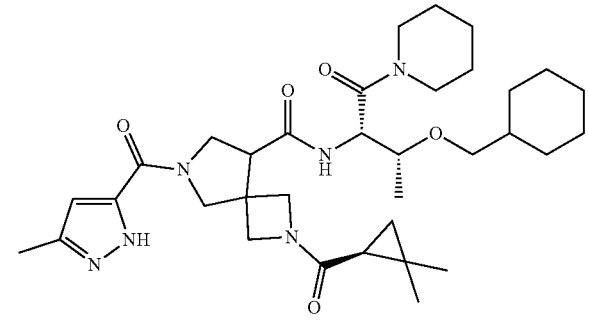 [SMILES: Cc1cc(C(=O)N2CC(C(=O)N[C@H](C(=O)N3CCCCC3)[C@@H](C)OCC3CCCCC3)C3(C2)CN(C(=O)[C@H]2CC2(C)C)C3)[nH]n1] |
| I-265 | 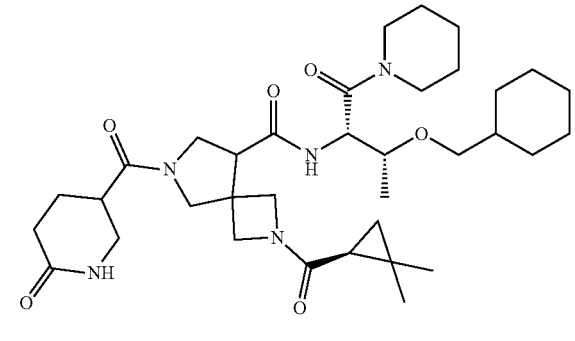 [SMILES: C[C@@H](OCC1CCCCC1)[C@H](NC(=O)C1CN(C(=O)C2CCC(=O)NC2)CC12CN(C(=O)[C@H]1CC1(C)C)C2)C(=O)N1CCCCC1] |
| I-266 | 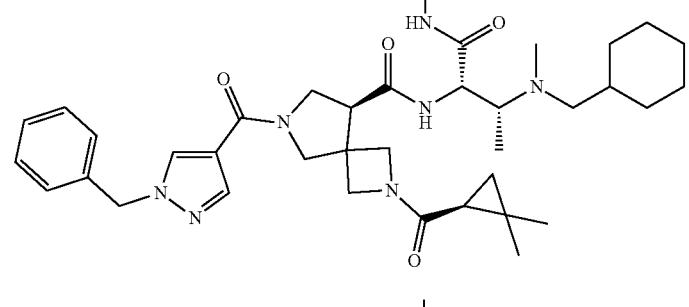 |
| I-267 | 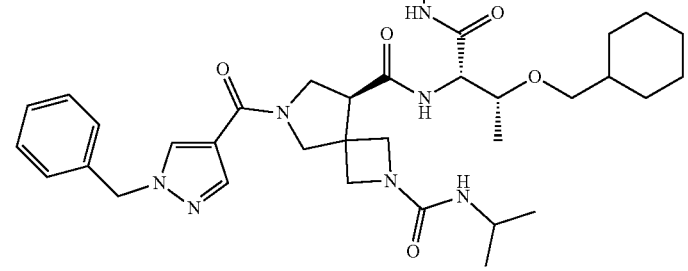 |

TABLE 1-continued

Exemplary Compounds

| Cmpd # | Structure |
|--------|-----------|
| I-268 | 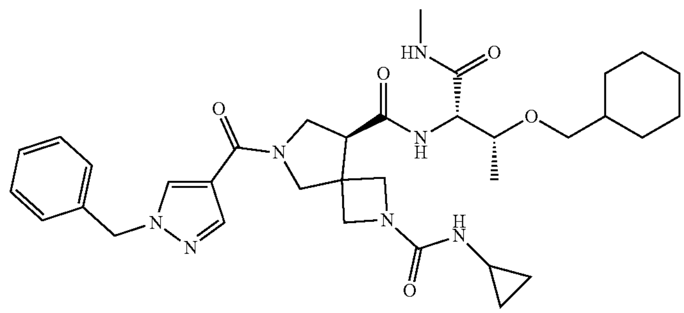 [SMILES: CNC(=O)[C@@H](NC(=O)[C@@H]1CN(C(=O)c2cnn(Cc3ccccc3)c2)CC12CN(C(=O)NC1CC1)C2)[C@@H](C)OCC1CCCCC1] |
| I-269 | 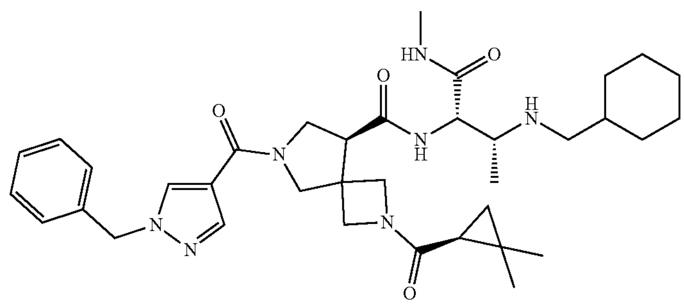 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)NCC1CCCCC1] |
| I-270 | 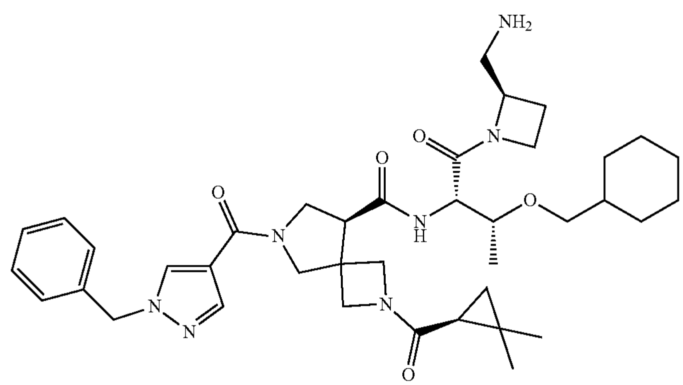 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CC[C@@H]1CN] |
| I-271 | 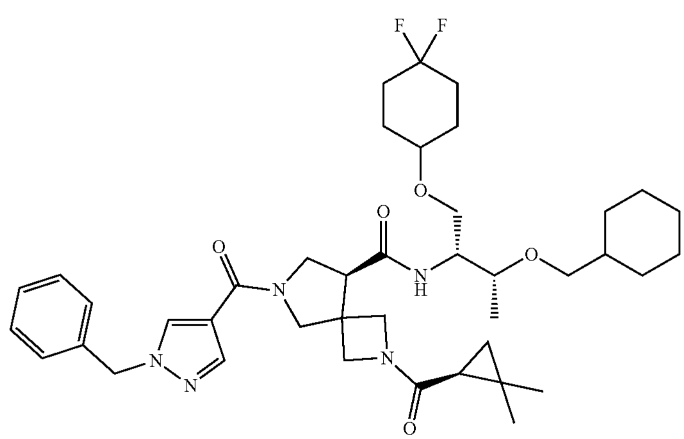 [SMILES: C[C@@H](OCC1CCCCC1)[C@@H](COC1CCC(F)(F)CC1)NC(=O)[C@@H]1CN(C(=O)c2cnn(Cc3ccccc3)c2)CC12CN(C(=O)[C@H]1CC1(C)C)C2] |

TABLE 1-continued

Exemplary Compounds

| Cmpd # | Structure |
|---|---|
| I-272 | 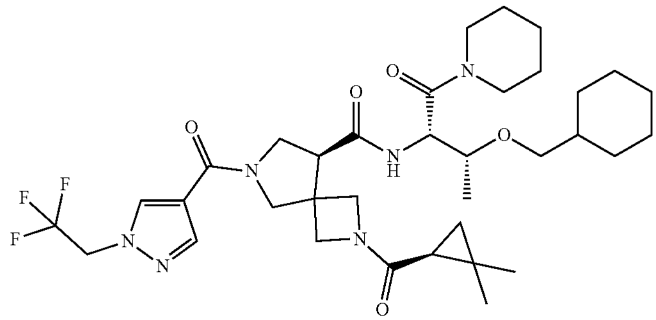 [SMILES: C[C@@H](OCC1CCCCC1)[C@H](NC(=O)[C@@H]1CN(C(=O)c2cnn(CC(F)(F)F)c2)CC12CN(C(=O)[C@H]1CC1(C)C)C2)C(=O)N1CCCCC1] |
| I-273 | 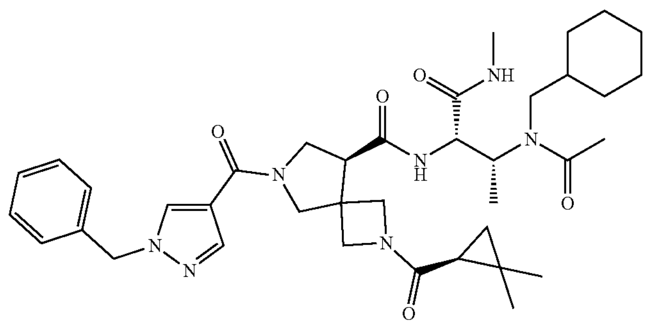 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)N(CC1CCCCC1)C(C)=O] |
| I-274 | 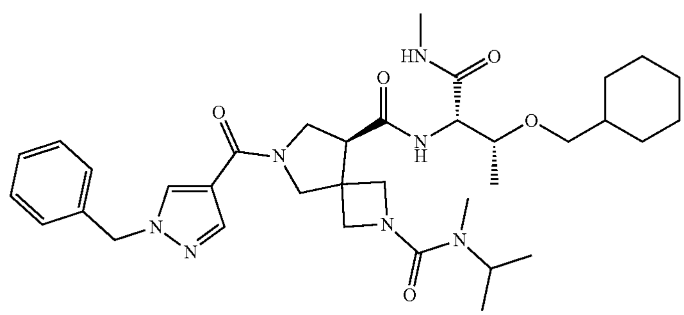 [SMILES: CNC(=O)[C@@H](NC(=O)[C@@H]1CN(C(=O)c2cnn(Cc3ccccc3)c2)CC12CN(C(=O)N(C)C(C)C)C2)[C@@H](C)OCC1CCCCC1] |
| I-275 | 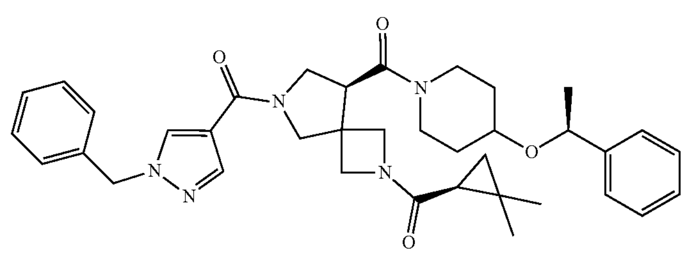 [SMILES: C[C@H](OC1CCN(C(=O)[C@@H]2CN(C(=O)c3cnn(Cc4ccccc4)c3)CC23CN(C(=O)[C@H]2CC2(C)C)C3)CC1)c1ccccc1] |
| I-276 | 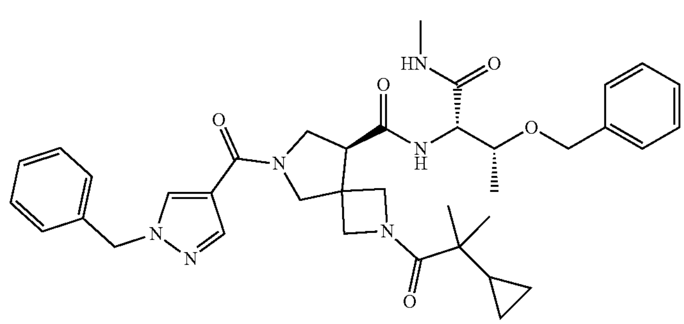 [SMILES: CNC(=O)[C@@H](NC(=O)[C@@H]1CN(C(=O)c2cnn(Cc3ccccc3)c2)CC12CN(C(=O)C(C)(C)C1CC1)C2)[C@@H](C)OCc1ccccc1] |

TABLE 1-continued

Exemplary Compounds

| Cmpd # | Structure |
|---|---|
| I-277 | 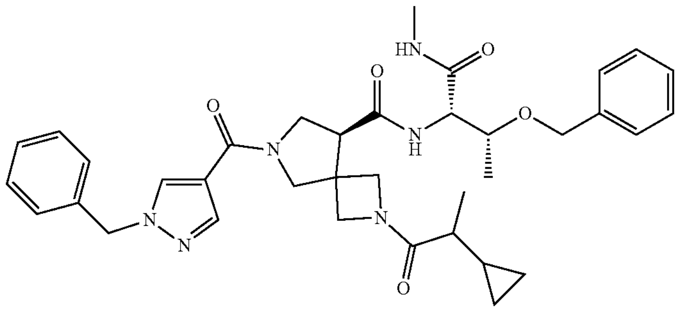 [SMILES: CNC(=O)[C@@H](NC(=O)[C@@H]1CN(C(=O)c2cnn(Cc3ccccc3)c2)CC12CN(C(=O)C(C)C1CC1)C2)[C@@H](C)OCc1ccccc1] |
| I-278 | 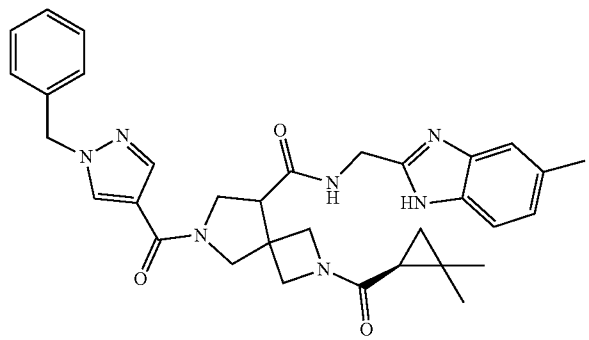 [SMILES: Cc1ccc2[nH]c(CNC(=O)C3CN(C(=O)c4cnn(Cc5ccccc5)c4)CC34CN(C(=O)[C@H]3CC3(C)C)C4)nc2c1] |
| I-279 | 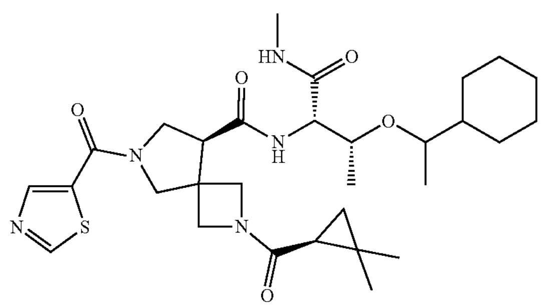 [SMILES: CNC(=O)[C@@H](NC(=O)[C@@H]1CN(C(=O)c2cncs2)CC12CN(C(=O)[C@H]1CC1(C)C)C2)[C@@H](C)OC(C)C1CCCCC1] |
| I-280 | 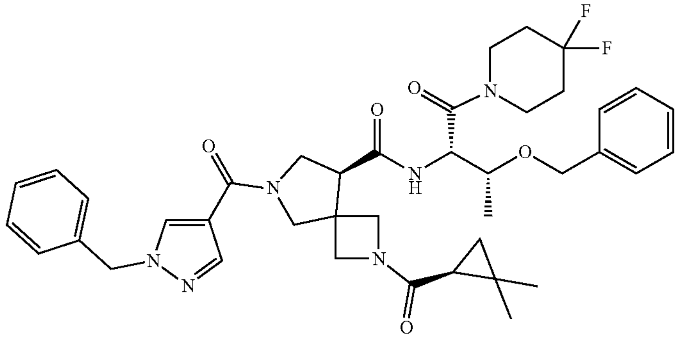 [SMILES: C[C@@H](OCc1ccccc1)[C@H](NC(=O)[C@@H]1CN(C(=O)c2cnn(Cc3ccccc3)c2)CC12CN(C(=O)[C@H]1CC1(C)C)C2)C(=O)N1CCC(F)(F)CC1] |

TABLE 1-continued

Exemplary Compounds

| Cmpd # | Structure |
|---|---|
| I-281 | 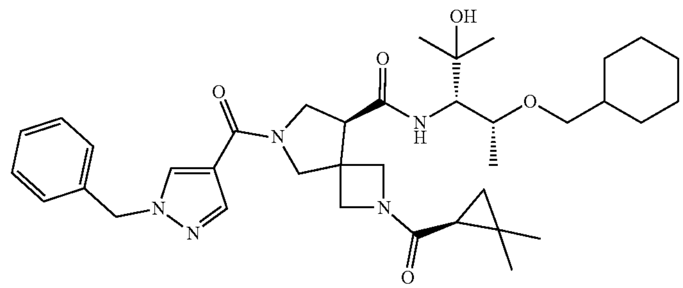 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(C)(C)O] |
| I-282 | 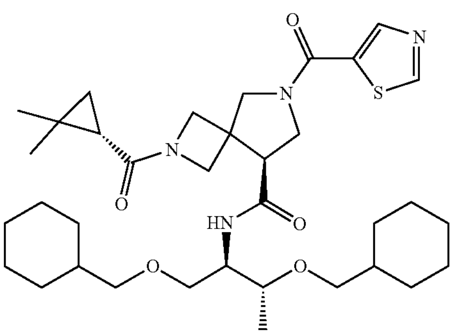 [SMILES: C[C@@H](OCC1CCCCC1)[C@@H](COCC1CCCCC1)NC(=O)[C@@H]1CN(C(=O)c2cncs2)CC12CN(C(=O)[C@H]1CC1(C)C)C2] |
| I-283 | 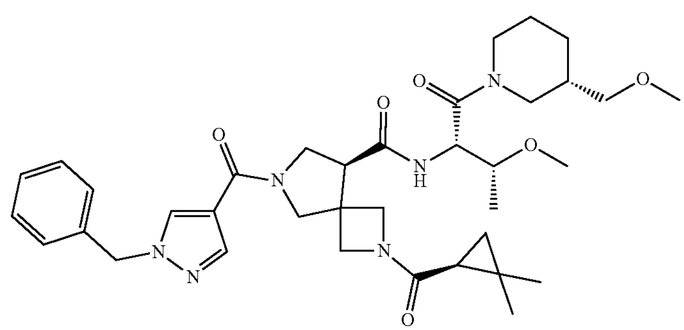 [SMILES: COC[C@H]1CCCN(C(=O)[C@@H](NC(=O)[C@@H]2CN(C(=O)c3cnn(Cc4ccccc4)c3)CC23CN(C(=O)[C@H]2CC2(C)C)C3)[C@@H](C)OC)C1] |
| I-284 | 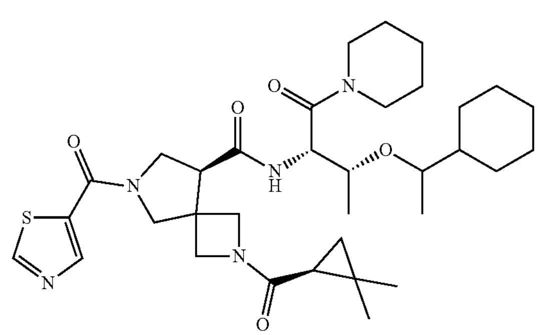 [SMILES: CC(O[C@H](C)[C@H](NC(=O)[C@@H]1CN(C(=O)c2cncs2)CC12CN(C(=O)[C@H]1CC1(C)C)C2)C(=O)N1CCCCC1)C1CCCCC1] |

TABLE 1-continued

Exemplary Compounds

| Cmpd # | Structure |
|---|---|
| I-285 | 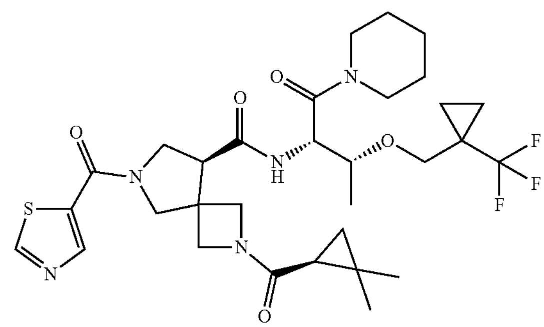 [SMILES: C[C@@H](OCC1(C(F)(F)F)CC1)[C@H](NC(=O)[C@@H]1CN(C(=O)c2cncs2)CC12CN(C(=O)[C@H]1CC1(C)C)C2)C(=O)N1CCCCC1] |
| I-286 | 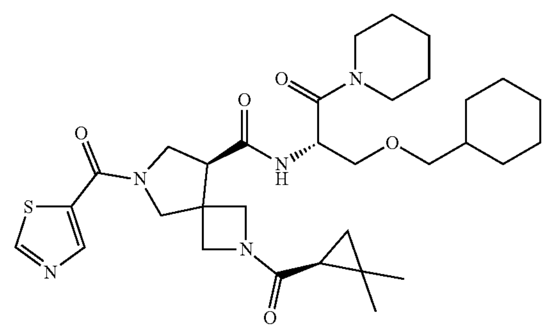 [SMILES: CC1(C)C[C@@H]1C(=O)N1CC2(CN(C(=O)c3cncs3)C[C@H]2C(=O)N[C@@H](COCC2CCCCC2)C(=O)N2CCCCC2)C1] |
| I-287 | 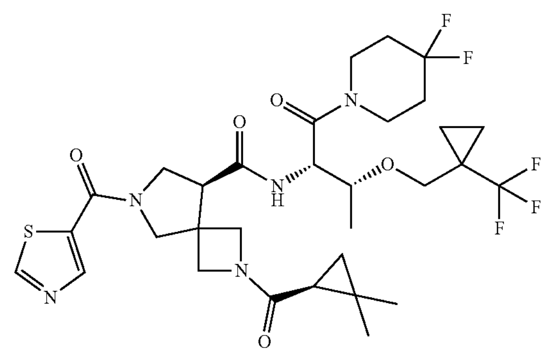 [SMILES: C[C@@H](OCC1(C(F)(F)F)CC1)[C@H](NC(=O)[C@@H]1CN(C(=O)c2cncs2)CC12CN(C(=O)[C@H]1CC1(C)C)C2)C(=O)N1CCC(F)(F)CC1] |
| I-288 | 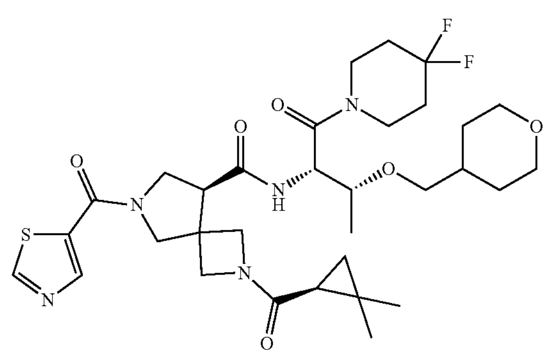 [SMILES: C[C@@H](OCC1CCOCC1)[C@H](NC(=O)[C@@H]1CN(C(=O)c2cncs2)CC12CN(C(=O)[C@H]1CC1(C)C)C2)C(=O)N1CCC(F)(F)CC1] |

TABLE 1-continued

Exemplary Compounds

| Cmpd # | Structure |
|---|---|
| I-289 | 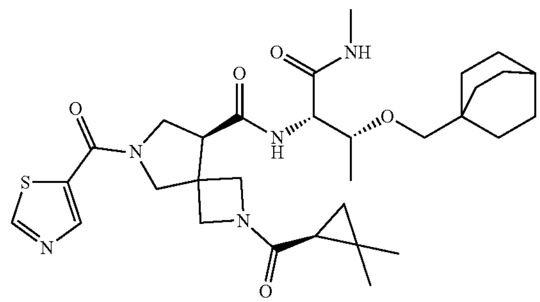 [SMILES: CNC(=O)[C@@H](NC(=O)[C@@H]1CN(C(=O)c2cncs2)CC12CN(C(=O)[C@H]1CC1(C)C)C2)[C@@H](C)OCC12CCC(CC1)CC2] |
| I-290 | 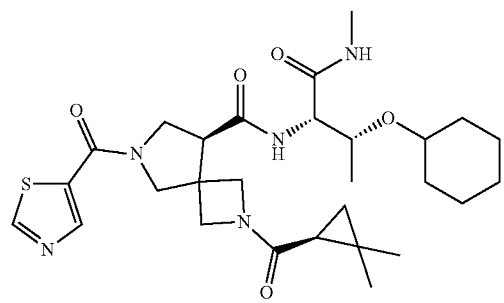 [SMILES: CNC(=O)[C@@H](NC(=O)[C@@H]1CN(C(=O)c2cncs2)CC12CN(C(=O)[C@H]1CC1(C)C)C2)[C@@H](C)OC1CCCCC1] |
| I-291 | 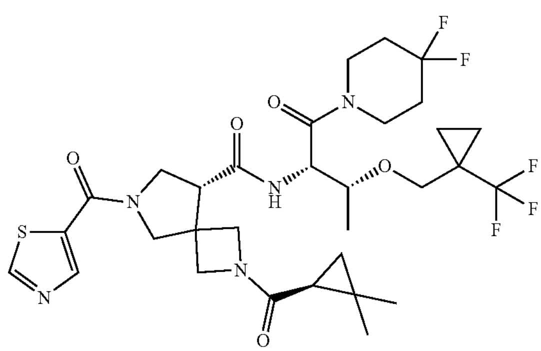 [SMILES: C[C@@H](OCC1(C(F)(F)F)CC1)[C@H](NC(=O)[C@H]1CN(C(=O)c2cncs2)CC12CN(C(=O)[C@H]1CC1(C)C)C2)C(=O)N1CCC(F)(F)CC1] |
| I-292 | 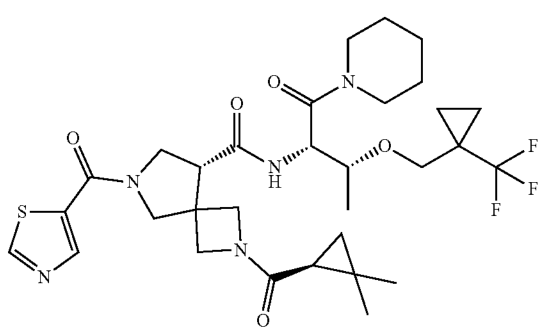 [SMILES: C[C@@H](OCC1(C(F)(F)F)CC1)[C@H](NC(=O)[C@H]1CN(C(=O)c2cncs2)CC12CN(C(=O)[C@H]1CC1(C)C)C2)C(=O)N1CCCCC1] |

TABLE 1-continued

Exemplary Compounds

| Cmpd # | Structure |
|---|---|
| I-293 | 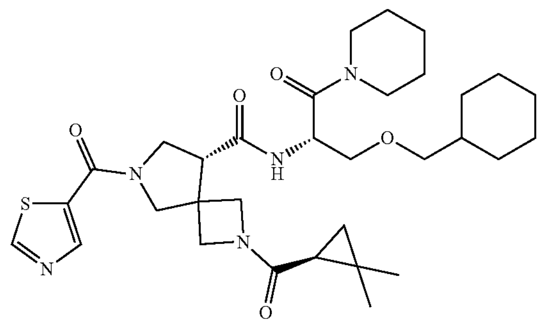 [SMILES: CC1(C)C[C@@H]1C(=O)N1CC2(CN(C(=O)c3cncs3)C[C@@H]2C(=O)N[C@@H](COCC2CCCCC2)C(=O)N2CCCCC2)C1] |
| I-294 | 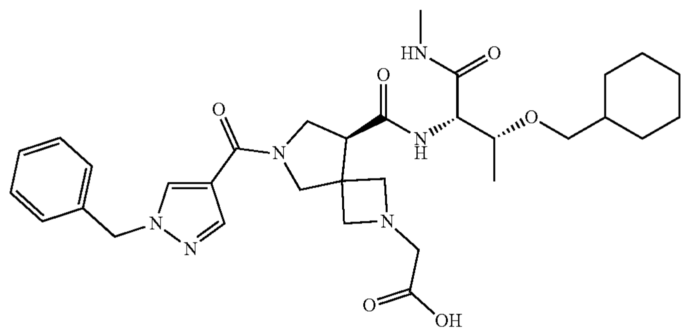 [SMILES: CNC(=O)[C@@H](NC(=O)[C@@H]1CN(C(=O)c2cnn(Cc3ccccc3)c2)CC12CN(CC(=O)O)C2)[C@@H](C)OCC1CCCCC1] |
| I-295 | 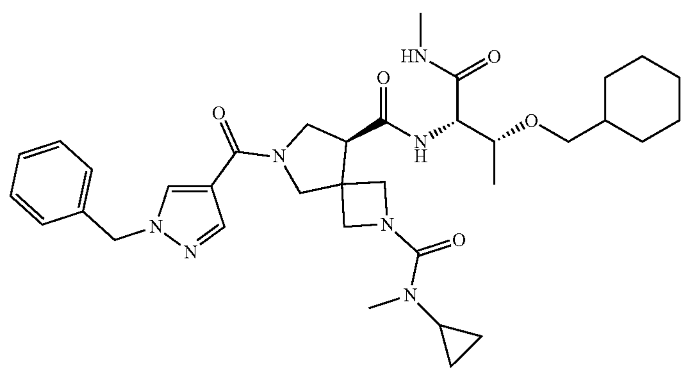 [SMILES: CNC(=O)[C@@H](NC(=O)[C@@H]1CN(C(=O)c2cnn(Cc3ccccc3)c2)CC12CN(C(=O)N(C)C1CC1)C2)[C@@H](C)OCC1CCCCC1] |
| I-296 | 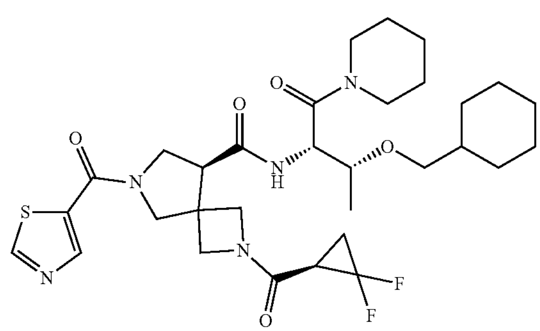 [SMILES: C[C@@H](OCC1CCCCC1)[C@H](NC(=O)[C@@H]1CN(C(=O)c2cncs2)CC12CN(C(=O)[C@H]1CC1(F)F)C2)C(=O)N1CCCCC1] |

TABLE 1-continued
Exemplary Compounds
| Cmpd # | Structure |
|---|---|
| I-297 | 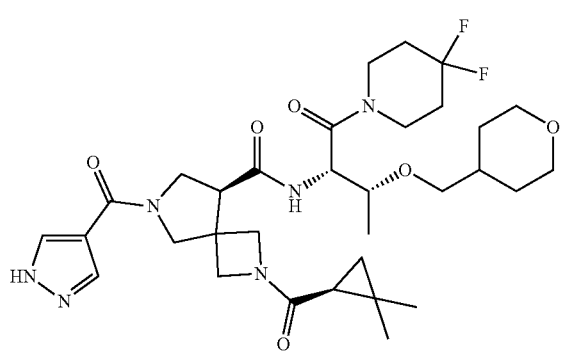 [SMILES: C[C@@H](OCC1CCOCC1)[C@H](NC(=O)[C@@H]1CN(C(=O)c2cn[nH]c2)CC12CN(C(=O)[C@H]1CC1(C)C)C2)C(=O)N1CCC(F)(F)CC1] |
| I-298 | 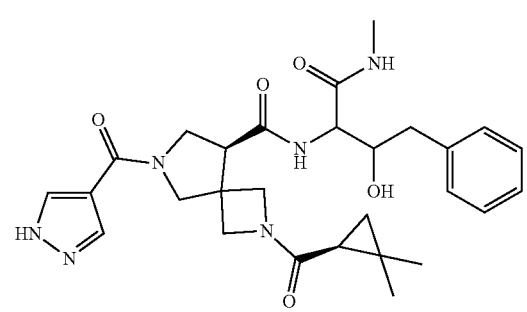 [SMILES: CNC(=O)C(NC(=O)[C@@H]1CN(C(=O)c2cn[nH]c2)CC12CN(C(=O)[C@H]1CC1(C)C)C2)C(O)Cc1ccccc1] |
| I-299 | 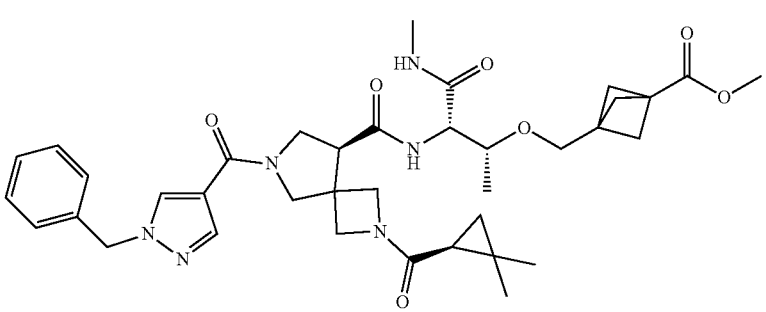 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC12CC(C(=O)OC)(C1)C2] |
| I-300 | 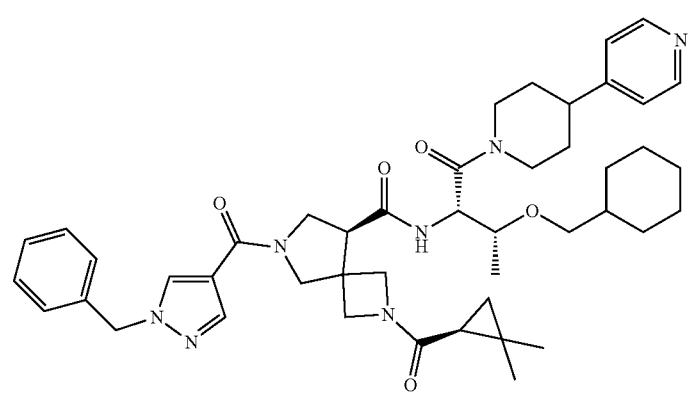 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(c2ccncc2)CC1] |

TABLE 1-continued

Exemplary Compounds

| Cmpd # | Structure |
| --- | --- |
| I-301 | 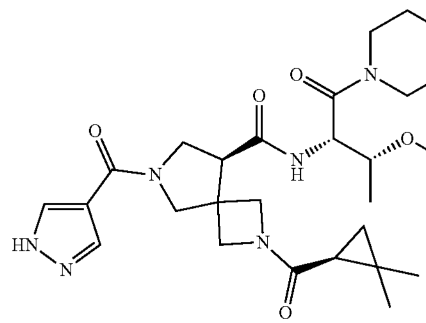 |
| I-302 | 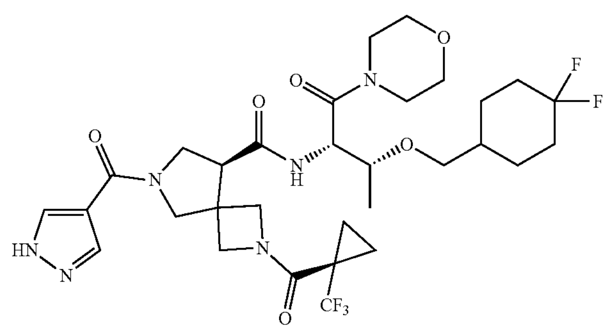 |
| I-303 | 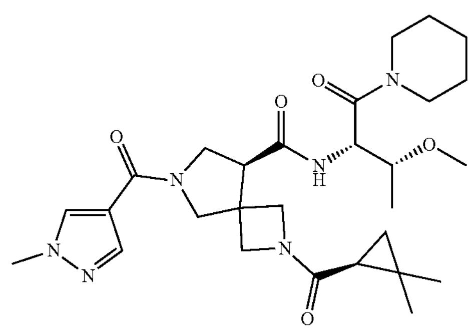 [SMILES: CO[C@H](C)[C@H](NC(=O)[C@@H]1CN(C(=O)c2cnn(C)c2)CC12CN(C(=O)[C@H]1CC1(C)C)C2)C(=O)N1CCCCC1] |
| I-304 | 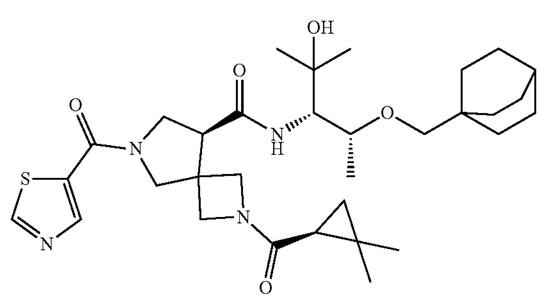 [SMILES: C[C@@H](OCC12CCC(CC1)CC2)[C@H](NC(=O)[C@@H]1CN(C(=O)c2cncs2)CC12CN(C(=O)[C@H]1CC1(C)C)C2)C(C)(C)O] |

TABLE 1-continued

Exemplary Compounds

| Cmpd # | Structure |
| --- | --- |
| I-305 | 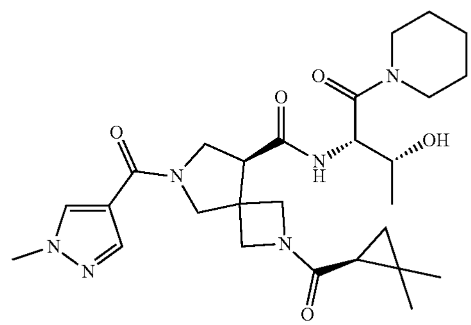 [SMILES: C[C@@H](O)[C@H](NC(=O)[C@@H]1CN(C(=O)c2cnn(C)c2)CC12CN(C(=O)[C@H]1CC1(C)C)C2)C(=O)N1CCCCC1] |
| I-306 | 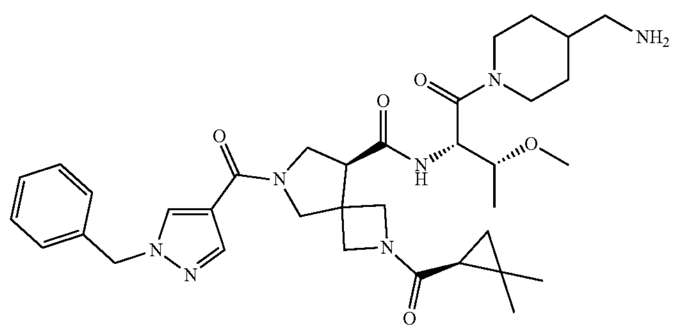 [SMILES: CO[C@H](C)[C@H](NC(=O)[C@@H]1CN(C(=O)c2cnn(Cc3ccccc3)c2)CC12CN(C(=O)[C@H]1CC1(C)C)C2)C(=O)N1CCC(CN)CC1] |
| I-307 | 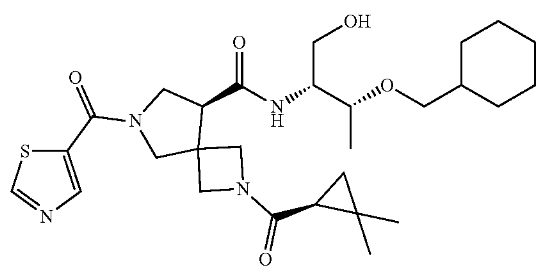 [SMILES: C[C@@H](OCC1CCCCC1)[C@@H](CO)NC(=O)[C@@H]1CN(C(=O)c2cncs2)CC12CN(C(=O)[C@H]1CC1(C)C)C2] |
| I-308 | 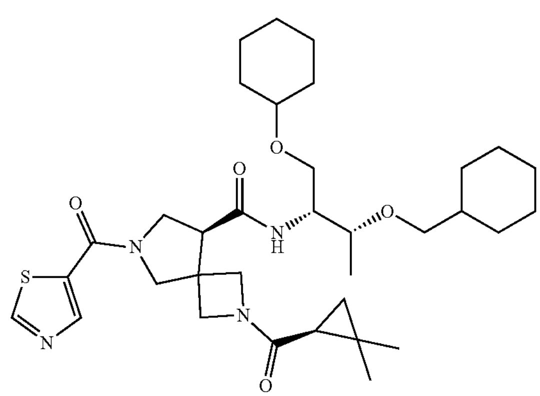 [SMILES: C[C@@H](OCC1CCCCC1)[C@@H](COC1CCCCC1)NC(=O)[C@@H]1CN(C(=O)c2cncs2)CC12CN(C(=O)[C@H]1CC1(C)C)C2] |

TABLE 1-continued

Exemplary Compounds

| Cmpd # | Structure |
|---|---|
| I-309 | 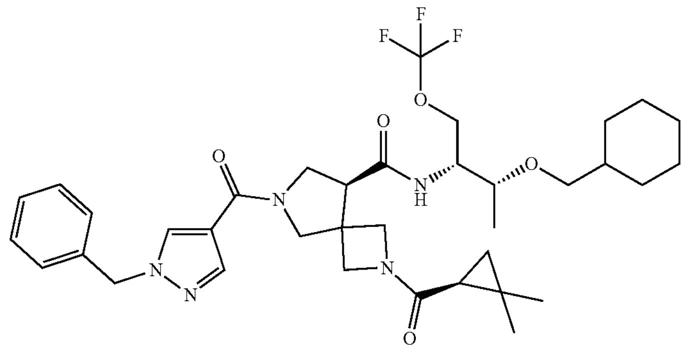 [SMILES: C[C@@H](OCC1CCCCC1)[C@@H](COC(F)(F)F)NC(=O)[C@@H]1CN(C(=O)c2cnn(Cc3ccccc3)c2)CC12CN(C(=O)[C@H]1CC1(C)C)C2] |
| I-310 | 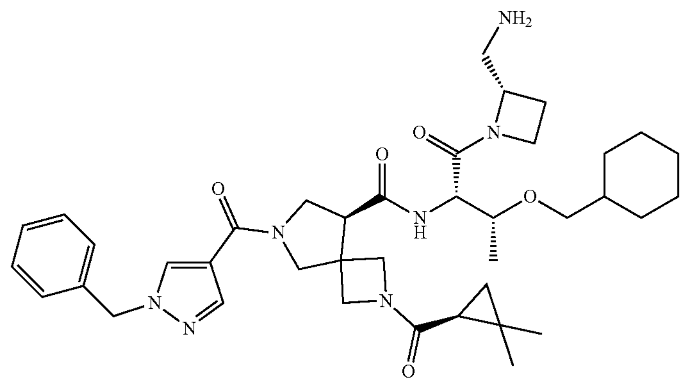 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CC[C@H]1CN] |
| I-311 | 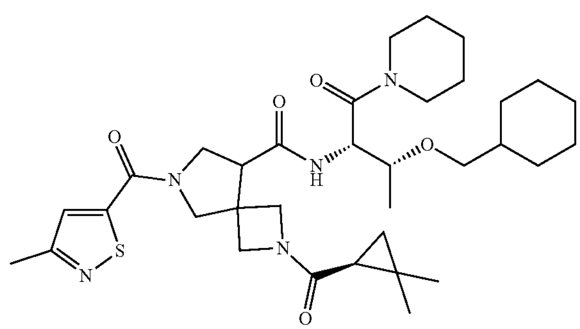 [SMILES: Cc1cc(C(=O)N2CC(C(=O)N[C@H](C(=O)N3CCCCC3)[C@@H](C)OCC3CCCCC3)C3(C2)CN(C(=O)[C@H]2CC2(C)C)C3)sn1] |
| I-312 | 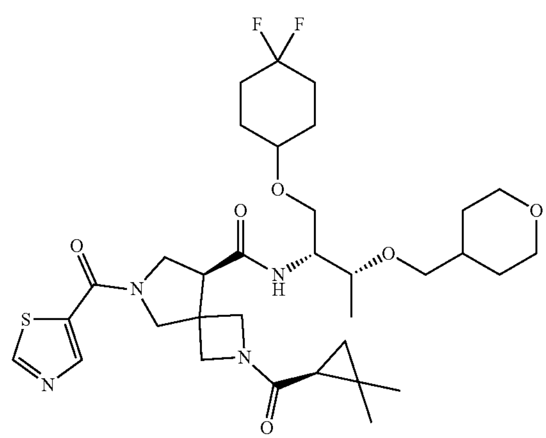 [SMILES: C[C@@H](OCC1CCOCC1)[C@@H](COC1CCC(F)(F)CC1)NC(=O)[C@@H]1CN(C(=O)c2cncs2)CC12CN(C(=O)[C@H]1CC1(C)C)C2] |

TABLE 1-continued

Exemplary Compounds

| Cmpd # | Structure |
|---|---|
| I-313 | 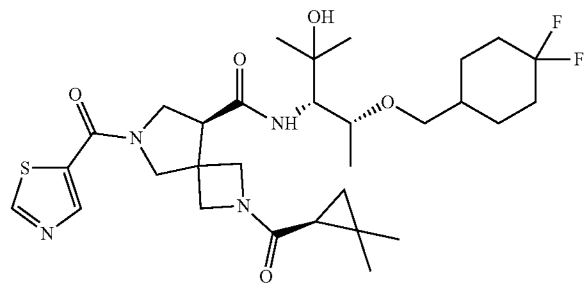 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(C)(C)O] |
| I-314 | 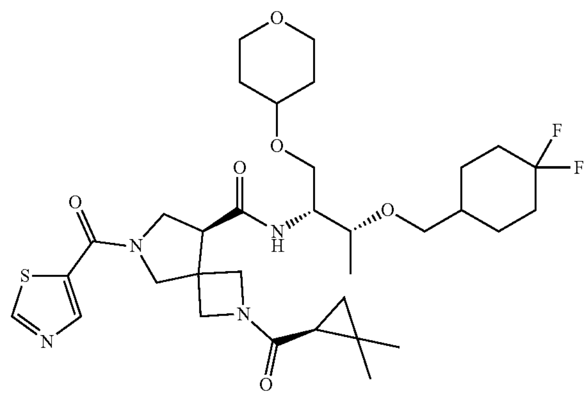 [SMILES: C[C@@H](OCC1CCC(F)(F)CC1)[C@@H](COC1CCOCC1)NC(=O)[C@@H]1CN(C(=O)c2cncs2)CC12CN(C(=O)[C@H]1CC1(C)C)C2] |
| I-315 | 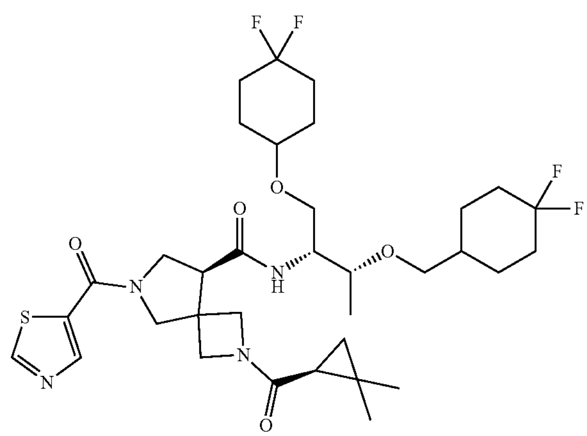 [SMILES: C[C@@H](OCC1CCC(F)(F)CC1)[C@@H](COC1CCC(F)(F)CC1)NC(=O)[C@@H]1CN(C(=O)c2cncs2)CC12CN(C(=O)[C@H]1CC1(C)C)C2] |
| I-316 | 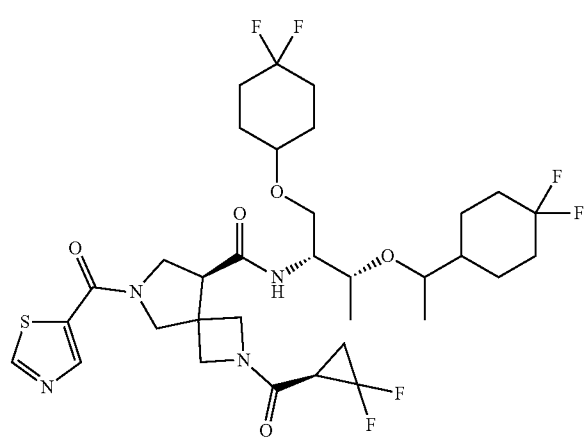 [SMILES: CC(O[C@H](C)[C@@H](COC1CCC(F)(F)CC1)NC(=O)[C@@H]1CN(C(=O)c2cncs2)CC12CN(C(=O)[C@H]1CC1(F)F)C2)C1CCC(F)(F)CC1] |

TABLE 1-continued

Exemplary Compounds

| Cmpd # | Structure |
|---|---|
| I-317 | 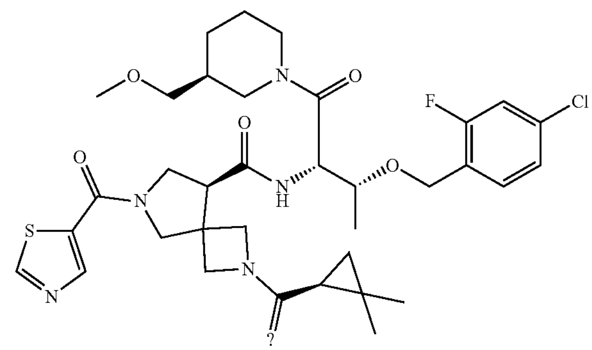 |
| I-318 | 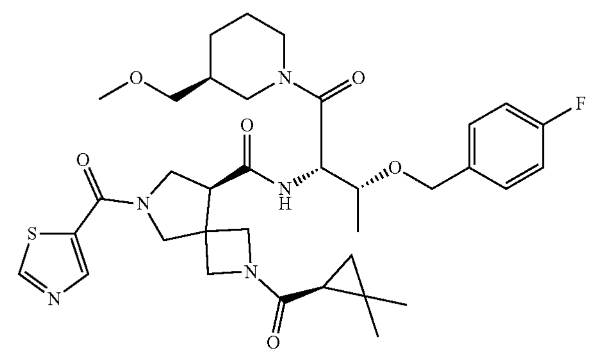 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OCc2ccc(F)cc2)C1] |
| I-319 | 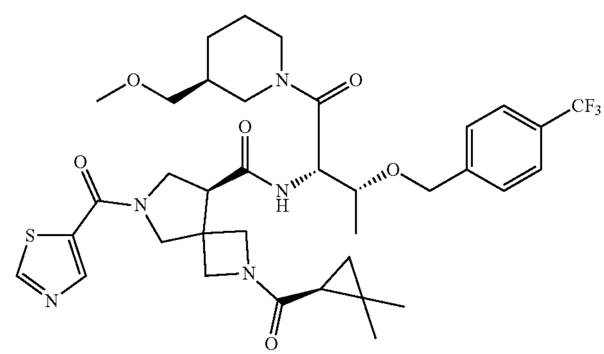 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OCc2ccc(C(F)(F)F)cc2)C1] |
| I-320 | 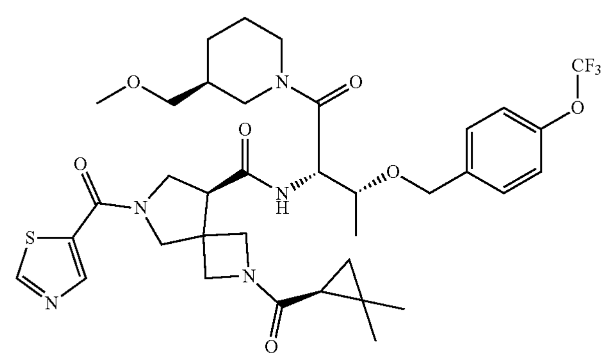 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OCc2ccc(OC(F)(F)F)cc2)C1] |

TABLE 1-continued
Exemplary Compounds
| Cmpd # | Structure |
|---|---|
| I-321 | 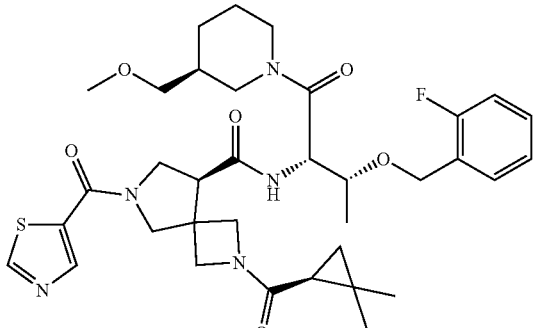 |
| I-322 | 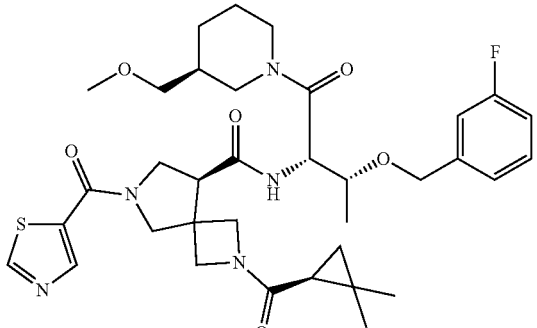 |
| I-323 | 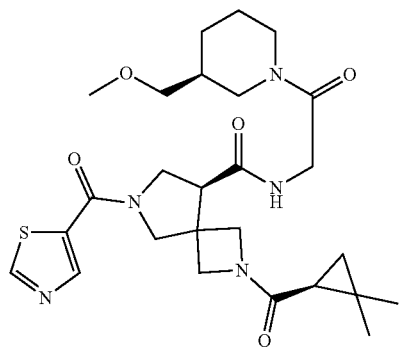 [SMILES: COC[C@H]1CCCN(C(=O)CNC(=O)[C@@H]2CN(C(=O)c3cncs3)CC23CN(C(=O)[C@H]2CC2(C)C)C3)C1] |
| I-324 | 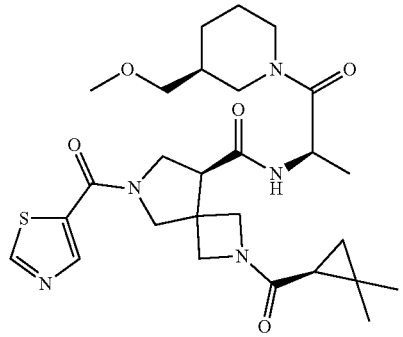 [SMILES: COC[C@H]1CCCN(C(=O)[C@@H](C)NC(=O)[C@@H]2CN(C(=O)c3cncs3)CC23CN(C(=O)[C@H]2CC2(C)C)C3)C1] |

TABLE 1-continued

Exemplary Compounds

| Cmpd # | Structure |
|---|---|
| I-325 | 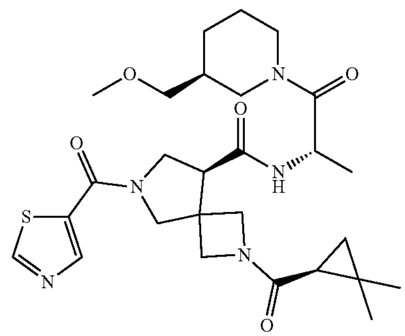 [SMILES: COC[C@H]1CCCN(C(=O)[C@H](C)NC(=O)[C@@H]2CN(C(=O)c3cncs3)CC23CN(C(=O)[C@H]2CC2(C)C)C3)C1] |
| I-326 | 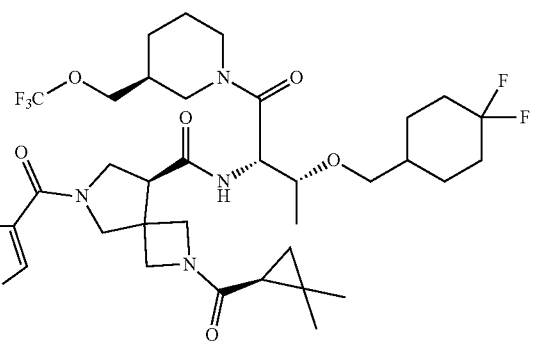 |
| I-327 | 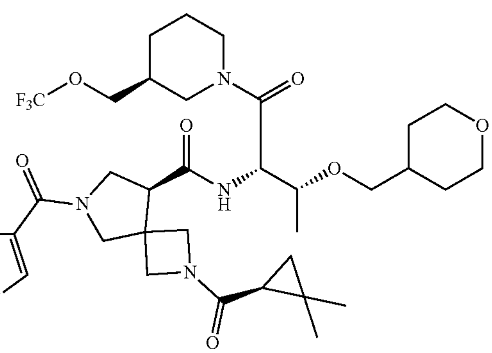 |
| I-328 | 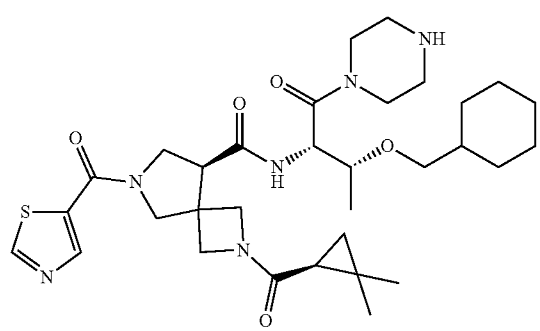 [SMILES: C[C@@H](OCC1CCCCC1)[C@H](NC(=O)[C@@H]1CN(C(=O)c2cncs2)CC12CN(C(=O)[C@H]1CC1(C)C)C2)C(=O)N1CCNCC1] |

TABLE 1-continued
Exemplary Compounds
| Cmpd # | Structure |
|---|---|
| I-329 | 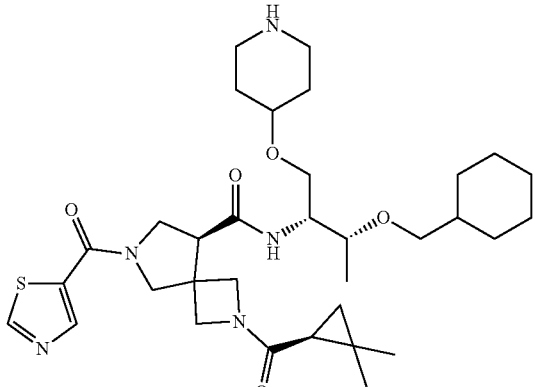 |
| I-330 | 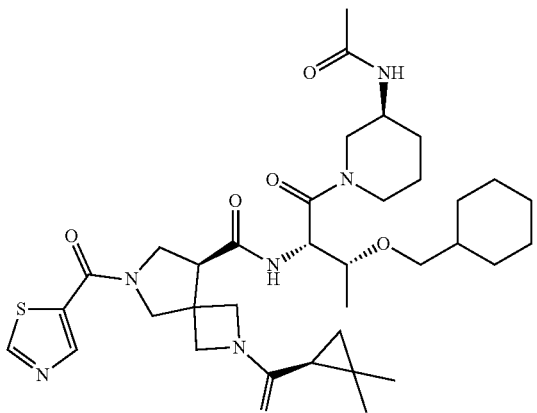 |
| I-331 | 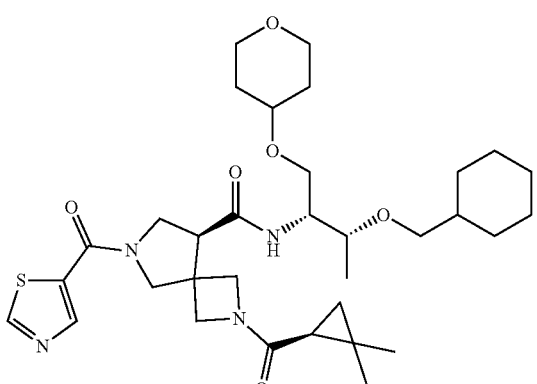 |

TABLE 1-continued
Exemplary Compounds
| Cmpd # | Structure |
|---|---|
| I-332 | 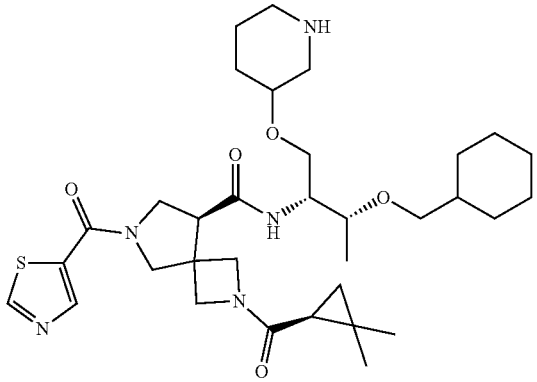 [SMILES: C[C@@H](OCC1CCCCC1)[C@@H](COC1CCCNC1)NC(=O)[C@@H]1CN(C(=O)c2cncs2)CC12CN(C(=O)[C@H]1CC1(C)C)C2] |
| I-333 | 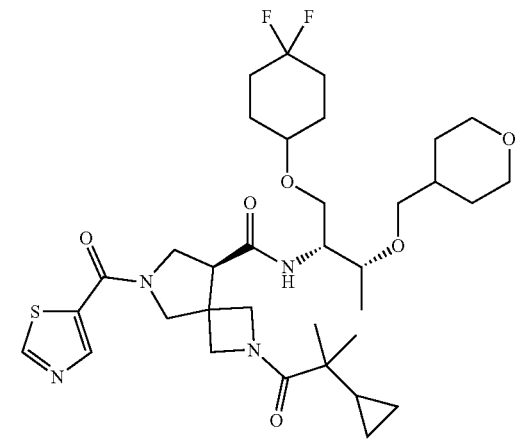 [SMILES: C[C@@H](OCC1CCOCC1)[C@@H](COC1CCC(F)(F)CC1)NC(=O)[C@@H]1CN(C(=O)c2cncs2)CC12CN(C(=O)C(C)(C)C1CC1)C2] |
| I-334 | 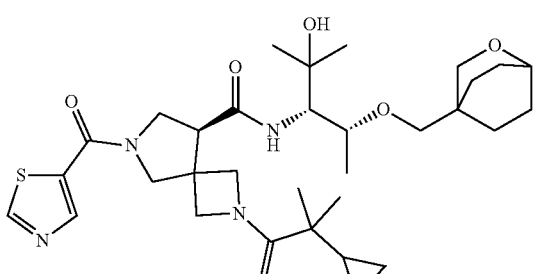 |
| I-335 | 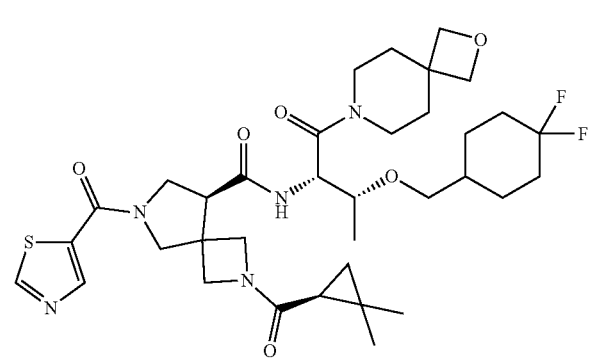 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CCC2(CC1)COC2] |

TABLE 1-continued

Exemplary Compounds

| Cmpd # | Structure |
|---|---|
| I-336 | 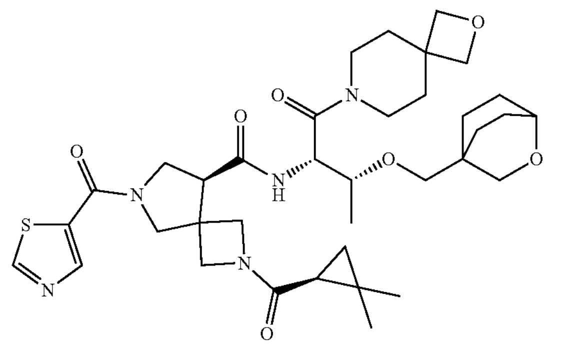 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC2(CC1)COC2] |
| I-337 | 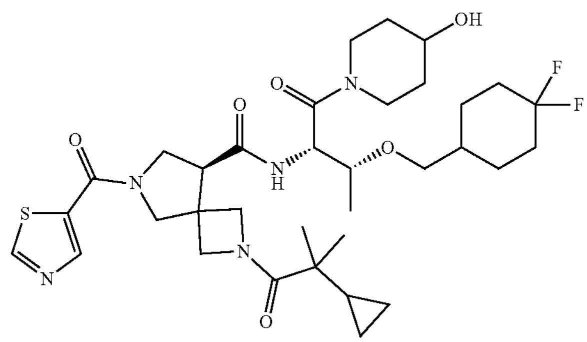 [SMILES: C[C@@H](OCC1CCC(F)(F)CC1)[C@H](NC(=O)[C@@H]1CN(C(=O)c2cncs2)CC12CN(C(=O)C(C)(C)C1CC1)C2)C(=O)N1CCC(O)CC1] |
| I-338 | 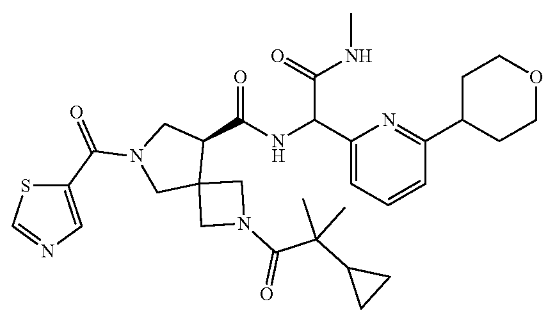 [SMILES: CNC(=O)C(NC(=O)[C@@H]1CN(C(=O)c2cncs2)CC12CN(C(=O)C(C)(C)C1CC1)C2)c1cccc(C2CCOCC2)n1] |
| I-339 | 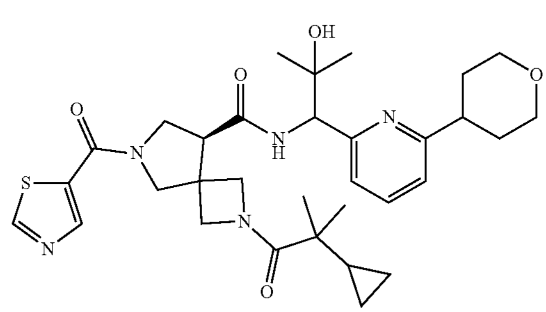 [SMILES: CC(C)(O)C(NC(=O)[C@@H]1CN(C(=O)c2cncs2)CC12CN(C(=O)C(C)(C)C1CC1)C2)c1cccc(C2CCOCC2)n1] |

TABLE 1-continued
Exemplary Compounds
| Cmpd # | Structure |
|---|---|
| I-340 | 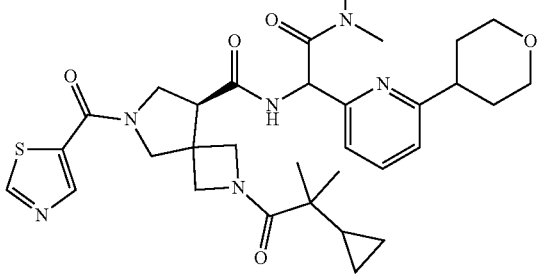 |
| I-341 | 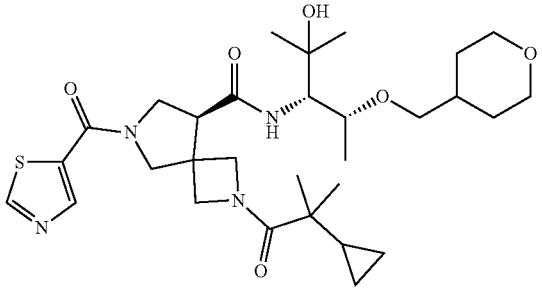 [SMILES: C[C@@H](OCC1CCOCC1)[C@H](NC(=O)[C@@H]1CN(C(=O)c2cncs2)CC12CN(C(=O)C(C)(C)C1CC1)C2)C(C)(C)O] |
| I-342 | 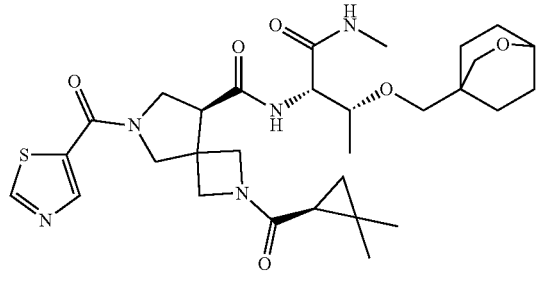 [SMILES: CNC(=O)[C@@H](NC(=O)[C@@H]1CN(C(=O)c2cncs2)CC12CN(C(=O)[C@H]1CC1(C)C)C2)[C@@H](C)OCC12CCC(CC1)OC2] |
| I-343 | 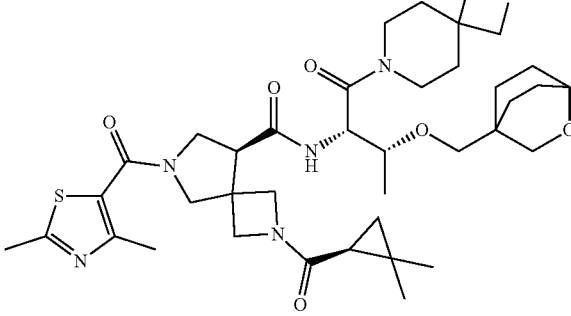 |
| I-344 | 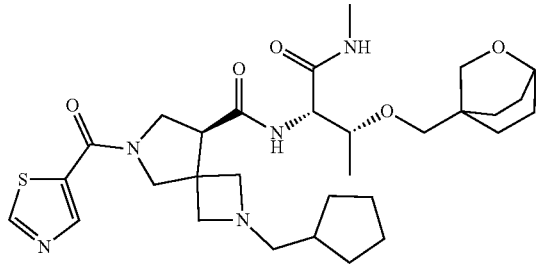 [SMILES: CNC(=O)[C@@H](NC(=O)[C@@H]1CN(C(=O)c2cncs2)CC12CN(CC1CCCC1)C2)[C@@H](C)OCC12CCC(CC1)OC2] |

TABLE 1-continued

Exemplary Compounds

| Cmpd # | Structure |
| --- | --- |
| I-345 | 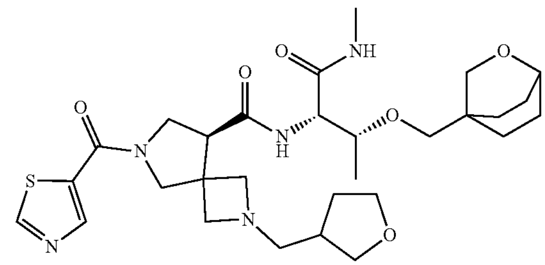 [SMILES: CNC(=O)[C@@H](NC(=O)[C@@H]1CN(C(=O)c2cncs2)CC12CN(CC1CCOC1)C2)[C@@H](C)OCC12CCC(CC1)OC2] |
| I-346 | 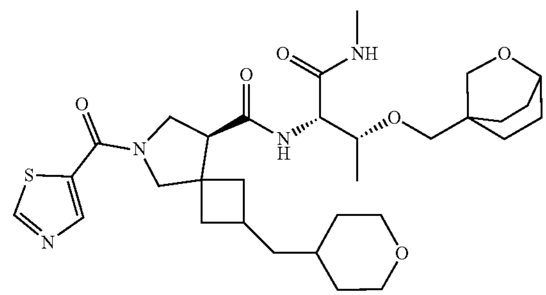 [SMILES: CNC(=O)[C@@H](NC(=O)[C@@H]1CN(C(=O)c2cncs2)CC12CC(CC1CCOCC1)C2)[C@@H](C)OCC12CCC(CC1)OC2] |
| I-347 | 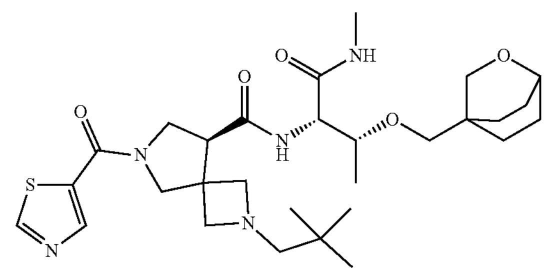 [SMILES: CNC(=O)[C@@H](NC(=O)[C@@H]1CN(C(=O)c2cncs2)CC12CN(CC(C)(C)C)C2)[C@@H](C)OCC12CCC(CC1)OC2] |
| I-348 | 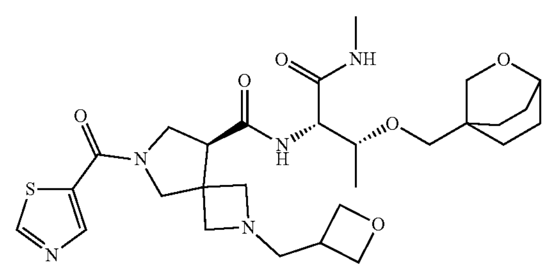 [SMILES: CNC(=O)[C@@H](NC(=O)[C@@H]1CN(C(=O)c2cncs2)CC12CN(CC1COC1)C2)[C@@H](C)OCC12CCC(CC1)OC2] |
| I-349 | 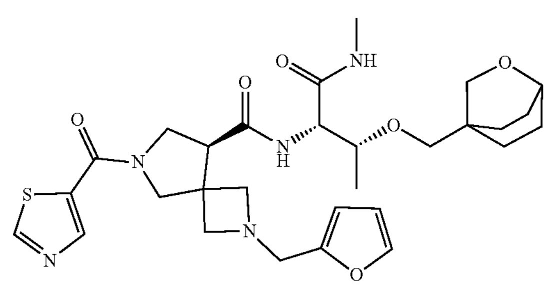 [SMILES: CNC(=O)[C@@H](NC(=O)[C@@H]1CN(C(=O)c2cncs2)CC12CN(Cc1ccco1)C2)[C@@H](C)OCC12CCC(CC1)OC2] |

TABLE 1-continued

Exemplary Compounds

| Cmpd # | Structure |
|---|---|
| I-350 | 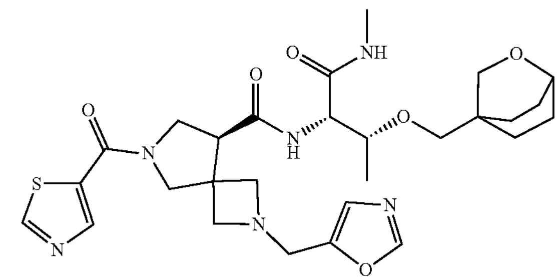 [SMILES: CNC(=O)[C@@H](NC(=O)[C@@H]1CN(C(=O)c2cncs2)CC12CN(Cc1cnco1)C2)[C@@H](C)OCC12CCC(CC1)OC2] |
| I-351 | 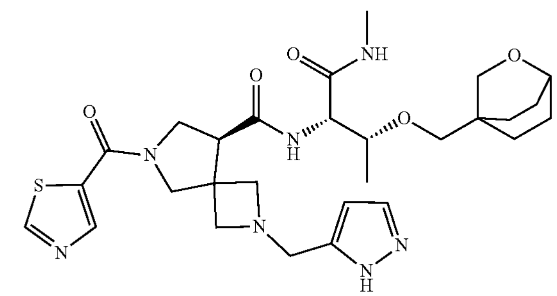 [SMILES: CNC(=O)[C@@H](NC(=O)[C@@H]1CN(C(=O)c2cncs2)CC12CN(Cc1ccn[nH]1)C2)[C@@H](C)OCC12CCC(CC1)OC2] |
| I-352 | 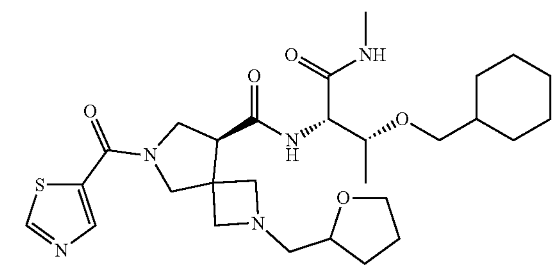 [SMILES: CNC(=O)[C@@H](NC(=O)[C@@H]1CN(C(=O)c2cncs2)CC12CN(CC1CCCO1)C2)[C@@H](C)OCC1CCCCC1] |
| I-353 | 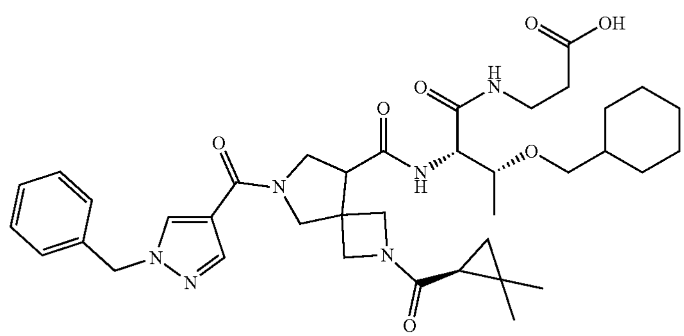 [SMILES: C[C@@H](OCC1CCCCC1)[C@H](NC(=O)C1CN(C(=O)c2cnn(Cc3ccccc3)c2)CC12CN(C(=O)[C@H]1CC1(C)C)C2)C(=O)NCCC(=O)O] |
| I-354 | 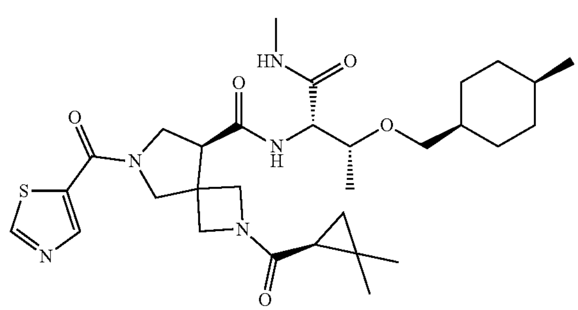 [SMILES: CNC(=O)[C@@H](NC(=O)[C@@H]1CN(C(=O)c2cncs2)CC12CN(C(=O)[C@H]1CC1(C)C)C2)[C@@H](C)OC[C@H]1CC[C@@H](C)CC1] |

TABLE 1-continued
Exemplary Compounds
| Cmpd # | Structure |
|---|---|
| I-355 | 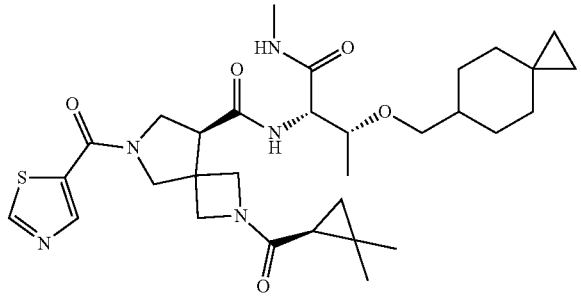 [SMILES: CNC(=O)[C@@H](NC(=O)[C@@H]1CN(C(=O)c2cncs2)CC12CN(C(=O)[C@H]1CC1(C)C)C2)[C@@H](C)OCC1CCC2(CC1)CC2] |
| I-356 | 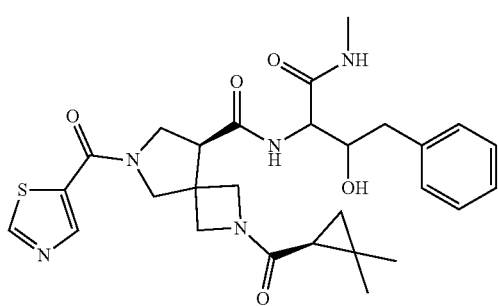 [SMILES: CNC(=O)C(NC(=O)[C@@H]1CN(C(=O)c2cncs2)CC12CN(C(=O)[C@H]1CC1(C)C)C2)C(O)Cc1ccccc1] |
| I-357 | 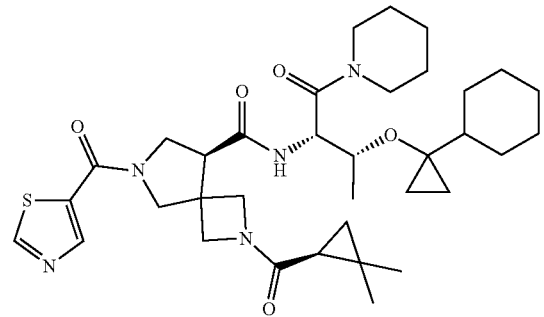 [SMILES: C[C@@H](OC1(C2CCCCC2)CC1)[C@H](NC(=O)[C@@H]1CN(C(=O)c2cncs2)CC12CN(C(=O)[C@H]1CC1(C)C)C2)C(=O)N1CCCCC1] |
| I-358 | 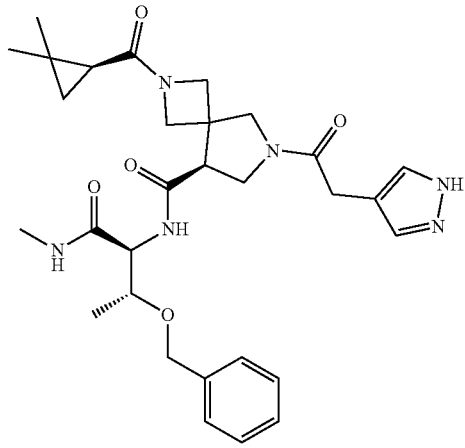 [SMILES: CNC(=O)[C@@H](NC(=O)[C@@H]1CN(C(=O)Cc2cn[nH]c2)CC12CN(C(=O)[C@H]1CC1(C)C)C2)[C@@H](C)OCc1ccccc1] |

TABLE 1-continued
Exemplary Compounds
| Cmpd # | Structure |
|---|---|
| I-359 | 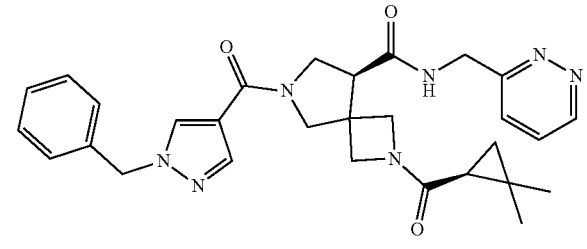 [SMILES: CC1(C)C[C@@H]1C(=O)N1CC2(CN(C(=O)c3cnn(Cc4ccccc4)c3)C[C@H]2C(=O)NCc2cccnn2)C1] |
| I-360 | 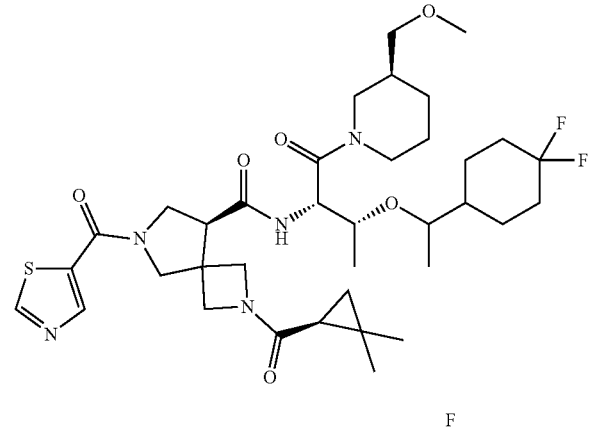 |
| I-361 | 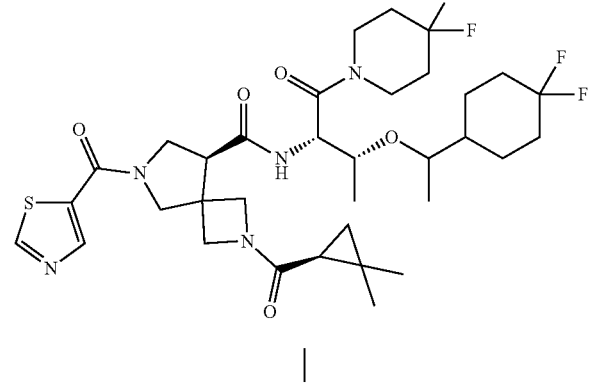 |
| I-362 | 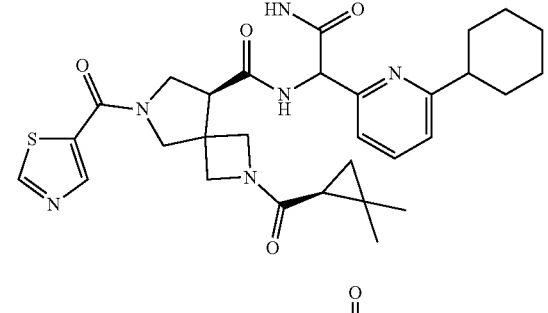 |
| I-363 | 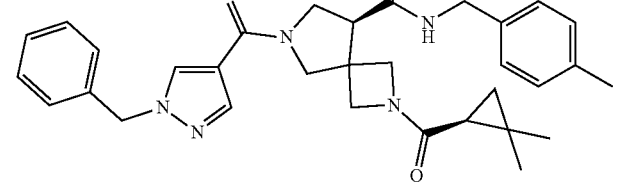 |

TABLE 1-continued
Exemplary Compounds
| Cmpd # | Structure |
|---|---|
| I-364 | 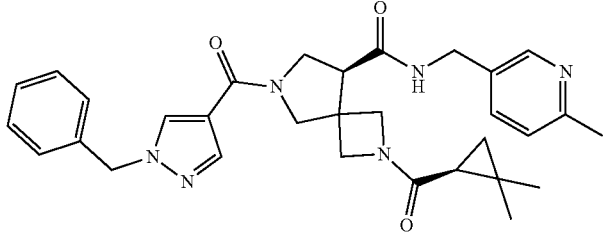 [SMILES: Cc1ccc(CNC(=O)[C@@H]2CN(C(=O)c3cnn(Cc4ccccc4)c3)CC23CN(C(=O)[C@H]2CC2(C)C)C3)cn1] |
| I-365 | 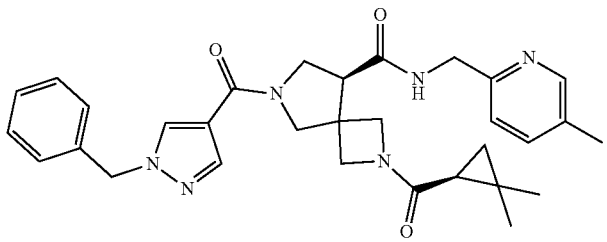 [SMILES: Cc1ccc(CNC(=O)[C@@H]2CN(C(=O)c3cnn(Cc4ccccc4)c3)CC23CN(C(=O)[C@H]2CC2(C)C)C3)nc1] |
| I-366 | 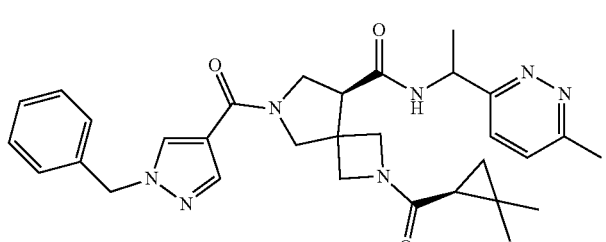 |
| I-367 | 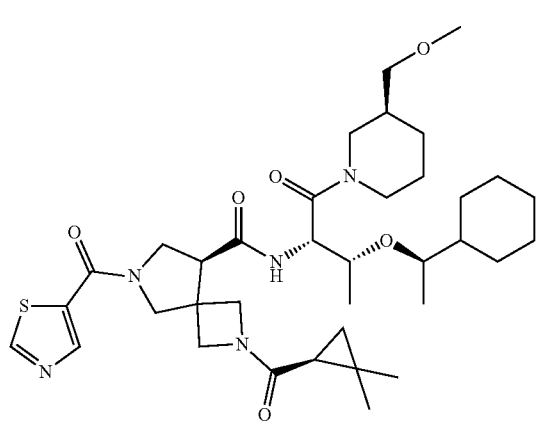 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)O[C@H](C)C2CCCCC2)C1] |

TABLE 1-continued

Exemplary Compounds

| Cmpd # | Structure |
|---|---|
| I-368 | 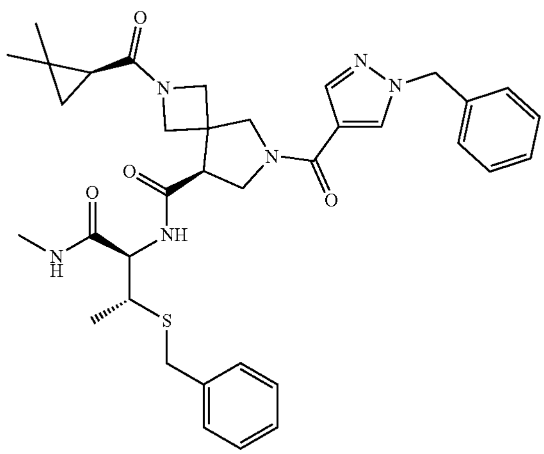 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)SCc1ccccc1] |
| I-369 | 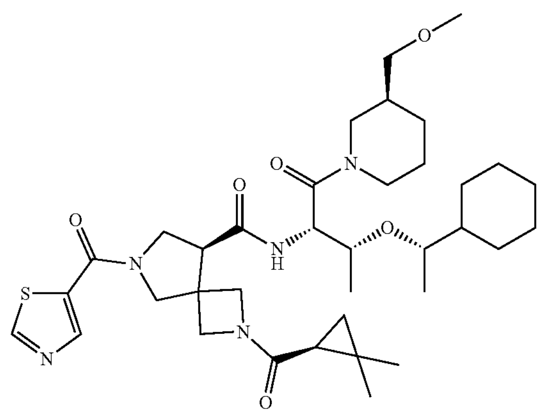 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)O[C@@H](C)C2CCCCC2)C1] |
| I-370 | 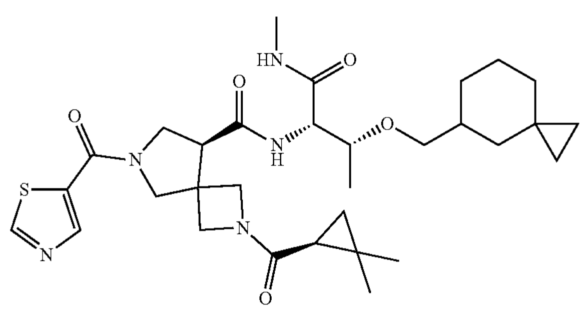 [SMILES: CNC(=O)[C@@H](NC(=O)[C@@H]1CN(C(=O)c2cncs2)CC12CN(C(=O)[C@H]1CC1(C)C)C2)[C@@H](C)OCC1CCCC2(CC2)C1] |
| I-371 | 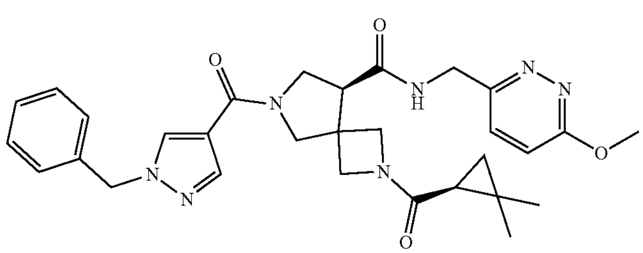 [SMILES: COc1ccc(CNC(=O)[C@@H]2CN(C(=O)c3cnn(Cc4ccccc4)c3)CC23CN(C(=O)[C@H]2CC2(C)C)C3)nn1] |

TABLE 1-continued

Exemplary Compounds

| Cmpd # | Structure |
|---|---|
| I-372 | 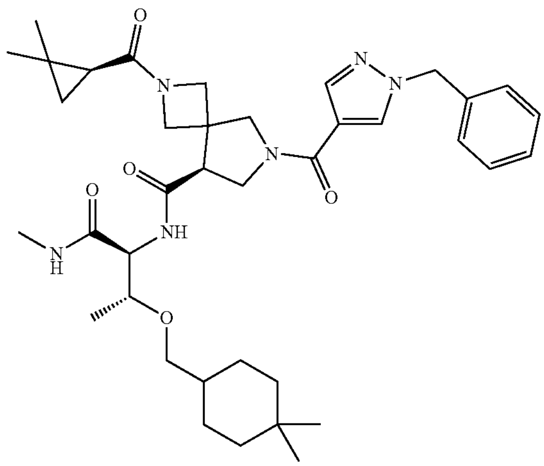 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC1CCC(C)(C)CC1] |
| I-373 | 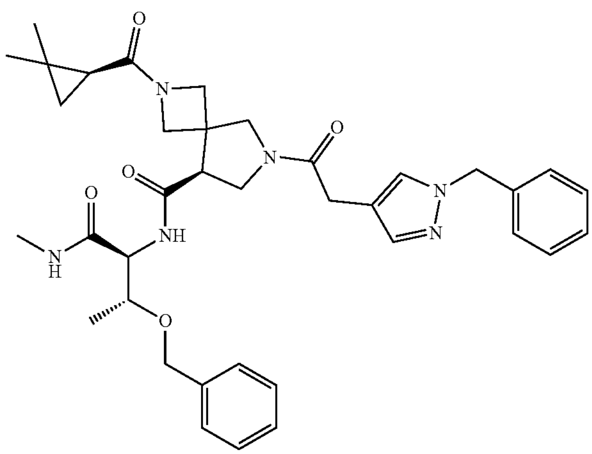 [SMILES: CNC(=O)[C@@H](NC(=O)[C@@H]1CN(C(=O)Cc2cnn(Cc3ccccc3)c2)CC12CN(C(=O)[C@H]1CC1(C)C)C2)[C@@H](C)OCc1ccccc1] |
| I-374 | 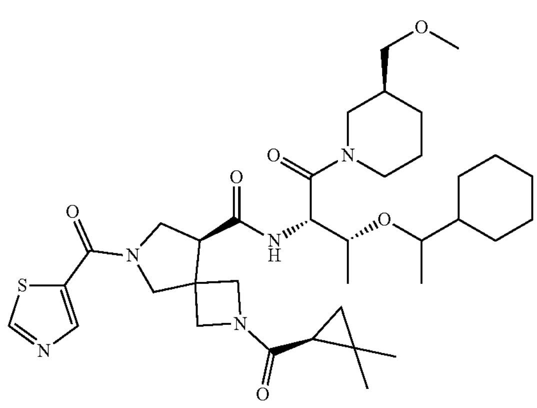 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OC(C)C2CCCCC2)C1] |

TABLE 1-continued

Exemplary Compounds

| Cmpd # | Structure |
|---|---|
| I-375 | 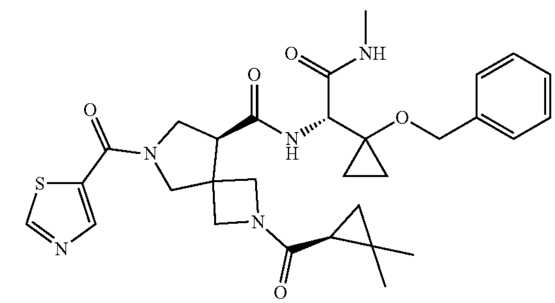 [SMILES: CNC(=O)[C@@H](NC(=O)[C@@H]1CN(C(=O)c2cncs2)CC12CN(C(=O)[C@H]1CC1(C)C)C2)C1(OCc2ccccc2)CC1] |
| I-376 | 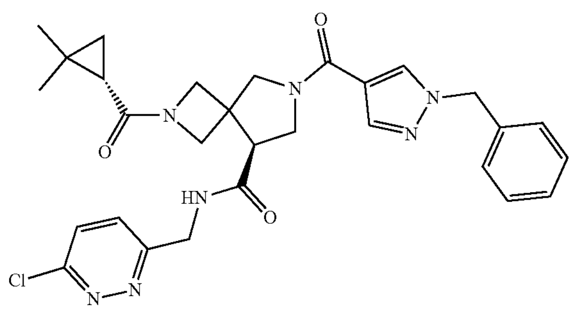 [SMILES: CC1(C)C[C@@H]1C(=O)N1CC2(CN(C(=O)c3cnn(Cc4ccccc4)c3)C[C@H]2C(=O)NCc2ccc(Cl)nn2)C1] |
| I-377 | 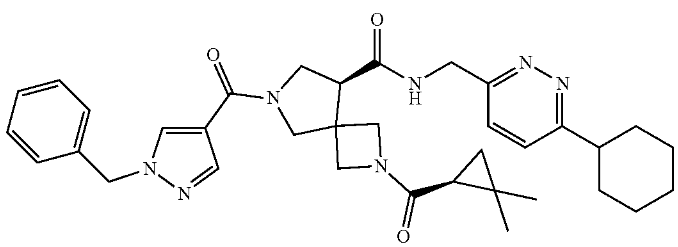 [SMILES: CC1(C)C[C@@H]1C(=O)N1CC2(CN(C(=O)c3cnn(Cc4ccccc4)c3)C[C@H]2C(=O)NCc2ccc(C3CCCCC3)nn2)C1] |
| I-378 | 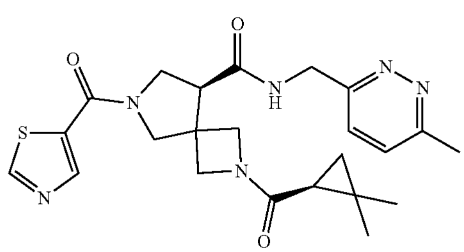 [SMILES: Cc1ccc(CNC(=O)[C@@H]2CN(C(=O)c3cncs3)CC23CN(C(=O)[C@H]2CC2(C)C)C3)nn1] |
| I-379 | 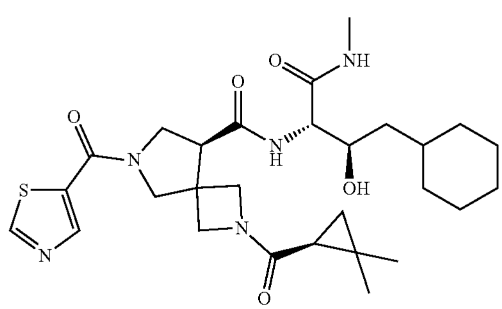 [SMILES: CNC(=O)[C@@H](NC(=O)[C@@H]1CN(C(=O)c2cncs2)CC12CN(C(=O)[C@H]1CC1(C)C)C2)[C@H](O)CC1CCCCC1] |

TABLE 1-continued
Exemplary Compounds
| Cmpd # | Structure |
|---|---|
| I-380 | 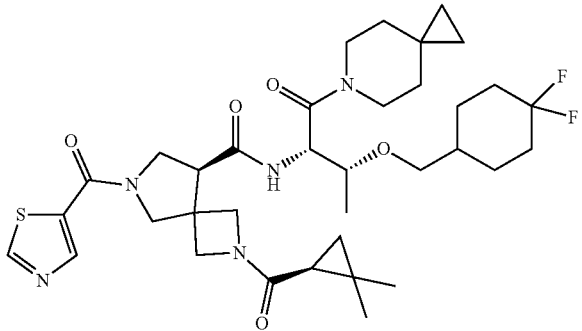 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CCC2(CC1)CC2] |
| I-381 | 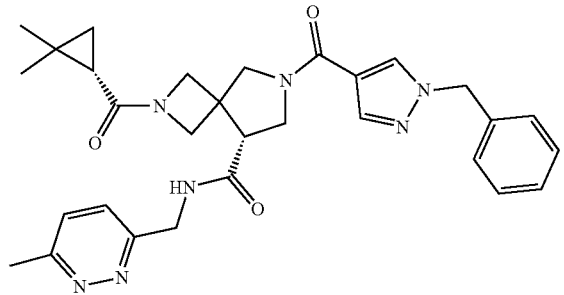 [SMILES: Cc1ccc(CNC(=O)[C@H]2CN(C(=O)c3cnn(Cc4ccccc4)c3)CC23CN(C(=O)[C@H]2CC2(C)C)C3)nn1] |
| I-382 | 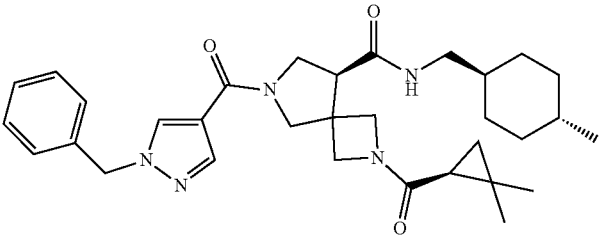 [SMILES: CC1(C)C[C@@H]1C(=O)N1CC2(CN(C(=O)c3cnn(Cc4ccccc4)c3)C[C@H]2C(=O)NC[C@H]2CC[C@H](C)CC2)C1] |
| I-383 | 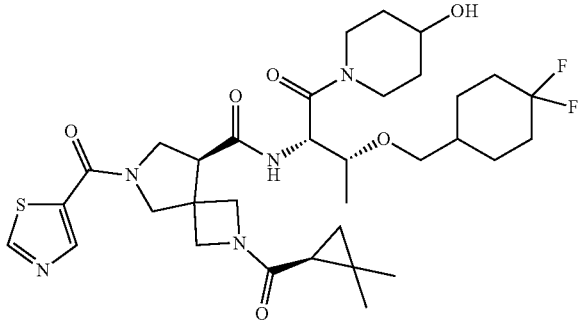 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CCC(O)CC1] |

TABLE 1-continued

Exemplary Compounds

| Cmpd # | Structure |
|---|---|
| I-384 | 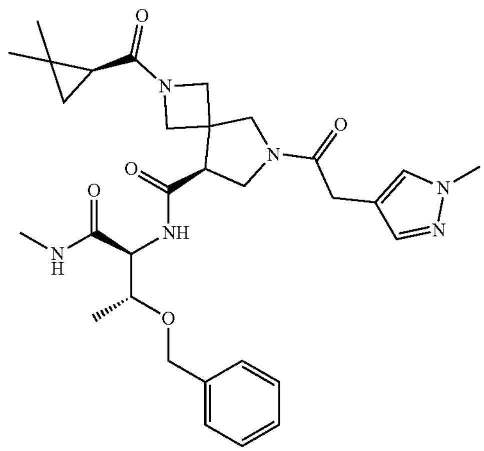 |
| I-385 | 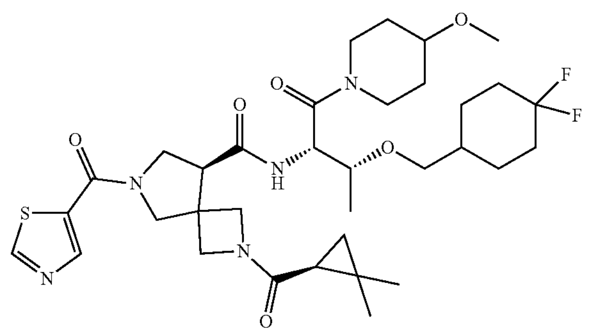 [SMILES: COC1CCN(C(=O)[C@@H](NC(=O)[C@@H]2CN(C(=O)c3cncs3)CC23CN(C(=O)[C@H]2CC2(C)C)C3)[C@@H](C)OCC2CCC(F)(F)CC2)CC1] |
| I-386 | 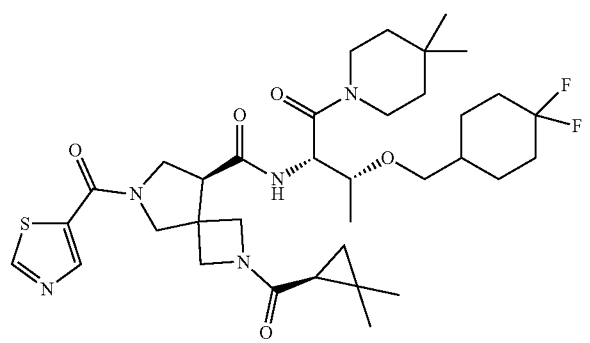 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CCC(C)(C)CC1] |
| I-387 | 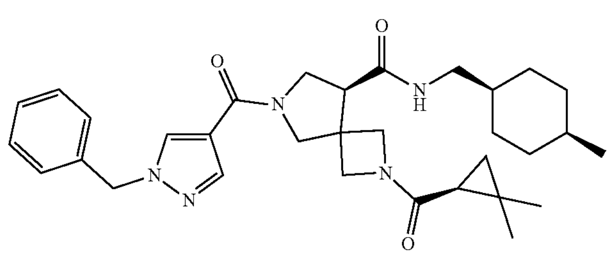 [SMILES: CC1(C)C[C@@H]1C(=O)N1CC2(CN(C(=O)c3cnn(Cc4ccccc4)c3)C[C@H]2C(=O)NC[C@H]2CC[C@@H](C)CC2)C1] |

TABLE 1-continued

Exemplary Compounds

| Cmpd # | Structure |
|---|---|
| I-388 | 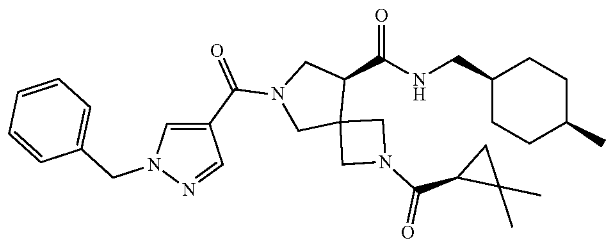 [SMILES: CC1(C)C[C@@H]1C(=O)N1CC2(CN(C(=O)c3cnn(Cc4ccccc4)c3)C[C@H]2C(=O)NC[C@H]2CC[C@@H](C)CC2)C1] |
| I-389 | 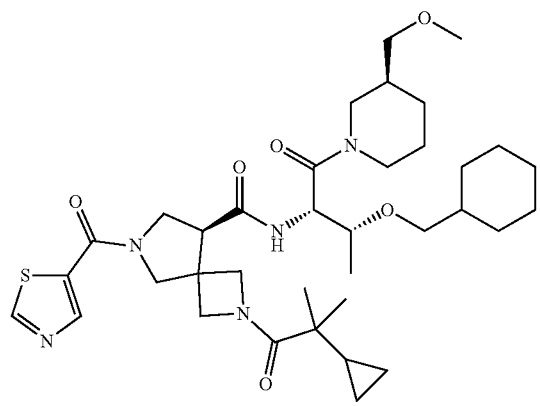 [SMILES: COC[C@H]1CCCN(C(=O)[C@@H](NC(=O)[C@@H]2CN(C(=O)c3cncs3)CC23CN(C(=O)C(C)(C)C2CC2)C3)[C@@H](C)OCC2CCCCC2)C1] |
| I-390 | 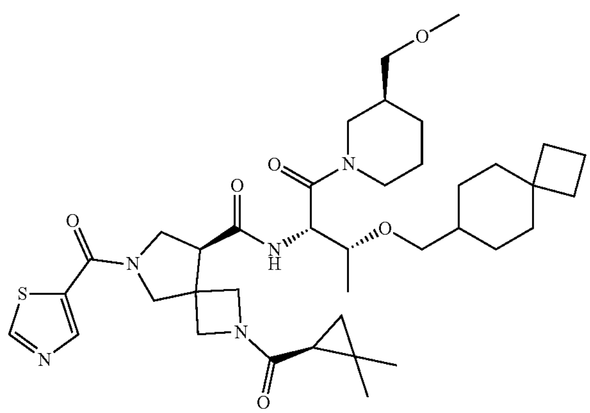 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OCC2CCC3(CCC3)CC2)C1] |
| I-391 | 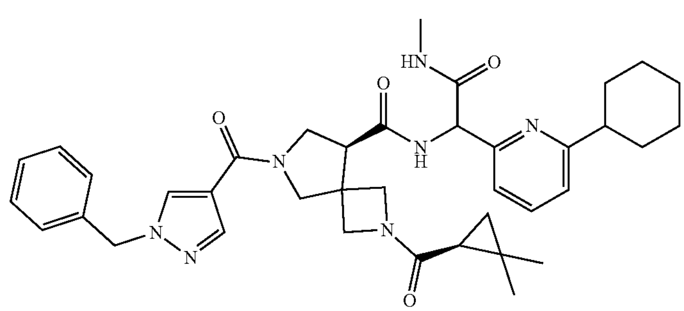 [SMILES: CNC(=O)C(NC(=O)[C@@H]1CN(C(=O)c2cnn(Cc3ccccc3)c2)CC12CN(C(=O)[C@H]1CC1(C)C)C2)c1cccc(C2CCCCC2)n1] |

TABLE 1-continued
Exemplary Compounds
| Cmpd # | Structure |
|---|---|
| I-392 | 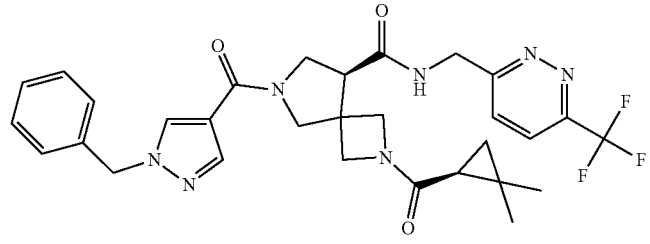 [SMILES: CC1(C)C[C@@H]1C(=O)N1CC2(CN(C(=O)c3cnn(Cc4ccccc4)c3)C[C@H]2C(=O)NCc2ccc(C(F)(F)F)nn2)C1] |
| I-393 | 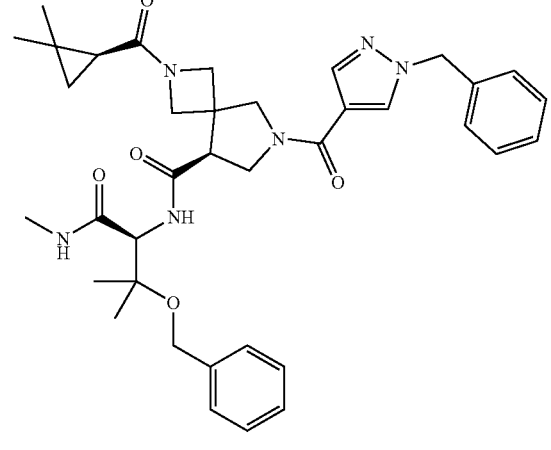 |
| I-394 | 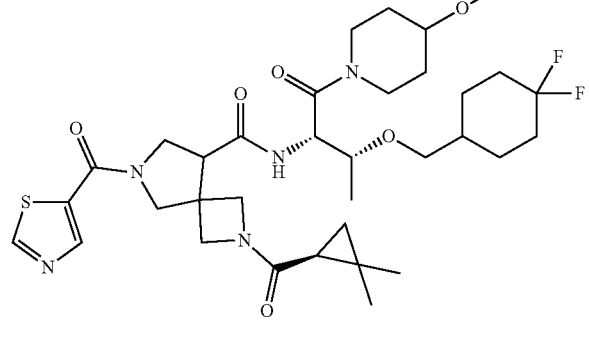 |
| I-395 | 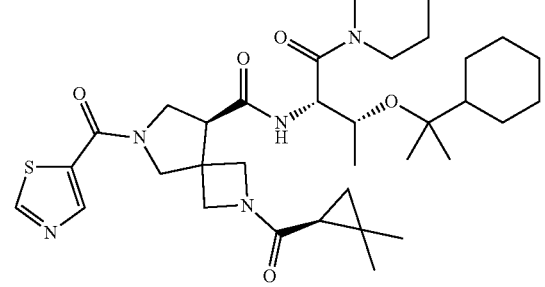 |

TABLE 1-continued

Exemplary Compounds

| Cmpd # | Structure |
|---|---|
| I-396 | 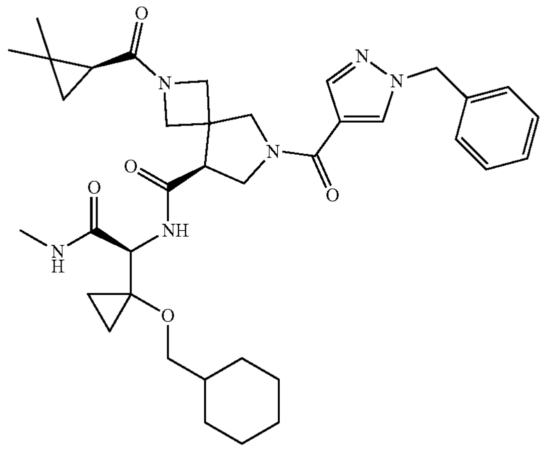 [SMILES: CNC(=O)[C@@H](NC(=O)[C@@H]1CN(C(=O)c2cnn(Cc3ccccc3)c2)CC12CN(C(=O)[C@H]1CC1(C)C)C2)C1(OCC2CCCCC2)CC1] |
| I-397 | 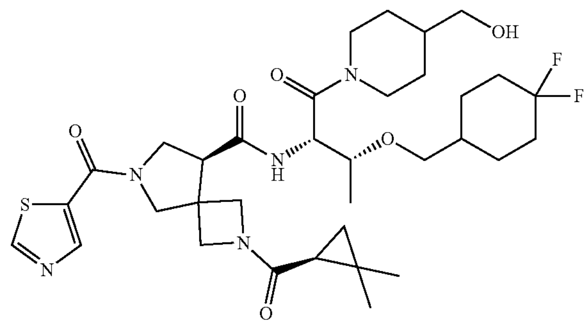 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CCC(CO)CC1] |
| I-398 | 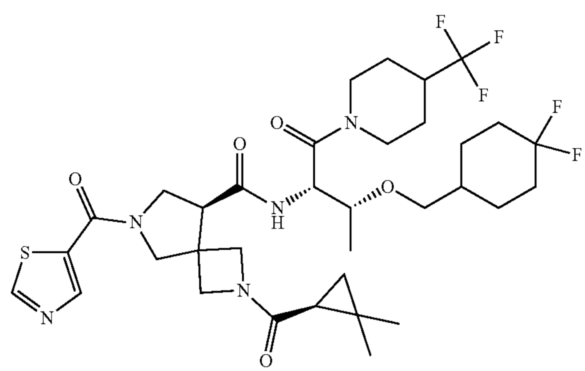 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CCC(C(F)(F)F)CC1] |
| I-399 | 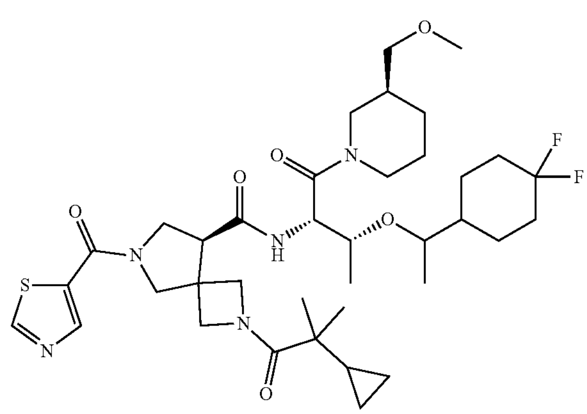 [SMILES: COC[C@H]1CCCN(C(=O)[C@@H](NC(=O)[C@@H]2CN(C(=O)c3cncs3)CC23CN(C(=O)C(C)(C)C2CC2)C3)[C@@H](C)OC(C)C2CCC(F)(F)CC2)C1] |

TABLE 1-continued

Exemplary Compounds

| Cmpd # | Structure |
|---|---|
| I-400 | 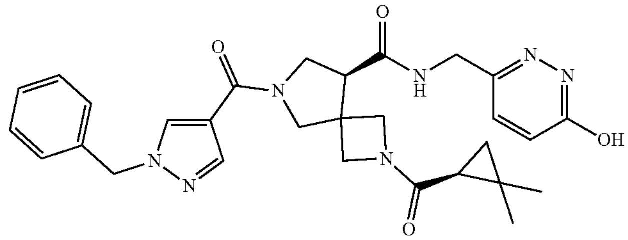 [SMILES: CC1(C)C[C@@H]1C(=O)N1CC2(CN(C(=O)c3cnn(Cc4ccccc4)c3)C[C@H]2C(=O)NCc2ccc(O)nn2)C1] |
| I-401 | 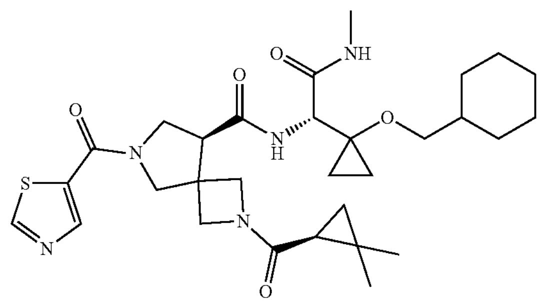 [SMILES: CNC(=O)[C@@H](NC(=O)[C@@H]1CN(C(=O)c2cncs2)CC12CN(C(=O)[C@H]1CC1(C)C)C2)C1(OCC2CCCCC2)CC1] |
| I-402 | 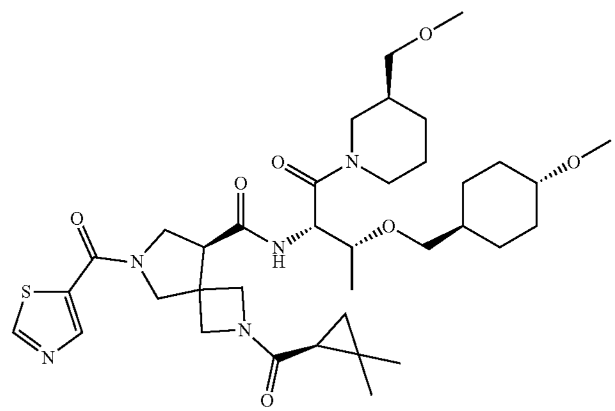 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OC[C@H]2CC[C@H](OC)CC2)C1] |
| I-403 | 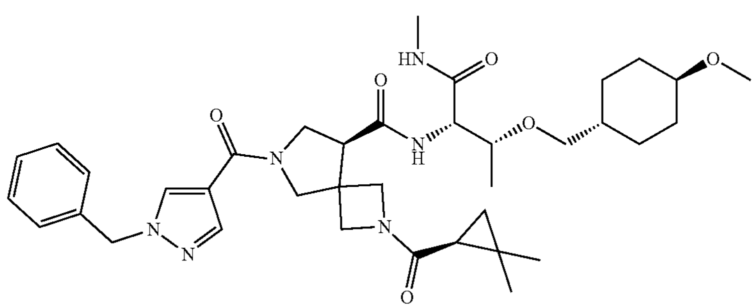 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OC[C@H]1CC[C@H](OC)CC1] |
| I-404 | 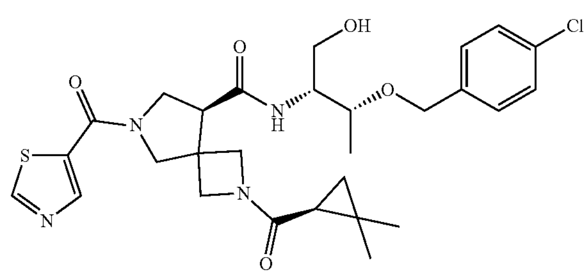 [SMILES: C[C@@H](OCc1ccc(Cl)cc1)[C@@H](CO)NC(=O)[C@@H]1CN(C(=O)c2cncs2)CC12CN(C(=O)[C@H]1CC1(C)C)C2] |

TABLE 1-continued
Exemplary Compounds
| Cmpd # | Structure |
|---|---|
| I-405 | 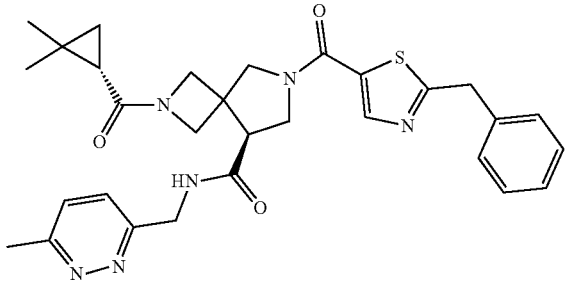 [SMILES: Cc1ccc(CNC(=O)[C@@H]2CN(C(=O)c3cnc(Cc4ccccc4)s3)CC23CN(C(=O)[C@H]2CC2(C)C)C3)nn1] |
| I-406 | 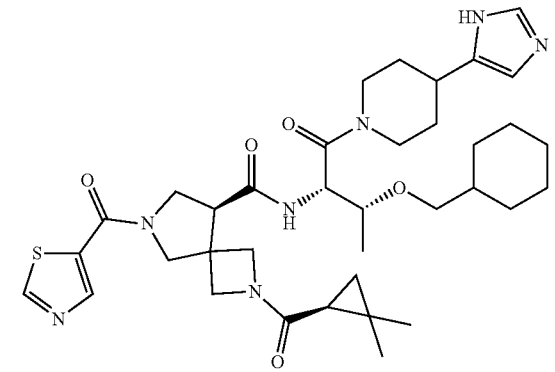 [SMILES: C[C@@H](OCC1CCCCC1)[C@H](NC(=O)[C@@H]1CN(C(=O)c2cncs2)CC12CN(C(=O)[C@H]1CC1(C)C)C2)C(=O)N1CCC(c2cnc[nH]2)CC1] |
| I-407 | 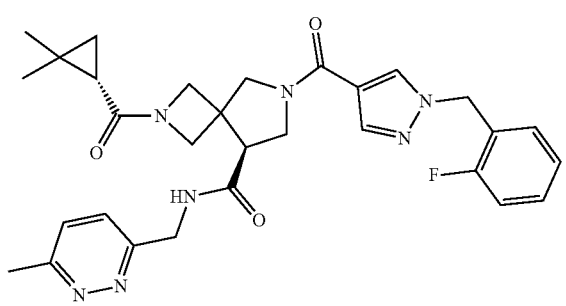 [SMILES: Cc1ccc(CNC(=O)[C@@H]2CN(C(=O)c3cnn(Cc4ccccc4F)c3)CC23CN(C(=O)[C@H]2CC2(C)C)C3)nn1] |
| I-408 | 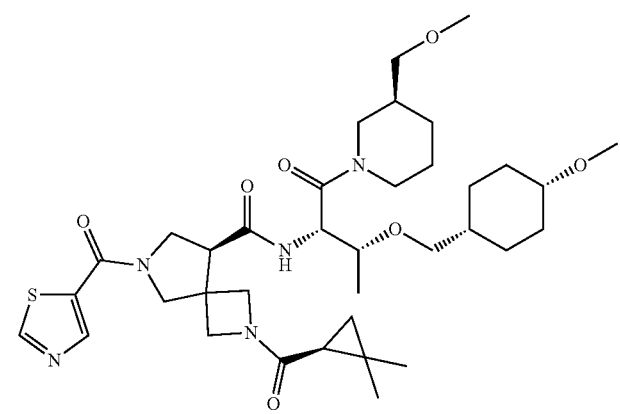 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OC[C@H]2CC[C@@H](OC)CC2)C1] |

TABLE 1-continued

Exemplary Compounds

| Cmpd # | Structure |
|---|---|
| I-409 | 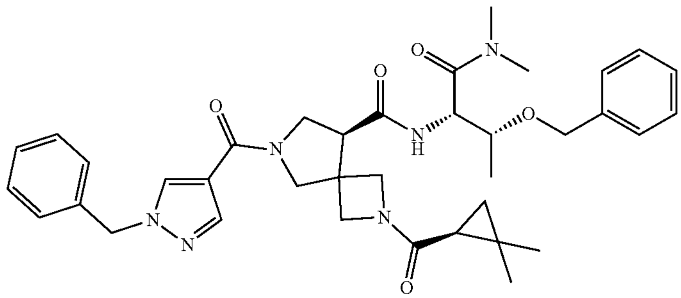 [SMILES: C[C@@H](OCc1ccccc1)[C@H](NC(=O)[C@@H]1CN(C(=O)c2cnn(Cc3ccccc3)c2)CC12CN(C(=O)[C@H]1CC1(C)C)C2)C(=O)N(C)C] |
| I-410 | 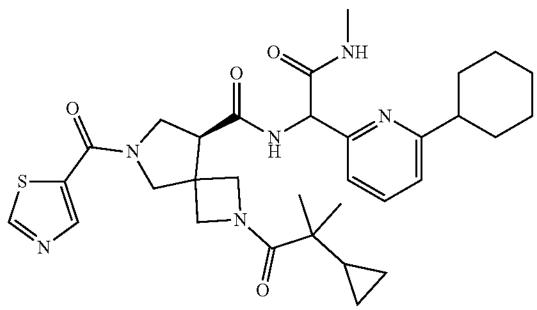 [SMILES: CNC(=O)C(NC(=O)[C@@H]1CN(C(=O)c2cncs2)CC12CN(C(=O)C(C)(C)C1CC1)C2)c1cccc(C2CCCCC2)n1] |
| I-411 | 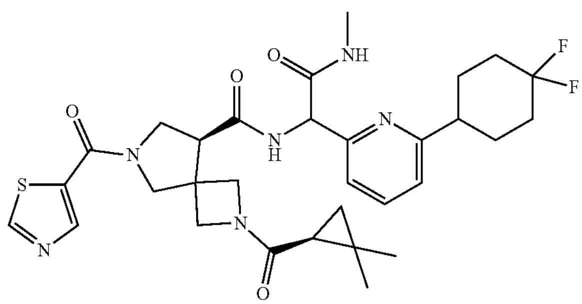 [SMILES: CNC(=O)C(NC(=O)[C@@H]1CN(C(=O)c2cncs2)CC12CN(C(=O)[C@H]1CC1(C)C)C2)c1cccc(C2CCC(F)(F)CC2)n1] |
| I-412 | 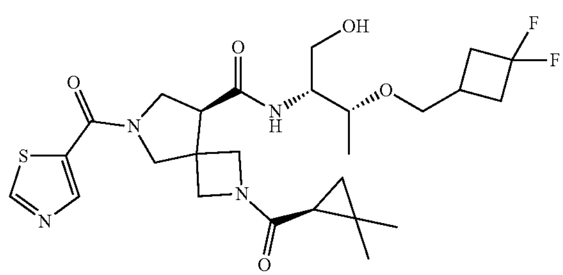 [SMILES: C[C@@H](OCC1CC(F)(F)C1)[C@@H](CO)NC(=O)[C@@H]1CN(C(=O)c2cncs2)CC12CN(C(=O)[C@H]1CC1(C)C)C2] |
| I-413 | 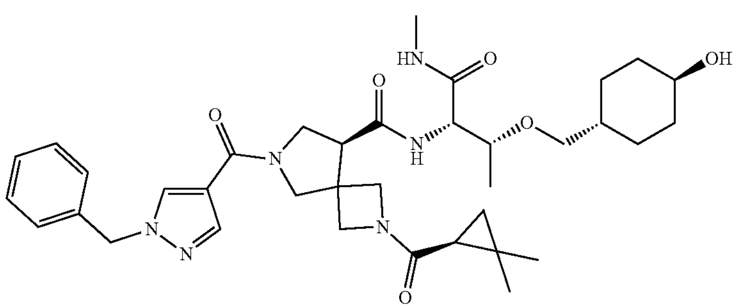 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OC[C@H]1CC[C@H](O)CC1] |

TABLE 1-continued

Exemplary Compounds

| Cmpd # | Structure |
|---|---|
| I-414 | 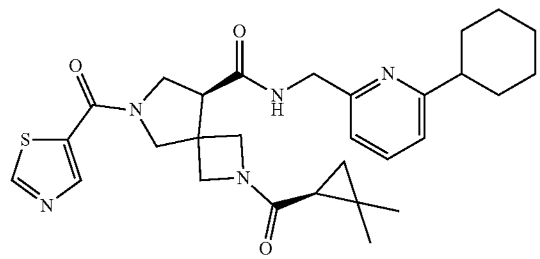 [SMILES: CC1(C)C[C@@H]1C(=O)N1CC2(CN(C(=O)c3cncs3)C[C@H]2C(=O)NCc2cccc(C3CCCCC3)n2)C1] |
| I-415 | 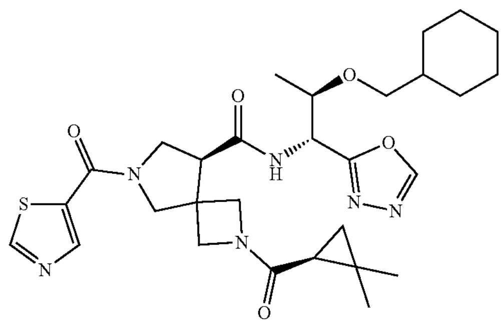 [SMILES: C[C@@H](OCC1CCCCC1)[C@@H](NC(=O)[C@@H]1CN(C(=O)c2cncs2)CC12CN(C(=O)[C@H]1CC1(C)C)C2)c1nnco1] |
| I-416 | 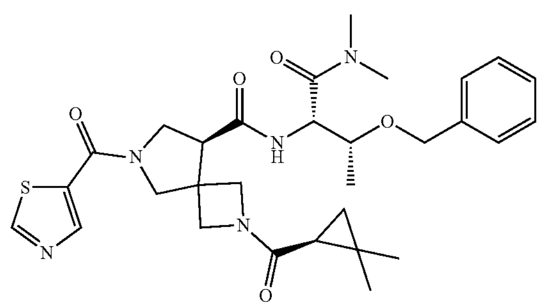 [SMILES: C[C@@H](OCc1ccccc1)[C@H](NC(=O)[C@@H]1CN(C(=O)c2cncs2)CC12CN(C(=O)[C@H]1CC1(C)C)C2)C(=O)N(C)C] |
| I-417 | 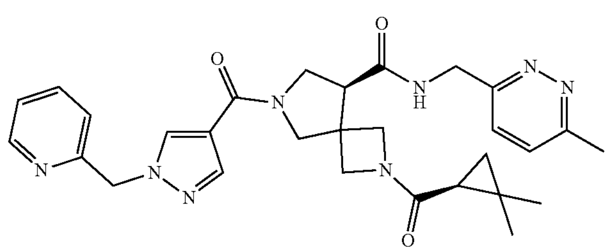 [SMILES: Cc1ccc(CNC(=O)[C@@H]2CN(C(=O)c3cnn(Cc4ccccn4)c3)CC23CN(C(=O)[C@H]2CC2(C)C)C3)nn1] |
| I-418 | 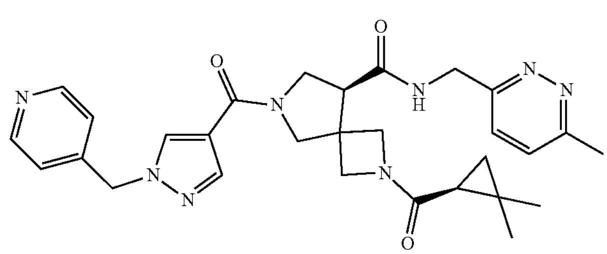 [SMILES: Cc1ccc(CNC(=O)[C@@H]2CN(C(=O)c3cnn(Cc4ccncc4)c3)CC23CN(C(=O)[C@H]2CC2(C)C)C3)nn1] |

TABLE 1-continued
Exemplary Compounds
| Cmpd # | Structure |
|---|---|
| I-419 | 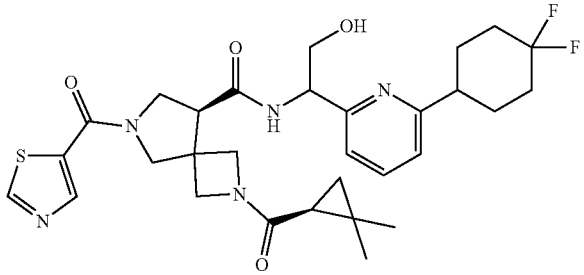 [SMILES: CC1(C)C[C@@H]1C(=O)N1CC2(CN(C(=O)c3cncs3)C[C@H]2C(=O)NC(CO)c2cccc(C3CCC(F)(F)CC3)n2)C1] |
| I-420 | 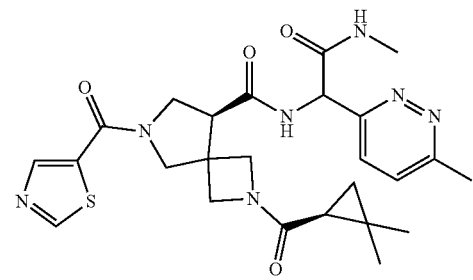 [SMILES: CNC(=O)C(NC(=O)[C@@H]1CN(C(=O)c2cncs2)CC12CN(C(=O)[C@H]1CC1(C)C)C2)c1ccc(C)nn1] |
| I-421 | 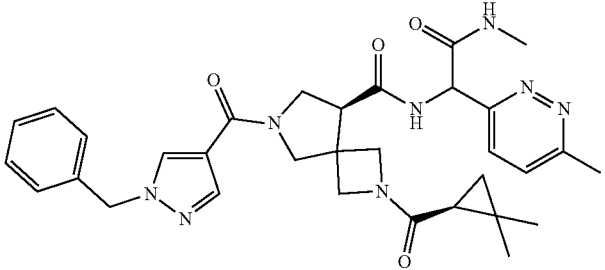 [SMILES: CNC(=O)C(NC(=O)[C@@H]1CN(C(=O)c2cnn(Cc3ccccc3)c2)CC12CN(C(=O)[C@H]1CC1(C)C)C2)c1ccc(C)nn1] |
| I-422 | 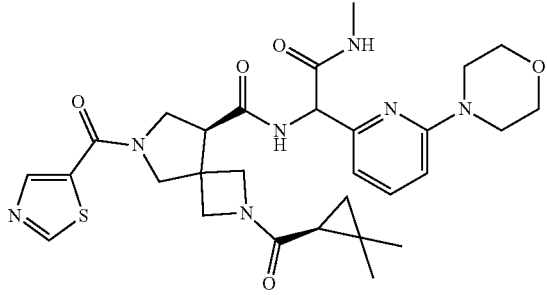 [SMILES: CNC(=O)C(NC(=O)[C@@H]1CN(C(=O)c2cncs2)CC12CN(C(=O)[C@H]1CC1(C)C)C2)c1cccc(N2CCOCC2)n1] |
| I-423 | 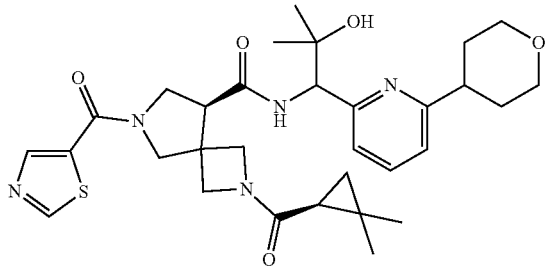 [SMILES: CC(C)(O)C(NC(=O)[C@@H]1CN(C(=O)c2cncs2)CC12CN(C(=O)[C@H]1CC1(C)C)C2)c1cccc(C2CCOCC2)n1] |

TABLE 1-continued

Exemplary Compounds

| Cmpd # | Structure |
|---|---|
| I-424 | 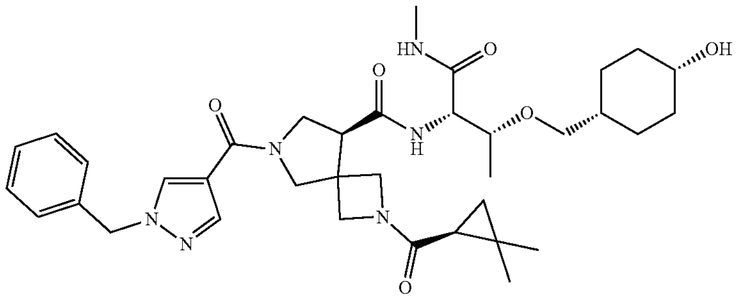 [SMILES: CNC(=O)[C@@H](NC(=O)[C@@H]1CN(C(=O)c2cnn(Cc3ccccc3)c2)CC12CN(C(=O)[C@H]1CC1(C)C)C2)[C@@H](C)OC[C@H]1CC[C@@H](O)CC1] |
| I-425 | 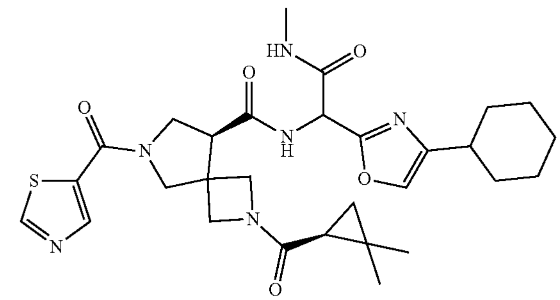 [SMILES: CNC(=O)C(NC(=O)[C@@H]1CN(C(=O)c2cncs2)CC12CN(C(=O)[C@H]1CC1(C)C)C2)c1nc(C2CCCCC2)co1] |
| I-426 | 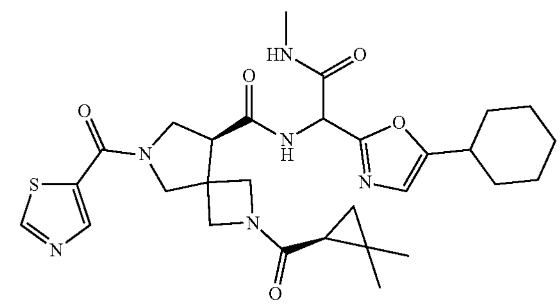 [SMILES: CNC(=O)C(NC(=O)[C@@H]1CN(C(=O)c2cncs2)CC12CN(C(=O)[C@H]1CC1(C)C)C2)c1ncc(C2CCCCC2)o1] |
| I-427 | 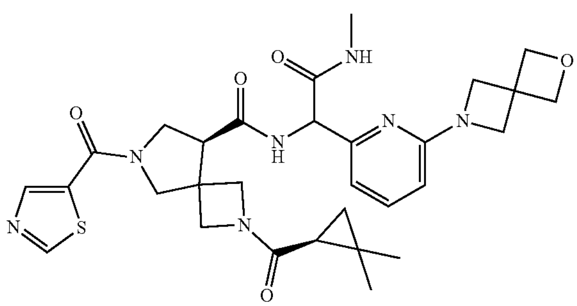 [SMILES: CNC(=O)C(NC(=O)[C@@H]1CN(C(=O)c2cncs2)CC12CN(C(=O)[C@H]1CC1(C)C)C2)c1cccc(N2CC3(COC3)C2)n1] |
| I-428 | 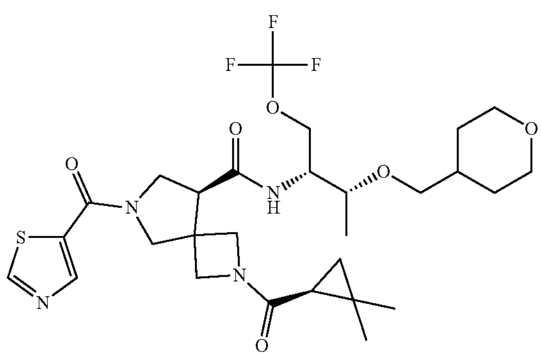 [SMILES: C[C@@H](OCC1CCOCC1)[C@@H](COC(F)(F)F)NC(=O)[C@@H]1CN(C(=O)c2cncs2)CC12CN(C(=O)[C@H]1CC1(C)C)C2] |

TABLE 1-continued

Exemplary Compounds

| Cmpd # | Structure |
|---|---|
| I-429 | 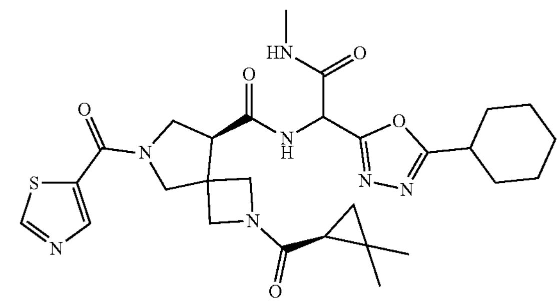 [SMILES: CNC(=O)C(NC(=O)[C@@H]1CN(C(=O)c2cncs2)CC12CN(C(=O)[C@H]1CC1(C)C)C2)c1nnc(C2CCCCC2)o1] |
| I-430 | 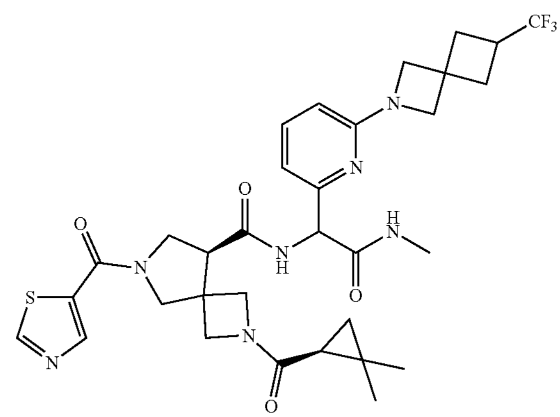 [SMILES: CNC(=O)C(NC(=O)[C@@H]1CN(C(=O)c2cncs2)CC12CN(C(=O)[C@H]1CC1(C)C)C2)c1cccc(N2CC3(CC(C(F)(F)F)C3)C2)n1] |
| I-431 | 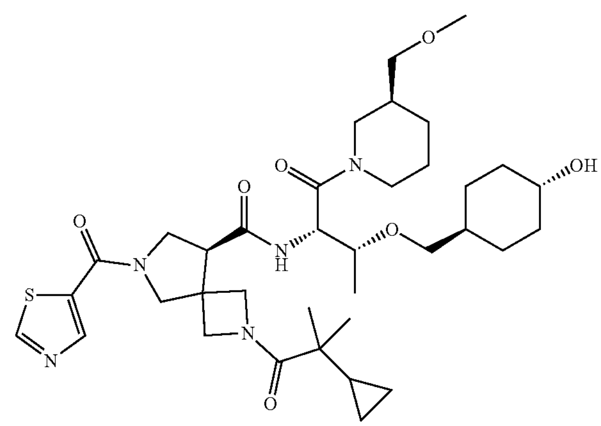 [SMILES: COC[C@H]1CCCN(C(=O)[C@@H](NC(=O)[C@@H]2CN(C(=O)c3cncs3)CC23CN(C(=O)C(C)(C)C2CC2)C3)[C@@H](C)OC[C@H]2CC[C@H](O)CC2)C1] |
| I-432 | 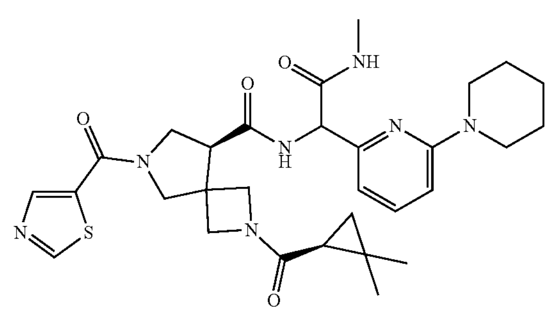 [SMILES: CNC(=O)C(NC(=O)[C@@H]1CN(C(=O)c2cncs2)CC12CN(C(=O)[C@H]1CC1(C)C)C2)c1cccc(N2CCCCC2)n1] |

TABLE 1-continued

Exemplary Compounds

| Cmpd # | Structure |
|---|---|
| I-433 | 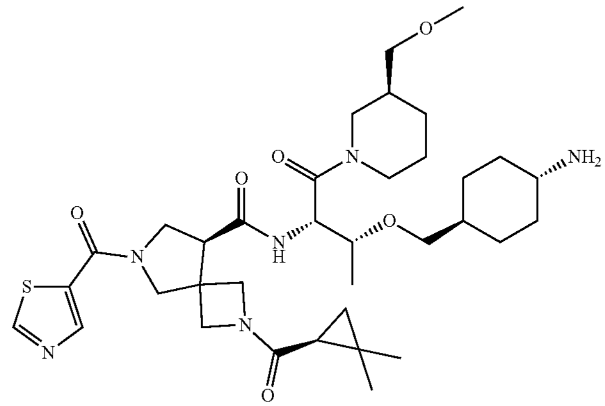 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OC[C@H]2CC[C@H](N)CC2)C1] |
| I-434 | 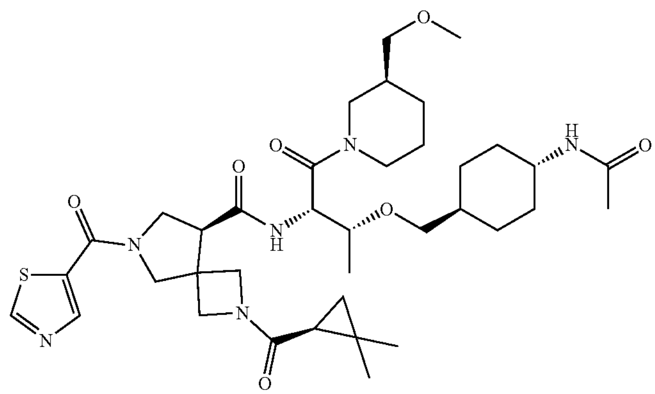 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OC[C@H]2CC[C@H](NC(C)=O)CC2)C1] |
| I-435 | 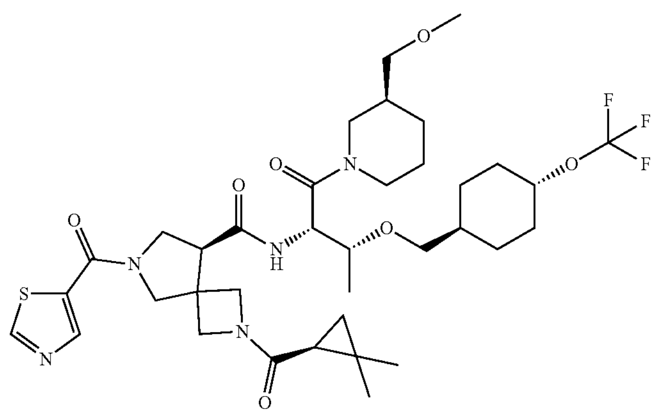 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)OC[C@H]2CC[C@H](OC(F)(F)F)CC2)C1] |
| I-436 | 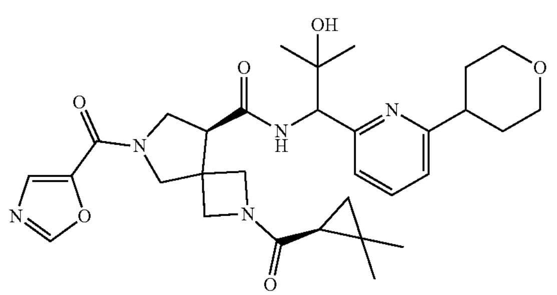 [SMILES: CC(C)(O)C(NC(=O)[C@@H]1CN(C(=O)c2cnco2)CC12CN(C(=O)[C@H]1CC1(C)C)C2)c1cccc(C2CCOCC2)n1] |

TABLE 1-continued

Exemplary Compounds

| Cmpd # | Structure |
|---|---|
| I-437 | 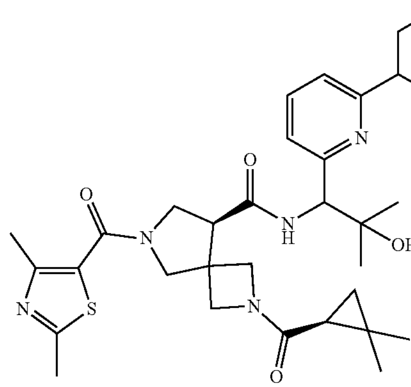 |
| I-438 | 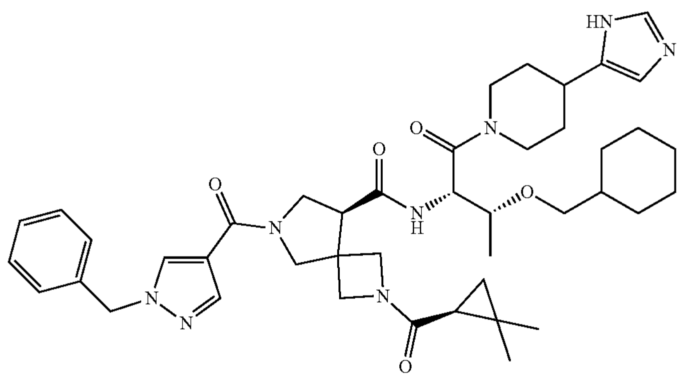 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(c2cnc[nH]2)CC1] |
| I-439 | 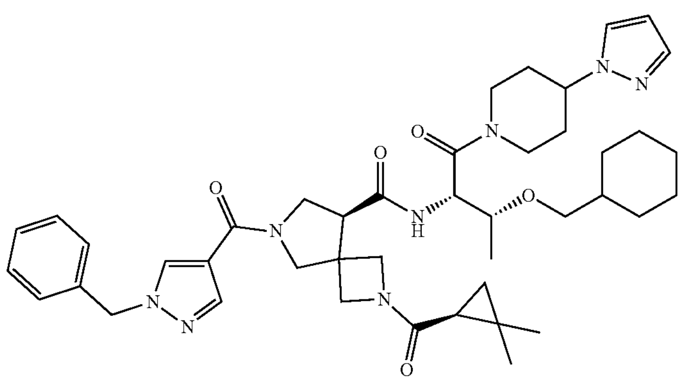 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(n2cccn2)CC1] |
| I-440 | 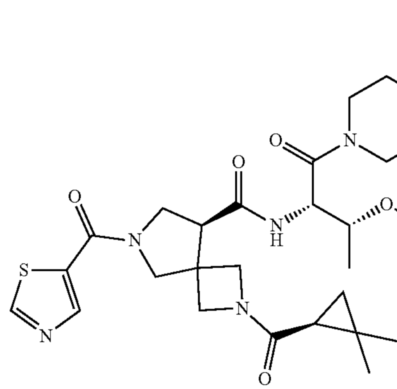 |

US 12,065,445 B2

393                                                                                                      394

TABLE 1-continued

Exemplary Compounds

| Cmpd # | Structure |
|--------|-----------|
| I-441  | 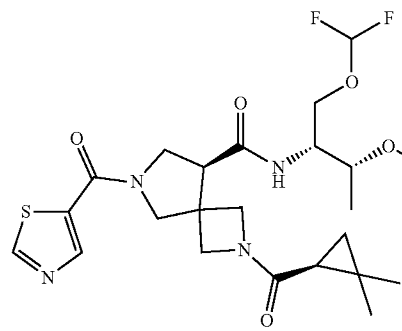          |
| I-442  | 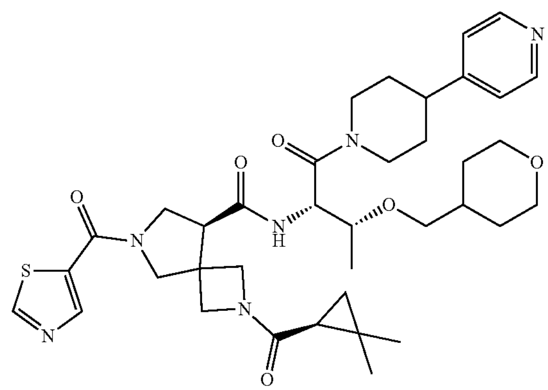 [SMILES: C[C@@H](OCC1CCOCC1)[C@H](NC(=O)[C@@H]1CN(C(=O)c2cncs2)CC12CN(C(=O)[C@H]1CC1(C)C)C2)C(=O)N1CCC(c2ccncc2)CC1]          |
| I-443  | 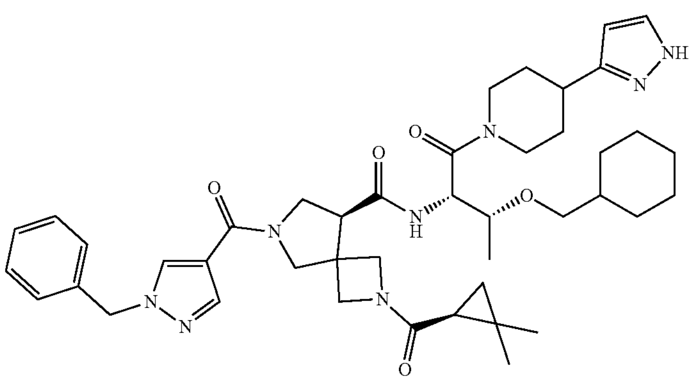 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(c2cc[nH]n2)CC1]          |
| I-444  | 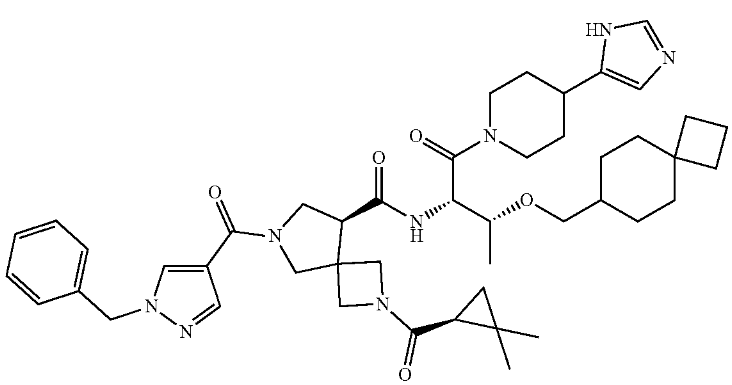 [SMILES: C[C@@H](OCC1CCC2(CCC2)CC1)[C@H](NC(=O)[C@@H]1CN(C(=O)c2cnn(Cc3ccccc3)c2)CC12CN(C(=O)[C@H]1CC1(C)C)C2)C(=O)N1CCC(c2cnc[nH]2)CC1]          |

TABLE 1-continued
Exemplary Compounds
| Cmpd # | Structure |
|---|---|
| I-445 | 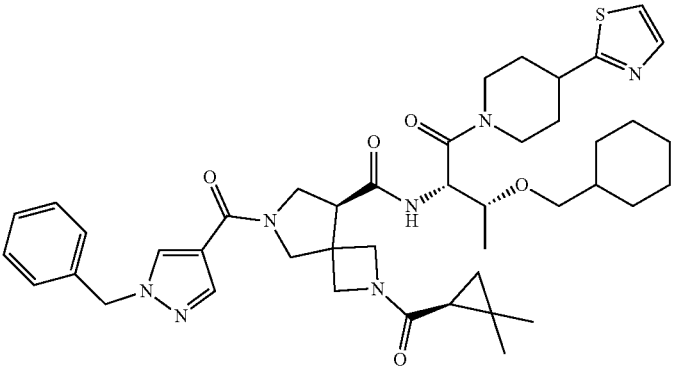 |
| I-446 | 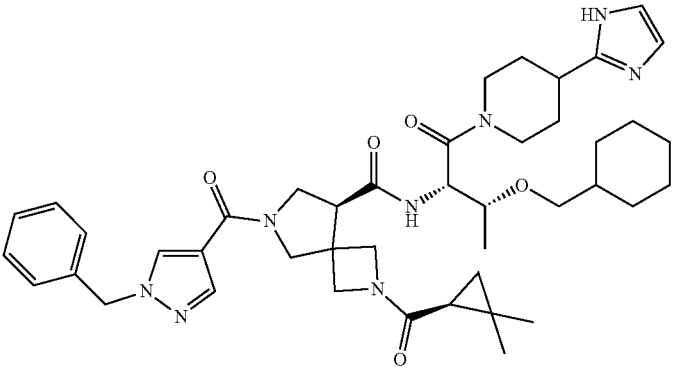 |
| I-447 | 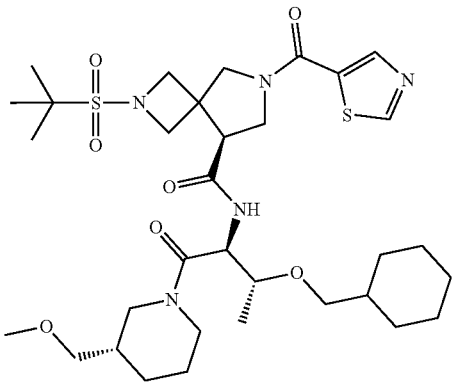 [SMILES: COC[C@H]1CCCN(C(=O)[C@@H](NC(=O)[C@@H]2CN(C(=O)c3cncs3)CC23CN(S(=O)(=O)C(C)(C)C)C3)[C@@H](C)OCC2CCCCC2)C1] |
| I-448 | 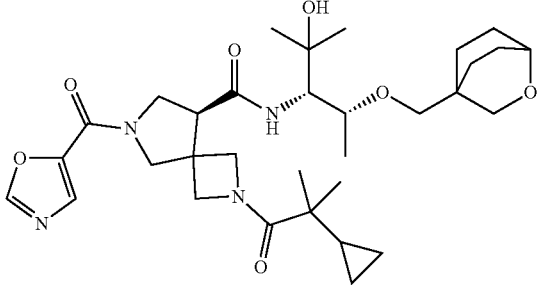 [SMILES: C[C@@H](OCC12CCC(CC1)OC2)[C@H](NC(=O)[C@@H]1CN(C(=O)c2cnco2)CC12CN(C(=O)C(C)(C)C1CC1)C2)C(C)(C)O] |

TABLE 1-continued

Exemplary Compounds

| Cmpd # | Structure |
|---|---|
| I-449 | 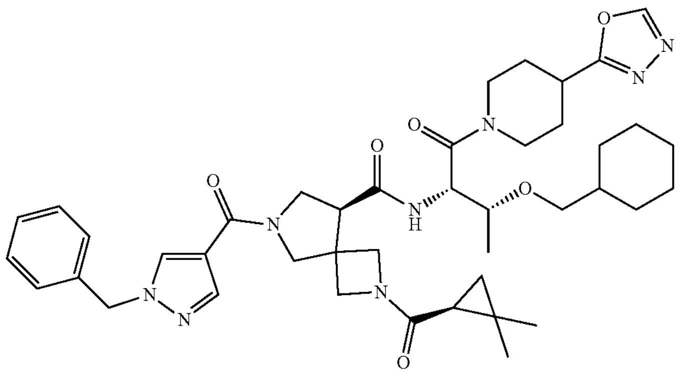 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(c2nnco2)CC1] |
| I-450 | 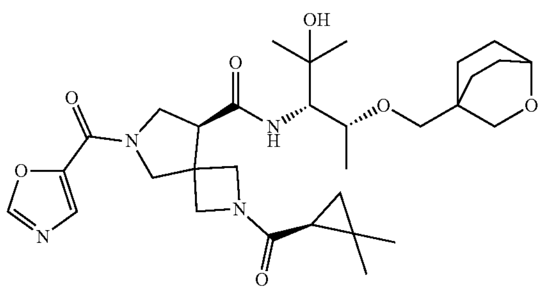 [SMILES: C[C@@H](OCC12CCC(CC1)OC2)[C@H](NC(=O)[C@@H]1CN(C(=O)c2cnco2)CC12CN(C(=O)[C@H]1CC1(C)C)C2)C(C)(C)O] |
| I-451 | 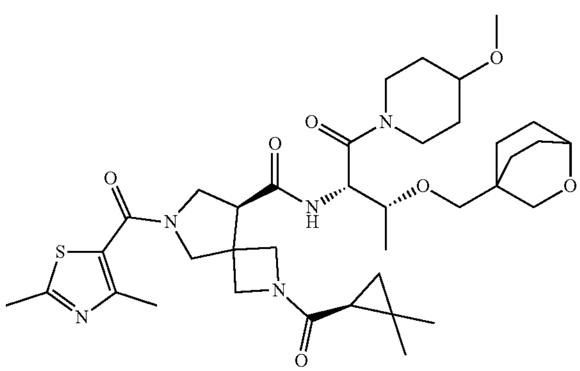 [SMILES: COC1CCN(C(=O)[C@@H](NC(=O)[C@@H]2CN(C(=O)c3sc(C)nc3C)CC23CN(C(=O)[C@H]2CC2(C)C)C3)[C@@H](C)OCC23CCC(CC2)OC3)CC1] |
| I-452 | 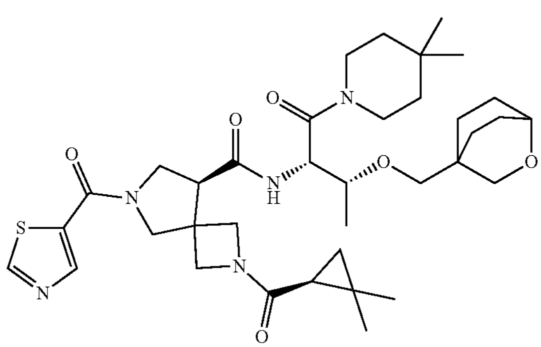 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC(C)(C)CC1] |

TABLE 1-continued

Exemplary Compounds

| Cmpd # | Structure |
|---|---|
| I-453 | 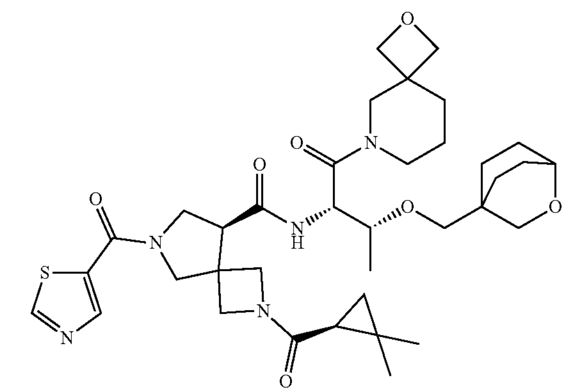 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCCC2(COC2)C1] |
| I-454 | 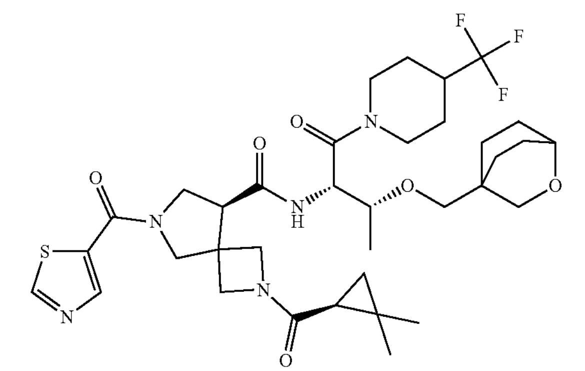 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC(C(F)(F)F)CC1] |
| I-455 | 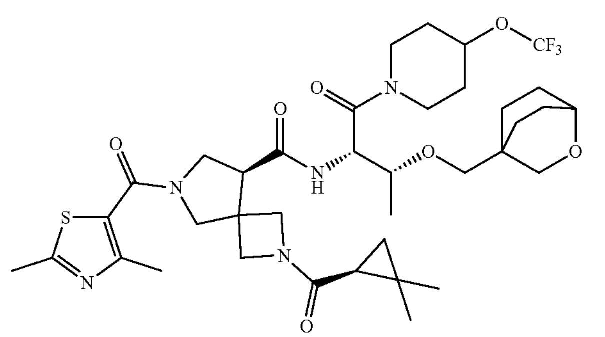 [SMILES: Cc1nc(C)c(C(=O)N2C[C@@H](C(=O)N[C@H](C(=O)N3CCC(OC(F)(F)F)CC3)[C@@H](C)OCC34CCC(CC3)OC4)C3(C2)CN(C(=O)[C@H]2CC2(C)C)C3)s1] |
| I-456 | 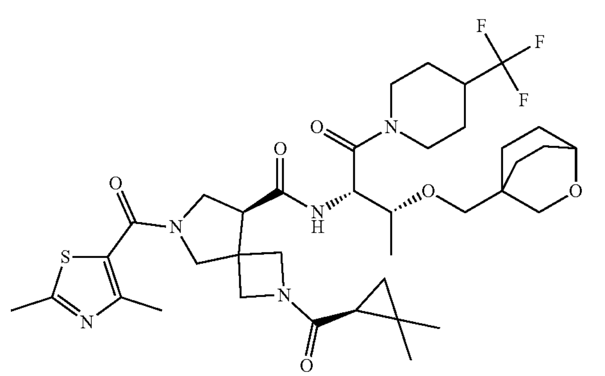 [SMILES: Cc1nc(C)c(C(=O)N2C[C@@H](C(=O)N[C@H](C(=O)N3CCC(C(F)(F)F)CC3)[C@@H](C)OCC34CCC(CC3)OC4)C3(C2)CN(C(=O)[C@H]2CC2(C)C)C3)s1] |

TABLE 1-continued

Exemplary Compounds

| Cmpd # | Structure |
|---|---|
| I-457 | 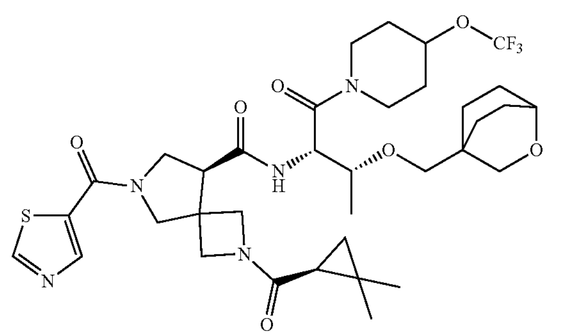 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC(OC(F)(F)F)CC1] |
| I-458 | 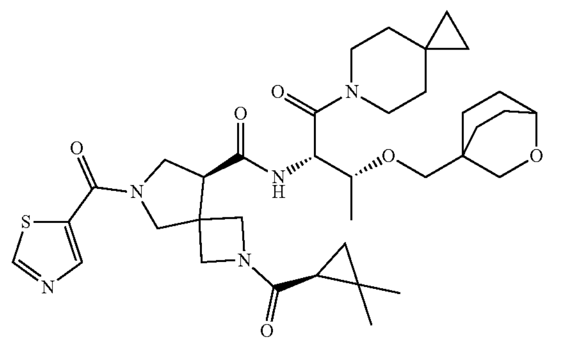 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC2(CC1)CC2] |
| I-459 | 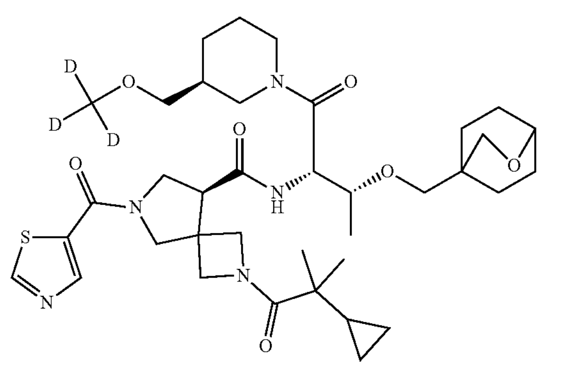 [SMILES: [2H]C([2H])([2H])OC[C@H]1CCCN(C(=O)[C@@H](NC(=O)[C@@H]2CN(C(=O)c3cncs3)CC23CN(C(=O)C(C)(C)C2CC2)C3)[C@@H](C)OCC23CCC(CC2)OC3)C1] |
| I-460 | 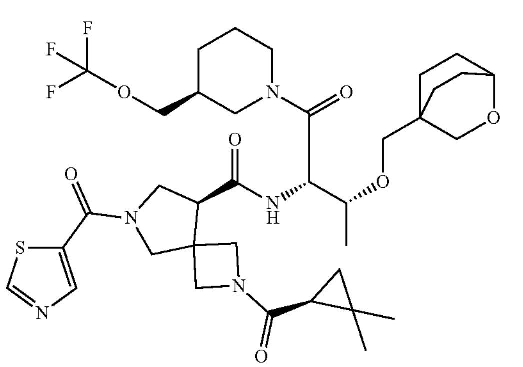 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC[C@H](COC(F)(F)F)C1] |

TABLE 1-continued

Exemplary Compounds

| Cmpd # | Structure |
|---|---|
| I-461 | 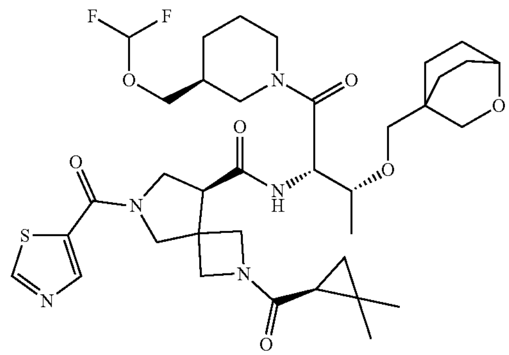 [SMILES: C[C@@H](OCC12CCC(CC1)OC2)[C@H](NC(=O)[C@@H]1CN(C(=O)c2cncs2)CC12CN(C(=O)[C@H]1CC1(C)C)C2)C(=O)N1CCC[C@H](COC(F)F)C1] |
| I-462 | 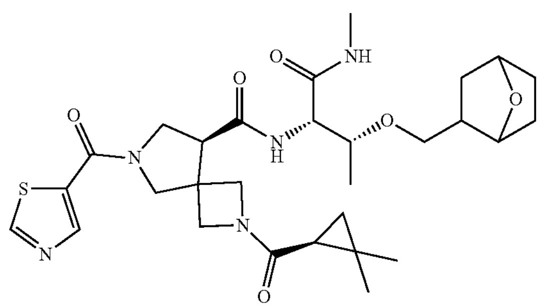 [SMILES: CNC(=O)[C@@H](NC(=O)[C@@H]1CN(C(=O)c2cncs2)CC12CN(C(=O)[C@H]1CC1(C)C)C2)[C@@H](C)OCC1CC2CCC1O2] |
| I-463 | 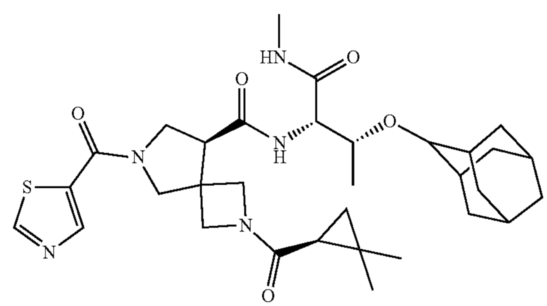 [SMILES: CNC(=O)[C@@H](NC(=O)[C@@H]1CN(C(=O)c2cncs2)CC12CN(C(=O)[C@H]1CC1(C)C)C2)[C@@H](C)OC1C2CC3CC(C2)CC1C3] |
| I-464 | 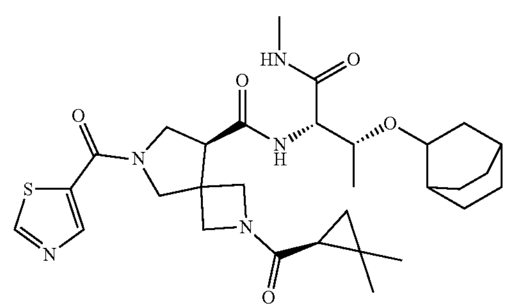 [SMILES: CNC(=O)[C@@H](NC(=O)[C@@H]1CN(C(=O)c2cncs2)CC12CN(C(=O)[C@H]1CC1(C)C)C2)[C@@H](C)OC1CC2CCC1CC2] |
| I-465 | 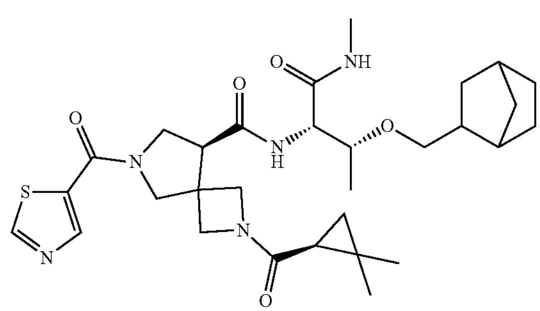 [SMILES: CNC(=O)[C@@H](NC(=O)[C@@H]1CN(C(=O)c2cncs2)CC12CN(C(=O)[C@H]1CC1(C)C)C2)[C@@H](C)OCC1CC2CCC1C2] |

TABLE 1-continued

Exemplary Compounds

| Cmpd # | Structure |
|---|---|
| I-466 | 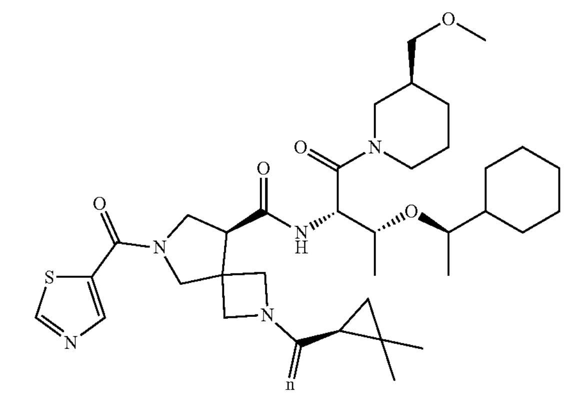 |
| I-467 | 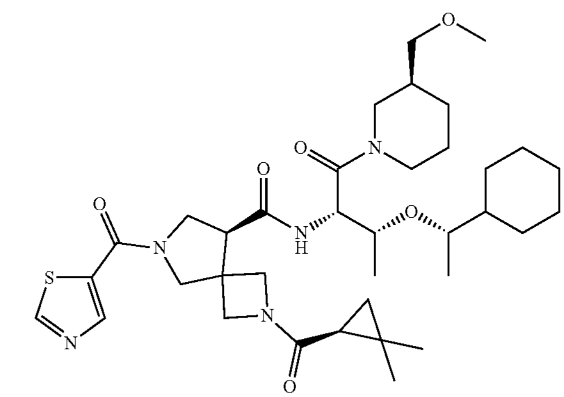 [SMILES: COC[C@H]1CCCN(C(=O)[C@@H](NC(=O)[C@@H]2CN(C(=O)c3cncs3)CC23CN(C(=O)[C@H]2CC2(C)C)C3)[C@@H](C)O[C@@H](C)C2CCCCC2)C1] |
| I-468 | 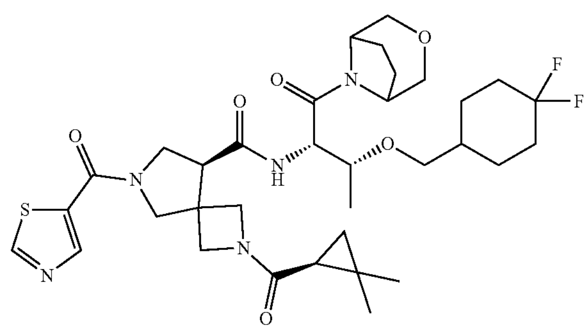 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1C2CCC1COC2] |
| I-469 | 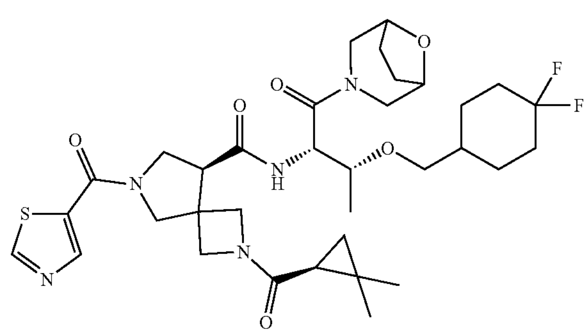 [SMILES: C[C@@H](OCC1CCC(F)(F)CC1)[C@H](NC(=O)[C@@H]1CN(C(=O)c2cncs2)CC12CN(C(=O)[C@H]1CC1(C)C)C2)C(=O)N1CC2CCC(C1)O2] |

TABLE 1-continued
Exemplary Compounds
| Cmpd # | Structure |
|---|---|
| I-470 | 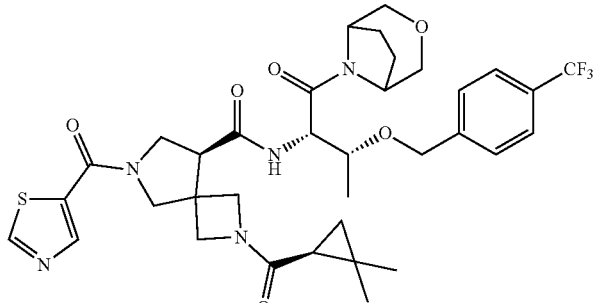 |
| I-471 | 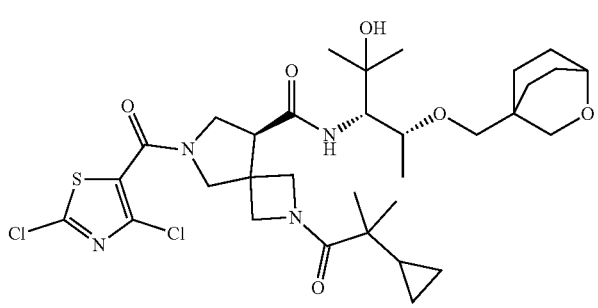 [SMILES: C[C@@H](OCC12CCC(CC1)OC2)[C@H](NC(=O)[C@@H]1CN(C(=O)c2sc(Cl)nc2Cl)CC12CN(C(=O)C(C)(C)C1CC1)C2)C(C)(C)O] |
| I-472 | 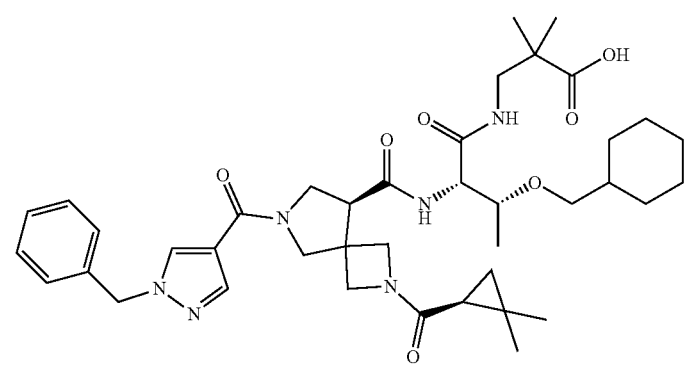 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)NCC(C)(C)C(=O)O] |
| I-473 | 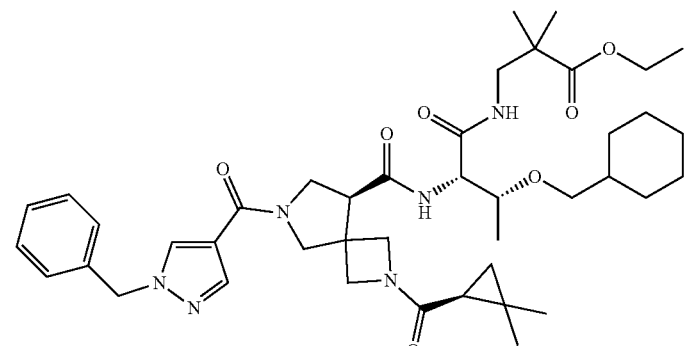 |

TABLE 1-continued
Exemplary Compounds
| Cmpd # | Structure |
|---|---|
| I-474 | 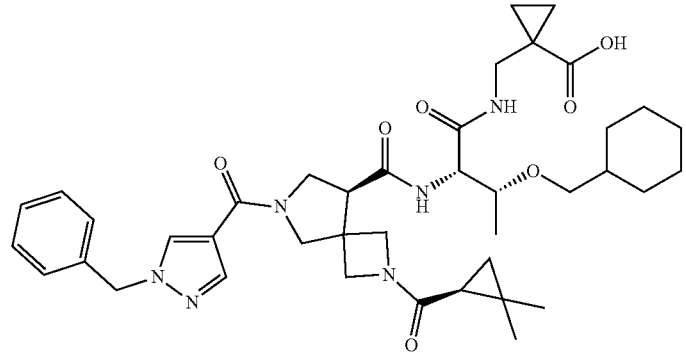 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)NCC1(C(=O)O)CC1] |
| I-475 | 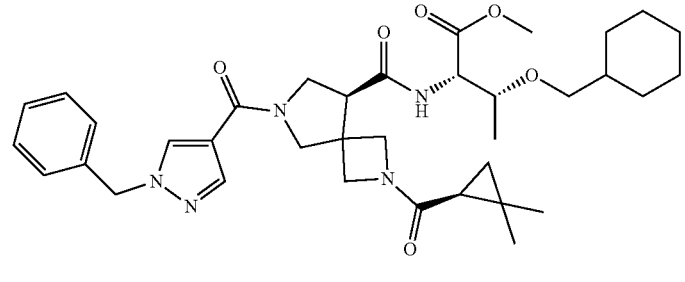 [SMILES: COC(=O)[C@@H](NC(=O)[C@@H]1CN(C(=O)c2cnn(Cc3ccccc3)c2)CC12CN(C(=O)[C@H]1CC1(C)C)C2)[C@@H](C)OCC1CCCCC1] |
| I-476 | 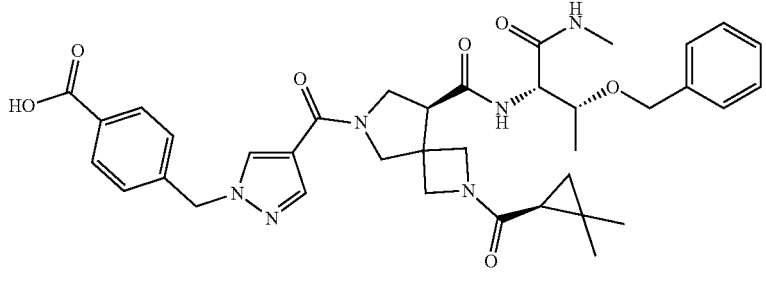 [SMILES: CNC(=O)[C@@H](NC(=O)[C@@H]1CN(C(=O)c2cnn(Cc3ccc(C(=O)O)cc3)c2)CC12CN(C(=O)[C@H]1CC1(C)C)C2)[C@@H](C)OCc1ccccc1] |
| I-477 | 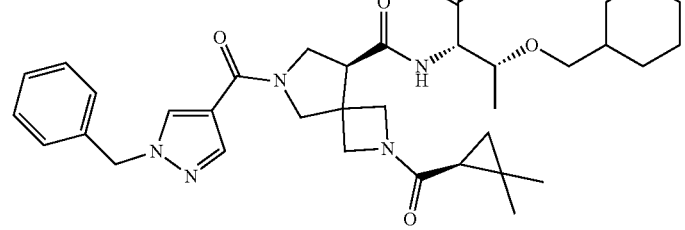 |

TABLE 1-continued

Exemplary Compounds

| Cmpd # | Structure |
|---|---|
| I-478 | 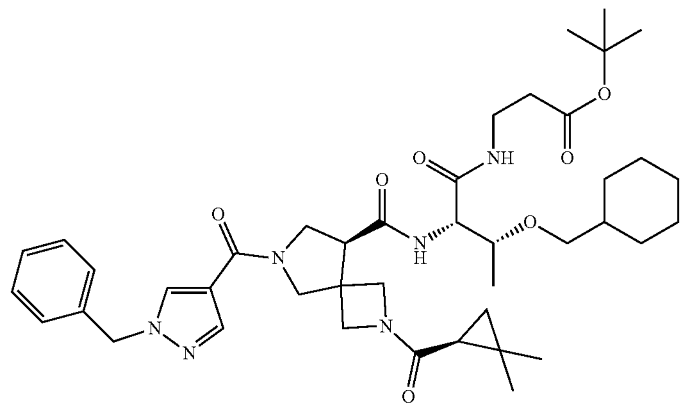 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)NCCC(=O)OC(C)(C)C] |
| I-479 | 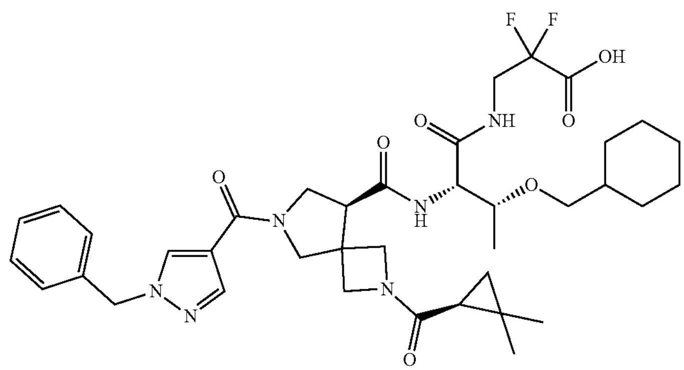 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)NCC(F)(F)C(=O)O] |
| I-480 | 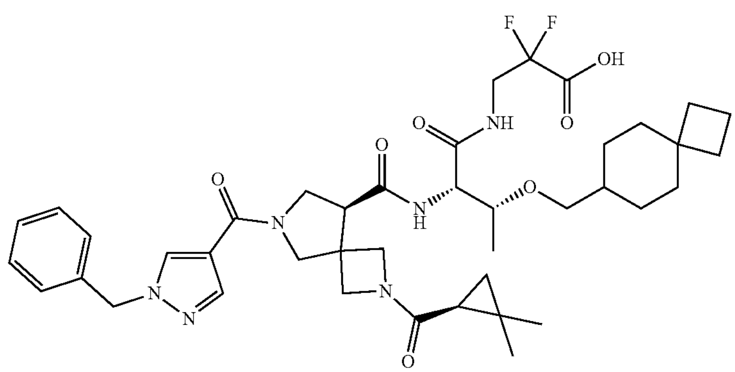 [SMILES: C[C@@H](OCC1CCC2(CCC2)CC1)[C@H](NC(=O)[C@@H]1CN(C(=O)c2cnn(Cc3ccccc3)c2)CC12CN(C(=O)[C@H]1CC1(C)C)C2)C(=O)NCC(F)(F)C(=O)O] |
| I-481 | 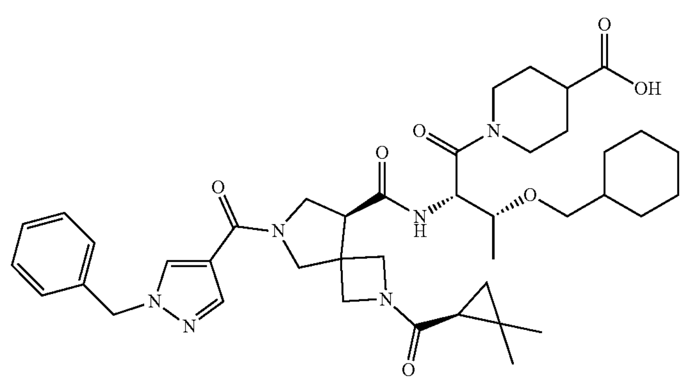 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCC(C(=O)O)CC1] |

TABLE 1-continued

Exemplary Compounds

| Cmpd # | Structure |
|---|---|
| I-482 | 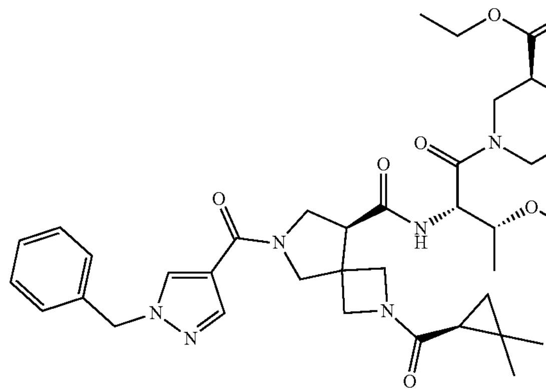 |
| I-483 | 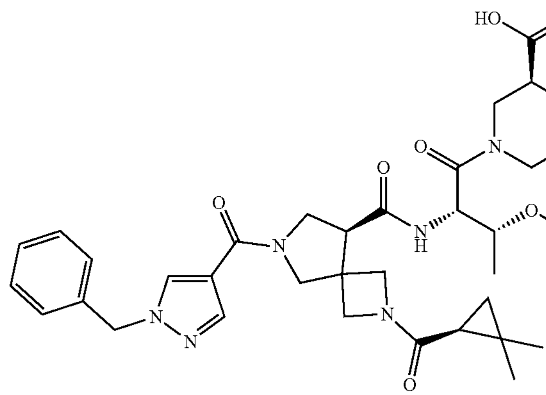 |
| I-484 | 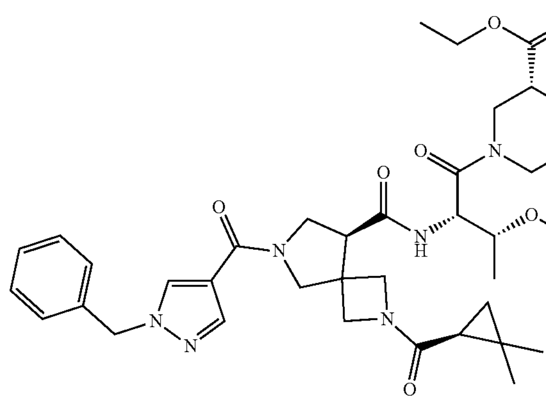 |
| I-485 | 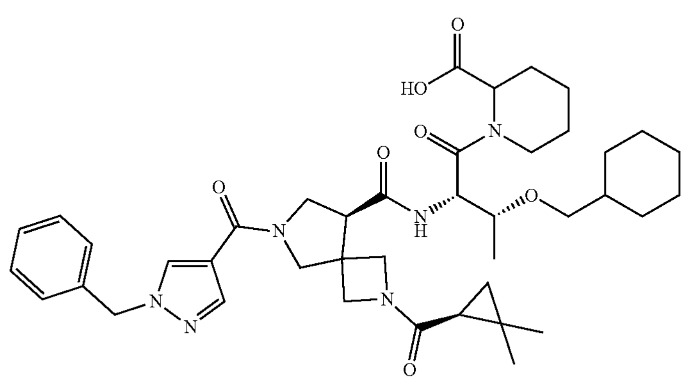 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)N1CCCCC1C(=O)O] |

415 416
TABLE 1-continued
Exemplary Compounds
| Cmpd # | Structure |
|---|---|
| I-486 | 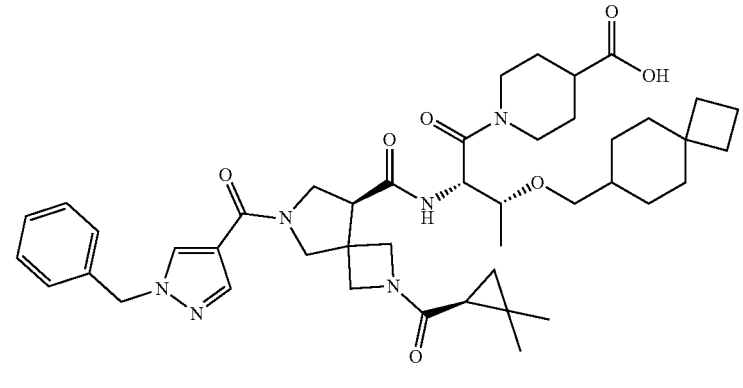 [SMILES: C[C@@H](OCC1CCC2(CCC2)CC1)[C@H](NC(=O)[C@@H]1CN(C(=O)c2cnn(Cc3ccccc3)c2)CC12CN(C(=O)[C@H]1CC1(C)C)C2)C(=O)N1CCC(C(=O)O)CC1] |
| I-487 | 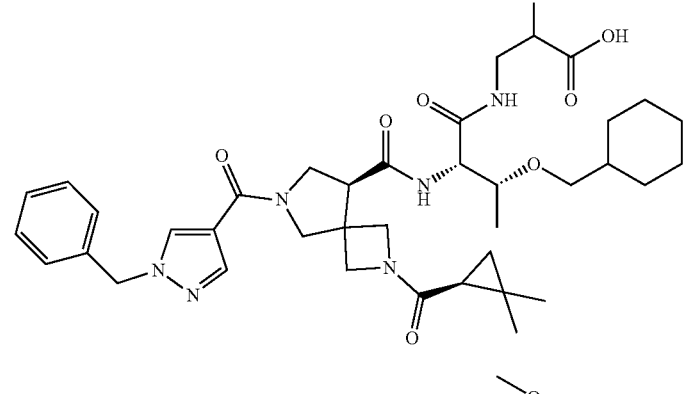 |
| I-488 | 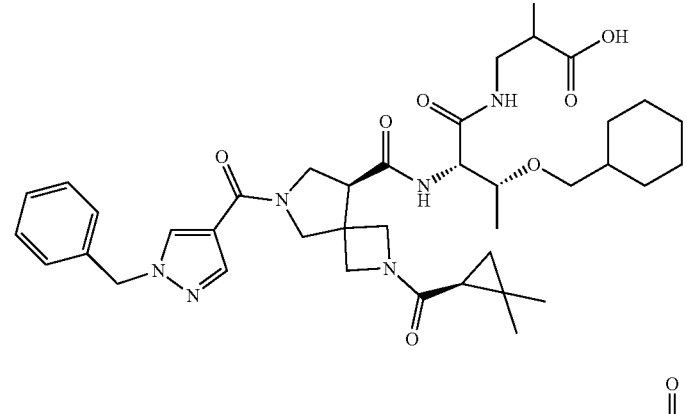 |
| I-489 | 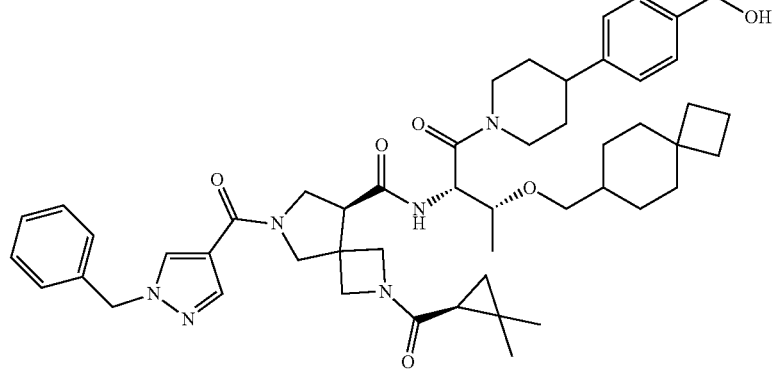 |

TABLE 1-continued

Exemplary Compounds

| Cmpd # | Structure |
|---|---|
| I-490 | 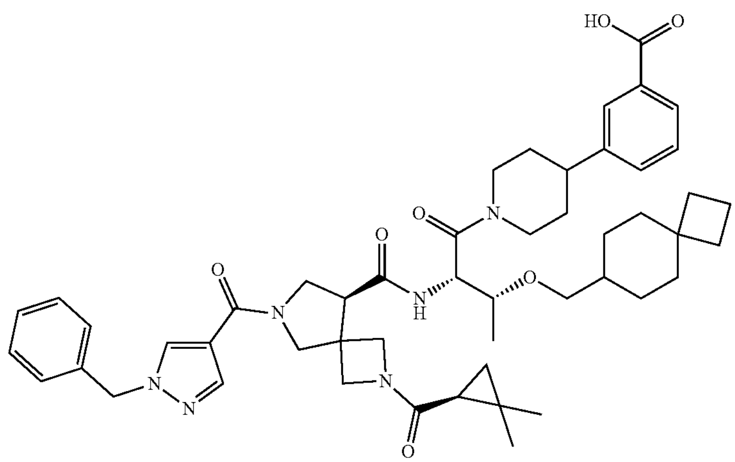 [SMILES: C[C@@H](OCC1CCC2(CCC2)CC1)[C@H](NC(=O)[C@@H]1CN(C(=O)c2cnn(Cc3ccccc3)c2)CC12CN(C(=O)[C@H]1CC1(C)C)C2)C(=O)N1CCC(c2cccc(C(=O)O)c2)CC1] |
| I-491 | 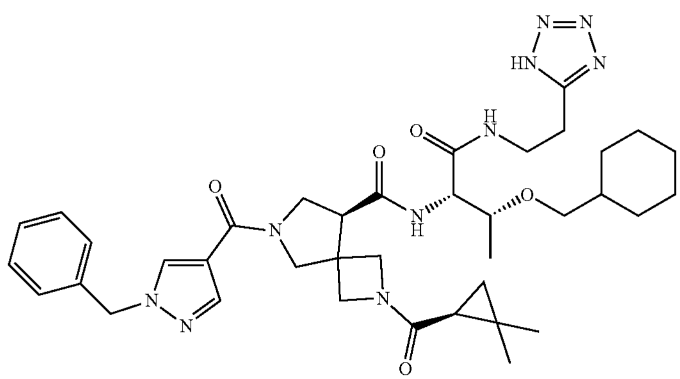 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)NCCc1nnn[nH]1] |
| I-492 | 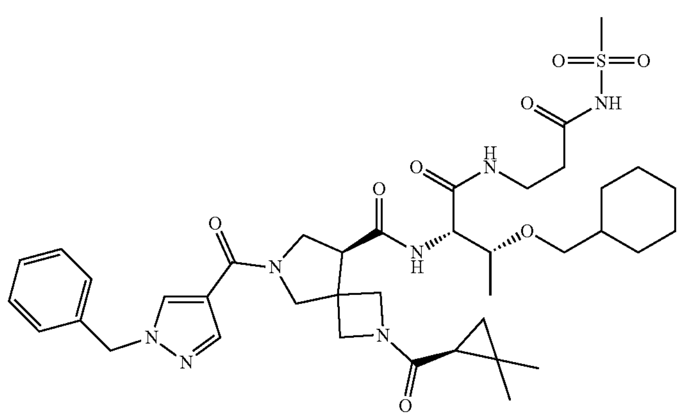 [SMILES: C[C@@H](OCC1CCCCC1)[C@H](NC(=O)[C@@H]1CN(C(=O)c2cnn(Cc3ccccc3)c2)CC12CN(C(=O)[C@H]1CC1(C)C)C2)C(=O)NCCC(=O)NS(C)(=O)=O] |
| I-493 | 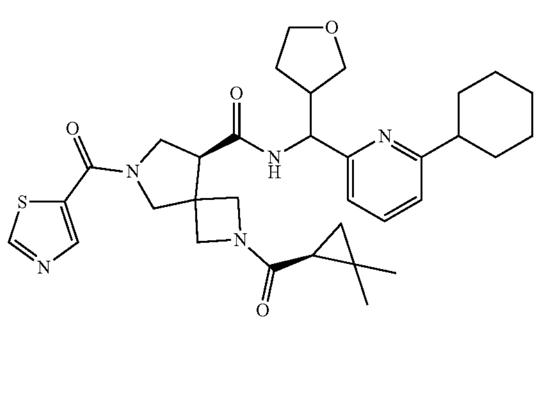 [SMILES: CC1(C)C[C@@H]1C(=O)N1CC2(CN(C(=O)c3cncs3)C[C@H]2C(=O)NC(c2cccc(C3CCCCC3)n2)C2CCOC2)C1] |

TABLE 1-continued
Exemplary Compounds
| Cmpd # | Structure |
|---|---|
| I-494 | 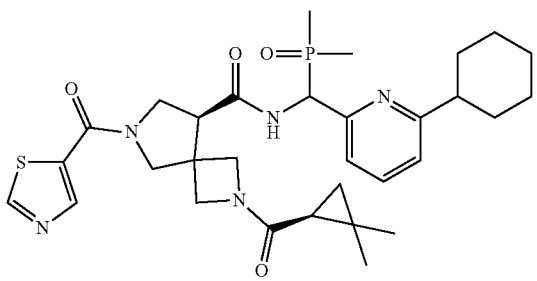 [SMILES: CC1(C)C[C@@H]1C(=O)N1CC2(CN(C(=O)c3cncs3)C[C@H]2C(=O)NC(c2cccc(C3CCCCC3)n2)P(C)(C)=O)C1] |
| I-495 | 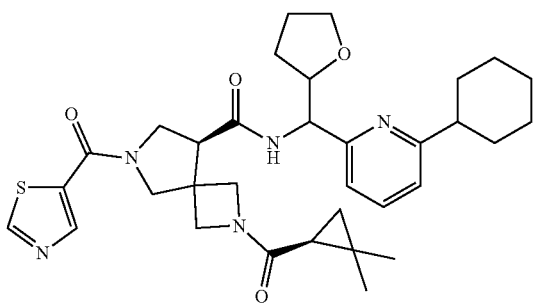 [SMILES: CC1(C)C[C@@H]1C(=O)N1CC2(CN(C(=O)c3cncs3)C[C@H]2C(=O)NC(c2cccc(C3CCCCC3)n2)C2CCCO2)C1] |
| I-496 | 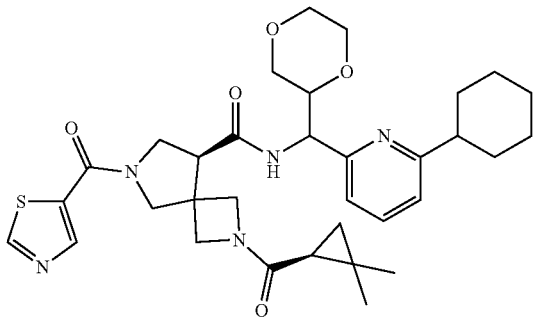 [SMILES: CC1(C)C[C@@H]1C(=O)N1CC2(CN(C(=O)c3cncs3)C[C@H]2C(=O)NC(c2cccc(C3CCCCC3)n2)C2COCCO2)C1] |
| I-497 | 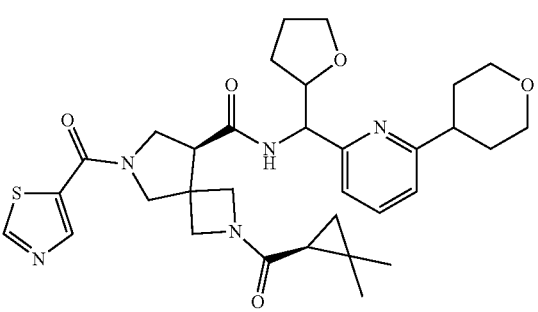 [SMILES: CC1(C)C[C@@H]1C(=O)N1CC2(CN(C(=O)c3cncs3)C[C@H]2C(=O)NC(c2cccc(C3CCOCC3)n2)C2CCCO2)C1] |
| I-498 | 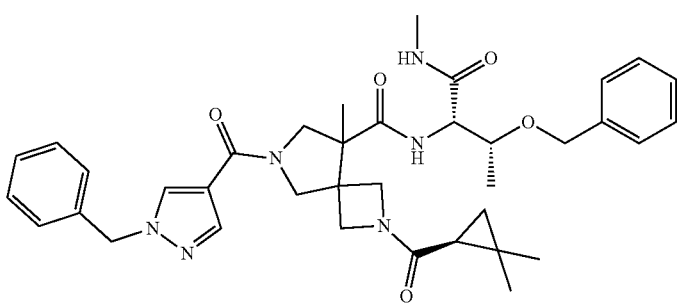 [SMILES: CNC(=O)[C@@H](NC(=O)C1(C)CN(C(=O)c2cnn(Cc3ccccc3)c2)CC12CN(C(=O)[C@H]1CC1(C)C)C2)[C@@H](C)OCc1ccccc1] |

TABLE 1-continued

Exemplary Compounds

| Cmpd # | Structure |
|---|---|
| I-499 | (A) |
| | (B) |
| I-500 | 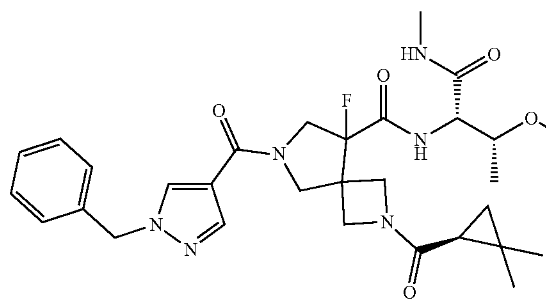 |
| I-501 | 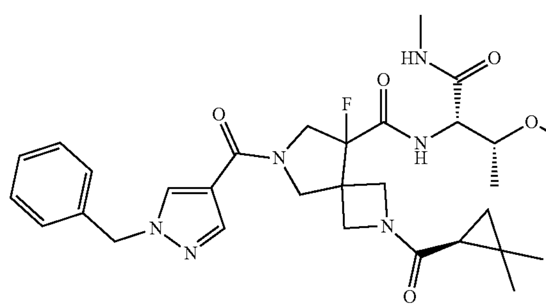 |

In some embodiments, the present disclosure provides a compound set forth in Table 1, above, or a pharmaceutically acceptable salt thereof. In some embodiments, the disclosure provides a compound set forth in Table 1, above, or a pharmaceutically acceptable salt thereof, and any enantiomers, diastereomers, or conformation isomers thereof. The present disclosure contemplates any and all enantiomers, diastereomers and conformation isomers of a compound shown herein.

In some embodiments, the present disclosure provides a pharmaceutical composition comprising a compound of the present disclosure, or a pharmaceutically acceptable salt thereof, together with a pharmaceutically acceptable carrier, excipient, vehicle, adjuvant or diluent. In some embodiments, the present disclosure provides a pharmaceutical composition comprising a compound set forth in Table 1 above, or a pharmaceutically acceptable salt thereof, together with a pharmaceutically acceptable carrier, excipient, vehicle, adjuvant or diluent. In some embodiments, the pharmaceutical composition further comprises an additional therapeutic agent.

In some embodiments, the present disclosure provides a complex comprising a CDK2 protein and a compound of the present disclosure.

In some embodiments, the present disclosure provides a method of inhibiting the activity of a cyclin-dependent kinase (CDK). In some embodiments, the method comprises contacting a compound of the present disclosure with a CDK. In some embodiments, the compound and the CDK are contacted in vivo. In some embodiments, the compound and the CDK are contacted in vitro. In some embodiments, the CDK is selected from CDK1, CDK2, CDK3, CDK4, CDK5, CDK6, CDK7, CDK8, CDK9, CDK10, CDK11, CDK12 and CDK13. In some embodiments, the CDK is CDK2. In some embodiments, the CDK is CDK3. In some embodiments, the CDK is CDK4. In some embodiments, the CDK is CDK6. In some embodiments, the method inhibits the activity of both CDK2 and CDK3. In some embodiments, the method inhibits the activity of CDK2 and one or both of CDK4 and CDK6.

In some embodiments, the compounds of the present disclosure inhibit the activity of one or more CDKs selected from CDK1, CDK2, CDK3, CDK4, CDK5, CDK6, CDK7, CDK8, CDK9, CDK10, CDK11, CDK12 and CDK13. In some embodiments, the compounds of the present disclosure inhibit CDK2. In some embodiments, the compounds of the present disclosure inhibit CDK3. In some embodiments, the compounds of the present disclosure inhibit CDK4. In some embodiments, the compounds of the present disclosure inhibit CDK5. In some embodiments, the compounds of the present disclosure inhibit CDK6. In some embodiments, the compounds of the present disclosure are CDK2/3 inhibitors. In some embodiments, the compounds of the present disclosure are CDK2/4/6 inhibitors.

In some embodiments, the present disclosure provides compounds that selectively inhibit CDK2 over other cyclin-dependent kinases (CDKs). In some embodiments, the compounds of the present disclosure selectively inhibit CDK2 over one or more other CDKs, selected from CDK1, CDK3, CDK4, CDK5, CDK6, CDK7, CDK8, CDK9, CDK10, CDK11, CDK12 and CDK13. In some embodiments, the compounds of the present disclosure selectively inhibit CDK2 over CDK4. In some embodiments, the compounds of the present disclosure selectively inhibit CDK2 over CDK6. In some embodiments, the compounds of the present disclosure selectively inhibit CDK2 over CDK4 and CDK6.

In some embodiments, the present disclosure provides compounds that selectively inhibit CDK2/cyclin E complexes over other CDK complexes.

4. General Methods of Providing the Present Compounds

The compounds of this disclosure may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like.

Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

Compounds of the present disclosure, including those of Formula I and the compounds of Table 1, can generally be prepared according the methods described below. Reagents and conditions can be modified and substituted using knowledge common to one of ordinary skill in the art, as needed, in order to arrive at the compounds of the present disclosure.

Scheme 1: Synthesis of Spirocyclic Core Structure

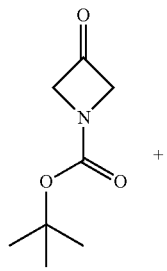

+

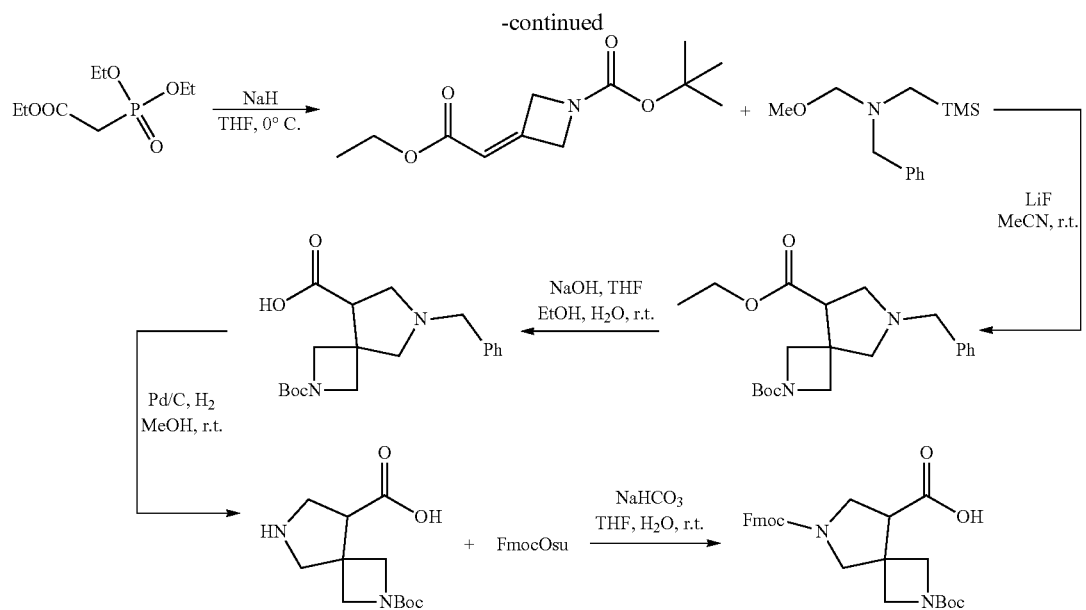
Scheme 2: Racemic Functionalization of Spirocyclic Core Structure
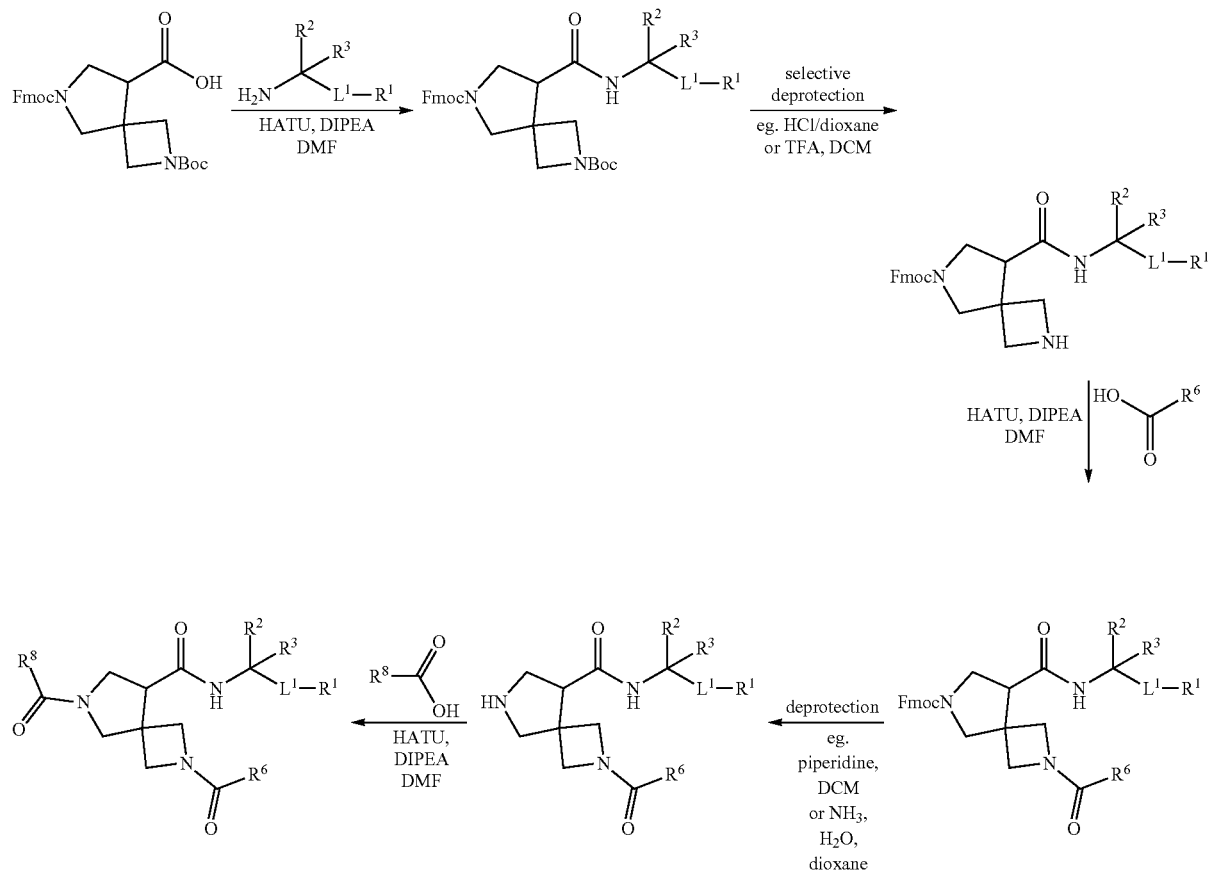

Scheme 3: Synthesis of Individual Enantiomers via Separation of Intermediates using Oxazolidinone Auxiliary
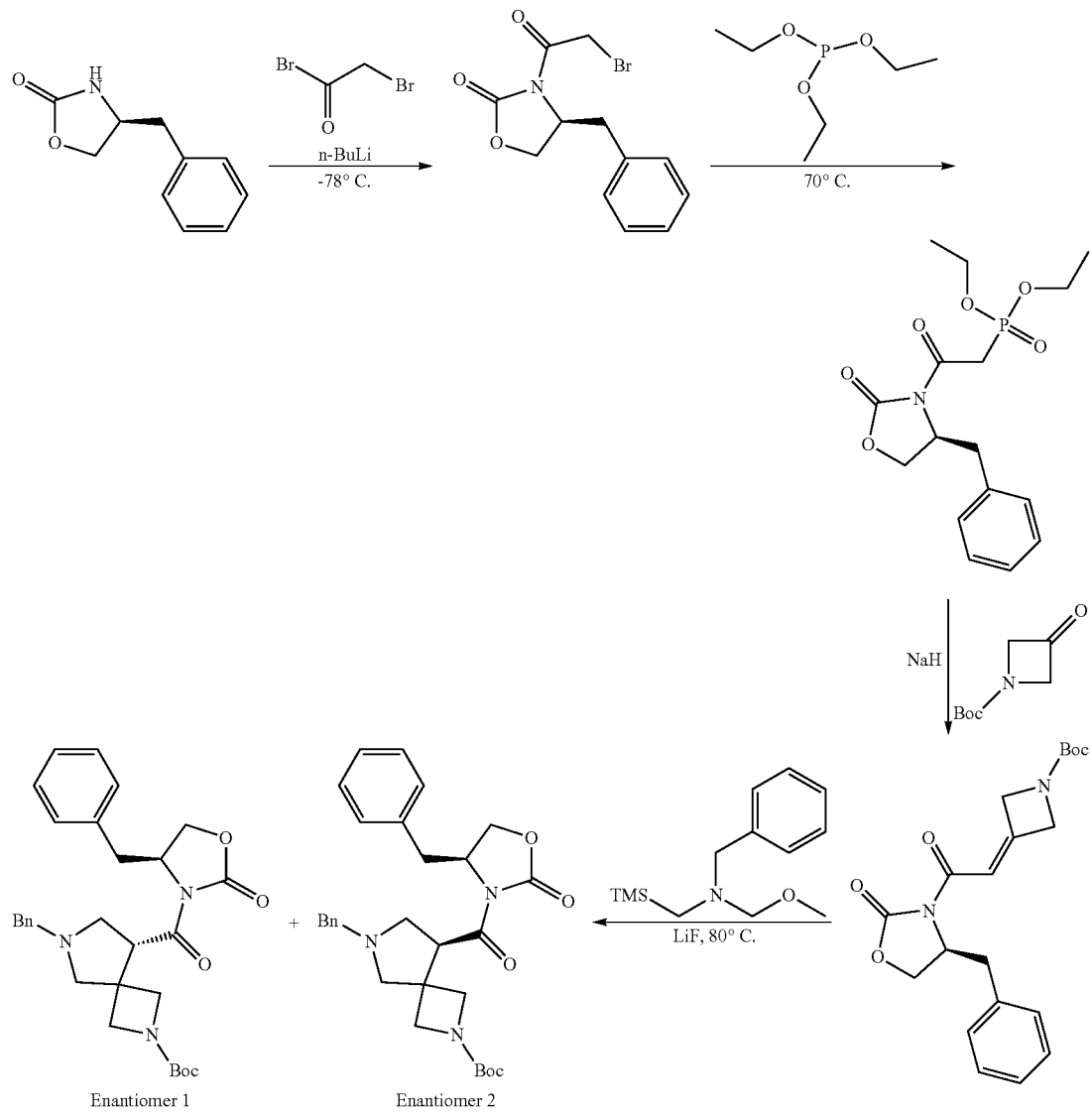
Scheme 4: Synthesis of Individual Enantiomers from Separated Intermediates
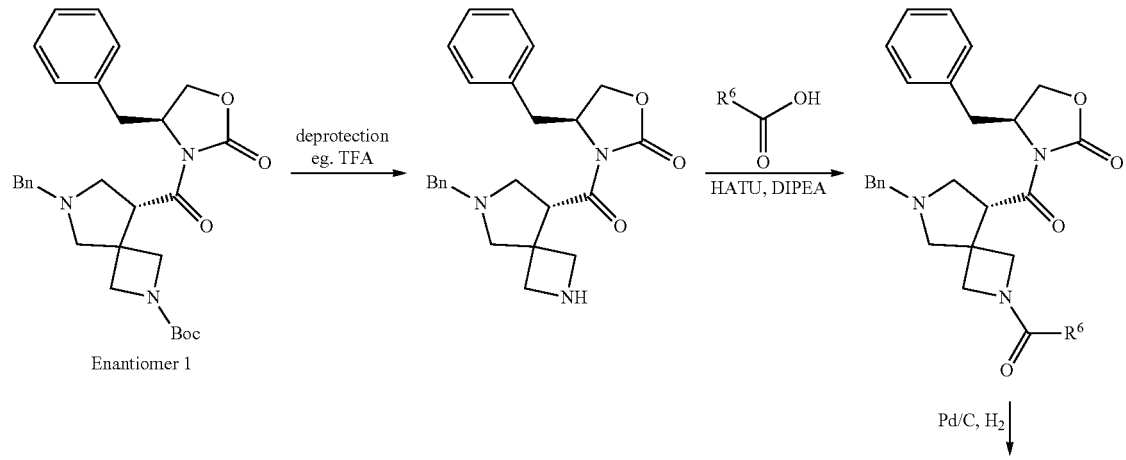

429 430
-continued
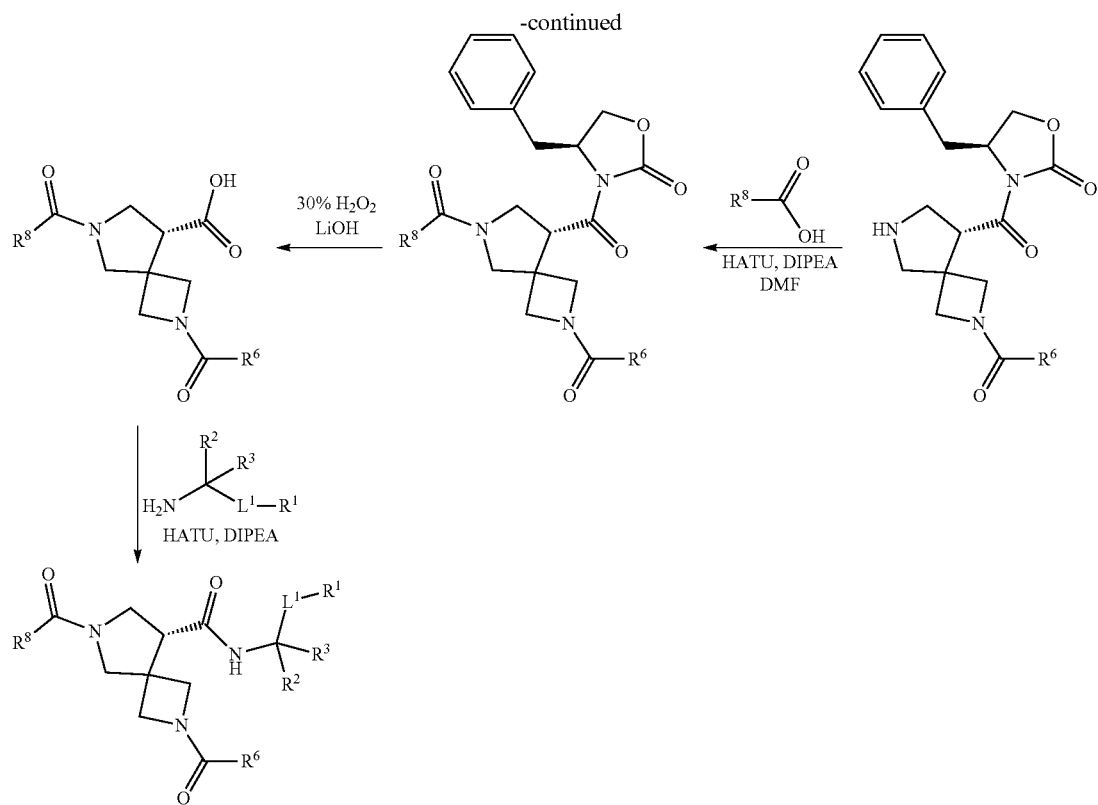
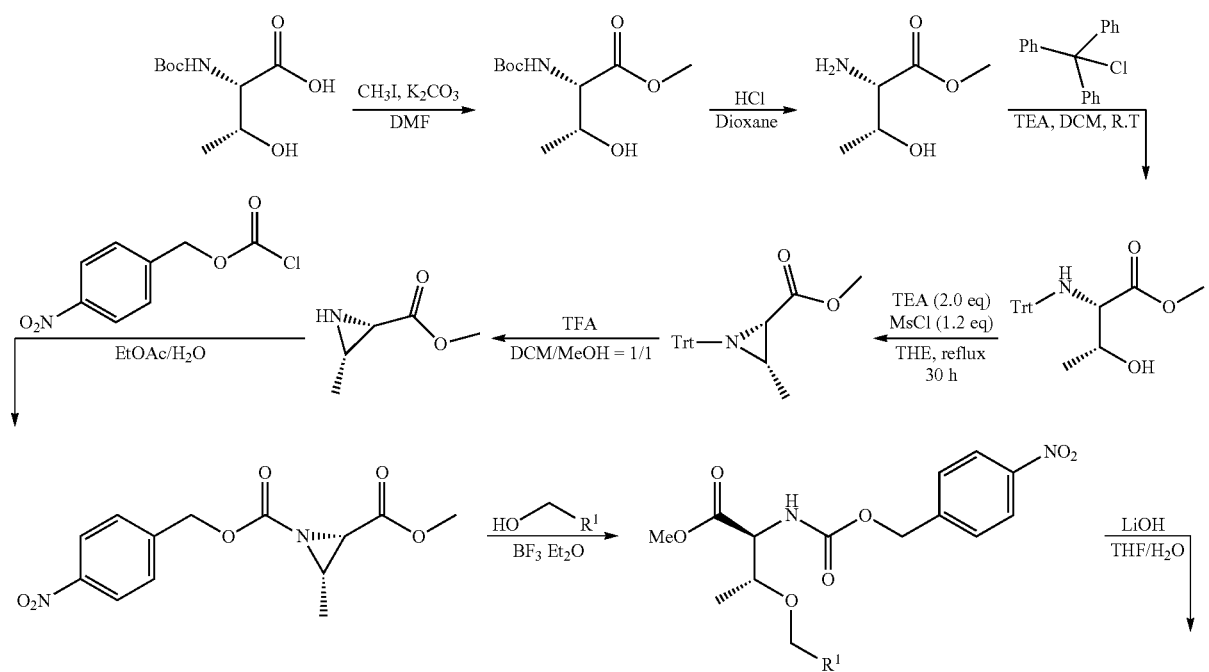
Scheme 5: Synthesis of compounds having a threonine derivative $R^A$ group, with desired stereochemistry -continued

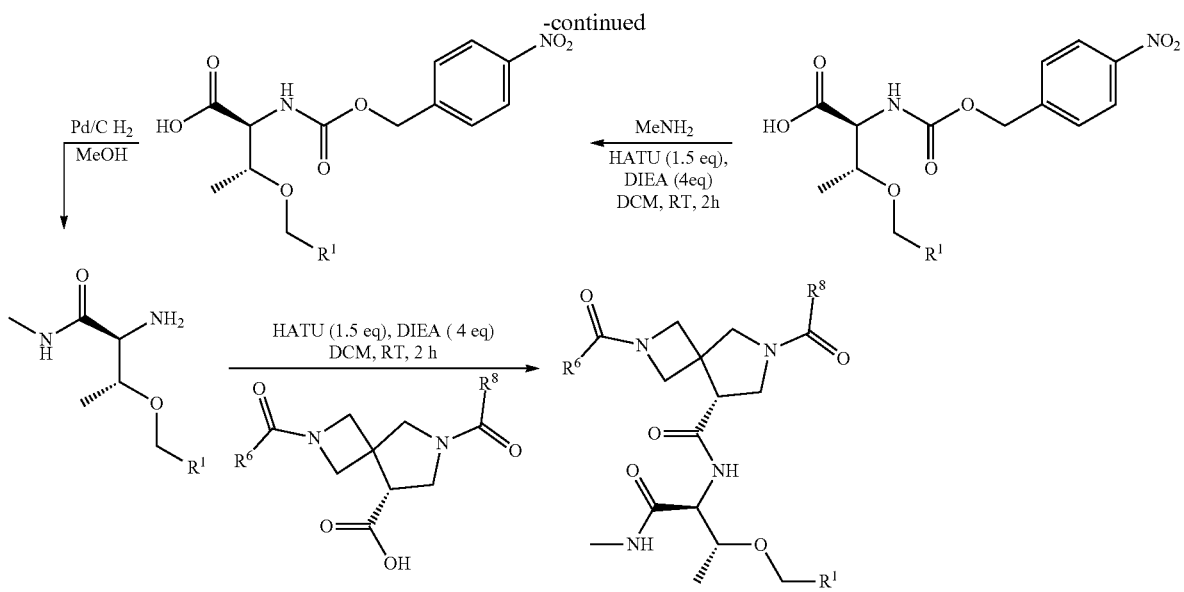

5. Uses, Formulation and Administration

Pharmaceutically Acceptable Compositions

According to another embodiment, the disclosure provides a composition comprising a compound of this disclosure or a pharmaceutically acceptable derivative thereof and a pharmaceutically acceptable carrier, adjuvant, or vehicle. The amount of compound in compositions of this disclosure is such that it is effective to measurably inhibit a CDK2 protein, or a mutant thereof, in a biological sample or in a patient. In certain embodiments, the amount of compound in compositions of this disclosure is such that it is effective to measurably inhibit a CDK2 protein, or a mutant thereof, in a biological sample or in a patient. In certain embodiments, a composition of this disclosure is formulated for administration to a patient in need of such composition. In some embodiments, a composition of this disclosure is formulated for oral administration to a patient.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered subcutaneously, orally, intraperitoneally or intravenously. In some embodiments, the compositions are administered orally. In some embodiments, the compositions are administered intraperitoneally. In some embodiments, the compositions are administered intravenously. In some embodiments, the compositions are administered subcutaneously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

Uses of Compounds and Pharmaceutically Acceptable Compositions

Compounds and compositions described herein are generally useful for the modulation of the activity CDK2. In some embodiments, the compounds and compositions described herein are CDK2 inhibitors.

In some embodiments, the compounds and compositions of the present disclosure are useful for treating diseases and disorders associated with CDK2 activity, including, but not limited to cancers, myeloproliferative disorders, autoimmune disorders, inflammatory disorders, viral infections, fibrotic disorders, and neurodegenerative disorders.

In some embodiments, the disclosure provides a method of inhibiting the activity of a CDK2, the method comprising contacting a compound of the present disclosure, or a pharmaceutically acceptable salt thereof with the CDK2. In some embodiments, the contacting takes place in vitro. In some embodiments, the contacting takes place in vivo.

In some embodiments, the disclosure provides a method of treating, preventing or lessening the severity of a disease or disorder associated with CDK2 activity in a patient, including, but not limited to cancers, myeloproliferative disorders, autoimmune disorders, inflammatory disorders, fibrotic disorders, and neurodegenerative disorders, said method comprising administering to a patient in need thereof, a compound of the present disclosure, or a pharmaceutically acceptable salt thereof, or a pharmaceutical composition comprising an effective amount of a compound of the present disclosure, or a pharmaceutically acceptable salt thereof.

The disclosure further provides a compound of the present disclosure, or a pharmaceutically acceptable salt thereof, or a pharmaceutical composition comprising an effective amount of a compound of the present disclosure, or a pharmaceutically acceptable salt thereof, for use in the treatment of a disease or disorder associated with CDK2 activity.

The disclosure further provides a compound of the present disclosure, or a pharmaceutically acceptable salt thereof, or a pharmaceutical composition comprising an effective amount of a compound of the present disclosure, or a pharmaceutically acceptable salt thereof, for use in the manufacture of a medicament for treating a disease or disorder associated with CDK2 activity.

In some embodiments, the disease or disorder associated with CDK2 activity is a CDK2-mediated disease or disorder. In some embodiments, the disease or disorder associated with CDK2 activity is a disease or disorder caused by CDK2 over-activity.

In some embodiments, the disease or disorder associated with CDK2 activity is cancer.

In some embodiments, the cancer is selected from breast cancer, ovarian cancer, bladder cancer, uterine cancer, prostate cancer, lung cancer, esophageal cancer, head and neck cancer, colorectal cancer, kidney cancer, liver cancer, pancreatic cancer, stomach cancer, melanoma and thyroid cancer.

In some embodiments, the cancer is characterized by amplification or overexpression of CCNE1 and/or CCNE2.

In some embodiments, the cancer is breast cancer. In some embodiments, the breast cancer is a breast cancer selected from ER-positive/HR-positive breast cancer, HER2-negative breast cancer, ER-positive/HR-positive breast cancer, HER2-positive breast cancer, triple negative breast cancer (TNBC), inflammatory breast cancer, endocrine resistant breast cancer, trastuzumab resistant breast cancer, breast cancer with primary or acquired resistance to CDK4/CDK6 inhibition, advanced breast cancer and metastatic breast cancer. In some embodiments the breast cancer is characterized by amplification or overexpression of CCNE1 and/or CCNE2.

In some embodiments, the cancer is ovarian cancer. In some embodiments, the ovarian cancer is high-grade serous ovarian cancer (HGSOC). In some embodiments the ovarian cancer is characterized by amplification or overexpression of CCNE1 and/or CCNE2.

In some embodiments, the cancer is bladder cancer. In some embodiments, the bladder cancer is characterized by amplification or overexpression of CCNE1 and/or CCNE2.

In some embodiments, the cancer is uterine cancer. In some embodiments, the uterine cancer is characterized by amplification or overexpression of CCNE1 and/or CCNE2.

In some embodiments, the cancer is prostate cancer. In some embodiments, the prostate cancer is characterized by amplification or overexpression of CCNE1 and/or CCNE2.

In some embodiments, the cancer is lung cancer. In some embodiments, the lung cancer is a lung cancer selected from non-small cell lung cancer, small cell lung cancer, squamous cell carcinoma, adenocarcinoma, and mesothelioma. In some embodiments, the lung cancer is characterized by amplification or overexpression of CCNE1 and/or CCNE2. In some embodiments, the lung cancer is CCNE1 amplified squamous cell carcinoma or CCNE1 amplified adenocarcinoma.

In some embodiments, the cancer is head and neck cancer. In some embodiments, the head and neck cancer is characterized by amplification or overexpression of CCNE1 and/or CCNE2.

In some embodiments, the cancer is colorectal cancer. In some embodiments, the colorectal cancer is characterized by amplification or overexpression of CCNE1 and/or CCNE2.

In some embodiments, the cancer is kidney cancer. In some embodiments, the kidney cancer is renal cell carcinoma (RCC). In some embodiments, the kidney cancer is characterized by amplification or overexpression of CCNE1 and/or CCNE2.

In some embodiments, the cancer is liver cancer. In some embodiments, the liver cancer is hepatocellular carcinoma (HCC). In some embodiments, the liver cancer is characterized by amplification or overexpression of CCNE1 and/or CCNE2.

In some embodiments, the cancer is pancreatic cancer. In some embodiments, the pancreatic cancer is characterized by amplification or overexpression of CCNE1 and/or CCNE2.

In some embodiments, the cancer is stomach cancer. In some embodiments, the stomach cancer is characterized by amplification or overexpression of CCNE1 and/or CCNE2.

In some embodiments, the cancer is melanoma. In some embodiments, the melanoma is characterized by amplification or overexpression of CCNE1 and/or CCNE2. CDK2 expression is regulated by essential melanocytic transcription factor MITF. It has been found that CDK2 depletion suppresses the growth of melanoma (Du et al., Cancer Cell. 2004 December; 6(6): 565-576)

In some embodiments, the cancer is thyroid cancer. In some embodiments, the thyroid cancer is characterized by amplification or overexpression of CCNE1 and/or CCNE2.

In some embodiments, the disease or disorder associated with CDK2 activity is a myeloproliferative disorder.

In some embodiments, the disease or disorder associated with CDK2 activity is a neurodegenerative disease or disorder. In some embodiments, the neurodegenerative disease or disorder is Alzheimer's disease (AD). It has been reported that neuronal cell death in subjects suffering from AD is preceded by cell cycle events. Inhibition of one or more CDKs can inhibit cell cycle events and therefore stave off neuronal cell death (Yang et al., J Neurosci. 2003 Apr. 1; 23(7):2557-2563).

In some embodiments, the disease or disorder associated with CDK2 activity is a liver disease.

In some embodiments, the disease or disorder associated with CDK2 activity is liver fibrosis. It has been reported that CCNE1 knockout mice do not develop liver fibrosis upon exposure to pro-fibrotic toxin $CCl_4$, suggesting that liver fibrosis can be treated via administration of a CDK2 inhibitor (Nevzorova, et al., *Hepatology*. 2012 September; 56(3): 1140-1149.)

In some embodiments, the disease or disorder associated with CDK2 activity is Cushing disease. Pituitary cyclin E/E2F1 signaling is a molecular mechanism underlying neuroendocrine regulation of the hypothalamic-pituitary-adrenal axis, and therefore provides a subcellular therapeutic target for CDK2 inhibitors of pituitary ACTH-dependent hypercortisolism, also known as Cushing disease (Liu, et al., *J Clin Endocrinol Metab*. 2015 July; 100(7): 2557-2564.).

In some embodiments, the disease or disorder associated with CDK2 activity is a kidney disease.

In some embodiments, the disease or disorder associated with CDK2 activity is polycystic kidney disease. It has been reported that CDK2/CDK5 inhibitor roscovitine yields effective arrest of cystic kidney disease in mouse models of polycystic kidney disease (Bukanov, et al., *Nature*. 2006 Dec. 14; 444(7121):949-52).

In some embodiments, the disease or disorder associated with CDK2 activity is an autoimmune disorder. CDK2 ablation has been shown to promote immune tolerance by supporting the function of regulatory T cells (Chunder et al., J Immunol. 2012 Dec. 15; 189(12):5659-66).

In some embodiments, the disease or disorder associated with CDK2 activity is an inflammatory disorder. Cyclin E ablation has been shown to attenuate hepatitis in mice, while p27 knockout mice display exacerbation of renal inflammation (Ehedego et al., Oncogene. 2018 June; 37(25):3329-3339; Ophascharoensuk et al., Nat Med. 1998 May; 4(5): 575-80.). In some embodiments, the inflammatory disorder is hepatitis.

In some embodiments, the compounds and compositions of the present disclosure are useful as male contraceptives. Based on the finding that male CDK2 knockout mice are sterile, CDK2 inhibitors have been studied as possible male contraceptives (Faber, et al., *Biol Reprod*. 2020 August; 103(2): 357-367.). In some embodiments, the present disclosure provides a method of reducing male fertility comprising administering to a patient in need thereof, a compound of the present disclosure, or a pharmaceutically acceptable salt thereof, or a pharmaceutical composition comprising an effective amount of a compound of the present disclosure, or a pharmaceutically acceptable salt thereof.

In some embodiments, the compounds and compositions of the present disclosure are useful for treating diseases and disorders associated with CDK5 activity, including, but not limited to cancers, myeloproliferative disorders, autoimmune disorders, inflammatory disorders, viral infections, fibrotic disorders, and neurodegenerative disorders. In some embodiments, the compounds and compositions of the present disclosure are useful for treating neurodegenerative disorders associated with CDK5 activity.

Combination Therapies

Depending upon the particular condition, or disease, to be treated, additional therapeutic agents, which are normally administered to treat that condition, may be administered in combination with compounds and compositions of this disclosure. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents that the compounds of the present disclosure may also be combined with include, without limitation: endocrine therapeutic agents, chemotherapeutic agents and other CDK inhibitory compounds.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of an endocrine therapeutic agent.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional CDK inhibitory compounds. In some embodiments, the one or more additional CDK inhibitory compounds are CDK4, or CDK4/CDK6 inhibitors. In some embodiments, the one or more additional CDK inhibitory compounds are CDK4, CDK6, CDK7 or CDK4/CDK6 inhibitors. In some embodiments, the one or more additional CDK inhibitory compounds are CDK4 inhibitors. In some embodiments, the one or more additional CDK inhibitory compounds are CDK6 inhibitors. In some embodiments, the one or more additional CDK inhibitory compounds are CDK7 inhibitors. In some embodiments, the one or more additional CDK inhibitory compounds are CDK4/CDK6 inhibitors.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of a chemotherapeutic agent. In some embodiments, the chemotherapeutic agent is a taxane. In some embodiments, the chemotherapeutic agent is a platinum agent. In some embodiments, the chemotherapeutic agent is trastuzumab.

As used herein, the term "combination," "combined," and related terms refers to the simultaneous or sequential administration of therapeutic agents in accordance with this disclosure. For example, a combination of the present disclosure may be administered with another therapeutic agent simultaneously or sequentially in separate unit dosage forms or together in a single unit dosage form.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the present disclosure, as part of a multiple dosage regimen. Alternatively, one or more other therapeutic agents may be part of a single dosage form, mixed together with a compound of this disclosure in a single composition. If administered as a multiple dosage regime, one or more other therapeutic agent and a compound or composition of the present disclosure may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition the present disclosure are administered as a multiple dosage regimen within greater than 24 hours apart.

In one embodiment, the present disclosure provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

EXAMPLES

As depicted in the Examples below, in certain exemplary embodiments, compounds are prepared according to the general procedures provided herein. It will be appreciated that, although the general methods depict the synthesis of certain compounds of the present disclosure, the general methods, and other methods known to one of ordinary skill in the art, can be applied to all compounds and subclasses and species of each of these compounds, as described herein.

Example 1: Synthesis of Intermediates

Intermediate 1: tert-butyl (R)-6-benzyl-8-((S)-4-benzyl-2-oxooxazolidine-3-carbonyl)-2,6-diazaspiro[3.4]octane-2-carboxylate and Intermediate 2: tert-butyl (S)-6-benzyl-8-((S)-4-benzyl-2-oxooxazolidine-3-carbonyl)-2,6-diazaspiro[3.4]octane-2-carboxylate

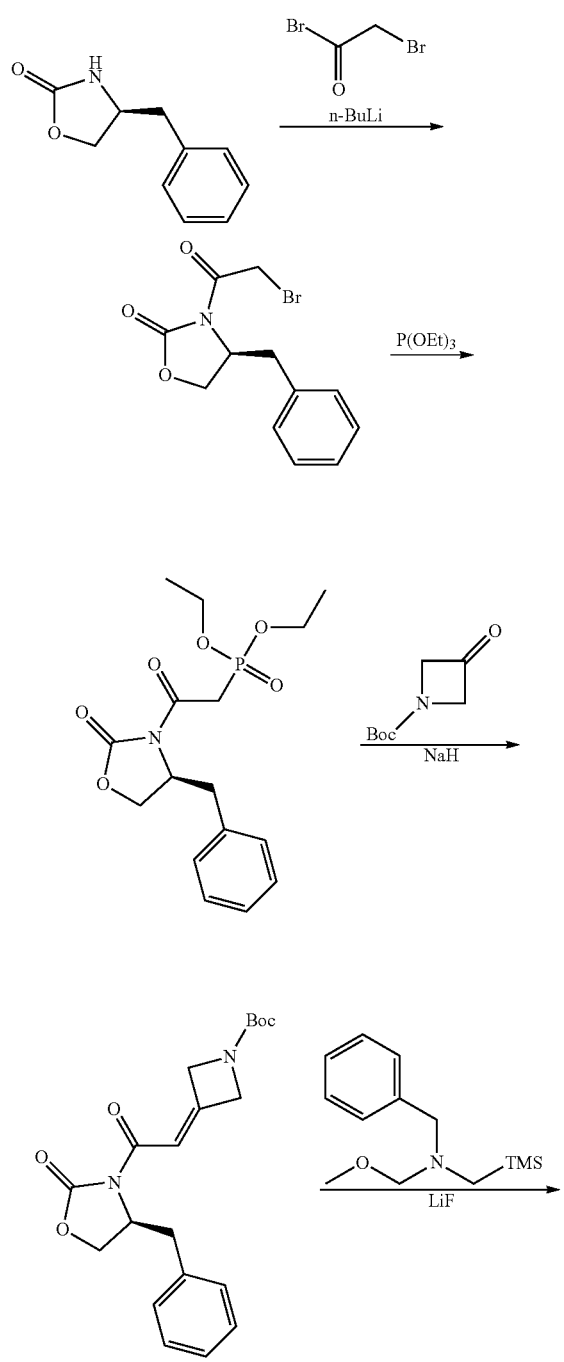

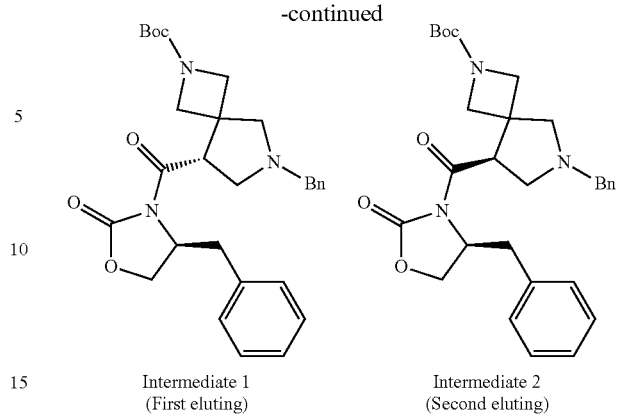

Intermediate 1 (First eluting)   Intermediate 2 (Second eluting)

Step 1: To a solution of (S)-4-benzyloxazolidin-2-one (40 g, 225 mmol) in anhydrous THF (400 mL) at −78° C. under a N₂ atmosphere was added n-BuLi (2.5 M in Hexanes, 99 mL, 248 mmol) dropwise.

The reaction mixture was stirred at −78° C. for 0.5 h then 2-bromoacetyl bromide (21 mL, 237 mmol) was added. The reaction was allowed to warm to room temperature and stirred for another 2 h. The mixture was diluted with EtOAc (600 mL), washed with water (200 mL×2), dried over Na₂SO₄, filtered and concentrated. The residue obtained was purified by column chromatography on silica gel (eluent: Pet. Ether EtOAc=10:1 to 3:1) to afford (S)-4-benzyl-3-(2-bromoacetyl)oxazolidin-2-one (50 g, 75%) as a yellow oil. ¹H NMR (400 MHz, CDCl₃) δ 7.38-7.26 (m, 3H), 7.24-7.19 (m, 2H), 4.70 (ddt, J=9.6, 7.8, 3.2 Hz, 1H), 4.61-4.48 (m, 2H), 4.30-4.20 (m, 2H), 3.33 (dd, J=13.6, 3.4 Hz, 1H), 2.81 (dd, J=13.4, 9.6 Hz, 1H).

Step 2: A mixture of (S)-4-benzyl-3-(2-bromoacetyl)oxazolidin-2-one (100 g, 335 mmol) in triethyl phosphite (279 g, 1.68 mol) was heated at 50° C. for 18 h. The excess triethyl phosphite was removed under vacuum at 70° C. to afford diethyl (S)-(2-(4-benzyl-2-oxooxazolidin-3-yl)-2-oxoethyl)phosphonate (110 g crude, 92%) as a yellow oil. LCMS m/z=356.0 [M+H]⁺; ¹H NMR (400 MHz, CDCl₃) δ 7.37-7.16 (m, 5H), 4.70 (ddt, J=10.4, 7.0, 3.4 Hz, 1H), 4.26-4.12 (m, 6H), 3.88-3.71 (m, 2H), 3.34 (dd, J=13.4, 3.4 Hz, 1H), 2.75 (dd, J=13.4, 9.8 Hz, 1H), 1.34 (t, J=7.0 Hz, 6H).

Step 3: To a solution of diethyl (S)-(2-(4-benzyl-2-oxooxazolidin-3-yl)-2-oxoethyl)phosphonate (30 g, 84 mmol) in anhydrous THF (300 mL) at 0° C. under N₂ atmosphere was added LiHMDS (1.0 M in THF, 85 mL, 85 mmol) dropwise. The reaction mixture was stirred at 0° C. for 30 min then tert-butyl 3-oxoazetidine-1-carboxylate (21.68 g, 127 mmol) was added. The reaction was allowed to warm to room temperature and stirred for another 1 h. The reaction was diluted with EtOAc (1 L) and the organic layer washed with sat. NH₄Cl (200 mL) and water (200 mL), dried over Na₂SO₄, filtered and concentrated. The residue obtained was purified by column chromatography on silica gel (eluent: Pet. Ether:EtOAc=10:1) to afford tert-butyl (S)-3-(2-(4-benzyl-2-oxooxazolidin-3-yl)-2-oxoethylidene)azetidine-1-carboxylate (17 g, 54%) as a yellow solid. LCMS m/z=373.1 [M+H]⁺; ¹H NMR (400 MHz, DMSO-d₆) δ 7.35-7.29 (m, 2H), 7.28-7.23 (m, 1H), 7.22-7.17 (m, 2H), 7.16-7.11 (m, 1H), 4.85-4.60 (m, 5H), 4.34 (t, J=8.4 Hz, 1H), 4.20 (dd, J=8.8, 2.8 Hz, 1H), 3.04 (dd, J=13.4, 3.2 Hz, 1H), 2.94 (dd, J=13.4, 7.6 Hz, 1H), 1.41 (s, 9H).

Step 4: A mixture of afford tert-butyl (S)-3-(2-(4-benzyl-2-oxooxazolidin-3-yl)-2-oxoethylidene)azetidine-1-carboxylate (10 g, 26.85 mmol), N-benzyl-1-methoxy-N-((trimethylsilyl)methyl)methanamine (8.29 g, 34.91 mmol) and LiF (2.09 g, 80.55 mmol) in acetonitrile (100 mL) was heated at 80° C. for 16 h. After cooling to room temperature, the mixture was diluted with water (200 mL) and extracted with EtOAc (300 mL×2). The combined organic layers were washed with brine, dried over $Na_2SO_4$, filtered and concentrated. The mixture was purified by column chromatography on silica gel (eluent: Pet. Ether:EtOAc=5:1) to afford tert-butyl (R)-6-benzyl-8-((S)-4-benzyl-2-oxooxazolidine-3-carbonyl)-2,6-diazaspiro[3.4]octane-2-carboxylate (Intermediate 1) (5 g, 37%) as a yellow oil as the first eluting isomer LCMS m/z=506.3 [M+H]$^+$; $^1$H NMR (400 MHz, DMSO-d$_6$) δ 7.36-7.31 (m, 4H), 7.30-7.23 (m, 4H), 7.20-7.18 (m, 2H), 4.66 (d, J=7.2 Hz, 1H), 4.33 (t, J=8.4 Hz, 1H), 4.23-4.20 (m, 1H), 4.05 (dd, J=8.0, 5.2 Hz, 1H), 3.90 (d, J=9.0 Hz, 1H), 3.75 (s, 1H), 3.73-3.55 (m, 4H), 3.19-3.09 (m, 1H), 3.00-2.92 (m, 3H), 2.74 (d, J=8.8 Hz, 1H), 2.45 (dd, J=9.6, 5.2 Hz, 1H), 1.35 (s, 9H). Further elution provided tert-butyl (S)-6-benzyl-8-((S)-4-benzyl-2-oxooxazolidine-3-carbonyl)-2,6-diazaspiro[3.4]octane-2-carboxylate (Intermediate 2) (5 g, 37%). LCMS m/z=506.3 [M+H]$^+$; $^1$H NMR (400 MHz, DMSO-d$_6$) δ 7.35--7.29 (m, 6H), 7.28-7.22 (m, 4H), 4.67--4.61 (m, 1H), 4.30 (t, J=8.4 Hz, 1H), 4.23 (dd, J=8.2, 6.2 Hz, 1H), 4.19--4.16 (m, 1H), 3.90 (br s, 1H), 3.83 (d, J=9.2 Hz, 1H), 3.68-3.66 (m, 2H), 3.62 (d, J=5.0 Hz, 2H), 3.12-3.05 (m, 1H), 3.02 (d, J=8.8 Hz, 1H), 2.97 (d, J=9.0 Hz, 1H), 2.86 (dd, J=13.4, 8.4 Hz, 1H), 2.65 (d, J=9.0 Hz, 1H), 2.55 (dd, J=9.4, 6.2 Hz, 1H), 1.36 (s, 9H).

Intermediate 4: (S)-6-(1-benzyl-1H-pyrazole-4-carbonyl)-2-((S)-2,2-dimethylcyclopropane-1-carbonyl)-2,6-diazaspiro[3.4]octane-8-carboxylic acid

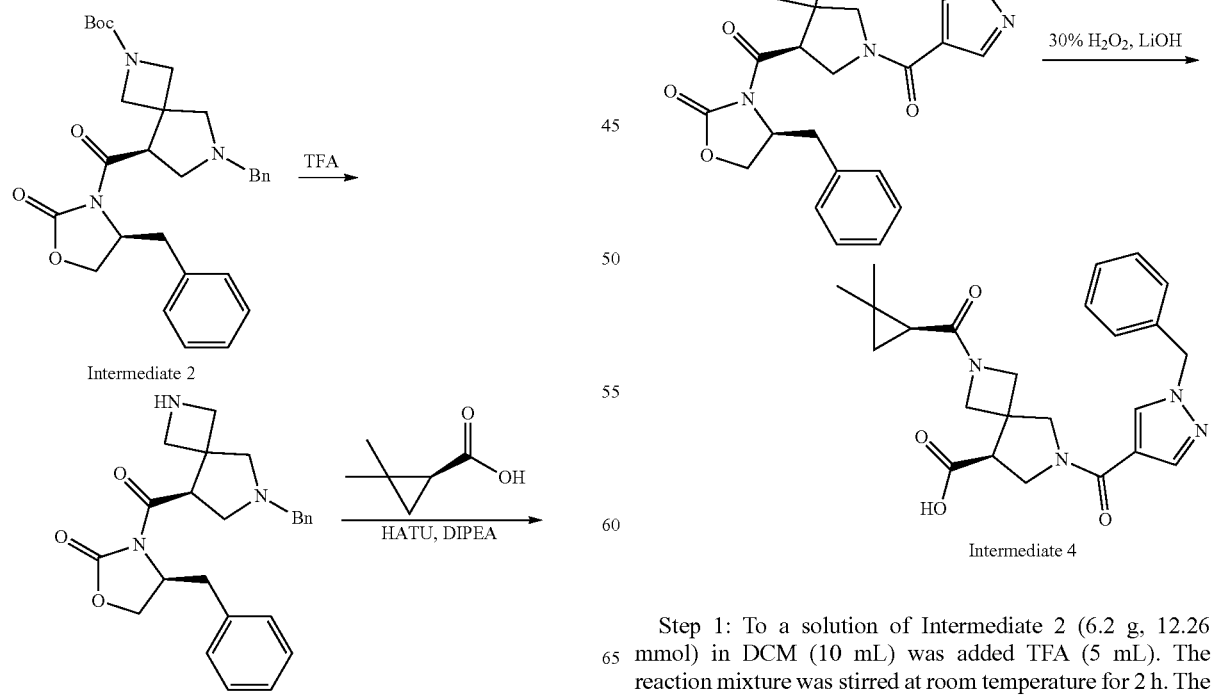

Step 1: To a solution of Intermediate 2 (6.2 g, 12.26 mmol) in DCM (10 mL) was added TFA (5 mL). The reaction mixture was stirred at room temperature for 2 h. The solvent was removed under vacuum to afford crude (S)-4- benzyl-3-((S)-6-benzyl-2,6-diazaspiro[3.4]octane-8-carbonyl)oxazolidin-2-one (5 g, 100%) which was used directly in the next step.

Step 2: To a solution of (S)-2,2-dimethylcyclopropane-1-carboxylic acid (1.55 g, 13.56 mmol) in DCM (50 mL) was added HATU (7.03 g, 18.50 mmol). The mixture was stirred at room temperature for 30 min. (S)-4-benzyl-3-((S)-6-benzyl-2,6-diazaspiro[3.4]octane-8-carbonyl)oxazolidin-2-one (5 g, 12.33 mmol) and DIPEA (6.37 g, 49.32 mmol) were added. The reaction mixture was stirred at room temperature for another 4 h. The mixture was diluted with water (100 mL), and then extracted with DCM (150 mL×2). The combined organic layers were washed with brine, dried over Na$_2$SO$_4$, filtered and concentrated. The mixture was purified by column chromatography on silica gel (eluent: Pet. Ether:EtOAc=3:1 to DCM/EtOAc=3/1) to afford (S)-4-benzyl-3-((S)-6-benzyl-2-((S)-2,2-dimethylcyclopropane-1-carbonyl)-2,6-diazaspiro[3.4]octane-8-carbonyl)oxazolidin-2-one (5.2 g, 84%) as a yellow solid. LCMS m/z=502.3 [M+H]$^+$; $^1$H NMR (400 MHz, DMSO-d$_6$) δ 7.53-7.36 (m, 5H), 7.35-7.21 (m, 5H), 4.67 (ddt, J=8.2, 5.6, 2.6 Hz, 1H), 4.58-4.46 (m, 1H), 4.37-3.93 (m, 7H), 3.89-3.79 (m, 1H), 3.57-3.40 (m, 2H), 3.10 (dt, J=13.4, 3.6 Hz, 1H), 2.88 (dd, J=13.4, 8.4 Hz, 1H), 1.35 (dd, J=8.0, 5.4 Hz, 1H), 1.13-0.96 (m, 6H), 0.86 (q, J=4.4 Hz, 1H), 0.70 (ddd, J=14.8, 8.0, 3.6 Hz, 1H).

Step 3: To a solution of (S)-4-benzyl-3-((S)-6-benzyl-2-((S)-2,2-dimethylcyclopropane-1-carbonyl)-2,6-diazaspiro[3.4]octane-8-carbonyl)oxazolidin-2-one (1.0 g, 1.99 mmol) in EtOAc (8 mL) was added 10% Pd/C (400 mg). The reaction mixture was stirred under a H$_2$ atmosphere for 24 h. Conversion was around 50%. The mixture was filtered through celite and concentrated. The residue was redissolved in EtOAc (8 mL) and another batch of 10% Pd/C (400 mg) was added. The reaction was stirred under H$_2$ atmosphere for another 24 h. The mixture was filtered and concentrated to afford (S)-4-benzyl-3-((S)-2-((S)-2,2-dimethylcyclopropane-1-carbonyl)-2,6-diazaspiro[3.4]octane-8-carbonyl)oxazolidin-2-one (800 mg, 98%) which was used directly in the next step. LCMS m/z=412.2 [M+H]$^+$.

Step 4: To a solution of 1-benzyl-1H-pyrazole-4-carboxylic acid (308 mg, 1.52 mmol) in DMF (10 mL) was added HATU (790 mg, 2.08 mmol). The mixture was stirred at room temperature for 30 min. (S)-4-benzyl-3-((S)-2-((S)-2,2-dimethylcyclopropane-1-carbonyl)-2,6-diazaspiro[3.4]octane-8-carbonyl)oxazolidin-2-one (570 mg, 1.39 mmol) and DIPEA (716 mg, 5.54 mmol) were added. The reaction mixture was stirred at room temperature for another 3 h. The mixture was diluted with water (100 mL), extracted with EtOAc (150 mL×2). The combined organic layers were washed with brine, dried over Na$_2$SO$_4$, filtered and concentrated. The mixture was purified by column chromatography on silica gel (eluent: DCM/MeOH=30/1) to afford the (S)-4-benzyl-3-((S)-6-(1-benzyl-1H-pyrazole-4-carbonyl)-2-((S)-2,2-dimethylcyclopropane-1-carbonyl)-2,6-diazaspiro[3.4]octane-8-carbonyl)oxazolidin-2-one (410 mg, 50%) as a yellow solid. LCMS m/z=596.3 [M+H]$^+$; $^1$H NMR (400 MHz, DMSO-d$_6$) δ 8.44-8.28 (m, 1H), 7.88-7.76 (m, 1H), 7.40-7.18 (m, 10H), 5.36 (d, J=4.4 Hz, 2H), 4.70-4.60 (m, 1H), 4.40-4.23 (m, 4H), 4.21-4.01 (m, 3H), 3.97-3.56 (m, 5H), 3.18-2.84 (m, 3H), 1.42-1.33 (m, 1H), 1.28-1.21 (m, 5H), 1.14-1.02 (m, 7H), 0.86 (d, J=7.2 Hz, 1H), 0.69 (d, J=6.4 Hz, 1H).

Step 5: To a solution of (S)-4-benzyl-3-((S)-6-(1-benzyl-1H-pyrazole-4-carbonyl)-2-((S)-2,2-dimethylcyclopropane-1-carbonyl)-2,6-diazaspiro[3.4]octane-8-carbonyl)oxazolidin-2-one (410 mg, 0.69 mmol) in THF/H$_2$O (16 mL/2 mL) at 0° C. was added lithium hydroxide monohydrate (58 mg, 1.38 mmol) in H$_2$O (1 mL) and 30% H$_2$O$_2$ (0.18 mL, 1.72 mmol) in H$_2$O (1 mL). The reaction mixture was stirred at 0° C. for 1 h then diluted with water (20 mL) and extracted with EtOAc (30 mL). The aqueous layer was collected and acidified with 1M HCl to pH ~ 2 and extracted with EtOAc (60 mL×3). The combined organic layers were washed with brine, dried over Na$_2$SO$_4$, filtered and concentrated to afford crude (S)-6-(1-benzyl-1H-pyrazole-4-carbonyl)-2-((S)-2,2-dimethylcyclopropane-1-carbonyl)-2,6-diazaspiro[3.4]octane-8-carboxylic acid (Intermediate 4) (245 mg, 82%) as a yellow solid. LCMS m/z=437.0 [M+H]$^+$; $^1$H NMR (400 MHz, DMSO-d$_6$) δ 12.69 (s, 1H), 8.38-8.28 (m, 1H), 7.88-7.79 (m, 1H), 7.37-7.23 (m, 6H), 5.36 (s, 2H), 4.37-4.24 (m, 1H), 4.17 (s, 1H), 4.11-3.61 (m, 7H), 1.42-1.32 (m, 1H), 1.09 (d, J=23.0 Hz, 6H), 0.90-0.85 (m, 1H), 0.72-0.64 (m, 1H).

Intermediate 3: (R)-6-(1-benzyl-1H-pyrazole-4-carbonyl)-2-((S)-2,2-dimethylcyclopropane-1-carbonyl)-2,6-diazaspiro[3.4]octane-8-carboxylic acid Intermediate 3 was made by the same method as Intermediate 4, starting from Intermediate 1 in place of Intermediate 2. Intermediate 3 (1.2 g, 40%) was isolated as a white solid which was used without purification. LCMS m/z=437.2 [M+H]$^+$.

Intermediate 5: 6-((9H-fluoren-9-yl)methyl) 2-(tert-butyl) (R)-8-(((2S,3R)-3-(benzyloxy)-1-(methylamino)-1-oxobutan-2-yl)carbamoyl)-2,6-diazaspiro[3.4]octane-2,6-dicarboxylate and Intermediate 6: 6-((9H-fluoren-9-yl)methyl) 2-(tert-butyl) (S)-8-(((2S,3R)-3-(benzyloxy)-1-(methylamino)-1-oxobutan-2-yl)carbamoyl)-2,6-diazaspiro[3.4]octane-2,6-dicarboxylate

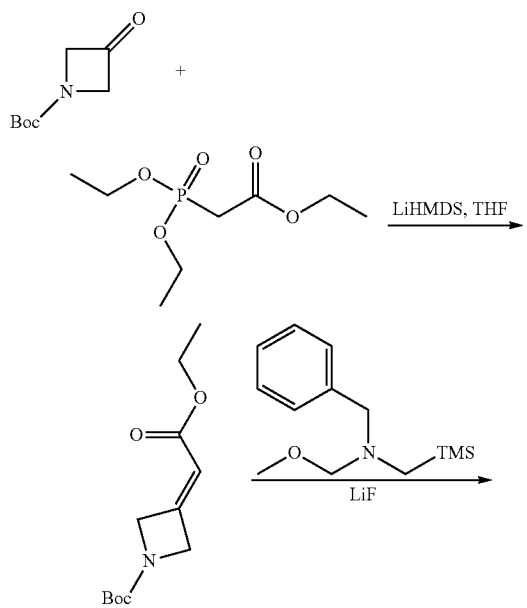

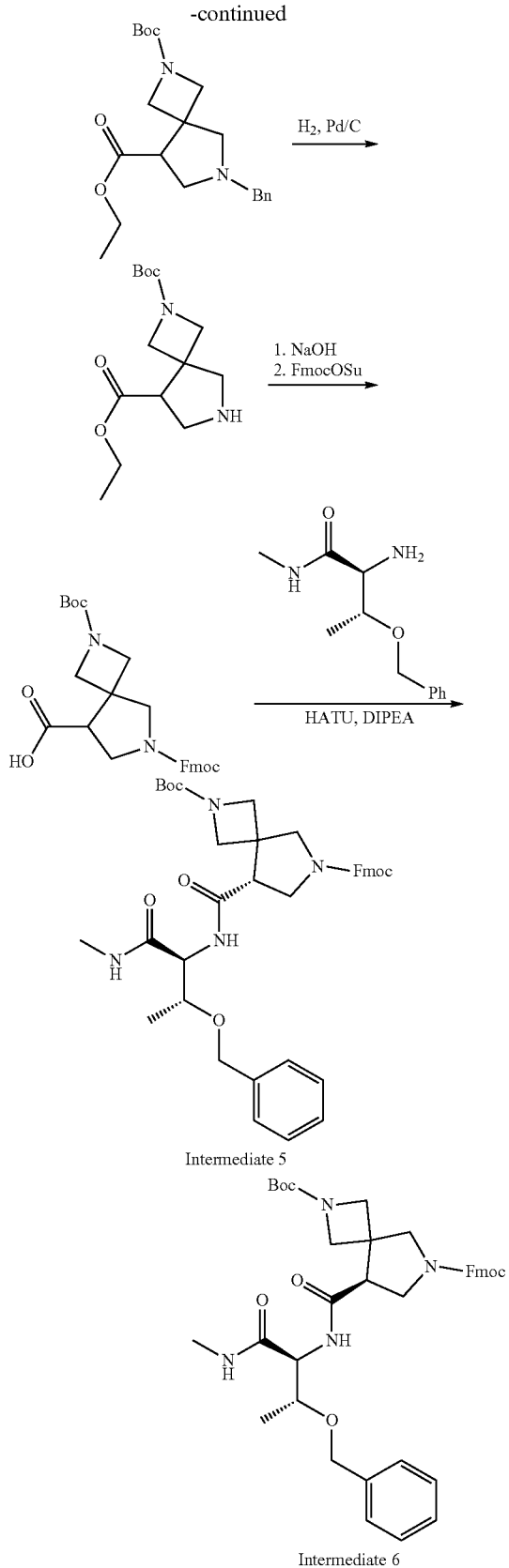

Intermediate 5

Intermediate 6

Step 1: To a solution of ethyl 2-(diethoxyphosphoryl) acetate (52 g, 0.23 mol) in anhydrous THF (200 mL) at 0° C. under $N_2$ atmosphere was added LiHMDS (1.0 M in THF, 234 mL, 0.23 mol) dropwise. The reaction mixture was stirred at 0° C. for 30 min. Tert-butyl 3-oxoazetidine-1-carboxylate (20 g, 0.12 mol) was added and the reaction allowed to warm to room temperature and stirred for another 1 h. The mixture was diluted with EtOAc (1 L) and the organic layer washed with sat. $NH_4Cl$ (200 mL) and water (200 mL), dried over $Na_2SO_4$, filtered and concentrated. The mixture was purified by column chromatography on silica gel (eluent: Pet. Ether:EtOAc=10:1) to afford tert-butyl 3-(2-ethoxy-2-oxoethylidene)azetidine-1-carboxylate (21 g, 75%) as a yellow solid. LCMS m/z=242.2 [M+H]$^+$; $^1$H NMR (400 MHz, Chloroform-d) δ 5.76 (p, J=2.4 Hz, 1H), 4.84-4.78 (m, 2H), 4.61-4.55 (m, 2H), 4.17 (qd, J=7.2, 0.8 Hz, 2H), 1.45 (s, 9H), 1.27 (t, J=7.2, 0.8 Hz, 3H).

Step 2: A mixture of tert-butyl 3-(2-ethoxy-2-oxoethylidene)azetidine-1-carboxylate (17 g, 70.46 mmol), N-benzyl-1-methoxy-N-((trimethylsilyl)methyl)methanamine (20 g, 84.55 mmol) and LiF (5.48 g, 0.21 mol) in acetonitrile (100 mL) was heated at 80° C. for 16 h. After cooling to room temperature, the mixture was diluted with water (200 mL) and extracted with EtOAc (300 mL×2). The combined organic layers were washed with brine, dried over $Na_2SO_4$, filtered and concentrated. The mixture was purified by column chromatography on silica gel (eluent: Pet. Ether:EtOAc=5:1) to afford 2-(tert-butyl) 8-ethyl 6-benzyl-2,6-diazaspiro[3.4]octane-2,8-dicarboxylate (20 g, 76%) as a yellow oil. $^1$H NMR (400 MHz, Chloroform-d) δ 7.31-7.26 (m, 3H), 7.25-7.17 (m, 2H), 4.20-4.10 (m, 2H), 3.79 (dd, J=12.6, 8.8 Hz, 2H), 3.69-3.63 (m, 2H), 3.60 (d, J=4.8 Hz, 2H), 3.03-2.87 (m, 3H), 2.76-2.64 (m, 2H), 1.38 (s, 9H), 1.24 (t, J=7.2 Hz, 4H).

Step 3: To a solution of 2-(tert-butyl) 8-ethyl 6-benzyl-2,6-diazaspiro[3.4]octane-2,8-dicarboxylate (20 g, 53.41 mmol) in EtOAc (120 mL) was added 10% Pd/C (5 g). The reaction mixture was stirred under an $H_2$ atmosphere for 4 days. The mixture was filtered through celite and concentrated to afford 2-(tert-butyl) 8-ethyl 2,6-diazaspiro[3.4]octane-2,8-dicarboxylate (15 g, 100%) which was used directly in the next step.

Steps 4 & 5: To a solution of 2-(tert-butyl) 8-ethyl 2,6-diazaspiro[3.4]octane-2,8-dicarboxylate (15 g, 52.75 mmol) in a mixture of THF and $H_2O$ (100 mL/50 mL) was added NaOH (4.2 g, 0.1 mol). The reaction mixture was stirred at room temperature for 5 hours. FmocOSu (20 g, 59.29 mmol) was added and the resulting mixture was stirred for another 3 h then diluted with water (50 mL) and extracted with EtOAc (100 mL). The aqueous layer was collected and acidified with 1M HCl to pH ~ 2 and extracted with EtOAc (200 mL×3). The combined organic layers were washed with brine, dried over $Na_2SO_4$, filtered and concentrated. The mixture was purified by column chromatography on silica gel (eluent: DCM/MeOH=20/1) to afford 6-(((9H-fluoren-9-yl)methoxy)carbonyl)-2-(tert-butoxycarbonyl)-2,6-diazaspiro[3.4]octane-8-carboxylic acid (10.5 g, 42%) as a white solid. LCMS m/z=479.3 [M+H]$^+$; $^1$H NMR (400 MHz, Chloroform-d) δ 7.77 (dd, J=7.6, 3.6 Hz, 2H), 7.58 (d, J=7.4 Hz, 2H), 7.44-7.36 (m, 2H), 7.36-7.28 (m, 2H), 4.48-4.34 (m, 2H), 4.23 (t, J=6.8 Hz, 1H), 4.10 (d, J=9.4 Hz, 1H), 3.99 (t, J=8.4 Hz, 1H), 3.92-3.53 (m, 6H), 3.18-3.07 (m, 1H), 1.46 (d, J=6.6 Hz, 9H).

Step 6: To a solution of 6-(((9H-fluoren-9-yl)methoxy)carbonyl)-2-(tert-butoxycarbonyl)-2,6-diazaspiro[3.4]octane-8-carboxylic acid (13 g, 27.20 mmol) in DMF (100 mL) was added HATU (15.5 g, 40.80 mmol) and the mixture stirred at room temperature for 30 min. (2S,3R)-2-amino-3-(benzyloxy)-N-methylbutanamide (7.2 g, 32.60 mmol)

and DIPEA (14 g, 0.11 mol) were added and the reaction stirred for another 3 h. The mixture was diluted with water (200 mL) and extracted with DCM (300 mL×2). The combined organic layers were washed with brine, dried over Na$_2$SO$_4$, filtered and concentrated. The residue obtained was purified by column chromatography on silica gel (eluent: Pet. Ether:EtOAc=1:1) to afford 6-((9H-fluoren-9-yl)methyl) 2-(tert-butyl) (R)-8-(((2S,3R)-3-(benzyloxy)-1-(methylamino)-1-oxobutan-2-yl)carbamoyl)-2,6-diazaspiro[3.4]octane-2,6-dicarboxylate (Intermediate 5) (6.8 g, 37%) as a white solid LCMS m/z=683.2 [M+H]$^+$; $^1$H NMR (400 MHz, Chloroform-d) δ 7.77 (d, J=7.0 Hz, 2H), 7.62-7.54 (m, 3H), 7.45-7.28 (m, 11H), 6.80 (d, J=6.2 Hz, 1H), 6.48 (s, 1H), 4.68-4.59 (m, 2H), 4.56 (dd, J=6.0, 3.2 Hz, 1H), 4.40 (t, J=5.8 Hz, 2H), 4.28-3.96 (m, 4H), 3.91-3.78 (m, 5H), 3.73-3.57 (m, 4H), 2.99 (t, J=5.6 Hz, 1H), 2.82 (d, J=4.8 Hz, 4H), 1.45 (d, J=8.0 Hz, 12H), 1.11 (dd, J=9.4, 6.2 Hz, 4H). Further elution provided 6-((9H-fluoren-9-yl)methyl) 2-(tert-butyl) (S)-8-(((2S,3R)-3-(benzyloxy)-1-(methylamino)-1-oxobutan-2-yl)carbamoyl)-2,6-diazaspiro[3.4]octane-2,6-dicarboxylate (Intermediate 6) (7 g, 38%) as a white solid. LCMS m/z=683.3 [M+H]$^+$; $^1$H NMR (400 MHz, DMSO-d$_6$) δ 8.30 (s, 1H), 7.92-7.83 (m, 3H), 7.69-7.62 (m, 2H), 7.42 (t, J=7.4 Hz, 2H), 7.35-7.25 (m, 7H), 4.54 (d, J=12.0 Hz, 1H), 4.44 (d, J=12.0 Hz, 1H), 4.38-4.24 (m, 5H), 4.02-3.83 (m, 3H), 3.74-3.35 (m, 8H), 2.61 (t, J=4.2 Hz, 3H), 1.38-1.34 (m, 9H), 1.10 (d, J=6.4 Hz, 3H).

Intermediate 7: (R)—N-((2S,3R)-3-(benzyloxy)-1-(methylamino)-1-oxobutan-2-yl)-2-((S)-2,2-dimethylcyclopropane-1-carbonyl)-2,6-diazaspiro[3.4]octane-8-carboxamide

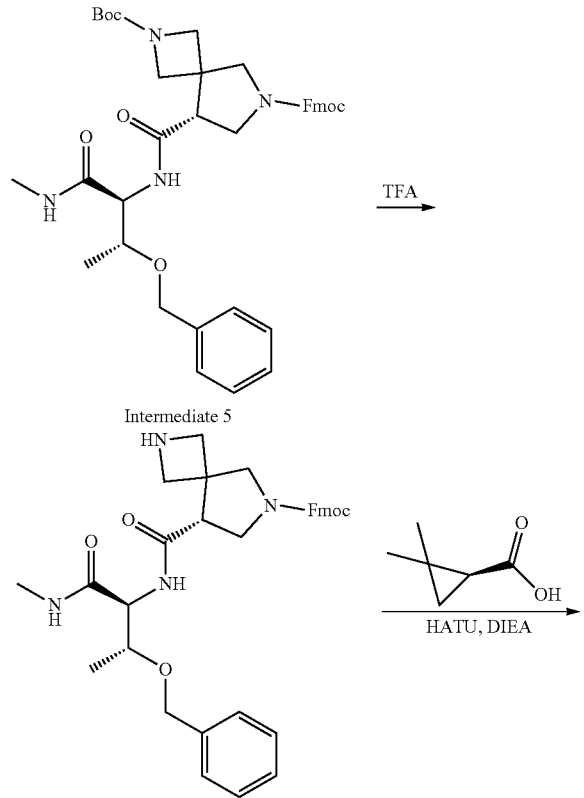

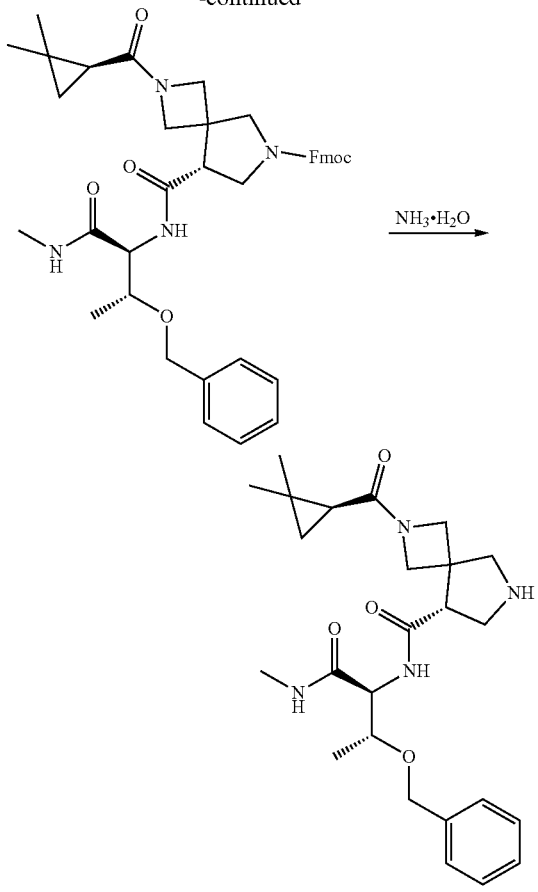

Intermediate 7

Step 1: To a solution of Intermediate 5 (0.2 g, 0.29 mmol) in DCM (1 mL) was added TFA (0.3 mL). The reaction mixture was stirred at room temperature for 1 h. The solvent was removed under vacuum to afford (9H-fluoren-9-yl)methyl (R)-8-(((2S,3R)-3-(benzyloxy)-1-(methylamino)-1-oxobutan-2-yl)carbamoyl)-2,6-diazaspiro[3.4]octane-6-carboxylate (170 mg, 100%) which was used directly in the next step. LCMS m/z=583.3 [M+H]$^+$.

Step 2: To a solution of (S)-2,2-dimethylcyclopropane-1-carboxylic acid (37 mg, 0.32 mmol) in DCM (2 mL) was added HATU (166 mg, 0.44 mmol). The mixture was stirred at room temperature for 30 min. (R)-8-(((2S,3R)-3-(benzyloxy)-1-(methylamino)-1-oxobutan-2-yl)carbamoyl)-2,6-diazaspiro[3.4]octane-6-carboxylate (170 mg, 0.29 mmol) and DIPEA (151 mg, 1.17 mmol) were added and the reaction mixture stirred at room temperature for another 1 h. The mixture was diluted with water (60 mL) and extracted with EtOAc (100 mL×2). The combined organic layers were washed with brine, dried over Na$_2$SO$_4$, filtered and concentrated. The mixture was purified by column chromatography on silica gel (eluent: DCM:MeOH=15:1) to afford (9H-fluoren-9-yl)methyl (R)-8-(((2S,3R)-3-(benzyloxy)-1-(methylamino)-1-oxobutan-2-yl)carbamoyl)-2-((S)-2,2-dimethylcyclopropane-1-carbonyl)-2,6-diazaspiro[3.4] octane-6-carboxylate (120 mg, 61%) as a white solid. LCMS m/z=679.4 [M+H]$^+$. $^1$H NMR (400 MHz, DMSO-d$_6$) δ 8.35 (dd, J=8.0 Hz, 1H), 7.99-7.85 (m, 3H), 7.72-7.59 (m, 2H), 7.54-7.19 (m, 9H), 4.54 (dd, J=12.2, 4.2 Hz, 1H), 4.46-4.38 (m, 1H), 4.37-4.19 (m, 4H), 4.13-4.02 (m, 1H), 4.00-3.85

(m, 2H), 3.82-3.68 (m, 1H), 3.67-3.53 (m, 2H), 3.50-3.39 (m, 3H), 3.31 (s, 1H), 2.61 (dd, J=4.6, 1.6 Hz, 3H), 1.41-1.31 (m, 1H), 1.15-1.03 (m, 9H), 0.89-0.85 (m, 1H), 0.74-0.65 (m, 1H).

Step 3: To a solution of (9H-fluoren-9-yl)methyl (R)-8-(((2S,3R)-3-(benzyloxy)-1-(methylamino)-1-oxobutan-2-yl)carbamoyl)-2-((S)-2,2-dimethylcyclopropane-1-carbonyl)-2,6-diazaspiro[3.4]octane-6-carboxylate (120 mg, 0.25 mmol) in 1,4-dioxane (2 mL) was added 25% ammonium hydroxide (2 mL). The reaction mixture was heated at 50° C. overnight and the solvent removed under vacuum. The residue was triturated with diethyl ether (10 mL×2) to afford (R)—N-((2S,3R)-3-(benzyloxy)-1-(methylamino)-1-oxobutan-2-yl)-2-((S)-2,2-dimethylcyclopropane-1-carbonyl)-2,6-diazaspiro[3.4]octane-8-carboxamide (Intermediate 7) (70 mg, 88%) as a white solid, LCMS m/z=457.3 [M+H]⁻

Intermediate 8: (S)—N-((2S,3R)-3-(benzyloxy)-1-(methylamino)-1-oxobutan-2-yl)-2-((S)-2,2-dimethylcyclopropane-1-carbonyl)-2,6-diazaspiro[3.4]octane-8-carboxamide Intermediate 8 was made by the same method as Intermediate 7, starting from Intermediate 6 in place of Intermediate 5. Intermediate 8 (550 mg, 40%) was isolated as a yellow solid. LCMS m/z=457.4 [M+H]⁺.

Intermediate 9: N-((2S,3R)-3-(benzyloxy)-1-(methylamino)-1-oxobutan-2-yl)-2-(2,2-dimethylcyclopropane-1-carbonyl)-2,6-diazaspiro[3.4]octane-8-carboxamide

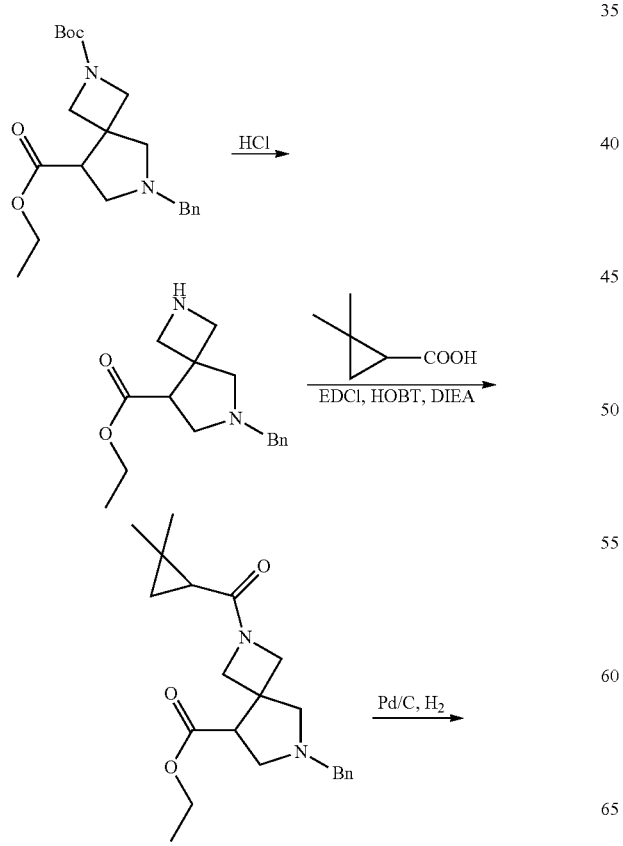

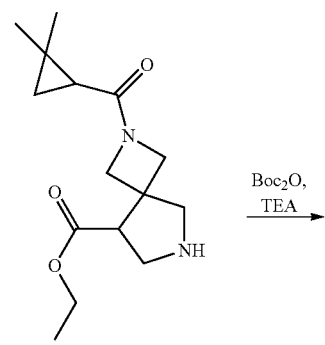

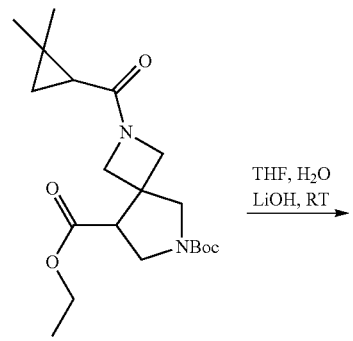

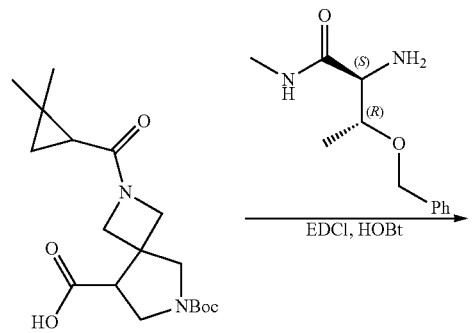

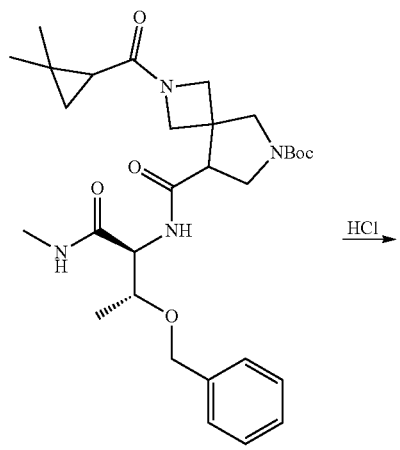

-continued

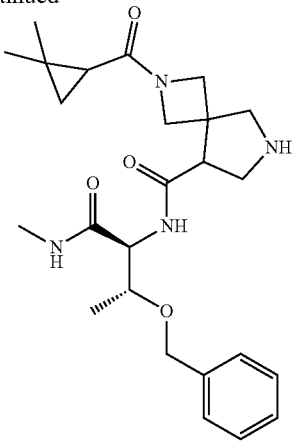

Step 1: To a solution of 2-(tert-butyl) 8-ethyl 6-benzyl-2,6-diazaspiro[3.4]octane-2,8-dicarboxylate (Intermediate 5-Step 2) (2.0 g, 5.3 mmol) in EtOH (2.0 mL) was added HCl/dioxane (4 M, 10 mL, 40 mmol). The mixture was stirred at room temperature for 1 h and then the solvent was removed under vacuum to afford ethyl 6-benzyl-2,6-diazaspiro[3.4]octane-8-carboxylate which was used in the next step directly. LCMS m/z=275.1 [M+H]$^+$.

Step 2: To a solution of 2,2-dimethylcyclopropane-1-carboxylic acid (500 mg, 4.38 mmol) in dry DMF (10 mL) was added EDCI (841 mg, 4.38 mmol), HOBt (591 mg, 4.38 mmol) and DIPEA (2.0 g, 14.6 mmol) and the mixture was stirred at room temperature for 1 h. Ethyl 6-benzyl-2,6-diazaspiro[3.4]octane-8-carboxylate (1.0 g, 3.65 mmol) was added and the reaction was stirred for an additional 14 h. The mixture was diluted with water (50 mL) and extracted with EtOAc (100 mL×2). The combined organic layers were washed with brine, dried over $Na_2SO_4$, filtered and concentrated. The residue obtained was purified by column chromatography on silica gel (eluent: Pet. Ether:EtOAc=1:1) to afford ethyl 6-benzyl-2-(2,2-dimethylcyclopropane-1-carbonyl)-2,6-diazaspiro[3.4]octane-8-carboxylate (590 mg, 43%) as a colorless oil. LCMS m/z=371.1 [M+H]$^+$; $^1$H NMR (400 MHz, CD$_3$OD) δ 7.53-7.02 (m, 5H), 4.37-3.70 (m, 6H), 3.67 (s, 2H), 3.22-3.12 (m, 1H), 3.02-2.77 (m, 4H), 1.42-1.35 (m, 1H), 1.32-1.23 (m, 3H), 1.19-1.05 (m, 6H), 1.04-0.97 (m, 1H), 0.79-0.71 (m, 1H).

Step 3: To a solution of ethyl 6-benzyl-2-(2,2-dimethylcyclopropane-1-carbonyl)-2,6-diazaspiro[3.4]octane-8-carboxylate (50 mg, 0.135 mmol) in MeOH (3.0 mL) was added 10% Pd/C (35 mg). The mixture was stirred under a H$_2$ atmosphere overnight. The mixture was filtered through celite and concentrated to afford ethyl 2-(2,2-dimethylcyclopropane-1-carbonyl)-2,6-diazaspiro[3.4]octane-8-carboxylate which was used directly in the next step. LCMS m/z=281.1 [M+H]$^+$.

Step 4: To a solution of ethyl 2-(2,2-dimethylcyclopropane-1-carbonyl)-2,6-diazaspiro[3.4]octane-8-carboxylate (430 mg, 1.5 mmol) in DCM (5 mL) was added (Boc)$_2$O (400 mg, 1.84 mmol) and TEA (227 mg, 2.25 mmol) and the mixture was stirred at room temperature for 4 h. The solvent was removed under vacuum and the residue was purified by column chromatography on silica gel (eluent: Pet. Ether:EtOAc=3:1) to afford 6-(tert-butyl) 8-ethyl 2-(2,2-dimethylcyclopropane-1-carbonyl)-2,6-diazaspiro[3.4]octane-6,8-dicarboxylate (522 mg, 89%) as a colorless oil. LCMS m/z=381.2 [M+H]$^+$.

Step 5: To a solution of 6-(tert-butyl) 8-ethyl 2-(2,2-dimethylcyclopropane-1-carbonyl)-2,6-diazaspiro[3.4]octane-6,8-dicarboxylate (522 mg, 1.37 mmol) in a mixture of THF and H$_2$O (4 mL/1 mL) was added LiOH (247 mg, 4.12 mmol). The reaction mixture was stirred at room temperature for 2 h then diluted with water (30 mL) and extracted with EtOAc (50 mL). The aqueous layer was collected and acidified with 1M HCl to pH ~ 2 and extracted with EtOAc (100 mL×3). The combined organic layers were washed with brine, dried over $Na_2SO_4$, filtered and concentrated to afford 6-(tert-butoxycarbonyl)-2-(2,2-dimethylcyclopropane-1-carbonyl)-2,6-diazaspiro[3.4]octane-8-carboxylic acid (457 mg, 94%) as a white solid which was used directly in the next step. LCMS m/z=353.2 [M+H]$^+$.

Step 6: To a solution of 6-(tert-butoxycarbonyl)-2-(2,2-dimethylcyclopropane-1-carbonyl)-2,6-diazaspiro[3.4]octane-8-carboxylic acid (100 mg, 0.284 mmol) in dry DMA (2 mL) was added EDCI (82 mg, 0.426 mmol), HOBt (57.5 mg, 0.426 mmol) and DIPEA (146 mg, 1.136 mmol) and the mixture stirred at room temperature for 1 h. (2S,3R)-2-amino-3-(benzyloxy)-N-methylbutanamide (75.7 mg, 0.341 mmol) was added and the reaction stirred a further 14 h. The mixture was diluted with water (20 mL) and extracted with EtOAc (60 mL×2). The combined organic layers were washed with brine, dried over $Na_2SO_4$, filtered and concentrated. The residue obtained was purified by column chromatography on silica gel (eluent: DCM:MeOH=50:1) to afford tert-butyl 8-(((2S,3R)-3-(benzyloxy)-1-(methylamino)-1-oxobutan-2-yl)carbamoyl)-2-(2,2-dimethylcyclopropane-1-carbonyl)-2,6-diazaspiro[3.4]octane-6-carboxylate (150 mg, 95%) as a white solid. LCMS m/z=557.4 [M+H]$^+$.

Step 7: To a solution of tert-butyl 8-(((2S,3R)-3-(benzyloxy)-1-(methylamino)-1-oxobutan-2-yl)carbamoyl)-2-(2,2-dimethylcyclopropane-1-carbonyl)-2,6-diazaspiro[3.4]octane-6-carboxylate (556 mg, 1 mmol) in dioxane (4.0 mL) was added a solution of HCl in dioxane (4 M, 3 mL, 12 mmol). The mixture was stirred at room temperature for 1 h then the solvent was removed under vacuum to afford N-((2S,3R)-3-(benzyloxy)-1-(methylamino)-1-oxobutan-2-yl)-2-(2,2-dimethylcyclopropane-1-carbonyl)-2,6-diazaspiro[3.4]octane-8-carboxamide as a white solid. LCMS m/z=457.2 [M+H]$^+$.

Intermediate 10: 6-(1-benzyl-1H-pyrazole-4-carbonyl)-N-((2S,3R)-3-methoxy-1-(methylamino)-1-oxobutan-2-yl)-2,6-diazaspiro[3.4]octane-8-carboxamide

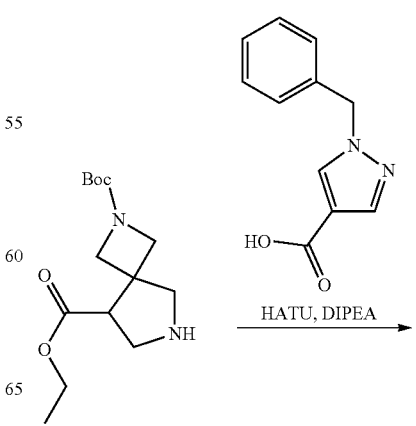

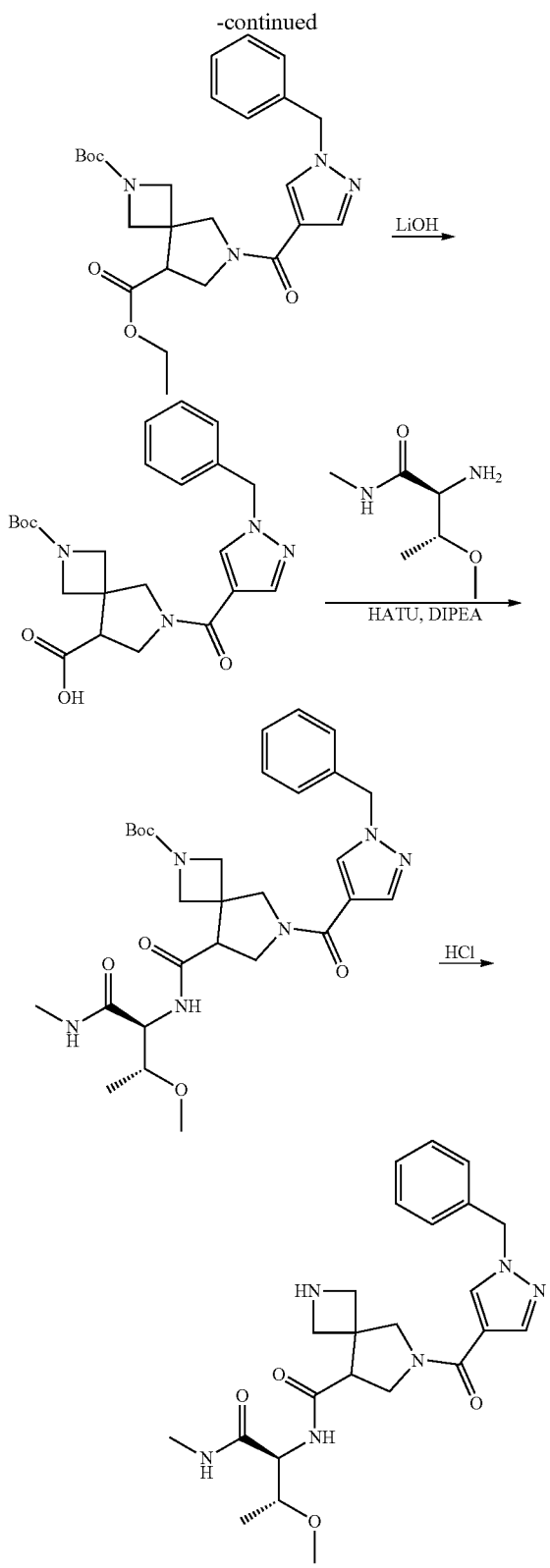

added and the reaction stirred for 4 h then diluted with water (50 mL) and extracted with EtOAc (100 mL×2). The combined organic layers were washed with brine, dried over $Na_2SO_4$, filtered and concentrated. The mixture was purified by column chromatography on silica gel (eluent: DCM: MeOH=50:1) to afford 2-(tert-butyl) 8-ethyl 6-(1-benzyl-1H-pyrazole-4-carbonyl)-2,6-diazaspiro[3.4]octane-2,8-dicarboxylate (2.9 g, 92%) as a white solid. LCMS m/z=469.1 [M+H]$^+$.

Step 2: To a solution of 2-(tert-butyl) 8-ethyl 6-(1-benzyl-1H-pyrazole-4-carbonyl)-2,6-diazaspiro[3.4]octane-2,8-dicarboxylate (1.0 g, 2.1 mmol) in a mixture of THF and $H_2O$ (8 mL/2 mL) was added LiOH (0.15 g, 6.4 mmol). The reaction mixture was stirred at room temperature for 2 h then diluted with water (30 mL) and extracted with ether (50 mL). The aqueous layer was collected and acidified with 1M HCl to pH ~ 2 and extracted with EtOAc (100 mL×3). The combined organic layers were washed with brine, dried over $Na_2SO_4$, filtered and concentrated to afford 6-(1-benzyl-1H-pyrazole-4-carbonyl)-2-(tert-butoxycarbonyl)-2,6-diazaspiro[3.4]octane-8-carboxylic acid (960 mg, 94%) as a white solid which was used directly in the next step. $^1$H NMR (400 MHz, DMSO-$d_6$) δ 8.36 (d, J=15.3 Hz, 1H), 7.82 (d, J=16.7 Hz, 1H), 7.40-7.23 (m, 5H), 5.35 (s, 2H), 4.03-3.55 (m, 9H), 2.85 (s, 1H), 1.37 (d, J=2.9 Hz, 9H).

Step 3: To a solution of 6-(1-benzyl-1H-pyrazole-4-carbonyl)-2-(tert-butoxycarbonyl)-2,6-diazaspiro[3.4]octane-8-carboxylic acid (200 mg, 0.46 mmol) in dry DMF (5 mL) was added HATU (260 mg, 0.68 mmol) and DIEA (234 mg, 1.81 mmol) and the mixture stirred at room temperature for 30 min. (2S,3R)-2-amino-3-methoxy-N-methylbutanamide (80 mg, 0.55 mmol) was added and the reaction stirred for a further 4 h then diluted with water (50 mL), extracted with EtOAc (100 mL×2). The combined organic layers were washed with brine, dried over $Na_2SO_4$, filtered and concentrated. The mixture was purified by column chromatography on silica gel (eluent: DCM:MeOH=50:1) to afford tert-butyl 6-(1-benzyl-1H-pyrazole-4-carbonyl)-8-(((2S,3R)-3-methoxy-1-(methylamino)-1-oxobutan-2-yl)carbamoyl)-2,6-diazaspiro[3.4]octane-2-carboxylate (118 mg, 46%) as a white solid. LCMS m/z=569.3 [M+H]$^+$.

Step 4: To a solution of tert-butyl 6-(1-benzyl-1H-pyrazole-4-carbonyl)-8-(((2S,3R)-3-methoxy-1-(methylamino)-1-oxobutan-2-yl)carbamoyl)-2,6-diazaspiro[3.4]octane-2-carboxylate (130 mg, 0.23 mmol) in dioxane (2.0 mL) was added a solution of HCl in dioxane (4 M, 2 mL, 8 mmol). The reaction was stirred at room temperature for 1 h then the solvent was removed under vacuum to afford 6-(1-benzyl-1H-pyrazole-4-carbonyl)-N-((2S,3R)-3-methoxy-1-(methylamino)-1-oxobutan-2-yl)-2,6-diazaspiro[3.4]octane-8-carboxamide (Intermediate 10) (120 mg) as a white solid.

Intermediate 11: tert-butyl (S)-6-benzyl-8-((R)-2-oxo-4-phenyloxazolidine-3-carbonyl)-2,6-diazaspiro[3.4]octane-2-carboxylate & Intermediate 12: tert-butyl (R)-6-benzyl-8-((R)-2-oxo-4-phenyloxazolidine-3-carbonyl)-2,6-diazaspiro[3.4]octane-2-carboxylate Step 1: To a solution of 1-benzyl-1H-pyrazole-4-carboxylic acid (1.1 g, 5.6 mmol) in dry DMF (10 mL) was added HATU (3.2 g, 8.4 mmol) and DIEA (2.89 g, 22.4 mmol) and the mixture was stirred at room temperature for 30 min. 2-(tert-butyl) 8-ethyl 2,6-diazaspiro[3.4]octane-2,8-dicarboxylate (Intermediate 5-Step 3) (1.9 g, 6.7 mmol) was

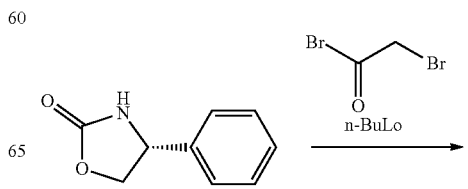

-continued

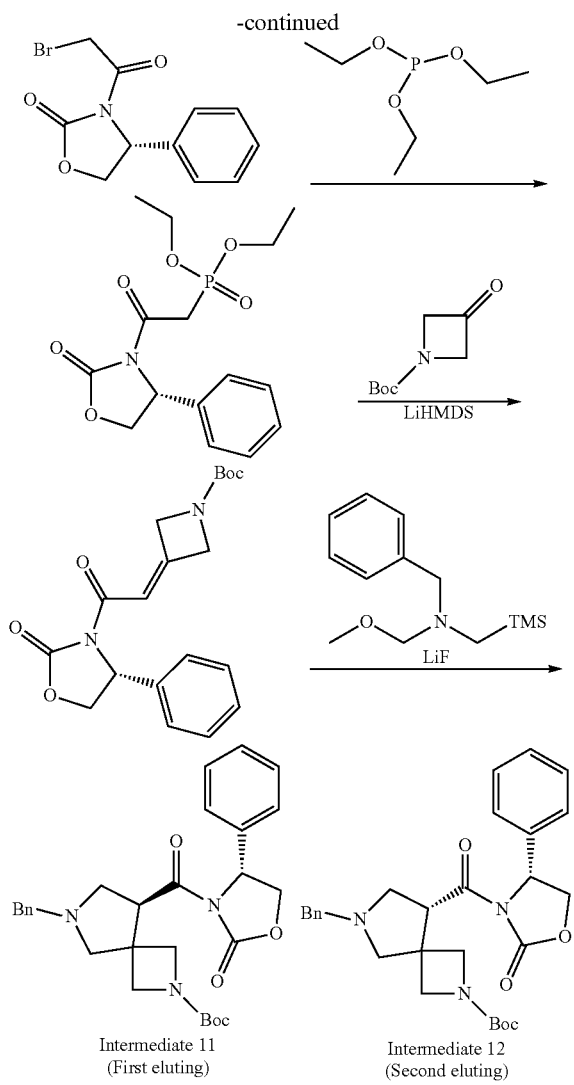

Intermediate 11
(First eluting)

Intermediate 12
(Second eluting)

Step 1: To a solution of (R)-4-phenyloxazolidin-2-one (10 g, 61 mmol) in anhydrous THF (100 mL) at −78° C. under a N₂ atmosphere was added n-BuLi (2.5 M in Hexanes, 27 mL, 67 mmol) dropwise. The reaction mixture was stirred at −78° C. for 0.5 h then 2-bromoacetyl bromide (5.6 mL, 64 mmol) was added. The reaction was allowed to warm to room temperature and stirred for another 2 h. The mixture was diluted with EtOAc (100 mL), quenched with sat. NH₄Cl (100 mL), extracted with EtOAc (100 mL×2), dried over Na₂SO₄, filtered and concentrated. The residue was purified by column chromatography on silica gel (eluent: Pet. Ether:EtOAc=10:1 to 3:1) to afford (R)-3-(2-bromoacetyl)-4-phenyloxazolidin-2-one (9 g, 52%) as a yellow oil. ¹H NMR (400 MHz, DMSO-d6) δ 7.42-7.37 (m, 2H), 7.36-7.30 (m, 3H), 5.52-5.46 (m, 1H), 4.83-4.75 (m, 2H), 4.56-4.50 (m, 1H), 4.24-4.18 (m, 1H).

Step 2: A mixture of (R)-3-(2-bromoacetyl)-4-phenyloxazolidin-2-one (10 g, 35 mmol) in triethyl phosphite (29 g, 175 mmol) was heated at 50° C. for 18 h. The excess triethyl phosphite was removed under vacuum at 70° C. to afford diethyl (R)-(2-oxo-2-(2-oxo-4-phenyloxazolidin-3-yl)ethyl)phosphonate (12 g crude, 99%) as a yellow oil. LCMS m/z=342.1 [M+H]⁺; ¹H NMR (400 MHz, CDCl₃) δ 7.41-7.29 (m, 5H), 5.55-5.48 (m, 1H), 4.78-4.70 (m, 1H), 4.20-4.14 (m, 1H), 4.03-3.96 (m, 5H), 3.60-3.48 (m, 1H), 1.27-1.15 (m, 8H).

Step 3: To a solution of diethyl (R)-(2-oxo-2-(2-oxo-4-phenyloxazolidin-3-yl)ethyl)phosphonate (10 g, 29 mmol) in anhydrous THF (100 mL) at 0° C. under N₂ atmosphere was added LiHMDS (1.0 M in THF, 29 mL, 29 mmol) dropwise. The reaction mixture was stirred at 0° C. for 30 min then tert-butyl 3-oxoazetidine-1-carboxylate (21.68 g, 127 mmol) was added. The reaction was warmed to room temperature and stirred for 1 h. The reaction was diluted with EtOAc (200 mL), and the organic layer was washed with sat. NH₄Cl (100 mL), dried over Na₂SO₄, filtered and concentrated. The residue was purified by column chromatography on silica gel (eluent: Pet. Ether:EtOAc=10:1) to afford tert-butyl (R)-3-(2-oxo-2-(2-oxo-4-phenyloxazolidin-3-yl)ethylidene)azetidine-1-carboxylate (10 g, 95%) as a yellow solid. LCMS m/z=492.0 [M+H]⁺; ¹H NMR (400 MHz, DMSO-d6) δ 7.41-7.36 (m, 2H), 7.34-7.28 (m, 3H), 7.20-7.15 (m, 1H), 5.53-5.46 (m, 1H), 4.79-4.73 (m, 1H), 4.61 (s, 4H), 4.21-4.14 (m, 1H), 1.37 (s, 9H).

Step 4: A mixture of tert-butyl (R)-3-(2-oxo-2-(2-oxo-4-phenyloxazolidin-3-yl)ethylidene)azetidine-1-carboxylate (10 g, 27.90 mmol), N-benzyl-1-methoxy-N-((trimethylsilyl)methyl)methanamine (8.61 g, 36.27 mmol) and LiF (2.17 g, 83.71 mmol) in acetonitrile (100 mL) was heated at 80° C. for 16 h. After cooling to room temperature, the mixture was diluted with water (100 mL) and extracted with EtOAc (100 mL×3). The combined organic layers were washed with brine, dried over Na₂SO₄, filtered and concentrated. The mixture was purified by column chromatography on silica gel (eluent: Pet. Ether:EtOAc=6:1) to afford tert-butyl (S)-6-benzyl-8-((R)-2-oxo-4-phenyloxazolidine-3-carbonyl)-2,6-diazaspiro[3.4]octane-2-carboxylate (Intermediate 11) (8 g, 58%) as a yellow solid as the first eluting isomer. LCMS m/z=492 [M+H]⁺; ¹H NMR (400 MHz, DMSO-d6) δ 7.41-7.22 (m, 10H), 5.49-5.43 (m, 1H), 4.75-4.69 (m, 1H), 4.23-4.11 (m, 2H), 3.93-3.85 (m, 1H), 3.79 (s, 1H), 3.65-3.58 (m, 2H), 3.56-3.51 (m, 2H), 3.24-3.15 (m, 1H), 2.94-2.87 (m, 1H), 2.57-2.52 (m, 1H), 2.35-2.27 (m, 1H), 1.36 (s, 9H). Further elution provided tert-butyl (R)-6-benzyl-8-((R)-2-oxo-4-phenyloxazolidine-3-carbonyl)-2,6-diazaspiro[3.4]octane-2-carboxylate (Intermediate 12) (4 g, 29%). LCMS m/z=492 [M+H]⁺; ¹H NMR (400 MHz, DMSO-d6) δ 7.37-7.24 (m, 10H), 5.47-5.41 (m, 1H), 4.76-4.69 (m, 1H), 4.35-4.28 (m, 1H), 4.21-4.14 (m, 1H), 4.00-3.92 (m, 1H), 3.66-3.60 (m, 1H), 3.59-3.55 (m, 2H), 3.36 (s, 2H), 3.19-3.15 (m, 1H), 3.06-2.98 (m, 1H), 2.94-2.88 (m, 1H), 2.55 (s, 1H), 1.36 (s, 9H).

Additional Building Block Compounds:

(S)-2-amino-3-(benzyloxy)-N-methylpropanamide

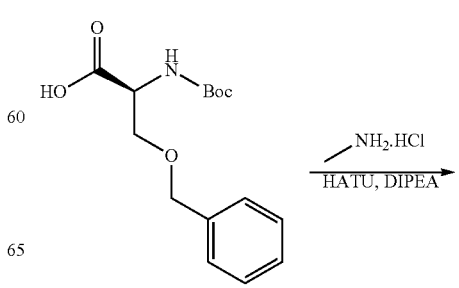

-continued

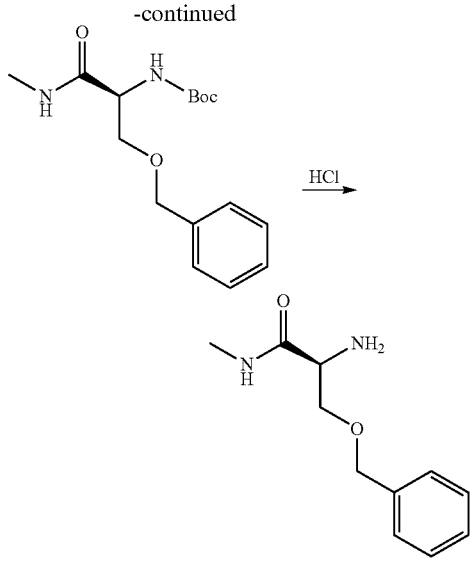

Step 1: To a solution of O-benzyl-N-(tert-butoxycarbonyl)-L-serine (1 g, 3.38 mmol) in DMF (10 mL) was added HATU (1.93 g, 5.07 mmol) and the mixture stirred at room temperature for 30 mi. Methylamine hydrochloride (274 mg, 4.06 mmol) and DIPEA (1.74 g, 13.52 mmol) were added and the reaction stirred for another 3 h then was diluted with water (60 mL) and, extracted with DCM (150 mL×3). The combined organic layers were washed with brine, dried over $Na_2SO_4$, filtered and concentrated. The mixture was purified by column chromatography on silica gel (eluent: DCM/MeOH=30/1) to afford tert-butyl (S)-(3-(benzyloxy)-1-(methylamino)-1-oxopropan-2-yl)carbamate (0.9 g, 87%) as a white solid. LCMS m/z=309.10 [M+H]$^+$; $^1$H NMR (400 MHz, CDCl$_3$) δ 7.39-7.25 (m, 5H), 4.61-4.46 (m, 2H), 3.91 (dd, J=9.3, 3.9 Hz, 1H), 3.61-3.52 (m, 1H), 2.83-2.79 (m, 4H), 1.44 (s, 9H).

Step 2: To a solution of tert-butyl (S)-(3-(benzyloxy)-1-(methylamino)-1-oxopropan-2-yl)carbamate (0.9 g, 2.92 mmol) in 1,4-dioxane (5 mL) was added a solution of HCl in Dioxane (4 M HCl in 1,4-dioxane (9 mL)). The reaction mixture was stirred at room temperature for 3 h then the solvent removed under vacuum to afford crude (S)-2-amino-3-(benzyloxy)-N-methylpropanamide (607 mg, 100%) which was used without purification. LCMS m/z=209.00 [M+H]$^+$.

The below compounds were synthesized according to the procedures outlined for (S)-2-amino-3-(benzyloxy)-N-methylpropanamide using the appropriate commercially available reagents.

| Compound | Characterization |
|---|---|
|  | LCMS m/z = 223.1 [M + H]$^+$; $^1$H NMR (400 MHz, DMSO-d$_6$) δ 8.73 (q, J = 4.6 Hz, 1H), 8.31 (d, J = 5.4 Hz, 2H), 7.37-7.26 (m, 5H), 4.59-4.47 (m, 2H), 3.90-3.77 (m, 2H), 2.65 (d, J = 4.6 Hz, 3H), 1.19 (d, J = 6.2 Hz, 3H). |
|  | $^1$HNMR (400 MHz, CD$_3$OD): δ 7.31-7.37 (m, 5H), 4.68 (d, J = 12.0 Hz, 1H), 4.49-4.53 (m, 2H); 3.90-3.92 (m, 1H), 3.83-3.86 (m, 1H), 3.60-3.63 (m, 1H), 3.46-3.52 (m, 1H), 3.39-3.42 (m, 1H), 1.81-1.95 (m, 4H), 1.36 (d, J = 6.4 Hz, 3H). |
|  | 207.00 [M + H]$^+$ |
|  | 225.1 [M + H]$^+$ |

(2S,3R)-2-amino-3-((4-fluorobenzyl)oxy)-N-methylbutanamide

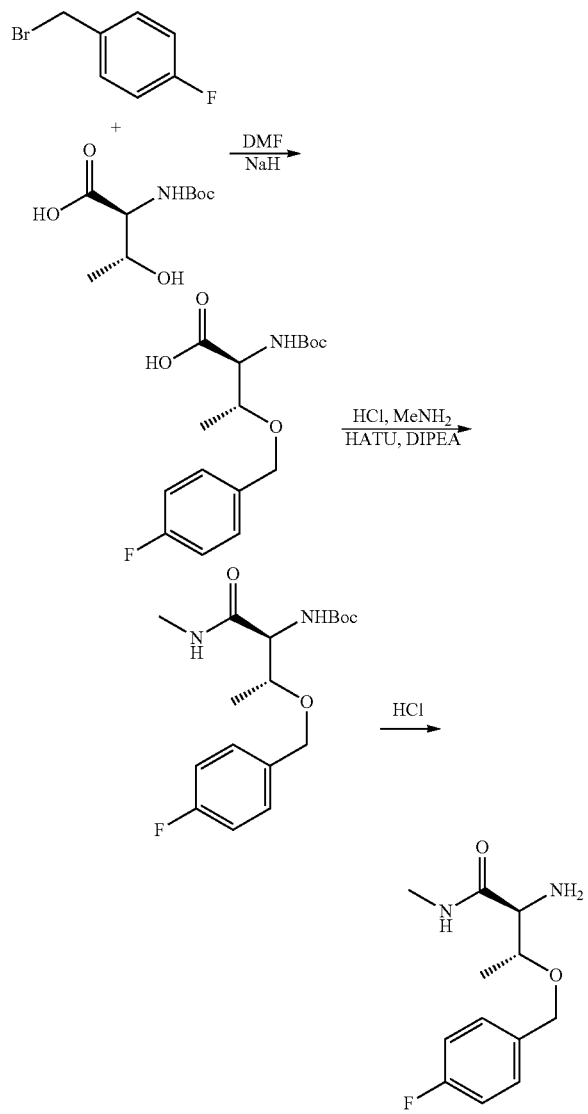

Step 1: To a solution of (tert-butoxycarbonyl)-L-threonine (1 g, 4.60 mmol) in dry DMF (5 mL) at 0° C. was added NaH (644 mg, 16.1 mmol). The mixture was stirred at 0° C. for 30 min. 1-(bromomethyl)-4-fluorobenzene (869 mg, 4.60 mmol) was added and the resulting reaction mixture was stirred overnight then diluted with water (30 mL) and extracted with EtOAc (50 mL). The aqueous layer was collected and acidified with 1M HCl to pH ~ 2 and extracted with EtOAc (100 mL×3). The combined organic layers were washed with brine, dried over $Na_2SO_4$, filtered and concentrated. The mixture was purified by reverse column (65% acetonitrile in water) to afford N-(tert-butoxycarbonyl)-O-(4-fluorobenzyl)-L-threonine (400 mg, 27%) as a yellow oil. LCMS m/z=350 [M+Na]$^+$; $^1$H NMR (400 MHz, DMSO-$d_6$) δ 7.40-7.29 (m, 2H), 7.21-7.10 (m, 2H), 6.53 (d, J=9.2 Hz, 1H), 4.52 (d, J=11.6 Hz, 1H), 4.37 (d, J=11.8 Hz, 1H), 4.12-3.90 (m, 2H), 1.39 (s, 9H), 1.14 (d, J=6.2 Hz, 3H).

Step 2: To a solution of N-(tert-butoxycarbonyl)-O-(4-fluorobenzyl)-L-threonine (400 mg, 1.20 mmol) in DMF (3 mL) was added HATU (684 mg, 1.80 mmol) and the mixture was stirred at room temperature for 30 min. Methylamine hydrochloride (97 mg, 1.40 mmol) and DIPEA (619 mg, 4.80 mmol) were added and the reaction stirred for another 6 h then diluted with water (30 mL) and extracted with DCM (100 mL×3). The combined organic layers were washed with brine, dried over $Na_2SO_4$, filtered and concentrated. The mixture was purified by column chromatography on silica gel (eluent: DCM/MeOH=50/1) to afford tert-butyl ((2S,3R)-3-((4-fluorobenzyl)oxy)-1-(methylamino)-1-oxobutan-2-yl)carbamate (320 mg, 77%) as a yellow solid. LCMS m/z=341.2 [M+H]$^+$; $^1$H NMR (400 MHz, DMSO-$d_6$) δ 7.82 (d, J=4.8 Hz, 1H), 7.37-7.27 (m, 2H), 7.19-7.09 (m, 2H), 6.40 (d, J=9.2 Hz, 1H), 4.49 (d, J=11.8 Hz, 1H), 4.37 (d, J=11.8 Hz, 1H), 4.02-3.95 (m, 1H), 3.86-3.78 (m, 1H), 2.59 (d, J=4.4 Hz, 3H), 1.38 (s, 9H), 1.07 (d, J=6.2 Hz, 3H).

Step 3: To a solution of tert-butyl ((2S,3R)-3-((4-fluorobenzyl)oxy)-1-(methylamino)-1-oxobutan-2-yl)carbamate (200 mg, 0.60 mmol) in 1,4-dioxane (2 mL) was added a solution of HCl in dioxane (4 M HCl in 1,4-dioxane, 3 mL). The reaction mixture was stirred at room temperature for 2 h then the solvent was removed under vacuum to afford (2S,3R)-2-amino-3-((4-fluorobenzyl)oxy)-N-methylbutanamide (180 mg, 100%). LCMS m/z=241.00 [M+H]$^+$.

The below compounds were synthesized according to the general procedures outlined for (2S,3R)-2-amino-3-((4-fluorobenzyl)oxy)-N-methylbutanamide using the appropriate commercially available reagents.

| Compound | Characterization |
| --- | --- |
|  | 224.1 [M + H]$^+$ |

| Compound | Characterization |
|---|---|
| (structure) | 224.1 [M + H]⁺ |
| (structure) | 224.1 [M + H]⁺ |
| (structure) | 227.1 [M + H]⁺ |
| (structure) | 301.1 [M + H]⁺ |
| (structure) | 248.0 [M + H]⁺ |

-continued

| Compound | Characterization |
|---|---|
| (structure: 3-(methoxymethyl)piperidine amide of threonine O-(2-fluoro-4-chlorobenzyl) ether) | LCMS not recorded |
| (structure: 3-(methoxymethyl)piperidine amide of threonine O-(4-fluorobenzyl) ether) | LCMS not recorded |
| (structure: 3-(methoxymethyl)piperidine amide of threonine O-(4-trifluoromethylbenzyl) ether) | LCMS not recorded |
| (structure: 3-(methoxymethyl)piperidine amide of threonine O-(4-trifluoromethoxybenzyl) ether) | LCMS not recorded |
| (structure: 3-(methoxymethyl)piperidine amide of threonine O-(2-fluorobenzyl) ether) | LCMS not recorded |
| (structure: 3-(methoxymethyl)piperidine amide of threonine O-(3-fluorobenzyl) ether) | LCMS not recorded |
| (structure: N-methyl amide of penicillamine S-benzyl) | 253.1 [M + H]$^+$ |

(2S,3R)-2-amino-3-(cyclohexylmethoxy)-N-methylbutanamide

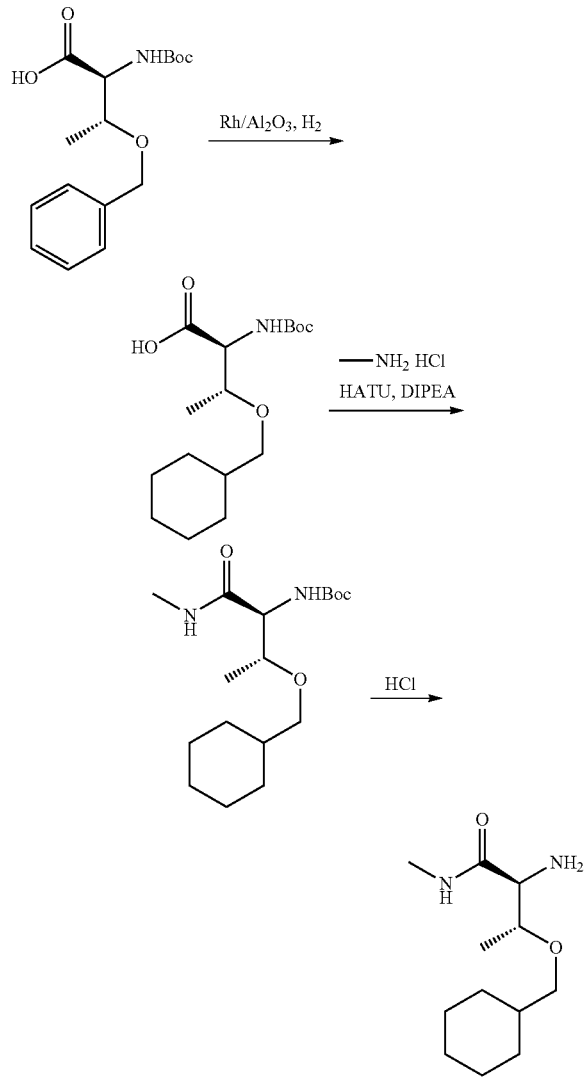

Step 1: To a solution of O-benzyl-N-(tert-butoxycarbonyl)-L-threonine (5 g, 16.16 mmol) in i-PrOH (30 mL) was added rhodium on $Al_2O_3$ (5%, 1.25 g) and the reaction stirred under a $H_2$ atmosphere for 48 h. The catalyst was removed by filtration through celite and the filtrate concentrated to afford N-(tert-butoxycarbonyl)-O-(cyclohexylmethyl)-L-threonine (5 g, 98%) as a colorless oil. $^1$H NMR (400 MHz, DMSO-$d_6$) δ 6.20 (d, J=9.2 Hz, 1H), 3.99 (dd, J=9.2, 3.4 Hz, 1H), 3.83-3.79 (m, 1H), 3.25 (dd, J=9.0, 6.2 Hz, 1H), 3.06 (dd, J=9.0, 6.6 Hz, 1H), 1.69-1.62 (m, 3H), 1.39 (s, 9H), 1.20-1.03 (m, 10H), 0.92-0.77 (m, 2H).

Step 2: To a solution of N-(tert-butoxycarbonyl)-O-(cyclohexylmethyl)-L-threonine (5.4 g, 17.12 mmol), methylamine hydrochloride (1.39 g, 20.54 mmol) and HATU (9.76 g, 25.68 mmol) in DMF (25 mL) was added DIPEA (8.85 g, 68.48 mmol). The reaction mixture was stirred at room temperature for 5 h then diluted with water (250 mL). The precipitate that formed was collected by filtration and washed with cold water (30 mL×2) to afford tert-butyl ((2S,3R)-3-(cyclohexylmethoxy)-1-(methylamino)-1-oxobutan-2-yl)carbamate (3.8 g, 68%) as a white solid. LCMS m/z=329.2 [M+H]$^+$; $^1$H NMR (400 MHz, DMSO-$d_6$) δ 7.74 (d, J=4.8 Hz, 1H), 6.22 (d, J=9.2 Hz, 1H), 3.89 (dd, J=9.2, 4.4 Hz, 1H), 3.64 (dt, J=10.4, 5.2 Hz, 1H), 3.22 (dd, J=9.2, 6.4 Hz, 1H), 3.06 (dd, J=9.2, 6.4 Hz, 1H), 2.58 (d, J=4.6 Hz, 3H), 1.69-1.60 (m, 5H), 1.38 (s, 9H), 1.26-1.08 (m, 4H), 1.00 (d, J=6.2 Hz, 3H), 0.90-0.79 (m, 2H).

Step 3: To a solution of tert-butyl ((2S,3R)-3-(cyclohexylmethoxy)-1-(methylamino)-1-oxobutan-2-yl)carbamate (3.8 g, 11.57 mmol) in 1,4-dioxane (50 mL) was added a solution of HCl in 1,4-dioxane (4 M, 15 mL). The reaction mixture was stirred at room temperature for 3 h the solvent was removed under vacuum to afford crude (2S,3R)-2-amino-3-(cyclohexylmethoxy)-N-methylbutanamide (3 g, 98%) as a white solid. $^1$H NMR (400 MHz, CDCl$_3$) δ 8.28-8.10 (m, 4H), 4.26 (s, 1H), 4.02 (s, 1H), 3.32 (ddd, J=24.0, 9.0, 6.4 Hz, 2H), 2.94 (s, 2H), 2.82 (d, J=3.4 Hz, 3H), 1.73-1.62 (m, 6H), 1.58-1.50 (m, 1H), 1.32-1.10 (m, 7H), 0.96-0.84 (m, 2H).

The below compounds were synthesized according to the procedures outlined for (2S,3R)-2-amino-3-(cyclohexylmethoxy)-N-methylbutanamide using the appropriate commercially available reagents.

| Compound | Characterization |
|---|---|
|  | 432.2 [M + H]$^+$ |

| Compound | Characterization |
|---|---|
| (structure: 3-Cbz-aminopiperidine amide with α-amino, β-(cyclohexylmethoxy)propanoyl) | 432.2 [M + H]⁺ |
| (structure: piperidine amide with α-amino, β-(cyclohexylmethoxy)propanoyl) | 283.2 [M + H]⁺ |
| (structure: morpholine amide with α-amino, β-(cyclohexylmethoxy)propanoyl) | 285.2 [M + H]⁺ |
| (structure: piperidine amide with α-amino, (cyclohexylmethoxy)methyl) | 269.2 [M + H]⁺ |
| (structure: 4-(pyridin-4-yl)piperidine amide with α-amino, β-(cyclohexylmethoxy)propanoyl) | 360.30 [M + H]⁺ |
| (structure: 2-amino-3-(cyclohexylmethoxy)-1-hydroxy-4-methylpentane with gem-dimethyl) | 230.2 [M + H]⁺<br>*Step 2: replace methylamine hydrochloride, HATU, DMF and DIPEA with methylmagnesium bromide in tetrahydrofuran at 0° C. |
| (structure: 3-(methoxymethyl)piperidine amide with α-amino, β-(cyclohexylmethoxy)propanoyl) | 327.3 [M + H]⁺; ¹H NMR (400 MHz, Chloroform-d) δ 8.27-8.18 (m, 2H), 7.57-7.50 (m, 2H), 5.59-5.43 (m, 1H), 5.33-5.18 (m, 3H), 4.37-4.24 (m, 1H), 4.19-3.99 (m, 1H), 3.86-3.69 (m, 4H), 3.68-3.61 (m, 1H), 3.34-3.19 (m, 1H), 2.19-2.06 (m, 4H), 202-1.83 (m, 2H), 1.79-1.54 (m, 7H), 1.39-1.31 (m, 6H), 1.08 (d, J = 6.3 Hz, 1H), 0.98 (d, J = 6.1 Hz, 1H). |

| Compound | Characterization |
|---|---|
| 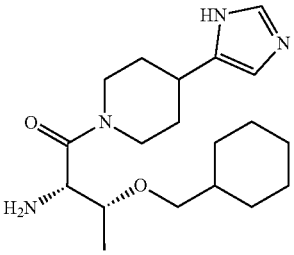 [SMILES: C[C@@H](OCC1CCCCC1)[C@H](N)C(=O)N1CCC(c2cnc[nH]2)CC1] | 349.2 [M + H]+ |
| 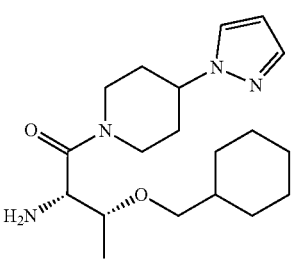 [SMILES: C[C@@H](OCC1CCCCC1)[C@H](N)C(=O)N1CCC(n2cccn2)CC1] | 349.2 [M + H]+ |
| 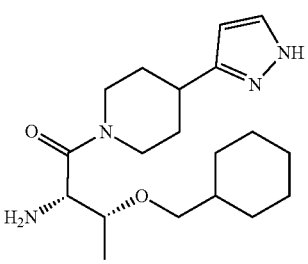 [SMILES: C[C@@H](OCC1CCCCC1)[C@H](N)C(=O)N1CCC(c2cc[nH]n2)CC1] | 349.2 [M + H]+ |
| 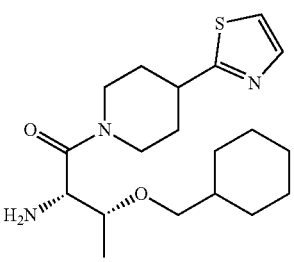 [SMILES: C[C@@H](OCC1CCCCC1)[C@H](N)C(=O)N1CCC(c2nccs2)CC1] | 366.2 [M + H]+ |
| 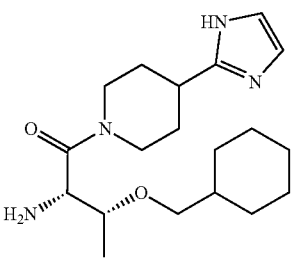 [SMILES: C[C@@H](OCC1CCCCC1)[C@H](N)C(=O)N1CCC(c2ncc[nH]2)CC1] | 349.2 [M + H]+ |

471
(S)-(3-aminopiperidin-1-yl)(phenyl)methanone

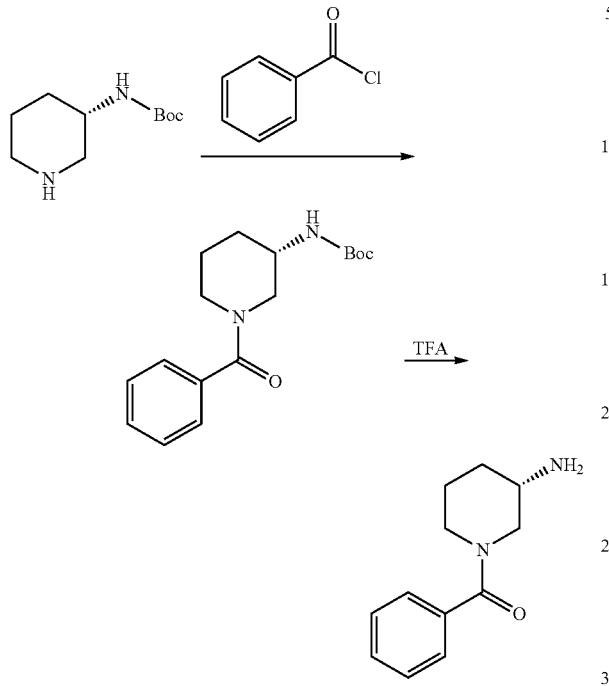

Step 1: To a solution of tert-butyl (S)-piperidin-3-ylcarbamate (1 g, 4.99 mmol) in DCM (10 mL) at 0° C. was added TEA (1.5 g, 14.97 mmol) and benzoyl chloride (1.05 g, 7.49 mmol). The resulting mixture was stirred at room temperature for 30 min then diluted with water (50 mL) and extracted with DCM (100 mL×3). The combined organic layers were washed with brine, dried over Na$_2$SO$_4$, filtered and concentrated to afford tert-butyl (S)-(1-benzoylpiperidin-3-yl)carbamate (1.5 g, 98%) as a yellow oil which was used directly in the next step. LCMS m/z=305.5 [M+H]$^+$.

Step 2: To a solution of tert-butyl (S)-(1-benzoylpiperidin-3-yl)carbamate (1.5 g, 4.90 mmol) in DCM (10 mL) was added TFA (3 mL). The reaction mixture was stirred at room temperature for 1 h then the solvent was removed under vacuum to afford crude (S)-(3-aminopiperidin-1-yl)(phenyl)methanone (1.5 g, 100%). LCMS m/z=205.2 [M+H]$^+$.

The compounds below were synthesized according to the procedures outlined in the synthesis of (S)-(3-aminopiperidin-1-yl)(phenyl)methanone using the appropriate commercially available reagents.

| Compound | Characterization |
|---|---|
| 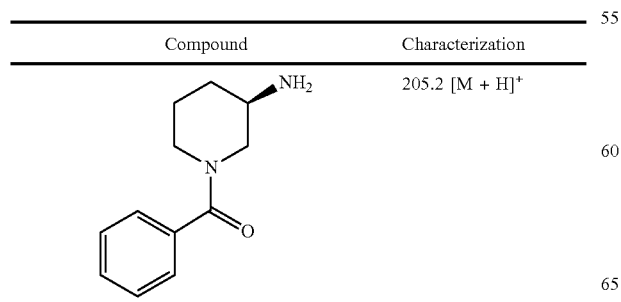 | 205.2 [M + H]$^+$ |

472
-continued

| Compound | Characterization |
|---|---|
| 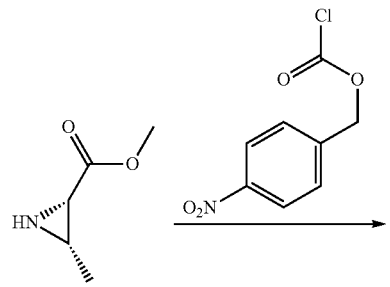 | 204.1 [M + H]$^+$ |

2-methyl 1-(4-nitrobenzyl) (2S,3S)-3-methylaziridine-1,2-dicarboxylate

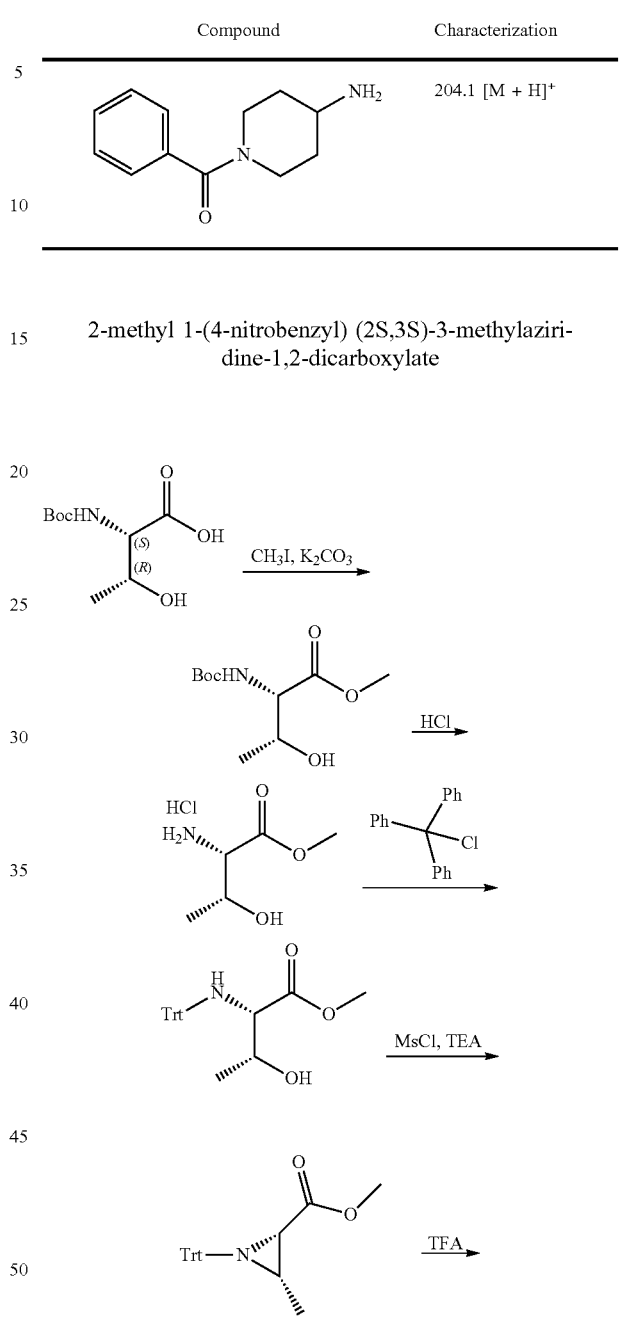

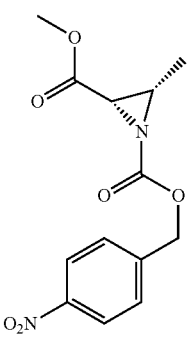

Step 1: To a solution of (tert-butoxycarbonyl)-L-threonine (25.0 g, 0.11 mol) in DMF (250 mL) was added K$_2$CO$_3$ (23.0 g, 0.16 mol) and CH$_3$I (19.4 g, 0.13 mol). The reaction mixture was stirred at room temperature for 4 h then diluted with water (300 mL) and extracted with EtOAc (500 mL×2). The combined organic layers were washed with brine, dried over Na$_2$SO$_4$, filtered and concentrated. The mixture was purified by column chromatography on silica gel (eluent: Pet. Ether:EtOAc=100:1 to 10:1) to afford methyl (tert-butoxycarbonyl)-L-threoninate (20 g, 80%) as a yellow oil. LCMS m/z=256.2 [M+Na]$^+$; $^1$H NMR (400 MHz, DMSO-d$_6$) δ 6.53 (d, J=8.8 Hz, 1H), 4.78 (d, J=7.2 Hz, 1H), 4.01-3.96 (m, 1H), 3.62 (s, 3H), 1.38 (s, 9H), 1.07 (d, J=6.2 Hz, 3H).

Step 2: A mixture of methyl (tert-butoxycarbonyl)-L-threoninate (20 g, 85.7 mmol) in a solution of HCl in 1,4-dioxane (4 M, 250 mL) was stirred at room temperature for 6 h. The solvent was removed under vacuum to afford crude methyl L-threoninate hydrochloride (14.5 g, 100%) which was used directly in the next step. LCMS m/z=134.2 [M+H]$^+$; $^1$H NMR (400 MHz, DMSO-d$_6$) δ 8.52 (s, 3H), 4.14-4.07 (m, 1H), 3.90 (d, J=3.8 Hz, 1H), 3.73 (s, 3H), 3.55 (s, 1H), 1.20 (d, J=6.6 Hz, 3H).

Step 3: To a solution of methyl L-threoninate hydrochloride (14.5 g, 85.5 mmol) in DCM (300 mL) was added TEA (45 g, 0.44 mol) and Trt-Cl (28.6 g, 102.6 mmol). The reaction mixture was stirred at room temperature overnight then diluted with water (200 mL) and extracted with DCM (300 mL×2). The combined organic layers were washed with brine, dried over Na$_2$SO$_4$, filtered and concentrated. The mixture was purified by column chromatography on silica gel (eluent: Pet. Ether:EtOAc=100:1 to 10:1) to afford methyl trityl-L-threoninate (24 g, 75%) as a white solid. $^1$H NMR (400 MHz, DMSO-d$_6$) δ 7.41 (d, J=7.4 Hz, 7H), 7.28 (d, J=7.4 Hz, 7H), 7.23-7.16 (m, 3H), 5.05 (d, J=4.8 Hz, 1H), 3.98-3.87 (m, 1H), 3.23-3.16 (m, 4H), 3.02 (s, 3H), 2.68 (d, J=10.0 Hz, 1H), 1.08 (d, J=6.4 Hz, 3H).

Step 4: To a solution of methyl trityl-L-threoninate (12 g, 32 mmol) in THF (130 mL) was added TEA (6.5 g, 64 mmol) and MsCl (5.4 g, 38.4 mmol). The reaction mixture was heated at 80° C. for 30 h then cooled to room temperature, diluted with water (100 mL) and extracted with EtOAc (250 mL×2). The combined organic layers were washed with brine, dried over Na$_2$SO$_4$, filtered and concentrated. The mixture was purified by column chromatography on silica gel (eluent: Pet. Ether:EtOAc=100:1 to 20:1) to afford methyl (2S,3 S)-3-methyl-1-tritylaziridine-2-carboxylate (8 g, 70%) as a white solid. $^1$H NMR (400 MHz, DMSO-d$_6$) δ 7.45-7.38 (m, 6H), 7.36-7.27 (m, 7H), 7.29-7.21 (m, 4H), 3.65 (s, 3H), 1.71 (d, J=6.6 Hz, 1H), 1.61-1.50 (m, 1H), 1.27 (d, J=5.4 Hz, 3H).

Steps 5 & 6: To a solution of methyl (2S,3S)-3-methyl-1-tritylaziridine-2-carboxylate (2 g, 5.6 mmol) in a mixture of DCM (20 mL) and MeOH (1 mL) was added TFA (10 mL). The mixture was stirred at room temperature for 30 min then diluted with water (20 mL) and extracted with Et$_2$O (30 mL×2). The aqueous layer was adjusted to pH ~ 9 using solid NaHCO$_3$ (LCMS: m/z=116.15 [M+H]$^+$). The aqueous layer was partitioned against EtOAc (20 mL) and 4-nitrobenzyl cholorformate (1.3 g, 5.6 mmol) was added. The mixture was stirred at room temperature overnight then extracted with EtOAc (50 mL×3). The combined organic layers were washed with brine, dried over Na$_2$SO$_4$, filtered and concentrated. The mixture was purified by column chromatography on silica gel (eluent: Pet. Ether: EtOAc=100:1 to 20:1) to afford 2-methyl 1-(4-nitrobenzyl) (2S,3S)-3-methylaziridine-1,2-dicarboxylate (500 mg, 31%) as a white solid. LCMS: m/z=295.0 [M+H]$^+$; $^1$H NMR (400 MHz, DMSO-d$_6$) δ 8.28-8.21 (m, 2H), 7.68-7.61 (m, 2H), 5.24 (s, 2H), 3.70 (s, 3H), 3.42 (d, J=6.8 Hz, 1H), 3.08-2.97 (m, 1H), 1.21 (d, J=5.6 Hz, 3H).

(2S,3R)-2-amino-N-methyl-3-(2,2,2-trifluoroethoxy)butanamide

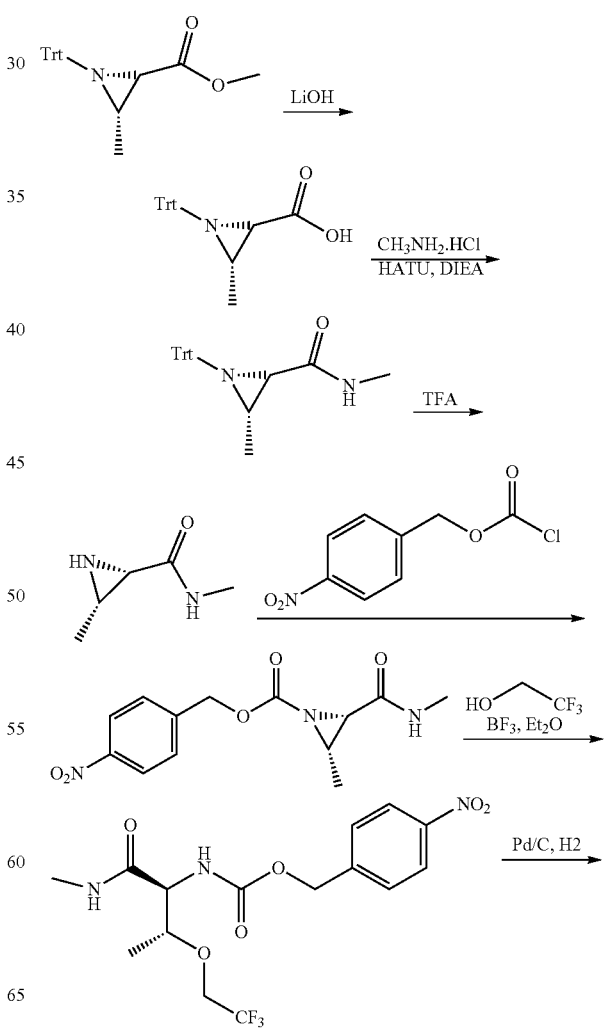

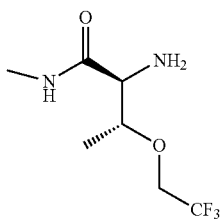

Step 1: To a solution of methyl (2S,3S)-3-methyl-1-tritylaziridine-2-carboxylate (5 g, 13.4 mmol) in a mixture of THF (18 mL), MeOH (6 mL) and water (6 mL) was added lithium hydroxide monohydrate (2 g, 46.9 mmol). The reaction was stirred at room temperature for 1 h, diluted with water (30 mL) and extracted with EtOAc (20 mL). The aqueous layer was collected and acidified to pH ~ 2 with 1M HCl and then extracted with EtOAc (20 mL×2). The combined organic layers were washed with brine, dried over Na$_2$SO$_4$, filtered and concentrated to afford (2S,3S)-3-methyl-1-tritylaziridine-2-carboxylic acid (2.9 g, 60%) as a yellow solid. LCMS m/z=342.05 [M+H]$^+$.

Step 2: To a solution of (2S,3S)-3-methyl-1-tritylaziridine-2-carboxylic acid (2.9 g, 8.4 mmol) in DCM (16 mL) was added HATU (4.8 g, 33.8 mmol) and the mixture stirred at room temperature for 30 min. Methylamine hydrochloride (0.86 g, 12.7 mmol) and DIPEA (4.36 g, 33.8 mmol) were then added and the reaction mixture stirred for another 2 h. Water (20 mL) was then added and the mixture extracted with DCM (20 mL×3). The combined organic layers were washed with brine, dried over Na$_2$SO$_4$, filtered and concentrated. The residue was purified by column chromatography on silica gel (eluent: Pet. Ether:EtOAc=5:1 to 2:1) to afford (2S,3S)—N,3-dimethyl-1-tritylaziridine-2-carboxamide (1.1 g, 36%) as a white solid. $^1$H NMR (400 MHz, DMSO-d$_6$) δ 7.90 (q, J=4.6 Hz, 1H), 7.50-7.40 (m, 6H), 7.35-7.21 (m, 9H), 2.66 (d, J=4.6 Hz, 3H), 1.64 (d, J=6.6 Hz, 1H), 1.39-1.33 (m, 1H), 1.23 (d, J=5.6 Hz, 3H).

Steps 3 & 4: To a solution of (2S,3S)—N,3-dimethyl-1-tritylaziridine-2-carboxamide (1.1 g, 3.1 mmol) in a mixture of DCM (3 mL) and MeOH (3 mL) was added TFA (2 mL). The mixture was stirred at room temperature for 30 min then diluted with water (10 mL) and extracted with Et$_2$O (10 mL×2). The pH of the aqueous layer was adjusted ~ 9 with solid NaHCO$_3$ and partitioned against EtOAc (10 mL). 4-nitrobenzyl chloroformate (82 mg, 0.38 mmol) was added and the mixture stirred at room temperature overnight then extracted with EtOAc (10 mL×3). The combined organic layers were washed with brine, dried over Na$_2$SO$_4$, filtered and concentrated. The mixture was purified by column chromatography on silica gel (eluent: Pet. Ether:EtOAc=2:1 to 1:1) to afford 4-nitrobenzyl (2S,3S)-2-methyl-3-(methylcarbamoyl)aziridine-1-carboxylate (0.5 g, 45%) as a white solid. LCMS: m/z=294.15 [M+H]$^+$; $^1$H NMR (400 MHz, DMSO-d$_6$) δ 8.27-8.23 (m, 2H), 7.92 (d, J=4.8 Hz, 1H), 7.68-7.64 (m, 2H), 5.24 (s, 2H), 3.17 (d, J=6.8 Hz, 1H), 2.94-2.88 (m, 1H), 2.60 (d, J=4.6 Hz, 3H), 1.16 (d, J=5.8 Hz, 3H).

Step 5: To a mixture of 4-nitrobenzyl (2S,3S)-2-methyl-3-(methylcarbamoyl)aziridine-1-carboxylate (200 mg, 0.68 mmol) and 2,2,2-trifluoroethan-1-ol (200 mg, 2 mmol) under a nitrogen atmosphere was added boron trifluoride etherate (190 mg, 1.4 mmol). The reaction mixture was stirred at room temperature for 4 h. The mixture was purified by reverse phase column (42% ACN in water) to afford 4-nitrobenzyl ((2S,3R)-1-(methylamino)-1-oxo-3-(2,2,2-trifluoroethoxy)butan-2-yl)carbamate (85 mg, 32%) as a yellow solid. LCMS m/z=394.15 [M+H]$^+$.

Step 6: To a solution of 4-nitrobenzyl ((2S,3R)-1-(methylamino)-1-oxo-3-(2,2,2-trifluoroethoxy)butan-2-yl)carbamate (85 mg, 0.22 mmol) in MeOH (10 mL) was added 10% Pd/C (34 mg). The reaction mixture was stirred under a H$_2$ atmosphere for 3 h. The catalyst was removed by filtration through celite and the filtrate concentrated to afford (2S,3R)-2-amino-N-methyl-3-(2,2,2-trifluoroethoxy)butanamide (42 mg, 90%) which was used without further purification. LCMS m/z=215.1 [M+H]$^+$.

The compounds below were synthesized according to the procedures outlined in the synthesis of (2S,3R)-2-amino-N-methyl-3-(2,2,2-trifluoroethoxy)butanamide using the appropriate commercially available reagents.

| Compound | LCMS |
|---|---|
| 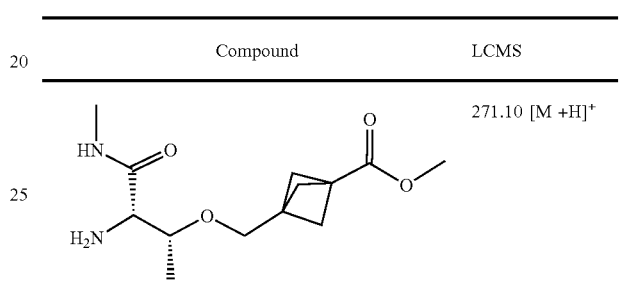 | 271.10 [M +H]$^+$ |

(2S,3R)-2-amino-3-(2-cyclohexylethoxy)-N-methylbutanamide

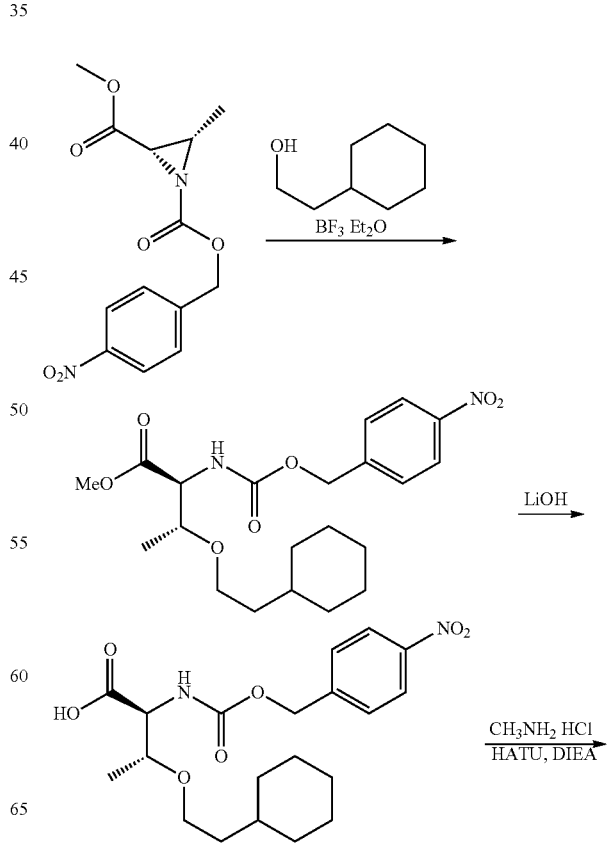

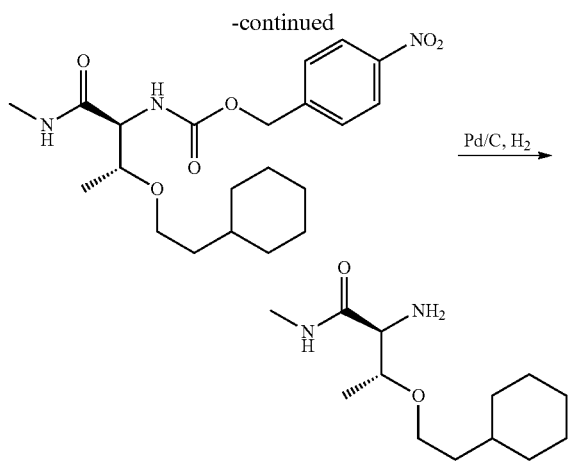

Step 1: To a solution of 2-methyl 1-(4-nitrobenzyl) (2S,3S)-3-methylaziridine-1,2-dicarboxylate (500 mg, 1.70 mmol) in toluene (2 mL) under a nitrogen atmosphere was added 2-cyclohexylethan-1-ol (435 mg, 3.40 mmol) and boron trifluoride etherate (0.2 mL). The reaction mixture was heated at reflux for 2 h then diluted with water (30 mL), extracted with EtOAc (100 mL×2). The combined organic layers were washed with brine, dried over $Na_2SO_4$, filtered and concentrated. The mixture was purified by column chromatography on silica gel (eluent: Pet. Ether:EtOAc=5:1) to afford methyl O-(2-cyclohexylethyl)-N-(((4-nitrobenzyl)oxy)carbonyl)-L-threoninate (160 mg, 22%) as a yellow solid. LCMS m/z=423.15 [M+H]$^+$.

Step 2: To a solution of methyl O-(2-cyclohexylethyl)-N-(((4-nitrobenzyl)oxy)carbonyl)-L-threoninate (150 mg, 0.36 mmol) in a mixture of THF (2 mL), MeOH (0.5 mL) and water (0.5 mL) was added lithium hydroxide monohydrate (43 mg, 1.07 mmol). The reaction was stirred at room temperature for 1 h then diluted with water (30 mL) and extracted with EtOAc (60 mL). The aqueous layer was collected and acidified with 1M HCl to pH ~ 2 then extracted with EtOAc (100 mL×2). The combined organic layers were washed with brine, dried over $Na_2SO_4$, filtered and concentrated to afford O-(2-cyclohexylethyl)-N-(((4-nitrobenzyl)oxy)carbonyl)-L-threonine (110 mg, 76%) as a white solid. LCMS m/z=409.15 [M+H]$^+$.

Step 3: To a solution of O-(2-cyclohexylethyl)-N-(((4-nitrobenzyl)oxy)carbonyl)-L-threonine (110 mg, 0.27 mmol) in DCM (2 mL) was added HATU (153 mg, 0.40 mmol) and the mixture stirred at room temperature for 30 min. Methylamine hydrochloride (27 mg, 0.40 mmol) and DIPEA (138 mg, 1.08 mmol) were added and the reaction stirred for another 2 h. The mixture was diluted with water (20 mL) and extracted with DCM (50 mL×3). The combined organic layers were washed with brine, dried over $Na_2SO_4$, filtered and concentrated. The mixture was purified by prep-TLC (eluent: DCM/MeOH=30/1) to afford 4-nitrobenzyl ((2S,3R)-3-(2-cyclohexylethoxy)-1-(methylamino)-1-oxobutan-2-yl)carbamate (50 mg, 44%) as a white solid. LCMS m/z=422.20 [M+H]$^+$; $^1$H NMR (400 MHz, Chloroform-d) δ 8.26-8.19 (m, 2H), 7.55-7.48 (m, 2H), 5.25-5.16 (m, 2H), 4.27-4.16 (m, 1H), 4.00-3.87 (m, 1H), 2.86-2.83 (m, 3H), 1.49-1.39 (m, 4H), 1.34-1.30 (m, 3H), 1.20-1.13 (m, 4H), 1.10-1.04 (m, 3H), 0.96-0.79 (m, 6H).

Step 4: To a solution of 4-nitrobenzyl ((2S,3R)-3-(2-cyclohexylethoxy)-1-(methylamino)-1-oxobutan-2-yl)carbamate (50 mg, 0.12 mmol) in MeOH (2 mL) was added 10% Pd/C (10 mg). The reaction mixture was stirred under a $H_2$ atmosphere for 3 h. The catalyst was removed by filtration through celite, and the filtrate concentrated to afford (2S,3R)-2-amino-3-(2-cyclohexylethoxy)-N-methylbutanamide (25 mg, 90%) which was used without purification. LCMS m/z=243.15 [M+H]$^+$.

The compounds below were synthesized according to the general procedures reported for (2S,3R)-2-amino-3-(2-cyclohexylethoxy)-N-methylbutanamide using the appropriate commercially available reagents.

| Compound | Characterization |
|---|---|
| (structure with tetrahydropyran) | 231.1 [M + H]$^+$ |
| (structure with cyclopentylmethyl) | 215.2 [M + H]$^+$ |

| Compound | Characterization |
|---|---|
| | 189.10 [M + H]⁺ |
| | 257.2 [M + H]⁺ |
| | 243.3 [M + H]⁺ |
| | 203.1 [M + H]⁺ |
| | 255.1 [M + H]⁺ |

| Compound | Characterization |
|---|---|
| | 201.1 [M + H]⁺ |
| | 251.2 [M + H]⁺ |
| | 355.1 [M + H]⁺ |
| | 265.2 [M + H]⁺ |
| | 297.3 [M + H]⁺ |
| | 309.1 [M + H]⁺ |

| Compound | Characterization |
|---|---|
| (structure) | 345.1 [M + H]+ |
| (structure) | 321.2 [M + H]+ |
| (structure) | 255.3 [M + H]+ |
| (structure) | 243.3 [M + H]+ |
| (structure) | 297.1 [M + H]+ |
| (structure) | 215.2 [M + H]+ |
| (structure) | LCMS not recorded//$^1$HNMR (400 MHz, CDCl$_3$): δ 3.61-3.73 (m, 9H), 3.43-3.52 (m, 2H), 3.20-3.24 (m, 1H), 2.07-2.14 (m, 2H), 1.78-1.84 (m, 2H), 1.66-1.76 (m, 2H), 1.25-1.36 (m, 3H), 1.11 (d, J = 6.4 Hz, 3H). |

-continued
| Compound | Characterization |
|---|---|
| 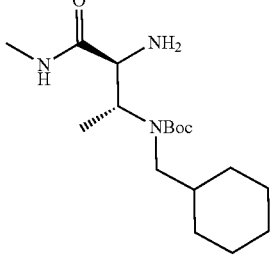 | 328.2 [M + H]+ |
| 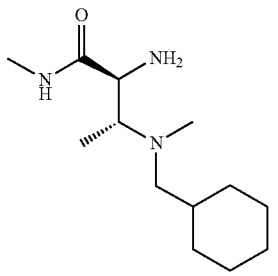 [SMILES: CNC(=O)[C@@H](N)[C@@H](C)N(C)CC1CCCCC1] | 242.2 [M + H]+ |
| 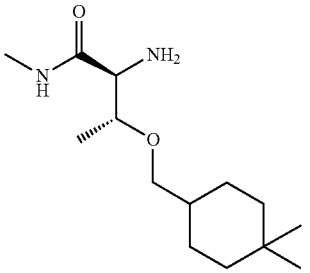 | m/z = 257.1 [M + H]+ |
| 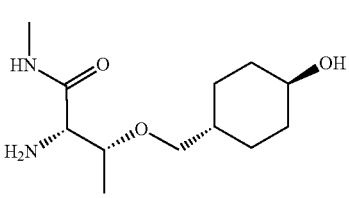 [SMILES: CNC(=O)[C@@H](N)[C@@H](C)OC[C@H]1CC[C@H](O)CC1] | m/z = 245.2 [M + H]+ |
| 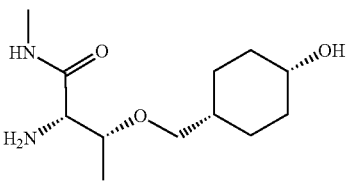 [SMILES: CNC(=O)[C@@H](N)[C@@H](C)OC[C@H]1CC[C@@H](O)CC1] | m/z = 245.2 [M + H]+ |
| 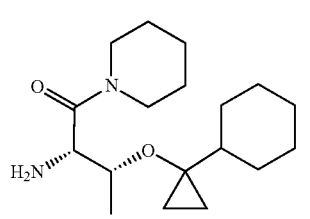 [SMILES: C[C@@H](OC1(C2CCCCC2)CC1)[C@H](N)C(=O)N1CCCCC1] | m/z = 309.2 [M + H]+ |

-continued

| Compound | Characterization |
|---|---|
| | m/z = 311.3 [M + H]+ |
| | m/z = 297.3 [M + H]+ |
| | m/z = 309.1 [M + H]+ |
| | m/z = 241.2 [M + H]+ |
| | m/z = 241.3 [M + H]+ |
| | m/z = 243.2 [M + H]+ |
| | m/z = 243.3 [M + H]+ |

-continued

| Compound | Characterization |
|---|---|
| (structure) | m/z = 255.2 [M + H]⁺ |
| (structure) | m/z = 255.2 [M + H]⁺ |
| (structure) | m/z = 257.3 [M + H]⁺ |
| (structure) | m/z = 267.2 [M + H]⁺ |
| (structure) | m/z = 377.2 [M + H]⁺ |
| (structure) | m/z = 369.1 [M + H]⁺ |

| Compound | Characterization |
|---|---|
| | m/z = 341.1 [M + H]+ |
| | m/z = 341.2 [M + H]+ |
| | m/z = 341.2 [M + H]+ |
| | m/z = 321.2 [M + H]+ |
| | m/z = 357.4 [M + H]+ |

| Compound | Characterization |
|---|---|
| | m/z = 357.4 [M + H]+ |
| | m/z = 367.4 [M + H]+ |
| | m/z = 335.2 [M + H]+ |
| | m/z = 349.2 [M + H]+ |
| | m/z = 349.2 [M + H]+ |
| | m/z = 347.2 [M + H]+ |

-continued
| Compound | Characterization |
|---|---|
| [structure] | m/z = 345.0 [M + H]⁺ |
| [structure] | m/z = 347.2 [M + H]⁺ |
| [structure] | m/z = 403.1 [M + H]⁺ |
| [structure] | m/z = 387.2 [M + H]⁺ |
| [structure] | m/z = 259.2 [M + H]⁺ |
(3S,4R)-4-(2-oxabicyclo[2.2.2]octan-4-ylmethoxy)-3-amino-2-methylpentan-2-ol
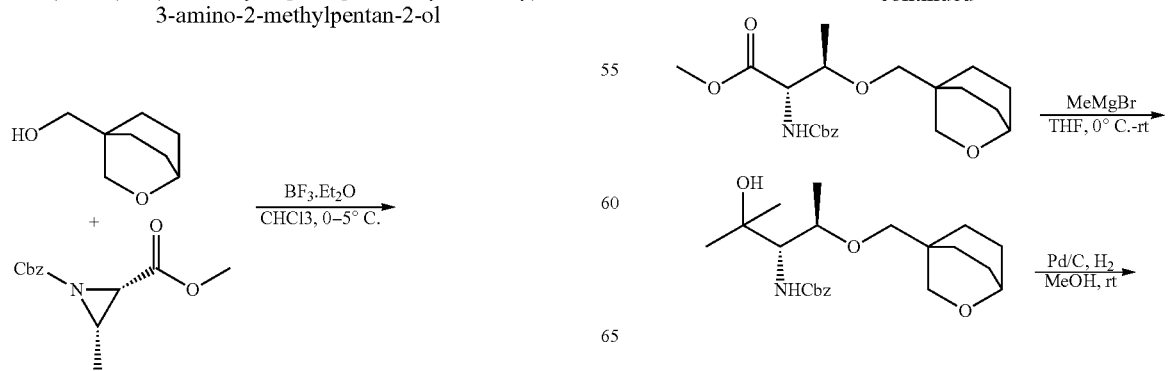
-continued -continued

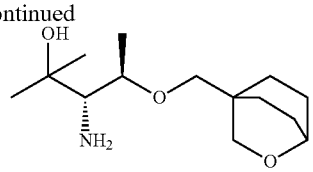

Step 1: To a mixture of 2-oxabicyclo[2.2.2]octan-4-yl-methanol (0.500 g, 3.52 mmol) and (2S,3S)-1-benzyl 2-methyl 3-methylaziridine-1,2-dicarboxylate (0.876 g, 3.52 mmol) in dichloromethane (10 mL) at 0-5° C. was added boron trifluoride etherate (100 mg, 0.70 mmol). The resulting mixture was stirred at 0° C. for an hour. The reaction mixture was concentrated under reduced pressure to give a crude residue which was purified by column chromatography using a 16% ethyl acetate in hexane gradient to afford (2S,3R)-methyl 3-(2-oxabicyclo[2.2.2]octan-4-ylmethoxy)-2-(((benzyloxy)carbonyl)amino)butanoate (0.376 g, 27%) as a colorless oil. MS: 392.2 [M+H]$^+$ Step 2: To a solution of (2S,3R)-methyl 3-(2-oxabicyclo[2.2.2]octan-4-ylmethoxy)-2-(((benzyloxy)carbonyl)amino) butanoate (0.376 g, 0.96 mmol) in tetrahydrofuran (5 mL) at 0-5° C. was added methylmagnesium bromide (3M in ether, 1.6 mL, 4.81 mmol). The resulting mixture was stirred at room temperature for an hour. The reaction mixture was quenched with water at 0-5° C. and extracted with ethyl acetate (10 mL×3). The combined organic layers were washed with brine (20 mL), dried over anhydrous sodium sulfate, and concentrated under reduced pressure to give a crude residue which was purified by silica gel column chromatography using a 20% ethyl acetate in hexane gradient to afford benzyl ((3S,4R)-4-(2-oxabicyclo[2.2.2]octan-4-ylmethoxy)-2-hydroxy-2-methylpentan-3-yl)carbamate (0.197 g, 14%) as a colorless oil. MS: 392.1 [M+H]$^+$ Step 3: To a solution of benzyl ((3S,4R)-4-(2-oxabicyclo[2.2.2]octan-4-ylmethoxy)-2-hydroxy-2-methylpentan-3-yl) carbamate (0.197 g, 0.50 mmol) in methanol (10 mL) was added Palladium on carbon (10%, 0.060 g). The resulting mixture was stirred at room temperature under H$_2$ atmosphere overnight. Palladium on carbon was removed through filtration and washed with methanol; the combined organic solution was concentrated under reduced pressure to give a crude residue which was purified by silica gel column chromatography using a 10% methanol in dichloromethane gradient to afford (3S,4R)-4-(2-oxabicyclo[2.2.2]octan-4-ylmethoxy)-3-amino-2-methylpentan-2-ol (0.100 g, 77%) as a colorless oil. MS: 258.1 [M+H]$^+$ The compounds below were synthesized according to the general procedures reported for (3S,4R)-4-(2-oxabicyclo[2.2.2]octan-4-ylmethoxy)-3-amino-2-methylpentan-2-ol using the appropriate commercially available reagents.

(2R,3R)-2-amino-3-(cyclohexylmethoxy)butan-1-ol

Step 1: To a solution of O-benzyl-N-(tert-butoxycarbonyl)-L-threonine (600 mg, 1.94 mmol) in isopropyl alcohol (5 mL) was added 5% Rh/Al$_2$O$_3$ (100 mg). The reaction mixture was stirred under a H$_2$ atmosphere for 16 h. The catalyst was removed by filtration through celite and the filtrate concentrated to afford crude N-(tert-butoxycarbo-

| Compound | Characterization |
|---|---|
| (structure) | 390.2 [M + H]$^+$ |
| (structure) | LCMS not recorded // $^1$HNMR (400 MHz, DMSO-d6): δ 12.40 (s, 1H), 8.25-8.26 (m, 1H), 7.86-7.91 (m, 1H), 7.55-7.60 (m, 1H), 7.48 (t, J = 2.0 Hz, 2H), 7.33 (t, J = 12.0 Hz, 2H). | nyl)-O-(cyclohexylmethyl)-L-threonine (400 mg, 65%) as a yellow oil which was used directly in the next step. LCMS m/z=314.4 [M−H]−; 1H NMR (400 MHz, Chloroform-d) δ 5.27 (d, J=11.8 Hz, 1H), 4.31 (d, J=2.2 Hz, 1H), 4.01 (s, 1H), 3.36-3.27 (m, 1H), 3.17-3.09 (m, 1H), 1.68 (s, 3H), 1.44 (s, 10H), 1.18 (s, 7H), 0.89 (d, J=11.6 Hz, 2H).

Step 2: To a solution of N-(tert-butoxycarbonyl)-O-(cyclohexylmethyl)-L-threonine (400 mg, 1.27 mmol) in dry THF (4 mL) at 0° C. was added BH$_3$-THF (2M, 1.58 mL, 3.17 mmol). The mixture was stirred at room temperature for 3 h then quenched by addition of MeOH (4 mL). The solvent was removed under vacuum and the cured residue obtained purified by column chromatography on silica gel (eluent: Pet. Ether:EtOAc=3:1) to afford tert-butyl ((2R,3R)-3-(cyclohexylmethoxy)-1-hydroxybutan-2-yl)carbamate (200 mg, 52%) as a yellow oil. LCMS m/z=302.4 [M+H]+; 1H NMR (400 MHz, Chloroform-d) δ 5.08 (d, J=7.6 Hz, 1H), 3.81-3.54 (m, 4H), 3.41-3.32 (m, 1H), 3.11-3.02 (m, 1H), 1.71 (d, J=12.0 Hz, 7H), 1.45 (s, 9H), 1.25 (d, J=6.0 Hz, 2H), 1.16 (d, J=6.2 Hz, 4H), 0.97-0.85 (m, 2H).

Step 3: To a solution of tert-butyl ((2R,3R)-3-(cyclohexylmethoxy)-1-hydroxybutan-2-yl)carbamate (200 mg, 0.66 mmol) in DCM (5 mL) was added TFA (2 mL). The reaction mixture was stirred at room temperature for 1 h then the solvent was removed under vacuum to afford (2R,3R)-2-amino-3-(cyclohexylmethoxy)butan-1-ol (642 mg, 100%) which was used without purification.

(R)-2-(benzyloxy)propan-1-amine

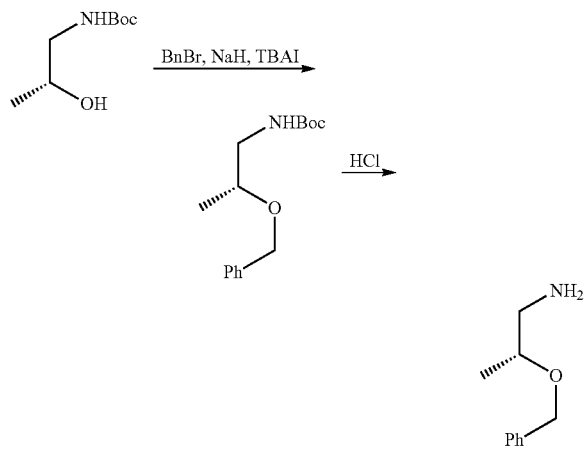

Step 1: To a solution of tert-butyl (R)-(2-hydroxypropyl)carbamate (200 mg, 1.14 mmol) in THF (5.0 mL) at 0° C. was added NaH (50 mg, 1.254 mmol) and TBAI (84 mg, 0.228 mmol) and the mixture was stirred at 0° C. for 30 min. Benzyl bromide (234 mg, 1.41 mmol) was added and the reaction was stirred overnight at room temperature. The reaction mixture was diluted with water (50 mL) and extracted with EtOAc (100 mL×2). The combined organic layers were washed with brine, dried over Na$_2$SO$_4$, filtered and concentrated. The mixture was purified by column chromatography on silica gel (eluent: Pet. Ether:EtOAc=5:1) to afford tert-butyl (R)-(2-(benzyloxy)propyl)carbamate (300 mg, 98%) as a colorless oil. LCMS m/z=288.1 [M+Na]+. 1H NMR (400 MHz, DMSO-d6) δ 7.40-7.18 (m, 5H), 6.82 (t, J=5.6 Hz, 1H), 4.58-4.37 (m, 2H), 3.55-3.47 (m, 1H), 3.09-2.91 (m, 2H), 1.37 (s, 9H), 1.07 (d, J=6.4 Hz, 3H).

Step 2: To a solution of tert-butyl (R)-(2-(benzyloxy)propyl)carbamate (300 mg, 1.13 mmol) in dioxane (2.0 mL) was added a solution of HCl in 1,4-dioxane (4 M, 2 mL, 8 mmol). The mixture was stirred at room temperature for 1 h then the solvent was removed under vacuum to afford the (R)-2-(benzyloxy)propan-1-amine (240 mg) as a white solid which was used without purification. LCMS m/z=166.2 [M+H]+.

(2S,3R)-2-amino-3-((tert-butyldimethylsilyl)oxy)-N-methylbutanamide

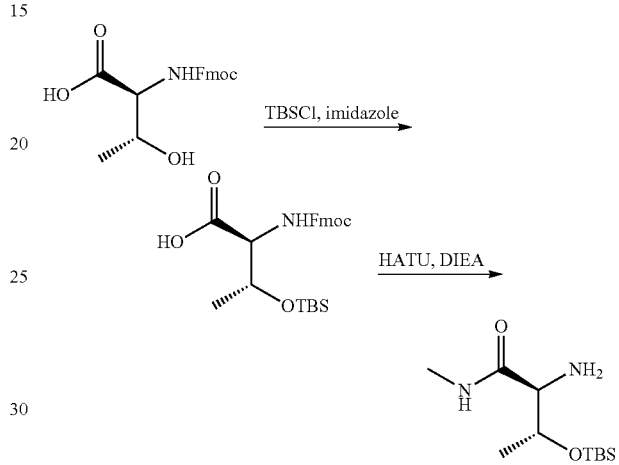

Step 1: To a solution of (((9H-fluoren-9-yl)methoxy)carbonyl)-L-threonine (5 g, 14.60 mmol) in dry DMF (50 mL) was added imidazole (2 g, 29.20 mmol) and tert-butyldimethylsilyl chloride (2.4 g, 16.06 mmol). The mixture was stirred at room temperature overnight then diluted with water (100 mL) and extracted with EtOAc (150 mL×3). The combined organic layers were washed with brine, dried over Na$_2$SO$_4$, filtered and concentrated. The mixture was purified by column chromatography on silica gel (eluent: DCM:MeOH=30:1) to afford N-(((9H-fluoren-9-yl)methoxy)carbonyl)-O-(tert-butyldimethylsilyl)-L-threonine (480 mg, 18%) as a yellow oil. Further elution provided recovered starting material (3 g). 1H NMR (400 MHz, DMSO-d6) δ 12.80 (s, 1H), 7.89 (d, J=7.6 Hz, 2H), 7.75 (t, J=6.8 Hz, 2H), 7.44-7.39 (m, 2H), 7.35-7.28 (m, 2H), 6.92 (d, J=9.4 Hz, 1H), 4.34-4.22 (m, 4H), 4.05 (dd, J=9.4, 3.2 Hz, 1H), 1.13 (d, J=6.2 Hz, 3H), 0.85 (s, 9H), 0.04 (d, J=11.8 Hz, 6H).

Step 2: To a solution of N-(((9H-fluoren-9-yl)methoxy)carbonyl)-O-(tert-butyldimethylsilyl)-L-threonine (480 mg, 1.05 mmol) in DMF (5 mL) was added HATU (440 mg, 1.16 mmol) and the mixture stirred at room temperature for 30 min. Methylamine hydrochloride (85 mg, 1.26 mmol) and DIPEA (545 mg, 4.20 mmol) were added and the reaction stirred for another 6 h. The mixture was diluted with water (20 mL), extracted with EtOAc (50 mL×3). The combined organic layers were washed with brine, dried over Na$_2$SO$_4$, filtered and concentrated. The mixture was purified by column chromatography on silica gel (eluent: DCM/MeOH=60/1) to afford (2S,3R)-2-amino-3-((tert-butyldimethylsilyl)oxy)-N-methylbutanamide (90 mg, 35%) as a white solid. LCMS m/z=247.25 [M+H]+.

501
2-(4-isopropoxyphenyl)acetic acid 502
1-(2-methoxyethyl)cyclopropane-1-carboxylic acid

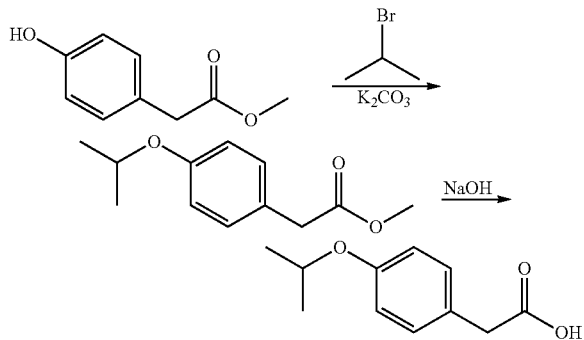

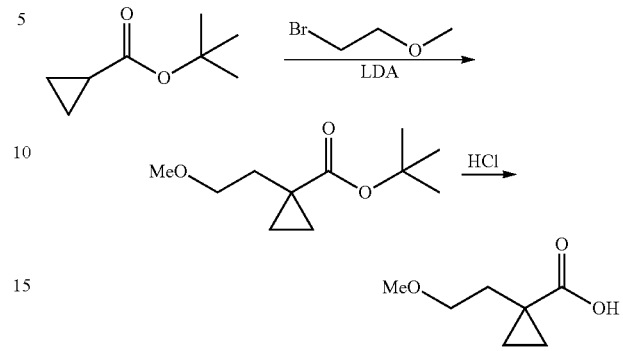

Step 1: To a solution of methyl 2-(4-hydroxyphenyl)acetate (1 g, 6.02 mmol) in DMF (5 mL) was added 2-bromopropane (888 mg, 7.22 mmol) and $K_2CO_3$ (1.25 g, 9.03 mmol). The mixture was heated at 50° C. overnight then cooled to room temperature, diluted with water (60 mL) and extracted with EtOAc (100 mL×2). The combined organic layers were washed with brine, dried over $Na_2SO_4$, filtered and concentrated. The residue obtained was purified by column chromatography on silica gel (eluent: Pet. Ether:EtOAc=20:1) to afford methyl 2-(4-isopropoxyphenyl)acetate (820 mg, 61%) as a white solid. LCMS m/z=209.1 $[M+H]^+$; $^1H$ NMR (400 MHz, DMSO-$d_6$) δ 7.22-7.09 (m, 2H), 6.88-6.80 (m, 2H), 4.56 (p, J=6.0 Hz, 1H), 3.60 (s, 3H), 3.58 (s, 2H), 1.24 (d, J=6.0 Hz, 6H).

Step 2: To a solution of methyl 2-(4-isopropoxyphenyl)acetate (820 mg, 3.94 mmol) in a mixture of MeOH (2 mL) and water (2 mL) was added NaOH (472 mg, 11.81 mmol). The mixture was heated at 50° C. overnight then cooled to room temperature, diluted with water (20 mL) and extracted with EtOAc (30 mL). The aqueous layer was collected and acidified with 1M HCl to pH ~ 2 and extracted with EtOAc (60 mL×3). The combined organic layers were washed with brine, dried over $Na_2SO_4$, filtered and concentrated to afford crude 2-(4-isopropoxyphenyl)acetic acid (730 mg, 96%) as a yellow solid which was used without purification. LCMS m/z=195.2 $[M+H]^+$.

Step 1: To a solution of LDA (2.1 mL, 2 M in THF) in dry THF (10 mL) at −80° C. under $N_2$ was added tert-butyl cyclopropanecarboxylate (500 mg, 3.50 mmol) dropwise. The mixture was stirred at −80° C. 5.5 h then a solution of 1-bromo-2-methoxyethane (1.5 g, 10.5 mmol) in dry THF (2 mL) was added dropwise to the reaction mixture. The mixture was allowed to warm to room temperature and stirred for another 6 h. The reaction was diluted EtOAc (50 mL), washed with brine and the organic layer was dried over $Na_2SO_4$, filtered and concentrated. The residue was purified by column chromatography on silica gel (eluent: Pet. Ether:EtOAc=20:1) to afford tert-butyl 1-(2-methoxyethyl)cyclopropane-1-carboxylate (200 mg, 28%) as a yellow oil. $^1H$ NMR (400 MHz, Chloroform-d) δ 3.52 (t, J=7.2 Hz, 2H), 3.33 (s, 3H), 1.79 (t, J=7.2 Hz, 2H), 1.43 (s, 9H), 1.13 (q, J=4.0 Hz, 2H), 0.68 (q, J=4.0 Hz, 2H).

Step 2: A mixture of tert-butyl 1-(2-methoxyethyl)cyclopropane-1-carboxylate (100 mg, 0.50 mmol) in a solution of HCl in 1,4-dioxane (4 M, 3 mL) was stirred at room temperature for 5 h. The solvent was removed under vacuum to afford 1-(2-methoxyethyl)cyclopropane-1-carboxylic acid as a yellow oil which was used without purification. $^1H$ NMR (400 MHz, Chloroform-d) δ 3.59-3.52 (m, 2H), 3.37 (d, J=1.4 Hz, 3H), 1.87-1.81 (m, 2H), 1.13-1.02 (m, 4H).

The compounds below were synthesized according to the general procedure outlined for 1-(2-methoxyethyl)cyclopropane-1-carboxylic acid using the appropriate commercially available reagents.

| Compound | $^1$HNMR |
| --- | --- |
| ![structure] | $^1$H NMR (400 MHz, Chloroform-d) δ 4.69 (t, J = 6.2 Hz, 1H), 4.57 (t, J = 6.2 Hz, 1H), 1.96-1.91 (m, 2H), 0.95-0.84 (m, 4H). |
| ![structure] | $^1$H NMR (400 MHz, DMSO-$d_6$) δ 12.11 (s, 1H), 1.46-1.42 (m, 2H), 1.07-1.03 (m, 1H), 1.02-0.99 (m, 2H), 0.77-0.73 (m, 2H), 0.38-0.32 (m, 2H), 0.07-0.02 (m, 2H). |
| ![structure] | $^1$H NMR (400 MHz, Chloroform-d) δ 1.52-1.48 (m, 2H), 1.45-1.40 (m, 2H), 1.29-1.24 (m, 4H), 0.89 (t, J = 7.2 Hz, 3H), 0.75 (q, J = 4.0 Hz, 2H). |

| Compound | ¹HNMR |
|---|---|
| 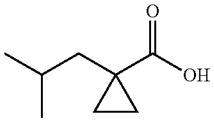 | ¹H NMR (400 MHz, DMSO-d$_6$) δ 12.02 (s, 1H), 1.90 (dt, J = 13.8, 6.8 Hz, 1H), 1.04-1.01 (m, 2H), 0.98 (t, J = 3.2 Hz, 2H), 0.86 (s, 3H), 0.85 (s, 3H), 0.68-0.62 (m, 2H). |

1-(4-fluorobenzyl)-1H-pyrazole-4-carboxylic acid

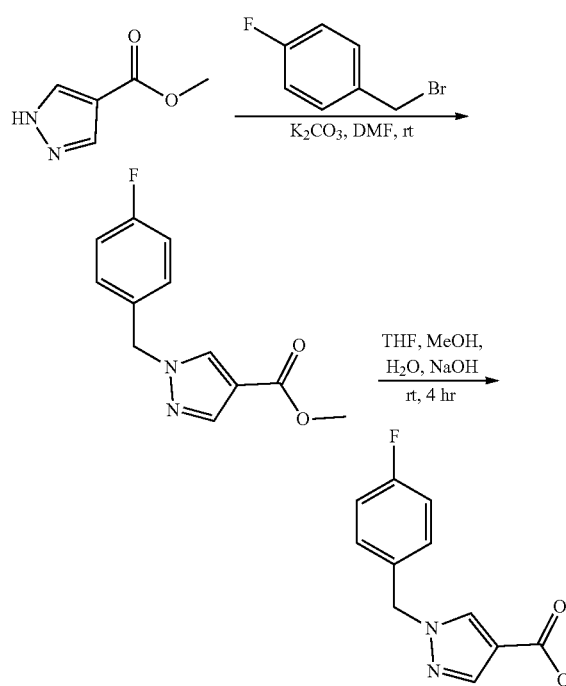

Step 1: To a solution of methyl 1H-pyrazole-4-carboxylate (1 g, 7.90 mmol) in DMF (10 mL) was added K$_2$CO$_3$ (3.3 g, 23.70 mmol) and 1-(bromomethyl)-4-fluorobenzene (1.5 g, 7.90 mmol). The reaction was stirred at room temperature overnight then diluted with water (60 mL) and extracted with EtOAc (150 mL×3). The combined organic layers were washed with brine, dried over Na$_2$SO$_4$, filtered and concentrated to afford methyl 1-(4-fluorobenzyl)-1H-pyrazole-4-carboxylate (1.8 g, 97%) as a white solid. LCMS m/z=235.0 [M+H]$^+$; ¹H NMR (400 MHz, DMSO-d$_6$) δ 8.48 (s, 1H), 7.88 (s, 1H), 7.37-7.30 (m, 2H), 7.21-7.14 (m, 2H), 5.35 (s, 2H), 3.73 (s, 3H).

Step 2: To a solution of methyl 1-(4-fluorobenzyl)-1H-pyrazole-4-carboxylate (1 g, 4.30 mmol) in a mixture of THF (4 mL) MeOH (1 mL) and H$_2$O (1 mL) was added 2M NaOH (2 mL). The mixture was stirred at room temperature for 4 h then diluted with water (50 mL) and extracted with EtOAc (80 mL). The aqueous layer was collected and acidified with 1M HCl to pH ~ 2 and extracted with EtOAc (150 mL×3). The combined organic layers were washed with brine, dried over Na$_2$SO$_4$, filtered and concentrated to afford 1-(4-fluorobenzyl)-1H-pyrazole-4-carboxylic acid (870 mg, 93R) as a white solid. LCMS m/z=221.0 [M+H]$^+$; ¹H NMR (400 MHz, DMSO-d$_6$) δ 12.34 (s, 1H), 8.37 (s, 10), 7.81 (d, J=1.8 Hz, 1H), 7.38-7.30 (m, 2H), 7.23-17.13 (m, 2H), 5.34 (s, 2H).

The compounds below were synthesized according to the general procedure outlined for 1-(4-fluorobenzyl)-1H-pyrazole-4-carboxylic acid using the appropriate commercially available reagents.

| Building Block Structure | ¹HNMR | LCMS |
|---|---|---|
| 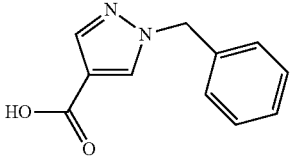 [SMILES: O=C(O)c1cnn(Cc2ccccc2)c1] | ¹H NMR (400 MHz, DMSO-d$_6$) δ 12.33 (s, 1H), 8.37 (s, 1H), 7.82 (s, 1H), 7.38-7.24 (m, 5H), 5.35 (s, 2H). | 203.05 [M + H]$^+$ |
| 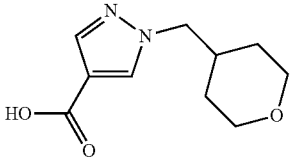 [SMILES: O=C(O)c1cnn(CC2CCOCC2)c1] | ¹H NMR (400 MHz, DMSO-d$_6$) δ 12.34 (s, 1H), 8.22 (s, 1H), 7.79 (s, 1H), 4.03 (d, J = 7.2 Hz, 2H), 3.81 (ddd, J = 11.4, 4.4, 1.8 Hz, 2H), 3.23 (td, J = 11.8, 2.2 Hz, 2H), 2.13-1.98 (m, 1H), 1.39-1.31 (m, 2H), 1.28-1.14 (m, 2H). | 211.2 [M + H]$^+$; |
| 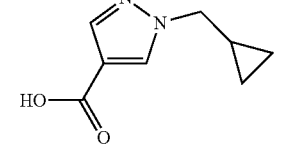 | ¹H NMR (400 MHz, DMSO-d$_6$) δ 12.32 (s, 1H), 8.26 (s, 1H), 7.79 (s, 1H), 3.98 (d, J = 7.2 Hz, 2H), 1.25 (tt, J = 7.6, 4.8 Hz, 1H), 0.55-0.49 (m, 2H), 0.40-0.32 (m, 2H). | 167.1 [M + H]$^+$ |

-continued

| Building Block Structure | ¹HNMR | LCMS |
|---|---|---|
| ![pyrazole CF3 carboxylic acid] | ¹H NMR (400 MHz, DMSO-d₆) δ 8.36 (s, 1H), 7.92 (d, J = 0.6 Hz, 1H), 5.19 (q, J = 9.0 Hz, 2H). | 195.2 [M + H]⁺; |
| ![pyrazole 2-pyridylmethyl carboxylic acid] | | 204.0 [M + H]⁺. |
| ![pyrazole 3-pyridylmethyl carboxylic acid] | | 204.0 [M + H]⁺. |
| ![pyrazole 4-pyridylmethyl carboxylic acid] | | 204.0 [M + H]⁺. |

1-benzyl-1H-pyrazole-4-sulfonyl chloride

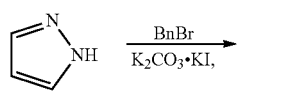
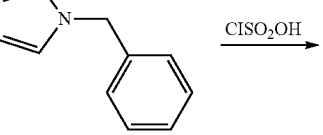

Step 1: To a solution of 1H-pyrazole (1 g, 25.2 mmol) in DMF (20 mL) was added K₂CO₃ (3.4 g, 25.2 mmol), KI (140 mg, 0.086 mmol) and (bromomethyl)benzene (2 mL, 16.8 mmol). The reaction mixture was heated at 80° C. overnight then diluted with water (60 mL) and extracted with DCM (150 mL×2). The combined organic layers were washed with brine, dried over Na₂SO₄, filtered and concentrated. The mixture was purified by column chromatography on silica gel (eluent: Pet. Ether:EtOAc=15:1) to afford 1-benzyl-1H-pyrazole (1.4 g, 60%) as yellow oil. LCMS m/z=159.2 [M+H]⁺.

Step 2: A mixture of 1-benzyl-1H-pyrazole (200 mg, 1.26 mmol) and chlorosulfonic acid (1 mL) was heated at 110° C. for 3 h. The mixture was cooled to room temperature, diluted DCM (50 mL) and washed with brine. The organic layer was dried over Na₂SO₄, filtered and concentrated to afford crude 1-benzyl-1H-pyrazole-4-sulfonyl chloride (70 mg, 22%) as a yellow oil which was used without purification. LCMS m/z=257.1 [M+H]⁺.

(2S,3R)-2-amino-3-((3-hydroxybenzyl)oxy)-N-methylbutanamide

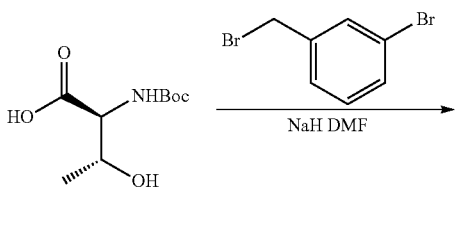

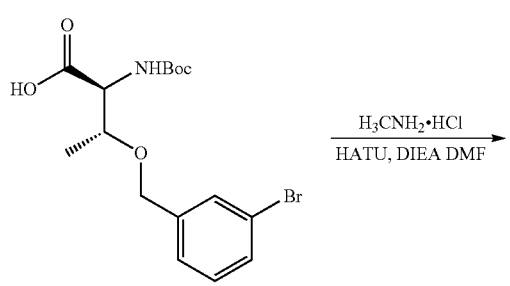

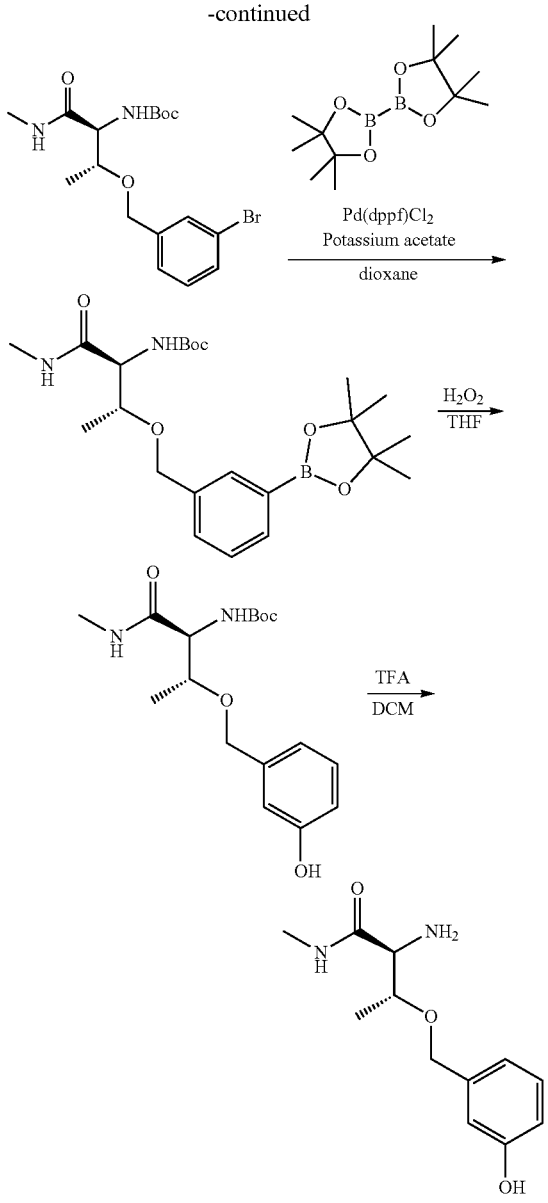

Step 1: To a solution of (tert-butoxycarbonyl)-L-threonine (3 g, 13.7 mmol) in anhydrous DMF (30 mL) at 0° C. was added NaH (1.9 g, 47.95 mmol). The reaction mixture was allowed to warm to room temperature and stirred 1 h. 1-bromo-3-(bromomethyl) benzene (3.4 g, 13.7 mmol) was then added and the reaction stirred at rt overnight. The mixture was diluted with EtOAc (60 mL), washed with water (100 mL×2), dried over $Na_2SO_4$, filtered and concentrated to afford O-(3-bromobenzyl)-N-(tert-butoxycarbonyl)-L-threonine (1.6 g, 30%) as a yellow oil. LCMS m/z=388.0 [M+H]$^+$; $^1$H NMR (400 MHz, DMSO-d$_6$) δ 7.54-7.50 (m, 1H), 7.47-7.44 (m, 1H), 7.35-7.24 (m, 3H), 4.64-4.53 (m, 2H), 4.40 (d, J=12.2 Hz, 1H), 4.09 (dd, J=9.1, 3.8 Hz, 1H), 1.41-1.38 (m, 9H), 1.15 (d, J=6.2 Hz, 3H).

Step 2: To a solution of O-(3-bromobenzyl)-N-(tert-butoxycarbonyl)-L-threonine (1.6 g, 4.13 mmol) in DCM (20 mL) was added HATU (2.3 g, 6.19 mmol) and the mixture stirred at room temperature for 30 min. Methylamine hydrochloride (332 mg, 4.96 mmol) and DIPEA (2.1 g, 16.5 mmol) were added and the reaction stirred for another 3 h. The reaction mixture was then diluted with water (60 mL) and extracted with DCM (150 mL×3). The combined organic layers were washed with brine, dried over $Na_2SO_4$, filtered and concentrated. The mixture was purified by reverse phase Biotage column (C18, 40 g, ACN/H$_2$O=60%) to afford tert-butyl ((2S,3R)-3-((3-bromobenzyl)oxy)-1-(methylamino)-1-oxobutan-2-yl)carbamate (750 mg, 45%) as a yellow oil. LCMS m/z=400.0 [M+H]$^+$; $^1$H NMR (400 MHz, DMSO-d$_6$) δ 7.84 (d, J=4.8 Hz, 1H), 7.51-7.43 (m, 2H), 7.28 (d, J=4.8 Hz, 2H), 6.48 (d, J=9.2 Hz, 1H), 4.52 (d, J=12.4 Hz, 1H), 4.39 (d, J=12.4 Hz, 1H), 4.02-3.97 (m, 1H), 3.88-3.79 (m, 1H), 2.61 (d, J=4.6 Hz, 3H), 1.39 (s, 9H), 1.08 (d, J=6.2 Hz, 3H).

Step 3: To a solution of tert-butyl ((2S,3R)-3-((3-bromobenzyl)oxy)-1-(methylamino)-1-oxobutan-2-yl)carbamate (750 mg, 1.87 mmol) in dioxane (10 mL) was added Bis(pinacolato)diboron (950 mg, 3.74 mmol), potassium acetate (550 mg, 5.61 mmol) and Pd(dppf)Cl$_2$ (82 mg, 0.11 mmol). The reaction was then heated at 80° C. overnight. The reaction was cooled to room temperature, diluted with water (20 mL) and extracted with EtOAc (20 mL). The combined organic layers were washed with brine, dried over $Na_2SO_4$, filtered and concentrated. The mixture was purified by reverse phase Biotage column (C18, 20 g, ACN/H$_2$O=50%) to afford tert-butyl ((2S,3R)-1-(methylamino)-1-oxo-3-((3-(4,4,5,5-tetramethyl-1,3,2-dioxaborolan-2-yl)benzyl)oxy)butan-2-yl)carbamate (500 mg, 59%) as a yellow oil. LCMS m/z=449.2 [M+H]$^+$.

Step 4: To a solution of tert-butyl ((2S,3R)-1-(methylamino)-1-oxo-3-((3-(4,4,5,5-tetramethyl-1,3,2-dioxaborolan-2-yl)benzyl)oxy)butan-2-yl)carbamate (500 mg, 1.11 mmol) in THF (10 mL) was added H$_2$O$_2$ (506 mg, 4.46 mmol) and the mixture stirred at room temperature overnight. Water (10 mL) was added and the mixture was extracted with EtOAc (20 mL). The combined organic layer was then separated, washed with brine, dried over $Na_2SO_4$, filtered and concentrated to afford tert-butyl ((2S,3R)-3-((3-hydroxybenzyl)oxy)-1-(methylamino)-1-oxobutan-2-yl)carbamate (350 mg, 93%) as a yellow oil. LCMS m/z=339.1 [M+H]$^+$.

Step 5: To a solution of tert-butyl ((2S,3R)-3-((3-hydroxybenzyl)oxy)-1-(methylamino)-1-oxobutan-2-yl)carbamate (300 mg, 0.88 mmol) in DCM (5 mL) was added TFA (1 mL) and the reaction mixture was stirred at room temperature for 1 h. The solvent was removed under vacuum to afford (2S,3R)-2-amino-3-((3-hydroxybenzyl)oxy)-N-methylbutanamide (211 mg, 100%). LCMS m/z=239.1 [M+H]$^+$.

(2S,3S)-2-amino-3-(cyclohexylmethoxy)-N-methylbutanamide

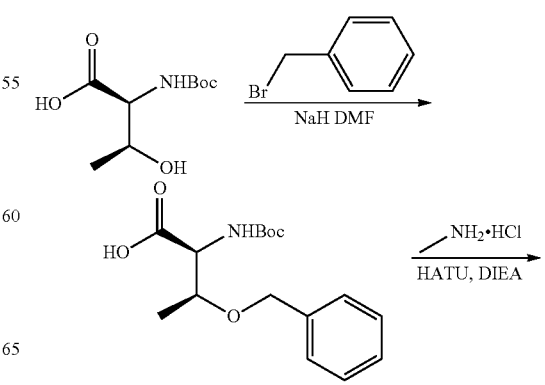

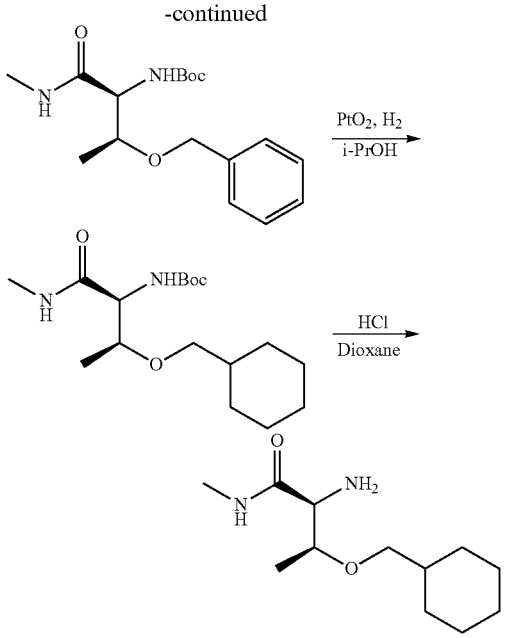

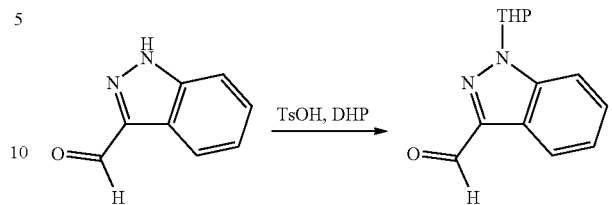

colorless oil. LCMS m/z=229.15 [M+H]⁺. 1-(tetrahydro-2H-pyran-2-yl)-1H-indazole-3-carbaldehyde To a solution of 1H-indazole-3-carbaldehyde (200 mg, 1.37 mmol) in MeCN (2 mL) were added TsOH (24 mg, 0.137 mmol) and 3,4-dihydropyran (230 mg, 2.74 mmol). The mixture was stirred at room temperature overnight under $N_2$. The mixture was diluted with water (30 mL) and extracted with EtOAc (50 mL×2). The combined organic layers were washed with brine, dried over $Na_2SO_4$, filtered and concentrated. The residue was purified by column chromatography on silica gel (eluent: Pet Ether:EtOAc=5:1) to afford 1-(tetrahydro-2H-pyran-2-yl)-1H-indazole-3-carbaldehyde (220 mg, 70%) as a white solid. LCMS m/z=230.9 [M+H]f; ¹H NMR (400 MHz, DMSO-$d_6$) δ 11.07 (s, 1H), 9.05-9.02 (m, 1H), 8.80-8.78 (m, 1H), 8.47-8.42 (m, 1H), 8.32-8.28 (m, 1H), 6.96-6.93 (m, 1H), 4.81-4.63 (m, 2H), 4.20 (s, 2H), 3.35-3.26 (m, 1H), 2.98-2.92 (m, 2H), 2.72-2.61 (m, 1H).

Step 1: To a solution of (tert-butoxycarbonyl)-L-allothreonine (800 mg, 3.65 mmol) in DMF (8 mL) at 0° C. under a $N_2$ atmosphere was added NaH (437 mg, 10.95 mmol). The reaction mixture was stirred at 0° C. for 1 h then benzylbromide (624 mg, 3.65 mmol) was added. The reaction was allowed to warm to room temperature and stirred overnight. The mixture was diluted with water (80 mL) and extracted with EtOAc (80 mL). The aqueous layer was then acidified to pH ~1 with 1M HCl and extracted with EtOAc (150 mL×3). The combined organic layers were washed with brine, dried over $Na_2SO_4$, filtered and concentrated to afford O-benzyl-N-(tert-butoxycarbonyl)-L-allothreonine (178 mg, 16%) as a yellow oil. LCMS m/z=308.05 [M−H]⁻.

Step 2: To a solution of O-benzyl-N-(tert-butoxycarbonyl)-L-allothreonine (200 mg, 0.65 mmol), methanamine hydrochloride (52 mg, 0.78 mmol), and HATU (368 mg, 0.97 mmol) in DMF (2 mL) was added DIEA (376 mg, 2.91 mmol). The mixture was stirred at room temperature for 2 h. The mixture was diluted with water (100 mL) and extracted with EtOAc (150 mL×2). The combined organic layers were washed with brine, dried over $Na_2SO_4$, filtered and concentrated. The mixture was purified by RP-column to afford tert-butyl ((2S,3S)-3-(benzyloxy)-1-(methylamino)-1-oxobutan-2-yl)carbamate (143 mg, 69%) as a white solid. LCMS m/z=323.10 [M+H]⁺.

Step 3: To a solution of tert-butyl ((2S,3S)-3-(benzyloxy)-1-(methylamino)-1-oxobutan-2-yl)carbamate (155 mg, 0.48 mmol) in AcOH (2 mL) was added $PtO_2$ (65 mg). The reaction was heated at 70° C. under a $H_2$ atmosphere overnight. The catalyst was removed by filtration through celite and the filtrate concentrated to afford tert-butyl ((2S,3S)-3-(cyclohexylmethoxy)-1-(methylamino)-1-oxobutan-2-yl)carbamate (148 mg, 94%) as a white solid. LCMS m/z=329.2 [M+H]⁺.

Step 4: To a solution of tert-butyl ((2S,3S)-3-(cyclohexylmethoxy)-1-(methylamino)-1-oxobutan-2-yl)carbamate (148 mg, 0.45 mmol) in 1,4-dioxane (2 mL) was added a solution of HCl in 1,4-dioxane (4 M, 2 mL). The mixture was stirred at room temperature for 1 h. The solvent was removed under vacuum to afford (2S,3S)-2-amino-3-(cyclohexylmethoxy)-N-methylbutanamide (87 mg, 85%) as a (R)-3-amino-1-methylpyrrolidin-2-one

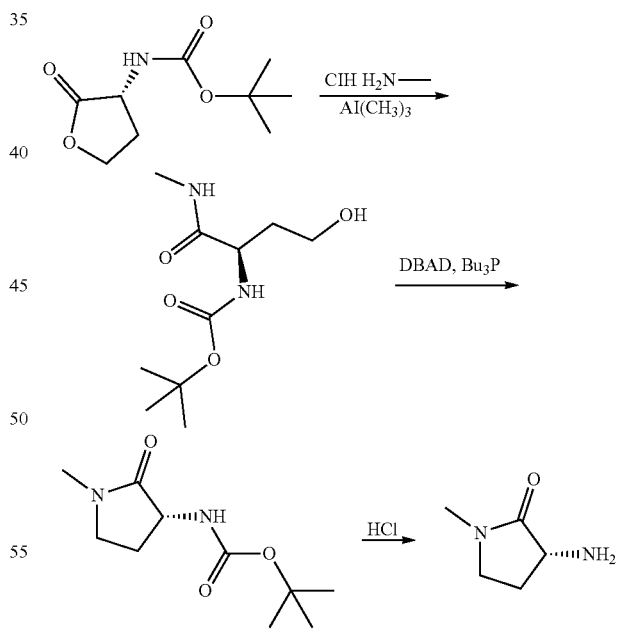

Step 1: To a solution of methylamine hydrochloride (202 mg, 2.99 mmol) in dry DCM at 0° C. (2 mL) under a nitrogen atmosphere was added trimethylaluminium (2.5 mL, 2 mol/L in hexane). The mixture was stirred at 0° C. for 15 min and then a solution of tert-butyl (R)-(2-oxotetrahydrofuran-3-yl)carbamate (500 mg, 2.49 mmol) in dry DCM (5 mL) was added. The reaction mixture was allowed to warm to room temperature and then stirred overnight. Water (30 mL) was added, and the mixture extracted with DCM (50 mL×3). The combined organic layers were washed with brine, dried over Na₂SO₄, filtered and concentrated to afford crude tert-butyl (S)-(4-hydroxy-1-(methylamino)-1-oxobutan-2-yl)carbamate (180 mg, 31%). LCMS m/z=233.1 [M+H]⁺.

Step 2: A solution of di-tert-butylazodicarboxylate (357 mg, 1.55 mmol) and Bu₃P (783 mg, 3.88 mmol) in dry THF (8 mL) at 0° C. was stirred for 30 min. To this, a solution of tert-butyl (S)-(4-hydroxy-1-(methylamino)-1-oxobutan-2-yl)carbamate (180 mg, 0.77 mmol) in THF (2 mL) was added and the resulting mixture heated at 60° C. overnight. The mixture was then diluted with water (30 mL) and extracted with EtOAc (50 mL×3). The combined organic layers were washed with brine, dried over Na₂SO₄, filtered and concentrated. The residue was purified by RP-column to afford tert-butyl (R)-(1-methyl-2-oxopyrrolidin-3-yl)carbamate (24 mg, 14%). LCMS m/z=215.1 [M+H]⁺; ¹H NMR (400 MHz, CDCl₃) δ 5.19-5.03 (m, 1H), 4.20-4.08 (m, 1H), 3.41-3.25 (m, 2H), 2.93-2.85 (m, 3H), 2.71-2.58 (m, 1H), 1.96-1.81 (m, 1H), 1.45 (s, 9H).

Step 3: To a solution of tert-butyl (R)-(1-methyl-2-oxopyrrolidin-3-yl)carbamate (24 mg, 0.11 mmol) in 1,4-dioxane (2 mL) was added a solution of HCl in dioxane (4 M, 0.5 mL). The reaction mixture was stirred at room temperature for 2 h, after which the solvent was removed under vacuum to afford (R)-3-amino-1-methylpyrrolidin-2-one (13 mg, 100%). LCMS m/z=115.0 [M+H]⁺.

The compounds below were synthesized according to the general procedure outlined for (R)-3-amino-1-methylpyrrolidin-2-one using the appropriate commercially available reagents.

| Compound | LCMS |
|---|---|
| 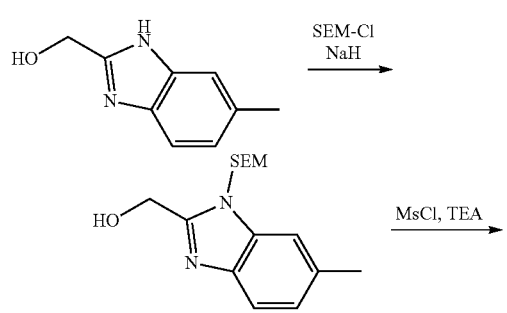 | 141.0 [M + H]⁺ |
| | 141.0 [M + H]⁺ |

(6-methyl-1-((2-(trimethylsilyl)ethoxy)methyl)-1H-benzo[d]imidazol-2-yl)methanamine

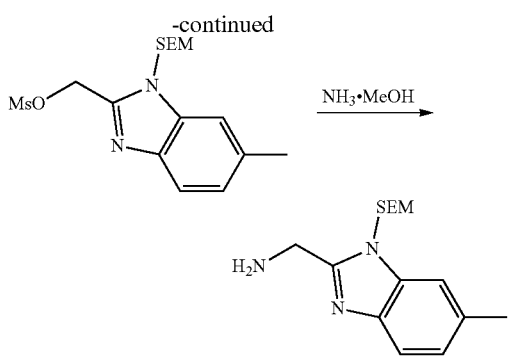

Step 1: To a solution of (6-methyl-1H-benzo[d]imidazol-2-yl)methanol (2 g, 6.47 mmol) in dry DMF (5 mL) was added 60% NaH (81 mg, 3.70 mmol) and the mixture stirred at room temperature for 30 min. SEM-Cl (370 mg, 2.20 mmol) was added slowly and the mixture was stirred at room temperature for another 4 hours. The reaction was then diluted with water (15 mL) and extracted with EtOAc (30 mL×3). The combined organic layers were washed with brine, dried over Na₂SO₄, filtered and concentrated. The residue was purified by column chromatography on silica gel (eluent: Pet. Ether:EtOAc=1:1) to afford (6-methyl-1-((2-(trimethylsilyl)ethoxy)methyl)-1H-benzo[d]imidazol-2-yl)methanol (300 mg, 56%) as a yellow oil. ¹H NMR (400 MHz, DMSO-d₆) δ 7.48 (dd, J=8.2, 2.8 Hz, 1H), 7.40 (td, J=1.8, 0.8 Hz, 1H), 7.05 (ddd, J=20.6, 8.2, 1.6 Hz, 1H), 5.66-5.62 (m, 3H), 4.72 (dd, J=5.8, 1.4 Hz, 2H), 3.55-3.49 (m, 2H), 2.41 (d, J=10.2 Hz, 3H), 0.83 (dt, J=7.8, 3.8 Hz, 2H), -0.09 (d, J=1.6 Hz, 9H).

Step 2: To a solution of (6-methyl-1-((2-(trimethylsilyl)ethoxy)methyl)-1H-benzo[d]imidazol-2-yl)methanol (100 mg, 0.34 mmol) and TEA (69 mg, 0.68 mmol) in DCM (2 mL) at 0° C. was added MsCl (47 mg, 0.41 mmol. The reaction mixture was stirred at room temperature for 1 h. Water (15 mL) was then added and the mixture extracted with DCM (30 mL×3). The combined organic layers were washed with brine, dried over Na₂SO₄, filtered and concentrated to afford crude (6-methyl-1-((2-(trimethylsilyl)ethoxy)methyl)-1H-benzo[d]imidazol-2-yl)methyl methanesulfonate (80 mg, 63%) as a brown oil. LCMS m/z=371.20 [M+H]⁺.

Step 3: A mixture of (6-methyl-1-((2-(trimethylsilyl)ethoxy)methyl)-1H-benzo[d]imidazol-2-yl)methyl methanesulfonate (350 mg, 1.20 mmol) and NH₃/MeOH (7 M, 4 mL) in a sealed-tube, was heated at 80° C. for 4 hours. The reaction was diluted with water (20 mL), extracted with DCM (50 mL×2), dried over Na₂SO₄ and concentrated. The residue was purified by prep-TLC (eluent: Pet. Ether:EtOAc=1:1 and then DCM:MeOH=20:1) to afford (6-methyl-1-((2-(trimethylsilyl)ethoxy)methyl)-1H-benzo[d]imidazol-2-yl)methanamine (70 mg, 25%) as a grey oil. LCMS m/z=292.10 [M+H]⁺.

(S)-2-amino-3-((tert-butyldiphenylsilyl)oxy)-N-methylpropanamide

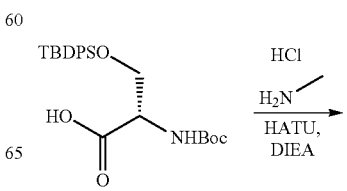

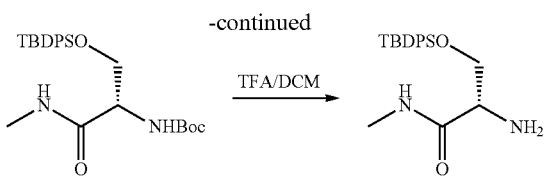

Step 1: To a solution of N-(tert-butoxycarbonyl)-O-(tert-butyldiphenylsilyl)-L-serine (200 mg, 0.45 mmol) in DCM (2 mL) was added HATU (188 mg, 0.495 mmol) and the reaction mixture stirred at room temperature for 30 min. Methanamine hydrochloride (36 mg, 0.54 mmol) and DIPEA (233 mg, 1.8 mmol) were added and the reaction mixture stirred for a further 3 h. The solvent was then removed under vacuum and the residue purified by prep-TLC (eluent: DCM/MeOH=20/1) to afford tert-butyl (S)-(3-((tert-butyldiphenylsilyl)oxy)-1-(methylamino)-1-oxopropan-2-yl)carbamate (195 mg, 95%) as a white solid. LCMS m/z=457.2 [M+H]$^+$; $^1$H NMR (400 MHz, DMSO-$d_6$) δ 7.95-7.93 (m, 1H), 7.62-7.59 (m, 4H), 7.47-7.40 (m, 6H), 6.68 (d, J=8.8 Hz, 1H), 4.20-4.15 (m, 1H), 3.82-3.68 (m, 2H), 2.6 (d, J=4.4 Hz, 3H), 1.39 (s, 9H), 0.96 (s, 9H).

Step 2: To a solution of tert-butyl (S)-(3-((tert-butyldiphenylsilyl)oxy)-1-(methylamino)-1-oxopropan-2-yl)carbamate (125 mg, 0.274 mmol) in DCM (3 mL) was added TFA (1 mL). The mixture was stirred at room temperature for 1 h and then the solvent was removed under vacuum to afford (S)-2-amino-3-((tert-butyldiphenylsilyl)oxy)-N-methylpropanamide (100 mg, 100%) as a yellow oil. LCMS m/z=357.3 [M+H]$^+$.

The compounds below were synthesized according to the general procedure outlined for (S)-2-amino-3-((tert-butyldiphenylsilyl)oxy)-N-methylpropanamide using the appropriate commercially available reagents.

| Compound | LCMS |
| --- | --- |
| TBDPSO–(structure)–NH$_2$ | 357.3 [M + H]$^+$ |

1-(methoxymethyl)cyclopropanamine (scheme: tert-butyl (1-(hydroxymethyl)cyclopropyl)carbamate → AgO, MeI → tert-butyl (1-(methoxymethyl)cyclopropyl)carbamate → HCl/1,4-Dioxane → 1-(methoxymethyl)cyclopropanamine·HCl)

Step 1: A mixture of tert-butyl (1-(hydroxymethyl)cyclopropyl)carbamate (500 mg, 2.67 mmol), AgO (1.24 g, 5.34 mmol), MeI (759 mg, 5.34 mmol) and DCE (2 mL) was heated at 60° C. overnight, in a sealed-tube. The solvent was then removed under vacuum and the residue purified by column chromatography on silica gel (eluent: Pet. Ether: EtOAc=20:1) to afford tert-butyl (1-(methoxymethyl)cyclopropyl)carbamate (200 mg, 37%) as a colorless oil. $^1$H NMR (CDCl$_3$, 400 MHz) δ, 5.04 (1H, s), 3.38 (2H, s), 3.36 (3H, s), 1.43 (9H, s), 0.81 (2H, d, J=4.8 Hz), 0.75 (2H, d, J=5.0 Hz).

Step 2: To a solution of tert-butyl (1-(methoxymethyl)cyclopropyl)carbamate (100 mg, 0.50 mmol) in DCM (2 mL) was added a solution of HCl in 1,4-dioxane (4 M, 1 mL). The reaction mixture was stirred at room temperature for 1 h. The solvent was then removed under vacuum to afford crude 1-(methoxymethyl)cyclopropanamine hydrochloride (68 mg, 100%) as a colorless oil. LCMS m/z=102.1 [M+H]$^+$.

The compounds below were synthesized according to the general procedure outlined for 1-(methoxymethyl)cyclopropanamine using the appropriate commercially available reagents.

| Compound | LCMS |
| --- | --- |
| MeO–(cyclopentyl)–NH$_2$ | 116.2 [M + H]$^+$ |
| iPrO–(cyclobutyl)–NH$_2$ | 130.2 [M + H]$^+$ |
| iPrO–(cyclobutyl)–NH$_2$ (stereoisomer) | 130.2 [M + H]$^+$ |

(S)-2-amino-5-cyclohexyl-N-methylpentanamide

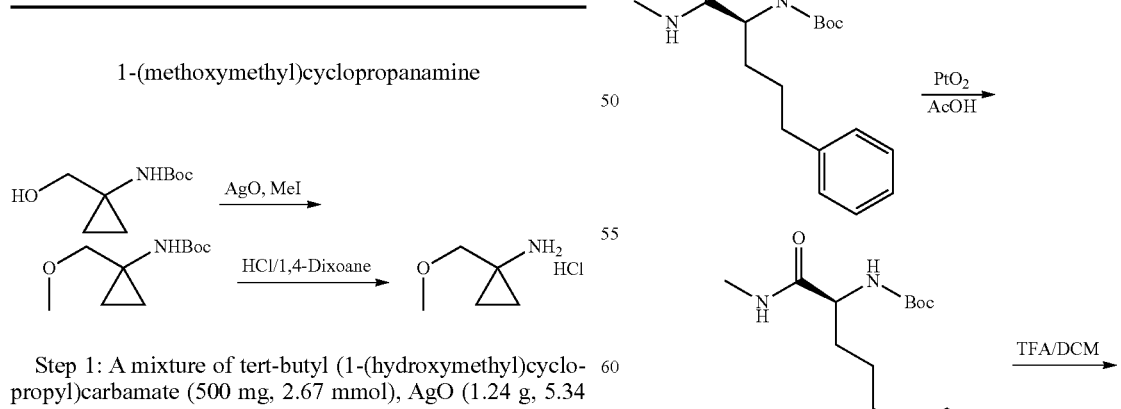

515

-continued

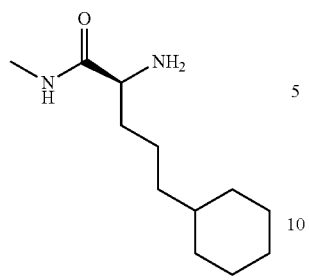

Step 1: To a solution of tert-butyl (S)-(1-(methylamino)-1-oxo-5-phenylpentan-2-yl)carbamate (350 mg, 1.14 mmol) in AcOH (8 mL) was added PtO$_2$ (50 mg). The reaction was heated at 70° C. overnight in a pressure vessel under 4 atm H$_2$. The catalyst was removed by filtration through celite and the filtrate concentrated to afford crude tert-butyl (S)-(5-cyclohexyl-1-(methylamino)-1-oxopentan-2-yl)carbamate (357 mg, 100%) as a yellow oil. LCMS m/z=313.2 [M+H]$^+$.

Step 2: To a solution of tert-butyl (S)-(5-cyclohexyl-1-(methylamino)-1-oxopentan-2-yl)carbamate (70 mg, 0.224 mmol) in DCM (4 mL) was added TFA (1 mL). The reaction mixture was stirred at room temperature for 1 h. The solvent was removed under vacuum to afford crude (S)-2-amino-5-cyclohexyl-N-methylpentanamide (48 mg, 100%). LCMS m/z=213.2 [M+H]$^+$.

(2S,3R)-2-amino-3-hydroxy-N-methyl-4-phenylbutanamide

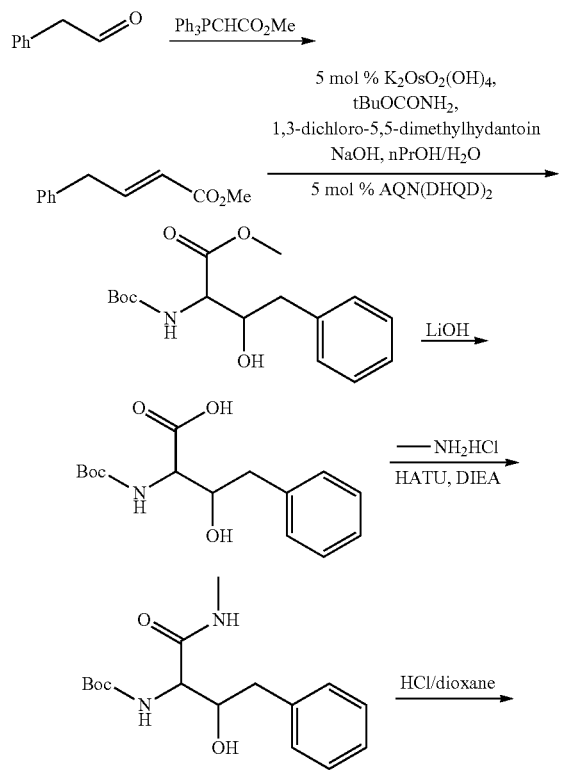

516

-continued

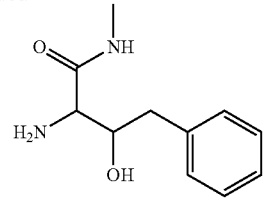

Step 1: To a solution of 2-phenylacetaldehyde (3.0 g, 24.97 mmol) in toluene (20 mL) at 25° C. was added Ph$_3$PCHCO$_2$Me (9.18 mg, 27.47 mmol). The reaction mixture was stirred at 90° C. for 16 h. The mixture was concentrated and the residue obtained was purified by column chromatography on silica gel (eluent: Pet. Ether:EtOAc=20:1) to afford methyl (E)-4-phenylbut-2-enoate (2.77 g, 62%) as a colorless oil. LCMS m/z=177.1 [M+H]$^+$.

Step 2: To a solution of t-BuOCONH$_2$ (1.99 g, 17.02 mmol) in n-PrOH/H$_2$O (5 mL/10 mL) at room temperature was added NaOH (0.68 g, 17.02 mmol), 1,3-dichloro-5,5-dimethylhydantoin (2.24 g, 11.35 mmol), AQN(DHQD)$_2$ (243 mg, 0.283 mmol) and K$_2$OsO$_2$(OH)$_4$ (104 mg, 0.283 mmol). The reaction mixture was stirred at room temperature for 16 h. The mixture was diluted with water (100 mL) and extracted with EtOAc (150 mL×2). The combined organic layers were washed with brine, dried over Na$_2$SO$_4$, filtered and concentrated. The residue obtained was purified by column chromatography on silica gel (eluent: Pet. Ether:EtOAc=5:1) to afford methyl (2S,3R)-2-((tert-butoxycarbonyl)amino)-3-hydroxy-4-phenylbutanoate (470 mg, 26%) as a yellowish oil. LCMS m/z=310.1 [M+H]$^+$. $^1$H NMR (400 MHz, CDCl$_3$) δ 7.36-7.28 (m, 3H), 7.26-7.20 (m, 2H), 5.51-5.33 (m, 1H), 4.44-4.26 (m, 2H), 3.75 (s, 2H), 3.70 (s, 1H), 2.93-2.74 (m, 2H), 1.61 (s, 2H), 1.51-1.41 (m, 9H).

Step 3: To a solution of methyl (2S,3R)-2-((tert-butoxycarbonyl)amino)-3-hydroxy-4-phenylbutanoate (0.1 g, 0.323 mmol) in a mixture of THF and water (2 mL/1 mL) was added LiOH (0.024 g, 0.969 mmol). The reaction mixture was stirred at room temperature for 2 h then diluted with water (10 mL) and extracted with ether (20 mL). The aqueous layer was collected and acidified with 1M HCl to pH 2 and extracted with EtOAc (10 mL×3). The combined organic layers were washed with brine, dried over Na$_2$SO$_4$, filtered and concentrated to afford (2S,3R)-2-((tert-butoxycarbonyl)amino)-3-hydroxy-4-phenylbutanoic acid (90 mg, 94%) as a white solid which was used directly in the next step. LCMS m/z=296.1 [M+H]$^+$.

Step 4: To a solution of (2S,3R)-2-((tert-butoxycarbonyl)amino)-3-hydroxy-4-phenylbutanoic acid (90 mg, 0.304 mmol) in DMF (1 mL) was added HATU (174 mg, 0.457 mmol). The mixture was stirred at room temperature for 30 min. Methylamine hydrochloride (31 mg, 0.457 mmol) and DIPEA (158 mg, 1.22 mmol) were then added and the reaction stirred for another 3 h. The mixture was diluted with water (20 mL), extracted with DCM (50 mL×3), the combined organic layers washed with brine, dried over Na$_2$SO$_4$, filtered and concentrated. The residue was purified by column chromatography on silica gel (eluent: DCM:MeOH=30:1) to afford tert-butyl ((2S,3R)-3-hydroxy-1-(methylamino)-1-oxo-4-phenylbutan-2-yl)carbamate (65 mg, 69%) as a white solid. LCMS m/z=309.1 [M+H]$^+$.

Step 5: To a solution of tert-butyl ((2S,3R)-3-hydroxy-1-(methylamino)-1-oxo-4-phenylbutan-2-yl)carbamate (65 mg, 0.210 mmol) in 1,4-dioxane (1 mL) was added a solution of HCl in Dioxane (4 M, 2 mL). The reaction mixture was stirred at room temperature for 3 h. The solvent was removed under vacuum to afford crude (2S,3R)-2-amino-3-hydroxy-N-methyl-4-phenylbutanamide (60 mg, 100%) which was used without purification. LCMS m/z=209.1 [M+H]+.

(S)-1-phenylpyrrolidin-3-amine HCl

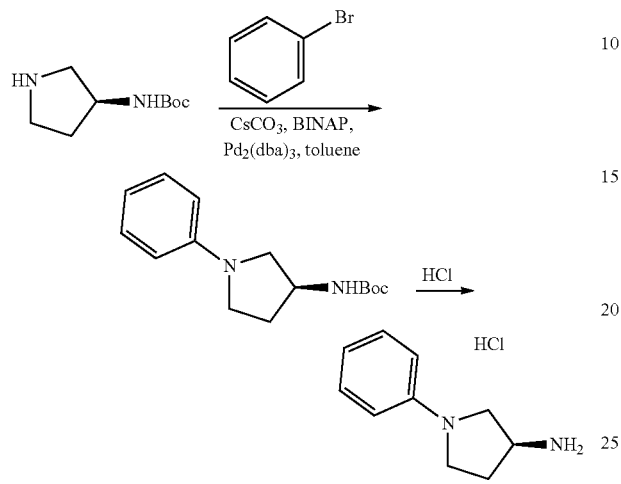

Step 1: To a solution of tert-butyl (S)-pyrrolidin-3-ylcarbamate (300 mg, 1.61 mmol) in toluene (20 mL) was added bromobenzene (316.2 mg, 2.01 mmol), Cs₂CO₃ (787.3 mg, 2.42 mmol), BINAP (160.5 mg, 0.26 mmol) and Pd₂(dba)₃ (118.0 mg, 0.13 mmol). The reaction mixture was heated at 110° C. under a N₂ atmosphere overnight. The reaction mixture was diluted with water (30 mL) and extracted with EtOAc (3×50 mL). The combined organic layers were washed with brine, dried over Na₂SO₄, filtered and concentrated. The residue was purified by prep-TLC (eluent: Pet. Ether:EtOAc=3:1) to afford (S)-1-phenylpyrrolidin-3-amine (200 mg, 47%) as a white solid. LCMS m/z=263.3 [M+H]+; ¹H NMR (400 MHz, DMSO-d₆) δ 7.18-7.15 (m, 1H), 7.15-7.14 (m, 1H), 7.14-7.11 (m, 1H), 6.58 (t, J=7.4, 1.0 Hz, 1H), 6.50 (s, 1H), 6.48 (s, 1H), 4.18-4.06 (m, 1H), 3.43 (dd, J=9.6, 6.6 Hz, 1H), 3.32-3.29 (m, 1H), 3.24-3.15 (m, 1H), 3.01 (q, J=9.6, 5.2 Hz, 1H), 2.20-2.09 (m, 1H), 1.93-1.81 (m, 1H), 1.39 (s, 9H).

Step 2: To a solution of tert-butyl (S)-(1-phenylpyrrolidin-3-yl)carbamate (100 mg, 0.38 mmol) in 1,4-dioxane (3 mL) was added HCl in 1,4-dioxane (4 M, 4 mL). The mixture was stirred at room temperature for 1 h. The solvent was removed under vacuum to afford crude (S)-1-phenylpyrrolidin-3-amine (62 mg, 100%) as a white solid. LCMS m/z=163.3 [M+H]+; ¹H NMR (400 MHz, DMSO-d₆) δ 8.45 (s, 3H), 7.19 (dd, 2H), 6.65 (t, J=7.2 Hz, 1H), 6.56 (d, J=8.0 Hz, 2H), 3.95-3.84 (m, 1H), 3.56-3.42 (m, 2H), 3.37-3.21 (m, 2H), 2.37-2.24 (m, 1H), 2.17-2.05 (m, 1H).

(R)-1-phenylpyrrolidin-3-amine HCl (R)-1-phenylpyrrolidin-3-amine was synthesized according to procedure outlined for (S)-1-phenylpyrrolidin-3-amine using the appropriate commercially available reagents. LCMS m/z=163.2 [M+H]+; ¹H NMR (400 MHz, DMSO-d₆) δ 8.46 (s, 3H), 7.23-7.16 (m, 2H), 6.65 (t, J=7.2 Hz, 1H), 6.56 (d, J=8.0 Hz, 2H), 3.95-3.85 (m, 1H), 3.56-3.41 (m, 2H), 3.36-3.22 (m, 2H), 2.37-2.23 (m, 1H), 2.16-2.03 (m, 1H).

4-(benzyloxy)piperidine

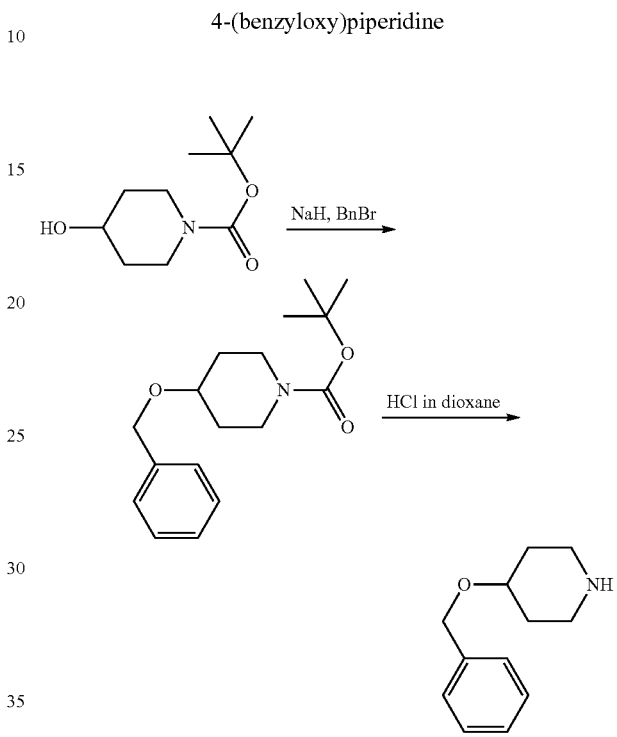

Step 1: To a solution of tert-butyl 4-hydroxypiperidine-1-carboxylate (500 mg, 2.5 mmol) in THF (5 mL) at 0° C. was added benzyl bromide (547 mg, 3.2 mmol) and 60% sodium hydride (120 mg, 3.0 mmol). The resulting mixture was allowed to warm to room temperature and stirred for 3 h. Water was added and the aqueous layer was extracted with EtOAc three times. The combined organic layers were washed with water, brine and dried over Na₂SO₄. The solvent was removed and the residue purified by silica gel column chromatography (4% MeOH/DCM) to afford tert-butyl 4-(benzyloxy)piperidine-1-carboxylate (633 mg, 85%) as a colorless oil. ¹H NMR (400 MHz, DMSO-d₆) δ 7.37-7.23 (m, 5H), 4.51 (s, 2H), 3.68-3.51 (m, 3H), 3.10-2.98 (m, 2H), 1.85-1.77 (m, 2H), 1.45-1.35 (m, 11H).

Step 2: A solution of tert-butyl 4-(benzyloxy)piperidine-1-carboxylate (100 mg, 0.34 mmol) in HCl (4 M in dioxane, 2 mL) was stirred for 1 hour. The solvent was removed to afford 4-(benzyloxy)piperidine (21 mg, 33%). LCMS m/z=192.1 [M+H]+.

(S)-4-(1-phenylethoxy)piperidine

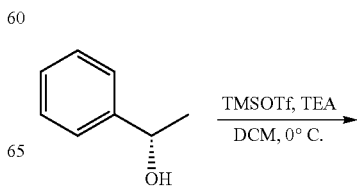

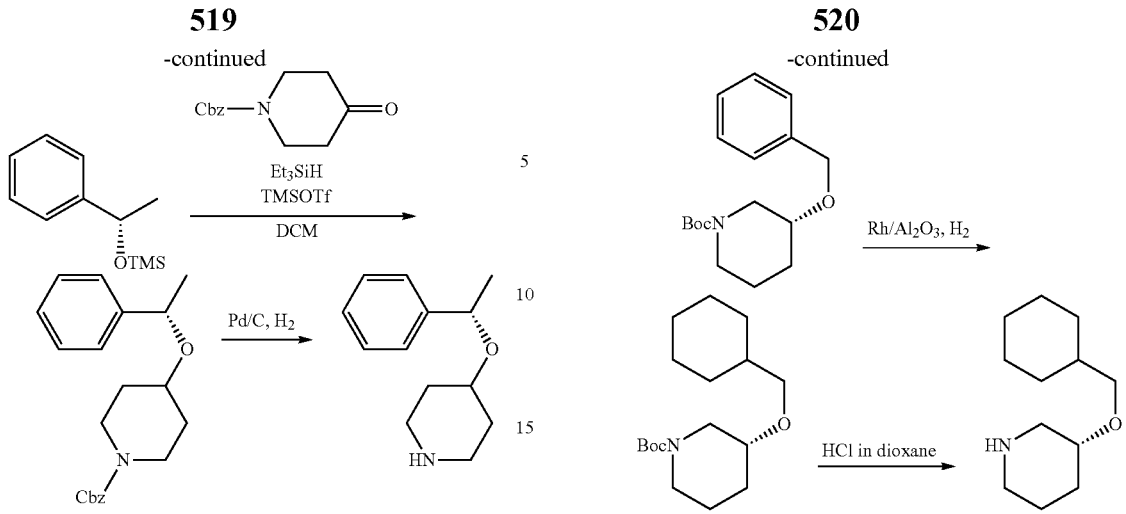

Step 1: TMSOTf (9.1 g, 40.9 mmol) was added dropwise to a solution of (S)-1-phenylethan-1-ol (2.0 g, 16.4 mmol) and TEA (8.3 g, 81.8 mmol) in DCM (20.0 mL) at 0° C. The resulting solution was allowed to warm to room temperature over 2 hours. Water was then added and the aqueous extracted with DCM. The combined organic layers were washed with water and brine and dried over Na$_2$SO$_4$. The solvent was removed and the residue purified by silica gel column chromatography (10% EtOAc/PE) to afford (S)-trimethyl(1-phenylethoxy)silane (2.4 g, 75%) as a colorless oil. $^1$H NMR (400 MHz, CD$_3$OD) δ 7.52-7.00 (m, 5H), 4.95-4.80 (m, 1H), 1.40 (d, J=6.4 Hz, 3H), 0.06 (s, 9H).

Step 2: To a solution of (S)-trimethyl(1-phenylethoxy)silane (150 mg, 0.77 mmol) in DCM (3.0 mL) was added benzyl 4-oxopiperidine-1-carboxylate (180 mg, 0.77 mmol), triethylsilane (99 mg, 0.85 mmol) and TMSOTf (86 mg, 0.39 mmol) at −78° C. The resulting solution was then warmed to 0° C. and stirred for 2 h. The reaction mixture was quenched with 1M H$_3$PO$_4$, water was added and the aqueous extracted with EtOAc. The combined organic layers were washed with water, brine and dried over Na$_2$SO$_4$. The solvent was removed and the residue purified by prep-HPLC to afford (S)-4-(1-phenylethoxy)piperidine-1-carboxylate (34 mg, 13%) as a yellow oil. LCMS m/z=340.1[M+H]$^+$; $^1$H NMR (400 MHz, CD$_3$OD) δ 7.38-7.20 (m, 10H), 5.09 (s, 2H), 4.64 (q, J=6.4 Hz, 1H), 3.88-3.66 (m, 2H), 3.49-3.39 (m, 1H), 3.25-3.01 (m, 2H), 1.92-1.80 (m, 1H), 1.72-1.59 (m, 1H), 1.59-1.40 (m, 2H), 1.38 (d, J=6.8 Hz, 3H).

Step 3: To a solution of (S)-4-(1-phenylethoxy)piperidine-1-carboxylate (30 mg, 0.09 mmol) in MeOH (2.0 mL) was added Pd/C (10%, 15 mg). The resulting mixture was stirred under an atmosphere of H$_2$ at room temperature for 4 h. The reaction mixture was filtered through celite and the filtrate concentrated under reduced pressure to afford (S)-4-(1-phenylethoxy)piperidine (18 mg, quant.). LCMS m/z=206.2 [M+H]$^+$.

(R)-3-(cyclohexylmethoxy)piperidine

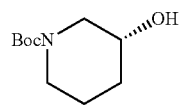 BnBr, NaH →

Step 1: To a solution of (R)-tert-butyl 3-hydroxypiperidine-1-carboxylate (200 mg, 0.99 mmol) in DMF (2 mL) was added NaH (79 mg, 1.99 mmol) at 0° C. and the mixture was stirred for 30 min. Benzyl bromide (153 mg, 0.89 mmol) was added and the reaction was allowed to warm to room temperature and stirred overnight. Water was added and the aqueous layer was extracted with EtOAc. The combined organic layers were washed with water, brine and dried over Na$_2$SO$_4$. The solvent was removed and the residue purified by silica gel column chromatography (20% EtOAc/PE) to afford (R)-tert-butyl 3-(benzyloxy)piperidine-1-carboxylate (240 mg, 83%) as a white solid. $^1$H NMR (400 MHz, DMSO-d$_6$) δ 7.38-7.25 (m, 5H), 4.57-4.46 (m, 2H), 3.37-3.06 (m, 4H), 1.82-1.36 (m, 14H).

Step 2: To a solution of (R)-tert-butyl 3-(benzyloxy)piperidine-1-carboxylate (150 mg, 0.51 mmol) in EtOAc (2 mL) was added Rh (5% on Al$_2$O$_3$, 15 mg). The mixture was stirred under an atmosphere of H$_2$ overnight. The mixture was filtered and the filtrate concentrated in vacuo to afford (R)-tert-butyl 3-(benzyloxy)piperidine-1-carboxylate (144 mg, 94%) as a white solid. $^1$H NMR (400 MHz, CDCl$_3$) δ 3.67-3.52 (m, 2H), 3.49-3.22 (m, 3H), 3.18-2.80 (m, 2H), 1.96-1.58 (m, 8H), 1.55-1.33 (m, 13H), 1.32-1.09 (m, 3H).

Step 3: To a solution of (R)-tert-butyl 3-(benzyloxy)piperidine-1-carboxylate (144 mg, 0.48 mmol) in DCM (1 mL) was added HCl (4M in dioxane, 1 mL). The mixture was stirred at room temperature for 3 h. The solvent was then removed in vacuo to afford (R)-3-(cyclohexylmethoxy)piperidine (112 mg, quant.) as a white solid. LCMS m/z=198.2 [M+H]$^+$.

The compounds below were synthesized according to the procedure outlined (R)-3-(cyclohexylmethoxy)piperidine using the appropriate commercially available reagents.

| Compound | LCMS |
|---|---|
| ![structure] | 198.2 [M + H]$^+$ |
| ![structure] | 184.2 [M + H]$^+$ |

| Compound | LCMS |
|---|---|
| 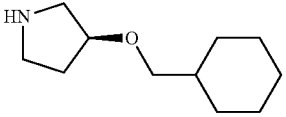 [SMILES: C1CCC(CO[C@H]2CCNC2)CC1] | 184.2 [M + H]+ |

(R)-1-(cyclohexylmethyl)piperidin-3-amine

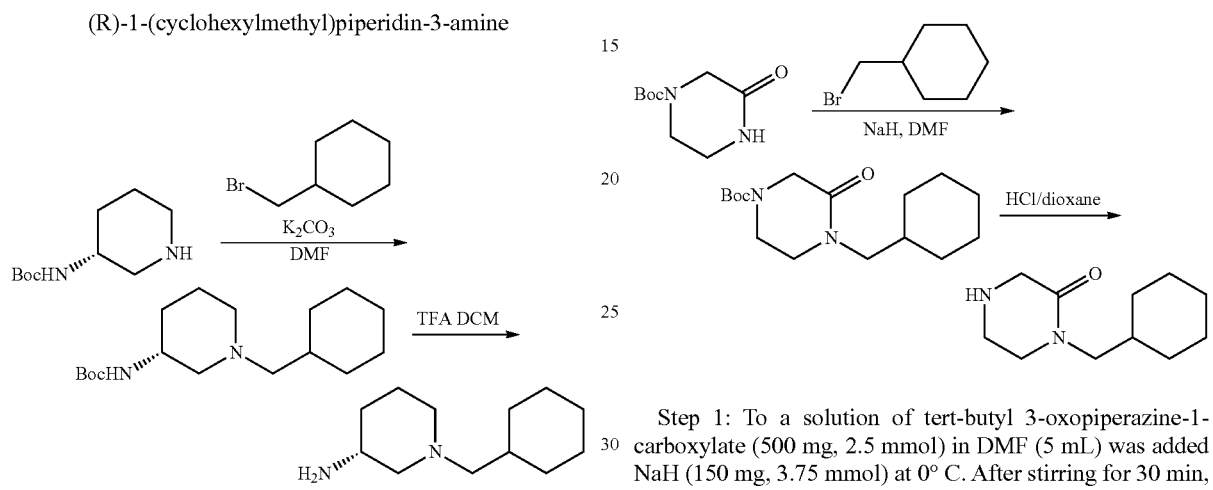

Step 1: To a solution of tert-butyl (R)-piperidin-3-ylcarbamate (500 mg, 2.50 mmol) in DMF (10.0 mL) was added (bromomethyl)cyclohexane (451 mg, 2.56 mmol) and K₂CO₃ (690 mg, 5.00 mmol). The resulting mixture was heated at 50° C. for 4 h. Water was added and the aqueous extracted with EtOAc three times. The combined organic layers were washed with water, brine and dried over Na₂SO₄. The solvent was removed and the residue purified by silica gel column chromatography (30% EtOAc/PE) to afford tert-butyl (R)-(1-(cyclohexylmethyl)piperidin-3-yl)carbamate (520 mg, 71%) as a colorless oil. ¹H NMR (400 MHz, CD₃OD) δ 3.64-3.45 (m, 1H), 2.87-2.52 (m, 2H), 2.18-2.08 (m, 2H), 2.06-1.51 (m, 11H), 1.47-1.41 (m, 9H), 1.33-1.17 (m, 4H), 0.96-0.83 (m, 2H).

Step 2: A solution of tert-butyl (R)-(1-(cyclohexylmethyl)piperidin-3-yl)carbamate (35 mg, 0.12 mmol) in HCl (4M in dioxane, 3 mL) was stirred at room temperature for 2 h. Solvent was removed to afford (R)-1-(cyclohexylmethyl)piperidin-3-amine (42 mg, quant.) as a colorless oil.

The compounds below were synthesized according to the procedure outlined (R)-1-(cyclohexylmethyl)piperidin-3-amine using the appropriate commercially available reagents.

| Compound | LCMS |
|---|---|
| 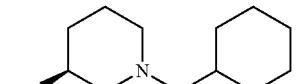 | LCMS not recorded |

| Compound | LCMS |
|---|---|
| 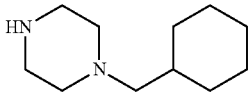 | 283.1 [M + H]+ |

1-(cyclohexylmethyl)piperazin-2-one

Step 1: To a solution of tert-butyl 3-oxopiperazine-1-carboxylate (500 mg, 2.5 mmol) in DMF (5 mL) was added NaH (150 mg, 3.75 mmol) at 0° C. After stirring for 30 min, (bromomethyl)cyclohexane (528 mg, 3.0 mmol) was added and the solution was heated at 40° C. for 3 h. Water was added and the aqueous extracted with EtOAc three times. The combined organic layers were washed with water, brine and dried over Na₂SO₄. The solvent was removed to afford tert-butyl 4-(cyclohexylmethyl)-3-oxopiperazine-1-carboxylate (340 mg, 46%) as a white solid. LCMS m/z=297.4 [M+H]+.

Step 2: A solution of tert-butyl 4-(cyclohexylmethyl)-3-oxopiperazine-1-carboxylate (100 mg, 1.1 mmol) in HCl (4M in dioxane, 3 mL) was stirred at room temperature for 4 h. The solvent was removed to afford 1-(cyclohexylmethyl)piperazin-2-one (66 mg, quant.).

(R)—N-cyclohexylpiperidine-3-carboxamide

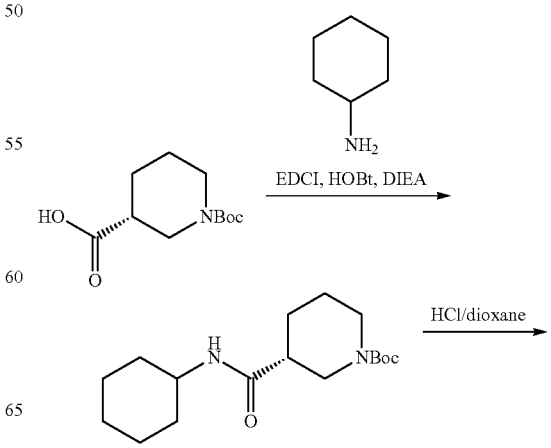

523
-continued

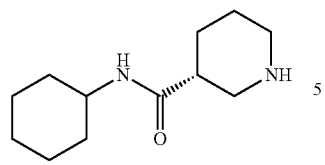

Step 1: To a solution of (R)-1-(tert-butoxycarbonyl)piperidine-3-carboxylic acid (100 mg, 0.44 mmol) in DMF (5 mL) was added cyclohexylamine (43 mg, 0.44 mmol), EDCI (88 mg, 0.66 mmol), HOBt (125 mg, 0.66 mmol) and DIPEA (169 mg, 1.31 mmol). The resulting mixture was stirred at room temperature overnight. Water was added and the aqueous extracted with EtOAc. The combined organic layers were washed with water, brine and dried over $Na_2SO_4$. The solvent was removed and the residue purified by silica gel column chromatography (5% MeOH/DCM) to afford tert-butyl (R)-3-(cyclohexylcarbamoyl)piperidine-1-carboxylate (113 mg, 84%) as a white solid. LCMS m/z=311.4 $[M+H]^+$; $^1H$ NMR (400 MHz, $CDCl_3$) δ 3.94-3.08 (m, 4H), 2.29-2.17 (m, 1H), 2.10-1.73 (m, 4H), 1.73-1.65 (m, 2H), 1.64-1.55 (m, 3H), 1.46 (s, 9H), 1.43-1.23 (m, 3H), 1.21-1.02 (m, 3H).

Step 2: To a solution of tert-butyl (R)-3-(cyclohexylcarbamoyl)piperidine-1-carboxylate (110 mg, 0.35 mmol) in DCM (3 mL) was added HCl (4M in dioxane, 3 mL). The resulting mixture was stirred at room temperature for 3 h. The solvent was removed to afford (R)—N-cyclohexylpiperidine-3-carboxamide (90 mg, quant.) LCMS m/z=211.3 $[M+H]^+$.

The compounds below were synthesized according to the general procedure outlined for (R)—N-cyclohexylpiperidine-3-carboxamide using the appropriate commercially available reagents.

| Compound | LCMS |
|---|---|
| ![structure] | 211.1 $[M + H]^+$ |
| ![structure] | 225.4 $[M + H]^+$ |
| ![structure] | 225.1 $[M + H]^+$ |

524
(R)-(3-aminopiperidin-1-yl)(cyclohexyl)methanone

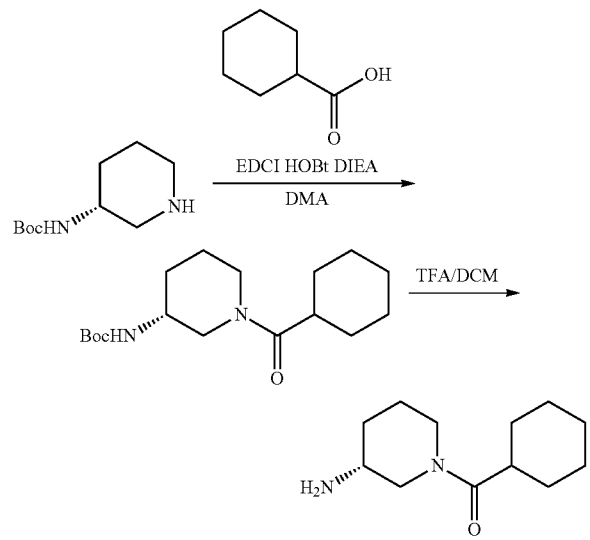

Step 1: To a solution of tert-butyl (R)-piperidin-3-ylcarbamate (300 mg, 1.50 mmol) in DMA (10 mL) was added cyclohexanecarboxylic acid (230 mg, 1.8 mmol), EDCI (432 mg, 2.3 mmol), HOBt (304 mg, 2.3 mmol) and DIPEA (774 mg, 6.0 mmol). The resulting mixture was stirred at room temperature overnight. Water was added and the aqueous extracted with EtOAc three times. The combined organic layers were washed with water, brine and dried over $Na_2SO_4$. The solvent was removed and the residue purified by silica gel column chromatography (50% EtOAc/PE) to afford tert-butyl (R)-(1-(cyclohexanecarbonyl)piperidin-3-yl)carbamate (338 mg, 76%) as a white solid. LCMS m/z=311.2 $[M+H]^+$.

Step 2: A solution of tert-butyl (R)-(1-(cyclohexanecarbonyl)piperidin-3-yl)carbamate (34 mg, 0.11 mmol) in HCl (4M in dioxane, 3 mL) was stirred at room temperature for 2 h. The solvent was removed to afford (R)-(3-aminopiperidin-1-yl)(cyclohexyl)methanone (41 mg, quant.) as a light yellow oil.

(S)-(3-aminopiperidin-1-yl)(cyclohexyl)methanone

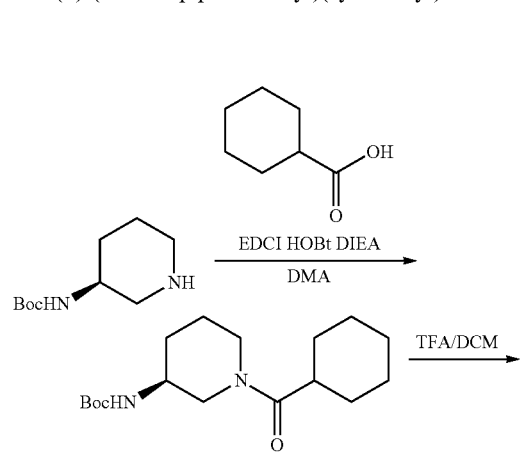

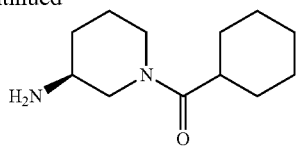

(S)-(3-aminopiperidin-1-yl)(cyclohexyl)methanone was synthesised using a similar procedure to that outlined for the preparation of (R)-(3-aminopiperidin-1-yl)(cyclohexyl)methanone. LCMS m/z=211.2 [M+H]$^+$.

(2S,3R)-2-amino-3-methoxy-1-(piperidin-1-yl)butan-1-one

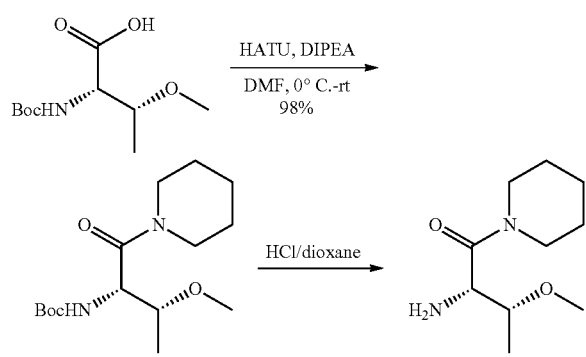

Step 1: To a solution of (2S,3R)-2-((tert-butoxycarbonyl)amino)-3-methoxybutanoic acid (500 mg, 2.15 mmol), piperidine (200 mg, 2.36 mmol), and N,N-Diisopropylethylamine (832 mg, 6.45 mmol) in N,N-Dimethylformamide (3 ml) was added HATU (980 mg, 2.58 mmol) at 0° C. The resulting mixture was stirred at room temperature under $N_2$ for 2 h. The reaction mixture was poured into water (10 mL) and extracted with ethyl acetate (10 mL×2). The combined organic layers were washed with brine (15 mL), dried over anhydrous sodium sulfate, and concentrated under reduced pressure to give a crude residue which was purified by column chromatography using a 20% ethyl acetate in hexane gradient to afford tert-butyl ((2S,3R)-3-methoxy-1-oxo-1-(piperidin-1-yl)butan-2-yl)carbamate (650 mg, 98% yield) as colorless oil. $^1$H NMR (400 MHz, DMSO-d6): δ 6.51 (d, J=8.6 Hz, 1H), 4.35-4.41 (m, 1H), 3.43-3.48 (m, 5H), 3.23 (s, 3H), 1.36-1.60 (m, 16H), 1.02 (d, J=6.2 Hz, 3H).

Step 2: To a solution of tert-butyl ((2S,3R)-3-methoxy-1-oxo-1-(piperidin-1-yl)butan-2-yl)carbamate (650 mg, 2.17 mmol) in dichloromethane (5 ml) was added hydrogen chloride solution in dioxane (4.0 M, 6 mL); the resulting mixture was stirred at room temperature for 3 hours. The reaction mixture was concentrated in vacuo to afford (2S,3R)-2-amino-3-methoxy-1-(piperidin-1-yl)butan-1-one (495 mg, 95% yield) as a light yellow oil.

The compounds below were synthesized according to the general procedure outlined for (2S,3R)-2-amino-3-methoxy-1-(piperidin-1-yl)butan-1-one using the appropriate commercially available reagents.

| Compound | Characterization |
|---|---|
| ![structure] | LCMS not recorded |
| ![structure] | LCMS not recorded // $^1$HNMR (400 MHz, CDCl$_3$): 67 4.64-4.67 (m, 2H), 4.04-4.08 (m, 1H), 3.65-3.66 (m, 1H), 3.38 (s, 3H), 3.00-3.05 (m, 3H), 2.54-2.62 (m, 1H), 1.69-1.77 (m, 6H), 1.44 (s, 9H), 1.09-1.23 (m, 5H). |
| ![structure] | LCMS: m/z 287.1 [M + H]$^+$ // $^1$HNMR (400 MHz, CDCl$_3$): δ 5.55 (s, 1H), 4.20-4.42 (m, 1H), 3.95-3.97 (m, 2H), 3.62 (q, J = 6.4 Hz, 1H), 3.32 (s, 3H), 3.16-3.27 (m, 2H), 2.55-3.02 (m, 2H), 1.65-1.86 (m, 4H), 1.45 (s, 9H),1.30-1.33 (m, 1H). |
| ![structure] | LCMS not recorded // $^1$H NMR (400 MHz, CDCl$_3$) δ 5.70 (t, J = 10.2 Hz, 1H), 4.58-4.70 (m, 1H), 4.26-4.41 (m, 1H), 3.74-3.88 (m, 1H), 3.31 (s, 3H), 3.15-3.29 (m, 2H), 2.86-3.06 (m, 1H), 2.53-2.83 (m, 1H), 1.68-1.87 (m, 3H), 1.43 (s, 9H), 1.34-1.38 (m, 1H), 1.29 (t, J = 6.0 Hz, 4H). |

-continued

| Compound | Characterization |
|---|---|
| (structure) | LCMS not recorded // ¹HNMR (400 MHz, CDCl₃): δ 5.59-5.60 (m, 1H), 4.60-4.65 (m, 1H), 4.35-4.41 (m, 1H), 3.71-3.85 (m, 1H), 3.32 (s, 3H), 3.22-3.28 (m, 2H) 3.05-3.11 (m, 0.5H), 2.84-2.90 (m, 0.5H), 2.57-2.72 (m, 1H), 1.79-1.83 (m, 2H), 1.44-1.48 (m, 11H), 1.28-1.30 (m, 4H). |
| (structure) | LCMS not recorded |
| (structure) | LCMS not recorded |
| (structure) | LCMS not recorded |
| (structure) | LCMS not recorded |
| (structure) | 353.1 [M + H]⁺ |

529

(2R,3R)-1,3-bis(cyclohexylmethoxy)butan-2-amine hydrochloride

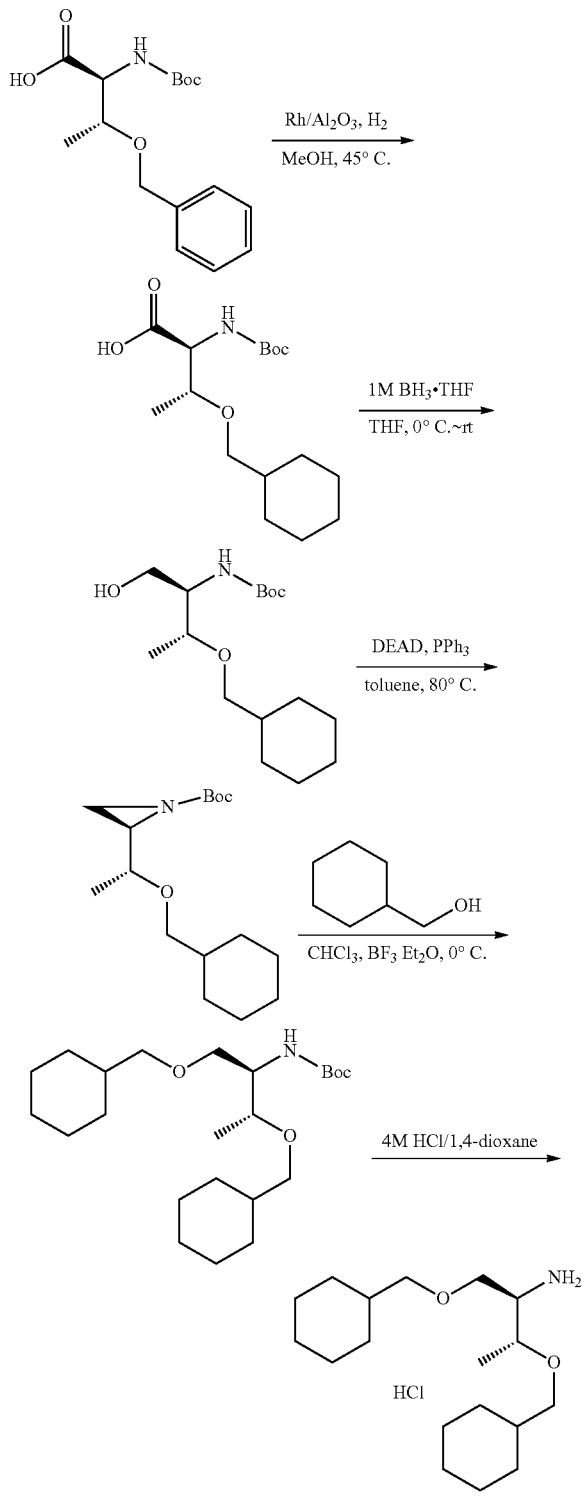

Step 1: A mixture of O-benzyl-N-(tert-butoxycarbonyl)-L-threonine (4.4 g, 14.2 mmol) and Rh/Al$_2$O$_3$ (880 mg, 20%) in methanol (50 mL) was stirred at 45° C. under hydrogen atmosphere (hydrogen balloon) overnight. The catalyst was removed through filtration and washed with methanol (20 mL×2). The combined filtrates were concentrated under reduced pressure to afford N-(tert-butoxycarbonyl)-O-(cyclohexylmethyl)-L-threonine (4.6 g, 100% yield) as colorless oil which was used in next step without further purification. LCMS: m/z 316.0 [M+H]$^+$. $^1$H NMR (400 MHz, CDCl$_3$) δ 4.31-4.39 (m, 1H), 3.97-4.06 (m, 1H), 3.36-3.43 (m, 1H), 3.21-3.29 (m, 1H), 1.52-1.74 (m, 5H), 1.46 (s, 9H), 1.10-1.29 (m, 7H), 0.83-0.96 (m, 2H).

Step 2: To a solution of N-(tert-butoxycarbonyl)-O-(cyclohexylmethyl)-L-threonine (4.9 g, 15.5 mmol) in tetrahydrofuran (40 mL) was added borane-tetrahydrofuran complex (1M, 31.1 mL) dropwise at 0° C. The resulting mixture was stirred at room temperature overnight. The reaction mixture was quenched with methanol at 0° C., and then concentrated under reduced pressure to give a crude residue which was purified by column chromatography using a 15-25% ethyl acetate/hexane gradient to afford tert-butyl ((2R,3R)-3-(cyclohexylmethoxy)-1-hydroxybutan-2-yl)carbamate (1.0 g, 22% yield) as a light yellow oil. LCMS: (ES$^+$): m/z 302.0 [M+H]$^+$. $^1$H NMR (400 MHz, CDCl$_3$) δ 5.00-5.15 (m, 1H), 3.55-3.80 (m, 4H), 3.34-3.41 (m, 1H), 3.04-3.11 (m, 1H), 2.74-2.85 (m, 1H), 1.64-1.78 (m, 5H), 1.45 (s, 9H), 1.12-1.29 (m, 7H), 0.85-0.99 (m, 2H).

Step 3: To a solution of tert-butyl ((2R,3R)-3-(cyclohexylmethoxy)-1-hydroxybutan-2-yl)(4.0 g, 13.3 mmol) in anhydrous toluene (50 mL) was added triphenylphosphine (5.2 g, 19.9 mmol) at room temperature; followed by addition of diethyl azodicarboxylate (3.1 mL, 19.9 mmol) at 0° C. The reaction mixture was stirred at 80° C. under nitrogen atmosphere overnight. The reaction mixture was concentrated under reduced pressure to give a crude residue which was purified by column chromatography using a 10-33% ethyl acetate/hexane gradient to afford tert-butyl (R)-2-((R)-1-(cyclohexylmethoxy)ethyl)aziridine-1-carboxylate (1.8 g, 48% yield) as a colorless oil. LCMS: m/z 284.0 [M+H]$^+$. $^1$H NMR (400 MHz, CDCl$_3$) δ 3.54-3.60 (m, 1H), 3.27-3.33 (m, 1H), 3.13-3.21 (m, 1H), 2.39-2.45 (m, 1H), 2.24 (d, J=6.8 Hz, 1H), 1.93 (d, J=3.6 Hz, 1H), 1.63-1.83 (m, 5H), 1.46 (s, 9H), 1.12-1.32 (m, 7H), 0.86-0.98 (m, 2H).

Step 4: To a mixture of tert-butyl (R)-2-((R)-1-(cyclohexylmethoxy)ethyl)aziridine-1-carboxylate (400 mg, 1.4 mmol) and cyclohexylmethanol (209.5 mg, 1.8 mmol) in dichloromethane (8 mL) was added boron trifluoride etherate (10.0 mg, 0.07 mmol) at 0° C. The resulting mixture was stirred at 0° C. for 30 minutes. The reaction mixture was quenched with saturated aqueous sodium bicarbonate solution at 0° C. and extracted with dichloromethane (10 mL×3). The combined organic layers were washed with brine, dried over anhydrous sodium sulfate, and concentrated under reduced pressure to give a crude residue which was purified by column chromatography using a 3% ethyl acetate/hexane gradient to afford tert-butyl ((2R,3R)-1,3-bis(cyclohexylmethoxy)butan-2-yl)carbamate (360 mg, yeild 64%). $^1$H NMR (400 MHz, CDCl$_3$): δ 4.78 (d, J=9.2 Hz, 1H), 3.60-3.73 (m, 2H), 3.38 (d, J=6.8 Hz, 2H), 3.32-3.37 (m, 1H), 3.17-3.26 (m, 2H), 3.04-3.11 (m, 1H), 1.62-1.80 (m, 10H), 1.50-1.53 (m, 1H), 1.44 (s, 9H), 1.15-1.26 (m, 7H), 1.12 (d, J=6.4 Hz, 3H), 0.85-0.97 (m, 4H).

Step 5: A mixture of tert-butyl ((2R,3R)-1,3-bis(cyclohexylmethoxy)butan-2-yl)carbamate (68 mg, 0.17 mmol) and hydrogen chloride in 1,4-dioxane (4M, 1 ml) in dichloromethane (2 mL) was stirred at room temperature for 1 hour. The volatiles were removed under reduced pressure to afford crude (2R,3R)-1,3-bis(cyclohexylmethoxy)butan-2-amine hydrochloride (crude 75 mg) as white solid. LCMS: m/z 298.4 [M+H]$^+$.

531

The compounds below were synthesized according to the general procedure outlined for (2R,3R)-1,3-bis(cyclohexylmethoxy)butan-2-amine hydrochloride using the appropriate commercially available reagents.

| Compound | LCMS |
|---|---|
| (structure) | LCMS not recorded |
| (structure) | 320.4 |
| (structure) | LCMS not recorded |

2,5-Dioxopyrrolidin-1-yl 2-cyclopropyl-2-methylpropanoate

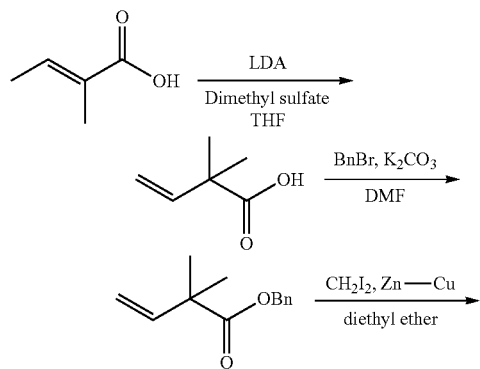

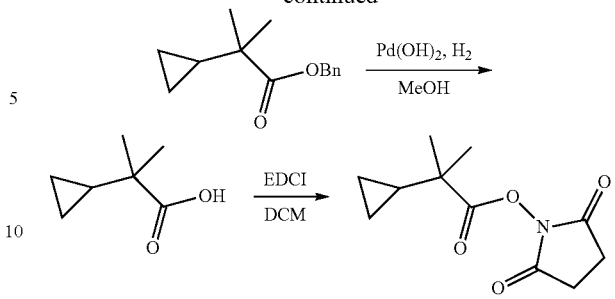

Step 1: To a solution of LDA (2 M, 55 ml, 109.87 mmol) in dry tetrahydrofuran (60 ml) at −70° C. was added a solution of (E)-2-methylbut-2-enoic acid (5.000 g, 49.94 mmol) in tetrahydrofuran (20 ml) dropwise slowly, and the resulting mixture was allowed to stirred at 0° C. for 30 minutes. The reaction mixture was cooled again to −70° C., followed by dropwise addition of the solution of dimethyl sulfate (6.30 g, 49.94 mmol) in dry tetrahydrofuran (20 ml). The resulting mixture was stirred at −70° C. for 1 h, then warmed to room temperature and stirred for 1 h. The reaction mixture was quenched with water (100 ml) and washed with diethyl ether (100 ml×3) to remove some impurity. The aqueous layer was acidified with hydrochloric acid (3.0 M) at 0° C., and extracted with ethyl acetate (100 ml×3). The combined organic layer was washed with brine (100 ml), dried over anhydrous sodium sulfate, and concentrated under reduced pressure to give a crude residue which was purified by column chromatography using 50% ethyl acetate in hexane gradient to afford 2,2-dimethylbut-3-enoic acid (3.500 g, 61%) as a colorless oil.

Step 2: To a stirred solution of 2,2-dimethylbut-3-enoic acid (2.200 g, 19.27 mmol) in dry N,N-dimethylformamide (30 mL) under $N_2$ atmosphere at room temperature was added potassium carbonate (5.300 g, 38.55 mmol). The resulting mixture was stirred at room temperature for 5 minutes, followed by addition of benzylbromide (3.600 g, 21.20 mmol), and the mixture was stirred at room temperature overnight. The reaction mixture was then poured into water (50 ml) and extracted with ethyl acetate (50 ml×2). The combined organic phases were washed with brine (50 ml×3), dried over anhydrous sodium sulfate, and concentrated under reduced pressure to give a crude residue which was purified by column chromatography using 100% hexane gradient to afford benzyl 2,2-dimethylbut-3-enoate (1.200 g, 31%) as a colorless oil. MS [MH]$^+$ 205.0

Step 3: To a suspension of Zn—Cu alloy (3 g) in diethyl ether (20 ml) at room temperature under an argon atmosphere was added diiodomethane (6.300 g, 23.50 mmol), followed by addition of 2,2-dimethylbut-3-enoate (1.200 g, 5.87 mmol). The resulting mixture was heated in a sealed tube at 60° C. for 16 hours. The reaction mixture was allowed to cool to room temperature, and diluted with Ethyl acetate (100 mL). The solid was removed through filtration, and the filter cake was washed with ethyl acetate (20 mL×2). The combined filtrates were washed with water (125 mL), dried over anhydrous sodium sulfate, and concentrated under reduced pressure to give a crude residue which was purified by column chromatography using 1% ethyl acetate in hexane gradient to afford benzyl 2-cyclopropyl-2-methylpropanoate (0.950 g, 74%) as a colorless oil. MS [MH]$^+$ 219.0

Step 4: To a solution of benzyl 2-cyclopropyl-2-methylpropanoate (950 mg, 4.36 mmol) in methanol (20 mL) was added Pd(OH)₂—C (100 mg), and the mixture was stirred under hydrogen atmosphere at room temperature overnight. Pd(OH)₂—C was removed through filtration and washed with ethanol (10 mL×2). The combined filtrates were concentrated under reduced pressure to afford 2-cyclopropyl-2-methylpropanoic acid (0.540 g, 97%) as colorless oil which was used in next step without further purification.

Step 5: To a solution of 2-cyclopropyl-2-methylpropanoic acid (0.540 g, 4.21 mmol) and 1-hydroxypyrrolidine-2,5-dione (0.582 g, 5.06 mmol) in dichloromethane (10 mL) at 0° C. was added N-(3-dimethylaminopropyl)-N'-ethylcarbodiimide hydrochloride (0.969 g, 5.06 mmol). The resulting mixture was stirred at room temperature overnight. The reaction mixture was then poured into water (30 mL) and extracted with dichloromethane (30 mL×2). The combined organic phases were washed with brine (20 mL×2), dried over anhydrous sodium sulfate, and concentrated under reduced pressure to give a crude residue which was purified by column chromatography using 10% ethyl acetate in hexane gradient to afford 2,5-dioxopyrrolidin-1-yl 2-cyclopropyl-2-methylpropanoate (730 mg, yield 77%) as colorless oil.

(2R,3R)-3-(cyclohexylmethoxy)-1-(trifluoromethoxy)butan-2-amine

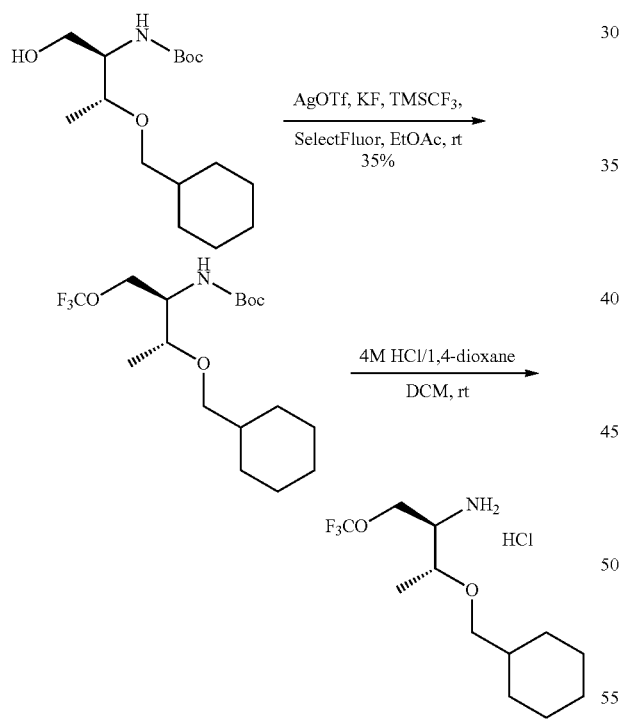

Step 1: To a mixture of tert-butyl ((2R,3R)-3-(cyclohexylmethoxy)-1-hydroxybutan-2-yl)carbamate (540 mg, 1.79 mmol), silver trifluoromethanesulfonate (921.2 mg, 3.59 mmol), potassium fluoride (312.0 mg, 5.37 mmol), and select fluour (951.3 mg, 2.69 mmol) in ethyl acetate (10 mL) was added 2-fluoro pyridine (348.6 mg, 3.59 mmol) and (Trifluoromethyl)trimethylsilane (510.5 mg, 3.59 mmol) at room temperature. The resulting mixture was stirred at room temperature under nitrogen atmosphere overnight. The mixture was filtered through a short pad and the filter cake was washed with ethyl acetate (8 mL×2); The combined filtrate were concentrated under reduced pressure to give a crude residue which was purified by column chromatography using 3.3% ethyl acetate/hexane gradient to afford tert-butyl ((2R,3R)-3-(cyclohexylmethoxy)-1-(trifluoromethoxy)butan-2-yl)carbamate (233 mg, 35% yeild) as a colorless oil. LCMS: m/z 370.0 [M+H]⁺. ¹H NMR (400 MHz, CDCl₃): δ 4.80 (d, J=10.0 Hz, 1H), 3.89-3.99 (m, 2H), 3.74-3.85 (m, 1H), 3.58-3.66 (m, 1H), 3.34-3.41 (m, 1H), 3.01-3.08 (m, 1H), 1.64-1.78 (m, 5H), 1.45 (s, 9H), 1.10-1.26 (m, 7H), 0.89-0.98 (m, 2H).

Step 2: To a solution of tert-butyl ((2R,3R)-3-(cyclohexylmethoxy)-1-(trifluoromethoxy)butan-2-yl)carbamate (100 mg, 0.27 mmol) in dichloromethane (2 mL) was added hydrogen chloride in 1,4-dioxane (4.0M, 2 mL). The resulting mixture was stirred at room temperature for one hour. The reaction mixture was concentrated in vacuo to give crude (2R,3R)-3-(cyclohexylmethoxy)-1-(trifluoromethoxy)butan-2-amine.

(2R,3R)-1-((4,4-difluorocyclohexyl)oxy)-3-((tetrahydro-2H-pyran-4-yl)methoxy)butan-2-amine

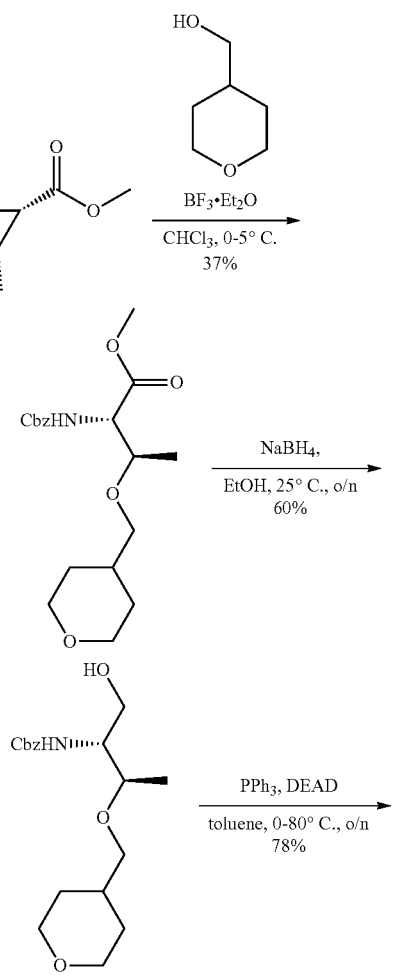

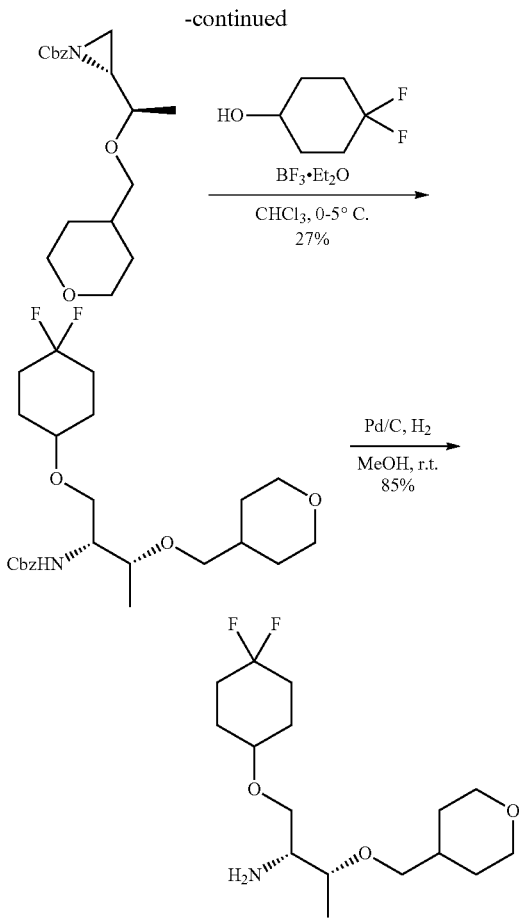

Step 1: To a solution of (tetrahydro-2H-pyran-4-yl)methanol (500 mg, 4.304 mmol) and 1-benzyl 2-methyl (2S,3S)-3-methylaziridine-1,2-dicarboxylate (1.07 g, 4.304 mmol) in chloroform (5 mL) at 0° C. was added boron trifluoride etherate (611 mg, 4.3 mmol) dropwise; the resulting mixture was stirred at 0° C. under nitrogen atmosphere for 4 hours. The reaction mixture was concentrated to give a crude residue which was purified by column chromatography using a 25% ethyl acetate in dichloromethane gradient to afford (2S,3R)-methyl 2-(((benzyloxy)carbonyl)amino)-3-((tetrahydro-2H-pyran-4-yl)methoxy)butanoate ((585 mg, 37% yield) as a yellow oil. LCMS: m/z 366.4[M+H]$^+$. $^1$H NMR (400 MHz, CDCl$_3$): δ 7.31-7.38 (m, 5H), 5.42 (d, J=4.6 Hz, 1H), 5.14 (s, 2H), 4.33-4.36 (m, 1H), 3.98-4.03 (m, 1H), 3.92-3.95 (m, 2H), 3.74 (s, 3H), 3.31-3.39 (m, 3H), 3.04-3.08 (m, 1H), 1.63-1.74 (m, 2H), 1.51-1.57 (m, 2H), 1.22-1.24 (m, 1H), 1.20 (d, J=3.2 Hz, 3H).

Step 2: To a solution of (2S,3R)-methyl 2-(((benzyloxy)carbonyl)amino)-3-((tetrahydro-2H-pyran-4-yl)methoxy)butanoate (250 mg, 0.684 mmol) in ethanol (3 mL) at 0° C. was added sodium borohydride (78 mg, 2.052 mmol); the resulting mixture was stirred at 25° C. under nitrogen atmosphere overnight. The reaction mixture was poured into water (6 mL) and extracted with dichloromethane (8 mL×4). The combined organic layers were washed with brine (8 mL), dried over anhydrous sodium sulfate and concentrated to give a crude residue which was purified by column chromatography using a 50% ethyl acetate in dichloromethane gradient to afford benzyl ((2R,3R)-1-hydroxy-3-((tetrahydro-2H-pyran-4-yl)methoxy)butan-2-yl)carbamate (150 mg, yield 65%) as a colorless oil. LCMS: m/z 338.5[M+H]$^+$. $^1$H NMR (400 MHz, CDCl$_3$): δ 7.33-7.38 (m, 5H), 5.26 (s, 1H), 5.12 (s, 2H), 3.94-3.98 (m, 2H), 3.69-3.77 (m, 4H), 3.34-3.44 (m, 3H), 3.14 (t, J=7.6 Hz, 1H), 2.47 (s, 1H), 1.77 (s, 1H), 1.61 (s, 2H), 1.31-1.38 (m, 2H), 1.19 (d, J=3.0 Hz, 3H).

Step 3: To a solution of benzyl ((2R,3R)-1-hydroxy-3-((tetrahydro-2H-pyran-4-yl)methoxy)butan-2-yl)carbamate (150 mg, 0.445 mmol) and triphenylphosphine (163 mg, 0.622 mmol) in toluene (2 mL) at 0° C. was added diethyl azodicarboxylate (108 mg, 0.622 mmol) dropwise; the resulting mixture was stirred at 80° C. under nitrogen atmosphere overnight. The mixture was concentrated to give a crude residue which was purified by column chromatography using a 10% ethyl acetate in dichloromethane gradient to afford (R)-benzyl 2-((R)-1-((tetrahydro-2H-pyran-4-yl)methoxy)ethyl)aziridine-1-carboxylate (130 mg, yield 78%) as a colorless oil. LCMS: m/z 320.2[M+H]$^+$. $^1$H NMR (400 MHz, CDCl$_3$): δ 7.31-7.35 (m, 5H), 5.09-5.17 (m, 2H), 3.89-3.94 (m, 2H), 3.60-3.64 (m, 1H), 3.29-3.38 (m, 3H), 3.14-3.20 (m, 1H), 3.49-3.54 (m, 1H), 2.33 (d, J=3.4 Hz, 1H), 2.02 (d, J=2.0 Hz, 1H), 1.73-1.80 (m, 1H), 1.62 (s, 1H), 1.54 (s, 1H), 1.28-1.33 (m, 2H), 1.20 (d, J=3.2 Hz, 3H).

Step 4: To a solution of (R)-benzyl 2-((R)-1-((tetrahydro-2H-pyran-4-yl)methoxy)ethyl)aziridine-1-carboxylate (130 mg, 0.407 mmol) and 4,4-difluorocyclohexanol (56 mg, 0.407 mmol) in chloroform (2 mL) was added boron trifluoride etherate (29 mg, 0.204 mmol) dropwise at 0° C.; the resulting mixture was stirred at 0° C. under nitrogen atmosphere for 4 hours. The reaction mixture was concentrated to give a crude residue which was purified by column chromatography using a 17% ethyl acetate in dichloromethane gradient to afford benzyl ((2R,3R)-1-((4,4-difluorocyclohexyl)oxy)-3-((tetrahydro-2H-pyran-4-yl)methoxy)butan-2-yl)carbamate (50 mg, 27% yield) as a colorless oil. $^1$H NMR (400 MHz, CDCl$_3$): δ 7.32-7.37 (m, 5H), 5.10 (d, J=2.4 Hz, 1H), 3.94-3.98 (m, 2H), 3.66-3.74 (m, 2H), 3.34-3.48 (m, 7H), 3.11 (t, J=7.8 Hz, 1H), 1.92-2.02 (m, 2H), 1.70-1.84 (m, 6H), 1.59-1.65 (m, 2H), 1.32-1.36 (m, 3H), 1.16 (d, J=3.0 Hz, 3H).

Step 5: To a solution of benzyl ((2R,3R)-1-((4,4-difluorocyclohexyl)oxy)-3-((tetrahydro-2H-pyran-4-yl)methoxy)butan-2-yl)carbamate (50 mg, 0.11 mmol) in methanol (10 mL) was added palladium on carbon (10%, 5 mg). The resulting mixture was stirred at room temperature under hydrogen atmosphere (hydrogen balloon) for 2 hours. Palladium on carbon was removed through filtration and washed with methanol (10 ml×2); the combined organic solution was concentrated under reduced pressure to afford (2R,3R)-1-((4,4-difluorocyclohexyl)oxy)-3-((tetrahydro-2H-pyran-4-yl)methoxy)butan-2-amine (30 mg crude) as a white solid. $^1$H NMR (400 MHz, CDCl$_3$): δ 3.95-3.98 (m, 2H), 3.30-3.50 (m, 7H), 3.12-3.16 (m, 1H), 2.78-2.84 (m, 1H), 1.97-2.09 (m, 2H), 1.70-1.91 (m, 6H), 1.64-1.67 (m, 2H), 1.31-1.38 (m, 2H), 1.20 (t, J=7.0 Hz, 1H), 1.14 (d, J=3.0 Hz, 3H).

The compounds below were synthesized according to the procedure outlined for (2R,3R)-1-((4,4-difluorocyclohexyl)oxy)-3-((tetrahydro-2H-pyran-4-yl)methoxy)butan-2-amine using the appropriate commercially available reagents.

| Compound | Characterization |
|---|---|
| (structure) | LCMS not recorded |
| (structure) | LCMS not recorded |
| (structure) | ¹HNMR (400 MHz, CDCl₃): δ 3.41-3.49 (m, 3H), 3.29-3.38 (m, 2H), 2.80-2.84 (m, 1H), 1.96-2.15 (m, 4H), 1.60-1.88 (m, 10H), 1.33-1.47 (m, 3H), 1.10-1.15 (m, 6H). |
| (structure) | ¹H NMR (400 MHz, CDCl₃) δ 3.69-3.80 (m, 5H), 3.55-3.59 (m, 1H), 3.35-3.39 (m, 1H), 3.18-3.27 (m, 2H), 3.09-3.15 (m, 2H), 1.84-1.85 (m, 3H), 1.65-1.76 (m, 7H), 1.45 (s, 9H), 1.13-1.24 (m, 5H), 0.86-0.94 (m, 3H). |
| (structure) | LCMS: m/z 385.5 [M + H]⁺. |

Example 2: Synthesis of Exemplary Compounds
Method 1A, Exemplified by the Synthesis of I-113A
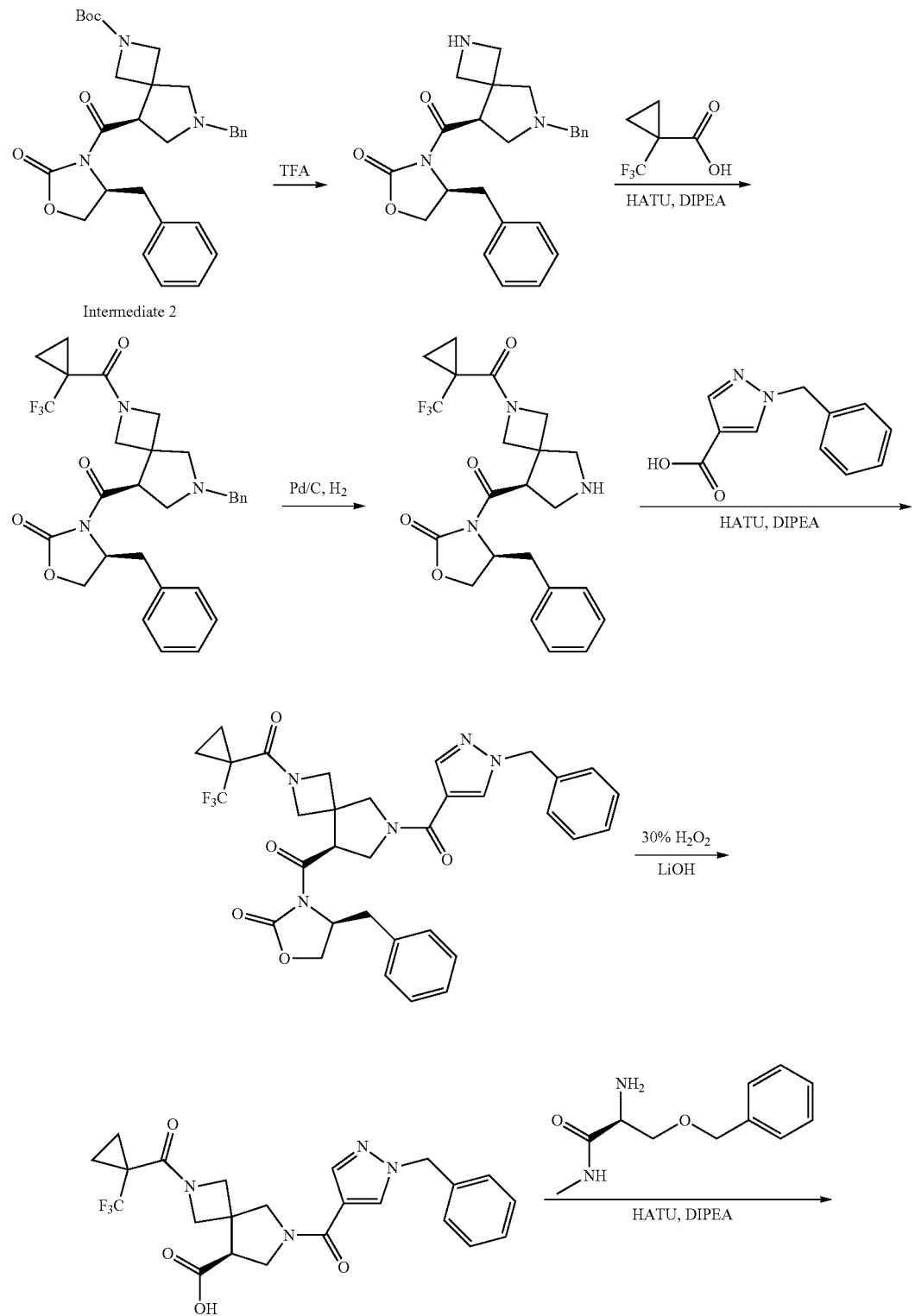

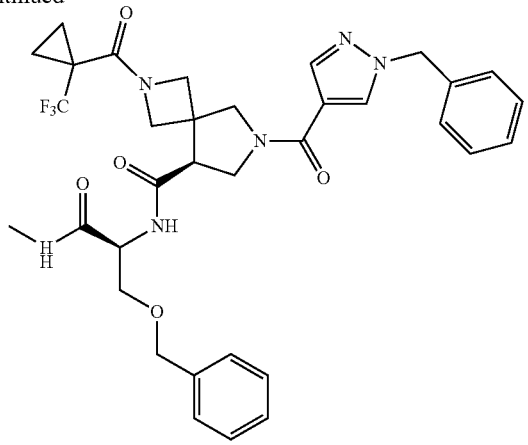

I-113A

Step 1: To a solution of Intermediate 2 (0.4 g, 0.79 mmol) in DCM (5 mL) was added TFA (1 mL) and the reaction mixture stirred at room temperature for 1 h. The solvent was removed under vacuum to afford (S)-4-benzyl-3-((S)-6-benzyl-2,6-diazaspiro[3.4]octane-8-carbonyl)oxazolidin-2-one (320 mg, 100%) which was used directly in the next step. LCMS m/z=406.1 [M+H]$^+$.

Step 2: To a solution of 1-(trifluoromethyl)cyclopropane-1-carboxylic acid (146 mg, 0.95 mmol) in DCM (5 mL) was added HATU (330 mg, 0.87 mmol) and the mixture stirred at room temperature for 30 min. (S)-4-benzyl-3-((S)-6-benzyl-2,6-diazaspiro[3.4]octane-8-carbonyl)oxazolidin-2-one (320 mg, 0.79 mmol) and DIPEA (408 mg, 3.16 mmol) were added and the reaction stirred at room temperature for another 2 h. The mixture was diluted with water (60 mL) and extracted with DCM (150 mL×2). The combined organic layers were washed with brine, dried over Na$_2$SO$_4$, filtered and concentrated. The mixture was purified by column chromatography on silica gel (eluent: Pet. Ether:EtOAc=3:1 to DCM/EtOAc=3/1) to afford (S)-4-benzyl-3-((S)-6-benzyl-2-(1-(trifluoromethyl)cyclopropane-1-carbonyl)-2,6-diazaspiro[3.4] octane-8-carbonyl)oxazolidin-2-one (0.4 g, 90%) as a yellow oil. LCMS m/z=542.2 [M+H]$^+$.

Step 3: To a solution of (S)-4-benzyl-3-((S)-6-benzyl-2-(1-(trifluoromethyl)cyclopropane-1-carbonyl)-2,6-diazaspiro[3.4] octane-8-carbonyl)oxazolidin-2-one (367 mg, 0.68 mmol) in EtOAc (8 mL) was added 10% Pd/C (145 mg). The reaction mixture was stirred under a H$_2$ atmosphere for 24 h. Conversion was around 50%. The mixture was filtered through celite and concentrated. The residue was redissolved in EtOAc (8 mL) and another batch of 10% Pd/C (145 mg) was added. The reaction was stirred under H$_2$ atmosphere for another 24 h. The mixture was filtered and concentrated to afford (S)-4-benzyl-3-((S)-2-(1-(trifluoromethyl)cyclopropane-1-carbonyl)-2,6-diazaspiro[3.4]octane-8-carbonyl)oxazolidin-2-one (305 mg, 100%) which was used directly in the next step. LCMS m/z=452.1 [M+H]$^+$;

Step 4: To a solution of 1-benzyl-1H-pyrazole-4-carboxylic acid (54 mg, 0.27 mmol) in DMF (2 mL) was added HATU (127 mg, 0.33 mmol). The mixture was stirred at room temperature for 30 min. (S)-4-benzyl-3-((S)-2-(1-(trifluoromethyl)cyclopropane-1-carbonyl)-2,6-diazaspiro[3.4]octane-8-carbonyl)oxazolidin-2-one (100 mg, 0.22 mmol) and DIPEA (115 mg, 0.89 mmol) were added and the reaction stirred at room temperature for another 2 h. The mixture was diluted with water (100 mL) and extracted with EtOAc (150 mL×2). The combined organic layers were washed with brine, dried over Na$_2$SO$_4$, filtered and concentrated. The mixture was purified by column chromatography on silica gel (eluent: DCM/MeOH=30/1) to afford (S)-4-benzyl-3-((S)-6-(1-benzyl-1H-pyrazole-4-carbonyl)-2-(1-(trifluoromethyl) cyclopropane-1-carbonyl)-2,6-diazaspiro [3.4]octane-8-carbonyl)oxazolidin-2-one (70 mg, 50%) as a yellow oil. LCMS m/z=636.3 [M+H]$^+$; $^1$H NMR (400 MHz, DMSO-d6) δ 8.46-8.28 (m, 1H), 7.89-7.81 (m, 1H), 7.37-7.08 (m, 10H), 5.40-5.33 (m, 2H), 4.68 (s, 1H), 4.41-4.32 (m, 2H), 4.27-4.10 (m, 4H), 4.05-4.04 (m, 1H), 3.87-3.68 (m, 3H), 2.99-2.83 (m, 2H), 1.16-1.15 (m, 3H).

Step 5: To a solution of (S)-4-benzyl-3-((S)-6-(1-benzyl-1H-pyrazole-4-carbonyl)-2-(1-(trifluoromethyl) cyclopropane-1-carbonyl)-2,6-diazaspiro[3.4]octane-8-carbonyl) oxazolidin-2-one (100 mg, 0.16 mmol) in a mixture of THF and H$_2$O (6 mL/0.5 mL) at 0° C. was added a solution of lithium hydroxide monohydrate (17 mg, 0.39 mmol) in H$_2$O (0.5 mL) and 30% H$_2$O$_2$ (11 mg, 0.31 mmol) in H$_2$O (0.5 mL). The reaction mixture was stirred at 0° C. for 2 h then diluted with water (50 mL) and extracted with EtOAc (80 mL). The aqueous layer was collected and acidified with 1M HCl to pH ~ 2 then extracted with EtOAc (150 mL×3). The combined organic layers were washed with brine, dried over Na$_2$SO$_4$, filtered and concentrated to afford (S)-6-(1-benzyl-1H-pyrazole-4-carbonyl)-2-(1-(trifluoromethyl)cyclopropane-1-carbonyl)-2,6-diazaspiro[3.4]octane-8-carboxylic acid (63 mg, 84%) as a white solid which was used directly in the next step. LCMS m/z=477.1 [M+H]$^+$.

Step 6: To a solution of (S)-6-(1-benzyl-1H-pyrazole-4-carbonyl)-2-(1-(trifluoromethyl)cyclopropane-1-carbonyl)-2,6-diazaspiro[3.4]octane-8-carboxylic acid (63 mg, 0.13 mmol) in DMF (2 mL) was added HATU (76 mg, 0.20 mmol) and the reaction stirred at room temperature for 30 min. (S)-2-amino-3-(benzyloxy)-N-methylpropanamide (33 mg, 0.16 mmol) and DIPEA (69 mg, 0.53 mmol) were added and the mixture stirred at room temperature for another 2 h. The solvent was removed under vacuum, the residue was purified by prep-HPLC to afford (S)-6-(1-benzyl-1H-pyrazole-4-carbonyl)-N—((S)-3-(benzyloxy)-1-(methylamino)-1-oxopropan-2-yl)-2-(1-(trifluoromethyl)cyclopropane-1-carbonyl)-2,6-diazaspiro[3.4]octane-8-carboxamide (I-113A) (26 mg, 30%) as a white solid. LCMS m/z=667.4 [M+H]$^+$; $^1$H NMR (400 MHz, DMSO-d6) δ 8.58 (s, 1H), 8.35 (d, J=8.0 Hz, 1H), 8.04 (s, 1H), 7.82 (d, J=12.2 Hz, 1H), 7.42-7.22 (m, 10H), 5.36 (s, 2H), 4.55 (s, 1H), 4.46 (s, 2H), 3.97-3.54 (m, 11H), 2.59 (dd, J=8.4, 4.6 Hz, 3H), 1.24 (dd, J=13.4, 6.8 Hz, 2H), 1.18-1.10 (m, 2H).

Method 1B: Exemplified by the Synthesis of
I-113B

I-113B was made by a similar process to Method 1A, starting from Intermediate 1, in place of Intermediate 2.

Method 2A: Exemplified by the Synthesis of
I-123A

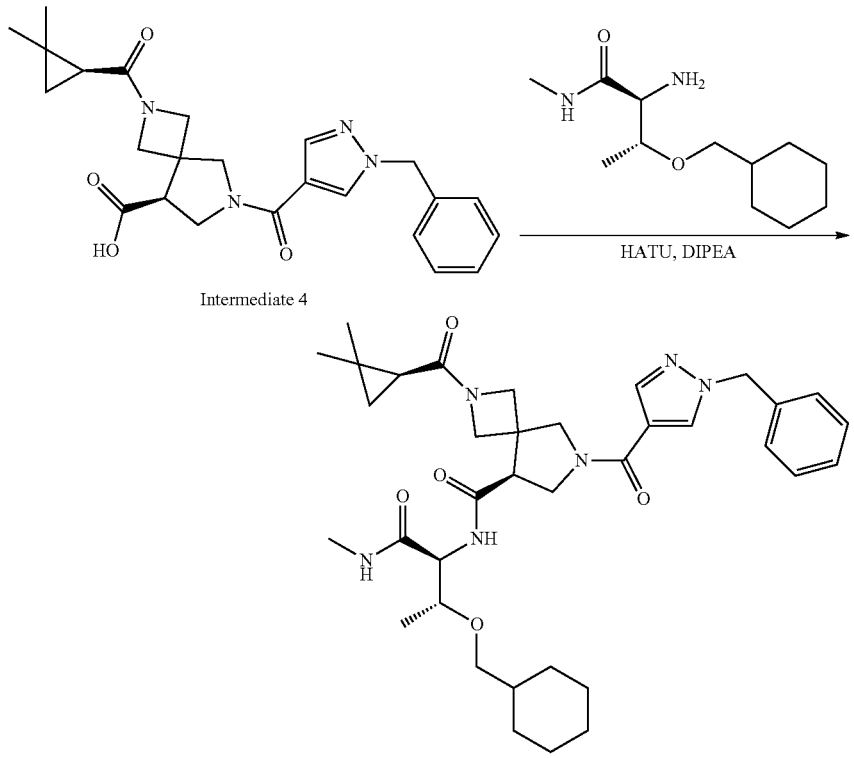

Intermediate 4

To a solution of (S)-6-(1-benzyl-1H-pyrazole-4-carbonyl)-2-((S)-2,2-dimethylcyclopropane-1-carbonyl)-2,6-diazaspiro[3.4]octane-8-carboxylic acid (Intermediate 4) (1.10 g, 2.52 mmol) in DCM (15 mL) was added HATU (1.44 g, 3.78 mmol) and the reaction mixture stirred at room temperature for 30 min. (2S,3R)-2-amino-3-(cyclohexylmethoxy)-N-methylbutanamide (633 mg, 2.77 mmol) and DIPEA (1.30 g, 10.08 mmol) were added and the reaction stirred for another 3 h. The solvent was removed under vacuum and the residue purified by reverse phase column (51% acetonitrile in water) to afford (S)-6-(1-benzyl-1H-pyrazole-4-carbonyl)-N-((2S,3R)-3-(cyclohexylmethoxy)-1-(methylamino)-1-oxobutan-2-yl)-2-((S)-2,2-dimethylcyclopropane-1-carbonyl)-2,6-diazaspiro[3.4]octane-8-carboxamide (I-123A) (1.15 g, 72%) as a white solid. LCMS m/z=647.5 [M+H]$^+$; $^1$H NMR (400 MHz, DMSO-d$_6$) δ 8.41-8.31 (m, 1H), 8.25-8.1 (m, 1H), 7.88-7.68 (m, 2H), 7.4-7.21 (m, 5H), 5.35 (s, 2H), 4.31-4.03 (m, 3H), 4.03-3.58 (m, 7H), 3.55-3.38 (m, 1H), 3.26-3.16 (m, 1H), 3.15-3.05 (m, 1H), 2.63-2.55 (m, 3H), 1.71-1.56 (m, 5H), 1.50-1.26 (m, 2H), 1.22-0.99 (m, 12H), 0.91-0.75 (m, 3H), 0.70-0.63 (m, 1H).

Method 2B: Exemplified by the Synthesis of
I-123B

I-123B was made by a similar process to Method 2A, starting from Intermediate 3, in place of Intermediate 4.

Method 3A: Exemplified by the Synthesis of I-25A

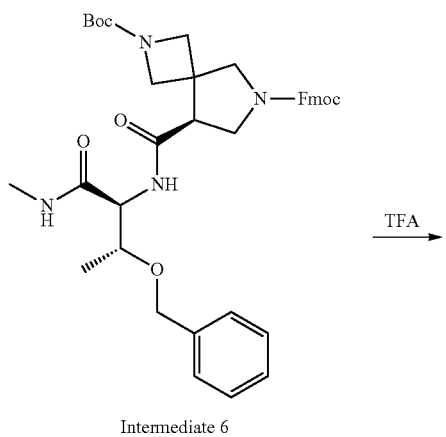

Intermediate 6

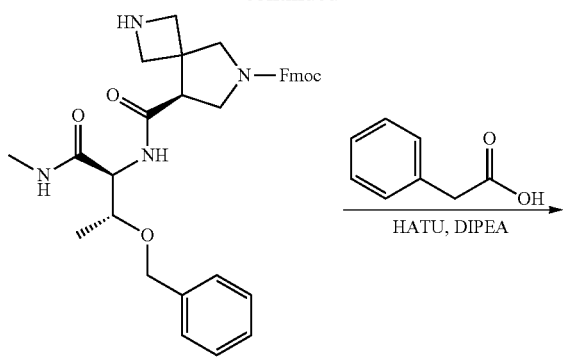

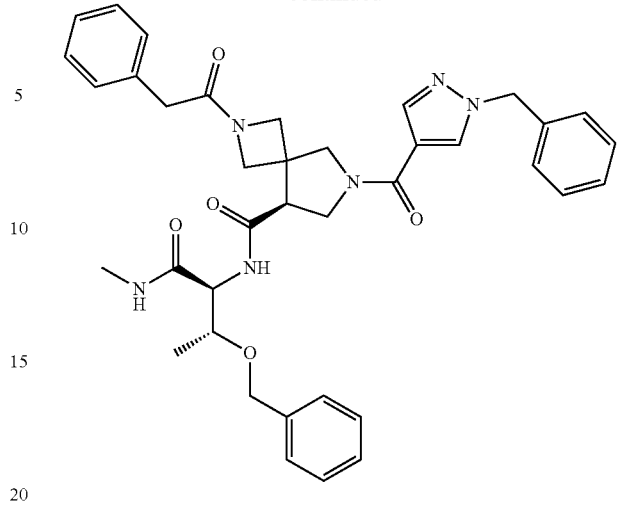

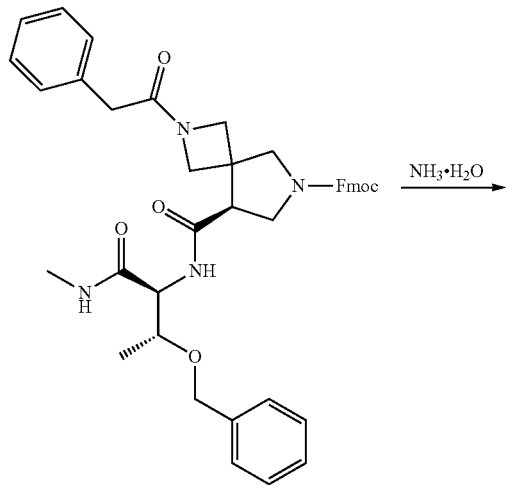

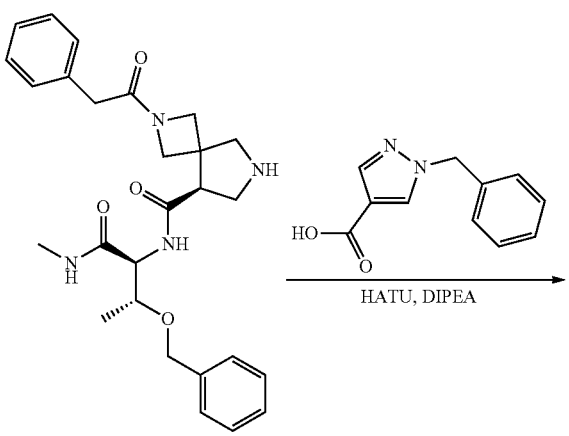

Step 1: To a solution of Intermediate 6 (0.2 g, 0.3 mmol) in DCM (5 mL) was added TFA (1 mL). The reaction mixture was stirred at room temperature for 1 h then the solvent was removed under vacuum to afford (9H-fluoren-9-yl)methyl (S)-8-(((2S,3R)-3-(benzyloxy)-1-(methylamino)-1-oxobutan-2-yl)carbamoyl)-2,6-diazaspiro[3.4]octane-6-carboxylate (171 mg, 100%) which was used directly in the next step. LCMS m/z=583.4 [M+H]⁺.

Step 2: To a solution of 2-phenylacetic acid (44 mg, 0.32 mmol) in DCM (5 mL) was added HATU (166 mg, 0.44 mmol) and the mixture stirred at room temperature for 30 min. (S)-8-(((2S,3R)-3-(benzyloxy)-1-(methylamino)-1-oxobutan-2-yl)carbamoyl)-2,6-diazaspiro[3.4]octane-6-carboxylate (170 mg, 0.29 mmol) and DIPEA (1.51 mg, 1.17 mmol) were added and the reaction stirred for another 2 h. The mixture was diluted with water (60 mL) and extracted with EtOAc (100 mL×2). The combined organic layers were washed with brine, dried over Na₂SO₄, filtered and concentrated. The mixture was purified by column chromatography on silica gel (eluent: DCM:MeOH=50:1) to afford (S)-8-(((2S,3R)-3-(benzyloxy)-1-(methylamino)-1-oxobutan-2-yl)carbamoyl)-2-(2-phenylacetyl)-2,6-diazaspiro[3.4]octane-6-carboxylate (150 mg, 73%) as a white solid. LCMS m/z=701.4 [M+H]⁺.

Step 3: To a solution of (S)-8-(((2S,3R)-3-(benzyloxy)-1-(methylamino)-1-oxobutan-2-yl)carbamoyl)-2-(2-phenylacetyl)-2,6-diazaspiro[3.4]octane-6-carboxylate (150 mg, 0.21 mmol) in 1,4-dioxane (5 mL) was added 25% ammonium hydroxide (5 mL). The reaction mixture was heated at 50° C. overnight. The solvent was removed under vacuum and the residue triturated with diethyl ether (20 mL×2) to afford (S)—N-((2S,3R)-3-(benzyloxy)-1-(methylamino)-1-oxobutan-2-yl)-2-(2-phenylacetyl)-2,6-diazaspiro[3.4]octane-8-carboxamide (40 mg, 30%) as a white solid. LCMS m/z=479.2 [M+H]⁺.

Step 4: To a solution of 1-benzyl-1H-pyrazole-4-carboxylic acid (16 mg, 0.08 mmol) in DMF (1 mL) was added HATU (49 mg, 0.13 mmol) and the mixture stirred at room temperature for 30 min. (S)-6-(1-benzyl-1H-pyrazole-4-carbonyl)-N-((2S,3R)-3-(benzyloxy)-1-(methylamino)-1-oxobutan-2-yl)-2-(2-phenylacetyl)-2,6-diazaspiro[3.4]octane-8-carboxamide (40 mg, 0.08 mmol) and DIPEA (41 mg, 0.32 mmol) were added and the reaction stirred for another 2 h. The mixture was diluted with water (60 mL) and extracted with EtOAc (100 mL×2). The combined organic layers were washed with brine, dried over Na₂SO₄, filtered and concentrated. The mixture was purified by prep-HPLC to afford (S)-6-(1-benzyl-1H-pyrazole-4-carbonyl)-N-((2S,3R)-3-(benzyloxy)-1-(methylamino)-1-oxobutan-2-yl)-2-(2-phenylacetyl)-2,6-diazaspiro[3.4]octane-8-carboxamide (I-25A) (20 mg, 45%) as a white solid. LCMS m/z=663.4 [M+H]⁺; ¹H NMR (400 MHz, DMSO-d₆) δ 8.39-8.29 (m, 2H), 7.82 (d, J=12.0 Hz, 2H), 7.38-7.23 (m, 13H), 7.21-7.13 (m, 2H), 5.35 (s, 2H), 4.56-4.40 (m, 2H), 4.38-4.10 (m, 2H), 4.07-3.86 (m, 4H), 3.82-3.69 (m, 2H), 3.68-3.35 (m, 3H), 3.30 (d, J=2.0 Hz, 2H), 2.64-2.56 (m, 3H), 1.04 (m, J=14.4, 7.0 Hz, 3H).

Method 3B: Exemplified by the Synthesis of I-25B

I-25B was made by a similar process to Method 3A, starting from Intermediate 5, in place of Intermediate 6.

Method 4A: Exemplified by the Synthesis of I-24A

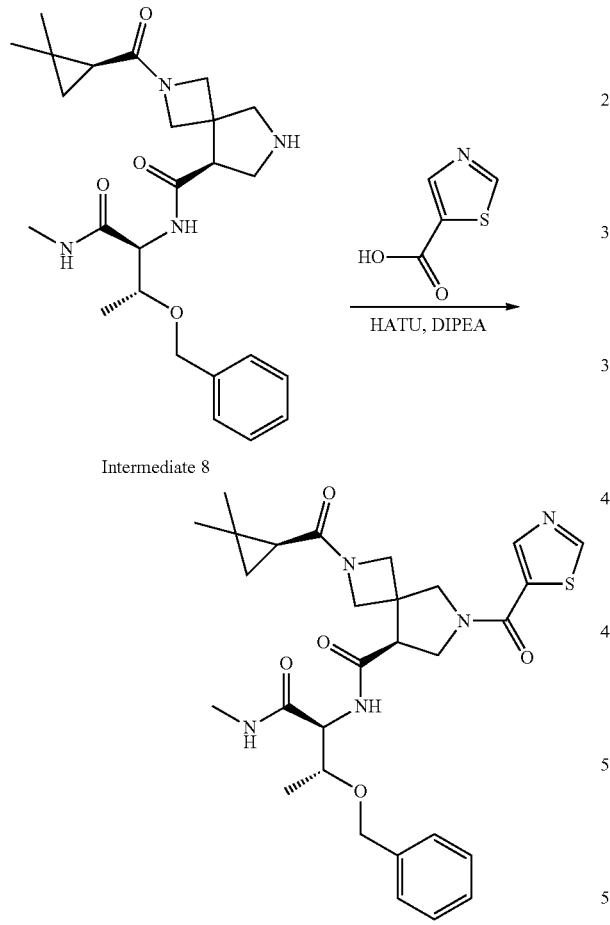

Intermediate 8

To a solution of thiazole-5-carboxylic acid (17 mg, 0.13 mmol) in DMF (3 mL) was added HATU (65 mg, 0.16 mmol). The mixture was stirred at room temperature for 30 min. Intermediate 8 (50 mg, 0.11 mmol) and DIPEA (60 mg, 0.44 mmol) were added and the reaction mixture was stirred at room temperature for another 1 h. The mixture was diluted with water (60 mL) and extracted with EtOAc (100 mL×2). The combined organic layers were washed with brine, dried over Na₂SO₄, filtered and concentrated. The mixture was purified by prep-HPLC to afford (S)—N-((2S,3R)-3-(benzyloxy)-1-(methylamino)-1-oxobutan-2-yl)-2-((S)-2,2-dimethylcyclopropane-1-carbonyl)-6-(thiazole-5-carbonyl)-2,6-diazaspiro[3.4]octane-8-carboxamide (I-24A) (17 mg, 28%) as a white solid. LCMS m/z=568.3 [M+H]⁺; ¹H NMR (400 MHz, DMSO-d₆) δ 9.26 (s, 1H), 8.45-8.35 (m, 2H), 7.89 (s, 1H), 7.40-7.20 (m, 5H), 4.56-4.40 (m, 2H), 4.39-4.16 (m, 2H), 4.15-3.94 (m, 4H), 3.93-3.70 (m, 3H), 3.70-3.43 (m, 2H), 2.62-2.58 (m, 3H), 1.31-1.25 (m, 1H), 1.10-1.02 (m, 9H), 0.84 (s, 1H), 0.64 (s, 1H).

Method 4B: Exemplified by the Synthesis of I-24B

I-24B was made by a similar process to Method 4A, starting from Intermediate 7, in place of Intermediate 8.

Method 5A: Exemplified by the Synthesis of I-77A

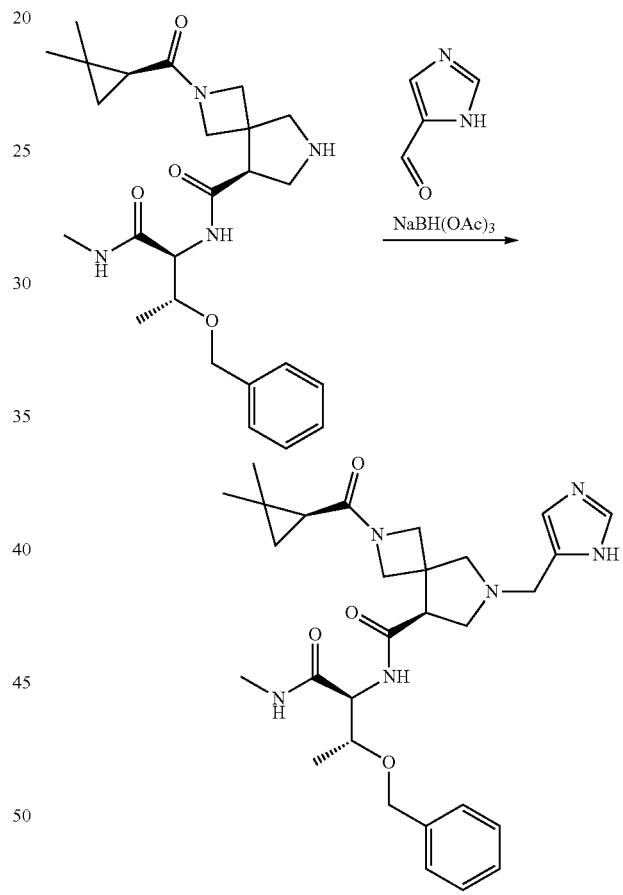

To a solution of Intermediate 8 (80 mg, 0.17 mmol) in DCE (2 mL) was added 1H-imidazole-5-carbaldehyde (18 mg, 0.18 mmol) and NaBH(OAc)₃ (148 mg, 0.70 mmol) followed by one drop of AcOH. The resulting mixture was stirred at room temperature overnight. The solvent was removed under vacuum and the residue purified by prep-HPLC to afford (S)-6-((1H-imidazol-5-yl)methyl)-N-((2S,3R)-3-(benzyloxy)-1-(methylamino)-1-oxobutan-2-yl)-2-((S)-2,2-dimethylcyclopropane-1-carbonyl)-2,6-diazaspiro[3.4]octane-8-carboxamide (I-77A) (35 mg, 37%) as a white solid. LCMS m/z=537.4 [M+H]⁺; ¹H NMR (400 MHz, DMSO-d₆) δ 8.23 (dd, J=8.6 Hz, 1H), 7.81 (dd, J=13.2, 5.6 Hz, 1H), 7.60-7.54 (m, 1H), 7.34-7.24 (m, 6H), 6.90 (s, 1H), 4.59-4.40 (m, 2H), 4.40-4.24 (m, 2H), 3.99-3.89 (m, 3H), 3.74-3.63 (m, 1H), 3.59-3.50 (m, 2H), 3.28-3.20 (m, 1H), 3.13-2.86 (m, 3H), 2.67-2.57 (m, 5H), 1.34-1.18 (m, 1H), 1.14-1.02 (m, 6H), 1.00 (d, J=10.4 Hz, 3H), 0.84-0.80 (m, 1H), 0.65-0.60 (m, 1H).

Method 5B: Exemplified by the Synthesis of I-77B

I-77B was made by a similar process to Method 5A, starting from Intermediate 5, in place of Intermediate 6.

Method 6A: Exemplified by the Synthesis of I-78A

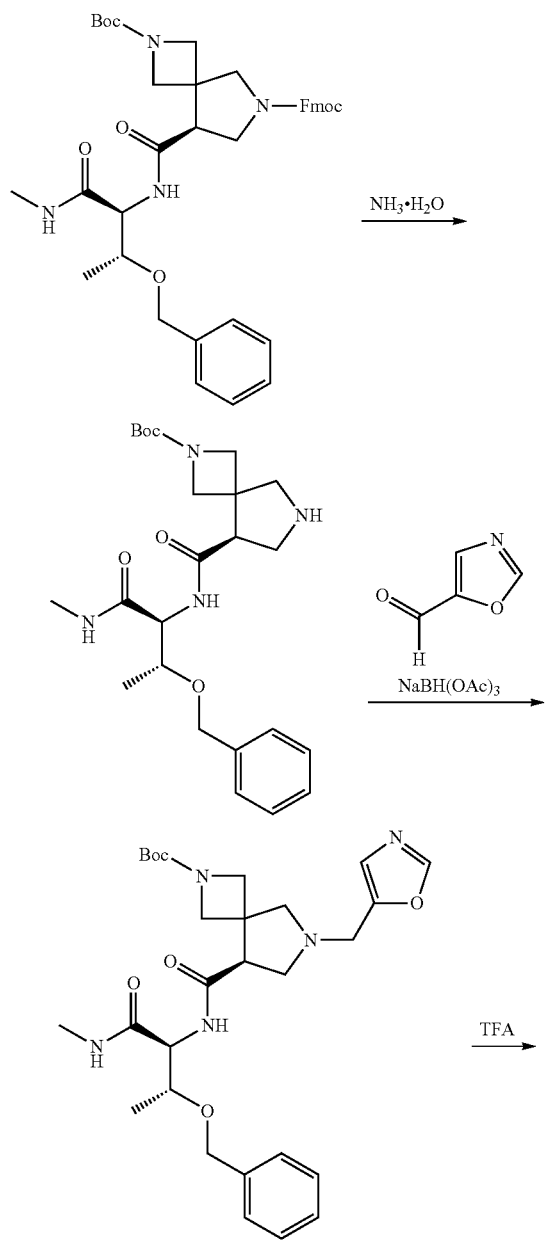

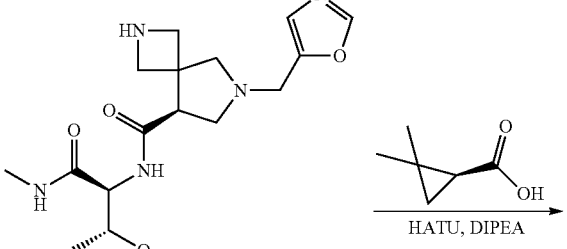

Step 1: To a solution of Intermediate 6 (2.25 g, 3.30 mmol) in 1,4-dioxane (14 mL) was added 25% ammonium hydroxide (9 mL). The reaction mixture was heated at 50° C. overnight then the solvent removed under vacuum. The residue was purified by column chromatography on silica gel (eluent: DCM:MeOH=10:1) to afford compound tert-butyl (S)-8-(((2S,3R)-3-(benzyloxy)-1-(methylamino)-1-oxobutan-2-yl)carbamoyl)-2,6-diazaspiro[3.4]octane-2-carboxylate (850 mg, 57%) as a yellow solid. LCMS m/z=461.2 $[M+H]^+$.

Step 2: To a solution of tert-butyl (S)-8-(((2S,3R)-3-(benzyloxy)-1-(methylamino)-1-oxobutan-2-yl)carbamoyl)-2,6-diazaspiro[3.4]octane-2-carboxylate (100 mg, 0.22 mmol) in DCE (2 mL) was added oxazole-5-carbaldehyde (25 mg, 0.26 mmol), $NaBH(OAc)_3$ (184 mg, 0.88 mmol) and one drop of AcOH. The resulting mixture was stirred at room temperature overnight. The mixture was diluted with water (60 mL) and extracted with EtOAc (100 mL×2). The combined organic layers were washed with brine, dried over $Na_2SO_4$, filtered and concentrated to afford tert-butyl (S)-8-(((2S,3R)-3-(benzyloxy)-1-(methylamino)-1-oxobutan-2-yl)carbamoyl)-6-(oxazol-5-ylmethyl)-2,6-diazaspiro[3.4]octane-2-carboxylate (95 mg, 81%) as a yellow solid. LCMS m/z=542.2 $[M+H]^+$.

Step 3: To a solution of (S)-8-(((2S,3R)-3-(benzyloxy)-1-(methylamino)-1-oxobutan-2-yl)carbamoyl)-6-(oxazol-5-ylmethyl)-2,6-diazaspiro[3.4]octane-2-carboxylate (95 mg, 0.18 mmol) in DCM (2.5 mL) was added TFA (0.5 mL). The reaction mixture was stirred at room temperature for 1 h. The solvent was removed under vacuum to afford (S)—N-((2S, 3R)-3-(benzyloxy)-1-(methylamino)-1-oxobutan-2-yl)-6-(oxazol-5-ylmethyl)-2,6-diazaspiro[3.4]octane-8-carboxamide (77 mg, 100%) which was used directly in the next step. LCMS m/z=442.1 [M+H]$^+$.

Step 4: To a solution of (S)-2,2-dimethylcyclopropane-1-carboxylic acid (24 mg, 0.21 mmol) in DCM (2 mL) was added HATU (100 mg, 0.26 mmol) and the mixture stirred at room temperature for 30 min. (S)—N-((2S,3R)-3-(benzyloxy)-1-(methylamino)-1-oxobutan-2-yl)-6-(oxazol-5-ylmethyl)-2,6-diazaspiro[3.4]octane-8-carboxamide (77 mg, 0.17 mmol) and DIPEA (90 mg, 0.70 mmol) were added and the reaction mixture stirred at room temperature for another 1 h. The mixture was diluted with water (30 mL) and extracted with EtOAc (60 mL×2). The combined organic layers were washed with brine, dried over Na$_2$SO$_4$, filtered and concentrated. The residue obtained was purified by prep-HPLC to afford (S)—N-((2S,3R)-3-(benzyloxy)-1-(methylamino)-1-oxobutan-2-yl)-2-((S)-2,2-dimethylcyclopropane-1-carbonyl)-6-(oxazol-5-ylmethyl)-2,6-diazaspiro[3.4]octane-8-carboxamide (I-78A) (12 mg, 13%) as a white solid. LCMS m/z=538.2 [M+H]$^+$; 1H NMR (400 MHz, DMSO-d$_6$) δ 8.28 (s, 1H), 8.26-8.18 (m, 1H), 7.86-7.74 (m, 1H), 7.34-7.24 (m, 5H), 7.06 (s, 1H), 4.54-4.48 (m, 1H), 4.46-4.40 (m, 1H), 4.36-4.30 (m, 1H), 3.98-3.88 (m, 3H), 3.74-3.62 (m, 3H), 3.28-3.24 (m, 1H), 3.00-2.88 (m, 2H), 2.68-2.64 (m, 1H), 2.62-2.54 (m, 4H), 1.28 (ddd, J=20.6, 8.0, 5.4 Hz, 1H), 1.12-1.08 (m, 3H), 1.06-0.98 (m, 6H), 0.84-0.78 (m, 1H), 0.66-0.58 (m, 1H).

Method 6B: Exemplified by the Synthesis of I-78B

I-78B was made by a similar process to Method 6A, starting from Intermediate 5, in place of Intermediate 6.

Method 7A: Exemplified by the Synthesis of I-67A Via I-3A

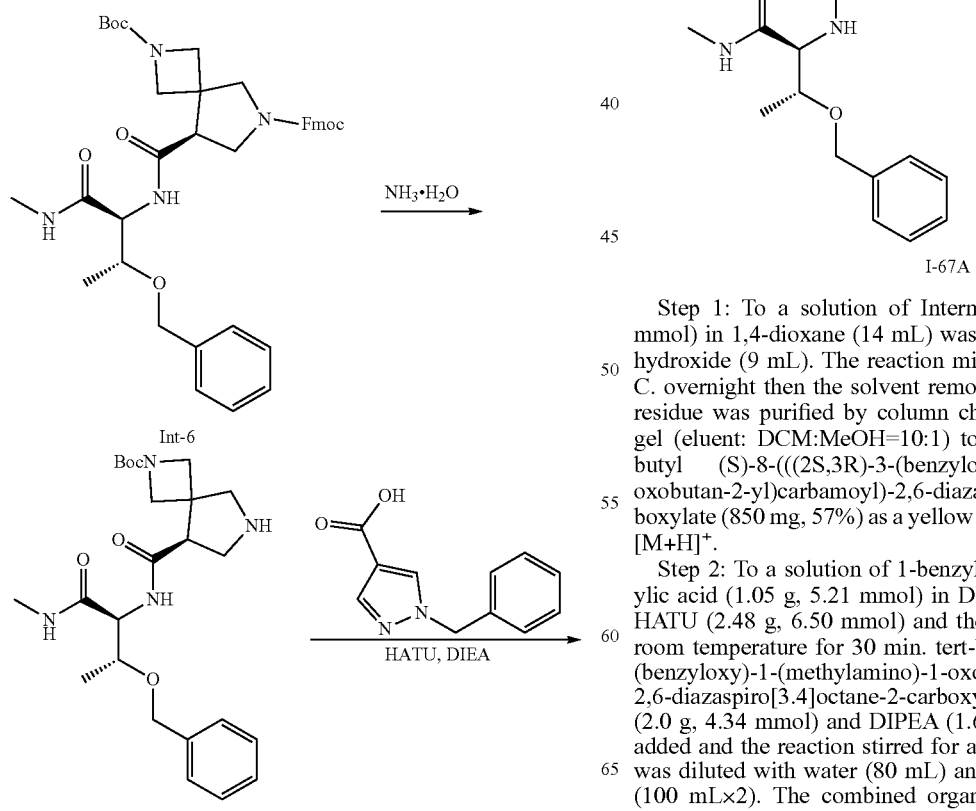

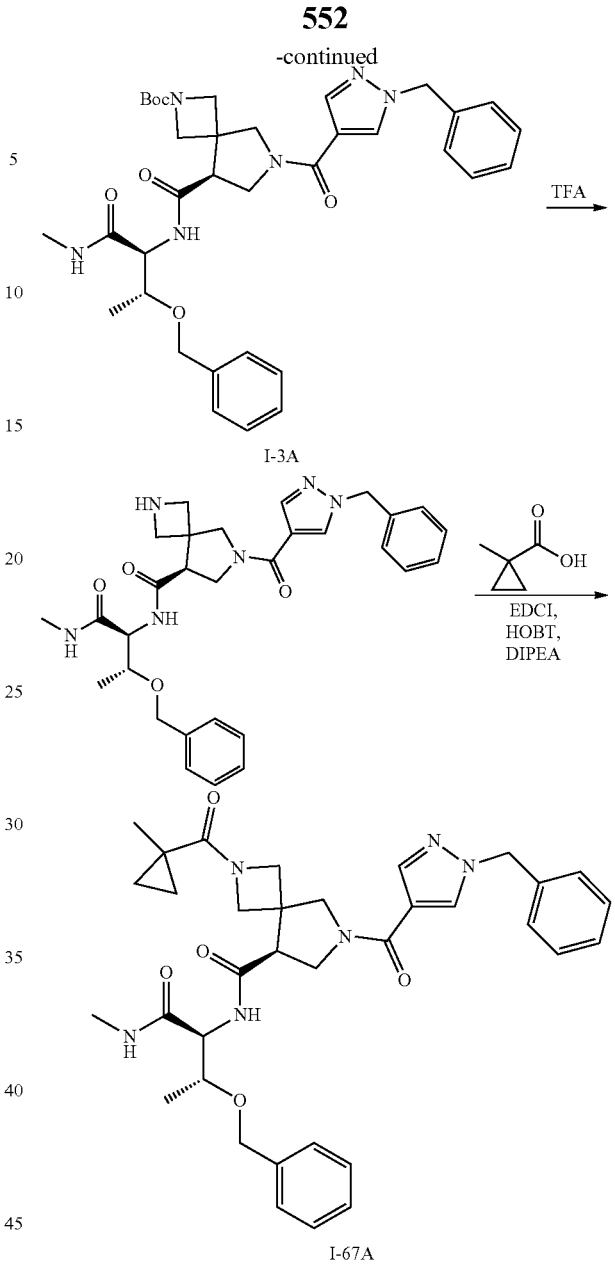

Step 1: To a solution of Intermediate 6 (2.25 g, 3.30 mmol) in 1,4-dioxane (14 mL) was added 25% ammonium hydroxide (9 mL). The reaction mixture was heated at 50° C. overnight then the solvent removed under vacuum. The residue was purified by column chromatography on silica gel (eluent: DCM:MeOH=10:1) to afford compound tert-butyl (S)-8-(((2S,3R)-3-(benzyloxy)-1-(methylamino)-1-oxobutan-2-yl)carbamoyl)-2,6-diazaspiro[3.4]octane-2-carboxylate (850 mg, 57%) as a yellow solid. LCMS m/z=461.2 [M+H]$^+$.

Step 2: To a solution of 1-benzyl-1H-pyrazole-4-carboxylic acid (1.05 g, 5.21 mmol) in DMF (20 mL) was added HATU (2.48 g, 6.50 mmol) and the mixture was stirred at room temperature for 30 min. tert-butyl (S)-8-(((2S,3R)-3-(benzyloxy)-1-(methylamino)-1-oxobutan-2-yl)carbamoyl)-2,6-diazaspiro[3.4]octane-2-carboxylate (See Method 6A) (2.0 g, 4.34 mmol) and DIPEA (1.68 g, 13.02 mmol) were added and the reaction stirred for another 3 h. The mixture was diluted with water (80 mL) and extracted with EtOAc (100 mL×2). The combined organic layers were washed with brine, dried over Na$_2$SO$_4$, filtered and concentrated.

553

The mixture was purified by column chromatography on silica gel (eluent: DCM:MeOH=50:1) to afford tert-butyl (S)-6-(1-benzyl-1H-pyrazole-4-carbonyl)-8-(((2S,3R)-3-(benzyloxy)-1-(methylamino)-1-oxobutan-2-yl)carbamoyl)-2,6-diazaspiro[3.4]octane-2-carboxylate (I-3A) (2.76 g, 99%) as a white solid. LCMS m/z=645.5 [M+H]+; 1H NMR (400 MHz, Methanol-d4) δ 8.19 (d, J=16.6 Hz, 1H), 7.90 (d, J=9.8 Hz, 1H), 7.30 (dd, J=16.8, 4.8 Hz, 10H), 5.39-5.35 (m, 2H), 4.62-4.43 (m, 3H), 4.15-3.75 (m, 10H), 2.73 (d, J=10.4 Hz, 3H), 1.41 (s, 9H), 1.21 (d, J=6.2 Hz, 3H).

Step 3: To a solution of tert-butyl (S)-6-(1-benzyl-1H-pyrazole-4-carbonyl)-8-(((2S,3R)-3-(benzyloxy)-1-(methylamino)-1-oxobutan-2-yl)carbamoyl)-2,6-diazaspiro[3.4]octane-2-carboxylate (70 mg, 0.11 mmol) in DCM (2 mL) was added TFA (1 mL). The reaction mixture was stirred at room temperature for 1 h. The solvent was removed under vacuum to afford (S)-6-(1-benzyl-1H-pyrazole-4-carbonyl)-N-((2S,3R)-3-(benzyloxy)-1-(methylamino)-1-oxobutan-2-yl)-2,6-diazaspiro[3.4]octane-8-carboxamide (54 mg, 100%) which was used directly in the next step. LCMS m/z=545.4 [M+H]+.

Step 4: To a solution of 1-methylcyclopropane-1-carboxylic acid (11 mg, 0.11 mmol) in DMA (1 mL) was added EDCI (27 mg, 0.14 mmol) and HOBt (19 mg, 0.12 mmol) and the mixture stirred at room temperature for 30 min. (S)-6-(1-benzyl-1H-pyrazole-4-carbonyl)-N-((2S,3R)-3-(benzyloxy)-1-(methylamino)-1-oxobutan-2-yl)-2,6-diazaspiro[3.4]octane-8-carboxamide (60 mg, 0.09 mmol) and DIPEA (48 mg, 0.37 mmol) were added. The reaction mixture was stirred at room temperature overnight then diluted with water (60 mL) and extracted with EtOAc (100 mL×2). The combined organic layers were washed with brine, dried over Na2SO4, filtered and concentrated. The mixture was purified by prep-HPLC to afford (S)-6-(1-benzyl-1H-pyrazole-4-carbonyl)-N-((2S,3R)-3-(benzyloxy)-1-(methylamino)-1-oxobutan-2-yl)-2-(1-methylcyclopropane-1-carbonyl)-2,6-diazaspiro[3.4]octane-8-carboxamide (I-67) (7 mg, 11%) as a white solid. LCMS m/z=627.5 [M+H]+; 1H NMR (400 MHz, DMSO-d6) δ 8.35 (d, J=13.4 Hz, 2H), 7.84-7.80 (m, 2H), 7.38-7.23 (m, 10H), 5.35 (s, 2H), 4.53 (d, J=12.0 Hz, 1H), 4.47-4.29 (m, 3H), 4.04-3.36 (m, 9H), 2.60 (dd, J=10.2, 4.4 Hz, 3H), 1.21-1.12 (m, 3H), 1.08 (t, J=5.4 Hz, 3H), 0.87 (s, 2H), 0.41 (s, 2H).

Method 7B: Exemplified by the Synthesis of I-67B Via I-3B

I-3B and I-67B were made by a similar process to Method 7A, starting from Intermediate 5, in place of Intermediate 6.

Method 8A: Exemplified by the Synthesis of I-66A

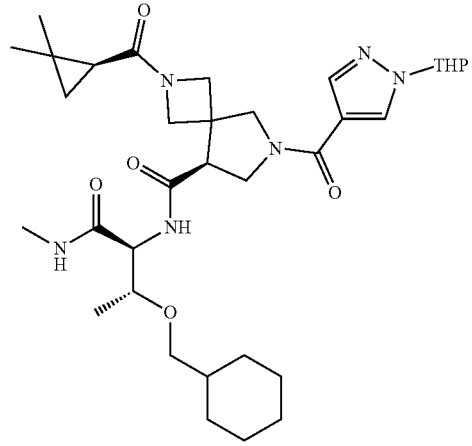

554

-continued

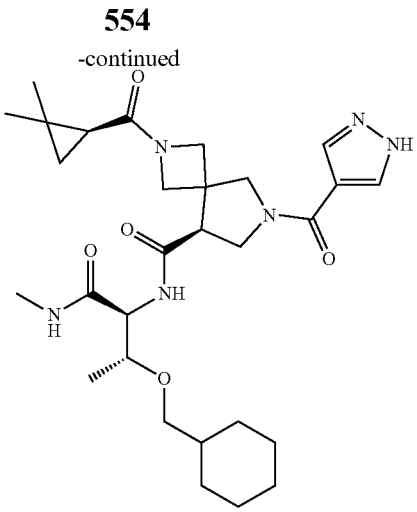

To a solution of (8S)—N-((2S,3R)-3-(cyclohexylmethoxy)-1-(methylamino)-1-oxobutan-2-yl)-2-((S)-2,2-dimethylcyclopropane-1-carbonyl)-6-(1-(tetrahydro-2H-pyran-2-yl)-1H-pyrazole-4-carbonyl)-2,6-diazaspiro[3.4]octane-8-carboxamide (100 mg, 0.156 mmol, synthesized from Intermediate 2 according to Method 1A) in DCM (2 mL) was added TFA (1 mL). The reaction mixture was stirred at room temperature for 1 h. The solvent was removed under vacuum. The residue was purified by prep-HPLC to afford (S)—N-((2S,3R)-3-(cyclohexylmethoxy)-1-(methylamino)-1-oxobutan-2-yl)-2-((S)-2,2-dimethylcyclopropane-1-carbonyl)-6-(1H-pyrazole-4-carbonyl)-2,6-diazaspiro[3.4]octane-8-carboxamide (30 mg, 35%) as a white solid. LCMS m/z=557.5 [M+H]7; 1H NMR (400 MHz, DMSO-d6) δ 8.17 (dd, J=19.0, 8.8 Hz, 1H), 8.01 (s, 1H), 7.82-7.67 (m, 1H), 4.28-3.46 (m, 11H), 3.25-3.21 (m, 1H), 3.10 (dd, J=9.4, 6.4 Hz, 1H), 2.60-2.56 (m, 3H), 1.70-1.60 (m, 5H), 1.44 (s, 1H), 1.36-1.27 (m, 1H), 1.19-1.12 (m, 3H), 1.08 (t, J=4.8 Hz, 3H), 1.06-1.00 (m, 6H), 0.88-0.78 (m, 3H), 0.67 (dd, J=8.0, 4.0 Hz, 1H).

Method 8B: Exemplified by the Synthesis of I-66B

I-66B was made by a similar process to Method 8A, starting from Intermediate 1, in place of Intermediate 2.

Method 9A: Exemplified by the Synthesis of I-88A

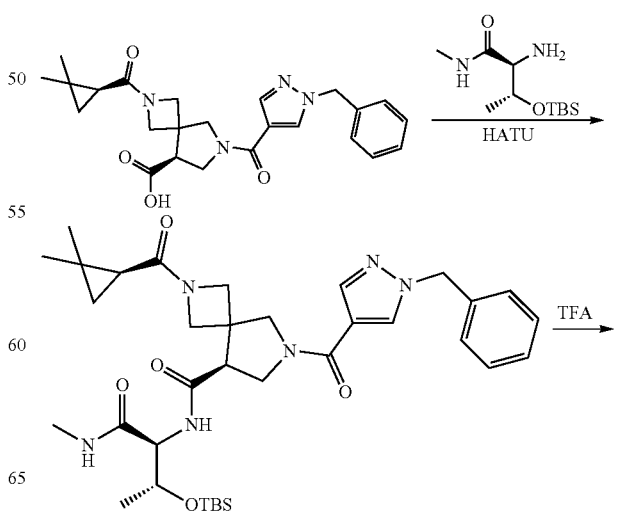

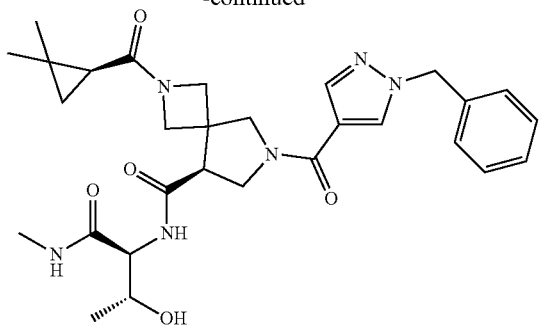

Step 1: (S)-6-(1-benzyl-1H-pyrazole-4-carbonyl)-N-((2S,3R)-3-((tert-butyldimethylsilyl)oxy)-1-(methylamino)-1-oxobutan-2-yl)-2-((S)-2,2-dimethylcyclopropane-1-carbonyl)-2,6-diazaspiro[3.4]octane-8-carboxamide was synthesized from Intermediate 4 according to the procedures outlined in Method 2A. LCMS m/z=665.5 [M+H]⁺.

Step 2: To a solution of (S)-6-(1-benzyl-1H-pyrazole-4-carbonyl)-N-((2S,3R)-3-((tert-butyldimethylsilyl)oxy)-1-(methylamino)-1-oxobutan-2-yl)-2-((S)-2,2-dimethylcyclopropane-1-carbonyl)-2,6-diazaspiro[3.4]octane-8-carboxamide (220 mg, 0.33 mmol) in DCM (3 mL) was added TFA (2 mL). The reaction mixture was stirred at room temperature overnight. The solvent was removed under vacuum, residue was purified by prep-HPLC to afford (S)-6-(1-benzyl-1H-pyrazole-4-carbonyl)-2-((S)-2,2-dimethylcyclopropane-1-carbonyl)-N-((2S,3R)-3-hydroxy-1-(methylamino)-1-oxobutan-2-yl)-2,6-diazaspiro[3.4]octane-8-carboxamide as a yellow solid. LCMS m/z=551.4 [M+H]⁺; $^1$H NMR (400 MHz, DMSO-d6) δ 8.38-8.34 (m, 1H), 8.19-8.13 (m, 1H), 7.84-7.70 (m, 2H), 7.37-7.25 (m, 5H), 5.35 (s, 2H), 4.26-4.13 (m, 2H), 4.09-3.90 (m, 5H), 3.78-3.73 (m, 4H), 3.48-3.33 (m, 1H), 2.61-2.56 (m, 2H), 1.35-1.31 (m, 1H), 1.12-1.01 (m, 9H), 0.86-0.84 (m, 1H), 0.69-0.64 (m, 1H).

Method 9B: Exemplified by the Synthesis of I-88B

I-88B was made by a similar process to Method 9A, starting from Intermediate 3, in place of Intermediate 4.

Method 10A: Exemplified by the Synthesis of I-41A

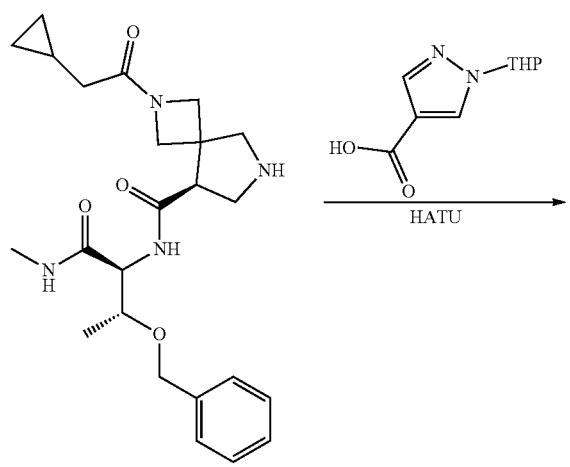

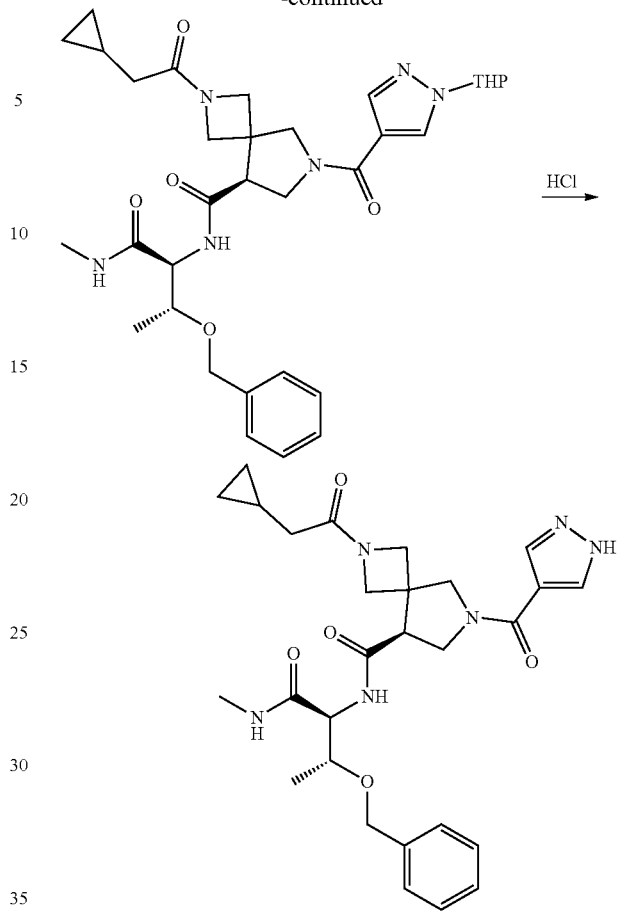

Step 1: (8S)—N-((2S,3R)-3-(benzyloxy)-1-(methylamino)-1-oxobutan-2-yl)-2-(2-cyclopropylacetyl)-6-(1-(tetrahydro-2H-pyran-2-yl)-1H-pyrazole-4-carbonyl)-2,6-diazaspiro[3.4]octane-8-carboxamide (30 mg, 27%) was synthesized from Intermediate 6 according to the procedures outlined in Method 3A, as a white solid. LCMS m/z=621.4 [M+H]⁺.

Step 2: A mixture of (8S)—N-((2S,3R)-3-(benzyloxy)-1-(methylamino)-1-oxobutan-2-yl)-2-(2-cyclopropylacetyl)-6-(1-(tetrahydro-2H-pyran-2-yl)-1H-pyrazole-4-carbonyl)-2,6-diazaspiro[3.4]octane-8-carboxamide (70 mg, 0.11 mmol) in 4M HCl/dioxane (1 mL) was stirred at room temperature for 6 h. The solvent was removed under vacuum. The residue was purified by prep-HPLC to afford (S)—N-((2S,3R)-3-(benzyloxy)-1-(methylamino)-1-oxobutan-2-yl)-2-(2-cyclopropylacetyl)-6-(1H-pyrazole-4-carbonyl)-2,6-diazaspiro[3.4]octane-8-carboxamide I-41A (16 mg, 36%) as a white solid. LCMS m/z=537.4 [M+H]⁺; $^1$H NMR (400 MHz, DMSO-d$_6$) δ 13.22 (s, 1H), 8.32 (dd, J=23.6, 9.0 Hz, 1H), 7.84 (s, 2H), 7.34-7.26 (m, 5H), 4.55-4.40 (m, 2H), 4.35 (dd, J=8.6, 3.4 Hz, 1H), 4.20-3.38 (m, 10H), 2.60 (dd, J=11.2, 4.4 Hz, 3H), 1.88 (dd, J=22.8, 6.4 Hz, 2H), 1.07 (d, J=5.4 Hz, 3H), 0.87 (s, 1H), 0.40 (s, 2H), 0.04 (d, J=7.6 Hz, 2H).

Method 10B: Exemplified by the Synthesis of I-41B

I-41B was made by a similar process to Method 10A, starting from Intermediate 5, in place of Intermediate 6.

Method 11A: Exemplified by the Synthesis of I-70A

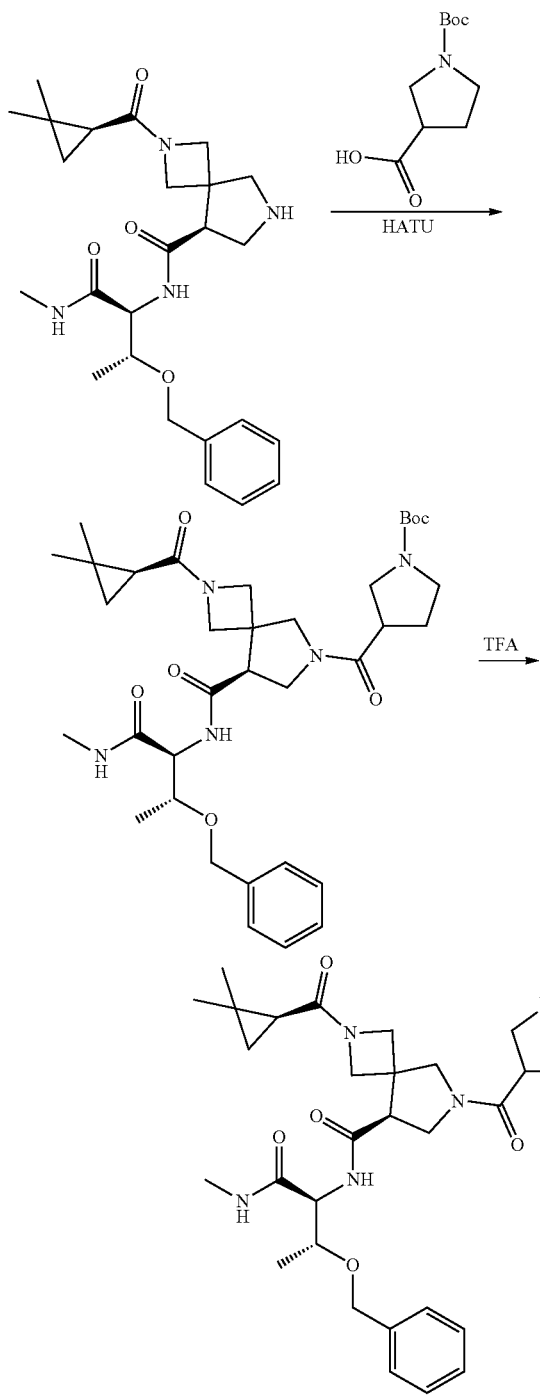

Step 1: tert-butyl 3-((S)-8-((((2S,3R)-3-(benzyloxy)-1-(methylamino)-1-oxobutan-2-yl)carbamoyl)-2-((S)-2,2-dimethylcyclopropane-1-carbonyl)-2,6-diazaspiro[3.4]octane-6-carbonyl)pyrrolidine-1-carboxylate was synthesized from Intermediate 8 according to Method 4A. LCMS m/z=654.3 [M+H]⁺.

Step 2: (8S)—N-((2S,3R)-3-(benzyloxy)-1-(methylamino)-1-oxobutan-2-yl)-2-((S)-2,2-dimethylcyclopropane-1-carbonyl)-6-(pyrrolidine-3-carbonyl)-2,6-diazaspiro[3.4]octane-8-carboxamide (I-70A) was made using a deprotection reaction, analogous to the conditions reported herein for Intermediate 7, Step 1. LCMS m/z=554.2 [M+H]⁺; ¹H NMR (400 MHz, DMSO-d₆) δ 8.39-8.29 (m, 2H), 7.92-7.82 (m, 1H), 7.35-7.24 (m, 5H), 4.57-4.49 (m, 1H), 4.47-4.40 (m, 1H), 4.38-4.30 (m, 1H), 4.23-4.11 (m, 1H), 4.04-3.90 (m, 3H), 3.84-3.74 (m, 2H), 3.65-3.53 (m, 3H), 3.47-3.39 (m, 2H), 3.18-3.09 (m, 2H), 3.01-2.93 (m, 2H), 2.61 (d, J=4.4 Hz, 3H), 2.07-1.96 (m, 1H), 1.91-1.78 (m, 1H), 1.35-1.22 (m, 1H), 1.11-1.00 (m, 9H), 0.87-0.80 (m, 1H), 0.68-0.60 (m, 1H).

Method 11B: Exemplified by the Synthesis of I-70B

I-70B was made by a similar process to Method 11A, starting from Intermediate 7, in place of Intermediate 8.

Method 12A: Exemplified by the Synthesis of I-48A

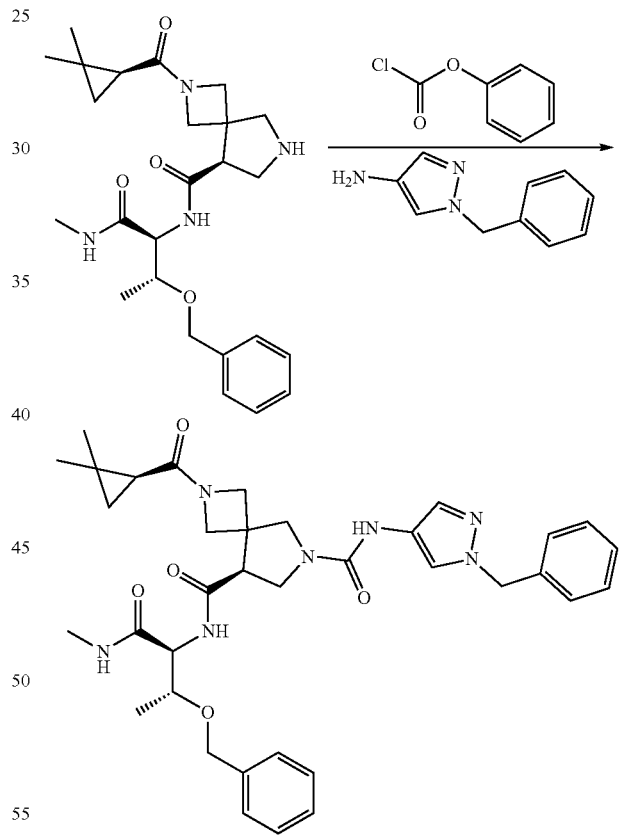

To a solution of 1-benzyl-1H-pyrazol-4-amine (34 mg, 0.164 mmol) in dry THF (1 mL) at 0° C. was added TEA (66 mg, 0.657 mmol) and phenylchloroformate (34 mg, 0.219 mmol). The reaction mixture was stirred at 0° C. for 3 h then diluted with EtOAc (20 mL) and washed with brine. The organic layer was dried over Na₂SO₄, filtered and concentrated to afford crude phenyl (1-benzyl-1H-pyrazol-4-yl) carbamate which was redissolved in dry DMF (1 mL). (S)—N-((2S,3R)-3-(benzyloxy)-1-(methylamino)-1-oxobutan-2-yl)-2-((S)-2,2-dimethylcyclopropane-1-carbonyl)-2,6- diazaspiro[3.4]octane-8-carboxamide (Intermediate 8) (50 mg, 0.110 mmol) was added to the mixture and the reaction stirred overnight at room temperature. The mixture was diluted with water (20 mL) and extracted with EtOAc (30 mL×2). The combined organic layers were washed with brine, dried over Na$_2$SO$_4$, filtered and concentrated. The mixture was purified by prep-TLC (eluent: DCM:MeOH=20:1) to afford (S)—N6-(1-benzyl-1H-pyrazol-4-yl)-N8-((2S,3R)-3-(benzyloxy)-1-(methylamino)-1-oxobutan-2-yl)-2-((S)-2,2-dimethylcyclopropane-1-carbonyl)-2,6-diazaspiro[3.4]octane-6,8-dicarboxamide (I-48A): (5 mg, 7%) as a white solid. LCMS m/z=656.1 [M+H]$^+$; $^1$H NMR (400 MHz, DMSO-d$_6$) δ 8.31-8.25 (m, 2H), 7.88-7.85 (m, 1H), 7.75 (s, 1H), 7.39 (d, J=0.6 Hz, 1H), 7.35-7.25 (m, 8H), 7.19 (s, 1H), 7.18 (s, 1H), 5.23 (s, 2H), 4.54-4.51 (m, 1H), 4.44-4.37 (m, 1H), 4.37-4.30 (m, 1H), 4.23-4.14 (m, 1H), 4.01-3.86 (m, 3H), 3.71 (dd, J=10.0, 5.4 Hz, 1H), 3.64-3.39 (m, 5H), 2.61 (d, J=4.6 Hz, 3H), 1.36-1.25 (m, 1H), 1.10-1.00 (m, 9H), 0.84 (t, J=4.6 Hz, 1H), 0.66-0.58 (m, 1H).

Method 12B: Exemplified by the Synthesis of I-48B

I-48B was made by a similar process to Method 12A, starting from Intermediate 7, in place of Intermediate 8.

Method 13: Exemplified by the Synthesis of I-14

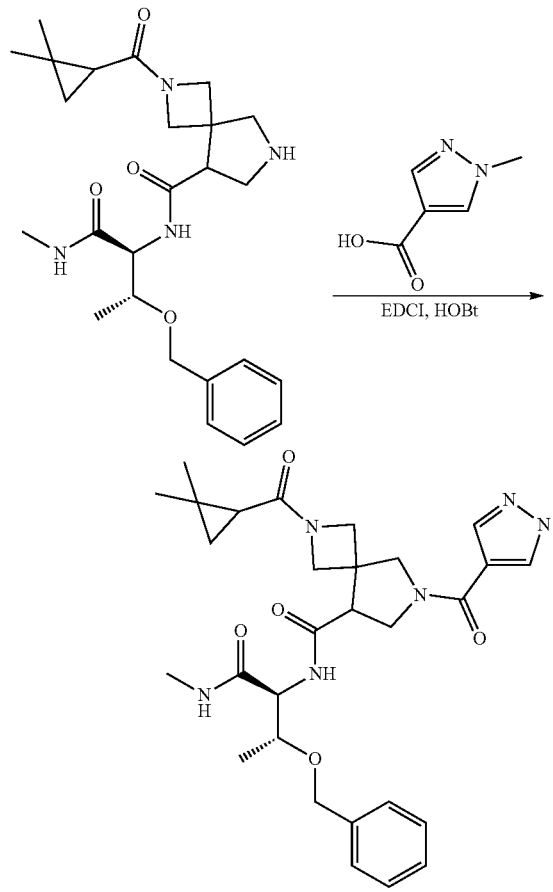

To a solution of 1-methyl-1H-pyrazole-4-carboxylic acid (18.4 mg, 0.146 mmol) in dry DMA (2 mL) was added EDCI (35 mg, 0.184 mmol), HOBt (25 mg, 0.183 mmol) and DIPEA (63 mg, 0.488 mmol) and the mixture stirred at room temperature for 1 h. N-((2S,3R)-3-(benzyloxy)-1-(methylamino)-1-oxobutan-2-yl)-2-(2,2-dimethylcyclopropane-1-carbonyl)-2,6-diazaspiro[3.4]octane-8-carboxamide (Intermediate 9) (60 mg, 0.122 mmol) was added and the resulting reaction stirred for 14 h. The mixture was diluted with water (20 mL) and extracted with EtOAc (60 mL×2). The combined organic layers were washed with brine, dried over Na$_2$SO$_4$, filtered and concentrated. The mixture was purified by column chromatography on silica gel (eluent: DCM:MeOH=50:1) to afford N-((2S,3R)-3-(benzyloxy)-1-(methylamino)-1-oxobutan-2-yl)-2-(2,2-dimethylcyclopropane-1-carbonyl)-6-(1-methyl-1H-pyrazole-4-carbonyl)-2,6-diazaspiro[3.4]octane-8-carboxamide (I-14) (41 mg, 61%) as a white solid. LCMS m/z=565.4 [M+H]$^+$; $^1$H NMR (400 MHz, Methanol-d$_4$) δ 8.12-8.01 (m, 1H), 7.90-7.80 (m, 1H), 7.36-7.23 (m, 5H), 4.65-3.83 (m, 15H), 3.39 (s, 1H), 2.74 (s, 3H), 1.53-1.36 (m, 1H), 1.24-1.09 (m, 9H), 1.03 (s, 1H), 0.77 (s, 1H).

Method 14: Exemplified by the Synthesis of I-2

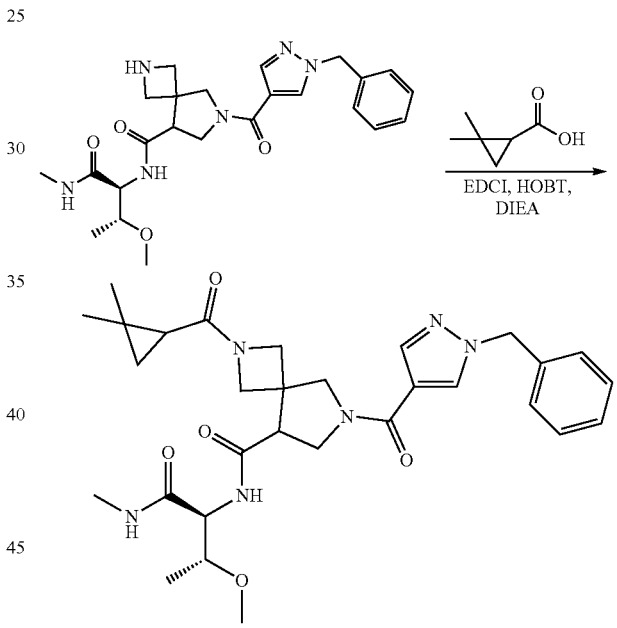

To a solution of 2,2-dimethylcyclopropane-1-carboxylic acid (15 mg, 0.127 mmol) in dry DMF (1 mL) was added EDCI (20 mg, 0.104 mmol), HOBt (14 mg, 0.106 mmol) and DIPEA (27 mg, 0.212 mmol) and the mixture was stirred at room temperature for 1 h. 6-(1-benzyl-1H-pyrazole-4-carbonyl)-N-((2S,3R)-3-methoxy-1-(methylamino)-1-oxobutan-2-yl)-2,6-diazaspiro[3.4]octane-8-carboxamide (Intermediate 10) (50 mg, 0.106 mmol) was added and the reaction was stirred for another 4 h then diluted with water (20 mL) and extracted with EtOAc (60 mL×2). The combined organic layers were washed with brine, dried over Na$_2$SO$_4$, filtered and concentrated. The mixture was purified by prep-HPLC to afford 6-(1-benzyl-1H-pyrazole-4-carbonyl)-2-(2,2-dimethylcyclopropane-1-carbonyl)-N-((2S,3R)-3-methoxy-1-(methylamino)-1-oxobutan-2-yl)-2,6-diazaspiro[3.4]octane-8-carboxamide (I-2) (6.3 mg, 10%) as a white solid. LCMS m/z=565.4 [M+H]$^+$; $^1$H NMR (400 MHz, Methanol-d$_4$) δ 8.20 (d, J=17.1 Hz, 1H), 7.92 (d, J=10.1 Hz, 1H), 7.38-7.25 (m, 5H), 5.37 (s, 2H), 4.59-3.37 (m, 13H), 2.78-2.70 (m, 3H), 1.22-0.99 (m, 11H), 0.82-0.73 (m, 1H).

Method 15: Exemplified by the Synthesis of I-97 Via I-9

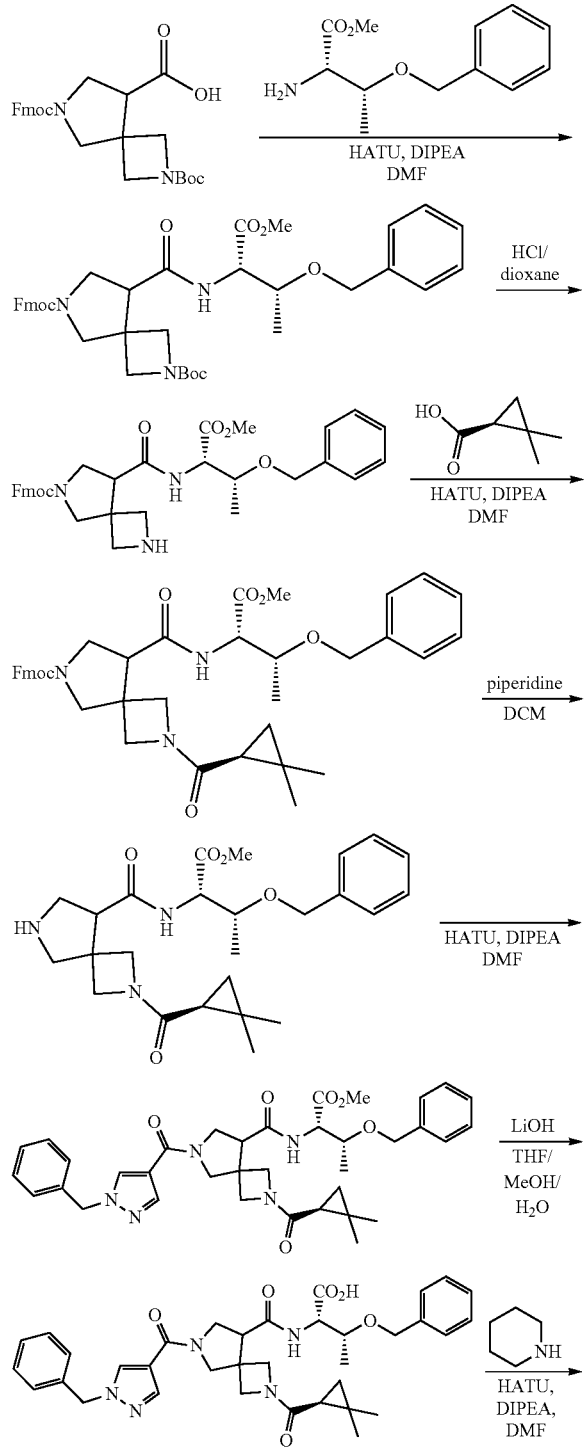

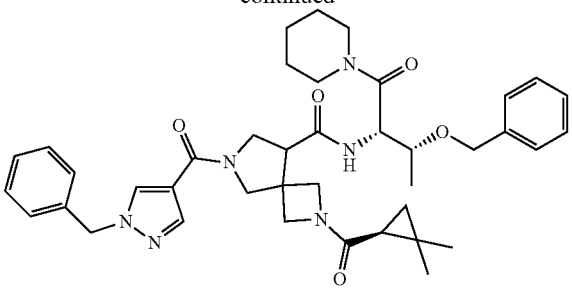

Step 1: To a solution of 6-(((9H-fluoren-9-yl)methoxy)carbonyl)-2-(tert-butoxycarbonyl)-2,6-diazaspiro[3.4]octane-8-carboxylic acid (3.5 g, 7.31 mmol) in N,N-dimethylformamide (30 ml) was added (2-(7-Aza-1H-benzotriazole-1-yl)-1,1,3,3-tetramethyluronium hexafluorophosphate) (3.6 g, 9.51 mmol) and N-ethyl-N-isopropylpropan-2-amine (2.8 g, 21.94 mmol). The resulting mixture was stirred at room temperature for 30 min, followed by addition of (2S,3R)-methyl 2-amino-3-(benzyloxy)butanoate hydrochloride (crude). The resulting mixture was stirred at room temperature for another 2 hours. The reaction mixture was poured into water (100 ml) and extracted with ethyl acetate (50 ml×3). The combined organic layers were washed with brine (50 ml×3), dried over anhydrous sodium sulfate, and concentrated under reduced pressure to give a crude residue which was purified by column chromatography using a 30-50% ethyl acetate/hexane gradient to afford 6-((9H-fluoren-9-yl)methyl) 2-tert-butyl 8-(((2S,3R)-3-(benzyloxy)-1-methoxy-1-oxobutan-2-yl)carbamoyl)-2,6-diazaspiro[3.4]octane-2,6-dicarboxylate (4.8 g, 96% yield) as a white solid. $^1$H NMR (400 MHz, CDCl$_3$): δ 7.76 (d, J=7.2 Hz, 2H), 7.58-7.60 (m, 2H), 7.30-7.40 (m, 7H), 7.24-7.25 (m, 2H), 6.34-6.38 (m, 1H), 4.56-4.64 (m, 2H), 4.34-4.40 (m, 3H), 4.17-4.23 (m, 2H), 4.03-4.09 (m, 1H), 3.66-3.87 (m, 10H), 2.98-3.03 (m, 1H), 1.43-1.46 (m, 9H), 1.26-1.28 (m, 3H).

Step 2: A mixture of 6-((9H-fluoren-9-yl)methyl) 2-tert-butyl 8-(((2S,3R)-3-(benzyloxy)-1-methoxy-1-oxobutan-2-yl)carbamoyl)-2,6-diazaspiro[3.4]octane-2,6-dicarboxylate (4.8 g, 7.02 mmol) in hydrogen chloride solution in dioxane (4M, 20 ml) was stirred at room temperature for 4 hours. The reaction mixture was concentrated in vacuo to give crude (9H-fluoren-9-yl)methyl 8-(((2S,3R)-3-(benzyloxy)-1-methoxy-1-oxobutan-2-yl)carbamoyl)-2,6-diazaspiro[3.4]octane-6-carboxylate hydrochloride which was used in next step without further purification. LCMS: m/z 585.0 [M+H]$^+$.

Step 3: To a solution of (S)-2, 2-dimethylcyclopropane-1-carboxylic acid (801 mg, 7.02 mmol) in N,N-dimethylformamide (40 ml) was added (2-(7-Aza-1H-benzotriazole-1-yl)-1,1,3,3-tetramethyluronium hexafluorophosphate) (3.2 g, 8.42 mmol) and N-ethyl-N-isopropylpropan-2-amine (3.7 ml, 21.06 mmol). The resulting mixture was stirred at room temperature for 30 min, followed by addition of (9H-fluoren-9-yl)methyl 8-(((2S,3R)-3-(benzyloxy)-1-methoxy-1-oxobutan-2-yl)carbamoyl)-2,6-diazaspiro[3.4]octane-6-carboxylate hydrochloride (crude, 7.02 mmol). The resulting mixture was stirred at room for another 2 hours. The reaction mixture was then poured into water (100 ml) and extracted with ethyl acetate (50 ml×3). The combined organic layers were washed with brine (50 ml×3), dried over anhydrous sodium sulfate, and concentrated under reduced pressure to give a crude residue which was purified by column chromatography using a 50% ethyl acetate/hexane gradient to afford (9H-fluoren-9-yl)methyl 8-(((2S,3R)-3-(benzyloxy)-1-methoxy-1-oxobutan-2-yl)carbamoyl)-2-((S)-2,2-dimethylcyclopropanecarbonyl)-2,6-diazaspiro[3.4]octane-6-carboxylate (2.99 g, 63% yield two steps) as a white solid. LCMS: 680.2 [M+H]$^+$. $^1$H NMR (400 MHz, CDCl$_3$): δ 7.76 (d, J=7.6 Hz, 2H), 7.58 (d, J=7.2 Hz, 2H), 7.30-7.40 (m, 7H), 7.24-7.25 (m, 2H), 6.41-6.54 (m, 1H), 4.55-4.63 (m, 2H), 4.08-4.45 (m, 7H), 3.89-4.03 (m, 3H), 3.63-3.77 (m, 6H), 3.03-3.07 (m, 1H), 1.14-1.23 (m, 11H), 0.75-0.78 (m, 1H).

Step 4: A solution of (9H-fluoren-9-yl)methyl 8-(((2S,3R)-3-(benzyloxy)-1-methoxy-1-oxobutan-2-yl)carbamoyl)-2-((S)-2,2-dimethylcyclopropanecarbonyl)-2,6-diazaspiro[3.4]octane-6-carboxylate (2.99 g, 4.40 mmol) and piperidine (2.0 ml) in dichloromethane (10 ml) was stirred at room temperature for 2 hours. The reaction mixture was then poured into water (50 ml) and extracted with ethyl acetate (50 ml×3). The combined organic layers were washed with ammonium chloride (50 ml×3) and then brine (50 ml), dried over anhydrous sodium sulfate, and concentrated under reduced pressure to give a crude residue which was purified column chromatography using a 10% methanol/dichloromethane gradient to afford (2S,3R)-methyl 3-(benzyloxy)-2-(2-((S)-2,2-dimethylcyclopropanecarbonyl)-2,6-diazaspiro[3.4]octane-8-carboxamido)butanoate (1.69 g, 84% yield) as a white solid. LCMS: m/z 458.9 [M+H]$^+$. $^1$H NMR (400 MHz, DMSO-d$_6$): δ 8.80-8.91 (m, 1H), 8.30 (br, 2H), 7.29-7.35 (m, 5H), 4.51-4.57 (m, 2H), 4.38-4.46 (m, 1H), 4.02-4.23 (m, 3H), 3.71-3.87 (m, 2H), 3.46-3.55 (m, 3H), 3.27-3.37 (m, 4H), 1.03-1.32 (m, 10H), 0.83-0.87 (m, 1H), 0.66-0.72 (m, 1H).

Step 5: To a solution of 1-benzyl-1H-pyrazole-4-carboxylic acid (747 mg, 3.69 mmol) in N,N-dimethylformamide (35 ml) was added (2-(7-Aza-1H-benzotriazole-1-yl)-1,1,3,3-tetramethyluronium hexafluorophosphate) (1.7 g, 4.43 mmol) and N-ethyl-N-isopropylpropan-2-amine (1.4 g, 11.08 mmol). The resulting mixture was stirred at room temperature for 30 min, followed by addition of (2S,3R)-methyl 3-(benzyloxy)-2-(2-((S)-2,2-dimethylcyclopropanecarbonyl)-2,6-diazaspiro[3.4]octane-8-carboxamido)butanoate (1.69 g, 3.69 mmol). The resulting mixture was stirred at room temperature for another 4 h. The reaction mixture was then poured into water (50 ml) and extracted with ethyl acetate (50 ml×3). The combined organic layers were washed with ammonium chloride (50 ml×2) and then brine (50 ml), dried over anhydrous sodium sulfate, concentrated under reduced pressure to give a crude residue which was purified by column and chromatography using 10% methanol/dichloromethane gradient to afford (2S,3R)-methyl 2-(6-(1-benzyl-1H-pyrazole-4-carbonyl)-2-((S)-2,2-dimethylcyclopropanecarbonyl)-2,6-diazaspiro[3.4]octane-8-carboxamido)-3-(benzyloxy)butanoate (1.9 g, 80% yield) as a white solid. LCMS: m/z 642.8 [M+H]$^+$. $^1$H NMR (400 MHz, CD$_3$OD): δ 8.13-8.25 (m, 1H), 7.92 (d, J=8.0 Hz, 1H), 7.27-7.34 (m, 10H), 3.35-5.37 (m, 2H), 4.59-4.64 (m, 2H), 4.31-4.42 (m, 2H), 3.78-4.25 (m, 8H), 3.66 (s, 2H), 3.60 (d, J=6.0 Hz, 1H), 3.38-3.48 (m, 1H), 2.81 (s, 1H), 1.30-1.44 (m, 2H), 1.17-1.26 (m, 4H), 1.10-1.15 (m, 4H), 1.02-1.04 (m, 1H), 0.74-0.79 (m, 1H).

Step 6: To a solution of (2S,3R)-methyl 2-(6-(1-benzyl-1H-pyrazole-4-carbonyl)-2-((S)-2,2-dimethylcyclopropanecarbonyl)-2,6-diazaspiro[3.4]octane-8-carboxamido)-3-(benzyloxy)butanoate (300 mg, 0.47 mmol) in tetrahydrofuran (6 ml)-methanol (3 ml)-water (1.5 ml) was added lithium hydroxide monohydrate (20 mg, 0.47 mmol, 1.0 eq.). The resulting mixture was stirred at 0° C. overnight. The reaction mixture was acidified to pH 4-5 with hydrochloric acid (2.0 N) and extracted with ethyl acetate (20 ml×3). The combined organic phases were washed with brine (10 ml), dried over anhydrous sodium sulfate, and concentrated under reduced pressure to give a crude residue which was purified by column chromatography using 10% methanol/dichloromethane gradient to afford (2S,3R)-2-(6-(1-benzyl-1H-pyrazole-4-carbonyl)-2-((S)-2,2-dimethylcyclopropanecarbonyl)-2,6-diazaspiro[3.4]octane-8-carboxamido)-3-(benzyloxy)butanoic acid (I-9) (240 mg, 82% yield) as a white solid. LCMS: m/z 628.6 [M+H]$^+$. $^1$H NMR (400 MHz, CD$_3$OD): δ 8.15-8.27 (m, 1H), 7.93-7.95 (m, 1H), 7.29-7.36 (m, 10H), 5.38-5.40 (m, 2H), 4.56-4.70 (m, 2H), 4.20-4.51 (m, 4H), 3.80-4.13 (m, 5H), 3.40-3.50 (m, 1H), 1.42-1.48 (m, 1H), 1.32-1.37 (m, 1H), 1.18-1.28 (m, 4H), 1.11-1.18 (m, 4H), 1.03-1.05 (m, 1H), 0.75-0.79 (m, 1H).

Step 7: To a stirring mixture of (2S,3R)-2-(6-(1-benzyl-1H-pyrazole-4-carbonyl)-2-((S)-2,2-dimethyl cyclopropanecarbonyl)-2,6-diazaspiro[3.4]octane-8-carboxamido)-3-(benzyloxy)butanoic acid (25 mg, 0.04 mmol), piperidine (4.09 mg, 0.048 mmol) and DIPEA (10.34 mg, 0.08 mmol) in DMF (10 ml) was added HATU (2-(7-Aza-1H-benzotriazole-1-yl)-1,1,3,3-tetramethyluronium hexafluorophosphate) (22.8 mg, 0.06 mmol) at 0° C. The resulting mixture was stirred at room temperature for 2 h. The reaction mixture was partitioned between ethyl acetate (30 ml) and water (20 ml); the organic layer was collected, and the aqueous layer was extracted with ethyl acetate (10 ml×2). The combined organic layers were washed with brine (30 ml), dried over anhydrous sodium sulfate, and concentrated under reduced pressure to give a crude residue which was purified by pre-TLC using 5% methanol/dichloromethane gradient to afford 6-(1-benzyl-1

H-pyrazole-4-carbonyl)-N-((2S,3R)-3-(benzyloxy)-1-oxo-1-(piperidin-1-yl)butan-2-yl)-2-((S)-2,2-dimethylcyclopropanecarbonyl)-2,6-diazaspiro[3.4]octane-8-carboxamide (I-97) (18 mg, 65% yield) as white solid. LCMS: m/z 695.5[M+H]$^+$. $^1$H NMR (400 MHz, CD$_3$OD): δ 8.14-8.23 (m, 1H), 7.87-7.93 (m, 1H), 7.17-7.42 (m, 10H), 5.33-5.38 (m, 2H), 4.93-4.98 (m, 1H), 4.60-4.65 (m, 1H), 4.50-4.56 (m, 1H), 3.84-4.20 (m, 8H), 3.43-3.58 (m, 4H), 3.37 (m, 1H), 2.19 (t, J=7.6 Hz, 1H), 2.02-2.03 (m, 1H), 1.58-1.62 (m, 3H), 1.43-1.53 (m, 4H), 1.18 (d, J=4.8 Hz, 2H), 1.10-1.12 (m, 4H), 1.02-1.04 (m, 1H), 0.90 (t, J=6.6 Hz, 2H), 0.74-0.79 (m, 1H).

Method 16A: Exemplified by the Synthesis of I-194A

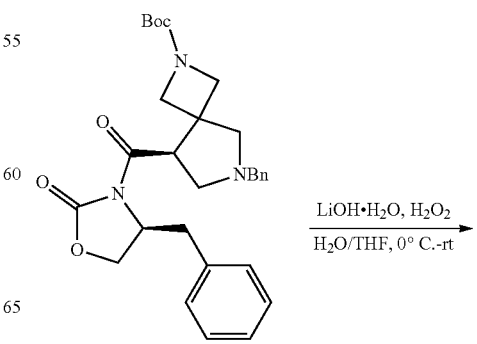

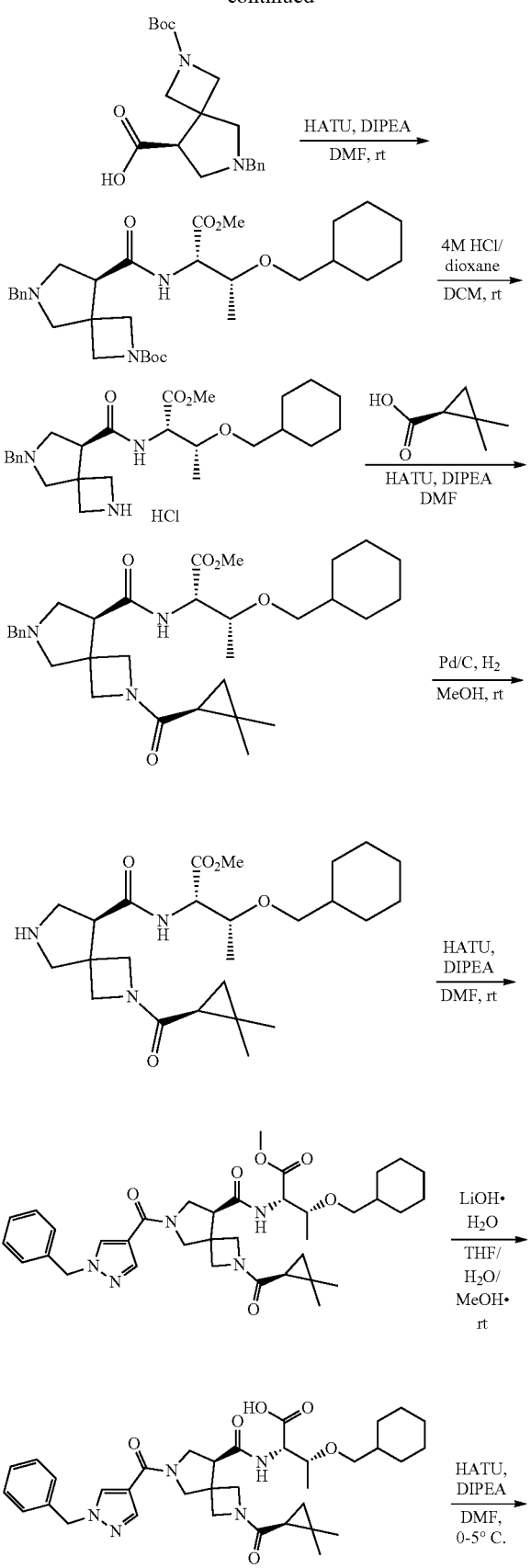

Step 1: To a solution of tert-butyl (S)-6-benzyl-8-((S)-4-benzyl-2-oxooxazolidine-3-carbonyl)-2,6-diazaspiro[3.4]octane-2-carboxylate (Intermediate 2) (4.00 g, 7.92 mmol) in tetrahydrofuran (30 mL) at 0-5° C. was added a solution of lithium hydroxide monohydrate (831 mg, 19.80 mmol) and hydrogen peroxide (30% in H₂O, 1.8 g, 15.8 mmol) in H₂O (2 mL). The resulting mixture was stirred at room temperature for 1 h. The reaction was quenched with aqueous sodium sulfite solution (10 mL), and extracted with ethyl acetate (20 mL×2). The aqueous layer was collected, acidified to pH 4 with diluted hydrochloride acid, and extracted with IPA/DCM mixture (1:3, 30 mL×3). The combined organic layer were washed with brine (20 ml), dried over anhydrous sodium sulfate, and concentrated under reduced pressure to give crude (S)-6-benzyl-2-(tert-butoxycarbonyl)-2,6-diazaspiro[3.4]octane-8-carboxylic acid (2.44 g, 89% yield) as a light yellow solid. $^1$H NMR (400 MHz, CDCl3) δ 7.41-7.60 (m, 5H), 4.24-4.46 (m, 2H), 3.89-4.14 (m, 4H), 3.40-3.82 (m, 5H), 1.38 (s, 9H).

Step 2: To a solution of (S)-6-benzyl-2-(tert-butoxycarbonyl)-2,6-diazaspiro[3.4]octane-8-carboxylic acid (2.74 g, 7.91 mmol), (2S,3R)-methyl 2-amino-3-(cyclohexylmethoxy)butanoate hydrochloride (1.99 g, 8.70 mmol), and N-ethyl-N-isopropylpropan-2-amine (4.09 g, 31.64 mmol) in N,N-dimethylformamide (20 mL) at 0-5° C. was added 2-(7-Aza-1H-benzotriazole-1-yl)-1,1,3,3-tetramethyluronium hexafluorophosphate (4.51 g, 11.86 mmol). The resulting mixture was stirred at room temperature for 2 hours. TLC showed the reaction was complete. The reaction mixture was partitioned between ethyl acetate (35 mL) and water (30 mL). The organic layer was collected, washed with saturated aqueous ammonium chloride solution (15 mL) and then brine (15 mL), dried over anhydrous sodium sulfate, and concentrated under reduced pressure to give a crude residue which was purified by silica gel flash chromatography using 25% ethyl acetate plus 25% dichloromethane/hexane gradient to afford tert-butyl (S)-6-benzyl-8-(((2S,3R)-3-(cyclohexylmethoxy)-1-methoxy-1-oxobutan-2-yl)carbamoyl)-2,6-diazaspiro[3.4]octane-2-carboxylate (3.30 g, 74% yield) as a white solid. $^1$H NMR (400 MHz, CDCl₃): δ 7.40-7.48 (m, 5H), 7.14 (br, 1H), 4.37-4.50 (m, 3H), 3.81-4.04 (m, 6H), 3.73 (s, 3H), 3.56-3.71 (m, 3H), 3.31-3.34 (m, 1H), 3.02-3.06 (m, 1H), 1.55-1.68 (m, 5H), 1.43-1.53 (m, 1H), 1.33-1.39 (m, 9H), 1.06-1.22 (m, 6H), 0.80-0.89 (m, 2H).

Step 3: To a mixture of tert-butyl (S)-6-benzyl-8-(((2S,3R)-3-(cyclohexylmethoxy)-1-methoxy-1-oxobutan-2-yl)carbamoyl)-2,6-diazaspiro[3.4]octane-2-carboxylate (3.30 g, 5.92 mmol) in dichloromethane (20 mL) was added hydrogen chloride dioxane solution (4.0 M, 10 mL). The resulting mixture was stirred at room temperature for an hour. TLC showed the reaction was complete. The reaction mixture was concentrated in vacuo to afford crude methyl N—((S)-6-benzyl-2,6-diazaspiro[3.4]octane-8-carbonyl)-

O-(cyclohexylmethyl)-L-threoninate which was used in next step without further purification.

Step 4: To a solution of (S)-2, 2-dimethylcyclopropane-1-carboxylic acid (743 mg, 6.51 mmol), crude methyl N—((S)-6-benzyl-2,6-diazaspiro[3.4]octane-8-carbonyl)-O-(cyclohexylmethyl)-L-threoninate (5.92 mmol), and N-ethyl-N-isopropylpropan-2-amine (4 mL, 23.67 mmol) in N,N-dimethylformamide (20 mL) at 0-5° C. was added 2-(7-Aza-1H-benzotriazole-1-yl)-1,1,3,3-tetramethyluronium hexafluorophosphate (2.70 g, 7.10 mmol). The resulting mixture was stirred at room temperature for 2 hours. TLC showed the reaction was complete. The reaction mixture was partitioned between ethyl acetate (35 mL) and water (30 mL). The organic layer was collected, washed with saturated aqueous ammonium chloride solution (15 mL) and then brine (15 mL), dried over anhydrous sodium sulfate, and concentrated under reduced pressure to give a crude residue which was purified by column chromatography using a 50% ethyl acetate/hexane gradient to afford methyl N—((S)-6-benzyl-2-((S)-2,2-dimethylcyclopropane-1-carbonyl)-2,6-diazaspiro[3.4]octane-8-carbonyl)-O-(cyclohexylmethyl)-L-threoninate (2.00 g, 61% yield over two steps) as a yellow solid. $^1$H NMR (400 MHz, CDCl$_3$): δ 8.16 (d, J=9.2 Hz, 1H), 7.27-7.37 (m, 5H), 4.56-4.59 (m, 1H), 4.20-4.25 (m, 1H), 3.88-4.09 (m, 4H), 3.67-3.75 (m, 5H), 3.29-3.41 (m, 2H), 3.01-3.07 (m, 2H), 2.92-2.96 (m, 1H), 2.70-2.73 (m, 1H), 2.61-2.65 (m, 1H), 1.60-1.65 (m, 4H), 1.07-1.22 (m, 15H), 0.79-0.94 (m, 3H), 0.67-0.72 (m, 1H).

Step 5: To a solution of methyl N—((S)-6-benzyl-2-((S)-2,2-dimethylcyclopropane-1-carbonyl)-2,6-diazaspiro[3.4]octane-8-carbonyl)-O-(cyclohexylmethyl)-L-threoninate (2.00 g, 3.61 mmol) in methanol (70 mL) was added palladium on carbon (10%, 400 mg). The resulting mixture was stirred at room temperature under H$_2$ overnight. TLC showed the reaction was complete. Palladium on carbon was removed through filtration and washed with methanol; the combined organic solution was concentrated under reduced pressure to give a crude residue which was purified by column chromatography using a 5-10% methanol/dichloromethane gradient to afford methyl 0-(cyclohexylmethyl)-N—((S)-2-((S)-2,2-dimethylcyclopropane-1-carbonyl)-2,6-diazaspiro[3.4]octane-8-carbonyl)-L-threoninate (1.29 g, 77% yield) as an off-white solid. $^1$H NMR (400 MHz, DMSO-d$_6$): δ 8.72 (dd, J=8.8, 20.4 Hz, 1H), 4.51-4.55 (m, 1H), 4.06-4.25 (m, 2H), 3.86-3.96 (m, 2H), 3.73-3.81 (m, 1H), 3.65 (s, 3H), 3.48-3.59 (m, 4H), 3.24-3.32 (m, 4H), 3.02-3.06 (m, 1H), 1.60-1.69 (m, 4H), 1.37-1.49 (m, 1H), 1.04-1.34 (m, 13H), 0.79-0.87 (m, 3H), 0.68-0.71 (m, 1H).

Step 6: To a solution of methyl 0-(cyclohexylmethyl)-N—((S)-2-((S)-2,2-dimethylcyclopropane-1-carbonyl)-2,6-diazaspiro[3.4]octane-8-carbonyl)-L-threoninate (150 mg, 0.32 mmol), 1-benzyl-1H-pyrazole-4-carboxylic acid (79 mg, 0.39 mmol), and N-ethyl-N-isopropylpropan-2-amine (125 mg, 0.97 mmol) in N,N-dimethylformamide (2 mL) at 0-5° C. was added (2-(7-Aza-1H-benzotriazole-1-yl)-1,1,3,3-tetramethyluronium hexafluorophosphate) (148 mg, 0.39 mmol). The resulting mixture was stirred at room temperature for 2 hours. TLC showed the reaction was complete. The reaction mixture was partitioned between ethyl acetate (25 mL) and water (25 mL). The organic layer was collected, washed with saturated aqueous ammonium chloride solution (15 mL) and then brine (15 mL), dried over anhydrous sodium sulfate, and concentrated under reduced pressure to give a crude residue which was purified by preparative TLC using a 5% methanol/dichloromethane gradient to afford methyl N—((S)-6-(1-benzyl-1H-pyrazole-4-carbonyl)-2-((S)-2,2-dimethylcyclopropane-1-carbonyl)-2,6-diazaspiro[3.4]octane-8-carbonyl)-O-(cyclohexylmethyl)-L-threoninate (144 mg, 68% yield) as a colorless oil. LCMS: m/z 648.4 [M+H]$^+$. $^1$H NMR (400 MHz, CD$_3$OD): δ 8.20-8.23 (m, 1H), 7.92 (d, J=10.0 Hz, 1H), 7.28-7.37 (m, 5H), 5.38 (s, 2H), 4.57-4.60 (m, 1H), 3.79-4.39 (m, 10H), 3.67-3.73 (m, 3H), 3.36-3.51 (m, 2H), 3.05-3.11 (m, 1H), 1.63-1.74 (m, 5H), 1.45-1.52 (m, 1H), 1.11-1.27 (m, 12H), 1.03-1.05 (m, 1H), 0.89-0.96 (m, 2H), 0.75-0.79 (m, 1H).

Step 7: To a solution of methyl N—((S)-6-(1-benzyl-1H-pyrazole-4-carbonyl)-2-((S)-2,2-dimethylcyclopropane-1-carbonyl)-2,6-diazaspiro[3.4]octane-8-carbonyl)-O-(cyclohexylmethyl)-L-threoninate (144 mg, 0.22 mmol) in tetrahydrofuran (2 mL)-methanol (1 mL)-water (1 mL) at 0-5° C. was added lithium hydroxide monohydrate (23 mg, 0.55 mmol, 2.5 eq.). The resulting mixture was stirred at 0-5° C. for 2 hours. TLC showed the reaction was complete. The reaction mixture was acidified to pH 4-5 with hydrochloric acid (2.0 N) and extracted with ethyl acetate (10 mL×2). The combined organic layers were washed with brine (10 mL), dried over anhydrous sodium sulfate, and concentrated under reduced pressure to give a crude residue which was purified by preparative TLC using a 10% methanol/dichloromethane gradient to afford N—((S)-6-(1-benzyl-1H-pyrazole-4-carbonyl)-2-((S)-2,2-dimethylcyclopropane-1-carbonyl)-2,6-diazaspiro[3.4]octane-8-carbonyl)-O-(cyclohexylmethyl)-L-threonine (104 mg, 73% yield) as a white solid. LCMS: m/z 634.4 [M+H]$^+$. $^1$H NMR (400 MHz, CD$_3$OD): δ 8.22-8.25 (m, 1H), 7.94 (d, J=8.4 Hz, 1H), 7.28-7.39 (m, 5H), 5.40 (s, 2H), 4.53-4.56 (m, 1H), 3.81-4.43 (m, 10H), 3.36-3.51 (m, 2H), 3.14-3.19 (m, 1H), 1.63-1.82 (m, 5H), 1.49-1.59 (m, 1H), 1.12-1.29 (m, 12H), 1.04-1.08 (m, 1H), 0.92-0.99 (m, 2H), 0.77-0.80 (m, 1H).

Step 8: To a solution of N—((S)-6-(1-benzyl-1H-pyrazole-4-carbonyl)-2-((S)-2,2-dimethylcyclopropane-1-carbonyl)-2,6-diazaspiro[3.4]octane-8-carbonyl)-O-(cyclohexylmethyl)-L-threonine (796 mg, 1.26 mmol), piperidine (128 mg, 1.51 mmol), and N-ethyl-N-isopropylpropan-2-amine (487 mg, 3.77 mmol) in N,N-dimethylformamide (7 mL) at 0-5° C. was added (2-(7-Aza-1H-benzotriazole-1-yl)-1,1,3,3-tetramethyluronium hexafluorophosphate) (573 mg, 1.51 mmol). The resulting mixture was stirred at room temperature for 2 hours. TLC showed the reaction was complete. The reaction mixture was then poured into water and extracted with ethyl acetate. The combined organic phases were washed with brine, dried over anhydrous sodium sulfate, and concentrated under reduced pressure to give a crude residue which was purified by column chromatography using 3.3% methanol/dichloromethane gradient to afford (S)-6-(1-benzyl-1H-pyrazole-4-carbonyl)-N-((2S,3R)-3-(cyclohexylmethoxy)-1-oxo-1-(piperidin-1-yl)butan-2-yl)-2-((S)-2,2-dimethylcyclopropane-1-carbonyl)-2,6-diazaspiro[3.4]octane-8-carboxamide (850 mg, 82% yield) as a white solid. LCMS: m/z 701.5 [M+H]$^+$. $^1$H NMR (400 MHz, CD$_3$OD): δ 8.19-8.23 (m, 1H), 7.92 (d, J=12.0 Hz, 1H), 7.26-7.36 (m, 5H), 5.38 (s, 2H), 4.91-4.94 (m, 1H), 3.71-4.41 (m, 10H), 3.50-3.60 (m, 4H), 3.33-3.46 (m, 2H), 3.17-3.22 (m, 1H), 1.38-1.76 (m, 13H), 1.10-1.24 (m, 11H), 1.03-1.05 (m, 1H), 0.87-0.97 (m, 2H), 0.76-0.81 (m, 1H).

Method 16B: Exemplified by the Synthesis of I-194B

I-194B was made by a similar process to Method 16A, starting from Intermediate 1, in place of Intermediate 2.

Method 17A: Exemplified by the Synthesis of I-196A

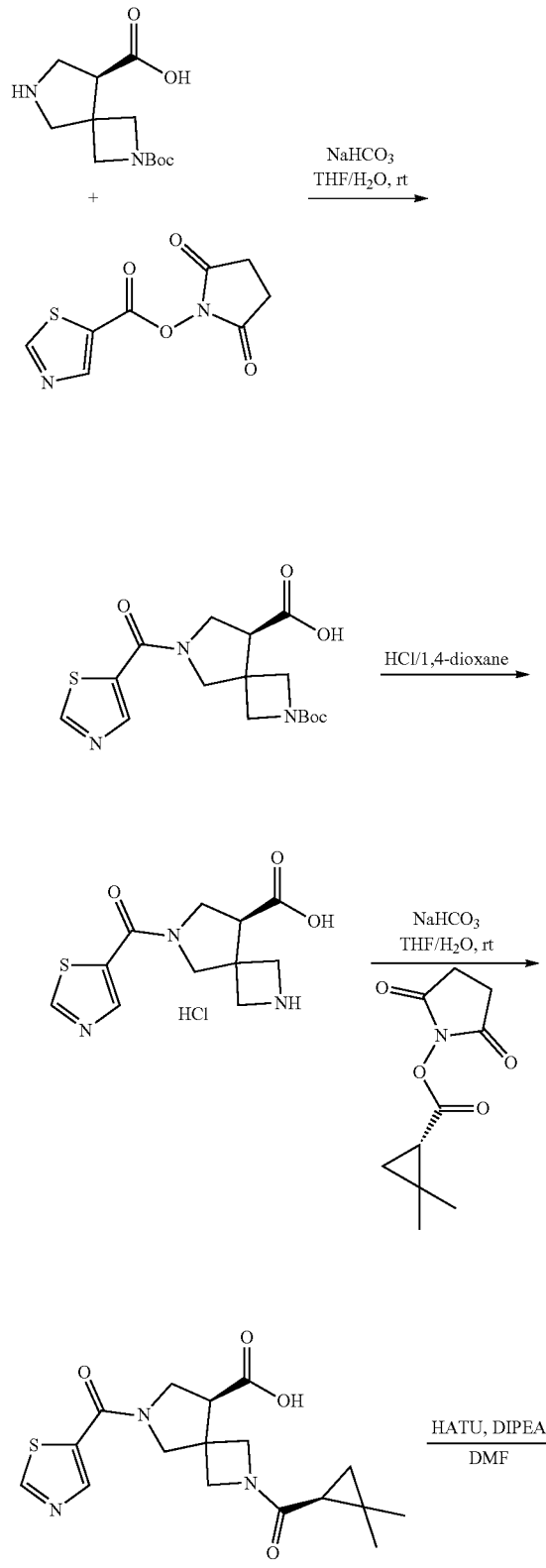

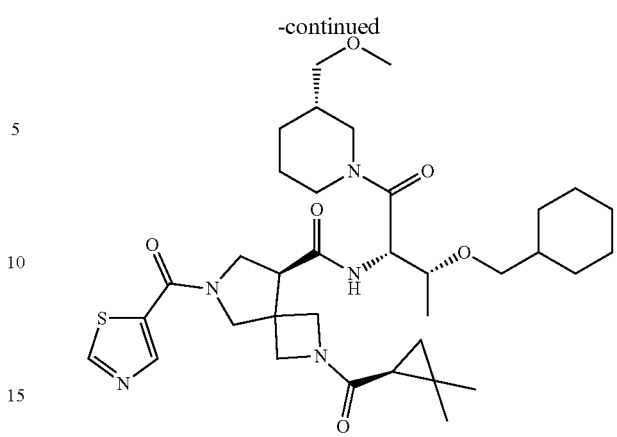

Step 1: To a solution of (S)-2-(tert-butoxycarbonyl)-2,6-diazaspiro[3.4]octane-8-carboxylic acid (See synthesis of Intermediate 6) (2 g, 7.80 mmol) in water (20 ml) was added NaHCO₃ (1.3 g, 15.60 mmol), followed by the dropwise addition of the solution of 2,5-dioxopyrrolidin-1-yl thiazole-5-carboxylate (1.7 g, 7.80 mmol) in THF, and the resulting mixture was stirred at room temperature for 1 hours. The reaction mixture was then poured into water (5 ml) and extracted with ethyl acetate (20 ml×2) to remove impurity. The aqueous layer was adjusted pH 3-4 with hydrochloric acid (2N) and extracted with 10% methanol in dichloromethane (20 ml×5). The combined organic phases were dried over anhydrous sodium sulfate, and concentrated in vacuo to give crude (S)-2-(tert-butoxycarbonyl)-6-(thiazole-5-carbonyl)-2,6-diazaspiro[3.4]octane-8-carboxylic acid (2.4 g, yeild 84%) which was used in next step without further purification. LCMS: m/z 311.8 [M−56]⁺. ¹H NMR (400 MHz, CDCl₃): δ 8.97 (s, 1H), 8.27 (d, J=3.6 Hz, 1H), 4.12-4.18 (m, 3H), 3.75-4.05 (m, 6H), 3.22-3.27 (m, 1H), 1.44 (d, J=5.6 Hz, 9H).

Step 2: To a solution of (S)-2-(tert-butoxycarbonyl)-6-(thiazole-5-carbonyl)-2,6-diazaspiro[3.4]octane-8-carboxylic acid (2.4 g, 6.53 mmol) in dichloromethane (20 ml) was added hydrogen chloride in dioxane (4.0M, 20 ml). The resulting mixture was stirred at room temperature for 6 hours. The reaction mixture was concentrated in vacuo to give crude (S)-6-(thiazole-5-carbonyl)-2,6-diazaspiro[3.4]octane-8-carboxylic acid which was used in next step without further purification. LCMS: m/z 267.8 [M+H]⁺.

Step 3: To a solution of (S)-6-(thiazole-5-carbonyl)-2,6-diazaspiro[3.4]octane-8-carboxylic acid (crude) in water (20 ml) was added NaHCO₃ (2.7 g, 32.66 mmol), followed by dropwise addition of the solution of (S)-2,5-dioxopyrrolidin-1-yl 2,2-dimethylcyclopropanecarboxylate (1.3 g, 6.53 mmol) in THF, and the resulting mixture was stirred at room temperature for 1 hours. The reaction mixture was then poured into water (5 ml) and extracted with ethyl acetate (20 ml×2) to remove impurity. The aqueous layer was adjusted pH 3-4 with hydrochloric acid (2N) and extracted with 10% methanol in dichloromethane (20 ml×5). The combined organic phases were dried over anhydrous sodium sulfate, and concentrated in vacuo to give crude (S)-2-((S)-2,2-dimethylcyclopropanecarbonyl)-6-(thiazole-5-carbonyl)-2,6-diazaspiro[3.4]octane-8-carboxylic acid (1.6 g, yield 67% two steps) which was used in next step without further purification. LCMS: m/z 364.0 [M+H]⁺. ¹H NMR (400 MHz, CDCl₃): δ 8.96 (s, 1H), 8.28 (d, J=6.0 Hz, 1H), 3.83-4.49 (m, 9H), 3.26-3.31 (m, 1H), 1.16-1.18 (m, 7H), 0.81-0.84 (m, 1H).

Step 4: To a solution of crude (S)-2-((S)-2,2-dimethylcyclopropanecarbonyl)-6-(thiazole-5-carbonyl)-2,6-diazaspiro[3.4]octane-8-carboxylic acid (1.6 g, 4.35 mmol) in N,N-dimethylformamide (15 ml) was added (2S,3R)-2-amino-3-(cyclohexylmethoxy)-1-((S)-3-(methoxymethyl)piperidin-1-yl)butan-1-one hydrochloride (1.7 g, 4.79 mmol), N-ethyl-N-isopropylpropan-2-amine (2.3 ml, 13.06 mmol), and (2-(7-Aza-1H-benzotriazole-1-yl)-1,1,3,3-tetramethyluronium hexafluorophosphate) (2.2 g, 5.66 mmol). The resulting mixture was stirred at room temperature for 1 hour. The reaction mixture was then poured into water (30 ml) and extracted with ethyl acetate (30 ml×2). The combined organic phases were washed with brine (30 ml×2), dried over anhydrous sodium sulfate, and concentrated under reduced pressure to give a crude residue which was purified by column chromatography using 50% ethyl acetate/hexane with 10% methanol gradient to afford (S)—N-((2S,3R)-3-(cyclohexylmethoxy)-1-((S)-3-(methoxymethyl)piperidin-1-yl)-1-oxobutan-2-yl)-2-((S)-2,2-dimethylcyclopropanecarbonyl)-6-(thiazole-5-carbonyl)-2,6-diazaspiro[3.4]octane-8-carboxamide (I-196A) (1.9 g, yield 64%) as a white solid. LCMS: m/z 672.4 [M+H]$^+$ $^1$H NMR (400 MHz, CD$_3$OD): δ 9.18 (s, 1H), 8.39 (d, J=13.2 Hz, 1H), 4.95-4.99 (m, 1H), 3.84-4.43 (m, 11H), 3.71-3.76 (m, 1H), 3.38-3.49 (m, 3H), 3.20-3.28 (m, 5H), 2.91-2.96 (m, 1H), 2.64-2.72 (m, 1H), 1.68-1.83 (m, 8H), 1.41-1.53 (m, 3H), 1.13-1.21 (m, 12H), 1.05-1.08 (m, 1H), 0.91-0.99 (m, 2H), 0.79-0.84 (m, 1H).

Method 17B: Exemplified by the Synthesis of I-196B

I-196B was made by a similar process to Method 17A, starting from (R)-2-(tert-butoxycarbonyl)-2,6-diazaspiro[3.4]octane-8-carboxylic acid.

Method 18: Exemplified by the Synthesis of I-284

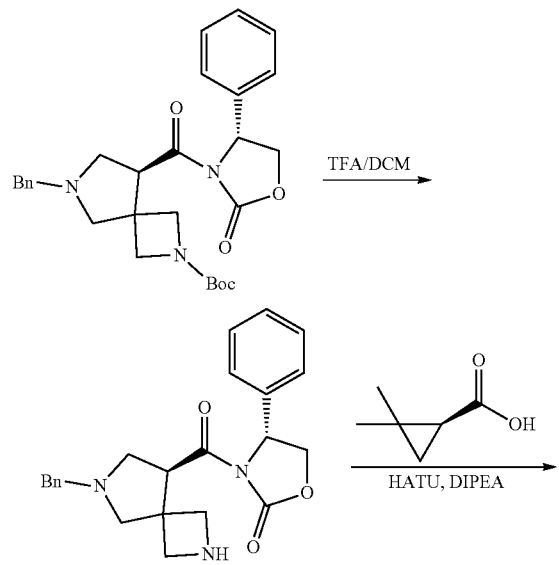

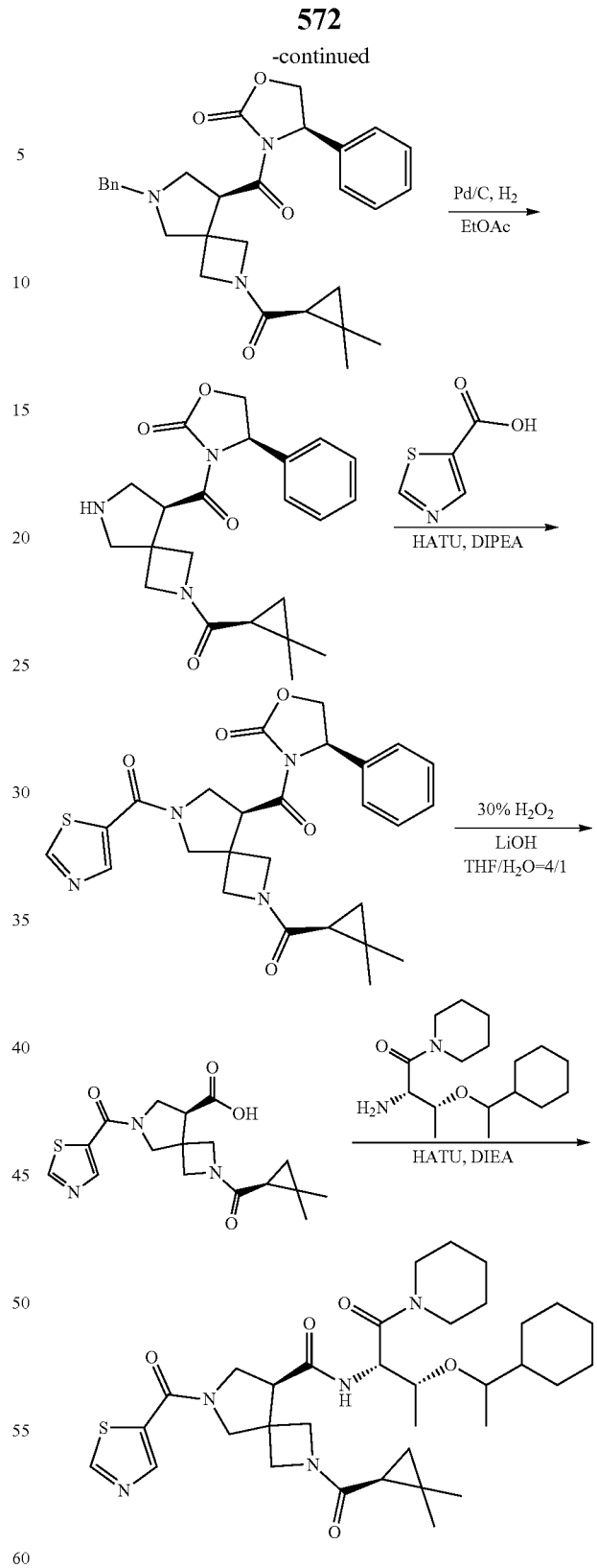

Step 1: To a solution of tert-butyl (S)-6-benzyl-8-((R)-2-oxo-4-phenyloxazolidine-3-carbonyl)-2,6-diazaspiro[3.4]octane-2-carboxylate (Intermediate 11) (1.1 g, 2.2 mmol) in DCM (4 mL) was added TFA (2 mL). The reaction mixture was stirred at room temperature for 2 h. The solvent was removed under vacuum to afford crude (R)-3-((S)-6-benzyl- 2,6-diazaspiro[3.4]octane-8-carbonyl)-4-phenyloxazolidin-2-one (876 mg, 100%) which was used directly in the next step.

Step 2: To a solution of (S)-2,2-dimethylcyclopropane-1-carboxylic acid (274 mg, 2.4 mmol) in DCM (10 mL) was added HATU (1.3 g, 3.3 mmol). The mixture was stirred at room temperature for 30 min. (S)-4-benzyl-3-((S)-6-benzyl-2,6-diazaspiro[3.4]octane-8-carbonyl)oxazolidin-2-one (876 mg, 2.2 mmol) and DIPEA (1.1 g, 8.8 mmol) were added and the reaction mixture stirred at room temperature for 4 h. The mixture was diluted with water (20 mL) and extracted with DCM (50 mL×2). The combined organic layers were washed with brine, dried over $Na_2SO_4$, filtered and concentrated. The crude was purified by column chromatography on silica gel (eluent: Pet. Ether:EtOAc=3:1 to DCM/EtOAc=3:1) to afford (R)-3-((S)-6-benzyl-2-((S)-2,2-dimethylcyclopropane-1-carbonyl)-2,6-diazaspiro[3.4]octane-8-carbonyl)-4-phenyloxazolidin-2-one (900 mg, 82%) as a yellow solid. LCMS m/z=488.1 [M+H]$^+$; $^1$H NMR (400 MHz, DMSO-d6) δ 7.44-7.24 (m, 10H), 5.53-5.46 (m, 1H), 4.78-4.71 (m, 1H), 4.50-3.48 (m, 9H), 3.21-2.53 (m, 3H), 1.39-1.32 (m, 1H), 1.28-1.22 (m, 2H), 1.10 (d, J=2.8 Hz, 3H), 1.03 (d, J=24.4 Hz, 3H), 0.87-0.82 (m, 1H), 0.71-0.64 (m, 1H).

Step 3: To a solution of (S)-4-benzyl-3-((S)-6-benzyl-2-((S)-2,2-dimethylcyclopropane-1-carbonyl)-2,6-diazaspiro[3.4]octane-8-carbonyl)oxazolidin-2-one (1.0 g, 2.1 mmol) in EtOAc (8 mL) was added 10% Pd/C (400 mg). The reaction mixture was stirred under a $H_2$ atmosphere for 24 h. Conversion was around 50%. The mixture was filtered through celite and concentrated. The residue was redissolved in EtOAc (8 mL) and another batch of 10% Pd/C (400 mg) was added. The reaction was stirred under $H_2$ atmosphere for another 24 h. The mixture was filtered and concentrated to afford (R)-3-((S)-2-((S)-2,2-dimethylcyclopropane-1-carbonyl)-2,6-diazaspiro[3.4]octane-8-carbonyl)-4-phenyloxazolidin-2-one (800 mg, 98%) which was used directly in the next step. LCMS m/z=398.1 [M+H]$^+$.

Step 4: To a solution of 1-benzyl-1H-pyrazole-4-carboxylic acid (1.63 g, 12.6 mmol) in DCM (50 mL) was added HATU (5.75 g, 15.1 mmol) and the mixture stirred at room temperature for 30 min. (S)-4-benzyl-3-((S)-2-((S)-2,2-dimethylcyclopropane-1-carbonyl)-2,6-diazaspiro[3.4]octane-8-carbonyl)oxazolidin-2-one (5 g, 12.6 mmol) and DIPEA (4.88 g, 37.8 mmol) were added and the reaction stirred at room temperature for another 3 h. The mixture was diluted with water (50 mL), extracted with DCM (150 mL×2) and the combined organic layers washed with brine, dried over $Na_2SO_4$ and filtered. The solvent was removed and the residue purified by column chromatography on silica gel (eluent: DCM:MeOH=30:1) to afford the (R)-3-((S)-2-((S)-2,2-dimethylcyclopropane-1-carbonyl)-6-(thiazole-5-carbonyl)-2,6-diazaspiro[3.4]octane-8-carbonyl)-4-phenyloxazolidin-2-one (4.2 g, 66%) as a yellow solid. LCMS m/z=509.2 [M+H]$^+$; $^1$H NMR (400 MHz, DMSO-d$_6$) δ 8.44-8.28 (m, 1H), 7.88-7.76 (m, 1H), 7.40-7.18 (m, 10H), 5.36 (d, J=4.4 Hz, 2H), 4.70-4.60 (m, 1H), 4.40-4.23 (m, 4H), 4.21-4.01 (m, 3H), 3.97-3.56 (m, 5H), 3.18-2.84 (m, 3H), 1.42-1.33 (m, 1H), 1.28-1.21 (m, 5H), 1.14-1.02 (m, 7H), 0.86 (d, J=7.2 Hz, 1H), 0.69 (d, J=6.4 Hz, 1H).

Step 5: To a solution of (S)-4-benzyl-3-((S)-6-(1-benzyl-1H-pyrazole-4-carbonyl)-2-((S)-2,2-dimethylcyclopropane-1-carbonyl)-2,6-diazaspiro[3.4]octane-8-carbonyl)oxazolidin-2-one (1 g, 2 mmol) in a mixture of THF/$H_2O$ (8 mL/1 mL) at 0° C. was added a solution of lithium hydroxide monohydrate (168 mg, 4 mmol) in $H_2O$ (0.5 mL) and 30% $H_2O_2$ (567 mL, 567 mmol) in $H_2O$ (0.5 mL). The reaction mixture was stirred at 0° C. for 1 h then diluted with water (20 mL) and extracted with EtOAc (30 mL). The aqueous layer was collected and acidified with 1M HCl to pH ~ 2 and extracted with EtOAc (60 mL×3). The combined organic layers were washed with brine, dried over $Na_2SO_4$, filtered and concentrated to afford crude (S)-2-((S)-2,2-dimethylcyclopropane-1-carbonyl)-6-(thiazole-5-carbonyl)-2,6-diazaspiro[3.4]octane-8-carboxylic acid (438 mg, 61%) as a yellow solid which was used directly in the next step. LCMS m/z=364.1 [M+H]$^+$; $^1$H NMR (400 MHz, DMSO-d6) δ 9.26 (s, 1H), 8.42-8.35 (m, 1H), 4.37-3.70 (m, 9H), 1.39-1.36 (m, 2H), 1.15-1.01 (m, 6H), 0.90-0.84 (m, 1H), 0.73-0.64 (m, 1H).

Step 6: To a solution of (S)-2-((S)-2,2-dimethylcyclopropane-1-carbonyl)-6-(thiazole-5-carbonyl)-2,6-diazaspiro[3.4]octane-8-carboxylic acid (44 mg, 0.12 mmol) in DCM (1 mL) was added HATU (42 mg, 0.11 mmol) and the mixture was stirred at room temperature for 30 min. (2S,3R)-2-amino-3-(1-cyclohexylethoxy)-1-(piperidin-1-yl)butan-1-one (30 mg, 0.10 mmol) and DIPEA (39 mg, 0.30 mmol) were then added and the reaction mixture stirred at room temperature for 2 h. The mixture was diluted with water (10 mL) and extracted with DCM (30 mL×2). The combined organic layers were washed with brine, dried over $Na_2SO_4$ and filtered. The solvent was removed and the crude was purified by prep-HPLC to afford (8S)—N-((2S,3R)-3-(1-cyclohexylethoxy)-1-oxo-1-(piperidin-1-yl)butan-2-yl)-2-((S)-2,2-dimethylcyclopropane-1-carbonyl)-6-(thiazole-5-carbonyl)-2,6-diazaspiro[3.4]octane-8-carboxamide (I-284) (16 mg, 25%) as a white solid. LCMS m/z=642.5 [M+H]$^+$; H NMR (400 MHz, DMSO-d$_6$) δ 9.25 (s, 1H), 8.40-8.24 (m, 2H), 4.83 (s, 1H), 4.20-3.64 (m, 9H), 3.53-3.45 (m, 5H), 3.25-3.16 (m, 1H), 1.66-1.29 (m, 13H), 1.12-0.86 (m, 18H), 0.67 (s, 1H).

Method 19: Exemplified by the Synthesis of I-291

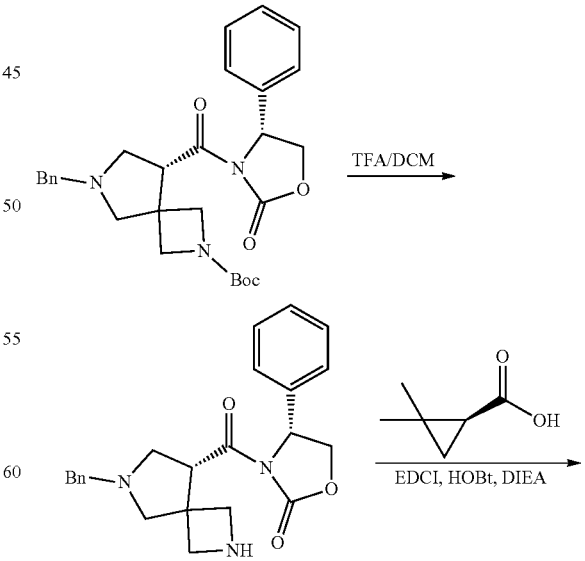

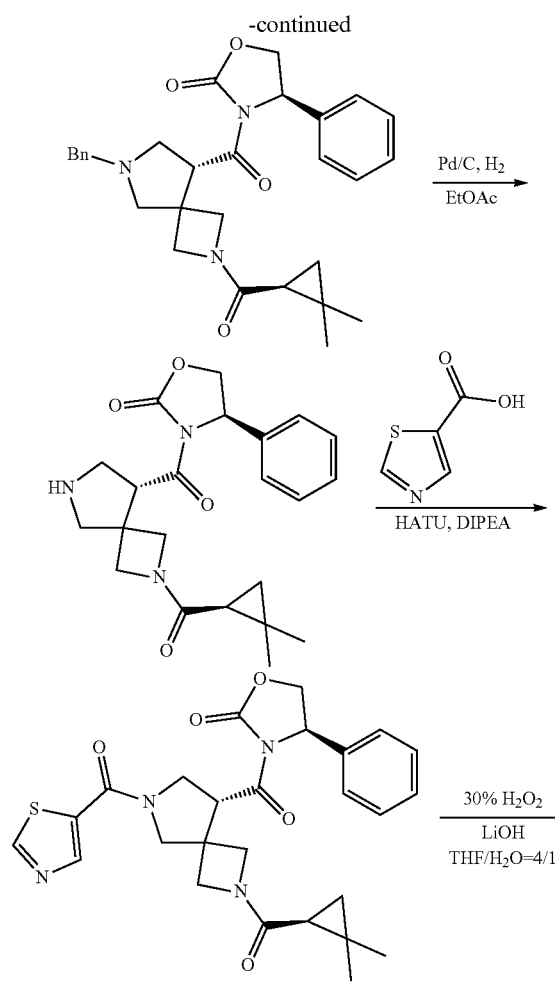
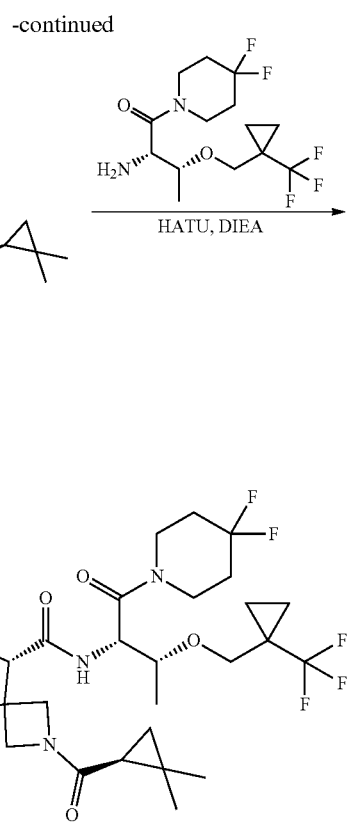
I-291 was made by a similar process to Method 18, starting from Intermediate 12.
Method 20: Exemplified by the Synthesis of I-294
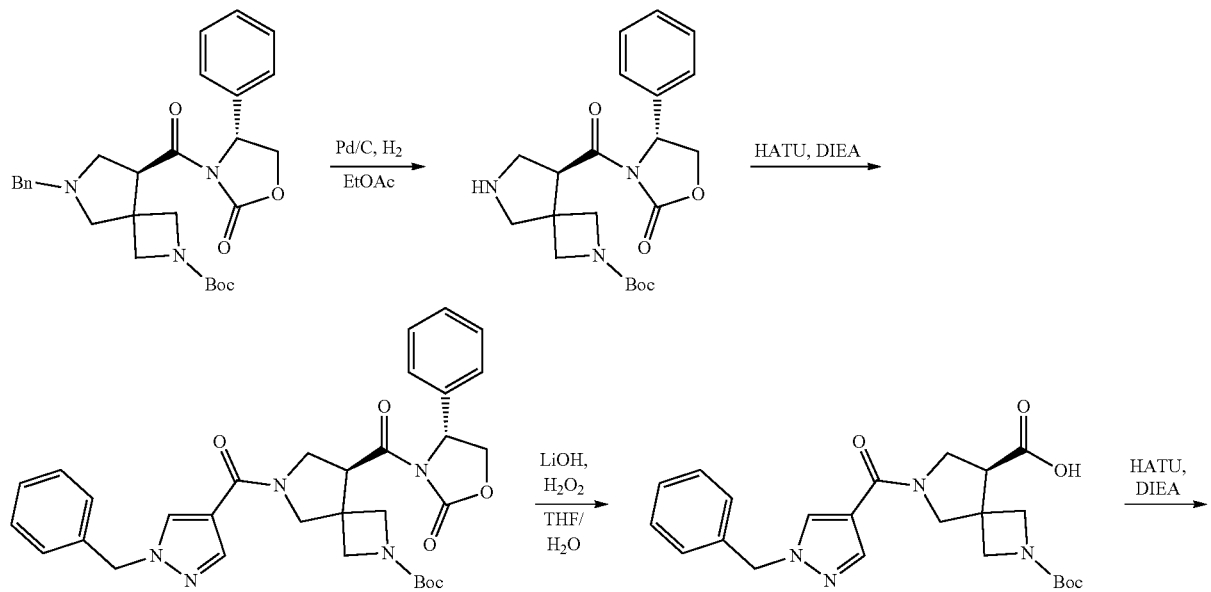

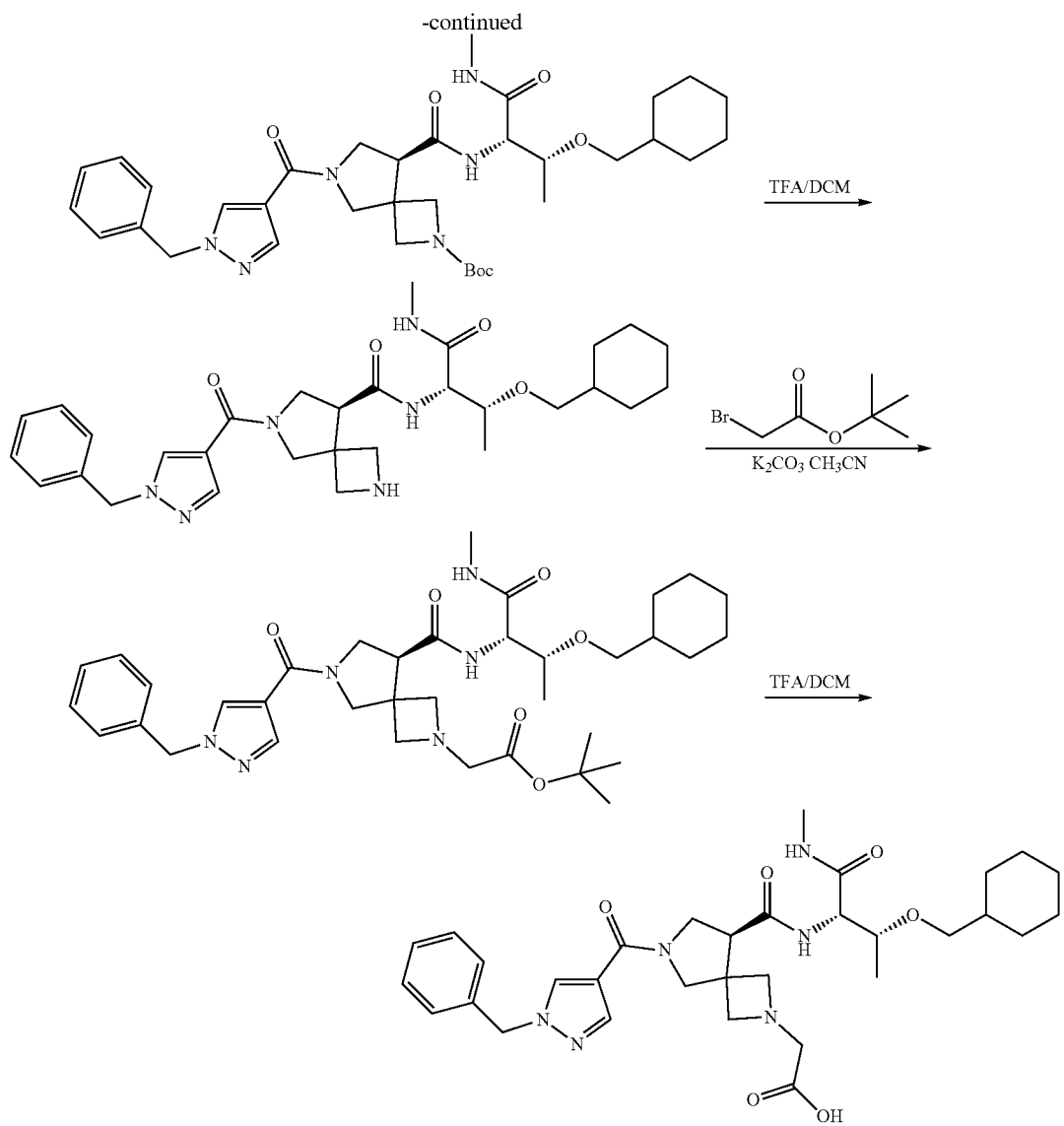

Step 1: To a solution of tert-butyl (S)-6-benzyl-8-((R)-2-oxo-4-phenyloxazolidine-3-carbonyl)-2,6-diazaspiro[3.4]octane-2-carboxylate (Intermediate 11) (1 g, 2.0 mmol) in EtOAc (10 mL) was added 10% Pd/C (300 mg). The reaction mixture was stirred under a $H_2$ atmosphere for 48 h. The mixture was filtered and concentrated to afford crude tert-butyl (S)-8-((R)-2-oxo-4-phenyloxazolidine-3-carbonyl)-2,6-diazaspiro[3.4]octane-2-carboxylate (800 mg, 100%) which was used directly in the next step without further purification. LCMS m/z=402.2 [M+H]$^+$.

Step 2: To a solution of 1-benzyl-1H-pyrazole-4-carboxylic acid (2.2 g, 11.0 mmol) in DCM (40 mL) was added HATU (4.79 g, 12.6 mmol) and the mixture was stirred at room temperature for 30 min. tert-butyl (S)-8-((R)-2-oxo-4-phenyloxazolidine-3-carbonyl)-2,6-diazaspiro[3.4]octane-2-carboxylate (4.2 g, 10.5 mmol) and DIPEA (2.03 g, 15.75 mmol) were added and the reaction stirred at room temperature for another 2 h. The mixture was diluted with water (100 mL) and extracted with EtOAc (150 mL×3). The combined organic layers were washed with brine, dried over $Na_2SO_4$, filtered and concentrated. The residue obtained was purified by column chromatography on silica gel (eluent: DCM:MeOH=30:1) to afford tert-butyl (S)-6-(1-benzyl-1H-pyrazole-4-carbonyl)-8-((R)-2-oxo-4-phenyloxazolidine-3-carbonyl)-2,6-diazaspiro[3.4]octane-2-carboxylate (4.7 g, 77%) as a yellow solid. LCMS m/z=586.3 [M+H]$^+$.

Step 3: To a solution of tert-butyl (S)-6-(1-benzyl-1H-pyrazole-4-carbonyl)-8-((R)-2-oxo-4-phenyloxazolidine-3-carbonyl)-2,6-diazaspiro[3.4]octane-2-carboxylate (100 mg, 0.17 mmol) in a mixture of THF and $H_2O$ (3 mL/0.25 mL) at 0° C. was added a solution of lithium hydroxide monohydrate (10 mg, 0.43 mmol) in water (0.25 mL) and 30% $H_2O_2$ (12 mg, 0.34 mmol) in water (0.25 mL). The reaction mixture was stirred at 0° C. for 1 h then diluted with water (15 mL) and extracted with EtOAc (30 mL). The aqueous layer was collected and acidified with 1M HCl to pH ~ 2 and extracted with EtOAc (80 mL×3). The combined organic layers were washed with brine, dried over $Na_2SO_4$, filtered and concentrated to afford crude (S)-6-(1-benzyl-1H-pyrazole-4-carbonyl)-2-(tert-butoxycarbonyl)-2,6-diazaspiro[3.4]octane-8-carboxylic acid (50 mg, 66%) as a white solid which was used directly in the next step. LCMS m/z=441.2 [M+H]$^+$.

Step 4: To a solution of (S)-6-(1-benzyl-1H-pyrazole-4-carbonyl)-2-(tert-butoxycarbonyl)-2,6-diazaspiro[3.4]octane-8-carboxylic acid (100 mg, 0.227 mmol) in DCM (2 mL) was added HATU (103 mg, 0.272 mmol) and the mixture was stirred at room temperature for 30 min. (2S, 3R)-2-amino-3-(cyclohexylmethoxy)-N-methylbutanamide hydrochloride (52 mg, 0.227 mmol) and DIPEA (117 mg, 0.908 mmol) were added and the reaction stirred at room temperature for another 2 h. The mixture was diluted with water (30 mL) and extracted with EtOAc (50 mL×3). The combined organic layers were washed with brine, dried over Na$_2$SO$_4$, filtered and concentrated. The residue obtained was purified by column chromatography on silica gel (eluent: DCM:MeOH=30:1) to afford tert-butyl (S)-6-(1-benzyl-1H-pyrazole-4-carbonyl)-8-(((2S,3R)-3-(cyclohexylmethoxy)-1-(methylamino)-1-oxobutan-2-yl)carbamoyl)-2,6-diazaspiro[3.4]octane-2-carboxylate (114 mg, 78%) as a yellow solid. LCMS m/z=651.4 [M+H]$^+$.

Step 5: To a solution of (S)-6-(1-benzyl-1H-pyrazole-4-carbonyl)-8-(((2S,3R)-3-(cyclohexylmethoxy)-1-(methylamino)-1-oxobutan-2-yl)carbamoyl)-2,6-diazaspiro[3.4]octane-2-carboxylate (50 mg, 0.077 mmol) in DCM (2 mL) was added TFA (1 mL). The reaction mixture was stirred at room temperature for 1 h. The solvent was removed under vacuum to afford (S)-6-(1-benzyl-1H-pyrazole-4-carbonyl)-N-((2S,3R)-3-(cyclohexylmethoxy)-1-(methylamino)-1-oxobutan-2-yl)-2,6-diazaspiro[3.4]octane-8-carboxamide (42 mg, 100%) which was used directly in the next step. LCMS m/z=551.3 [M+H]$^+$.

Step 6: To a solution of (S)-6-(1-benzyl-1H-pyrazole-4-carbonyl)-N-((2S,3R)-3-(cyclohexylmethoxy)-1-(methylamino)-1-oxobutan-2-yl)-2,6-diazaspiro[3.4]octane-8-carboxamide (85 mg, 1.54 mmol) in CH$_3$CN (2 mL) was added tert-butyl 2-bromoacetate (30 mg, 1.54 mmol) and K$_2$CO$_3$ (85 mg, 6.17 mmol). The mixture was stirred at room temperature overnight. The mixture was diluted with water (20 mL) and extracted with EtOAc (50 mL×2). The combined organic layers were washed with brine, dried over Na$_2$SO$_4$, filtered and concentrated. The residue obtained was purified by prep-TLC (eluent: DCM/MeOH=30:1) to afford tert-butyl 2-((S)-6-(1-benzyl-1H-pyrazole-4-carbonyl)-8-(((2S,3R)-3-(cyclohexylmethoxy)-1-(methylamino)-1-oxobutan-2-yl)carbamoyl)-2,6-diazaspiro[3.4]octan-2-yl)acetate (25 mg, 24%) as a colorless oil. LCMS m/z=665.50 [M+H]$^+$.

Step 7: To a solution of tert-butyl 2-((S)-6-(1-benzyl-1H-pyrazole-4-carbonyl)-8-(((2S,3R)-3-(cyclohexylmethoxy)-1-(methylamino)-1-oxobutan-2-yl)carbamoyl)-2,6-diazaspiro[3.4]octan-2-yl)acetate (25 mg, 0.37 mmol) in DCM (0.6 mL) was added TFA (0.2 mL). The mixture was stirred at room temperature for 2 h. The solvent was removed under vacuum. The residue was purified by prep-HPLC to afford 2-((S)-6-(1-benzyl-1H-pyrazole-4-carbonyl)-8-(((2S,3R)-3-(cyclohexylmethoxy)-1-(methylamino)-1-oxobutan-2-yl)carbamoyl)-2,6-diazaspiro[3.4]octan-2-yl)acetic acid (I-294) (11 mg, 50%) as a white solid. LCMS m/z=609.4 [M+H]$^+$; $^1$H NMR (400 MHz, DMSO-d6) δ 8.36-8.28 (m, 1H), 8.15-8.06 (m, 1H), 7.83-7.74 (m, 2H), 7.38-7.23 (m, 5H), 5.38-5.33 (m, 2H), 4.27-4.20 (m, 1H), 4.06-3.99 (m, 1H), 3.92-3.44 (m, 11H), 3.38-3.32 (m, 3H), 3.26-3.21 (m, 1H), 3.14-3.09 (m, 1H), 2.60-2.55 (m, 3H), 1.70-1.58 (m, 5H), 1.49-1.38 (m, 1H), 1.20-1.04 (m, 6H), 0.89-0.79 (m, 2H).

Method 21: Exemplified by the Synthesis of I-268

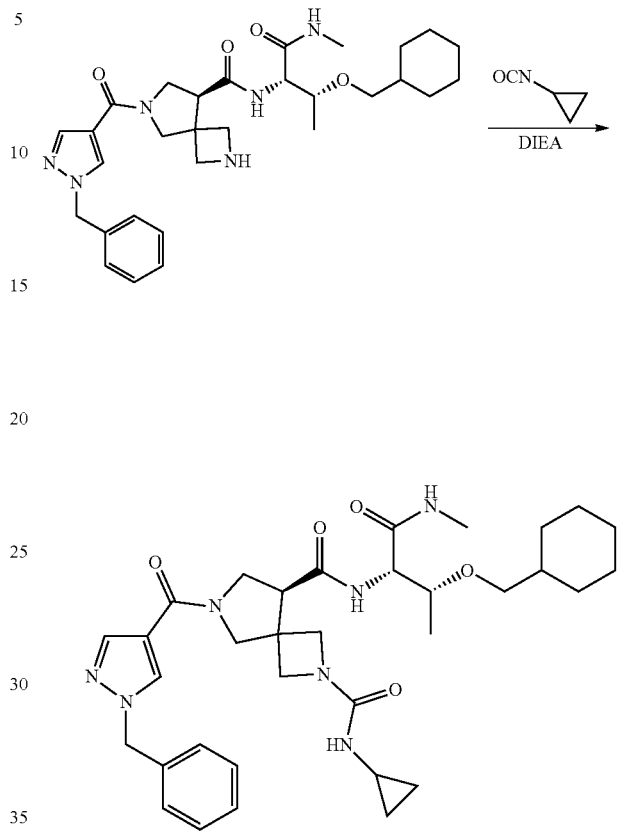

To a solution of (S)-6-(1-benzyl-1H-pyrazole-4-carbonyl)-N-((2S,3R)-3-(cyclohexylmethoxy)-1-(methylamino)-1-oxobutan-2-yl)-2,6-diazaspiro[3.4]octane-8-carboxamide (See Method 20-Step 5) (42 mg, mmol) in THF (1 mL) was added cyclopropylisocyanate (6 mg, 0.076 mmol) and DIEA (29 mg, 0.229 mmol). The mixture was stirred at room temperature for 2 h. The solvent was removed under vacuum and the residue purified by prep-HPLC to afford (S)-6-(1-benzyl-1H-pyrazole-4-carbonyl)-N8-((2S,3R)-3-(cyclohexylmethoxy)-1-(methylamino)-1-oxobutan-2-yl)-N2-cyclopropyl-2,6-diazaspiro[3.4]octane-2,8-dicarboxamide (25 mg, 51%) as a white solid. LCMS m/z=634.3 [M+H]$^+$; $^1$H NMR (400 MHz, DMSO-d$_6$) δ 8.38-8.33 (m, 1H), 8.15-8.11 (m, 1H), 7.83-7.70 (m, 2H), 7.37-7.25 (m, 5H), 6.43 (d, J=3.2 Hz, 1H), 5.35 (s, 2H), 4.26-4.24 (m, 1H), 3.98-3.71 (m, 6H), 3.67-3.57 (m, 3H), 3.55-3.45 (m, 1H), 3.26-3.22 (m, 1H), 3.12-3.08 (m, 1H), 2.59-2.55 (m, 3H), 2.42-2.39 (m, 1H), 1.68-1.63 (m, 5H), 1.45-1.43 (m, 1H), 1.19-1.09 (m, 3H), 1.04-1.01 (m, 3H), 0.87-0.81 (m, 2H), 0.54-0.51 (m, 2H), 0.33-0.32 (m, 2H).

Method 22: Exemplified by the Synthesis of I-274

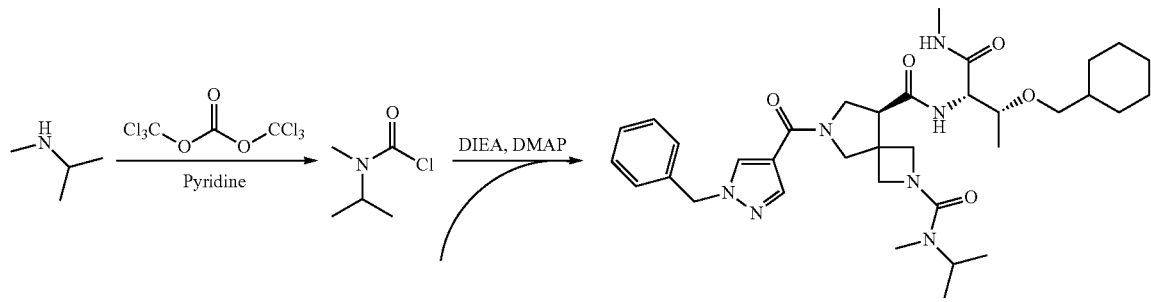

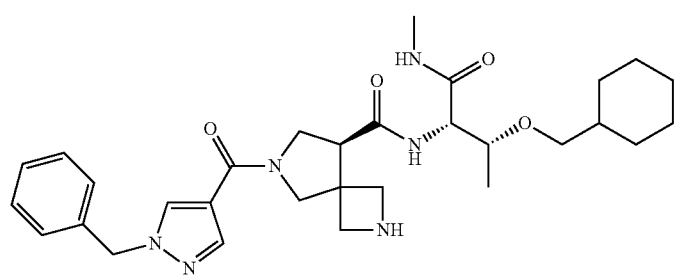

Step 1: To a solution of N-methylpropan-2-amine (100 mg, 1.37 mmol) and pyridine (215.2 mg, 2.72 mmol) in anhydrous THF (4 mL) at 0° C. was added a solution of triphosgene (202 mg, 0.68 mmol) in anhydrous THF (4 mL). The reaction mixture was stirred at room temperature for 3.5 h. The solvent was then removed under vacuum. The residue was diluted with 0.1 N HCl (20 mL) and extracted with EtOAc (10 mL×3). The combined organic layers were dried over Na$_2$SO$_4$, filtered and concentrated to afford crude isopropyl(methyl)carbamic chloride (110 mg, 59%) which was used directly in the next step. $^1$H NMR (400 MHz, DMSO-d$_6$) δ 3.16 (p, J=6.4 Hz, 1H), 2.45 (s, 3H), 1.22 (d, J=6.4 Hz, 6H).

Step 2: To a solution of (S)-6-(1-benzyl-1H-pyrazole-4-carbonyl)-N-((2S,3R)-3-(cyclohexylmethoxy)-1-(methylamino)-1-oxobutan-2-yl)-2,6-diazaspiro[3.4]octane-8-carboxamide (See Method 20-Step 5) (50 mg, 0.09 mmol), DIEA (23.5 mg, 0.18 mmol) and DMAP (1.0 mg, 0.009 mmol), in anhydrous DCM (0.5 mL) at 0° C., was added a solution of isopropyl(methyl)carbamic chloride (18.3 mg, 0.136 mmol) in anhydrous DCM (0.5 mL). The reaction mixture was stirred at room temperature for 2 h then the solvent was removed under vacuum. The residue was purified by prep-HPLC to afford (S)-6-(1-benzyl-1H-pyrazole-4-carbonyl)-N8-((2S,3R)-3-(cyclohexylmethoxy)-1-(methylamino)-1-oxobutan-2-yl)-N2-isopropyl-N2-methyl-2,6-diazaspiro[3.4]octane-2,8-dicarboxamide (35 mg, 43%). LCMS m/z=650.50 [M+1]$^+$; $^1$H NMR (400 MHz, DMSO-d$_6$) δ 8.35 (d, J=21.4 Hz, 1H), 8.14 (t, J=7.0 Hz, 1H), 7.81 (d, J=16.4 Hz, 1H), 7.75-7.66 (m, 1H), 7.44-7.19 (m, 5H), 5.35 (d, J=2.2 Hz, 2H), 4.27 (dd, J=8.8, 3.4 Hz, 1H), 4.13-3.95 (m, 3H), 3.94-3.87 (m, 1H), 3.86-3.73 (m, 3H), 3.73-3.63 (m, 2H), 3.62-3.52 (m, 1H), 3.49-3.34 (m, 1H), 3.27-3.18 (m, 1H), 3.10 (dd, J=9.2, 6.8 Hz, 1H), 2.57 (dd, J=13.8, 3.4 Hz, 6H), 1.63 (q, J=13.8, 12.6 Hz, 5H), 1.42 (d, J=10.2 Hz, 1H), 1.21-1.08 (m, 3H), 1.05-0.98 (m, 9H), 0.84 (t, J=11.8 Hz, 2H).

Method 23: Exemplified by the Synthesis of I-269

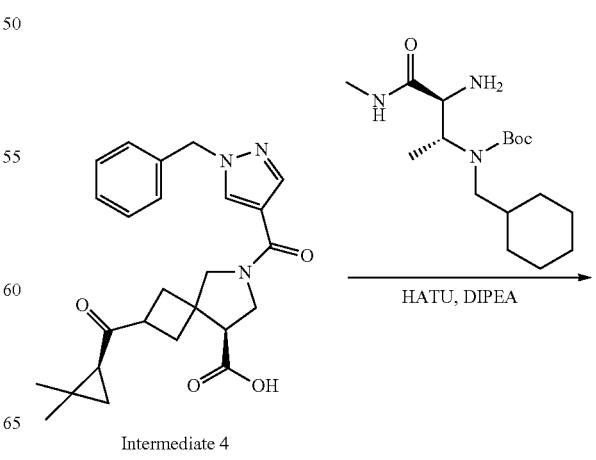

Intermediate 4

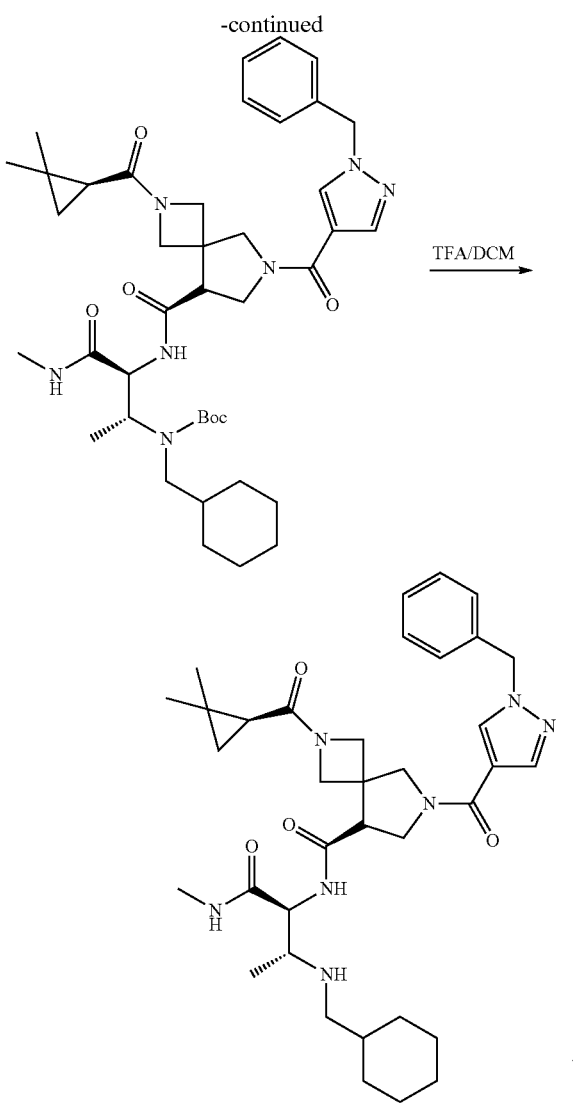

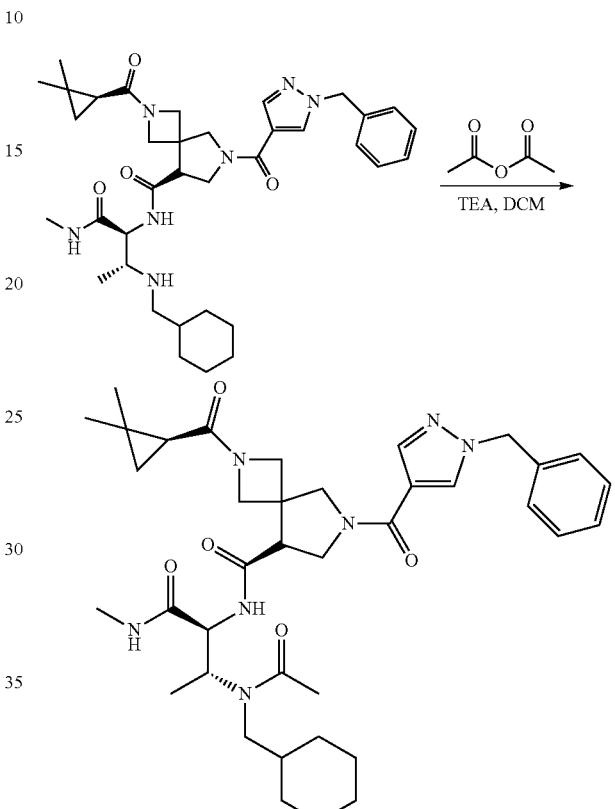

4.81-4.72 (m, 1H), 4.23-3.94 (m, 4H), 3.86-3.63 (m, 4H), 3.29-3.15 (m, 2H), 2.95-2.75 (m, 2H), 2.68-2.63 (m, 2H), 2.60 (d, J=4.6 Hz, 1H), 1.82-1.56 (m, 6H), 1.38-1.31 (m, 1H), 1.24-1.12 (m, 6H), 1.12-1.04 (m, 6H), 1.01-0.92 (m, 2H), 0.89-0.84 (m, 1H), 0.74-0.65 (m, 1H).

Method 24: Exemplified by the Synthesis of I-273

Step 1: tert-butyl ((2R,3S)-3-((S)-6-(1-benzyl-1H-pyrazole-4-carbonyl)-2-((S)-2,2-dimethylcyclopropane-1-carbonyl)-2,6-diazaspiro[3.4]octane-8-carboxamido)-4-(methylamino)-4-oxobutan-2-yl)(cyclohexylmethyl)carbamate was synthesized from (S)-6-(1-benzyl-1H-pyrazole-4-carbonyl)-2-((S)-2,2-dimethylcyclopropane-1-carbonyl)-2,6-diazaspiro[3.4]octane-8-carboxylic acid (Intermediate 4) and tert-butyl ((2R,3S)-3-amino-4-(methylamino)-4-oxobutan-2-yl)(cyclohexylmethyl)carbamate according to the procedures outlined in Method 2A using the appropriate commercially available reagents and/or intermediates described elsewhere. LCMS m/z=746.4 [M+H]+.

Step 2: (S)-6-(1-benzyl-1H-pyrazole-4-carbonyl)-N-((2S,3R)-3-((cyclohexylmethyl)amino)-1-(methylamino)-1-oxobutan-2-yl)-2-((S)-2,2-dimethylcyclopropane-1-carbonyl)-2,6-diazaspiro[3.4]octane-8-carboxamide (I-269) was synthesized from tert-butyl ((2R,3S)-3-((S)-6-(1-benzyl-1H-pyrazole-4-carbonyl)-2-((S)-2,2-dimethylcyclopropane-1-carbonyl)-2,6-diazaspiro[3.4]octane-8-carboxamido)-4-(methylamino)-4-oxobutan-2-yl)(cyclohexylmethyl) carbamate via deprotection using the appropriate commercially available reagents. LCMS m/z=646.5; 1H NMR (400 MHz, DMSO-d6) δ 8.78-8.70 (m, 1H), 8.41-8.31 (m, 3H), 7.87-7.78 (m, 1H), 7.40-7.23 (m, 5H), 5.36 (s, 2H), To a solution of (S)-6-(1-benzyl-1H-pyrazole-4-carbonyl)-N-((2S,3R)-3-((cyclohexylmethyl)amino)-1-(methylamino)-1-oxobutan-2-yl)-2-((S)-2,2-dimethylcyclopropane-1-carbonyl)-2,6-diazaspiro[3.4]octane-8-carboxamide (I-269, Method 23) (50 mg, 0.077 mmol) in DCM (5 mL) was added TEA (16 mg, 0.154 mmol) and acetic anhydride (12 mg, 0.116 mmol). The reaction mixture was stirred at room temperature for 2 h. The mixture was diluted with water (20 mL) and extracted with DCM (50 mL×2). The combined organic layers were washed with brine, dried over Na2SO4, filtered and concentrated. The residue was purified by prep-TLC (eluent: DCM/MeOH=15/1, v/v) to afford (S)-6-(1-benzyl-1H-pyrazole-4-carbonyl)-N-((2S,3R)-3-(N-(cyclohexylmethyl)acetamido)-1-(methylamino)-1-oxobutan-2-yl)-2-((S)-2,2-dimethylcyclopropane-1-carbonyl)-2,6-diazaspiro[3.4]octane-8-carboxamide (I-273) (20 mg, 40%) as a white solid. LCMS m/z=688.5 [M+H]+; 1H NMR (400 MHz, DMSO-d6) δ 8.70-8.50 (m, 1H), 8.39-8.28 (m, 1H), 8.16-8.07 (m, 1H), 7.86-7.77 (m, 1H), 7.38-7.22 (m, 5H), 5.35 (s, 2H), 4.72-4.43 (m, 1H), 4.25-3.52 (m, 10H), 3.26-3.10 (m, 1H), 3.08-3.00 (m, 1H), 2.64-2.53 (m, 3H), 2.13 (d, J=2.8 Hz, 1H), 1.99-1.89 (m, 2H), 1.72-1.53 (m, 6H), 1.41-1.32 (m, 1H), 1.24-1.22 (m, 1H), 1.19-1.14 (m, 3H), 1.12-1.02 (m, 8H), 0.93-0.78 (m, 3H), 0.71-0.63 (m, 1H).

Method 25: Exemplified by the Synthesis of I-199

Method 26A: Exemplified by the Synthesis of I-139

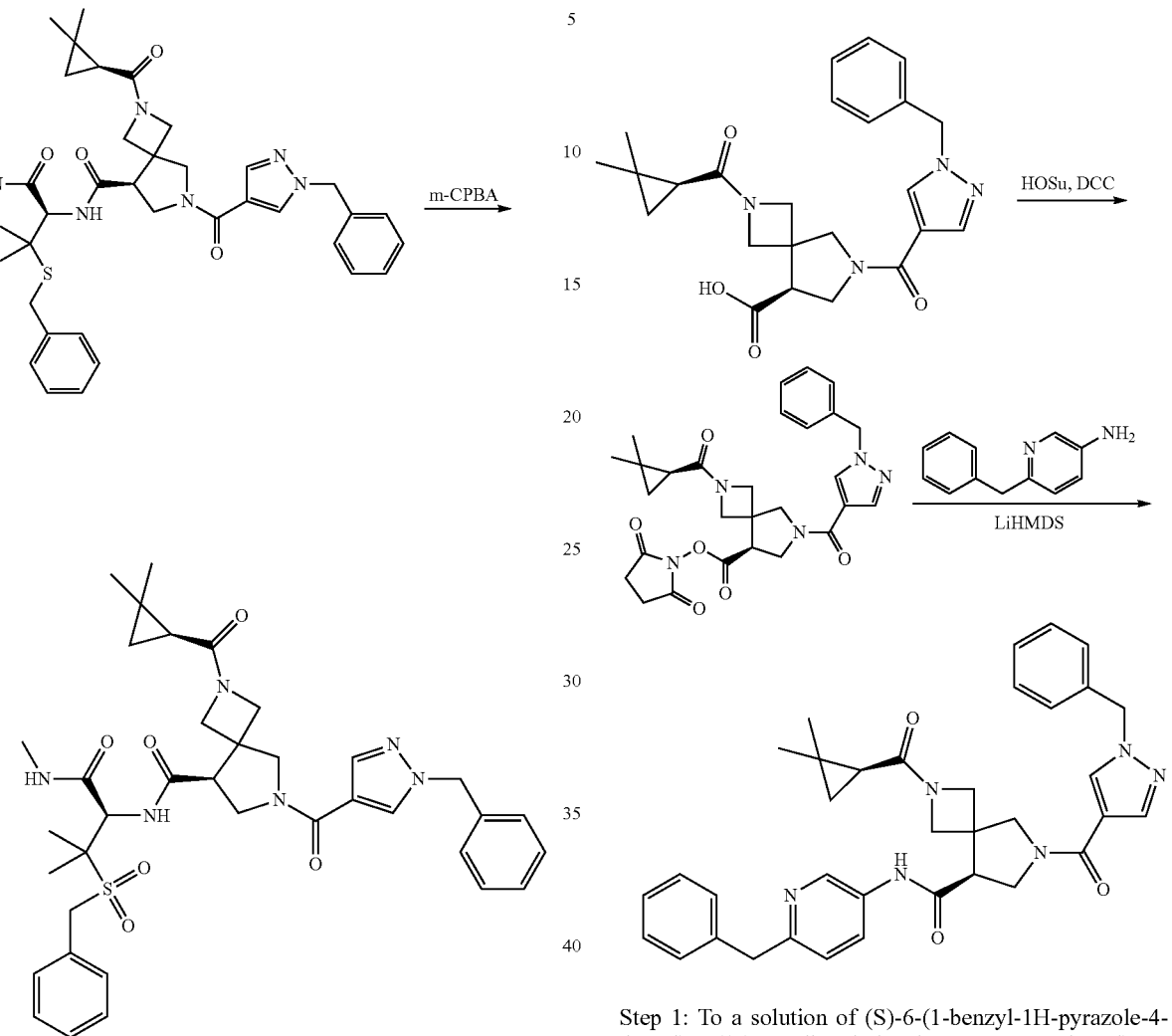

To a solution of (S)-6-(1-benzyl-1H-pyrazole-4-carbonyl)-N—((R)-3-(benzylthio)-3-methyl-1-(methylamino)-1-oxobutan-2-yl)-2-((S)-2,2-dimethylcyclopropane-1-carbonyl)-2,6-diazaspiro[3.4]octane-8-carboxamide (I-171A) (40 mg, 0.06 mmol) in DCM (2 mL) was added m-CPBA (31 mg, 0.18 mmol) under $N_2$ at 0° C. The reaction mixture was then stirred at room temperature for 8 h. The solvent was removed under vacuum and the residue purified by prep-HPLC to afford (S)-6-(1-benzyl-1H-pyrazole-4-carbonyl)-N—((R)-3-(benzylsulfonyl)-3-methyl-1-(methylamino)-1-oxobutan-2-yl)-2-((S)-2,2-dimethylcyclopropane-1-carbonyl)-2,6-diazaspiro[3.4]octane-8-carboxamide (I-199) (29 mg, 69%) as a white solid. LCMS m/z=703.40 [M+H]+; $^1$H NMR (400 MHz, DMSO-$d_6$) δ 8.79 (t, J=8.8 Hz, 1H), 8.47-8.27 (m, 2H), 7.82 (dd, J=25.8, 8.2 Hz, 1H), 7.39-7.07 (m, 10H), 5.38-5.30 (m, 2H), 5.20-5.11 (m, 1H), 4.71 (t, J=12.8 Hz, 1H), 4.20 (dd, J=42.4, 10.8 Hz, 2H), 4.11-4.00 (m, 2H), 3.88 (s, 1H), 3.78 (m, 3H), 3.56 (m, 1H), 3.46-3.33 (m, 1H), 2.62 (m, 3H), 1.48 (d, J=11.8 Hz, 3H), 1.39 (s, 3H), 1.35 (t, J=7.2 Hz, 1H), 1.11 (t, J=6.0 Hz, 3H), 1.05 (t, J=4.2 Hz, 3H), 0.90-0.83 (m, 1H), 0.72-0.65 (m, 1H).

Step 1: To a solution of (S)-6-(1-benzyl-1H-pyrazole-4-carbonyl)-2-((S)-2,2-dimethylcyclopropane-1-carbonyl)-2,6-diazaspiro[3.4]octane-8-carboxylic acid (Intermediate 4) 45 mg, 0.103 mmol) in dry THF (1 mL) were added HOSu (18 mg, 0.155 mmol) and DCC (25.5 mg, 0.124 mmol) at 0° C. The mixture was stirred at room temperature overnight under a $N_2$ atmosphere. The mixture was filtered through celite and the filtrate concentrated in vacuo to afford 2,5-dioxopyrrolidin-1-yl (S)-6-(1-benzyl-1H-pyrazole-4-carbonyl)-2-((S)-2,2-dimethylcyclopropane-1-carbonyl)-2,6-diazaspiro[3.4]octane-8-carboxylate, which was used directly for the next step. LCMS m/z=534.1 [M+H]+.

Step 2: To a solution of 6-benzylpyridin-3-amine (19 mg, 0.103 mmol) in dry THF (1 mL) was added LiHMDS (26 mg, 0.155 mmol) and the reaction mixture was stirred at room temperature for 0.5 h. A solution of 2,5-dioxopyrrolidin-1-yl (S)-6-(1-benzyl-1H-pyrazole-4-carbonyl)-2-((S)-2,2-dimethylcyclopropane-1-carbonyl)-2,6-diazaspiro[3.4]octane-8-carboxylate (55 mg, 0.103 mmol) in dry THF (1 mL) was then added and the resulting mixture was stirred at room temperature for 6 h. The solvent was removed and the residue purified by prep-HPLC to afford (S)-6-(1-benzyl-1H-pyrazole-4-carbonyl)-N-(6-benzylpyridin-3-yl)-2-((S)-2,2-dimethylcyclopropane-1-carbonyl)-2,6-diazaspiro[3.4]octane-8-carboxamide (3.4 mg, 5%) as an off-white solid.

LCMS m/z=603.0 [M+H]⁺; ¹H NMR (400 MHz, DMSO-d₆) δ 8.66-8.60 (m, 1H), 8.26-8.18 (m, 2H), 7.95-7.89 (m, 2H), 7.36-7.19 (m, 10H), 5.39-5.37 (m, 2H), 4.44-4.14 (m, 3H), 4.12-3.76 (m, 7H), 3.48-3.35 (m, 1H), 1.41-1.33 (m, 1H), 1.20-1.13 (m, 2H), 1.11-1.09 (m, 2H), 1.01-0.96 (m, 1H), 0.90-0.84 (m, 2H), 0.77-0.71 (m, 1H).

Method 26B: Exemplified by the Synthesis of I-168

I-168 was made by a similar process to Method 26A, starting from Intermediate 3, in place of Intermediate 4.

Method 27: Exemplified by the Synthesis of I-301

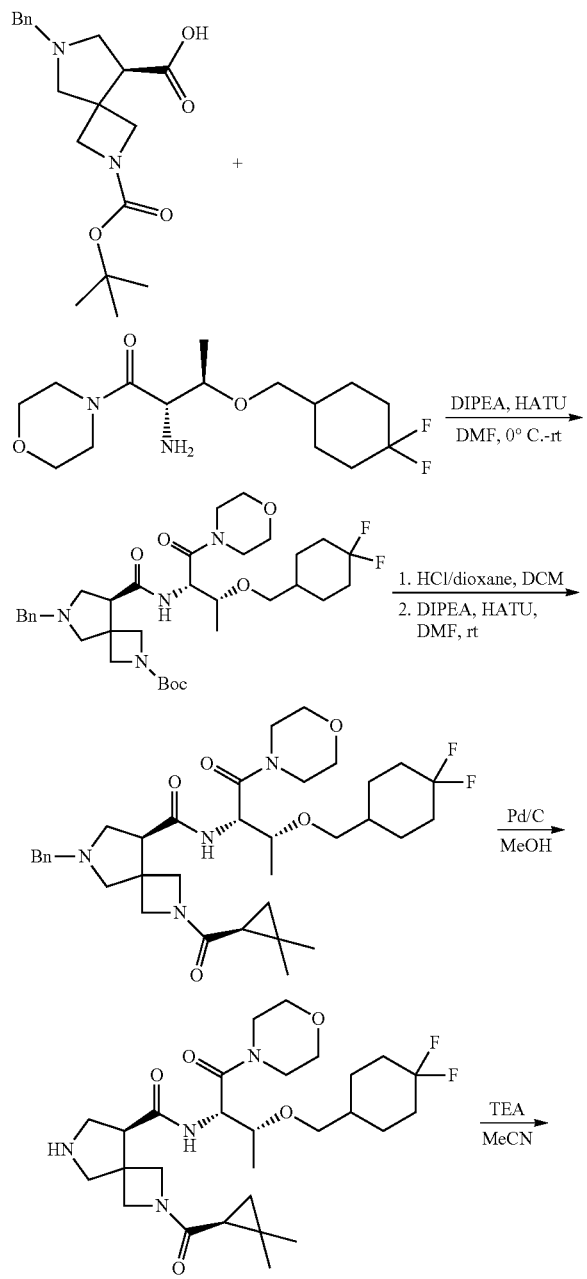

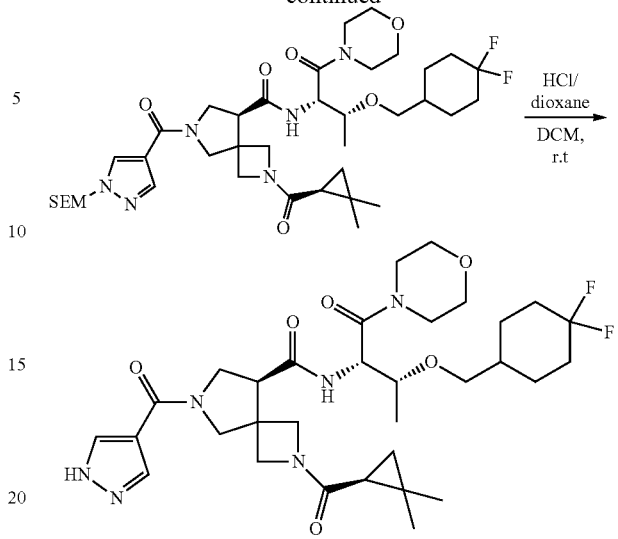

Step 1: To a solution of (2S,3R)-2-amino-3-((4,4-difluorocyclohexyl)methoxy)-1-morpholinobutan-1-one (240 mg, 0.75 mmol), (S)-6-benzyl-2-(tert-butoxycarbonyl)-2,6-diazaspiro[3.4]octane-8-carboxylic acid (346 mg, 1.0 mmol), and N-ethyl-N-isopropylpropan-2-amine (292.5 mg, 2.2 mmol) in N,N-dimethylformamide (8 mL) was added 2-(7-Aza-1H-benzotriazole-1-yl)-1,1,3,3-tetramethyluronium hexafluorophosphate (427.8 mg, 1.13 mmol) at 0-5° C. The resulting mixture was stirred at room temperature for 0.5 hour. The reaction mixture was poured into water (30 ml) and extracted with ethyl acetate (10 ml×3). The combined organic layers were washed with brine (20 ml×2), dried over anhydrous sodium sulfate, and concentrated under reduced pressure to give a crude residue which was purified by column chromatography using a 2% methanol in dichloromethane gradient to afford tert-butyl (S)-6-benzyl-8-(((2S,3R)-3-((4,4-difluorocyclohexyl)methoxy)-1-morpholino-1-oxobutan-2-yl)carbamoyl)-2,6-diazaspiro[3.4]octane-2-carboxylate (270 mg, 60% yield) as a light yellow oil. LCMS: m/z 649.6 [M+H]⁺. ¹H NMR (400 MHz, DMSO-d6): δ 8.37 (d, J=8.4 Hz, 1H), 7.25-7.34 (m, 6H), 4.80-4.84 (m, 1H), 3.85-3.88 (m, 1H), 3.46-3.73 (m, 15H), 3.19-3.23 (m, 1H), 3.12-3.15 (m, 1H), 2.78-2.85 (s, 2H), 2.59-2.61 (m, 1H), 1.93-2.01 (m, 2H), 1.70-1.84 (m, 4H), 1.57-1.61 (m, 1H), 1.34 (s, 9H), 1.10-1.19 (m, 2H), 1.06 (d, J=5.6 Hz, 3H).

Step 2: A mixture of (S)-6-benzyl-8-(((2S,3R)-3-((4,4-difluorocyclohexyl)methoxy)-1-morpholino-1-oxobutan-2-yl)carbamoyl)-2,6-diazaspiro[3.4]octane-2-carboxylate (100 mg, 0.15 mmol) in hydrogen chloride in dioxane (4.0 M, 2 ml)-dichloromethane (2 ml) was stirred at room temperature for 1 hour, after which The volatiles were evaporated under reduced pressure. The residue was taken up in N,N-dimethylformamide (2 ml), followed by sequential addition of (S)-2,2-dimethylcyclopropane-1-carboxylic acid (16.4 mg, 0.14 mmol), N-ethyl-N-isopropylpropan-2-amine (77.6 mg, 0.6 mmol), and HATU (2-(7-Aza-1H-benzotriazole-1-yl)-1,1,3,3-tetramethyluronium hexafluorophosphate) (68.4 mg, 0.18 mmol) at 0° C. The resulting mixture was allowed to warm up to room temperature and stirred for 30 min. The resulting mixture was diluted with water (10 ml) and extracted with ethyl acetate (5 ml×3). The combined organic phases were washed with brine, dried over anhydrous sodium sulfate, and concentrated under reduced pressure to give a crude residue which was purified by silica gel flash chromatography using a 2.5% methanol in dichloromethane gradient to afford (S)-6-benzyl-N-((2S,3R)-3-((4,4-difluorocyclohexyl)methoxy)-1-morpholino-1-oxobutan-2-yl)-2-((S)-2,2-dimethylcyclopropane-1-carbonyl)-2,6-diazaspiro[3.4]octane-8-carboxamide (50 mg, 53% yield) as a white solid. ¹H NMR (400 MHz, DMSO-d6): δ 8.32-8.43 (m, 1H), 7.25-7.33 (m, 6H), 4.79-4.88 (m, 1H), 4.20 (d, J=8.4 Hz, 1H), 3.85-3.98 (m, 2H), 3.46-3.74 (m, 14H), 3.12-3.24 (m, 3H), 2.81-2.89 (m, 2H), 2.59-2.68 (m, 1H), 1.90-2.019 (m, 3H), 1.67-1.80 (m, 4H), 1.55-1.60 (m, 1H), 1.30-1.35 (m, 1H), 0.98-1.08 (m, 9H), 0.80-0.84 (m, 1H), 0.63-0.66 (m, 1H). LCMS: m/z 645.3 [M+H]⁺.

Step 3: To a solution of (S)-6-benzyl-N-((2S,3R)-3-((4,4-difluorocyclohexyl)methoxy)-1-morpholino-1-oxobutan-2-yl)-2-((S)-2,2-dimethylcyclopropane-1-carbonyl)-2,6-diazaspiro[3.4]octane-8-carboxamide (50 mg, 0.078 mmol) in methanol (20 mL) was added palladium on carbon (10%, 10 mg). The resulting mixture was stirred at room temperature under hydrogen atmosphere (hydrogen balloon) for 3 hours. Palladium on carbon was removed through filtration and washed with methanol (10 ml×2); the combined organic solution was concentrated under reduced pressure to afford (S)—N-((2S,3R)-3-((4,4-difluorocyclohexyl)methoxy)-1-morpholino-1-oxobutan-2-yl)-2-((S)-2,2-dimethylcyclopropane-1-carbonyl)-2,6-diazaspiro[3.4]octane-8-carboxamide (40 mg, 93% yield) as a white solid. ¹H NMR (400 MHz, DMSO-d6): δ 8.30-8.53 (m, 1H), 4.81-4.88 (m, 1H), 4.16-4.21 (m, 1H), 3.96-4.03 (m, 1H), 3.41-3.87 (m, 12H), 3.13-3.29 (m, 5H), 2.87-3.10 (m, 2H), 2.59-2.74 (m, 1H), 1.90-2.02 (m, 2H), 1.68-1.85 (m, 4H), 1.54-1.64 (m, 1H), 1.28-1.35 (m, 1H), 1.04-1.12 (m, 10H), 0.81-0.86 (m, 1H), 0.64-0.69 (m, 1H).

Step 4: To a stirred solution of (S)—N-((2S,3R)-3-((4,4-difluorocyclohexyl)methoxy)-1-morpholino-1-oxobutan-2-yl)-2-((S)-2,2-dimethylcyclopropane-1-carbonyl)-2,6-diazaspiro[3.4]octane-8-carboxamide (40 mg, 0.07 mmol) and triethylamine (14.2 mg, 0.14 mmol) in acetonitrile (2 mL) was added 2,5-dioxopyrrolidin-1-yl 1-((2-(trimethylsilyl)ethoxy)methyl)-1H-pyrazole-4-carboxylate (26.9 mg, 0.08 mmol) at 0° C. The resulting mixture was stirred at room temperature for 3 hours. The reaction mixture was then concentrated to remove the solvent. The residue was diluted with water (10 ml) and extracted with ethyl acetate (10 ml×3). The combined organic phases were washed with brine, dried over anhydrous sodium sulfate, and concentrated under reduced pressure to give a crude residue which was purified by preparative TLC using a 7% methanol in dichloromethane gradient to afford (S)—N-((2S,3R)-3-((4,4-difluorocyclohexyl)methoxy)-1-morpholino-1-oxobutan-2-yl)-2-((S)-2,2-dimethylcyclopropane-1-carbonyl)-6-(1-((2-(trimethylsilyl)ethoxy)methyl)-1H-pyrazole-4-carbonyl)-2,6-diazaspiro[3.4]octane-8-carboxamide (26 mg, 46% yield) as a white solid. LCMS: m/z 779.4 [M+H]⁺.

Step 5: A solution of (S)—N-((2S,3R)-3-((4,4-difluorocyclohexyl)methoxy)-1-morpholino-1-oxobutan-2-yl)-2-((S)-2,2-dimethylcyclopropane-1-carbonyl)-6-(1-((2-(trimethylsilyl)ethoxy)methyl)-1H-pyrazole-4-carbonyl)-2,6-diazaspiro[3.4]octane-8-carboxamide (28 mg, 0.028 mmol) in hydrogen chloride in dioxane (4.0 M, 2 ml)-dichloromethane (2 ml) was stirred at room temperature for 1 hour. The volatiles were removed under reduced pressure to give a crude residue which was adjusted to pH 8-9 with aqueous sodium carbonate solution and extracted with ethyl acetate (10 ml×3). The combined organic layers were washed with brine (20 ml), dried over sodium sulfate, and concentrated under reduced pressure to give the crude residue which was purified by preparative TLC using a 10% methanol in dichloromethane gradient to afford (S)—N-((2S,3R)-3-((4,4-difluorocyclohexyl)methoxy)-1-morpholino-1-oxobutan-2-yl)-2-((S)-2,2-dimethylcyclopropane-1-carbonyl)-6-(1H-pyrazole-4-carbonyl)-2,6-diazaspiro[3.4]octane-8-carboxamide (I-301) (14 mg, 60% yield) as a white solid. LCMS: 649.4 [M+H]⁺. ¹H NMR (400 MHz, DMSO-d6): δ 13.20-13.25 (m, 1H), 8.44-8.47 (m, 1H), 8.17-8.20 (m, 1H), 7.82-7.85 (m, 1H), 4.81-4.89 (m, 1H), 3.83-4.23 (m, 5H), 3.42-3.81 (m, 11H), 3.38-3.40 (m, 1H), 3.28-3.30 (s, 1H), 3.20-3.25 (m, 1H), 1.94-2.03 (m, 2H), 1.54-1.87 (m, 5H), 1.23-1.45 (m, 4H), 1.05-1.45 (m, 9H), 0.84-0.88 (m, 1H), 0.66-0.68 (m, 1H).

Method 28: Exemplified by the Synthesis of I-333

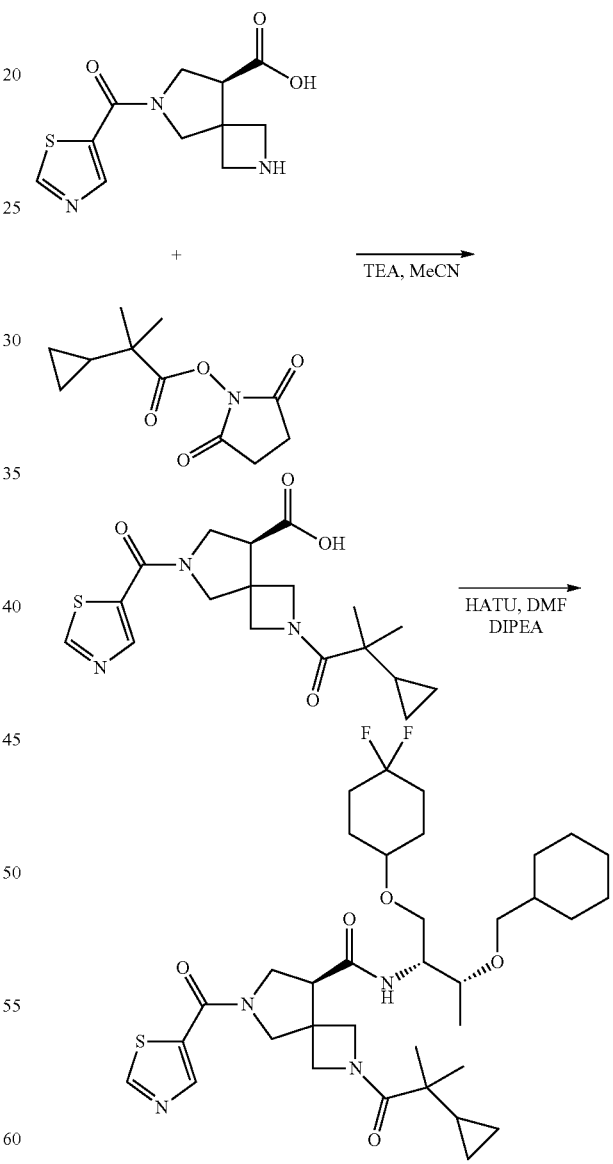

Step 1: To a stirred solution of (S)-6-(thiazole-5-carbonyl)-2,6-diazaspiro[3.4]octane-8-carboxylic acid hydrochloride (See Method 17A) (673 mg, 2.22 mmol) in acetonitrile (10 ml) was added triethylamine (0.9 ml, 6.66 mmol), followed by slow addition of a solution of 2,5-dioxopyrrolidin-1-yl 2-cyclopropyl-2-methylpropanoate (500 mg, 2.22 mmol) in acetonitrile (5 ml), and the resulting mixture was stirred at room temperature for 1 hour. The reaction mixture was then poured into water (5 mL) and extracted with ethyl acetate (10 ml×2) to remove some impurity. The aqueous layer was adjusted pH 3-4 with diluted hydrochloric acid (2.0 N) and extracted with 10% methanol in dichloromethane (20 mL×5). The combined organic phases were dried over anhydrous sodium sulfate, and concentrated in vacuo to give crude (S)-2-(2-cyclopropyl-2-methylpropanoyl)-6-(thiazole-5-carbonyl)-2,6-diazaspiro[3.4]octane-8-carboxylic acid (0.400 g, 48%) as a shite solid which was used in next step without further purification. MS [MH]+ 378.3

Step 2: To a solution of crude (S)-2-(2-cyclopropyl-2-methylpropanoyl)-6-(thiazole-5-carbonyl)-2,6-diazaspiro[3.4]octane-8-carboxylic acid (0.050 g, 0.13 mmol) in N,N-dimethylformamide (1.5 mL) was added (2R,3R)-1-((4,4-difluorocyclohexyl)oxy)-3-((tetrahydro-2H-pyran-4-yl)methoxy)butan-2-amine (0.043 g, 0.13 mmol), N-ethyl-N-isopropylpropan-2-amine (0.1 ml, 0.40 mmol), and (2-(7-Aza-1H-benzotriazole-1-yl)-1,1,3,3-tetramethyluronium hexafluorophosphate) (0.060 g, 0.16 mmol). The resulting mixture was stirred at room temperature for 1 hour. The reaction mixture was then poured into water (10 mL) and extracted with ethyl acetate (10 mL×2). The combined organic phases were washed with brine (10 mL×2), dried over anhydrous sodium sulfate, and concentrated under reduced pressure to give a crude residue which was purified by column chromatography using 10% methanol in dichloromethane gradient to afford (S)-2-(2-cyclopropyl-2-methylpropanoyl)-N-((2R,3R)-1-((4,4-difluorocyclohexyl)oxy)-3-((tetrahydro-2H-pyran-4-yl)methoxy)butan-2-yl)-6-(thiazole-5-carbonyl)-2,6-diazaspiro[3.4]octane-8-carboxamide (I-333) (0.028 g, 31%) as a white solid. $^1$H NMR (400 MHz, CD$_3$OD): δ 9.06 (s, 1H), 8.26 (d, J=20.8 Hz, 1H), 7.24-7.18 (m, 0.5H), 4.60-4.38 (m, 2H), 4.18-3.76 (m, 9H), 3.58-3.25 (m, 8H), 3.13-3.08 (m, 1H), 1.92-1.55 (m, 10H), 1.27-1.19 (m, 3H), 1.02-0.91 (m, 10H), 0.39-0.26 (m, 4H). MS [MH]+ 681.7

Method 29: Exemplified by the Synthesis of I-344

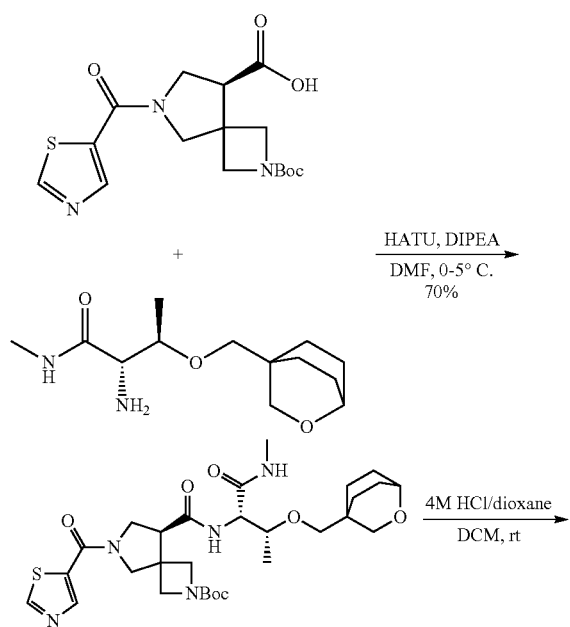

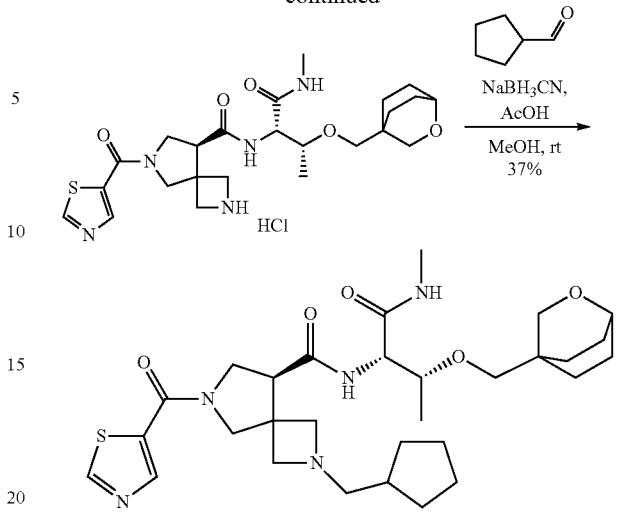

Step 1: To a stirred solution of (S)-2-(tert-butoxycarbonyl)-6-(thiazole-5-carbonyl)-2,6-diazaspiro[3.4]octane-8-carboxylic acid (See Method 17A) (0.198 g, 0.54 mmol), (2S,3R)-3-(2-oxabicyclo[2.2.2]octan-4-ylmethoxy)-2-amino-N-methylbutanamide (0.145 g, 0.57 mmol), and N-ethyl-N-isopropylpropan-2-amine (0.140 g, 1.08 mmol) in N,N-dimethylformamide (2 mL) at 0-5° C. was added HATU (2-(7-Aza-1H-benzotriazole-1-yl)-1,1,3,3-tetramethyluronium hexafluorophosphate) (0.246 g, 0.65 mmol), the resulting mixture was allowed to warm to room temperature and stirred at room temperature for an hour. The mixture was poured into water (20 mL) and extracted with ethyl acetate (15 mL×2). The organic layers were collected, washed with brine (20 mL), dried over anhydrous sodium sulfate, and concentrated under reduced pressure to give a crude residue which was purified by column chromatography using 50% ethyl acetate in dichloromethane containing 5% methanol gradient to afford (S)-tert-butyl 8-(((2S,3R)-3-(2-oxabicyclo[2.2.2]octan-4-ylmethoxy)-1-(methylamino)-1-oxobutan-2-yl)carbamoyl)-6-(thiazole-5-carbonyl)-2,6-diazaspiro[3.4]octane-2-carboxylate (0.230 g, 70%) as a white solid. $^1$H NMR (400 MHz, CDCl$_3$): δ 8.90 (s, 1H), 8.24 (s, 1H), 6.98-6.90 (m, 1H), 6.48-6.37 (m, 1H), 4.54-4.43 (m, 1H), 4.11-3.81 (m, 10H), 3.74-3.69 (m, 2H), 3.29-3.24 (m, 2H), 3.14-3.06 (m, 1H), 2.87 (d, J=4.8 Hz, 3H), 2.09-1.99 (m, 2H), 1.69-1.66 (m, 1H), 1.63-1.58 (m, 2H), 1.57-1.48 (m, 2H), 1.43 (s, 9H), 1.04 (d, J=6.4 Hz, 3H).

Step 2: To a mixture of (S)-tert-butyl 8-(((2S,3R)-3-(2-oxabicyclo[2.2.2]octan-4-ylmethoxy)-1-(methylamino)-1-oxobutan-2-yl)carbamoyl)-6-(thiazole-5-carbonyl)-2,6-diazaspiro[3.4]octane-2-carboxylate (0.055 g, 0.09 mmol) in dichloromethane (3 mL) was added hydrogen chloride in 1,4-dioxane (4M, 1 mL), the resulting mixture was stirred at room temperature for 30 min. The volatiles were evaporated under reduced pressure to afford crude (S)—N-((2S,3R)-3-((2-oxabicyclo[2.2.2]octan-4-yl)methoxy)-1-(methylamino)-1-oxobutan-2-yl)-6-(thiazole-5-carbonyl)-2,6-diazaspiro[3.4]octane-8-carboxamide hydrochloride which was used in next step without further purification.

Step 3: To a mixture of (S)—N-((2S,3R)-3-((2-oxabicyclo[2.2.2]octan-4-ylmethoxy)-1-(methylamino)-1-oxobutan-2-yl)-6-(thiazole-5-carbonyl)-2,6-diazaspiro[3.4]octane-8-carboxamide hydrochloride (0.09 mmol) in methanol (2 mL) was added triethylamine (0.5 mL). The mixture was stirred at room temperature for 10 min. To the reusing mixture was added cyclopentanecarbaldehyde (0.013 g, 0.14 mmol) and acetic acid (0.2 mL), and the resulting mixture was stirred at room temperature for 20 min, followed by the addition of sodium cyanoborohydride (0.011 g, 0.18 mmol). The resulting mixture was stirred at room temperature for 30 min. The reaction mixture was poured into aqueous sodium bicarbonate solution (10 mL) and extracted with dichloromethane (10 mL×2). The combined organic layers were washed with brine (10 mL), dried over anhydrous sodium sulfate, and concentrated under reduced pressure to give a crude residue which was purified by preparative TLC using a 10% methanol in dichloromethane gradient to afford (S)—N-((2S,3R)-3-(2-oxabicyclo[2.2.2]octan-4-ylmethoxy)-1-(methylamino)-1-oxobutan-2-yl)-2-(cyclopentylmethyl)-6-(thiazole-5-carbonyl)-2,6-diazaspiro[3.4]octane-8-carboxamide (I-344) (0.020 g, 37%) as a pink solid. $^1$H NMR (400 MHz, CD$_3$OD): δ 9.15 (d, J=3.2 Hz, 1H), 8.34 (d, J=7.2 Hz, 1H), 4.31 (dd, J=3.2, 8.8 Hz, 1H), 4.12-4.02 (m, 2H), 3.92-3.37 (m, 12H), 3.27-3.25 (m, 1H), 3.01-2.98 (m, 1H), 2.74 (d, J=14.8 Hz, 3H), 2.64-2.57 (m, 2H), 2.03-1.42 (m, 18H), 1.19 (d, J=6.4 Hz, 3H). MS: [MH]$^+$ 588.45.

Method 30: Exemplified by the Synthesis of I-387

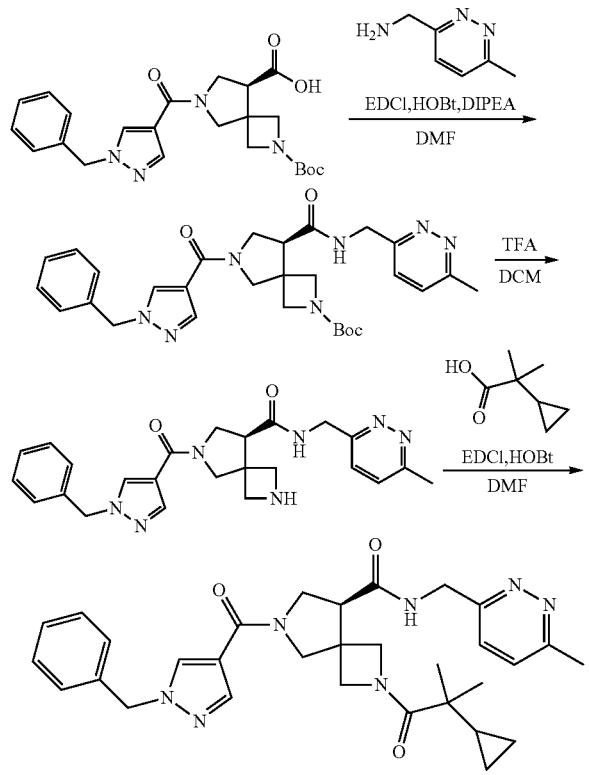

Step 1: To a solution of (S)-6-(1-benzyl-1H-pyrazole-4-carbonyl)-2-(tert-butoxycarbonyl)-2,6-diazaspiro[3.4]octane-8-carboxylic acid (Method 20-Step 3) (75 mg, 0.17 mmol) in DMF (2.0 mL) was added (6-methylpyridazin-3-yl)methanamine (42 mg, 0.20 mmol), EDCI (49 mg, 0.26 mmol), HOBt (34.5 mg, 0.26 mmol) and DIPEA (88 mg, 0.68 mmol). The resulting mixture was stirred at room temperature for 14 h then the solvent was removed under vacuum. The residue obtained was purified by prep-TLC (DCM:MeOH=12:1) to afford (S)-6-(1-benzyl-1H-pyrazole-4-carbonyl)-8-(((6-methylpyridazin-3-yl)methyl)carbamoyl)-2,6-diazaspiro[3.4]octane-2-carboxylate (25 mg, 26%) as a colorless solid. LCMS m/z=546.1 [M+H]$^+$.

Step 2: To a solution of (S)-6-(1-benzyl-1H-pyrazole-4-carbonyl)-8-(((6-methylpyridazin-3-yl)methyl)carbamoyl)-2,6-diazaspiro[3.4]octane-2-carboxylate (25 mg, 0.046 mmol) in DCM (3 mL) was added TFA (1 mL). The resulting mixture was stirred for 2 h, then the solvent removed under reduced pressure to afford (S)-6-(1-benzyl-1H-pyrazole-4-carbonyl)-N-((6-methylpyridazin-3-yl)methyl)-2,6-diazaspiro[3.4]octane-8-carboxamide 2,2,2-trifluoroacetate (30 mg, quant.) which was used directly in the next step.

Step 3: To a solution of (S)-6-(1-benzyl-1H-pyrazole-4-carbonyl)-N-((6-methylpyridazin-3-yl)methyl)-2,6-diazaspiro[3.4]octane-8-carboxamide 2,2,2-trifluoroacetate (30 mg, 0.045 mmol) in DMF (1.0 mL) was added 2-cyclopropyl-2-methylpropanoic acid (7 mg, 0.055 mmol), EDCI (13 mg, 0.068 mmol), HOBt (9 mg, 0.067 mmol) and DIPEA (17.4 mg, 0.13 mmol). The resulting mixture was stirred at room temperature for 14 h then the solvent was removed under vacuum. The residue was purified by prep-HPLC to give (S)-6-(1-benzyl-1H-pyrazole-4-carbonyl)-2-(2-cyclopropyl-2-methylpropanoyl)-N-((6-methylpyridazin-3-yl)methyl)-2,6-diazaspiro[3.4]octane-8-carboxamide (11 mg, 44%) as a yellow solid. LCMS m/z=556.4 [M+H]$^+$; $^1$H NMR (400 MHz, Methanol-d$_4$) δ 8.21 (d, J=14.0 Hz, 1H), 8.04-7.74 (m, 3H), 7.40-7.20 (m, 5H), 5.37 (s, 2H), 4.76-3.72 (m, 9H), 3.28-3.16 (m, 1H), 2.76 (s, 3H), 1.08-0.87 (m, 7H), 0.52-0.21 (m, 4H).

Method 31: Exemplified by the Synthesis of I-415

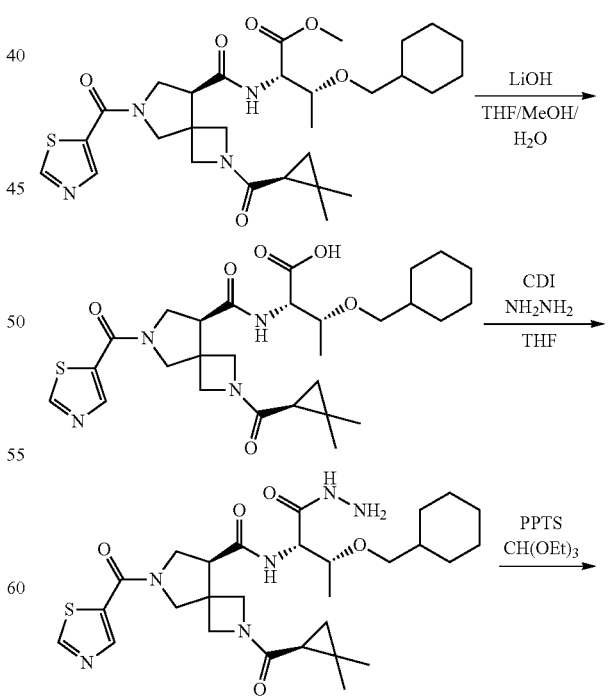

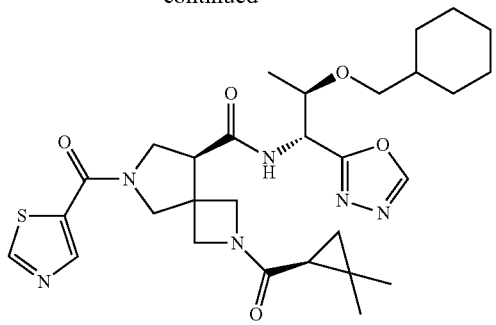

Methyl O-(cyclohexylmethyl)-N—((S)-2-((S)-2,2-dimethylcyclopropane-1-carbonyl)-6-(thiazole-5-carbonyl)-2,6-diazaspiro[3.4]octane-8-carbonyl)-L-threoninate was synthesized from Intermediate 11 according to the procedures outlined in Method 18 using the appropriate commercially available reagents and/or intermediates described elsewhere. LCMS m/z=575.3 [M+H]⁺; ¹H NMR (400 MHz, DMSO-d6) δ 9.25 (s, 1H), 8.59-8.46 (m, 1H), 8.41-8.34 (m, 1H), 4.52 (d, J=9.6 Hz, 1H), 4.20-4.05 (m, 3H), 3.96-3.55 (m, 11H), 3.06 (d, J=9.0 Hz, 1H), 1.65 (d, J=12.4 Hz, 6H), 1.18-1.02 (m, 13H), 0.85 (s, 3H), 0.68 (d, J=7.4 Hz, 1H).

Step 1: To a solution of methyl O-(cyclohexylmethyl)-N—((S)-2-((S)-2,2-dimethylcyclopropane-1-carbonyl)-6-(thiazole-5-carbonyl)-2,6-diazaspiro[3.4]octane-8-carbonyl)-L-threoninate (800 mg, 1.39 mmol) in a mixture of THF and H₂O (8 mL/2 mL) was added LiOH (67 mg, 2.78 mmol). The reaction mixture was stirred at room temperature for 2 h then diluted with water (30 mL) and extracted with ether (50 mL). The aqueous layer was collected and acidified to pH 2 with 1M HCl and extracted with EtOAc (50 mL×2). The combined organic layers were washed with brine, dried over Na₂SO₄, filtered and concentrated to afford O-(cyclohexylmethyl)-N—((S)-2-((S)-2,2-dimethylcyclopropane-1-carbonyl)-6-(thiazole-5-carbonyl)-2,6-diazaspiro[3.4]octane-8-carbonyl)-L-threonine (500 mg, 64%) as a white solid which was used directly in the next step. LCMS m/z=561.2 [M+H]⁺.

Step 2: To a solution of O-(cyclohexylmethyl)-N—((S)-2-((S)-2,2-dimethylcyclopropane-1-carbonyl)-6-(thiazole-5-carbonyl)-2,6-diazaspiro[3.4]octane-8-carbonyl)-L-threonine (500 mg, 0.89 mmol) in THF (10 mL) was added CDI (180 mg, 1.07 mmol). The mixture was stirred at room temperature for 1 h then NH₂NH₂ (70 mg, 1.33 mmol) was added. The reaction mixture was stirred at room temperature overnight then the mixture was diluted with water (20 mL) and extracted with EtOAc (30 mL×2). The combined organic layers were washed with brine, dried over Na₂SO₄, filtered and concentrated. The residue was purified by prep-TLC (DCM/MeOH=10/1) to afford (S)—N-((2S,3R)-3-(cyclohexylmethoxy)-1-hydrazinyl-1-oxobutan-2-yl)-2-((S)-2,2-dimethylcyclopropane-1-carbonyl)-6-(thiazole-5-carbonyl)-2,6-diazaspiro[3.4]octane-8-carboxamide (80 mg, 15%) as a white solid. LCMS m/z=575.3 [M+H]⁺.

Step 3: To a solution of (S)—N-((2S,3R)-3-(cyclohexylmethoxy)-1-hydrazinyl-1-oxobutan-2-yl)-2-((S)-2,2-dimethylcyclopropane-1-carbonyl)-6-(thiazole-5-carbonyl)-2,6-diazaspiro[3.4]octane-8-carboxamide (80 mg, 0.13 mmol) in triethyl orthoformate (10 mL) was added p-toluenesulfonic acid (1 mg). The mixture was stirred at 150° C. for 1 h in a microwave reactor. The solvent was removed under reduced pressure and the residue obtained purified by prep-HPLC to afford (S)—N-((1S,2R)-2-(cyclohexylmethoxy)-1-(1,3,4-oxadiazol-2-yl)propyl)-2-((S)-2,2-dimethylcyclopropane-1-carbonyl)-6-(thiazole-5-carbonyl)-2,6-diazaspiro[3.4]octane-8-carboxamide (8.7 mg, 10%) as a white solid. LCMS m/z=585.5 [M+H]⁺; ¹H NMR (400 MHz, DMSO-d6) δ 9.23 (d, J=18.4 Hz, 2H), 9.01-8.91 (m, 1H), 8.37 (d, J=18.6 Hz, 1H), 5.34 (s, 1H), 4.25-4.00 (m, 4H), 3.95-3.78 (m, 4H), 3.70 (s, 1H), 3.58-3.47 (m, 1H), 3.06 (s, 1H), 1.63-1.49 (m, 5H), 1.39-1.35 (m, 1H), 1.16-1.04 (m, 13H), 0.86 (d, J=5.2 Hz, 1H), 0.80-0.65 (m, 3H).

Method 32: Exemplified by the Synthesis of I-410

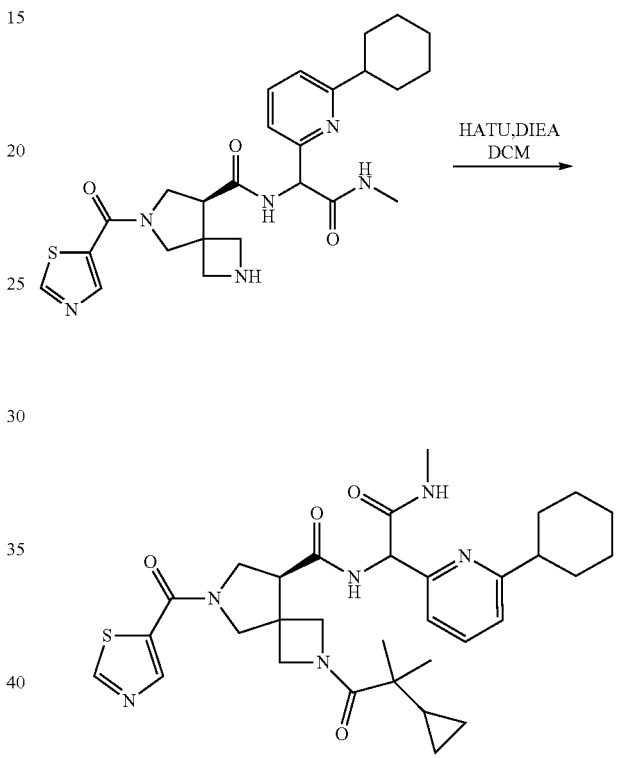

To a solution of 2-cyclopropyl-2-methylpropanoic acid (7 mg, 0.06 mmol) in DCM (2 mL) was added HATU (23 mg, 0.06 mmol) and the mixture was stirred at room temperature for 30 min. (8S)—N-(1-(6-cyclohexylpyridin-2-yl)-2-(methylamino)-2-oxoethyl)-6-(thiazole-5-carbonyl)-2,6-diazaspiro[3.4]octane-8-carboxamide (made by a method analogous to Method 20) (29 mg, 0.06 mmol) and DIPEA (23 mg, 0.06 mmol) were added and the reaction stirred at room temperature for another 2 h. The mixture was diluted with water (10 mL) and extracted with DCM (50 mL). The combined organic layers were washed with brine, dried over Na₂SO₄, filtered and concentrated. The residue obtained was purified by prep-HPLC to afford (8S)—N-(1-(6-cyclohexylpyridin-2-yl)-2-(methylamino)-2-oxoethyl)-2-(2-cyclopropyl-2-methylpropanoyl)-6-(thiazole-5-carbonyl)-2,6-diazaspiro[3.4]octane-8-carboxamide (30 mg, 43%) as a white solid. LCMS m/z=512.2 [M+H]⁺; ¹H NMR (400 MHz, DMSO-d₆) δ 9.28-9.20 (m, 1H), 9.08-8.76 (m, 1H), 8.41-8.30 (m, 1H), 8.21-8.09 (m, 1H), 7.74-7.58 (m, 1H), 7.30-7.11 (m, 2H), 5.48 (s, 1H), 4.65-4.16 (m, 2H), 4.12-3.63 (m, 6H), 3.59-3.44 (m, 1H), 2.70-2.55 (m, 4H), 1.89-1.68 (m, 5H), 1.53-1.17 (m, 5H), 1.04-0.71 (m, 7H), 0.47-0.05 (m, 4H).

Method 33: Exemplified by the Synthesis of I-454

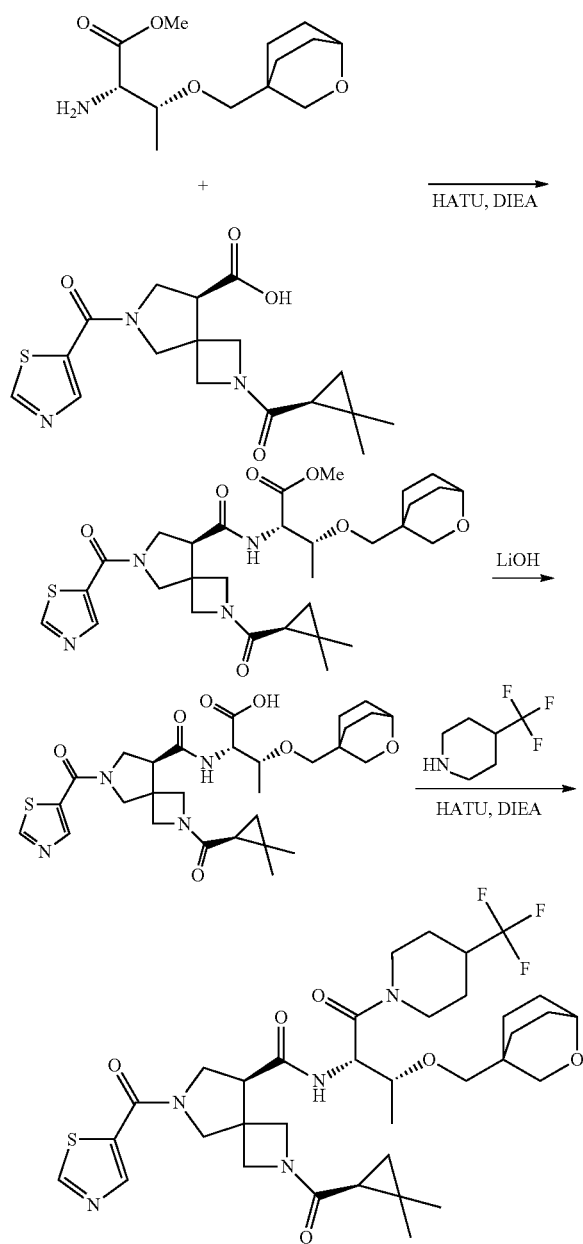

Step 1: To a solution of (S)-2-((S)-2,2-dimethylcyclopropane-1-carbonyl)-6-(thiazole-5-carbonyl)-2,6-diazaspiro[3.4]octane-8-carboxylic acid (see Method 17A) (835 mg, 2.3 mmol) in DCM (6 mL) was added HATU (874 mg, 2.3 mmol) and DIPEA (742 mg, 5.75 mmol) and the mixture stirred at room temperature for 30 min. Methyl O-((2-oxabicyclo[2.2.2]octan-4-yl)methyl)-L-threoninate (600 mg, 2.3 mmol) was added and the reaction was stirred for another 2 h. The reaction was quenched with water (30 mL) and extracted with DCM (40 mL×3). The combined organic layers were washed with brine, dried over Na$_2$SO$_4$, filtered and concentrated. The residue obtained was purified by column chromatography on silica gel (eluent: DCM: MeOH=50:1) to afford methyl O-((2-oxabicyclo[2.2.2]octan-4-yl)methyl)-N—((S)-2-((S)-2,2-dimethylcyclopropane-1-carbonyl)-6-(thiazole-5-carbonyl)-2,6-diazaspiro[3.4]octane-8-carbonyl)-L-threoninate (850 mg, 62%) as a yellow oil. LCMS m/z=603.1 [M+H]$^+$; $^1$H NMR (400 MHz, CDCl$_3$) δ 8.91 (s, 1H), 8.27 (s, 1H), 4.70-4.57 (m, 1H), 4.40-3.96 (m, 10H), 3.79-3.72 (m, 4H), 3.65-3.58 (m, 1H), 3.52-3.42 (m, 1H), 3.23-3.09 (m, 2H), 2.05-1.94 (m, 2H), 1.58-1.51 (m, 4H), 1.48-1.41 (m, 2H), 1.19-1.11 (m, 12H), 0.83-0.71 (m, 1H).

Step 2: To a solution of methyl O-((2-oxabicyclo[2.2.2]octan-4-yl)methyl)-N—((S)-2-((S)-2,2-dimethylcyclopropane-1-carbonyl)-6-(thiazole-5-carbonyl)-2,6-diazaspiro[3.4]octane-8-carbonyl)-L-threoninate (850 mg, 1.41 mmol) in a mixture of THF (8 mL), MeOH (2 mL) and H$_2$O (2 mL) was added LiOH (97 mg, 4.23 mmol). The reaction was stirred at room temperature for 4 h then diluted with water (50 mL) and extracted with EtOAc (30 mL×2). The aqueous phase was acidified to pH 2 with 1M HCl and extracted with EtOAc (50 mL×3). The combined organic layers were washed with brine, dried over Na$_2$SO$_4$ and concentrated to afford O-((2-oxabicyclo[2.2.2]octan-4-yl)methyl)-N—((S)-2-((S)-2,2-dimethylcyclopropane-1-carbonyl)-6-(thiazole-5-carbonyl)-2,6-diazaspiro[3.4]octane-8-carbonyl)-L-threonine (600 mg, 72%) as a yellow oil. LCMS m/z=589.2 [M+H]$^+$.

Step 3: To a solution of O-((2-oxabicyclo[2.2.2]octan-4-yl)methyl)-N—((S)-2-((S)-2,2-dimethylcyclopropane-1-carbonyl)-6-(thiazole-5-carbonyl)-2,6-diazaspiro[3.4]octane-8-carbonyl)-L-threonine (50 mg, 0.085 mmol) in DCM (2 mL) was added HATU (32 mg, 0.085 mmol) and DIPEA (27 mg, 0.213 mmol). The mixture was stirred at room temperature for 30 min then 4-(trifluoromethyl)piperidine (14 mg, 0.094 mmol) was added and the reaction was stirred for another 2 h. The solvent was removed under reduced pressure, the residue obtained was purified by prep-HPLC to afford (S)—N-((2S,3R)-3-((2-oxabicyclo[2.2.2]octan-4-yl)methoxy)-1-oxo-1-(4-(trifluoromethyl)piperidin-1-yl)butan-2-yl)-2-((S)-2,2-dimethylcyclopropane-1-carbonyl)-6-(thiazole-5-carbonyl)-2,6-diazaspiro[3.4]octane-8-carboxamide (20 mg, 33%). LCMS m/z=724.4 [M+H]$^+$; $^1$H NMR (400 MHz, CD$_3$OD) δ 9.15 (s, 1H), 8.37 (m, 1H), 4.95 (s, 1H), 4.58 (m, 1H), 4.43-3.82 (m, 10H), 3.72 (m, 3H), 3.45 (m, 1H), 3.27-3.13 (m, 2H), 3.02 (s, 1H), 2.69 (s, 1H), 2.51 (s, 1H), 1.96 (m, 4H), 1.65 (m, 4H), 1.57-1.36 (m, 5H), 1.21-1.10 (m, 9H), 1.05 (s, 1H), 0.79 (m, 1H).

Method 34: Exemplified by the Synthesis of I-447

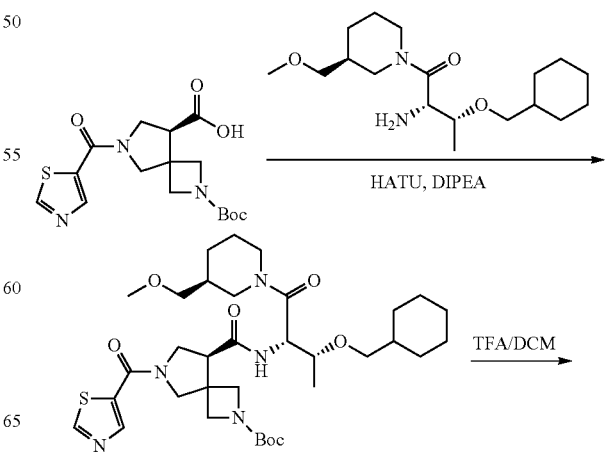

-continued

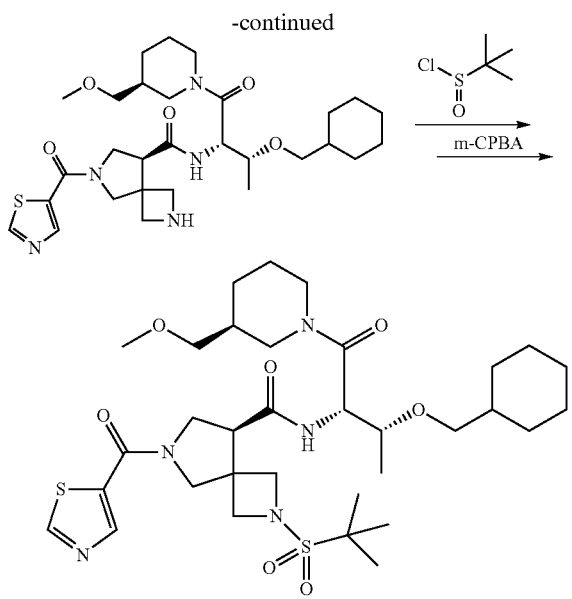

Step 1: To a solution of (S)-2-(tert-butoxycarbonyl)-6-(thiazole-5-carbonyl)-2,6-diazaspiro[3.4]octane-8-carboxylic acid (see Method 17A) (200 mg, 0.54 mmol) in DCM (5 mL) was added HATU (205 mg, 0.54 mmol) and DIPEA (279 mg, 2.16 mmol). The mixture was stirred at room temperature for 30 min then (2S,3R)-2-amino-3-(cyclohexylmethoxy)-1-((S)-3-(methoxymethyl)piperidin-1-yl)butan-1-one (176 mg, 0.54 mmol) was added and the reaction stirred for another 2 h. The mixture was diluted with water (50 mL) and extracted with DCM (50 mL×3). The combined organic layers were washed with brine, dried over $Na_2SO_4$, filtered and concentrated. The residue obtained was purified by prep-TLC (eluent: DCM:MeOH=20:1) to afford tert-butyl (S)-8-(((2S,3R)-3-(cyclohexylmethoxy)-1-((S)-3-(methoxymethyl)piperidin-1-yl)-1-oxobutan-2-yl)carbamoyl)-6-(thiazole-5-carbonyl)-2,6-diazaspiro[3.4]octane-2-carboxylate (250 mg, 68%) as a yellow oil. LCMS m/z=676.3 [M+H]+.

Step 2: To a solution of tert-butyl (S)-8-(((2S,3R)-3-(cyclohexylmethoxy)-1-((S)-3-(methoxymethyl)piperidin-1-yl)-1-oxobutan-2-yl)carbamoyl)-6-(thiazole-5-carbonyl)-2,6-diazaspiro[3.4]octane-2-carboxylate (100 mg, 0.15 mmol) in DCM (2 mL) was added TFA (0.5 mL). The reaction was stirred for 1 h then the solvent was removed under vacuum to afford (S)—N-((2S,3R)-3-(cyclohexylmethoxy)-1-((S)-3-(methoxymethyl)piperidin-1-yl)-1-oxobutan-2-yl)-6-(thiazole-5-carbonyl)-2,6-diazaspiro[3.4]octane-8-carboxamide (85 mg, 100%) which was used directly in the next step. LCMS m/z=576.3 [M+H]+.

Step 3: To a solution of (S)—N-((2S,3R)-3-(cyclohexylmethoxy)-1-((S)-3-(methoxymethyl)piperidin-1-yl)-1-oxobutan-2-yl)-6-(thiazole-5-carbonyl)-2,6-diazaspiro[3.4]octane-8-carboxamide (42 mg, 0.07 mmol) and TEA (28 mg, 0.28 mmol) in DCM (2 mL) at 0° C. was added 2-methylpropane-2-sulfinic chloride (10 mg, 0.07 mmol). The reaction mixture was stirred at room temperature for 2 h then concentrated and the residue was purified by prep-HPLC to afford (8S)-2-(tert-butylsulfinyl)-N-((2S,3R)-3-(cyclohexylmethoxy)-1-((S)-3-(methoxymethyl)piperidin-1-yl)-1-oxobutan-2-yl)-6-(thiazole-5-carbonyl)-2,6-diazaspiro[3.4]octane-8-carboxamide (15 mg, 31%) as a white solid. LCMS m/z=680.5 [M+H]+; 1H NMR (400 MHz, DMSO-d6) δ 9.24 (d, J=4.9 Hz, 1H), 8.49-8.30 (m, 2H), 4.84 (s, 1H), 4.34-4.18 (m, 1H), 4.12-3.32 (m, 12H), 3.27-3.10 (m, 7H), 3.07-2.74 (m, 1H), 1.72-1.57 (m, 8H), 1.50-1.39 (m, 1H), 1.24-1.13 (m, 4H), 1.10-1.00 (m, 13H), 0.94-0.82 (m, 2H).

Step 4: To a solution of (8S)-2-(tert-butylsulfinyl)-N-((2S,3R)-3-(cyclohexylmethoxy)-1-((S)-3-(methoxymethyl)piperidin-1-yl)-1-oxobutan-2-yl)-6-(thiazole-5-carbonyl)-2,6-diazaspiro[3.4]octane-8-carboxamide (30 mg, 0.04 mmol) in DCM (2 mL) at 0° C. was added m-CPBA (8 mg, 0.05 mmol). The reaction mixture was stirred at room temperature for 2 h then the solvent was removed and the residue purified by prep-HPLC to afford (S)-2-(tert-butylsulfonyl)-N-((2S,3R)-3-(cyclohexylmethoxy)-1-((S)-3-(methoxymethyl)piperidin-1-yl)-1-oxobutan-2-yl)-6-(thiazole-5-carbonyl)-2,6-diazaspiro[3.4]octane-8-carboxamide (16 mg, 52%) as a white solid. LCMS m/z=696.5 [M+H]+; 1H NMR (400 MHz, DMSO-d6) δ 9.29-9.23 (m, 1H), 8.57-8.47 (m, 1H), 8.44-8.30 (m, 1H), 4.86 (s, 1H), 4.35-4.22 (m, 1H), 4.17-3.36 (m, 12H), 3.28-3.08 (m, 7H), 3.06-2.74 (m, 1H), 1.75-1.53 (m, 8H), 1.52-1.32 (m, 2H), 1.30-1.00 (m, 16H), 0.92-0.79 (m, 2H).

Method 35: Exemplified by the Synthesis of I-498

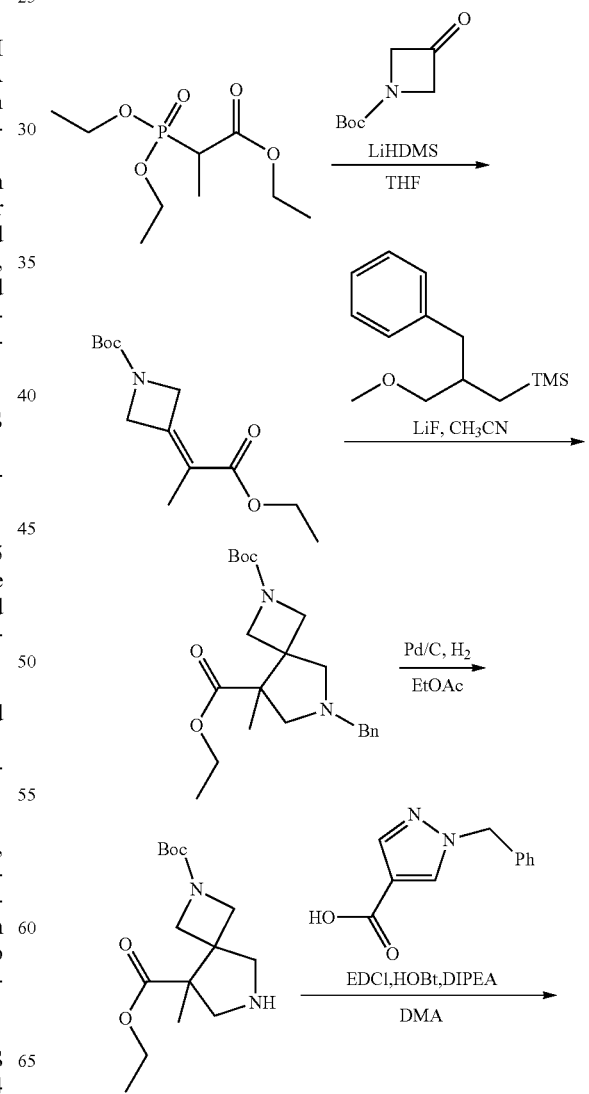

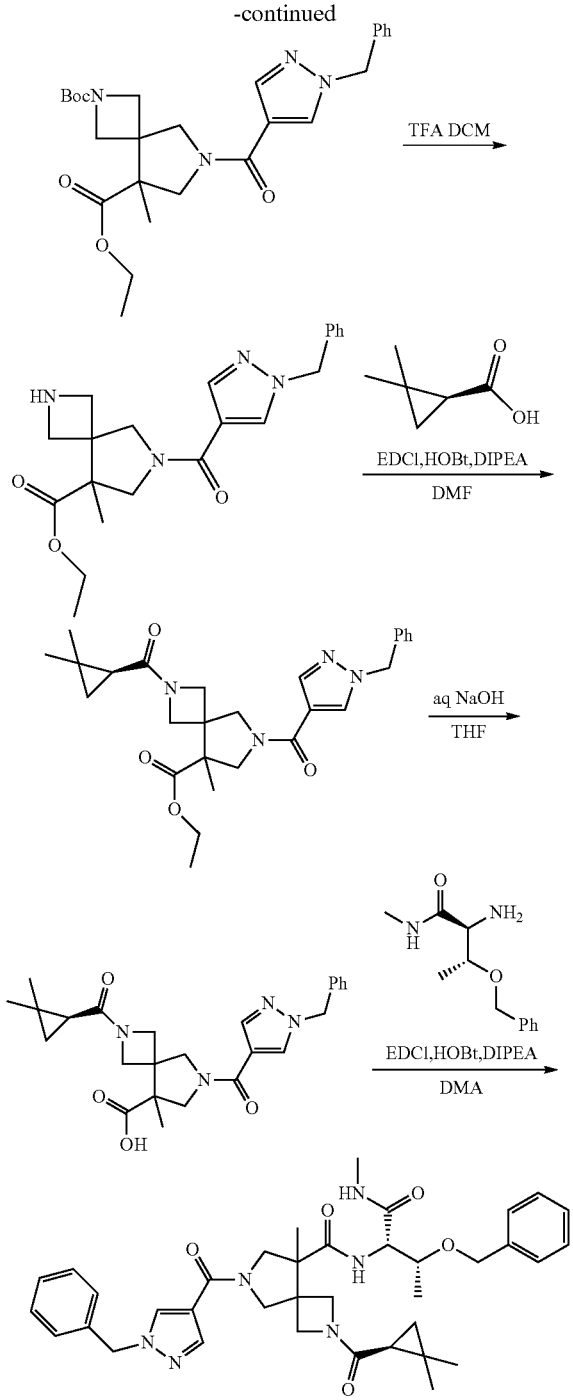

Step 1: A solution of LiHMDS (1M in THF, 4.2 mL, 4.2 mmol) was added dropwise to a solution of ethyl 2-(diethoxyphosphoryl)propanoate (1.0 g, 4.2 mmol) in THF (6 mL) at 0° C. After stirring for 30 min, a solution of tert-butyl 3-oxoazetidine-1-carboxylate (647 mg, 3.8 mmol) in THF (5.0 mL) was added and the resulting solution was stirred at room temperature for 1 h. Water was added and the aqueous extracted with EtOAc. The combined organic layers were washed with water, brine and dried over $Na_2SO_4$.

The solvent was removed and the crude purified by silica gel column chromatography (20% EtOAc/PE) to afford tert-butyl 3-(1-ethoxy-1-oxopropan-2-ylidene)azetidine-1-carboxylate (552 mg, 52%) as a white solid. LCMS m/z=256.2 [M+H]$^+$; $^1$H NMR (400 MHz, DMSO-d$_6$) δ 4.60 (s, 2H), 4.52 (s, 2H), 4.10 (q, J=7.2 Hz, 2H), 1.67-1.65 (m, 3H), 1.39 (s, 9H), 1.21 (t, J=7.1 Hz, 3H)

Step 2: To a solution of tert-butyl 3-(1-ethoxy-1-oxopropan-2-ylidene)azetidine-1-carboxylate (540 mg, 2.1 mmol) and LiF (165 mg, 6.3 mmol) in ACN (10.0 mL) was added N-benzyl-N-(methoxymethyl)-2-(trimethylsilyl)ethan-1-amine (603 mg, 2.5 mmol) dropwise at room temperature. The mixture was then heated at reflux overnight. The reaction mixture was cooled, water added and the aqueous extracted with EtOAc. The combined organic layers were washed with water, brine and dried over $Na_2SO_4$. The solvent was removed and the crude purified by silica gel column chromatography (30% EtOAc/PE) to afford 2-(tert-butyl) 8-ethyl 6-benzyl-8-methyl-2,6-diazaspiro[3.4]octane-2,8-dicarboxylate (378 mg, 44%). LCMS m/z=389.2 [M+H]$^+$.

Step 3: To a solution of 2-(tert-butyl) 8-ethyl 6-benzyl-8-methyl-2,6-diazaspiro[3.4]octane-2,8-dicarboxylate (378 mg, 0.97 mmol) in EtOAc (5.0 mL) was added Pd/C (10%, 100 mg). The resulting mixture was stirred for 5 h at 50° C. under an atmosphere of $H_2$. The reaction mixture was filtered through celite and the filtrate was concentrated under reduced pressure to afford 2-(tert-butyl) 8-ethyl 8-methyl-2,6-diazaspiro[3.4]octane-2,8-dicarboxylate (234 mg, 88%).

Step 4: To a solution of 2-(tert-butyl) 8-ethyl 8-methyl-2,6-diazaspiro[3.4]octane-2,8-dicarboxylate (224 mg, 0.75 mmol) in DMA (3.0 mL) was added 1-benzyl-1H-pyrazole-4-carboxylic acid (183 mg, 0.9 mmol), EDCI (216 mg, 1.1 mmol), HOBt (122 mg, 0.9 mmol) and DIPEA (292 mg, 2.3 mmol). The resulting mixture was stirred at room temperature overnight. Water was added and the aqueous extracted with EtOAc. The combined organic layers were washed with water, brine and dried over $Na_2SO_4$. The solvent was removed and the crude purified by silica gel column chromatography (5% MeOH/DCM) to afford 2-(tert-butyl) 8-ethyl 6-(1-benzyl-1H-pyrazole-4-carbonyl)-8-methyl-2,6-diazaspiro[3.4]octane-2,8-dicarboxylate (190 mg, 52%) as a white solid. LCMS m/z=427.2 [M+H−56]$^+$ Step 5: To a solution of 2-(tert-butyl) 8-ethyl 6-(1-benzyl-1H-pyrazole-4-carbonyl)-8-methyl-2,6-diazaspiro[3.4]octane-2,8-dicarboxylate (190 mg, 1.93 mmol) in DCM (10 mL) was added TFA (2 mL). The resulting mixture was stirred for 2 h then the solvent was removed under reduced pressure to afford ethyl 6-(1-benzyl-1H-pyrazole-4-carbonyl)-8-methyl-2,6-diazaspiro[3.4]octane-8-carboxylate (151 mg, quant.).

Step 6: Made using a similar method as described for the synthesis of 2-(tert-butyl) 8-ethyl 6-(1-benzyl-1H-pyrazole-4-carbonyl)-8-methyl-2,6-diazaspiro[3.4]octane-2,8-dicarboxylate (Step 4 of Method 35), using (S)-2,2-dimethylcyclopropane-1-carboxylic acid. LCMS m/z=479.4 [M+H]$^+$.

Step 7: To a solution of ethyl 6-(1-benzyl-1H-pyrazole-4-carbonyl)-2-((S)-2,2-dimethylcyclopropane-1-carbonyl)-8-methyl-2,6-diazaspiro[3.4]octane-8-carboxylate (112 mg, 0.23 mmol) in MeOH (1.0 mL) was added 10% aqueous NaOH (4.0 mL). The resulting mixture was stirred for 3 h then the solvent removed under vacuum. The residue obtained was diluted with water and the pH adjusted to ~1 by addition of 1M HCl. The aqueous layer was extracted with EtOAc three times and the combined organic layers were washed with water, brine, dried over $Na_2SO_4$ and concentrated to afford 6-(1-benzyl-1H-pyrazole-4-carbonyl)-2-((S)-2,2-dimethylcyclopropane-1-carbonyl)-8- methyl-2,6-diazaspiro[3.4]octane-8-carboxylic acid (105 mg, quant.) as an off-white solid. LCMS m/z=451.3 [M+H]⁺.

Step 8: Made using a similar method as described for the synthesis of 2-(tert-butyl) 8-ethyl 6-(1-benzyl-1H-pyrazole-4-carbonyl)-8-methyl-2,6-diazaspiro[3.4]octane-2,8-dicarboxylate (Step 4 of Method 35) to give 6-(1-benzyl-1H-pyrazole-4-carbonyl)-N-((2S,3R)-3-(benzyloxy)-1-(methylamino)-1-oxobutan-2-yl)-2-((S)-2,2-dimethylcyclopropane-1-carbonyl)-8-methyl-2,6-diazaspiro[3.4]octane-8-carboxamide (I-498) after purification by prep-HPLC. LCMS m/z=655.5 [M+H]⁺; ¹H NMR (400 MHz, CD₃OD) δ 8.27-8.17 (m, 1H), 7.96-7.93 (m, 1H), 7.41-7.19 (m, 10H), 5.35 (d, J=11.3 Hz, 2H), 4.70-3.58 (m, 13H), 2.72 (t, J=2.8 Hz, 3H), 1.49-1.25 (m, 6H), 1.22-1.15 (m, 4H), 1.10-1.02 (m, 3H), 0.78-0.73 (m, 1H).

TABLE 2

Characterization Data of Exemplary Compounds
Table 2 below contains the characterization data for the compounds of Table 1. Additionally, Table 2 discloses the method of Example 2 that best describes the process by which each compound of Table 1 was made. The appropriate reagents, starting materials, conditions, and modifications from the Exemplary synthesis method necessary for synthesizing the compounds of Table 1 would be apparent to a Person of ordinary skill in the art. LCMS values are shown [M + H]+ unless otherwise specified.

| Compound Number | Method | ¹HNMR | LCMS |
|---|---|---|---|
| I-1 | 14 | ¹H NMR (400 MHz, Methanol-d₄) δ 8.27-8.12 (m, 1H), 7.96-7.88 (m, 1H), 7.60-6.99 (m, 10H), 5.37 (s, 2H), 4.70-4.30 (m, 4H), 4.27-3.58 (m, 10H), 2.73 (s, 3H), 1.48-1.29 (m, 1H), 1.19-1.07 (m, 6H), 1.03 (s, 1H), 0.83-0.67 (m, 1H). | 627.4 |
| I-2 | 14 | ¹H NMR (400 MHz, Methanol-d₄) δ 8.20 (d, J = 17.1 Hz, 1H), 7.92 (d, J = 10.1 Hz, 1H), 7.38-7.25 (m, 5H), 5.37 (s, 2H), 4.59-3.37 (m, 13H), 2.78-2.70 (m, 3H), 1.22-0.99 (m, 11H), 0.82-0.73 (m, 1H). | 565.4 |
| I-3A | 7A | ¹H NMR (400 MHz, Methanol-d₄) δ 8.19 (d, J = 16.6 Hz, 1H), 7.90 (d, J = 9.8 Hz, 1H), 7.30 (dd, J = 16.8. 4.8 Hz, 10H), 5.39-5.35 (m, 2H), 4.62-4.43 (m, 3H), 4.15-3.75 (m, 10H), 2.73 (d, J = 10.4 Hz, 3H), 1.41 (s. 9H), 1.21 (d. J = 6.2 Hz, 3H). | 645.5 |
| I-3B | 7B | ¹H NMR (400 MHz, DMSO-d₆) δ 8.39-8.27 (m, 2H), 7.92-7.76 (m, 2H), 7.39-7.20 (m, 10H), 5.75 (s, 1H), 5.34 (s, 2H), 4.59-4.27 (m, 3H), 4.07-3.36 (m, 11H), 2.61 (d, J = 4.4 Hz, 3H), 1.37 (s, 10H), 1.28-1.22 (m, 4H), 1.06 (dd, J = 20.2, 6.2 Hz, 3H). | 645.5 |
| I-4A | 7A | ¹H NMR (400 MHz, Methanol-d₄) δ 8.23-8.12 (m, 1H), 7.94-7.85 (m, 1H), 7.36-7.22 (m, 10H), 5.36 (s, 2H), 4.65-4.53 (m, 1H), 4.52-4.35 (m, 2H), 4.31-3.73 (m, 9H), 3.41-3.33 (m, 1H), 3.03 (ddt, J = 38.0, 17.0, 8.6 Hz, 1H), 2.79-2.68 (m, 3H), 2.07-1.75 (m, 4H), 1.24-1.13 (m, 6H), 1.09-1.03 (m, 3H). | 655.5 |
| I-4B | 7B | ¹H NMR (400 MHz, Methanol-d₄) δ 8.23-8.13 (m, 1H), 7.89 (d, J = 19.0 Hz, 1H), 7.37-7.20 (m, 10H), 5.35 (d, J = 4.8 Hz, 2H), 4.69-4.29 (m, 4H), 4.24-3.71 (m, 9H), 3.16-3.01 (m, 1H), 2.76-2.70 (m, 3H), 2.04-1.86 (m, 4H), 1.22-1.10 (m, 6H), 1.06 (s, 3H). | 655.4 |
| I-5 | 14 | ¹H NMR (400 MHz, Methanol-d₄) δ 8.12-8.01 (m, 2H), 7.36-7.24 (m, 5H), 4.73-4.36 (m, 4H), 4.29-3.69 (m, 9H), 3.40 (s, 1H), 2.74 (dd, J = 7.0, 4.4 Hz, 3H), 1.52-1.33 (m, 1H), 1.25-1.09 (m, 9H), 1.03 (s, 1H), 0.77 (s, 1H). | 550.3 |
| I-6 | 14 | ¹H NMR (400 MHz, Methanol-d₄) δ 8.27-8.12 (m, 1H), 7.90 (d, J = 22.2 Hz, 1H), 7.74-7.42 (m, 4H), 7.40-7.23 (m, 5H), 5.37 (s, 2H), 4.73-3.77 (m, 12H), 3.42 (s, 1H), 2.80-2.72 (m, 3H), 1.53-1.36 (m, 1H), 1.25-1.08 (m, 9H), 1.06-1.00 (m, 1H), 0.82-0.74 (m, 1H). | 666.5 |
| I-7 | 14 | ¹H NMR (400 MHz, Methanol-d₄) δ 8.16 (d, J = 22.2 Hz, 1H), 7.90 (d,J = 14.6 Hz, 1H), 7.42-7.17 (m, 10H), 5.37 (s, 2H), 4.67-4.27 (m, 3H), 4.25-3.58 (m, 9H), 3.29-3.08 (m, 2H), 1.43-1.32 (m, 1H), 1.20-1.08 (m, 9H), 1.02 (s, 1H), 0.79-0.67 (m, 1H). | 584.4 |
| I-8A | 7A | ¹H NMR (400 MHz, Methanol-d₄) δ 8.26-8.11 (m, 1H), 7.91 (s, 1H), 7.43-7.21 (m, 10H), 5.45-5.28 (m, 2H), 4.67-4.55 (m, 1H), 4.52-4.42 (m, 2H), 4.40-3.72 (m, 9H), 3.45-3.34 (m, 1H), 2.73 (s, 3H), 2.13-1.87 (m, 2H), 1.43-1.13 (m, 4H), 0.93 (s, 1H), 0.50 (s, 1H), 0.13 (s, 2H). | 627.4 |
| I-8B | 7B | ¹H NMR (400 MHz, Methanol-d₄) δ 8.32-8.12 (m, 1H), 7.89 (d, J = 18.8 Hz, 1H), 7.42-7.17 (m, 10H), 5.36 (s, 2H), 4.65-4.52 (m, 1H), 4.50-4.35 (m, 2H), 4.35-3.64 (m, 8H), 3.37 (s, 1H), 2.72 (s, 3H), 2.14-1.93 (m, 2H), 1.47-0.80 (m, 6H), 0.51 (s, 2H), 0.16 (s, 2H). | 627.4 |
| I-9 | 15 | ¹H NMR (400 MHz, CD₃OD): δ 8.15-8.27 (m, 1H), 7.93-7.95 (m, 1H), 7.29-7.36 (m, 10H), 5.38-5.40 (m, 2H), 4.56-4.70 (m, 2H), 4.20-4.51 (m, 4H), 3.80-4.13 (m, 5H), 3.40- | 628.6 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 3.50 (m, 1H), 1.42-1.48 (m, 1H), 1.32-1.37 (m, 1H), 1.18-1.28 (m, 4H), 1.11-1.18 (m, 4H), 1.03-1.05 (m, 1H), 0.75-0.79 (m, 1H). | |
| I-10 | 14 | $^1$H NMR (400 MHz, Methanol-d$_4$) δ 8.18-8.02 (m, 1H), 7.95-7.82 (m, 1H), 7.39-7.16 (m, 5H), 4.67-4.55 (m, 1H), 4.52-3.73 (m, 13H), 3.47-3.34 (m, 1H), 2.81-2.66 (m, 3H), 1.99-1.82 (m, 1H), 1.80-1.65 (m, 3H), 1.63-1.50 (m, 2H), 1.49-1.27 (m, 2H), 1.26-0.93 (m, 15H), 0.82-0.69 (m, 1H). | 647.5 |
| I-11 | 13 | $^1$H NMR (400 MHz, Methanol-d$_4$) δ 8.66 (s, 1H), 8.38-8.26 (m, 1H), 8.18-7.90 (m, 2H), 7.64 (s, 1H), 7.54-7.38 (m, 1H), 7.36-7.25 (m, 5H), 5.62 (s, 2H), 4.67-4.31 (m, 4H), 4.30-3.77 (m, 9H), 3.42 (s, 1H), 2.74 (t, J = 5.8 Hz, 3H), 1.43-1.34 (m, 1H), 1.27-1.10 (m, 9H), 1.07-0.96 (m, 1H), 0.84-0.68 (m, 1H). | 642.4 |
| I-12 Mix | 14 | $^1$H NMR (400 MHz, Methanol-d$_4$) δ 8.25-8.16 (m, 1H), 7.95-7.88 (m, 1H), 7.38-7.24 (m, 5H), 4.56-3.76 (m, 10H), 3.48-3.33 (m, 2H), 3.22-3.10 (m, 1H), 2.77-2.69 (m, 3H), 1.79-1.62 (m, 6H), 1.57-1.38 (m, 2H), 1.37-1.08 (m, 14H), 1.07-1.00 (m, 2H), 0.91 (q, J = 11.8 Hz, 2H), 0.77 (dd, J = 7.6, 4.0 Hz, 1H). | 647.5 |
| I-13 | 13 | $^1$H NMR (400 MHz, Methanol-d$_4$) δ 8.79 (s, 2H), 8.39-8.30 (m, 1H), 8.07-7.96 (m, 1H), 7.79-7.67 (m, 2H), 7.39-7.21 (m, 5H), 5.74 (d, J = 8.6 Hz, 2H), 4.65-4.29 (m, 4H), 4.26-3.79 (m, 8H), 3.61 (q, J = 7.0 Hz, 1H), 3.49-3.37 (m, 1H), 2.74 (t, J = 6.2 Hz, 3H), 1.24-1.17 (m, 5H), 1.16-1.11 (m, 4H), 1.07-1.00 (m, 1H), 0.83-0.72 (m, 1H). | 642.4 |
| I-14 | 13 | $^1$H NMR (400 MHz, Methanol-d$_4$) δ 8.12-8.01 (m, 1H), 7.90-7.80 (m, 1H), 7.36-7.23 (m, 5H), 4.65-3.83 (m, 15H), 3.39 (s, 1H), 2.74 (s, 3H), 1.53-1.36 (m, 1H), 1.24-1.09 (m, 9H), 1.03 (s, 1H), 0.77 (s, 1H). | 565.4 |
| I-15 | 13 | $^1$H NMR (400 MHz, Methanol-d$_4$) δ 8.79 (s, 2H), 8.44-8.26 (m, 2H), 8.02-7.93 (m, 2H), 7.37-7.22 (m, 5H), 5.64 (s, 2H), 4.66-4.56 (m, 1H), 4.51-3.77 (m, 11H), 3.42 (br s, 1H), 2.79-2.69 (m, 3H), 1.34-1.28 (m, 2H), 1.23-1.18 (m, 3H), 1.16-1.11 (m, 4H), 1.03 (br s, 1H), 0.83-0.68 (m, 1H). | 642.4 |
| I-16A | 5A | $^1$H NMR (400 MHz, Methanol-d$_4$) δ 7.66 (d, J = 5.8 Hz, 1H), 7.51 (s, 1H), 7.34-7.18 (m, 10H), 5.28 (d, J = 3.3 Hz, 2H), 4.61-4.26 (m, 4H), 4.14-3.77 (m, 5H), 3.60 (s, 2H), 3.21-3.12 (m, 1H), 3.01-2.79 (m, 4H), 2.73 (s, 3H), 1.40-1.34 (m, 1H), 1.20-1.16 (m, 4H), 1.12-1.07 (m, 4H), 1.03-0.99 (m, 1H), 0.74 (dt, J = 7.8, 4.0 Hz, 1H). | 627.4 |
| I-16B | 5B | $^1$H NMR (400 MHz, Methanol-d$_4$) δ 7.92 (s, 1H), 7.69 (s, 1H), 7.37-7.24 (m, 10H), 5.36 (s, 2H), 4.66-4.32 (m, 6H), 4.29-3.85 (m, 6H), 3.59-3.51 (m, 2H), 2.72 (s, 3H), 1.52 (t, J = 6.6 Hz, 1H), 1.39-1.28 (m, 1H), 1.26-1.15 (m, 7H), 1.12 (s, 3H), 1.06-1.01 (m, 1H), 0.80 (dd, J = 8.2, 4.2 Hz, 1H). | 627.5 |
| I-17A | 4A | $^1$H NMR (400 MHz, Methanol-d$_4$) δ 8.13 (d, J = 11.0 Hz, 1H), 7.91 (d, J = 9.6 Hz, 1H), 7.39-7.21 (m, 5H), 4.61 (d, J = 11.8 Hz, 1H), 4.57-4.31 (m, 4H), 4.24-3.82 (m, 11H), 3.50-3.37 (m, 1H), 3.14-3.03 (m, 1H), 2.77-2.68 (m, 3H), 2.60 (t, J = 12.6 Hz, 1H), 2.19 (t, J = 7.6 Hz, 1H), 2.03 (q, J = 7.0, 6.4 Hz, 1H), 1.61 (s, 1H), 1.43-1.32 (m, 2H), 1.25-1.08 (m, 11H), 1.03 (t, J = 4.6 Hz, 1H), 0.77 (d, J = 9.6 Hz, 1H). | 690.4 |
| I-17B | 4B | $^1$H NMR (400 MHz, Methanol-d$_4$) δ 8.12 (d, J = 25.6 Hz, 1H), 7.90 (d, J = 19.4 Hz, 1H), 7.36-7.23 (m, 5H), 4.64-4.41 (m, 5H), 4.27-4.07 (m, 5H), 4.04-3.87 (m, 6H), 3.84-3.75 (m, 1H), 3.46-3.36 (m, 1H), 3.07 (q, J = 11.2. 10.4 Hz, 1H), 2.74 (d, J = 2.0 Hz, 3H), 2.58 (q, J = 11.4, 11.0 Hz, 1H), 2.23-2.14 (m, 1H), 2.08 (s, 3H), 1.60 (s, 2H), 1.51-1.41 (m, 1H), 1.22-1.18 (m, 5H), 1.16-1.11 (m, 5H), 1.06-1.02 (m, 1H), 0.81-0.75 (m, 1H). | 690.4 |
| I-18 | 18 | $^1$H NMR (400 MHz, DMSO-d$_6$) δ 9.25 (d, J = 2.6 Hz, 1H), 8.80 (t, J = 15.6 Hz, 1H), 8.41-8.32 (m, 1H), 8.08-7.98 (m, 1H), 7.51 (m, 1H), 6.72 (d, J = 8.8 Hz, 2H), 5.35 (d, J = | 599.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
| --- | --- | --- | --- |
| | | 8.2 Hz, 1H), 4.15 (m, 4H), 3.96-3.74 (m, 3H), 3.72-3.53 (m, 6H), 3.46 (s, 4H), 1.40-1.21 (m, 1H), 1.13-1.00 (m, 5H), 0.90 (d, J = 5.0 Hz, 1H), 0.86-0.58 (m, 2H). | |
| I-19A | 11A | $^1$H NMR (400 MHz, Methanol-d$_4$) δ 8.16-8.10 (m, 1H), 7.90 (d, J = 9.6 Hz, 1H), 7.35-7.23 (m, 5H), 4.61 (d, J = 11.6 Hz, 1H), 4.52-4.31 (m, 3H), 4.24-3.81 (m, 11H), 3.48-3.35 (m, 1H), 3.04 (d, J = 12.4 Hz, 2H), 2.77-2.71 (m, 3H), 2.55 (t, J = 12.2 Hz, 2H), 2.09-1.98 (m, 1H), 1.55 (d, J = 13.2 Hz, 2H), 1.40-1.29 (m, 2H), 1.26-1.19 (m, 5H), 1.15-1.09 (m, 6H), 1.03 (t, J = 4.6 Hz, 1H), 0.77 (dd, J = 12.0, 5.4 Hz, 1H). | 648.4 |
| I-19B | 11B | $^1$H NMR (400 MHz, Methanol-d$_4$) δ 8.17-8.08 (m, 1H), 7.93-7.86 (m, 1H), 7.41-7.20 (m, 5H), 4.67-4.36 (m, 4H), 4.30-4.12 (m, 3H), 4.10-3.79 (m, 9H), 3.46-3.37 (m, 1H), 3.06-3.00 (m, 2H), 2.74 (s, 3H), 2.59-2.50 (m, 2H), 2.04 (s, 1H), 1.60-1.47 (m, 3H), 1.23-1.17 (m, 6H), 1.15-1.12 (m, 4H), 1.07-1.02 (m, 1H), 0.83-0.74 (m, 1H). | 648.5 |
| I-20 | 15 | $^1$H NMR (400 MHz, CD$_3$OD): δ 8.13-8.03 (m, 1H), 7.83-7.78 (m, 1H), 7.24-7.18 (m, 10H), 8.28-8.26 (m, 2H), 4.52-4.34 (m, 3H), 4.10-3.75 (m, 12H), 3.37-3.29 (m, 1H), 1.27-1.19 (m, 2H), 1.11-0.93 (m, 9H), 0.80-0.64 (m, 2H). | 695.9 |
| I-21 | 15 | $^1$H NMR (400 MHz, DMSO-d$_6$) δ 8.38-8.30 (m, 2H), 8.03-7.93 (m, 1H), 7.84-7.79 (m, 1H), 7.70-7.25 (m, 10H), 5.35-5.32 (m, 2H), 4.58-4.38 (m, 4H), 4.20-3.60 (m, 9H), 3.48-3.09 (m, 13H), 2.03-1.95 (m, 1H), 1.37-1.01 (m, 11H). | 759.9 |
| I-22 | 15 | $^1$H NMR (400 MHz, DMSO-d$_6$) δ 8.68-8.31 (m, 3H), 7.84-7.78 (m, 1H), 7.37-7.25 (m, 10H), 5.35-5.31 (m, 2H), 5.00-4.85 (m, 1H), 4.54-3.58 (m, 14H), 2.02-1.95 (m, 2H), 1.10-1.03 (m, 10H), 0.87-0.82 (m, 6H), 0.72-0.65 (m, 5H). | 723.8 |
| I-23A | 4A | $^1$H NMR (400 MHz, Methanol-d$_4$) δ 8.17-8.10 (m, 1H), 7.90 (d, J = 9.6 Hz, 1H), 7.36-7.22 (m, 5H), 4.61 (d, J = 11.8 Hz, 1H), 4.51-4.31 (m, 3H), 4.24-3.80 (m, 10H), 3.49-3.34 (m, 1H), 2.87 (d, J = 11.6 Hz, 2H), 2.80-2.68 (m, 3H), 2.08-1.83 (m, 3H), 1.57 (d, J = 13.6 Hz, 2H), 1.40-1.28 (m, 5H), 1.25-1.18 (m, 3H), 1.15-1.08 (m, 6H), 1.03 (t, J = 4.6 Hz, 1H), 0.76 (dt, J = 12.6, 5.6 Hz, 1H). | 662.5 |
| I-23B | 4B | $^1$H NMR (400 MHz, Methanol-d$_4$) δ 8.20-8.11 (m, 1H), 7.95-7.87 (m, 1H), 7.34-7.25 (m, 5H), 4.66-4.55 (m, 2H), 4.50-4.40 (m, 2H), 4.31-4.11 (m, 5H), 4.07-3.75 (m, 6H), 3.55-3.39 (m, 3H), 3.02-2.83 (m, 5H), 2.74 (s, 3H), 2.27-2.16 (m, 1H), 1.85 (s, 2H), 1.58-1.49 (m, 2H), 1.24-1.18 (m, 5H), 1.16-1.11 (m, 4H), 1.05 (s, 1H), 0.79 (s, 1H). | 662.5 |
| I-24A | 4A | $^1$H NMR (400 MHz, DMSO-d$_6$) δ 9.26 (s, 1H), 8.45-8.35 (m, 2H), 7.89 (s, 1H), 7.40-7.20 (m, 5H), 4.56-4.40 (m, 2H), 4.39-4.16 (m, 2H), 4.15-3.94 (m, 4H), 3.93-3.70 (m, 3H), 3.70-3.43 (m, 2H), 2.62-2.58 (m, 3H), 1.31-1.25 (m, 1H), 1.10-1.02 (m, 9H), 0.84 (s, 1H), 0.64 (s, 1H). | 568.3 |
| I-24B | 4B | $^1$H NMR (400 MHz, DMSO-d$_6$) δ 9.25 (s, 1H), 8.44-8.31 (m, 2H), 7.96-7.84 (m, 1H), 7.35-7.23 (m, 5H), 4.58-4.30 (m, 3H), 4.21-4.00 (m, 3H), 3.94-3.62 (m, 5H), 3.57-3.44 (m, 1H), 3.30 (s, 1H), 2.61 (t, J = 2.6 Hz, 3H), 1.38-1.31 (m, 1H), 1.14-1.01 (m, 9H), 0.86 (s, 1H), 0.70 (dd, J = 8.6, 4.4 Hz, 1H). | 568.4 |
| I-25A | 3A | $^1$H NMR (400 MHz, DMSO-d$_6$) δ 8.39-8.29 (m, 2H), 7.82 (d, J = 12.0 Hz, 2H), 7.38-7.23 (m, 13H), 7.21-7.13 (m, 2H), 5.35 (s, 2H), 4.56-4.40 (m, 2H), 4.38-4.10 (m, 2H), 4.07-3.86 (m, 4H), 3.82-3.69 (m, 2H), 3.68-3.35 (m, 3H), 3.30 (d, J = 2.0 Hz, 2H), 2.64-2.56 (m, 3H), 1.04 (m, J = 14.4, 7.0 Hz, 3H). | 663.4 |
| I-25B | 3B | $^1$H NMR (400 MHz, DMSO-d$_6$) δ 8.39-8.30 (m, 2H), 7.92-7.78 (m, 2H), 7.36-7.26 (m, 11H), 7.22 (d, J = 7.2 Hz, 4H), 5.35 (s, 2H), 4.57-4.48 (m, 1H), 4.45-4.28 (m, 3H), 4.14-3.89 (m, 4H), 3.88-3.57 (m, 5H), 3.37 (s, 1H), 2.61 (dd, J = 11.0, 4.6 Hz, 3H), 1.11-1.02 (m, 3H). | 663.2 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-26A | 3A | $^1$H NMR (400 MHz, DMSO-$d_6$) δ 8.35 (q, J = 13.2, 12.4 Hz, 2H), 7.82 (d, J = 16.6 Hz, 2H), 7.62 (d, J = 7.4 Hz, 1H), 7.56 (s, 1H), 7.48 (d, J = 7.6 Hz, 1H), 7.41 (t, J = 7.4 Hz, 2H), 7.36-7.21 (m, 10H), 5.35 (s, 2H), 4.56-4.09 (m, 6H), 4.04-3.73 (m, 5H), 3.67-3.41 (m, 2H), 2.60-2.57 (m, 3H), 1.13-0.95 (m, 3H). | 649.4 |
| I-26B | 3B | $^1$H NMR (400 MHz, DMSO-$d_6$) δ 8.42-8.27 (m, 2H), 7.96-7.76 (m, 2H), 7.68-7.63 (m, 2H), 7.55-7.41 (m. 3H), 7.36-7.23 (m, 10H), 5.35 (s, 2H), 4.53 (t, J = 9.6 Hz, 1H), 4.48-4.36 (m, 2H), 4.33-4.20 (m, 3H), 4.10-3.79 (m, 5H), 3.77-3.41 (m, 3H), 2.64-2.51 (m, 3H), 1.12-0.99 (m, 3H). | 649.2 |
| I-27A | 3A | $^1$H NMR (400 MHz, DMSO-$d_6$) δ 8.35 (d, J = 11.6 Hz, 2H), 7.89-7.80 (m, 2H), 7.37-7.25 (m, 10H), 5.35 (s, 2H), 4.53 (dd, J = 12.0, 4.8 Hz, 1H), 4.44 (d, J = 12.2 Hz, 1H), 4.36 (s, 1H), 4.07-3.83 (m, 5H), 3.80-3.57 (m, 3H), 3.37 (s, 1H), 3.30 (s, 1H), 2.60 (dd, J = 10.6, 4.4 Hz, 3H), 2.46 (d, J = 7.4 Hz, 1H), 2.18-1.90 (m, 4H), 1.81-1.70 (m, 2H), 1.62-1.52 (m, 2H), 1.08 (d, J = 6.2 Hz, 3H). | 641.4 |
| I-27B | 3B | $^1$H NMR (400 MHz, DMSO-$d_6$) δ 8.40-8.29 (m, 2H), 7.90 (d, J = 17.2 Hz, 1H), 7.81 (d, J = 15.6 Hz, 1H), 7.37-7.25 (m, 10H), 5.35 (s, 2H), 4.52 (1.7 = 11.6 Hz, 1H), 4.46-4.21 (m, 2H), 4.13-3.52 (m, 8H), 3.50-3.37 (m, 1H), 2.60 (t, J = 4.4 Hz, 3H), 2.57-2.52 (m, 1H), 2.14 (t, J = 6.4 Hz, 2H), 2.01 (s, 2H), 1.78 (q, J = 8.2 Hz, 2H), 1.63 (t, J = 9.0 Hz, 2H), 1.12-0.99 (m, 3H). | 641.4 |
| I-28 | 15 | $^1$H NMR (400 MHz, CDCl3): δ 8.84-8.60 (m, 3H), 7.96-7.78 (m, 3H), 7.37-7.27 (m, 6H), 7.25-7.19 (m, 2H), 5.28 (s, 2H), 4.61-4.43 (m, 3H), 4.24-3.41 (m, 15H), 1.28-1.06 (m, 12H), 0.77-0.68 (m, 1H). | 694.9 |
| I-29 | 15 | $^1$H NMR (400 MHz, CD$_3$OD): δ 8.15-8.04 (m, 1H), 7.94-7.78 (m, 2H), 7.25-7.17 (m, 9H), 5.27 (d, J = 6.4 Hz, 2H), 4.52-4.23 (m, 4H), 4.11-3.69 (m, 8H), 3.41-3.27 (m, 3H), 2.42-2.38 (m, 2H), 1.21-1.19 (m, 2H), 1.12-0.98 (m, 8H), 0.95-0.91 (m, 1H), O.71-O.61 (m, 1H) | 699.7 |
| I-30 | 15 | $^1$H NMR (400 MHz, CD$_3$OD): δ 8.15-8.04 (m, 1H), 7.83-7.78 (m, 1H), 7.45-7.03 (m, 10H), 5.28-5.23 (m, 2H), 4.53-4.34 (m, 3H), 4.33-4.16 (m, 1H), 4.14-3.63 (m, 8H), 3.50-3.45 (m, 2H), 3.36-3.25 (m, 1H), 2.13-1.91 (m, 1H), 1.52-1.29 (m, 1H), 1.19 (s. 2H), 1.13-0.98 (m, 8H), 0.92 (s, 1H), 0.69-0.62 (m, 1H). | 671.9 |
| I-31 | 15 | $^1$H NMR (400 MHz, DMSO-$d_6$) δ 8.38-8.33 (m, 2H), 7.96-7.79 (s, 2H), 7.37-7.26 (m, 9H), 5.35 (s, 2H), 4.56-4.36 (m, 3H), 4.24-3.89 (s. 5H), 3.81-3.40 (m, 5H), 3.14-3.05 (m, 2H), 2.59-2.55 (m, 1H), 2.08-1.96 (m, 1H), 1.23 (s, 3H), 1.11-1.01 (m, 7H), 0.86-0.81 (d, J = 6.8 Hz, 2H), 0.70-0.57 (m, 2H) | 670.5 |
| I-32 | 15 | $^1$H NMR (400 MHz, CD$_3$OD) δ 8.23-8.16 (m, 1H), 7.93-7.88 (m, 1H), 7.37-7.28 (m, 10H), 5.38-5.37 (m, 2H), 5.00-4.92 (m, 1H), 4.65-4.44 (m, 3H), 4.39-4.24 (m, 1H), 4.22-3.81 (m, 8H), 3.60-3.48 (m, 4H), 2.91-2.70 (m, 4H), 1.37-1.33 (m, 1H), 1.24-1.10 (m, 9H), 1.03-1.02 (m, 1H), 0.79-0.74 (m, 1H). | 696.9 |
| I-33A | 4A | $^1$H NMR (400 MHz, DMSO-$d_6$) δ 8.38-8.26 (m, 1H), 8.17 (d, J = 13.4 Hz, 1H), 7.86-7.74 (m, 2H), 7.35-7.26 (m, 5H), 4.55-4.40 (m, 2H), 4.35 (d, J = 8.4 Hz, 1H), 4.25-4.14 (m, 1H), 4.08-3.90 (m, 4H), 3.86 (s, 3H), 3.81-3.59 (m, 3H), 3.58-3.40 (m, 2H), 2.60 (dd, J = 9.0, 4.4 Hz, 3H), 1.34-1.25 (m, 1H), 1.12-1.03 (m, 8H), 1.01 (s, 1H), 0.84 (t, J = 4.6 Hz, 1H), 0.64 (q, J = 8.2, 5.8 Hz, 1H). | 565.4 |
| I-33B | 4B | $^1$H NMR (400 MHz, DMSO-$d_6$) δ 8.41-8.3 1 (m, 1H), 8.19-8.13 (m, 1H), 7.94-7.82 (m, 1H), 7.80-7.72 (m, 1H), 7.35-7.27 (m, 5H), 4.52 (t, J = 11.2 Hz, 1H), 4.46-4.29 (m, 2H), 4.17-3.94 (m, 3H), 3.94-3.56 (m, 8H), 3.54-3.39 (m, 1H), 3.30 (s, 1H), 2.61 (d, J = 4.4 Hz, 3H), 1.36 (t, J = 6.6 Hz, 1H), 1.15-1.02 (m, 9H), 0.89-0.82 (m, 1H), 0.71-0.65 (m, 1H). | 565.2 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | ¹HNMR | LCMS |
|---|---|---|---|
| I-34A | 3A | ¹H NMR (400 MHz, DMSO-$d_6$) δ 8.38-8.28 (m, 2H), 7.82 (d, J = 12.0 Hz, 2H), 7.37-7.22 (m, 10H), 7.06 (dd, J = 15.2, 8.2 Hz, 2H), 6.85-6.75 (m, 2H), 5.35 (s, 2H), 4.54-4.41 (m, 3H), 4.36-4.32 (m, 1H), 4.27-4.05 (m, 1H), 4.05-3.84 (m, 4H), 3.83-3.68 (m, 2H), 3.68-3.58 (m, 2H), 3.41-3.20 (m, 3H), 2.63-2.56 (m, 3H), 1.23 (d, J = 6.0 Hz, 6H), 1.05 (dd, J = 13.4, 6.4 Hz, 3H). | 721.4 |
| I-34B | 3B | ¹H NMR (400 MHz, DMSO-$d_6$) δ 8.40-8.29 (m, 2H), 7.92-7.77 (m, 2H), 7.35-7.25 (m, 10H), 7.11 (d, J = 8.2 Hz, 2H), 6.85-6.79 (m, 2H), 5.35 (s, 2H), 4.60-4.47 (m, 2H), 4.45-4.31 (m, 2H), 4.21-3.33 (m, 12H), 2.61 (dd, J = 10.4, 4.6 Hz, 3H), 1.24 (dd, J = 6.0, 2.8 Hz, 6H), 1.12-1.02 (m, 3H). | 721.2 |
| I-35 | 1A | ¹H NMR (400 MHz, Methanol-$d_4$) δ 8.50-8.47 (m, 1H), 8.37-8.29 (m, 2H), 8.00-7.94 (m, 1H), 7.71-7.61 (m, 2H), 7.16-7.10 (m, 1H), 5.57 (s, 2H), 4.81-4.58 (m, 2H), 4.45-4.28 (m, 1H), 4.27-4.16 (m, 2H), 4.14-3.98 (m, 3H), 3.97-3.84 (m, 2H), 3.30-3.22 (m, 1H), 2.71-2.66 (m, 3H), 1.43-1.32 (m, 1H), 1.21-1.11 (m, 4H), 1.10-1.07 (m, 2H), 1.05-1.01 (m, 1H), 0.80-0.73 (m, 1H). | 561.5 |
| I-36A | 3A | ¹H NMR (400 MHz, DMSO-$d_6$) δ 8.44-8.26 (m, 1H), 8.19-8.12 (m, 1H), 7.89-7.73 (m, 2H), 7.35-7.24 (m, 5H), 4.56-4.40 (m, 2H), 4.35 (dd, J = 8.8, 4.0 Hz, 1H), 4.21-3.88 (m, 5H), 3.85 (s, 3H), 3.78-3.38 (m, 5H), 2.60 (dd, J = 9.2, 4.4 Hz, 3H), 1.94-1.83 (m, 2H), 1.10-1.04 (m, 3H), 0.93-0.80 (m, 1H), 0.40 (t, J = 7.0 Hz, 2H), 0.08-0.01 (m, 2H). | 551.4 |
| I-36B | 3B | ¹H NMR (400 MHz, DMSO-$d_6$) δ 8.36-8.29 (m, 1H), 8.22-8.09 (m, 1H), 7.93-7.72 (m, 2H), 7.35-7.26 (m, 5H), 4.52 (t, J = 10.6 Hz, 1H), 4.45-4.22 (m, 2H), 4.05-3.93 (m, 3H), 3.85 (d, J = 4.4 Hz, 5H), 3.76-3.36 (m, 5H), 2.62-2.58 (m, 3H), 1.96 (t, J = 7.4 Hz, 2H), 1.09-1.05 (m, 3H), 0.90 (d, J = 6.8 Hz, 1H), 0.46-0.38 (m, 2H), 0.09 (s, 2H). | 551.2 |
| I-37A | 3A | ¹H NMR (400 MHz, DMSO-$d_6$) δ 8.40-8.28 (m, 2H), 7.88-7.77 (m, 2H), 7.38-7.23 (m, 10H), 5.35 (s, 2H), 4.53 (d, J = 12.2 Hz, 1H), 4.44 (d, J = 12.0 Hz, 1H), 4.35 (d, J = 9.0 Hz, 1H), 4.19-3.84 (m, 5H), 3.81-3.53 (m, 3H), 3.52-3.35 (m, 1H), 3.30 (s, 1H), 2.60 (dd, J = 10.4, 4.4 Hz, 3H), 1.92-1.72 (m, 2H), 1.59 (s, 6H), 1.25-0.98 (m, 6H), 0.84 (d, J = 9.4 Hz, 2H). | 669.2 |
| I-37B | 3B | ¹H NMR (400 MHz, DMSO-$d_6$) δ 8.40-8.27 (m, 2H), 7.93-7.77 (m, 2H), 7.38-7.20 (m, 10H), 5.35 (s, 2H), 4.52 (t, J = 11.6 Hz, 1H), 4.46-4.20 (m, 2H), 4.11-3.79 (m, 5H), 3.77-3.51 (m, 3H), 3.49-3.38 (m, 1H), 2.60 (d, J = 4.4 Hz, 3H), 1.89 (s, 2H), 1.63 (s, 6H), 1.26-1.01 (m, 7H), 0.91-0.85 (m, 2H). | 669.2 |
| I-38A | 4A | ¹H NMR (400 MHz, DMSO-$d_6$) δ 8.36-8.19 (m, 1H), 7.84 (dd, J = 11.0, 4.8 Hz, 1H), 7.35-7.25 (m, 5H), 4.56-4.39 (m, 2H), 4.38-4.32 (m, 1H), 4.23-4.10 (m, 1H), 4.05-3.33 (m, 13H), 2.66 (d, J = 11.1 Hz, 1H), 2.61 (d, J = 4.5 Hz, 3H), 1.57-1.52 (m, 4H), 1.36-1.20 (m, 1H), 1.11-1.00 (m, 9H), 0.83 (q, J = 4.6 Hz, 1H), 0.68-0.60 (m, 1H). | 569.5 |
| I-38B | 4B | ¹H NMR (400 MHz, DMSO-$d_6$) δ 8.40-8.27 (m, 1H), 7.95-7.80 (m, 1H), 7.36-7.25 (m, 5H), 4.57-4.28 (m, 3H), 4.15-3.92 (m, 2H), 3.91-3.78 (m, 4H), 3.77-3.59 (m, 2H), 3.59-3.41 (m, 3H), 3.30 (s, 2H), 2.60 (d, J = 4.2 Hz, 3H), 1.54 (s, 4H), 1.37-1.34 (m, 1H), 1.11 (s, 3H), 1.10-1.02 (m, 6H), 0.86 (s, 1H), 0.69 (dt, J = 7.8, 4.2 Hz, 1H). | 569.4 |
| I-39A | 4A | ¹H NMR (400 MHz, DMSO-$d_6$) δ 8.58 (d, J = 1.8 Hz, 1H), 8.41-8.33 (m, 1H), 7.88-7.78 (m, 2H), 7.35-7.25 (m, 5H), 4.53 (d, J = 12.2 Hz, 1H), 4.43 (d, J = 12.2 Hz, 1H), 4.34 (d, J = 8.6 Hz, 1H), 4.27-3.66 (m, 9H), 3.65-3.43 (m, 1H), 2.60 (dd, J = 7.4, 4.4 Hz, 3H), 1.32-1.23 (m, 1H), 1.11-1.02 (m, 9H), 0.84 (t, J = 4.6 Hz, 1H), 0.69-0.60 (m, 1H). | 552.4 |
| I-39B | 4B | ¹H NMR (400 MHz, DMSO-$d_6$) δ 8.58-8.56 (m, 1H), 8.46-8.39 (m, 1H), 7.96-7.84 (m, 1H), 7.83-7.75 (m, | 552.1 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 1H), 7.35-7.26 (m, 5H), 4.55-4.50 (m, 1H), 4.45-4.31 (m, 2H), 4.20-3.39 (m, 10H), 2.64-2.59 (m, 3H), 1.38-1.32 (m, 1H), 1.13-1.05 (m, 9H), 0.87 (t, J = 5.0 Hz, 1H), 0.68 (dq, J = 7.8, 4.4, 3.6 Hz, 1H). | |
| I-40A | 5A | $^1$H NMR (400 MHz, DMSO-d$_6$) δ 8.49-8.47 (m, 1H), 8.26-8.19 (m, 1H), 8.17 (s, 1H), 7.84-7.72 (m, 2H), 7.44 (d, J = 7.8 Hz, 1H), 7.33-7.24 (m, 6H), 4.55-4.41 (m, 2H), 4.37-4.28 (m, 1H), 3.99-3.91 (m, 3H), 3.75-3.65 (m, 4H), 3.55 (d, J = 10.0 Hz, 1H), 2.97-2.90 (m, 2H), 2.73-2.62 (m, 2H), 2.59 (d, J = 4.6 Hz, 3H), 1.34-1.26 (m, 1H), 1.13-0.99 (m, 9H), 0.85-0.79 (m, 1H), 0.65-0.60 (m, 1H). | 548.4 |
| I-40B | 5B | $^1$H NMR (400 MHz, DMSO-d$_6$) δ 8.49-8.45 (m, 1H), 8.27 (dd, J = 8.8, 4.8 Hz, 1H), 7.84 (dd, J = 22.8. 4.8 Hz, 1H), 7.73 (tdd, J = 7.6, 5.8, 1.8 Hz, 1H), 7.42 (d, J = 7.8 Hz, 1H), 7.32-7.22 (m, 6H), 4.52 (dd, J = 12.0, 1.6 Hz, 1H), 4.42 (dd, J = 12.0, 2.4 Hz, 1H), 4.35 (ddd, J = 13.8, 8.8, 4.4 Hz, 1H), 4.15-4.03 (m, 1H), 3.94-3.65 (m, 5H), 3.22 (q, J = 6.8 Hz, 1H), 3.06-2.90 (m, 2H), 2.73-2.65 (m, 1H), 2.64-2.56 (m, 4H), 1.33 (ddd, J = 23.8, 8.0, 5.4 Hz, 1H), 1.12-0.99 (m, 9H), 0.83 (dd, J = 5.4, 3.8 Hz, 1H), 0.65 (dd, J = 8.0, 3.8 Hz, 1H). | 548.4 |
| I-41A | 10A | $^1$H NMR (400 MHz, DMSO-d$_6$) δ 13.22 (s, 1H), 8.32 (dd, J = 23.6, 9.0 Hz, 1H), 7.84 (s, 2H), 7.34-7.26 (m, 5H), 4.55-4.40 (m, 2H), 4.35 (dd, J = 8.6, 3.4 Hz, 1H), 4.20-3.38 (m, 10H), 2.60 (dd, J = 11.2, 4.4 Hz, 3H), 1.88 (dd, J = 22.8, 6.4 Hz, 2H), 1.07 (d, J = 5.4 Hz, 3H), 0.87 (s, 1H), 0.40 (s, 2H), 0.04 (d, J = 7.6 Hz, 2H). | 537.4 |
| I-41B | 10B | $^1$H NMR (400 MHz, DMSO-d$_6$) δ 13.22 (s, 1H), 8.32 (t, J = 10.2 Hz, 1H), 8.23-8.00 (m, 1H), 7.97-7.76 (m, 2H), 7.35-7.24 (m, 5H), 4.52 (t, J = 12.2 Hz, 1H), 4.45-4.21 (m, 2H), 4.11-3.95 (m, 3H), 3.90-3.80 (m, 2H), 3.77-3.38 (m, 5H), 2.60 (d, J = 4.2 Hz, 3H), 2.00-1.92 (m, 2H), 1.10-1.03 (m, 3H), 0.91 (s, 1H), 0.42 (t, J = 6.4 Hz, 2H), 0.09 (t, J = 6.0 Hz, 2H). | 537.1 |
| I-42A | 4A | $^1$H NMR (400 MHz, DMSO-d$_6$) δ 8.73-8.66 (m, 2H), 8.43-8.24 (m, 1H), 7.99-7.70 (m, 1H), 7.52-7.44 (m, 1H), 7.35-7.22 (m, 5H), 4.52 (dd, J = 12.2, 6.0 Hz, 1H), 4.46-4.07 (m, 3H), 4.04-3.57 (m, 7H), 3.54-3.38 (m, 1H), 3.30 (s, 1H), 2.64-2.54 (m, 3H), 1.33-1.20 (m, 1H), 1.11-0.96 (m, 9H), 0.85-0.78 (m, 1H), 0.70-0.57 (m, 1H). | 562.4 |
| I-42B | 4B | $^1$H NMR (400 MHz, DMSO-d$_6$) δ 8.72-8.63 (m, 2H), 8.47-8.25 (m, 1H), 7.95-7.79 (m, 2H), 7.48 (dd, J = 7.6, 4.8 Hz, 1H), 7.37-7.16 (m, 5H), 4.59-4.30 (m, 3H), 4.28-4.00 (m, 1H), 3.98-3.63 (m, 6H), 3.60-3.34 (m, 2H), 3.31 (d, J = 4.8 Hz, 1H), 2.60 (dt, J = 7.4, 3.2 Hz, 3H), 1.41-1.22 (m, 1H), 1.16-1.01 (m, 7H), 1.00-0.92 (m, 2H), 0.90-0.80 (m, 1H), 0.72-0.61 (m, 1H). | 562.2 |
| I-43A | 3A | $^1$H NMR (400 MHz, DMSO-d$_6$) δ 8.42-8.28 (m, 2H), 7.93 (d, J = 12.8 Hz, 1H), 7.85 (d, J = 4.8 Hz, 1H), 7.36-7.23 (m, 5H), 5.18 (q, J = 9.0 Hz, 2H), 4.56-4.49 (m, 1H), 4.43 (d, J = 12.2 Hz, 1H), 4.35 (d, J = 8.6 Hz, 1H), 4.20-3.88 (m, 5H), 3.87-3.47 (m, 4H), 3.41 (dt, J = 12.6, 6.2 Hz, 1H), 2.60 (dd, J = 10.4, 4.5 Hz, 3H), 1.95-1.88 (m, 1H), 1.85 (dd, J = 6.9, 2.6 Hz, 1H), 1.12-1.04 (m, 3H), 0.87 (dt, J = 13.8, 6.6 Hz, 1H), 0.44-0.36 (m, 2H), 0.08-0.00 (m, 2H). | 619.3 |
| I-43B | 3B | $^1$H NMR (400 MHz, DMSO-d$_6$) δ 8.38-8.29 (m, 2H), 8.02-7.73 (m, 2H), 7.36-7.21 (m, 5H), 5.17 (q, J = 9.0 Hz, 2H), 4.52 (t, J = 11.2 Hz, 1H), 4.46-4.27 (m, 2H), 4.27-4.01 (m, 2H), 4.00-3.52 (m, 7H), 3.51-3.38 (m, 1H), 2.60 (dd, J = 4.6, 2.4 Hz, 3H), 1.96 (t, J = 7.4 Hz, 2H), 1.13-1.01 (m, 3H), 0.90 (d, J = 8.2 Hz, 1H), 0.43 (d, J = 7.8 Hz, 2H), 0.10-0.05 (m, 2H). | 619.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-44A | 4A | $^1$H NMR (400 MHz, DMSO-$d_6$) δ 8.31 (s, 1H), 7.89-7.80 (m, 1H), 7.72 (s, 1H), 7.65 (s, 1H), 7.41-7.26 (m, 5H), 4.53 (d, J = 12.2 Hz, 1H), 4.43 (d, J = 12.2 Hz, 1H), 4.39-4.09 (m, 3H), 4.07-3.36 (m, 8H), 2.60 (dd, J = 9.6, 4.4 Hz, 3H), 1.35-1.24 (m, 1H), 1.12-1.00 (m, 9H), 0.84 (br s, 1H), 0.63 (br s, 1H). | 551.1 |
| I-44B | 4B | $^1$H NMR (400 MHz, DMSO-$d_6$) δ 8.38-8.32 (m, 1H), 7.92-7.86 (m, 1H), 7.75-7.68 (m, 1H), 7.64 (s, 1H), 7.35-7.27 (m, 5H), 4.58-4.26 (m, 4H), 4.25-4.05 (m, 2H), 4.04-3.84 (m, 2H), 3.84-3.77 (m, 2H), 3.65 (s, 2H), 2.61 (d, J = 4.0 Hz, 3H), 1.39-1.35 (m, 1H), 1.12-1.04 (m, 9H), 0.86 (br s, 1H), 0.68 (br s, 1H). | 551.4 |
| I-45A | 4A | $^1$H NMR (400 MHz, DMSO-$d_6$) δ 8.63-8.60 (m, 1H), 8.41-8.25 (m, 1H), 7.97-7.75 (m, 3H), 7.54-7.49 (m, 1H), 7.35-7.23 (m, 5H), 4.54-4.50 (m, 1H), 4.45-4.26 (m, 2H), 4.22-4.03 (m, 2H), 4.02-3.85 (m, 4H), 3.84-3.64 (m, 3H), 3.60-3.41 (m, 1H), 2.64-2.54 (m, 3H), 1.37-1.21 (m, 1H), 1.11-0.98 (m, 9H), 0.83 (dq, J = 12.6, 4.6, 4.0 Hz, 1H), 0.67-0.60 (m, 1H). | 562.2 |
| I-45B | 4B | $^1$H NMR (400 MHz, DMSO-$d_6$) δ 8.66-8.55 (m, 1H), 8.44-8.27 (m, 1H), 8.01-7.68 (m, 3H), 7.51 (ddd, J = 7.6, 4.6. 1.2 Hz, 1H), 7.40-7.16 (m, 5H), 4.59-4.11 (m, 4H), 4.10-3.53 (m, 8H), 3.49-3.38 (m, 1H), 2.60 (td, J = 5.2, 4.8, 2.6 Hz, 3H), 1.40-1.30 (m, 1H), 1.13-0.95 (m, 9H), 0.88-0.81 (m, 1H), 0.70-0.62 (m, 1H). | 562.4 |
| I-46A | 4A | $^1$H NMR (400 MHz, DMSO-$d_6$) δ 8.71-8.65 (m, 2H), 8.44-8.26 (m, 1H), 7.89-7.74 (m, 1H), 7.51-7.45 (m, 2H), 7.35-7.22 (m, 5H), 4.52 (dd, J = 12.2, 6.2 Hz, 1H), 4.45-4.25 (m, 2H), 4.23-4.07 (m, 1H), 4.03-3.81 (m, 3H), 3.78-3.37 (m, 6H), 2.63 (d, J = 4.6 Hz, 2H), 2.56 (dd, J = 4.6, 2.0 Hz, 1H), 1.35-1.19 (m, 1H), 1.11-0.96 (m, 9H), 0.87-0.77 (m, 1H), 0.69-0.56 (m, 1H). | 562.1 |
| I-46B | 4B | $^1$H NMR (400 MHz, DMSO-$d_6$) δ 8.69-8.65 (m, 2H), 8.45-8.25 (m, 1H), 7.94-7.79 (m, 1H), 7.46-7.43 (m, 2H), 7.36-7.18 (m, 5H), 4.58-4.19 (m, 4H), 4.14-4.01 (m, 1H), 3.97-3.81 (m, 2H), 3.80-3.75 (m, 1H), 3.73-3.65 (m, 3H), 3.62-3.46 (m, 1H), 3.40-3.35 (m, 1H), 2.62-2.58 (m, 3H), 1.39-1.27 (m, 1H), 1.13-0.94 (m, 9H), 0.85 (dt, J = 20.8, 4.8 Hz, 1H), 0.66 (ddt, J = 16.0, 8.0, 3.8 Hz, 1H). | 562.2 |
| I-47A | 5A | $^1$H NMR (400 MHz, DMSO-$d_6$) δ 8.27 (q, J = 8.4, 7.8 Hz, 1H), 8.15 (s, 1H), 7.86-7.77 (m, 1H), 7.60 (d, J = 1.8 Hz, 1H), 7.39-7.22 (m, 5H), 4.59-4.49 (m, 1H), 4.43 (d, J = 12.2 Hz, 1H), 4.37-4.24 (m, 1H), 3.99-3.89 (m, 3H), 3.79 (d, J = 5.8 Hz, 3H), 3.73-3.62 (m, 1H), 3.53 (dd, J = 15.4, 9.2 Hz, 2H), 3.25 (t, J = 7.6 Hz, 1H), 3.13 (dd, J = 14.2, 7.6 Hz, 1H), 3.00-2.91 (m, 2H), 2.71-2.54 (m, 5H), 1.28 (m, 1H), 1.19 (d, J = 6.4 Hz, 1H), 1.12-0.96 (m, 8H), 0.85-0.79 (m, 1H), 0.66-0.60 (m, 1H). | 551.40 |
| I-47B | 5B | $^1$H NMR (400 MHz, DMSO-$d_6$) δ 8.28-8.23 (m, 2H), 7.86-7.79 (m, 1H), 7.55 (d, 1H), 7.34-7.23 (m, 5H), 4.55-4.51 (m, 1H), 4.44-4.40 (m, 1H), 4.37-4.30 (m, 1H), 4.10-4.01 (m, 2H), 3.91-3.83 (m, 2H), 3.77 (d, 2H), 3.73-3.70 (m, 1H), 3.65-3.62 (m, 1H), 3.51-3.49 (m, 1H), 3.43-3.42 (m, 2H), 3.16 (q, J = 6.8 Hz, 1H), 2.95-2.83 (m, 2H), 2.61-2.58 (m, 3H), 2.54 (d, 1H), 1.36-1.27 (m, 1H), 1.1-1.0 (m, 9H), 0.84-0.82 (m, 1H), 0.66-0.63 (m, 1H). | 551.2 |
| I-48A | 12A | $^1$H NMR (400 MHz, DMSO-$d_6$) δ 8.31-8.25 (m, 2H), 7.88-7.85 (m, 1H), 7.75 (s, 1H), 7.39 (d, J = 0.6 Hz, 1H), 7.35-7.25 (m, 8H), 7.19 (s, 1H), 7.18 (s, 1H), 5.23 (s, 2H), 4.54-4.51 (m, 1H), 4.44-4.37 (m, 1H), 4.37-4.30 (m, 1H), 4.23-4.14 (m, 1H), 4.01-3.86 (m, 3H), 3.71 (dd, J = 10.0, 5.4 Hz, 1H), 3.64-3.39 (m, 5H), 2.61 (d, J = 4.6 Hz, 3H), 1.36-1.25 (m, 1H), 1.10-1.00 (m, 9H), 0.84 (t, J = 4.6 Hz, 1H), 0.66-0.58 (m, 1H). | 656.1 |
| I-48B | 12B | $^1$H NMR (400 MHz, DMSO-$d_6$) δ 8.31 (d, J = 8.8 Hz, 1H), 8.27 (d, J = 5.0 Hz, 1H), 7.91-7.84 (m, 1H), 7.74 (t. J = 0.8 Hz, 1H), 7.38 (s, 1H), 7.35-7.23 (m, 8H), 7.19 (d, J = 1.4 Hz, 1H), 7.19-7.15 (m, 1H), 5.23 (s, 2H), 4.56-4.49 (m, 1H), 4.47-4.38 (m, 1H), 4.37-4.30 (m, 1H), 4.12- | 656.2 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 4.05 (m, 1H), 4.01-3.69 (m, 3H), 3.66-3.35 (m, 6H), 2.61 (dd, J = 4.6, 1.8 Hz, 3H), 1.36 (ddd, J = 10.6.7.8.5.4 Hz, 1H), 1.14-1.04 (m, 9H), 0.86 (q, J = 4.8 Hz, 1H), 0.68 (td, J = 7.6, 3.8 Hz, 1H). | |
| I-49A | 5A | $^1$H NMR (400 MHz, DMSO-$d_6$) δ 8.51 (s, 1H), 8.46 (dd, J = 4.8, 1.6 Hz, 1H), 8.25-8.19 (m, 1H), 7.86-7.77 (m, 1H), 7.73 (dt, J = 7.8, 2.0 Hz, 1H), 7.37-7.31 (m, 2H), 7.30-7.24 (m, 4H), 4.52 (dd, J = 12.2. 5.2 Hz, 1H), 4.43 (d, J = 12.2 Hz, 1H), 4.34 (dt, J = 8.8, 3.6 Hz, 1H), 4.02-3.97 (m, 1H), 3.94-3.91 (m, J = 13.8, 6.8 Hz, 2H), 3.75-3.65 (m, 1H), 3.63 (d, J = 3.2 Hz, 2H), 3.54 (d, J = 10.0 Hz, 1H), 3.30-3.20 (m, 1H), 2.89 (t, J = 9.4 Hz, 2H), 2.65 (dd, J = 9.0, 2.2 Hz, 1H), 2.59 (t, J = 4.2 Hz, 4H), 1.37-1.25 (m, 1H), 1.18-0.95 (m, 9H), 0.86-0.77 (m, 1H), 0.62 (dt, J = 8.4, 4.0 Hz, 1H). | 548.4 |
| I-49B | 5B | $^1$H NMR (400 MHz, DMSO-$d_6$) δ 8.52 (d, J = 2.4 Hz, 1H), 8.50-8.47 (m, 1H), 8.30 (dd, J = 9.0, 3.6 Hz, 1H), 7.90-7.83 (m, 1H), 7.74 (d, J = 7.8 Hz, 1H), 7.37-7.26 (m, 6H), 4.56 (d, J = 12.0 Hz, 1H), 4.44 (dd, J = 12.0. 2.8 Hz, 1H), 4.37 (ddd, J = 13.6, 8.8, 4.4 Hz, 1H), 4.17-4.10 (m, 1H), 3.97-3.86 (m, 1H), 3.79 (dd, J = 18.2. 9.4 Hz, 1H). 3.69-3.67 (m, 1H), 3.65 (s, 1H), 3.62-3.52 (m, 1H), 3.23 (q, J = 6.3 Hz, 1H), 3.03-2.86 (m, 2H), 2.71-2.64 (m, 1H), 2.64-2.56 (m, 4H), 1.39-1.30 (m, 1H), 1.15-1.01 (m, 9H), 0.88-0.82 (m, 1H), 0.67 (dd, J = 8.0, 3.8 Hz, 1H). | 548.4 |
| I-50A | 5A | $^1$H NMR (400 MHz, DMSO-$d_6$) δ 8.23 (t, J = 8.2 Hz, 1H), 8.18 (s, 1H), 7.79 (dd, J = 8.8, 4.4 Hz, 1H), 7.53-7.48 (m, 2H), 7.34-7.22 (m, 5H), 4.50 (d, J = 5.6 Hz, 1H), 4.43 (d, 12.2 Hz, 1H), 4.36-4.30 (m, 1H), 3.99-3.87 (m, 3H), 3.66 (dd, J = 20.5, 9.8 Hz, 1H), 3.57-3.40 (m, 3H), 3.25-3.20 (m, 1H), 2.93-2.83 (m, 2H), 2.64-2.52 (m, 5H), 1.33-1.23 (m, 1H), 1.13-0.97 (m, 9H), 0.84-0.78 (m, 1H), 0.66-0.59 (m, 1H). | 537.4 |
| I-50B | 5B | $^1$H NMR (400 MHz, DMSO-$d_6$) δ 8.28-8.25 (m, 1H), 7.87-7.78 (m, 1H), 7.48 (d, 2H), 7.33-7.23 (m, 5H), 4.54-4.51 (m, 1H), 4.44-4.40 (m, 1H), 4.37-4.30 (m, 1H), 4.10-4.01 (m, 1.5H), 3.91-3.81 (m, 1.5H), 3.77-3.62 (m, 2H), 3.51-3.43 (m, 4H), 3.16 (q, J = 6.8 Hz, 1H), 2.94-2.83 (m, 2H), 2.61-2.58 (m, 3H), 1.36-1.27 (m, 1H), 1.1-1.0 (m, 9H), 0.84-0.82 (m, 1H), 0.65-0.62 (m, 1H). | 537.2 |
| I-51A | 5A | $^1$H NMR (400 MHz, DMSO-$d_6$) δ 9.02 (d, J = 1.8 Hz, 1H), 8.26-8.15 (m, 1H), 7.84-7.76 (m, 2H), 7.35-7.23 (m, 5H), 4.52 (dd, J = 12.2, 5.6 Hz, 1H), 4.47-4.39 (m, 1H), 4.36-4.25 (m, 1H), 4.02-3.81 (m, 5H), 3.74-3.50 (m, 1H), 3.31-3.26 (m, 2H), 2.95 (p, J = 10.2, 9.4 Hz, 2H), 2.61 (dd, J = 14.6, 6.8 Hz, 5H), 1.29 (ddd, J = 14.2, 8.0, 5.4 Hz, 1H), 1.14-0.98 (m, 9H), 0.85-0.79 (m, 1H), 0.62 (ddd, J = 7.8, 6.0, 3.8 Hz, 1H). | 554.4 |
| I-51B | 6B | $^1$H NMR (400 MHz, DMSO-$d_6$) δ 9.01 (d, J = 1.4 Hz, 1H), 8.23 (d, J = 8.8 Hz, 1H), 7.84 (dd, J = 21.4, 4.6 Hz, 1H), 7.77 (s, 1H), 7.34-7.23 (m, 5H), 4.54-4.40 (m, 2H), 4.34 (ddd, J = 16.6, 8.9, 4.6 Hz, 1H), 4.15-3.99 (m, 1H), 3.93-3.81 (m, 4H), 3.78-3.73 (m, 1H), 3.64-3.48 (m, 1H), 3.27-3.19 (m, 1H), 3.07-2.87 (m, 2H), 2.68-2.52 (m, 5H), 1.33 (ddd, J = 23.2, 8.0, 5.4 Hz, 1H), 1.11-1.00 (m, 9H), 0.85-0.81 (m, 1H), 0.64 (dd, J = 8.0. 3.8 Hz, 1H). | 554.4 |
| I-52 | 15 | $^1$H NMR (400 MHz, CD$_3$OD): δ 8.24-8.14 (m, 1H), 7.97-7.87 (m, 2H), 7.51-7.06 (m, 10H), 5.37-5.33 (m, 2H), 4.63-4.30 (m, 4H), 4.08-3.78 (m, 8H), 3.46-3.35 (m, 1H), 3.20-3.15 (m, 2H), 3.01-2.95 (m, 2H), 1.50-1.41 (m, 13H), 1.38-1.25 (m, 4H), 1.25-1.09 (m, 8H), 1.06-1.00 (m, 1H), 0.82-0.70 (m, 1H) | 812.5 |
| I-53A | 3A | $^1$H NMR (400 MHz, DMSO-$d_6$) δ 8.39-8.28 (m, 1H), 8.21 (d, J = 7.6 Hz, 1H), 7.85-7.77 (m, 2H), 7.36-7.24 (m, 5H), 4.53 (dd, J = 12.2, 3.2 Hz, 1H), 4.43 (d, J = 12.0 Hz, 1H), 4.35 (dd, J = 8.8, 3.8 Hz, 1H), 4.20-3.84 (m, 8H), 3.80-3.37 (m, 4H), 2.60 (dd, J = 10.2, 4.4 Hz, 3H). 1.92 (dd, J = 7.0, 4.6 Hz, 1H), 1.86 (dd, J = 6.8, 2.4 Hz, | 591.2 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 1H), 1.27-1.21 (m, 1H), 1.08 (p, J = 3.0 Hz, 3H), 0.86 (dq, J = 12.6, 6.6 Hz, 1H), 0.52 (d, J = 7.6 Hz, 2H), 0.42-0.36 (m, 4H), 0.08-0.01 (m, 2H). | |
| I-53B | 3B | $^1$H NMR (400 MHz, DMSO-d$_6$) δ 8.33 (q, J = 11.4, 9.2 Hz, 1H), 8.24-8.16 (m, 1H), 7.93-7.75 (m, 2H), 7.35-7.24 (m, 5H), 4.52 (t, J = 11.4 Hz, 1H), 4.45-4.22 (m, 2H), 4.15-3.36 (m, 12H), 2.60 (d, J = 4.4 Hz, 3H), 1.96 (t, J = 7.6 Hz, 2H), 1.25 (d, J = 7.6 Hz, 1H), 1.10-1.03 (m, 3H), 0.91 (t, J = 6.2 Hz, 1H), 0.55-0.34 (m, 6H), 0.11-0.08 (m, 2H). | 591.2 |
| I-54A | 7A | $^1$H NMR (400 MHz, DMSO-d$_6$) δ 8.42-8.27 (m, 2H), 7.86-7.79 (m, 2H), 7.37-7.25 (m, 10H), 5.35 (s, 2H), 4.53 (dd, J = 12.2, 4.2 Hz, 1H), 4.45-4.32 (m, 2H), 4.25-4.06 (m, 2H), 4.00-3.85 (m, 4H), 3.81-3.60 (m, 3H), 3.57-3.40 (m, 1H), 2.63-2.57 (m, 3H), 2.40-2.22 (m, 1H), 1.09-1.04 (m, 3H), 0.98-0.86 (m, 6H). | 615.1 |
| I-54B | 7B | $^1$H NMR (400 MHz, DMSO-d$_6$) δ 8.39-8.27 (m, 2H), 7.92-7.78 (m, 2H), 7.37-7.26 (m, 10H), 5.35 (s, 2H), 4.52 (t, J = 11.4 Hz, 1H), 4.46-4.27 (m, 3H), 4.16-3.97 (m, 3H), 3.95-3.78 (m, 2H), 3.77-3.53 (m, 4H), 3.51-3.38 (m, 1H), 2.60 (d, J = 4.4 Hz, 3H), 2.40 (p, J = 6.6 Hz, 1H), 1.10-1.02 (m, 3H), 0.98-0.94 (m, 6H). | 615.2 |
| I-55A | 5A | $^1$H NMR (400 MHz, DMSO-d$_6$) δ 8.50-8.48 (m, 2H), 8.26-8.20 (m, 1H), 7.80 (dd, J = 12.0, 4.8 Hz, 1H), 7.35-7.25 (m, 7H), 4.56-4.41 (m, 2H), 4.36-4.27 (m, 1H), 4.03-3.89 (m, 3H), 3.75-3.50 (m, 4H), 2.94-2.87 (m, 2H), 2.67 (t, J = 7.8 Hz, 1H), 2.59 (d, J = 4.6 Hz, 3H), 1.30 (ddd, J = 13.6.8.0.5.2 Hz, 1H), 1.13-0.99 (m, 9H), 0.82 (q, J = 5.2 Hz, 1H), 0.63 (dd, J = 8.0, 3.8 Hz, 1H). | 548.5 |
| I-55B | 5B | $^1$H NMR (400 MHz, DMSO-d$_6$) δ 8.50-8.47 (m, 2H), 8.28 (dd, J = 9.0, 4.8 Hz, 1H), 7.90-7.83 (m, 1H), 7.33-7.29 (m, 3H), 7.29-7.22 (m, 4H), 4.55-4.51 (m, 1H), 4.46-4.28 (m, 2H), 4.15-4.05 (m, 1H), 3.96-3.67 (m, 3H), 3.65-3.49 (m, 2H), 3.33-3.18 (m, 2H), 3.01-2.86 (m, 2H), 2.70-2.51 (m, 5H), 1.33 (ddd, J = 25.4, 8.0, 5.2 Hz, 1H), 1.13-0.97 (m, 9H), 0.83 (dd, J = 5.4, 3.8 Hz, 1H), 0.65 (dd, J = 8.0, 3.8 Hz, 1H). | 548.2 |
| I-56A | 1A | $^1$H NMR (400 MHz, DMSO-d$_6$) δ 8.39-8.31 (m, 1H), 8.26-8.12 (m, 1H), 7.86-7.70 (m, 2H), 7.38-7.23 (m, 5H), 5.35 (s, 2H), 4.30-4.24 (m, 1H), 4.22-4.04 (m, 1H), 4.04-3.79 (m, 4H), 3.79-3.52 (m, 4H), 3.52-3.35 (m, 1H), 3.26-3.19 (m, 1H), 3.14-3.06 (m, 1H), 2.61-2.54 (m, 3H), 1.98-1.89 (m, 2H), 1.70-1.56 (m, 5H), 1.43 (s, 1H), 1.26-1.06 (m, 3H), 1.04-0.98 (m, 3H), 0.95-0.77 (m, 3H), 0.47-0.39 (m, 2H), 0.12-0.04 (m, 2H). | 633.3 |
| I-56B | 1B | $^1$H NMR (400 MHz, DMSO-d$_6$) δ 8.40-8.29 (m, 1H), 8.28-8.10 (m, 1H), 7.93-7.70 (m, 2H), 7.38-7.21 (m, 5H), 5.35 (s, 2H), 4.31-4.21 (m, 1H), 4.11-3.84 (m, 3H), 3.83-3.51 (m, 4H), 3.50-3.37 (m, 1H), 3.27-2.62 (m, 3H), 2.61-2.53 (m, 3H), 1.99-1.90 (m, 2H), 1.71-1.50 (m, 6H), 1.50-1.30 (m, 1H), 1.17-1.07 (m, 3H), 1.02-0.78 (m, 6H), 0.46-0.39 (m, 2H), 0.12-0.05 (m, 2H). | 633.55 |
| I-57 | 15 | $^1$H NMR (400 MHz, CD$_3$OD): δ 8.25-8.14 (m, 1H), 7.93-7.87 (m, 1H), 7.57-7.03 (m, 10H), 5.38-5.34 (s, 2H), 4.64-4.32 (m, 4H), 4.23-3.78 (m, 8H), 3.74-3.46 (m, 1H), 3.45-3.32 (m, 1H), 3.25-3.13 (m, 2H), 2.91-2.78 (m, 2H), 1.65-1.57 (m, 2H), 1.55-1.44 (m, 2H), 1.40-1.32 (m, 3H), 1.25-1.08 (m, 9H), 1.03-1.01 (m, 1H), 0.79-0.73 (m, 1H). | 712.5 |
| I-58A | 2A | $^1$H NMR (400 MHz, DMSO-d$_6$) δ 8.43-8.29 (m, 1H), 7.87-7.76 (m, 1H), 7.39-7.23 (m, 7H), 7.18 (d, J = 7.6 Hz, 3H), 5.35 (d, J = 4.9 Hz, 2H), 4.34 (d, J = 12.5 Hz, 1H), 4.30-4.12 (m, 1H), 4.13-3.89 (m, 4H), 3.88-3.55 (m, 5H), 3.11-2.93 (m, 1H), 2.58-2.50 (m, 9H), 2.46 (s, 1H), 1.77 (s, 1H), 1.68-1.49 (m, 2H), 1.46-1.21 (m, 1H), 1.19-0.92 (m, 8H), 0.90-0.82 (m, 1H), 0.68 (dd, J = 12.1, 7.3 Hz, 1H). | 593.34 |
| I-58B | 2B | $^1$H NMR (400 MHz, DMSO-d$_6$) δ 8.43-8.28 (m, 1H), 7.88-7.77 (m, 1H), 7.38-7.19 (m, 8H), 7.19-7.13 (m, | 594.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 2H), 5.35 (t, J = 5.2 Hz, 2H), 4.35 (d, 1H), 4.28-4.02 (m, 3H), 4.00-3.78 (m, 4H), 3.76-3.57 (m, 3H), 2.99 (d, 1H), 2.53 (s, 2H), 1.75 (s, 1H), 1.59 (d, J = 11.2 Hz, 2H), 1.46-1.34 (m, 1H), 1.13 (d, 4H), 1.07-0.98 (m, 3H), 0.86 (d, J = 12.1 Hz, 1H), 0.74-0.61 (m, 1H). | |
| I-59A | 2A | $^1$H NMR (400 MHz, DMSO-d$_6$) δ 8.40-8.25 (m, 2H), 7.86-7.78 (m, 1H), 7.45-7.24 (m, 10H), 5.36 (s, 2H), 4.25-3.55 (m, 11H), 3.20-2.87 (m, 3H), 1.90-1.72 (m, 2H), 1.57-1.40 (m, 2H), 1.38-1.28 (m, 1H), 1.12-1.01 (m, 6H), 0.90-0.81 (m, 1H), 0.72-0.63 (m, 1H). | 623.5 |
| I-59B | 2B | $^1$H NMR (400 MHz, DMSO-d$_6$) δ 8.40-8.20 (m, 2H), 7.82 (d, J = 11.8 Hz, 1H), 7.45-7.24 (m, 10H), 5.35 (s, 2H), 4.32-3.55 (m, 11H), 3.10 (br s, 3H), 1.84 (s, 2H), 1.50 (s, 2H), 1.36-1.23 (m, 1H), 1.12-0.97 (m, 6H), 0.86-0.67 (m, 2H). | 623.5 |
| I-60A | 7A | $^1$H NMR (400 MHz, DMSO-d$_6$) δ 8.32 (dd, J = 24.8, 10.2 Hz, 2H), 7.83 (t, J = 10.6 Hz, 2H), 7.38-7.21 (m, 10H), 5.35 (s, 2H), 4.57-4.39 (m, 2H), 4.35 (d, J = 7.4 Hz, 1H), 4.18-3.40 (m, 10H), 2.60 (dd, J = 10.8, 4.6 Hz, 3H), 1.90 (dh, J = 24.8, 8.0 Hz, 2H), 1.43 (dq, J = 11.4, 7.2 Hz, 2H), 1.08 (d, J = 6.0 Hz, 3H), 0.81 (dd, J = 8.6, 7.2 Hz, 3H). | 615.45 |
| I-60B | 7B | $^1$H NMR (400 MHz, DMSO-d$_6$) δ 8.39-8.28 (m, 2H), 7.97-7.76 (m, 2H), 7.46-7.09 (m, 10H), 5.35 (s, 2H), 4.56-4.48 (m, 1H), 4.45-4.29 (m, 2H), 4.27-3.92 (m, 4H), 3.88-3.38 (m, 6H), 2.64-2.54 (m, 3H), 2.03-1.95 (m, 2H), 1.52-1.44 (m, 2H), 1.10-1.01 (m, 3H), 0.89-0.83 (m, 3H). | 615.40 |
| I-61A | 2A | $^1$H NMR (DMSO, 400 MHz) δ 0.75 (2H, d, J = 70.6 Hz), 0.97-1.47 (9H, m), 1.75 (2H, s), 3.01-3.18 (2H, m), 3.35-4.41 (11H, m), 5.35 (2H, s), 7.22-7.39 (7H, m), 7.44 (3H, dt, J = 5.0, 2.4 Hz), 7.82 (1H, d, J = 12.2 Hz), 8.22-8.38 (2H, m). | 623.50 |
| I-61B | 2B | $^1$H NMR (400 MHz, DMSO-d$_6$) δ 8.41-8.24 (m, 2H), 7.83 (d, J = 12.7 Hz, 1H), 7.45-7.23 (m, 10H), 5.35 (s, 2H), 4.28-3.54 (m, 11H), 3.15-3.02 (m, 2H), 1.96-1.62 (m, 2H), 1.43-0.98 (m, 10H), 0.93-0.60 (m, 2H). | 623.45 |
| I-62A | 7A | $^1$H NMR (400 MHz, DMSO-d$_6$) δ 8.37-8.29 (m, 2H), 7.83-7.80 (m, 2H), 7.37-7.25 (m, 10H), 5.35 (d, 2H), 4.55-4.52 (m, 1H), 4.45-4.42 (m, 1H), 4.36-4.34 (m, 1H), 4.21-4.01 (m, 1.5H), 3.98-3.86 (m, 4H), 3.77-3.61 (m, 3H), 3.58-3.36 (m, 1.5H), 2.6 (dd, J = 4.8 Hz, 3H), 1.93-1.80 (m, 2H), 1.09-1.07 (m, 3H), 0.95-0.91 (m, 9H). | 643.2 |
| I-62B | 7B | $^1$H NMR (400 MHz, DMSO-d$_6$) δ 8.37-8.27 (m, 2H), 7.90-7.79 (m, 2H), 7.36-7.25 (m, 10H), 5.35 (s, 2H), 4.55-4.49 (m, 1H), 4.45-4.32 (m, 2H), 4.25-4.09 (m, 1H), 4.02-3.96 (m, 3H), 3.91-3.81 (m, 2H), 3.76-3.68 (m, 2H), 3.65-3.53 (m, 1H), 3.46-3.37 (m, 1H), 2.60 (d, J = 4.8 Hz, 1H), 1.94-1.86 (m, 2H), 1.09-1.02 (m, 3H), 0.97-0.96 (m, 9H). | 643.2 |
| I-63A | 2A | $^1$H NMR (400 MHz, DMSO-d$_6$) δ 10.42-10.37 (m, 1H), 8.43-8.36 (m, 1H), 7.99-7.91 (m, 1H), 7.89-7.82 (m, 1H), 7.63-7.51 (m, 3H), 7.50-7.25 (m, 10H), 5.38-5.34 (m, 2H), 4.33-3.64 (m, 7H), 3.30-3.28 (m, 1H), 1.39-1.33 (m, 1H), 1.12-0.78 (m, 7H), 0.71-0.60 (m, 1H). | 588.1 |
| I-63B | 2B | $^1$H NMR (400 MHz, DMSO-d$_6$) δ 10.39 (d, J = 12.6 Hz, 1H), 8.44-8.34 (m, 1H), 7.96 (d, J = 8.6 Hz, 1H), 7.86 (d, J = 15.2 Hz, 1H), 7.65-7.53 (m, 3H), 7.50-7.21 (m, 10H), 5.36 (s, 2H), 4.42-4.24 (m, 1H), 4.23-3.99 (m, 3H), 3.98-3.79 (m, 3H), 3.78-3.66 (m, 1H), 1.38 (tt, J = 34.0 Hz, 1H), 1.13-0.88 (m, 6H), 0.86-0.58 (m, 3H). | 588.4 |
| I-64 | 15 | $^1$H NMR (400 MHz, CD$_3$OD): δ 8.14-8.22 (m, 1H), 7.87-7.93 (m, 1H), 7.27-7.36 (m, 10H), 5.38 (s, 2H), 4.94-4.99 (m, 1H), 4.29-4.64 (m, 4H), 3.76-4.21 (m, 10H), 3.09-3.29 (m, 5H), 2.49-2.98 (m, 3H), 1.46-1.80 (m, 4H), 1.19-1.30 (m, 6H), 1.10-1.12 (m, 5H), 0.74-0.79 (m, 1H). | 739.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-65A | 7A | $^1$H NMR (400 MHz, DMSO-d$_6$) δ 8.35 (d, J = 12.2 Hz, 2H), 7.82 (d, J = 16.0 Hz, 2H), 7.30 (m, 10H), 5.35 (s, 2H), 4.56-4.40 (m, 2H), 4.37 (dd, J = 8.6, 3.2 Hz, 1H), 4.23 (d, J = 45.8 Hz, 1H), 4.10-3.82 (m, 4H), 3.78 (m, 2H), 3.62 (m, 1H), 3.44 (m, 1H), 2.60 (dd, J = 10.0, 4.4 Hz, 3H), 1.39-1.16 (m, 1H), 1.05 (d, J = 15.4 Hz, 12H). | 629.45 |
| I-65B | 7B | $^1$H NMR (400 MHz, DMSO-d$_6$) δ 8.34 (d, J = 21.8 Hz, 2H), 7.94-7.76 (m, 2H), 7.38-7.20 (m, 10H), 5.35 (d, J = 2.4 Hz, 2H), 4.58-4.20 (m, 5H), 4.03-3.78 (m, 4H), 3.73-3.41 (m, 4H), 2.59 (dd, J = 4.6. 2.1 Hz, 3H), 1.13-1.04 (m, 12H). | 629.5 |
| I-66A | 8A | $^1$H NMR (400 MHz, DMSO-d$_6$) δ 8.17 (dd, J = 19.0, 8.8 Hz, 1H), 8.01 (s, 1H), 7.82-7.67 (m, 1H), 4.28-3.46 (m, 11H), 3.25-3.21 (m, 1H), 3.10 (dd, J = 9.4, 6.4 Hz, 1H), 2.60-2.56 (m, 3H), 1.70-1.60 (m, 5H), 1.44 (s, 1H), 1.36-1.27 (m, 1H), 1.19-1.12 (m, 3H), 1.08 (t, J = 4.8 Hz, 3H), 1.06-1.00 (m, 6H), 0.88-0.78 (m, 3H), 0.67 (dd, J = 8.0, 4.0 Hz, 1H). | 557.5 |
| I-66B | 8B | $^1$H NMR (400 MHz, DMSO-d$_6$) δ 8.25-8.18 (m, 1H), 8.01-7.97 (m, 2H), 7.86-7.79 (m, 1H), 4.36-4.29 (m, 1H), 4.26-4.12 (m, 1H), 4.06-3.88 (m, 3H), 3.83-3.59 (m, 6H), 3.27-3.19 (m, 1H), 3.12-3.04 (m, 1H), 3.59 (t, J = 4.8 Hz, 3H), 1.63-1.60 (m, 5H), 1.39-1.33 (m, 2H), 1.19-1.11 (m, 6H), 1.06-1.05 (m, 3H), 1.02-0.95 (m, 3H), 0.88-0.78 (m, 3H), 0.71-0.65 (m, 1H). | 557.1 |
| I-67A | 7A | $^1$H NMR (400 MHz, DMSO-d$_6$) δ 8.35 (d, J = 13.4 Hz, 2H), 7.84-7.80 (m, 2H), 7.38-7.23 (m, 10H), 5.35 (s, 2H), 4.53 (d, J = 12.0 Hz, 1H), 4.47-4.29 (m, 3H), 4.04-3.36 (m, 9H), 2.60 (dd, J = 10.2, 4.4 Hz, 3H), 1.21-1.12 (m, 3H), 1.08 (t, J = 5.4 Hz, 3H), 0.87 (s, 2H), 0.41 (s, 2H). | 627.5 |
| I-67B | 7B | $^1$H NMR (400 MHz, DMSO-d$_6$) δ 8.40-8.29 (m, 2H), 7.83 (t, J = 16.6 Hz, 2H), 7.37-7.23 (m, 11H), 5.35 (s, 2H), 4.57-4.26 (m, 4H), 4.03-3.38 (m, 9H), 2.60 (d, J = 4.6 Hz, 4H), 1.22 (s, 3H), 1.07 (dd, J = 17.6, 6.2 Hz, 4H), 0.90 (s, 2H), 0.45 (d, J = 2.6 Hz, 2H). | 627.5 |
| I-68A | 5A | $^1$H NMR (400 MHz, DMSO-d$_6$) δ 8.20 (t, J = 8.2 Hz, 1H), 7.84-7.76 (m, 1H), 7.35-7.22 (m, 5H), 4.55-4.48 (m, 1H), 4.43 (d, J = 12.2 Hz, 1H), 4.38-4.22 (m, 1H), 4.00-3.87 (m, 3H), 3.84-3.76 (m, 2H), 3.68 (dd, J = 23.5, 9.6 Hz, 1H), 3.54 (d, J = 10.0 Hz, 1H), 3.39-3.32 (m, 1H), 3.31-3.16 (m, 4H), 2.91-2.83 (m, 2H), 2.65-2.52 (m, 5H), 2.29-2.24 (m, 2H), 1.65-1.59 (m, 2H), 1.35-1.26 (m, 1H), 1.13-1.05 (m, 6H), 1.04-0.99 (m, 4H), 0.86-0.79 (m, 1H), 0.67-0.60 (m, 1H). | 555.5 |
| I-68B | 5B | $^1$H NMR (400 MHz, DMSO-d$_6$) δ 8.23 (d, J = 8.8 Hz, 1H), 8.14 (s, 1H), 7.82 (dd, J = 23.2. 4.8 Hz, 1H), 7.34-7.23 (m, 5H), 4.56-4.39 (m, 2H), 4.33 (m, 1H), 4.14-4.02 (m, 2H), 3.95-3.84 (m, 1H), 3.81 (d, J = 9.6 Hz, 1H), 3.79-3.72 (m, 2H), 3.59 (dd, J = 51.2, 9.6 Hz, 2H), 3.27 (q, J = 2.0 Hz, 1H), 3.23 (dt, J = 11.8, 2.4 Hz, 2H), 3.15 (q, J = 6.2 Hz, 1H), 2.97-2.84 (m, 2H), 2.63-2.55 (m, 4H), 2.25 (dd, J = 7.0, 2.8 Hz, 2H), 1.60 (t, J = 15.2 Hz, 3H), 1.33 (m, 1H), 1.12-1.06 (m, 7H), 1.06-1.02 (m, 4H). 0.84 (dd, J = 5.4, 3.8 Hz, 1H), 0.65 (dd, J = 8.0, 3.8 Hz, 1H). | 555.50 |
| I-69A | 7A | $^1$H NMR (400 MHz, DMSO-d$_6$) δ 8.34 (d, J = 10.4 Hz, 2H), 7.82 (d, J = 12.8 Hz, 2H), 7.39-7.23 (m, 10H), 5.35 (s, 2H), 4.53 (d, J = 12.2 Hz, 1H), 4.43 (d, J = 12.2 Hz, 1H), 4.39-4.32 (m, 1H), 4.17-3.83 (m, 5H), 3.80-3.60 (m, 3H), 3.56-3.38 (m, 2H), 2.60 (dd, J = 10.4, 4.4 Hz, 3H), 1.96-1.76 (m, 3H), 1.08 (d, J = 6.0 Hz, 3H), 0.86-0.80 (m, 6H). | 629.45 |
| I-69B | 7B | $^1$H NMR (400 MHz, DMSO-d$_6$) δ 8.41-8.27 (m, 2H), 7.95-7.78 (m, 2H), 7.38-7.22 (m, 10H), 5.35 (s, 2H), 4.56-4.48 (m, 1H), 4.45-4.21 (m, 2H), 4.12-3.79 (m, 5H), 3.76-3.52 (m, 3H), 3.49-3.36 (m, 1H), 2.60 (d, J = 4.4 Hz, 3H), 1.99-1.86 (m, 3H), 1.11-1.00 (m, 3H), 0.90-0.85 (m, 6H). | 629.2 |
| I-70A | 11A | $^1$H NMR (400 MHz, DMSO-d$_6$) δ 8.39-8.29 (m, 2H), 7.92-7.82 (m, 1H), 7.35-7.24 (m, 5H), 4.57-4.49 (m, | 554.2 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 1H), 4.47-4.40 (m, 1H), 4.38-4.30 (m, 1H), 4.23-4.11 (m, 1H), 4.04-3.90 (m, 3H), 3.84-3.74 (m, 2H), 3.65-3.53 (m, 3H), 3.47-3.39 (m, 2H), 3.18-3.09 (m, 2H), 3.01-2.93 (m, 2H), 2.61 (d, J = 4.4 Hz, 3H), 2.07-1.96 (m, 1H), 1.91-1.78 (m, 1H), 1.35-1.22 (m, 1H), 1.11-1.00 (m, 9H), 0.87-0.80 (m, 1H), 0.68-0.60 (m, 1H). | |
| I-70B | 11B | $^1$H NMR (400 MHz, DMSO-d$_6$) δ 8.42-8.34 (m, 1H), 7.92-7.84 (m, 1H), 7.36-7.25 (m, 5H), 4.56-4.52 (m, 1H), 4.47-4.42 (m, 1H), 4.39-4.28 (m, 1H), 4.16-4.05 (m, 1H), 4.02-3.82 (m, 3H), 3.80-3.69 (m, 2H), 3.63-3.56 (m, 2H), 3.52-3.45 (m, 2H), 3.43-3.40 (m, 1H), 3.31-3.29 (m, 1H), 3.26-3.23 (m, 2H), 3.15-3.09 (m, 2H), 2.62-2.60 (m, 3H), 2.2-2.13 (m, 1H), 1.92-1.84 (m, 1H), 1.38-1.31 (m, 1H), 1.12-1.03 (m, 9H), 0.89-0.86 (m, 1H), 0.73-0.66 (m, 1H). | 554.2 |
| I-71A | 7A | $^1$H NMR (400 MHz, DMSO-d$_6$) δ 8.42-8.32 (m, 2H), 7.84-7.80 (m, 2H), 7.37-7.24 (m, 10H), 5.35 (s, 2H), 4.55-4.42 (m, 3H), 4.38-4.20 (m, 2H), 4.13-3.97 (m, 3H), 3.91-3.88 (m, 1H), 3.83-3.67 (m, 2H), 3.63-3.58 (m, 1H), 3.56-3.46 (m, 1H), 2.62-2.58 (m, 3H), 1.25-1.15 (m, 4H), 1.11-1.06 (m, 3H). | 631.1 |
| I-71B | 7B | $^1$H NMR (400 MHz, DMSO-d$_6$) δ 8.41-8.29 (m, 2H), 7.88-7.77 (m, 2H), 7.39-7.20 (m, 10H), 5.35 (d, J = 3.2 Hz, 2H), 4.60-4.23 (m, 5H), 4.19-4.04 (m, 1H), 4.02-3.77 (m, 4H), 3.73-3.62 (m, 2H), 3.45 (s, 1H), 2.60 (d, J = 4.8 Hz, 3H), 1.31-1.15 (m, 4H), 1.10-1.03 (m, 3H). | 631.4 |
| I-72A | 4A | $^1$H NMR (400 MHz, DMSO-d$_6$) δ 11.65 (s, 1H), 8.39-8.28 (m, 1H), 8.11-8.01 (m, 1H), 7.91-7.75 (m, 2H), 7.43 (d, J = 8.0 Hz, 1H), 7.36-7.23 (m, 5H), 7.19-7.04 (m, 2H), 4.53 (d, J = 12.2 Hz, 1H), 4.44 (d, J = 12.2 Hz, 1H), 4.39-4.33 (m, 1H), 4.29-4.14 (m, 1H), 4.10-3.86 (m, 5H), 3.79-3.65 (m, 2H), 3.54-3.41 (m, 1H), 3.30 (s. 1H), 2.60 (s, 3H), 1.37-1.18 (m, 2H), 1.12-1.08 (m, 3H), 1.07-1.03 (m, 3H), 1.01 (s, 2H), 0.87-0.79 (m, 1H), 0.67-0.58 (m, 1H). | 600.4 |
| I-72B | 4B | $^1$H NMR (400 MHz, DMSO-d$_6$) δ 11.65 (s, 1H), 8.34 (t, J = 8.0 Hz, 1H), 8.05 (d, J = 8.0 Hz, 1H), 7.96-7.77 (m, 2H), 7.46-7.40 (m, 1H), 7.27 (s, 5H), 7.15 (ddd, J = 8.0, 7.0, 1.2 Hz, 1H), 7.08 (tt, J = 7.0, 1.0 Hz, 1H), 4.51 (s, 1H), 4.44-4.33 (m, 2H), 4.18-3.65 (m, 9H), 3.45 (q, J = 6.2, 5.6 Hz, 1H), 2.61 (dd, J = 4.4, 2.8 Hz, 3H), 1.35 (dd, J = 7.8, 5.2 Hz, 1H), 1.11-1.05 (m, 9H), 0.86 (d, J = 4.8 Hz, 1H), 0.73-0.62 (m, 1H). | 600.1 |
| I-73A | 7A | $^1$H NMR (400 MHz, DMSO-d$_6$) δ 8.36 (d, J = 12.8 Hz, 2H), 7.83 (d, J = 15.6 Hz, 2H), 7.37-7.24 (m, 10H), 5.36 (d, J = 1.4 Hz, 2H), 4.68-4.34 (m, 5H), 4.11-3.44 (m, 8H), 2.60 (dd, J = 10.6, 4.6 Hz, 3H), 1.50 (dd, J = 24.6, 7.0 Hz, 4H), 1.10 (d, J = 6.4 Hz, 3H). | 638.45 |
| I-73B | 7B | $^1$H NMR (400 MHz, DMSO-d$_6$) δ 8.43-8.23 (m, 2H), 7.91-7.76 (m, 2H), 7.38-7.23 (m, 10H), 5.35 (d, J = 4.8 Hz, 2H), 4.66-4.48 (m, 2H), 4.47-4.30 (m, 3H), 4.17-4.05 (m, 1H), 4.00-3.39 (m, 7H), 2.60 (d, J = 4.6 Hz, 3H), 1.55-1.48 (m, 4H), 1.13-1.01 (m, 3H). | 638.4 |
| I-74A | 7A | $^1$H NMR (400 MHz, DMSO-d$_6$) δ 8.47-8.35 (m, 2H), 7.90-7.85 (m, 2H), 7.42-7.29 (m, 10H), 5.40 (s, 2H), 4.61-4.37 (m, 3H), 4.25-3.44 (m, 10H), 2.65 (dd, J = 10.7, 4.4 Hz, 3H), 2.11-1.93 (m, 1H), 1.46-1.27 (m, 4H), 1.14 (d, J = 6.2 Hz, 3H), 0.88-0.75 (m, 6H). | 643.5 |
| I-74B | 7B | $^1$H NMR (400 MHz, DMSO-d$_6$) δ 8.41-8.22 (m, 2H), 7.93-7.77 (m, 2H), 7.39-7.20 (m, 10H), 5.35 (s, 2H), 4.52 (t, J = 11.6 Hz, 1H), 4.46-4.31 (m, 2H), 4.30-3.42 (m, 9H), 3.41-3.34 (m, 1H), 2.63-2.57 (m, 3H), 2.08-1.97 (m, 1H), 1.49-1.37 (m, 2H), 1.35-1.21 (m, 2H), 1.11-1.00 (m, 3H), 0.83-0.75 (m, 6H). | 643.5 |
| I-75A | 2A | $^1$H NMR (400 MHz, DMSO-d$_6$) δ 10.21 (d, J = 5.2 Hz, 1H), 8.42-8.34 (m, 1H), 7.88-7.8 (m, 1H), 7.49-7.40 (m, 2H), 7.39-7.14 (m, 11H), 6.95 (d, J = 7.6 Hz, 1H), 5.38-8.3 (m, 2H), 4.28-3.60 (m, 10H), 3.41-3.255 (m, 1H), 1.34 (q, J = 7.0 Hz, 1H), 1.12-1.02 (m, 4H), 0.96-0.77 (m, 3H), 0.68-0.60 (m, 1H). | 602.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-75B | 2B | $^1$H NMR (400 MHz, DMSO-$d_6$) δ 10.22 (d, J = 9.8 Hz, 1H), 8.41-8.32 (m, 1H), 7.84 (d, J = 16.6 Hz, 1H), 7.49-7.40 (m, 2H), 7.38-7.14 (m, 11H), 6.95 (d, J = 7.2 Hz, 1H), 5.39-5.32 (m, 2H), 4.21 (d, J = 8.4 Hz, 1H), 4.18-4.07 (m, 1H), 4.07-3.94 (m, 2H), 3.92-3.79 (m, 4H), 3.78-3.62 (m, 2H), 1.43-1.31 (m, 1H), 1.13-1.01 (m, 5H), 0.91-0.85 (m, 1H), 0.84-0.78 (m, 1H), 0.69-0.58 (m, 1H). | 602.5 |
| I-76A | 7A | $^1$H NMR (400 MHz, DMSO-$d_6$) δ 8.42-8.31 (m, 2H), 7.89-7.80 (m, 2H), 7.38-7.23 (m, 10H), 5.35 (s, 2H). 4.64-3.38 (m, 12H), 3.31-3.29 (m, 1H), 2.64-2.56 (m, 3H), 1.49-1.39 (m, 6H), 1.12-1.04 (m, 3H). | 640.2 |
| I-76B | 7B | $^1$H NMR (400 MHz, DMSO-$d_6$) δ 8.41-8.30 (m, 2H), 7.93-7.77 (m, 2H), 7.38-7.22 (m, 10H), 5.35 (s, 2H), 4.64-4.31 (m, 5H), 4.20-3.40 (m, 8H), 2.60 (d, J = 4.4 Hz, 3H), 1.50-1.46 (m, 6H), 1.09 (d, J = 6.2 Hz, 2H), 1.05 (d, J = 5.8 Hz, 1H). | 640.2 |
| I-77A | 5A | $^1$H NMR (400 MHz, DMSO-$d_6$) δ 8.23 (dd, J = 8.6 Hz, 1H), 7.81 (dd, J = 13.2, 5.6 Hz, 1H), 7.60-7.54 (m, 1H), 7.34-7.24 (m, 6H), 6.90 (s, 1H), 4.59-4.40 (m, 2H), 4 40-4.24 (m, 2H), 3.99-3.89 (m, 3H), 3.74-3.63 (m, 1H), 3.59-3.50 (m, 2H), 3.28-3.20 (m, 1H), 3.13-2.86 (m, 3H), 2.67-2.57 (m, 5H), 1.34-1.18 (m, 1H), 1.02 (m, 6H), 1.00 (d, J = 10.4 Hz, 3H), 0.84-0.80 (m, 1H), 0.65-0.60 (m, 1H). | 537.4 |
| I-77B | 5B | $^1$H NMR (400 MHz, DMSO-$d_6$) δ 8.27 (dd, J = 7.6 Hz, 1H), 8.18 (s, 1H), 7.87-7.80 (m, 1H), 7.55 (s, 1H), 7.31-7.25 (m, 5H), 6.89 (s, 1H), 4.52 (d, J = 12.2 Hz, 1H), 4.42 (dd, J = 12.0, 2.8 Hz, 1H), 4.34 (ddd, J = 13.8, 8.6, 4.4 Hz, 1H), 4.14-3.71 (m, 4H), 3.66-3.46 (m, 3H), 3.18 (d, J = 7.2 Hz, 1H), 3.05-2.86 (m, 2H), 2.69-2.53 (m, 5H), 1.32 (dt, J = 20.0, 7.0 Hz, 1H), 1.11-1.00 (m, 9H), 0.83 (t, J = 4.6 Hz, 1H), 0.64 (dd, J = 8.0, 3.6 Hz, 1H). | 537.4 |
| I-78A | 6A | $^1$H NMR (400 MHz, DMSO-$d_6$) δ 8.28 (s, 1H), 8.26-8.18 (m, 1H), 7.86-7.74 (m, 1H), 7.34-7.24 (m, 5H), 7.06 (s, 1H), 4.54-4.48 (m, 1H), 4.46-4.40 (m, 1H), 4.36-4.30 (m, 1H), 3.98-3.88 (m, 3H), 3.74-3.62 (m, 3H), 3.28-3.24 (m, 1H), 3.00-2.88 (m, 2H), 2.68-2.64 (m, 1H), 2.62-2.54 (m, 4H), 1.28 (ddd, J = 20.6. 8.0. 5.4 Hz, 1H), 1.12-1.08 (m, 3H), 1.06-0.98 (m, 6H), 0.84-0.78 (m, 1H), 0.66-0.58 (m, 1H). | 538.2 |
| I-78B | 6B | $^1$H NMR (400 MHz, DMSO-$d_6$) δ 8.28 (s, 1H), 8.24 (d, J = 8.8 Hz, 1H), 8.13 (s, 1H), 7.83 (dd, J = 22.4. 4.6 Hz, 1H), 7.33-7.23 (m, 5H), 7.05 (s, 1H), 4.52 (dd, J = 12.0, 1.6 Hz, 1H), 4.42 (dd, J = 12.0, 3.0 Hz, 1H), 4.34 (ddd, J = 17.4, 8.8, 4.6 Hz, 1H), 4.13-4.02 (m, 1H), 3.91-3.63 (m, 5H), 3.50 (d, J = 10.0 Hz, 1H), 3.24-3.20 (m, 1H), 2.98 (ddd, J = 21.8, 9.0, 5.0 Hz, 2H), 2.66 (dd, J = 13.6, 8.8 Hz, 1H), 2.59 (dd, J = 6.4, 4.6 Hz, 4H), 1.33 (ddd, J = 21.4, 8.0, 5.4 Hz, 1H), 1.10-1.01 (m, 9H), 0.83 (t, J = 4.6 Hz, 1H), 0.65 (dd, J = 8.2, 3.8 Hz, 1H). | 538.5 |
| I-79A | | $^1$H NMR (400 MHz, DMSO-$d_6$) δ 8.28 (q, J = 9.2 Hz, 1H), 7.87 (t, J = 2.6 Hz, 1H), 7.85-7.47 (m, 5H), 7.38 (dd, J = 8.6, 2.0 Hz, 2H), 7.34-7.22 (m, 5H), 6.29 (dt, J = 10.0, 2.2 Hz, 1H), 5.47 (s, 2H), 4.51-4.34 (m, 2H), 4.24 (td, J = 8.6, 3.2 Hz, 1H), 4.13-3.87 (m, 2H), 3.81-3.65 (m, 2H), 3.54-3.35 (m, 6H), 2.60 (dd, J = 4.6, 1.6 Hz, 3H), 1.24-1.14 (m, 1H), 1.08-1.01 (m, 6H), 1.01-0.93 (m, 3H), 0.79 (d, J = 4.5 Hz, 1H), 0.66-0.55 (m, 1H). | 677.45 |
| I-79B | | $^1$H NMR (400 MHz, DMSO-$d_6$) δ 8.29 (d, J = 9.6 Hz, 1H), 7.90-7.62 (m, 4H), 7.58-7.48 (m, 1H), 7.39-7.25 (m, 6H), 6.36-6.27 (m, 1H), 5.49 (d, J = 2.4 Hz, 2H), 4.53 (d, J = 11.8 Hz, 1H), 4.42 (dd, J = 12.0, 4.8 Hz, 1H), 4.29-4.14 (m, 1H), 4.08-3.36 (m, 9H), 3.23 (d, J = 4.2 Hz, 1H), 2.59 (dd, J = 4.6, 2.0 Hz, 3H), 1.31-1.23 (m, 1H), 1.11 (t, J = 3.2 Hz, 3H), 1.08-1.00 (m, 6H), 0.84 (d, J = 4.6 Hz, 1H), 0.68 (dd, J = 8.0, 3.8 Hz, 1H). | 677.40 |
| I-80A | 7A | $^1$H NMR (400 MHz, DMSO-$d_6$) δ 8.37-8.20 (m, 2H), 7.90-7.73 (m, 2H), 7.37-7.22 (m, 12H), 7.15 (dd, J = 20.0, 7.8 Hz, 2H), 5.34 (d, J = 5.8 Hz, 2H), 4.58-4.23 (m, | 745.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
|  |  | 3H), 4.15-3.34 (m, 9H), 3.29-3.15 (m, 1H), 2.58 (dd, J = 10.2, 4.4 Hz, 3H), 1.22 (d, J = 8.4 Hz, 12H), 1.10-0.96 (m, 4H). |  |
| I-80B | 7B | $^1$H NMR (400 MHz, DMSO-d$_6$) δ 8.39-8.19 (m, 2H), 7.95-7.74 (m, 2H), 7.28 (tdd, J = 27.4, 14.9, 8.1 Hz, 14H), 5.35 (d, J = 7.4 Hz, 2H), 4.53 (t, J = 11.9 Hz, 1H), 4.46-4.28 (m, 2H), 4.11-3.87 (m, 2H), 3.86-3.54 (m, 5H), 3.50-3.38 (m, 2H), 3.29-3.16 (m, 1H), 2.72-2.61 (m, 3H), 1.35-1.21 (m, 11H), 1.12-1.00 (m, 4H), 0.99-0.84 (m, 1H). | 745.5 |
| I-81A | 2A | $^1$H NMR (400 MHz, DMSO-d$_6$) δ 10.38 (d, J = 4.6 Hz, 1H), 8.44-8.35 (m, 1H), 7.86 (d, J = 12.8 Hz, 1H), 7.69 (d, J = 4.6 Hz, 2H), 7.67-7.60 (m, 4H), 7.44 (dd, J = 8.2, 7.0 Hz, 2H), 7.39-7.23 (m, 6H), 5.37 (s, 2H), 4.34-3.62 (m, 8H), 3.47-3.34 (m, 1H), 1.41-1.31 (m, 1H), 1.15-1.02 (m, 5H), 0.88 (s, 1H), 0.87-0.78 (m, 1H), 0.66 (s, 1H). | 588.40 |
| I-81B | 2B | $^1$H NMR (400 MHz, DMSO-d$_6$) δ 10.38 (d, J = 10.8 Hz, 1H), 8.39 (d, J = 12.4 Hz, 1H), 7.86 (d, J = 14.4 Hz, 1H), 7.70 (d, J = 7.8 Hz, 2H), 7.63 (d, J = 7.4 Hz, 4H), 7.44 (t, J = 7.6 Hz, 2H), 7.32 (dt, J = 19.8, 9.2 Hz, 6H), 5.37 (s, 2H), 4.43-3.99 (m, 4H), 3.84 (m, 4H), 1.39 (m, 1H), 1.07 (d, J = 14.8 Hz, 6H), 0.92 (d, J = 7.6 Hz, 1H), 0.83 (s, 1H), 0.66 (s, 1H). | 588.40 |
| I-82A | 7A | $^1$H NMR (400 MHz, DMSO-d$_6$) δ 8.38-8.28 (m, 2H), 7.87-7.79 (m, 2H), 7.37-7.24 (m, 10H), 5.35 (s, 2H), 4.55-4.41 (m, 2H), 4.38-4.32 (m, 1H), 4.20-3.40 (m, 11H), 3.20 (d, J = 6.0 Hz, 1H), 3.16 (s, 2H), 3.15-3.12 (m, 1H), 2.60 (dd, J = 11.2, 4.6 Hz, 3H), 2.13-1.90 (m, 2H), 1.10-1.05 (m, 3H), 0.40-0.33 (m, 4H). | 671.45 |
| I-82B | 7B | $^1$H NMR (400 MHz, DMSO-d$_6$) δ 8.46-8.27 (m, 2H), 7.95-7.76 (m, 2H), 7.38-7.19 (m, 10H), 5.34 (s, 2H), 4.57-4.47 (m, 1H), 4.46-4.29 (m, 2H), 4.11-3.56 (m, 8H), 3.50-3.37 (m, 2H), 3.23-3.13 (m, 5H), 2.60 (d, J = 4.4 Hz, 3H), 2.19-1.98 (m, 2H), 1.12-0.99 (m, 3H), 0.48-0.32 (m, 4H). | 671.2 |
| I-83A | 2A | $^1$H NMR (400 MHz, DMSO-d$_6$) δ 8.52-8.21 (m, 2H), 7.88-7.78 (m, 1H), 7.71-7.15 (m, 10H), 5.36 (s, 2H), 4.54-3.50 (m, 11H), 3.23-2.65 (m, 3H), 2.00-1.30 (m, 5H), 1.16-0.88 (m, 6H), 0.87-0.80 (m, 1H), 0.73-0.57 (m, 1H). | 623.50 |
| I-83B | 2B | $^1$H NMR (400 MHz, DMSO-d$_6$) δ 8.32 (d, J = 30.6 Hz, 2H), 7.82 (d, J = 13.4 Hz, 1H), 7.46-7.35 (m, 5H), 7.34-7.22 (m, 5H), 5.35 (s, 2H), 4.17 (m, 1H), 3.96 (m, 3H), 3.73 (m, 4H), 3.56-3.34 (m, 3H), 3.09 (m, 2H), 1.85 (m, 2H), 1.49 (m, 2H), 1.30 (m, 2H), 1.12-1.08 (m, 3H), 1.05 (m, 3H), 0.85 (s, 1H), 0.68 (d, J = 7.8 Hz, 1H). | 623.45 |
| I-84A | 2A | $^1$H NMR (400 MHz, DMSO-d$_6$) δ 10.28-10.21 (m, 1H), 8.42-8.36 (m, 1H), 7.88-7.81 (m, 1H), 7.53-7.46 (m, 2H), 7.39-7.23 (m, 7H), 7.22-7.14 (m, 5H), 5.38-5.34 (m, 2H), 4.28-3.63 (m, 10H), 1.39-1.30 (m, 1H), 1.12-1.08 (m, 1H), 1.06-1.02 (m, 3H), 0.91-0.87 (m, 1H), 0.86-0.76 (m, 2H), 0.69-0.60 (m, 1H). | 602.1 |
| I-84B | 2B | $^1$H NMR (400 MHz, DMSO-d$_6$) δ 10.26-10.18 (m, 1H), 8.42-8.33 (m, 1H), 7.88-7.80 (m, 1H), 7.54-7.47 (m, 2H), 7.37-7.24 (m, 7H), 7.21-7.13 (m, 5H), 5.38-5.33 (m, 2H), 4.39-3.90 (m, 4H), 3.88-3.62 (m, 4H), 3.33 (s, 3H), 1.43-1.29 (m, 1H), 1.12-0.99 (m, 5H), 0.89-0.76 (m, 2H), 0.68-0.60 (m, 1H). | 602.2 |
| I-85 | 15 | $^1$H NMR (400 MHz, CDCl3): δ 7.83 (d, J = 3.2 Hz, 2H), 7.29-7.37 (m, 7.4H), 7.23 (m, 2.6H), 6.85 (d, J = 7.2 Hz, 1H), 5.31-5.36 (m, 2H), 4.98-5.02 (m, 1H), 4.62 (d, J = 11.6 Hz, 1H), 4.42-4.46 (m, 1H), 3.75-4.21 (m, 11H), 3.43-3.54 (m, 4H), 3.06 (m, 1H), 2.23 (t, J = 7.6 Hz, 0.5H), 1.99-2.05 (m, 1.5H), 1.13-1.22 (m, 10H), 0.88 (t, J = 6.6 Hz, 1H), 0.72-0.77 (m, 1H). | 731.5 |
| I-86 | 15 | $^1$H NMR (400 MHz, CD$_3$OD): δ 8.15-8.23 (m, 1H), 7.90 (t, J = 10.2 Hz, 1H), 7.26-7.36 (m, 10H), 5.33-5.38 (m, 2H), 4.90-4.97 (m, 1H), 4.42-4.66 (m, 3H), 4.04-4.22 (m, 3H), 3.84-4.00 (m, 5H), 3.35-3.53 (m, 8H), 2.19 (t, J = 7.6 Hz, | 697.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 0.4H), 2.00-2.05 (m, 0.7H), 1.58-1.61 (m, 0.5H), 1.45-1.49 (m, 0.5H), 1.22-1.24 (m, 2H), 1.17-1.18 (m, 2H), 1.10-1.13 (m, 4H), 1.03 (m, 1H), 0.90 (t, J = 6.8 Hz, 1H), 0.74-0.79 (m, 1H). | |
| I-87A | 7A | $^1$H NMR (400 MHz, DMSO-d$_6$) δ 8.39-8.30 (m, 2H), 7.83-7.75 (m, 2H), 7.38-7.22 (m, 10H), 5.35 (s, 2H), 4.56-3.44 (m, 12H), 3.30 (s, 3H), 2.60 (dd, J = 11.4, 4.2 Hz, 3H), 1.09 (d, J = 6.6 Hz, 3H). | 655.4 |
| I-87B | 7B | $^1$H NMR (400 MHz, DMSO-d$_6$) δ 8.40-8.28 (m, 2H), 7.95-7.75 (m, 2H), 7.37-7.23 (m, 10H), 5.35 (s, 2H), 4.59-4.35 (m, 2H), 4.33-4.20 (m, 1H), 4.17-3.99 (m, 2H), 3.98-3.84 (m, 2H), 3.84-3.67 (m, 2H), 3.65-3.58 (m, 1H), 3.51-3.34 (m, 2H), 3.30-3.22 (m, 1H), 2.60 (q, J = 3.8 Hz, 3H), 1.30-1.24 (m, 1H), 1.11-1.01 (m, 4H). | 655.4 |
| I-88 - Mix | 14 | $^1$H NMR (400 MHz, Methanol-d$_4$) δ 8.24-8.18 (m, 1H), 7.96-7.89 (m, 1H), 7.40-7.24 (m, 5H), 5.38 (s, 2H), 4.55-3.82 (m, 10H), 3.39 (s, 1H), 2.78-2.71 (m, 3H), 1.51-1.37 (m, 1H), 1.22-1.09 (m, 9H), 1.03 (s, 1H), 0.78 (s, 1H). | 551.4 |
| I-88A | 9A | $^1$H NMR (400 MHz, DMSO-d$_6$) δ 8.38-8.34 (m, 1H), 8.19-8.13 (m, 1H), 7.84-7.70 (m, 2H), 7.37-7.25 (m, 5H), 5.35 (s, 2H), 4.26-4.13 (m, 2H), 4.09-3.90 (m, 5H), 3.78-3.73 (m, 4H), 3.48-3.33 (m, 1H), 2.61-2.56 (m, 2H), 1.35-1.31 (m, 1H), 1.12-1.01 (m, 9H), 0.86-0.84 (m, 1H), 0.69-0.64 (m, 1H). | 551.4 |
| I-88B | 9B | $^1$H NMR (400 MHz, DMSO-d$_6$) δ 8.38-8.32 (m, 1H), 8.19-8.10 (m, 1H), 7.84-7.78 (m, 2H), 5.35 (s, 2H), 4.15-4.10 (m, 2H), 4.05-3.99 (m, 4H), 3.83-3.62 (m, 5H), 2.59 (t, J = 4.8 Hz, 3H), 1.36-1.35 (m, 1H), 1.12-0.95 (m, 9H), 0.87-0.86 (m, 1H), 0.69-0.68 (m, 1H). | 551.4 |
| I-89A | 7A | $^1$H NMR (400 MHz, DMSO-d$_6$) δ 8.43-8.27 (m, 2H), 7.88-7.80 (m, 2H), 7.43-7.19 (m, 10H), 5.35 (s, 2H), 4.56-4.50 (m, 1H), 4.43 (d, J = 12.0 Hz, 1H), 4.39-4.33 (m, 1H), 4.21-3.38 (m, 10H), 2.60 (dd, J = 10.6, 4.4 Hz, 3H), 1.17-1.04 (m, 15H), 0.92-0.86 (m, 1H). | 669.5 |
| I-89B | 7B | $^1$H NMR (400 MHz, DMSO-d$_6$) δ 8.44-8.26 (m, 2H), 7.96-7.75 (m, 2H), 7.45-7.12 (m, 10H), 5.35 (s, 2H), 4.52 (t, J = 11.6 Hz, 1H), 4.45-4.21 (m, 2H), 4.11-3.77 (m, 5H), 3.77-3.46 (m, 4H), 3.43-3.39 (m, 1H), 2.61 (t, J = 3.6 Hz, 3H), 1.18-0.92 (m, 16H). | 669.5 |
| I-90A | 7A | $^1$H NMR (400 MHz, DMSO-d$_6$) δ 8.41-8.31 (m, 2H), 7.88-7.78 (m, 2H), 7.38-7.23 (m, 10H), 5.35 (s, 2H), 4.57-4.40 (m, 2H), 4.39-3.42 (m, 11H), 2.60 (dd, J = 10.6, 4.4 Hz, 3H), 1.52-1.35 (m, 6H), 1.10-1.05 (m, 3H). | 633.5 |
| I-90B | 7B | $^1$H NMR (400 MHz, DMSO-d$_6$) δ 8.39-8.28 (m, 2H), 7.92-7.78 (m, 2H), 7.37-7.22 (m, 10H), 5.35 (s, 2H), 4.55-3.38 (m, 13H), 2.61-2.58 (m, 3H), 1.47 (d, J = 22.0 Hz, 6H), 1.11-1.01 (m, 3H). | 633.45 |
| I-91A | 2A | $^1$H NMR (400 MHz, DMSO-d$_6$) δ 8.41-8.30 (m, 1H), 7.86-7.76 (m, 1H), 7.39-7.10 (m, 10H), 5.34-5.23 (m, 2H), 4.35-3.49 (m, 11H), 3.20-2.59 (m, 2H), 2.43-2.33 (m, 1H), 1.79-1.31 (m, 4H), 1.31-0.98 (m, 9H), 0.90-0.63 (m, 2H). | 594.5 |
| I-91B | 2B | $^1$H NMR (400 MHz, DMSO-d$_6$) δ 8.42-8.28 (m, 1H), 7.87-7.75 (m, 1H), 7.38-7.09 (m, 10H), 5.35 (s, 2H), 4.29-3.90 (m, 5H), 3.87-3.49 (m, 5H), 3.17-2.94 (m, 1H), 2.90-2.63 (m, 1H), 2.44-2.35 (m, 1H), 1.80-1.51 (m, 3H), 1.49-1.28 (m, 2H), 1.27-1.15 (m, 2H), 1.14-1.00 (m, 6H), 0.90-0.80 (m, 1H), 0.71-0.62 (m, 1H). | 594.45 |
| I-92A | 7A | $^1$H NMR (400 MHz, DMSO-d$_6$) δ 8.37-8.29 (m, 2H), 7.86-7.80 (m, 2H), 7.37-7.24 (m, 10H), 5.35 (s, 2H), 4.61-4.59 (m, 1H), 4.55-4.42 (m, 2H), 4.37-4.34 (m, 1H), 4.19-3.86 (m, 6H), 3.79-3.63 (m, 3H), 3.58-3.4 (m, 1H), 3.28-3.16 (m, 2H), 2.60 (dd, J = 4.8 Hz, 3H), 2.24-2.12 (m, 1H), 2.04-1.91 (m, 1H), 1.09-1.06 (m, 3H), 0.36-0.29 (m, 4H). | 657.1 |
| I-92B | 7B | $^1$H NMR (400 MHz, DMSO-d$_6$) δ 8.41-8.30 (m, 2H), 7.96-7.79 (m, 2H), 7.45-7.18 (m, 10H), 5.37 (s, 2H), 4.71-4.61 (m, 1H), 4.54 (t, J = 11.7 Hz, 1H), 4.47-4.25 (m, 2H), 4.15-3.98 (m, 3H), 3.96-3.40 (m, 7H), 3.28 (d, | 657.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-93 | 2B | J = 11.2 Hz, 2H), 2.63 (d, J = 4.5 Hz, 3H), 2.28-2.04 (m, 2H), 1.17-0.99 (m, 3H), 0.45-0.29 (m, 4H).<br>$^1$H NMR (400 MHz, DMSO-d$_6$) δ 8.42-8.34 (m, 1H), 7.88-7.78 (m, 1H), 7.64-7.52 (m, 2H), 7.48-7.17 (m, 10H), 5.38-5.28 (m, 2H), 4.38-3.58 (m, 10H), 1.12-0.92 (m, 7H), 0.84 (s, 1H), 0.70-0.58 (m, 1H). | 579.1 |
| I-94A | 7A | $^1$H NMR (400 MHz, DMSO-d$_6$) δ 8.39-8.28 (m, 2H), 7.88-7.77 (m, 2H), 7.38-7.22 (m, 10H), 5.35 (s, 2H), 4.55-4.35 (m, 3H), 4.02-3.37 (m, 10H), 2.60 (dd, J = 10.6, 4.6 Hz, 3H), 1.28 (d, J = 44.0 Hz, 6H), 1.08 (t, J = 5.4 Hz, 3H), 0.81 (dq, J = 13.2, 6.4, 6.0 Hz, 5H), 0.41 (s, 2H). | 669.50 |
| I-94B | 7B | $^1$H NMR (400 MHz, DMSO-d$_6$) δ 8.42-8.21 (m, 2H), 7.88-7.77 (m, 2H), 7.39-7.13 (m, 10H), 5.35 (d, J = 3.2 Hz, 2H), 4.56-4.35 (m, 3H), 4.33-3.44 (m, 10H), 2.60 (d, J = 4.6 Hz, 3H), 1.49-1.31 (m, 2H), 1.26 (t, J = 6.4 Hz, 4H), 1.06 (dd, J = 17.6, 6.2 Hz, 3H), 0.87-0.81 (d, J = 8.6 Hz, 5H), 0.49-0.39 (m, 2H). | 669.5 |
| I-95A | 4A | $^1$H NMR (400 MHz, DMSO-d$_6$) δ 8.40-8.27 (m, 1H), 8.20 (d, J = 11.6 Hz, 1H), 7.90-7.75 (m, 2H), 7.36-7.23 (m, 5H), 4.56-4.5 (m, 1H), 4.47-4.4 (m, 1H), 4.38-4.31 (m, 1H), 4.27-4.21 (m, 1H), 4.08-3.39 (m, 13H), 3.24 (t, J = 11.6 Hz, 2H), 2.65-2.56 (m, 3H), 2.07 (s, 1H), 1.41-1.17 (m, 5H), 1.11-1.01 (m, 9H), 0.84 (t, J = 4.6 Hz, 1H), 0.68-0.61 (m, 1H). | 649.2 |
| I-95B | 4B | $^1$H NMR (400 MHz, Methanol-d$_4$) δ 8.18-8.07 (m, 1H), 7.94-7.85 (m, 1H), 7.37-7.22 (m, 5H), 4.61-4.56 (m, 1H), 4.49-4.40 (m, 2H), 4.29-4.12 (m, 3H), 4.05 (dt, J = 22.2, 7.2 Hz, 4H), 3.96-3.86 (m, 5H), 3.85-3.75 (m, 1H), 3.43-3.34 (m, 3H), 2.74 (s, 3H), 2.21-2.11 (m, 1H), 1.53-1.42 (m, 3H), 1.40-1.29 (m, 3H), 1.21-1.17 (m, 4H), 1.15-1.11 (m, 4H), 1.07-1.02 (m, 1H), 0.81-0.75 (m, 1H). | 649.5 |
| I-96A | 2A | $^1$H NMR (400 MHz, DMSO-d$_6$) δ 8.45-8.32 (m, 2H), 7.88-7.77 (m, 1H), 7.40-7.21 (m, 10H), 5.35 (d, J = 2.6 Hz, 2H), 4.50-4.42 (m, 2H), 4.23-4.02 (m, 2H), 4.00-3.41 (m, 8H), 3.31-3.04 (m, 3H), 1.39-1.22 (m, 1H). 1.11-0.97 (m, 6H), 0.87-0.82 (m, 1H), 0.69-0.59 (m, 1H). | 570.4 |
| I-96B | 2B | $^1$H NMR (400 MHz, DMSO-d$_6$) δ 8.48-8.32 (m, 2H), 7.87-7.79 (m, 1H), 7.41-7.22 (m, 10H), 5.38-5.33 (m, 2H), 4.52-4.40 (m, 2H), 4.33-3.54 (m, 8H), 3.51-3.35 (m, 3H), 3.29-3.05 (m, 2H), 1.40-1.21 (m, 1H), 1.11-1.02 (m, 6H), 0.90-0.81 (m, 1H), 0.71-0.59 (m, 1H). | 570.1 |
| I-97 | 15 | $^1$H NMR (400 MHz, CD$_3$OD): δ 8.14-8.23 (m, 1H), 7.87-7.93 (m, 1H), 7.17-7.42 (m, 10H), 5.33-5.38 (m, 2H), 4.93-4.98 (m, 1H), 4.60-4.65 (m, 1H), 4.50-4.56 (m, 1H), 3.84-4.20 (m, 8H), 3.43-3.58 (m, 4H), 3.37 (m, 1H), 2.19 (t, J = 7.6 Hz, 1H), 2.02-2.03 (m, 1H), 1.58-1.62 (m, 3H), 1.43-1.53 (m, 4H), 1.18 (d, J = 4.8 Hz, 2H), 1.10-1.12 (m, 4H), 1.02-1.04 (m, 1H), 0.90 (t, J = 6.6 Hz, 2H), 0.74-0.79 (m, 1H). | 695.5 |
| I-98 | 15 | $^1$H NMR (400 MHz, CD$_3$OD): δ 8.15-8.23 (m, 1H), 7.87-7.93 (m, 1H), 7.19-7.36 (m, 10H), 5.33-5.38 (m, 2H), 4.95-5.02 (m, 1H), 4.30-4.65 (m, 5H), 3.81-4.21 (m, 10H), 3.35-4.43 (m, 2H), 2.41-2.98 (m, 5H), 2.19 (t, J = 7.4 Hz, 0.4H), 2.00-2.05 (m, 0.7 H), 1.60-1.78 (m, 3H), 1.18 (d, J = 5.2 Hz, 2H), 1.10-1.12 (m, 4H), 1.01-1.04 (m, 1H), 0.90 (t, J = 6.8 Hz, 1H), 0.73-0.79 (m, 1H). | 725.5 |
| I-99 | 15 | $^1$H NMR (400 MHz, CDCl3): δ 7.82-7.83 (m, 2H), 7.24-7.38 (m, 10H), 6.70-6.77 (m, 1H), 4.62 (d, J = 12.0 Hz, 1H), 4.50-4.57 (m, 1H), 4.454.48 (m, 1H), 3.60-4.20 (m, 14H), 3.05 (s, 1H), 1.99-2.03 (m, 1H), 1.12-1.24 (m, 16H), 0.85-0.90 (m, 1H), 0.72-0.75 (m, 1H). | 695.5 |
| I-100A | 1A | $^1$H NMR (400 MHz, DMSO-d$_6$) δ 8.59-8.53 (m, 1H), 8.35 (d, J = 11.6 Hz, 1H), 8.03-8.02 (m, 1H), 7.84-7.80 (m, 1H), 7.37-7.25 (m, 10H), 5.35 (s, 2H), 4.55-4.42 (m, 4H), 4.28-3.87 (m, 4H), 3.78-3.62 (m, 3H), 3.56-3.54 (m, 2H), 3.26-3.25 (m, 1H), 2.60-2.57 (m, 3H), 1.07-1.02 (m, 9H). | 615.2 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
| --- | --- | --- | --- |
| I-100B | 1B | $^1$H NMR (400 MHz, DMSO-$d_6$) δ 8.57-8.47 (m, 1H), 8.35 (d, 1H), 8.07-7.90 (m, 1H), 7.83-7.79 (m, 1H), 7.38-7.20 (m, 10H), 5.35 (d, J = 4.2 Hz, 2H), 4.54-4.43 (m, 3H), 4.32-4.20 (m, 1H), 4.01-3.76 (m, 3H), 3.76-3.65 (m, 2H), 3.63-3.53 (m, 3H), 3.30-3.26 (m, 1H), 2.59 (d, J = 4.4 Hz, 3H), 1.09 (s, 9H). | 615.2 |
| I-101A | 2A | $^1$H NMR (400 MHz, DMSO-$d_6$) δ 8.51-8.41 (m, 1H), 8.38-8.35 (m, 1H), 7.95 (t, 1H), 7.86-7.79 (m, 1H), 7.41-7.07 (m, 10H), 5.39-5.32 (m, 2H), 4.28-3.80 (m, 6H), 3.80-3.57 (m, 3H), 3.27-3.21 (m, 1H), 2.58-2.52 (m, 5H), 1.67-1.47 (m, 4H), 1.35-1.22 (m, 1H), 1.10-1.07 (m, 1H), 1.06-1.00 (m, 5H), 0.88-0.82 (m, 1H), 0.67-0.60 (m, 1H). | 625.2 |
| I-101B | 2B | $^1$H NMR (400 MHz, DMSO-$d_6$) δ 8.47-8.30 (m, 2H), 8.01-7.78 (m, 2H), 7.38-7.08 (m, 10H), 5.35 (s, 2H), 4.38-4.10 (m, 2H), 4.09-3.85 (m, 3H), 3.85-3.53 (m, 4H), 3.27-3.21 (m, 1H), 2.61-2.51 (m, 5H), 1.73-1.40 (m, 4H), 1.34 (dd, J = 7.6, 5.6 Hz, 1H), 1.14-1.03 (m, 6H), 0.85 (q, J = 4.8 Hz, 1H), 0.72-0.62 (m, 1H). | 625.2 |
| I-102A | 7A | $^1$H NMR (400 MHz, DMSO-$d_6$) δ 8.35 (d, J = 11.4 Hz, 2H), 7.89-7.76 (m, 2H), 7.38-7.20 (m, 10H), 5.35 (s, 2H), 4.53 (d, J = 12.0 Hz, 1H), 4.46-4.33 (m, 2H), 4.21-3.42 (m, 10H), 3.16 (d, J = 18.8 Hz, 3H), 2.60 (dd, J = 10.8, 4.6 Hz, 3H), 1.70-1.53 (m, 2H), 1.07 (t, J = 5.6 Hz, 3H), 0.78 (s, 2H), 0.49 (s, 2H). | 671.45 |
| I-102B | 7B | $^1$H NMR (400 MHz, DMSO-$d_6$) δ 8.45-8.26 (m, 2H), 7.96-7.7 (m, 2H), 7.39-7.20 (m, 10H), 5.35 (s, 2H), 4.52 (t, J = 12.0 Hz, 1H), 4.46-4.30 (m, 2H), 4.24-3.37 (m, 10H), 3.30 (s, 2H), 3.18 (d, J = 18.0 Hz, 3H), 2.60 (d, J = 4.4 Hz, 3H), 1.76-1.56 (m, 2H), 1.06 (dd, J = 18.6, 6.2 Hz, 3H), 0.87-0.77 (m, 2H), 0.53 (s, 2H). | 671.5 |
| I-103A | 1A | $^1$H NMR (400 MHz, DMSO-$d_6$) δ 9.25 (s, 1H), 8.38-8.34 (m, 1H), 8.23 (dd, J = 8.4 Hz, 1H), 7.80-7.73 (m, 1H), 4.28-4.21 (m, 1H), 4.18-3.96 (m, 4H), 3.93-3.86 (m, 1H), 3.82-3.71 (m, 3H), 3.70-3.60 (m, 1H), 3.52-3.42 (m, 1H), 3.25-3.20 (m, 1H), 3.12-3.07 (m, 1H), 2.59 (d, J = 4.4 Hz, 2H), 2.57-2.55 (m, 1H), 1.98-1.92 (m, 2H), 1.68-1.63 (m, 5H), 1.44-1.42 (m, 1H), 1.19-1.09 (m, 3H), 1.03-1.00 (m, 3H), 0.91-0.81 (m, 3H), 0.43-0.40 (m, 2H), 0.10-0.05 (m, 2H). | 560.1 |
| I-103B | 1B | $^1$H NMR (DMSO, 400 MHz) δ 0.06-0.12 (2H, m), 0.40-0.46 (2H, m), 0.77-0.98 (4H, m), 1.02 (2H, d, J = 6.2 Hz), 1.08-1.21 (3H, m), 1.41 (1H, s), 1.61 (5H, d, J = 12.4 Hz), 1.93-2.01 (2H, m), 2.59 (3H, s), 3.09 (1H, m), 3.19-3.27 (1H, m), 3.46 (1H, m), 3.61-3.89 (5H, m), 3.94-4.17 (4H, m), 4.20-4.33 (1H, m), 7.77-7.89 (1H, m), 8.20-8.31 (1H, m), 8.33-8.39 (1H, m), 9.25 (1H, s). | 560.40 |
| I-104 | 15 | $^1$H NMR (400 MHz, CD$_3$OD): δ 8.08-8.16 (m, 1H), 7.80-7.83 (d, J = 13.2 Hz, 1H), 7.19-7.27 (m, 5H), 5.28 (s, 2H), 4.79-4.86 (m, 1H), 3.50-4.49 (m, 13H), 3.21-3.32 (m, 2H), 3.04-3.10 (m, 1H), 2.45-2.55 (m, 1H), 1.93-2.03 (m, 1H), 1.74-1.78 (m, 1H), 1.55-1.66 (m, 6H), 1.30-1.41 (m, 3H), 1.00-1.07 (m, 10H), 0.67-0.83 (m, 11H). | 729.5 |
| I-105 | 15 | $^1$H NMR (400 MHz, CD$_3$OD) δ 8.21 (d, J = 14.8 Hz, 1H), 7.92 (d, J = 12.0 Hz, 1H), 7.28-7.37 (m, 5H), 5.38 (s, 2H), 4.91-4.99 (m, 1H), 3.70-4.41 (m, 12H), 3.35-3.51 (m, 3H), 3.11-3.24 (m, 2H), 2.84-3.04 (m, 1H), 2.52-2.70 (m, 1H), 1.55-1.88 (m, 9H), 1.04-1.29 (m, 13H), 1.03-1.05 (m, 1H), 0.88-0.97 (m, 3H), 0.76-0.80 (m, 1H). | 731.5 |
| I-106 | 15 | $^1$H NMR (400 MHz, CDCl3): δ 8.15-8.23 (m, 1H), 7.88-7.93 (m, 1H), 7.27-7.36 (m, 10H), 5.33-5.38 (m, 2H), 4.28-4.66 (m, 4H), 3.76-4.23 (m, 12H), 3.35-3.37 (m, 1H), 2.02-2.21 (m, 5H), 1.78-1.82 (m, 2H), 1.29-1.30 (m, 6H), 1.18-1.24 (m, 4H), 1.09-1.15 (m, 4H), 1.01-1.04 (m, 1H), 0.88-0.91 (m, 1H), 0.76-0.79 (m, 1H). | 707.5 |
| I-107 | 15 | $^1$H NMR (400 MHz, CD$_3$OD) δ 8.17-8.25 (m, 2H), 7.89-7.93 (m, 1H), 7.28-7.36 (m, 5H), 5.38 (s, 2H), 4.50-4.56 (m, 1H), 3.70-4.43 (m, 15H), 3.31-3.36 (m, 1H), 3.17-3.23 (m, 1H), 2.11-2.25 (m, 4H), 1.82-1.89 (m, 2H), 1.65-1.77 (m, 5H), 1.02-1.20 (m, 13H), 0.86-0.97 (m, 2H), 0.76-0.80 (m, 1H). | 713.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-108A | 7A | $^1$H NMR (400 MHz, DMSO-d$_6$) δ 8.34 (d, J = 8.6 Hz, 2H), 7.82 (d, J = 15.0 Hz, 2H), 7.41-7.23 (m, 10H), 5.35 (s, 2H), 4.53 (d, J = 12.2 Hz, 1H), 4.50-4.26 (m, 3H), 3.92 (m, 4H), 3.77 (m, 2H), 3.62-3.38 (m, 2H), 3.30 (s, 1H), 2.60 (dd, J = 10.8, 4.5 Hz, 3H), 1.21-1.05 (m, 7H). | 681.4 |
| I-108B | 7B | $^1$H NMR (400 MHz, DMSO-d$_6$) δ 8.36-8.31 (m, 2H), 7.88-7.79 (m, 2H), 7.37-7.23 (m, 10H), 5.35-5.34 (m, 2H), 4.52 (t, J = 12 Hz, 1H), 4.44-4.34 (m, 3H), 4.12-3.96 (m, 3H), 3.90-3.85 (m, 2H), 3.79-3.62 (m, 3H), 3.49-3.40 (m, 1H), 2.61-2.59 (m, 3H), 1.28-1.04 (m, 7H). | 681.4 |
| I-109A | 7A | $^1$H NMR (400 MHz, DMSO-d$_6$) δ 8.36 (d, J = 11.0 Hz, 2H), 7.83 (d, J = 16.0 Hz, 2H), 7.38-7.23 (m, 10H), 5.36 (s, 2H), 4.56-4.41 (m, 2H), 4.39-3.37 (m, 11H), 3.30 (s, 1H), 2.60 (dd, J = 10.4, 4.4 Hz, 3H), 1.63 (s, 1H), 1.24 (s, 1H), 1.09 (d, J = 5.6 Hz, 3H), 1.00-0.92 (m, 1H), 0.84 (s, 8H), 0.40 (s, 2H). | 669.45 |
| I-109B | 7B | $^1$H NMR (400 MHz, DMSO-d$_6$) δ 8.35 (d, J = 22.6 Hz, 2H), 7.82 (d, J = 20.0 Hz, 1H), 7.39-7.21 (m, 10H), 5.35 (d, J = 3.8 Hz, 2H), 4.52 (t, J = 11.6 Hz, 1H), 4.44-3.44 (m, 12H), 2.60 (d, J = 4.4 Hz, 3H), 1.66 (s, 1H), 1.38-1.23 (m, 2H), 1.06 (dd, J = 16.6, 6.2 Hz, 3H), 0.86 (d, J = 6.2 Hz, 8H), 0.43 (s, 2H). | 669.45 |
| I-110A | 2A | $^1$H NMR (400 MHz, DMSO-d$_6$) δ 8.36 (d, J = 14.4 Hz, 1H), 8.25-8.13 (m, 1H), 7.86-7.69 (m, 2H), 7.38-7.24 (m, 5H), 5.35 (s, 2H), 4.31-3.53 (m, 11H), 3.29 (d, J = 7.4 Hz, 1H), 3.21-3.11 (m, 1H), 2.58 (dd, J = 10.0, 4.4 Hz, 3H), 2.08-1.98 (m, 1H), 1.63-1.29 (m, 7H), 1.17-1.00 (m, 11H), 0.85 (d, J = 4.4 Hz, 1H), 0.67 (d, J = 8.0 Hz, 1H). | 633.4 |
| I-110B | 2B | $^1$H NMR (400 MHz, DMSO-d$_6$) δ 8.41-8.18 (m, 2H), 7.82 (d, J = 17.8 Hz, 2H), 7.38-7.22 (m, 5H), 5.35 (s, 2H), 4.38-3.49 (m, 11H), 3.33-3.26 (m, 1H), 3.15 (d, J = 7.4 Hz, 1H), 2.59 (t, J = 5.0 Hz, 3H), 1.99 (m, 1H), 1.63-1.33 (m, 7H), 1.16-0.94 (m, 11H), 0.91-0.81 (m, 1H), 0.68 (m, 1H). | 633.5 |
| I-111 | 15 | $^1$H NMR (400 MHz, CD$_3$OD) δ 8.18-8.24 (m, 1H), 7.92 (d, J = 12.0 Hz, 1H), 7.28-7.37 (m, 5H), 5.38 (s, 2H), 4.88-4.96 (m, 1H), 3.64-4.56 (m, 13H), 3.33-3.39 (m, 2H), 3.13-3.28 (m, 4H), 2.44-3.05 (m, 3H), 1.61-1.85 (m, 8H), 1.45-1.56 (m, 2H), 1.01-1.22 (m, 13H), 0.83-0.97 (m, 3H), 0.74-0.79 (m, 1H). | 745.5 |
| I-112A | 4A | $^1$H NMR (400 MHz, DMSO-d$_6$) δ 13.59-13.56 (m, 1H), 8.39-8.31 (m, 1H), 8.25-8.16 (m, 1H), 7.93-7.80 (m, 1H), 7.65-7.61 (m, 1H), 7.42 (t, J = 7.6 Hz, 1H), 7.36-7.21 (m, 6H), 4.56-4.51 (m, 1H), 4.46-4.41 (m, 1H), 4.38-4.29 (m, 2H), 4.26-4.05 (m, 3H), 4.03-3.92 (m, 2H), 3.90-3.78 (m, 2H), 3.75-3.62 (m, 1H), 3.57-3.45 (m, 1H), 2.63-2.57 (m, 3H), 1.37-1.23 (m, 1H), 1.18-1.01 (m, 9H), 0.85-0.83 (m, 1H), 0.67-0.61 (m, 1H). | 601.5 |
| I-112B | 4B | $^1$H NMR (400 MHz, DMSO-d$_6$) δ 13.58 (s, 1H), 8.40-8.34 (m, 1H), 8.16 (d, J = 8.4 Hz, 1H), 7.93-7.84 (m, 1H), 7.63-7.60 (m, 1H), 7.42 (t, J = 7.6 Hz, 1H), 7.35-7.20 (m, 6H), 4.57-4.30 (m, 4H), 4.25-4.20 (m, 1H), 4.16-4.13 (m, 1H), 4.10-4.02 (m, 1H), 3.99-3.86 (m, 2H), 3.83-3.64 (m, 3H), 3.54-3.45 (m, 1H), 2.63-2.60 (m, 3H), 1.41-1.34 (m, 1H), 1.14-1.06 (m, 7H), 1.04-0.98 (m, 2H), 0.89-0.83 (m, 1H), 0.72-0.63 (m, 1H). | 601.5 |
| I-113A | 1A | $^1$H NMR (400 MHz, DMSO-d$_6$) δ 8.58 (s, 1H), 8.35 (d, J = 8.0 Hz, 1H), 8.04 (s, 1H), 7.82 (d, J = 12.2 Hz, 1H), 7.42-7.22 (m, 10H), 5.36 (s, 2H), 4.55 (s, 1H), 4.46 (s, 2H), 3.97-3.54 (m, 11H), 2.59 (dd, J = 8.4, 4.6 Hz, 3H), 1.24 (dd, J = 13.4, 6.8 Hz, 2H), 1.18-1.10 (m, 2H). | 667.4 |
| I-113B | 1B | $^1$H NMR (400 MHz, DMSO-d$_6$) δ 8.51-8.49 (m, 1H), 8.36-8.32 (m, 1H), 8.00-7.99 (m, 1H), 7.84-7.80 (m, 1H), 7.37-7.24 (m, 10H), 5.35-5.34 (m, 2H), 4.48-4.45 (m, 3H), 4.04-3.91 (m, 2H), 3.79-3.71 (m, 2H), 3.60-3.56 (m, 3H), 3.38-3.36 (m, 1H), 3.29-3.27 (m, 2H), 2.60 (d, J = 4.4 Hz, 3H), 2.51 (s, 1H), 1.27-1.23 (m, 2H), 1.17-1.14 (m, 2H). | 667.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-114A | 7A | $^1$H NMR (400 MHz, DMSO-d$_6$) δ 8.36 (d, J = 14.6 Hz, 2H), 7.83 (d, J = 16.6 Hz, 2H), 7.36-7.24 (m, 10H), 5.36 (s, 2H), 4.57-4.47 (m, 2H), 4.46-4.34 (m, 3H), 4.03-3.40 (m, 8H), 2.63-2.57 (m, 3H), 1.31-1.16 (m, 1H), 1.11-1.04 (m, 3H), 0.75 (s, 2H), 0.34 (s, 4H), 0.02 (s, 2H). | 653.45 |
| I-114B | 7B | $^1$H NMR (400 MHz, DMSO-d$_6$) δ 8.42-8.29 (m, 2H), 7.96-7.75 (m, 2H), 7.38-7.21 (m, 10H), 5.35 (d, J = 3.2 Hz, 2H), 4.52 (t, J = 11.6 Hz, 1H), 4.46-4.30 (m, 3H), 4.09-3.95 (m, 2H), 3.93-3.41 (m, 7H), 2.63-2.57 (m, 3H), 1.33-1.24 (m, 1H), 1.07 (dd, J = 17.2, 6.2 Hz, 3H), 0.85-0.72 (m, 2H), 0.44-0.34 (m, 4H), 0.12-0.01 (m, 2H). | 653.45 |
| I-115 | 1A | $^1$H NMR (400 MHz, DMSO-d$_6$) δ 8.91-8.90 (m, 1H), 8.41-8.35 (m, 1H), 8.26-8.24 (m, 1H), 4.88-4.86 (m, 1H), 4.21-4.02 (m, 3H), 3.98-3.83 (m, 2H), 3.79-3.69 (m, 2H), 3.61-3.40 (m, 7H), 3.26-3.16 (m, 2H), 1.66-1.58 (m, 7H), 1.46-1.30 (m, 6H), 1.17-1.09 (m, 6H), 1.07-1.03 (m, 6H), 0.87-0.84 (m, 3H), 0.69-0.66 (m, 1H). | 679.4 |
| I-116A | 7A | $^1$H NMR (400 MHz, Methanol-d$_4$) δ 8.23-8.18 (m, 1H), 7.94-7.89 (m, 1H), 7.38-7.24 (m, 10H), 5.40-5.36 (m, 2H), 4.64-4.58 (m, 1H), 4.50-4.41 (m, 2H), 4.34-4.31 (m, 1H), 4.20-3.94 (m, 6H), 3.87-3.83 (m, 1H), 3.61-3.58 (m, 2H), 2.73 (d, J = 11.2 Hz, 3H), 1.46-1.37 (m, 2H), 1.22-1.15 (m, 4H), 0.93-0.71 (m, 4H), 0.48-0.37 (m, 2H), 0.11-0.05 (m, 2H). | 667.45 |
| I-116B | 7B | $^1$H NMR (400 MHz, DMSO-d$_6$) δ 8.40-8.27 (m, 2H), 7.94-7.77 (m, 2H), 7.39-7.17 (m, 10H), 5.35 (s, 2H), 4.57-4.47 (m, 1H), 4.46-4.34 (m, 2H), 4.29-3.58 (m, 8H), 3.50-3.33 (m, 2H), 2.60 (d, J = 4.6 Hz, 3H), 1.47-1.29 (m, 2H), 1.13-1.00 (m, 3H), 0.80 (s, 2H), 0.74-0.61 (m, 1H), 0.54 (s, 2H), 0.40-0.28 (m, 2H), 0.08--0.01 (m, 2H). | 667.4 |
| I-117A | 7A | $^1$H NMR (400 MHz, DMSO-d$_6$) δ 8.35 (d, J = 9.8 Hz, 2H), 7.85-7.79 (m, 2H), 7.37-7.32 (m, 3H), 7.31-7.24 (m, 7H), 5.35 (s, 2H), 4.55-4.34 (m, 6H), 3.99-3.44 (m, 9H), 2.62-2.58 (m, 3H), 1.86-1.72 (m, 2H), 1.09-1.05 (m, 3H), 0.84 (s, 2H), 0.55 (s, 2H). | 659.45 |
| I-117B | 7B | $^1$H NMR (400 MHz, Chloroform-d) δ 7.83 (s, 2H), 7.42-7.27 (m, 10H), 5.31 (s, 2H), 4.69-4.42 (m, 5H), 4.35-3.76 (m, 9H), 3.10 (s, 1H), 2.89-2.78 (m, 3H), 1.96-1.83 (m, 2H), 1.16-0.93 (m, 5H), 0.64 (s, 2H). | 659.45 |
| I-118 | 1A | $^1$H NMR (400 MHz, DMSO-d$_6$) δ 8.35-8.28 (m, 1H), 4.90-4.82 (m, 1H), 4.21-4.12 (m, 1H), 4.09-3.95 (m, 1H), 3.93-3.66 (m, 3H), 3.63-3.48 (m, 5H), 3.46-3.35 (m, 4H), 3.27-3.21 (m, 1H), 3.17-3.13 (m, 1H), 1.94-1.91 (m, 3H), 1.69-1.58 (m, 7H), 1.47-1.37 (m, 5H), 1.36-1.26 (m, 1H), 1.20-1.08 (m, 6H), 1.06-1.02 (m, 6H), 0.89-0.83 (m, 3H), 0.70-0.66 (m, 1H). | 559.4 |
| I-119A | 2A | $^1$H NMR (400 MHz, DMSO-d$_6$) δ 8.36 (d, J = 14.2 Hz, 1H), 8.26-8.16 (m, 1H), 7.82 (d, J = 15.6 Hz, 2H), 7.39-7.23 (m, 5H), 5.35 (s, 2H), 4.29-3.57 (m, 14H), 3.25-3.14 (m, 2H), 2.61-2.55 (m, 3H), 1.69 (s, 1H), 1.53 (d, J = 12.8 Hz, 2H), 1.32 (d, J = 19.8 Hz, 1H), 1.18-0.99 (m, 12H), 0.85 (s, 1H), 0.68 (d, J = 8.0 Hz, 1H). | 649.45 |
| I-119B | 2B | $^1$H NMR (400 MHz, Methanol-d$_4$) δ 8.29-8.14 (m, 1H), 7.98-7.88 (m, 1H), 7.40-7.24 (m, 5H), 4.65-4.49 (m, 1H), 4.46-4.34 (m, 1H), 4.27-3.81 (m, 10H), 3.48-3.33 (m, 4H), 3.20 (ddd, J = 14.6, 9.2, 6.6 Hz, 1H), 2.74 (s, 3H), 1.86-1.69 (m, 1H), 1.60 (t, J = 16.0 Hz, 2H), 1.52-1.35 (m, 1H), 1.33-1.09 (m, 11H), 1.04 (q, J = 5.8, 4.8 Hz, 2H), 0.83-0.73 (m, 1H). | 649.5 |
| I-120A | 2A | $^1$H NMR (400 MHz, DMSO-d$_6$) δ 8.64 (dd, J = 18.8, 8.0 Hz, 1H), 8.44-8.31 (m, 1H), 7.85 (d, J = 10.2 Hz, 1H), 7.43-7.08 (m, 8H), 5.36 (s, 2H), 5.31-5.2 (m, 1H), 4.27-3.59 (m, 8H), 3.24-3.03 (m, 1H), 2.99-2.75 (m, 2H), 2.44-2.31 (s, 1H), 1.98-1.73 (m, 1H), 1.41-1.28 (m, 1H), 1.15-1.03 (m, 6H), 0.86 (s, 1H), 0.67 (dd, J = 8.4, 4.2 Hz, 1H). | 586.0 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-120B | 2B | $^1$H NMR (400 MHz, DMSO-d$_6$) δ 8.67 (q, J = 9.8, 8.8 Hz, 1H), 8.42-8.34 (m, 1H), 7.84 (d, J = 14.6 Hz, 1H), 7.43-7.08 (m, 8H), 5.36 (s, 2H), 5.28 (dq, J = 16.4, 7.8 Hz, 1H), 4.35 (t, J = 10.4 Hz, 1H), 4.18-4.02 (m, 2H), 3.94 (d, J = 10.4 Hz, 1H), 3.83 (d, J = 17.2 Hz, 2H), 3.64 (d, J = 14.2 Hz, 2H), 3.19-3.04 (m, 1H), 2.98-2.77 (m, 2H), 2.41 (s, 1H), 1.86 (dq, J = 17.2, 8.9 Hz, 1H), 1.35 (d, J = 18.4 Hz, 1H), 1.14-1.03 (m, 6H), 0.86 (d, J = 6.4 Hz, 1H), 0.71 (dd, J = 8.6, 4.2 Hz, 1H). | 586.3 |
| I-121A | 1A | $^1$H NMR (400 MHz, DMSO-d$_6$) δ 8.25-8.13 (m, 2H), 7.84-7.70 (m, 2H), 4.31-4.11 (m, 2H), 4.10-3.99 (m, 3H), 3.99-3.38 (m, 10H), 3.30-3.18 (m, 3H), 3.15-3.06 (m, 1H), 2.64-2.54 (m, 3H), 2.14-1.99 (m, 1H), 1.71-1.56 (m, 5H), 1.49-0.98 (m, 18H), 0.91-0.77 (m, 3H), 0.71-0.62 (m, 1H). | 655.1 |
| I-121B | 1B | $^1$H NMR (400 MHz, DMSO-d$_6$) δ 8.28-8.16 (m, 2H), 7.88-7.77 (m, 2H), 4.39-3.95 (m, 7H), 3.91-3.46 (m, 8H), 3.27-3.19 (m, 3H), 3.12-3.05 (m, 1H), 2.59 (t, J = 4.8 Hz, 3H), 2.12-2.01 (m, 1H), 1.62 (s, 5H), 1.44-1.33 (m, 4H), 1.27-1.17 (m, 3H), 1.14-0.99 (m, 10H), 0.95 (d, J = 6.6 Hz, 1H), 0.89-0.78 (m, 3H), 0.69 (td, J = 7.8, 4.0 Hz, 1H). | 655.5 |
| I-122A | 2A | $^1$H NMR (400 MHz, DMSO-d$_6$) δ 8.39-8.30 (m, 2H), 7.85-7.80 (m, 1H), 7.38-7.23 (m, 5H), 5.35 (s, 2H), 4.25-3.54 (m, 9H), 3.28-3.01 (m, 6H), 1.40-1.29 (m, 1H), 1.15-1.01 (m, 6H), 0.89-0.82 (m, 1H), 0.71-0.64 (m, 1H). | 494.35 |
| I-122B | 2B | $^1$H NMR (400 MHz, DMSO-d$_6$) δ 8.40-8.31 (m, 2H), 7.86-7.79 (m, 1H), 7.40-7.22 (m, 5H), 5.35 (s, 2H), 4.32-3.59 (m, 9H), 3.30 (s, 1H), 3.26-3.21 (m, 3H), 3.21-3.05 (m, 2H), 1.40-1.30 (m, 1H), 1.14-1.02 (m, 6H), 0.85 (s, 1H), 0.71-0.63 (m, 1H). | 494.0 |
| I-123 - Mix | 14 | $^1$H NMR (400 MHz, Methanol-d$_4$) δ 8.25-8.16 (m, 1H), 7.95-7.88 (m, 1H), 7.38-7.24 (m, 5H), 4.56-3.76 (m, 10H), 3.48-3.33 (m, 2H), 3.22-3.10 (m, 1H), 2.77-2.69 (m, 3H), 1.79-1.62 (m, 6H), 1.57-1.38 (m, 2H), 1.37-1.08 (m, 14H), 1.07-1.00 (m, 2H), 0.91 (q, J = 11.8 Hz, 2H), 0.77 (dd, J = 7.6, 4.0 Hz, 1H). | 647.5 |
| I-123A | 2A | $^1$H NMR (400 MHz, DMSO-d$_6$) δ 8.41-8.31 (m, 1H), 8.25-8.1 (m, 1H), 7.88-7.68 (m, 2H), 7.4-7.21 (m, 5H), 5.35 (s, 2H), 4.31-4.03 (m, 3H), 4.03-3.58 (m, 7H), 3.55-3.38 (m, 1H), 3.26-3.16 (m, 1H), 3.15-3.05 (m, 1H), 2.63-2.55 (m, 3H), 1.71-1.56 (m, 5H), 1.50-1.26 (m, 2H), 1.22-0.99 (m, 12H), 0.91-0.75 (m, 3H), 0.70-0.63 (m, 1H). | 647.5 |
| I-123B | 2B | $^1$H NMR (400 MHz, DMSO-d$_6$) δ 8.40-8.16 (m, 2H), 7.88-7.68 (m, 2H), 7.38-7.20 (m, 5H), 5.35 (s, 2H), 4.39-4.19 (m, 2H), 4.13 (t, J = 8.4 Hz, 1H), 4.04-3.99 (m, 2H), 3.78-3.60 (m, 5H), 3.48-3.40 (m, 1H), 3.27-3.19 (m, 1H), 3.10-3.06 (m, 1H), 2.61-2.57 (m, 3H), 1.62 (br s, 6H), 1.43-1.33 (m, 2H), 1.11 (s, 5H), 1.07-1.05 (m, 3H), 1.02-0.99 (m, 2H), 0.96 (t, J = 6.4 Hz, 1H), 0.87-0.78 (m, 3H), 0.71-0.66 (m, 1H). | 647.5 |
| I-125 | 15 | $^1$H NMR (400 MHz, CD$_3$OD): δ 7.91-7.97 (m, 2H), 7.18-7.22 (m, 5H), 4.88-4.93 (m, 1H), 4.32-4.57 (m, 4H), 3.71-4.17 (m, 10H), 3.27 (m, 1H), 2.25-2.43 (m, 2H), 1.89-1.99 (m, 1H), 1.58-1.72 (m, 1H), 1.19-1.23 (m, 1H), 1.08-1.16 (m, 5H), 1.02 (d, J = 9.6 Hz, 3H), 0.92-0.95 (m, 1H), 0.78-0.81 (m, 4H), 0.58-0.69 (m, 4H). | 633.5 |
| I-125A | 2A | $^1$H NMR (400 MHz, DMSO-d$_6$) δ 8.40-8.14 (m, 2H), 7.87-7.67 (m, 2H), 7.37-7.24 (m, 5H), 5.35 (s, 2H), 4.29-4.10 (m, 2H), 4.08-3.40 (m, 11H), 2.61-2.55 (m, 3H), 1.68-1.58 (m, 5H), 1.38-1.27 (m, 4H), 1.20-1.12 (m, 2H), 1.13-1.01 (m, 10H), 0.89-0.79 (m, 3H), 0.70-0.62 (m, 1H). | 661.50 |
| I-125B | 2B | $^1$H NMR (400 MHz, DMSO-d$_6$) δ 8.39-8.13 (m, 2H), 7.85-7.73 (m, 2H), 7.38-7.22 (m, 5H), 5.35 (s, 2H), 4.39-4.13 (m, 2H), 4.12-3.39 (m, 11H), 2.63-2.57 (m, 3H), 1.61 (s, 5H), 1.39-1.27 (m, 4H), 1.14-0.93 (m, 12H), 0.89-0.79 (m, 3H), 0.73-0.64 (m, 1H). | 661.65 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-126A | 2A | $^1$H NMR (400 MHz, DMSO-$d_6$) δ 8.77 (t, J = 6.2 Hz, 1H), 8.37 (d, J = 8.2 Hz, 1H), 7.83 (d, J = 10.6 Hz, 1H), 7.62 (t, J = 7.6 Hz, 1H), 7.38-7.24 (m, 5H), 6.84 (q, J = 8.0, 7.4 Hz, 1H), 6.67 (d, J = 8.2 Hz, 1H), 5.35 (s, 2H), 4.43-4.07 (m, 4H), 4.02-3.63 (m, 9H), 3.28-3.15 (m, 1H), 1.38-1.28 (m, 1H), 1.13-0.96 (m, 6H), 0.86 (d, J = 9.2 Hz, 1H), 0.67 (td, J = 8.2, 3.6 Hz, 1H). | 557.40 |
| I-126B | 2B | $^1$H NMR (400 MHz, DMSO-$d_6$) δ 8.87-8.72 (m, 1H), 8.36 (d, J = 8.7 Hz, 1H), 7.83 (d, J = 11.3 Hz, 1H), 7.67-7.53 (m, 1H), 7.39-7.23 (m, 5H), 6.89-6.78 (m, 1H), 6.67 (d, J = 6.8 Hz, 1H), 5.35 (s, 2H), 4.40 (dd, J = 16.2, 6.0 Hz, 1H), 4.28-4.08 (m, 2H), 4.00 (d, J = 24.0 Hz, 3H), 3.83 (d, J = 9.3 Hz, 5H), 3.75-3.62 (m, 2H), 3.27-3.16 (m, 1H), 1.39-1.34 (m, 1H), 1.31-1.27 (m, 1H), 1.13-1.08 (m, 3H), 1.07-1.02 (m, 3H), 0.88-0.83 (m, 1H), 0.71-0.63 (m, 1H). | 557.4 |
| I-127A | 2A | $^1$H NMR (400 MHz, DMSO-$d_6$) δ 8.79-8.65 (m, 1H), 8.39-8.30 (m, 1H), 7.81 (d, J = 14.4 Hz, 1H), 7.41-7.00 (m, 9H), 5.34 (d, J = 5.6 Hz, 2H), 5.01-4.91 (m, 1H), 4.30-3.84 (m, 5H), 3.83-3.65 (m, 2H), 3.67-3.57 (m, 1H), 3.21-3.05 (m, 1H), 1.40-1.30 (m, 4H), 1.14-1.03 (m, 7H), 0.90-0.84 (m, 1H), 0.73-0.64 (m, 1H). | 558.35 |
| I-127B | 2B | $^1$H NMR (400 MHz, DMSO-$d_6$) δ 8.78-8.64 (m, 1H), 8.38-8.33 (m, 1H), 7.84-7.79 (m, 1H), 7.36-6.99 (m, 9H), 5.36-5.33 (m, 2H), 4.96-4.89 (m, 1H), 4.16-3.96 (m, 2H), 3.95-3.84 (m, 2H), 3.84-3.67 (m, 3H), 3.64 (s, 1H), 3.23-3.10 (m, 1H), 1.39-1.34 (m, 3H), 1.12-0.80 (m, 8H), 0.65 (d, J = 8.0 Hz, 1H). | 558.4 |
| I-128A | 2A | $^1$H NMR (400 MHz, DMSO-$d_6$) δ 8.71 (m, 1H), 8.37 (s, 1H), 7.83 (d, J = 5.8 Hz, 1H), 7.39-7.22 (m, 6H), 7.15 (t, J = 7.9 Hz, 2H), 7.04 (t, J = 8.7 Hz, 1H), 5.35 (s, 2H), 5.02-4.88 (m, 1H), 4.23-3.59 (m, 8H), 3.26-3.07 (m, 1H), 1.37 (d, J = 7.4 Hz, 3H), 1.26 (m, 1H), 1.12-0.90 (m, 6H), 0.82 (m, 1H), 0.70-0.60 (m, 1H). | 558.4 |
| I-128B | 2B | $^1$H NMR (400 MHz, DMSO-$d_6$) δ 8.75-8.69 (m, 1H), 8.36-8.32 (m, 1H), 7.83-7.79 (m, 1H), 7.37-7.23 (m, 6H), 7.16-7.12 (m, 2H), 8.75-8.69 (m, 1H), 7.37-7.23 (m, 6H), 7.16-7.12 (m, 2H), 7.07-7.05 (m, 1H), 5.35-5.34 (m, 2H), 4.97-4.93 (m, 1H), 4.34-4.18 (m, 1H), 4.13-3.96 (m, 2H), 3.93-3.89 (m, 1H), 3.83-3.74 (m, 2H), 3.71-3.61 (m, 2H), 3.21-3.13 (m, 1H), 1.38-1.35 (m, 4H), 1.12-1.02 (m, 6H), 0.86-0.85 (m, 1H), 0.71-0.68 (m, 1H). | 558.4 |
| I-129A | 1A | $^1$H NMR (400 MHz, DMSO-$d_6$) δ 9.27-9.22 (m, 1H), 8.42-8.32 (m, 1H), 8.27-8.18 (m, 1H), 7.81-7.68 (m, 1H), 4.29-4.05 (m, 4H), 4.03-3.77 (m, 4H), 3.77-3.44 (m, 3H), 3.26-3.19 (m, 1H), 3.14-3.06 (m, 1H), 2.61-2.54 (m, 3H), 1.70-1.58 (m, 5H), 1.48-1.38 (m, 1H), 1.37-1.27 (m, 1H), 1.26-1.11 (m, 4H), 1.10-1.06 (m, 3H), 1.05-0.99 (m, 5H), 0.90-0.77 (m, 3H), 0.71-0.64 (m, 1H). | 574.4 |
| I-129B | 1B | $^1$H NMR (DMSO, 400 MHz) δ 0.68 (1H, m), 0.77-0.89 (3H, m), 0.96 (1H, t, J = 5.8 Hz), 1.02 (2H, d, J = 6.2 Hz), 1.06 (3H, d, J = 6.0 Hz), 1.08-1.23 (6H, m), 1.34 (2H, m), 1.56-1.68 (5H, m), 2.59 (3H, t, J = 4.8 Hz), 3.04-3.12 (1H, m), 3.17-3.29 (2H, m), 3.42-3.52 (1H, m), 3.63-3.87 (5H, m), 3.98-4.27 (4H, m), 4.29-4.41 (1H, m), 7.77-7.89 (1H, m), 8.24-8.41 (2H, m), 9.25 (1H, s). | 574.40 |
| I-130A | 2A | $^1$H NMR (400 MHz, DMSO-$d_6$) δ 8.40-8.32 (m, 1H), 8.14-8.04 (m, 1H), 7.87-7.79 (m, 1H), 7.79-7.69 (m, 1H), 7.39-7.22 (m, 5H), 5.36 (s, 2H), 4.33-3.59 (m, 11H), 3.15-3.08 (m, 1H), 3.00-2.90 (m, 1H), 2.61-2.55 (m, 3H), 1.37-1.20 (m, 2H), 1.12-1.01 (m, 9H), 0.85-0.81 (m, 9H), 0.69-0.65 (m, 1H). | 621.45 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
| --- | --- | --- | --- |
| I-130B | 2B | $^1$H NMR (400 MHz, DMSO-$d_6$) δ 8.40-8.12 (m, 2H), 7.90-7.70 (m, 2H), 7.39-7.22 (m, 5H), 5.35 (s, 2H), 4.37-4.25 (m, 1H), 4.17-3.55 (m, 9H), 3.51-3.37 (m, 1H), 3.15-3.06 (m, 1H), 2.99-2.89 (m, 1H), 2.62-2.55 (m, 3H), 1.40-1.31 (m, 1H), 1.14-1.09 (m, 3H), 1.07-1.01 (m, 5H), 1.00-0.96 (m, 1H), 0.89-0.85 (m, 1H). 0.85-0.80 (m, 6H), 0.80-0.77 (m, 3H), 0.72-0.64 (m, 1H). | 621.1 |
| I-131A | 2A | $^1$H NMR (400 MHz, DMSO-$d_6$) δ 8.40-8.24 (m, 2H), 7.87-7.81 (m, 1H), 7.39-7.23 (m, 5H), 5.36 (s, 2H), 4.26-3.56 (m, 12H), 3.31-3.27 (m, 4H), 3.09-3.04 (m, 2H), 1.84-1.73 (m, 1H), 1.44-1.30 (m, 2H), 1.13-1.03 (m, 6H), 0.89-0.82 (m, 1H), 0.71-0.65 (m, 1H). | 550.4 |
| I-131B | 2B | $^1$H NMR (400 MHz, DMSO-$d_6$) δ 8.40-8.25 (m, 2H), 7.87-7.79 (m, 1H), 7.40-7.22 (m, 5H), 5.35 (s, 2H), 4.34-3.58 (m, 12H), 3.30 (s, 2H), 3.25-3.22 (m, 1H), 3.18-2.99 (m, 3H), 1.78 (s, 1H), 1.48-1.29 (m, 2H), 1.14-1.03 (m, 6H), 0.88-0.81 (m, 1H), 0.73-0.64 (m, 1H). | 550.0 |
| I-132 | 1A | $^1$H NMR (400 MHz, DMSO-$d_6$) δ 8.48-8.40 (m, 1H), 8.36-8.33 (m, 1H), 7.96-7.91 (m, 1H), 5.17 (q, J = 9.2 Hz, 2H), 4.88-4.85 (m, 1H), 4.24-3.94 (m, 4H), 3.89-3.82 (m, 1H), 3.77-3.67 (m, 2H), 3.61-3.58 (m, 2H), 3.51-3.40 (m, 5H), 3.25-3.22 (m, 1H), 3.17-3.13 (m, 1H), 1.69-1.58 (m, 6H), 1.44-1.23 (m, 7H), 1.19-1.09 (m, 6H), 1.06-1.03 (m, 6H), 0.86-0.85 (m, 1H), 0.69-0.67 (m, 1H). | 693.3 |
| I-133A | 2A | $^1$H NMR (400 MHz, DMSO-$d_6$) δ 8.76-8.62 (m, 1H), 8.42-8.35 (m, 1H), 7.88-7.80 (m, 1H), 7.41-7.22 (m, 6H), 7.21-7.06 (m, 2H), 5.36 (s, 2H), 5.33-5.26 (m, 1H), 4.29-3.75 (m, 7H), 3.69-3.63 (m, 1H), 3.23-3.01 (m, 1H), 2.99-2.90 (m, 1H), 2.88-2.77 (m, 1H), 2.46-2.39 (m, 1H), 1.90-1.75 (m, 1H), 1.41-1.21 (m, 1H), 1.11-0.99 (m, 6H), 0.90-0.83 (m, 1H), 0.71-0.64 (m, 1H). | 586.35 |
| I-133B | 2B | $^1$H NMR (400 MHz, DMSO-$d_6$) δ 8.66-8.60 (m, 1H), 8.41-8.36 (m, 1H), 7.88-7.81 (m, 1H), 7.38-7.14 (m, 8H), 5.36 (s, 2H), 5.27-5.20 (m, 1H), 4.35-4.02 (m, 3H), 3.99-3.80 (m, 3H), 3.78-3.64 (m, 2H), 3.21-3.04 (m, 1H), 2.97-2.75 (m, 2H), 2.46-2.31 (m, 1H), 1.87-1.76 (m, 1H), 1.39-1.33 (m, 1H), 1.14-1.09 (m, 3H), 1.07-1.04 (m, 3H), 0.88-0.83 (m, 1H), 0.73-0.66 (m, 1H). | 586.30 |
| I-134A | 2A | $^1$H NMR (400 MHz, DMSO-$d_6$) δ 8.38-8.36 (m, 1H), 8.27-8.16 (m, 1H), 7.84-7.81 (m, 1H), 7.37-7.27 (m, 5H), 5.35 (s, 2H), 4.26-4.15 (m, 1H), 4.12-3.86 (m, 6H), 3.77-3.71 (m, 3H), 3.66-3.61 (m, 1H), 3.43-3.38 (m, 1H), 3.31-3.21 (m, 6H), 1.75-1.73 (m, 1H), 1.46-1.44 (m, 1H), 1.35-1.30 (m, 1H), 1.12-1.02 (m, 6H), 0.86-0.84 (m, 1H), 0.70-0.65 (m, 1H). | 550.4 |
| I-134B | 2B | $^1$H NMR (400 MHz, DMSO-$d_6$) δ 8.37-8.35 (m, 1H), 8.30-8.17 (m, 1H), 7.84-7.81 (m, 1H), 7.35-7.25 (m, 5H), 5.35 (s, 2H), 4.36-4.16 (m, 1H), 4.08-3.83 (m, 6H), 3.80-3.57 (m, 5H), 3.28-3.20 (m, 6H), 1.76-1.74 (m, 1H), 1.46-1.44 (m, 1H), 1.38-1.24 (m, 1H), 1.11-1.05 (m, 6H), 0.86-0.83 (m, 1H), 0.70-0.68 (m, 1H). | 550.3 |
| I-135A | 2A | $^1$H NMR (400 MHz, DMSO-$d_6$) δ 8.36 (d, J = 11.0 Hz, 1H), 7.93-7.79 (m, 2H), 7.40-7.22 (m, 5H), 5.35 (s, 2H), 4.69-4.54 (m, 1H), 4.32-3.92 (m, 4H), 3.89-3.68 (m, 4H), 3.66-3.38 (m, 4H), 3.28-3.22 (m, 1H), 3.16-3.08 (m, 1H), 1.78-1.58 (m, 5H), 1.48 (s, 1H), 1.32 (d, J = 30.6 Hz, 1H), 1.24-1.12 (m, 3H), 111102 (m, 6H), 1.01-0.94 (m, 3H), 0.92-0.81 (m, 3H), 0.72-0.61 (m, 1H). | 620.5 |
| I-135B | 2B | $^1$H NMR (400 MHz, DMSO-$d_6$) δ 8.36 (d, J = 12.4 Hz, 1H), 7.91-7.74 (m, 2H), 7.41-7.20 (m, 5H), 5.35 (s, 2H), 4.62 (dd, J = 10.4, 5.4 Hz, 1H), 4.35 (t, J = 8.2 Hz, 1H), 4.10-3.90 (m, 3H), 3.85-3.70 (m, 4H), 3.65-3.38 (m, 4H), 3.29-3.23 (m, 1H), 3.10 (t, J = 8.2 Hz, 1H), 1.71-1.63 (m, 5H), 1.46 (s, 1H), 1.35 (s, 1H), 1.25-1.14 (m, | 620.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
| --- | --- | --- | --- |
| | | 3H), 1.13-1.09 (m, 5H), 1.05 (d, J = 3.4 Hz, 2H), 1.01-0.92 (m, 3H), 0.86 (s, 2H), 0.68 (s, 1H). | |
| I-136A | 1A | $^1$H NMR (400 MHz, DMSO-d$_6$) δ 8.42-8.27 (m, 2H), 7.9-7.78 (m, 2H), 7.39-7.28 (m, 4H), 7.16 (q, J = 9.4 Hz, 4H), 5.34 (s, 2H), 4.56-4.30 (m, 3H), 4.26-4.12 (m, 1H), 4.09-3.59 (m, 8H), 3.56-3.38 (m, 1H), 2.64-2.55 (m, 3H), 1.35-1.21 (m, 1H), 1.15-0.99 (m, 9H), 0.84 (t, J = 4.8 Hz, 1H), 0.69-0.56 (m, 1H). | 677.5 |
| I-136B | 1B | $^1$H NMR (400 MHz, DMSO-20 δ 8.40-8.30 (m, 2H), 7.94-7.77 (m, 2H), 7.37-7.26 (m, 4H), 7.21-7.09 (m, 4H), 5.34 (s, 2H), 4.50 (t, J = 13.0 Hz, 1H), 4.42-4.29 (m, 2H), 4.13 (t, J = 8.2 Hz, 1H), 4.08-3.91 (m, 3H), 3.90-3.76 (m, 2H), 3.75-3.64 (m, 2H), 3.63-3.57 (m, 1H), 3.53-3.39 (m, 1H), 2.62-2.58 (m, 3H), 1.39-1.32 (m, 1H), 1.13-1.00 (m, 9H), 0.89-0.83 (m, 1H), 0.73-0.64 (m, 1H). | 677.45 |
| I-137A | 2A | $^1$H NMR (400 MHz, DMSO-2, ) δ 8.36 (d, J = 14.6 Hz, 1H), 8.25-8.15 (m, 1H), 7.82 (d, J = 15.4 Hz, 1H), 7.79-7.71 (m, 1H), 7.40-7.21 (m, 5H), 5.35 (s, 2H), 4.29-4.02 (m, 3H), 4.00-3.56 (m, 7H), 3.53-3.39 (m, 1H), 3.22-3.15 (m, 1H), 3.11-3.03 (m, 1H), 2.61-2.55 (m, 3H), 1.71 (dt, J = 13.4, 6.6 Hz, 1H), 1.38-1.27 (m, 1H), 1.13-1.01 (m, 9H), 0.88-0.84 (m, 1H), 0.82 (d, J = 6.6 Hz, 6H), 0.69-0.64 (m, 1H). | 607.45 |
| I-137B | 2B | $^1$H NMR (400 MHz, Methanol-d$_4$) δ 8.25-8.16 (m, 1H), 7.91 (d, J = 16.8 Hz, 1H), 7.38-7.25 (m, 5H), 5.38 (s, 2H), 4.58 (s, 1H), 4.37 (q, J = 4.8 Hz, 1H), 4.27-3.77 (m, 9H), 3.47-3.37 (m, 1H), 3.14-3.08 (m, 1H), 2.75 (s, 3H), 1.77 (dq, J = 12.8, 6.2 Hz, 1H), 1.52-1.39 (m, 1H), 1.19-1.11 (m, 8H), 1.04 (d, J = 6.7 Hz, 2H), 0.87 (ddd, J = 11.2, 5.4, 2.4 Hz, 6H), 0.79 (dd, J = 8.0, 4.2 Hz, 1H). | 607.45 |
| I-138 | 15 | $^1$H NMR (400 MHz, CD$_3$OD): δ 9.16 (s, 1H), 8.37 (d, J = 12.4 Hz, 1H), 4.89-4.95 (m, 1H), 4.22-4.40 (m, 3H), 3.87-4.18 (m, 6H), 3.55-3.75 (m, 10H), 3.33-3.38 (m, 1H), 3.19-3.24 (m, 1H), 1.66-1.76 (m, 5H), 1.49-1.55 (m, 1H), 1.11-1.22 (m, 12H), 0.90-0.90 (m, 3H), 0.76-0.82 (m, 1H). | 630.4 |
| I-139 | 26A | $^1$H NMR (400 MHz, DMSO-d$_6$) δ 8.66-8.60 (m, 1H), 8.26-8.18 (m, 2H), 7.95-7.89 (m, 2H), 7.36-7.19 (m, 10H), 5.39-5.37 (m, 2H), 4.44-4.14 (m, 3H), 4.12-3.76 (m, 7H), 3.48-3.35 (m, 1H), 1.41-1.33 (m, 1H), 1.20-1.13 (m, 2H), 1.11-1.09 (m, 2H), 1.01-0.96 (m, 1H), 0.90-0.84 (m, 2H), 0.77-0.71 (m, 1H). | 603.0 |
| I-140A | 2A | $^1$H NMR (400 MHz, DMSO-d$_6$) δ 8.64-8.55 (m, 1H), 8.36 (d, J = 8.0 Hz, 1H), 7.83 (d, J = 11.8 Hz, 1H), 7.40-7.14 (m, 8H), 7.10-7.03 (m, 1H), 5.35 (s, 2H), 4.27-3.60 (m, 8H), 3.15-2.96 (m, 1H), 2.83 (s, 1H), 1.93 (d, J = 43.0 Hz, 1H), 1.41-1.31 (m, 1H), 1.28-1.15 (m, 2H), 1.14-1.02 (m, 5H), 0.97 (d, J = 9.8 Hz, 1H), 0.90-0.82 (m, 1H), 0.73-0.63 (m, 1H). | 586.3 |
| I-140B | 2B | $^1$H NMR (400 MHz, Methanol-A) δ 8.26-8.17 (m, 1H), 7.92 (d, J = 10.6 Hz, 1H), 7.39-7.12 (m, 8H), 7.09-7.02 (m, 1H), 5.37 (s, 2H), 4.51-3.78 (m, 8H), 3.19-3.07 (m, 1H), 2.93-2.82 (m, 1H), 2.10-1.90 (m, 1H), 1.47-1.37 (m, 1H), 1.28-1.04 (m, 9H), 0.78 (td J = 8.4, 4.0 Hz, 1H). | 586.3 |
| I-141A | 2A | $^1$H NMR (400 MHz, Methanol-A) δ 8.28-8.15 (m, 1H), 7.92 (d, J = 10.0 Hz, 1H), 7.47-7.16 (m, 5H), 5.38 (s, 2H), 4.58 (s, 1H), 4.43-4.30 (m, 2H), 4.26-4.15 (m, 2H), 4.08-3.98 (m, 3H), 3.92-3.80 (m, 2H), 3.57-3.41 (m, 2H), 2.77-2.72 (m, 3H), 2.18 (d, J = 11.6 Hz, 1H), 1.88 (s, 1H), 1.67 (d, J = 11.8 Hz, 4H), 1.55-1.50 (m, 3H), 1.45-1.38 (m, 1H), 1.37-1.32 (m, 1H), 1.30 (d, J = 7.6 Hz, 1H), 1.21-1.17 (m, 3H), 1.16 (d, J = 4.2 Hz, 3H), 1.13 (d, J = 5.4 Hz, 1H), 1.11 (s, 2H), 1.03 (d, J = 5.2 Hz, 1H), 0.77 (dd, J = 8.0, 4.2 Hz, 1H). | 715.5 |
| I-141B | 2B | $^1$H NMR (400 MHz, Metlianol-0/4) δ 8.29-8.14 (m, 1H), 7.91 (d, J = 17.0 Hz, 1H), 7.41-7.22 (m, 5H), 5.38 (s, 2H), 4.64-4.51 (m, 1H), 4.43-4.34 (m, 1H), 4.27-4.07 (m, 3H), 3.99-3.85 (m, 4H), 3.84-3.74 (m, 1H), 3.55-3.40 (m, 2H), 2.74 (d, J-2.8 Hz, 3H), 2.14 (s, 1H), 1.86 | 715.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | (s, 1H), 1.66 (d, J = 10.0 Hz, 3H), 1.50 (dd, J = 8.0, 5.4 Hz, 4H), 1.30 (d, J = 10.6 Hz, 1H), 1.21-1.13 (m, 6H), 1.12 (d, J = 4.8 Hz, 2H), 1.08-1.02 (m, 2H), 0.79 (dd, J = 7.8, 4.2 Hz, 1H). | |
| I-142A | 2A | $^1$H NMR (400 MHz, DMSO-d$_6$) δ 9.51 (d, J = 3.8 Hz, 1H), 8.36 (d, J = 12.0 Hz, 1H), 7.83 (d, J = 10.8 Hz, 1H), 7.47-7.13 (m, 5H), 5.35 (s, 2H), 4.91-4.78 (m, 2H), 4.58-4.45 (m, 2H), 4.35-3.94 (m, 4H), 3.92 (d, J = 9.8 Hz, 1H), 3.78 (dd, J = 15.0, 8.8 Hz, 2H), 3.65 (dd, J = 15.6, 5.8 Hz, 4H), 3.25-3.11 (m, 1H), 1.44-1.29 (m, 1H), 1.13-1.08 (m, 3H), 1.06 (d, J = 11.2 Hz, 3H), 0.86 (s, 1H), 0.69 (dd, J = 8.0, 3.8 Hz, 1H). | 550.3 |
| I-142B | 2B | $^1$H NMR (400 MHz, DMSO-d$_6$) δ 9.47 (d, J = 16.4 Hz, 1H), 8.33 (d, J = 12.0 Hz, 1H), 7.79 (d, J = 12.0 Hz, 1H), 7.40-7.20 (m, 5H), 5.32 (s, 2H), 4.89-4.78 (m, 2H), 4.50 (dd, J = 11.8, 5.4 Hz, 2H), 4.30 (d, J = 9.4 Hz, 1H), 4.14 (d, J = 13.2 Hz, 1H), 4.02-3.86 (m, 4H), 3.79-3.67 (m, 2H), 3.64-3.58 (m, 4H), 3.14 (d, J = 5.4 Hz, 1H), 1.32 (d, J = 6.8 Hz, 1H), 1.08 (t, J = 2.4 Hz, 3H), 1.03 (d, J = 7.8 Hz, 3H), 0.83 (s, 1H), 0.66 (s, 1H). | 550.3 |
| I-143 | 4B | $^1$H NMR (400 MHz, DMSO-d$_6$) δ 13.50 (s, 1H), 10.61 (s, 0.5H), 8.72-8.68 (m, 1H), 7.94-7.92 (m, 2H), 7.61 (d, J = 8.4 Hz, 1H), 7.44 (t, J = 7.2 Hz, 1H), 7.33-7.22 (m, 5.5H), 4.87-4.72 (m, 2H), 4.56-4.53 (m, 1H), 4.46-4.42 (m, 1H), 4.36-4.34 (m, 1H), 4.25-4.08 (m, 1H), 4.00-3.85 (m, 4H), 3.70-3.65 (m, 5H), 2.60-2.59 (m, 3H), 1.31-1.23 (m, 1H), 1.11-1.03 (m, 9H), 0.86-0.84 (m, 1H), 0.70-0.68 (m, 7H). | 587 |
| I-144A | 2A | $^1$H NMR (400 MHz, DMSO-d$_6$) δ 8.36 (d, J = 14.4 Hz, 1H), 8.27-8.15 (m, 1H), 7.86-7.70 (m, 2H), 7.38-7.22 (m, 5H), 5.35 (s, 2H), 4.29-3.62 (m, 10H), 3.51-3.37 (m, 2H), 3.29 (s, 1H), 2.62-2.55 (m, 3H), 2.46-2.38 (m, 1H), 1.98-1.88 (m, 2H), 1.84-1.76 (m, 2H), 1.70-1.59 (m, 2H), 1.38-1.26 (m, 1H), 1.12-1.01 (m, 9H), 0.88-0.83 (m, 1H), 0.70-0.64 (m, 1H). | 619.45 |
| I-144B | 2B | $^1$H NMR (400 MHz, DMSO-d$_6$) δ 8.37-8.27 (m, 1H), 8.21 (d, J = 8.6 Hz, 1H), 7.81 (d, J = 17.8 Hz, 2H), 7.36-7.21 (m, 5H), 5.33 (s, 2H), 4.38-3.74 (m, 12H), 3.28-3.23 (m, 1H), 2.60-2.56 (m, 3H), 2.42-2.31 (m, 1H), 1.95-1.82 (m, 2H), 1.80-1.70 (m, 2H), 1.66-1.53 (m, 2H), 1.38-1.31 (m, 1H), 1.12-0.95 (m, 9H), 0.89-0.81 (m, 1H), 0.72-0.64 (m, 1H). | 619.4 |
| I-145A | 1A | $^1$H NMR (400 MHz, DMSO-d$_6$) δ 8.29-8.16 (m, 2H), 7.83-7.66 (m, 1H), 4.72 (s, 2H), 4.29-3.64 (m, 11H), 3.62-3.46 (m, 1H), 3.32 (s, 4H), 3.26-3.19 (m, 1H), 3.14-3.07 (m, 1H), 2.58 (dd, J = 11.4, 4.4 Hz, 3H), 1.71-1.58 (m, 5H), 1.49-1.26 (m, 2H), 1.20-1.00 (m, 12H), 0.89-0.75 (m, 3H), 0.69-0.63 (m, 1H). | 618.0 |
| I-145B | 1B | $^1$H NMR (400 MHz, DMSO-d$_6$) δ 8.38-8.16 (m, 2H), 7.91-7.77 (m, 1H), 4.71 (d, J = 2.0 Hz, 2H), 4.39-4.29 (m, 1H), 4.25 (dd, J = 8.8, 4.4 Hz, 1H), 4.21-4.10 (m, 1H), 4.03 (m, 2H), 3.75 (m, 5H), 3.54-3.44 (m, 1H), 3.42 (d, J = 1.6 Hz, 3H), 3.29-3.18 (m, 2H), 3.09 (dt, J = 9.6, 6.8 Hz, 1H), 2.59 (t, J = 4.8 Hz, 3H), 1.61 (d, J = 13.0 Hz, 5H), 1.34 (m, 2H), 1.17 (m, 2H), 1.13-1.11 (m, 3H), 1.08-1.05 (m, 3H), 1.04-1.00 (m, 2H), 0.96 (t, J = 5.4 Hz, 1H), 0.86 (d, J = 9.6 Hz, 2H), 0.80 (m, 1H), 0.68 (m, 1H). | 618.5 |
| I-146 | 1B | $^1$H NMR (400 MHz, DMSO-d$_6$) δ 8.28 (q, J = 16.0, 9.0 Hz, 1H), 8.06-8.00 (m, 2H), 7.91-7.77 (m, 1H), 4.51-4.33 (m, 1H), 4.30-3.98 (m, 4H), 3.92-3.59 (m, 5H), 3.53-3.39 (m, 1H), 3.28-3.20 (m, 1H), 3.13-3.02 (m, 1H), 2.61-2.57 (m, 3H), 1.68-1.55 (m, 5H), 1.45-1.33 (m, 2H), 1.28-1.10 (m, 6H), 1.07-1.04 (m, 3H), 1.02 (dd, J = 6.4, 2.4 Hz, 2H), 0.97 (t, J = 5.8 Hz, 1H), 0.90-0.78 (m, 3H), 0.71-0.65 (m, 1H). | 574.4 |
| I-147 | 16A | $^1$H NMR (400 MHz, DMSO-d$_6$) δ 8.48-8.30 (m, 2H), 7.93-7.78 (m, 3H), 7.39-7.22 (m, 7H), 5.35 (s, 2H), 4.97-4.88 (m, 1H), 4.60-4.49 (m, 1H), 4.22-3.91 (m, 5H), 3.83 (s, 3H), 3.76-3.59 (m, 4H), 3.28-3.09 (m, 4H), 2.95-2.84 (m, 1H), 2.64-2.54 (m, 4H), 2.46-2.41 | 835.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | (m, 1H), 1.90-1.81 (m, 1H), 1.70-1.56 (m, 5H), 1.50-1.29 (m, 3H), 1.12-1.04 (m, 10H), 0.90-0.81 (m, 3H), 0.71-0.64 (m, 1H). | |
| I-148A | 2A | $^1$H NMR (400 MHz, DMSO-d$_6$) δ 8.39-8.27 (m, 2H), 7.83 (d, J = 11.8 Hz, 1H), 7.44-7.18 (m, 5H), 5.36 (s, 2H), 4.28-4.12 (m, 1H), 4.10-4.05 (m, 1H), 4.05-3.81 (m, 4H), 3.80-3.67 (m, 4H), 3.63 (t, J = 5.2 Hz, 1H), 3.31-3.28 (m, 3H), 3.24 (d, J = 2.8 Hz, 1H), 3.16-2.98 (m, 3H), 1.77 (d, J = 13.0 Hz, 1H), 1.45-1.28 (m, 2H), 1.14-1.08 (m, 3H), 1.07-1.01 (m, 3H), 0.85 (dd, J = 5.4, 3.6 Hz, 1H), 0.72-0.62 (m, 1H). | 550.4 |
| I-148B | 2B | $^1$H NMR (400 MHz, DMSO-d$_6$) δ 8.41-8.18 (m, 2H), 7.83 (d, J = 13.0 Hz, 1H), 7.38-7.23 (m, 5H), 5.35 (s, 2H), 4.37-3.55 (m, 12H), 3.30-3.25 (m, 3H), 3.18-3.01 (m, 3H), 1.82-1.73 (m, 1H), 1.46-1.27 (m, 2H), 1.14-1.02 (m, 6H), 0.88-0.83 (m, 1H), 0.71-0.65 (m, 1H). | 550.4 |
| I-149 - Mix | 15 | $^1$H NMR (400 MHz, CD$_3$CD) δ 8.17-8.23 (m, 2H), 7.95 (d, J = 12.4 Hz, 1H), 7.27-7.36 (m, 5H), 5.37 (s, 2H), 4.30-4.40 (m, 1H), 3.92-4.25 (m, 6H), 3.66-3.87 (m, 18H), 3.54-3.60 (m, 1H), 3.30-3.46 (m, 2H), 3.18-3.23 (m, 1H), 1.88-2.12 (m, 4H), 1.65-1.75 (m, 4H), 1.39-1.55 (m, 2H), 1.24-1.33 (m, 3H), 1.10-1.18 (m, 9H), 1.02-1.04 (m, 1H), 0.86-0.92 (m, 2H), 0.72-0.80 (m, 1H). | 737.5 |
| I-149A | 16A | $^1$H NMR (400 MHz, CD$_3$OD): δ 8.21-8.26 (m, 1H), 7.94 (d, J = 12.8 Hz, 1H), 7.29-7.39 (m, 5H), 5.40 (s, 2H), 4.95-4.98 (m, 1H), 4.53-4.56 (m, 0.6H), 3.72-4.29 (m, 11.3H), 3.38-3.41 (m, 2H), 3.18-3.24 (m, 1H), 1.97-2.07 (m, 4H), 1.40-1.73 (m, 7H), 1.12-1.31 (m, 13H), 1.06 (s, 1H), 0.92-0.96 (m, 2H), 0.78-0.81 (m, 1H). | 737.5 |
| I-149B | 16B | $^1$H NMR(400 MHz, CD$_3$OD): δ 8.18-8.23 (m, 1H), 7.92 (d, J = 12.8 Hz, 1H), 7.26-7.37 (m, 5H), 5.36-5.38 (m, 2H), 4.95-4.99 (m, 1H), 3.55-4.40 (m, 15H), 3.33-3.38 (m, 1H), 3.19-3.24 (m, 1H), 1.86-2.05 (m, 4H), 1.65-1.77 (m, 5H), 1.03-1.25 (m, 14H), 0.91-0.97 (m, 2H), 0.76-0.80 (m, 1H). | 737.4 |
| I-150 - Mix | 15 | $^1$H NMR(400 MHz, MeOD):5 8.46-8.49 (m, 1H), 8.20-8.25 (m, 1H), 7.92-7.95 (m, 1H), 7.31-7.37 (m, 5H), 5.40 (s, 2H), 3.59-4.64 (m, 13H), 3.37-3.40 (m, 2H), 3.20-3.24 (m, 1H), 2.48-2.91 (m, 3H), 2.10-2.19 (m, 1H), 1.92-2.02 (m, 1H), 1.13-1.89 (m, 21H), 1.04-1.08 (m, 1H), 0.90-1.00 (m, 2H), 0.79-0.83 (m, 1H), Isolated as HCl salt | 717.1 |
| I-150A | 16A | $^1$H NMR (400 MHz, CD$_3$OD): δ 8.21-8.26 (m, 1H), 7.92-7.95 (m, 1H), 7.29-7.39 (m, 5H), 5.40 (s, 2H), 4.90-4.94 (m, 1H), 3.67-4.39 (m, 12H), 3.36-3.66 (m, 4H), 3.18-3.28 (m, 2H), 2.08-2.16 (m, 1H), 1.85-1.99 (m, 1H), 1.50-1.80 (m, 9H), 1.13-1.27 (m, 12H), 0.94-1.00 (m, 2H), 0.78-0.81 (m, 1H). | 717.1 |
| I-150B | 16B | $^1$H NMR (400 MHz, CD$_3$OD): δ 8.21-8.26 (m, 1H), 7.92-7.95 (m, 1H), 7.29-7.39 (m, 5H), 5.40 (s, 2H), 4.90-4.94 (m, 1H), 3.67-4.39 (m, 12H), 3.36-3.66 (m, 4H), 3.18-3.28 (m, 2H), 2.08-2.16 (m, 1H), 1.85-1.99 (m, 1H), 1.50-1.80 (m, 9H), 1.13-1.27 (m, 12H), 0.94-1.00 (m, 2H), 0.78-0.81 (m, 1H). | 717.1 |
| I-151A | 16A | $^1$H NMR (400 MHz, CD$_3$OD): δ 8.16-8.20 (m, 1H), 7.96-7.99 (m, 1H), 4.93-4.97 (m, 1H), 4.54-4.58 (m, 1H), 3.71-4.29 (m, 9H), 3.57-3.64 (m, 4H), 3.35-3.42 (m, 2H), 3.15-3.23 (m, 1H), 1.42-1.72 (m, 12H), 1.03-1.31 (m, 13H), 0.90-0.97 (m, 2H), 0.76-0.81 (m, 1H). | 611.5 |
| I-151B | 16B | $^1$H NMR (400 MHz, CD$_3$OD): δ 7.93-8.28 (m, 2H), 4.93-4.95 (m, 2H), 3.74-4.56 (m, 9H), 3.45-3.64 (m, 4H), 3.35-3.44 (m, 2H), 3.17-3.25 (m, 1H), 1.37-1.76 (m, 12H), 1.11-1.35 (m, 12H), 1.00-1.05 (m, 1H), 0.89-0.97 (m, 2H), 0.75-0.85 (m, 1H). | 611.4 |
| I-152 - Mix | 15 | $^1$H NMR (400 MHz, CDCl3) δ 7.80-7.84 (m, 2H), 7.33-7.39 (m, 3H), 7.21-7.25 (m, 1H), 6.81-6.91 (m, 1H), 5.31 (s, 2H), 4.91-4.96 (m, 1H), 3.45-4.22 (m, 18H), 3.29-3.33 (m, 1H), 3.15-3.20 (m, 1H), 3.02-3.07 (m, 1H), 1.67-1.74 (m, 6H), 1.44-1.51 (m, 1H), 1.07-1.22 (m, 12H), 0.86-0.92 (m, 2H), 0.72-0.76 (m, 1H). | 703.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-152A | 16A | $^1$H NMR (400 MHz, CD$_3$OD): δ 8.21-8.26 (m, 1H), 7.94 (d, J = 13.6 Hz, 1H), 7.31-7.39 (m, 5H), 5.40 (s, 2H), 4.89-4.93 (m, 1H), 4.53-4.57 (m, 0.6H), 3.62-4.29 (m, 15.4H), 3.37-3.42 (m, 2H), 3.18-3.24 (m, 1H), 1.71-1.77 (m, 5H), 1.13-1.50 (m, 15H), 1.04-1.06 (m, 1H), 0.91-0.96 (m, 2H), 0.80 (dd, J = 8.2, 4.2 Hz, 1H). | 703.5 |
| I-152B | 16B | $^1$H NMR(400 MHz, CD$_3$OD): δ 8.21 (d, J = 18.4 Hz, 1H), 7.92 (d, J = 12.8 Hz, 1H), 7.28-7.35 (m, 5H), 5.38 (s, 2H), 4.90-4.93 (m, 1H), 3.60-4.37 (m, 18H), 3.33-3.45 (m, 2H), 3.18-3.25 (m, 1H), 1.64-1.78 (m, 5H), 1.47-1.57 (m, 1H), 1.04-1.24 (m, 13H), 0.89-0.94 (m, 2H), 0.74-0.82 (m, 1H). | 703.4 |
| I-153 - Mix | 15 | $^1$H NMR (400 MHz, CD$_3$CD) δ 8.19-8.24 (m, 2H), 7.89-7 95 (m, 1H), 7 28-7 36 (m, 5H), δ 37 (s, 2H), 4 34-4 57 (m, 2H), 3.91-4.25 (m, 8H), 3.66-3.77 (m, 4H), 3.54-3.62 (m, 1H), 3.31-3.42 (m, 2H), 3.18-3.23 (m, 1H), 1.67-1.76 (m, 4H), 1.48-1.56 (m, 4H), 1.24-1.30 (m, 9H), 1.10-1.18 (m, 10H), 1.02-1.04 (m, 1H), 0.86-0.94 (m, 2H), 0.76-0.80 (m, 1H). | 701.5 |
| I-153A | 16A | $^1$H NMR (400 MHz, CD$_3$OD): δ 8.20-8.26 (m, 1H), 7.94 (d, J = 15.2 Hz, 1H), 7.31-7.39 (m, 5H), 5.40 (s, 2H), 4.39-4.58 (m, 2H), 3.62-4.26 (m, 13H), 3.36-3.43 (m, 2H), 3.20-3.26 (m, 1H), 1.69-1.76 (m, 5H), 1.13-1.53 (m, 20H), 1.04-1.08 (m, 1H), 0.94-0.98 (m, 2H), 0.80 (dd, J = 8.0, 4.2 Hz, 1H). | 701.5 |
| I-153B | 16B | $^1$H NMR(400 MHz, CD$_3$OD): δ 8.19-8.23 (m, 1H), 7.92 (d, J = 12.0 Hz, 1H), 7.27-7.37 (m, 5H), 5.38 (s, 2H), 3.59-4.46 (m, 16H), 3.35-3.37 (m, 1H), 3.22-3.26 (m, 1H), 1.49-1.80 (m, 7H), 1.10-1.26 (m, 16H), 1.03-1.05 (m, 1H), 0.89-0.97 (m, 3H), 0.76-0.80 (m, 1H). | 701.4 |
| I-154A | 16A | $^1$H NMR(400 MHz, DMSO-d$_6$): δ 13.22 (brs, 1H), 8.49-5.57 (m, 1H), 8.14-8.19 (m, 1H), 7.80-7.84 (m, 1H), 4.85-4.87 (m, 1H), 3.89-4.28 (m, 4H), 3.59-3.79 (m, 7H), 3.35-3.48 (m, 1H), 3.24-3.29 (m, 1H), 3.13-3.17 (m, 1H), 1.86-2.02 (m, 4H), 1.59-1.68 (m, 4H), 1.32-1.47 (m, 2H), 1.21-1.31 (m, 3H), 1.02-1.15 (m, 10H), 0.80-0.87 (m, 5H), 0.66-0.68 (m, 1H). | 647.4 |
| I-154B | 16B | $^1$H NMR (400 MHz, CD$_3$OD): δ 7.95-8.16 (m, 2H), 5.00 (s, 1H), 3.50-4.39 (m, 12H), 3.35-3.48 (m, 2H), 3.20 (s, 1H), 1.84-2.19 (m, 4H), 1.37-1.80 (m, 7H), 0.78-1.25 (m, 15H). | 647.4 |
| I-155A | 2A | $^1$H NMR (400 MHz, DMSO-d$_6$) δ 8.50-8.33 (m, 2H), 7.94-7.87 (m, 1H), 7.82 (d, J = 13.6 Hz, 1H), 7.38-7.23 (m, 5H), 5.35 (s, 2H), 4.26-4.09 (m, 2H), 4.08-4.01 (m, 1H), 3.99-3.88 (m, 2H), 3.86-3.56 (m, 4H), 3.29-3.13 (m, 1H), 2.59-2.54 (m, 3H), 1.70-1.56 (m, 6H), 1.49-1.39 (m, 1H), 1.37-1.26 (m, 2H), 1.22-1.08 (m, 10H), 1.06-1.02 (m, 3H), 0.89-0.77 (m, 3H), 0.66 (dd, J = 7.8, 3.8 Hz, 1H). | 631.5 |
| I-155B | 2B | $^1$H NMR (400 MHz, DMSO-d$_6$) δ 8.40-8.31 (m, 2H), 7.98-7.76 (m, 2H), 7.39-7.29 (m, 3H), 7.28-7.23 (m, 2H), 5.35 (s, 2H), 4.38-4.10 (m, 2H), 4.09-3.88 (m, 3H), 3.85-3.54 (m, 4H), 3.31-3.19 (m, 1H), 2.57 (t, J = 4.8 Hz, 3H), 1.74-1.63 (m, 1H), 1.62-1.52 (m, 5H), 1.51-1.43 (m, 1H), 1.35 (t, J = 6.8 Hz, 1H), 1.25-1.09 (m, 10H), 1.08-1.01 (m, 4H), 0.91-0.74 (m, 3H), 0.73-0.60 (m, 1H). | 631.5 |
| I-156A | 1A | $^1$H NMR (400 MHz, DMSO-d$_6$) δ 8.29-8.16 (m, 1H), 8.14-8.04 (m, 1H), 7.84-7.68 (m, 1H), 4.29-4.04 (m, 4H), 4.00-3.60 (m, 6H), 3.57-3.42 (m, 1H), 3.26-3.19 (m, 1H), 3.14-3.06 (m, 1H), 2.67 (s, 3H), 2.62-2.54 (m, 3H), 1.72-1.57 (m, 5H), 1.50-1.27 (m, 2H), 1.20-1.00 (m, 12H), 0.89-0.77 (m, 3H), 0.70-0.62 (m, 1H). | 588.0 |
| I-156B | 1B | $^1$H NMR(400 MHz, DMSO-d$_6$) δ 8.41-8.25 (m, 1H), 8.11-8.06 (m, 1H), 7.88-7.81 (m, 1H), 4.37-4.30 (m, 1H), 4.26-4.16 (m, 1H), 4.12-4.03 (m, 2H), 4.01-3.97 (m, 1H), 3.86-3.63 (m, 5H), 3.50-3.42 (m, 1H), 3.27-3.19 (m, 2H), 3.12-3.04 (m, 1H), 2.66 (s, 3H), 2.59 (t, J = 4.8 Hz, 3H), 1.63-1.60 (m, 5H), 1.38-1.32 (m, 2H), 1.12-1.11 (m, 4H), 1.06-1.05 (m, 3H), 1.02-0.95 (m, 3H), 0.88-0.66 (m, 5H). | 588.4 |
| I-157A | 1A | $^1$H NMR (400 MHz, DMSO-d$_6$) δ 9.24-9.22 (m, 1H), 8.28-8.16 (m, 1H), 7.86-7.68 (m, 1H), 4.29-3.99 (m, | 608.9 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
|  |  | 3H), 3.97-3.77 (m, 3H), 3.73-3.45 (m, 5H), 3.26-3.19 (m, 1H), 3.14-3.05 (m, 1H), 2.62-2.54 (m, 3H), 1.70-1.57 (m, 5H), 1.49-1.26 (m, 2H), 1.19-0.98 (m, 12H), 0.90-0.77 (m, 3H), 0.70-0.61 (m, 1H). |  |
| I-157B | 1B | $^1$H NMR (400 MHz, DMSO-d$_6$) δ 9.23 (s, 1H), 8.41-8.15 (m, 1H), 7.91-7.73 (m, 1H), 4.39-4.18 (m, 2H), 4.16-4.02 (m, 1H), 4.01-3.90 (m, 1H), 3.88-3.77 (m, 2H), 3.76-3.64 (m, 3H), 3.62-3.55 (m, 1H), 3.50-3.42 (m, 1H), 3.29-3.19 (m, 1H), 3.15-3.02 (m, 1H), 2.61-2.56 (m, 3H), 1.71-1.55 (m, 5H), 1.49-1.37 (m, 1H), 1.36-1.25 (m, 1H), 1.21-1.09 (m, 5H), 1.08-1.03 (m, 4H), 1.03-0.98 (m, 2H), 0.96-0.91 (m, 1H), 0.90-0.74 (m, 3H), 0.72-0.62 (m, 1H). | 608.4 |
| I-158A | 2A | $^1$H NMR (400 MHz, DMSO-d$_6$) δ 9.14-9.01 (m, 1H), 8.42-8.32 (m, 1H), 7.83 (d, J = 11.4 Hz, 1H), 7.39-7.21 (m, 5H), 5.35 (s, 2H), 5.23-5.09 (m, 1H), 4.27-4.04 (m, 2H), 4.03-3.92 (m, 2H), 3.92-3.76 (m, 2H), 3.75-3.58 (m, 2H), 3.23-3.07 (m, 1H), 2.35-2.25 (m, 3H), 1.52-1.43 (m, 3H), 1.41-1.30 (m, 1H), 1.14-1.08 (m, 3H), 1.08-1.00 (m, 3H), 0.86 (s, 1H), 0.72-0.65 (m, 1H). | 546.4 |
| I-158B | 2B | $^1$H NMR (400 MHz, DMSO-d$_6$) δ 9.14-9.02 (m, 1H), 8.41-8.33 (m, 1H), 7.86-7.79 (m, 1H), 7.38-7.23 (m, 5H), 5.35 (s, 2H), 5.20-5.08 (m, 1H), 4.38-4.13 (m, 1H), 4.10-3.61 (m, 7H), 3.27-3.13 (m, 1H), 2.34-2.26 (m, 3H), 1.53-1.45 (m, 3H), 1.39-1.27 (m, 1H), 1.14-1.02 (m, 6H), 0.89-0.83 (m, 1H), 0.73-0.65 (m, 1H). | 546.4 |
| I-159 | 4A | $^1$H NMR (400 MHz, DMSO-d$_6$) & 13.52 (s, 1H), 10.67 (s, 1H), 8.70-8.64 (m, 1H), 7.96-7.88 (m, 2H), 7.62-7.60 (m, 1H), 7.46-7.42 (m, 1H), 7.34-7.22 (m, 5H), 4.89-4.73 (m, 2H), 4.55-4.51 (m, 1H), 4.44-4.41 (m, 1H), 4.34-4.25 (m, 1H), 4.14-4.06 (m, 1H), 4.03-3.82 (m, 4H), 3.74-3.64 (m, 5H), 2.62-2.61 (m, 3H), 1.27-1.23 (m, 1H), 1.16-1.02 (m, 9H), 0.85-0.82 (m, 1H), 0.69-0.66 (m, 1H). | 587 |
| I-160A | 1A | $^1$H NMR (400 MHz, DMSO-d$_6$) δ 9.11-9.08 (m, 1H), 8.28-8.12 (m, 1H), 7.84-7.66 (m, 1H), 4.29-3.48 (m, 11H), 3.26-3.19 (m, 1H), 3.13-3.06 (m, 1H), 2.62-2.53 (m, 3H), 2.44-2.40 (m, 3H), 1.70-1.57 (m, 5H). 1.48-1.25 (m, 2H), 1.20-0.98 (m, 12H), 0.89-0.77 (m, 3H), 0.70-0.62 (m, 1H). | 588.4 |
| I-160B | 1B | $^1$H NMR (400 MHz, DMSO-d$_6$) δ 9.09 (s, 1H), 8.41-8.17 (m, 1H), 7.92-7.75 (m, 1H), 4.38-3.42 (m, 11H), 3.25-3.01 (m, 2H), 2.59 (t, J = 4.8 Hz, 3H), 2.41 (s, 3H), 1.61 (d, J = 22.0 Hz, 5H), 1.46-1.27 (m, 2H), 1.16-1.00 (m, 10H), 0.96-0.61 (m, 6H). | 588.5 |
| I-161A | 1A | $^1$H NMR (400 MHz, DMSO-d$_6$) δ 8.62-8.50 (m, 1H), 8.33-8.18 (m, 1H), 7.83-7.67 (m, 1H), 4.29-3.68 (m, 10H), 3.62-3.46 (m, 1H), 3.26-3.20 (m, 1H), 3.14-3.06 (m, 1H), 2.63-2.55 (m, 3H), 1.71-1.55 (m, 5H), 1.49-1.38 (m, 1H), 1.36-1.27 (m, 1H), 1.21-1.00 (m, 12H), 0.89-0.77 (m, 3H), 0.70-0.64 (m, 1H). | 642.0 |
| I-161B | 1B | $^1$H NMR (400 MHz, DMSO-d$_6$) & 8.58-8.54 (m, 1H), 8.36-8.28 (m, 1H), 7.88-7.79 (m, 1H), 4.38-4.30 (m, 1H), 4.27-4.21 (m, 1H), 4.19-4.13 (m, 1H), 4.11-4.09 (m, 1H), 4.06-4.00 (m, 1H), 3.86-3.78 (m, 2H), 3.76-3.61 (m, 3H), 3.53-3.48 (m, 1H), 2.61-2.58 (m, 3H), 1.62-1.59 (m, 5H), 1.42-1.31 (m, 2H), 1.15-1.09 (m, 6H), 1.07-1.05 (m, 3H), 1.03-1.01 (m, 2H), 0.98-0.95 (m, 1H), 0.87-0.81 (m, 3H), 0.72-0.66 (m, 1H). | 641.9 |
| I-162A | 1A | $^1$H NMR (400 MHz, DMSO-d$_6$) δ 8.28-8.11 (m, 1H), 7.86-7.65 (m, 1H), 4.68 (s, 2H), 4.28-3.40 (m, 14H), 3.26-3.19 (m, 1H), 3.13-3.06 (m, 1H), 2.59 (s, 3H), 2.38 (s, 3H), 1.70-1.57 (m, 5H), 1.49-1.27 (m, 2H), 1.23-0.98 (m, 12H), 0.89-0.76 (m, 3H), 0.70-0.61 (m, 1H). | 632.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-162B | 1B | $^1$H NMR (400 MHz, DMSO-d$_6$) δ 8.34-8.19 (m, 1H), 7.90-7.77 (m, 1H), 4.67 (s, 2H), 4.31 (m, 2H), 4.15-3.89 (m, 2H), 3.78-3.39 (m, 10H), 3.24 (m, 1H), 3.08 (m, 1H), 2.59 (t, J = 4.8 Hz, 3H), 2.37 (d, J = 3.2 Hz, 3H), 1.47 (m, 8H), 1.10 (d, J = 9.6 Hz, 5H), 1.05 (s, 2H), 1.02-0.92 (m, 3H), 0.76 (m, 5H). | 632.5 |
| I-163A | 1A | $^1$H NMR (400 MHz, DMSO-d$_6$) δ 9.38-9.31 (m, 1H), 8.27-8.12 (m, 1H), 7.85-7.64 (m, 1H), 4.29-4.08 (m, 2H), 4.00-3.36 (m, 9H), 3.26-3.19 (m, 1H), 3.13-3.05 (m, 1H), 2.62-2.53 (m, 3H), 1.70-1.57 (m, 5H), 1.48-1.25 (m, 2H), 1.21-0.98 (m, 12H), 0.89-0.77 (m, 3H), 0.71-0.62 (m, 1H). | 642.9 |
| I-163B | 1B | $^1$H NMR (400 MHz, DMSO-d$_6$) δ 9.34 (d, J = 3.0 Hz, 1H), 8.37-8.17 (m, 1H), 7.90-7.74 (m, 1H), 4.37-3.82 (m, 4H), 3.82-3.69 (m, 2H), 3.66-3.42 (m, 4H), 3.30-3.19 (m, 2H), 3.15-3.01 (m, 1H), 2.61-2.55 (m, 3H), 1.70-1.51 (m, 5H), 1.49-1.26 (m, 2H), 1.24-1.08 (m, 5H), 1.07-1.01 (m, 5H), 0.99 (s, 1H), 0.95 (d, J = 6.2 Hz, 1H), 0.89-0.72 (m, 3H), 0.67 (dq, J = 8.6, 4.2 Hz, 1H). | 642.4 |
| I-164A | 1A | $^1$H NMR (400 MHz, DMSO-d$_6$) δ 8.46 (d, J = 8.4 Hz, 1H), 8.40-8.32 (m, 1H), 7.82 (dd, J = 15.4, 3.2 Hz, 1H), 7.33 (dd, J = 8.8, 5.2 Hz, 2H), 7.23-7.13 (m, 2H), 5.34 (s, 2H), 4.95-4.86 (m, 1H), 4.25-3.81 (m, 5H), 3.80-3.44 (m, 9H), 3.42-3.33 (m, 1H), 3.27-3.20 (m, 1H), 2.04-1.53 (m, 11H), 1.39-1.27 (m, 1H), 1.20-1.03 (m, 11H), 0.85 (s, 1H), 0.68 (dd, J = 8.0, 3.6 Hz, 1H). | 791.5 |
| I-164B | 1B | $^1$H NMR (400 MHz, DMSO-d$_6$) δ 8.61-8.48 (m, 1H), 8.40-8.31 (m, 1H), 7.85-7.78 (m, 1H), 7.32 (dd, J = 8.6, 5.2 Hz, 2H), 7.17 (t, J = 8.6 Hz, 2H), 5.34 (s, 2H), 4.89-4.82 (m, 1H), 4.30-3.40 (m, 15H), 3.24-3.17 (m, 1H), 2.08-1.83 (m, 7H), 1.79-1.65 (m, 4H), 1.61-1.51 (m, 1H), 1.38-1.26 (m, 1H), 1.12-1.03 (m, 10H), 0.88-0.82 (m, 1H), 0.70-0.64 (m, 1H). | 791.5 |
| I-165 | 2B | $^1$H NMR (400 MHz, DMSO-d$_6$) δ 8.41-8.23 (m, 2H), 8.03-7.89 (m, 1H), 7.86-7.74 (m, 1H), 7.37-7.21 (m, 5H), 5.35 (s, 2H), 4.51-4.41 (m, 1H), 4.16-3.91 (m, 3H), 3.81-3.52 (m, 5H), 3.44-3.37 (m, 1H), 3.30-3.29 (m, 1H), 3.21-3.08 (m, 2H), 2.60-2.55 (m, 3H), 1.66-1.48 (m, 5H), 1.38-1.30 (m, 2H), 1.24-1.22 (m, 1H), 1.12-0.99 (m, 11H), 0.88-0.78 (m, 3H), 0.71-0.64 (m, 1H). | 647.1 |
| I-166A | 2A | $^1$H NMR (400 MHz, DMSO-d$_6$) δ 8.36 (d, J = 15.0 Hz, 1H), 8.25-8.13 (m, 1H), 7.86-7.70 (m, 2H), 7.39-7.24 (m, 5H), 5.35 (s, 2H), 4.30-3.51 (m, 11H), 3.23-3.16 (m, 1H), 3.11-3.04 (m, 1H), 2.62-2.55 (m, 3H), 1.70-1.33 (m, 12H), 1.11-1.00 (m, 11H), 0.88-0.82 (m, 1H), 0.70-0.63 (m, 1H) | 661.6 |
| I-166B | 2B | $^1$H NMR (400 MHz, DMSO-d$_6$) δ 8.40-8.30 (m, 1H), 8.28-8.19 (m, 1H), 7.89-7.75 (m, 2H), 7.38-7.22 (m, 5H), 5.35 (s, 2H), 4.40-3.44 (m, 11H), 3.26-3.16 (m, 1H), 3.10-3.02 (m, 1H), 2.62-2.55 (m, 3H), 1.65-1.31 (m, 12H), 1.12-0.94 (m, 11H), 0.89-0.83 (m, 1H), 0.72-0.64 (m, 1H). | 661.5 |
| I-167 | 1B | $^1$H NMR (400 MHz, Methanol-d$_4$) δ 8.26-8.17 (m, 1H), 7.95-7.87 (m, 1H), 7.33 (tt, J = 5.8, 3.2 Hz, 2H), 7.11-7.05 (m, 2H), 5.36 (d, J = 2.6 Hz, 2H), 4.56 (dd, J = 10.2, 6.6 Hz, 1H), 4.40-4.35 (m, 1H), 4.26-4.08 (m, 3H), 4.00-3.80 (m, 5H), 3.45-3.37 (m, 2H), 3.25-3.17 (m, 1H), 2.75 (d, J = 2.8 Hz, 3H), 2.00 (s, 2H), 1.83-1.73 (m, 3H), 1.69-1.57 (m, 2H), 1.51-1.37 (m, 1H), 1.24-1.10 (m, 10H), 1.05 (t, J = 5.6 Hz, 2H), 0.82-0.74 (m, 1H). | 701.5 |
| I-168 | 26b | $^1$H NMR (400 MHz, DMSO-d$_6$) δ 10.55-10.54 (m, 1H), 8.62-8.59 (m, 1H), 8.47-8.36 (m, 1H), 8.23-8.22 (m, 1H), 7.90-7.82 (m, 2H), 7.36-7.18 (m, 10H), 5.36-5.35 (m, 2H), 4.36-3.73 (m, 7H), 3.52-3.50 (m, 4H), 1.76-1.58 (m, 2H), 1.35-1.27 (m, 2H), 1.11-1.08 (m, 2H), 0.86-0.75 (m, 2H), 0.64-0.63 (m, 1H). | 603.0 |
| I-169 | 1A | $^1$H NMR (400 MHz, DMSO-d$_6$) δ 8.27-8.18 (m, 1H), 8.07-8.02 (m, 2H), 7.82-7.71 (m, 1H), 4.44-4.35 (m, 1H), 4.28-4.08 (m, 4H), 3.97-3.89 (m, 1H), 3.88-3.69 | 574.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | (m, 4H), 3.58-3.45 (m, 1H), 3.26-3.20 (m, 1H), 3.13-3.06 (m, 1H), 2.62-2.56 (m, 3H), 1.71-1.57 (m, 5H), 1.49-1.21 (m, 3H), 1.17-1.11 (m, 3H), 1.10-1.06 (m, 3H), 1.05-1.01 (m, 5H), 0.89-0.79 (m, 3H), 0.69-0.64 (m, 1H). | |
| I-170 | 1A | $^1$H NMR (400 MHz, DMSO-d$_6$) δ 8.36 (d, J = 13.4 Hz, 1H), 8.28-8.18 (m, 1H), 7.86-7.72 (m, 2H), 7.36-7.30 (m, 2H), 7.18 (t, J = 8.8 Hz, 2H), 5.34 (s, 2H), 4.35-4.02 (m, 4H), 3.99-3.61 (m, 7H), 3.51-3.39 (m, 1H), 3.18 (dd, J = 9.4, 6.2 Hz, 1H), 2.60-2.55 (m, 3H), 2.02-1.93 (m, 2H), 1.86-1.65 (m, 5H), 1.59 (s, 1H), 1.37-1.27 (m, 1H), 1.12-1.02 (m, 10H), 0.88-0.82 (m, 1H), 0.70-0.64 (m, 1H). | 701.5 |
| I-171A | 2A | $^1$H NMR (400 MHz, DMSO-d$_6$) δ 8.50 (m, 1H), 8.44-8.18 (m, 2H), 7.89-7.76 (m, 1H), 7.38-7.03 (m, 10H), 5.36 (d, J = 6.8 Hz, 2H), 4.73-4.64 (m, 1H), 4.20-4.01 (m, 3H), 3.95-3.80 (m, 3H), 3.79-3.69 (m, 3H), 3.66-3.38 (m, 2H), 2.61 (dd, J = 7.2, 4.4 Hz, 3H), 1.38 (d, J = 9.4 Hz, 3H), 1.34 (dd, J = 8.0, 3.2 Hz, 1H), 1.25 (d, J = 11.8 Hz, 3H), 1.11 (t, J = 5.8 Hz, 3H), 1.04 (d, J = 5.2 Hz, 3H), 0.86 (s, 1H), 0.68 (m, 1H). | 671.4 |
| I-171B | 2B | $^1$H NMR (400 MHz, DMSO-d$_6$) δ 8.60-8.45 (m, 1H), 8.38 (d, J = 6.6 Hz, 1H), 8.30 (dd, J = 12.0. 4.8 Hz, 1H), 7.89-7.80 (m, 1H), 7.44-7.13 (m, 10H), 5.36 (d, J = 5.2 Hz, 2H), 4.81-4.66 (m, 1H), 4.44 (dd, J = 23.4, 8.6 Hz, 1H), 4.15-4.00 (m, 2H), 3.97-3.82 (m, 3H), 3.80-3.67 (m, 3H), 3.65-3.48 (m, 2H), 2.61 (dd, J = 8.8, 4.2 Hz, 3H), 1.38 (d, J = 8.4 Hz, 3H), 1.27 (d, J = 3.0 Hz, 3H), 1.08-1.04 (m, 2H), 0.98-0.88 (m, 4H), 0.82 (d, J = 6.4 Hz, 1H), 0.67 (d, J = 14.6 Hz, 1H), 0.37-0.26 (m, 1H). | 671.5 |
| I-172 | 15 | $^1$H NMR(400 MHz, CD$_3$OD), δ 9.15 (s, 1H), 8.37 (d, J = 14.4 Hz, 1H), 4.89-4.95 (m, 1H), 3.62-4.50 (m, 12H), 3.33-3.47 (m, 2H), 3.16-3.24 (m, 1H), 2.50-2.63 (m, 1H), 2.01-2.14 (m, 1H), 1.62-1.76 (m, 6H), 1.38-1.61 (m, 4H), 1.04-1.22 (m, 12H), 0.88-0.95 (m, 8H), 0.72-0.82 (m, 2H). | 656.4 |
| I-173 - Mix | 15 | $^1$H NMR(400 MHz, CD$_3$OD): δ 8.01-8.21 (m, 1H), 7.91-8.00 (m, 1H), 4.91-4.97 (m, 1H), 4.43-4.52 (m, 2H), 3.83-4.21 (m, 9H), 3.64-3.73 (m, 1H), 3.34-3.38 (m, 2H), 3.12-3.20 (m, 1H), 2.52-2.67 (m, 1H), 2.06-2.14 (m, 1H), 1.81-1.87 (m, 1H), 1.66-1.69 (m, 5H), 1.41-1.52 (m, 3H), 1.03-1.24 (m, 11H), 0.89-0.95 (m, 8H), 0.81-0.85 (m, 1H), 0.76-0.78 (m, 1H). | 639.7 |
| I-173A | 15 | $^1$H NMR(400 MHz, CD$_3$OD): δ 8.01-8.21 (m, 1H), 7.91-8.00 (m, 1H), 4.91-4.97 (m, 1H), 4.43-4.52 (m, 2H), 3.83-4.21 (m, 9H), 3.64-3.73 (m, 1H), 3.34-3.38 (m, 2H), 3.12-3.20 (m, 1H), 2.52-2.67 (m, 1H), 2.06-2.14 (m, 1H), 1.81-1.87 (m, 1H), 1.66-1.69 (m, 5H), 1.41-1.52 (m, 3H), 1.03-1.24 (m, 11H), 0.89-0.95 (m, 8H), 0.81-0.85 (m, 1H), 0.76-0.78 (m, 1H). | 639.7 |
| I-173B | 15 | $^1$H NMR(400 MHz, CD$_3$OD): δ 8.01-8.21 (m, 1H), 7.91-8.00 (m, 1H), 4.91-4.97 (m, 1H), 4.43-4.52 (m, 2H), 3.83-4.21 (m, 9H), 3.64-3.73 (m, 1H), 3.34-3.38 (m, 2H), 3.12-3.20 (m, 1H), 2.52-2.67 (m, 1H), 2.06-2.14 (m, 1H), 1.81-1.87 (m, 1H), 1.66-1.69 (m, 5H), 1.41-1.52 (m, 3H), 1.03-1.24 (m, 11H), 0.89-0.95 (m, 8H), 0.81-0.85 (m, 1H), 0.76-0.78 (m, 1H). | 639.7 |
| I-174A | 1A | $^1$H NMR (400 MHz, DMSO-d$_6$) δ 8.35 (d, J = 14.0 Hz, 1H), 8.21 (s, 1H), 7.82 (d, J = 17.2 Hz, 1H), 7.76 (s, 1H), 7.45-7.19 (m, 5H), 5.36 (s, 2H), 4.28 (dd, J = 8.8, 3.4 Hz, 2H), 3.95 (d, J = 39.6 Hz, 3H), 3.84-3.70 (m, 3H), 3.62 (s, 1H), 3.48 (s, 1H), 3.40 (d, J = 6.4 Hz, 1H), 3.22 (t, J = 8.4 Hz, 1H), 3.10 (t, J = 8.0 Hz, 1H), 2.58 (dd, J = 9.8, 4.4 Hz, 3H), 1.65 (s, 5H), 1.43 (s, 1H), 1.20-1.05 (m, 12H), 1.01 (s, 3H), 0.84 (t, J = 11.8 Hz, 2H). | 635.5 |
| I-174B | 1B | $^1$H NMR (400 MHz, DMSO-d$_6$) δ 8.35 (d, J = 18.4 Hz, 1H), 8.22 (s, 1H), 7.81 (d, J = 17.6 Hz, 2H), 7.38-7.22 (m, 5H), 5.35 (s, 2H), 4.32-3.53 (m, 10H), 3.30-3.29 (m, 1H), 3.26-3.19 (m, 1H), 3.08 (s, 1H), 2.61-2.55 (m, 3H), 1.68-1.56 (m, 5H), 1.45-1.35 (m, 1H), 1.16-1.05 (m, 12H), 1.03-0.95 (m, 3H), 0.89-0.76 (m, 2H). | 635.4 |

TABLE 2-continued

Characterization Data of Exemplary Compounds
Table 2 below contains the characterization data for the compounds of Table 1. Additionally, Table 2 discloses the method of Example 2 that best describes the process by which each compound of Table 1 was made. The appropriate reagents, starting materials, conditions, and modifications from the Exemplary synthesis method necessary for synthesizing the compounds of Table 1 would be apparent to a Person of ordinary skill in the art. LCMS values are shown [M + H]+ unless otherwise specified.

| Compound Number | Method | $^1$HNMR | LCMS |
|---|---|---|---|
| I-175A | 1A | $^1$H NMR (400 MHz, DMSO-$d_6$) δ 8.27-8.15 (m, 2H), 7.82-7.67 (m, 1H), 4.70 (s, 2H), 4.30-4.17 (m, 2H), 4.15-3.95 (m, 3H), 3.92-3.64 (m, 5H), 3.58-3.44 (m, 1H), 3.26-3.19 (m, 1H), 3.15-3.06 (m, 1H), 2.61-2.55 (m, 3H), 1.70-1.59 (m, 5H), 1.48-1.40 (m, 1H), 1.35-1.27 (m, 1H), 1.24 (s, 9H), 1.19-1.01 (m, 12H), 0.88-0.78 (m, 3H), 0.71-0.64 (m, 1H). | 660.0 |
| I-175B | 1B | $^1$H NMR (400 MHz, DMSO-$d_6$) δ 8.31-8.24 (m, 1H), 8.20-8.14 (m, 1H), 7.88-7.81 (m, 1H), 4.70 (s, 2H), 4.36-4.30 (m, 1H), 4.26-4.17 (m, 1H), 4.13-3.98 (m, 3H), 3.83-3.72 (m, 3H), 3.68-3.63 (m, 2H), 3.45-3.43 (m, 1H), 3.27-3.19 (m, 1H), 3.12-3.08 (m, 1H), 2.59 (t, J = 4.8 Hz, 3H), 1.62-1.59 (m, 5H), 1.40-1.32 (m, 2H), 1.24 (s, 9H), 1.12-1.05 (m, 9H), 1.02-0.95 (m, 3H), 0.87-0.78 (m, 3H), 0.71-0.68 (m, 1H). | 660.0 |
| I-176A | 7A | $^1$H NMR (400 MHz, DMSO-$d_6$) δ 8.38-8.23 (m, 2H), 7.85-7.81 (m, 1H), 7.40-7.19 (m, 12H), 5.35 (s, 2H), 4.56-4.53 (m, 1H), 4.48-4.45 (m, 1H), 4.38-4.35 (m, 1H), 4.26-4.15 (m, 1H), 4.09-3.96 (m, 3H), 3.94-3.81 (m, 2H), 3.77-3.59 (m, 3H), 3.55-3.35 (m, 1H), 1.34-1.25 (m, 1H), 1.11-1.01 (m, 9H), 0.84-0.82 (m, 1H), 0.66-0.61 (m, 1H). | 627.0 |
| I-176B | 2B | $^1$H NMR (400 MHz, DMSO-$d_6$) δ 8.47-8.38 (m, 1H), 8.32-8.29 (m, 1H), 7.84-7.80 (m, 1H), 7.42-7.14 (m, 12H), 5.35 (s, 2H), 4.57-4.33 (m, 4H), 4.14-4.12 (m, 1H), 4.02-3.96 (m, 3H), 3.76-3.61 (m, 4H), 3.45-3.43 (m, 1H), 1.36-1.33 (m, 1H), 1.15-1.06 (m, 9H), 0.87-0.86 (m, 1H), 0.68-0.66 (m, 1H). | 627.0 |
| I-177A | 1A | $^1$H NMR (400 MHz, DMSO-$d_6$) δ 8.28-8.17 (m, 1H), 8.17-8.09 (m, 1H), 7.82-7.68 (m, 1H), 4.28-4.19 (m, 2H), 4.15-3.62 (m, 9H), 3.58-3.43 (m, 1H), 3.25-3.20 (m, 1H), 3.14-3.06 (m, 1H), 2.88 (d, J = 7.2 Hz, 2H), 2.61-2.55 (m, 3H), 1.69-1.59 (m, 5H), 1.50-1.28 (m, 2H), 1.18-1.01 (m, 13H), 0.88-0.79 (m, 3H), 0.70-0.64 (m, 1H), 0.61-0.55 (m, 2H), 0.31 (q, J = 5.2 Hz, 2H). | 628.4 |
| I-177B | 1B | $^1$H NMR (400 MHz, DMSO-$d_6$) δ 8.31-8.24 (m, 1H), 8.16-8.10 (m, 1H), 7.88-7.81 (m, 1H), 4.36-4.32 (m, 1H), 4.27-4.17 (m, 1H), 4.14-3.98 (m, 3H), 3.80-3.63 (m, 5H), 3.50-3.43 (m, 1H), 3.27-3.19 (m, 1H), 3.12-3.06 (m, 1H), 2.88 (d, J = 7.2 Hz, 2H), 2.59 (t, J = 4.8 Hz, 3H), 1.63-1.59 (m, 5H), 1.36-1.33 (m, 2H), 1.12-1.05 (m, 10H), 1.03-0.95 (m, 3H), 0.87-0.78 (m, 3H), 0.71-0.68 (m, 1H), 0.60-0.55 (m, 2H), 0.31-0.30 (m, 1H). | 628.0 |
| I-178A | 1A | $^1$H NMR (400 MHz, DMSO-$d_6$) δ 8.21 (dd, J = 20.2, 8.6 Hz, 1H), 8.03 (d, J = 16.4 Hz, 1H), 7.84-7.62 (m, 1H), 4.30-4.06 (m, 3H), 4.05-3.88 (m, 2H), 3.87-3.53 (m, 5H), 3.52-3.38 (m, 1H), 3.23 (dd, J = 9.4, 6.6 Hz, 1H), 3.10 (dd, J = 9.4, 6.4 Hz, 1H), 2.58 (t, J = 6.4 Hz, 3H), 2.48-2.39 (m, 1H), 1.64 (d, J = 11.8 Hz, 5H), 1.43 (s, 1H), 1.35-1.23 (m, 1H), 1.21-1.13 (dt, J = 8.1, 3.5 Hz, 4H), 1.10 (d, J = 15.8 Hz, 4H), 1.07-0.94 (m, 8H), 0.83 (d, J = 14.0 Hz, 3H), 0.71-0.63 (m, 1H). | 614.5 |
| I-178B | 1B | $^1$H NMR (400 MHz, DMSO-$d_6$) δ 8.34-8.22 (m, 1H), 8.08-7.98 (m, 1H), 7.90-7.76 (m, 1H), 4.36-4.15 (m, 2H), 4.12-3.95 (m, 3H), 3.85-3.74 (m, 2H), 3.69-3.60 (m, 2H), 3.53-3.40 (m, 1H), 3.30-3.19 (m, 2H), 3.14-3.03 (m, 1H), 2.59 (t, J = 4.8 Hz, 3H), 2.46-2.39 (m, 1H), 1.67-1.55 (m, 5H), 1.46-1.32 (m, 2H), 1.20-1.14 (m, 3H), 1.13-1.03 (m, 8H), 1.03-0.95 (m, 5H), 0.90-0.77 (m, 3H), 0.73-0.64 (m, 1H). | 614.5 |
| I-179 | 2A | $^1$HNMR (400 MHz, CD$_3$OD) δ 8.29-8.15 (m, 1H), 7.97-7.88 (m, 1H), 7.39-7.22 (m, 5H), 5.39-5.35 (m, 2H), 4.49-3.37 (m, 13H), 3.28-2.57 (m, 6H), 1.93-1.53 (m, 9H), 1.51-1.31 (m, 5H), 1.19-1.01 (m, 8H), 0.74-0.80 (m, 1H). | 643.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-180 | 2A | $^1$H NMR (400 MHz, CD$_3$OD) δ 8.29-8.16 (m, 1H), 7.97-7.87 (m, 1H), 7.39-7.23 (m, 5H), 5.39-5.36 (m, 2H), 4.49-3.86 (m, 9H), 3.84-3.39 (m, 3H), 3.27-2.34 (m, 2H), 2.32-1.44 (m, 10H), 1.43-1.01 (m, 14H), 0.82-0.74 (m, 1H) | 629.5 |
| I-181 | 2A | $^1$H NMR (400 MHz, CD$_3$OD) δ 8.27-8.15 (m, 1H), 7.96-7.86 (m, 1H), 7.38-7.23 (m, 5H), 5.38-5.35 (m, 2H). 4.51-3.71 (m, 12H), 3.00-2.65 (m, 5H), 1.94-1.25 (m, 15H), 1.20-1.07 (m, 7H), 1.06-1.00 (m, 1H), 0.82-0.72 (m, 1H) | 643.5 |
| I-182 | 2A | $^1$H NMR (400 MHz, CD$_3$OD) δ 8.32-8.17 (m, 1H), 7.97-7.88 (m, 1H), 7.53-7.14 (m, 5H), 5.38 (s, 2H), 4.44-3.64 (m, 11H), 3.24-2.92 (m, 2H), 2.68-2.53 (m, 1H), 2.05-0.99 (m, 23H), 0.82-0.73 (m, 1H). | 629.5 |
| I-183 | 2A | $^1$H NMR (400 MHz, DMSO-d$_6$) δ 9.54-9.35 (m, 0.5H), 8.60-8.43 (m, 0.5 H), 8.42-8.33 (m, 1H), 7.87-7.79 (m, 1H), 7.41-7.23 (m, 5H), 5.36 (s, 2H), 4.30-4.06 (m, 3H), 4.04-3.60 (m, 6H), 3.48-3.38 (m, 1H), 3.24-2.60 (m, 5H) , 1.84-1.58 (m, 9H), 1.40-1.22 (m, 6H), 1.14-0.63 (m, 14H). | 615.6 |
| I-184 | 1A | $^1$H NMR (400 MHz, Methanol-d$_4$) δ 7.44 (s, 1H), 4.59 (s, 1H), 4.42-4.31 (m, 2H), 4.23-3.81 (m, 8H), 3.38-3.35 (m, 1H), 3.18-3.13 (m, 1H), 2.75 (s, 3H), 1.71 (m, 5H), 1.52 (s, 1H), 1.43-1.37 (m, 1H), 1.30-1.21 (m, 4H), 1.18-1.11 (m, 8H), 1.06-1.01 (m, 1H), 0.92 (d, J = 11.8 Hz, 2H), 0.78 (dd, J = 8.0, 4.2 Hz, 1H). | 590.3 |
| I-185A | 1A | $^1$H NMR (400 MHz, DMSO-d$_6$) δ 9.02 (s, 1H), 8.27-8.15 (m, 1H), 7.84-7.68 (m, 1H), 4.28-3.61 (m, 11H), 3.25-3.20 (m, 1H), 3.09 (t, J = 8.0 Hz, 1H), 2.62-2.54 (m, 3H), 2.24-2.17 (m, 1H), 1.71-1.57 (m, 5H), 1.47-1.39 (m, 1H), 1.37-1.26 (m, 1H), 1.17-0.92 (m, 15H), 0.88-0.80 (m, 3H), 0.70-0.63 (m, 1H). | 614.4 |
| I-185B | 1B | $^1$H NMR (400 MHz, DMSO-d$_6$) δ 9.01 (s, 1H), 8.34-8.17 (m, 1H), 7.90-7.76 (m, 1H), 4.38-3.47 (m, 11H), 3.27-3.19 (m, 1H), 3.14-3.01 (m, 1H), 2.61-2.56 (m, 3H), 2.23-2.14 (m, 1H), 1.74-1.24 (m, 8H), 1.16-0.85 (m, 18H), 0.71-0.63 (m, 1H). | 614.5 |
| I-186A | 1A | $^1$H NMR (400 MHz, DMSO-d$_6$) δ 9.25 (s, 1H), 8.36 (d, J = 20.2 Hz, 1H), 8.24 (s, 1H), 7.76 (s, 1H), 4.64-4.16 (m, 3H), 4.13-3.93 (m, 2H), 3.90-3.73 (m, 3H), 3.67 (d, J = 5.8 Hz, 1H), 3.55-3.41 (m, 1H), 3.29 (s, 1H), 3.22 (t, J = 8.0 Hz, 1H), 3.10 (dd, J = 9.6, 6.2 Hz, 1H), 2.58 (dd, J = 12.4, 4.4 Hz, 3H), 1.64 (d, J = 10.8 Hz, 5H), 1.43 (s, 1H), 1.28-1.12 (m, 3H), 1.08 (s, 9H), 1.01 (s, 3H), 0.84 (t, J = 12.0 Hz, 2H). | 562.4 |
| I-186B | 1B | $^1$H NMR (400 MHz, DMSO-d$_6$) δ 9.25 (s, 1H), 8.40-8.20 (m, 2H), 7.82 (d, J = 41.8 Hz, 1H), 4.38-3.36 (m, 11H), 3.28-3.19 (m, 1H), 3.13-3.03 (m, 1H), 2.58 (d, J = 4.4 Hz, 3H), 1.60 (d, J = 13.6 Hz, 5H), 1.48-1.33 (m, 1H), 1.19-1.06 (m, 12H), 0.99 (dd, J = 21.0, 6.2 Hz, 3H), 0.90-0.73 (m, 2H). | 562.6 |
| I-187A | 2A | $^1$H NMR (400 MHz, DMSO-d$_6$) δ 8.68-8.66 (m, 1H), 8.39-8.35 (m, 1H), 7.84-7.81 (m, 1H), 7.37-7.25 (m, 5H), 5.35 (s, 2H), 5.11 (s, 1H), 4.41-4.34 (m, 1H), 4.29-4.14 (m, 1H), 4.11-4.01 (m, 2H), 3.93-3.88 (m, 1H). 3.79-3.71 (m, 3H), 3.65-3.54 (m, 5H), 3.44-3.43 (m, 1H), 3.29-3.26 (m, 1H), 1.36-1.32 (m, 1H), 1.12-1.05 (m, 6H), 0.86-0.84 (m, 1H), 0.70-0.66 (m, 1H). | 538.0 |
| I-187B | 2B | $^1$H NMR (400 MHz, DMSO-d$_6$) δ 8.64-8.62 (m, 1H), 8.38-8.35 (m, 1H), 7.84-7.81 (m, 1H), 7.37-7.25 (m, 5H), 5.35 (s, 2H), 5.14-5.07 (m, 1H), 4.39-4.35 (m, 1H), 4.31-4.14 (m, 1H), 4.11-3.82 (m, 4H), 3.78-3.69 (m, 3H), 3.63-3.62 (m, 3H), 3.58-3.57 (m, 1H), 3.38-3.35 (m, 1H), 3.30-3.28 (m, 1H), 1.37-1.34 (m, 1H), 1.11-1.05 (m, 6H), 0.87-0.85 (m, 1H), 0.70-0.67 (m, 1H). | 538.0 |
| I-188A | 1A + 8A | $^1$H NMR (400 MHz, DMSO-d$_6$) δ 13.24 (s, 1H), 8.53-7.84 (m, 3H), 4.91 (s, 1H), 4.37-4.17 (m, 2H), 4.05-3.87 (m, 3H), 3.73-3.45 (m, 9H), 3.26-3.22 (m, 2H), 2.03-1.59 (m, 13H), 1.15-1.12 (m, 4H), 1.05 (d, J = 6.0 Hz, 3H). | 722.9 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-188B | 1B + 8B | $^1$H NMR (400 MHz, DMSO-d$_6$) δ 8.54 (d, J = 8.6 Hz, 1H), 7.99 (d, J = 14.6 Hz, 2H), 4.85 (s, 1H), 4.21 (m, 2H), 3.98 (m, 3H), 3.73-3.60 (m, 7H), 3.37-3.31 (m, 2H), 3.23-3.17 (m, 1H), 1.95 (s, 6H), 1.73 (m, 4H), 1.27-1.03 (m, 10H). | 723.4 |
| I-189A | 1A | $^1$H NMR (400 MHz, DMSO-d$_6$) δ 8.29-8.11 (m, 2H), 7.81-7.67 (m, 1H), 4.48-4.23 (m, 1H), 4.22-3.85 (m, 5H), 3.84-3.44 (m, 5H), 3.25-3.20 (m, 1H), 3.13-3.07 (m, 1H), 2.62-2.55 (m, 3H), 1.73-1.54 (m, 5H), 1.45-1.25 (m, 2H), 1.20-0.98 (m, 12H), 0.90-0.76 (m, 3H), 0.71-0.63 (m, 1H). | 608.4 |
| I-189B | 1B | $^1$H NMR (400 MHz, DMSO-d$_6$) δ 8.35-8.24 (m, 1H), 8.20-8.11 (m, 1H), 7.89-7.78 (m, 1H), 4.38-4.29 (m, 1H), 4.26-4.00 (m, 4H), 3.83-3.61 (m, 5H), 3.54-3.43 (m, 1H), 3.27-3.19 (m, 1H), 3.12-3.05 (m, 1H), 2.61-2.58 (m, 3H), 1.67-1.58 (m, 5H), 1.41-1.31 (m, 2H), 1.15-1.05 (m, 9H), 1.03-0.97 (m, 3H), 0.89-0.79 (m, 3H), 0.73-0.66 (m, 1H). | 608.4 |
| I-190A | 1A | $^1$H NMR (400 MHz, DMSO-d$_6$) δ 8.49-8.33 (m, 2H), 7.83-7.79 (m, 1H), 7.34-7.30 (m, 2H), 7.20-7.15 (m, 2H), 5.34-5.33 (m, 2H), 4.92-4.84 (m, 1H), 4.37-3.85 (m, 6H), 3.74-3.46 (m, 8H), 3.37-3.33 (m, 1H), 3.26-3.23 (m, 1H), 1.99-1.59 (m, 12H), 1.16-1.12 (m, 5H), 1.05 (d, J = 6.4 Hz, 3H). | 828.9 [M-H]' |
| I-190B | 1B | $^1$H NMR (400 MHz, DMSO-d$_6$) δ 8.54 (d, J = 8.6 Hz, 1H), 8.34 (d, J = 12.8 Hz, 1H), 7.81 (d, J = 17.0 Hz, 1H), 7.32 (dd, J = 8.4, 5.6 Hz, 2H), 7.17 (t, J = 8.8 Hz, 2H), 5.33 (d, J = 5.0 Hz, 2H), 4.84 (s, 1H), 4.43-4.12 (m, 2H), 3.95 (dd, J = 24.2, 14.0 Hz, 3H), 3.79-3.59 (m, 7H), 3.52 (s, 1H), 3.44 (q, J = 7.0 Hz, 2H), 3.21 (dd, J = 92, 6.8 Hz, 1H), 1.95 (s, 5H), 1.70 (s, 3H), 1.55 (s, 1H), 1.25 (d, J = 7.6 Hz, 2H), 1.20-1.10 (m, 4H), 1.06 (t, J = 7.0, 4H). | 831.5 |
| I-191A | 2A | $^1$H NMR (400 MHz, DMSO-d$_6$) δ 8.77 (s, 1H), 8.40-8.33 (m, 1H), 7.86-7.80 (m, 1H), 7.38-7.23 (m, 5H), 5.37-5.34 (m, 2H), 4.39-4.31 (m, 1H), 4.24-4.15 (m, 1H), 4.11-3.57 (m, 8H), 3.30-3.29 (m, 1H), 3.25-3.09 (m, 1H), 1.38-1.30 (m, 1H), 1.12-1.08 (m, 3H), 1.06-1.01 (m, 3H), 0.88-0.81 (m, 1H), 0.71-0.65 (m, 1H). | 517.3 |
| I-191B | 2B | $^1$H NMR (400 MHz, DMSO-d$_6$) δ 8.79 (s, 1H), 8.39-8.31 (m, 1H), 7.86-7.80 (m, 1H), 7.38-7.23 (m, 5H), 5.37-5.33 (m, 2H), 4.42-4.34 (m, 2H), 4.17-3.90 (m, 4H), 3.84-3.59 (m, 5H), 1.38-1.32 (m, 1H), 1.13-1.02 (m, 6H), 0.88-0.83 (m, 1H), 0.72-0.64 (m, 1H). | 517.4 |
| I-192 - Mix | 15 | $^1$H NMR (400 MHz, CD$_3$OD): δ 9.16 (s, 1H), 8.37 (d, J = 12.8 Hz, 1H), 4.96-5.01 (m, 1H), 3.57-4.40 (m, 14H), 3.34-3.48 (m, 2H), 3.16-3.25 (m, 1H), 1.88-2.00 (m, 2H), 1.62-1.76 (m, 5H), 1.47-1.58 (m, 1H), 1.41-1.46 (m, 1H), 1.02-1.24 (m, 14H), 0.90-0.97 (m, 2H), 0.75-0.81 (m, 1H). | 664.4 |
| I-192A | 15 | $^1$H NMR (400 MHz, CD$_3$OD): δ 9.16 (s, 1H), 8.37 (d, J = 12.8 Hz, 1H), 4.96-5.01 (m, 1H), 3.57-4.40 (m, 14H), 3.34-3.48 (m, 2H), 3.16-3.25 (m, 1H), 1.88-2.00 (m, 2H), 1.62-1.76 (m, 5H), 1.47-1.58 (m, 1H), 1.41-1.46 (m, 1H), 1.02-1.24 (m, 14H), 0.90-0.97 (m, 2H), 0.75-0.81 (m, 1H). | 664.4 |
| I-192B | 15 | $^1$H NMR (400 MHz, CD$_3$OD): δ 9.16 (s, 1H), 8.37 (d, J = 12.8 Hz, 1H), 4.96-5.01 (m, 1H), 3.57-4.40 (m, 14H), 3.34-3.48 (m, 2H), 3.16-3.25 (m, 1H), 1.88-2.00 (m, 2H), 1.62-1.76 (m, 5H), 1.47-1.58 (m, 1H), 1.41-1.46 (m, 1H), 1.02-1.24 (m, 14H), 0.90-0.97 (m, 2H), 0.75-0.81 (m, 1H). | 664.4 |
| I-193 | 15 | $^1$H NMR(400 MHz, CD$_3$OD): δ 9.18 (s, 1H), 8.39 (d, J = 12.0 Hz, 1H), 4.96-5.05 (m, 2H), 4.60 (s, 1H), 3.74-4.43 (m, 10H), 3.41-3.49 (m, 3H), 3.16-3.24 (m, 2H), 2.90-2.97 (m, 1H), 2.60-2.72 (m, 1H), 1.55-1.85 (m, 9H), 1.41-1.47 (m, 2H), 1.07-1.26 (m, 12H), 0.85-0.99 (m, 3H), 0.77-0.81 (m, 1H). | 658.4 |
| I-194 - Mix | 15 | $^1$H NMR (400 MHz, CD$_3$OD) δ 8.19-8.24 (m, 1H), 7.90-7.93 (m, 1H), 7.28-7.37 (m, 5H), 5.38 (s, 2H), 4.91-4.94 (m, 1H), 3.70-4.41 (m, 10H), 3.48-3.62 (m, 4H), 3.33-3.41 (m, 2H), 3.12-3.22 (m, 1H), 1.45-1.76 (m, 13H), 1.01-1.19 (m, 11H), 0.86-0.97 (m, 3H), 0.76-0.79 (m, 1H). | 701.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-194A | 16A | $^1$H NMR(400 MHz, CD$_3$OD): δ 8.19-8.23 (m, 1H), 7.92 (d, J = 12.0 Hz, 1H), 7.26-7.36 (m, 5H), 5.38 (s, 2H), 4.91-4.94 (m, 1H), 3.71-4.41 (m, 10H), 3.50-3.60 (m, 4H), 3.33-3.46 (m, 2H), 3.17-3.22 (m, 1H), 1.38-1.76 (m, 13H), 1.10-1.24 (m, 11H), 1.03-1.05 (m, 1H), 0.87-0.97 (m, 2H), 0.76-0.81 (m, 1H). | 701.5 |
| I-194B | 16B | $^1$H NMR(400 MHz, CD$_3$OD): δ 8.19-8.23 (m, 1H), 7.92 (d, J = 12.4 Hz, 1H), 7.26-7.36 (m, 5H), 5.37 (s, 2H), 4.91-4.94 (m, 1H), 3.71-4.41 (m, 10H), 3.50-3.60 (m, 4H), 3.33-3.46 (m, 2H), 3.17-3.22 (m, 1H), 1.46-1.76 (m, 13H), 1.03-1.21 (m, 12H), 0.89-0.97 (m, 2H), 0.75-0.80 (m, 1H). | 701.4 |
| I-195 | 15 | $^1$H NMR (400 MHz, CD$_3$OD): δ 9.15 (s, 1H), 8.37 (d, J = 12.5 Hz, 1H), 4.92-4.97 (m, 1H), 3.86-4.41 (m, 9H), 3.69-3.76 (m, 2H), 3.40-3.48 (m, 1H), 3.23 (dd, J = 14.9, 7.4 Hz, 3H), 2.93-3.08 (m, 1H), 2.60 (dd, J = 24.9, 12.1 Hz, 1H), 1.66-1.80 (m, 6H), 1.31-1.52 (m, 12H), 1.10-1.27 (m, 11H), 1.04 (s, 1H), 0.92 (dd, J = 24.0, 11.6 Hz, 2H), 0.76-0.79 (m, 1H). | 672.4 |
| I-196 - Mix | 15 | $^1$H NMR (400 MHz, CD$_3$OD): δ 9.15 (s, 1H), 8.37 (d, J = 12.8 Hz, 1H), 4.91-4.96 (m, 2H), 4.23-4.40 (m, 4H), 3.99-4.17 (m, 4H), 3.84-3.97 (m, 3H), 3.70-3.78 (m, 1H), 3.35-3.46 (m, 2H), 3.18-3.27 (m, 4H), 2.88-2.96 (m, 1H), 2.61-2.71 (m, 1H), 1.66-1.81 (m, 8H), 1.36-1.53 (m, 4H), 1.10-1.24 (m, 12H), 1.04-1.07 (m, 1H), 0.89-0.97 (m, 2H), 0.76-0.81 (m, 1H). | 672.4 |
| I-196A | 17A | $^1$H NMR(400 MHz, CD$_3$OD): δ 9.18 (s, 1H), 8.39 (d, J = 13.2 Hz, 1H), 4.95-4.99 (m, 1H), 3.84-4.43 (m, 11H), 3.71-3.76 (m, 1H), 3.38-3.49 (m, 3H), 3.20-3.28 (m, 5H), 2.91-2.96 (m, 1H), 2.64-2.72 (m, 1H), 1.68-1.83 (m, 8H), 1.41-1.53 (m, 3H), 1.13-1.21 (m, 12H), 1.05-1.08 (m, 1H), 0.91-0.99 (m, 2H), 0.79-0.84 (m, 1H). | 672.4 |
| I-196B | 17B | $^1$H NMR(400 MHz, CD$_3$OD): δ 9.16 (s, 1H), 8.35-8.40 (m, 1H), 4.94-5.00 (m, 1H), 3.69-4.58 (m, 13H), 3.39-3.42 (m, 3H), 3.11-3.28 (m, 5H), 2.92-2.99 (m, 1H), 2.54-2.76 (m, 1H), 1.69-1.83 (m, 9H), 1.40-1.54 (m, 3H), 1.11-1.19 (m, 11H), 1.03-1.05 (m, 1H), 0.88-0.94 (m, 2H), 0.77-0.79 (m, 1H). | 672.3 |
| I-197 | 15 | $^1$H NMR (400 MHz, CD$_3$OD): δ 9.16 (s, 1H), 8.37 (d, J = 12.4 Hz, 1H), 4.91-5.00 (m, 1H), 3.75-4.41 (m, 12H), 3.34-3.51 (m, 4H), 3.13-3.24 (m, 2H), 2.87-3.04 (m, 1H), 1.66-1.81 (m, 7H), 1.35-1.41 (m, 3H), 1.00-1.24 (m, 14H), 0.91-0.97 (m, 2H), 0.75-0.81 (m, 1H). | 658.4 |
| I-198 | 17A | $^1$H NMR (400 MHz, CD$_3$OD): δ 9.16 (s, 1H), 8.37 (d, J = 12.4 Hz, 1H), 4.89-4.95 (m, 1H), 4.22-4.40 (m, 3H), 3.87-4.18 (m, 6H), 3.55-3.75 (m, 10H), 3.33-3.38 (m, 1H), 3.19-3.24 (m, 1H), 1.66-1.76 (m, 5H), 1.49-1.55 (m, 1H), 1.11-1.22 (m, 12H), 0.90-0.90 (m, 3H), 0.76-0.82 (m, 1H). | 630.4 |
| I-199 | 25 | $^1$H NMR (400 MHz, DMSO-d$_6$) δ 8.79 (t, J = 8.8 Hz, 1H), 8.47-8.27 (m, 2H), 7.82 (dd, J = 25.8. 8.2 Hz, 1H), 7.39-7.07 (m, 10H), 5.38-5.30 (m, 2H), 5.20-5.11 (m, 1H), 4.71 (t, J = 12.8 Hz, 1H), 4.20 (dd, J = 42.4. 10.8 Hz, 2H), 4.11-4.00 (m, 2H), 3.88 (s, 1H), 3.78 (m, 3H), 3.56 (m, 1H), 3.46-3.33 (m, 1H), 2.62 (m, 3H), 1.48 (d, J = 11.8 Hz, 3H), 1.39 (s, 3H), 1.35 (t, J = 7.2 Hz, 1H), 1.11 (t, J = 6.0 Hz, 3H), 1.05 (t, J = 4.2 Hz, 3H), 0.90-0.83 (m, 1H), 0.72-0.65 (m, 1H). | 703.40 |
| I-200 | 7A | $^1$H NMR (400 MHz, DMSO-d$_6$) δ 8.36 (d, J = 15.0 Hz, 1H), 8.20-8.08 (m, 1H), 7.82 (d, J = 16.0 Hz, 1H), 7.39-7.11 (m, 7H), 5.35 (s, 2H), 4.33-4.12 (m, 2H), 4.10-3.77 (m, 6H), 3.73-3.46 (m, 3H), 3.26-3.21 (m, 1H), 3.18-3.12 (m, 1H), 1.73-1.59 (m, 5H), 1.51-1.39 (m, 1H), 1.37-1.26 (m, 1H), 1.22-1.08 (m, 6H), 1.07-1.01 (m, 6H), 0.90-0.80 (m, 3H), 0.70-0.63 (m, 1H). | 633.0 |
| I-201A | 2A | $^1$H NMR (400 MHz, DMSO-d$_6$) δ 8.40-8.32 (m, 1H), 8.28-8.17 (m, 1H), 7.86-7.78 (m, 1H), 7.39-7.22 (m, 5H), 5.35 (s, 2H), 5.23-5.09 (m, 1H), 4.26-4.12 (m, 3H), 4.10-3.83 (m, 4H), 3.80-3.57 (m, 3H), 3.29-3.18 (m, 1H), 2.07-1.90 (m, 2H), 1.83-1.72 (m, 2H), 1.39-1.31 (m, 1H), 1.12-1.01 (m, 6H), 0.88-0.81 (m, 1H), 0.71-0.62 (m, 1H). | 506.0 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-201B | 2B | $^1$H NMR (400 MHz, DMSO-$d_6$) δ 8.39-8.33 (m, 1H), 8.32-8.16 (m, 1H), 7.86-7.79 (m, 1H), 7.40-7.21 (m, 5H), 5.37-5.33 (m, 2H), 5.22-5.05 (m, 1H), 4.48-4.41 (m, 1H), 4.26-4.17 (m, 2H), 4.16-3.93 (m, 3H), 3.91-3.81 (m, 1H), 3.80-3.69 (m, 2H), 3.68-3.53 (m, 2H), 3.26-3.17 (m, 1H), 2.08-1.94 (m, 2H), 1.86-1.72 (m, 2H), 1.41-1.33 (m, 1H), 1.12-1.04 (m, 6H), 0.89-0.82 (m, 1H), 0.71-0.64 (m, 1H). | 506.0 |
| I-202 | 2A | $^1$H NMR (400 MHz, Methanol-$d_4$) δ 8.20 (d, J = 16.0 Hz, 1H), 7.91 (d, J = 10.2 Hz, 1H), 7.37-7.23 (m, 5H), 5.37 (s, 2H), 4.41-4.28 (m, 2H), 4.20-3.79 (m, 8H), 3.47-3.38 (m, 2H), 3.26-3.18 (m, 1H), 2.73 (d, J = 8.4 Hz, 3H), 2.02-1.95 (m, 2H), 1.85-1.74 (m, 3H), 1.70-1.58 (m, 2H), 1.43-1.33 (m, 1H), 1.29-1.21 (m, 2H), 1.18-1.13 (m, 6H), 1.09 (s, 2H), 1.06-1.00 (m, 1H), 0.80-0.74 (m, 1H). | 683.5 |
| I-203 | 1A | $^1$H NMR (400 MHz, DMSO-$d_6$) δ 8.36 (d, J = 13.8 Hz, 1H), 8.24-8.11 (m, 1H), 7.82 (d, J = 15.8 Hz, 1H), 7.38-7.25 (m, 3H), 7.18 (t, J = 8.8 Hz, 3H), 5.34 (s, 2H), 4.30 (s, 1H), 4.25-3.37 (m, 11H), 3.21 (t, J = 8.0 Hz, 1H), 2.03-1.91 (m, 2H), 1.83-1.58 (m, 5H), 1.38-1.26 (m, 1H), 1.17-1.02 (m, 11H), 0.88-0.82 (m, 1H), 0.70-0.63 (m, 1H). | 687.4 |
| I-204 | 2A | $^1$H NMR (400 MHz, DMSO-$d_6$) δ 8.47-8.33 (m, 2H), 7.94-7.78 (m, 2H), 7.40-7.21 (m, 5H), 5.35 (s, 2H), 4.34 (q, J = 4.8 Hz, 1H), 4.19 (m, 1H), 4.04 (m, 6H), 3.88 (dd, J = 16.8, 7.6 Hz, 1H), 3.77 (t, J = 9.0 Hz, 1H), 3.73-3.60 (m, 2H), 3.52-3.35 (m, 1H), 2.59 (dd, J = 8.8, 4.2 Hz, 3H), 1.37-1.27 (m, 1H), 1.08 (m, 9H), 0.85 (m, 1H), 0.67 (dd, J = 8.0, 3.6 Hz, 1H). | 633.4 |
| I-205A | 2A | $^1$H NMR(400 MHz, DMSO-$d_6$) δ 8.36 (d, J = 15.4 Hz, 1H), 8.26-8.16 (m, 1H), 7.87-7.73 (m, 2H), 7.40-7.21 (m, 5H), 5.36 (s, 2H), 4.33-4.26 (m, 1H), 4.23-4.04 (m, 2H), 4.01-3.59 (m, 8H), 3.54-3.36 (m, 2H), 2.62-2.55 (m, 3H), 1.37-1.24 (m, 1H), 1.12-1.02 (m, 9H), 0.93-0.81 (m, 5H), 0.70-0.63 (m, 1H). | 673.4 |
| I-205B | 2B | $^1$H NMR (400 MHz, DMSO-$d_6$) δ 8.40-8.20 (m, 2H), 7.91-7.76 (m, 2H), 7.41-7.19 (m, 5H), 5.35 (s, 2H), 4.37-4.12 (m, 2H), 4.09-3.90 (m, 3H), 3.84-3.57 (m, 6H), 3.52-3.35 (m, 2H), 2.59 (t, J = 5.2 Hz, 3H), 1.40-1.31 (m, 1H), 1.13-1.08 (m, 3H), 1.07-0.97 (m, 6H), 0.92-0.77 (m, 5H), 0.73-0.63 (m, 1H). | 673.0 |
| I-206 | 2A | $^1$H NMR (400 MHz, DMSO-$d_6$) δ 8.59 (dt, J = 18.4, 6.6 Hz, 1H), 8.41-8.33 (m, 1H), 7.83 (d, J = 14.2 Hz, 1H), 7.41-7.21 (m, 5H), 7.16 (t, J = 8.4, 7.0 Hz, 2H), 6.60 (t, J = 7.2 Hz, 1H), 6.56-6.50 (m, 2H), 5.35 (d, J = 3.6 Hz, 2H), 4.42 (s, 1H), 4.24-3.59 (m, 8H), 3.52-3.44 (m, 1H), 3.36 (d, J = 8.0 Hz, 1H), 3.29-3.16 (m, 1H), 3.16-3.01 (m, 2H), 2.22-2.11 (m, 1H), 1.91-1.80 (m, 1H), 1.41-1.28 (m, 1H), 1.14-1.03 (m, 6H), 0.89-0.83 (m, 1H), 0.73-0.65 (m, 1H). | 581.5 |
| I-207 | 2A | $^1$H NMR (400 MHz, DMSO-$d_6$) δ 8.65-8.50 (m, 1H), 8.43-8.32 (m, 1H), 7.83 (d, J = 11.8 Hz, 1H), 7.38-7.24 (m, 5H), 7.19-7.12 (m, 2H), 6.60 (t, J = 7.0 Hz, 1H), 6.51 (t, J = 8.2 Hz, 2H), 5.36 (s, 2H), 4.49-4.36 (m, 1H), 4.22-3.45 (m, 9H), 3.43-3.35 (m, 1H), 3.29-3.21 (m, 1H), 3.21-3.07 (m, 1H), 3.07-2.99 (m, 1H), 2.26-2.12 (m, 1H), 1.98-1.83 (m, 1H), 1.40-1.20 (m, 1H), 1.13-1.00 (m, 6H), 0.90-0.80 (m, 1H), 0.72-0.61 (m, 1H). | 581.5 |
| I-208A | 1A | $^1$H NMR (400 MHz, DMSO-$d_6$) δ 8.28-8.14 (m, 1H), 7.83-7.67 (m, 1H), 4.29-4.01 (m, 3H), 3.98-3.77 (m, 3H), 3.75-3.58 (m, 4H), 3.52-3.42 (m, 1H), 3.26-3.19 (m, 1H), 3.12-3.06 (m, 1H), 2.62-2.54 (m, 3H), 2.38-2.34 (m, 3H), 1.70-1.58 (m, 5H), 1.48-1.38 (m, 1H), 1.36-1.26 (m, 1H), 1.25-0.97 (m, 13H), 0.87-0.81 (m, 2H), 0.70-0.63 (m, 1H). | 622.4 |
| I-208B | 1B | $^1$H NMR (400 MHz, DMSO-$d_6$) δ 8.37-8.17 (m, 1H), 7.91-7.77 (m, 1H), 4.37-3.90 (m, 4H), 3.84-3.70 (m, 3H), 3.66-3.58 (m, 2H), 3.53-3.40 (m, 1H), 3.30-3.19 (m, 2H), 3.14-3.03 (m, 1H), 2.59 (t, J = 4.7 Hz, 3H), 2.39- | 622.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-209A | 2A | 2.31 (m, 3H), 1.69-1.56 (m, 5H), 1.46-1.32 (m, 2H), 1.21-1.08 (m, 6H), 1.07-1.04 (m, 2H), 1.04-0.93 (m, 4H), 0.89-0.76 (m, 3H), 0.72-0.64 (m, 1H). $^1$H NMR (400 MHz, DMSO-d$_6$) δ 8.71-8.55 (m, 1H), 8.37 (d, J = 10.2 Hz, 1H), 7.83 (d, J = 11.4 Hz, 1H), 7.44-7.20 (m, 5H), 5.35 (s, 2H), 5.10 (q, J = 6.0 Hz, 1H), 4.38 (s, 1H), 4.24-4.05 (m, 2H), 4.04-3.82 (m, 3H), 3.80-3.67 (m, 3H), 3.61 (d, J = 18.4 Hz, 5H), 3.30 (s, 1H), 1.34 (d, J = 7.6 Hz, 1H), 1.12-1.08 (m, 3H), 1.07-1.02 (m, 3H), 0.85 (s, 1H), 0.67 (s, 1H). | 538.4 |
| I-209B | 2B | $^1$H NMR (400 MHz, DMSO-d$_6$) δ 8.82-8.61 (m, 1H), 8.41-8.31 (m, 1H), 7.88-7.76 (m, 1H), 7.46-7.14 (m, 5H), 5.35 (s, 2H), 5.15 (s, 1H), 4.46-4.32 (m, 1H), 4.20-3.99 (m, 2H), 3.98-3.84 (m, 2H), 3.83-3.59 (m, 8H). 3.40 (s, 1H), 3.30 (s, 1H), 1.42-1.29 (m, 1H), 1.15-1.10 (m, 3H), 1.09-1.04 (m, 3H), 0.92-0.81 (m, 1H), 0.75-0.61 (m, 1H). | 538.4 |
| I-210 | 2A | $^1$H NMR(400 MHz, CD$_3$OD) δ 8.25-8.11 (m, 1H), 7.96-7.79 (m, 1H), 7.36-7.15 (m, 10H), 5.39-5.35 (m, 2H), 4.39-4.16 (m, 3H), 4.14-3.69 (m, 9H), 3.69-3.36 (m, 2H), 3.28-2.49 (m, 4H), 1.46-1.31 (m, 1H), 1.19-1.00 (m, 7H), 0.80-0.72 (m, 1H). | 596.4 |
| I-211 | 2A | $^1$H NMR (400 MHz, CD$_3$OD) δ 8.29-8.17 (m, 1H), 7.97-7.89 (m, 1H), 7.41-7.25 (m, 5H), 5.41-5.38 (m, 2H), 4.46-3.55 (m, 12H), 3.52-3.37 (m, 1H), 3.28-2.85 (m, 1H), 2.49-2.18 (m, 1H), 2.02-1.75 (m, 6H), 1.66-1.51 (m, 2H), 1.48-1.29 (m, 4H), 1.27-1.03 (m, 11H), 0.85-0.74 (m, 1H) | 629.5 |
| I-212 | 2A | $^1$H NMR (400 MHz, CD$_3$OD) δ 8.28-8.16 (m, 1H), 7.97-7.87 (m, 1H), 7.41-7.17 (m, 5H), 5.43-5.33 (m, 2H), 4.45-3.73 (m, 9H), 3.66-3.44 (m, 2H), 3.26-2.56 (m, 5H), 2.13-1.98 (m, 2H), 1.95-1.70 (m, 7H), 1.68-1.34 (m, 4H), 1.27-1.10 (m, 7H), 1.08-0.76 (m, 4H). | 615.5 |
| I-213A | 1A | $^1$H NMR (400 MHz, DMSO-d$_6$) δ 8.25-8.12 (m, 1H), 7.84-7.65 (m, 1H), 4.27-3.99 (m, 3H), 3.97-3.50 (m, 8H), 3.26-3.19 (m, 1H), 3.13-3.06 (m, 1H), 2.64-2.61 (m, 3H), 2.60-2.54 (m, 3H), 2.34 (s, 3H), 1.68-1.57 (m, 5H), 1.47-1.38 (m, 1H), 1.36-1.26 (m, 1H), 1.21-0.98 (m, 13H), 0.86-0.81 (m, 2H), 0.69-0.63 (m, 1H). | 602.4 |
| I-213B | 1B | $^1$H NMR (400 MHz, DMSO-d$_6$) δ 8.26 (s, 1H), 7.91-7.74 (m, 1H), 4.40-3.87 (m, 4H), 3.81-3.57 (m, 6H), 3.44 (s, 1H), 3.24 (s, 1H), 3.08 (s, 1H), 2.61 (s, 3H), 2.59 (t, J = 4.6 Hz, 3H), 2.33 (d, J = 3.6 Hz, 3H), 1.63 (s, 5H), 1.33 (s, 2H), 1.08 (d, J = 24.4 Hz, 12H), 0.85 (s, 3H), 0.68 (s, 1H). | 602.4 |
| I-214 | 2A | $^1$H NMR (400 MHz, CD$_3$OD) δ 8.26-8.15 (m, 1H), 7.95-7.87 (m, 1H), 7.40-7.19 (m, 10H), 5.40-5.34 (m, 2H), 4.62-4.55 (m, 2H), 4.39-4.20 (m, 2H), 4.16-3.71 (m, 10H), 3.51-3.35 (m, 2H), 2.05-1.54 (m, 5H), 1.46-1.27 (m, 3H), 1.21-1.00 (m, 6H), 0.82-0.74 (m, 1H) | 610.5 |
| I-215 | 2A | $^1$H NMR (400 MHz, CD$_3$OD) δ 8.27-8.16 (m, 1H), 7.98-7.85 (m, 1H), 7.48-7.17 (m, 5H), 5.43-5.30 (m, 2H), 4.41-3.67 (m, 11H), 3.22-2.57 (m, 4H), 2.10-1.52 (m, 9H), 1.49-0.99 (m, 14H), 0.84-0.74 (m, 1H). | 629.5 |
| I-216 | 27 | $^1$H NMR (400 MHz, CD$_3$OD): δ 7.68-7.78 (m, 1H), 6.75-6.78 (m, 1H), 5.51 (d, J = 12.2 Hz, 0.5H), 4.91-4.96 (m, 1H), 3.86-4.64 (m, 9H), 3.71-3.75 (m, 1H), 3.55-3.56 (m, 4H), 3.32-3.41 (m, 2H), 3.17-3.23 (m, 1H), 1.51-1.76 (m, 11H), 1.37-1.47 (m, 1H), 1.11-1.28 (m, 12H), 1.01-1.07 (m, 1H), 0.91-0.97 (m, 2H), 0.74-0.81 (m, 1H). | 611.3 |
| I-217 | 27 | $^1$H NMR (400 MHz, CD$_3$OD): δ 8.55-8.56 (m, 1H), 7.72-7.75 (m, 1H), 4.91-4.95 (m, 1H), 3.70-4.41 (m, 10H), 3.33-3.56 (m, 6H), 3.17-3.23 (m, 1H), 1.50-1.76 (m, 11H), 1.11-1.45 (m, 13H), 1.02-1.07 (m, 1H), 0.89-0.97 (m, 2H), 0.76-0.80 (m, 1H). | 628.4 |
| I-218 | 16A | $^1$H NMR (400 MHz, CDCl3): δ 8.45-8.71 (m, 2H), 7.84-7.93 (m, 2H), 7.30-7.33 (m, 5H), 5.30-5.35 (m, 2H), 4.79-4.98 (m, 1H), 3.79-4.48 (m, 9H), 3.49-3.64 (m, 2H), 2.81-3.25 (m, 10H), 1.93-2.26 (m, 2H), 1.54-1.75 (m, 5H), 1.44-1.47 (m, 1H), 1.02-1.32 (m, 15H), 0.76-0.88 (m, 1H). | 716.6 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-219 | 16A | $^1$H NMR (400 MHz, CD$_3$OD): δ 8.22 (d, J = 22.0 Hz, 1H), 7.92 (d, J = 14.0 Hz, 1H), 7.27-7.37 (m, 5H), 5.38 (s, 2H), 4.91-4.95 (m, 1H), 4.47-4.60 (m, 1H), 3.63-4.39 (m, 12H), 3.33-3.41 (m, 1H), 3.12-3.24 (m, 2H), 2.80-2.88 (m, 2H), 2.64-2.71 (m, 1H), 1.83-1.98 (m, 2H), 1.62-1.80 (m, 6H), 1.47-1.56 (m, 1H), 1.01-1.24 (m, 16H), 0.90-0.97 (m, 2H), 0.75-0.81 (m, 1H). | 731.0 |
| I-220 | 16A | $^1$H NMR(400 MHz, CD$_3$OD): δ 8.20-8.25 (m, 1H), 7.89-7.93 (m, 1H), 7.24-7.37 (m, 5H), 5.38 (s, 2H), 4.68-4.71 (m, 1H), 3.72-4.38 (m, 12H), 3.60-3.68 (m, 1H), 3.50-3.43 (m, 2H), 3.22-3.26 (m, 1H), 3.08-3.13 (m, 1H), 2.95-3.02 (m, 1H), 1.90-2.21 (m, 4H), 1.67-1.84 (m, 6H), 1.50-1.60 (m, 1H), 1.37-1.44 (m, 1H), 1.11-1.26 (m, 12H), 1.02-1.06 (m, 1H), 0.94-1.00 (m, 2H), 0.76-0.81 (m, 1H). | 717.1 |
| I-221 | 2A | $^1$H NMR (400 MHz, DMSO-d$_6$) δ 8.39-8.25 (m, 2H), 7.87-7.79 (m, 1H), 7.37-7.25 (m, 5H), 5.37-5.34 (m, 2H), 4.25-3.52 (m, 10H), 3.26-2.89 (m, 4H), 1.74 (s, 1H), 1.56-1.22 (m, 6H), 1.12-1.04 (m, 6H), 0.88-0.82 (m, 1H), 0.70-0.65 (m, 1H). | 534.4 |
| I-222 | 1A | $^1$H NMR (400 MHz, DMSO-d$_6$) δ 8.40-8.32 (m, 1H), 8.14-8.04 (m, 1H), 7.87-7.79 (m, 1H), 7.79-7.69 (m, 1H), 7.39-7.22 (m, 5H), 5.36 (s, 2H), 4.33-3.59 (m, 11H), 3.15-3.08 (m, 1H), 3.00-2.90 (m, 1H), 2.61-2.55 (m, 3H), 1.37-1.20 (m, 2H), 1.12-1.01 (m, 9H), 0.85-0.81 (m, 9H), 0.69-0.65 (m, 1H). | 662.45 |
| I-223 | 2A | $^1$H NMR (400 MHz, DMSO-d$_6$) δ 8.47-8.31 (m, 2H), 7.83 (d, J = 12.4 Hz, 1H), 7.59-7.52 (m, 1H), 7.39-7.21 (m, 5H), 5.35 (s, 2H), 4.23-3.56 (m, 9H), 3.21-3.00 (m, 3H), 2.46-2.33 (m, 1H), 2.12-1.98 (m, 1H), 1.82 (s, 1H), 1.60 (s, 1H), 1.39-1.29 (m, 1H), 1.13-1.01 (m, 6H), 0.89-0.82 (m, 1H), 0.72-0.64 (m, 1H). | 533.4 |
| I-224A | 1A | $^1$H NMR (400 MHz, Methanol-d$_4$) δ 9.00 (s, 1H), 4.40-4.26 (m, 2H), 4.16-3.76 (m, 6H), 3.68 (s, 1H), 3.49-3.39 (m, 1H), 3.39-3.32 (m, 2H), 3.20-3.11 (m, 1H), 2.74 (d, J = 19.6 Hz, 3H), 2.03 (d, J = 5.2 Hz, 2H), 1.90-1.65 (m, 11H), 1.51 (s, 1H), 1.38 (s, 1H), 1.30-1.02 (m, 14H), 0.97-0.87 (m, 2H), 0.78 (s, 1H). | 642.5 |
| I-224B | 1B | $^1$H NMR (400 MHz, DMSO-d$_6$) δ 9.08 (s, 1H), 8.35-8.16 (m, 1H), 7.84 (d, J = 26.8 Hz, 1H), 4.37-3.43 (m, 10H), 3.30-3.21 (m, 2H), 3.14-3.01 (m, 1H), 2.62-2.55 (m. 3H), 1.98-1.81 (m, 2H), 1.78-1.30 (m, 13H), 1.17-0.62 (m, 17H). | 642.4 |
| I-225 | 2A | $^1$H NMR (400 MHz, DMSO-d$_6$) δ 8.65-8.56 (m, 1H), 8.41-8.33 (m, 1H), 8.12 (t, J = 5.2 Hz, 1H), 7.87-7.79 (m, 1H), 7.37-7.22 (m, 10H), 5.36 (d, J = 3.8 Hz, 2H), 4.54-4.44 (m, 1H), 4.32-4.19 (m, 1H), 4.10-4.00 (m, 2H), 3.94-3.83 (m, 1H), 3.80-3.57 (m, 6H), 3.27 (d, J = 12.0 Hz, 1H), 3.25-3.15 (m, 1H), 2.79-2.70 (m, 1H), 2.62-2.57 (m, 3H), 1.33-1.24 (m, 1H), 1.12-1.00 (m, 5H), 0.97 (s, 1H), 0.87-0.80 (m, 1H), 0.67-0.60 (m, 1H). | 643.4 |
| I-226 | 25, starting from I-225 | $^1$H NMR (400 MHz, Methanol-d$_4$) δ 8.26-8.15 (m, 1H), 7.92 (d, J = 13.4 Hz, 1H), 7.49-7.24 (m, 10H), 5.37 (d, J = 6.2 Hz, 2H), 5.04-4.93 (m, 1H), 4.62-4.51 (m, 1H), 4.49-4.44 (m, 2H), 4.26-3.73 (m, 8H), 3.70-3.60 (m, 1H), 3.26-3.17 (m, 1H), 2.72 (d, J = 15.8 Hz, 3H), 1.44-1.28 (m, 2H), 1.15-1.10 (m, 2H), 1.09-1.07 (m, 3H), 1.03-0.97 (m, 1H), 0.76-0.63 (m, 1H). | 675.40 |
| I-227A | 1A | $^1$H NMR (400 MHz, DMSO-d$_6$) δ 8.28-8.13 (m, 1H), 7.75 (s, 1H), 4.26-3.42 (m, 11H), 3.28-3.19 (m, 2H), 3.13-3.06 (m, 1H), 2.62-2.54 (m, 3H), 2.36 (s, 3H), 1.69-1.56 (m, 5H), 1.49-1.27 (m, 8H), 1.19-1.00 (m, 12H), 0.89-0.75 (m, 3H), 0.70-0.62 (m, 1H). | 630.5 |
| I-227B | 1B | $^1$H NMR (400 MHz, DMSO-d$_6$) δ 8.26 (s, 1H), 7.93-7.74 (m, 1H), 4.39-3.88 (m, 4H), 3.78-3.60 (m, 5H), 3.54-3.35 (m, 2H), 3.28-3.19 (m, 2H), 3.14-3.03 (m, 1H), 2.62-2.56 (m, 3H), 2.40-2.30 (m, 3H), 1.62 (s, 5H), 1.40-1.28 (m, 8H), 1.20-0.95 (m, 12H), 0.85 (s, 3H), 0.71-0.63 (m, 1H). | 630.0 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-228A | 1A + 8A | $^1$H NMR (400 MHz, DMSO-$d_6$) δ 8.50-8.40 (m, 1H), 8.09-7.92 (m, 2H), 4.96-4.86 (m, 1H), 4.22-3.83 (m, 6H), 3.78-3.47 (m, 9H), 3.40-3.32 (m, 1H), 3.27-3.20 (m, 1H), 2.02-1.70 (m, 10H), 1.66-1.56 (m, 1H), 1.39-1.24 (m, 1H), 1.19-1.04 (m, 11H), 0.89-0.82 (m, 1H), 0.71-0.65 (m, 1H). | 683.5 |
| I-228B | 1B + 8B | $^1$H NMR (400 MHz, DMSO-$d_6$) δ 13.23 (s, 1H), 8.55 (dt, J = 25.4, 9.6 Hz, 1H), 8.17 (d, J = 18.2 Hz, 1H), 7.83 (d, J = 14.2 Hz, 1H), 4.87 (t, J = 7.2 Hz, 1H), 4.30-4.11 (m, 1H), 4.10-3.90 (m, 3H), 3.84-3.56 (m, 9H), 3.47-3.33 (m, 2H), 3.20 (q, J = 9.4, 8.8 Hz, 1H), 2.06-1.86 (m, 6H), 1.81-1.65 (m, 4H), 1.54 (dd, J = 13.8, 3.4 Hz, 1H), 1.39-1.26 (m, 1H), 1.15-1.01 (m, 11H), 0.89-0.82 (m, 1H), 0.67 (dd, J = 8.0, 4.0 Hz, 1H) | 683.0 |
| I-229A | 1A | $^1$H NMR (400 MHz, DMSO-$d_6$) δ 8.27-8.17 (m, 1H), 8.16-8.10 (m, 1H), 7.82-7.68 (m, 1H), 4.29-4.04 (m, 4H), 4.00-3.63 (m, 6H), 3.58-3.43 (m, 1H), 3.26-3.19 (m, 1H), 3.13-3.07 (m, 1H), 2.61-2.55 (m, 3H), 1.71-1.60 (m, 5H), 1.48-1.36 (m, 11H), 1.16-1.00 (m, 12H), 0.89-0.77 (m, 3H), 0.70-0.64 (m, 1H). | 630.5 |
| I-229B | 1B | $^1$H NMR (400 MHz, DMSO-$d_6$) δ 8.33-8.23 (m, 1H), 8.16-8.08 (m, 1H), 7.90-7.76 (m, 1H), 4.36-3.44 (m, 11H), 3.27-3.18 (m, 1H), 3.12-3.03 (m, 1H), 2.59 (t, J = 4.8 Hz, 3H), 1.68-1.56 (m, 5H), 1.41-1.32 (m, 11H), 1.15-0.94 (m, 12H), 0.89-0.77 (m, 3H), 0.73-0.64 (m, 1H). | 630.4 |
| I-230 | 2A | $^1$H NMR (400 MHz, DMSO-$d_6$) δ 9.13-9.04 (m, 1H), 8.40-8.33 (m, 1H), 7.86-7.81 (m, 1H), 7.71-7.62 (m, 2H), 7.42-7.21 (m, 7H), 5.35 (s, 2H), 4.76-4.50 (m, 2H), 4.38-4.23 (m, 1H), 4.20-3.88 (m, 4H), 3.87-3.63 (m, 3H), 3.31-3.18 (m, 1H), 1.37-1.32 (m, 1H), 1.13-0.98 (m, 6H), 0.87-0.83 (m, 1H), 0.69-0.64 (m, 1H). | 567.4 |
| I-231A | 1A | $^1$H NMR (400 MHz, DMSO-$d_6$) δ 9.06-9.03 (m, 1H), 8.25-8.09 (m, 1H), 7.83-7.68 (m, 1H), 4.31-3.93 (m, 3H), 3.92-3.73 (m, 3H), 3.71-3.49 (m, 3H), 3.47-3.35 (m, 2H), 3.26-3.19 (m, 1H), 3.13-3.04 (m, 1H), 2.61-2.54 (m, 3H), 1.71-1.55 (m, 5H), 1.49-1.36 (m, 1H), 1.34-1.26 (m, 10H), 1.18-0.98 (m, 12H), 0.89-0.77 (m, 3H), 0.71-0.62 (m, 1H). | 630.4 |
| I-231B | 1B | $^1$H NMR (400 MHz, DMSO-$d_6$) δ 9.04 (d, J = 4.8 Hz, 1H), 8.32-8.17 (m, 1H), 7.90-7.79 (m, 1H), 4.34-4.16 (m, 2H), 4.11-4.01 (m, 1H), 3.91 (t, J = 9.4 Hz, 1H), 3.83-3.74 (m, 2H), 3.67 (m, 1H), 3.59 (m, 2H), 3.49-3.46 (m, 1H), 3.30-3.18 (m, 2H), 3.12-3.02 (m, 1H), 2.58 (td, J = 4.5, 2.2 Hz, 3H), 1.60 (d, J = 31.2 Hz, 6H), 1.30 (dd, J = 6.8, 3.6 Hz, 12H), 1.11 (d, J = 4.2 Hz, 3H), 1.06 (dd, J = 6.2, 2.8 Hz, 4H), 1.02 (dd, J = 6.4, 2.0 Hz, 2H), 0.99-0.96 (m, 2H), 0.84 (d, J = 10.7 Hz, 2H), 0.70-0.65 (m, 1H). | 630.4 |
| I-232A | 1A | $^1$H NMR (400 MHz, Methanol-$d_4$) δ 4.43-3.79 (m, 9H), 3.50-3.33 (m, 2H), 3.19-3.12 (m, 1H), 2.78-2.71 (m, 3H), 1.78-1.65 (m, 5H), 1.57-1.47 (m, 1H), 1.37-1.13 (m, 11H), 1.11 (s, 2H), 1.08-1.00 (m, 1H), 0.97-0.85 (m, 2H), 0.81-0.74 (m, 1H). | 642.3 |
| I-232B | 1B | $^1$H NMR (400 MHz, Methanol-$d_4$) δ 4.60-4.51 (m, 1H), 4.41-4.34 ($_m$, 1H), 4.29-3.69 (m, 9H), 3.50-3.34 (m, 3H), 3.20-3.12 (m, 1H), 2.75 (s, 3H), 1.78-1.65 (m, 5H), 1.56-1.43 (m, 2H), 1.33-1.05 (m, 15H), 0.98-0.87 (m, 2H), 0.81-0.75 (m, 1H). | 642.3 |
| I-233 | 2A | $^1$H NMR (400 MHz, DMSO-$d_6$) δ 8.69-8.55 (m, 1H), 8.46-8.37 (m, 1H), 7.87 (d, J = 12.6 Hz, 1H), 7.43-7.25 (m, 5H), 5.40 (s, 2H), 4.27-4.10 (m, 4H), 4.10-3.87 (m, 3H), 3.85-3.71 (m, 2H), 3.67-3.62 (m, 1H), 3.54 (q, J = 6.2 Hz, 1H), 3.17-3.01 (m, 1H), 2.22-2.08 (m, 4H), 1.42-1.35 (m, 1H), 1.17-1.09 (m, 6H), 1.09-1.06 (m, 6H), 0.91-0.86 (m, 1H), 0.74-0.68 (m, 1H). | 548.3 |
| I-234 | 2A | $^1$H NMR (400 MHz, DMSO-$d_6$) δ 8.51-8.42 (m, 1H), 8.37 (d, J = 6.6 Hz, 1H), 7.83 (d, J = 11.2 Hz, 1H), 7.39-7.24 (m, 5H), 5.36 (s, 2H), 4.22-3.97 (m, 3H), 3.94-3.84 (m, 2H), 3.81-3.66 (m, 4H), 3.62-3.49 (m, 2H), 3.12-2.94 (m, 1H), 2.60-2.52 (m, 2H), 1.82-1.68 (m, | 548.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
|  |  | 2H), 1.38-1.31 (m, 1H), 1.13-1.05 (m, 6H), 1.05-1.02 (m, 6H), 0.87-0.84 (m, 1H), 0.71-0.63 (m, 1H). |  |
| I-235 | 2A | $^1$H NMR (400 MHz, CD$_3$OD) δ 8.28-8.15 (m, 1H), 7.96-7.86 (m, 1H), 7.38-7.28 (m, 5H), 5.40-5.33 (m, 2H), 4.36-3.37 (m, 13H), 3.29-3.20 (m, 1H), 2.19-1.90 (m, 2H), 1.80-1.61 (m, 5H), 1.58-0.85 (m, 16H), 0.82-0.72 (m, 1H). | 602.5 |
| I-236 | 2A | $^1$H NMR (400 MHz, CD$_3$OD) δ 8.27-8.15 (m, 1H), 7.96-7.86 (m, 1H), 7.39-7.22 (m, 5H), 5.38-5.36 (m, 2H), 4.39-4.21 (m, 2H), 4.17-3.72 (m, 8H), 3.66-3.47 (m, 2H), 3.25-3.17 (m, 1H), 2.10-0.76 (m, 27H). | 616.5 |
| I-237 | 2A | $^1$H NMR(400 MHz, CD$_3$OD) δ 8.31-8.14 (m, 1H), 7.97-7.86 (m, 1H), 7.38-7.23 (m, 5H), 5.38 (s, 2H), 4.37-4.22 (m, 2H), 4.18-3.48 (m, 11H), 2.57-2.16 (m, 6H), 1.91-1.62 (m, 5H), 1.60-1.37 (m, 2H), 1.33-1.23 (m, 3H), 1.18-0.77 (m, 10H) | 601.5 |
| I-238 | 16A | $^1$H NMR(400 MHz, DMSO-d$_6$): δ 8.10-8.14 (m, 1H), 7.80-7.84 (m, 1H), 7.19-7.27 (m, 5H), 5.28 (s, 2H), 4.53-4.60 (m, 1H), 3.99-4.27 (m, 5H), 3.69-3.91 (m, 7H), 3.54-3.59 (m, 1H), 3.25-3.30 (m, 2H), 3.12-3.15 (m, 1H), 2.81-2.92 (m, 2H), 1.73-2.00 (m, 5H), 1.56-1.63 (m, 5H), 1.29-1.43 (m, 2H), 1.01-1.11 (m, 10H), 0.95 (s, 1H), 0.82-0.85 (m, 2H), 0.67-0.69 (m, 1H). | 716.9 |
| I-239 | 16A | $^1$H NMR(400 MHz, CD$_3$OD): δ 8.09-8.14 (m, 1H), 7.80-7.84 (m, 1H), 7.17-7.27 (m, 5H), 5.28 (s, 2H), 3.57-4.46 (m, 16H), 3.23-3.27 (m, 1H), 3.12-3.21 (m, 1H), 2.98-3.03 (m, 2H), 2.73-2.82 (m, 1H), 1.57-1.70 (m, 5H), 1.39-1.52 (m, 2H), 1.13-1.16 (m, 2H), 1.01-1.09 (m, 10H), 0.93-0.95 (m, 1H), 0.80-0.90 (m, 3H), 0.65-0.70 (m, 1H). | 702.9 |
| I-240 | 16A | $^1$H NMR (400 MHz, DMSO-d$_6$): δ 8.12 (d, J = 17.6 Hz, 1H), 7.82 (d, J = 13.6 Hz, 1H), 7.19-7.27 (m, 5H), 5.28 (s, 2H), 4.42-4.44 (m, 1H), 4.28-4.35 (m, 2H), 3.63-4.25 (m, 16H), 3.25-3.33 (m, 2H), 3.10-3.15 (m, 1H), 1.56-1.65 (m, 5H), 1.27-1.45 (m, 3H), 1.13-1.19 (m, 6H), 1.00-1.02 (m, 3H), 0.80-0.94 (m, 5H), 0.68-0.69 (m, 1H). | 714.9 |
| I-241 | 16A | $^1$H NMR (400 MHz, CD$_3$OD): δ 4.93-4.99 (m, 1H), 3.85-4.59 (m, 9H), 3.73-3.77 (m, 1H), 3.52-3.64 (m, 4H), 3.35-3.46 (m, 2H), 3.20-3.25 (m, 1H), 2.49 (d, J = 6.6 Hz, 3H), 1.54-1.79 (m, 11H), 1.39-1.48 (m, 1H), 1.14-1.31 (m, 12H), 1.05-1.09 (m, 1H), 0.94-0.99 (m, 2H), 0.78-0.82 (m, 1H). | 626.4 |
| I-242 | 15 | $^1$H NMR (400 MHz, CD$_3$OD): δ 4.94-4.97 (m, 1H), 3.50-4.38 (m, 15H), 3.37-3.47 (m, 2H), 3.21-3.24 (m, 1H), 3.09-3.15 (m, 1H), 2.97 (s, 3H), 2.42-2.47 (m, 2H), 1.92-2.07 (m, 2H), 1.52-1.79 (m, 11H), 1.15-1.45 (m, 14H), 1.05-1.09 (m, 1H), 0.94-0.99 (m, 2H), 0.78-0.83 (m, 1H). | 656.4 |
| I-243 | 2A | $^1$H NMR (400 MHz, DMSO-d$_6$) δ 8.59 (m, 1H), 8.38 (d, J = 4.8 Hz, 1H), 7.83 (d, J = 10.2 Hz, 1H), 7.39-7.24 (m, 5H), 5.36 (s, 2H), 4.36 (m, 1H), 4.24-4.13 (m, 1H), 4.12-3.87 (m, 4H), 3.87-3.65 (m, 3H), 3.64 (m, 1H), 3.27-3.10 (m, 3H), 2.70-2.64 (m, 1H), 2.23 (m, 1H), 1.66 (p, J = 10.8 Hz, 1H), 1.37-1.29 (m, 1H), 1.11-1.02 (m, 6H), 0.84 (d, J = 4.6 Hz, 1H), 0.69-0.63 (m, 4H). | 559.40 |
| I-244 | 2A | $^1$H NMR (400 MHz, DMSO-d$_6$) δ 8.54-8.48 (m, 2H), 8.43-8.34 (m, 2H), 7.94-7.79 (m, 2H), 7.39-7.21 (m, 7H), 5.36 (s, 2H), 4.63-4.45 (m, 2H), 4.41-4.34 (m, 1H), 4.28-4.14 (m, 1H), 4.10-3.50 (m, 9H), 2.65-2.56 (m, 3H), 1.34-1.20 (m, 1H), 1.13-0.99 (m, 9H), 0.86-0.80 (m, 1H), 0.67-0.57 (m, 1H). | 642.3 |
| I-245 | 23 | $^1$H NMR (400 MHz, DMSO-d$_6$) δ 8.41-8.28 (m, 2H), 8.21 (s, 1H), 7.82 (d, J = 12.4 Hz, 1H), 7.45-7.18 (m, 5H), 5.35 (s, 2H), 4.16 (d, J = 8.8 Hz, 1H), 4.13-4.03 (m, 2H), 3.99 (d, J = 9.6 Hz, 2H), 3.87 (t, J = 11.8 Hz, 2H), 3.79-3.74 (m, 2H), 3.66-3.54 (m, 4H), 3.29-3.07 (m, 2H), 2.99 (s, 1H), 2.81 (s, 2H), 1.41-1.26 (m, 1H), 1.14-1.08 (m, 3H), 1.05 (d, J = 8.6 Hz, 3H), 0.85 (d, J = 5.2 Hz, 1H), 0.74-0.62 (m, 1H). | 535.3 |
| I-246 | 1A | $^1$H NMR (400 MHz, DMSO-d$_6$) δ 9.78 (s, 1H), 8.30-8.19 (m, 1H), 7.82-7.72 (m, 1H), 4.44-4.07 (m, 5H), 3.99-3.69 (m, 5H), 3.62-3.48 (m, 1H), 3.26-3.20 (m, 1H), | 575.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 3.15-3.07 (m, 1H), 2.62-2.55 (m, 3H), 1.73-1.57 (m, 5H), 1.50-1.39 (m, 1H), 1.37-1.25 (m, 1H), 1.21-1.07 (m, 7H), 1.06-1.01 (m, 5H), 0.91-0.78 (m, 3H), 0.72-0.64 (m, 1H). | |
| I-247 | 2A | $^1$H NMR (400 MHz, DMSO-d$_6$) δ 8.58 (t, J = 7.6 Hz, 2H), 8.43-8.33 (m, 2H), 7.93-7.80 (m, 3H), 7.56-7.50 (m, 1H), 7.39-7.22 (m, 5H), 5.36 (s, 2H), 4.67-4.59 (m, 1H), 4.54-4.47 (m, 1H), 4.41-4.34 (m, 1H), 4.15-3.56 (m, 10H), 2.62-2.56 (m, 3H), 1.25 (q, J = 6.4 Hz, 1H), 1.13-0.98 (m, 9H), 0.83 (t, J = 4.6 Hz, 1H), 0.69-0.59 (m, 1H). | 642.4 |
| I-248 | 2A | $^1$H NMR (400 MHz, DMSO-d$_6$) δ 8.41-8.33 (m, 1H), 8.29-8.19 (m, 1H), 7.86-7.79 (m, 1H), 7.39-7.22 (m, 5H), 5.35 (s, 2H), 4.23-4.00 (m, 3H), 3.99-3.83 (m, 3H), 3.80-3.69 (m, 3H), 3.65-3.57 (m, 1H), 3.19-3.14 (m, 3H), 3.13-2.99 (m, 1H), 2.21-2.11 (m, 1H), 1.85-1.74 (m, 1H), 1.72-1.61 (m, 2H), 1.50-1.38 (m, 2H), 1.36-1.21 (m, 1H), 1.13-1.01 (m, 6H), 0.88-0.80 (m, 1H), 0.71-0.61 (m, 1H). | 534.4 |
| I-249 | 2A | $^1$H NMR (400 MHz, DMSO-d$_6$) δ 8.36 (d, J = 14.8 Hz, 1H), 8.24-8.13 (m, 1H), 7.86-7.70 (m, 2H), 7.37-7.24 (m, 5H), 5.35 (s, 2H), 4.30-3.60 (m, 11H), 3.26-3.20 (m, 1H), 3.13-3.05 (m, 1H), 2.61-2.56 (m, 3H), 1.67-1.56 (m, 3H), 1.40-1.29 (m, 3H), 1.12-0.99 (m, 10H), 0.85 (d, J = 6.4 Hz, 7H), 0.70-0.63 (m, 1H), 0.50-0.37 (m, 3H). | 675.6 |
| I-250 | 2A | $^1$H NMR (400 MHz, DMSO-d$_6$) δ 8.62-8.53 (m, 1H), 8.39-8.34 (m, 1H), 7.87-7.78 (m, 1H), 7.38-7.22 (m, 5H), 5.35 (s, 2H), 4.20-3.58 (m, 8H), 3.37-3.29 (m, 2H), 3.23 (dd, J = 10.6, 3.6 Hz, 3H), 3.11-2.94 (m, 1H), 1.38-1.25 (m, 1H), 1.13-1.04 (m, 6H), 0.88-0.82 (m, 1H), 0.71-0.57 (m, 5H). | 520.4 |
| I-251 | 2A | $^1$H NMR (400 MHz, DMSO-d$_6$) δ 9.51 (s, 1H), 8.41-8.26 (m, 2H), 7.89-7.77 (m, 2H), 7.38-7.29 (m, 3H), 7.28-7.21 (m, 3H), 7.10-7.04 (m, 1H), 6.85-6.71 (m, 2H), 5.36 (s, 2H), 4.52-4.35 (m, 3H), 4.29-3.87 (m, 6H), 3.78-3.47 (m, 4H), 2.63-2.57 (m, 3H), 1.35-1.21 (m, 1H), 1.12-1.07 (m, 3H), 1.07-1.02 (m, 6H), 0.86-0.81 (m, 1H), 0.68-0.59 (m, 1H). | 657.4 |
| I-252 | 2A | $^1$H NMR (400 MHz, DMSO-d$_6$) δ 8.95 (d, J = 5.4 Hz, 1H), 8.36 (d, J = 9.0 Hz, 1H), 7.83 (d, J = 10.6 Hz, 1H), 7.52-7.38 (m, 2H), 7.38-7.22 (m, 5H), 5.35 (s, 2H), 4.68-4.43 (m, 2H), 4.27-4.13 (m, 1H), 4.08 (dd, J = 17.4, 8.6 Hz, 1H), 3.98 (d, J = 8.0 Hz, 1H), 3.96-3.76 (m, 3H), 3.75-3.68 (m, 1H), 3.66 (d, J = 5.8 Hz, 1H), 3.25-3.13 (m, 1H), 2.58 (d, J = 2.4 Hz, 3H), 1.38-1.24 (m, 1H), 1.12-0.96 (m, 6H), 0.84 (d, J = 5.6 Hz, 1H), 0.70-0.61 (m, 1H). | 542.4 |
| I-253 | 2A | $^1$H NMR (400 MHz, CD$_3$OD) δ 8.27-8.16 (m, 1H), 7.96-7.87 (m, 1H), 7.39-7.24 (m, 5H), 5.40-5.35 (m, 2H), 4.40-3.79 (m, 13H), 3.56-3.36 (m, 2H), 3.30-3.20 (m, 2H), 1.80-1.60 (m, 6H), 1.50-1.35 (m, 1H), 1.33-0.90 (m, 13H), 0.83-0.72 (m, 1H) | 615.4 |
| I-254 | 2A | $^1$H NMR (400 MHz, CD$_3$OD) δ 8.28-8.15 (m, 1H), 7.97-7.86 (m, 1H), 7.40-7.21 (m, 5H), 5.40-5.36 (m, 2H), 4.43-4.22 (m, 2H), 4.16-3.38 (m, 11H), 3.28-2.98 (m, 2H), 2.10-1.51 (m, 9H), 1.48-1.22 (m, 6H), 1.18-1.09 (m, 7H), 1.07-0.96 (m, 3H). | 616.5 |
| I-255 | 2A | $^1$H NMR (400 MHz, CD$_3$OD) δ 8.28-8.15 (m, 1H), 7.97-7.89 (m, 1H), 7.38-7.20 (m, 10H), 5.39-5.33 (m, 2H), 4.44-3.34 (m, 15H), 2.94-2.54 (m, 3H), 1.46-1.31 (m, 1H), 1.22-1.03 (m, 7H), 0.80-0.77 (m, 1H). | 596.4 |
| I-256 | 2A | $^1$H NMR (400 MHz, CD$_3$OD) δ 8.29-8.16 (m, 1H), 7.97-7.87 (m, 1H), 7.40-7.24 (m, 5H), 5.40-5.35 (m, 2H), 4.38-4.23 (m, 2H), 4.18-3.35 (m, 12H), 3.30-3.21 (m, 2H), 2.22-1.96 (m, 2H), 1.81-1.63 (m, 5H), 1.60-0.87 (m, 15H), 0.83-0.73 (m, 1H). | 602.5 |
| I-257 | 2A | $^1$H NMR (400 MHz, DMSO-d$_6$) δ 0.63 (1H, s), 0.82 (1H, s), 0.99 (1H, s), 1.03-1.08 (4H, m), 1.09-1.15 (3H, m). 1.24-1.33 (2H, m), 2.57-2.65 (3H, m), 3.63-3.86 (7H, | 642.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
|  |  | m), 4.17-4.23 (2H, m), 4.40 (2H, s), 4.68 (2H, d, J = 20.4 Hz), 5.36 (2H, s), 7.23-7.40 (5H, m), 7.58 (2H, d, J = 41.0 Hz), 7.81 (1H, d), 8.07 (2H, s), 8.32-8.40 (1H, m), 8.42-8.56 (1H, m), 8.65 (1H, s). |  |
| I-258 | 2A | $^1$H NMR (400 MHz, DMSO-d$_6$) δ 8.61-8.52 (m, 1H), 8.42-8.34 (m, 1H), 7.87-7.80 (m, 1H), 7.39-7.23 (m, 5H), 5.35 (s, 2H), 4.41-3.82 (m, 6H), 3.80-3.58 (m, 3H), 3.32-3.08 (m, 3H), 2.74 (d, J = 1.8 Hz, 3H), 2.34-2.22 (m, 1H), 1.83-1.68 (m, 1H), 1.41-1.30 (m, 1H), 1.14-1.03 (m, 6H), 0.88-0.83 (m, 1H), 0.70-0.65 (m, 1H). | 533.4 |
| I-259 | 2A | $^1$H NMR (400 MHz, DMSO-d$_6$) δ 8.61-8.50 (m, 1H), 8.41-8.33 (m, 1H), 7.87-7.80 (m, 1H), 7.39-7.22 (m, 5H), 5.38-5.33 (m, 2H), 4.45-3.70 (m, 8H), 3.66-3.57 (m, 1H), 3.23-3.05 (m, 3H), 2.69-2.62 (m, 1H), 2.29-2.16 (m, 1H), 1.78-1.65 (m, 1H), 1.42-1.31 (m, 1H), 1.15-1.01 (m, 6H), 0.91-0.82 (m, 1H), 0.73-0.60 (m, 5H). | 559.4 |
| I-260 | 23 | $^1$H NMR (400 MHz, DMSO-d$_6$) & 8.37-8.3 (m, 2H), 7.84-7.81 (m, 2H), 7.37-7.25 (m, 5H), 5.35 (s, 2H), 4.94-4.88 (m, 1H), 4.26-3.53 (m, 12H), 2.59-2.56 (m, 3H), 1.35-1.31 (m, 3H), 1.11-1.04 (m, 6H), 0.86-0.84 (m, 1H), 0.69-0.64 (m, 1H). | 537.4 |
| I-261 | 23 | $^1$H NMR (400 MHz, DMSO-d$_6$) δ 8.38-8.25 (m, 2H), 7.84-7.81 (m, 2H), 7.37-7.25 (m, 5H), 5.35 (s, 2H), 4.91-4.88 (m, 1H), 4.26-3.55 (m, 12H), 2.59-2.57 (m, 3H), 1.35-1.34 (m, 1H), 1.11-1.04 (m, 6H), 0.86-0.84 (m, 1H), 0.69-0.66 (m, 1H). | 537.4 |
| I-262 | 2A | $^1$H NMR (400 MHz, DMSO-d$_6$) δ 9.31 (d, J = 5.0 Hz, 1H), 8.41-8.26 (m, 2H), 7.82 (d, J = 15.0 Hz, 2H), 7.39-7.24 (m, 5H), 7.10 (t, J = 7.8 Hz, 1H), 6.74-6.61 (m, 3H), 5.35 (s, 2H), 4.46-3.60 (m, 13H), 2.64-2.56 (m, 3H), 1.36-1.22 (m, 1H), 1.10-0.99 (m, 9H), 0.85 (d, J = 5.0 Hz, 1H), 0.68-0.61 (m, 1H). | 657.5 |
| I-263 | 2A | $^1$H NMR (400 MHz, DMSO-d$_6$) δ 8.41-8.29 (m, 2H), 7.88-7.78 (m, 2H), 7.52 (d, J = 8.0 Hz, 2H), 7.38-7.22 (m, 7H), 5.36 (s, 2H), 4.50 (d, J = 12.6 Hz, 1H), 4.44-4.31 (m, 2H), 4.26-4.11 (m, 1H), 4.06 (t, J = 9.6 Hz, 1H), 3.98-3.40 (m, 8H), 2.59 (dd, J = 10.4, 4.6 Hz, 3H), 1.35-1.20 (m, 1H), 1.10-0.99 (m, 9H), 0.87-0.81 (m, 1H), 0.67-0.59 (m, 1H). | 719.3 |
| I-264 | 15 | $^1$H NMR (400 MHz, CD$_3$OD): δ 6.49 (d, J = 5.6 Hz, 1H), 4.93-4.99 (m, 1H), 3.86-4.59 (m, 9H), 3.73-3.77 (m, 1H), 3.50-3.64 (m, 4H), 3.35-3.39 (m, 2H), 3.19-3.25 (m, 1H), 2.34 (d, J = 5.0 Hz, 3H), 1.51-1.78 (m, 11H), 1.39-1.46 (m. 1H), 1.13-1.35 (m, 12H), 1.04-1.09 (m, 1H), 0.93-0.10 (m, 2H), 0.77-0.82 (m, 1H). | 625.4 |
| I-265 | 15 | $^1$H NMR (400 MHz, CD$_3$OD): δ 4.94-4.96 (m, 1H), 3.35-4.39 (m, 17H), 3.20-3.24 (m, 1H), 2.98-3.05 (m, 1H), 2.42-2.45 (m, 2H), 1.90-2.10 (m, 2H), 1.52-1.78 (m, 11H), 1.46 (m, 14H), 1.05-1.09 (m, 1H), 0.93-0.99 (m, 2H), 0.78-0.83 (m, 1H). | 642.5 |
| I-266 | 2A | $^1$H NMR (400 MHz, DMSO-d$_6$) δ 8.40-8.32 (m, 1H), 8.18-8.01 (m, 2H), 7.87-7.77 (m, 1H), 7.39-7.22 (m, 5H), 5.35 (s, 2H), 4.28-3.94 (m, 5H), 3.90-3.71 (m, 3H), 3.62-3.56 (m, 1H), 2.82-2.73 (m, 1H), 2.58-2.53 (m, 4H), 2.19-2.05 (m, 5H), 1.81-1.69 (m, 2H), 1.67-1.58 (m, 3H), 1.39-1.33 (m, 2H), 1.29-1.21 (m, 4H), 1.11-1.03 (m, 6H), 0.87-0.84 (m, 1H), 0.82-0.77 (m, 4H), 0.71-0.64 (m, 1H). | 660.6 |
| I-267 | 21 | $^1$H NMR (400 MHz, DMSO-d$_6$) δ 8.36 (d, J = 22.0 Hz, 1H), 8.13 (t, J = 8.6 Hz, 1H), 7.82 (d, J = 15.8 Hz, 1H), 7.75-7.66 (m, 1H), 7.41-7.22 (m, 5H), 6.03 (d, J = 7.8 Hz, 1H), 5.35 (s, 2H), 4.25 (dd, J = 8.8, 3.2 Hz, 1H), 4.00-3.75 (m, 5H), 3.73-3.52 (m, 5H), 3.49-3.36 (m, 1H), 3.24 (dd, J = 9.2, 6.4 Hz, 1H), 3.10 (d, J = 9.2, 6.8 Hz, 1H), 2.57 (dd, J = 11.6, 4.6 Hz, 3H), 1.70-1.58 (m, 5H), 1.49-1.37 (m, 1H), 1.21-1.10 (m, 3H), 1.06-0.98 (m, 9H), 0.84 (dd, J = 13.8, 9.6 Hz, 2H). | 636.5 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-268 | 21 | $^1$H NMR (400 MHz, DMSCM.) δ 8.38-8.33 (m, 1H), 8.15-8.11 (m, 1H), 7.83-7.70 (m, 2H), 7.37-7.25 (m, 5H), 6.43 (d, J = 3.2 Hz, 1H), 5.35 (s, 2H), 4.26-4.24 (m, 1H), 3.98-3.71 (m, 6H), 3.67-3.57 (m, 3H), 3.55-3.45 (m, 1H), 3.26-3.22 (m, 1H), 3.12-3.08 (m, 1H), 2.59-2.55 (m, 3H), 2.42-2.39 (m, 1H), 1.68-1.63 (m, 5H), 1.45-1.43 (m, 1H), 1.19-1.09 (m, 3H), 1.04-1.01 (m, 3H), 0.87-0.81 (m, 2H), 0.54-0.51 (m, 2H), 0.33-0.32 (m, 2H). | 634.3 |
| I-269 | 23 | $^1$H NMR (400 MHz, DMSO-d$_6$) δ 7.37-7.24 (m, 10H), 5.47-5.41 (m, 1H), 4.76-4.69 (m, 1H), 4.35-4.28 (m, 1H), 4.21-4.14 (m, 1H), 4.00-3.92 (m, 1H), 3.66-3.60 (m, 1H), 3.59-3.55 (m, 2H), 3.36 (s, 2H), 3.19-3.15 (m, 1H), 3.06-2.98 (m, 1H), 2.94-2.88 (m, 1H), 2.55 (s, 1H), 1.36 (s, 9H). | 492 |
| I-270 | 16A | $^1$H NMR(400 MHz, DMSO-d$_6$): δ 8.44-8.51 (m, 1H), 8.37-8.39 (m, 1H), 8.05 (br, 2H), 7.81-7.85 (m, 1H), 7.26-7.37 (m, 5H), 5.36 (s, 2H), 4.48-4.56 (m, 1H), 4.34-4.41 (m, 1H), 4.05-4.21 (m, 4H), 3.85-3.98 (m, 2H), 3.48-3.81 (m, 5H), 3.36-3.42 (m, 1H), 3.05-3.26 (m, 5H), 2.30-2.39 (m, 1H), 2.05-2.14 (m, 1H), 1.59-1.74 (m, 5H), 1.44-1.53 (m, 1H), 1.28-1.36 (m, 1H), 1.14-1.25 (m, 3H), 1.05-1.09 (m, 8H), 0.86-0.93 (m, 3H), 0.66-0.69 (m, 1H). | 702.9 |
| I-271 | 2A | $^1$H NMR(400 MHz, CD$_3$OD): δ 8.16-8.25 (m, 1H), 7.88-7.95 (m, 1H), 7.25-7.38 (m, 5H), 5.35-5.41 (m, 2H), 3.78-4.41 (m, 10H), 3.35-3.68 (m, 6H), 3.11-3.18 (m, 1H), 1.91-2.03 (m, 2H), 1.66-1.83 (m, 10H), 1.08-1.45 (m, 14H), 1.01-1.06 (m, 1H), 0.91-1.00 (m, 2H), 0.74-0.81 (m, 1H). | 738.4 |
| I-272 | 25 | $^1$H NMR (400 MHz, DMSO-d$_6$) δ 8.79 (t, J = 8.8 Hz, 1H), 8.47-8.27 (m, 2H), 7.82 (dd, J = 25.8, 8.2 Hz, 1H), 7.39-7.07 (m, 10H), 5.38-5.30 (m, 2H), 5.20-5.11 (m, 1H), 4.71 (t, J = 12.8 Hz, 1H), 4.20 (dd, J = 42.4, 10.8 Hz, 2H), 4.11-4.00 (m, 2H), 3.88 (s, 1H), 3.78 (m, 3H), 3.56 (m, 1H), 3.46-3.33 (m, 1H), 2.62 (m, 3H), 1.48 (d, J = 11.8 Hz, 3H), 1.39 (s, 3H), 1.35 (t, J = 7.2 Hz, 1H), 1.11 (t, J = 6.0 Hz, 3H), 1.05 (t, J = 4.2 Hz, 3H), 0.90-0.83 (m, 1H), 0.72-0.65 (m, 1H). | 703.40 |
| I-273 | 23 + 24 | $^1$H NMR (400 MHz, DMSO-d$_6$) δ 8.70-8.50 (m, 1H), 8.39-8.28 (m, 1H), 8.16-8.07 (m, 1H), 7.86-7.77 (m, 1H), 7.38-7.22 (m, 5H), 5.35 (s, 2H), 4.72-4.43 (m, 1H), 4.25-3.52 (m, 10H), 3.26-3.10 (m, 1H), 3.08-3.00 (m, 1H), 2.64-2.53 (m, 3H), 2.13 (d, J = 2.8 Hz, 1H), 1.99-1.89 (m, 2H), 1.72-1.53 (m, 6H), 1.41-1.32 (m, 1H), 1.24-1.22 (m, 1H), 1.19-1.14 (m, 3H), 1.12-1.02 (m, 8H), 0.93-0.78 (m, 3H), 0.71-0.63 (m, 1H). | 688.5 |
| I-274 | 22 | $^1$H NMR (400 MHz, DMSO-d$_6$) δ 8.35 (d, J = 21.4 Hz, 1H), 8.14 (t, J = 7.0 Hz, 1H), 7.81 (d, J = 16.4 Hz, 1H), 7.75-7.66 (m, 1H), 7.44-7.19 (m, 5H), 5.35 (d, J = 2.2 Hz, 2H), 4.27 (dd, J = 8.8. 3.4 Hz, 1H), 4.13-3.95 (m, 3H), 3.94-3.87 (m, 1H), 3.86-3.73 (m, 3H), 3.73-3.63 (m, 2H), 3.62-3.52 (m, 1H), 3.49-3.34 (m, 1H), 3.27-3.18 (m, 1H), 3.10 (dd, J = 9.2, 6.8 Hz, 1H), 2.57 (dd, J = 13.8, 3.4 Hz, 6H), 1.63 (q, J = 13.8, 12.6 Hz, 5H), 1.42 (d, J = 10.2 Hz, 1H), 1.21-1.08 (m, 3H), 1.05-0.98 (m, 9H), 0.84 (t, J = 11.8 Hz, 2H). | 650.50 |
| I-275 | 2A | $^1$H NMR (400 MHz, CD$_3$OD) δ 8.27-8.11 (m, 1H), 7.95-7.84 (m, 1H), 7.37-7.22 (m, 10H), 5.40-5.33 (m, 2H), 4.67-3.75 (m, 12H), 2.04-1.52 (m, 4H), 1.43-1.32 (m, 6H), 1.22-1.00 (m, 8H), 0.93-0.72 (m, 3H). | 624.5 |
| I-276 | 7A | $^1$H NMR (400 MHz, DMSO-d$_6$) δ 8.35 (d, J = 11.8 Hz, 2H), 7.82 (d, J = 15.4 Hz, 2H), 7.38-7.23 (m, 10H), 5.35 (s, 2H), 4.52 (d, J = 12.0 Hz, 1H), 4.46-4.29 (m, 3H), 4.26-3.59 (m, 8H), 3.49 (m, 1H), 2.60 (m, 3H), 1.07 (s, 3H), 0.88 (s, 7H), 0.27 (d, J = 34.4 Hz, 4H). | 655.4 |
| I-277 | 7A | $^1$H NMR (400 MHz, DMSO-d$_6$) δ 8.39-8.31 (m, 2H), 7.87-7.78 (m, 2H), 7.37-7.24 (m, 10H), 5.35 (s, 2H), 4.56-4.49 (m, 1H), 4.46-4.40 (m, 1H), 4.38-4.32 (m, 1H), 4.22-4.08 (m, 1H), 4.06-3.87 (m, 5H), 3.79-3.60 | 641.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | (m, 3H), 3.53-3.36 (m, 1H), 2.64-2.56 (m, 3H), 1.68-1.49 (m, 1H), 1.12-1.04 (m, 3H), 1.03-0.93 (m, 3H). 0.88-0.73 (m, 1H), 0.41-0.28 (m, 2H), 0.18--0.01 (m, 2H). | |
| I-278 | 23 | $^1$H NMR (DMSO, 400 MHz) δ 9.05 (1H, s), 8.35 (1H, m), 7.83 (1H, d, J = 7.8 Hz), 7.57 (1H, m), 7.48 (1H, m), 7.21-7.37 (6H, m), 5.35 (2H, s), 4.62 (2H, m), 3.70-4.24 (9H, m), 2.45 (3H, d, J = 3.4 Hz), 1.34 (1H, d, J = 6.6 Hz), 1.11 (2H, m), 1.04 (3H, d, J = 2, 4 Hz), 1.00 (1H, s), 0.84 (1H, d, J = 5.0 Hz), 0.66 (1H, dd, J = 7.8, 3.8 Hz). | 580.4 |
| I-279 | 18 | $^1$H NMR (400 MHz, DMSO-$d_6$) δ 8.25-9.22 (m, 1H), 8.40-8.35 (m, 1H), 8.10-8.00 (m, 1H), 7.76-7.72 (m, 1H), 4.29-4.10 (m, 4H), 3.99-3.70 (m, 6H), 3.62-3.47 (m, 1H), 3.24-3.10 (m, 1H), 2.61-2.55 (m, 3H), 1.66-1.58 (m, 5H), 1.36-1.24 (m, 2H), 1.12-0.98 (m, 13H), 0.95-0.86 (m, 5H), 0.68-0.66 (m, 1H). | 588.3 |
| I-280 | 2A | $^1$H NMR (400 MHz, CD$_3$OD): δ 8.24 (d, J = 16.8 Hz, 1H), 7.93 (d, J = 12.0 Hz, 1H), 7.28-7.38 (m, 10H), 5.39 (d, J = 2.4 Hz, 2H), 4.99-5.03 (m, 1H), 4.64-4.68 (m, 1H), 4.48-4.52 (m, 1H), 4.33-4.40 (m, 1H), 4.13-4.24 (m, 2H), 3.96-4.10 (m, 3H), 3.75-3.92 (m, 4H), 3.65-3.66 (m, 1H), 3.36-3.53 (m, 3H), 1.78-1.94 (m, 4H), 1.26-1.27 (m, 3H), 1.12-1.18 (m, 6H), 1.04-1.07 (m, 1H), 0.77-0.80 (m, 1H). | 731.4 |
| I-281 | 2A | $^1$H NMR (400 MHz, CD$_3$OD): δ 8.19-8.26 (m, 1H), 7.90-7.95 (m, 1H), 7.23-7.39 (m, 5H), 5.36-5.41 (m, 2H), 3.78-4.44 (m, 11H), 3.39-3.49 (m, 2H), 3.13-3.18 (m, 1H), 1.66-1.85 (m, 5H), 1.51-1.61 (m, 1H), 1.35-1.46 (m, 1H), 0.98-1.29 (m, 20H), 0.75-0.81 (m, 1H). | 648.4 |
| I-282 | 17A | $^1$H NMR(400 MHz, CD$_3$OD): δ 9.17 (s, 1H), 8.34-8.41 (m, 1H), 3.84-4.41 (m, 9H), 3.33-3.64 (m, 5H), 3.13-3.28 (m, 3H), 1.64-1.86 (m, 9H), 1.49-1.61 (m, 2H), 0.87-1.42 (m, 21H), 0.75-0.81 (m, 1H). | 643.4 |
| I-283 | 2A | $^1$H NMR (400 MHz, DMSO) d ppm 1.33-1.43 (m, 1H), 0.63-0.72 (m, 1H), 1.59-1.77 (m, 2H), 0.82-0.89 (m, 1H), 1.00-1.11 (m, 6H), 1.25 (dd, J = 12.00, 6.40 Hz, 9H), 3.31 (s, 3H), 3.08-3.26 (m, 7H), 3.49-4.33 (m, 11H), 4.76-4.88 (m, 1H), 5.36 (s, 1H), 8.48-8.61 (m, 1H), 8.33-8.43 (m, 1H), 7.25-7.36 (m, 3H), 7.78-7.89 (m, 1H) | 663.7 |
| I-284 | 18 | $^1$H NMR (400 MHz, DMSO-$d_6$) δ 9.25 (s, 1H), 8.40-8.24 (m, 2H), 4.83 (s, 1H), 4.20-3.64 (m, 9H), 3.53-3.45 (m, 5H), 3.25-3.16 (m, 1H), 1.66-1.29 (m, 13H), 1.12-0.86 (m, 18H), 0.67 (s, 1H). | 642.5 |
| I-285 | 18 | $^1$H NMR (400 MHz, DMSO-$d_6$) δ 9.25 (s, 1H), 8.51-8.32 (m, 2H), 4.91-4.82 (m, 1H), 4.26-4.06 (m, 3H), 4.05-3.71 (m, 4H), 3.69-3.59 (m, 3H), 3.58-3.37 (m, 6H), 1.61-1.29 (m, 7H), 1.13-1.03 (m, 9H), 0.96-0.80 (m, 5H), 0.72-0.64 (m, 1H). | 654.3 |
| I-286 | 18 | $^1$H NMR (400 MHz, DMSO-$d_6$) δ 9.26-9.24 (m, 1H), 8.70-8.56 (m, 1H), 8.40-8.34 (m, 1H), 5.01-4.92 (m, 1H), 4.22-3.91 (m, 4H), 3.90-3.71 (m, 3H), 3.69-3.62 (m, 1H), 3.59-3.35 (m, 7H), 3.26-3.13 (m, 2H), 1.68-1.53 (m, 7H), 1.51-1.36 (m, 5H), 1.35-1.28 (m, 1H), 1.20-1.04 (m, 9H), 0.91-0.80 (m, 3H), 0.71-0.66 (m, 1H). | 614.4 |
| I-287 | 18 | $^1$H NMR (400 MHz, DMSO-$d_6$) δ 9.25 (s, 1H), 8.49 (dt, J = 22.0, 8.2 Hz, 1H), 8.37 (dd, J = 19.6, 3.8 Hz, 1H), 4.96 (m, 1H), 4.25-4.06 (m, 3H), 4.01-3.72 (m, 4H), 3.69-3.40 (m, 9H), 1.98 (m, 4H), 1.40-1.25 (m, 1H), 1.12-1.03 (m, 9H), 0.94-0.82 (m, 5H), 0.67 (d, J = 7.6 Hz, 1H). | 690.3 |
| I-288 | 18 | $^1$H NMR (400 MHz, DMSO-$d_6$) δ 9.25 (s, 1H), 8.53-8.44 (m, 1H), 8.41-8.33 (m, 1H), 4.92 (s, 1H), 4.23-4.06 (m, 3H), 4.03-3.93 (m, 1H), 3.86-3.75 (m, 4H), 3.69-3.48 (m, 7H), 3.47-3.39 (m, 1H), 3.30-3.17 (m, 4H), 1.94 (s, 4H), 1.70 (s, 1H), 1.60-1.50 (m, 2H), 1.38-1.27 (m, 1H), 1.18-1.04 (m, 11H), 0.88-0.83 (m, 1H), 0.72-0.64 (m, 1H). | 666.3 |
| I-289 | 18 | $^1$H NMR (400 MHz, DMSO-$d_6$) δ 9.25 (s, 1H), 8.40-8.35 (m, 1H), 8.11-8.05 (m, 1H), 7.76-7.67 (m, 1H), 4.27-4.07 (m, 4H), 4.02-3.66 (m, 6H), 3.58-3.45 (m, 1H), | 600.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 3.03 (d, J = 8.8 Hz, 1H), 2.87 (d, J = 8.8 Hz, 1H), 2.60-2.56 (m, 3H), 1.51-1.46 (m, 7H), 1.32-1.28 (m, 7H), 1.12-0.99 (m, 9H), 0.87-0.86 (m, 1H), 0.68-0.66 (m, 1H). | |
| I-290 | 18 | $^1$H NMR (400 MHz, DMSO-d$_6$) δ 9.25 (s, 1H), 8.44-8.30 (m, 1H), 8.19-8.05 (m, 1H), 7.79-7.64 (m, 1H), 4.30-4.16 (m, 2H), 4.15-4.06 (m, 2H), 4.03-3.93 (m, 2H), 3.92-3.73 (m, 3H), 3.68 (dd, J = 13.0, 6.4 Hz, 1H), 3.57 (s, 2H), 3.27 (s, 1H), 2.58 (dd, J = 13.0, 4.6 Hz, 3H), 1.73 (s, 2H), 1.64 (d, J = 9.6 Hz, 2H), 1.43 (d, J = 7.8 Hz, 1H), 1.38-1.28 (m, 1H), 1.22 (d, J = 8.4 Hz, 2H), 1.18-1.14 (m, 2H), 1.12 (s, 1H), 1.08 (dd, J = 6.4, 4.2 Hz, 3H), 1.03 (d, J = 8.2 Hz, 5H), 0.86 (t, J = 5.0 Hz, 1H), 0.72-0.63 (m, 1H). | 560.4 |
| I-291 | 19 | $^1$H NMR (400 MHz, DMSO-d$_6$) δ 9.25 (s, 1H), 8.68-8.51 (m, 1H), 8.41-8.32 (m, 1H), 4.94-4.85 (m, 1H), 4.27-4.01 (m, 3H), 3.89-3.39 (m, 13H), 2.05-1.84 (m, 4H), 1.38-1.25 (m, 1H), 1.11-1.03 (m, 9H), 0.93-0.77 (m, 5H), 0.70-0.65 (m, 1H). | 690.35 |
| I-292 | 19 | $^1$H NMR (400 MHz, DMSO-d$_6$) δ 9.25 (s, 1H), 8.66-8.49 (m, 1H), 8.42-8.32 (m, 1H), 4.89-4.78 (m, 1H), 4.31-4.15 (m, 1H), 4.08-4.00 (m, 2H), 3.93-3.75 (m, 3H), 3.71-3.64 (m, 3H), 3.59-3.37 (m, 7H), 1.62-1.53 (m, 2H), 1.49-1.38 (m, 4H), 1.30-1.22 (m, 1H), 1.14-1.09 (m, 3H), 1.07-1.01 (m, 6H), 0.91 (s, 1H), 0.88-0.81 (m, 3H), 0.80-0.74 (m, 1H), 0.71-0.64 (m, 1H). | 654.4 |
| I-293 | 19 | $^1$H NMR (400 MHz, DMSO-d$_6$) δ 9.25 (s, 1H), 8.70-8.55 (m, 1H), 8.36 (dd, J = 23.6, 2.0 Hz, 1H), 4.96 (s, 1H), 4.32-3.90 (m, 4H), 3.88-3.70 (m, 3H), 3.67 (d, J = 5.8 Hz, 1H), 3.60-3.33 (m, 7H), 3.24-3.10 (m, 2H), 1.59 (d, J = 11.2 Hz, 7H), 1.45 (d, J = 28.0 Hz, 5H), 1.35-1.26 (m, 1H), 1.17-1.03 (m, 9H), 0.85 (d, J = 10.0 Hz, 3H), 0.68 (dd, J = 8.6, 3.8 Hz, 1H). | 614.4 |
| I-294 | 20 | $^1$H NMR (400 MHz, DMSO-d$_6$) δ 8.36-8.28 (m, 1H), 8.15-8.06 (m, 1H), 7.83-7.74 (m, 2H), 7.38-7.23 (m, 5H), 5.38-5.33 (m, 2H), 4.27-4.20 (m, 1H), 4.06-3.99 (m, 1H), 3.92-3.44 (m, 11H), 3.38-3.32 (m, 3H), 3.26-3.21 (m, 1H), 3.14-3.09 (m, 1H), 2.60-2.55 (m, 3H), 1.70-1.58 (m, 5H), 1.49-1.38 (m, 1H), 1.20-1.04 (m, 6H), 0.89-0.79 (m, 2H). | 609.4 |
| I-295 | 22 | $^1$H NMR (400 MHz, DMSO-d$_6$) δ 8.35 (d, J = 20.2 Hz, 1H), 8.16 (dd, J = 9.0. 3.8 Hz, 1H), 7.88-7.64 (m, 2H), 7.41-7.18 (m, 5H), 5.35 (d, J = 4.2 Hz, 2H), 4.27 (dd, J = 8.6, 3.4 Hz, 1H), 4.08 (dd, J = 19.6, 8.4 Hz, 1H), 4.01-3.91 (m, 2H), 3.88-3.68 (m, 5H), 3.63-3.54 (m, 1H), 3.46 (t, J = 6.0 Hz, 2H), 3.23 (t, J = 7.6 Hz, 1H), 3.15-3.07 (m, 1H), 2.71 (d, J = 2.4 Hz, 3H), 2.58 (dd, J = 10.8. 4.6 Hz, 3H), 1.64 (q, J = 13.6. 12.4 Hz, 5H), 1.49-1.38 (m, 1H), 1.24-1.08 (m, 3H), 1.03 (dd, J = 6.4, 3.2 Hz, 3H), 0.83 (q, J = 12.4 Hz, 2H), 0.69 (t, J = 6.4 Hz, 2H), 0.64-0.55 (m, 2H). | 648.5 |
| I-296 | 1A | $^1$H NMR (400 MHz, DMSO-d$_6$) δ 9.25 (s, 1H), 8.51-8.29 (m, 2H), 4.84 (m, 1H), 4.30-4.14 (m, 2H), 4.12-3.92 (m, 2H), 3.89-3.74 (m, 2H), 3.68-3.36 (m, 7H), 3.23 (d, J = 6.8 Hz, 1H), 3.15 (m, 1H), 2.60 (m, 1H), 1.93-1.80 (m, 2H), 1.63 (q, J = 15.8. 14.6 Hz, 7H), 1.45 (s, 5H), 1.23-1.08 (m, 3H), 1.02 (s, 3H), 0.86 (t, J = 12.0 Hz, 2H). | 636.3 |
| I-297 | 1A + 8A | $^1$H NMR (400 MHz, DMSO-d$_6$) δ 13.22 (s, 1H), 8.43 (s, 1H), 8.17 (s, 1H), 7.84 (s, 1H), 4.96-4.89 (m, 1H), 4.21-3.35 (m, 18H), 3.27-3.22 (m, 2H), 2.06-1.87 (m, 4H), 1.76-1.65 (m, 1H), 1.54 (d, J = 13.2 Hz, 2H), 1.38-1.27 (m, 1H), 1.16-1.02 (m, 11H), 0.86 (s, 1H), 0.71-0.65 (m, 1H). | 649.45 |
| I-298A | 1A + 8A | $^1$H NMR (400 MHz, DMSO-d$_6$) δ 13.20 (s, 1H), 8.64-8.56 (m, 1H), 8.29-7.73 (m, 2H), 7.62 (s, 1H), 7.36-7.13 (m, 5H), 5.11 (s, 1H), 4.90-4.79 (m, 1H), 4.36-4.20 (m, 1H), 4.16-3.67 (m, 7H), 3.62-3.52 (m, 1H), 3.41 (s, 1H), 2.54 (s, 3H), 2.21-2.04 (m, 2H), 1.39 (s, 1H), 1.16-1.02 (m, 6H), 0.87 (s, 1H), 0.73-0.65 (m, 1H). | 537.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-299 | 2A | $^1$H NMR (400 MHz, DMSO-$d_6$) δ 8.40-8.32 (m, 1H), 8.25-8.13 (m, 1H), 7.88-7.72 (m, 2H), 7.38-7.29 (m, 3H), 7.28-7.24 (m, 2H), 5.35 (s, 2H), 4.31-4.02 (m, 4H), 4.00-3.94 (m, 1H), 3.92-3.83 (m, 2H), 3.81-3.69 (m, 2H), 3.68-3.62 (m, 1H), 3.58 (s, 3H), 3.47-3.35 (m, 3H), 2.64-2.56 (m, 3H), 1.90-1.87 (m, 5H), 1.38-1.25 (m, 1H), 1.14-1.00 (m, 10H), 0.89-0.82 (m, 1H), 0.71-0.63 (m, 1H). | 689.3 |
| I-300 | 1A | $^1$H NMR (400 MHz, CD$_3$OD): δ 8.48-8.39 (m, 2H), 8.24-8.16 (m, 1H), 7.94-7.88 (m, 1H), 7.37-7.26 (m, 7H), 5.37 (s, 2H), 5.02-4.95 (m, 1H), 4.76-4.58 (m, 1H), 4.38-3.73 (m, 10H), 3.45-3.36 (m, 1H), 3.28-3.16 (m, 2H), 2.96-2.86 (m, 1H), 2.83-2.73 (m, 1H), 2.04-1.86 (m, 2H), 1.81-1.35 (m, 10H), 1.25-1.10 (m, 12H), 1.07-1.02 (m, 1H), 0.99-0.90 (m, 2H), 0.80-0.74 (m, 1H). | 778.45 |
| I-301 | 27 | $^1$H NMR(400 MHz, DMSO-$d_6$): δ 13.20-13.25 (m, 1H), 8.44-8.47 (m, 1H), 8.17-8.20 (m, 1H), 7.82-7.85 (m, 1H), 4.81-4.89 (m, 1H), 3.83-4.23 (m, 5H), 3.42-3.81 (m, 11H), 3.38-3.40 (m, 1H), 3.28-3.30 (s, 1H), 3.20-3.25 (m, 1H), 1.94-2.03 (m, 2H), 1.54-1.87 (m, 5H), 1.23-1.45 (m, 4H), 1.05-1.45 (m, 9H), 0.84-0.88 (m, 1H), 0.66-0.68 (m, 1H). | 649.4 |
| I-302 | 27 | $^1$H NMR(400 MHz, DMSO-$d_6$): δ 13.22 (br, 1H), 8.43-8.47 (m, 1H), 8.09-8.23 (m, 1H), 7.75-7.93 (m, 1H), 4.86 (br, 1H), 4.11-4.42 (m, 2H), 3.67-4.09 (m, 5H), 3.41-3.64 (m, 10H), 3.36-3.68 (m, 1H), 3.21-3.25 (m, 1H), 1.94-2.01 (m, 2H), 1.67-1.86 (m, 4H), 1.56-1.64 (m, 10H), 1.04-1.24 (m, 1H) | 689.3 |
| I-303 | 27 | $^1$H NMR (400 MHz, CDCl3): δ 8.11 (s, 1H), 7.90 (d, J = 10.6 Hz, 1H), 3.48-4.52 (m, 17H), 3.33-3.38 (m, 4H), 1.53-1.74 (m, 6H), 1.39 (d, J = 6.4 Hz, 3H), 1.11-1.17 (m, 8H), 1.06 (d, J = 4.4 Hz, 1H), 0.77-0.84 (m, 1H). | 543.6 |
| I-304 | 17A | $^1$H NMR (400 MHz, CD$_3$OD): δ 9.16 (s, 1H), 8.35-8.40 (m, 1H), 3.82-4.45 (m, 11H), 3.47-3.56 (m, 1H), 3.18-3.20 (m, 1H), 2.92-2.96 (m, 1H), 1.57-1.60 (m, 7H), 1.43-1.45 (m, 6H), 1.25-1.28 (m, 3H), 1.14-1.20 (m, 5H), 1.03-1.11 (m, 8H), 0.76-0.81 (m, 1H). | 601.5 |
| I-305 | 27 | $^1$H NMR (400 MHz, CDCl3) d 0.73-0.80 (m, 1H), 1.16 (dd, J = 11.44, 7.00 Hz, 9H), 1.45 (d, J = 6.6 Hz, 2H), 1.56 (dd, J = 12.2, 6.8 Hz, 5H), 1.62-1.69 (m, 2H), 3.08-3.14 (m, 1H), 3.52 (s, 5H), 3.95 (s, 6H), 4.04-4.15 (m, 3H), 4.22-4.30 (m, 1H), 4.81-4.94 (m, 1H), 7.82 (d, J = 21.2 Hz, 2H) | 529.5 |
| I-306 | 2A | $^1$H NMR(400 MHz, DMSO-$d_6$): δ 8.52-8.61 (m, 1H), 8.37-8.40 (m, 1H), 7.69-7.85 (m, 4H), 7.26-7.37 (m, 4H), 5.36 (s, 2H), 4.83-4.85 (m, 1H), 4.33-4.39 (m, 1H), 4.17-4.24 (m, 1H), 3.97-4.10 (m, 3H), 3.86-3.90 (m, 1H), 3.67-3.80 (m, 2H), 3.40-3.62 (m, 3H), 3.24-3.26 (m, 3H), 2.91-3.10 (m, 3H), 2.57-2.72 (m, 3H), 1.66-1.88 (m, 3H), 1.30-1.38 (m, 1H), 1.23 (s, 1H), 0.93-1.15 (m, 10H), 0.85-0.86 (m, 1H), 0.65-0.70 (m, 1H). | 648.9 |
| I-307 | 17A | $^1$H NMR (400 MHz, CD$_3$OD): δ 9.16 (s, 1H), 8.37 (d, J = 12.0 Hz, 1H), 3.82-4.45 (m, 9H), 3.55-3.72 (m, 3H), 3.32-3.42 (m, 2H), 3.13-3.20 (m, 1H), 1.64-1.85 (m, 5H), 1.49-1.60 (m, 1H), 1.36-1.46 (m, 1H), 1.03-1.32 (m, 13H), 0.92-1.12 (m, 2H), 0.74-0.81 (m, 1H). | 547.5 |
| I-308 | 17A | $^1$H NMR (400 MHz, CD$_3$OD): δ 9.16 (s, 1H), 8.34-8.39 (m, 1H), 3.82-4.39 (m, 10H), 3.33-3.65 (m, 6H), 3.12-3.17 (m, 1H), 1.67-1.88 (m, 11H), 1.50-1.60 (m, 2H), 1.09-1.26 (m, 16H), 0.92-0.98 (m, 2H), 0.75-0.80 (m, 1H). | 629.5 |
| I-309 | 2A | $^1$H NMR(400 MHz, CD$_3$OD): δ 8.21 (dd, J = 3.6, 20.0 Hz, 1H), 7.90-7.93 (m, 1H), 7.25-7.37 (m, 5H), 5.37-5.38 (m, 2H), 3.80-4.40 (m, 12H), 3.61-3.66 (m, 1H), 3.25-3.42 (m, 2H), 3.11-3.15 (m, 1H), 1.65-1.82 (m, 5H), 1.50-1.60 (m, 1H), 1.35-1.46 (m, 1H), 1.18-1.26 (m, 3H), 1.10-1.16 (m, 8H), 0.94-1.07 (m, 3H), 0.75-0.80 (m, 1H). | 688.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
| --- | --- | --- | --- |
| I-310 | 16A | $^1$H NMR (400 MHz, CD$_3$OD): δ 8.19-8.24 (m, 1H), 7.90-7.94 (m, 1H), 7.27-7.37 (m, 5H), 5.38 (s, 2H), 4.55-4.66 (m, 1H), 3.75-4.44 (m, 13H), 3.34-3.45 (m, 2H), 3.15-3.25 (m, 3H), 2.40-2.50 (m, 1H), 2.08-2.16 (m, 1H), 1.48-1.79 (m, 7H), 1.11-1.23 (m, 11H), 0.95-1.05 (m, 3H), 0.76-0.79 (m, 1H). | 703.1 |
| I-311 | 27 | $^1$H NMR (400 MHz, CD$_3$OD): δ 7.50-7.55 (m, 1H), 4.90-4.95 (m, 1H), 3.71-4.40 (m, 10H), 3.34-3.56 (m, 6H), 3.16-3.22 (m, 1H), 2.51 (d, J = 5.4 Hz, 3H), 1.53-1.76 (m, 11H), 1.10-1.29 (m, 13H), 1.02-1.07 (m, 1H), 0.90-0.97 (m, 2H), 0.75-0.81 (m, 1H). | 642.3 |
| I-312 | 17A | $^1$H NMR (400 MHz, CD$_3$OD): δ 9.16 (s, 1H), 8.36 (d, J = 9.0 Hz, 1H), 3.80-4.40 (m, 12H), 3.37-3.70 (m, 8H), 3.20-3.23 (m, 1H), 1.94-2.05 (m, 2H), 1.66-1.86 (m, 9H), 1.40-1.47 (m, 1H), 1.11-1.19 (m, 9H), 1.02-1.06 (m, 1H), 0.90 (t, J = 6.6 Hz, 1H), 0.77-0.79 (m, 1H). | 667.8 |
| I-313 | 17A | $^1$H NMR (400 MHz, CDCl3): δ 8.92 (s, 1H), 8.26 (d, J = 8.0 Hz, 1H), 6.33-6.39 (m, 1H), 4.08-4.51 (m, 4H), 3.89-4.07 (m, 5H), 3.75-3.85 (m, 1H), 3.44-3.53 (m, 2H), 3.08-3.19 (m, 2H), 1.99-2.12 (m, 2H), 1.65-1.78 (m, 5H), 1.30-1.34 (m, 6H), 1.10-1.22 (m, 12H), 0.75-0.78 (m, 1H). | 611.2 |
| I-314 | 17A | $^1$H NMR (400 MHz, CDCl3): δ 8.94 (s, 1H), 8.27 (s, 1H), 5.89-5.91 (m, 1H), 3.88-4.37 (m, 11H), 3.75-3.76 (m, 1H), 3.40-3.54 (m, 6H), 3.14-3.22 (m, 1H), 2.99-3.07 (m, 1H), 2.06-2.19 (m, 2H), 1.72-1.91 (m, 6H), 1.46-1.64 (s, 4H), 1.14-1.15 (m, 8H), 1.25 (s, 4H), 0.74-0.78 (m, 1H), LC_MS: m/z 667.3 [M + H]$^+$. | 667.3 |
| I-315 | 17A | $^1$H NMR(400 MHz, DMSO-d$_6$): δ 8.92 (s, 1H), 8.25-8.28 (m, 1H), 5.86-5.93 (m, 1H), 3.84-4.44 (m, 9H), 3.70-3.77 (m, 1H), 3.40-3.53 (m, 4H), 3.11-3.20 (m, 1H), 2.98-3.08 (m, 1H), 1.94-2.17 (m, 4H), 1.72-1.87 (m, 8H), 1.63-1.67 (m, 1H), 1.13-1.36 (m, 15H), 00.73-0.80 (m, 1H). | 701.2 |
| I-316 | 17A | $^1$H NMR (400 MHz, CD$_3$OD): δ 9.16 (s, 1H), 8.34-8.39 (m, 1H), 3.81-4.47 (m, 9H), 3.70-3.80 (m, 1H), 3.59-3.67 (m. 1H), 3.34-3.57 (m, 4H), 2.49-2.62 (m, 1H), 1.64-2.10 (m, 16H), 1.29-1.56 (m, 4H), 1.09-1.13 (m, 6H). | 723.2 |
| I-317 | 17A | $^1$H NMR (400 MHz, CD$_3$OD) δ 9.15 (s, 1H), 8.34-8.37 (m, 1H), 7.43-7.46 (m, 1H), 7.17-7.22 (m, 2H), 4.98-4.99 (m, 1H), 4.64-4.67 (m, 1H), 4.52-4.56 (m, 1H), 3.88-4.39 (m, 12H), 3.44-3.48 (m, 1H), 3.12-3.28 (m, 5H), 2.78-2.81 (m, 1H), 2.59-2.62 (m, 1H), 1.67-1.77 (m, 3H), 1.32-1.35 (m, 2H), 1.22-1.28 (m, 5H), 1.09-1.13 (m, 5H), 0.98-1.03 (m, 1H), 0.70-0.76 (m, 1H). | 718.2 |
| I-318 | 17A | $^1$H NMR (400 MHz, CD$_3$OD): δ 9.16 (s, 1H), 8.37 (d, J = 10.0 Hz, 1H), 7.32-7.40 (m, 2H), 7.07-7.09 (m, 2H), 4.95-5.00 (m, 1H), 4.58-4.63 (m, 1H), 3.82-4.50 (m, 12H), 3.36-3.48 (m, 1H), 3.08-3.29 (m, 5H), 2.71-2.88 (m, 1H), 2.57-2.65 (m, 1H), 1.60-1.80 (m, 3H), 1.21-1.41 (m, 7H), 1.10-1.14 (m, 5H), 1.01-1.06 (m, 1H), 0.73-0.80 (m, 1H). | 684.3 |
| I-319 | 17A | $^1$H NMR (400 MHz, CD$_3$OD) δ 9.15 (s, 1H), 8.37 (d, J = 5.0 Hz, 1H), 7.64 (d, J = 3.4 Hz, 2H), 7.54 (d, J = 3.4 Hz, 2H), 4.98-5.02 (m, 1H), 4.69-4.74 (m, 1H), 4.58-4.61 (m, 1H), 4.32-4.40 (m, 2H), 4.18-4.30 (m, 2H), 4.15 (d, J = 5.2 Hz, 1H), 3.77-4.08 (m, 7H), 3.40-3.49 (m, 1H), 3.13-3.28 (m, 5H), 3.73-3.83 (m, 1H), 2.60-2.63 (m, 1H), 1.68 (t, J = 9.6 Hz, 3H), 1.33-1.40 (m, 2H), 1.20-1.31 (m, 6H), 1.08 (d, J = 3.0 Hz, 3H), 1.02 (t, J = 3.8 Hz, 1H). | 734.3 |
| I-320 | 17A | $^1$H NMR (400 MHz, CD$_3$OD): δ 9.16 (s, 1H), 8.37 (d, J = 10.0 Hz, 1H), 7.44-7.46 (m, 2H), 7.24-7.26 (m, 2H), 4.95-5.01 (m, 1H), 4.63-4.68 (m, 1H), 4.49-4.55 (m, 1H), 3.81-4.40 (m, 12H), 3.38-3.48 (m, 1H), 3.13-3.28 (m, 5H), 2.58-2.85 (m, 2H), 1.58-1.82 (m, 3H), 1.22-1.29 (m, 5H), 1.09-1.15 (m, 6H), 1.00-1.04 (m, 1H), 0.71-0.78 (m, 1H). | 750.7 |
| I-321 | 17A | $^1$H NMR (400 MHz, CD$_3$OD) δ 9.15 (s, 1H), 8.34-8.37 (m, 1H), 7.42-7.46 (m, 1H), 7.29-7.35 (m, 1H), 7.14-7.18 (m, 1H), 7.05-7.09 (m, 1H), 4.96-4.99 (m, 1H), 4.66-4.69 (m, 1H), 4.56-4.60 (m, 1H), 3.81-4.41 (m, 11H), 3.41-3.48 (m, 1H), 3.07-3.27 (m, 5H), 2.75-2.81 (m, 1H), 2.59-2.65 (m, 1H), 1.64-1.76 (m, 3H), 1.28-1.36 (m, 2H), 1.21-1.26 (m, | 684.7 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 4H), 1.12-1.19 (m, 5H), 1.02-1.06 (m, 1H), 0.70-0.75 (m, 1H). | |
| I-322 | 17A | $^1$H NMR (400 MHz, CD$_3$OD) δ 9.15 (s, 1H), 8.36 (d, J = 4.2 Hz, 1H), 7.31-7.37 (m, 1H), 7.11-7.13 (m, 2H), 6.96-7.05 (m, 1H), 4.96-5.01 (m, 1H), 4.64 (d, J = 6.2 Hz, 1H), 4.48-4.54 (m, 1H), 4.31-4.41 (m, 2H), 4.18-4.28 (m, 2H), 4.01-4.16 (m, 3H), 3.73-3.99 (m, 5H), 3.38-3.49 (m, 1H), 3.26 (d, J = 3.4 Hz, 3H), 3.20-3.23 (m, 1H), 3.10-3.17 (m, 1H), 2.73-2.83 (m, 1H), 2.59-2.69 (m, 1H), 1.65-1.77 (m, 3H), 1.24-1.41 (m, 5H), 1.09-1.13 (m, 6H), 1.00-1.04 (m, 1H), 0.71-0.79 (m, 1H). | 684.7 |
| I-323 | 17A | $^1$H NMR (400 MHz, CD$_3$OD): δ 9.16 (s, 1H), 8.37 (d, J = 7.6 Hz, 1H), 4.40-4.54 (m, 1H), 4.15-4.36 (m, 4H), 3.99-4.09 (m, 4H), 3.82-3.89 (m, 3H), 3.72-3.76 (m, 1H), 3.33-3.34 (m, 2H), 2.95-3.12 (m, 2H), 2.00-2.22 (m, 1H), 1.68-1.88 (m, 3H), 1.40-1.46 (m, 2H), 1.09-1.19 (m, 7H), 1.03-1.04 (m, 1H), 0.88-0.92 (m, 2H), 0.76-0.78 (m, 1H). | 532.1 |
| I-324 | 17A | $^1$H NMR (400 MHz, CD$_3$OD) δ 9.15 (s, 1H), 8.37 (d, J = 5.2 Hz, 1H), 4.91 (s, 1H), 4.32-4.54 (m, 2H), 3.83-4.25 (m, 9H), 3.48-3.74 (m, 1H), 3.33 (s,2H), 2.85-3.25 (m, 4H), 2.56-2.62 (m, 1H), 1.60-1.82 (m, 4H), 1.38-1.45 (m, 3H), 1.02-1.19 (m, 8H), 0.77 (s, 1H). | 546.4 |
| I-325 | 17A | $^1$H NMR (400 MHz, CD$_3$OD): δ 9.18 (s, 1H), 8.52-8.61 (m, 1H), 8.39-8.40 (m, 1H), 3.83-4.36 (m, 9H), 3.14-3.25 (m, 6H), 2.71-2.96 (m, 2H), 1.74-2.05 (m, 3H), 1.33-1.44 (m, 7H), 1.15-1.21 (m, 2H), 1.03-1.06 (m, 1H), 0.80-0.93 (m, 3H). | 546.4 |
| I-326 | 17A | $^1$H NMR (400 MHz, CD$_3$OD): δ 9.15 (s, 1H), 8.36 (d, J = 14.0 Hz, 1H), 4.93-4.97 (m, 1H), 3.74-4.48 (m, 13H), 3.42-3.47 (m, 2H), 3.25-3.29 (m, 2H), 2.94-3.09 (m, 1H), 2.64-2.84 (m, 1H), 2.00-2.02 (m, 2H), 1.64-1.85 (m, 8H), 1.40-1.44 (m, 2H), 1.12-1.29 (m, 11H), 1.03-1.05 (m, 1H), 0.78-0.79 (m, 2H). | 762.3 |
| I-327 | 17A | $^1$H NMR (400 MHz, CD$_3$OD): δ 9.16 (s, 1H), 8.36 (d, J = 14.0 Hz, 1H), 4.92-4.96 (m, 1H), 3.90-4.44 (m, 14H), 3.70-3.75 (m, 1H), 3.39-3.48 (m, 4H), 3.22-3.25 (m, 1.5 H), 2.96-3.03 (m, 0.5H), 2.76-2.83 (m, 0.5H), 2.62-2.67 (m, 0.5H), 1.80-1.99 (m, 4H), 1.62-1.65 (m, 2H), 1.40-1.46 (m, 2H), 1.26-1.31 (m, 3H), 1.11-1.19 (m, 8H), 1.03-1.05 (m, 1H), 0.77-0.79 (m, 1H). | 728.6 |
| I-328 | 17A | $^1$H NMR (400 MHz, CD$_3$OD): δ 9.18 (s, 1H), 8.39 (d, J = 12.0 Hz, 1H), 6.97-7.38 (m, 1H), 4.94-4.98 (m, 1H), 3.36-4.48 (m, 8H), 3.58-5.76 (m, 5H), 3.21-3.23 (m, 1H), 2.78-2.87 (m, 4H), 1.69-1.78 (m, 5H), 1.42-1.56 (m, 2H), 1.26-1.33 (m, 4H), 1.15-1.26 (m, 9H), 0.93-1.06 (m, 4H), 0.76-0.83 (m, 1H). | 629.8 |
| I-329 | 17A | $^1$H NMR (400 MHz, CD$_3$OD) δ 9.17 (s, 1H), 8.34-8.40 (m, 1H), 3.84-4.40 (m, 10H), 3.64-3.66 (m, 3H), 3.54 (t, J = 8.6 Hz, 3H), 3.35-3.42 (m, 2H), 3.22-3.25 (m, 2H), 3.12-3.16 (m, 1H), 3.04-3.08 (m, 2H), 1.94-1.98 (m, 2H), 1.67-1.83 (m, 7H), 1.56 (s, 1H), 1.38-1.45 (m, 1H), 1.23-1.29 (m, 3H), 1.11-1.17 (m, 8H), 0.93-1.05 (m, 3H), 0.77-0.79 (m, 1H) | 630.7 |
| I-330 | 17A | $^1$H NMR (400 MHz, CD$_3$OD): δ 9.15 (s, 1H), 8.35-8.39 (m, 1H), 4.91-4.99 (m, 1H), 3.68-4.40 (m, 13H), 3.34-3.46 (m, 2H), 3.11-3.27 (m, 2H), 2.75-3.05 (m, 1H), 1.85-1.97 (m, 5H), 1.65-1.76 (m, 6H), 1.48-1.62 (m, 3H), 1.13-1.24 (m, 11H), 1.02-1.07 (m, 1H), 0.89-0.98 (m, 2H), 0.74-0.81 (m, 1H). | 685.4 |
| I-331 | 17A | $^1$H NMR (400 MHz, CD$_3$OD): δ 9.16 (s, 1H), 8.34-8.39 (m, 1H), 3.81-4.40 (m, 11H), 3.58-3.68 (m, 2H), 3.38-3.53 (m. 5H), 3.13-3.18 (m, 1H), 1.67-1.90 (m, 7H), 1.35-1.60 (m, 5H), 1.09-1.26 (m, 12H), 0.95-1.06 (m, 3H), 0.77-0.82 (m, 1H). | 631.3 |
| I-332 | 17A | $^1$H NMR(400 MHz, CDCl3): δ 8.90 (s, 1H), 8.25-8.27 (m, 2H), 4.23-4.45 (m, 3H), 4.02-4.13 (m, 3H), 3.77-3.97 (m, 4H), 2.87-3.70 (m, 11H), 1.92-2.23 (m, 3H), 1.65-1.70 (m, 5H), 1.40-1.57 (m, 5H), 1.08-1.25 (m, 9H), 0.87-0.91 (m, 3H), 0.67-0.76 (m, 1H). | 630.8 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-333 | 28 | $^1$H NMR (400 MHz, CD$_3$OD): δ 9.06 (s, 1H), 8.26 (d, J = 20.8 Hz, 1H), 7.24-7.18 (m, 0.5H), 4.60-4.38 (m, 2H), 4.18-3.76 (m, 9H), 3.58-3.25 (m, 8H), 3.13-3.08 (m, 1H), 1.92-1.55 (m, 10H), 1.27-1.19 (m, 3H), 1.02-0.91 (m, 10H), 0.39-0.26 (m, 4H). | 681.7 |
| I-334 | 28 | $^1$H NMR (400 MHz, CD$_3$OD): δ 9.18 (s, 1H), 8.40 (d, J = 18.4 Hz, 1H), 4.75-4.50 (m, 2H), 4.32-3.82 (m, 8H), 3.77 (s, 3H), 3.54-3.47 (m, 1H), 3.29-3.27 (m, 1H), 3.05-3.01 (m, 1H), 2.06-2.00 (m, 2H), 1.72-1.57 (m, 6H), 1.27-1.02- (m, 17H), 0.48-0.38 (m, 4H). | 617.6 |
| I-335 | 17A | $^1$H NMR(400 MHz, CD$_3$OD): δ 9.18 (s, 1H), 8.39 (d, J = 16.0 Hz, 1H), 4.98-4.96 (m, 1H), 4.51-4.45 (m, 4H), 4.30-3.86 (m, 8H), 3.75-3.59 (m, 8H), 3.28-3.24 (m, 1H), 2.04-1.61 (m, 12H), 1.47-1.38 (m, 1H), 1.19-1.13 (m, 8H), 1.06-1.05 (m, 1H), 0.94-0.90 (m, 2H), 0.81-0.79 (m, 1H). | 706.7 |
| I-336 | 17A | $^1$H NMR (400 MHz, CD$_3$OD): δ 9.16 (s, 1H), 8.37 (d, J = 16.0 Hz, 1H), 4.95-4.90 (m, 1H), 4.50-3.82 (m, 13H), 3.76-3.70 (m, 5H), 3.50-3.36 (m, 3H), 3.23 (d, J = 7.2 Hz, 1H), 3.04-2.98 (m, 1H), 1.98-1.82 (m, 5H), 1.68-1.62 (m, 3H), 1.52-1.44 (m, 2H), 1.37 (d, J = 6.4 Hz, 6H), 1.20-1.11 (m, 8H), 0.82-0.75 (m, 1H). | 698.7 |
| I-337 | 28 | $^1$H NMR (400 MHz, CDCl3) δ 9.15 (s, 1H), 8.37 (d, J = 7.4 Hz, 1H), 4.97-4.94 (m, 1H), 4.71-4.44 (m, 2H), 4.08-3.75 (m, 10H), 3.45-3.34 (m, 3H), 3.26-3.23 (m, 2H), 3.13-3.07 (m, 1H), 2.05-1.99 (m, 2H), 1.92-1.39 (m, 10H), 1.23 (s, 1H), 1.17 (t, J = 5.6 Hz, 3H), 1.02 (d, J = 4.4 Hz, 7H), 0.48-0.43 (m, 2H), 0.36-0.35 (m, 2H). | 694.6 |
| I-338 | 28 | $^1$H NMR(400 MHz, CD$_3$OD): δ 9.18 (s, 1H), 8.41-8.35 (m, 1H), 7.75 (d, J = 7.6 Hz, 1H), 7.35-7.26 (m, 1H), 5.61-5.57 (m 1H), 4.64-4.44 (m, 2H), 4.25-3.94 (m, 7H), 3.66-3.45 (m, 3H), 3.05-2.98 (m, 3H), 2.76-2.75 (m, 3H), 1.97-1.84 (m, 3H), 1.40-1.32 (m, 3H), 1.06 (d, J = 6.8 Hz, 2H), 0.95-0.90 (m, 4H), 0.52 (s, 1H), 0.40-0.24 (m, 3H). | 609.5 |
| I-339 | 28 | $^1$H NMR(400 MHz, CD$_3$OD): δ 9.15-9.12 (m, 1H), 8.35-8.19 (m, 2H), 7.77-7.68 (m, 2H), 5.10 (s, 2H), 4.50-3.42 (m, 13H), 3.22 (s, 1H), 1.91 (s, 4H), 1.31-0.78 (m, 13H), 0.48-0.20 (m, 4H). | 610.5 |
| I-340 | 28 | $^1$H NMR (400 MHz, CD$_3$OD): δ 9.15 (s, 1H), 8.38-8.32 (m, 1H), 7.77-7.69 (m, 1H), 7.31-7.21 (m, 2H), 6.08 (s, 1H), 4.55-3.76 (m, 11H), 3.56 (t, J = 11.0 Hz, 2H), 3.45-3.39 (m, 1H), 3.09-3.06 (m, 3H), 3.00-2.93 (m, 4H), 1.90-1.80 (m, 4H), 1.37 (d, J = 6.6 Hz, 1H), 1.04 (d, J = 7.7 Hz, 3H), 0.96-0.88 (m, 4H), 0.48-0.30 (m, 4H). | 623.6 |
| I-341 | 28 | $^1$H NMR (400 MHz, DMSO-d$_6$): δ 9.15 (s, 1H), 8.37 (d, J = 17.6 Hz, 1H), 7.87-7.79 (m, 1H), 4.76-4.46 (m, 2H), 4.31-3.82 (m, 10H), 3.48-3.38 (m, 4H), 3.23-3.17 (m, 1H), 1.87-1.78 (m, 1H), 1.70-1.67 (m, 2H), 1.38-1.00 (m, 18H), 0.48-0.36 (m, 4H). | 591.6 |
| I-342 | 17A | $^1$H NMR (400 MHz, CDCl3): δ 9.15 (s, 1H), 8.37 (d, J = 9.2 Hz, 1H), 4.40-3.88 (m, 11H), 3.74-3.68 (m, 3H), 3.27-3.23 (m, 1H), 3.01-2.96 (m, 1H), 2.75 (d, J = 11.6 Hz, 3H), 2.02-1.92 (m, 2H), 1.71-1.59 (m, 4H), 1.53-1.44 (m, 2H), 1.37 (d, J = 6.4 Hz, 3H), 1.19-1.11 (m, 8H), 1.06-1.01 (m, 1H), 0.80-0.75 (m, 1H). | 602.25 |
| I-343 | 17A | $^1$H NMR (400 MHz, CD$_3$OD): δ 4.97-4.92 (m, 1H), 4.50-4.45 (m, 4H), 4.34-3.40 (m, 17H), 3.21 (d, J = 9.2 Hz, 1H), 3.02-3.00 (m, 1H), 2.68 (s, 3H), 2.42 (s, 3H), 1.96-1.85 (m, 6H), 1.67-1.62 (m, 4H), 1.50-1.38 (m, 3H), 1.17-1.03 (m, 10H), 0.78-0.77 (m, 1H). | 726.6 |
| I-344 | 29 | $^1$H NMR (400 MHz, CD$_3$OD): δ 9.15 (d, J = 3.2 Hz, 1H), 8.34 (d, J = 7.2 Hz, 1H), 4.31 (dd, J = 3.2, 8.8 Hz, 1H), 4.12-4.02 (m, 2H), 3.92-3.37 (m, 12H), 3.27-3.25 (m, 1H), 3.01-2.98 (m, 1H), 2.74 (d, J = 14.8 Hz, 3H), 2.64-2.57 (m, 2H), 2.03-1.42 (m, 18H), 1.19 (d, J = 6.4 Hz, 3H). | 588.45 |
| I-345 | 29 | $^1$H NMR (400 MHz, CD$_3$OD) δ9.15 (d, J = 1.8 Hz, 1H), 8.34 (d, J = 4.0 Hz, 1H), 4.33-4.30 (m, 1H), 4.08-4.03 (m, 2H), 3.94-3.72 (m, 10H), 3.56-3.35 (m, 6H), 3.28-3.25 (m, 1H), 3.01-2.98 (m, 1H), 2.74 (d, J = 7.2 Hz, 3H), 2.66-2.60 (m, 2H), 2.32-2.25 (m, 1H), 2.07-1.95 (m, 3H), 1.69-1.49 (m, 8H), 1.19 (d, J = 3.0 Hz, 3H). | 590.45 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-346 | 29 | $^1$H NMR (400 MHz, CD$_3$OD): δ 9.06 (s, 1H), 8.25 (d, J = 6.4 Hz, 1H), 4.23-4.21 (m, 1H), 4.01-3.94 (m, 2H), 3.83-3.78 (m, 5H), 3.64-3.54 (m, 4H), 3.45-3.29 (m, 6H), 3.16 (d, J = 9.6 Hz, 1H), 2.90 (d, J = 9.2 Hz, 1H), 2.64 (d, J = 14.4 Hz, 3H), 2.55-2.48 (m, 2H), 1.92-1.85 (m, 2H), 1.59-1.54 (m, 7H), 1.42-1.36 (m, 2H), 1.16 (s, 1H), 1.09 (d, J = 6.0 Hz, 3H). | 604.85 |
| I-347 | 29 | $^1$H NMR (400 MHz, CD$_3$OD) δ9.05 (d, J = 2.4 Hz, 1H), 8.25 (d, J = 4.8 Hz, 1H), 4.24-4.21 (m, 1H), 4.04-3.93 (m, 2H), 3.83-3.62 (m, 7H), 3.47-3.25 (m, 4H), 3.18-3.15 (m, 1H), 2.91-2.88 (m, 1H), 2.65 (d, J = 7.2 Hz, 3H), 2.41-2.36 (m, 2H), 1.92-1.85 (m, 2H), 1.59-1.53 (m, 4H), 1.42-1.39 (m, 2H), 1.09 (d, J = 3.2 Hz, 3H), 0.84-0.81 (m, 9H). | 576.40 |
| I-348 | 29 | $^1$H NMR (400 MHz, CD$_3$OD) δ9.05 (d, J = 2.0 Hz, 1H), 8.24 (d, J = 4.2 Hz, 1H), 4.69-4.64 (m, 2H), 4.34-4.29 (m, 2H), 4.22-4.19 (m, 1H), 3.97-3.62 (m, 8H), 3.37-3.25 (m, 3H), 3.18-3.16 (m, 3H), 2.98-2.89 (m, 2H), 2.79-2.74 (m. 2H), 2.64 (d, J = 7.4 Hz, 1H), 1.92-1.83 (m, 2H), 1.60-1.54 (m, 4H), 1.45-1.42 (m, 6H), 1.08 (d, J = 3.0 Hz, 3H). | 576.45 |
| I-349 | 29 | $^1$H NMR (400 MHz, CD$_3$OD): δ 9.04 (d, J = 4.8 Hz, 1H), 8.23 (d, J = 9.2 Hz, 1H), 7.37-7.35 (m, 1H), 6.27-6.25 (m, 1H), 6.20-6.16 (m, 1H), 4.19-4.15 (m, 1H), 3.94-3.90 (m, 2H), 3.82-3.73 (m, 2H), 3.68-3.57 (m, 6H), 3.41-3.30 (m, 4H), 3.17-3.14 (m, 2H), 2.89-2.86 (m, 1H), 2.63 (d, J = 16.4 Hz, 3H), 1.91-1.85 (m, 2H), 1.59-1.53 (m, 4H), 1.41-1.38 (m, 2H), 1.07-1.04 (m, 3H). | 586.85 |
| I-350 | 29 | $^1$H NMR (400 MHz, CD$_3$OD) δ 9.17 (d, J = 4.4 Hz, 1H), 8.36 (d, J = 10.0 Hz, 1H), 8.21 (d, J = 6.0 Hz, 1H), 7.07 (d, J = 8.4 Hz, 1H), 4. 32-4. 28 (m, 1H), 4.08-4.04 (m, 2H), 3.93-3.86 (m, 2H), 3.83-3.73 (m, 6H), 3.52-3.25 (m, 7H), 3.01-2.97 (m, 1H), 2.76 (d, J = 15.6 Hz, 3H), 1.95-2.04 (m, 2H), 1.64-1.72 (m, 4H), 1.45-1.54 (m, 2H), 1.15-1.18 (m, 3H). | 587.40 |
| I-351 | 29 | $^1$H NMR(400 MHz, CD$_3$OD): δ 9.16 (d, J = 5.6 Hz, 1H), 8.36 (d, J = 10.4 Hz, 1H), 7.6 (s, 1H), 6.29 (d, J = 9.6 Hz, 1H), 4.32-4.29 (m, 1H), 4.08-4.04 (m, 2H), 3.93-3.88 (m, 2H), 3.83-3.73 (m, 6H), 3.50-3.37 (m, 5H), 3.28-3.25 (m, 1H), 3.01-2.97 (m, 1H), 2.75 (d, J = 16.0 Hz, 3H), 1.99-1.97 (m, 2H), 1.70-1.65 (m, 4H), 1.52-1.49 (m, 2H), 1.18-1.16 (m, 3H). | 586.45 |
| I-352 | 29 | $^1$H NMR(400 MHz, CD$_3$OD): δ 9.18 (s, 1H), 8.37 (s, 1H), 4.36 (s, 1H), 4.19-3.76 (m, 12H), 3.57-3.50 (m, 1H), 3.39 (t, J = 8.4 Hz, 1H), 3.20 (t, J = 8.4 Hz , 1H), 3.04-3.01 (m, 2H), 2.75 (d, J = 13.6 Hz, 3H), 2.09-2.07 (m, 2H), 1.94-1.92 (m, 2H), 1.77-1.68 (m, 5H), 1.58-1.54 (m, 2H), 1.31-1.19 (m, 6H), 0.95-0.93 (m, 2H). | 562.6 |
| I-353 | 16A | $^1$H NMR (400 MHz, CD$_3$OD): δ 8.22 (d, J = 8.8 Hz, 1H), 7.93 (d, J = 6.4 Hz, 1H), 7.42-7.23 (m, 5H), 5.38 (s, 2H), 4.45-4.31 (m, 5.83 Hz, 2H), 4.22-3.80 (m, 8H), 3.52-3.33 (m, 4H), 3.23-3.12 (m, 1H), 2.53-2.49 (m, 2H), 1.76-1.66 (m, 5H), 1.53 (s, 1H), 1.44-1.32 (m, 2H), 1.27-1.19 (m, 3H), 1.06-1.01 (m, 1H), 1.11 (s, 2H), 1.15 (d, J = 7.2 Hz, 6H), 0.97-0.90 (m, 2H), 0.78-0.75 (m, 1H). | 705.10 |
| I-354 | 18 | $^1$H NMR (400 MHz, DMSO-d$_6$) & 9.25 (s, 1H), 8.40-8.35 (m, 1H), 8.27-8.19 (m, 1H), 7.79-7.69 (m, 1H), 4.28-4.19 (m, 2H), 4.13-3.93 (m, 3H), 3.90-3.69 (m, 5H), 3.46-3.34 (m, 2H), 3.23-3.19 (m, 1H), 2.60-2.55 (m, 3H), 1.61-1.59 (m, 2H), 1.38-1.29 (m, 7H), 1.18-1.16 (m, 2H), 1.12-1.04 (m, 10H), 0.87 (d, J = 6.8 Hz, 3H), 0.68-0.66 (m, 1H). | 588.4 |
| I-355 | 18 | $^1$H NMR (400 MHz, DMSO-d$_6$) δ 9.25 (s, 1H), 8.37 (d, J = 17.8 Hz, 1H), 8.24 (m, 1H), 7.82-7.68 (m, 1H), 4.23 (m, 2H), 4.14-4.07 (m, 2H), 4.01-3.67 (m, 6H), 3.58-3.46 (m, 1H), 3.29-3.25 (m, 1H), 3.16 (t, J = 7.8 Hz, 1H), 2.58 (dd, J = 13.0, 4.4 Hz, 3H), 1.63 (m, 4H), 1.48 (s, 1H), 1.37-1.28 (m, 1H), 1.13-0.98 (m, 11H), 0.85 (d, J = 11.0 Hz, 3H), 0.67 (s, 1H), 0.26-0.20 (m, 2H), 0.14 (m, 2H). | 600.4 |
| I-356 | 18 | $^1$H NMR (400 MHz, DMSO-d$_6$) δ 9.26 (s, 1H), 8.44-8.26 (m, 2H), 7.78-7.64 (m, 1H), 7.30-7.24 (m, 2H), 7.21-7.12 (m, 3H), 5.22-5.17 (m, 1H), 4.38-4.26 (m, 1H), 4.26-4.04 (m, 5H), 4.01-3.69 (m, 4H), 3.62-3.47 (m, | 554.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 1H), 2.68-2.53 (m, 5H), 1.38-1.29 (m, 1H), 1.13-1.02 (m, 3H), 0.94-0.88 (m, 3H), 0.84-0.78 (m, 1H), 0.67-0.56 (m, 1H). | |
| I-357 | 18 | $^1$H NMR (400 MHz, DMSO-d$_6$) δ 9.25 (s, 1H), 8.41-8.24 (m, 2H), 4.83-4.72 (m, 1H), 4.20-4.05 (m, 3H), 4.01-3.92 (m, 1H), 3.89-3.75 (m, 4H), 3.64 (s, 1H), 3.43 (s, 5H), 1.70-1.56 (m, 8H), 1.49-1.39 (m, 4H), 1.20-1.16 (m, 1H), 1.12-1.03 (m, 11H), 0.88-0.65 (m, 5H), 0.58 (s, 2H), 0.49-0.41 (m, 2H). | 654.4 |
| I-358 | 4A | $^1$H NMR (400 MHz, DMSO-d$_6$) δ 8.34-8.25 (m, 1H), 7.86-7.82 (m, 1H), 7.46-7.44 (m, 1H), 7.34-7.26 (m, 5H), 4.54-4.32 (m, 3H), 4.23-4.10 (m, 1H), 4.00-3.78 (m, 4H), 3.75-3.42 (m, 7H), 2.61 (t, J = 3.6 Hz, 3H), 1.31-1.21 (m, 1H), 1.10-1.00 (m, 9H), 0.85-0.83 (m, 1H), 0.67-0.64 (m, 1H). | 565.4 |
| I-359 | 2A | $^1$H NMR (400 MHz, Methanol-d$_4$) δ 9.09 (s, 1H), 8.19 (s, 1H), 7.92 (d, J = 9.5 Hz, 1H), 7.76-7.59 (m, 2H), 7.45-7.19 (m, 5H), 5.38 (s, 2H), 4.80-4.61 (m, 2H), 4.47-3.76 (m, 8H), 1.41 (s, 1H), 1.36-1.33 (m, 1H), 1.15 (s, 3H), 1.08 (s, 3H), 1.03 (d, J = 4.7 Hz, 1H), 0.89 (d, J = 7.5 Hz, 1H), 0.79-0.73 (m, 1H). | 528.3 |
| I-360 | 18 | $^1$H NMR (400 MHz, DMSO-d$_6$) δ 9.25 (s, 1H), 8.44-8.29 (m, 2H), 4.84 (s, 1H), 4.41-3.59 (m, 11H), 3.28-3.10 (m, 6H), 3.08-2.78 (m, 1H), 1.98 (s, 2H), 1.85-1.51 (m, 7H), 1.42-1.14 (m, 5H), 1.12-0.97 (m, 13H), 0.86 (s, 1H), 0.68 (s, 1H). | 722.3 |
| I-361 | 18 | $^1$H NMR (400 MHz, DMSO-d$_6$) δ 9.25 (s, 1H), 8.47-8.33 (m, 2H), 4.97-4.86 (m, 1H), 4.24-3.37 (m, 15H), 2.04-1.64 (m, 10H), 1.49-1.33 (m, 1H), 1.32-1.16 (m, 2H), 1.14-0.99 (m, 13H), 0.89-0.83 (m, 1H), 0.73-0.64 (m, 1H). | 714.1 |
| I-362 | 18 | $^1$H NMR (400 MHz, DMSO-d$_6$) δ 9.25 (t, J = 3.6 Hz, 1H), 8.95-8.79 (m, 1H), 8.41-8.31 (m, 1H), 8.21-8.05 (m, 1H), 7.72-7.57 (m, 1H), 7.29-7.20 (m, 1H), 7.17 (d, J = 8.0 Hz, 1H), 5.56-5.41 (m, 1H), 4.30-3.96 (m, 4H), 3.94-3.64 (m, 4H), 3.61-3.46 (m, 1H), 2.72-2.63 (m, 1H), 2.59 (dd, J = 8.5, 4.2 Hz, 3H), 1.91-1.76 (m, 4H), 1.70 (d, J = 12.6 Hz, 1H), 1.55-1.43 (m, 2H), 1.38 (t, J = 11.9 Hz, 2H), 1.32-1.18 (m, 2H), 1.14-1.07 (m, 3H), 1.06-0.99 (m, 2H), 0.92-0.73 (m, 2H), 0.70-0.58 (m, 1H). | 593.4 |
| I-363 | 2A | $^1$H NMR (400 MHz, Methanol-d$_4$) δ 8.25-8.17 (m, 1H), 7.92 (d, J = 13.2 Hz, 1H), 7.38-7.24 (m, 5H), 7.19-7.09 (m, 4H), 5.37 (s, 2H), 4.49-3.81 (m, 10H), 3.25-3.07 (m, 1H), 2.29 (s, 3H), 1.48-1.20 (m, 2H), 1.17-1.02 (m, 7H), 0.79-0.73 (m, 1H). | 540.3 |
| I-364 | 2A | $^1$H NMR (400 MHz, Methanol-d$_4$) δ 8.39-8.34 (m, 1H), 8.25-8.16 (m, 1H), 7.94-7.88 (m, 1H), 7.70-7.61 (m, 1H), 7.38-7.20 (m, 6H), 5.38 (s, 2H), 4.49-4.33 (m, 2H), 4.33-3.77 (m, 8H), 3.25-3.09 (m, 1H), 2.50 (s, 3H), 1.46-1.31 (m, 2H), 1.20-1.10 (m, 4H), 1.09-0.99 (m, 3H), 0.93-0.83 (m, 1H). | 541.3 |
| I-365 | 2A | $^1$H NMR (400 MHz, Methanol-d$_4$) δ 8.31 (d, J = 8.9 Hz, 1H), 8.21 (d, J = 14.3 Hz, 1H), 7.92 (d, J = 9.0 Hz, 1H), 7.60 (s, 1H), 7.31 (d, J = 18.0 Hz, 6H), 5.38 (s, 2H), 4.61-3.77 (m, 10H), 2.32 (s, 3H), 1.41 (s, 2H), 1.19-1.01 (m, 8H), 0.77 (s, 1H). | 541.3 |
| I-366 | 2A | $^1$H NMR (400 MHz, Methanol-d$_4$) δ 8.23-8.14 (m, 1H), 7.93-7.86 (m, 1H), 7.63-7.47 (m, 2H), 7.39-7.22 (m, 5H), 5.36 (s, 2H), 5.27-5.17 (m, 1H), 4.48-3.73 (m, 8H), 3.28-3.14 (m, 1H), 2.65 (s, 3H), 1.59-1.51 (m, 3H), 1.42-1.25 (m, 1H), 1.20-0.93 (m, 7H), 0.83-0.70 (m, 1H). | 556.3 |
| I-367 | 18 | $^1$H NMR (400 MHz, DMSO-d$_6$) δ 9.25 (s, 1H), 8.41-8.31 (m, 2H), 4.86 (s, 1H), 4.22-3.71 (m, 10H), 3.70-3.60 (m, 3H), 3.23-3.11 (m, 7H), 1.83-1.53 (m, 11H), 1.14-0.95 (m, 17H), 0.87 (s, 2H), 0.67 (s, 1H). | 686.4 |
| I-368 | 2A | $^1$H NMR (400 MHz, Methanol-d$_4$) δ 8.21 (d, J = 17.2 Hz, 1H), 7.92 (d, J = 12.8 Hz, 1H), 7.29 (m, 10H), 5.38 (d, J = 4.8 Hz, 2H), 4.74-4.33 (m, 3H), 4.21-3.77 (m, 9H), 3.12 (d, J = 8.8 Hz, 1H), 2.74 (d, J = 10.6 Hz, 3H), 1.51-1.00 (m, 13H), 0.73 (d, J = 8.0 Hz, 1H). | 657.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-369 | 18 | $^1$H NMR (400 MHz, Methanol-d$_4$) δ 9.15 (s, 1H), 8.37 (d, J = 13.8 Hz, 1H), 4.92 (s, 2H), 4.46-3.79 (m, 12H), 3.48 (s, 1H), 3.27-2.58 (m, 6H), 1.71 (m, 8H), 1.39 (s, 3H), 1.20-0.95 (m, 19H), 0.78 (s, 1H). | 686.4 |
| I-370 | 18 | $^1$H NMR (400 MHz, DMSO-d$_6$) δ 9.25 (s, 1H), 8.44-8.32 (m, 1H), 8.27-8.14 (m, 1H), 7.80-7.63 (m, 1H), 4.32-4.06 (m, 4H), 4.03-3.61 (m, 6H), 3.58-3.44 (m, 1H), 3.24 (dd, J = 14.8, 7.0 Hz, 1H), 3.13 (dt, J = 15.8, 7.8 Hz, 1H), 2.57 (dd, J = 13.0, 4.4 Hz, 3H), 1.75-1.49 (m, 4H), 1.31 (p, J = 13.0, 12.4 Hz, 3H), 1.13-0.99 (m, 9H), 0.95-0.81 (m, 4H), 0.75-0.56 (m, 1H), 0.27-0.10 (m, 4H). | 600.4 |
| I-371 | 2A | $^1$H NMR (400 MHz, Methanol-d$_4$) δ 8.24-8.18 (m, 1H), 7.92 (d, J = 9.3 Hz, 1H), 7.56-7.51 (m, 1H), 7.38-7.24 (m, 5H), 7.17-7.09 (m, 1H), 5.38 (s, 2H), 4.71-4.49 (m, 2H), 4.42-4.09 (m, 3H), 4.06 (s, 3H), 4.04-3.81 (m, 4H), 1.43-1.32 (m, 3H), 1.18-1.13 (m, 3H), 1.13-1.07 (m, 3H), 1.04-1.01 (m, 1H), 0.79-0.73 (m, 1H). | 558.3 |
| I-372 | 2A | $^1$H NMR (400 MHz, Methanol-d$_4$) δ 8.25-8.10 (m, 2H), 7.92 (d, J = 9.9 Hz, 1H), 7.32 (dq, J = 15.1, 5.9, 4.6 Hz, 5H), 5.38 (s, 2H), 4.50-4.27 (m, 2H), 4.25-4.11 (m, 2H), 4.10-4.00 (m, 2H), 3.95 (dd, J = 12.8, 7.4 Hz, 2H), 3.90-3.77 (m, 2H), 3.47-3.34 (m, 2H), 3.21 (dd, J = 9.2, 6.3 Hz, 1H), 2.74 (d, J = 8.6 Hz, 3H), 1.57 (d, J = 11.2 Hz, 2H), 1.47-1.28 (m, 5H), 1.18 (d, J = 4.3 Hz, 3H), 1.15 (d, J = 7.3 Hz, 6H), 1.10 (s, 3H), 1.07-1.01 (m, 1H), 0.89 (d, J = 6.8 Hz, 6H), 0.77 (dd, J = 8.0, 4.2 Hz, 1H). | 675.5 |
| I-373 | 4A | $^1$H NMR (400 MHz, DMSO-d$_6$) δ 8.33-8.24 (m, 1H), 7.86-7.81 (m, 1H), 7.66-7.65 (m, 1H), 7.34-7.19 (m, 11H), 5.27 (s, 2H), 4.54-4.33 (m, 3H), 4.21-4.11 (m, 1H), 4.00-3.59 (m, 7H), 3.53-3.36 (m, 4H), 2.62-2.60 (m, 3H), 1.32-1.20 (m, 1H), 1.12-1.00 (m, 9H), 0.85-0.83 (m, 1H), 0.67-0.60 (m, 1H). | 655.4 |
| I-374 | 18 | $^1$H NMR (400 MHz, DMSO-d$_6$) δ 9.25 (s, 1H), 8.40-8.31 (m, 2H), 4.87 (s, 1H), 4.26-3.65 (m, 13H), 3.22-3.13 (m, 7H), 1.78-1.59 (m, 9H), 1.31-1.09 (m, 9H), 1.07-0.96 (m, 10H), 0.87-0.86 (m, 2H), 0.68-0.66 (m, 1H). | 686.5 |
| I-375 | 18 | $^1$H NMR (400 MHz, DMSO-d$_6$) δ 9.25 (s, 1H), 8.70-8.59 (m, 1H), 8.41-8.33 (m, 1H), 8.19-8.07 (m, 1H), 7.35-7.21 (m, 5H), 4.82-4.67 (m, 1H), 4.61-4.44 (m, 2H), 4.27-4.17 (m, 1H), 4.13-3.91 (m, 3H), 3.88-3.62 (m, 4H), 3.59-3.41 (m, 1H), 2.65-2.57 (m, 3H), 1.27-1.18 (m, 1H), 1.08-0.96 (m, 6H), 0.93-0.74 (m, 4H), 0.70-0.55 (m, 2H). | 580.2 |
| I-376 | 2A | $^1$H NMR (400 MHz, Methanol-d$_4$) δ 8.21 (d, J = 13.7 Hz, 1H), 7.91 (d, J = 9.6 Hz, 1H), 7.69 (m, J = 26.0, 8.6, 4.5 Hz, 2H), 7.41-7.22 (m, 5H), 5.37 (s, 2H), 4.79-4.58 (m, 2H), 4.44-3.81 (m, 9H), 1.47-1.27 (m, 3H), 1.20-1.13 (m, 4H), 1.08 (s, 3H), 0.76 (m, J = 8.0, 4.3 Hz, 1H). | 562.2 |
| I-377 | 2A | $^1$H NMR (400 MHz, Methanol-d$_4$) δ 8.21 (d, J = 12.0 Hz, 1H), 8.18-7.95 (m, 2H), 7.91 (d, J = 9.4 Hz, 1H), 7.37-7.24 (m, 5H), 5.37 (s, 2H), 4.83-4.61 (m, 2H), 4.44-3.73 (m, 8H), 3.40-3.33 (m, 1H), 3.11-2.97 (m, 1H), 2.05-1.88 (m, 4H), 1.85-1.78 (m, 1H), 1.70-1.32 (m, 7H), 1.20-1.10 (m, 5H), 1.08-0.99 (m, 2H). | 610.4 |
| I-378 | 18 | $^1$H NMR (400 MHz, Methanol-d$_4$) δ 9.16 (s, 1H), 8.37 (d, J = 9.8 Hz, 1H), 7.62-7.47 (m, 2H), 4.78-4.57 (m, 2H), 4.40 (m 1H), 4.32-4.19 (m, 2H), 4.19-4.00 (m, 3H), 4.01-3.80 (m, 3H), 2.66 (m, 3H), 1.47-1.26 (m, 2H), 1.19-1.01 (m, 7H), 0.76 (m, 1H). | 469.2 |
| I-379 | 18 | $^1$H NMR (400 MHz, DMSO-d$_6$) δ 9.25 (s, 1H), 8.42-8.33 (m, 1H), 8.21-8.12 (m, 1H), 7.77-7.63 (m, 1H), 4.90-4.81 (m, 1H), 4.27-3.61 (m, 10H), 3.56-3.40 (m, 1H), 2.62-2.53 (m, 3H), 1.75-1.51 (m, 5H), 1.41-1.24 (m, 3H), 1.22-0.99 (m, 10H), 0.95-0.75 (m, 3H), 0.72-0.65 (m, 1H). | 560.2 |
| I-380 | 18 | $^1$H NMR (400 MHz, DMSO-d$_6$) δ 9.25 (s, 1H), 8.49-8.35 (m, 2H), 4.87 (s, 1H), 4.22-3.95 (m, 4H), 3.86-3.75 (m, 3H), 3.65-3.42 (m, 8H), 3.23-3.19 (m, 1H), 1.97-1.95 (m, 2H), 1.76-1.69 (m, 4H), 1.30-1.24 (m, 5H), 1.12-1.04 (m, 12H), 0.87-0.85 (m, 1H), 0.68-0.66 (m, 1H), 0.31 (s, 4H). | 690.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-381 | 2B | $^1$H NMR (400 MHz, Methanol-$d_4$) δ 8.26-8.16 (m, 1H), 7.96-7.87 (m, 1H), 7.55 (t, J = 8.8 Hz, 2H), 7.39-7.23 (m, 5H), 5.38 (s, 2H), 4.77-4.46 (m, 2H), 4.32-3.77 (m, 8H), 3.26 (q, J = 5.3 Hz, 1H), 2.65 (s, 3H), 1.44-1.37 (m, 1H), 1.19-1.02 (m, 7H), 0.82-0.72 (m, 1H). | 542.3 |
| I-382 | 2A | $^1$H NMR (400 MHz, Methanol-$d_4$) δ 8.25-8.15 (m, 1H), 7.92 (d, J = 13.2 Hz, 1H), 7.49-7.19 (m, 5H), 5.38 (s, 2H), 4.39-3.76 (m, 8H), 3.24-2.89 (m, 3H), 1.82-1.64 (m, 4H), 1.46-1.36 (m, 2H), 1.22-1.08 (m, 6H), 1.06-0.87 (m, 9H), 0.81-0.73 (m, 1H). | 546.3 |
| I-383 | 18 | $^1$H NMR (400 MHz, DMSO-$d_6$) δ 9.25 (s, 1H), 8.46-8.33 (m, 2H), 4.86 (d, J = 5.2 Hz, 1H), 4.73 (d, J = 17.9 Hz, 1H), 4.25-3.59 (m, 13H), 3.47 (d, J = 33.1 Hz, 1H), 3.22 (s, 2H), 3.05 (s, 7H), 1.97 (s, 2H), 1.73 (s, 7H), 1.31 (s, 2H), 1.18-1.02 (m, 12H), 0.85 (s, 1H), 0.68 (s, 1H). | 680.4 |
| I-384 | 4A | $^1$H NMR (400 MHz, DMSO-$d_6$) δ 8.33-8.24 (m, 1H), 7.87-7.81 (m, 1H), 7.53-7.51 (m, 1H), 7.35-7.24 (m, 5H), 4.54-4.51 (m, 1H), 4.45-4.41 (m, 1H), 4.38-3.83 (m, 6H), 3.79-3.78 (m, 3H), 3.74-3.35 (m, 7H), 2.62-2.60 (m, 3H), 1.35-1.28 (m, 1H), 1.10-1.00 (m, 9H), 0.85-0.83 (m, 1H), 0.67-0.60 (m, 1H). | 579.3 |
| I-385 | 18 | H NMR (400 MHz, DMSO-$d_6$) δ 9.25 (s, 1H), 8.48-8.33 (m, 2H), 4.92-4.83 (m, 1H), 4.25-3.93 (m, 4H), 3.92-3.69 (m, 5H), 3.67-3.58 (m, 2H), 3.44-3.37 (m, 2H), 3.31-3.18 (m, 6H), 3.18-3.08 (m, 1H), 2.03-1.92 (m, 2H), 1.85-1.68 (m, 6H), 1.66-1.56 (m, 1H), 1.41-1.23 (m, 3H), 1.15-1.02 (m, 11H), 0.88-0.83 (m, 1H), 0.70-0.64 (m, 1H). | 694.3 |
| I-386 | 18 | $^1$H NMR (400 MHz, DMSO-$d_6$) δ 9.25 (s, 1H), 8.48-8.33 (m, 2H), 4.91-4.82 (m, 1H), 4.25-3.71 (m, 7H), 3.68-3.59 (m, 2H), 3.54-3.38 (m, 5H), 3.38-3.32 (m, 1H), 3.26-3.18 (m, 1H), 2.04-1.90 (m, 2H), 1.85-1.54 (m, 5H), 1.36-1.04 (m, 16H), 0.96-0.83 (m, 7H), 0.71-0.65 (m, 1H). | 692.3 |
| I-387 | 30 | $^1$H NMR (400 MHz, Methanol-$d_4$) δ 8.21 (d, J = 14.0 Hz, 1H), 8.04-7.74 (m, 3H), 7.40-7.20 (m, 5H), 5.37 (s, 2H), 4.76-3.72 (m, 9H), 3.28-3.16 (m, 1H), 2.76 (s, 3H), 1.08-0.87 (m, 7H), 0.52-0.21 (m, 4H). | 556.4 |
| I-388 | 2A | $^1$H NMR (400 MHz, Methanol-$d_4$) δ 8.27-8.11 (m, 1H), 7.91 (d, J = 13.2 Hz, 1H), 7.44-7.19 (m, 5H), 5.37 (d, J = 2.8 Hz, 2H), 4.42-4.02 (m, 4H), 4.02-3.74 (m, 4H), 3.27-3.00 (m, 3H), 1.78-1.58 (m, 2H), 1.55-1.26 (m, 8H), 1.19-1.16 (m, 2H), 1.16-1.07 (m, 4H), 1.06-1.00 (m, 1H), 0.99-0.82 (m, 4H), 0.81-0.75 (m, 1H). | 546.4 |
| I-389 | 20 | $^1$H NMR (400 MHz, Methanol-$d_4$) δ 9.15 (s, 1H), 8.37 (d, J = 13.8 Hz, 1H), 4.96-3.61 (m, 13H), 3.41-2.55 (m, 5H), 2.39-1.35 (m, 12H), 1.26-0.88 (m, 18H), 0.65-0.09 (m, 5H). | 686.5 |
| I-390 | 18 | $^1$H NMR (400 MHz, DMSO-$d_6$) δ 9.25 (s, 1H), 8.40-8.34 (m, 2H), 4.87 (s, 1H), 4.14-4.09 (m, 3H), 3.88-3.78 (m, 5H), 3.65-3.56 (m, 4H), 3.20-3.15 (m, 9H), 1.81-1.77 (m, 3H), 1.70-1.63 (m, 7H), 1.54-1.51 (m, 3H), 1.36-1.29 (m, 3H), 1.24-1.09 (m, 8H), 1.06-1.04 (m, 4H), 0.87-0.86 (m, 3H), 0.68-0.67 (m, 1H). | 712.6 |
| I-391 | 2A | $^1$H NMR (400 MHz, Methanol-$d_4$) δ 8.26-8.09 (m, 1H), 7.95-7.86 (m, 1H), 7.81-7.63 (m, 1H), 7.39-7.17 (m, 7H), 5.60-5.31 (m, 2H), 4.54-4.11 (m, 3H), 4.08-3.78 (m, 5H), 3.55-3.34 (m, 1H), 2.81-2.65 (m, 4H), 1.90 (dd, J = 28.4, 12.8 Hz, 4H), 1.76 (d, J = 12.6 Hz, 1H), 1.56 (q, J = 12.2, 11.8 Hz, 2H), 1.48-1.40 (m, 2H), 1.39-1.24 (m, 2H), 1.22-1.03 (m, 6H), 1.01-0.89 (m, 1H), 0.81-0.66 (m, 1H). | 666.5 |
| I-392 | 2A | $^1$H NMR (400 MHz, Methanol-$d_4$) δ 8.28-8.16 (m, 1H), 8.08-8.01 (m, 1H), 7.95-7.81 (m, 2H), 7.43-7.24 (m, 5H), 5.37 (s, 2H), 4.92-4.85 (m, 1H), 4.82-4.72 (m, 1H), 4.50-4.31 (m, 1H), 4.26-3.75 (m, 7H), 3.38-3.32 (m, 1H), 1.47-1.35 (m, 1H), 1.19-1.00 (m, 7H), 0.79-0.72 (m, 1H), $^{19}$F NMR (376 MHz, Methanol-$d_4$) δ-68.47. | 596.4 |
| I-393 | 2A | $^1$H NMR (400 MHz, DMSO-$d_6$) δ 8.46-8.31 (m, 2H), 8.01 (m, 1H), 7.85-7.79 (m, 1H), 7.29 (m, 10H), 5.35 (d, J | 655.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | = 7.2 Hz, 2H), 4.69-4.58 (m, 1H), 4.46 (s, 2H), 4.23-4.11 (m, 1H), 4.05-3.91 (m, 2H), 3.90-3.74 (m, 2H), 3.73-3.62 (m, 2H), 3.61-3.42 (m, 2H), 2.62-2.55 (m, 3H), 1.25 (t, J = 7.6 Hz, 6H), 1.18 (m, 1H), 1.10-0.99 (m, 6H), 0.83 (q, J = 4.6 Hz, 1H), 0.63 (m, 1H). | |
| I-394 | 18 | $^1$H NMR (400 MHz, DMSO-d$_6$) δ 9.25 (s, 1H), 8.51-8.41 (m, 1H), 8.41-8.33 (m, 1H), 4.94-4.84 (m, 1H), 4.73-4.63 (m, 1H), 4.26-3.36 (m, 14H), 3.27-3.18 (m, 2H), 2.03-1.86 (m, 4H), 1.82-1.67 (m, 4H), 1.66-1.49 (m, 3H), 1.41-1.25 (m, 1H), 1.17-1.02 (m, 11H), 0.90-0.82 (m, 1H), 0.73-0.64 (m, 1H). | 748.2 |
| I-395 | 18 | $^1$H NMR (400 MHz, DMSO-d$_6$) δ 9.25 (s, 1H), 8.40-8.34 (m, 1H), 8.22-8.16 (m, 1H), 4.87-4.74 (m, 1H), 4.32-4.18 (m, 1H), 4.14-3.92 (m, 3H), 3.89-3.65 (m, 5H), 1.77-1.69 (m, 4H), 1.62-1.26 (m, 9H), 1.12-1.00 (m, 18H), 0.94-0.84 (m, 3H), 0.67-0.64 (m, 1H). | 656.4 |
| I-396 | 2A | $^1$H NMR (400 MHz, DMSO-d$_6$) δ 8.49-8.39 (m, 1H), 8.39-8.32 (m, 1H), 8.05-7.97 (m, 1H), 7.87-7.78 (m, 1H), 7.42-7.20 (m, 5H), 5.35 (s, 2H), 4.67-4.58 (m, 1H), 4.29-4.14 (m, 1H), 4.11-3.79 (m, 4H), 3.78-3.68 (m, 2H), 3.62-3.55 (m, 1H), 3.53-3.39 (m, 1H), 3.27-3.21 (m, 2H), 2.60-2.54 (m, 3H), 1.66-1.56 (m, 5H). 1.38-1.28 (m, 2H), 1.16-1.03 (m, 9H), 0.89-0.76 (m, 4H), 0.71-0.54 (m, 4H). | 659.3 |
| I-397 | 18 | $^1$H NMR (400 MHz, DMSO-d$_6$) δ 9.25 (s, 1H), 8.47-8.32 (m, 2H), 4.87 (s, 1H), 4.51-4.30 (m, 2H), 4.25-3.39 (m, 12H), 3.22 (m, 3H), 3.07-2.92 (m, 1H), 1.97 (s, 2H), 1.83-1.56 (m, 8H), 1.39-1.25 (m, 1H), 1.19-1.02 (m, 12H), 0.92 (s, 1H), 0.85 (s, 1H), 0.67 (d, J = 4.2 Hz, 1H). | 694.4 |
| I-398 | 18 | $^1$H NMR (400 MHz, DMSO-d$_6$) δ 9.25 (s, 1H), 8.54-8.30 (m, 2H), 4.89 (ddd, J = 13.4, 8.3, 4.4 Hz, 1H), 4.47 (s, 1H), 4.27-3.71 (m, 8H), 3.64 (s, 2H), 3.48 (dt, J = 34.2, 5.7 Hz, 1H), 3.22 (dd, 1H), 3.09 (dd, J = 15.3 Hz, 1H), 2.61 (s, 2H), 2.04-1.70 (m, 8H), 1.60 (s, 1H), 1.32 (ddd, J = 22.3, 8.5, 5.0 Hz, 2H), 1.25-1.12 (m, 3H), 1.11-1.00 (m, 9H), 0.85 (p, J = 4.2 Hz, 1H), 0.68 (dq, J = 7.1, 3.3 Hz, 1H). | 732.3 |
| I-399 | 20 | $^1$H NMR (400 MHz, Methanol-d$_4$) δ 9.15 (s, 1H), 8.37 (d, J = 16.6 Hz, 1H), 5.04-4.89 (m, 1H), 4.78-3.72 (m, 12H), 3.42-3.33 (m, 1H), 3.24-2.84 (m, 2H), 2.70-2.61 (m, 1H), 2.10-1.92 (m, 3H), 1.85-1.61 (m, 7H), 1.51-0.97 (m, 21H), 0.49-0.48 (m, 2H), 0.41-0.35 (m, 2H). | 736.6 |
| I-400 | 2A | $^1$H NMR (400 MHz, Methanol-d$_4$) δ 8.26-8.17 (m, 1H), 7.92 (d, J = 11.2 Hz, 1H), 7.49-7.22 (m, 6H), 6.93 (t, J = 8.5 Hz, 1H), 5.38 (s, 2H), 4.55-3.75 (m, 11H), 3.29-3.15 (m, 1H), 1.46-1.27 (m, 2H), 1.19-1.10 (m, 5H), 1.06 (s, 2H), 0.78 (dd, J = 8.0, 4.4 Hz, 1H). | 544.2 |
| I-401 | 18 | $^1$H NMR (400 MHz, DMSO-d$_6$) δ 9.25 (s, 1H), 8.54-8.43 (m, 1H), 8.42-8.33 (m, 1H), 8.06-7.96 (m, 1H), 4.69-4.56 (m, 1H), 4.30-4.15 (m, 1H), 4.13-3.93 (m, 3H), 3.88-3.62 (m, 4H), 3.54-3.40 (m, 1H), 3.28-3.19 (m, 2H), 2.62-2.53 (m, 3H), 1.66-1.55 (m, 5H), 1.38-1.28 (m, 2H), 1.17-1.03 (m, 9H), 0.90-0.77 (m, 4H), 0.71-0.54 (m, 4H). | 586.2 |
| I-402 | 18 | $^1$H NMR (400 MHz, DMSO-d$_6$) δ 9.24 (s, 1H), 8.45-8.16 (m, 2H), 4.87 (s, 1H), 4.33-4.04 (m, 4H), 4.00-3.61 (m, 6H), 3.54 (d, J = 24.3 Hz, 2H), 3.31 (s, 11H), 3.10-2.93 (m, 2H), 1.97 (d, 2H), 1.78-1.55 (m, 5H), 1.46-1.33 (m, 2H), 1.28-1.14 (m, 2H), 1.10 (d, J = 11.4 Hz, 4H), 1.06-0.99 (m, 7H), 0.93-0.82 (m, 3H), 0.67 (t, J = 5.6 Hz, 1H). | 702.4 |
| I-403 | 2A | $^1$H NMR (400 MHz, DMSO-d$_6$) δ 8.38 (d, 1H), 8.19 (dd, J = 18.3, 8.8 Hz, 1H), 7.86-7.69 (m, 2H), 7.39-7.20 (m, 5H), 5.35 (s, 2H), 4.34-4.12 (m, 2H), 4.10-3.82 (m, 4H), 3.79-3.49 (m, 4H), 3.46-3.36 (m, 1H), 3.21 (s, 4H), 3.10 (t, J = 7.8 Hz, 1H), 3.05-2.96 (m, 1H), 2.58 (dd, J = 9.4 Hz, 3H), 1.96 (d, J = 12.4 Hz, 2H), 1.72 (d, J = 13.1 Hz, 2H), 1.45-1.27 (m, 2H), 1.12-1.06 (m, 4H), 1.02 (d, J = 6.6 Hz, 7H), 0.93-0.87 (m, 1H), 0.86-0.78 (m, 2H), 0.70-0.62 (m, 1H). | 677.4 |
| I-404 | 18 | $^1$H NMR (400 MHz, DMSO-d$_6$) δ 9.25 (s, 1H), 8.38 (d, J = 17.8 Hz, 1H), 8.07-7.96 (m, 1H), 7.40 (d, J = 3.2 Hz, | 575.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 4H), 4.70 (s, 1H), 4.60-4.41 (m, 2H), 4.19-4.04 (m, 3H), 3.98-3.64 (m, 7H), 3.55-3.39 (m, 2H), 3.17 (s, 1H), 1.35-1.18 (m, 1H), 1.09-0.99 (m, 9H), 0.84 (d, J = 4.9 Hz, 1H), 0.69-0.57 (m, 1H). | |
| I-405 | 1A | $^1$H NMR(400 MHz, Methanol-d$_4$) δ 8.19-7.97 (m, 3H), 7.37-7.19 (m, 5H), 4.82-4.60 (m , 2H), 4.40-3.82 (m, 10H), 3.37 (s, 1H), 2.84-2.73 (m, 3H), 1.44-1.34 (m, 1H), 1.17-0.99 (m, 7H), 0.80-0.73 (m, 1H). | 559.4 |
| I-406 | 18 | $^1$H NMR (400 MHz, DMSO-d$_6$) δ 9.25 (s, 1H), 8.37 (m, 2H), 7.12 (d, J = 22.2 Hz, 1H), 4.92 (s, 1H), 4.41 (m, 1H), 4.11 (dd, J = 20.4, 10.8 Hz, 4H), 3.80 (m, 2H), 3.65 (m, 3H), 3.37-3.16 (m, 5H), 2.88 (m, 1H), 2.74 (m, 1H), 1.95 (m, 2H), 1.65 (m, 5H), 1.39 (d, J = 34.6 Hz, 4H), 1.07 (t, J = 9.8 Hz, 12H), 0.86 (s, 3H), 0.68 (m, 1H). | 694.4 |
| I-407 | 1A | $^1$H NMR (400 MHz, Methanol-d$_4$) δ 8.50-8.47 (m, 1H), 8.37-8.29 (m, 2H), 8.00-7.94 (m, 1H), 7.71-7.61 (m, 2H), 7.16-7.10 (m, 1H), 5.57 (s, 2H), 4.81-4.58 (m, 2H), 4.45-4.28 (m, 1H), 4.27-4.16 (m, 2H), 4.14-3.98 (m, 3H), 3.97-3.84 (m, 2H), 3.30-3.22 (m, 1H), 2.71-2.66 (m, 3H), 1.43-1.32 (m, 1H), 1.21-1.11 (m, 4H), 1.10-1.07 (m, 2H), 1.05-1.01 (m, 1H), 0.80-0.73 (m, 1H). | 561.5 |
| I-408 | 18 | $^1$H NMR (400 MHz, DMSO-d$_6$) δ 9.25 (s, 1H), 8.40-8.34 (m, 2H), 4.87 (s, 1H), 4.27-3.77 (m, 10H), 3.73-3.34 (m, 5H), 3.20-3.17 (m, 9H), 3.02-3.00 (m, 1H), 1.75-1.72 (m, 4H), 1.39-1.29 (m, 7H), 1.24-1.19 (m, 4H), 1.12-1.04 (m, 9H), 0.87-0.86 (m, 1H), 0.69-0.67 (m, 1H). | 702.5 |
| I-409 | 2A | $^1$H NMR (400 MHz, DMSO-d$_6$) δ 8.53-8.42 (m, 1H), 8.36 (d, J = 10.8 Hz, 1H), 7.82 (d, J = 13.6 Hz, 1H), 7.38-7.23 (m, 10H), 5.38-5.33 (m, 2H), 4.91 (m, 1H), 4.58-4.45 (m, 2H), 4.25-4.12 (m, 1H), 4.05-3.96 (m, 2H), 3.87 (s, 1H), 3.76 (m, 3H), 3.63-3.54 (m, 1H), 3.53-3.32 (m, 2H), 2.96 (d, J = 4.4 Hz, 3H), 2.81 (d, J = 9.6 Hz, 3H), 1.27 (m, 1H), 1.12-1.01 (m, 9H), 0.84 (m, 1H), 0.63 (s, 1H). | 655.4 |
| I-410 | 32 | $^1$H NMR (400 MHz, DMSO-d$_6$) δ 9.28-9.20 (m, 1H), 9.08-8.76 (m, 1H), 8.41-8.30 (m, 1H), 8.21-8.09 (m, 1H), 7.74-7.58 (m, 1H), 7.30-7.11 (m, 2H), 5.48 (s, 1H), 4.65-4.16 (m, 2H), 4.12-3.63 (m, 6H), 3.59-3.44 (m, 1H), 2.70-2.55 (m, 4H), 1.89-1.68 (m, 5H), 1.53-1.17 (m, 5H), 1.04-0.71 (m, 7H), 0.47-0.05 (m, 4H). | 512.2 |
| I-411 | 18 | $^1$H NMR (400 MHz, DMSO-d$_6$) δ 9.25 (d, J = 4.4 Hz, 1H), 9.02-8.83 (m, 1H), 8.41-8.31 (m, 1H), 8.27-8.13 (m, 1H), 7.78-7.63 (m, 1H), 7.33-7.18 (m, 2H), 5.56-5.47 (m, 1H), 4.28-3.98 (m, 4H), 3.94-3.62 (m, 4H), 3.57-3.39 (m, 1H), 3.00-2.79 (m, 1H), 2.59 (s, 3H), 2.15-1.88 (m, 6H), 1.83-1.71 (m, 2H), 1.40-1.23 (m, 1H), 1.15-1.00 (m, 5H), 0.91-0.76 (m, 2H), 0.71-0.57 (m, 1H). | 629.3 |
| I-412 | 18 | $^1$H NMR (400 MHz, DMSO-d$_6$) δ 9.25 (s, 1H), 8.43-8.33 (m, 1H), 8.01-7.89 (m, 1H), 4.65 (s, 1H), 4.26-3.60 (m, 11H), 3.55-3.45 (m, 2H), 3.43-3.37 (m, 2H), 2.68-2.55 (m, 2H), 2.42-2.27 (m, 3H), 1.41-1.25 (m, 1H), 1.14-0.99 (m, 9H), 0.89-0.82 (m, 1H), 0.72-0.64 (m, 1H). | 555.4 |
| I-413 | 2A | $^1$H NMR (400 MHz, DMSO-d$_6$) δ 8.35 (d, J = 14.6 Hz, 1H), 8.15 (dd, J = 20.4 Hz, 1H), 7.82 (d, J = 15.8 Hz, 1H), 7.78-7.66 (m, 1H), 7.39-7.23 (m, 5H), 5.35 (s, 2H), 4.44 (d, 1H), 4.32-4.13 (m, 2H), 4.08 (dd, J = 12.3 Hz, 1H), 4.00-3.88 (m, 2H), 3.84-3.61 (m, 4H), 3.56-3.37 (m, 1H), 3.31-3.25 (m, 2H), 3.21 (t, J = 8.0 Hz, 1H), 3.10 (t, J = 7.7 Hz, 1H), 2.62-2.54 (m, 3H), 1.79 (d, J = 12.3 Hz, 2H), 1.67 (d, J = 12.6 Hz, 2H), 1.38-1.27 (m, 2H), 1.14-1.00 (m, 11H), 0.90-0.79 (m, 3H), 0.66 (t, 1H). | 663.6 |
| I-414 | 18 | $^1$H NMR (400 MHz, Methanol-d$_4$) δ 9.16 (s, 1H), 8.37 (d, J = 10.1 Hz, 1H), 7.68 (q, J = 8.4 Hz, 1H), 7.16 (d, J = 8.1 Hz, 2H), 4.60-4.42 (m, 2H), 4.40-4.22 (m, 2H), 4.22-4.09 (m, 2H), 4.12-3.84 (m, 4H), 3.42-3.30 (m, 4H), | 536.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 2.69 (d, J = 10.3 Hz, 1H), 1.87 (t, J = 14.8 Hz, 4H), 1.77 (d, J = 12.8 Hz, 1H), 1.61-1.49 (m, 2H), 1.44 (d, J = 11.9 Hz, 2H), 1.39-1.27 (m, 2H), 1.17 (d, J = 13.9 Hz, 4H), 1.13-1.00 (m, 4H), 0.77 (d, 1H). | |
| I-415 | 31 | $^1$H NMR (400 MHz, DMSO-d$_6$) δ 9.23 (d, J = 18.4 Hz, 2H), 9.01-8.91 (m, 1H), 8.37 (d, J = 18.6 Hz, 1H), 5.34 (s, 1H), 4.25-4.00 (m, 4H), 3.95-3.78 (m, 4H), 3.70 (s, 1H), 3.58-3.47 (m, 1H), 3.06 (s, 1H), 1.63-1.49 (m, 5H), 1.39-1.35 (m, 1H), 1.16-1.04 (m, 13H), 0.86 (d, J = 5.2 Hz, 1H), 0.80-0.65 (m, 3H). | 585.5 |
| I-416 | 18 | HNMR (400 MHz, DMSO-d$_6$) δ 9.25 (s, 1H), 8.57-8.45 (m, 1H), 8.41-8.34 (m, 1H), 7.37-7.24 (m, 5H), 4.96-4.87 (m, 1H), 4.58-4.44 (m, 2H), 4.23-3.95 (m, 4H), 3.92-3.63 (m, 5H), 3.56-3.41 (m, 1H), 2.99-2.93 (m, 3H), 2.84-2.77 (m, 3H), 1.31-1.22 (m, 1H), 1.13-1.01 (m, 9H), 0.87-0.81 (m, 1H), 0.68-0.61 (m, 1H). | 582.4 |
| I-417 | 18 | $^1$H NMR (400 MHz, DMSO-d$_6$) δ 8.99-8.93 (m, 1H), 8.56-8.51 (m, 1H), 8.41-8.36 (m, 1H), 7.89-7.82 (m, 1H), 7.81-7.75 (m, 1H), 7.52-7.40 (m, 2H), 7.34-7.29 (m, 1H), 7.13-7.08 (m, 1H), 5.47 (s, 2H), 4.66-4.45 (m, 2H), 4.21-3.67 (m, 8H), 3.25-3.14 (m, 1H), 2.58 (s, 3H), 1.36-1.27 (m, 1H), 1.24-1.16 (m, 1H), 1.11-1.03 (m, 4H), 1.00-0.98 (m, 1H), 0.88-0.82 (m, 1H), 0.69-0.64 (m, 1H). | 543.3 |
| I-418 | 18 | $^1$H NMR (400 MHz, DMSO-d$_6$) δ 8.98-8.91 (m, 1H), 8.58-8.51 (m, 2H), 8.45-8.40 (m, 1H), 7.92-7.85 (m, 1H), 7.52-7.40 (m, 2H), 7.19-7.12 (m, 2H), 5.43 (s, 2H), 4.67-4.44 (m, 2H), 4.27-4.14 (m, 1H), 4.13-4.04 (m, 1H), 4.04-3.98 (m, 1H), 3.95-3.84 (m, 2H), 3.82-3.64 (m, 3H), 3.28-3.12 (m, 1H), 2.60-2.56 (m, 3H), 1.31-1.23 (m, 1H), 1.12-0.98 (m, 6H), 0.88-0.81 (m, 1H), 0.70-0.63 (m, 1H). | 543.2 |
| I-419 | 18 | $^1$H NMR (400 MHz, DMSO-d$_6$) δ9.25-9.24 (m, 1H), 8.71-8.65 (m, 1H), 8.39-8.34 (m, 1H), 7.70-7.59 (m, 1H), 7.20-7.13 (m, 2H), 4.91-4.89 (m, 1H), 4.28-3.65 (m, 11H), 2.88-2.82 (m, 1H), 2.10-1.77 (m, 9H), 1.38-1.27 (m, 1H), 1.13-1.00 (m, 6H), 0.87-0.85 (m, 1H), 0.70-0.67 (m, 1H). | 602.5 |
| I-420 | 18 | $^1$H NMR (400 MHz, CD$_3$OD) δ 9.15 (d, J = 4.3 Hz, 1H), 8.40-8.28 (m, 1H), 8.03 (dddd, J = 45.9, 31.7, 10.6, 6.9 Hz, 2H), 4.50-3.81 (m, 9H), 3.56-3.38 (m, 1H), 2.77 (td, J = 11.2, 9.5, 7.0 Hz, 6H), 1.41 (ddd, J = 34.3, 10.8, 6.3 Hz, 1H), 1.21-1.07 (m, 6H), 1.07-0.99 (m, 1H), 0.93 (dd, J = 23.1, 5.0 Hz, 1H), 0.82-0.69 (m, 1H). | 526.4 |
| I-421 | 2A | $^1$H NMR (400 MHz, CD$_3$OD) δ 8.23-8.16 (m, 1H), 7.93-7.86 (m, 1H), 7.74-7.49 (m, 2H), 7.32 (ddt, J = 19.9, 14.7, 7.0 Hz, 5H), 5.85-5.72 (m, 1H), 5.37 (d, J = 5.8 Hz, 2H), 4.56-3.81 (m, 8H), 3.41 (dtd, J = 17.7, 12.4, 6.3 Hz, 1H), 2.78-2.70 (m, 3H), 2.67 (d, J = 2.5 Hz, 3H), 1.50-1.30 (m, 1H), 1.21-0.90 (m, 7H), 0.75 (ddd, J = 25.6, 8.2, 4.2 Hz, 1H). | 599.4 |
| I-422 | 18 | $^1$H NMR (400 MHz, DMSO-d$_6$) δ 9.33-9.16 (m, 1H), 8.86-8.72 (m, 1H), 8.40-8.34 (m, 1H), 8.11-8.01 (m, 1H), 7.56-7.45 (m, 1H), 6.75-6.69 (m, 2H), 5.38-5.33 (m, 1H), 4.26-3.96 (m, 5H), 3.71-3.66 (m, 6H), 3.49-3.42 (m, 5H), 2.61-2.57 (m, 3H), 1.36-1.22 (m, 1H), 1.15-0.99 (m, 7H), 0.91-0.80 (m, 2H), 0.71-0.59 (m, 1H). | 596.5 |
| I-423 | 18 | $^1$H NMR (400 MHz, DMSO-d$_6$) δ 9.28-9.20 (m, 1H), 8.54 (q, J = 11.2, 10.2 Hz, 1H), 8.41-8.27 (m, 1H), 7.66 (dq, J = 15.4, 7.6 Hz, 1H), 7.26-7.13 (m, 2H), 5.08-4.97 (m, 1H), 4.92-4.81 (m, 1H), 4.31-4.08 (m, 2H), 4.07-3.91 (m, 4H), 3.90-3.69 (m, 3H), 3.67-3.49 (m, 2H), 3.48-3.40 (m, 2H), 2.92 (d, J = 5.6 Hz, 1H), 1.83-1.67 (m, 4H), 1.39-1.24 (m, 1H), 1.14-0.91 (m, 12H), 0.89-0.81 (m, 1H), 0.67 (td, J = 25.2, 24.2, 16.4 Hz, 1H). | 596.3 |
| I-424 | 2A | $^1$H NMR (400 MHz, DMSO-d$_6$) δ 8.36 (d, J = 14.4 Hz, 1H), 8.24-8.13 (m, 1H), 7.86-7.70 (m, 2H), 7.39-7.23 (m, 5H), 5.35 (s, 2H), 4.31-4.13 (m, 3H), 4.10-4.03 (m, 1H), 4.00-3.87 (m, 2H), 3.84-3.69 (m, 4H), 3.67-3.35 | 663.6 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
|  |  | (m, 3H), 3.28-3.23 (m, 1H), 3.18-3.09 (m, 1H), 2.62-2.55 (m, 3H), 1.56-1.45 (m, 3H), 1.41-1.27 (m, 7H), 1.13-1.07 (m, 3H), 1.06-1.01 (m, 6H), 0.90-0.81 (m, 1H), 0.72-0.62 (m, 1H). |  |
| I-425 | 18 | $^1$H NMR (400 MHz, CD$_3$OD) δ 9.21 (s, 1H), 8.39 (s, 1H), 7.63-7.50 (m, 1H), 4.54-3.79 (m, 8H), 3.43 (m, 1H), 2.78 (m, 3H), 2.55-2.40 (m, 1H), 2.06-1.89 (m, 2H). 1.84-1.67 (m, 3H), 1.39 (m, 6H), 1.21-0.99 (m, 7H), 0.81-0.72 (m, 1H). | 583.4 |
| I-426 | 18 | $^1$H NMR (400 MHz, CD$_3$OD) δ 9.15 (s, 1H), 8.39-8.34 (m, 1H), 6.79-6.70 (m, 1H), 4.59-3.83 (m, 9H), 3.50-3.35 (m, 1H), 2.81-2.78 (m, 3H), 2.70 (s, 1H), 2.00 (s, 2H), 1.79 (s, 2H), 1.74-1.67 (m, 1H), 1.47-1.35 (m, 5H), 1.21-1.03 (m, 7H), 0.77 (s, 1H). | 583.5 |
| I-427 | 18 | $^1$H NMR (400 MHz, DMSO-d$_6$) δ 9.27-9.21 (m, 1H), 8.83-8.67 (m, 1H), 8.42-8.32 (m, 1H), 8.05 (s, 1H), 7.54-7.40 (m, 1H), 6.74-6.62 (m, 1H), 6.32-6.19 (m, 1H), 5.37-5.24 (m, 1H), 4.75-4.66 (m, 4H), 4.28-4.15 (m, 1H), 4.14-4.04 (m, 6H), 4.03-3.41 (m, 6H), 2.62-2.55 (m, 3H), 1.38-1.24 (m, 1H), 1.14-1.00 (m, 5H), 0.92-0.76 (m, 2H), 0.72-0.58 (m, 1H). | 608.3 |
| I-428 | 18 | $^1$H NMR (400 MHz, DMSO-d$_6$) δ 9.26-9.23 (m, 1H), 8.41-8.34 (m, 1H), 8.33-8.24 (m, 1H), 4.22-3.99 (m, 7H), 3.89-3.77 (m, 5H), 3.71-3.65 (m, 1H), 3.60-3.54 (m, 1H), 3.40-3.33 (m, 2H), 3.29-3.24 (m, 2H), 3.18-3.12 (m, 1H), 1.79-1.69 (m, 1H), 1.62-1.54 (m, 2H), 1.35-1.17 (m, 3H), 1.13-1.03 (m, 9H), 0.89-0.83 (m, 1H), 0.71-0.65 (m, 1H). | 617.4 |
| I-429 | 18 | $^1$H NMR (400 MHz, Methanol-d$_4$) δ 9.16 (s, 1H), 8.42-8.31 (m, 1H), 4.54-4.12 (m, 4H), 4.10-3.84 (m, 4H), 3.50-3.36 (m, 1H), 3.02-2.88 (m, 1H), 2.83-2.75 (m, 3H), 2.06 (s, 2H), 1.89-1.52 (m, 5H), 1.51-1.25 (m, 5H), 1.21-1.02 (m, 7H), 0.78 (s, 1H). | 584.4 |
| I-430 | 18 | $^1$H NMR (400 MHz, CD$_3$OD) δ 9.15 (dd, J = 5.3, 2.6 Hz, 1H), 8.41-8.31 (m, 1H), 7.48 (t, J = 7.7 Hz, 1H), 6.72 (t, J = 7.0 Hz, 1H), 6.30 (dd, J = 8.8, 5.6 Hz, 1H), 5.43-5.36 (m, 1H), 4.56-3.82 (m, 13H), 3.61-3.41 (m, 1H), 3.06-2.93 (m, 1H), 2.74 (dd, J = 6.4, 3.4 Hz, 3H), 2.54-2.46 (m, 2H), 2.38 (dd, J = 13.2, 7.2 Hz, 2H), 1.37-1.30 (m, 2H), 1.22-1.14 (m, 3H), 1.11-1.05 (m, 2H), 0.97 (d, J = 8.6 Hz, 2H), 0.81-0.67 (m, 1H). | 674.4 |
| I-431 | 32 | $^1$H NMR (400 MHz, Methanol-d$_4$) δ 9.15 (s, 1H), 8.37 (d, J = 13.8 Hz, 1H), 5.01-4.89 (m, 1H), 4.75-4.23 (m, 4H), 4.18-3.83 (m, 7H), 3.73 (s, 1H), 3.51-3.33 (m, 4H), 3.28-3.10 (m, 4H), 2.91 (s, 1H), 2.74-2.57 (m, 1H), 1.93 (d, 2H), 1.84-1.69 (m, 5H), 1.45 (s, 1H), 1.38-1.29 (m, 2H), 1.22 (d, J = 12.3 Hz, 2H), 1.16 (t, 3H), 1.03 (d, J = 7.8 Hz, 8H), 0.99-0.93 (m, 1H), 0.47 (t, 2H), 0.37 (s, 2H). | 702.6 |
| I-432 | 18 | $^1$H NMR (400 MHz, Methanol-d$_4$) δ 9.16 (s, 1H), 8.38 (s, 1H), 7.47 (t, J = 7.5 Hz, 1H), 6.75-6.58 (m, 2H), 5.50-5.28 (m, 1H), 4.56-4.28 (m, 1H), 4.22-4.05 (m, 3H), 4.02-3.86 (m, 3H), 3.64-3.35 (m, 6H), 2.74 (d, J = 6.3 Hz, 3H), 1.69-1.58 (m, 6H), 1.32 (d, J = 17.3 Hz, 2H). 1.20 (s, 1H), 1.16 (d, J = 6.3 Hz, 2H), 1.08 (t, J = 7.0 Hz, 2H), 0.98 (s, 1H), 0.81-0.66 (m, 1H). | 594.4 |
| I-433 | 18 | $^1$H NMR (400 MHz, DMSO-d$_6$) δ 9.25 (s, 1H), 8.38 (d, J = 28.1 Hz, 4H), 4.90 (s, 1H), 4.28 (s, 3H), 4.07 (s, 5H), 3.80 (s, 4H), 3.65 (s, 2H), 3.59 (s, 3H), 3.46 (s, 2H), 3.05 (s, 1H), 2.78 (s, 2H), 1.88 (s, 2H), 1.72 (s, 4H), 1.37 (d, J = 25.1 Hz, 3H), 1.20 (s, 4H), 1.12 (s, 1H), 1.09 (s, 2H), 1.05 (s, 4H), 0.93 (s, 1H), 0.89 (s, 1H), 0.86 (s, 1H), 0.68 (s, 1H). | 687.4 |
| I-434 | 18 | $^1$H NMR (400 MHz, DMSO-d$_6$) δ 9.25 (s, 1H), 8.48-8.31 (m, 2H), 7.69-7.61 (m, 1H), 4.88 (s, 1H), 4.35-4.07 (m, 4H), 4.02-3.73 (m, 5H), 3.70-3.49 (m, 3H), 3.48-3.36 (m, 2H), 3.22-3.16 (m, 5H), 3.04-2.78 (m, 1H), 1.83-1.54 (m, 11H), 1.48-1.16 (m, 5H), 1.13-1.02 (m, 11H), 0.98-0.82 (m, 3H), 0.71-0.63 (m, 1H). | 729.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-435 | 18 | $^1$H NMR (400 MHz, DMSO-$d_6$) δ 9.25 (s, 1H), 8.43-8.32 (m, 2H), 4.86 (s, 1H), 4.31-4.02 (m, 7H), 3.90-3.73 (m, 4H), 3.62 (d, J = 24.8 Hz, 3H), 3.46-3.39 (m, 1H), 3.23-3.14 (m, 7H), 1.99 (d, J = 12.4 Hz, 2H), 1.79-1.67 (m, 4H), 1.48-1.37 (m, 4H), 1.26-1.18 (m, 2H), 1.11-1.00 (m, 12H), 0.90-0.82 (m, 1H), 0.72-0.64 (m, 1H). | 756.5 |
| I-436 | 18 | $^1$H NMR (400 MHz, DMSO-$d_6$) δ 8.54 (d, J = 18.8 Hz, 2H), 7.77 (d, J = 26.5 Hz, 1H), 7.66 (t, J = 8.1 Hz, 1H), 7.24-7.13 (m, 2H), 5.07-4.97 (m, 1H), 4.91-4.82 (m, 1H), 4.31-4.08 (m, 2H), 4.07-4.01 (m, 1H), 3.99-3.90 (m, 3H), 3.89-3.80 (m, 1H), 3.77-3.71 (m, 1H), 3.69-3.40 (m, 5H), 2.99-2.85 (m, 1H), 1.80-1.72 (m, 4H), 1.41-1.31 (m, 1H), 1.23-1.14 (m, 1H), 1.13-1.09 (m, 4H), 1.07-1.04 (m, 4H), 1.02-0.93 (m, 2H), 0.90-0.73 (m, 2H), 0.72-0.57 (m, 1H). | 580.3 |
| I-437 | 32 | $^1$H NMR (400 MHz, DMSO-$d_6$) δ 8.51 (1H. s), 7.60-7.73 (1H, m), 7.16 (2H, m), 5.03 (1H, d, J = 5.6 Hz), 4.87 (1H. d, J = 6.6 Hz), 3.88-4.27 (5H, m), 3.62-3.71 (2H. m), 3.75 (1H, s), 3.40-3.48 (3H, m), 2.97 (2H. m), 2.62 (3H. d, J = 2.8 Hz), 2.30-2.36 (2H, m), 2.23 (1H. s), 1.72 (5H. m), 1.34 (1H, s), 1.10 (4H, s), 1.04 (5H, d, J = 9.0 Hz), 0.94 (1H, s), 0.86 (1H, s), 0.80 (1H, s), 0.56-0.72 (1H, m). | 624.4 |
| I-438 | 2A | $^1$H NMR (400 MHz, DMSO-$d_6$) δ 8.48-8.10 (m, 3H), 7.86-7.77 (m, 1H), 7.40-7.03 (m, 6H), 5.35 (s, 2H), 4.99-4.86 (m, 1H), 4.48-4.33 (m, 1H), 4.25-3.48 (m, 12H), 3.21-3.13 (m, 2H), 2.96-2.70 (m, 2H), 2.07-1.85 (m, 2H), 1.71-1.56 (m, 5H), 1.52-1.27 (m, 4H), 1.19-1.03 (m, 12H), 0.92-0.79 (m, 3H), 0.71-0.65 (m, 1H). | 767.5 |
| I-439 | 2A | $^1$H NMR (400 MHz, DMSO-$d_6$) δ 8.44-8.32 (m, 2H), 7.86-7.79 (m, 1H), 7.75-7.72 (m, 1H), 7.46-7.39 (m, 1H), 7.37-7.23 (m, 5H), 6.25-6.19 (m, 1H), 5.37-5.33 (m, 2H), 4.99-4.89 (m, 1H), 4.50-4.40 (m, 2H), 4.22-3.48 (m, 12H), 3.24-3.15 (m, 2H), 2.85-2.73 (m, 1H), 2.08-1.99 (m, 2H), 1.88-1.54 (m, 8H), 1.48-1.28 (m, 2H), 1.14-1.01 (m, 11H), 0.92-0.79 (m, 3H), 0.70-0.64 (m, 1H). | 767.6 |
| I-440 | 18 + step 7 of 15 | $^1$H NMR (400 MHz, Methanol-$d_4$) δ 9.16 (s, 1H), 8.37 (d, J = 10.4 Hz, 1H), 8.21 (s, 1H), 7.34 (s, 1H), 7.13 (d, J = 14.4 Hz, 1H), 5.01-4.89 (m, 2H), 4.78-4.43 (m, 3H), 4.42-4.29 (m, 2H), 4.27-3.97 (m, 5H), 3.95-3.75 (m, 4H), 3.51-3.33 (m, 5H), 2.90-2.76 (m, 1H), 2.31-1.95 (m, 3H), 1.93-1.75 (m, 2H), 1.69-1.59 (m, 2H), 1.48-1.10 (m, 13H), 1.08-1.02 (m, 1H), 0.83-0.76 (m, 1H). | 696.4 |
| I-441 | 18 | $^1$H NMR (400 MHz, CD$_3$OD) δ 9.16 (s, 1H), 8.41-8.33 (m, 1H), 6.61-6.14 (m, 1H), 4.40-3.85 (m, 13H), 3.73-3.62 (m, 1H), 3.49-3.34 (m, 4H), 3.26-3.18 (m, 1H), 1.90-1.79 (m, 1H), 1.74-1.62 (m, 2H), 1.46-1.28 (m, 3H), 1.20-1.10 (m, 9H), 1.09-1.00 (m, 1H), 0.83-0.75 (m, 1H). | 599.3 |
| I-442 | 18 + step 7 of 15 | $^1$H NMR (400 MHz, DMSO-$d_6$) δ 9.25 (s, 1H), 8.82 (s, 2H), 8.56-8.31 (m, 2H), 7.93 (d, J = 5.6 Hz, 2H), 4.94 (s, 1H), 4.57 (s, 1H), 4.26-3.90 (m, 7H), 3.83-3.78 (m, 3H), 3.54-3.43 (m, 1H), 3.37-3.06 (m, 7H), 2.69 (d, J = 13.6 Hz, 1H), 2.01-1.83 (m, 2H), 1.71 (s, 1H), 1.55 (d, J = 13.4 Hz, 4H), 1.39-1.26 (m, 1H), 1.21-0.99 (m, 12H), 0.86 (d, J = 5.6 Hz, 1H), 0.73-0.64 (m, 1H). | 707.5 |
| I-443 | 2A | $^1$H NMR (400 MHz, DMSO-$d_6$) δ 8.36 (d, J = 13.0 Hz, 2H), 7.82 (d, J = 15.8 Hz, 1H), 7.47 (m, 1H), 7.36-7.21 (m, 5H), 6.02 (s, 1H), 5.35 (s, 2H), 4.91 (m, 1H), 4.39 (m, 1H), 4.18 (d, J = 7.6 Hz, 1H), 4.11-3.81 (m, 5H), 3.77-3.43 (m, 5H), 3.17 (d, J = 8.6 Hz, 3H), 2.89 (m, 1H), 2.73 (m, 1H), 1.92 (m, 2H), 1.65 (m, 6H), 1.50-1.28 (m, 4H), 1.15-1.04 (m, 11H), 0.86 (s, 3H), 0.71-0.64 (m, 1H). | 767.6 |
| I-444 | 2A | $^1$H NMR (400 MHz, DMSO-$d_6$) δ 8.36 (d, J = 12.8 Hz, 2H), 8.17 (s, 1H), 7.82 (d, J = 16.1 Hz, 1H), 7.50 (s, 1H), 7.38-7.23 (m, 5H), 6.72 (s, 1H), 5.35 (s, 2H), 4.91 (s, 1H), 4.20-3.49 (m, 13H), 4.05 (m, 1H), 3.15 (d, J = 8.8 | 807.7 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | Hz, 2H), 2.74 (s, 1H), 1.93 (s, 2H), 1.78 (s, 2H), 1.63 (s, 6H), 1.52 (d, J = 12.2 Hz, 2H), 1.35 (s, 3H), 1.24-1.02 (m, 12H), 0.86 (s, 3H), 0.71-0.63 (m, 1H). | |
| I-445 | 2A | $^1$H NMR (400 MHz, DMSO-d$_6$) δ 8.40 (d, J = 18.5 Hz, 2H), 7.87-7.54 (m, 3H), 7.39-7.22 (m, 5H), 5.35 (s, 2H), 4.93 (s, 1H), 4.43 (s, 1H), 4.26-3.38 (m, 12H), 3.30-3.12 (m, 3H), 2.87-2.72 (m, 1H), 2.14-1.99 (m, 2H), 1.71-1.54 (m, 6H), 1.51-1.24 (m, 3H), 1.18-1.02 (m, 12H), 0.85 (s, 3H), 0.70-0.64 (m, 1H). | 784.5 |
| I-446 | 2A | $^1$H NMR (400 MHz, DMSO-d$_6$) δ 8.36 (d, J = 13.7 Hz, 2H), 8.15 (s, 1H), 7.82 (d, J = 13.9 Hz, 1H), 7.37-7.22 (m, 5H), 6.87 (s, 2H), 5.35 (s, 2H), 4.91 (s, 1H), 4.37-3.57 (m, 12H), 3.17 (s, 2H), 2.97-2.77 (m, 2H), 1.92 (s, 2H), 1.73-1.20 (m, 10H), 1.19-1.02 (m, 12H), 0.86 (s, 3H), 0.70-0.64 (m, 1H). | 767.6 |
| I-447 | 34 | $^1$H NMR (400 MHz, DMSO-d$_6$) δ 9.29-9.23 (m, 1H), 8.57-8.47 (m, 1H), 8.44-8.30 (m, 1H), 4.86 (s, 1H), 4.35-4.22 (m, 1H), 4.17-3.36 (m, 12H), 3.28-3.08 (m, 7H), 3.06-2.74 (m, 1H), 1.75-1.53 (m, 8H), 1.52-1.32 (m, 2H), 1.30-1.00 (m, 16H), 0.92-0.79 (m, 2H). | 696.5 |
| I-448 | 32 | $^1$H NMR (400 MHz, Methanol-d$_4$) δ 8.38 (d, J = 3.4 Hz, 1H), 7.79 (d, J = 13.6 Hz, 1H), 5.73-5.55 (m, 2H), 4.54 (d, J = 22.0 Hz, 1H), 4.39-3.98 (m, 5H), 3.85 (d, J = 32.2 Hz, 3H), 3.53-3.40 (m, 4H), 3.28-3.16 (m, 1H), 2.05 (d, J = 9.6 Hz, 2H), 1.86 (s, 2H), 1.65-1.50 (m, 2H), 1.34-0.91 (m, 18H), 0.41 (dd, J = 38.4. 6.8 Hz, 4H). | 601.4 |
| I-449 | 2A | $^1$H NMR (400 MHz, Methanol-d$_4$) δ 8.87 (m, 1H), 8.21 (d, J = 15.2 Hz, 1H), 7.96-7.88 (m, 1H), 7.39-7.25 (m, 5H), 5.38 (d, J = 2.6 Hz, 2H), 4.99 (s, 1H), 4.60 (s, 1H), 4.47-3.71 (m, 11H), 3.35 (s, 3H), 3.21 (q, J = 5.4. 5.0 Hz, 1H), 3.00 (s, 1H), 2.16 (m, 2H), 1.88 (d, J = 6.6 Hz, 1H), 1.74 (m, 6H), 1.51 (dt, J = 8.0. 3.6 Hz, 1H), 1.39-1.12 (m, 13H), 1.04 (t, J = 4.6 Hz, 1H), 0.92 (m, 2H), 0.81-0.76 (m, 1H). | 769.5 |
| I-450 | 32 | $^1$H NMR (400 MHz, Methanol-d$_4$) δ 8.38 (d, J = 2.6 Hz, 1H), 7.81-7.62 (m, 2H), 4.42-4.25 (m, 3H), 4.23-4.04 (m, 3H), 4.04-3.82 (m, 5H), 3.75 (s, 2H), 3.67-3.42 (m, 2H), 3.28-3.22 (m, 1H), 3.04 (d, J = 8.6 Hz, 1H), 1.99 (d, J = 13.6 Hz, 1H), 1.90-1.62 (m, 5H), 1.56 (d, J = 7.8 Hz, 2H), 1.44 (t, J = 6.8 Hz, 1H), 1.38 (d, J = 7.4 Hz, 1H), 1.24 (d, J = 4.6 Hz, 3H), 1.21-1.14 (m, 7H), 1.13 (d, J = 6.0 Hz, 2H), 1.06 (dt, J = 12.0, 5.6 Hz, 3H), 0.83-0.77 (m, 1H). | 587.45 |
| I-451 | 33 | $^1$H NMR (400 MHz, DMSO-d$_6$) δ 8.28 (s, 1H), 4.85 (s, 1H), 4.70-4.32 (m, 4H), 4.26-3.99 (m, 3H), 3.88-3.65 (m, 6H), 3.46-3.38 (m, 2H), 3.25 (s, 5H), 3.18-3.06 (m, 2H), 3.01-2.93 (m, 1H), 2.62 (s, 3H), 2.36-2.32 (m, 3H), 1.86-1.63 (m, 4H), 1.57-1.27 (m, 9H), 1.11-0.98 (m, 9H), 0.88-0.82 (m, 1H), 0.71-0.63 (m, 1H). | 714.5 |
| I-452 | 33 | $^1$H NMR (400 MHz, Methanol-d$_4$) δ 9.15 (s, 1H), 8.37 (d, J = 12.3 Hz, 1H), 4.97-4.91 (m, 1H), 4.45-4.21 (m, 3H), 4.19-4.03 (m, 3H), 4.00-3.82 (m, 3H), 3.71 (d, 4H), 3.63-3.53 (m, 4H), 3.23-3.01 (m, 1H), 2.02-1.93 (m, 2H), 1.67 (t, J = 12.3 Hz, 4H), 1.49 (d, 2H), 1.45-1.41 (m, 2H), 1.32 (d, J = 19.2 Hz, 3H), 1.16 (dd, J = 18.1, 9.1 Hz, 10H), 1.02 (d, 4H), 0.98 (s, 2H), 0.82-0.75 (m, 1H). | 684.4 |
| I-453 | 33 | $^1$H NMR (400 MHz, DMSO-d$_6$) δ 9.25 (s, 1H), 8.39 (m, 2H), 5.65-5.48 (m, 1H), 4.83 (m, 1H), 4.16 (m, 10H), 3.79 (m, 3H), 3.65 (m, 3H), 3.55 (m, 2H), 3.40 (m, 2H), 2.98 (s, 1H), 1.79 (d, J = 27.6 Hz, 6H), 1.52 (d, J = 11.4 Hz, 4H), 1.39 (m, 5H), 1.10-1.08 (m, 3H), 1.06 (d, J = 9.6 Hz, 4H), 0.86 (m, 1H), 0.68 (m, 1H). | 698.4 |
| I-454 | 33 | $^1$H NMR (400 MHz, CD$_3$OD) δ 9.15 (s, 1H), 8.37 (m, 1H), 4.95 (s, 1H), 4.58 (m, 1H), 4.43-3.82 (m, 10H), 3.72 (m, 3H), 3.45 (m, 1H), 3.27-3.13 (m, 2H), 3.02 (s, 1H), 2.69 (s, 1H), 2.51 (s, 1H), 1.96 (m, 4H), 1.65 (m, 4H), 1.57-1.36 (m, 5H), 1.21-1.10 (m, 9H), 1.05 (s, 1H), 0.79 (m, 1H). | 724.4 |
| I-455 | 33 | H NMR (400 MHz, DMSO-d$_6$) δ 8.40-8.24 (m, 1H), 4.90-4.82 (m, 1H), 4.70 (s, 1H), 4.24-3.99 (m, 3H), 3.95- | 768.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 3.71 (m, 6H), 3.65-3.58 (m, 3H), 3.57-3.50 (m, 3H), 3.48-3.40 (m, 2H), 3.14-3.06 (m, 1H), 3.03-2.95 (m, 1H), 2.63-2.60 (m, 3H), 2.36-2.32 (m, 3H), 2.02-1.76 (m, 5H), 1.69-1.61 (m, 1H), 1.60-1.45 (m, 6H), 1.44-1.25 (m, 4H), 1.05-0.99 (m, 6H), 0.88-0.81 (m, 1H), 0.70-0.63 (m, 1H). | |
| I-456 | 33 | $^1$H NMR (400 MHz, DMSO-d$_6$) δ 8.35-8.22 (m, 1H), 5.65-5.48 (m, 2H), 4.95-4.80 (m, 1H), 4.55-4.42 (m, 1H), 4.31-3.96 (m, 4H), 3.89-3.38 (m, 8H), 3.24-3.09 (m, 3H), 2.70-2.57 (m, 5H), 2.34 (s, 3H), 1.97-1.70 (m, 6H), 1.66-1.14 (m, 6H), 1.14-0.91 (m, 10H), 0.89-0.81 (m, 1H), 0.72-0.62 (m, 1H). | 752.4 |
| I-457 | 33 | $^1$H NMR (400 MHz, CD$_3$OD) δ 9.16 (s, 1H), 8.39-8.36 (m, 2H), 4.96-4.92 (m, 1H), 4.64-4.56 (m, 2H), 4.40-3.89 (m, 9H), 3.73-3.35 (m, 7H), 3.24-3.23 (m, 1H), 3.04-3.02 (m, 1H), 1.98-1.97 (m, 4H), 1.81-1.63 (m, 5H), 1.50-1.29 (m, 4H), 1.20-1.11 (m, 9H), 1.09-1.05 (m, 1H), 0.80-0.79 (m, 1H). | 740.5 |
| I-458 | 33 | $^1$H NMR (400 MHz, DMSO-d$_6$) δ 9.25 (s, 1H), 8.41-8.32 (m, 2H), 4.87 (s, 1H), 4.19-3.47 (m, 17H), 3.13 (d, J = 9.2 Hz, 1H), 2.99 (t, J = 8.6 Hz, 1H), 1.82 (s, 2H), 1.59-1.48 (m, 4H), 1.38-1.20 (m, 6H), 1.16-0.99 (m, 10H), 0.86 (s, 1H), 0.67 (t, J = 7.8, 4.0 Hz, 1H), 0.32 (s, 4H). | 682.3 |
| I-459 | 32 | $^1$H NMR (400 MHz, Methanol-d$_4$) δ 9.15 (s, 1H), 8.37 (d, J = 15.0 Hz, 1H), 4.99-4.93 (m, 1H), 4.63-4.49 (m, 4H), 4.16-3.99 (m, 4H), 3.92-3.82 (m, 2H), 3.75-3.64 (m, 5H), 3.50-3.47 (m, 1H), 3.26-3.19 (m, 2H), 3.17-2.86 (m, 2H), 2.75-2.60 (m, 1H), 2.01-1.93 (m, 2H), 1.87-1.78 (m, 2H), 1.70-1.61 (m, 5H), 1.55-1.45 (m, 3H), 1.37-1.33 (m, 1H), 1.31-1.29 (m, 1H), 1.18-1.10 (m, 4H), 1.06-1.03 (m, 3H), 1.02-1.01 (m, 2H), 0.53-0.42 (m, 2H), 0.41-0.33 (m, 2H). | 717.4 |
| I-460 | 18 | $^1$H NMR (400 MHz, DMSO-d$_6$) δ 9.25 (s, 1H), 8.43-8.26 (m, 2H), 5.57 (q, J = 11.0 Hz, 1H), 4.88 (d, J = 29.0 Hz, 1H), 4.35-4.02 (m, 5H), 3.96 (m, 3H), 3.80 (d, J = 10.0 Hz, 3H), 3.65 (m, 2H), 3.50 (d, J = 33.0 Hz, 3H), 3.27-2.63 (m, 5H), 1.91 (m, 1H), 1.75 (m, 5H), 1.59-1.47 (m, 2H), 1.43-1.23 (m, 5H), 1.13-0.97 (m, 9H), 0.86 (m, 1H), 0.72-0.64 (m, 1H). | 754.3 |
| I-461 | 18 | $^1$H NMR (400 MHz, DMSO-d$_6$) δ 9.25 (s, 1H), 8.51-8.27 (m, 2H), 5.57 (q, J = 11.2 Hz, 1H), 4.96-4.78 (m, 1H), 4.30-3.52 (m, 16H), 3.25-2.80 (m, 4H), 1.96-1.61 (m, 7H), 1.57-1.51 (m, 1H), 1.42-1.24 (m, 5H), 1.12-1.00 (m, 10H), 0.86 (s, 1H), 0.71-0.64 (m, 1H). | 736.4 |
| I-462 | 18 | $^1$H NMR (400 MHz, DMSO-d$_6$) δ 9.28 (s, 1H), 8.46-8.27 (m, 2H), 7.88-7.71 (m, 1H), 4.45 (s, 1H), 4.33-4.21 (m, 3H), 4.20-4.02 (m, 3H), 3.99-3.72 (m, 5H), 3.69-3.48 (m, 1H), 3.23-3.12 (m, 1H), 3.08-2.99 (m, 1H), 2.62 (dd, J = 12.6, 4.4 Hz, 3H), 1.98-1.86 (m, 1H), 1.62-1.49 (m, 3H), 1.45-1.35 (m, 3H), 1.26 (d, J = 4.2 Hz, 1H), 1.17-1.10 (m, 3H), 1.07 (d, J = 3.3 Hz, 5H), 1.04-0.96 (m, 1H), 0.91-0.86 (m, 1H), 0.75-0.66 (m, 1H). | 588.4 |
| I-463 | 18 | $^1$H NMR (DMSO, 400 MHz) δ 9.26 (1H, s), 8.33-8.42 (1H, m), 8.01-8.12 (1H, m), 7.69-7.82 (1H, m), 3.67-4.27 (10H, m), 3.50-3.62 (1H, m), 3.43 (1H, t, J = 3.2 Hz), 2.54-2.61 (3H, m), 2.03 (1H, d, J = 12.4 Hz), 1.93 (1H, d, J = 11.8 Hz), 1.85 (2H, d, J = 7.2 Hz), 1.75 (3H, d, J = 10.0 Hz), 1.62 (5H, m), 1.27-1.40 (3H, m), 1.02-1.12 (9H, m), 0.85 (1H, t, J = 5.Q Hz), 0.63-0.70 (1H, m) | 612.4 |
| I-464 | 18 | $^1$H NMR (400 MHz, DMSO-d$_6$) δ 9.25 (s, 1H), 8.40-8.35 (m, 1H), 8.13-8.07 (m, 1H), 7.76-7.67 (m, 1H), 4.22-4.10 (m, 4H), 3.94-3.69 (m, 6H), 3.56-3.49 (m, 2H), 2.62-2.54 (m, 3H), 1.84-1.69 (m, 2H), 1.59-1.29 (m, 11H), 1.12-1.03 (m, 9H), 0.87-0.86 (m, 1H), 0.68-0.66 (m, 1H). | 586.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| I-465 | 18 | $^1$H NMR (400 MHz, DMSO-$d_6$) δ 9.28-9.23 (m, 1H), 8.42-8.33 (m, 1H), 8.31-8.18 (m, 1H), 7.83-7.67 (m, 1H), 4.29-3.66 (m, 11H), 3.36-3.28 (m, 1H), 3.19-2.98 (m, 1H), 2.62-2.55 (m, 3H), 2.19-2.09 (m, 2H), 2.04-1.94 (m, 1H), 1.64-1.54 (m, 1H), 1.49-1.37 (m, 2H), 1.33-1.18 (m, 4H), 1.12-1.01 (m, 10H), 0.89-0.83 (m, 1H), 0.71-0.62 (m, 1H), 0.60-0.51 (m, 1H). | 586.4 |
| I-466 | 18 | $^1$H NMR (400 MHz, DMSO-$d_6$) δ 9.25 (s, 1H), 8.41-8.31 (m, 2H), 4.86 (s, 1H), 4.22-3.71 (m, 10H), 3.70-3.60 (m, 3H), 3.23-3.11 (m, 7H), 1.83-1.53 (m, 11H), 1.14-0.95 (m, 17H), 0.87 (s, 2H), 0.67 (s, 1H). | 686.4 |
| I-467 | 18 | $^1$H NMR (400 MHz, Methanol-$d_4$) δ 9.15 (s, 1H), 8.37 (d, J = 13.8 Hz, 1H), 4.92 (s, 2H), 4.46-3.79 (m, 12H), 3.48 (s, 1H), 3.27-2.58 (m, 6H), 1.71 (m, 8H), 1.39 (s, 3H), 1.20-0.95 (m, 19H), 0.78 (s, 1H). | 686.4 |
| I-468 | 18 | $^1$H NMR (400 MHz, DMSO-$d_6$) δ 9.25 (s, 1H), 8.53 (s, 1H), 8.41-8.32 (m, 1H), 4.74-3.36 (m, 18H), 3.28-3.17 (m, 1H), 2.02-1.57 (m, 11H), 1.39-1.26 (m, 1H), 1.19-1.01 (m, 11H), 0.89-0.82 (m, 1H), 0.71-0.64 (m, 1H). | 692.3 |
| I-469 | 18 | $^1$H NMR (400 MHz, DMSO-$d_6$) δ 9.25 (s, 1H), 8.63-8.43 (m, 1H), 8.41-8.33 (m, 1H), 4.77 (s, 1H), 4.37-3.93 (m, 7H), 3.90-3.56 (m, 7H), 3.49 (m, 1H), 3.30-3.18 (m, 2H), 2.85-2.67 (m, 1H), 1.97 (s, 2H), 1.72 (t, J = 36.8 Hz, 9H), 1.40 (m, 2H), 1.07 (m, 10H), 0.86 (s, 1H), 0.68 (s, 1H). | 692.3 |
| I-470 | 18 | $^1$H NMR (400 MHz, DMSO-$d_6$) δ 9.25 (s, 1H), 8.70-8.56 (m, 1H), 8.47-8.35 (m, 1H), 7.71-7.68 (m, 2H), 7.62-7.48 (m, 2H), 4.83-4.55 (m, 3H), 4.48-4.27 (m, 2H), 4.24-3.96 (m, 4H), 3.92-3.65 (m, 5H), 3.58-3.40 (m, 5H), 1.88-1.61 (m, 4H), 1.28-1.12 (m, 4H), 1.08-0.96 (m, 6H), 0.88-0.82 (m, 1H), 0.68-0.57 (m, 1H). | 718.4 |
| I-471 | 32 | $^1$H NMR (400 MHz, Methanol-$d_4$) δ 5.70-5.56 (m, 1H), 4.76-4.35 (m, 2H), 4.24-3.69 (m, 9H), 3.54-3.38 (m, 3H), 3.28-3.17 (m, 1H), 2.11-1.94 (m, 2H), 1.90-1.48 (m, 5H), 1.34-0.85 (m, 17H), 0.50-0.31 (m, 4H). | 685.3 |
| I-472 | 16A | $^1$H NMR (400 MHz, DMSO-$d_6$) δ 8.40-8.20 (m, 2H), 7.82 (d, J = 17.8 Hz, 1H), 7.57 (d, J = 22.6 Hz, 1H), 7.37-7.23 (m, 5H), 5.35 (s, 2H), 4.42 (dd, J = 8.8, 3.4 Hz, 1H), 4.25-4.10 (m, 1H), 4.07-3.85 (m, 3H), 3.78-3.59 (m, 4H), 3.56-3.40 (m, 2H), 3.17 (m, 4H), 1.67 (dd, J = 25.2, 13.2 Hz, 5H), 1.49-1.25 (m, 2H), 1.21 (d, J = 18.6 Hz, 4H), 1.09-1.01 (m, 14H), 0.84 (d, J = 12.4 Hz, 3H), 0.69-0.64 (m, 1H). | 733.3 |
| I-473 | 16A | $^1$H NMR (400 MHz, DMSO-$d_6$) δ 8.30 (dd, J = 40.8, 17.2 Hz, 2H), 7.82 (d, J = 18.2 Hz, 1H), 7.61 (d, J = 23.6 Hz, 1H), 7.37-7.23 (m, 5H), 5.35 (s, 2H), 4.42 (s, 1H), 4.26-3.80 (m, 8H), 3.78-3.57 (m, 5H), 3.24-3.08 (m, 3H), 1.68 (m, 5H), 1.35 (m, 1H), 1.17 (d, J = 13.6 Hz, 7H), 1.09-1.01 (m, 15H), 0.85 (s, 3H), 0.67 (m, 1H). | 761.5 |
| I-474 | 16A | $^1$H NMR(400 MHz, DMSO-$d_6$) δ 8.36 (d, J = 14.8 Hz, 1H), 8.30-8.18 (m, 1H), 7.86-7.79 (m, 1H), 7.74 (d, J = 22.6 Hz, 1H), 7.38-7.23 (m, 5H), 5.35 (s, 2H), 4.43-4.35 (m, 1H), 4.24-4.04 (m, 2H), 3.98-3.85 (m, 2H), 3.83-3.59 (m, 5H), 3.58-3.37 (m, 2H), 3.23-3.12 (m, 2H), 1.73-1.59 (m, 5H), 1.50-1.41 (m, 1H), 1.38-1.34 (m, 1H), 1.30-1.11 (m, 6H), 1.08-0.99 (m, 8H), 0.89-0.79 (m, 6H), 0.66 (d, J = 7.2 Hz, 1H). | 731.4 |
| I-475 | 16A | $^1$H NMR (400 MHz, DMSO-$d_6$) δ 8.40-8.33 (m, 1H), 8.17 (s, 1H), 7.83 (d, J = 13.0 Hz, 1H), 7.37-7.22 (m, 5H), 5.35 (s, 2H), 4.52 (d, J = 8.6 Hz, 1H), 4.12-4.04 (m, 1H), 3.99-3.87 (m, 3H), 3.74 (dd, J = 20.8, 13.2 Hz, 2H), 3.66-3.59 (m, 5H), 3.28 (d, J = 9.0 Hz, 1H), 3.13 (m, 2H), 3.07-3.01 (m, 1H), 1.65 (d, J = 12.4 Hz, 5H), 1.39 (d, J = 29.8 Hz, 2H), 1.20-1.10 (m, 4H), 1.06 (m, 8H), 0.85 (m, 3H), 0.67 (m, 1H). | 648.3 |
| I-476 | 16A | $^1$H NMR (400 MHz, Chloroform-d) δ 7.96 (t, J = 7.6 Hz, 4H), 7.84 (s, 1H), 7.34 (q, J = 7.0 Hz, 7H), 6.56 (d, J = 26.2 Hz, 1H), 5.36 (s, 2H), 4.64 (d, J = 9.2 Hz, 3H), 4.19-3.89 (m, 9H), 3.16 (m, 1H), 2.82 (d, J = 4.6 Hz, 3H), 1.19 (d, J = | 685.3 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | $^1$HNMR | LCMS |
|---|---|---|---|
| | | 7.2 Hz, 1H), 1.12 (dd, J = 6.6, 3.0 Hz, 10H), 0.75 (d, J = 7.0 Hz, 1H). | |
| I-477 | 16A | $^1$H NMR (400 MHz, DMSO-d$_6$) δ 8.39-8.34 (m, 1H), 7.82 (d, J = 13.2 Hz, 1H), 7.37-7.23 (m, 5H), 5.35 (s, 2H), 4.40 (s, 1H), 4.14 (m, 2H), 3.99-3.83 (m, 3H), 3.72 (m, 2H), 3.60 (d, J = 9.2 Hz, 1H), 3.51-3.43 (m, 1H), 3.32 (s, 3H), 3.08 (t, J = 7.8 Hz, 1H), 1.73-1.58 (m, 5H), 1.45 (m, 1H), 1.32 (d, J = 23.6 Hz, 1H), 1.19-1.10 (m, 4H), 1.09-1.02 (m, 8H), 0.84 (d, J = 10.2 Hz, 3H), 0.69-0.63 (m, 1H). | 634.3 |
| I-478 | 16A | $^1$H NMR (400 MHz, CD$_3$OD): 5 7.92 (d, J = 8.16 Hz, 1H), 8.21 (d, J = 11.6 Hz, 1H), 7.43-7.20 (m, 5H), 5.38 (s, 2H), 4.43-3.81 (m, 10H), 3.50-3.32 (m, 5H), 3.19 (d, J = 2.0 Hz, 1H), 2.47-2.44 (m, 2H), 1.74 (t, J = 13.2 Hz, 5H), 1.43 (d, J = 9.6 Hz, 9H), 1.30-1.22 (m, J = 24.0, 6.8 Hz, 5H), 1.15 (d, J = 8.0 Hz, 6H), 1.11 (s, 2H), 1.06-1.01 (m, 1H), 0.97-0.89 (m, 2H), 0.81-0.74 (m, 1H) | 761.5 |
| I-479 | | | |
| I-480 | | | |
| I-481 | | | |
| I-482 | 16A | $^1$H NMR (400 MHz, DMSO-d$_6$) δ 8.46-8.30 (m, 2H), 7.82 (d, J = 16.2 Hz, 1H), 7.40-7.21 (m, 5H), 5.35 (s, 2H), 4.97-4.82 (m, 1H), 4.44-3.53 (m, 14H), 3.33-2.69 (m, 5H), 2.01-1.82 (m, 1H), 1.72-1.53 (m, 7H), 1.48-1.32 (m, 2H), 1.23-0.97 (m, 16H), 0.92-0.77 (m, 3H), 0.70-0.63 (m, 1H). | 773.4 |
| I-483 | 16A | $^1$H NMR (400 MHz, DMSO-d$_6$) δ 12.30 (s, 1H), 8.45-8.31 (m, 2H), 7.82 (d, J = 14.8 Hz, 1H), 7.39-7.22 (m, 5H), 5.35 (s, 2H), 4.96-4.85 (m, 1H), 4.56-3.36 (m, 12H), 3.27-3.08 (m, 2H), 3.05-2.59 (m, 2H), 2.41-2.14 (m, 1H), 2.05-1.87 (m, 1H), 1.78-1.53 (m, 7H), 1.49-1.27 (m, 3H), 1.24-0.99 (m, 12H), 0.91-0.79 (m, 3H), 0.70-0.64 (m, 1H). | 745.3 |
| I-484 | 16A | $^1$H NMR (400 MHz, DMSO-d$_6$) δ 8.48-8.25 (m, 2H), 7.82 (d, J = 16.4 Hz, 1H), 7.39-7.21 (m, 5H), 5.35 (d, J = 3.4 Hz, 2H), 5.07-4.78 (m, 1H), 4.27-3.81 (m, 9H), 3.79-3.44 (m, 6H), 3.25-3.14 (m, 3H), 3.06-2.83 (m, 2H), 2.00-1.80 (m, 1H), 1.72-1.57 (m, 7H), 1.47-1.28 (m, 3H), 1.19-0.98 (m, 15H), 0.92-0.76 (m, 3H), 0.70-0.62 (m, 1H). | 773.4 |
| I-485 | | | |
| I-486 | | | |
| I-487 | | | |
| I-488 | | | |
| I-489 | | | |
| I-490 | | | |
| I-491 | | | |
| I-492 | | | |
| I-493 | 18 | $^1$H NMR (400 MHz, DMSO-d$_6$) δ 9.25 (d, J = 4.6 Hz, 1H), 8.84-8.67 (m, 1H), 8.38 (d, J = 3.2 Hz, 1H), 7.64 (m, 1H), 7.14 (m, 2H), 4.87 (m, 1H), 4.18-3.96 (m, 4H), 3.81-3.52 (m, 8H), 2.76 (d, J = 8.0 Hz, 1H), 2.64 (s, 1H), 1.89-1.78 (m, 4H), 1.70 (d, J = 12.4 Hz, 2H), 1.49 (s, 2H), 1.39-1.33 (m, 3H), 1.23 (d, J = 4.2 Hz, 3H), 1.11-0.98 (m, 5H), 0.86 (d, J = 7.3 Hz, 1H), 0.80 (m, 1H), 0.70-0.60 (m, 1H). | 606.5 |
| I-494 | 18 | $^1$H NMR (400 MHz, DMSO-d$_6$) δ 9.25 (s, 1H), 8.38 (d, J = 28.1 Hz, 4H), 4.90 (s, 1H), 4.28 (s, 3H), 4.07 (s, 5H), 3.80 (s, 4H), 3.65 (s, 2H), 3.59 (s, 3H), 3.46 (s, 2H), 3.05 (s, 1H), 2.78 (s, 2H), 1.88 (s, 2H), 1.72 (s, 4H), 1.37 (d, J = 25.1 Hz, 3H), 1.20 (s, 4H), 1.12 (s, 1H), 1.09 (s, 2H), 1.05 (s, 4H), 0.93 (s, 1H), 0.89 (s, 1H), 0.86 (s, 1H), 0.68 (s, 1H). | 612.3 |
| I-495 | 18 | $^1$H NMR (400 MHz, Methanol-d$_4$) δ 9.19-9.09 (m, 1H), 8.40-8.26 (m, 1H), 7.70-7.56 (m, 1H), 7.24-7.05 (m, 2H), 5.17-4.98 (m, 1H), 4.59-3.64 (m, 10H), 3.52-3.35 (m, 1H), 2.70-2.64 (m, 1H), 2.04-1.69 (m, 9H), 1.66-1.21 (m, 7H), 1.21-0.91 (m, 6H), 0.90-0.64 (m, 2H). | 606.4 |
| I-496 | 18 | $^1$H NMR (400 MHz, CD$_3$OD) δ 9.19-9.09 (m, 1H), 8.40-8.28 (m, 1H), 7.70-7.58 (m, 1H), 7.22-7.05 (m, 2H), | 622.4 |

TABLE 2-continued

Characterization Data of Exemplary Compounds
Table 2 below contains the characterization data for the compounds of Table 1. Additionally,
Table 2 discloses the method of Example 2 that best describes the process by which each compound of
Table 1 was made. The appropriate reagents, starting materials, conditions, and modifications from the
Exemplary synthesis method necessary for synthesizing the compounds of Table 1 would be apparent to a
Person of ordinary skill in the art. LCMS values are shown [M + H]+ unless otherwise specified.

| Compound Number | Method | ¹HNMR | LCMS |
|---|---|---|---|
| I-497 | 18 | 5.18-4.97 (m, 1H), 4.63-3.73 (m, 10H), 3.72-3.32 (m, 6H), 2.76-2.64 (m, 1H), 1.99-1.81 (m, 4H), 1.81-1.72 (m, 1H), 1.64-1.24 (m, 6H), 1.23-0.64 (m, 8H). $^1$H NMR (400 MHz, CD$_3$OD) δ 9.29-9.10 (m, 1H), 8.41-8.26 (m, 1H), 7.79-7.60 (m, 1H), 7.34-7.12 (m, 2H), 5.19-4.96 (m, 1H), 4.56-4.09 (m, 5H), 4.09-3.91 (m, 5H), 3.90-3.50 (m, 5H), 3.49-3.33 (m, 1H), 3.16-2.68 (m, 1H), 2.03-1.42 (m, 9H), 1.22-0.96 (m, 6H), 0.93-0.67 (m, 2H). | 608.4 |
| I-498 | 35 | $^1$H NMR (400 MHz, CD$_3$OD) δ 8.27-8.17 (m, 1H), 7.96-7.93 (m, 1H), 7.41-7.19 (m, 10H), 5.35 (d, J = 11.3 Hz, 2H), 4.70-3.58 (m, 13H), 2.72 (t, J = 2.8 Hz, 3H), 1.49-1.25 (m, 6H), 1.22-1.15 (m, 4H), 1.10-1.02 (m, 3H), 0.78-0.73 (m, 1H). | 655.5 |
| I-499A | 35 | $^1$H NMR (400 MHz, CD$_3$OD) δ 8.25-8.18 (m, 1H), 7.95-7.90 (m, 1H), 7.38-7.27 (m, 5H), 5.38 (s, 2H), 4.62-3.59 (m, 10H), 2.75-2.74 (m, 3H), 1.69-1.66 (m, 5H), 1.50-1.39 (m, 5H), 1.24-1.00 (m, 14H), 0.94-0.70 (m, 4H). | 661.5 |
| I-499B | 35 | $^1$H NMR (400 MHz, CD$_3$OD) δ 8.30-8.22 (m, 1H), 7.98-7.95 (m, 1H), 7.37-7.23 (m, 5H), 5.39 (s, 2H), 4.70-3.61 (m, 10H), 3.37-3.33 (m, 1H), 3.22-3.10 (m, 1H), 1.72-1.64 (m, 5H), 1.51-1.33 (m, 6H), 1.24-1.07 (m. 12H), 1.04-1.00 (m, 1H), 0.97-0.84 (m, 3H), 0.79-0.72 (m, 1H). | 661.5 |
| I-500 | 35 | $^1$H NMR (400 MHz, CD$_3$OD) δ 8.29-8.17 (m, 1H), 8.01-7.84 (m, 1H), 7.38-7.19 (m, 10H), 5.38 (s, 2H), 4.65-3.78 (m, 13H), 2.77-2.70 (m, 3H), 1.46-1.31 (m, 1H), 1.22-0.99 (m, 10H), 0.79-0.67 (m, 1H). | 659.4 |
| I-501 | 35 | $^1$H NMR(400 MHz, CD$_3$OD) δ 8.34-8.15 (m, 1H), 8.01-7.85 (m, 1H), 7.40-7.22 (m, 5H), 5.38-3.78 (m, 13H), 3.36-3.18 (m, 2H), 2.80-2.73 (m, 3H), 1.70-1.46 (m, 7H), 1.23-1.04 (m, 12H), 0.94-0.77 (m, 4H) | 665.5 |

Example A1: CDK2/Cyclin E1 Caliper Assay

Inhibition of CDK2/Cyclin E1 activity in the presence of compounds of the present disclosure was evaluated using a Caliper LabChip® EZ Reader mobility shift assay. In the assay, CDK2/Cyclin E1 (Eurofins, 14-475) catalyzed the phosphorylation of a fluorescently tagged peptide 5-FAM-QSPKKG-CONH2 (PerkinElmer, FL Peptide 18) which induced a difference in capillary electrophoresis mobility. The peptide substrate and product were measured, and the conversion ratio was used to determine the inhibition (as % activity and IC50 values) of CDK2/Cyclin E1. Reactions contained 50 mM HEPES pH 7.5, 10 mM MgCl2, 1 mM EDTA, 2 mM DTT, 0.01% Brij35, 0.5 mg/mL BSA, 0.1% DMSO, 2.5 nM CDK2/Cyclin E1, 100 µM ATP, and 1.5 µM fluorescent peptide substrate.

Dose titrations of inhibitors in 100% DMSO were combined with 3.25 nM CDK2/Cyclin E1 and 130 µM of ATP in reaction buffer. The mixtures were incubated for 30 minutes before the addition of fluorescent peptide substrate to initiate the kinase reaction. The final conditions were 2.5 nM CDK2/Cyclin E1, 100 µM ATP, and 1.5 µM fluorescent peptide. The reactions were stopped after 100 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the IC50 for each compound.

The results of the Caliper Assay are reported in Table 3, below. Compounds with an IC$_{50}$ less than or equal to 0.01 µM are designated as "A". Compounds with an IC$_{50}$ greater than 0.01 µM and less than or equal to 0.1 µM are designated as "B". Compounds with an IC$_{50}$ greater than 0.1 µM and less than or equal to 1.0 µM are designated as "C". Compounds with an IC$_{50}$ greater than 1.0 µM and less than or equal to 10.0 µM are designated as "D". Compounds with an IC$_{50}$ greater than 10.0 µM are designated as "E".

Example A2: BrdU Cell Proliferation Assay

A BrdU assay was used as a measure of proliferation based on the DNA replication process of proliferating cells. BrdU, a pyrimidine analog, is added to the cell culture and incorporated into the DNA of proliferating cells. The presence of the BrdU analog was then measured through a colorimetric ELISA. After fixation and permeabilization of cells, peroxidase-conjugated antibody recognizing BrdU is added and allowed to incubate, followed by thorough washing to remove unbound antibody. In order to quantify the amount of bound antibody, peroxidase substrate is added and produces a color that can be measured at 450 nm.

On day −1, Kuramochi cells (Sekisui XenoTech JCRB0098) were seeded at 2,000 cells/well in columns 2-12 of a 96 well plate (Corning, CLS3596) in 150 µL media and allowed to adhere overnight at 37 degree with 5% CO$_2$.

On day 0, the source plate was prepared by adding 10 mM compounds and performing 3-fold serial dilutions for a 10-point dose response of each compound. Using a multi-channel pipette, 2 µL of the contents of the source plate were stamped into an intermediate plate with 500 µL of RPMI 1640 Media, GlutaMAX Supplement (Life Technologies, 61870127) in each well of a Nunc 96 DeepWell™ plate, non-treated 96 DeepWell plate, 2 mL/well, sterile, natural, 60/cs (Sigma Z717274) and mixed thoroughly. 50 µL from each well of this intermediate plate were added to 4 wells of a 96-well plate with previously seeded Kuramochi cells.

On day 4, the plates were developed using the BrdU ELISA Cell Proliferation Assay according to manufacturer's instructions (Roche, 11647229001). Briefly, BrdU was diluted 1:100 in Gibco®, OptiMEM® and 20 µL/well was added, shaken for 10 minutes at 350 rpm, and then returned to the incubator for 1 hour. Following incubation, the medium was discarded, and the cells were fixed by adding 200 µL of Fix/Denature solution. The anti-BrdU peroxidase antibody was diluted 1:1000 in OptiMEM, added at 100 µL/well, and incubated while shaking (350 rpm) for one hour. Three washes with PBS were performed to remove any unbound antibody, followed by the addition of 100 µL of substrate solution to each well. 25 µL/well of 1M sulfuric acid solution was then added to halt the reaction, and plates were read out using an Envision spectrophotometer (Perkin Elmer) set to read 450 nm absorbance. Background absorbance values from empty wells were subtracted from all samples and then normalized to DMSO treated wells.

The results of the BrdU cell proliferation assay are reported in Table 3, below. Compounds with an $IC_{50}$ less than or equal to 0.5 µM are designated as "A". Compounds with an $IC_{50}$ greater than 0.5 µM and less than or equal to 5.0 µM are designated as "B". Compounds with an $IC_{50}$ greater than 5.0 µM and less than or equal to 10.0 µM are designated as "C". Compounds with an $IC_{50}$ greater than 10.0 µM are designated as "D".

Example A3: HotSpot® Kinase Inhibition Assay

Inhibition of CDK2/CCNE1 activities in the presence of compounds of the present disclosure was evaluated using the HotSpot™ assay (proprietary to Reaction Biology Corporation). In the assay, CDK2/Cyclin E1 (Signalchem C29-18G) catalyzed the transfer of radioactive phosphate to amino acid residues of Histone H1 (Sigma, H5505), which are detected radiometrically. After subtraction of background derived from control reactions containing inactive enzyme, kinase activity data is expressed as the percent remaining kinase activity in test samples compared to reactions without inhibitor present. Reactions contained 20 mM HEPES pH 7.5, 10 mM $MgCl_2$, 1 mM EGTA, 2 mM DTT, 0.02% Brij35, 0.02 mg/mL BSA, 0.1 mM $Na_3VO_4$, 1% DMSO, 1.5 nM CDK2/Cyclin E1, 10 µM ATP, and 20 µM Histone H1.

CDK2/Cyclin E1 and Histone H1 were mixed in reaction buffer. To this mixture dose titrations of inhibitors in 100% DMSO were added in by acoustic transfer. The compound mixtures were incubated for 20 minutes, then the kinase reactions were initiated by the addition of a mixture of ATP and $^{33}P$ ATP for final concentrations of 10 µM total ATP, 20 µM Histone H1, and 1.5 nM CDK2/Cyclin E1. The reactions were carried out for 120 minutes, then spotted on a P81 ion exchange filter paper, and extensively washed with 0.75% phosphoric acid. The resulting radioactive counts were normalized to yield % activity, plotted against compound concentration, and fit to a four-parameter equation to determine the $IC_{50}$ for each compound.

The results of the HotSpot™ assay are reported in Table 3, below. Compounds with an $IC_{50}$ less than or equal to 1.0 µM are designated as "A". Compounds with an $IC_{50}$ greater than 1.0 µM and less than or equal to 10 µM are designated as "B". Compounds with an $IC_{50}$ greater than 10 µM and less than or equal to 100 µM are designated as "C". Compounds with an $IC_{50}$ greater than 100 µM are designated as "D".

Example A4: IncuCyte® Cell Proliferation Assay

IncuCyte® assay was used to measure the effect of disclosed compounds on cell proliferation. Fluorescent microscopy images of cells were taken immediately after compound treatment and 72 hours later. Image analysis software was used to obtain cell counts as a function of compound concentration. Kuramochi cells labeled with mApple-H2B were seeded on 384-well assay-ready plates. Plates were placed in an IncuCyte® (Sartorius) and scanned at 0 and 72 hours. IncuCyte® software was used to count the number of fluorescent nuclei in each well. The fold change in cell count from 0 to 72 hours in wells treated with increasing compounds concentrations (10 pts, ½ log dilution, 20 µM top concentration) was normalized to DMSO control wells. The normalized cell counts were fit with dose response curves and a G150 was calculated.

The results of the IncuCyte® cell proliferation assay are reported in Table 3, below. Compounds with an $IC_{50}$ less than or equal to 0.5 µM are designated as "A". Compounds with an $IC_{50}$ greater than 0.5 µM and less than or equal to 5.0 µM are designated as "B". Compounds with an $IC_{50}$ greater than 5.0 µM and less than or equal to 20.0 µM are designated as "C". Compounds with an $IC_{50}$ greater than 20.0 µM are designated as "D".

TABLE 3

Assay Results

| Cmpd # | Caliper Assay (CDK2/CCNE1): IC50 (µM) | BrdU - KURAMOCHI.1: IC50 (µM) | Kinase Assay (CDK2/CCNE): IC50 (µM) | IncuCyte ® Assay: IC50 (µM) |
|---|---|---|---|---|
| I-1 | | | B | |
| I-2 | | | C | |
| I-3A | C | | A | |
| I-3B | E | | B | D |
| I-4A | | | C | |
| I-4B | | | D | |
| I-5A | | | A | |
| I-5B | | | B | |
| I-6 | | | D | |
| I-7 | | D | A | |
| I-8A | D | | B | |

TABLE 3-continued

Assay Results

| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
|---|---|---|---|---|
| I-8B | D | | C | |
| I-9 | C | D | | |
| I-10 | C | | A | |
| I-11 | C | | A | |
| I-12 | | B | A | |
| I-13 | C | | A | |
| I-14 | D | | B | |
| I-15 | C | D | | |
| I-16A | E | D | | |
| I-16B | E | D | | |
| I-17A | | D | | |
| I-17B | E | D | | |
| I-18 | D | | | D |
| I-19A | C | D | | |
| I-19B | E | D | | |
| I-20 | B | D | | |
| I-21 | B | D | | |
| I-22 | B | B | | |
| I-23A | D | D | | |
| I-23B | E | D | | |
| I-24A | C | D | | |
| I-24B | E | D | | |
| I-25A | E | D | | |
| I-25B | E | D | | |
| I-26A | D | D | | |
| I-26B | E | D | | |
| I-27A | D | D | | |
| I-27B | E | D | | |
| I-28 | C | D | | |
| I-29 | C | D | | |
| I-30 | B | D | | |
| I-31 | C | D | | |
| I-32 | B | D | | |
| I-33A | C | D | | |
| I-33B | E | D | | |
| I-34A | E | D | | |
| I-34B | E | D | | |
| I-35 | E | | | D |
| I-36A | E | D | | |
| I-36B | E | D | | |
| I-37A | E | D | | |
| I-37B | E | D | | |
| I-38A | E | D | | |
| I-38B | E | D | | |
| I-39A | C | D | | |
| I-39B | E | D | | |
| I-40A | E | D | | |
| I-40B | E | D | | |
| I-41A | E | D | | |
| I-41B | E | D | | |
| I-42A | D | D | | |
| I-42B | E | D | | |
| I-43A | E | D | | |
| I-43B | E | D | | |
| I-44A | E | D | | |
| I-44B | E | D | | |
| I-45A | E | D | | |
| I-45B | E | D | | |
| I-46A | E | D | | |
| I-46B | E | D | | |
| I-47A | E | D | | |
| I-47B | E | D | | |
| I-48A | E | D | | |
| I-48B | E | D | | |
| I-49A | E | D | | |
| I-49B | E | D | | |
| I-50A | E | D | | |
| I-50B | E | D | | |
| I-51A | E | C | | C |
| I-51B | E | D | | |
| I-52 | B | B | | B |
| I-53A | E | D | | |
| I-53B | E | D | | |
| I-54A | C | D | | |

TABLE 3-continued

| | Assay Results | | | |
|---|---|---|---|---|
| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
| I-54B | E | D | | |
| I-55A | E | D | | |
| I-55B | E | D | | |
| I-56A | C | D | | |
| I-56B | D | D | | |
| I-57 | B | D | | |
| I-58A | C | D | | |
| I-58B | D | D | | |
| I-59A | E | D | | |
| I-59B | E | D | | |
| I-60A | D | D | | |
| I-60B | E | D | | |
| I-61A | D | D | | |
| I-61B | E | D | | |
| I-62A | C | D | | |
| I-62B | E | D | | |
| I-63A | D | C | | |
| I-63B | D | D | | |
| I-64 | B | B | | |
| I-65A | B | D | | |
| I-65B | E | D | | |
| I-66A | B | D | | |
| I-66B | D | D | | |
| I-67A | C | D | | |
| I-67B | E | D | | |
| I-68A | E | D | | |
| I-68B | E | D | | |
| I-69A | C | D | | |
| I-69B | E | D | | |
| I-70A | E | D | | |
| I-70B | E | D | | |
| I-71A | C | D | | |
| I-71B | E | D | | |
| I-72A | E | D | | |
| I-72B | E | D | | |
| I-73A | D | D | | |
| I-73B | E | D | | |
| I-74A | D | D | | |
| I-74B | E | D | | |
| I-75A | D | B | | |
| I-75B | D | D | | |
| I-76A | D | D | | |
| I-76B | E | D | | |
| I-77A | E | D | | |
| I-77B | E | D | | |
| I-78A | E | D | | |
| I-78B | E | D | | |
| I-79A | E | D | | |
| I-79B | E | D | | |
| I-80A | E | D | | |
| I-80B | E | D | | |
| I-81A | C | | | |
| I-81B | D | C | | |
| I-82A | E | D | | |
| I-82B | E | D | | |
| I-83A | D | D | | |
| I-83B | E | D | | |
| I-84A | D | | | |
| I-84B | D | C | | |
| I-85 | B | B | | |
| I-86 | B | D | | |
| I-87A | C | D | | |
| I-87B | E | D | | |
| I-88 mixture | | | C | |
| I-88A | E | D | | |
| I-88B | E | D | | |
| I-89A | D | D | | |
| I-89B | E | D | | |
| I-90A | C | D | | |
| I-90B | E | D | | |
| I-91A | E | D | | |
| I-91B | E | D | | |
| I-92A | E | D | | |
| I-92B | E | D | | |

TABLE 3-continued

| | Assay Results | | | |
|---|---|---|---|---|
| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
| I-93 | D | D | | |
| I-94A | E | D | | |
| I-94B | E | D | | |
| I-95A | C | D | | |
| I-95B | E | D | | |
| I-96A | C | D | | |
| I-96B | E | D | | |
| I-97 | B | B | | B |
| I-98 | B | D | | |
| I-99 | B | B | | C |
| I-100A | D | D | | |
| I-100B | E | D | | |
| I-101A | C | D | | |
| I-101B | E | D | | |
| I-102A | E | D | | |
| I-102B | E | D | | |
| I-103A | C | D | | |
| I-103B | E | D | | |
| I-104 | B | A | | B |
| I-105 | A | A | | A |
| I-106 | B | B | | |
| I-107 | A | A | | A |
| I-108A | C | D | | |
| I-108B | E | D | | |
| I-109A | E | D | | |
| I-109B | E | D | | |
| I-110A | B | B | | |
| I-110B | C | C | | C |
| I-111 | B | A | | B |
| I-112A | D | D | | |
| I-112B | E | D | | |
| I-113A | D | D | | |
| I-113B | E | D | | |
| I-114A | C | D | | |
| I-114B | E | D | | |
| I-115 | C | D | | C |
| I-116A | E | D | | |
| I-116B | E | D | | |
| I-117A | D | D | | |
| I-117B | E | D | | |
| I-118 | E | D | | D |
| I-119A | C | D | | |
| I-119B | D | D | | |
| I-120A | C | D | | |
| I-120B | D | D | | |
| I-121A | B | C | | |
| I-121B | D | D | | |
| I-122A | E | D | | |
| I-122B | E | D | | |
| I-123A | A | A | | B |
| I-123B | C | D | | |
| I-124 | C | D | | |
| I-125A | A | A | | A |
| I-125B | B | B | | B |
| I-126A | E | D | | |
| I-126B | E | D | | |
| I-127A | D | D | | |
| I-127B | E | D | | |
| I-128A | E | D | | |
| I-128B | E | D | | |
| I-129A | B | B | | B |
| I-129B | D | D | | |
| I-130A | B | C | | C |
| I-130B | C | D | | |
| I-131A | E | D | | D |
| I-131B | E | D | | |
| I-132 | B | B | | B |
| I-133A | D | D | | |
| I-133B | D | D | | D |
| I-134A | E | D | | D |
| I-134B | E | D | | D |
| I-135A | B | B | | B |
| I-135B | C | D | | C |
| I-136A | B | B | | C |

TABLE 3-continued

| | Assay Results | | | |
|---|---|---|---|---|
| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
| I-136B | C | D | | |
| I-137A | C | D | | D |
| I-137B | D | D | | D |
| I-138 | A | A | | A |
| I-139 | C | D | | |
| I-140A | C | D | | C |
| I-140B | E | D | | |
| I-141A | B | B | | |
| I-141B | C | B | | C |
| I-142A | E | D | | |
| I-142B | E | D | | |
| I-143 | E | D | | |
| I-144A | B | D | | |
| I-144B | D | D | | |
| I-145A | B | B | | |
| I-145B | D | D | | |
| I-146 | E | D | | |
| I-147 | A | | | |
| I-148A | E | D | | |
| I-148B | E | D | | |
| I-149 mixture | A | A | | A |
| I-149A | A | A | | A |
| I-149B | C | D | | |
| I-150A | A | B | | |
| I-150B | D | D | | |
| I-151A | | B | | B |
| I-151B | D | D | | |
| I-152 mixture | A | A | | A |
| I-152A | A | A | | A |
| I-152B | D | D | | C |
| I-153 mixture | A | A | | A |
| I-153A | | A | | A |
| I-153B | D | D | | |
| I-154A | | B | | B |
| I-154B | D | D | | |
| I-155A | C | D | | |
| I-155B | D | D | | |
| I-156A | B | C | | |
| I-156B | E | D | | D |
| I-157A | B | B | | B |
| I-157B | C | D | | |
| I-158A | E | D | | |
| I-158B | E | D | | |
| I-159 | E | D | | |
| I-160A | B | B | | |
| I-160B | E | D | | |
| I-161A | E | D | | |
| I-161B | E | D | | |
| I-162A | B | B | | C |
| I-162B | E | D | | |
| I-163A | E | D | | D |
| I-163B | E | D | | |
| I-164A | A | A | | A |
| I-164B | B | B | | B |
| I-165 | E | D | | |
| I-166A | A | A | | A |
| I-166B | C | B | | |
| I-167 | C | D | | |
| I-168 | D | D | | |
| I-169 | E | D | | |
| I-170 | A | B | | |
| I-171A | C | D | | |
| I-171B | E | D | | |
| I-172 | A | A | | |
| I-173A | A | A | | B |
| I-173B | D | D | | |
| I-174A | B | B | | B |
| I-174B | C | D | | |
| I-175A | A | A | | A |
| I-175B | C | D | | C |
| I-176A | B | D | | D |
| I-176B | D | D | | |
| I-177A | C | B | | C |
| I-177B | D | D | | |

TABLE 3-continued

| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
|---|---|---|---|---|
| I-178A | C | D | | C |
| I-178B | E | D | | |
| I-179 | D | D | | |
| I-180 | C | D | | |
| I-181 | D | D | | |
| I-182 | D | C | | |
| I-183 | E | D | | |
| I-184 | C | | | |
| I-185A | E | D | | |
| I-185B | E | D | | |
| I-186A | B | B | | |
| I-186B | E | D | | |
| I-187A | E | D | | |
| I-187B | E | D | | |
| I-188A | B | D | | |
| I-188B | D | D | | |
| I-189A | C | D | | C |
| I-189B | E | D | | D |
| I-190A | B | A | | A |
| I-190B | C | B | | C |
| I-191A | E | D | | D |
| I-191B | E | D | | D |
| I-192A | A | A | | A |
| I-192B | D | D | | |
| I-193 | | A | | A |
| I-194 mixture | A | A | | A |
| I-194A | | A | | A |
| I-194B | | B | | C |
| I-195 | A | A | | A |
| I-196 mixture | A | A | | B |
| I-196A | A | A | A | A |
| I-196B | A | A | | B |
| I-197 | A | B | | A |
| I-198 | A | A | | A |
| I-199 | C | D | | |
| I-200 | A | B | | |
| I-201A | E | D | | |
| I-201B | E | D | | |
| I-202 | A | B | | |
| I-203 | A | B | | B |
| I-204 | D | D | | |
| I-205A | C | D | | |
| I-205B | D | D | | |
| I-206 | C | D | | |
| I-207 | D | A | | C |
| I-208A | B | A | | A |
| I-208B | C | D | | |
| I-209A | D | D | | |
| I-209B | E | D | | |
| I-210 | E | D | | |
| I-211 | D | D | | |
| I-212 | D | D | | |
| I-213A | B | B | | B |
| I-213B | E | D | | D |
| I-214 | D | D | | |
| I-215 | D | D | | |
| I-216 | C | D | | |
| I-217 | A | A | | |
| I-218 | A | C | | |
| I-219 | A | B | | |
| I-220 | B | D | | |
| I-221 | E | D | | |
| I-222 | B | D | | |
| I-223 | E | D | | |
| I-224A | D | D | | D |
| I-224B | E | D | | |
| I-225 | C | D | | |
| I-226 | D | D | | |
| I-227A | C | D | | D |
| I-227B | E | D | | |
| I-228A | A | D | | D |
| I-228B | C | D | | |
| I-229A | E | B | | B |
| I-229B | E | D | | |

TABLE 3-continued

| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
|---|---|---|---|---|
| I-230 | D | D | | |
| I-231A | D | D | | D |
| I-231B | E | D | | |
| I-232A | B | B | | B |
| I-232B | D | D | | |
| I-233 | E | D | | |
| I-234 | E | D | | |
| I-235 | C | D | | |
| I-236 | D | D | | |
| I-237 | C | D | | |
| I-238 | B | D | | |
| I-239 | A | D | | |
| I-240 | A | D | | |
| I-241 | D | D | | |
| I-242 | D | D | | |
| I-243 | E | D | | |
| I-244 | D | D | | |
| I-245 | D | D | | |
| I-246 | C | B | | C |
| I-247 | C | D | | |
| I-248 | E | D | | |
| I-249 | B | B | | B |
| I-250 | E | D | | |
| I-251 | C | D | | |
| I-252 | C | C | A | C |
| I-253 | C | C | B | C |
| I-254 | E | D | | |
| I-255 | E | D | | |
| I-256 | C | C | B | |
| I-257 | D | D | | D |
| I-258 | E | D | | D |
| I-259 | E | D | | D |
| I-260 | E | D | | D |
| I-261 | E | D | | D |
| I-262 | C | D | | D |
| I-263 | A | B | | B |
| I-264 | D | D | | D |
| I-265 | D | D | | D |
| I-266 | D | D | | D |
| I-267 | D | D | | D |
| I-268 | E | D | | D |
| I-269 | C | D | | C |
| I-270 | B | D | | C |
| I-271 | A | A | | A |
| I-272 | B | B | | B |
| I-273 | E | D | | D |
| I-274 | C | C | | C |
| I-275 | C | D | | D |
| I-276 | D | D | | D |
| I-277 | D | D | | D |
| I-278 | D | D | | D |
| I-279 | B | B | | B |
| I-280 | A | B | | B |
| I-281 | A | B | A | A |
| I-282 | A | A | | A |
| I-283 | D | D | | D |
| I-284 | B | B | | B |
| I-285 | C | | | D |
| I-286 | B | B | | B |
| I-287 | C | D | | C |
| I-288 | B | D | | C |
| I-289 | A | A | | A |
| I-290 | C | D | | C |
| I-291 | C | | | D |
| I-292 | B | | | D |
| I-293 | D | D | | D |
| I-294 | E | D | | D |
| I-295 | C | C | | C |
| I-296 | B | B | | B |
| I-297 | B | | | D |
| I-298 | E | D | | D |
| I-299 | B | D | | D |
| I-300 | A | | | A |
| I-301 | A | | | D |

TABLE 3-continued

Assay Results

| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte ® Assay: IC50 (μM) |
|---|---|---|---|---|
| I-302 | B | D | | D |
| I-303 | E | D | | |
| I-304 | A | B | | B |
| I-305 | E | B | | |
| I-306 | D | D | | D |
| I-307 | B | B | | B |
| I-308 | A | A | | B |
| I-309 | B | B | | B |
| I-310 | | | | C |
| I-311 | A | A | | A |
| I-312 | B | | | B |
| I-313 | A | | | B |
| I-314 | A | | | A |
| I-315 | A | | | B |
| I-316 | C | | | D |
| I-317 | A | B | | B |
| I-318 | A | B | | B |
| I-319 | A | A | | B |
| I-320 | A | | | B |
| I-321 | B | B | | B |
| I-322 | A | B | | B |
| I-323 | D | D | | D |
| I-324 | D | D | | D |
| I-325 | D | D | | D |
| I-326 | A | A | | A |
| I-327 | B | | | C |
| I-328 | A | B | | B |
| I-329 | A | | | B |
| I-330 | A | C | | B |
| I-331 | A | | | A |
| I-332 | A | | | C |
| I-333 | B | | | C |
| I-334 | C | | | D |
| I-335 | A | | | B |
| I-336 | A | D | | C |
| I-337 | A | | | B |
| I-338 | E | | | D |
| I-339 | D | | | D |
| I-340 | D | | | D |
| I-341 | C | D | | D |
| I-342 | B | B | | B |
| I-343 | A | | | D |
| I-344 | E | D | | D |
| I-345 | E | D | | D |
| I-346 | E | D | | D |
| I-347 | E | | | D |
| I-348 | D | | | D |
| I-349 | E | | | D |
| I-350 | E | | | D |
| I-351 | E | | | D |
| I-352 | E | | | D |
| I-353 | A | | | C |
| I-354 | A | B | | A |
| I-355 | A | B | | A |
| I-356 | E | D | | D |
| I-357 | B | C | | C |
| I-358 | E | D | | D |
| I-359 | E | D | | D |
| I-360 | A | B | | B |
| I-361 | A | B | | B |
| I-362 | B | B | | C |
| I-363 | D | C | | C |
| I-364 | E | D | | C |
| I-365 | D | D | | D |
| I-366 | D | B | | B |
| I-367 | A | B | A | B |
| I-368 | C | D | | C |
| I-369 | A | B | | B |
| I-370 | A | A | | A |
| I-371 | E | D | | D |
| I-372 | A | A | | A |
| I-373 | E | D | | D |
| I-374 | A | B | | B |
| I-375 | C | D | | D |

TABLE 3-continued

Assay Results

| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte® Assay: IC50 (μM) |
|---|---|---|---|---|
| I-376 | D | D | B | D |
| I-377 | C | D | A | D |
| I-378 | E | D | C | D |
| I-379 | E | D |   | D |
| I-380 | A | A |   | A |
| I-381 | E | D |   | D |
| I-382 | D | D |   | D |
| I-383 | A | C |   | B |
| I-384 | E | D |   | D |
| I-385 | A | A |   | A |
| I-386 | A | A |   | A |
| I-387 | E |   |   | D |
| I-388 | E |   |   | B |
| I-389 | A |   |   | B |
| I-390 | A |   |   | A |
| I-391 | A |   |   | B |
| I-392 | D |   |   | D |
| I-393 | B |   |   | C |
| I-394 | A |   |   | A |
| I-395 | B |   |   | B |
| I-396 | A |   |   | B |
| I-397 | A |   |   | B |
| I-398 | A | A |   | A |
| I-399 | A | B |   | B |
| I-400 | E | D |   | D |
| I-401 | B | B |   | B |
| I-402 | B | B |   | B |
| I-403 | B | D |   | D |
| I-404 | B |   |   | D |
| I-405 | E |   |   | D |
| I-406 | A | B |   | B |
| I-407 | E |   |   | D |
| I-408 | B |   |   | B |
| I-409 | A |   |   | B |
| I-410 | B |   |   | B |
| I-411 | B |   |   | D |
| I-412 | B |   |   | D |
| I-413 | C |   |   | D |
| I-414 | B |   |   | B |
| I-415 | B |   |   | B |
| I-416 | B |   |   | C |
| I-417 | E |   |   | D |
| I-418 | E |   |   | D |
| I-419 | C |   |   | D |
| I-420 | E |   |   | D |
| I-421 | D |   |   | D |
| I-422 | D | D |   | D |
| I-423 | D |   |   | D |
| I-424 | B | D |   | D |
| I-425 | C | D |   | D |
| I-426 | C | D |   | D |
| I-427 | D | D |   | D |
| I-428 | C | D |   | D |
| I-429 | D | D |   | D |
| I-430 | C | D |   | D |
| I-431 | C |   |   | D |
| I-432 | C | D |   | D |
| I-433 | D |   |   | D |
| I-434 | C |   |   | D |
| I-435 | A |   |   | B |
| I-436 | E |   |   | D |
| I-437 | E |   |   | D |
| I-438 | A |   |   | B |
| I-439 | A |   |   | A |
| I-440 | B |   |   | D |
| I-441 | C |   |   | D |
| I-442 | A |   |   | C |
| I-443 | A |   |   | A |
| I-444 | A |   |   | A |
| I-445 | A |   |   | A |
| I-446 | A |   |   | B |
| I-447 | C | D |   |   |
| I-448 | D |   |   | D |
| I-449 | A |   |   | A |

TABLE 3-continued

Assay Results

| Cmpd # | Caliper Assay (CDK2/CCNE1): IC50 (μM) | BrdU - KURAMOCHI.1: IC50 (μM) | Kinase Assay (CDK2/CCNE): IC50 (μM) | IncuCyte® Assay: IC50 (μM) |
|---|---|---|---|---|
| I-450 | C | | | D |
| I-451 | B | | | C |
| I-452 | A | | | A |
| I-453 | A | | | C |
| I-454 | A | | | B |
| I-455 | B | | | B |
| I-456 | A | | | B |
| I-457 | B | | | B |
| I-458 | A | | | B |
| I-459 | B | | | C |
| I-460 | A | | | B |
| I-461 | A | | | B |
| I-462 | C | D | | D |
| I-463 | B | B | | B |
| I-464 | B | B | | B |
| I-465 | A | B | | A |
| I-466 | A | B | A | B |
| I-467 | A | B | | B |
| I-468 | A | A | | A |
| I-469 | A | B | | A |
| I-470 | A | | | B |
| I-471 | D | | | D |
| I-472 | A | | | |
| I-473 | A | | | |
| I-474 | A | | | |
| I-475 | A | | | |
| I-476 | D | | | D |
| I-477 | A | | | D |
| I-478 | A | | | A |
| I-479 | | | | |
| I-480 | | | | |
| I-481 | | | | |
| I-482 | A | | | |
| I-483 | A | | | |
| I-484 | A | | | |
| I-485 | | | | |
| I-486 | | | | |
| I-487 | | | | |
| I-488 | | | | |
| I-489 | | | | |
| I-490 | | | | |
| I-491 | | | | |
| I-492 | | | | |
| I-493 | B | | | C |
| I-494 | C | D | | D |
| I-495 | B | | | B |
| I-496 | B | D | | C |
| I-497 | D | | | D |
| I-498 | D | | | D |
| I-499A | D | | | D |
| I-499B | E | | | D |
| I-500 | C | | | |
| I-501 | B | | | B |

Example A5: CDK1/Cyclin B1 Caliper Assay

Inhibition of CDK1/Cyclin B1 activity in the presence of compounds of the present disclosure was evaluated using a Caliper LabChip® EZ Reader mobility shift assay. In the assay, CDK1/Cyclin B1 (Carna Biosciences, 04-102) catalyzed the phosphorylation of a fluorescently tagged peptide 5-FAM-GGGPATPKKAKKL-CONH2 (PerkinElmer, FL Peptide 29) which induced a difference in capillary electrophoresis mobility. The peptide substrate and product were measured, and the conversion ratio was used to determine the inhibition (as % activity and $IC_{50}$ values) of CDK1/Cyclin B1. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 1.25 nM CDK1/Cyclin B1, 10 μM ATP, and 1.5 μM fluorescent peptide substrate.

Dose titrations of inhibitors in 100% DMSO were combined with 1.625 nM CDK1/Cyclin B1 and 13 μM of ATP in reaction buffer. The mixtures were incubated for 30 minutes before the addition of fluorescent peptide substrate to initiate the kinase reaction. The final conditions were 1.25 nM CDK1/Cyclin B1, 10 μM ATP, and 1.5 μM fluorescent peptide. The reactions were stopped after 90 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

Certain compounds of the present invention were tested in the above method of Example A5 and found to be selective for inhibition of CDK2/Cyclin E1 over CDK1/Cyclin B1. In some embodiments, the tested compounds were found to be greater than 5000-fold more selective for CDK2/Cyclin E1 over CDK1/Cyclin B1. In some embodiments, the tested compounds were found to be greater than 1000-fold more selective for CDK2/Cyclin E1 over CDK1/Cyclin B1. In some embodiments, the tested compounds were found to be greater than 500-fold more selective for CDK2/Cyclin E1 over CDK1/Cyclin B1. In some embodiments, the tested compounds were found to be greater than 200-fold more selective for CDK2/Cyclin E1 over CDK1/Cyclin B1.

Example A6: CDK2/Cyclin A2 Caliper Assay

Inhibition of CDK2/Cyclin A2 activity in the presence of compounds of the present disclosure was evaluated using a Caliper LabChip® EZ Reader mobility shift assay. In the assay, CDK2/Cyclin A2 (Carna Biosciences, 04-103) catalyzed the phosphorylation of a fluorescently tagged peptide 5-FAM-QSPKKG-CONH2 (PerkinElmer, FL Peptide 18) which induced a difference in capillary electrophoresis mobility. The peptide substrate and product were measured, and the conversion ratio was used to determine the inhibition (as % activity and $IC_{50}$ values) of CDK2/Cyclin A2. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 1.5 nM CDK2/Cyclin A2, 10 µM ATP, and 1.5 µM fluorescent peptide substrate.

Dose titrations of inhibitors in 100% DMSO were combined with 2 nM CDK2/Cyclin A2 and 13 µM of ATP in reaction buffer. The mixtures were incubated for 30 minutes before the addition of fluorescent peptide substrate to initiate the kinase reaction. The final conditions were 1.5 nM CDK2/Cyclin A2, 10 µM ATP, and 1.5 µM fluorescent peptide. The reactions were stopped after 120 minutes with the addition of EDTA (400 mM final EDTA concentration). The stopped reactions were analyzed on a Caliper LabChip© EZ Reader II. The conversion ratios were normalized to yield % activity, plotted against compound concentration, and fit to a four-parameter equation to determine the $IC_{50}$ for each compound.

Certain compounds of the present invention were tested in the above method of Example A6 and found to be selective for inhibition of CDK2/Cyclin E1 over CDK2/Cyclin A2. In some embodiments, the tested compounds were found to be greater than 5000-fold more selective for CDK2/Cyclin E1 over CDK2/Cyclin A2. In some embodiments, the tested compounds were found to be greater than 1000-fold more selective for CDK2/Cyclin E1 over CDK2/Cyclin A2. In some embodiments, the tested compounds were found to be greater than 500-fold more selective for CDK2/Cyclin E1 over CDK2/Cyclin A2. In some embodiments, the tested compounds were found to be greater than 200-fold more selective for CDK2/Cyclin E1 over CDK2/Cyclin A2.

Example A7: CDK3/Cyclin E1 Caliper Assay

Inhibition of CDK3/Cyclin E1 activity in the presence of compounds of the present disclosure was evaluated using a Caliper LabChip® EZ Reader mobility shift assay. In the assay, CDK3/Cyclin E1 (Carna Biosciences, 04-104) catalyzed the phosphorylation of a fluorescently tagged peptide 5-FAM-GGGPATPKKAKKL-CONH2 (PerkinElmer, FL Peptide 29) which induced a difference in capillary electrophoresis mobility. The peptide substrate and product were measured, and the conversion ratio was used to determine the inhibition (as % activity and $IC_{50}$ values) of CDK3/Cyclin E1. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 0.31 nM CDK3/Cyclin E1, 1 mM ATP, and 1.5 µM fluorescent peptide substrate.

Dose titrations of inhibitors in 100% DMSO were combined with 0.4 nM CDK3/Cyclin E1 and 1.3 mM of ATP in reaction buffer. The mixtures were incubated for 30 minutes before the addition of fluorescent peptide substrate to initiate the kinase reaction. The final conditions were 0.31 nM CDK3/Cyclin E1, 1 mM ATP, and 1.5 µM fluorescent peptide. The reactions were stopped after 120 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

Certain compounds of the present invention were tested in the above method of Example A7 and found to be selective for inhibition of CDK2/Cyclin E1 over CDK3/Cyclin E1. In some embodiments, the tested compounds were found to be greater than 2-fold more selective for CDK2/Cyclin E1 over CDK3/Cyclin E1.

Example A8: CDK4/Cyclin D3 Caliper Assay

Inhibition of CDK4/Cyclin D3 activity in the presence of compounds of the present disclosure was evaluated using a Caliper LabChip® EZ Reader mobility shift assay. In the assay, CDK4/Cyclin D3 (Carna Biosciences, 04-105) catalyzed the phosphorylation of a fluorescently tagged peptide 5-FAM-RRRFRPASPLRGPPK-COOH (PerkinElmer, FL Peptide 34) which induced a difference in capillary electrophoresis mobility. The peptide substrate and product were measured, and the conversion ratio was used to determine the inhibition (as % activity and $IC_{50}$ values) of CDK4/Cyclin D3. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 5 nM CDK4/Cyclin D3, 100 µM ATP, and 1.5 µM fluorescent peptide substrate.

Dose titrations of inhibitors in 100% DMSO were combined with 6.5 nM CDK4/Cyclin D3 and 130 µM of ATP in reaction buffer. The mixtures were incubated for 30 minutes before the addition of fluorescent peptide substrate to initiate the kinase reaction. The final conditions were 5 nM CDK4/Cyclin D3, 100 µM ATP, and 1.5 µM fluorescent peptide. The reactions were stopped after 120 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

Certain compounds of the present invention were tested in the above method of Example A8 and found to be selective for inhibition of CDK2/Cyclin E1 over CDK4/Cyclin D3. In some embodiments, the tested compounds were found to be greater than 5000-fold more selective for CDK2/Cyclin E1 over CDK4/Cyclin D3. In some embodiments, the tested compounds were found to be greater than 1000-fold more selective for CDK2/Cyclin E1 over CDK4/Cyclin D3. In some embodiments, the tested compounds were found to be greater than 500-fold more selective for CDK2/Cyclin E1 over CDK4/Cyclin D3. In some embodiments, the tested compounds were found to be greater than 200-fold more selective for CDK2/Cyclin E1 over CDK4/Cyclin D3.

Example A9: CDK5/p35 Caliper Assay

Inhibition of CDK5/p35 activity in the presence of compounds of the present disclosure was evaluated using a Caliper LabChip® EZ Reader mobility shift assay. In the assay, CDK5/p35 (Signalchem, C33-10BG) catalyzed the phosphorylation of a fluorescently tagged peptide 5-FAM-GGGPATPKKAKKL-CONH2 (PerkinElmer, FL Peptide 29) which induced a difference in capillary electrophoresis mobility. The peptide substrate and product were measured, and the conversion ratio was used to determine the inhibition (as % activity and $IC_{50}$ values) of CDK5/p35. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 60 µM CDK5/p35, M ATP, and 1.5 µM fluorescent peptide substrate.

Dose titrations of inhibitors in 100% DMSO were combined with 78 µM CDK5/p35 and 13 µM of ATP in reaction buffer. The mixtures were incubated for 30 minutes before the addition of fluorescent peptide substrate to initiate the kinase reaction. The final conditions were 60 µM CDK5/p35, 10 µM ATP, and 1.5 µM fluorescent peptide. The reactions were stopped after 60 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

Certain compounds of the present invention were tested in the above method of Example A9 and found to be selective for inhibition of CDK2/Cyclin E1 over CDK5/p35. In some embodiments, the tested compounds were found to be greater than 1000-fold more selective for CDK2/Cyclin E1 over CDK5/p35. In some embodiments, the tested compounds were found to be greater than 500-fold more selective for CDK2/Cyclin E1 over CDK5/p35. In some embodiments, the tested compounds were found to be greater than 200-fold more selective for CDK2/Cyclin E1 over CDK5/p35.

Example A10: CDK6/Cyclin D3 Caliper Assay

Inhibition of CDK6/Cyclin D3 activity in the presence of compounds of the present disclosure was evaluated using a Caliper LabChip® EZ Reader mobility shift assay. In the assay, CDK6/Cyclin D3 (Carna Biosciences, 04-107) catalyzed the phosphorylation of a fluorescently tagged peptide 5-FAM-RRRFRPASPLRGPPK-COOH (PerkinElmer, FL Peptide 34) which induced a difference in capillary electrophoresis mobility. The peptide substrate and product were measured, and the conversion ratio was used to determine the inhibition (as % activity and $IC_{50}$ values) of CDK6/Cyclin D3. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 5 nM CDK6/Cyclin D3, 100 µM ATP, and 1.5 µM fluorescent peptide substrate.

Dose titrations of inhibitors in 100% DMSO were combined with 6.5 nM CDK6/Cyclin D3 and 130 µM of ATP in reaction buffer. The mixtures were incubated for 30 minutes before the addition of fluorescent peptide substrate to initiate the kinase reaction. The final conditions were 5 nM CDK6/Cyclin D3, 100 µM ATP, and 1.5 µM fluorescent peptide. The reactions were stopped after 120 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

Certain compounds of the present invention were tested in the above method of Example A10 and found to be selective for inhibition of CDK2/Cyclin E1 over CDK6/Cyclin D3. In some embodiments, the tested compounds were found to be greater than 5000-fold more selective for CDK2/Cyclin E1 over CDK6/Cyclin D3. In some embodiments, the tested compounds were found to be greater than 1000-fold more selective for CDK2/Cyclin E1 over CDK6/Cyclin D3. In some embodiments, the tested compounds were found to be greater than 500-fold more selective for CDK2/Cyclin E1 over CDK6/Cyclin D3. In some embodiments, the tested compounds were found to be greater than 200-fold more selective for CDK2/Cyclin E1 over CDK6/Cyclin D3.

Example A11: CDK7/Cyclin H/MAT1 Caliper Assay

Inhibition of CDK7/Cyclin H/MAT1 activity in the presence of compounds of the present disclosure was evaluated using a Caliper LabChip® EZ Reader mobility shift assay. In the assay, CDK7/Cyclin H/MAT1 (Carna Biosciences, 04-108) catalyzed the phosphorylation of a fluorescently tagged peptide 5-FAM-FLAKSFGSPNRAYKK-COOH (Pharmaron, CDK7tide) which induced a difference in capillary electrophoresis mobility. The peptide substrate and product were measured, and the conversion ratio was used to determine the inhibition (as % activity and $IC_{50}$ values) of CDK7/Cyclin H/MAT1. Reactions contained 50 mM HEPES pH 7.5, 10 mM $MgCl_2$, 1 mM EDTA, 2 mM DTT, 0.01% Brij35, 0.5 mg/mL BSA, 0.1% DMSO, 5 nM CDK7/Cyclin H/MAT1, 40 µM ATP, and 1.5 µM fluorescent peptide substrate.

Dose titrations of inhibitors in 100% DMSO were combined with 6.5 nM CDK7/Cyclin H/MAT1 and 52 µM of ATP in reaction buffer. The mixtures were incubated for 30 minutes before the addition of fluorescent peptide substrate to initiate the kinase reaction. The final conditions were 5 nM CDK7/Cyclin H/MAT1, 40 µM ATP, and 1.5 µM fluorescent peptide. The reactions were stopped after 120 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the $IC_{50}$ for each compound.

Certain compounds of the present invention were tested in the above method of Example A11 and found to be selective for inhibition of CDK2/Cyclin E1 over CDK7/Cyclin H/MAT1. In some embodiments, the tested compounds were found to be greater than 5000-fold more selective for CDK2/Cyclin E1 over CDK7/Cyclin H/MAT1. In some embodiments, the tested compounds were found to be greater than 1000-fold more selective for CDK2/Cyclin E1 over CDK7/Cyclin H/MAT1. In some embodiments, the tested compounds were found to be greater than 500-fold more selective for CDK2/Cyclin E1 over CDK7/Cyclin H/MAT1. In some embodiments, the tested compounds were found to be greater than 200-fold more selective for CDK2/Cyclin E1 over CDK7/Cyclin H/MAT1.

Example A12: CDK9/Cyclin T1 Caliper Assay

Inhibition of CDK9/Cyclin T1 activity in the presence of compounds of the present disclosure was evaluated using a Caliper LabChip® EZ Reader mobility shift assay. In the assay, CDK9/Cyclin T1 (Carna Biosciences, 04-110) catalyzed the phosphorylation of a fluorescently tagged peptide 5-FAM-RRRFRPASPLRGPPK-COOH (PerkinElmer, FL Peptide 34) which induced a difference in capillary electrophoresis mobility. The peptide substrate and product were measured, and the conversion ratio was used to determine the inhibition (as % activity and IC$_{50}$ values) of CDK9/Cyclin T1. Reactions contained 50 mM HEPES pH 7.5, 10 mM MgCl$_2$, 1 mM EDTA, 2 mM DTT, 0.01% Brij35, 0.5 mg/mL BSA, 0.1% DMSO, 2.5 nM CDK9/Cyclin T1, 10 µM ATP, and 1.5 µM fluorescent peptide substrate.

Dose titrations of inhibitors in 100% DMSO were combined with 3.25 nM CDK9/Cyclin T1 and 13 µM of ATP in reaction buffer. The mixtures were incubated for 30 minutes before the addition of fluorescent peptide substrate to initiate the kinase reaction. The final conditions were 2.5 nM CDK9/Cyclin T1, 10 µM ATP, and 1.5 µM fluorescent peptide. The reactions were stopped after 120 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the IC$_{50}$ for each compound.

Certain compounds of the present invention were tested in the above method of Example A12 and found to be selective for inhibition of CDK2/Cyclin E1 over CDK9/Cyclin T1. In some embodiments, the tested compounds were found to be greater than 5000-fold more selective for CDK2/Cyclin E1 over CDK9/Cyclin T1. In some embodiments, the tested compounds were found to be greater than 1000-fold more selective for CDK2/Cyclin E1 over CDK9/Cyclin T1. In some embodiments, the tested compounds were found to be greater than 500-fold more selective for CDK2/Cyclin E1 over CDK9/Cyclin T1. In some embodiments, the tested compounds were found to be greater than 200-fold more selective for CDK2/Cyclin E1 over CDK9/Cyclin T1.

Example A13: CDK2/Cyclin E2 Caliper Assay

Inhibition of CDK2/Cyclin E2 activity in the presence of compounds of the present disclosure was evaluated using a Caliper LabChip® EZ Reader mobility shift assay. In the assay, CDK2/Cyclin E2 (Biortus, BP469/4624/691) catalyzed the phosphorylation of a fluorescently tagged peptide 5-FAM-QSPKKG-CONH2 (PerkinElmer, FL Peptide 18) which induced a difference in capillary electrophoresis mobility. The peptide substrate and product were measured, and the conversion ratio was used to determine the inhibition (as % activity and IC$_{50}$ values) of CDK2/Cyclin E2. Reactions contained 50 mM HEPES pH 7.5, 10 mM MgCl$_2$, 1 mM EDTA, 2 mM DTT, 0.01% Brij35, 0.5 mg/mL BSA, 0.1% DMSO, 5 nM CDK2/Cyclin E2, 200 µM ATP, and 1.5 µM fluorescent peptide substrate.

Dose titrations of inhibitors in 100% DMSO were combined with 6.5 nM CDK2/Cyclin E2 and 260 µM of ATP in reaction buffer. The mixtures were incubated for 30 minutes before the addition of fluorescent peptide substrate to initiate the kinase reaction. The final conditions were 5 nM CDK2/Cyclin E2, 200 µM ATP, and 1.5 µM fluorescent peptide. The reactions were stopped after 90 minutes with the addition of EDTA (400 mM final EDTA concentration). The stopped reactions were analyzed on a Caliper LabChip® EZ Reader II. The conversion ratios were normalized to yield % activity, plotted against compound concentration, and fit to a four-parameter equation to determine the IC$_{50}$ for each compound.

Certain compounds of the present invention were tested in the above method of Example A13 and found to be selective for inhibition of CDK2/Cyclin E1 over CDK2/Cyclin E2. In some embodiments, the tested compounds were found to be 1000-fold more selective for CDK2/Cyclin E1 over CDK2/Cyclin E2. In some embodiments, the tested compounds were found to be greater than 500-fold more selective for CDK2/Cyclin E1 over CDK2/Cyclin E2. In some embodiments, the tested compounds were found to be greater than 200-fold more selective for CDK2/Cyclin E1 over CDK2/Cyclin E2.

We claim:
1. A compound, wherein the compound is of Formula I:

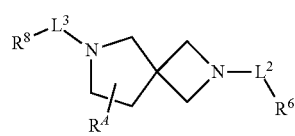

or a pharmaceutically acceptable salt thereof, wherein:

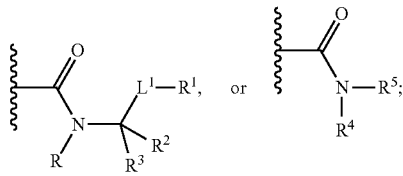

$R^4$ is
$L^1$ is a covalent bond or a saturated or unsaturated, straight or branched, optionally substituted bivalent $C_{1-6}$ hydrocarbon chain, wherein 0-2 methylene units of $L^1$ are independently replaced by —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or —NRC(O)NR—;

$R^1$ is hydrogen, an optionally substituted $C_{1-6}$ aliphatic group, or an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur);

$R^2$ is hydrogen, an optionally substituted $C_{1-6}$ aliphatic group, —C$_{1-6}$ alkylene-OR, —C$_{1-3}$ alkylene-O—

$C_{1-3}$ alkylene-R, —C(O)OR, or —C(O)NR$_2$; and R$^3$ is hydrogen; or R$^2$ and R$^3$ together with the intervening carbon atom form an optionally substituted 3-7 membered saturated or partially unsaturated carbocyclic ring, or an optionally substituted 3-7 membered saturated or partially unsaturated heterocyclic ring (having 1-2 heteroatoms independently selected from nitrogen, oxygen, and sulfur);

R$^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur); and R$^5$ is hydrogen; or R$^4$ and R$^5$ together with the intervening nitrogen atom form an optionally substituted 4-7 membered saturated, or partially unsaturated heterocyclic ring (having 0-2 heteroatoms, in addition to the nitrogen, independently selected from nitrogen, oxygen, and sulfur), or an optionally substituted heteroaryl ring (having 0-3 heteroatoms, in addition to the nitrogen, independently selected from nitrogen, oxygen, and sulfur);

L$^2$ is a saturated or unsaturated, straight or branched, optionally substituted bivalent $C_{1-4}$ hydrocarbon chain, wherein 0-2 methylene units of L$^2$ are independently replaced by —O—, —NR—, —C(O)O—, —C(O)—, —S(O)$_2$—, or —C(O)NR;

R$^6$ is an optionally substituted $C_{1-6}$ aliphatic group, or a cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R$^7$;

each instance of R$^7$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

L$^3$ is a saturated or unsaturated, straight or branched, optionally substituted bivalent $C_{1-4}$ hydrocarbon chain, wherein 0-2 methylene units of L$^3$ are independently replaced by —O—, —NR—, —C(O)O—, —C(O)—, S(O)$_2$—, or —C(O)NR;

R$^8$ is a cyclic group selected from a 3-8 membered saturated or partially unsaturated monocyclic heterocyclic ring (having 1-2 heteroatoms independently selected from nitrogen, oxygen, and sulfur), a 7-12 membered saturated or partially unsaturated bicyclic heterocyclic ring (having 1-4 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur), wherein the cyclic group is optionally substituted with one or more instances of R$^9$;

each instance of R$^9$ is independently halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, an optionally substituted $C_{1-6}$ aliphatic group, an optionally substituted $C_{1-6}$ aliphatic-Cy group, or Cy;

each Cy is independently an optionally substituted cyclic group selected from a 3-8 membered saturated or partially unsaturated monocyclic carbocyclic ring, phenyl, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur); and each R is independently hydrogen, or an optionally substituted $C_{1-6}$ aliphatic group, an optionally substituted phenyl, an optionally substituted 3-7 membered saturated or partially unsaturated carbocyclic ring, an optionally substituted 3-7 membered saturated or partially unsaturated heterocyclic ring (having 1-2 heteroatoms independently selected from nitrogen, oxygen, and sulfur), or an optionally substituted 5-6 membered heteroaryl ring (having 1-4 heteroatoms independently selected from nitrogen, oxygen, and sulfur); or two R groups on the same nitrogen are taken together with their intervening atoms to form an optionally substituted 4-7 membered saturated, partially unsaturated, or heteroaryl ring (having 0-3 heteroatoms, in addition to the nitrogen, independently selected from nitrogen, oxygen, and sulfur);

wherein the compound is not 6-(1-benzyl-1H-pyrazole-4-carbonyl)—N-(3-(benzyloxy)-1-(methylamino)-1-oxobutan-2-yl)-2-(2,2-dimethylcyclopropane-1-carbonyl)-2,6-diazaspiro[3.4]octane-8-carboxamide.

2. The compound of claim 1, wherein $R^4$ is

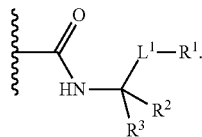

3. The compound of claim 1, wherein $L^1$ is a covalent bond; or
   $L^1$ is an optionally substituted straight or branched $C_{1-4}$ alkylene chain, wherein 1-2 methylene units of $L^1$ are independently replaced by —O—, —NR—, —S—, —C(O)O—, —C(O)—, —S(O)$_2$—, or —NRC(O).
4. The compound of claim 1, wherein $R^1$ is hydrogen: or
   $R^1$ is an optionally substituted $C_{1-6}$ aliphatic group; or
   $R^1$ is an optionally substituted cyclic group selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), a 5-6 membered monocyclic heteroaromatic ring (having 1-4 heteroatoms independently selected from nitrogen, oxygen, and sulfur), and an 8-10 membered bicyclic heteroaromatic ring (having 1-5 heteroatoms independently selected from nitrogen, oxygen, and sulfur).
5. The compound of claim 1, wherein $R^2$ is hydrogen, methyl, —CH$_2$OR, —CH$_2$OCH$_2$R, —C(O)OR, or —C(O)NR$^2$ and $R^3$ is hydrogen; or
   $R^2$ and $R^3$ together with the intervening carbon atom form an optionally substituted oxetanyl, cyclopropyl, cyclobutyl, cyclopentyl, tetrahydropyranyl, piperidinyl, piperazinyl, morpholinyl, pyrrolidinyl, or 1,4-oxazepanyl.
6. The compound of claim 1, wherein $R^4$ is

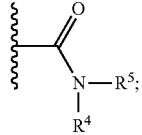

or
   $R^4$ is a group selected from the group consisting of:

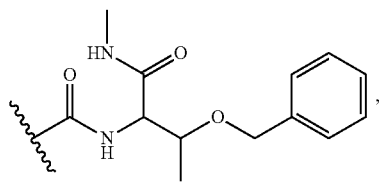

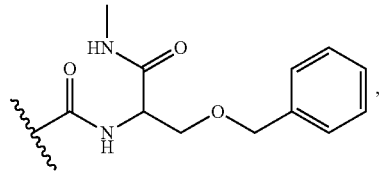

-continued

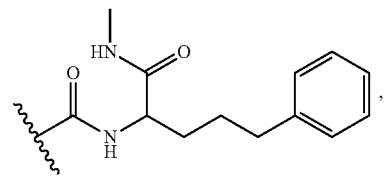

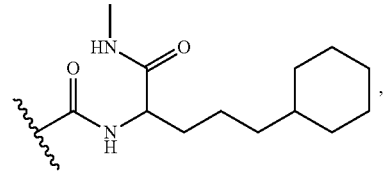

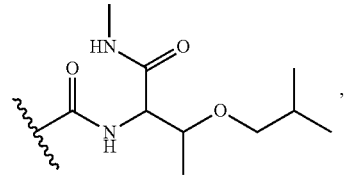

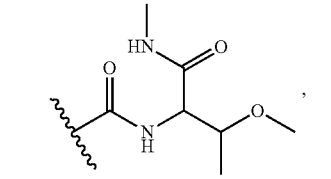

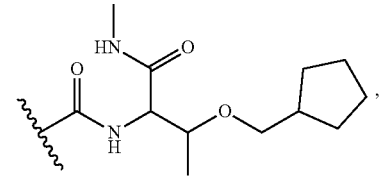

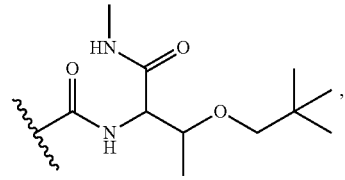

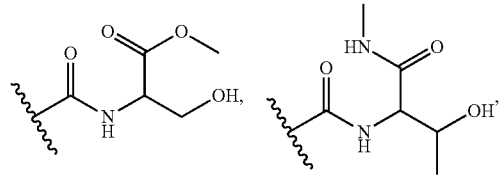

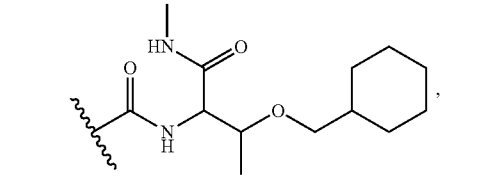

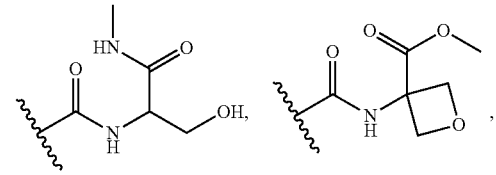

755
-continued
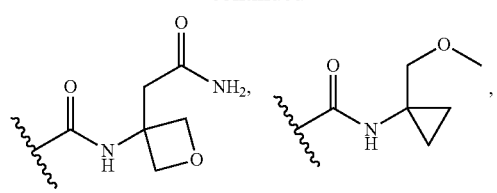
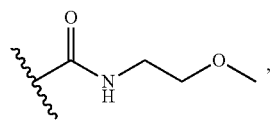
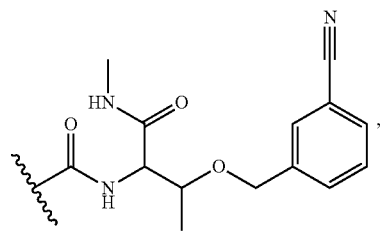
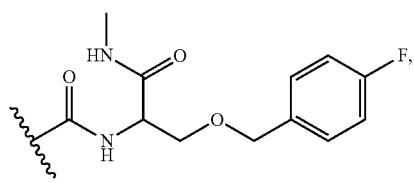
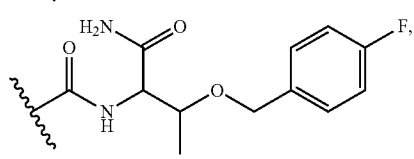
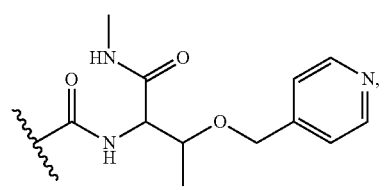
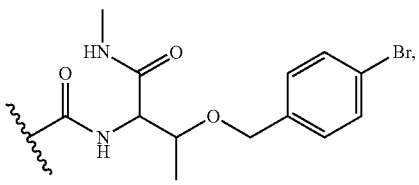
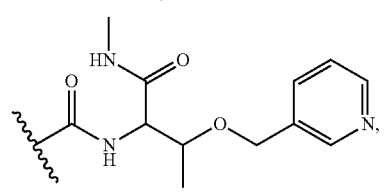
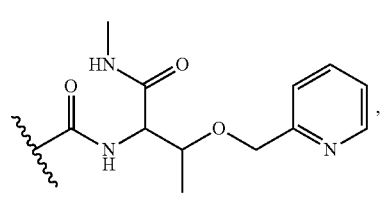
756
-continued
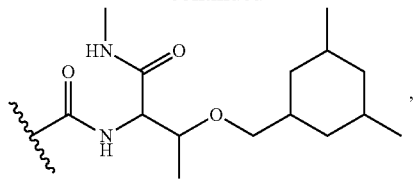
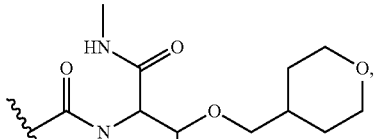
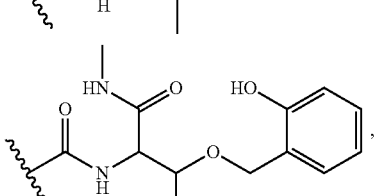
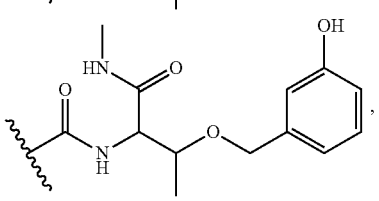
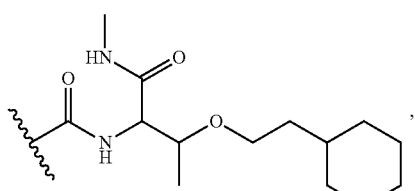
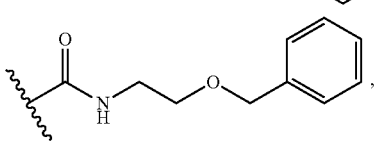
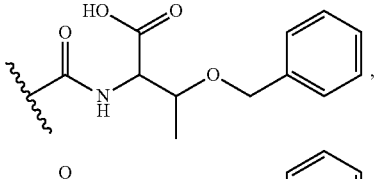
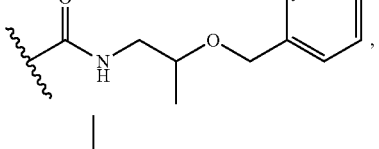
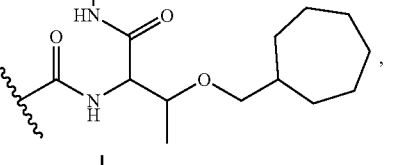
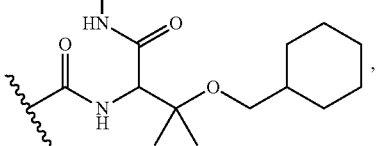

757
-continued
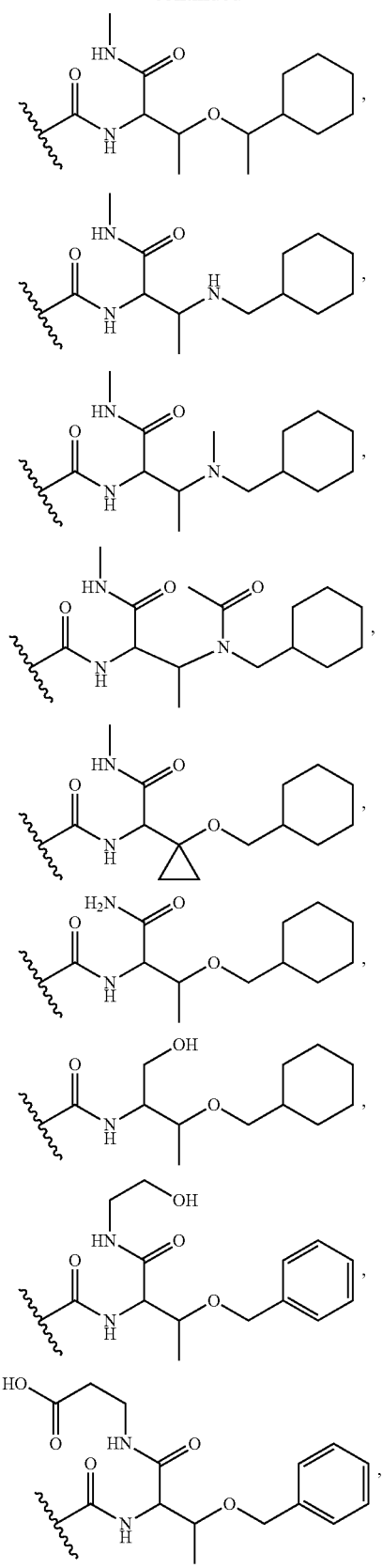
758
-continued
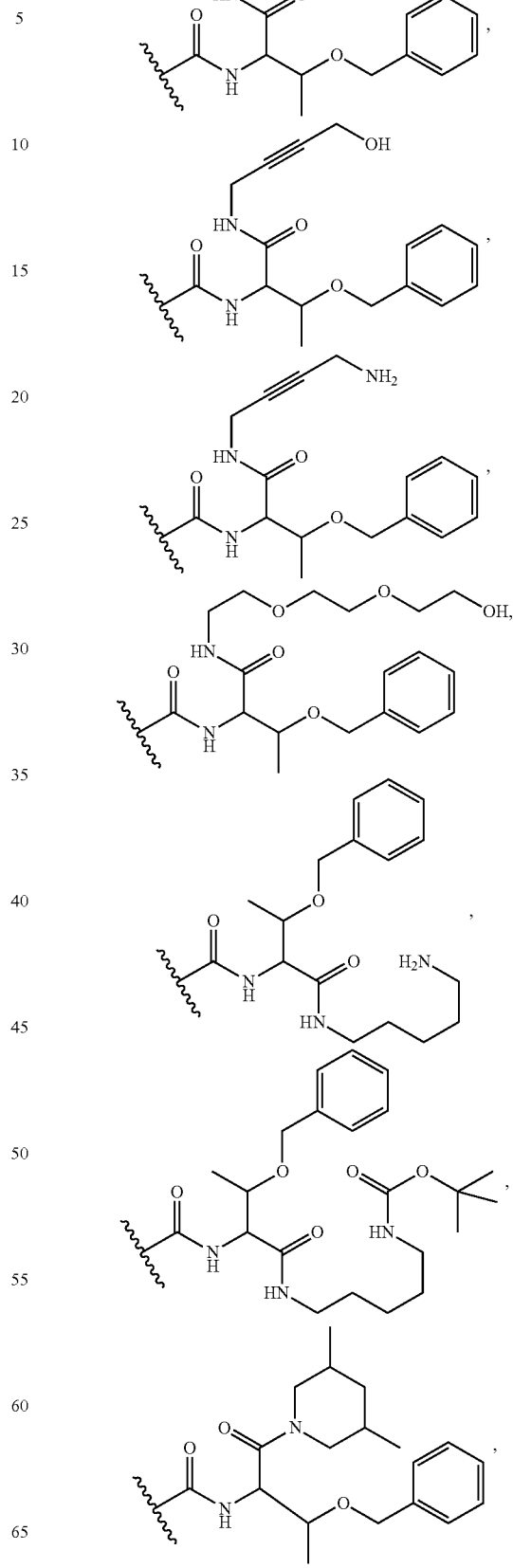

759
-continued
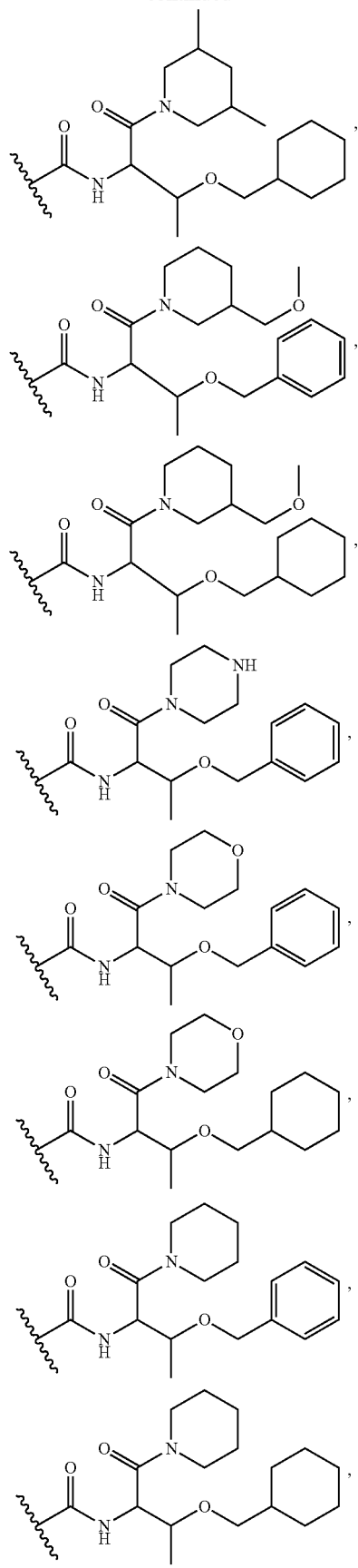
760
-continued
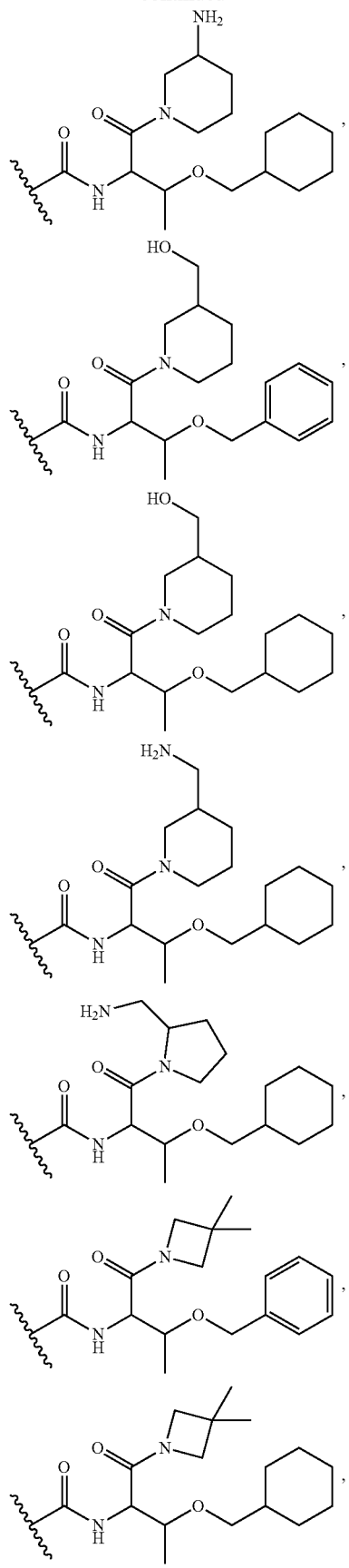

761
-continued
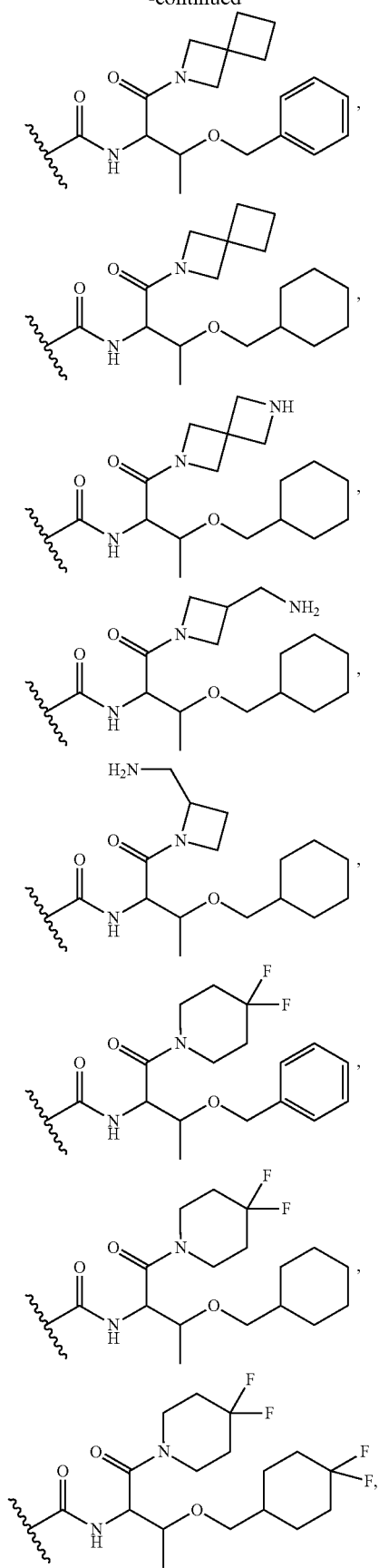
762
-continued
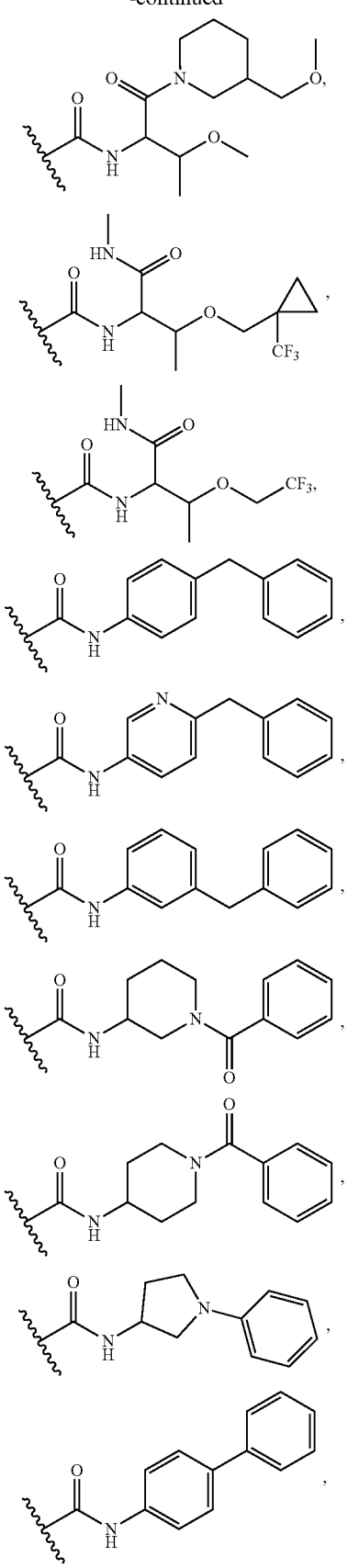

763
-continued
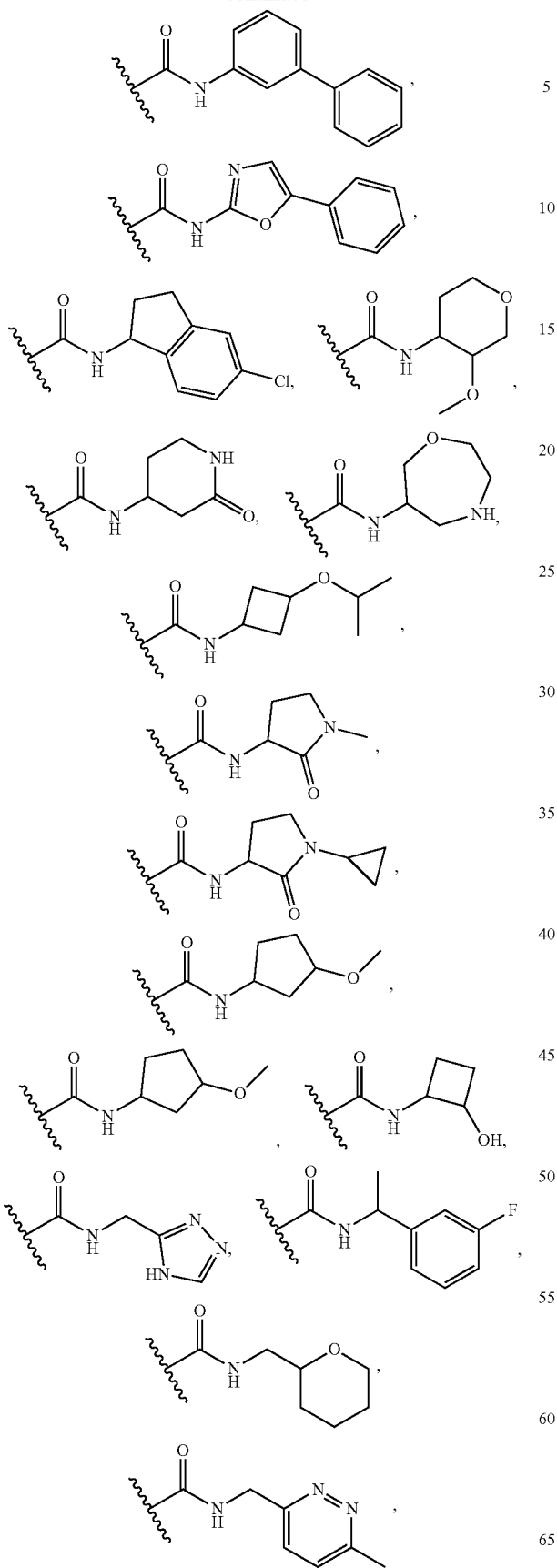
764
-continued
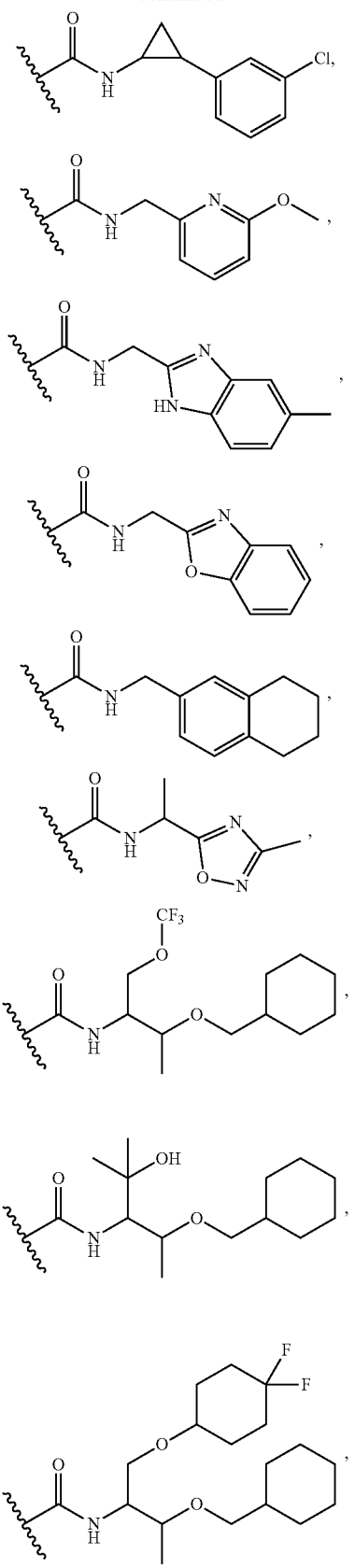

765
-continued
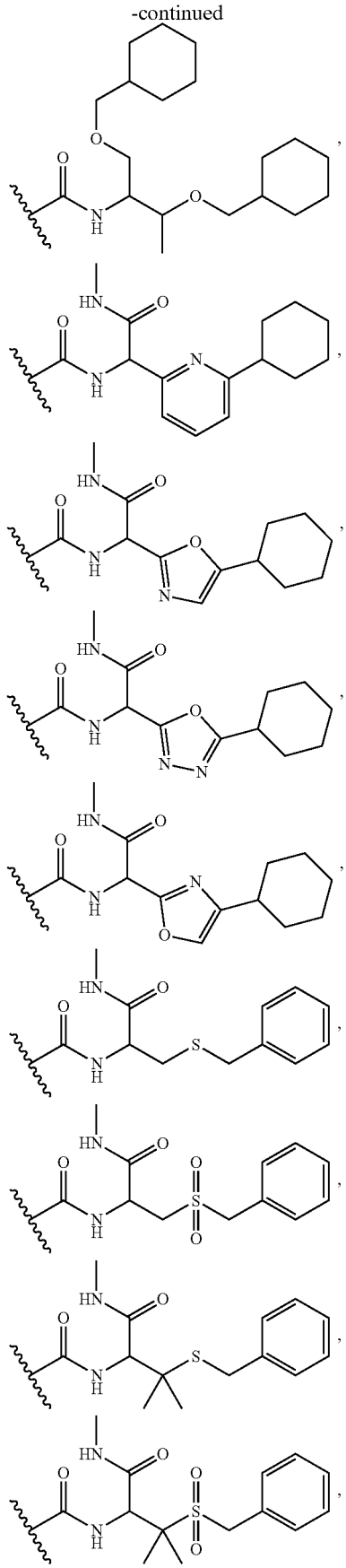
766
-continued
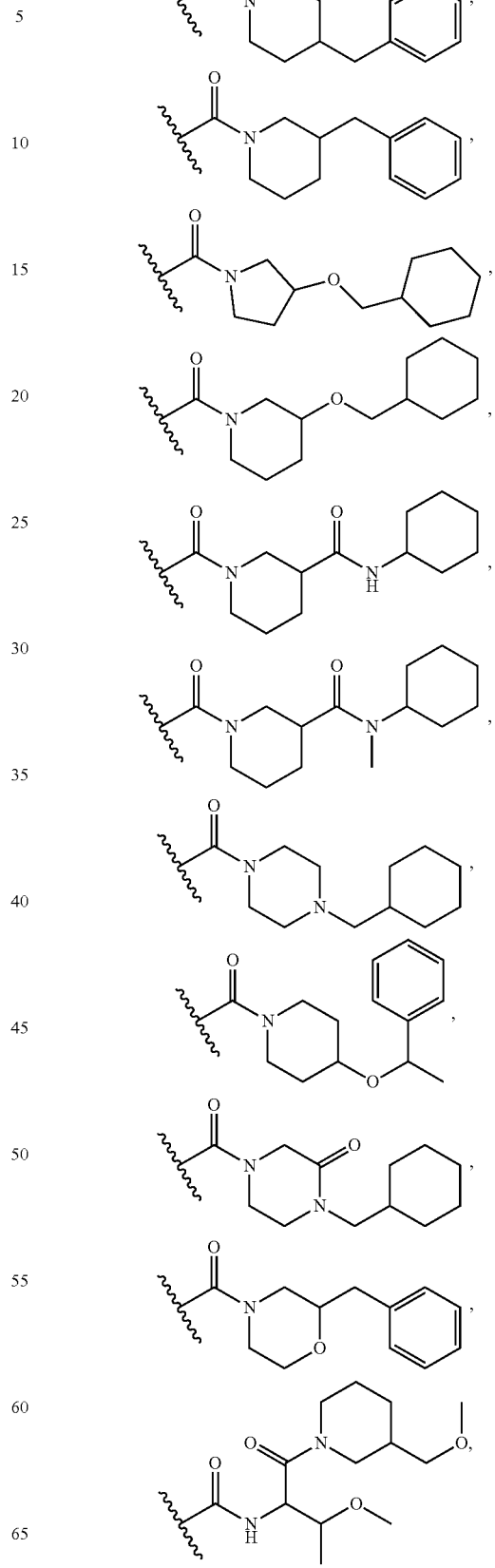

767
-continued
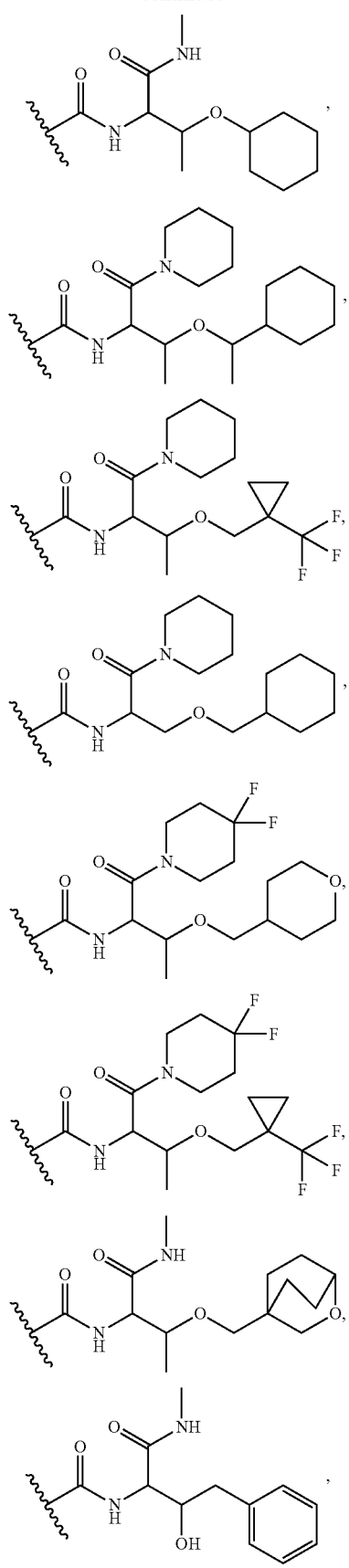
768
-continued
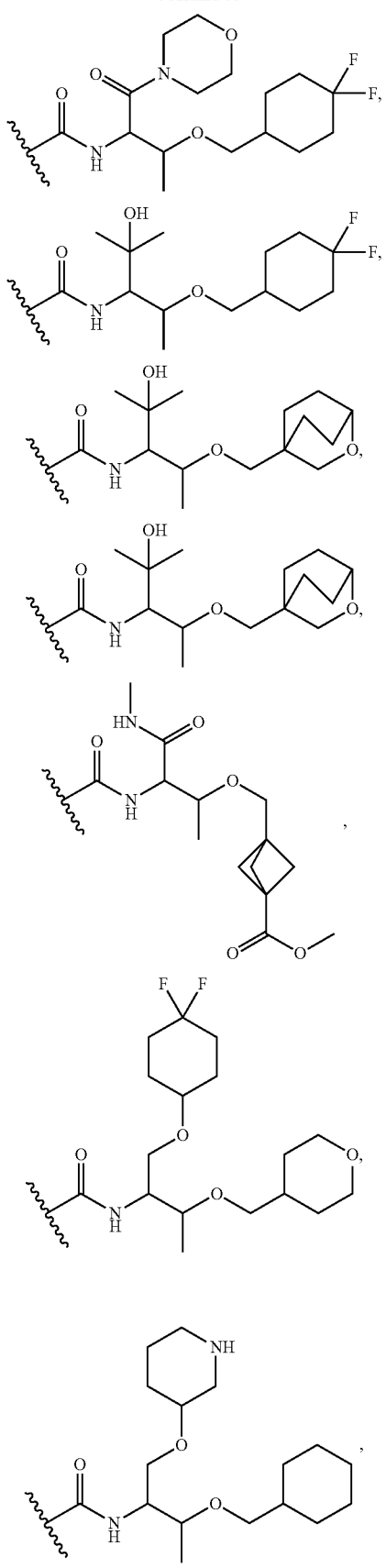

769
-continued
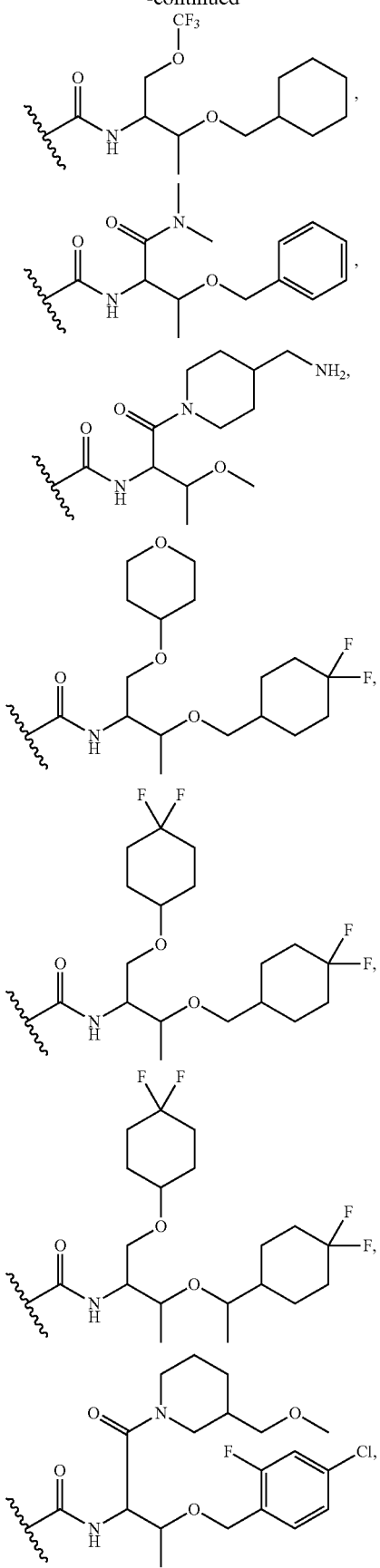
770
-continued
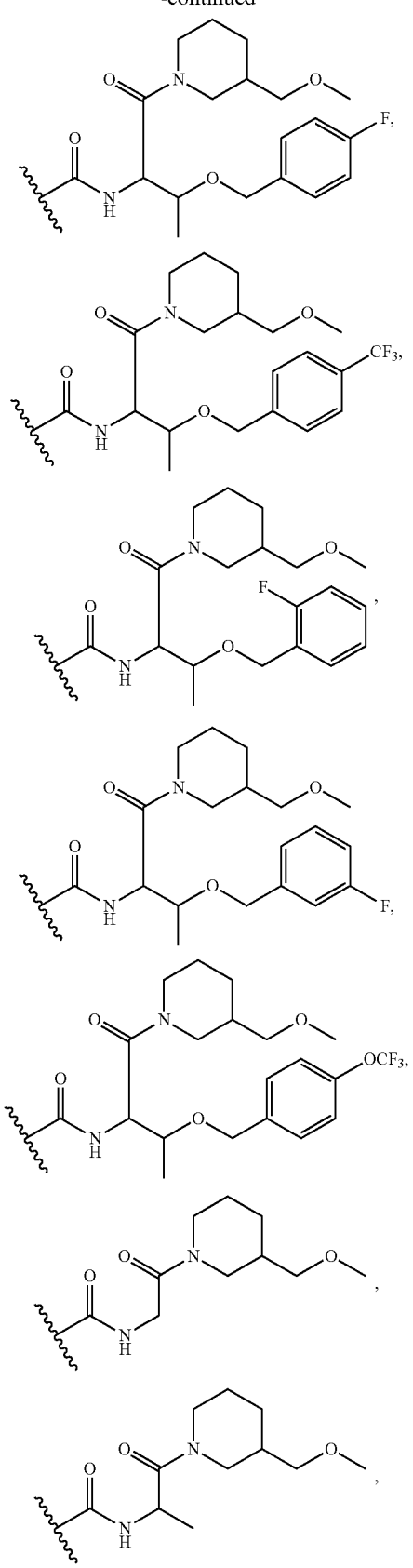

771
-continued
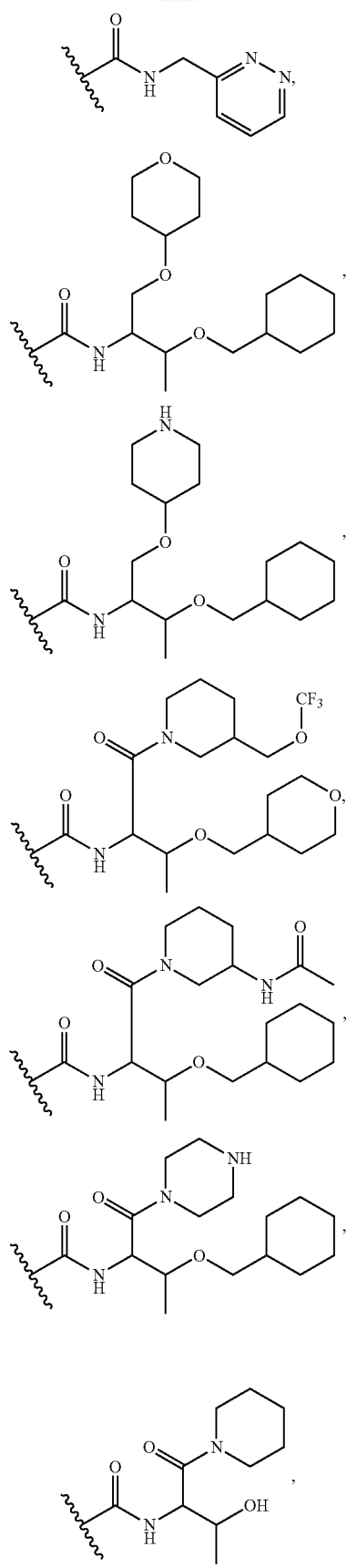
772
-continued
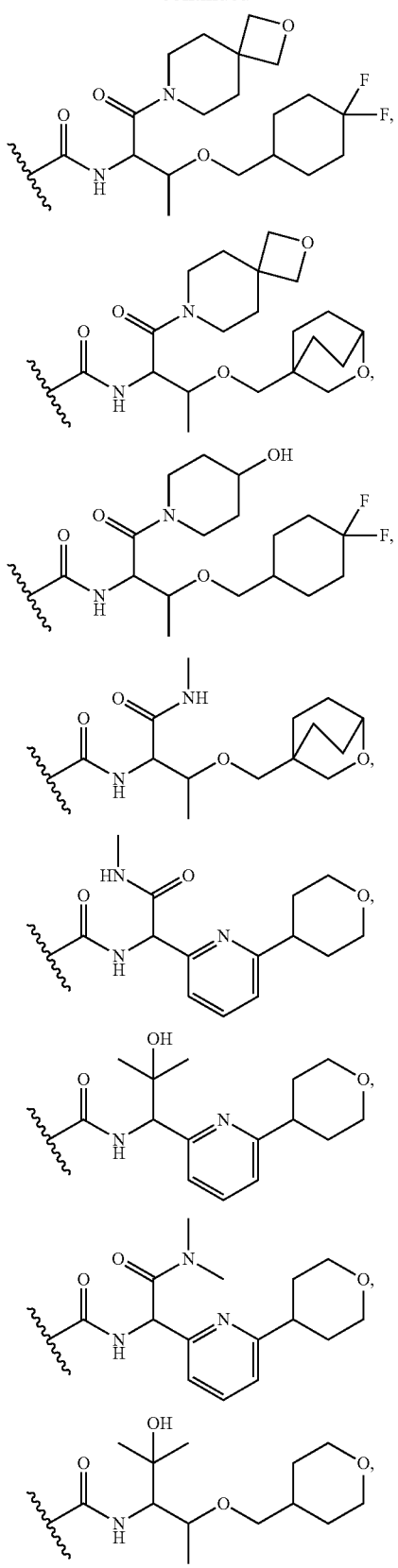

773
-continued
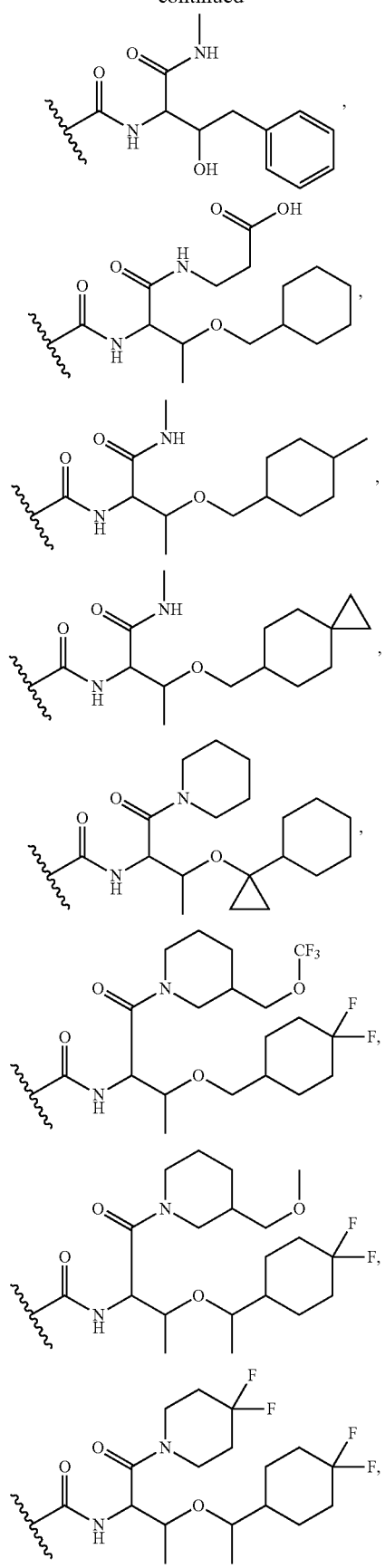
774
-continued
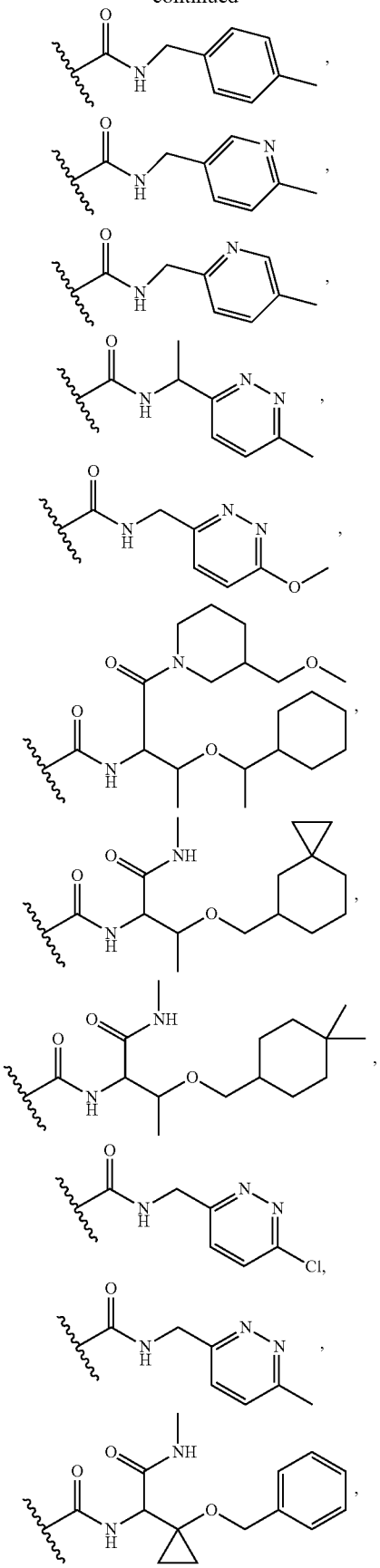

775
-continued
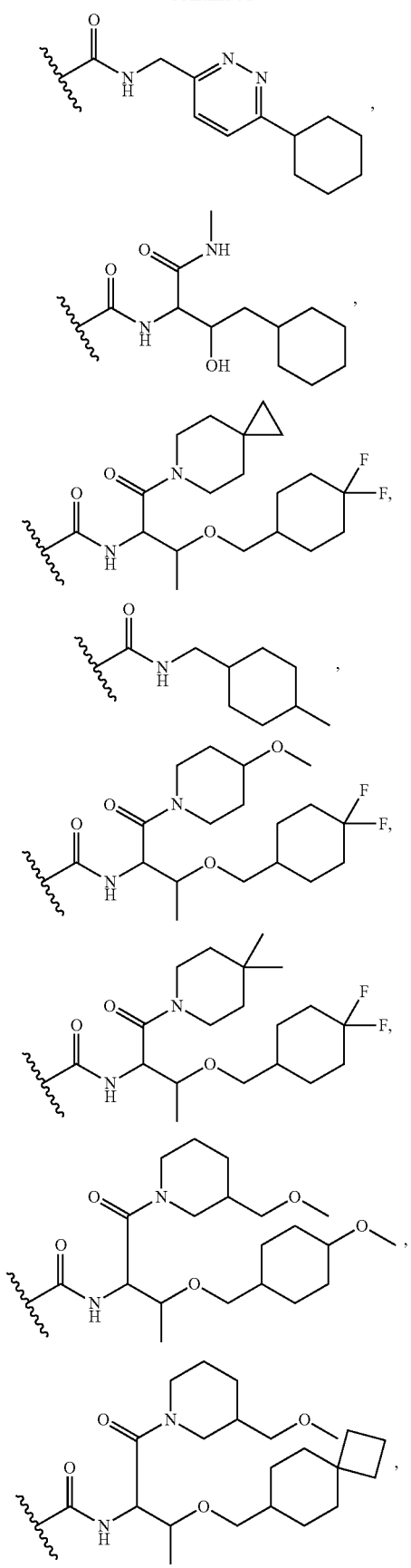
776
-continued
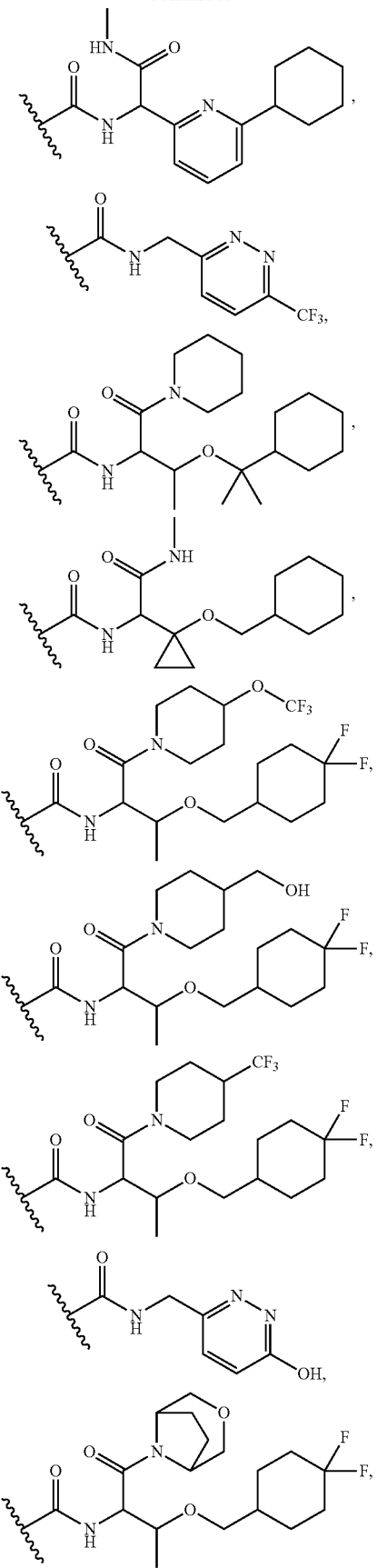

777
-continued
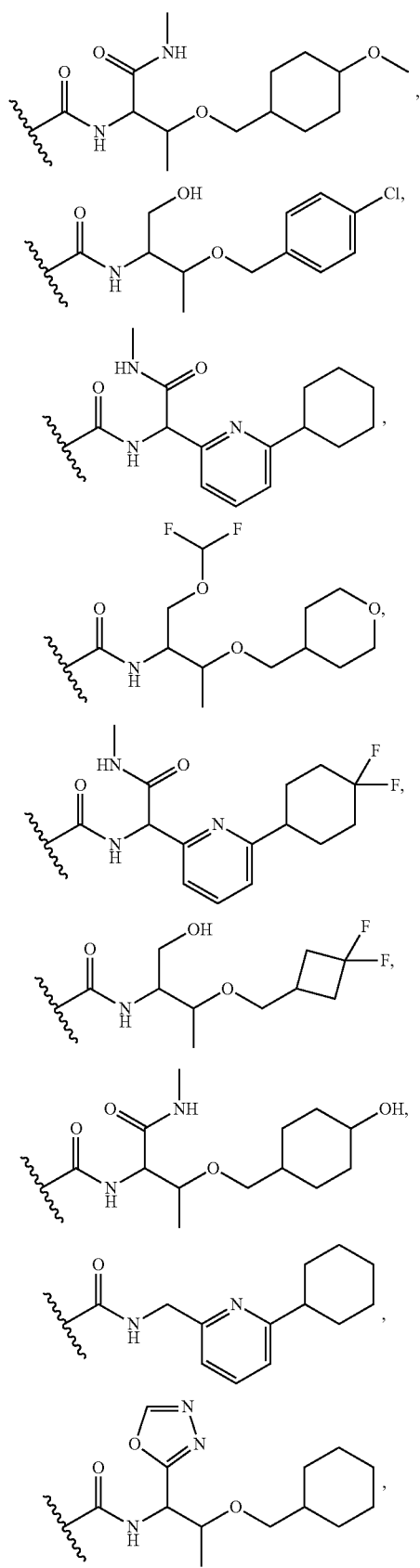
778
-continued
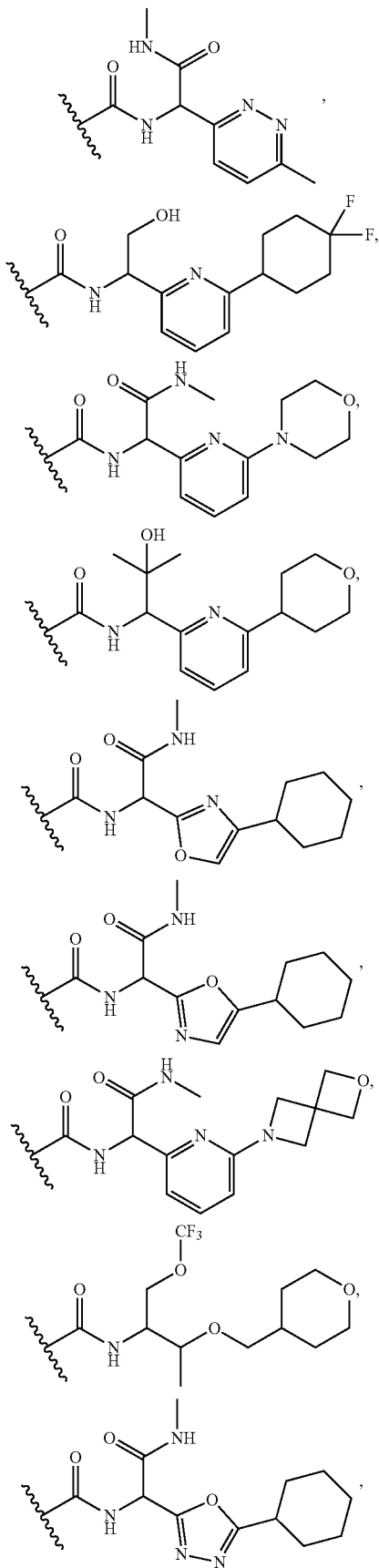

779
-continued
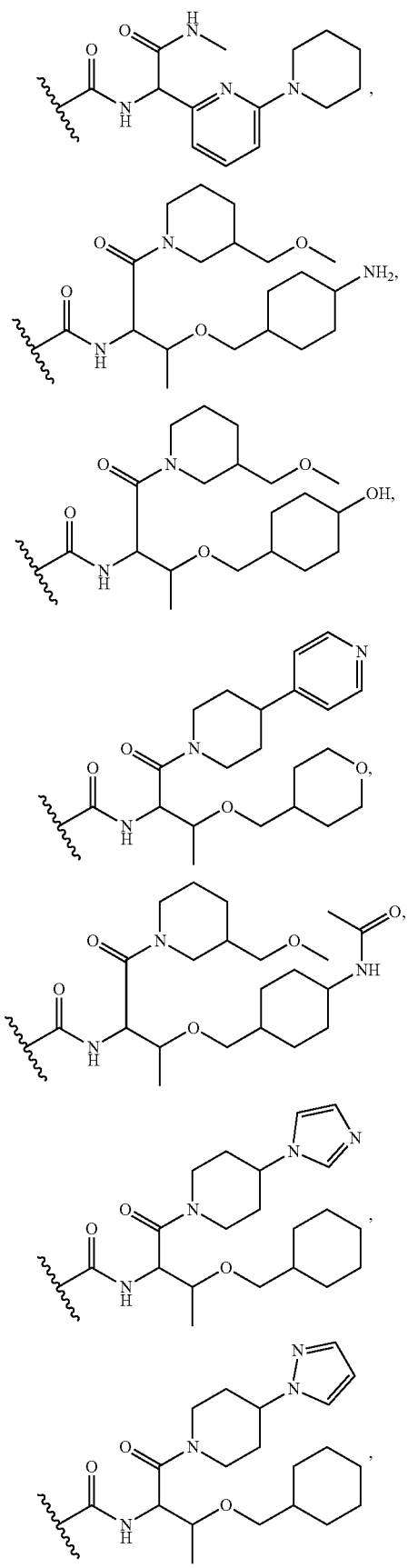
780
-continued
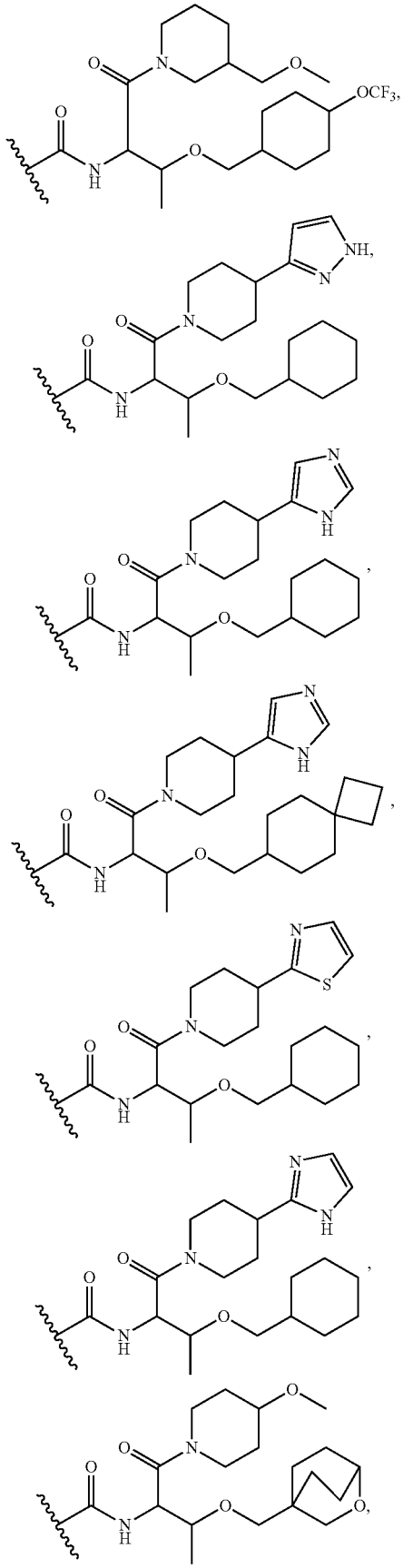

781
-continued
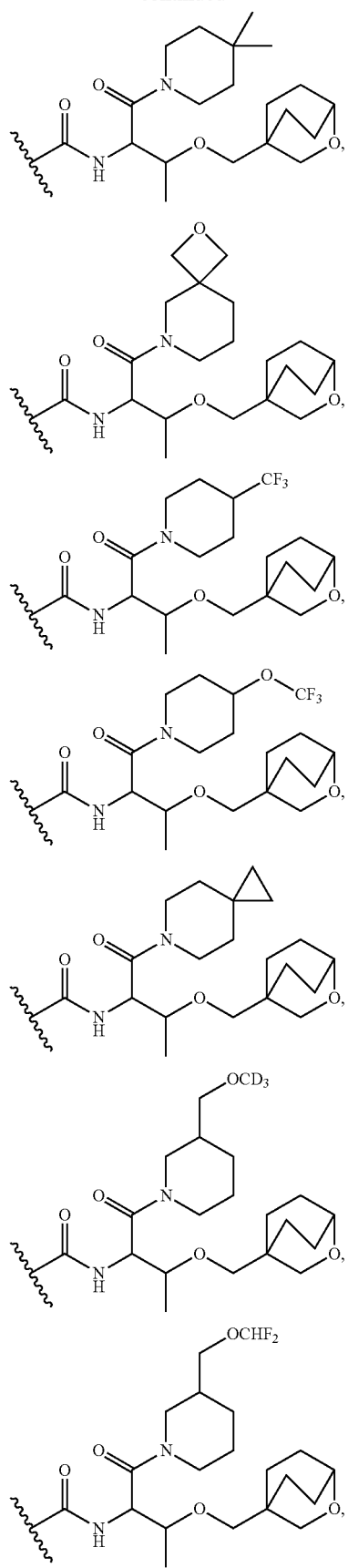
782
-continued
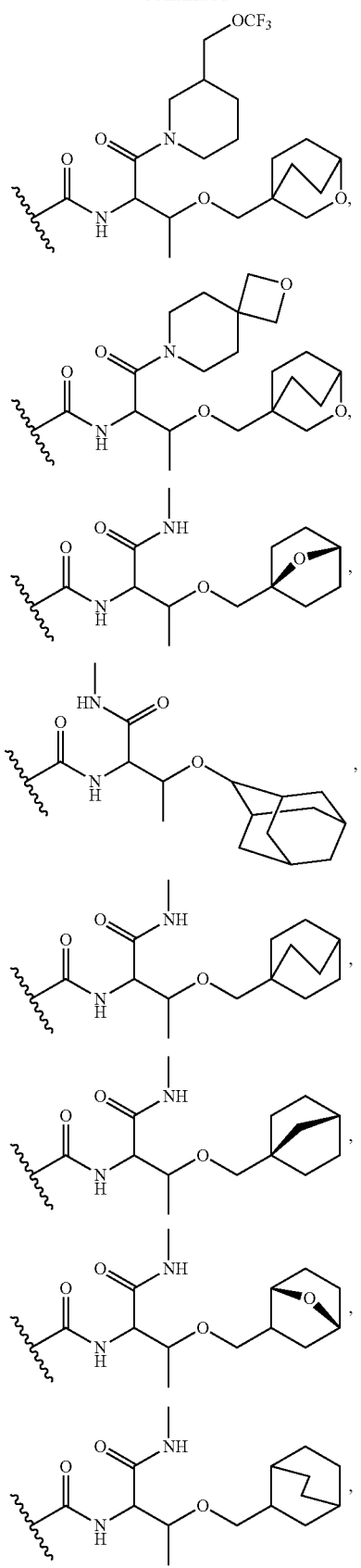

-continued
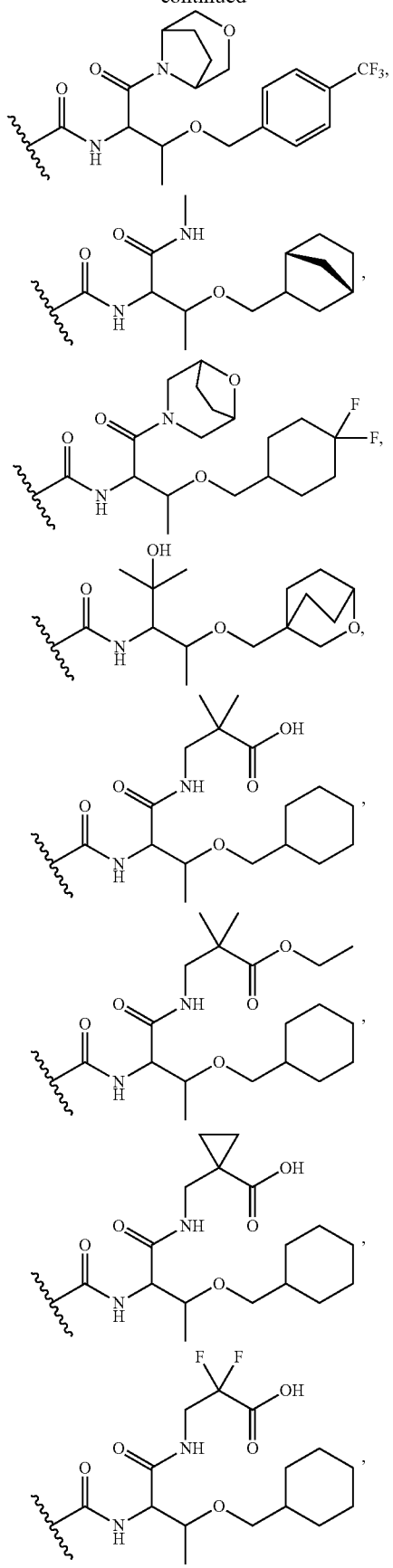
-continued
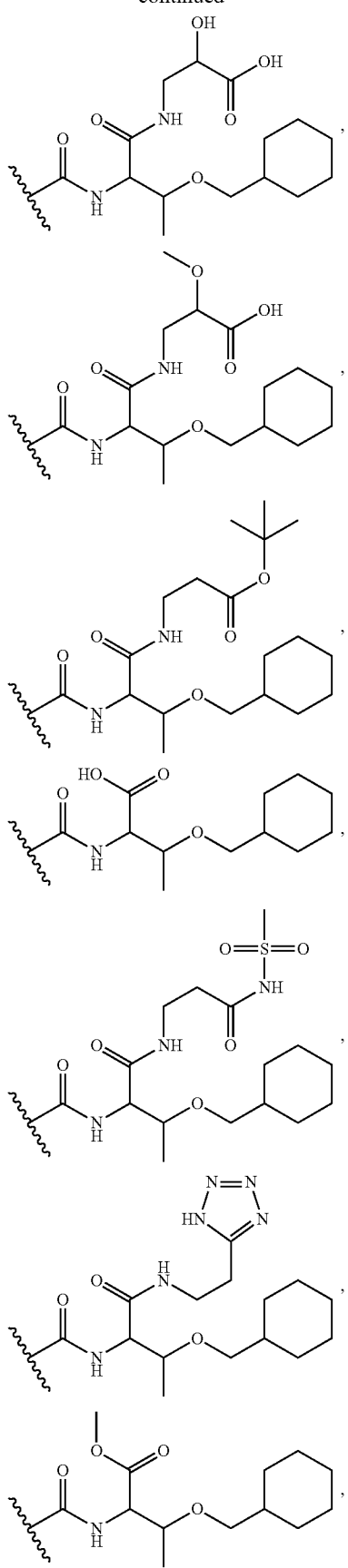

785
-continued
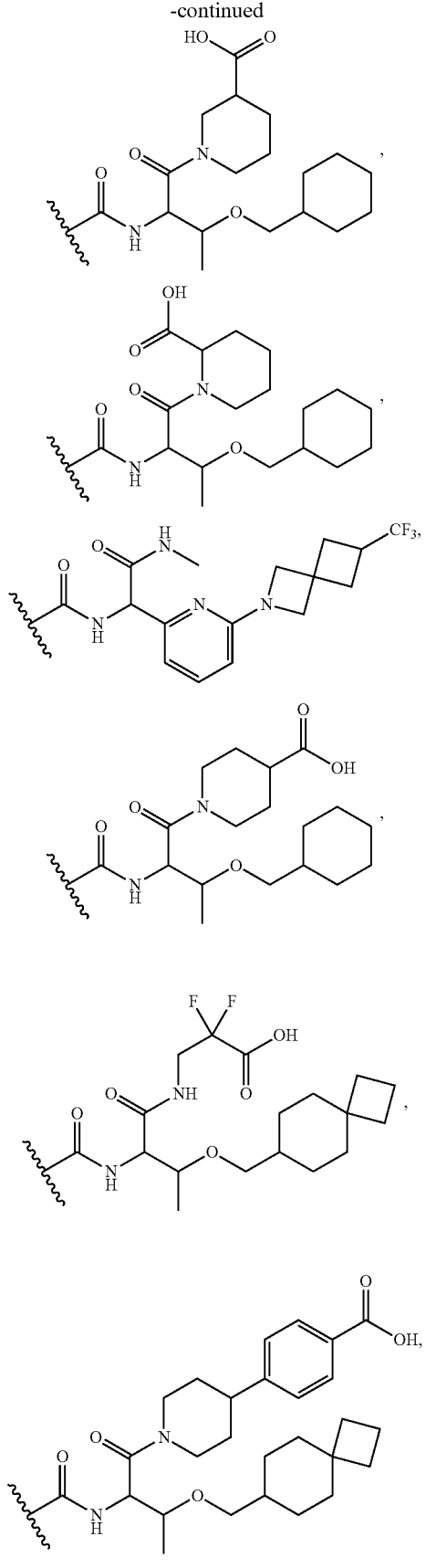
786
-continued
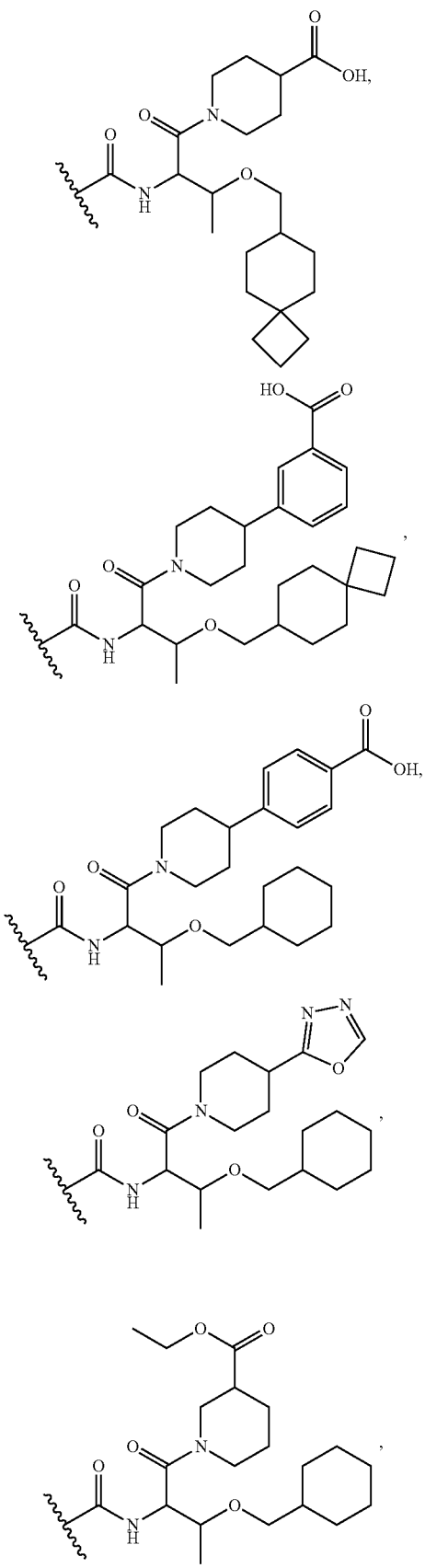

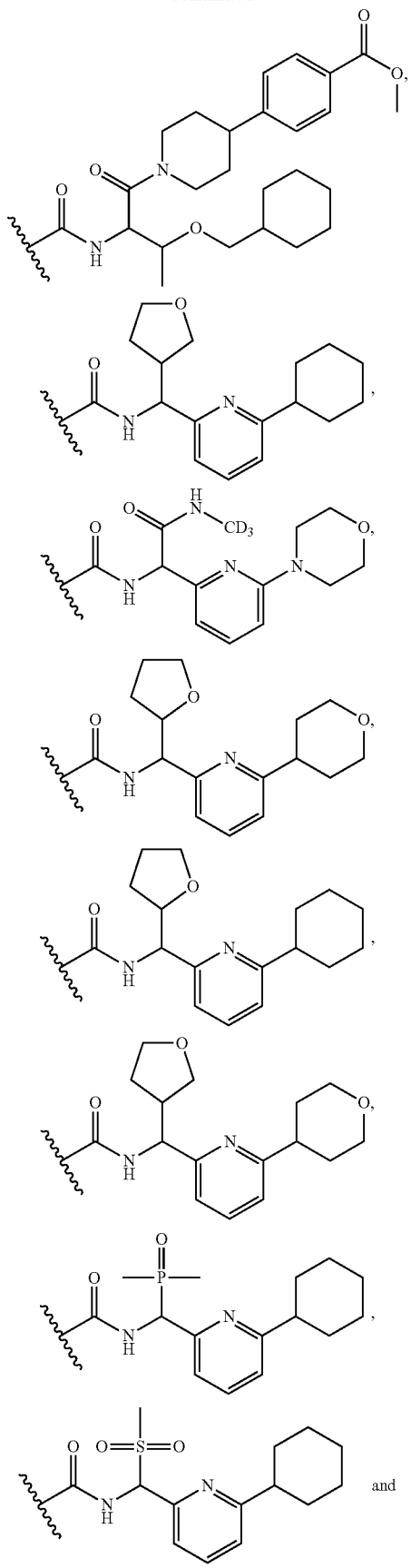

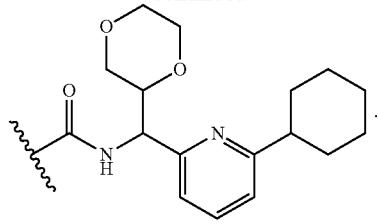

7. The compound of claim 1, wherein $R^4$ is an optionally substituted cyclic group selected from a 3-8 membered saturated or partially unsaturated monocyclic carbocyclic ring, a 7-12 membered saturated or partially unsaturated bicyclic carbocyclic ring, phenyl, an 8-10 membered bicyclic aromatic carbocyclic ring, a 3-8 membered saturated or partially unsaturated monocyclic heterocyclic ring (having 1-2 heteroatoms independently selected from nitrogen, oxygen, and sulfur), and a 5-6 membered monocyclic heteroaromatic ring (having 1-4 heteroatoms independently selected from nitrogen, oxygen, and sulfur) and $R^5$ is hydrogen; or $R^4$ and $R^5$ together with the intervening nitrogen atom form an optionally substituted cyclic group selected from piperindinyl, piperazinyl, morpholinyl, and pyrrolidinyl wherein the cyclic group formed by $R^4$ and $R^5$ together with the intervening nitrogen atom is optionally substituted with a group selected from —$C_{1-6}$ alkylene-phenyl, —O—$C_{1-6}$ alkylene-phenyl, —$C_{1-6}$ alkylene-cyclohexyl, and —O—$C_{1-6}$ alkylene-cyclohexyl.

8. The compound of claim 1, wherein $L^2$ is a saturated or unsaturated, straight or branched, optionally substituted bivalent $C_{1-4}$ hydrocarbon chain, wherein 0-2 methylene units of $L^2$ are independently replaced by —C(O)O—, —C(O)—, or —C(O)NR—.

9. The compound of claim 1, wherein $R^6$ is an optionally substituted $C_{1-6}$ aliphatic group; or $R^6$ is phenyl, optionally substituted with one or more instances of $R^7$; or $R^6$ is a 3-8 membered saturated or partially unsaturated monocyclic carbocyclic ring, optionally substituted with one or more instances of $R^7$; or optionally wherein each instance of $R^7$ is independently —F, methyl, ethyl, isopropyl, isobutyl, —CN, optionally substituted phenyl, optionally substituted benzyl, —$CF_3$, —$CH_2OH$, —$CH_2OCH_3$, —$CH_2CH_2OCH_3$, —$CH_2CH_2F$, cyclopropyl or —$CH_2$-(cyclopropyl).

10. The compound of claim 1, wherein -$L^2$-$R^6$ is a substituent selected from the group consisting of:

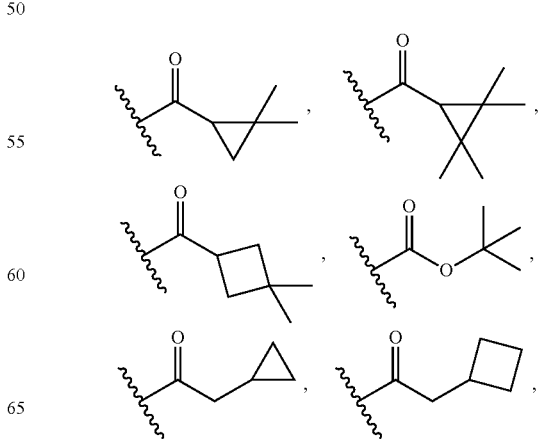

11. The compound of claim 1, wherein $L^3$ is a saturated or unsaturated, straight or branched, optionally substituted bivalent $C_{1-4}$ hydrocarbon chain, wherein 0-2 methylene units of $L^3$ are independently replaced by —S(O)$_2$—, —C(O)NR—, or —C(O)—.

12. The compound of claim 1, wherein $R^8$ is a cyclic group selected from pyrazolyl, oxazolyl, thiazolyl, pyrrolidinyl, tetrahydropyranyl, pyridinyl, imidazolyl, indolyl, 1,2,4-triazolyl, 1,2,4-thiadiazolyl, piperidinyl, and indazolyl, wherein the cyclic group is optionally substituted with one or more instances of $R^9$.

13. The compound of claim 1, wherein each instance of $R^9$ is independently halogen, an optionally substituted $C_{1-6}$ aliphatic group, an optionally substituted $C_{1-6}$ aliphatic-Cy group, or Cy.

14. The compound of claim 1, wherein -$L^3$-$R^8$ is a substituent selected from the group consisting of:

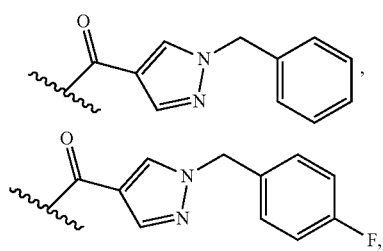

791
-continued
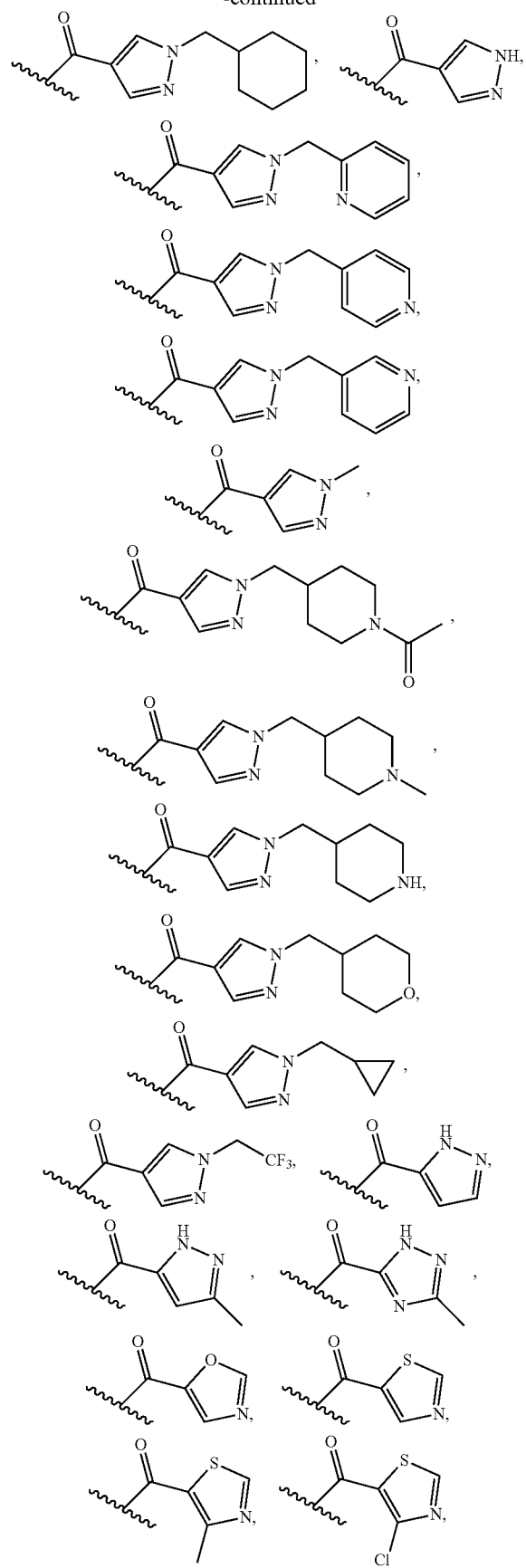
792
-continued
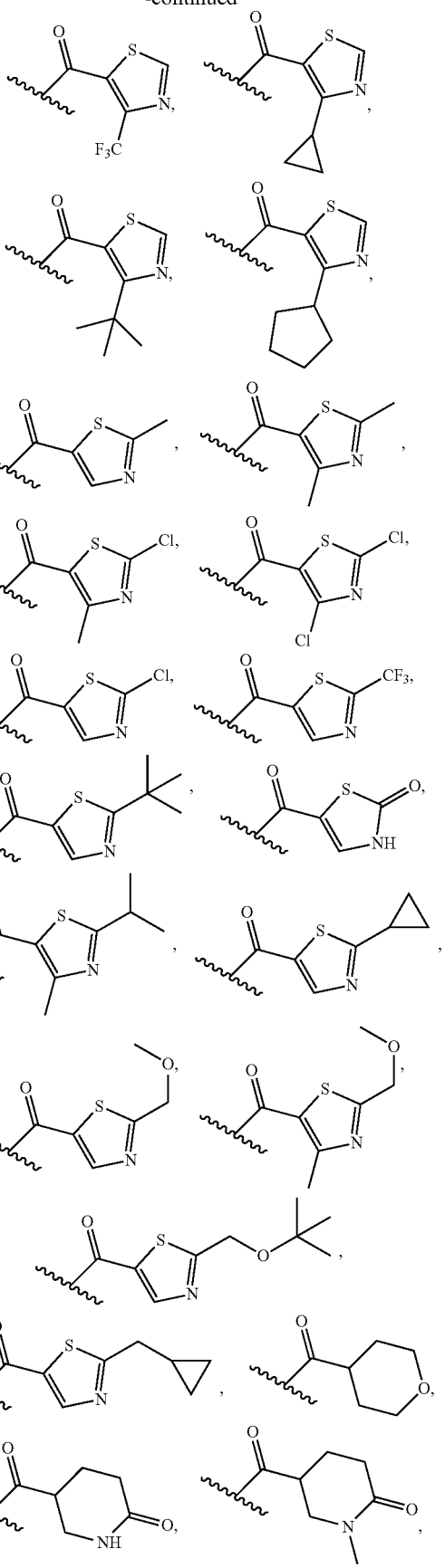

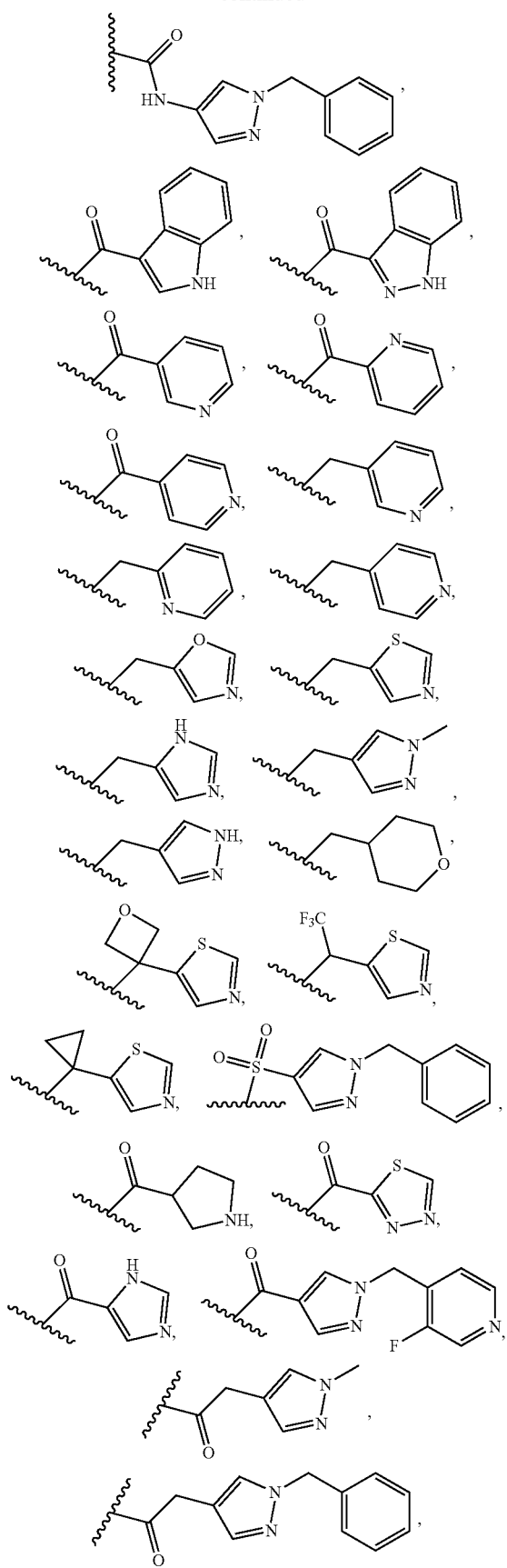
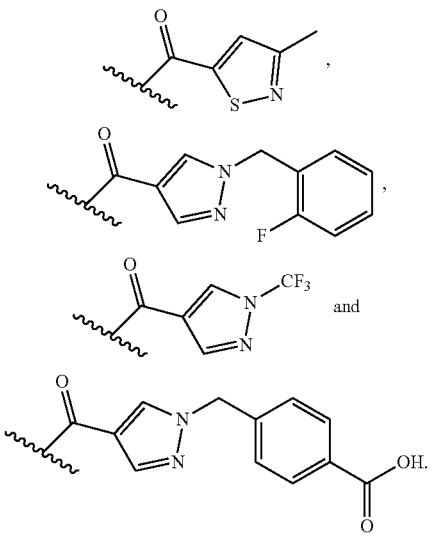
15. The compound of claim 1, wherein the compound of Formula I is a compound of any of Formulae II, IIIa, IVa, IVb, IVc, Va, Vb, VIa, VIb, VIa, VIb, VIc, VIIa, VIIb, VIIc, VIIIa, VIIIb, VIIIc, IXb*, or IXc*:
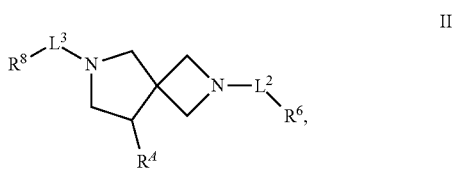
II
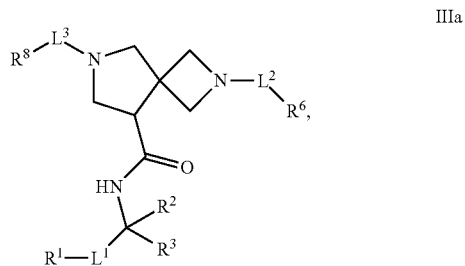
IIIa
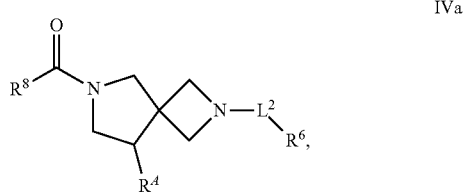
IVa
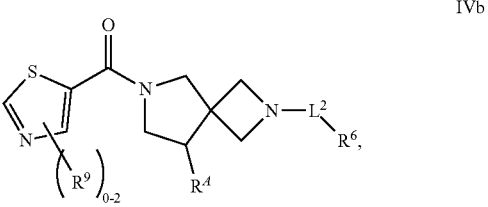
IVb IVc
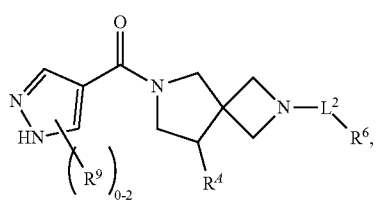
Va
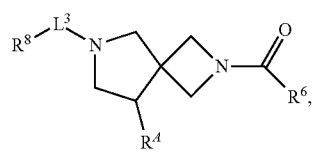
Vb
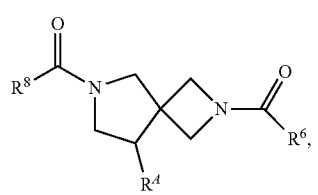
VIa
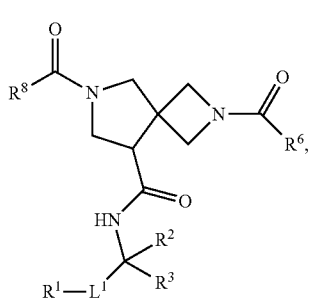
VIb
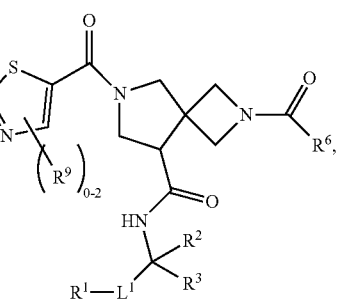
VIc
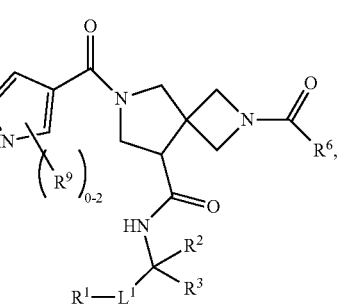
VIIa
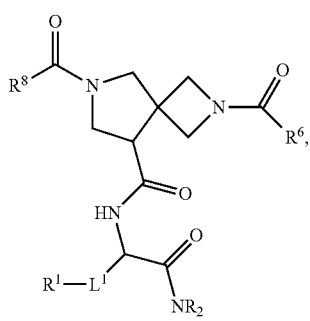
VIIb
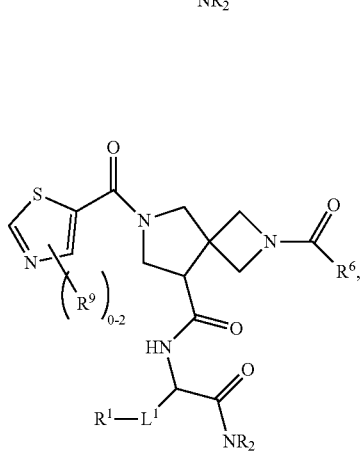
VIIc
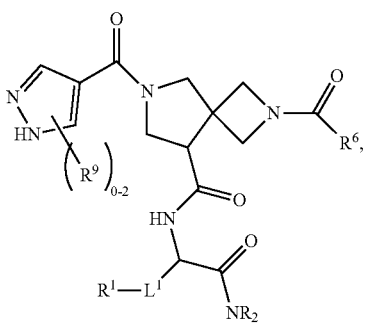
VIIIa
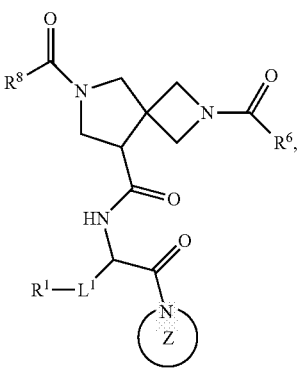

-continued

VIIIb
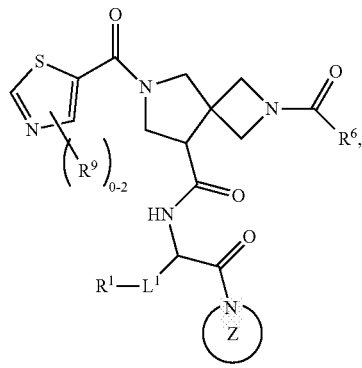

VIIIc
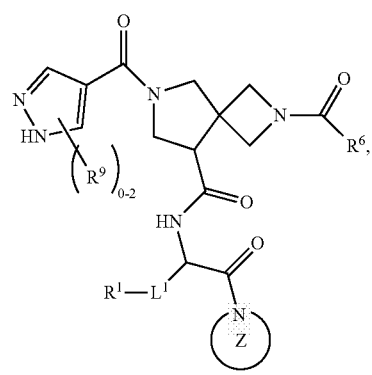

IXb*
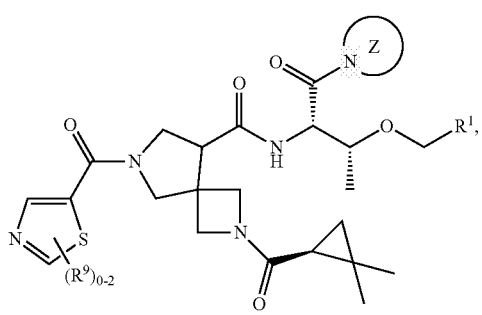

IXc*
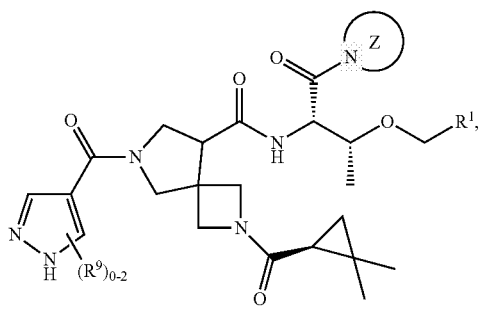

or a pharmaceutically acceptable salt thereof, wherein cyclic moiety Z is formed from two R groups, taken together with the intervening nitrogen atom to form an optionally substituted 4-7 membered saturated ring having 0-3 heteroatoms, in addition to the nitrogen, independently selected from nitrogen, oxygen, and sulfur.

16. The compound of claim 1, wherein the compound is selected from the group consisting of:

I-1
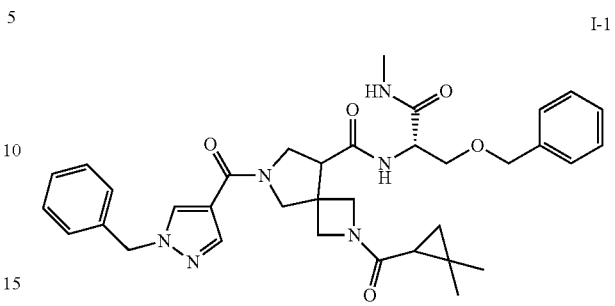

I-2
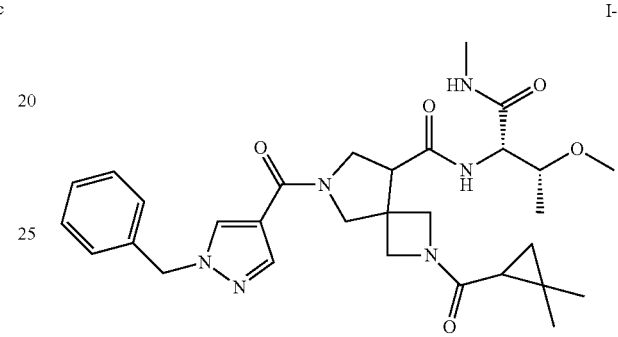

I-3
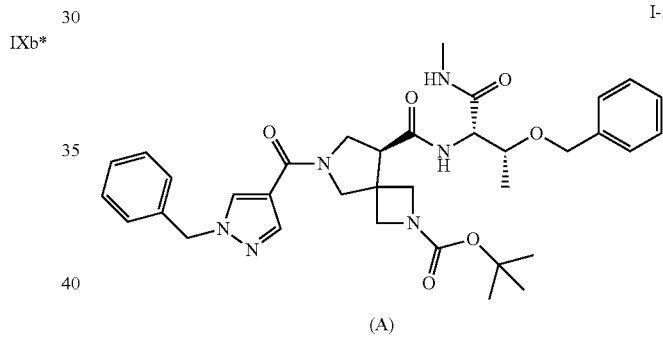

(A)

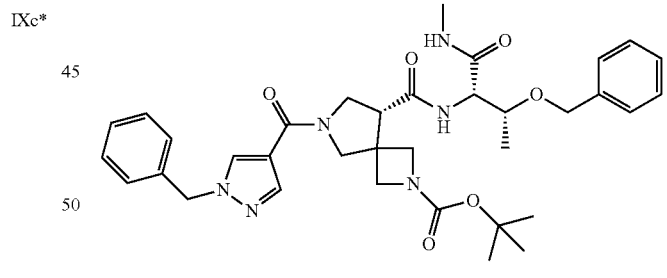

(B)

I-4
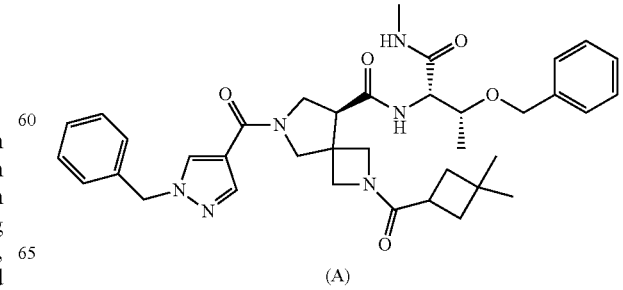

(A)

-continued
(B)
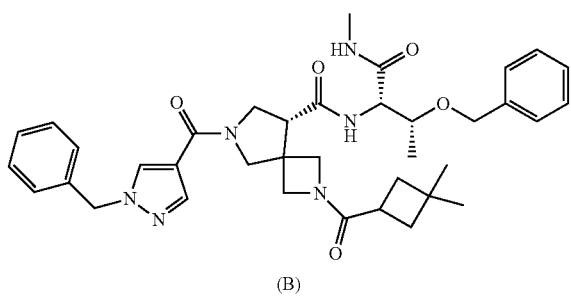
I-5
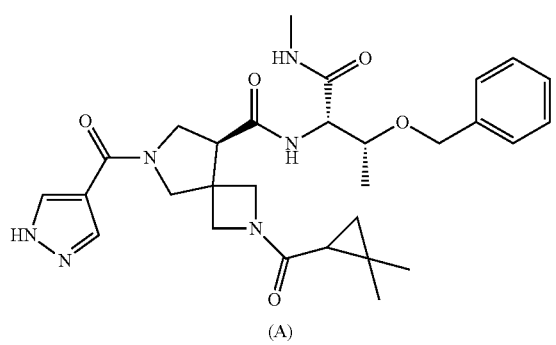
(A)
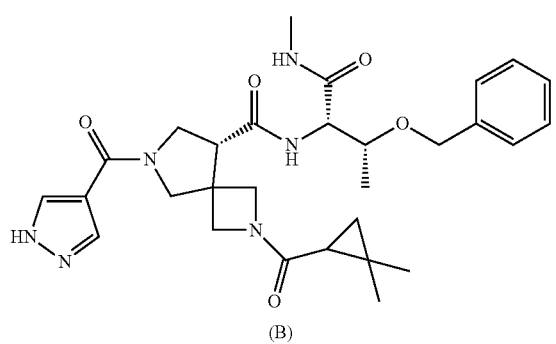
(B)
I-6
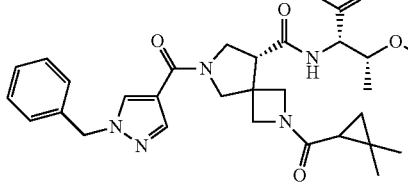
I-7
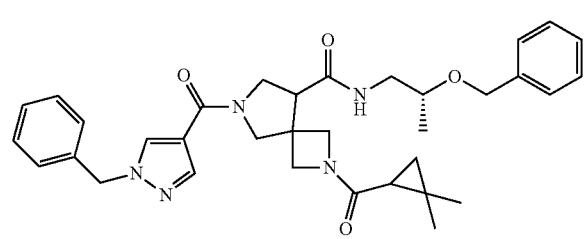
-continued
I-8
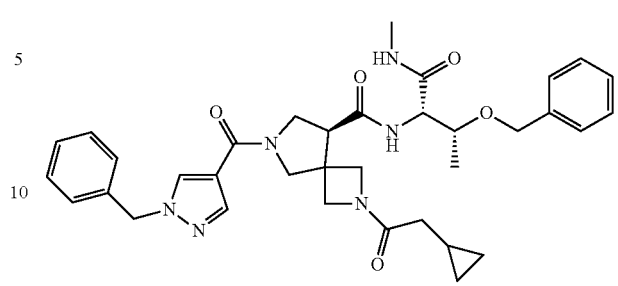
(A)
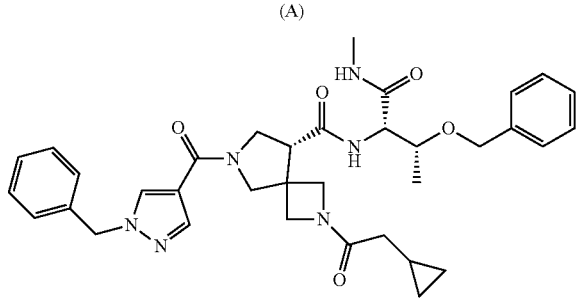
(B)
I-9
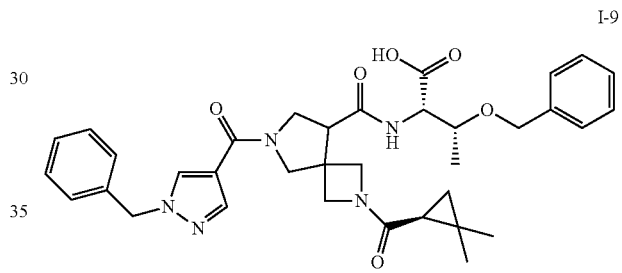
I-10
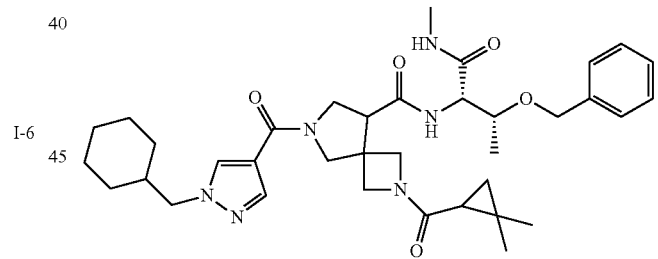
I-11
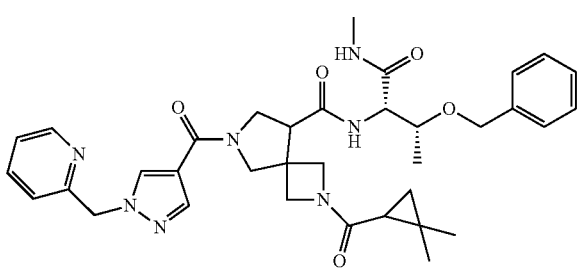

I-12
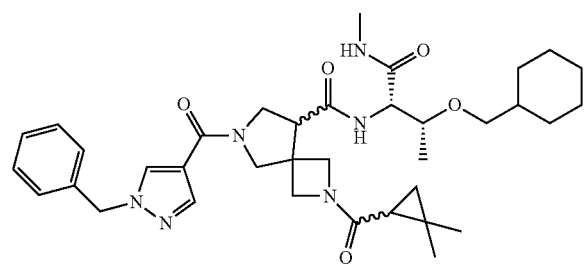
Mixture
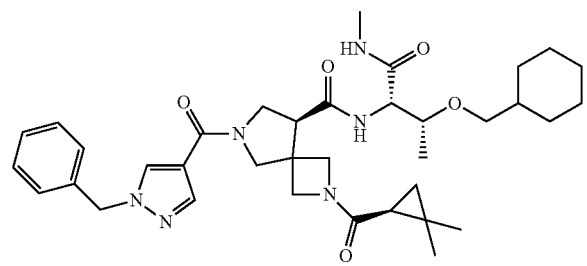
(A)
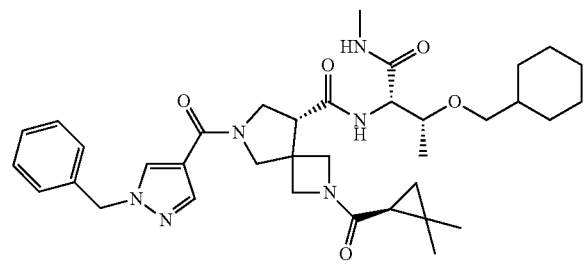
(B)
I-13
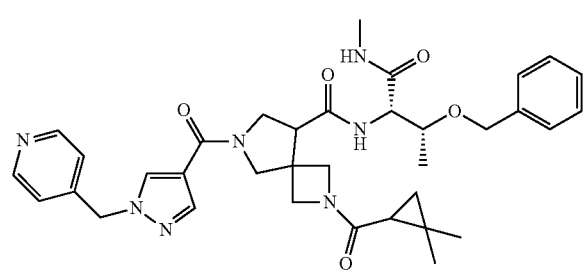
I-14
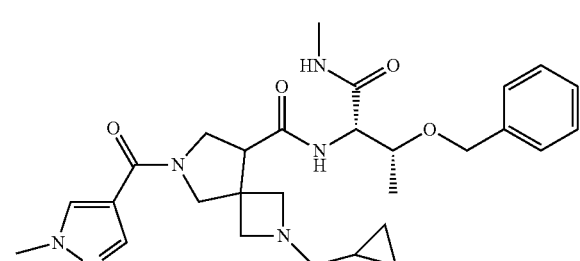
I-15
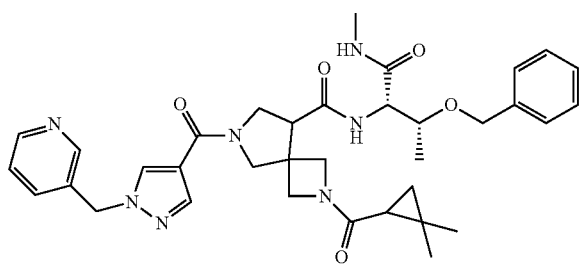
I-16
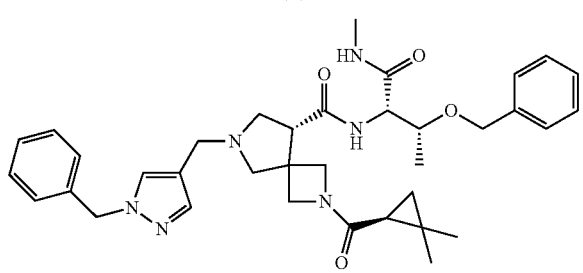
(A)
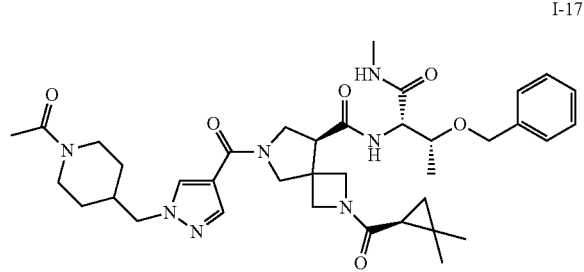
(B)
I-17
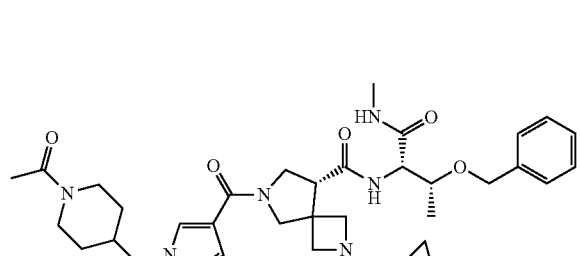
(A)
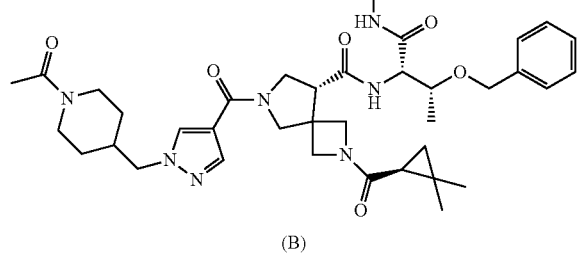
(B)

I-18
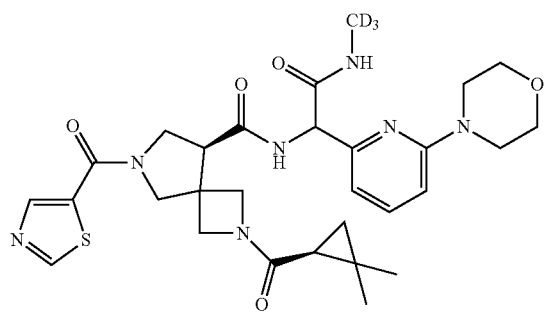
I-19
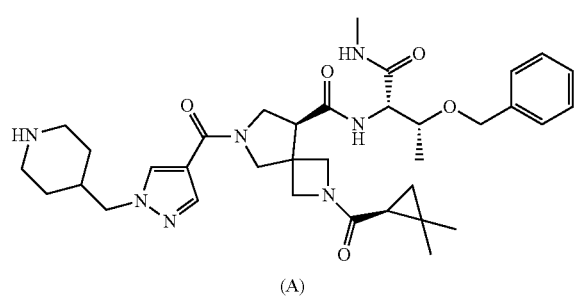
(A)
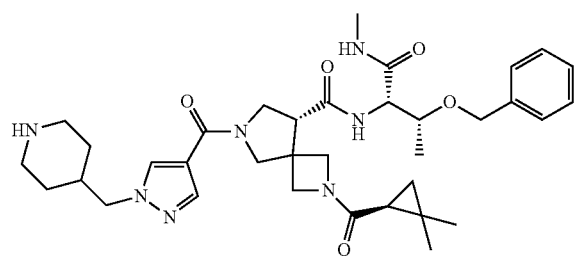
(B)
I-20
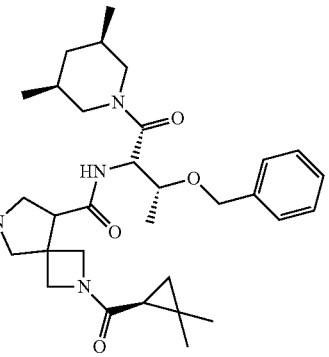
I-21
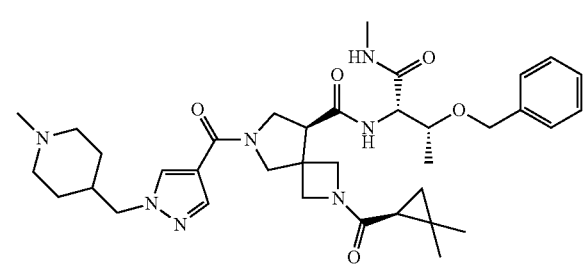
I-22
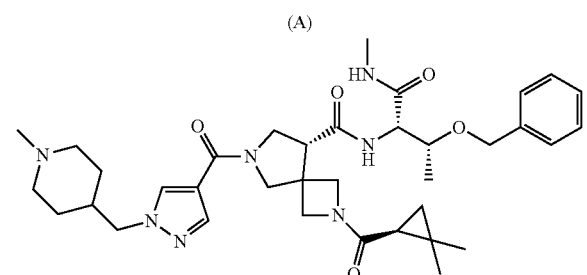
I-23
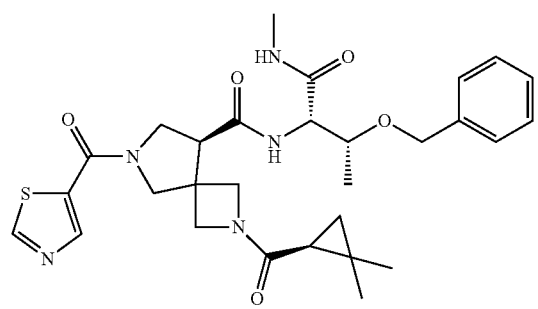
(A)
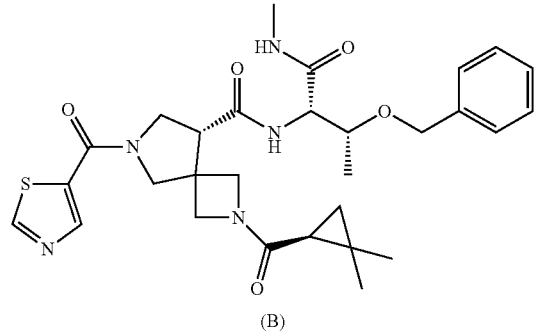
(B)
I-24
(A)
(B)

I-25
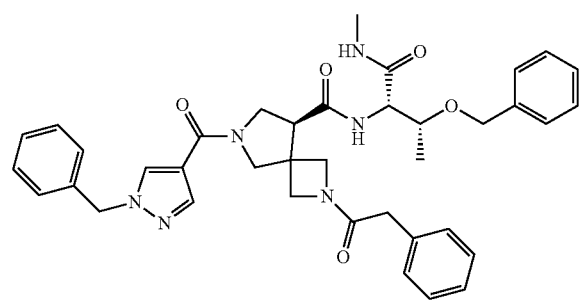
(A)
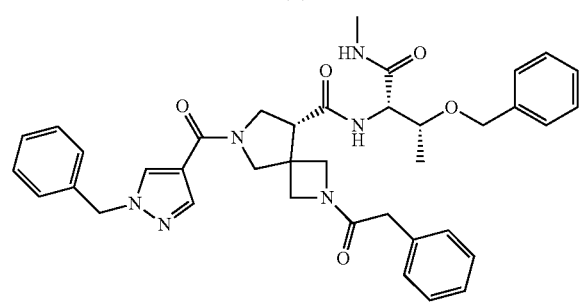
(B)
I-26
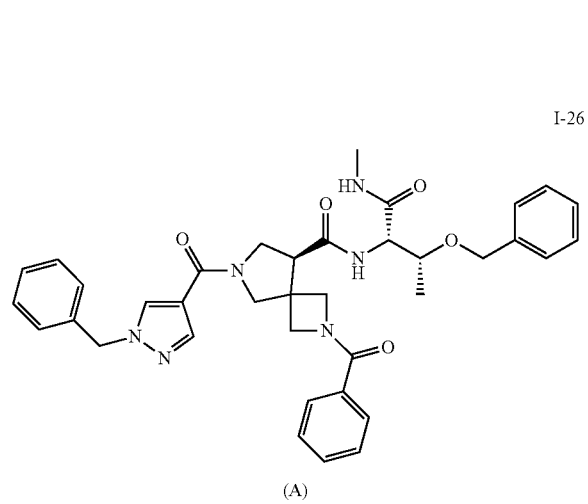
(A)
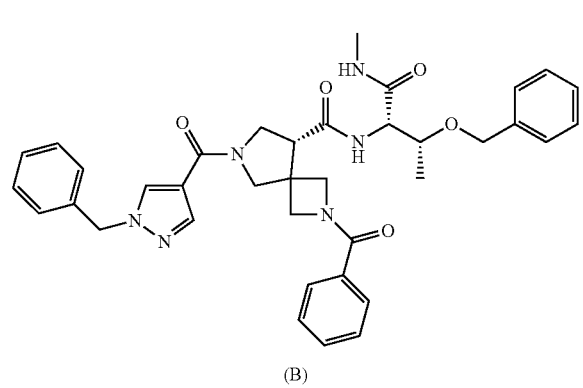
(B)
I-27
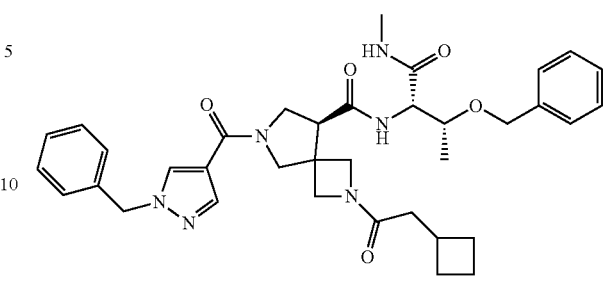
(A)
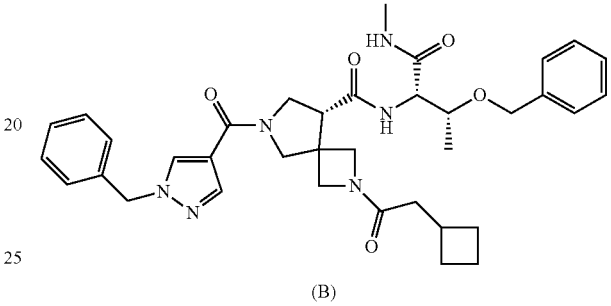
(B)
I-28
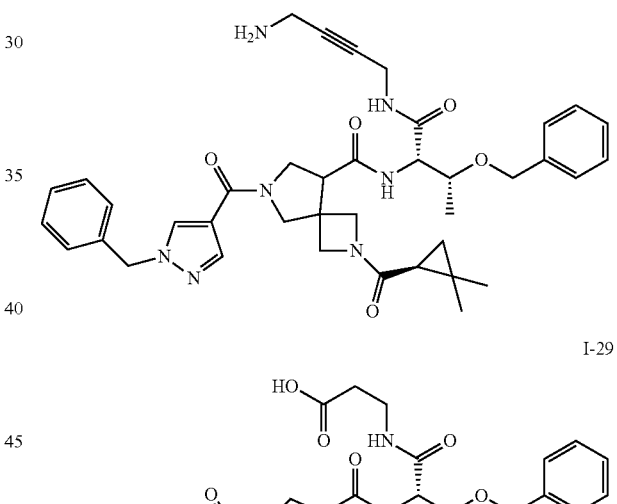
I-29
I-30
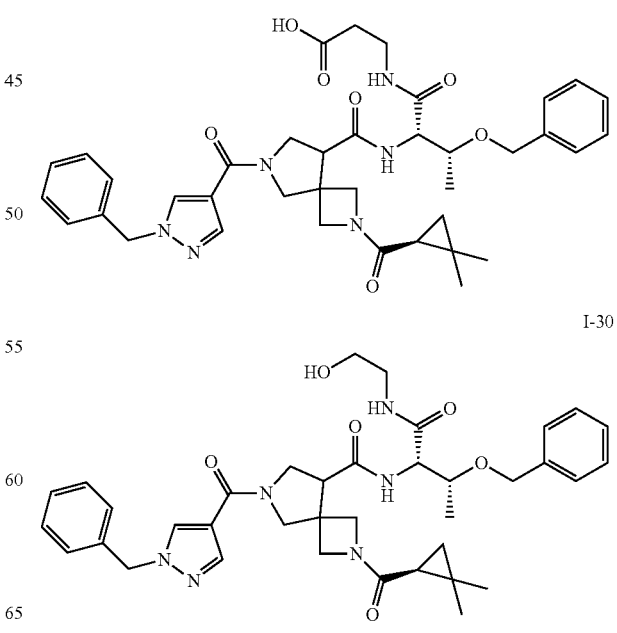

I-31
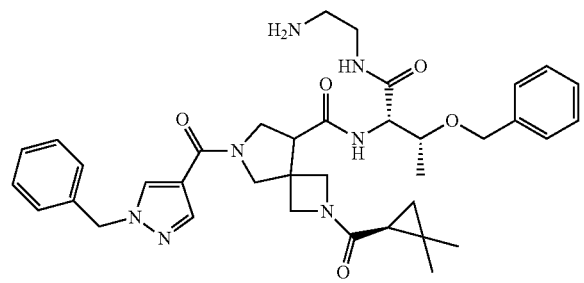
I-32
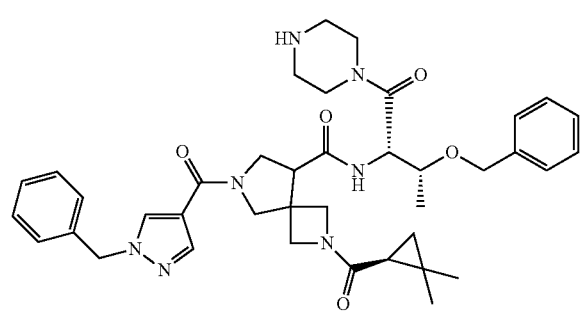
I-33
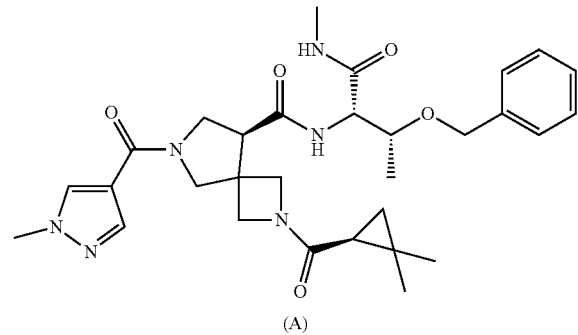
(A)
(B)
I-34
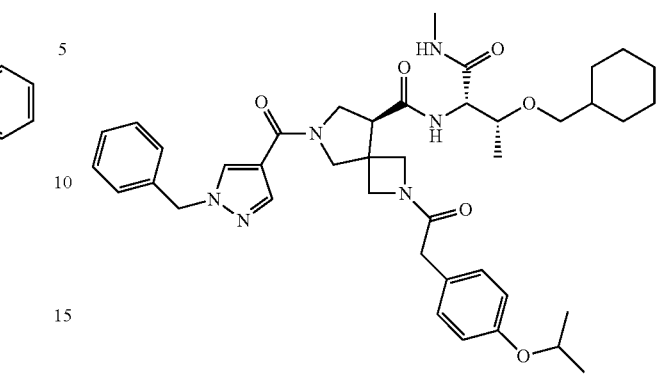
(A)
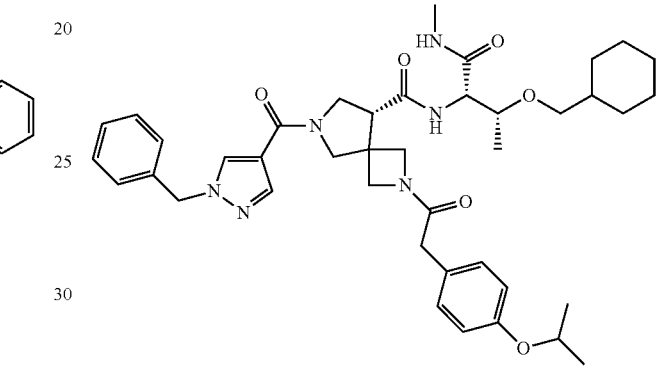
(B)
I-35
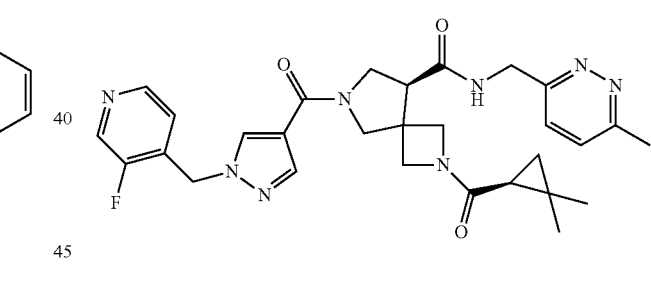
I-36
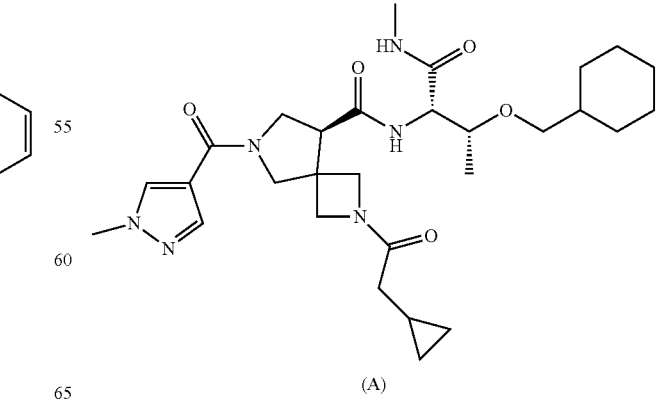
(A)

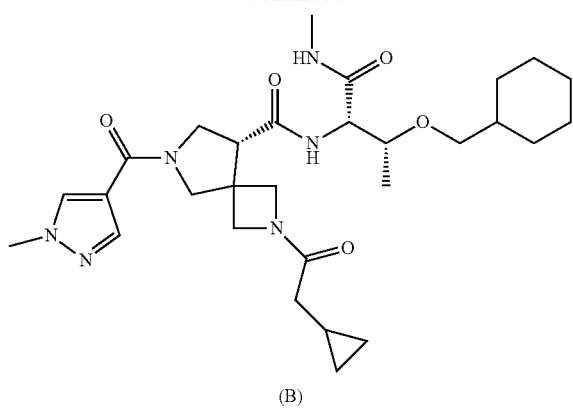
(B)
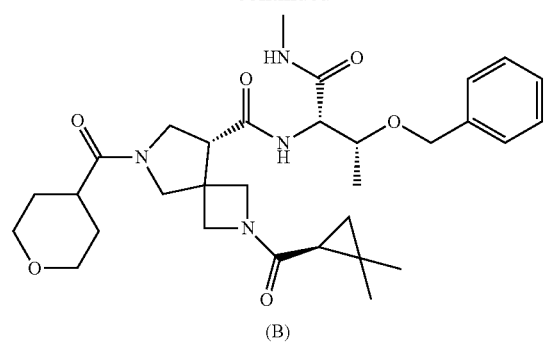
(B)
I-37
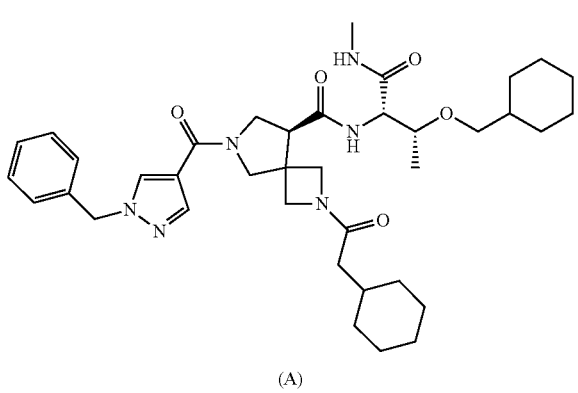
(A)
I-39
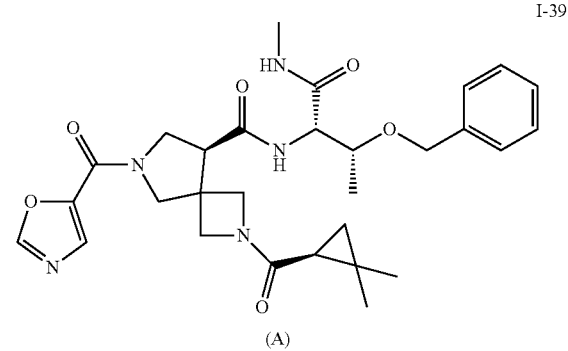
(A)
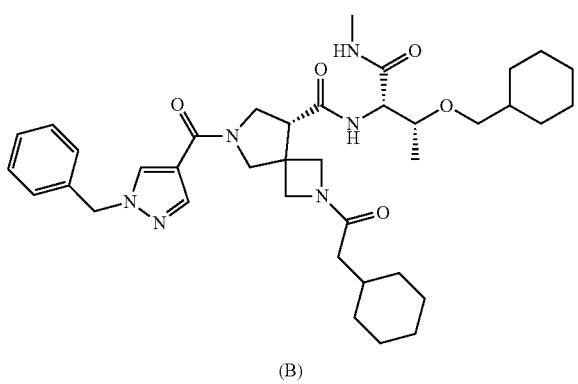
(B)
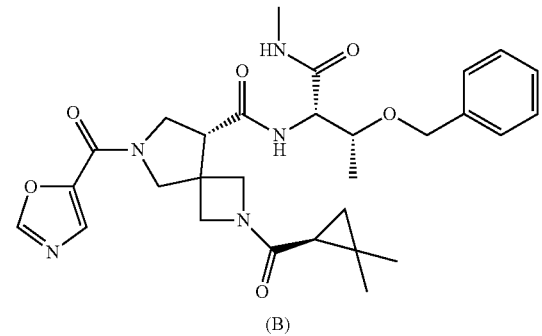
(B)
I-38
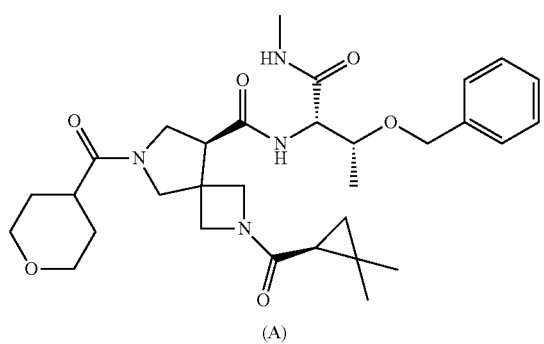
(A)
I-40
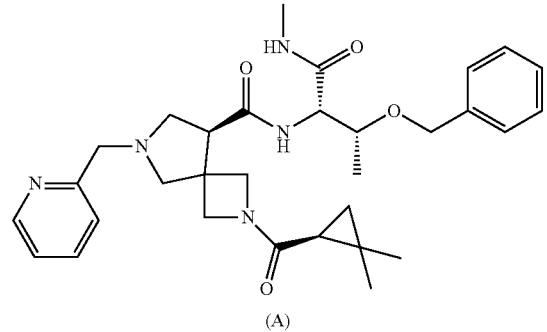
(A)

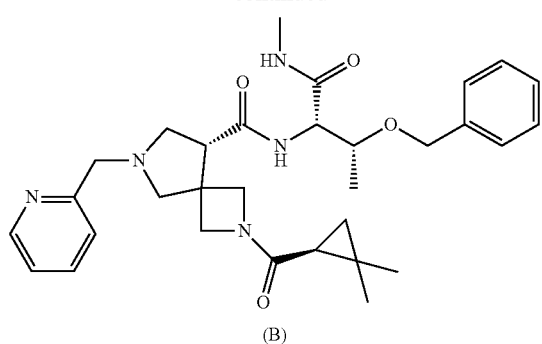
(B)
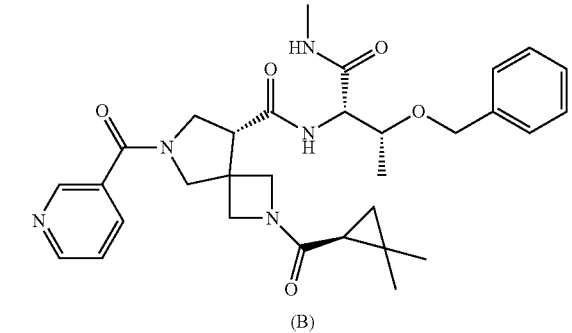
(B)
I-41
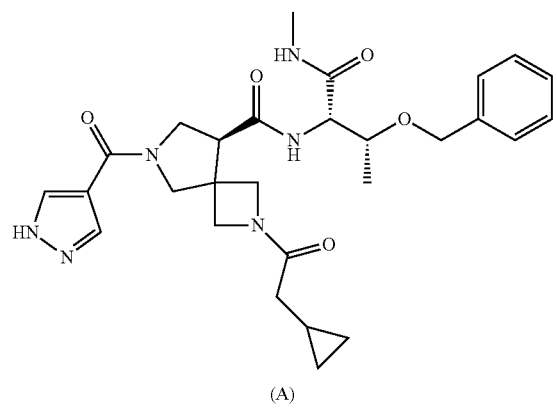
(A)
I-43
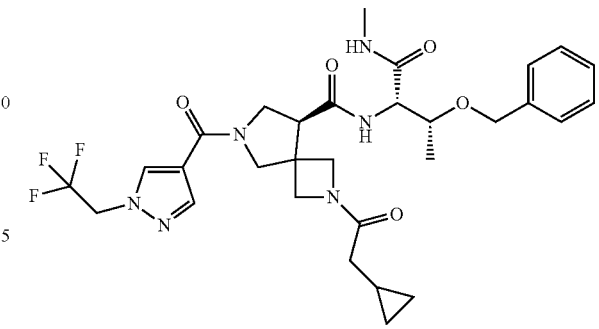
(A)
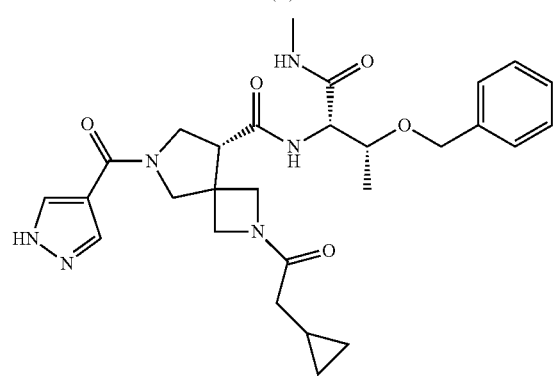
(B)
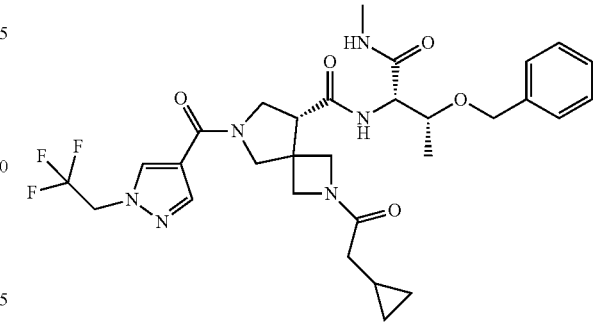
(B)
I-42
I-44
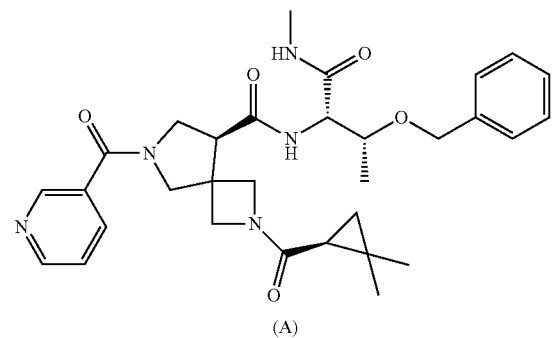
(A)
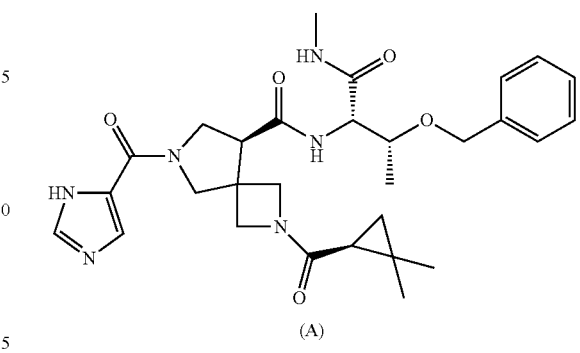
(A)

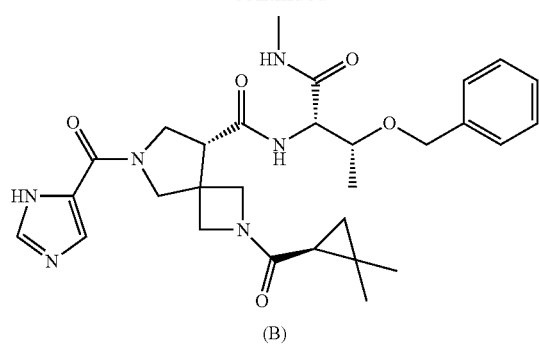
(B)
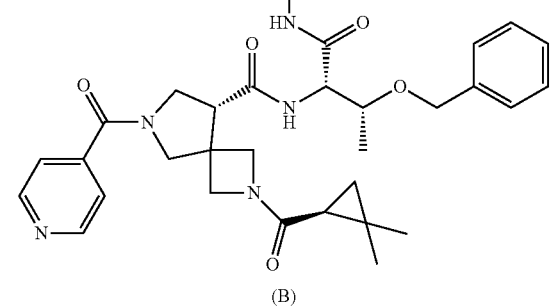
(B)
I-45
I-47
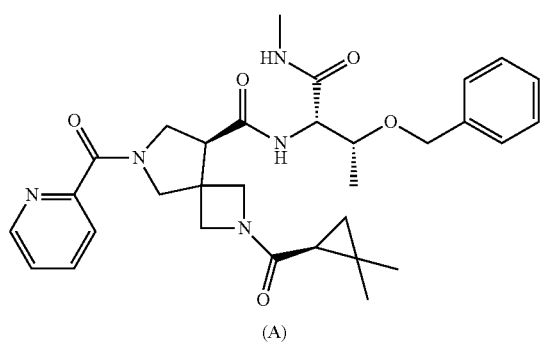
(A)
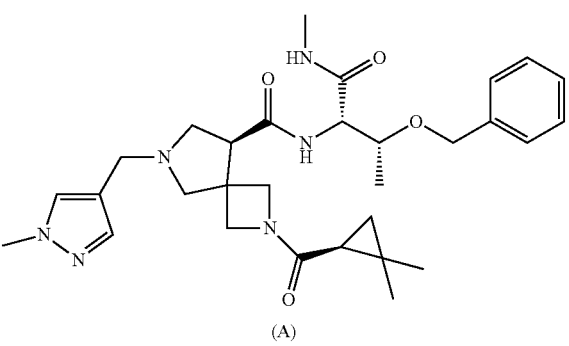
(A)
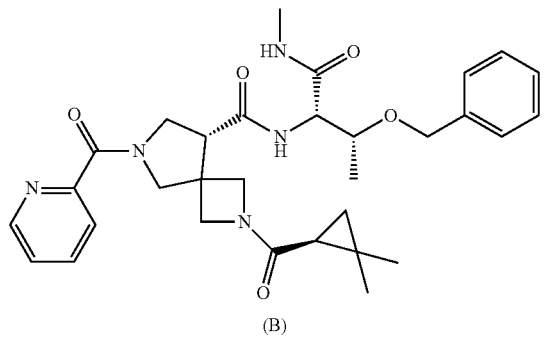
(B)
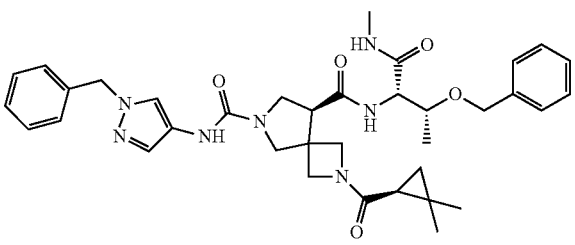
(B)
I-46
I-48
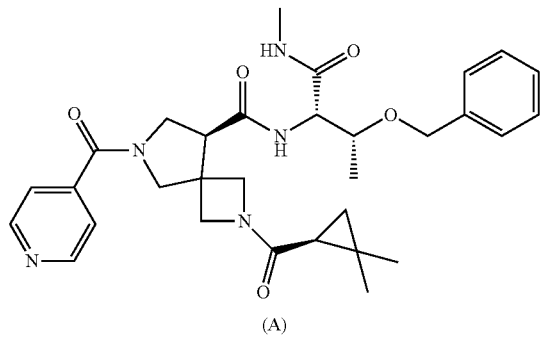
(A)
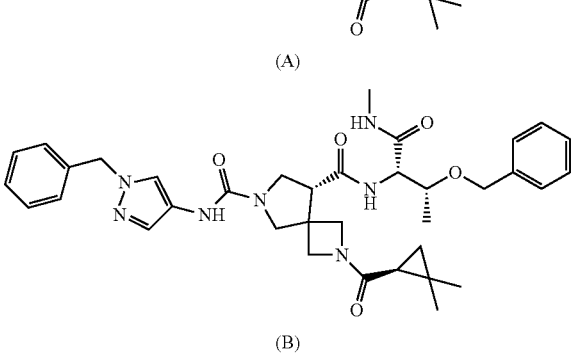
(B)

I-49
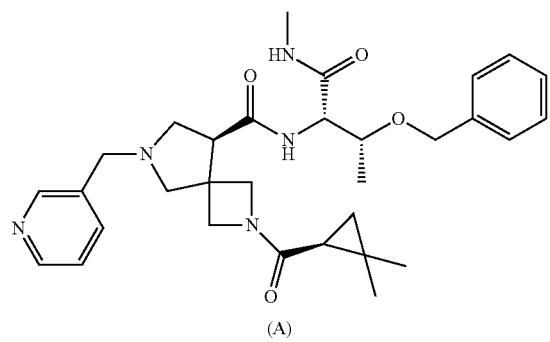
(A)
(B)
I-50
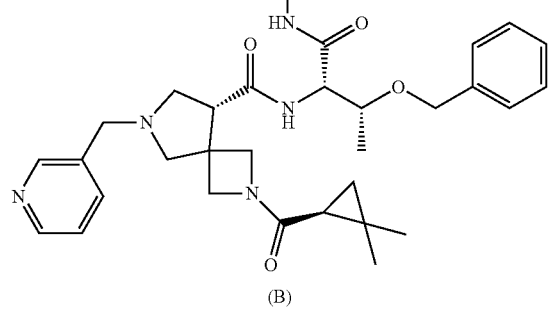
(A)
(B)
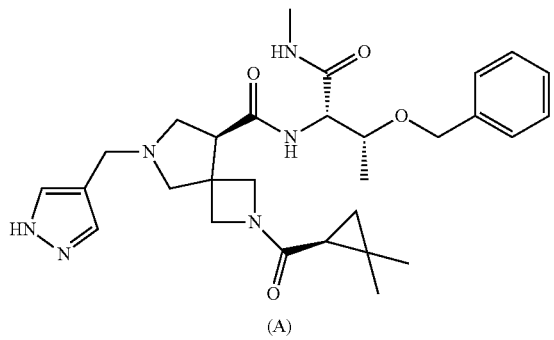
I-51
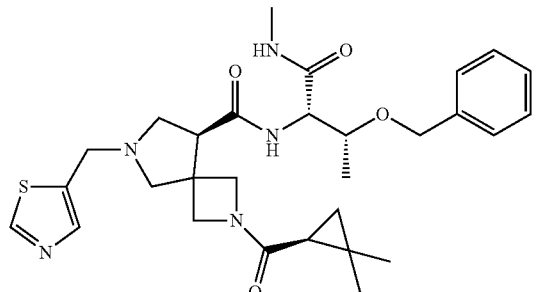
(A)
(B)
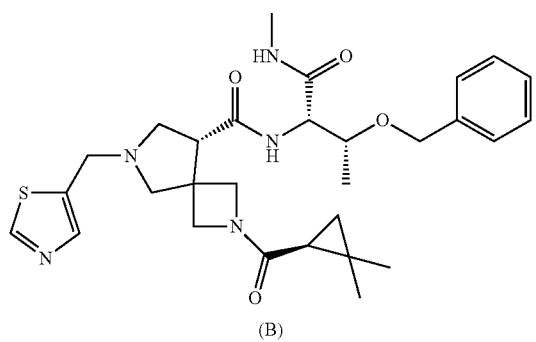
I-52
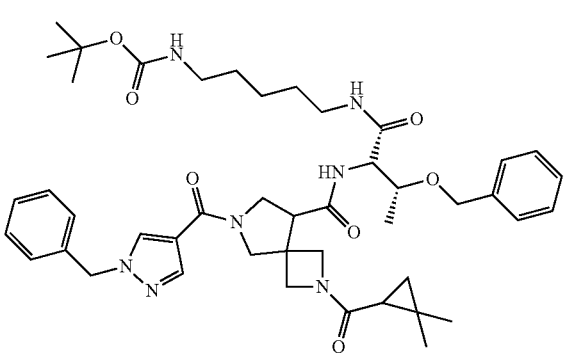
I-53
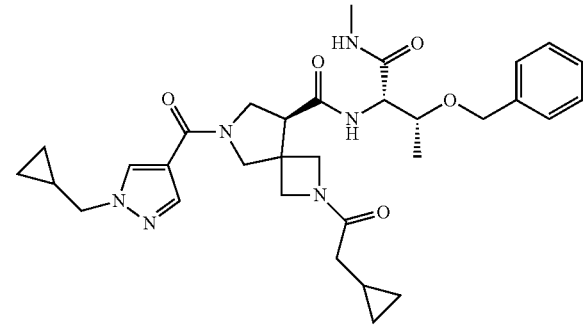
(A)
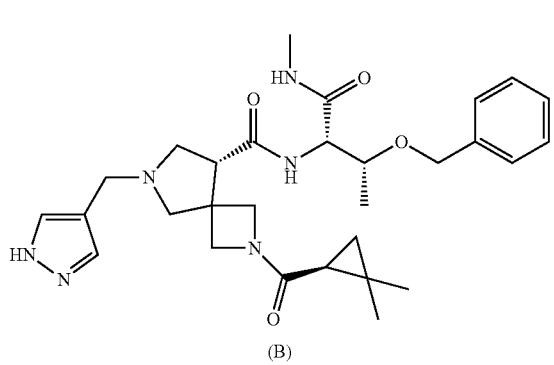

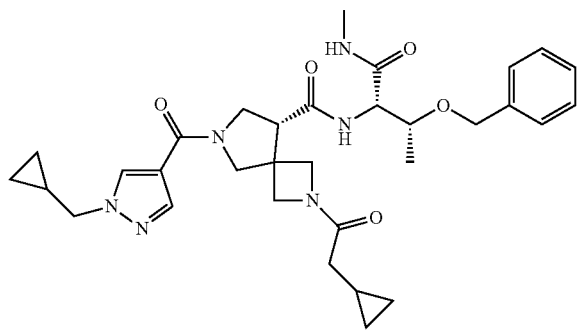
(B)
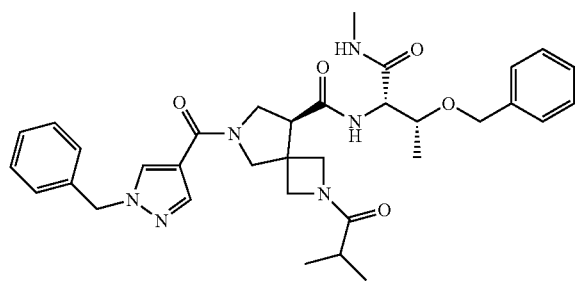
(A)
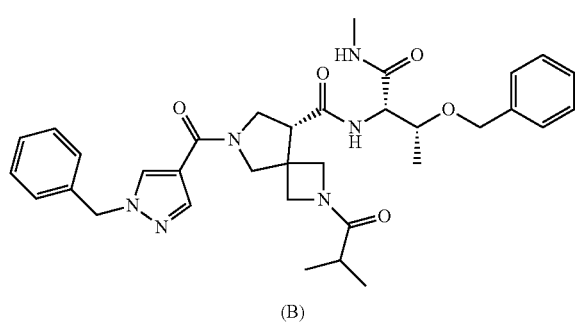
(B)
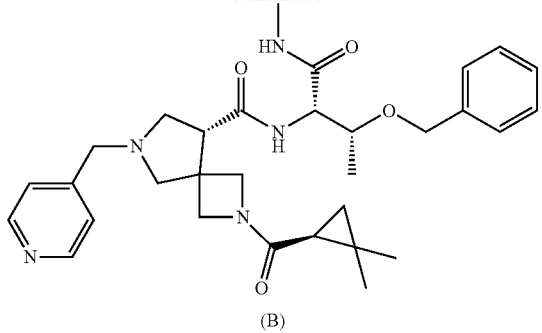
(B)
I-54
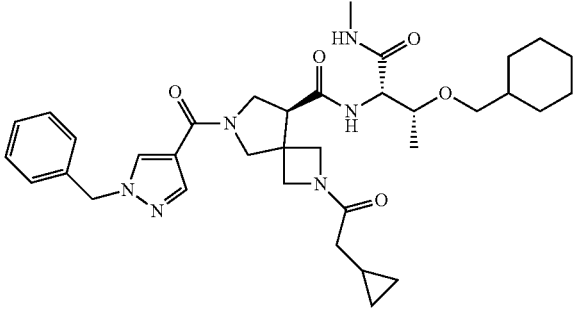
(A)
I-55
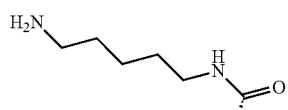
I-56
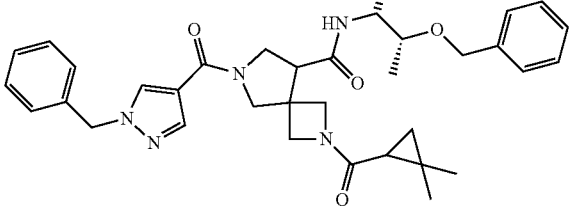
I-57
I-58
(A)

819
-continued
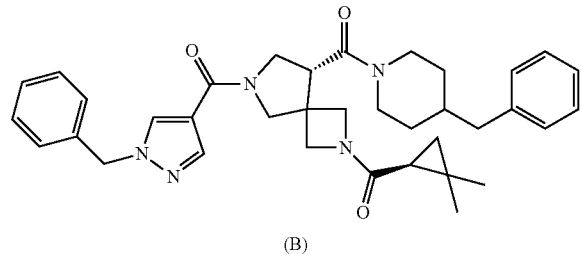
(B)
I-59
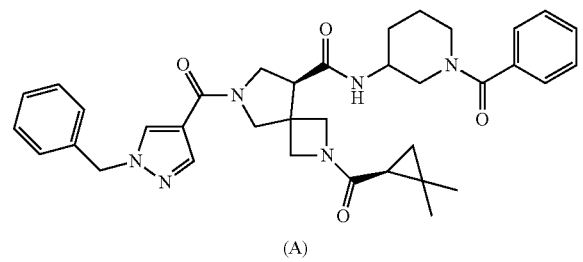
(A)
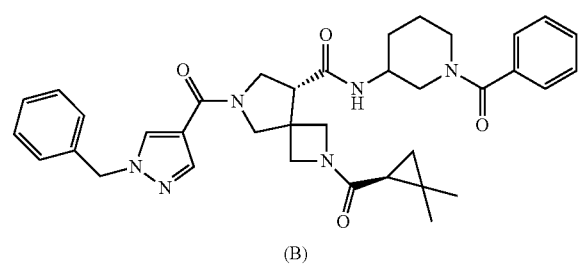
(B)
I-60
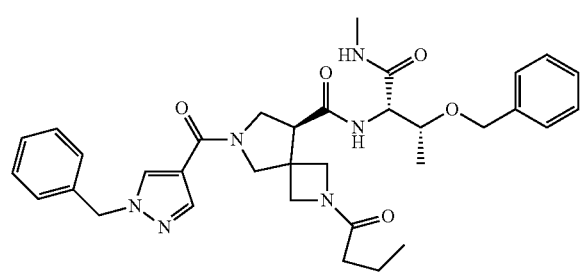
(A)
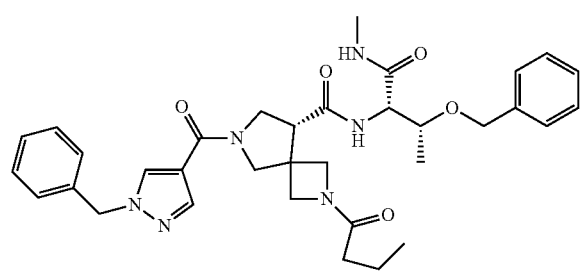
(B)
820
-continued
I-61
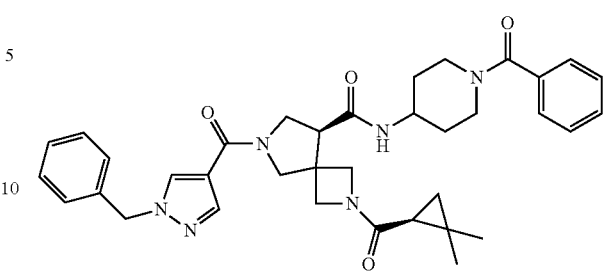
(A)
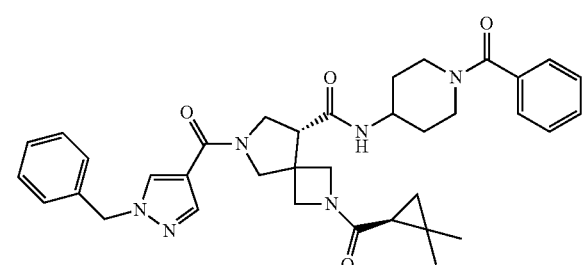
(B)
I-62
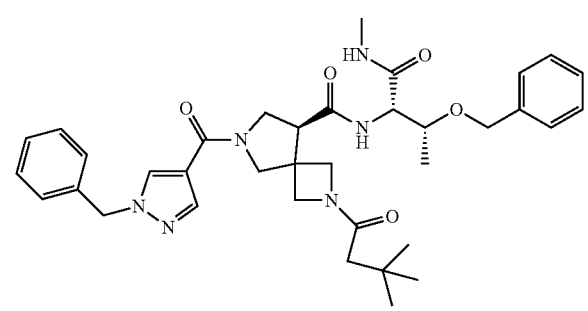
(A)
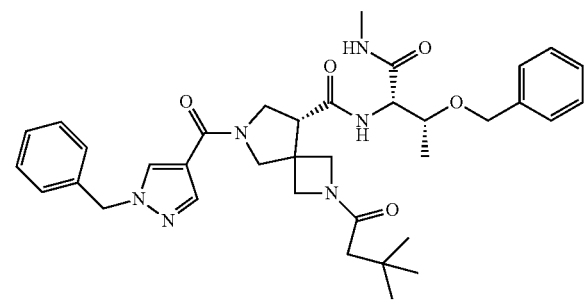
(B)
I-63
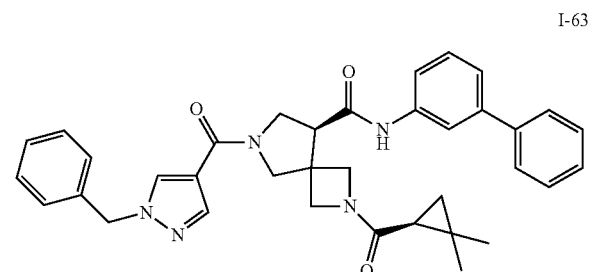
(A)

821
-continued
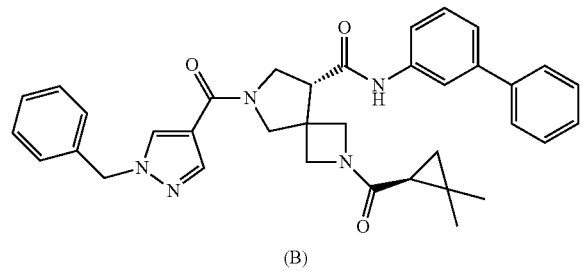
(B)
I-64
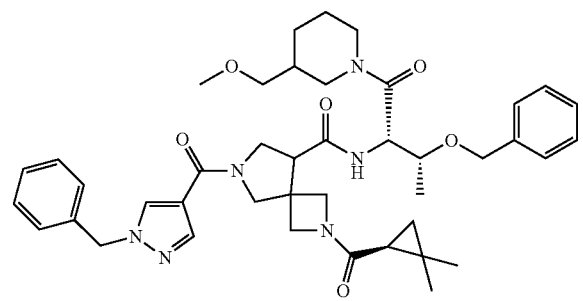
I-65
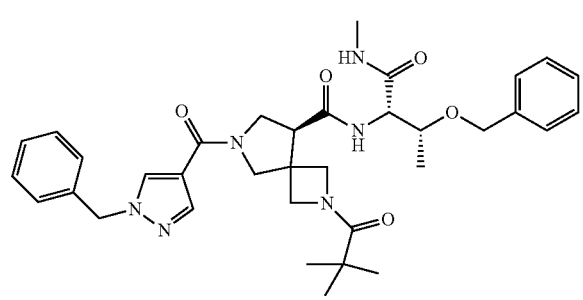
(A)
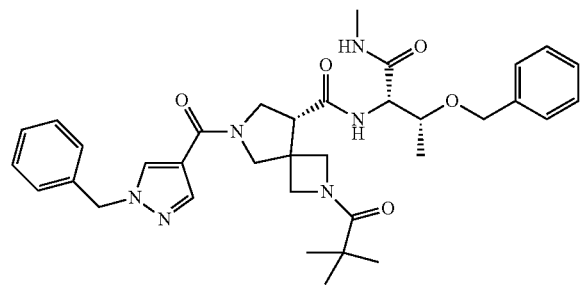
(B)
I-66
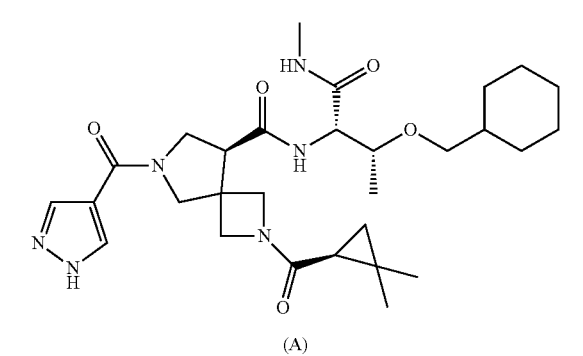
(A)
822
-continued
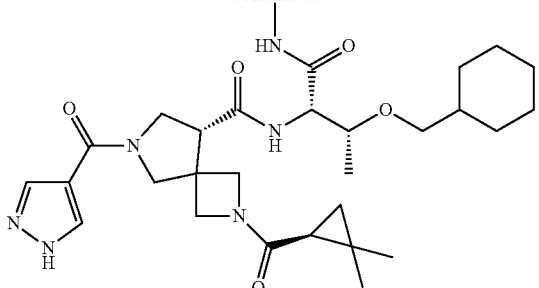
(B)
I-67
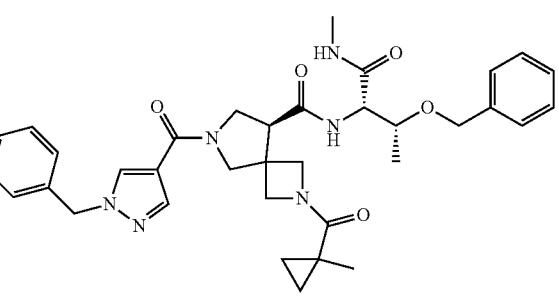
(A)
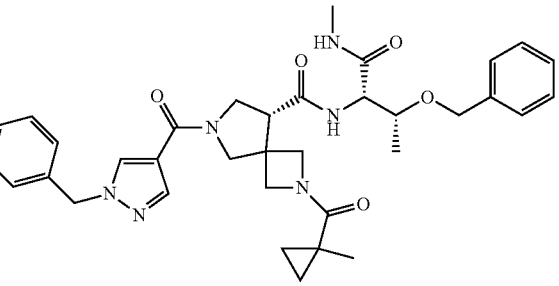
(B)
I-68
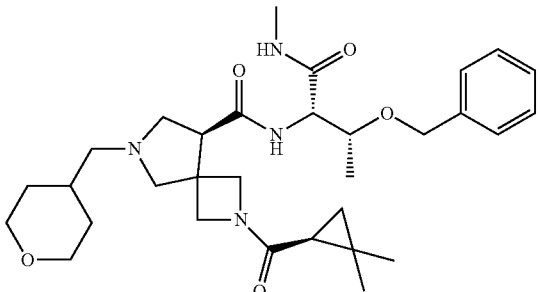
(A)
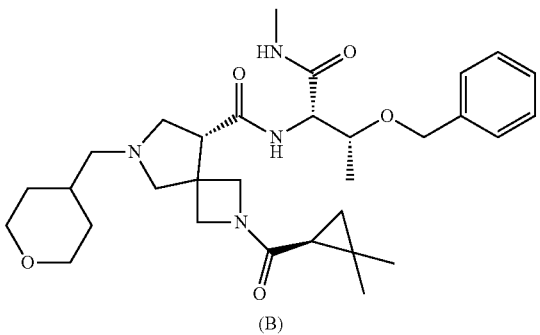
(B)

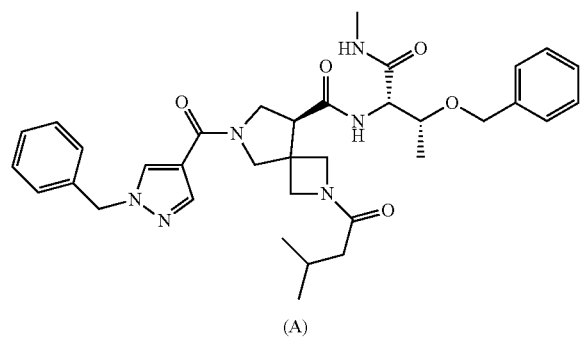
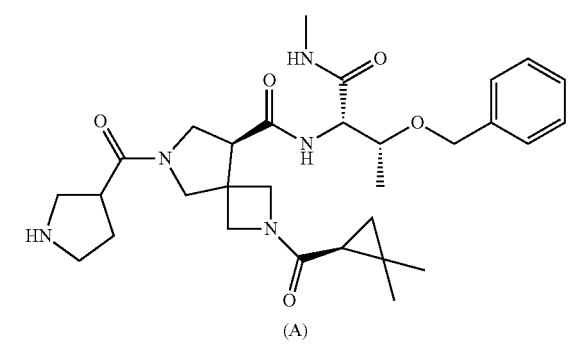

I-73
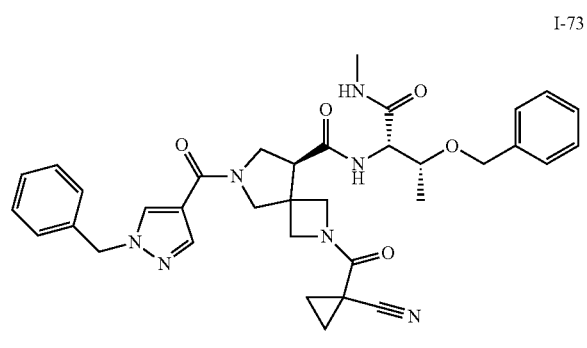
(A)
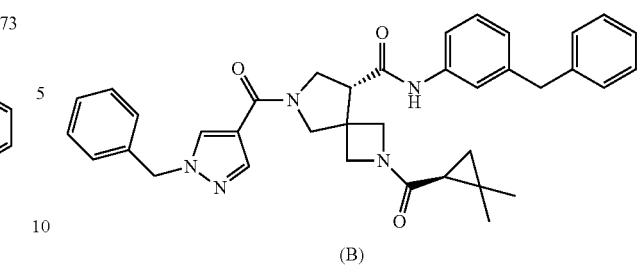
(B)
I-74
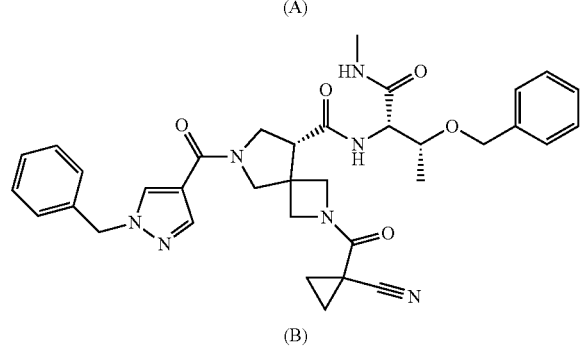
(A)
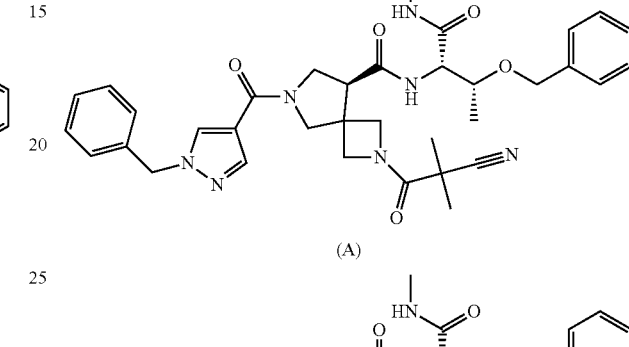
I-76
(A)
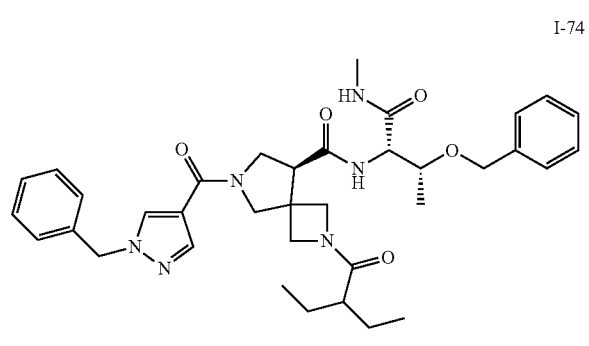
(B)
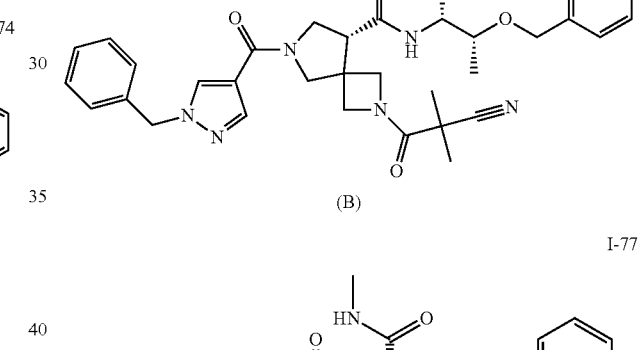
(B)
I-75
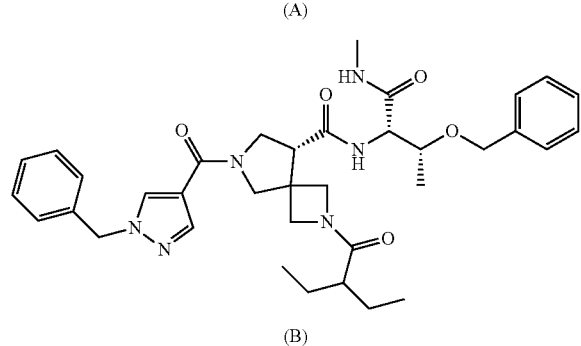
(A)
I-77
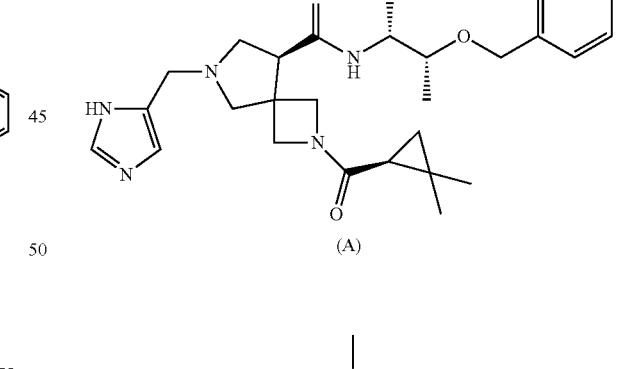
(A)
(B)

I-78
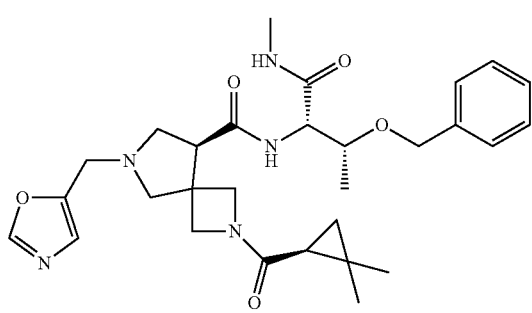
(A)
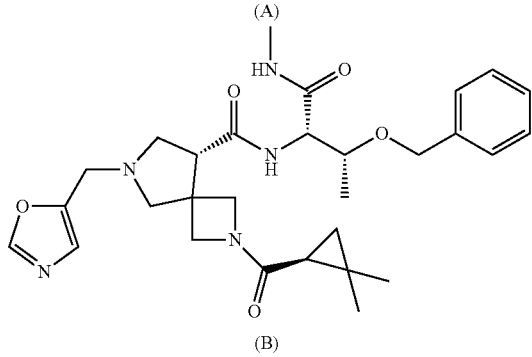
(B)
I-79
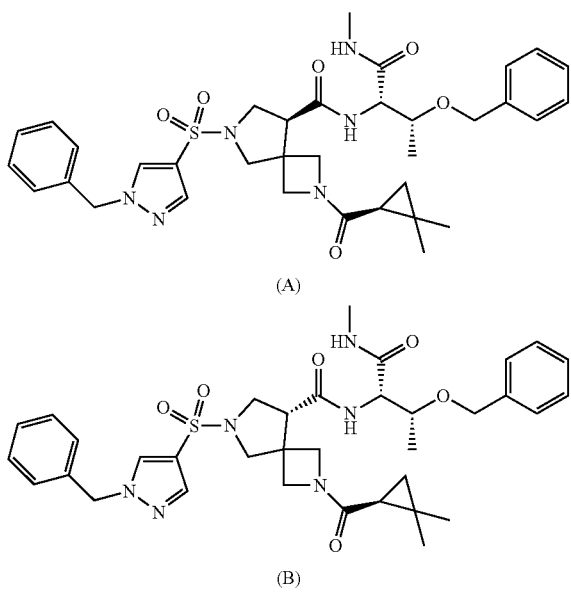
(A)
(B)
I-80
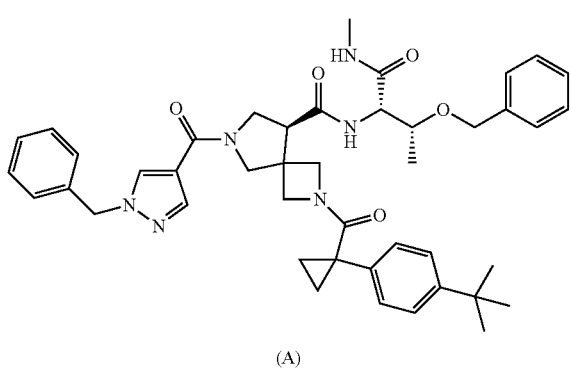
(A)
I-81
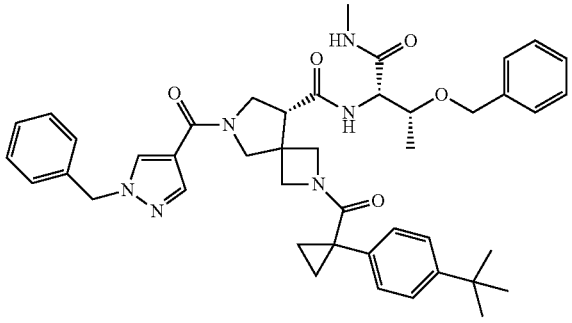
(B)
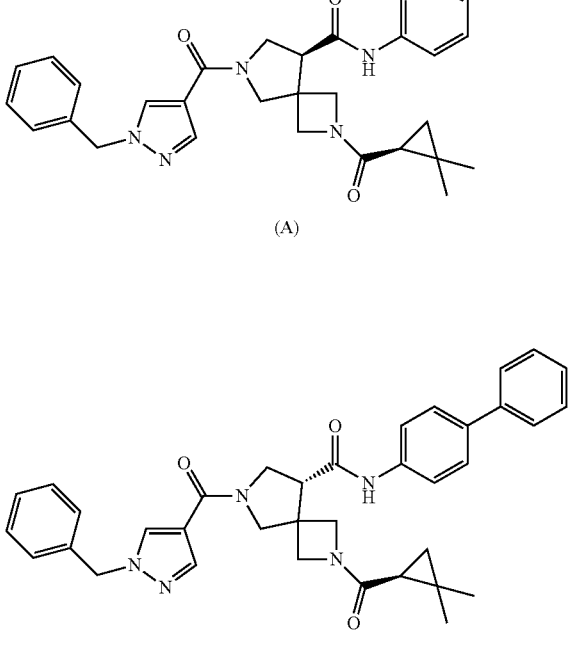
(A)
(B)
I-82
(A)

-continued
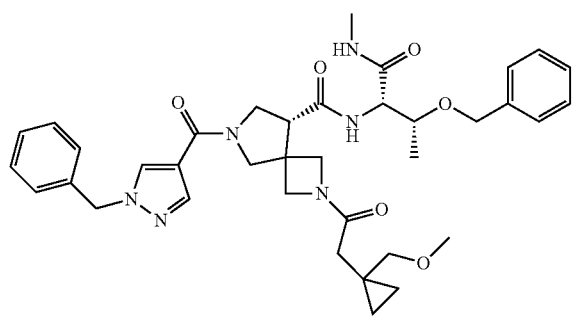
(B)
I-83
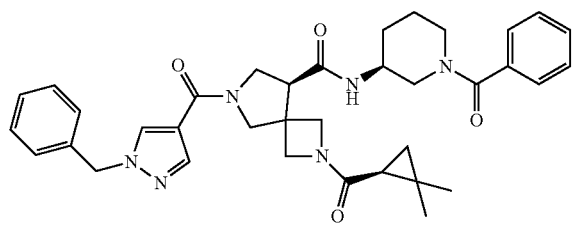
(A)
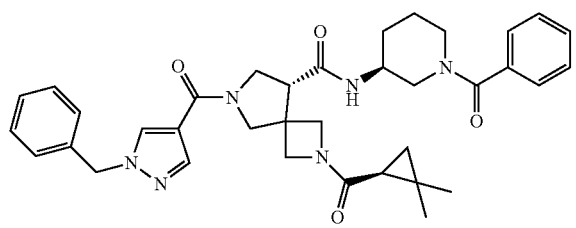
(B)
I-84
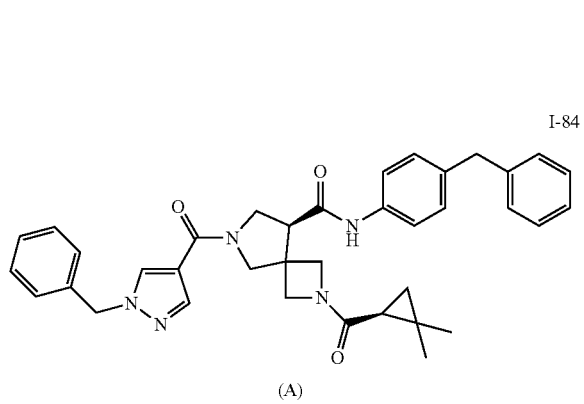
(A)
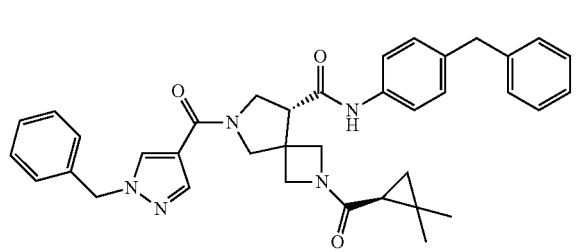
(B)
-continued
I-85
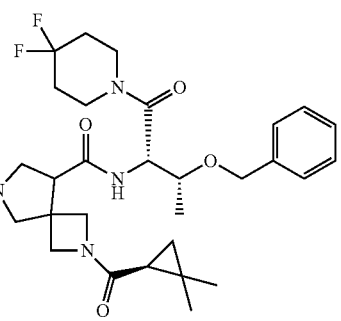
I-86
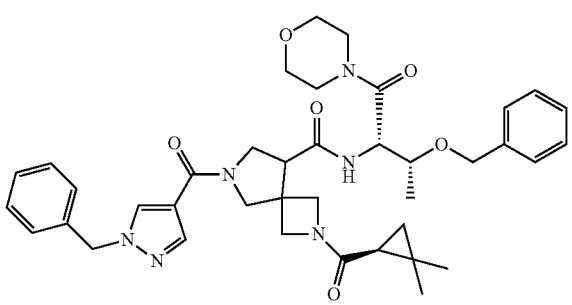
I-87
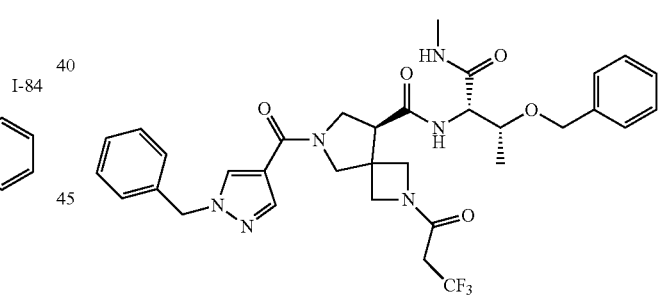
(A)
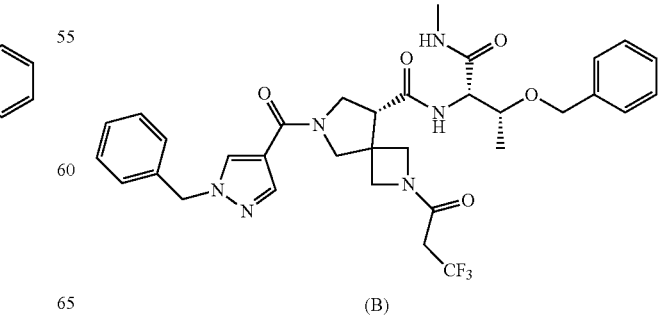
(B)

831
-continued
I-88
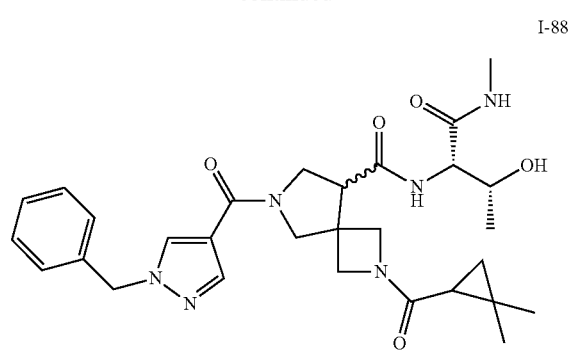
Mixture
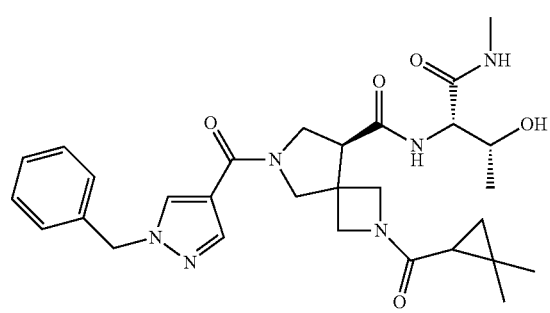
(A)
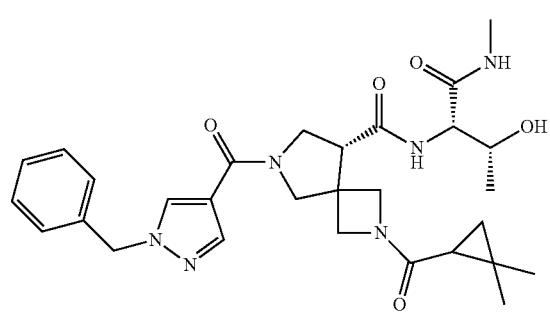
(B)
I-89
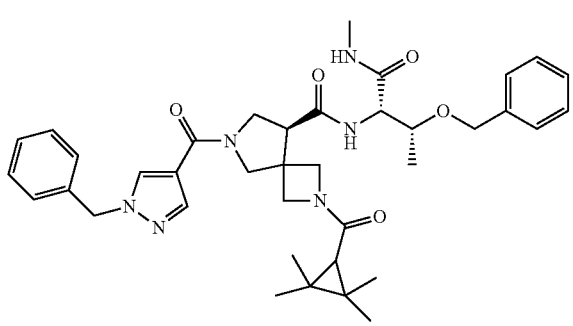
(A)
832
-continued
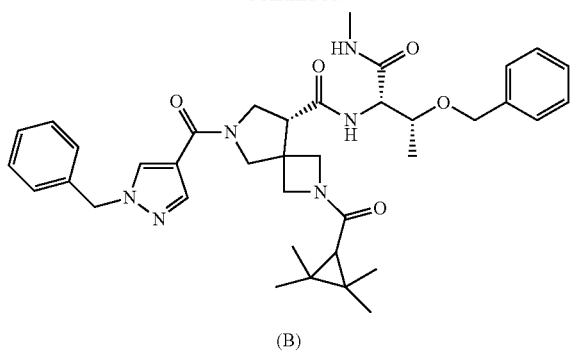
(B)
I-90
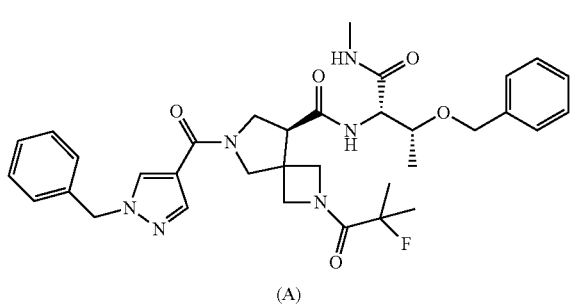
(A)
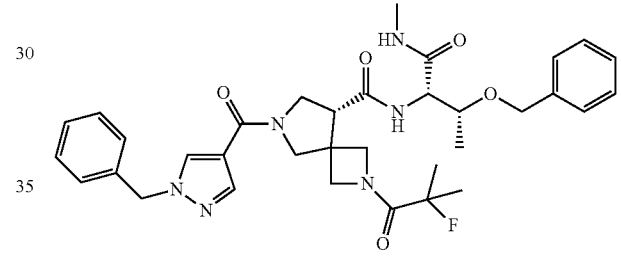
(B)
I-91
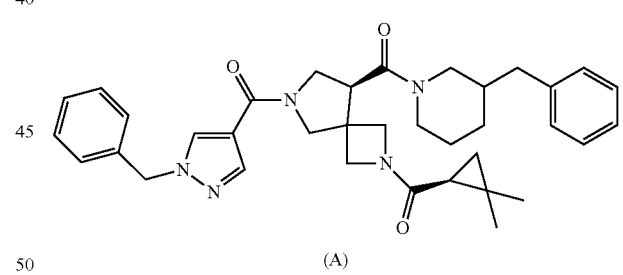
(A)
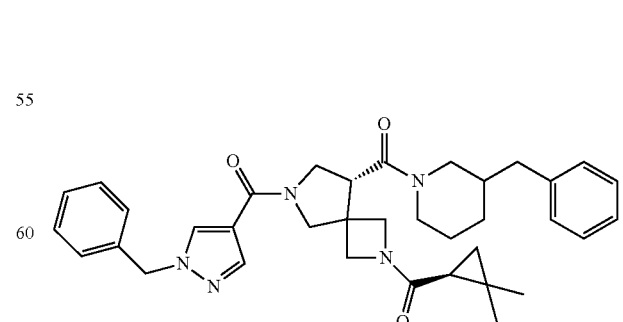
(B)

I-92
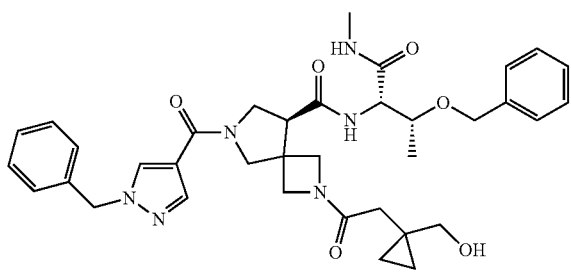
(A)
(B)
I-93
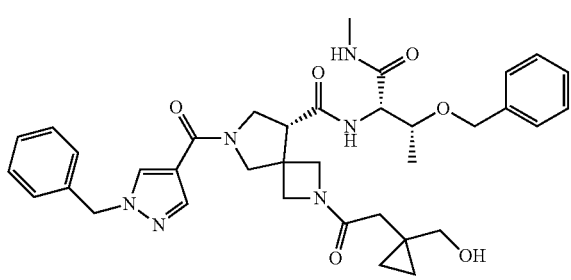
I-94
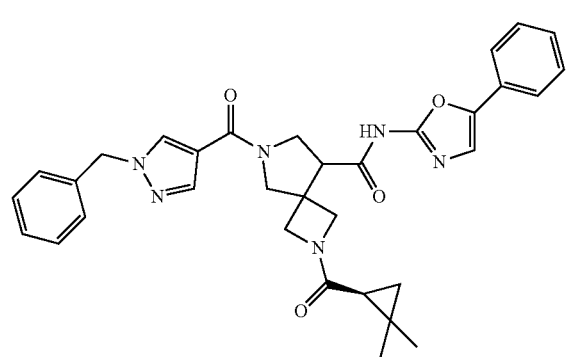
(A)
(B)
I-95
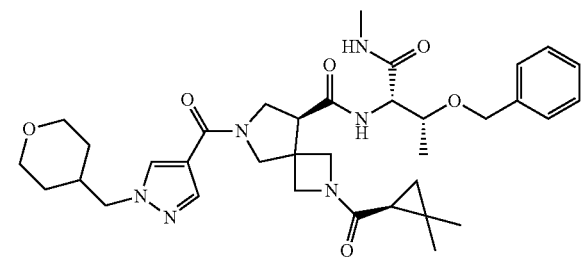
(A)
(B)
I-96
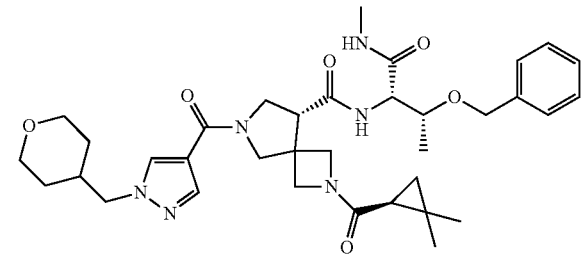
(A)
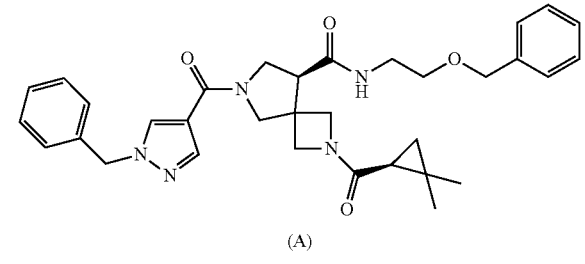
(B)
I-97
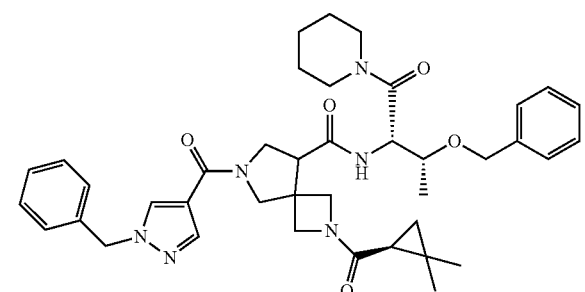

I-98
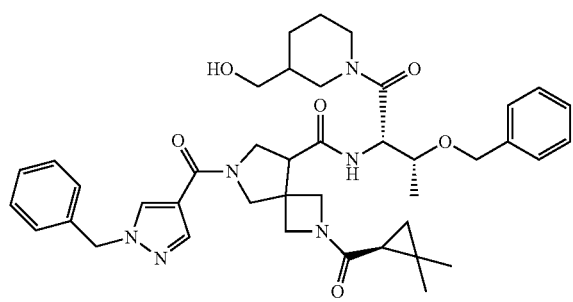
I-99
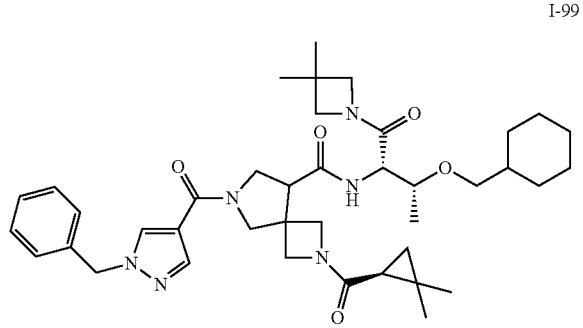
I-100
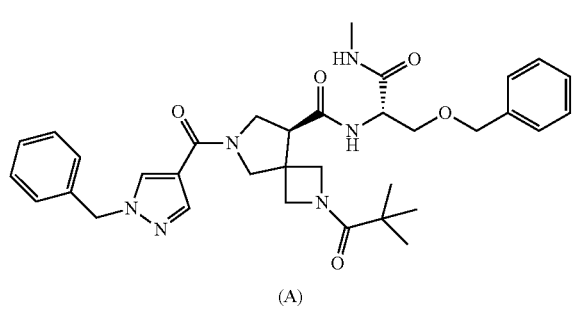
(A)
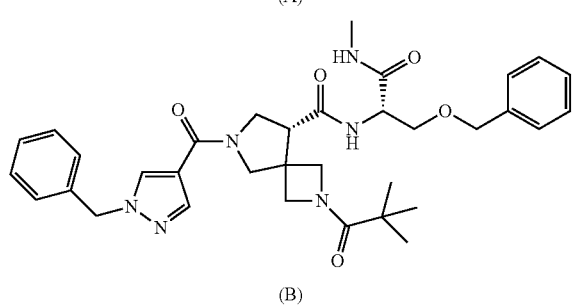
(B)
I-101
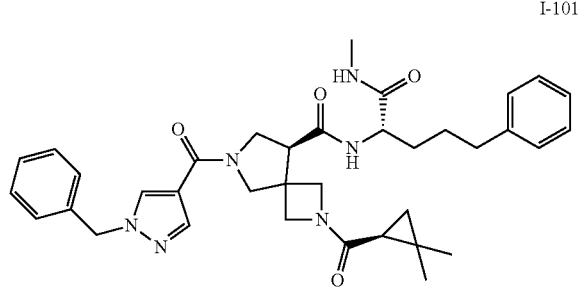
(A)
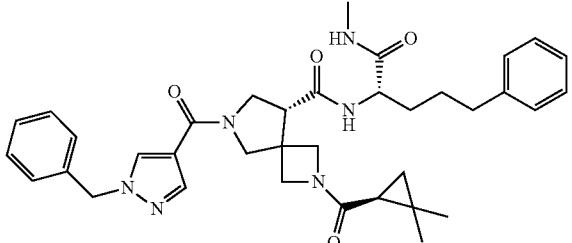
(B)
I-102
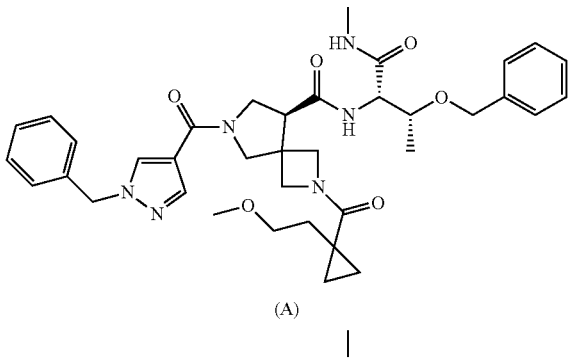
(A)
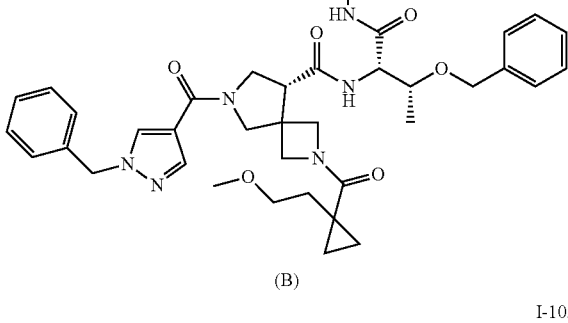
(B)
I-103
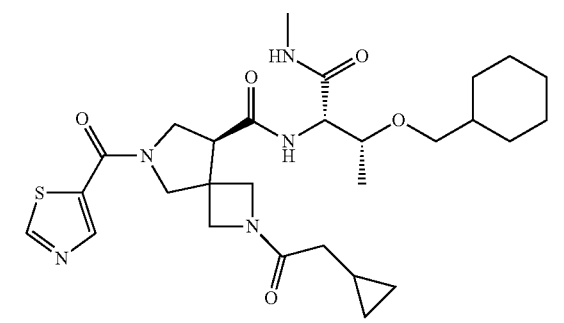
(A)
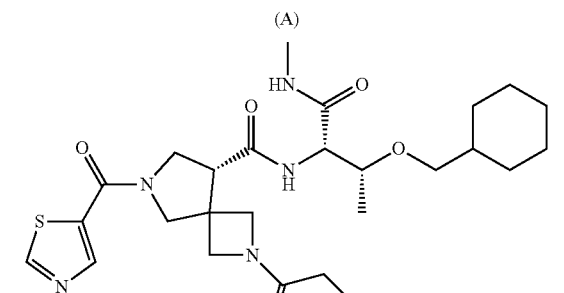
(B)

I-104
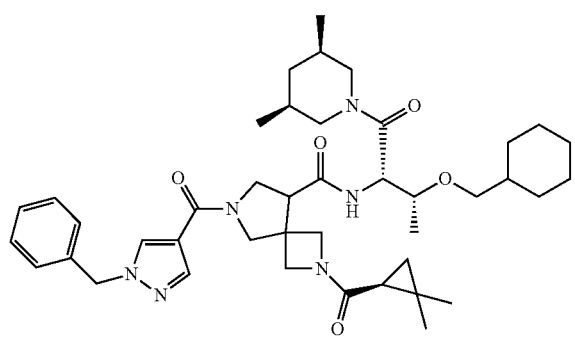
I-105
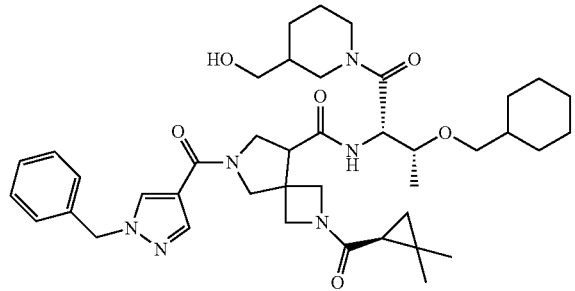
I-106
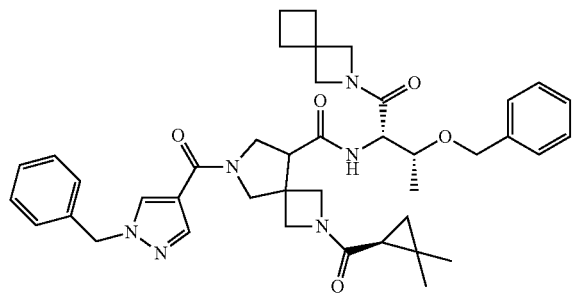
I-107
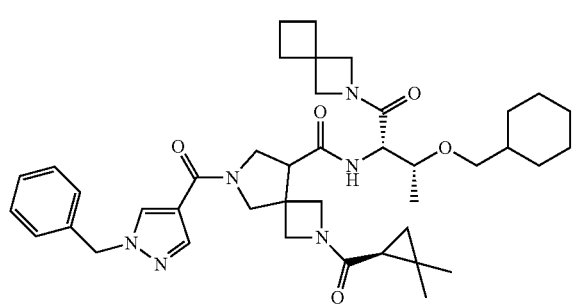
I-108
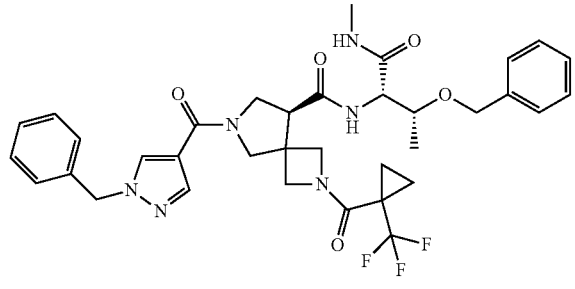
(A)
I-108
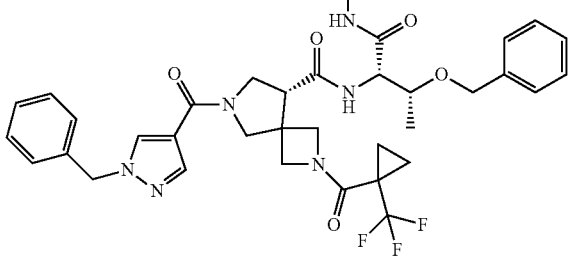
(B)
I-109
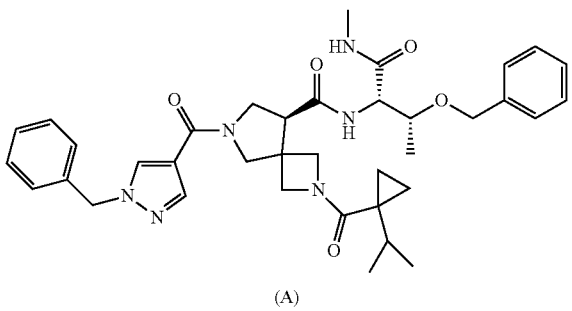
(A)
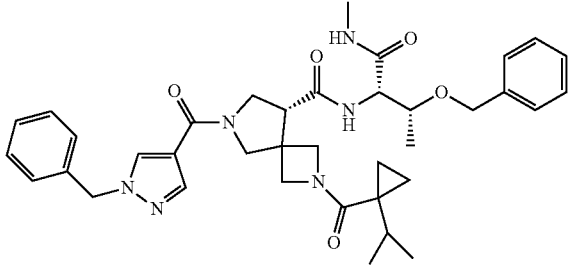
(B)
I-110
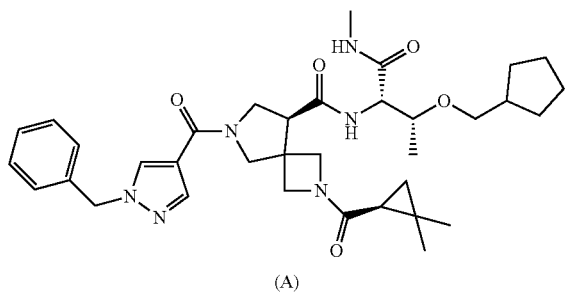
(A)
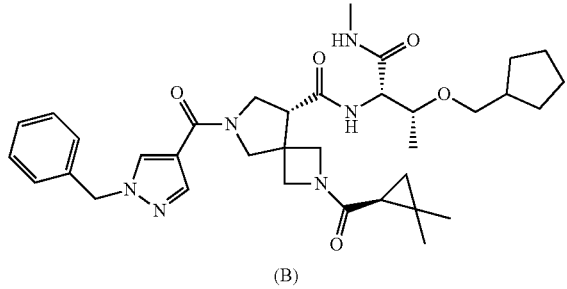
(B)

839
-continued
I-111
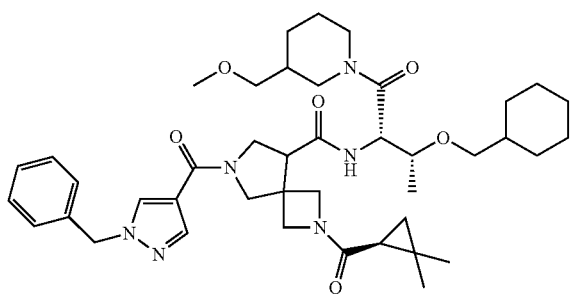
I-112
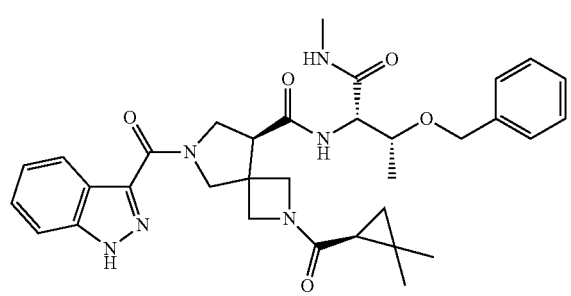
(A)
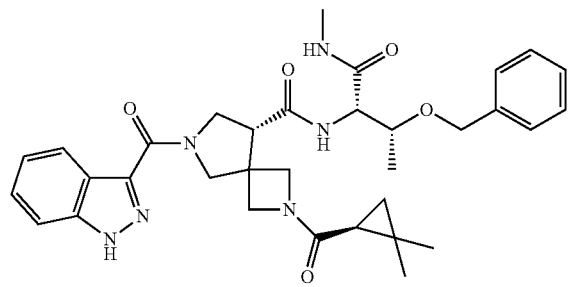
(B)
I-113
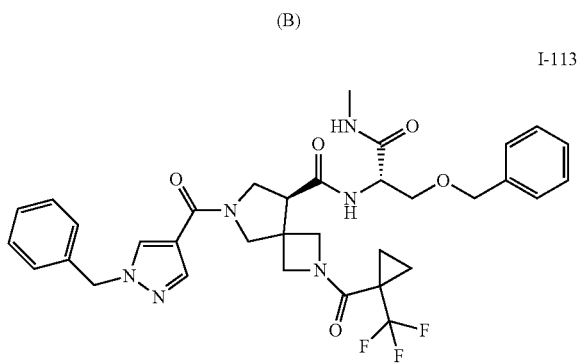
(A)
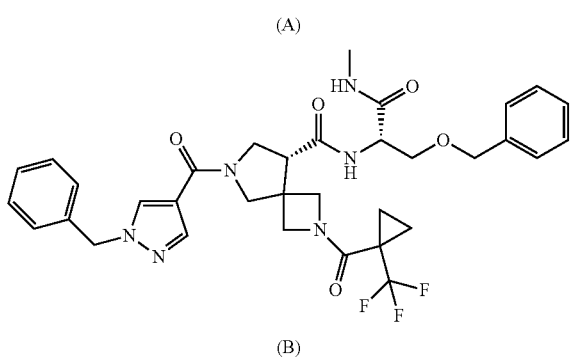
(B)
840
-continued
I-114
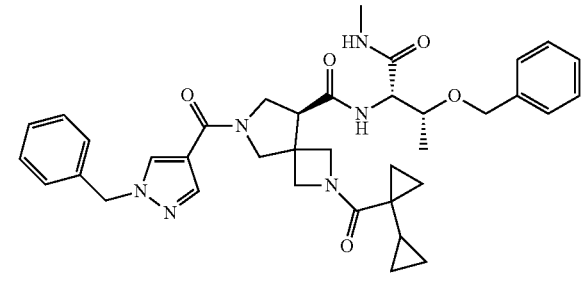
(A)
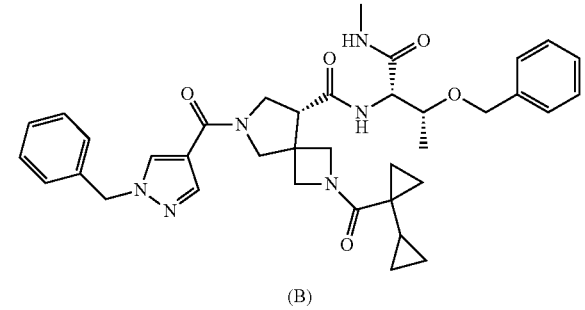
(B)
I-115
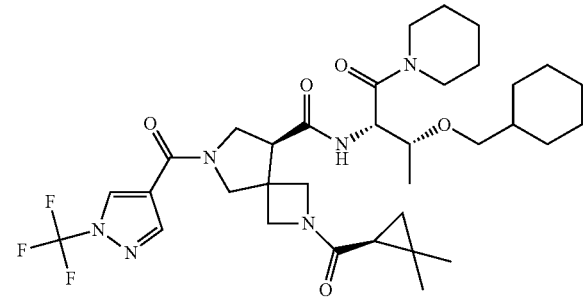
I-116
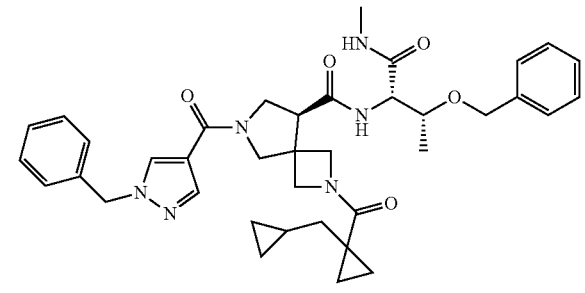
(A)
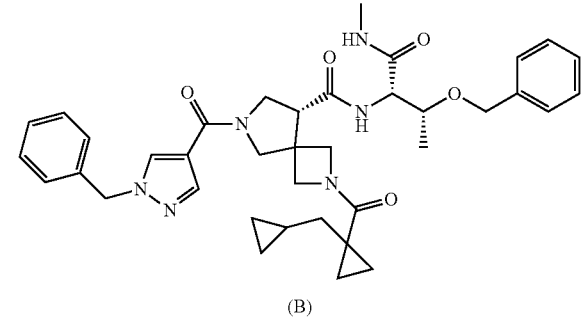
(B)

I-117
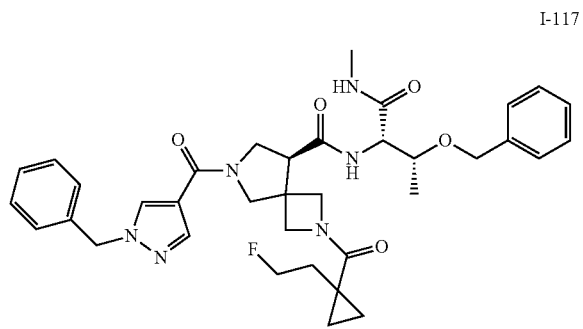
(A)
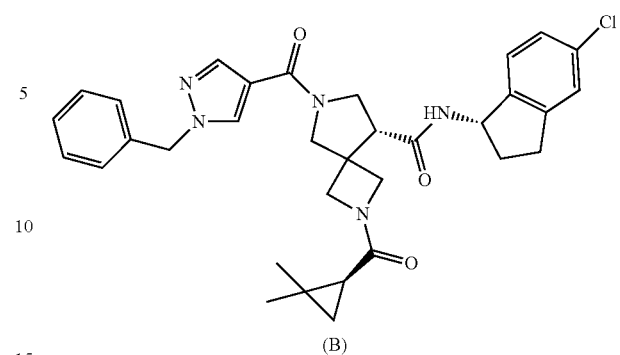
(B)
I-121
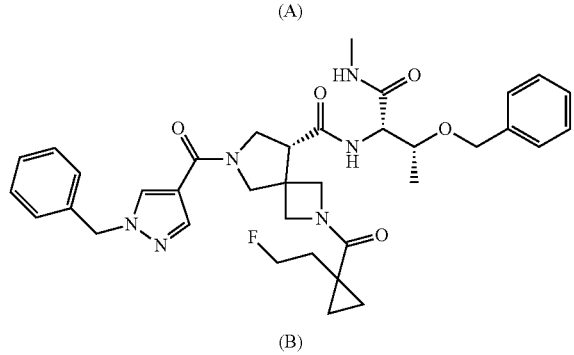
(B)
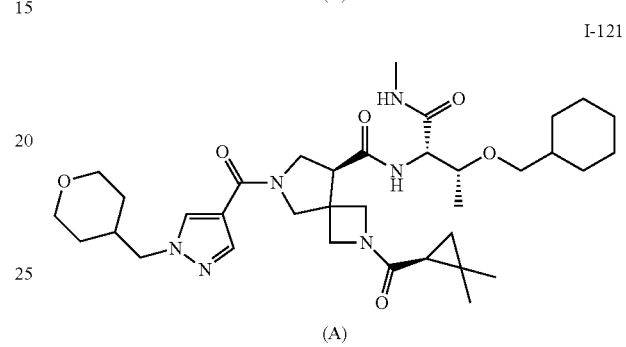
(A)
I-119
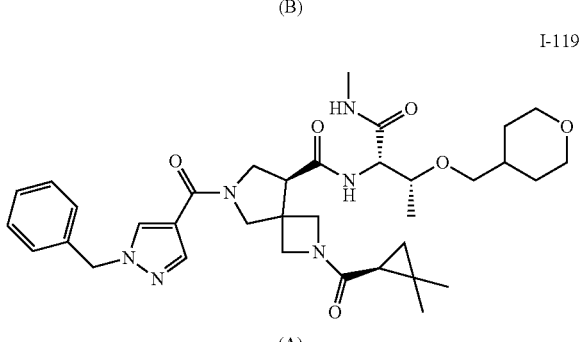
(A)
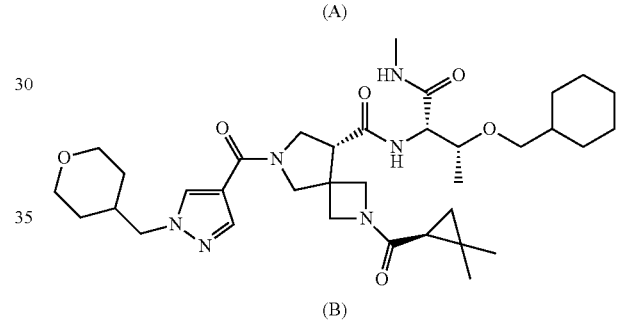
(B)
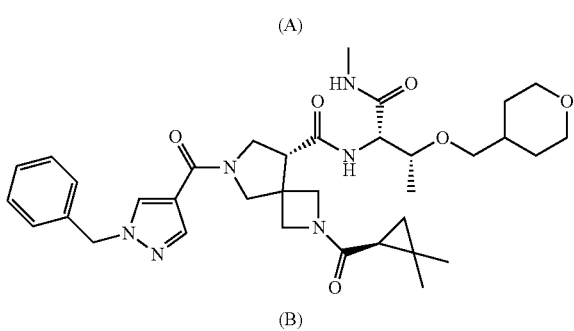
(B)
I-122
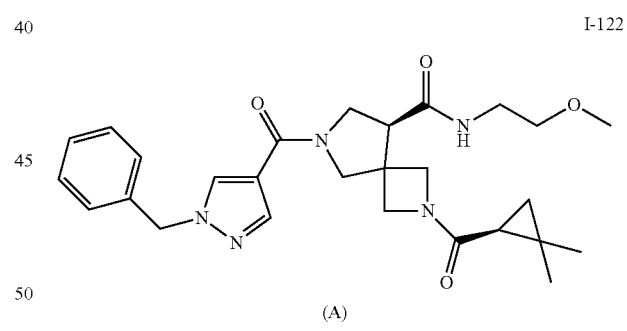
(A)
I-120
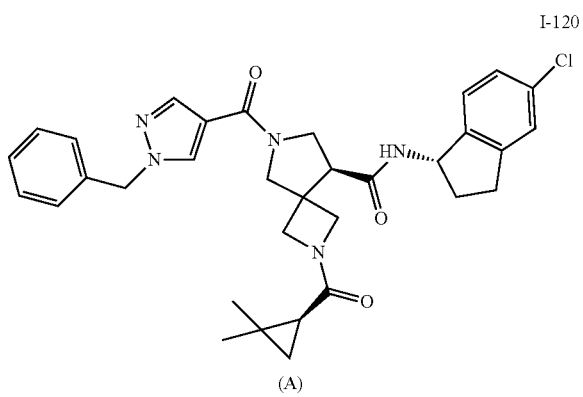
(A)
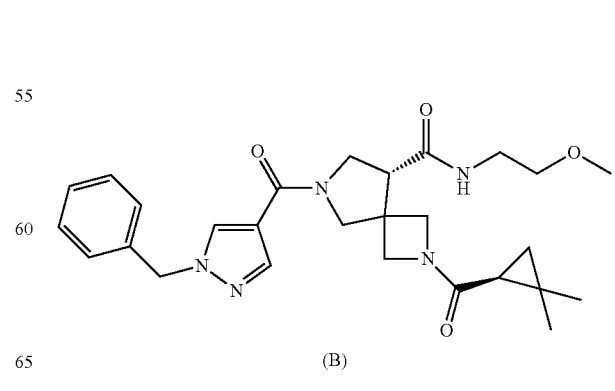
(B)

I-123
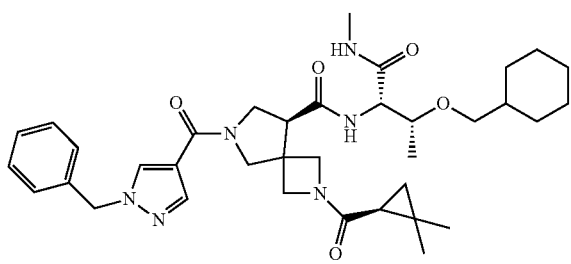
(A)
(B)
I-124
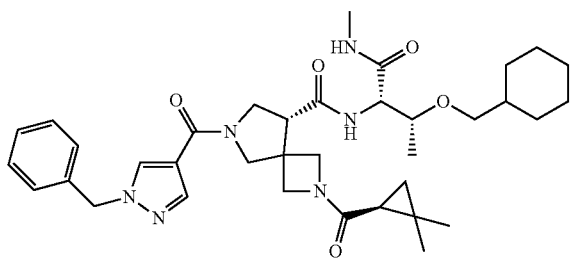
I-125
I-126
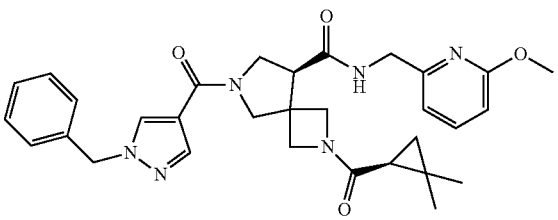
(A)
(B)
I-127
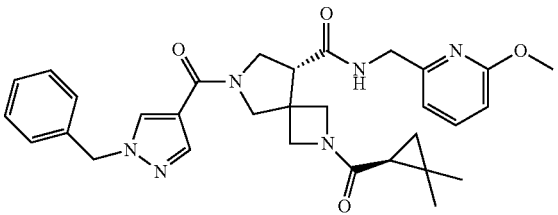
(A)
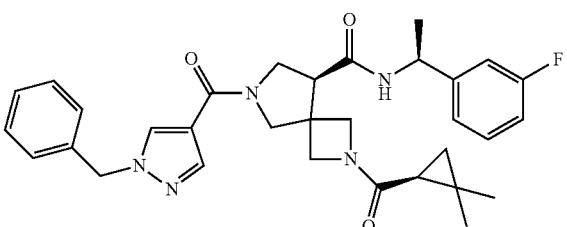
(B)
I-128
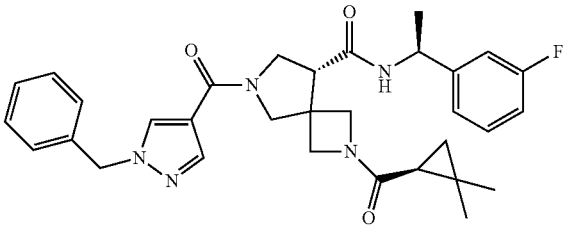
(A)
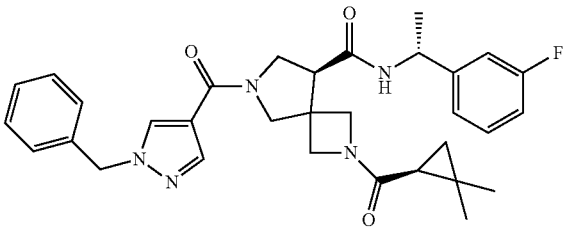
(A)
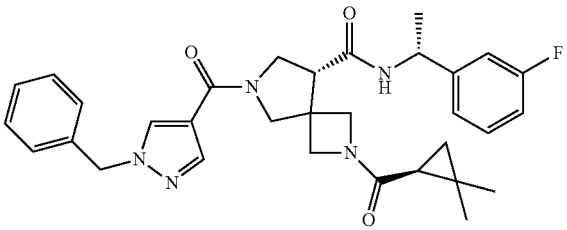
(B)

I-129
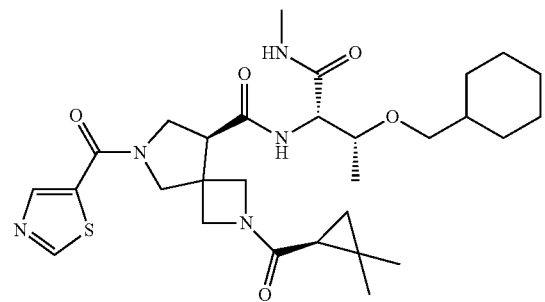
(A)
(B)
I-130
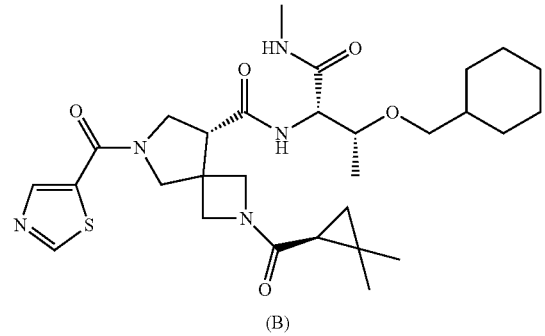
(A)
(B)
I-131
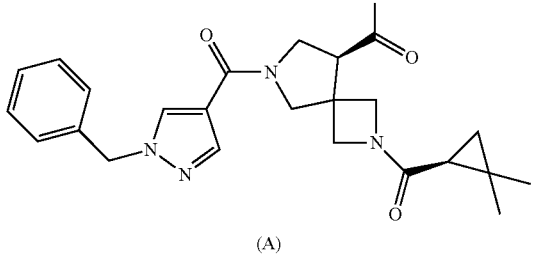
(A)
(B)
I-132
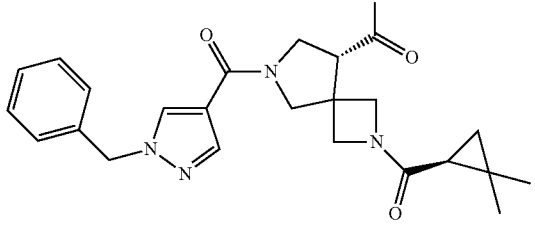
I-133
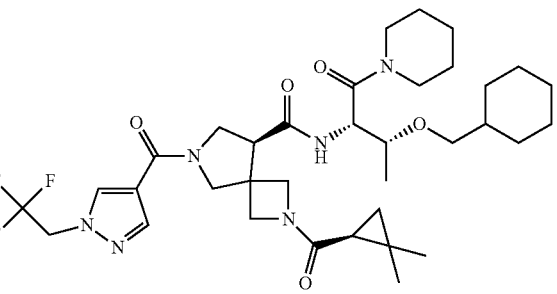
(A)
(B)

I-134
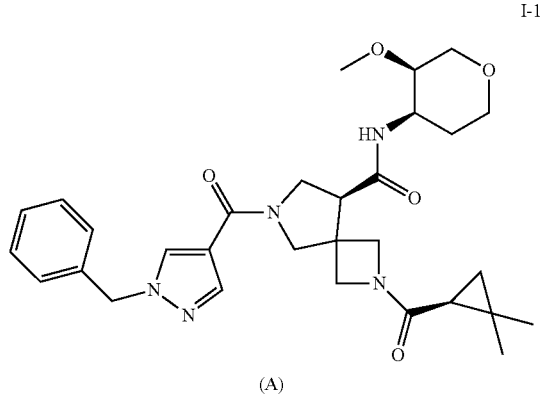
(A)
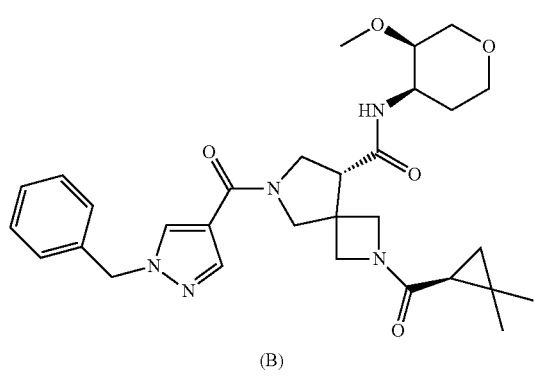
(B)
I-135
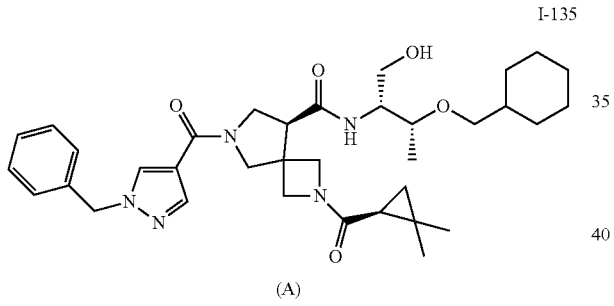
(A)
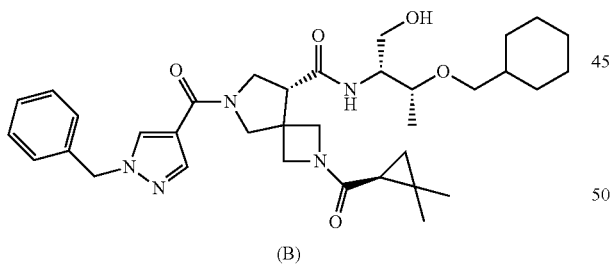
(B)
I-136
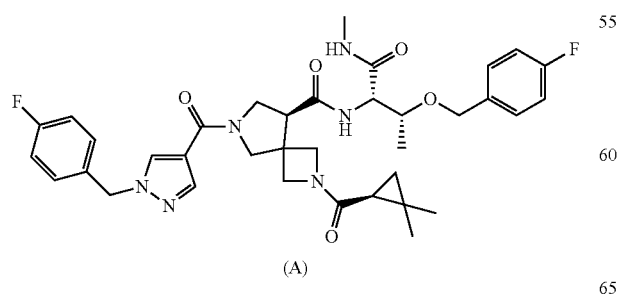
(A)
I-137
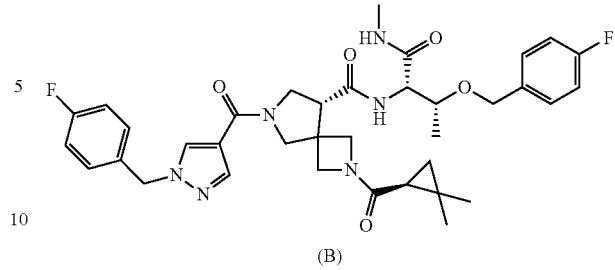
(B)
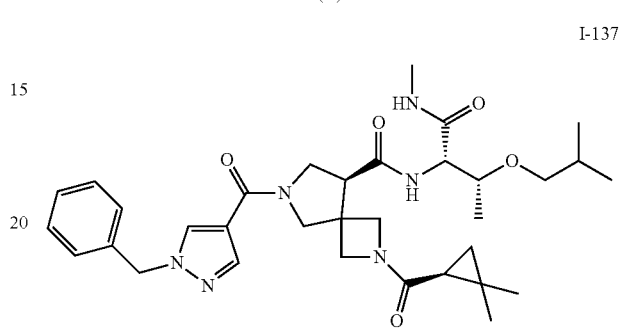
(A)
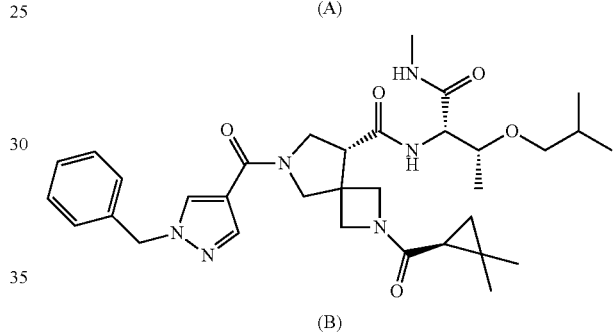
(B)
I-138
I-139
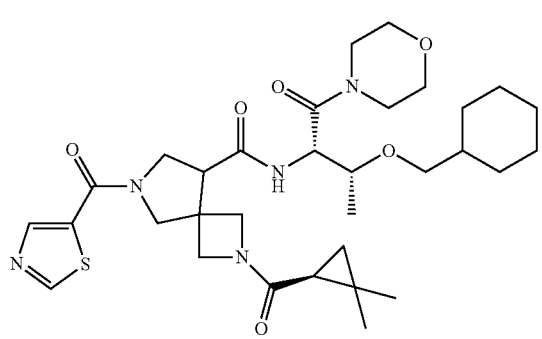

I-140
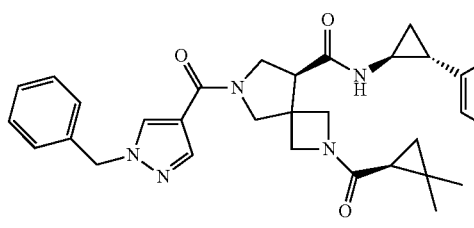
(A)
(B)
I-141
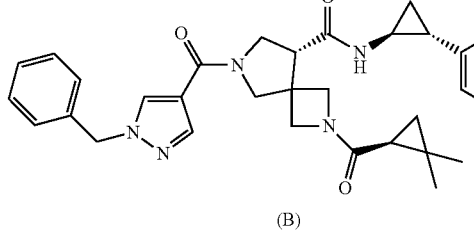
(A)
(B)
I-142
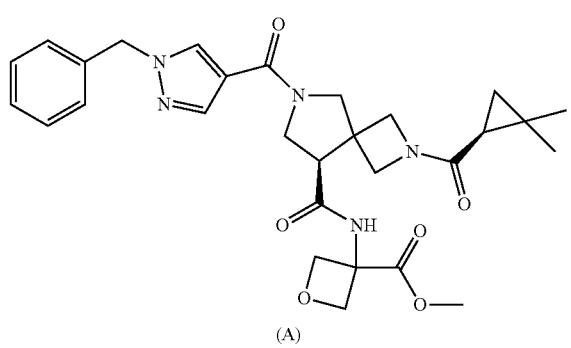
(A)
-continued
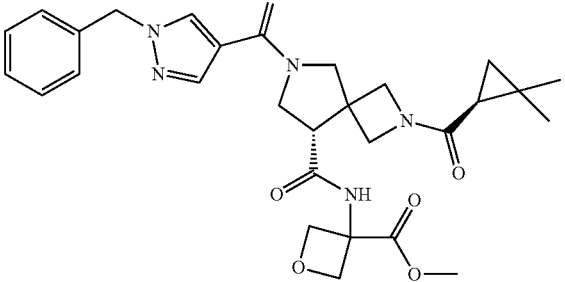
(B)
I-143
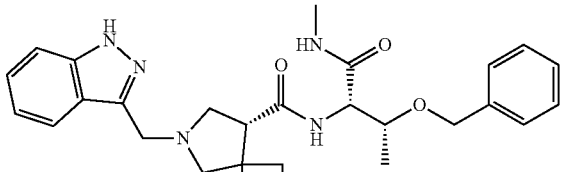
I-144
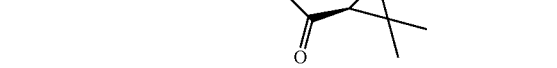
(A)
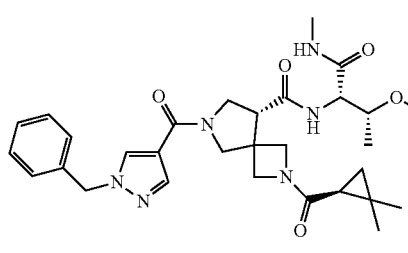
(B)
I-145
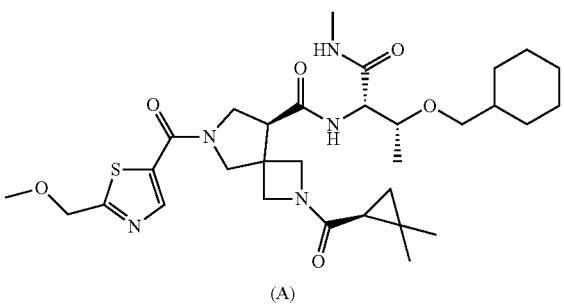
(A)

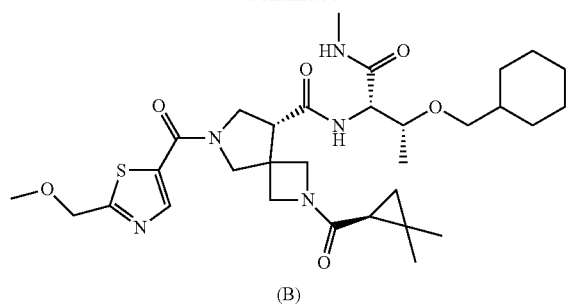
(B)
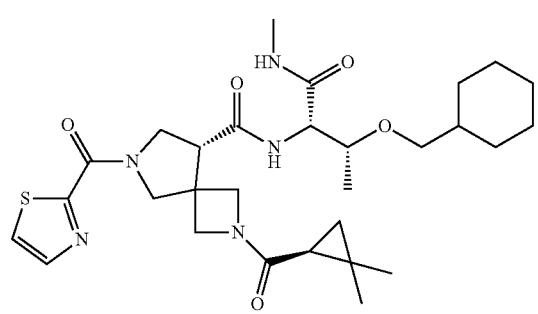
I-147
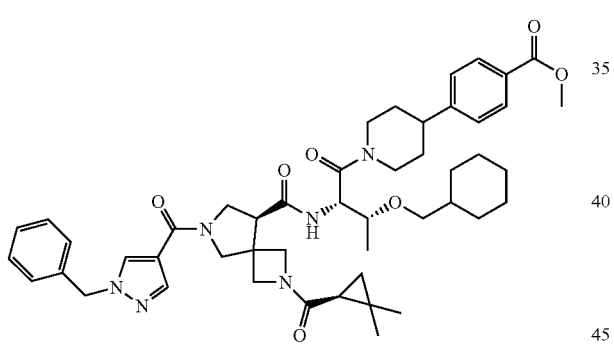
I-148
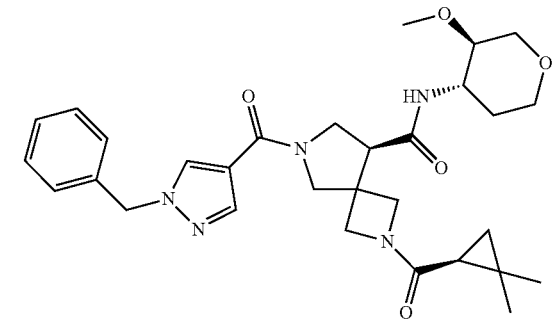
(A)
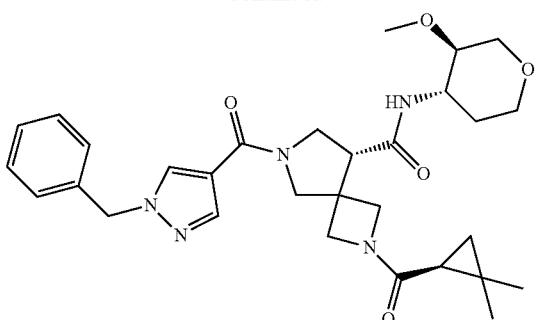
(B)
I-146
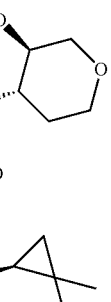
I-149
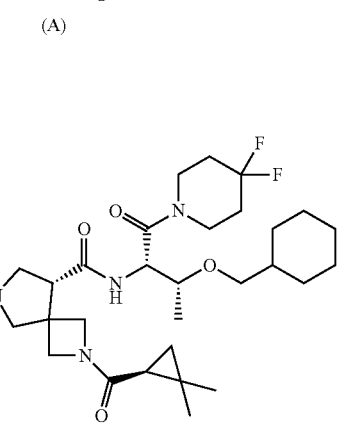
Mixture
(A)
(B)

I-150
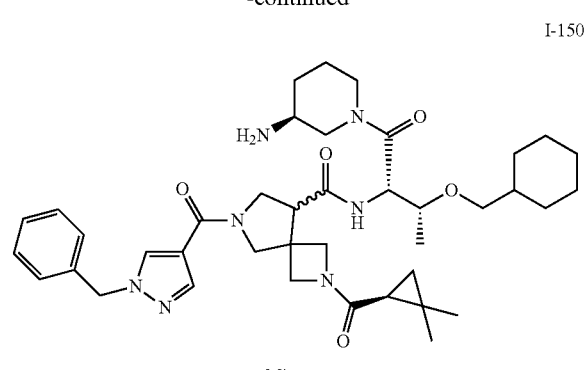
Mixture
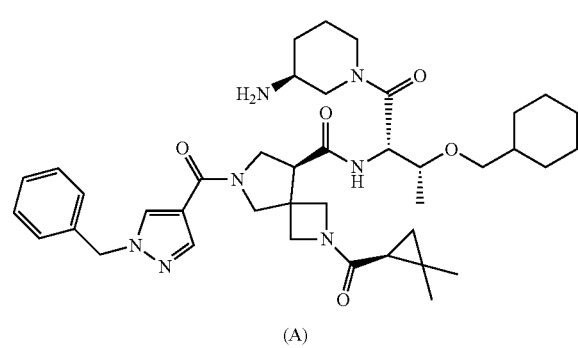
(A)
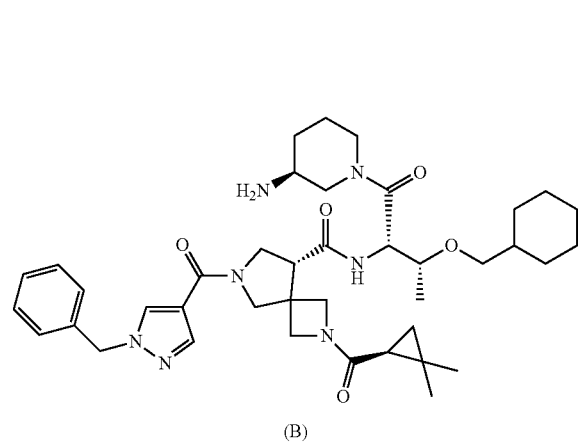
(B)
I-151
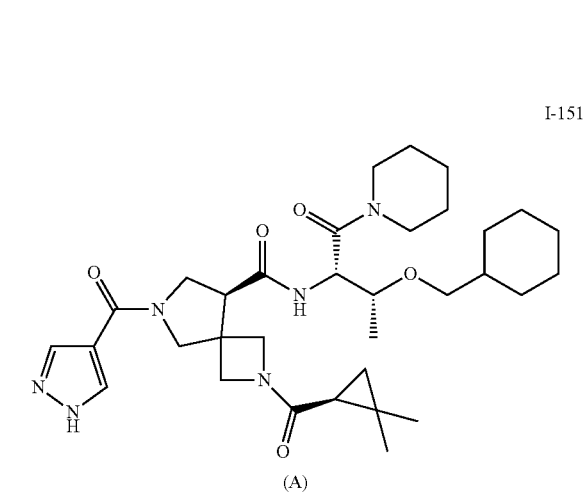
(A)
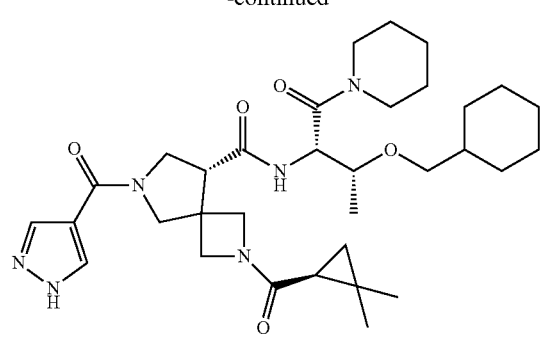
(B)
I-152
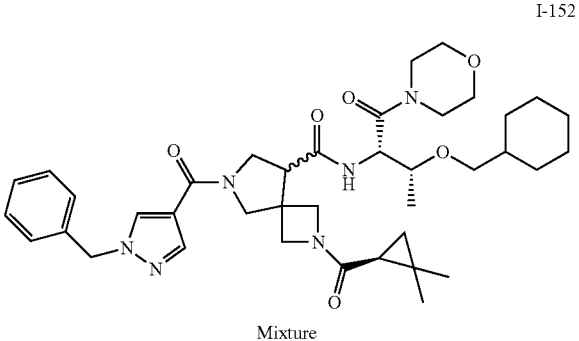
Mixture
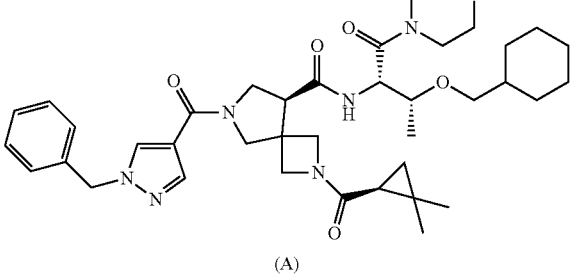
(A)
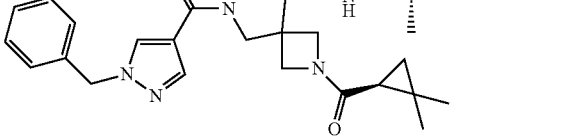
(B)
I-153
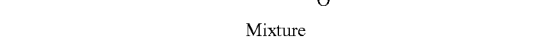
Mixture

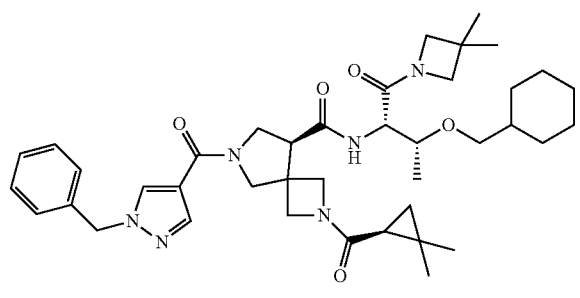
(A)
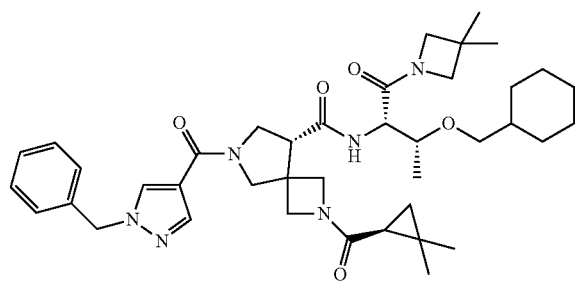
(B)
I-154
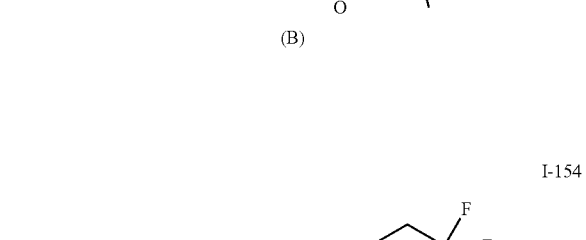
(A)
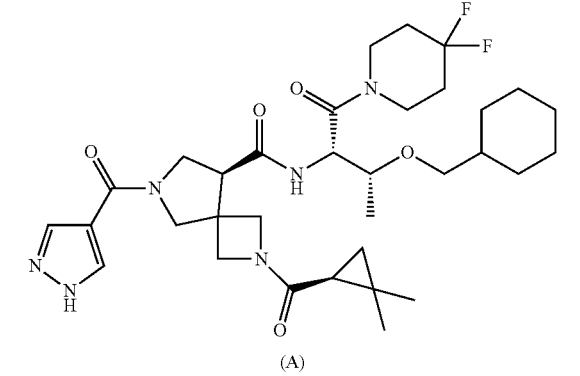
(B)
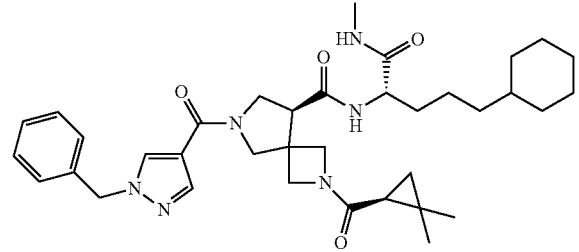
(A)
I-155
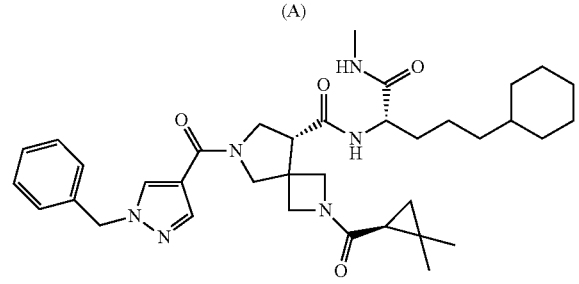
(B)
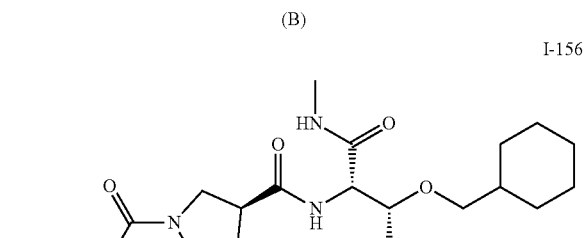
(A)
I-156
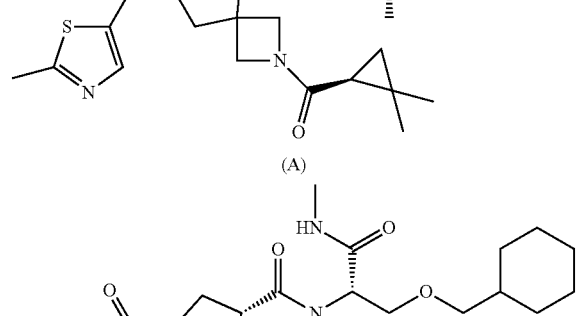
(B)
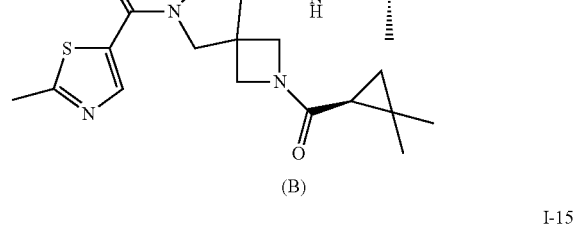
(A)
I-157
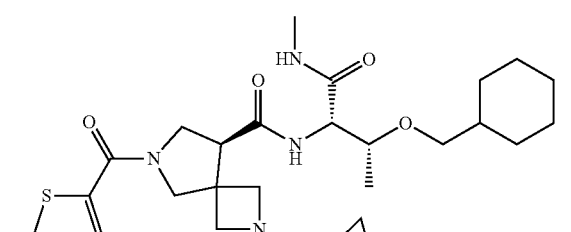
(A)

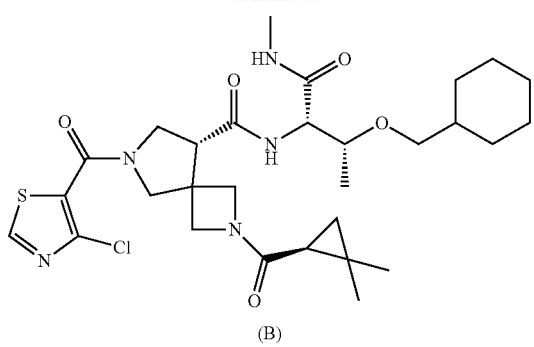
I-158
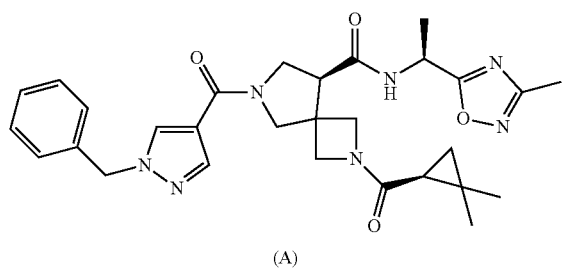
I-159
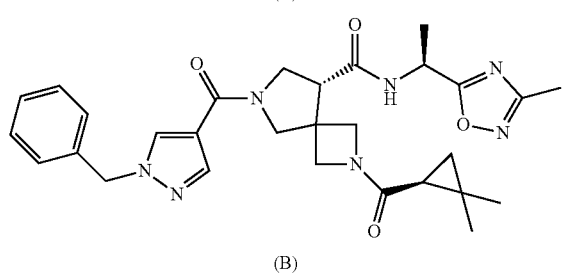
I-160
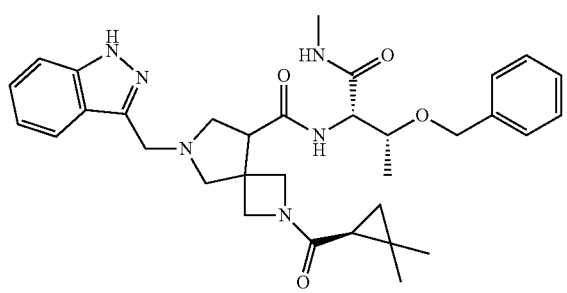
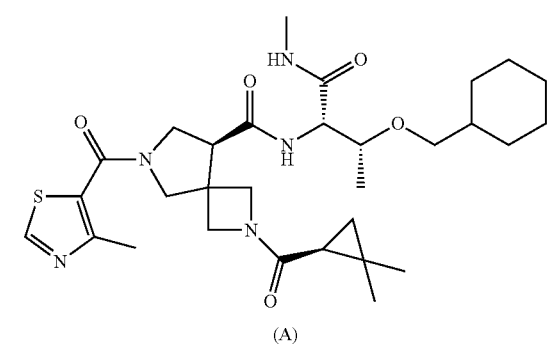
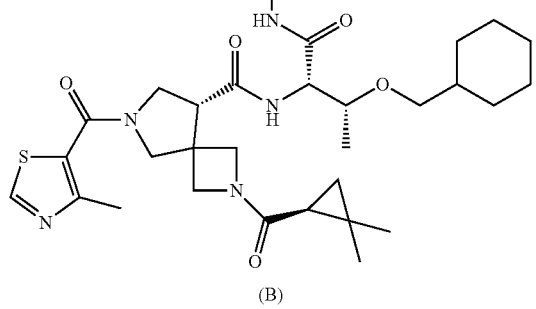
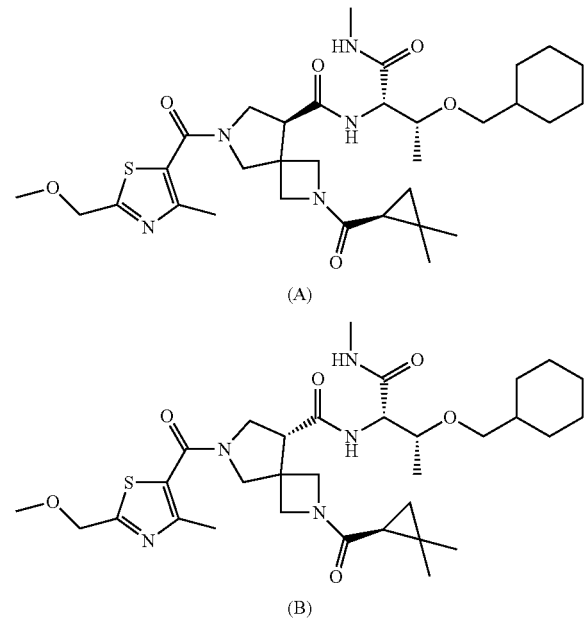
I-161
I-162

I-163
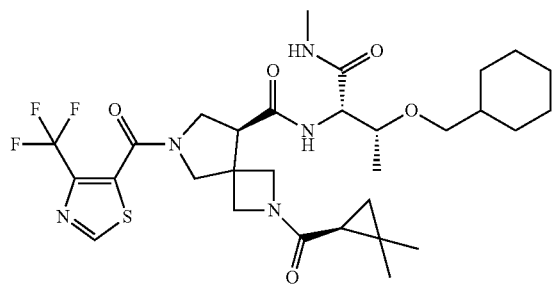
(A)
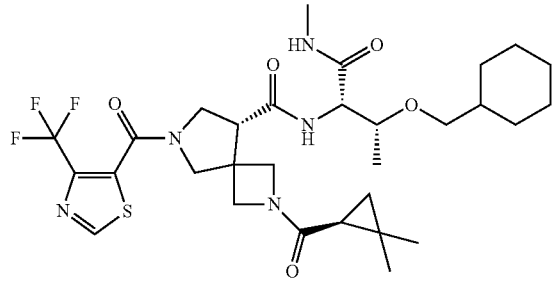
(B)
I-164
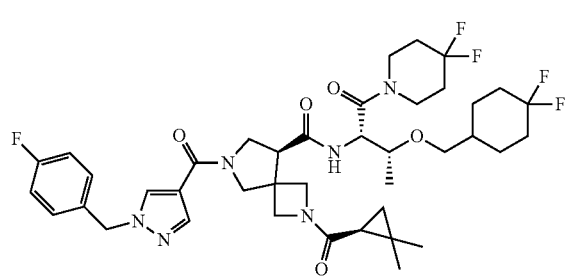
(A)
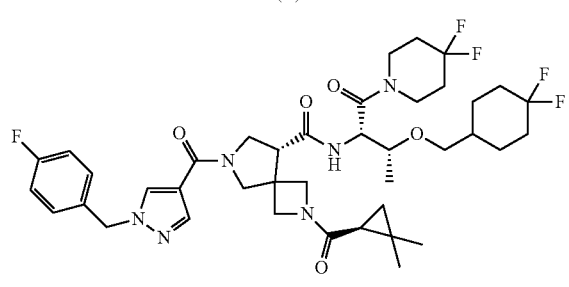
(B)
I-165
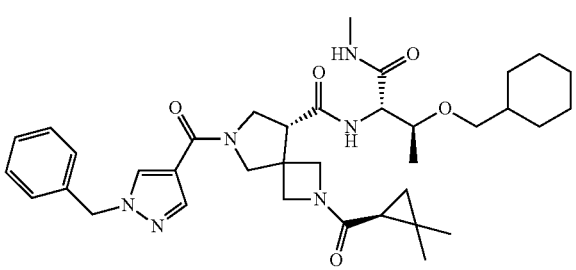
I-166
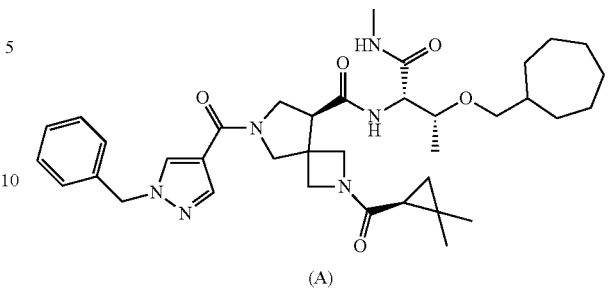
(A)
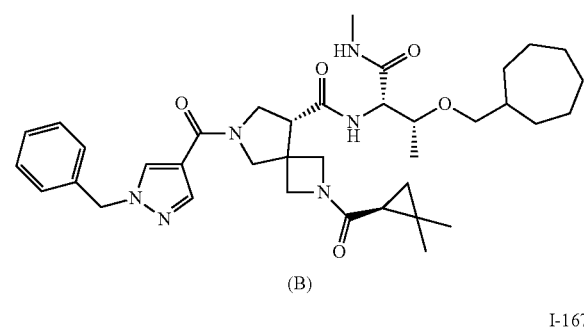
(B)
I-167
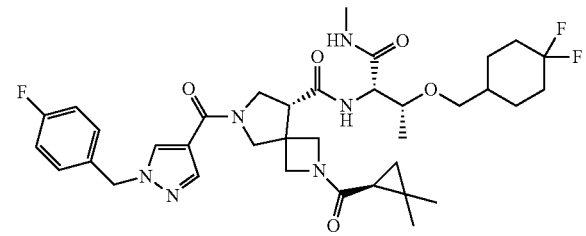
I-168
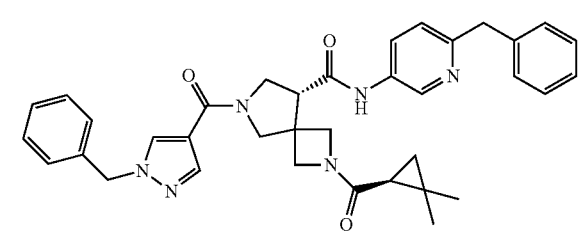
I-169
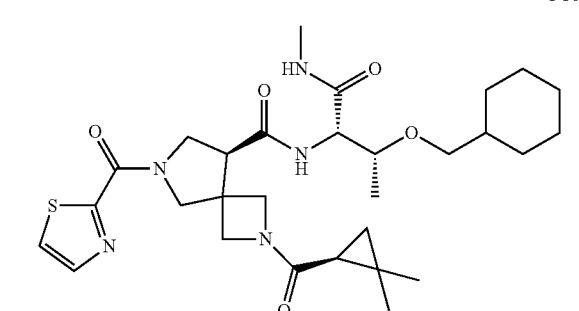

861
-continued
I-170
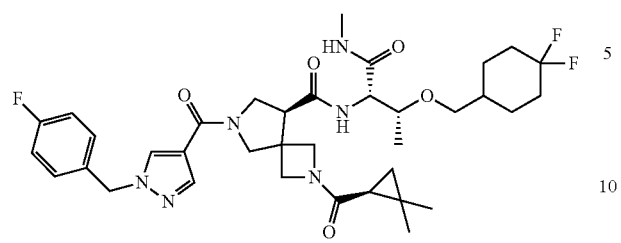
I-171
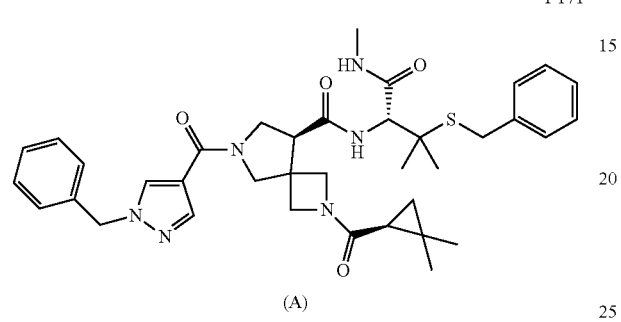
(A)
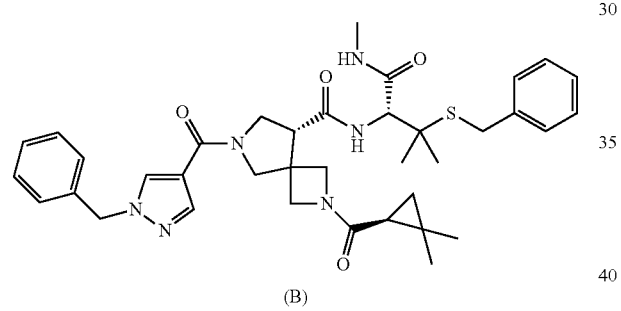
(B)
I-172
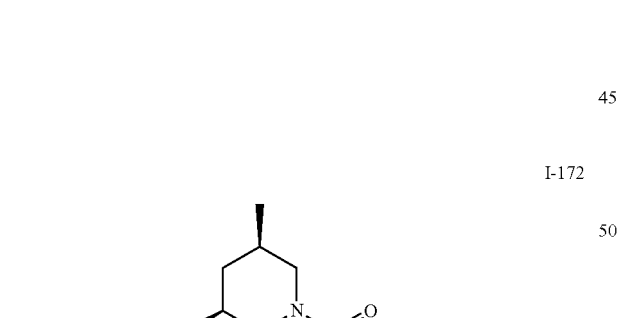
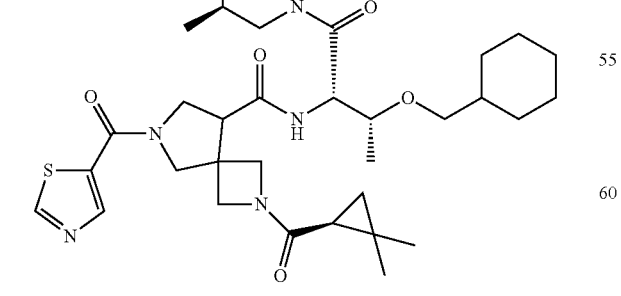
862
-continued
I-173
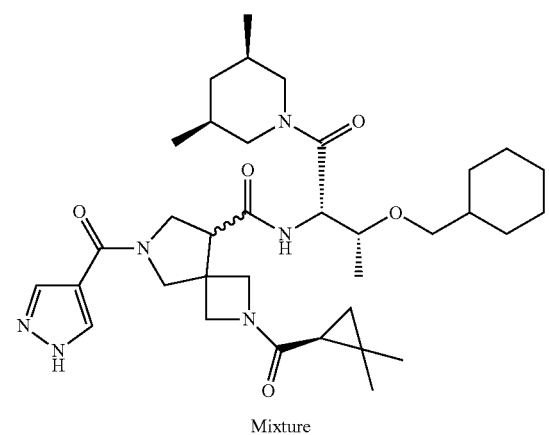
Mixture
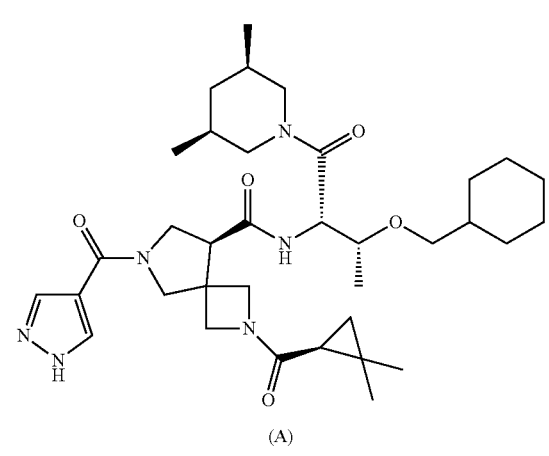
(A)
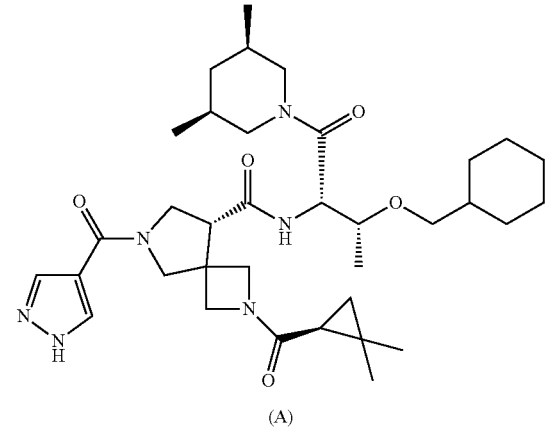
(A)
I-174
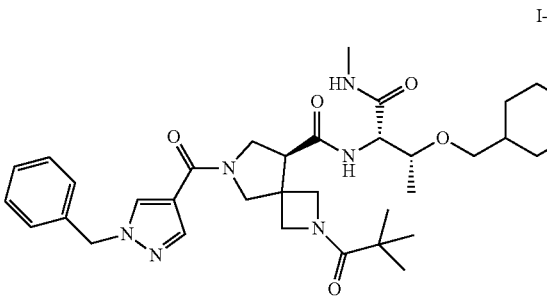
(A)

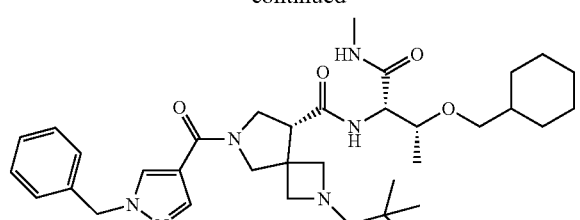
(B)
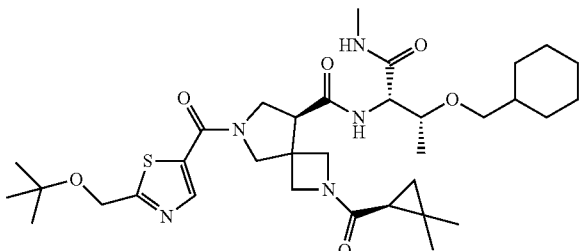
I-175
(A)
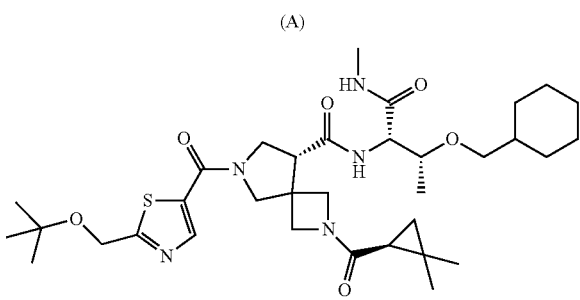
(B)
I-176
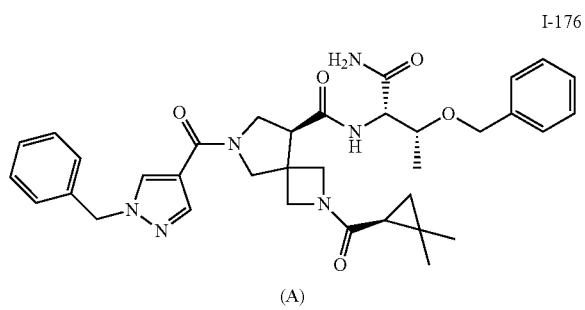
(A)
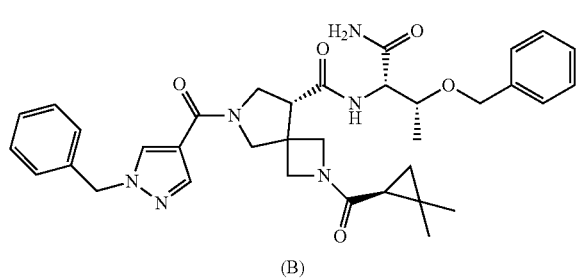
(B)
I-177
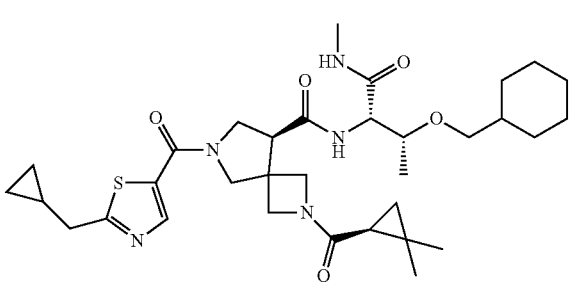
(A)
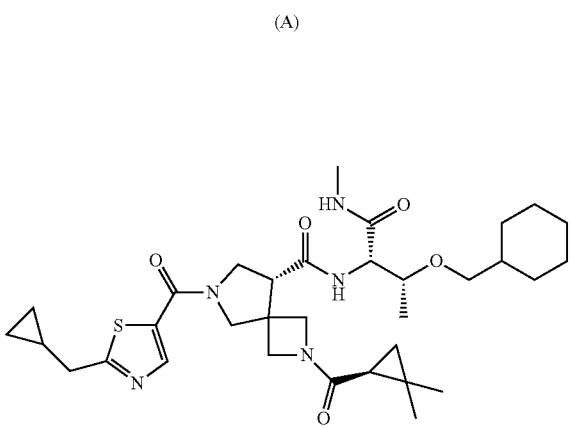
(B)
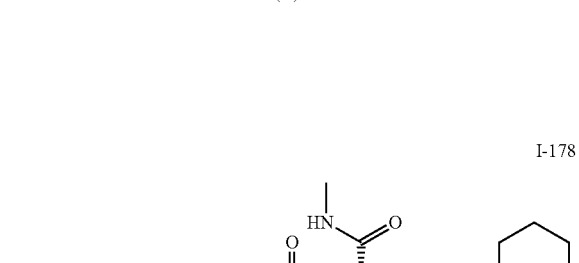
I-178
(A)
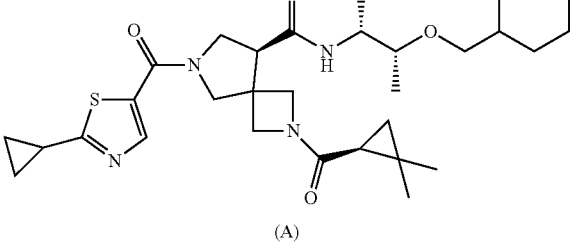
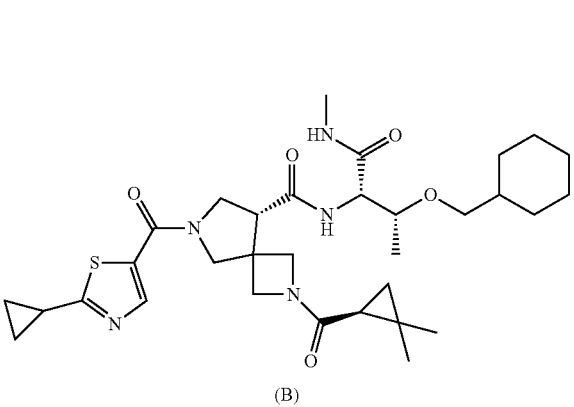
(B)

865
-continued
I-179
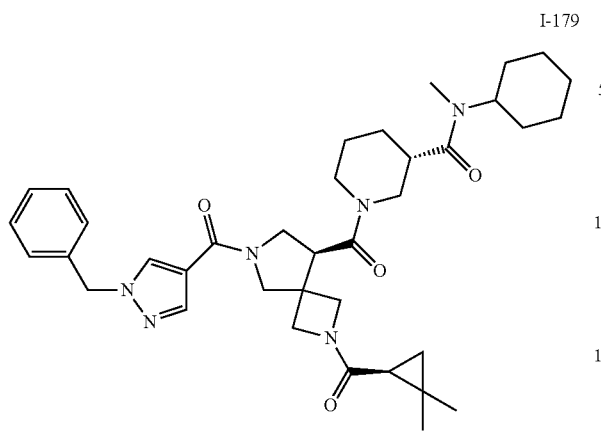
I-180
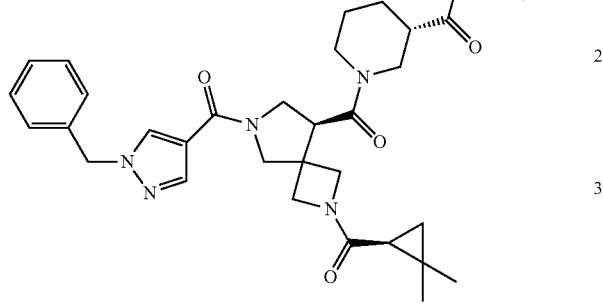
I-181
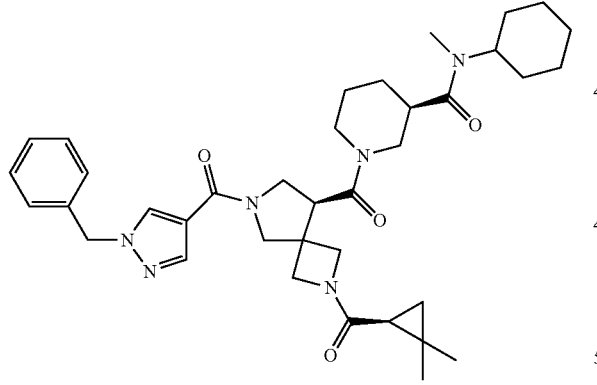
I-182
866
-continued
I-183
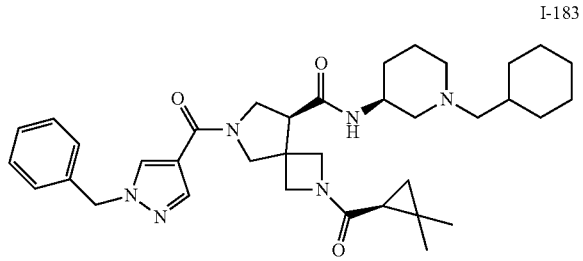
I-184
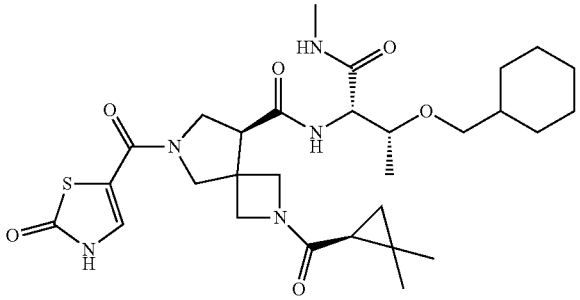
I-185
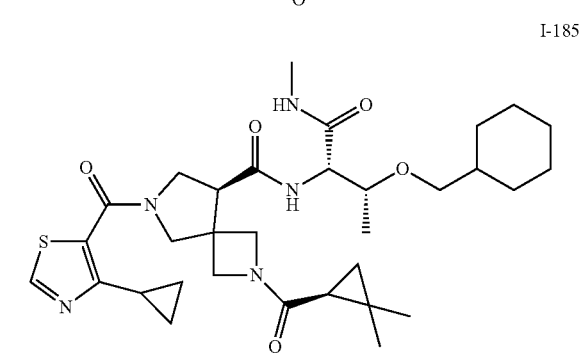
(A)
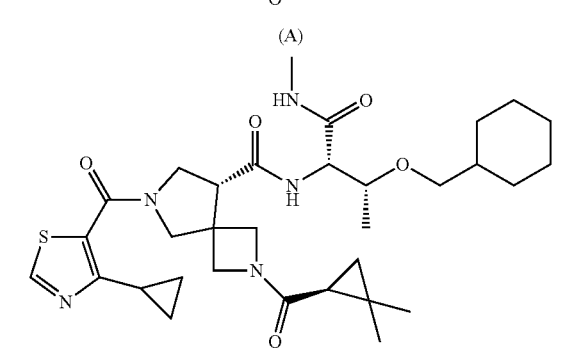
(B)
I-186
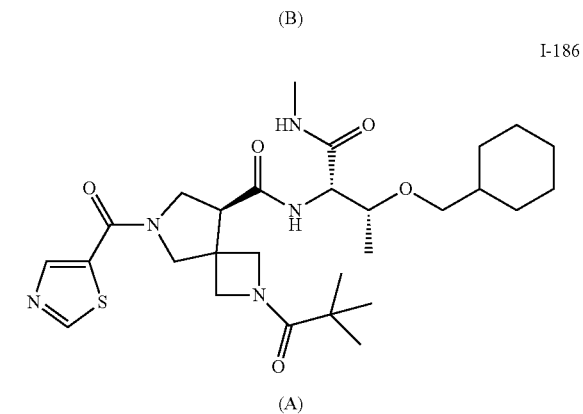
(A)

-continued
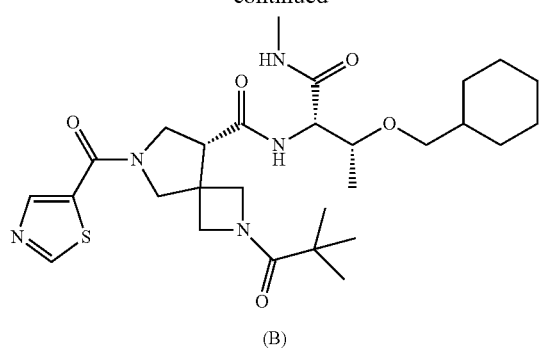
(B)
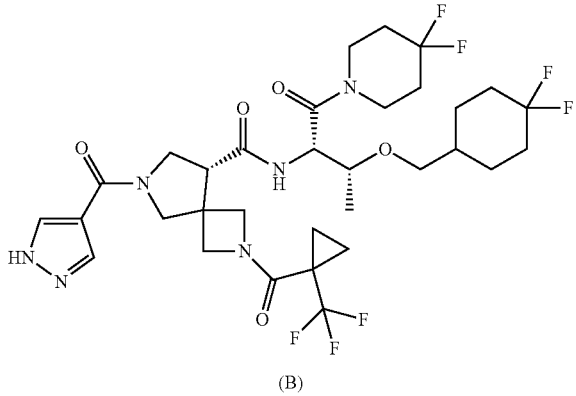
(B)
I-187
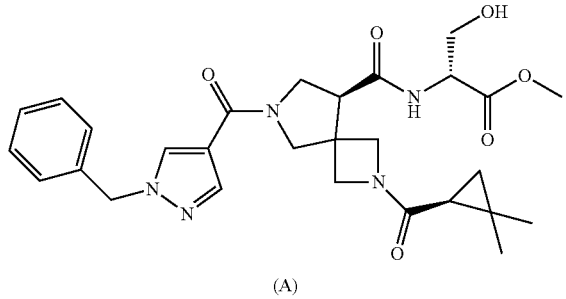
(A)
I-189
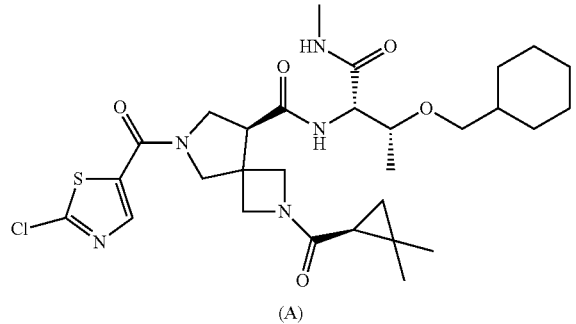
(A)
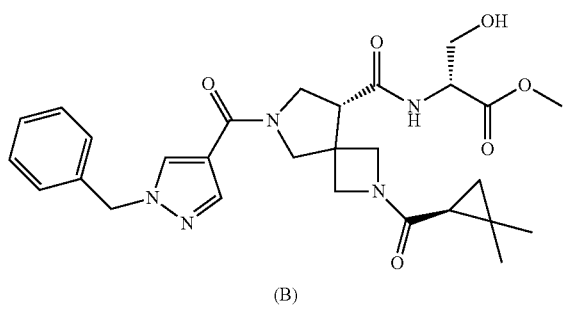
(B)
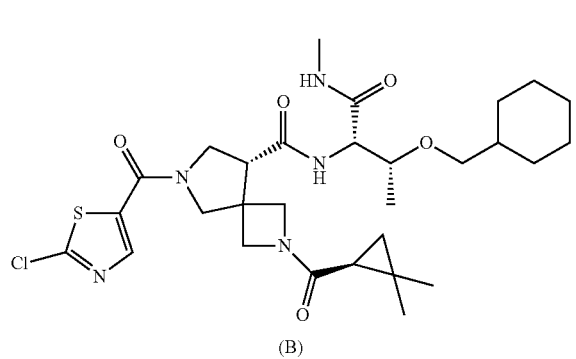
(B)
I-188
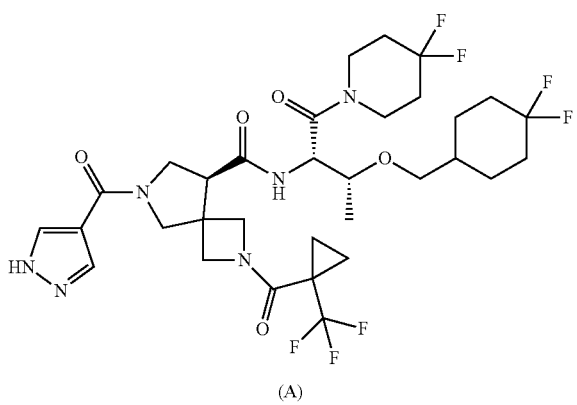
(A)
I-190
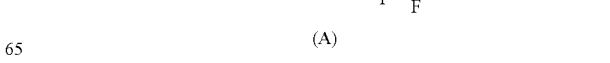
(A)

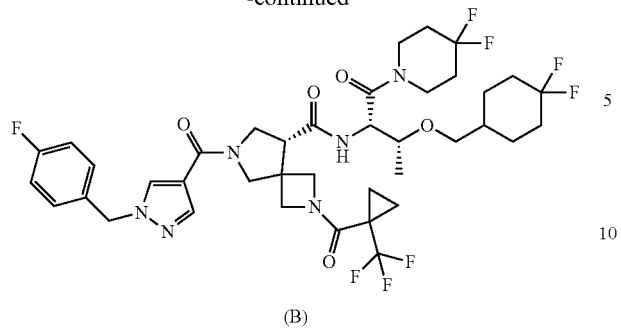
I-191
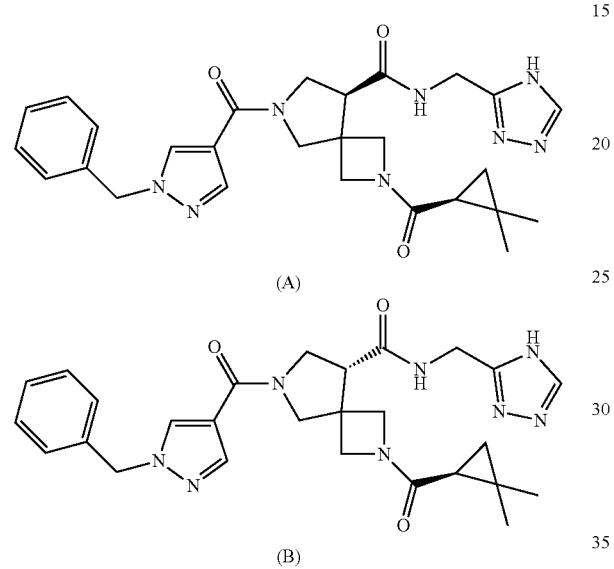
I-192
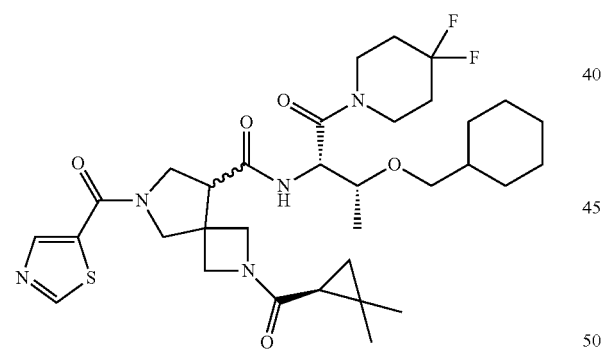
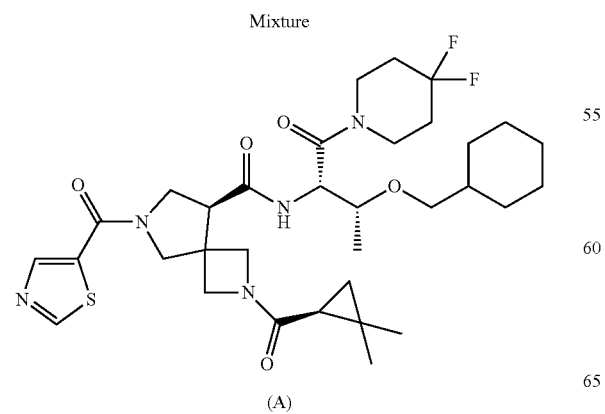
(A)
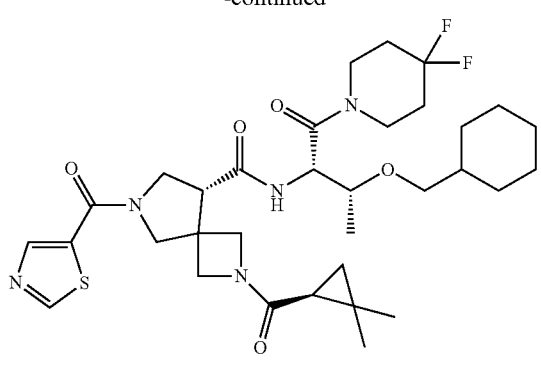
I-193
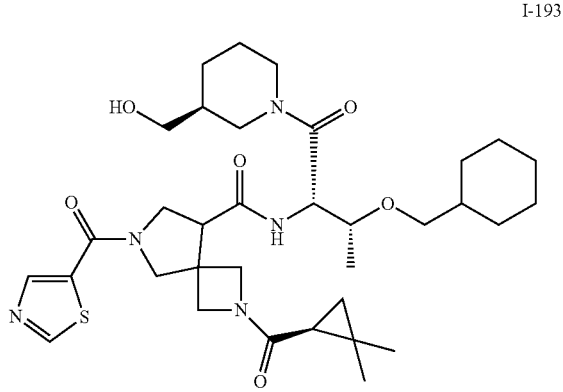
I-194
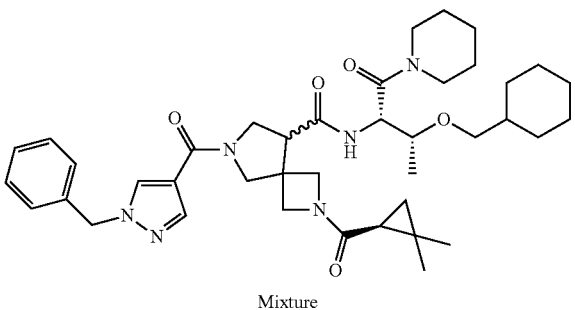
Mixture
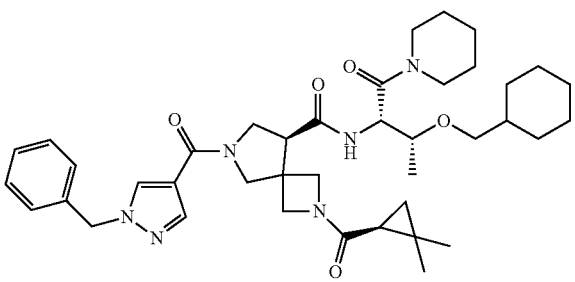
(A)

-continued
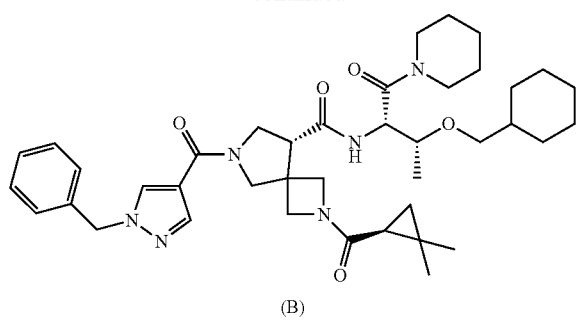
(B)
I-195
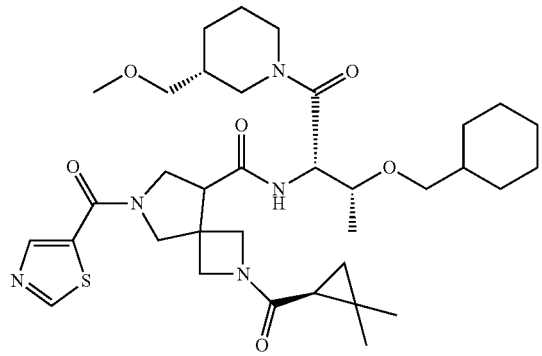
I-196
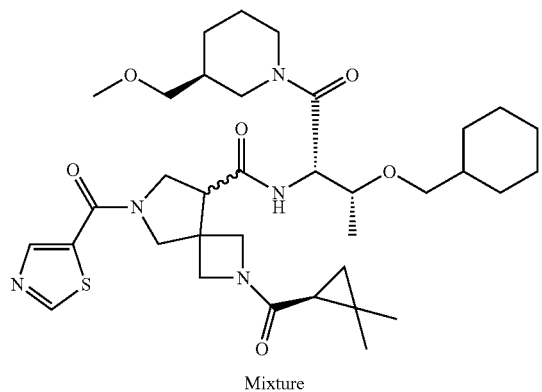
Mixture
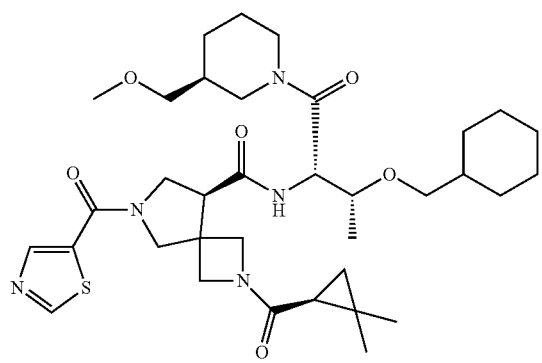
(A)
-continued
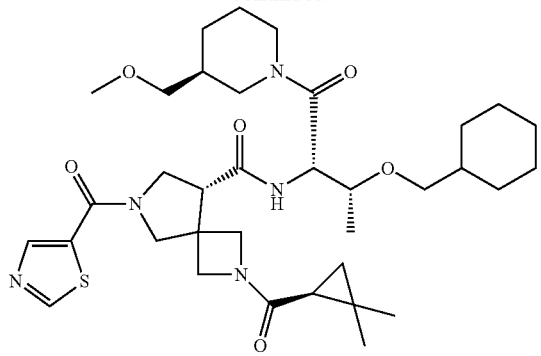
(B)
I-197
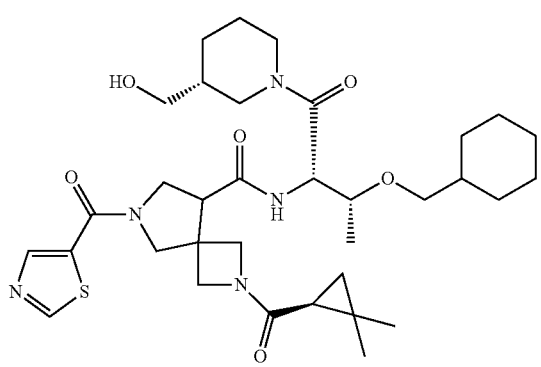
I-198
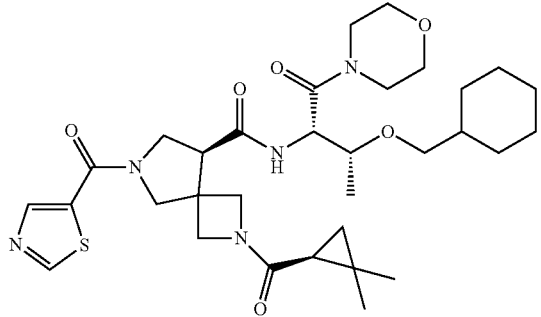
I-199
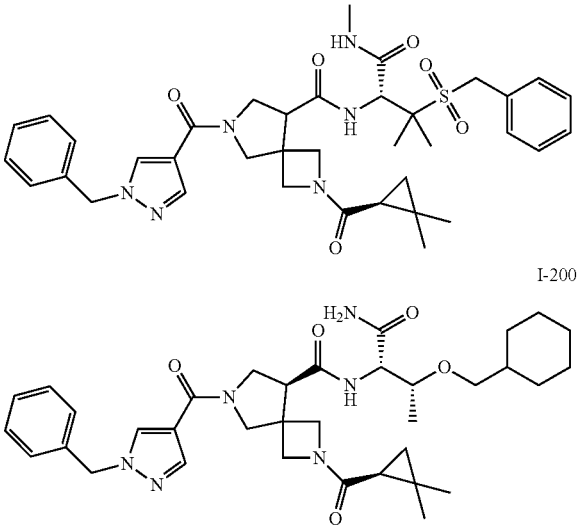
I-200

I-201
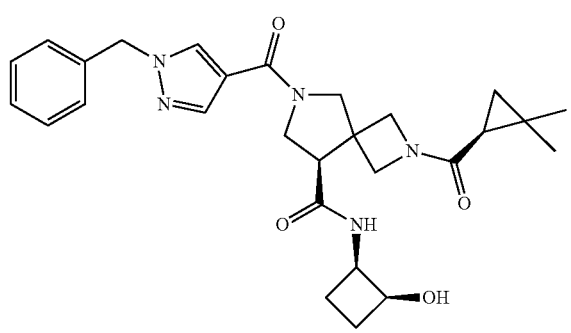
(A)
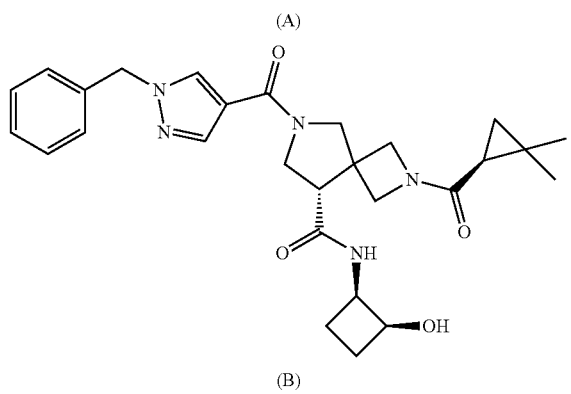
(B)
I-202
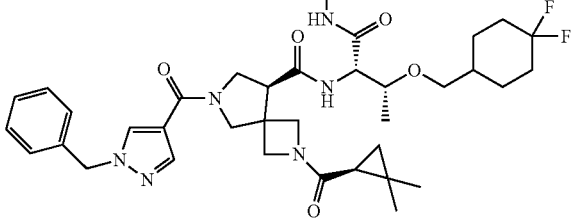
I-203
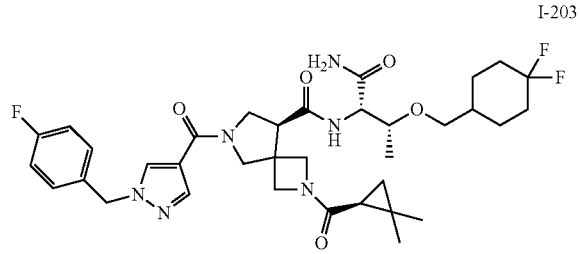
I-204
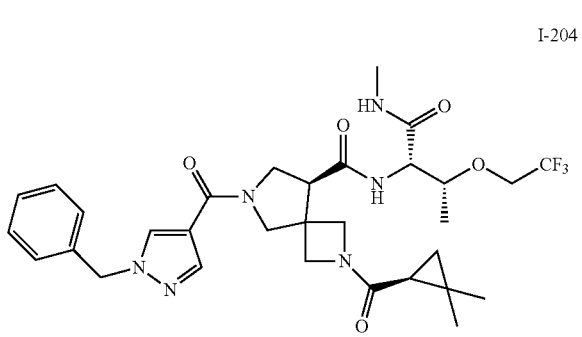
I-205
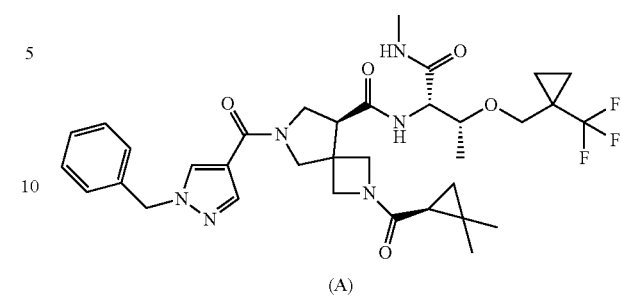
(A)
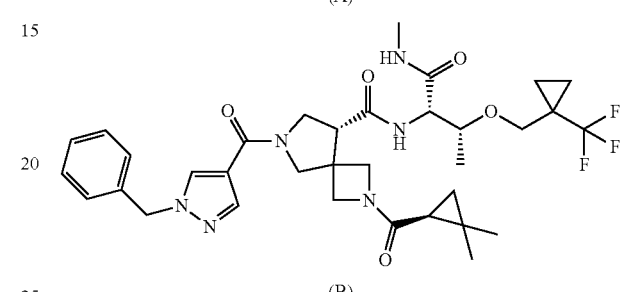
(B)
I-206
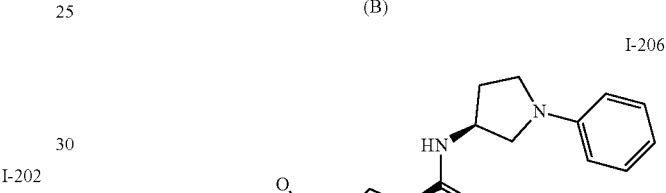
I-207
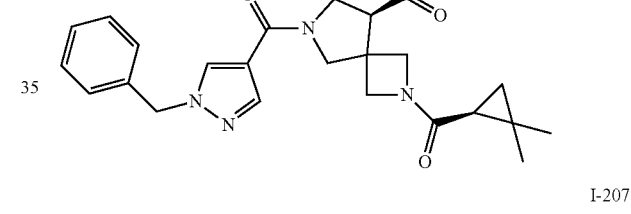
I-208
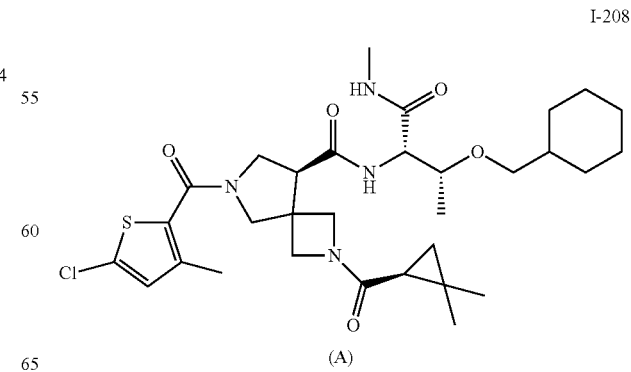
(A)

875
-continued
(B)
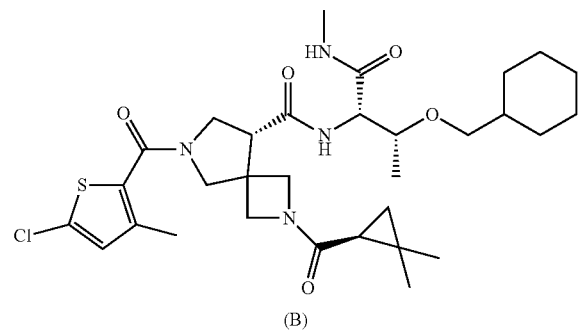
I-209
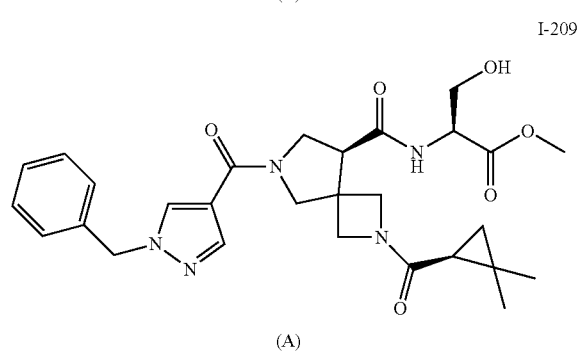
(A)
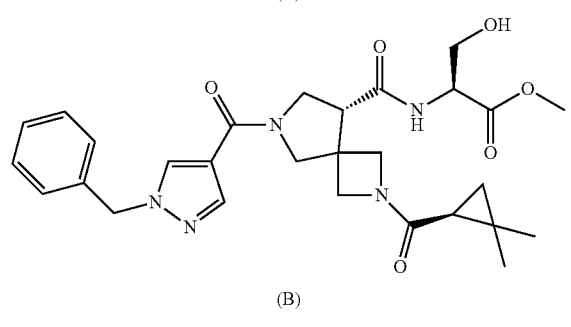
(B)
I-210
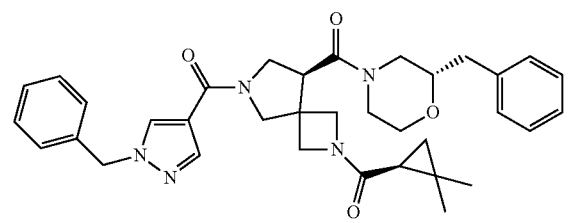
I-211
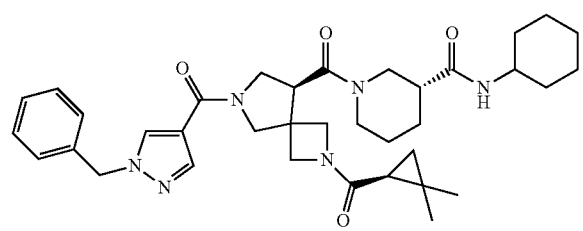
876
-continued
I-212
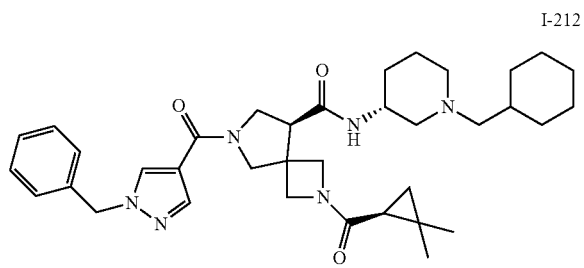
I-213
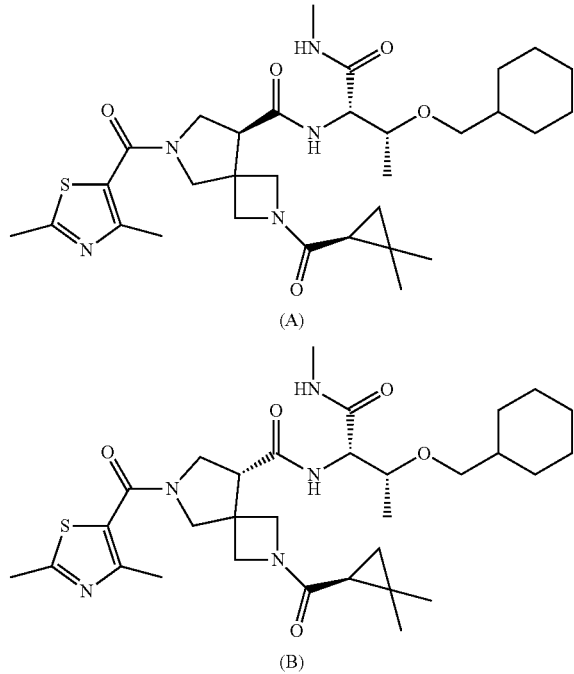
(A)
(B)
I-214
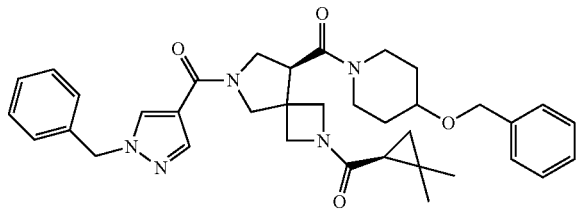
I-215
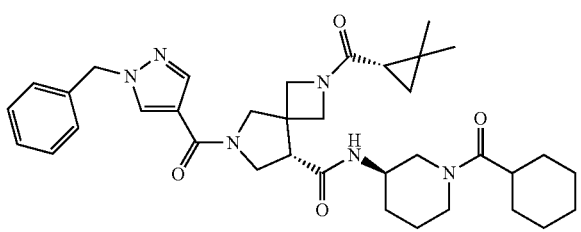

-continued
I-216
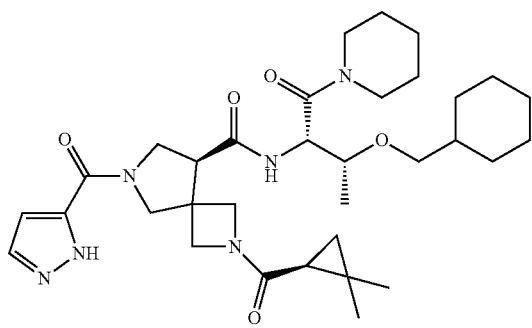
I-217
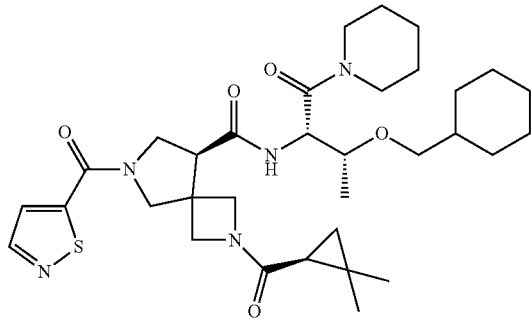
I-218
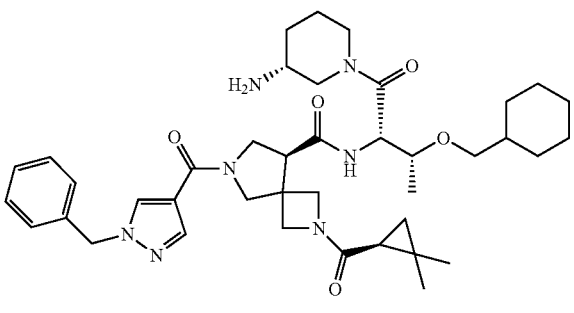
I-219
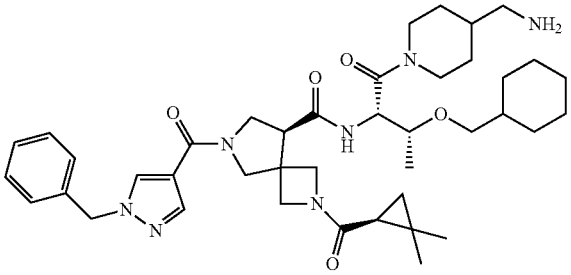
I-220
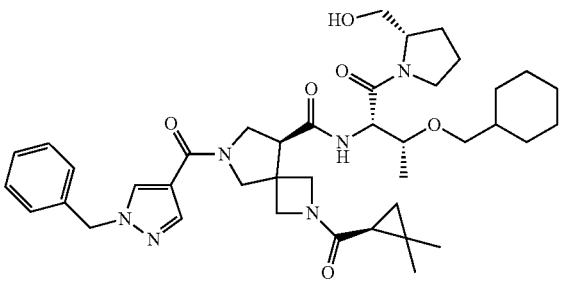
-continued
I-221
I-222
I-223
I-224
(A)
(B)

I-225
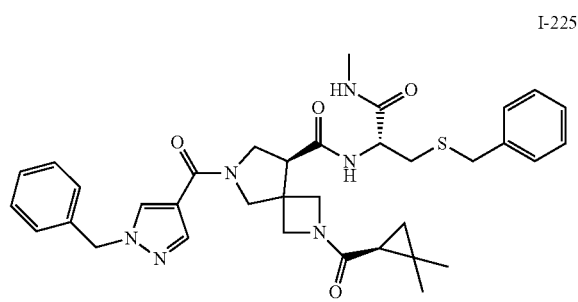
I-226
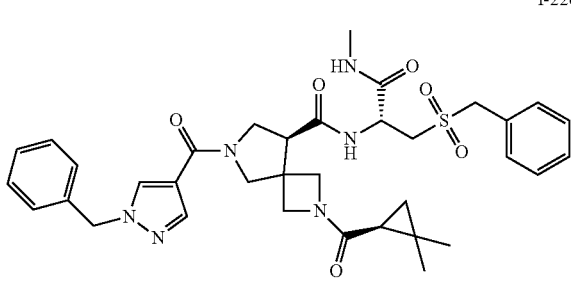
I-227
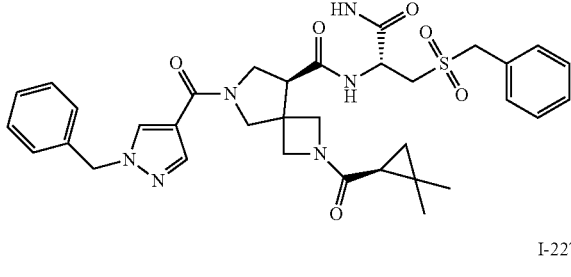
(A)
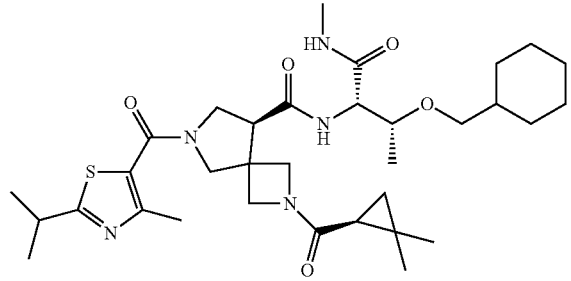
(B)
I-228
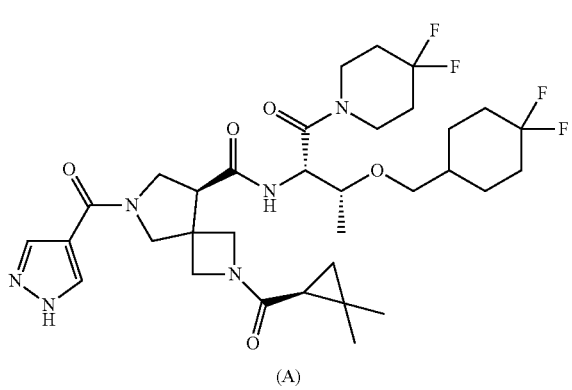
(A)
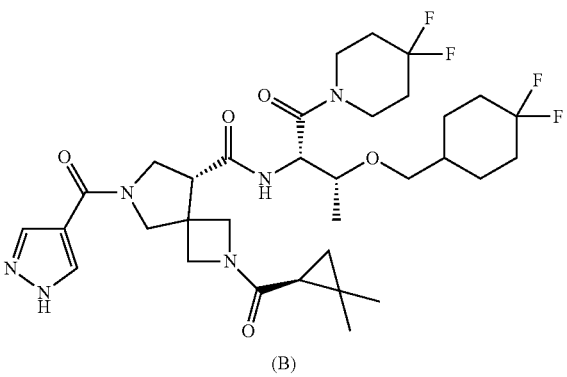
(B)
I-229
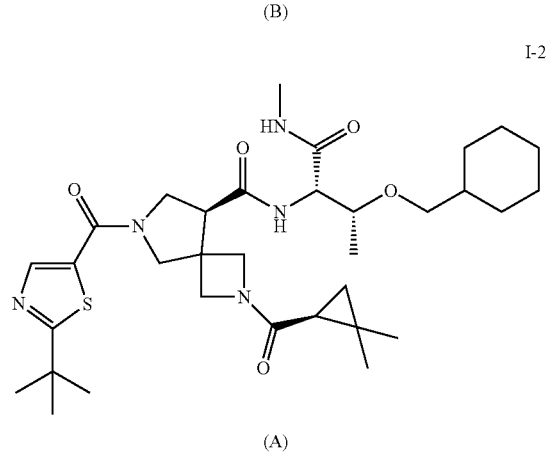
(A)
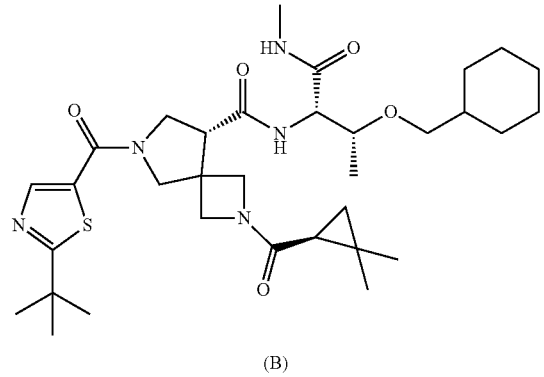
(B)
I-230
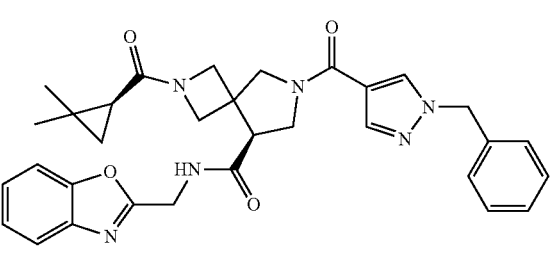

881
-continued
I-231
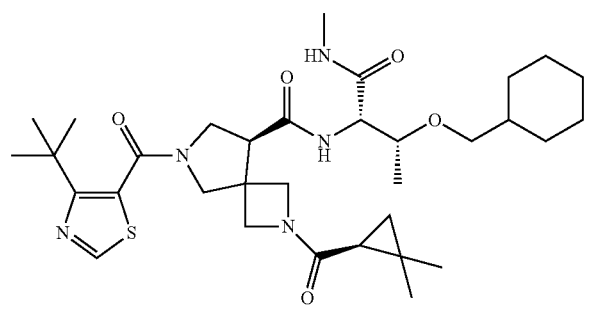
(A)
(B)
I-232
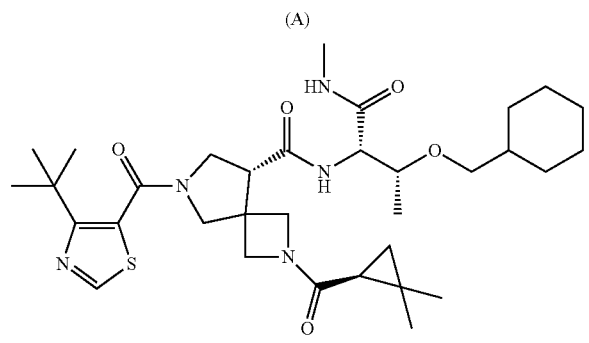
(A)
(B)
I-233
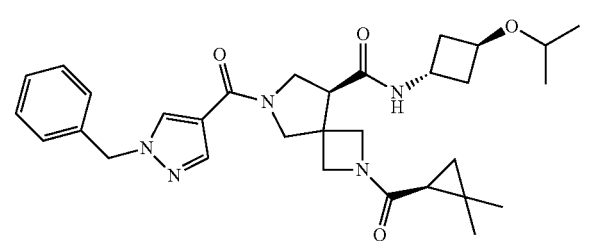
882
-continued
I-234
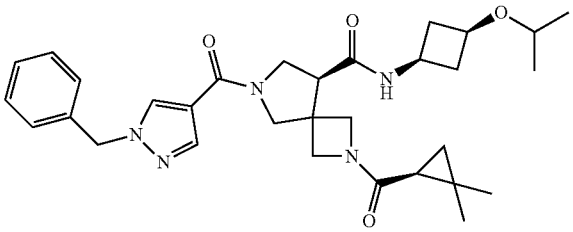
I-235
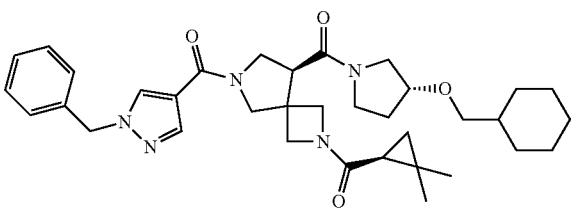
I-236
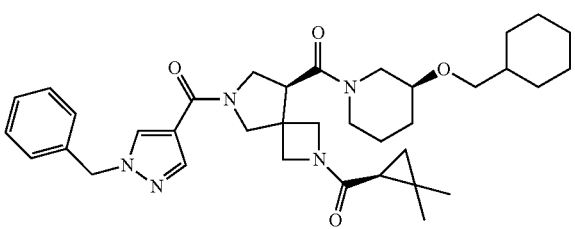
I-237
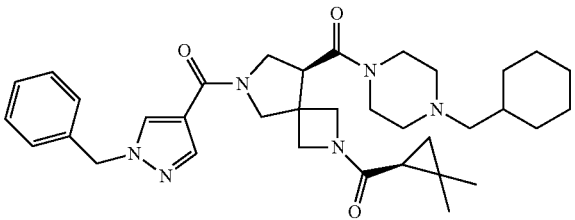
I-238
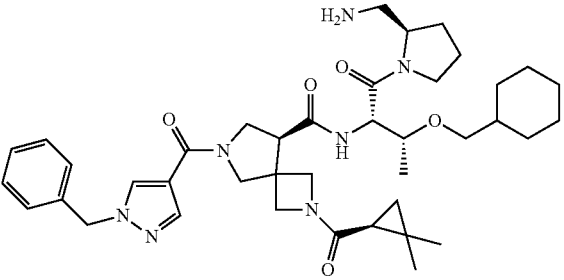
I-239
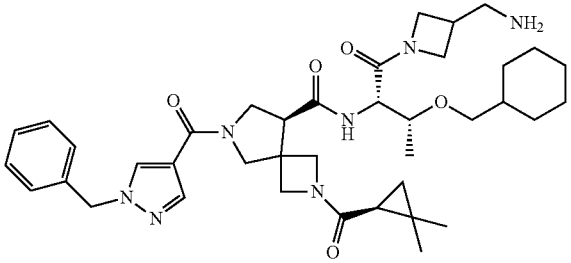

I-240
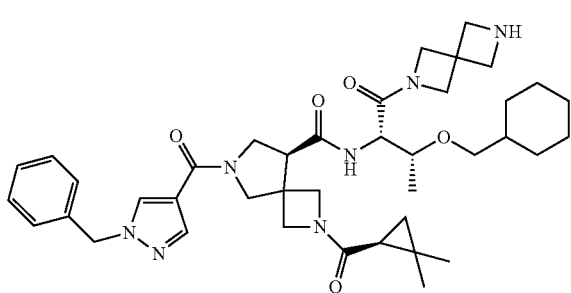
I-241
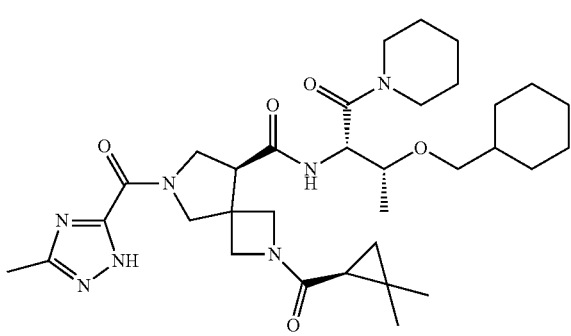
I-242
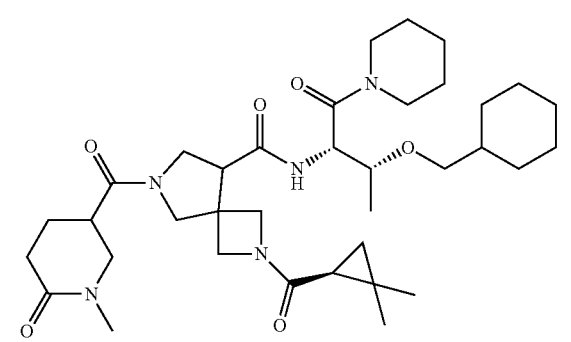
I-243
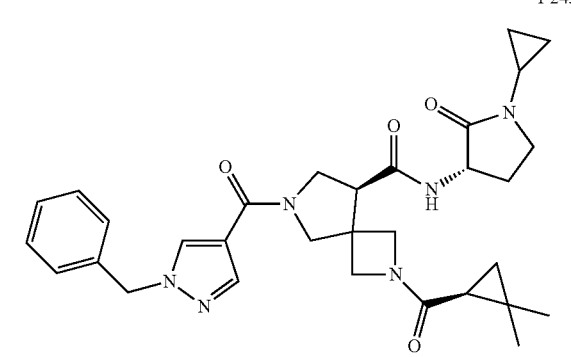
I-244
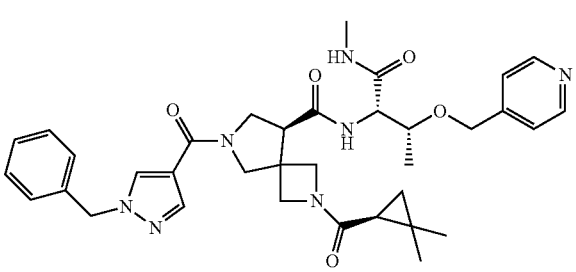
I-245
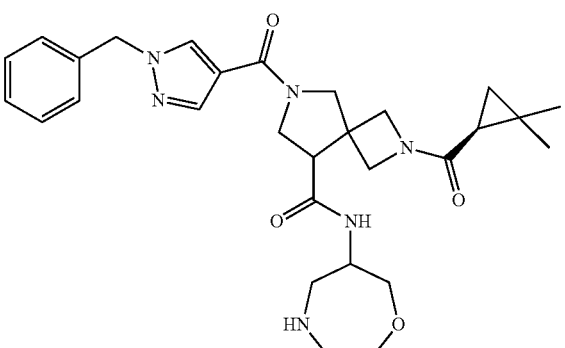
I-246
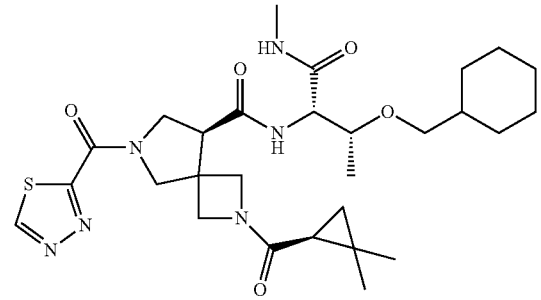
I-247
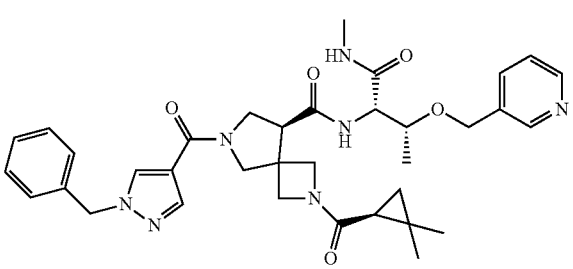
I-248
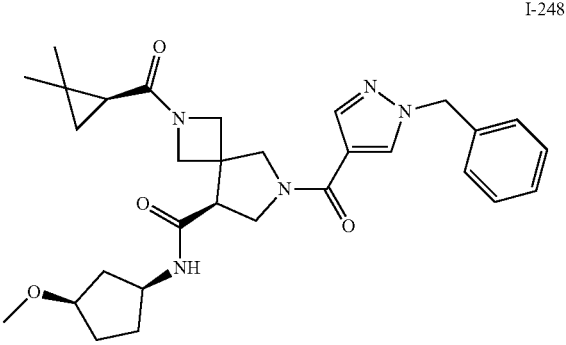
I-249
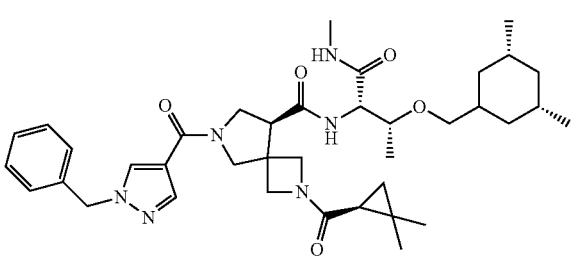

I-250
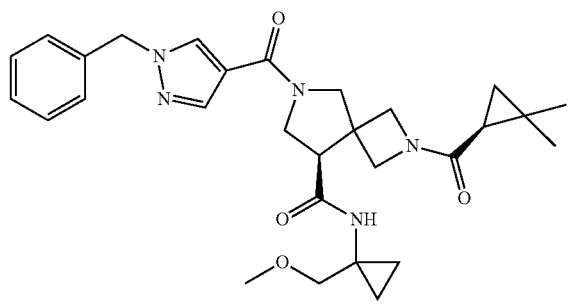
I-251
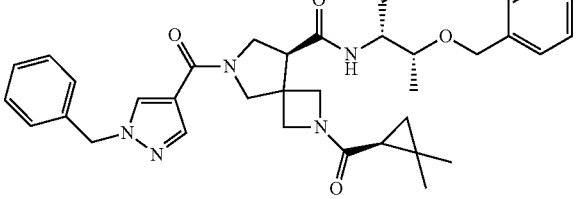
I-252
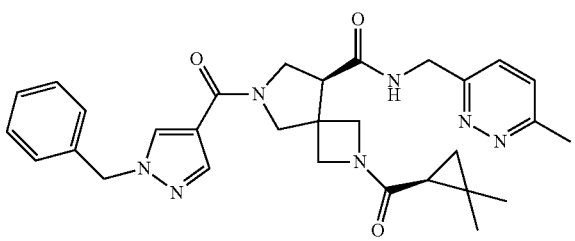
I-253
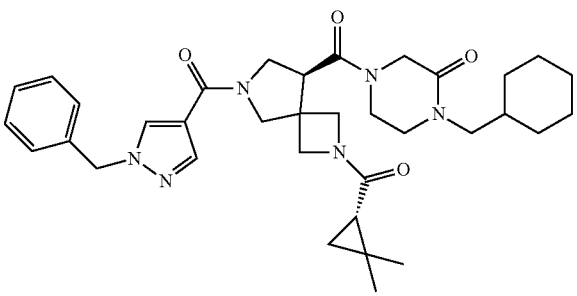
I-254
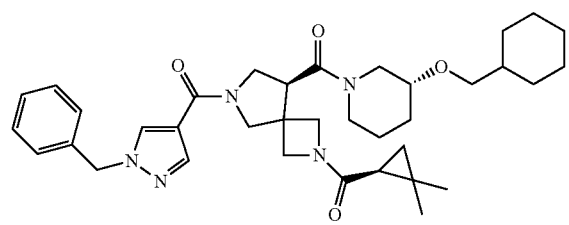
I-255
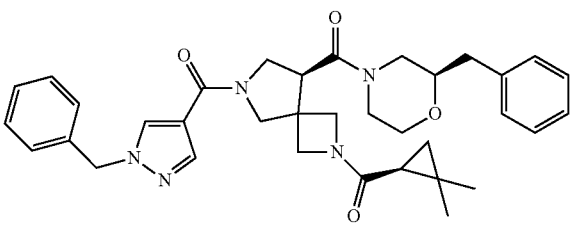
I-256
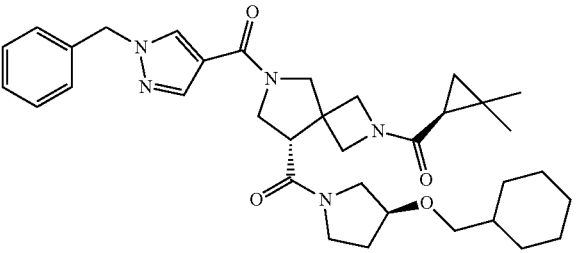
I-257
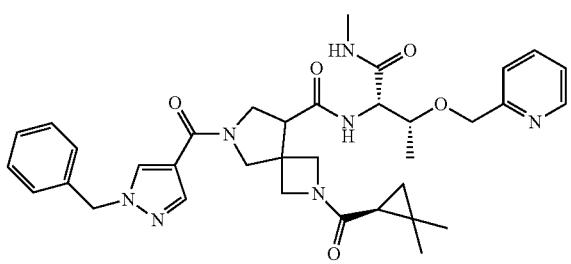
I-258
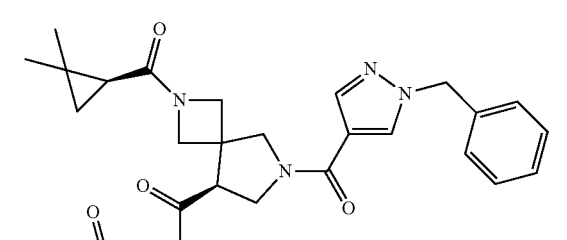
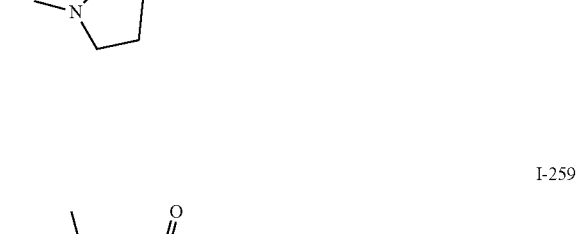
I-259
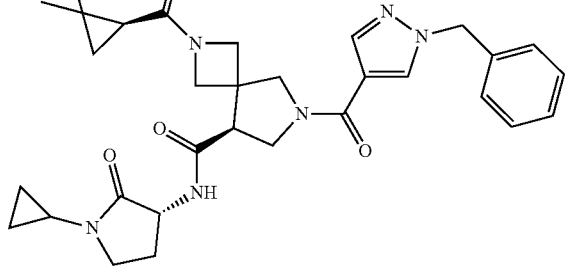

I-260
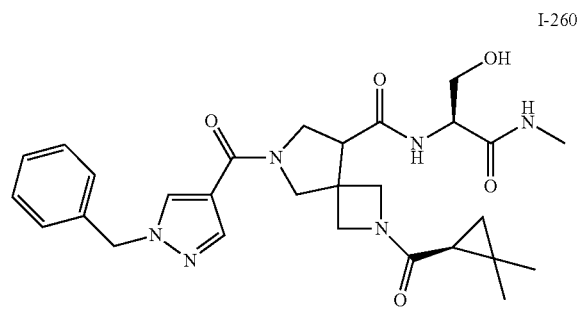
I-261
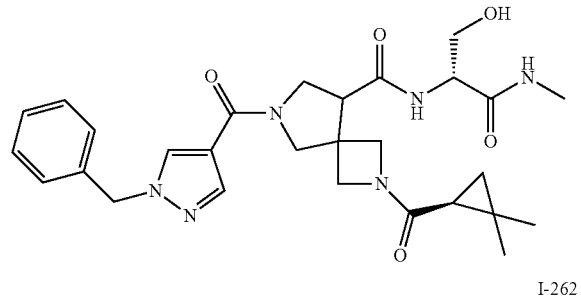
I-262
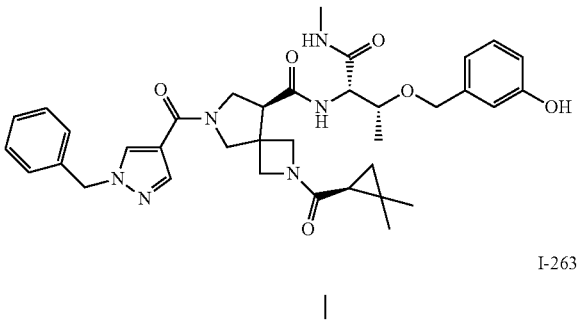
I-263
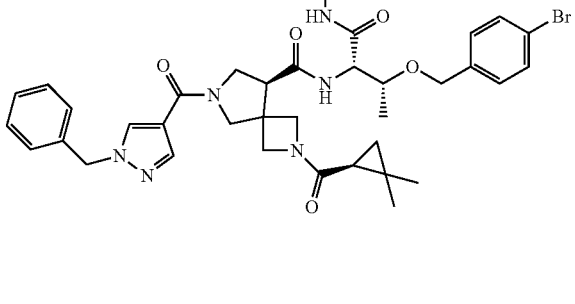
I-264
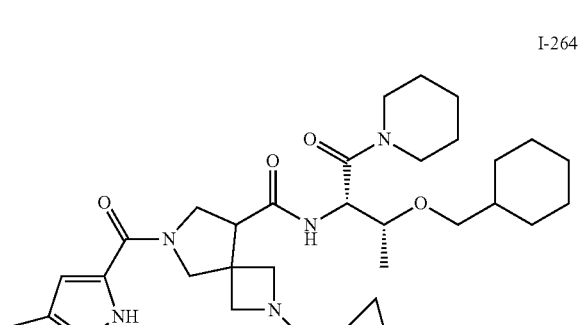
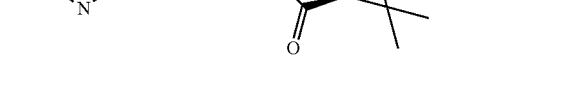
I-265
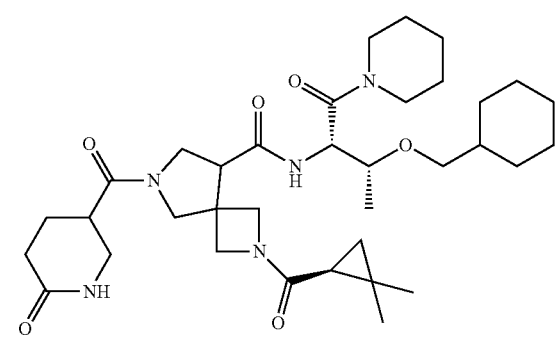
I-266
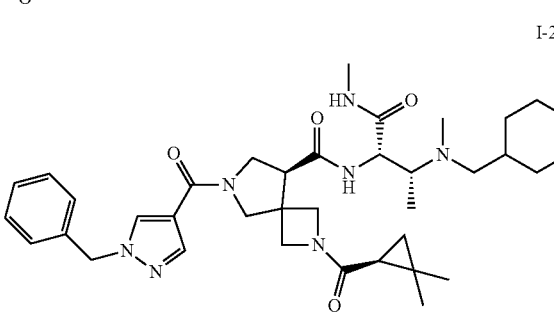
I-267
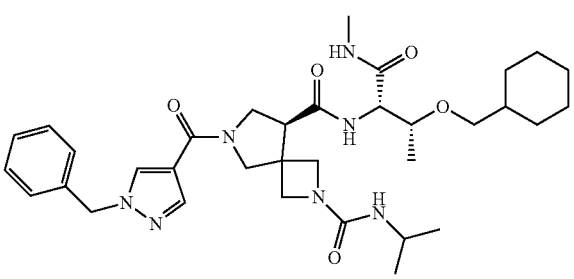
I-268
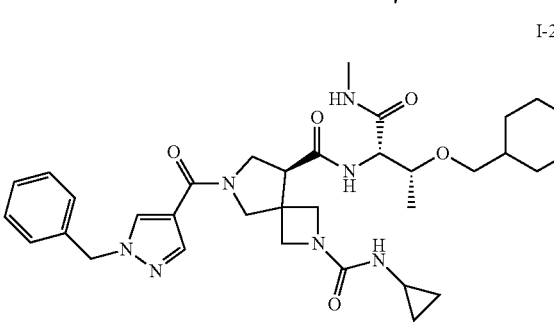
I-269
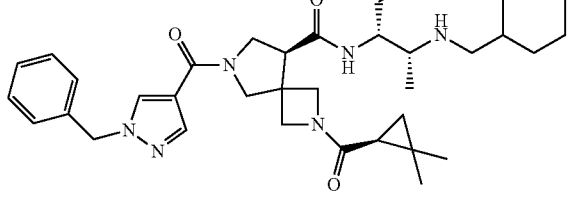

I-270
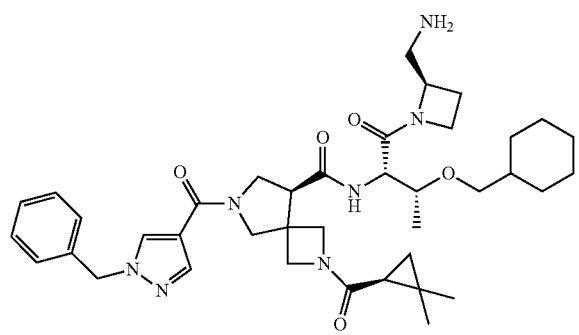
I-274
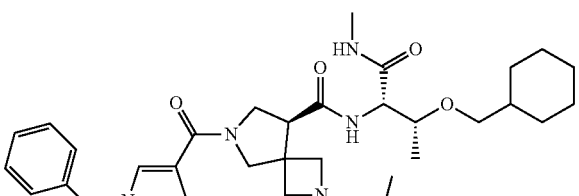
I-271
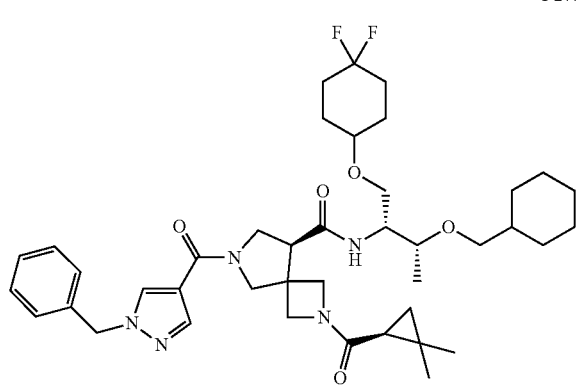
I-275
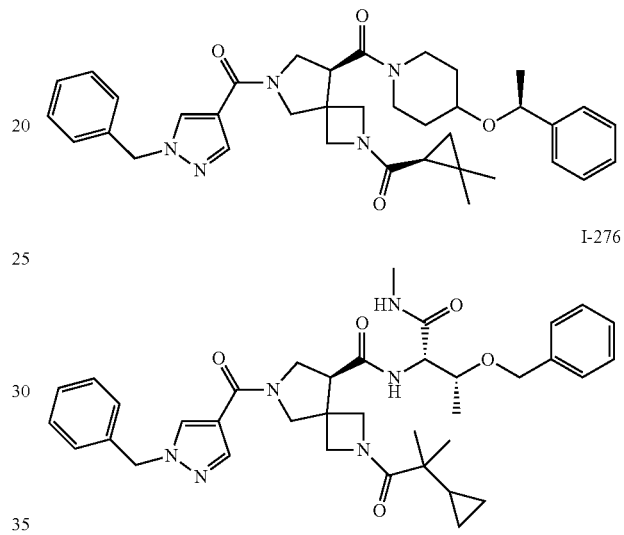
I-272
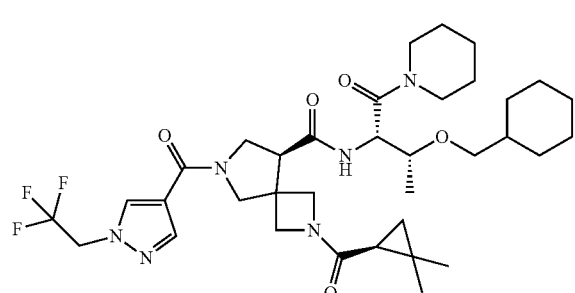
I-276
I-277
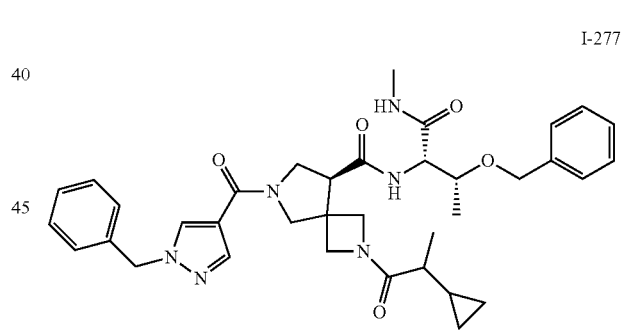
I-273
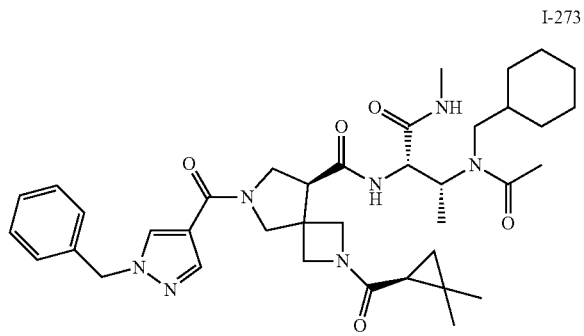
I-278
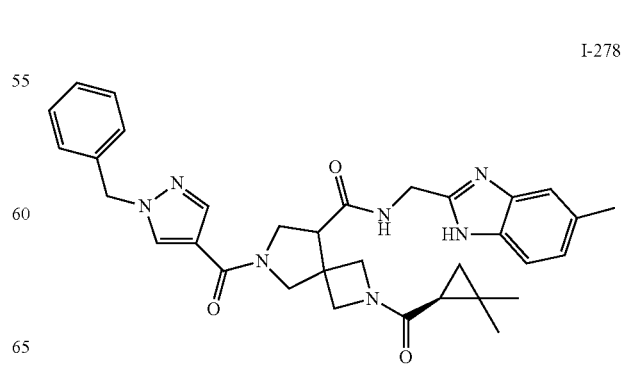

I-279
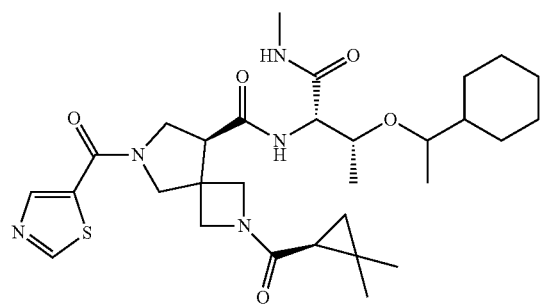
I-280
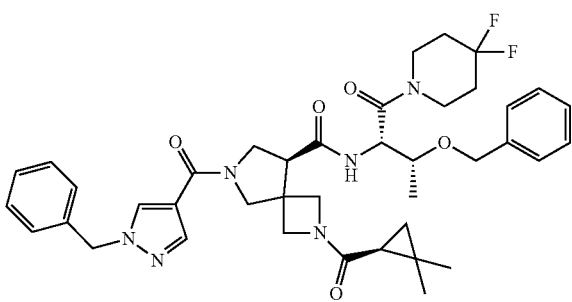
I-281
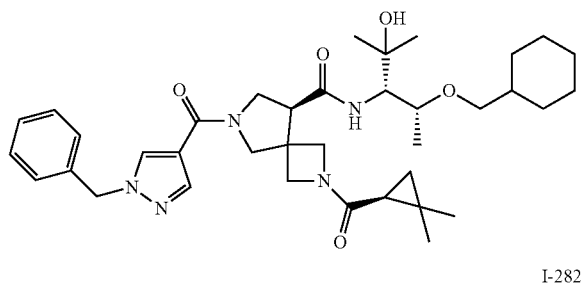
I-282
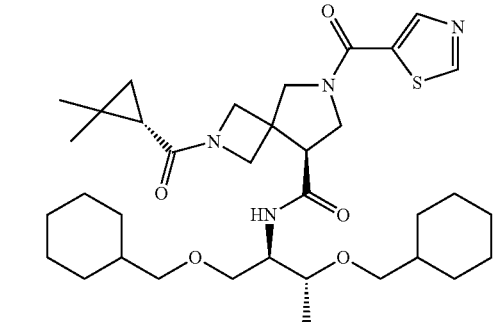
I-283
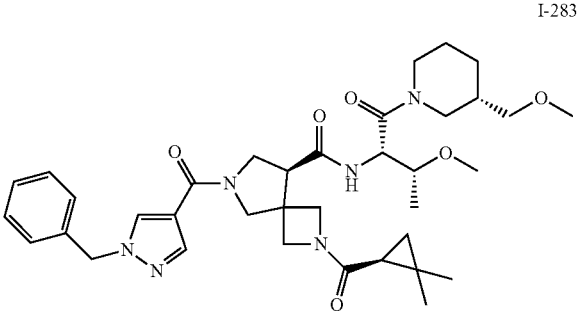
I-284
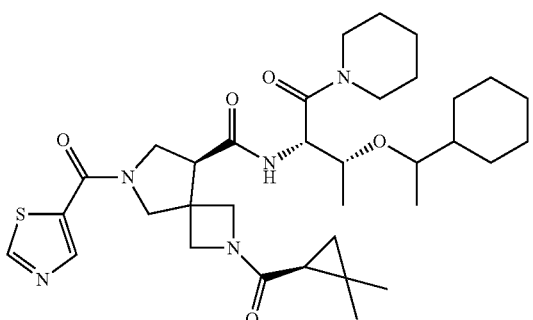
I-285
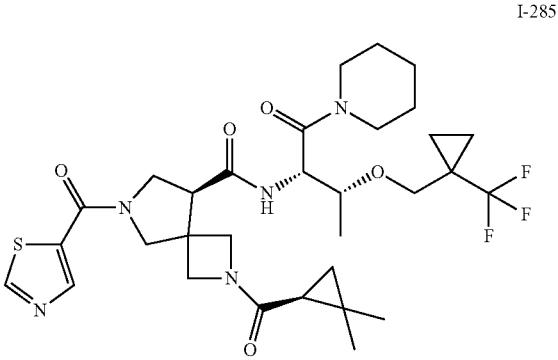
I-286
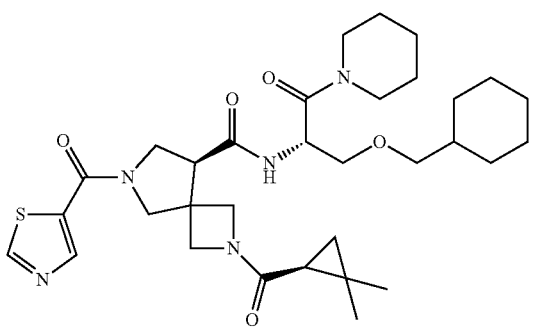
I-287
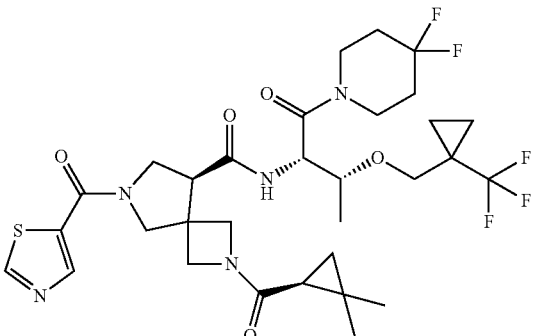

I-288
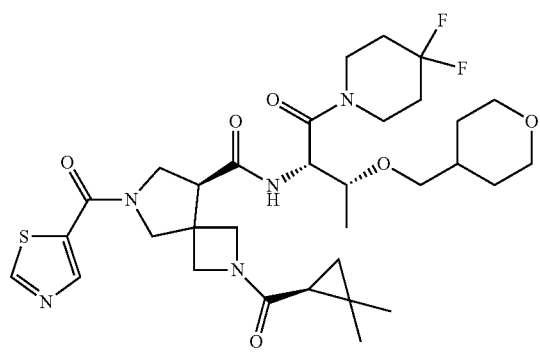
I-292
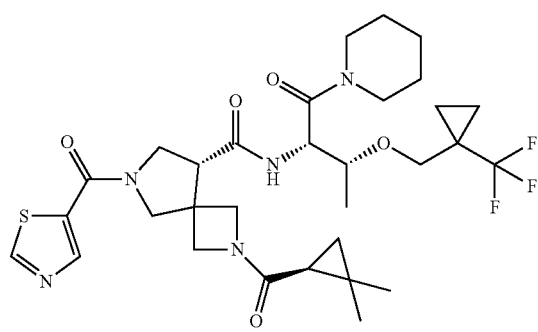
I-289
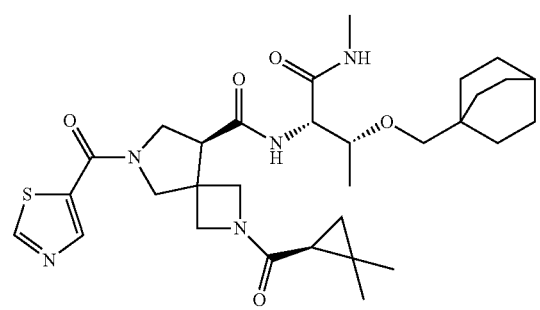
I-293
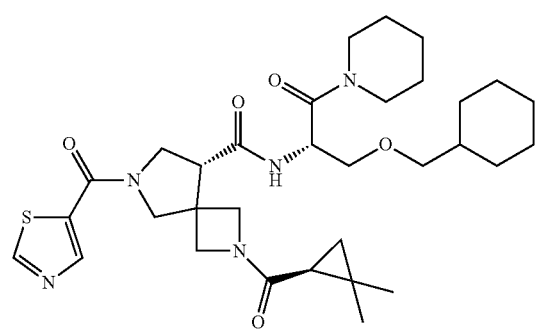
I-290
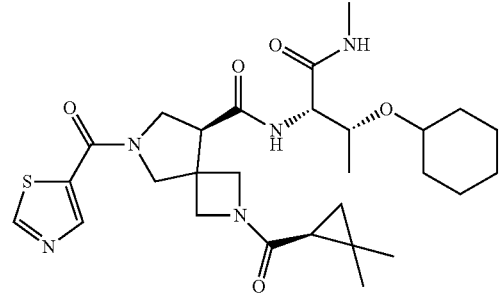
I-294
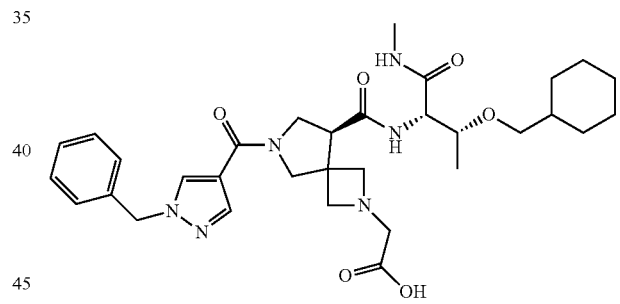
I-291
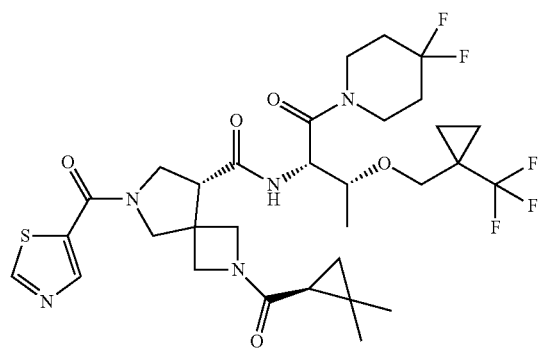
I-295
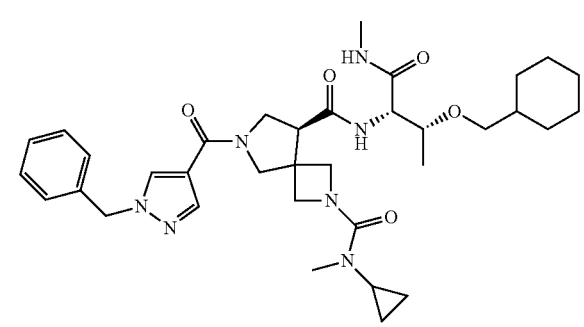

I-296
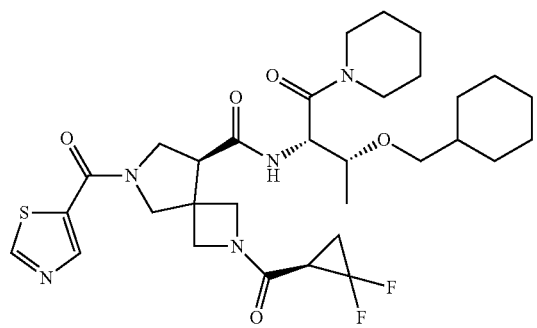
I-297
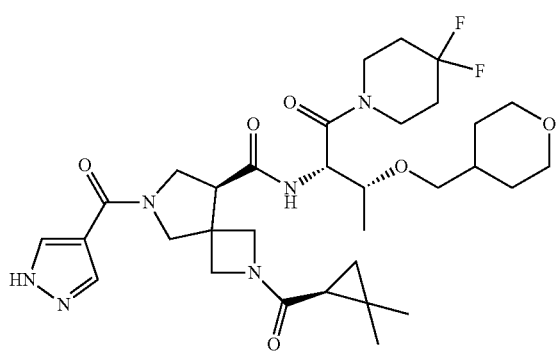
I-298
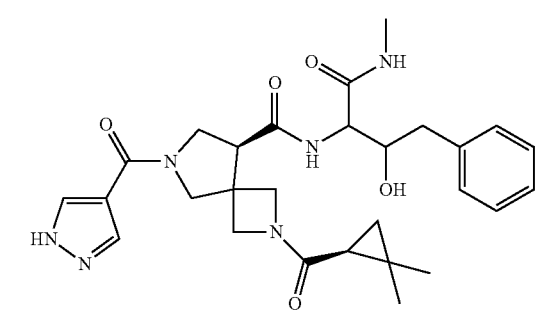
I-299
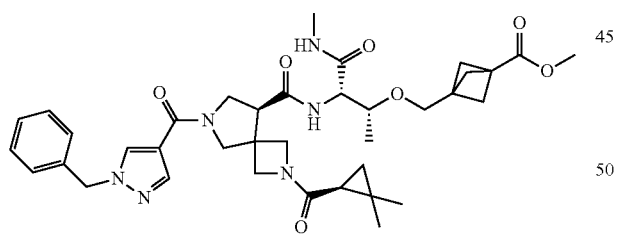
I-300
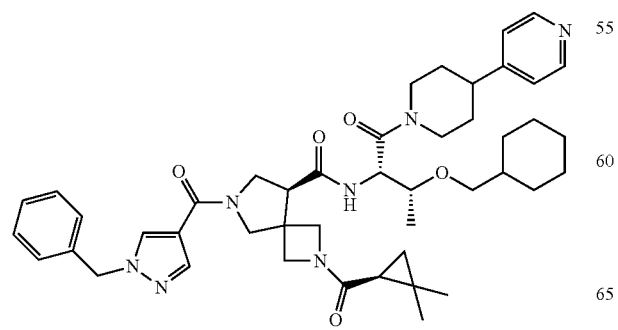
I-301
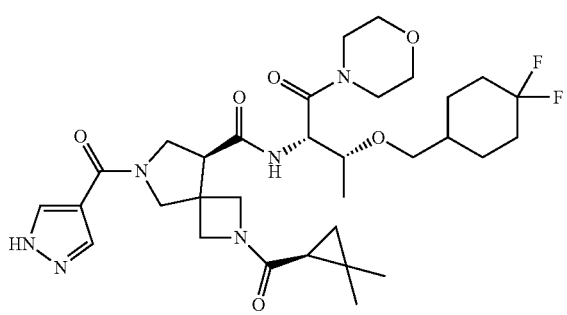
I-302
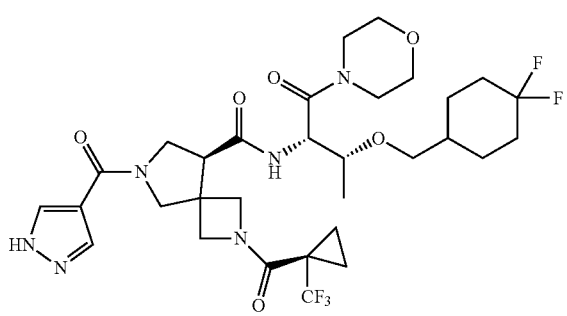
I-303
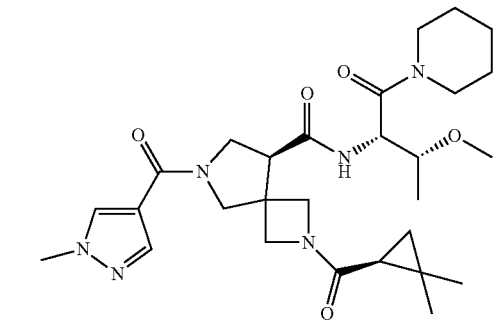
I-304
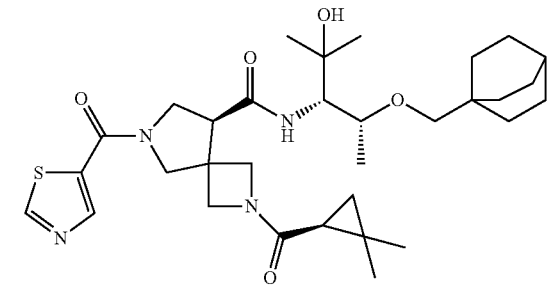
I-305
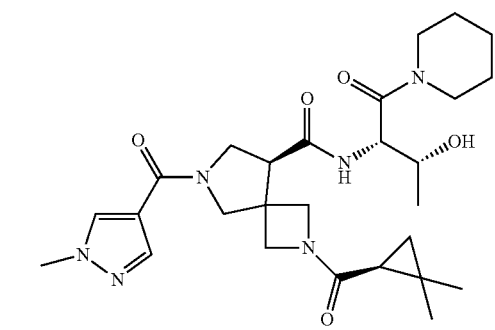

I-306
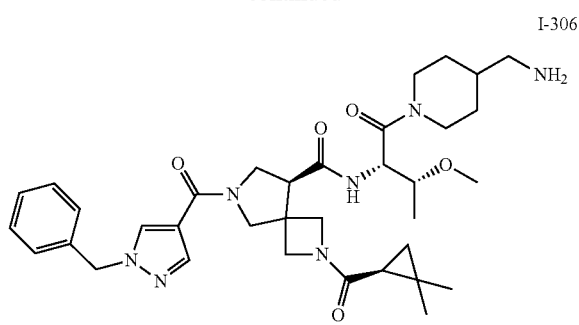
I-307
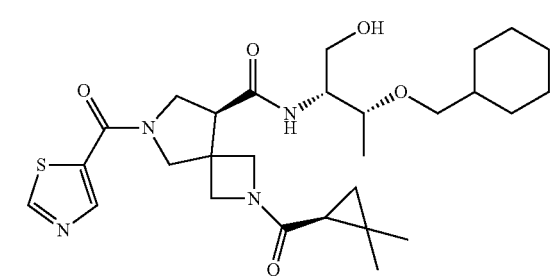
I-308
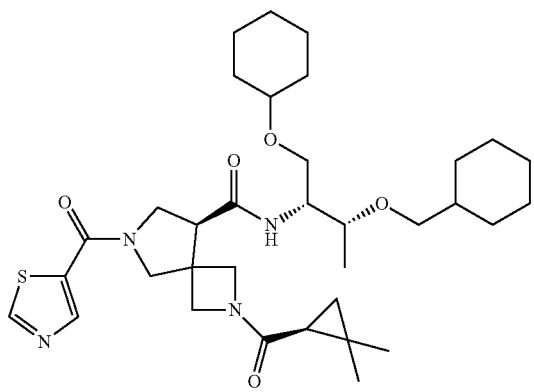
I-309
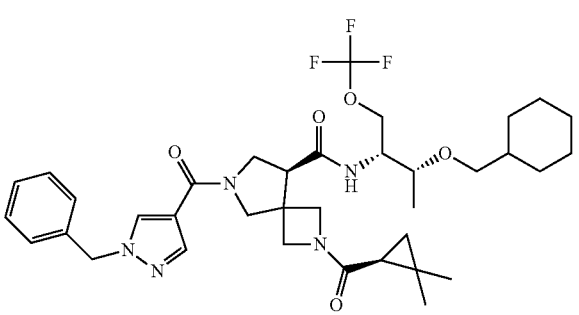
I-310
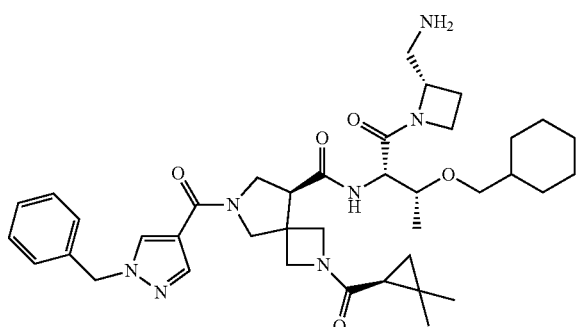
I-311
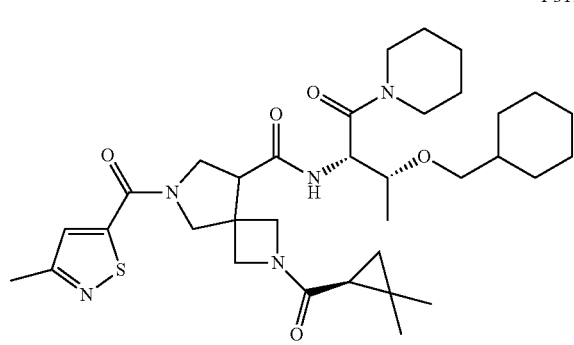
I-312
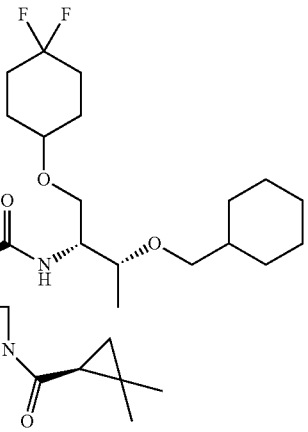
I-313
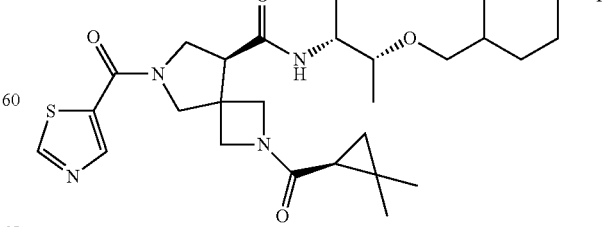

I-314 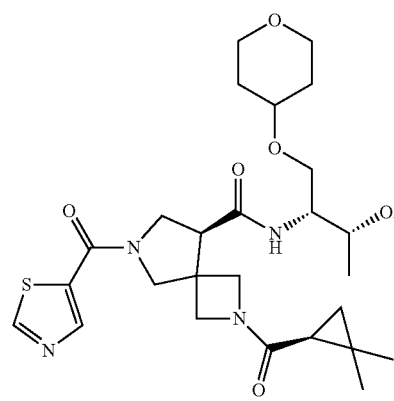
I-317 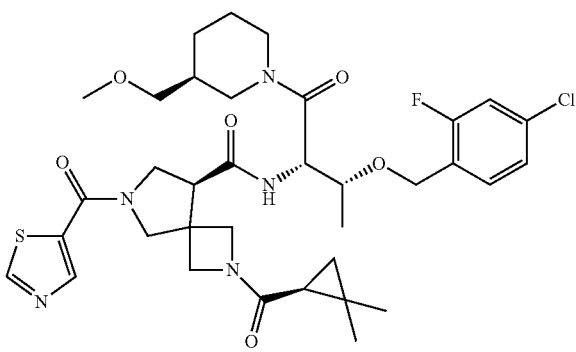
I-315 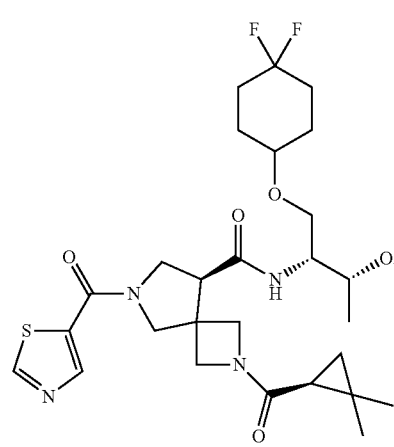
I-318 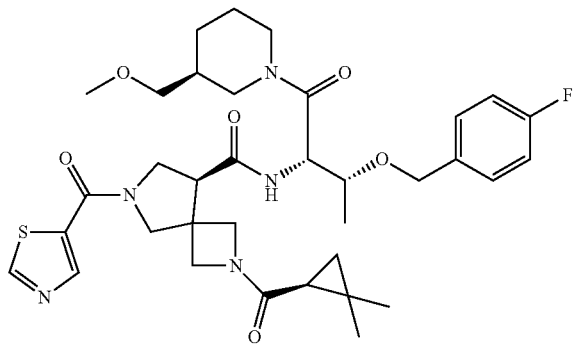
I-316 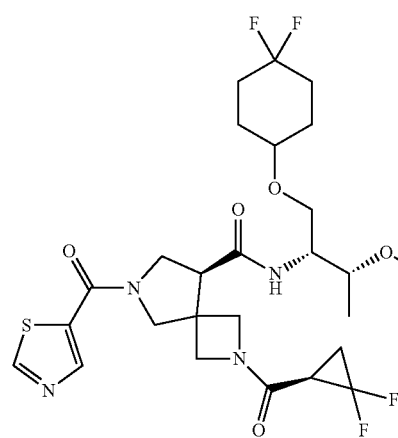
I-319 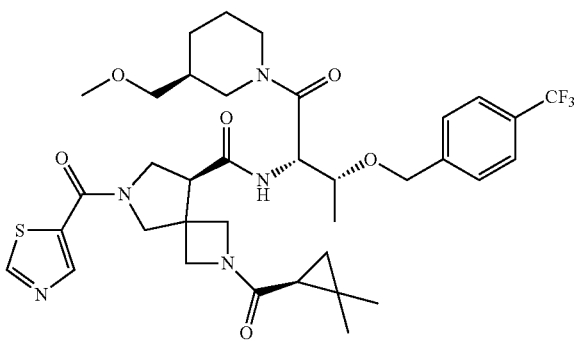
I-320 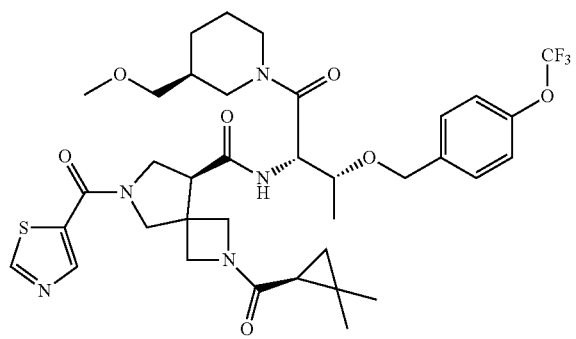

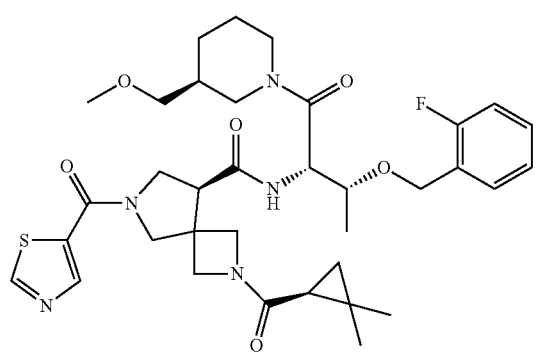
I-321
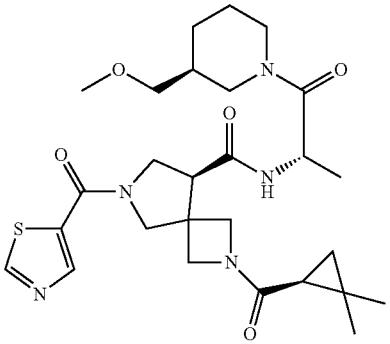
I-325
I-322
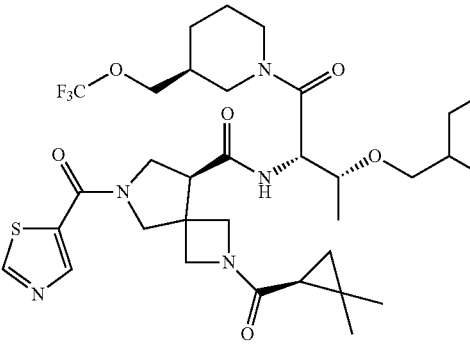
I-326
I-323
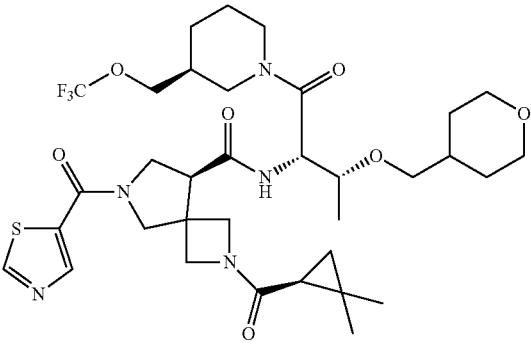
I-327
I-324
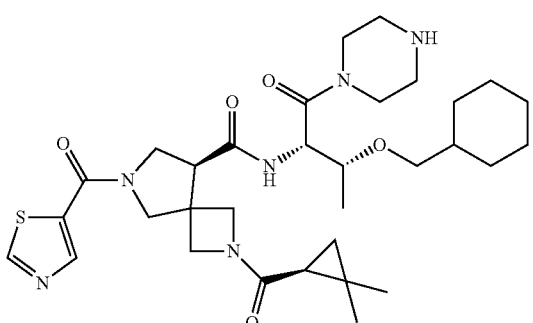
I-328

I-329
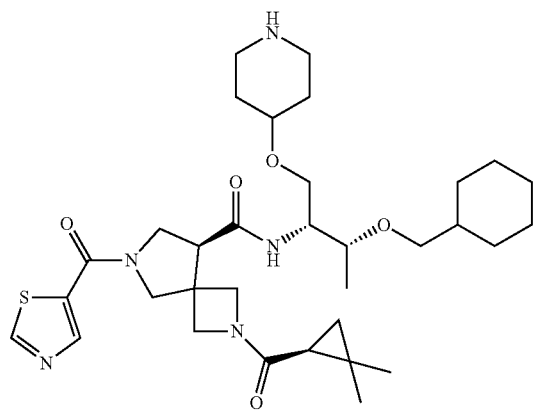
I-330
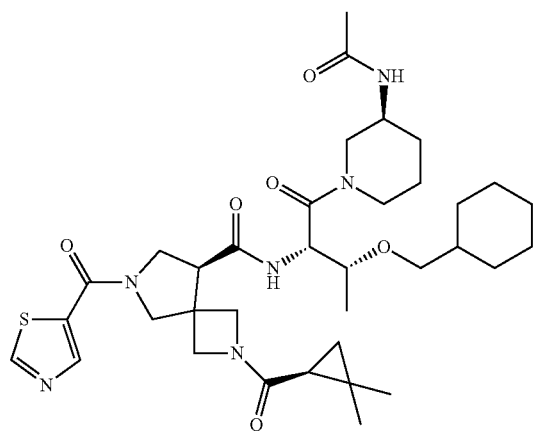
I-331
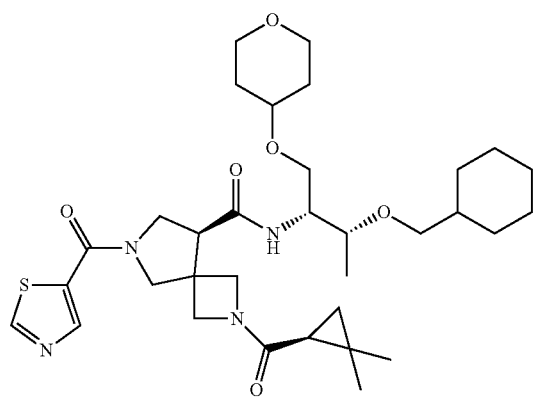
I-332
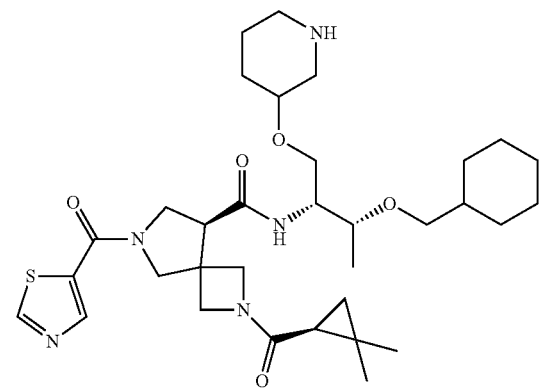
I-333
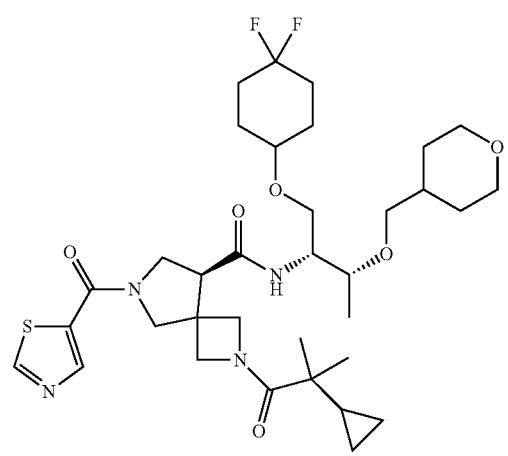
I-334
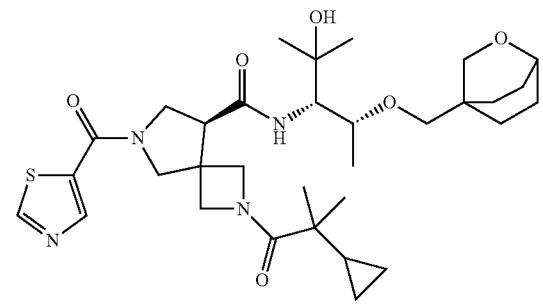
I-335
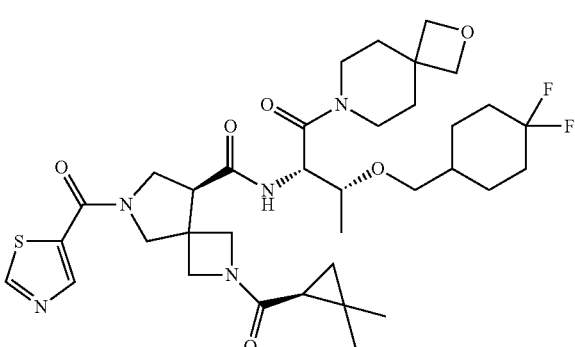

I-336
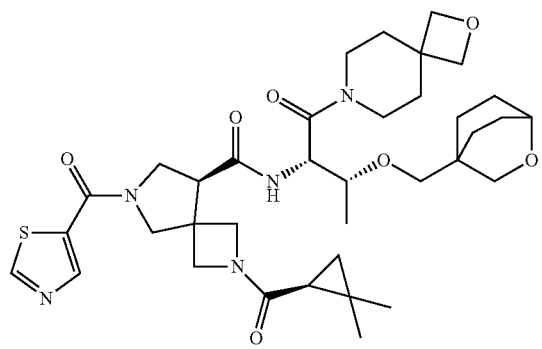
I-340
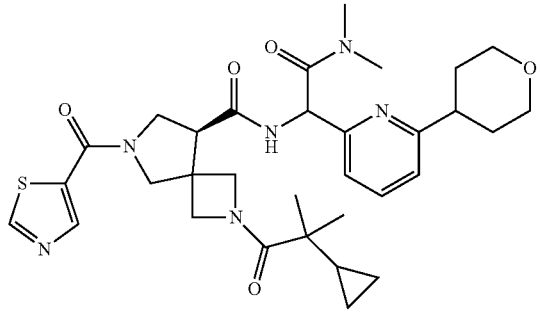
I-337
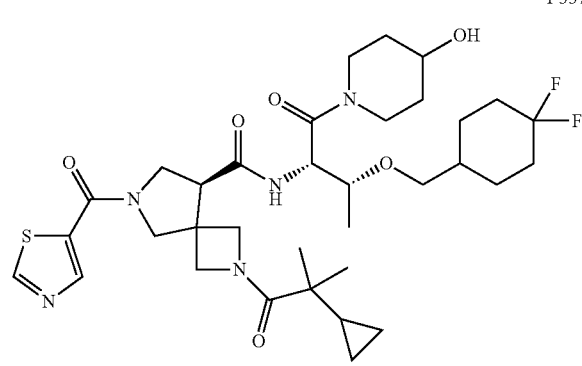
I-341
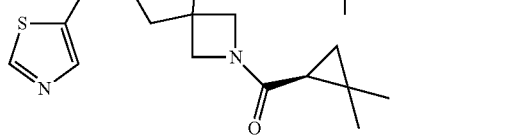
I-338
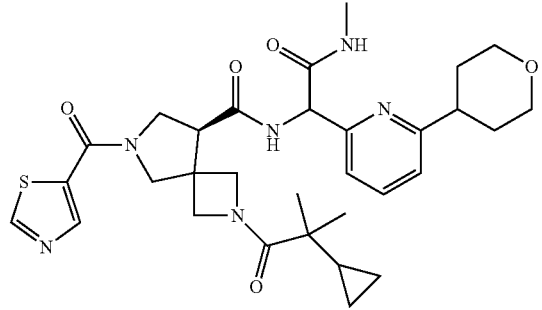
I-342
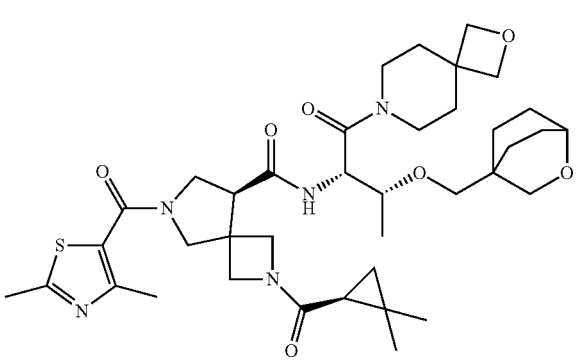
I-339
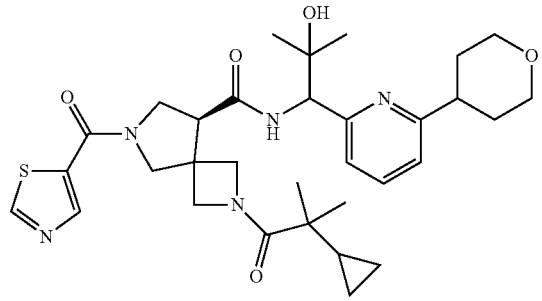
I-343
I-344
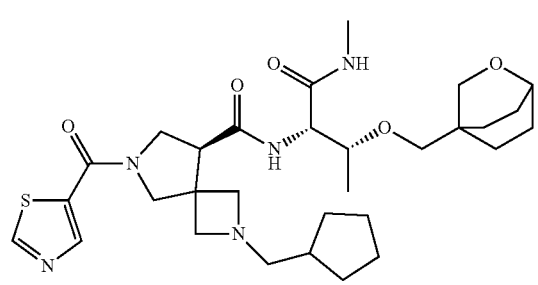

I-345
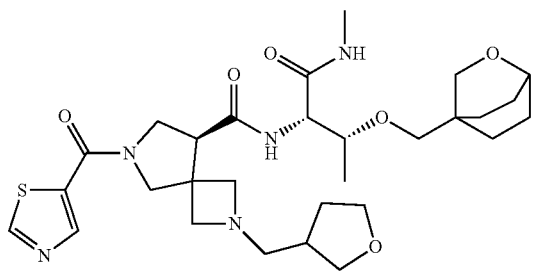
I-346
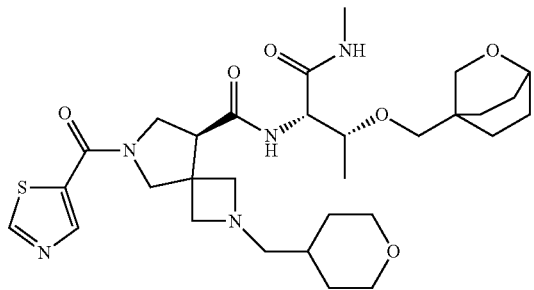
I-347
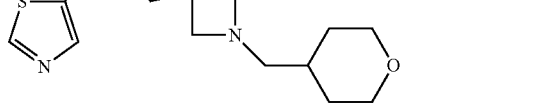
I-348
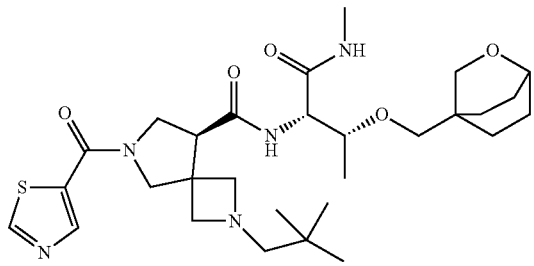
I-349
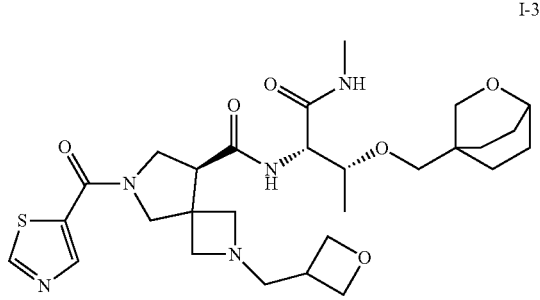
I-350
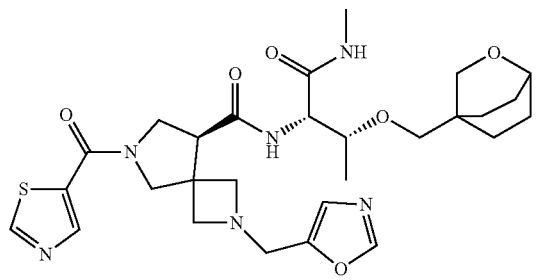
I-351
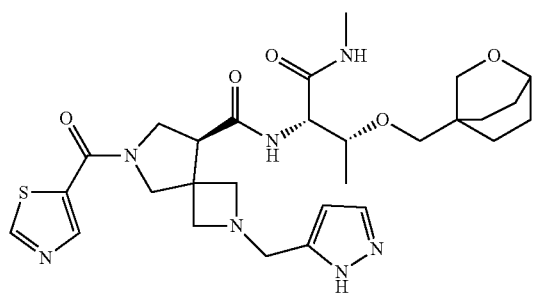
I-352
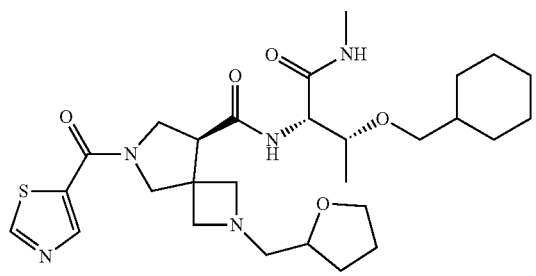
I-353
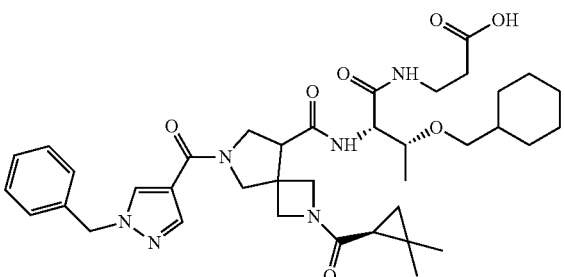
I-354
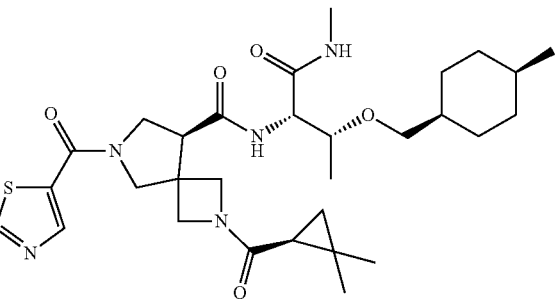

I-355
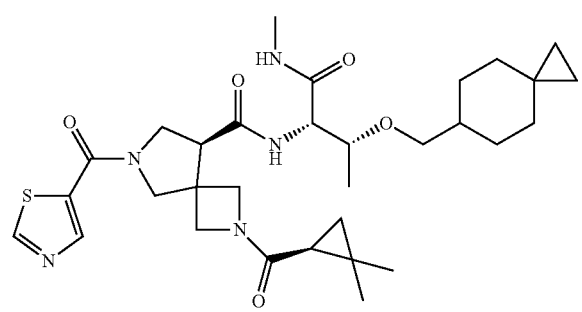
I-356
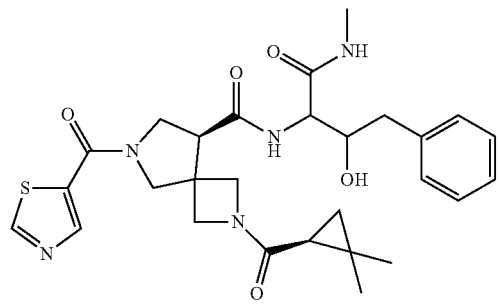
I-357
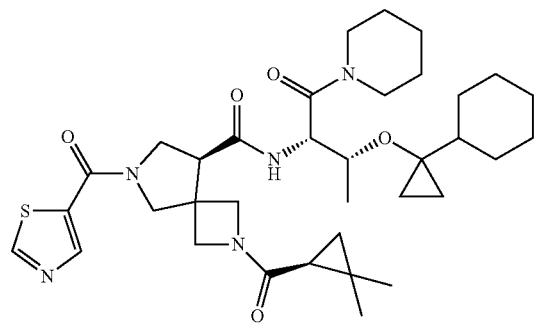
I-358
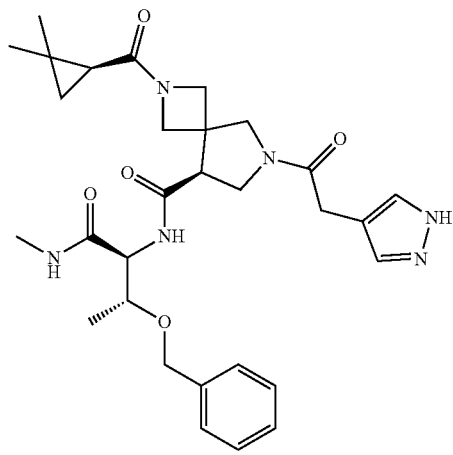
I-359
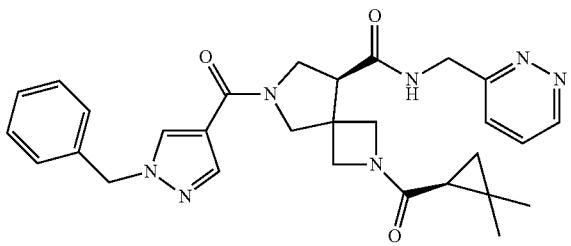
I-360
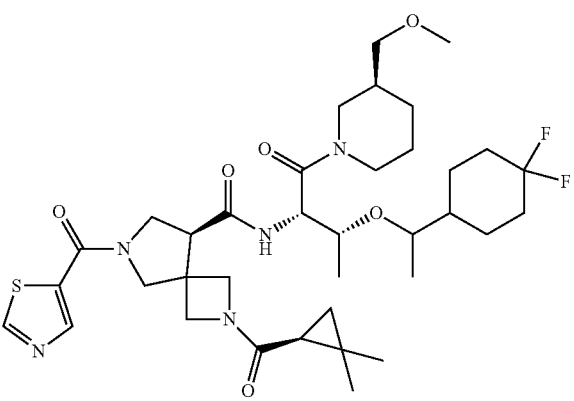
I-361
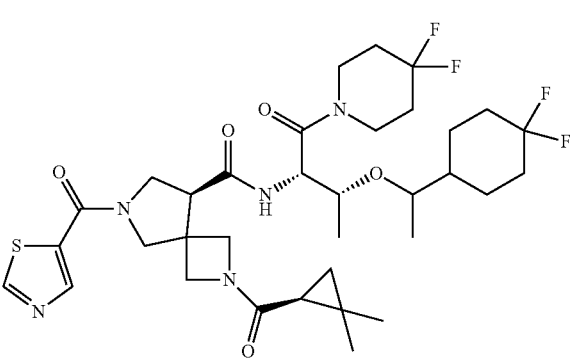
I-362
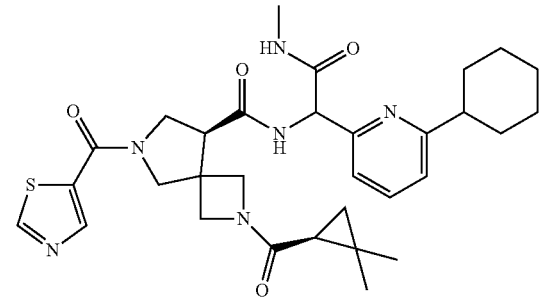
I-363
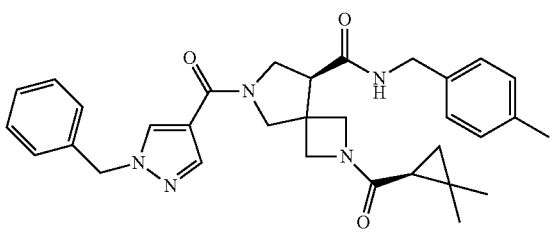

I-364
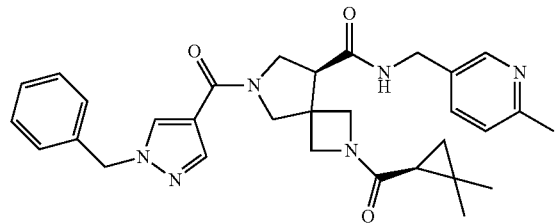
I-365
I-368
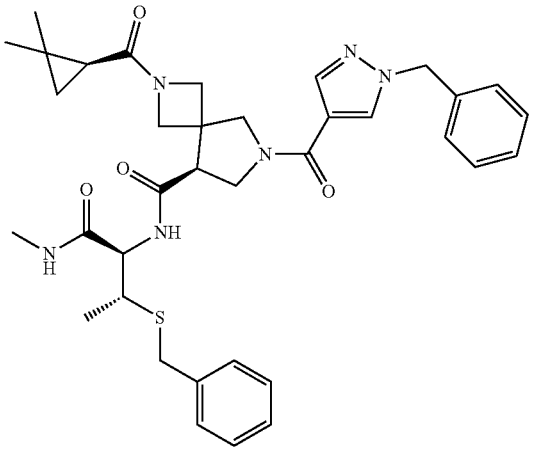
I-369
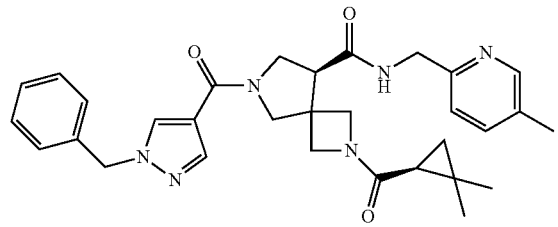
I-366
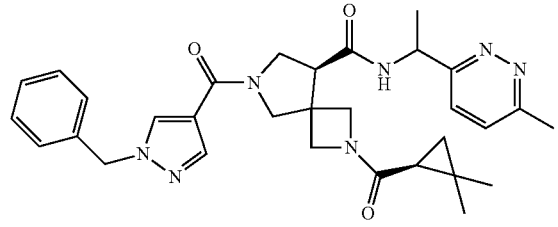
I-367
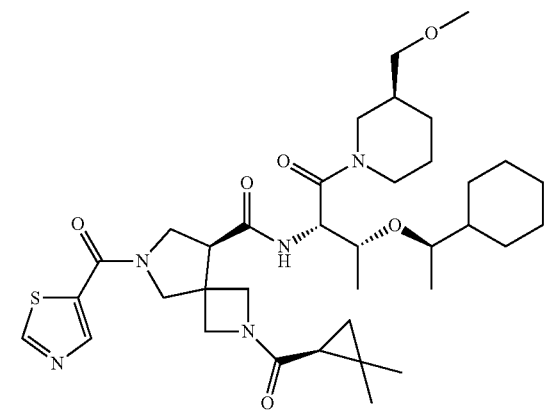
I-370
I-371
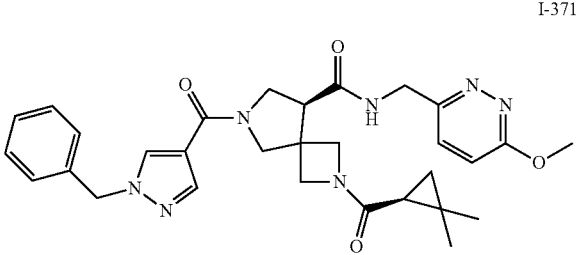

I-372
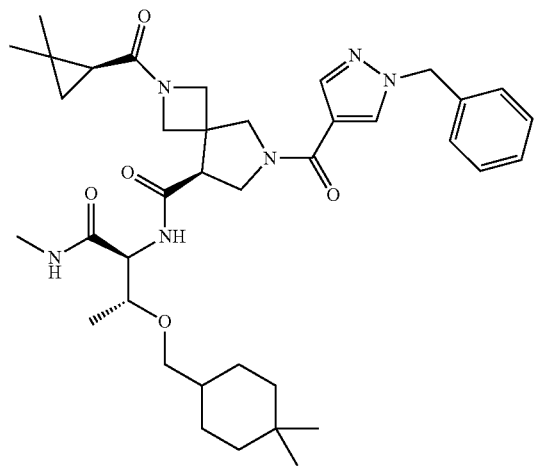
I-373
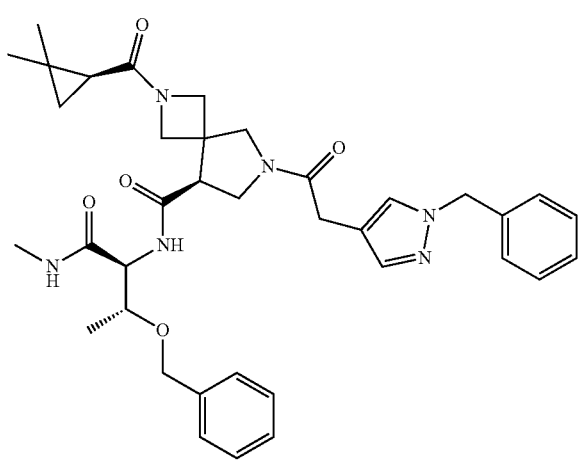
I-374
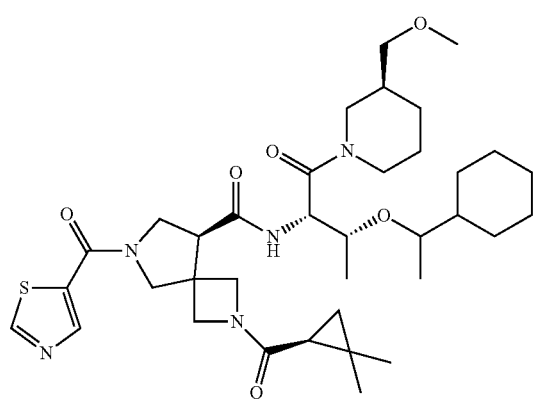
I-375
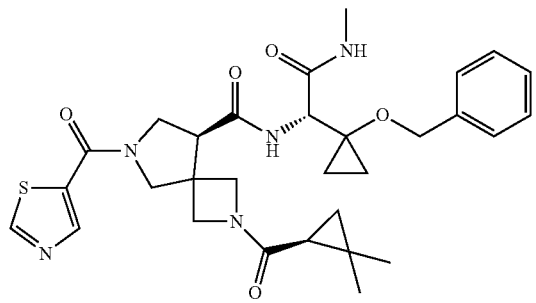
I-376
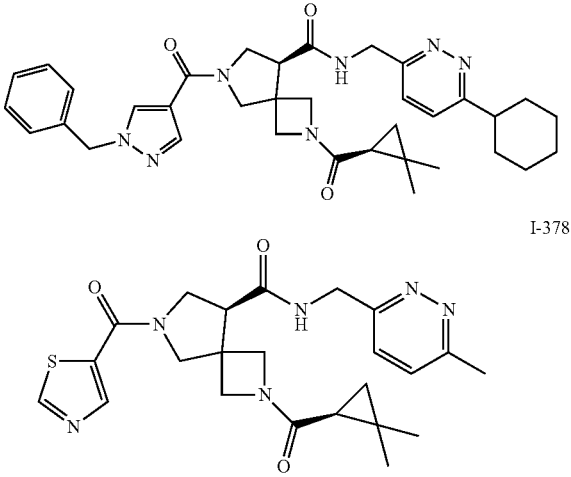
I-377
I-378
I-379
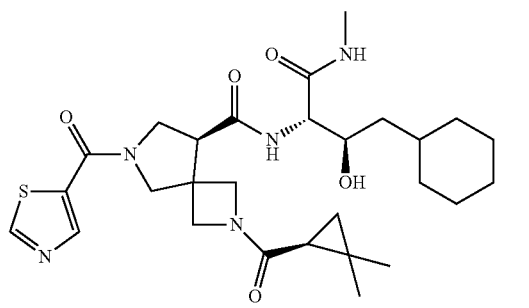

I-380
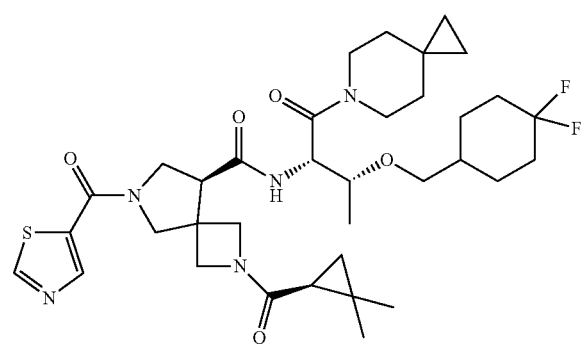
I-384
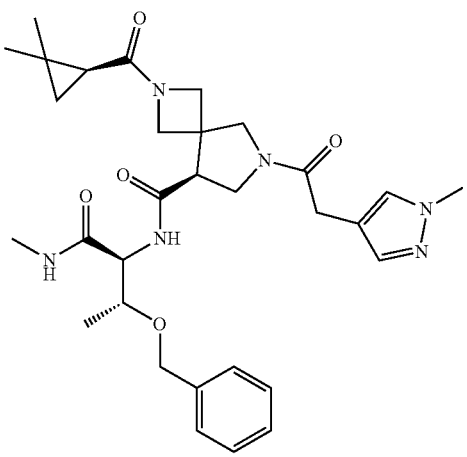
I-381
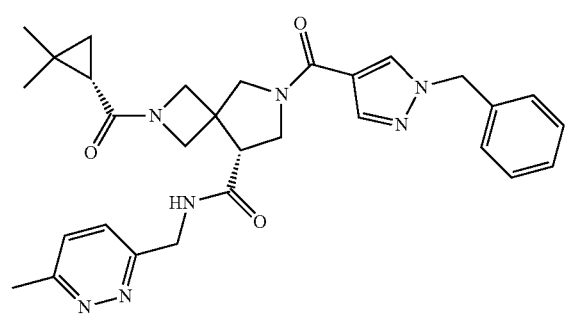
I-385
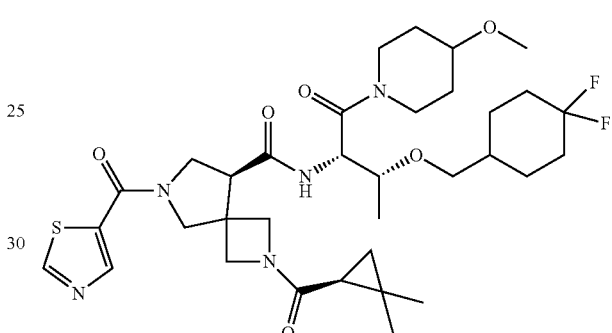
I-382
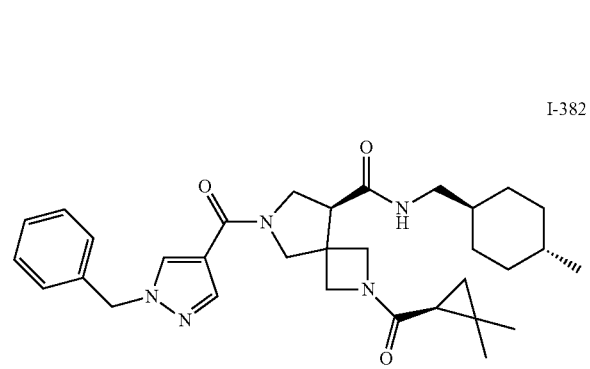
I-386
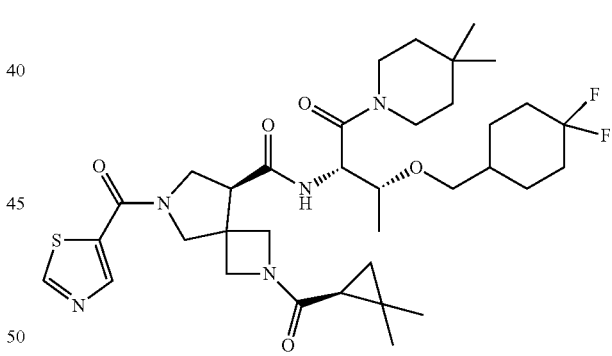
I-383
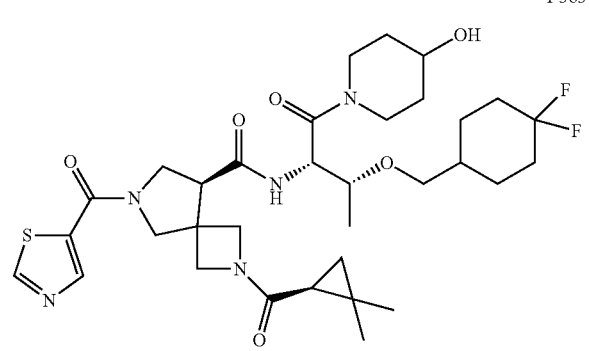
I-387
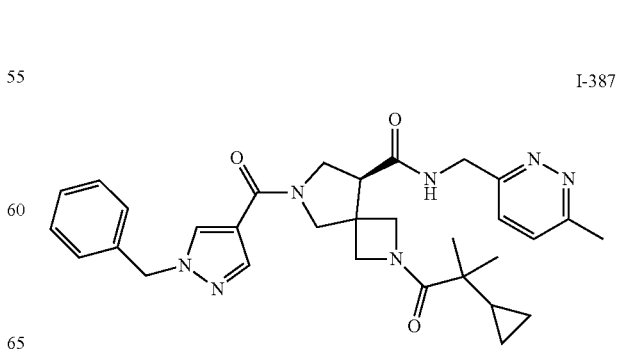

I-388
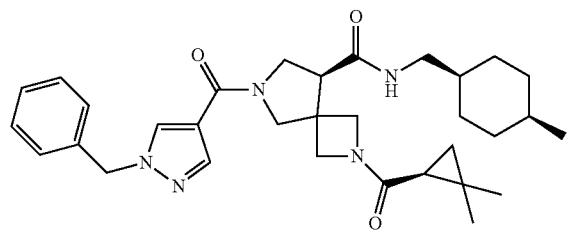
I-389
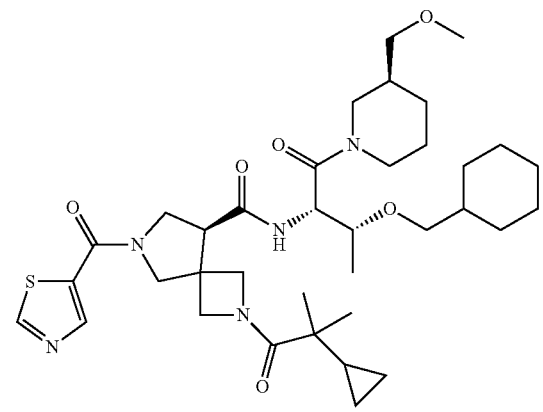
I-390
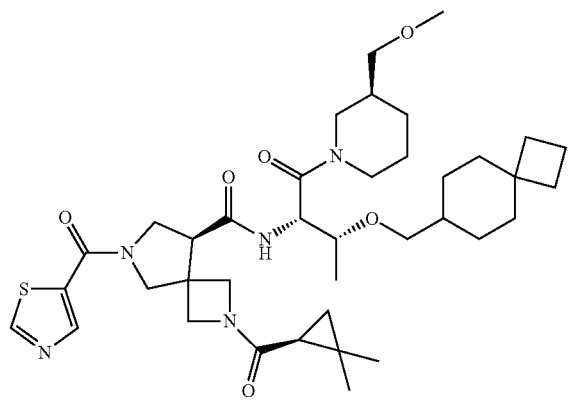
I-393
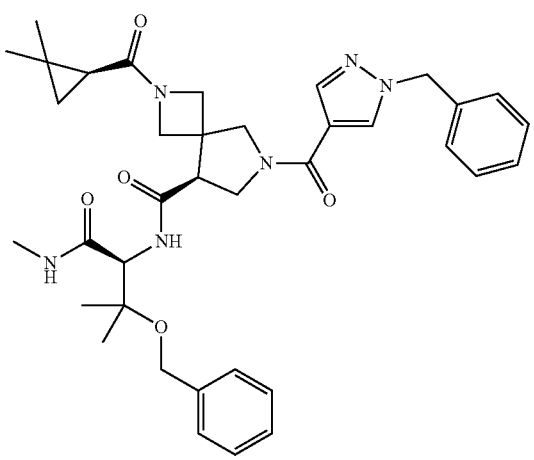
I-394
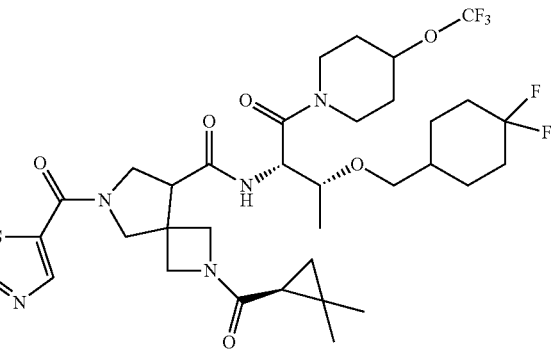
I-395
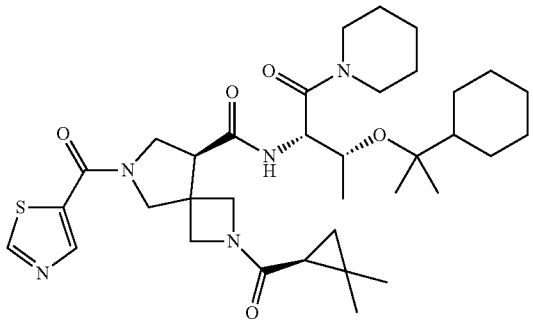
I-391
I-392

I-396
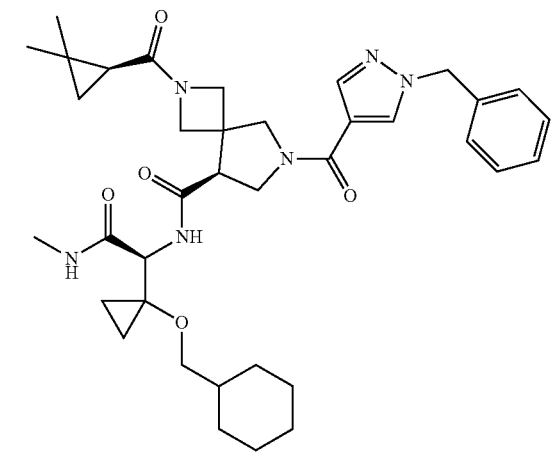
I-397
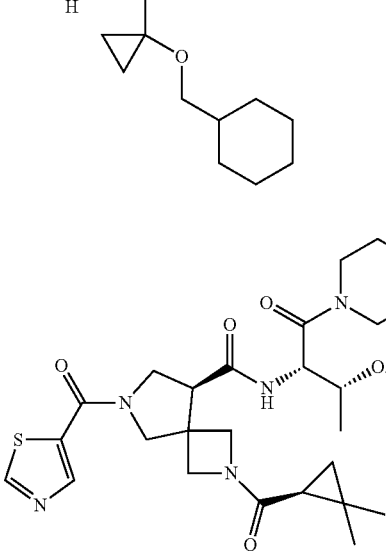
I-398
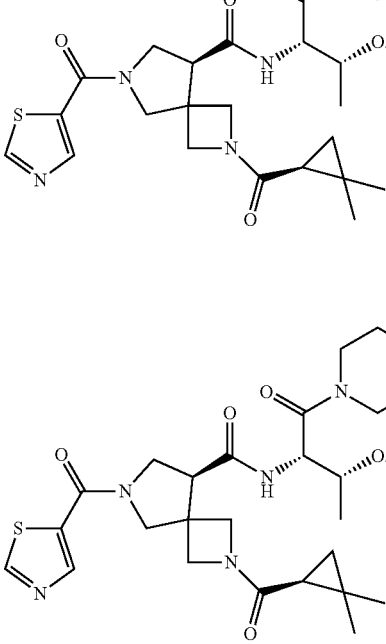
I-399
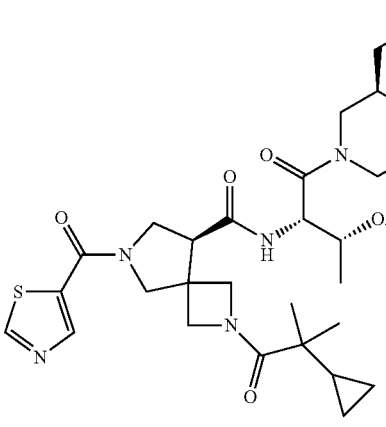
I-400
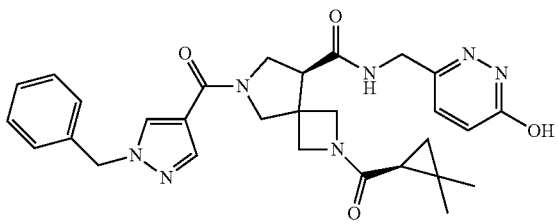
I-401
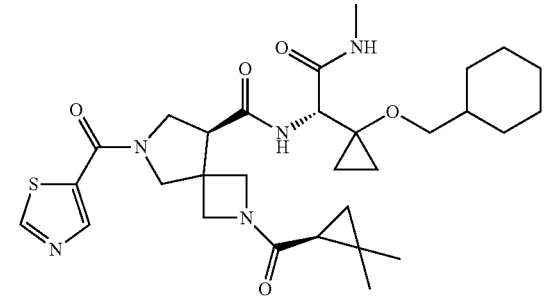
I-402
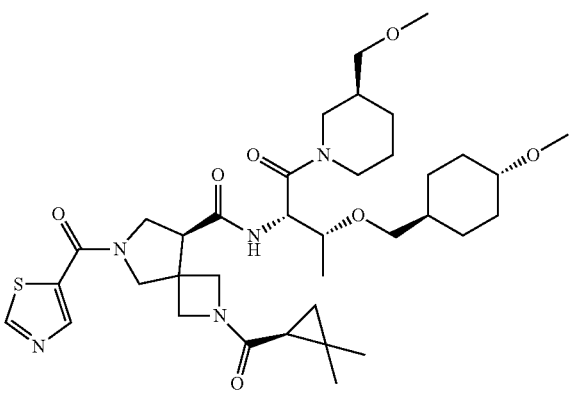
I-403
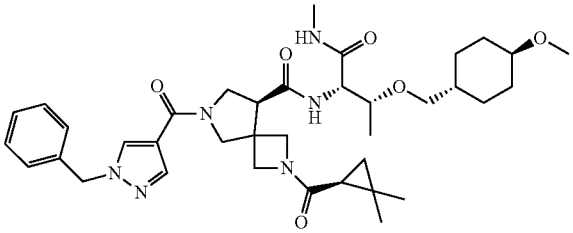
I-404
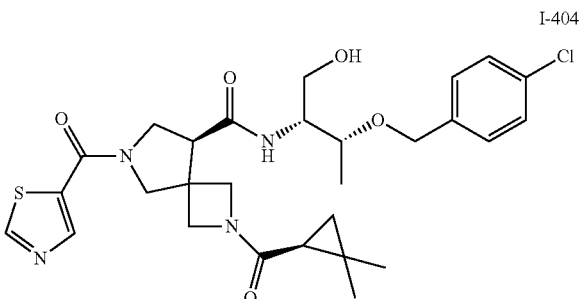

I-405
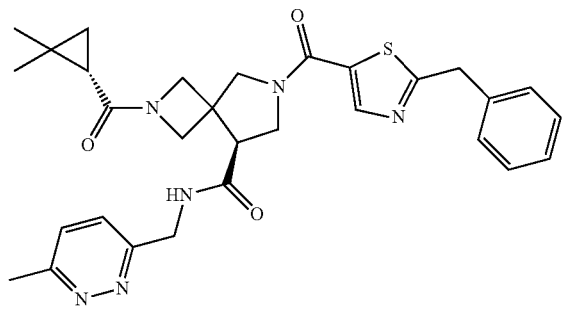
I-406
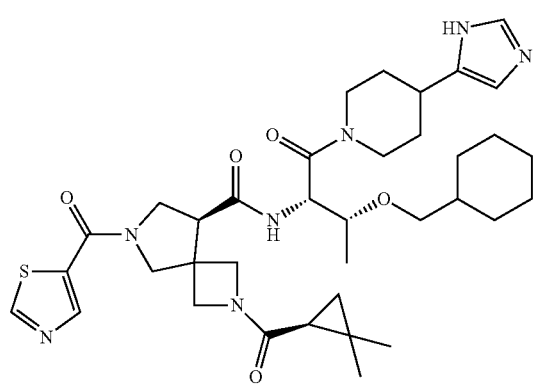
I-407
I-408
I-409
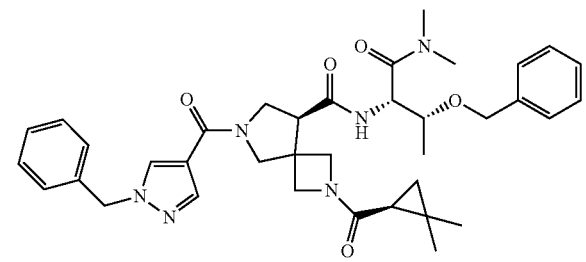
I-410
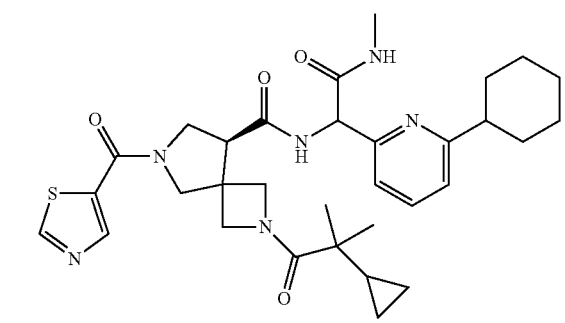
I-411
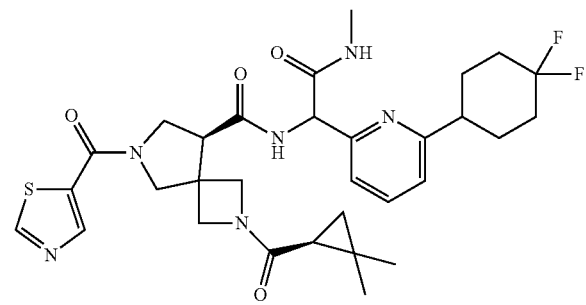
I-412
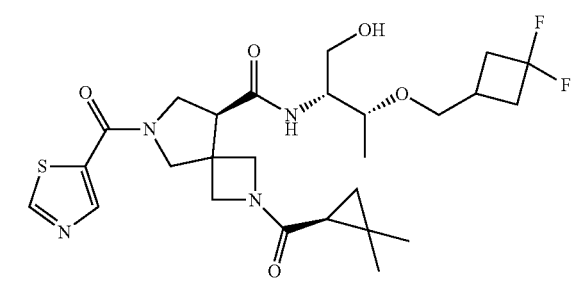
I-413
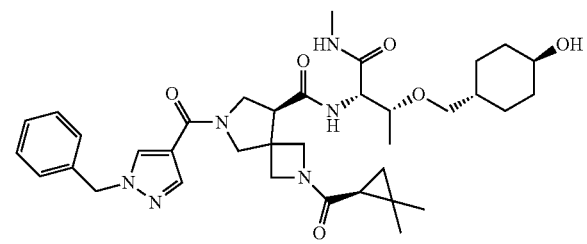

I-414
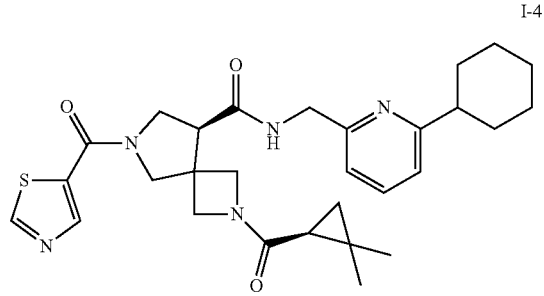
I-415
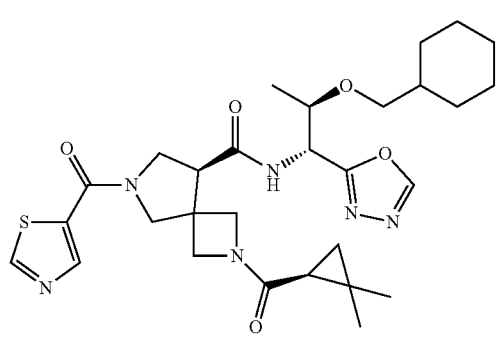
I-416
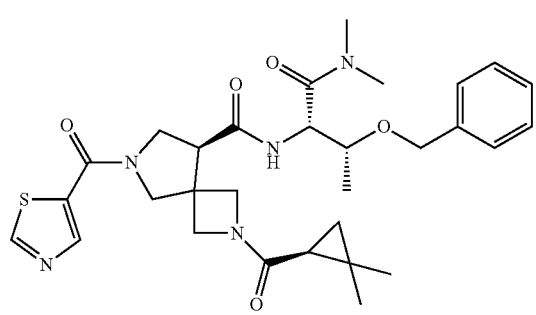
I-417
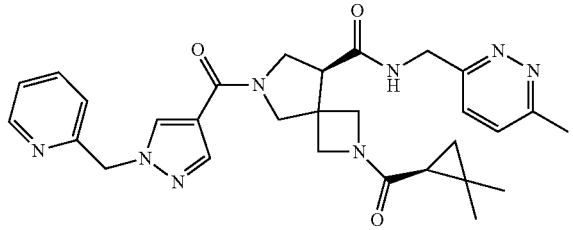
I-418
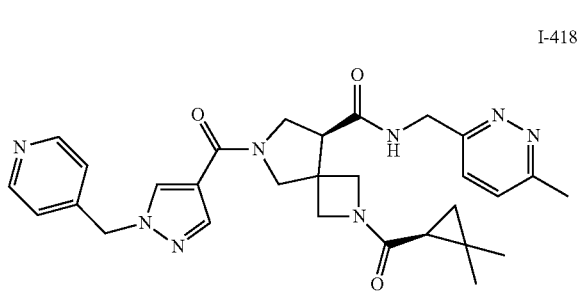
I-419
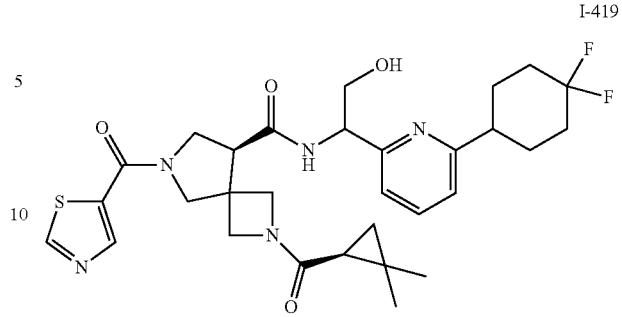
I-420
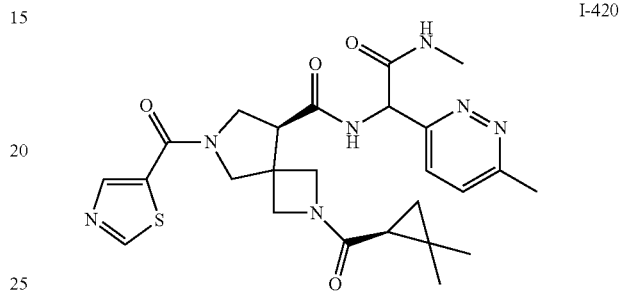
I-421
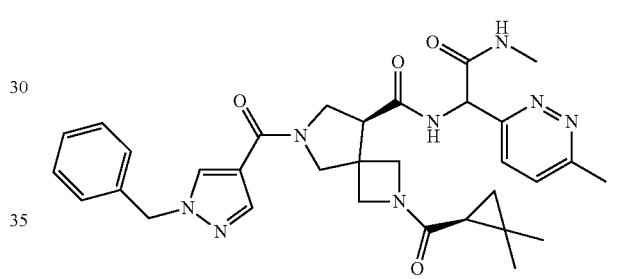
I-422
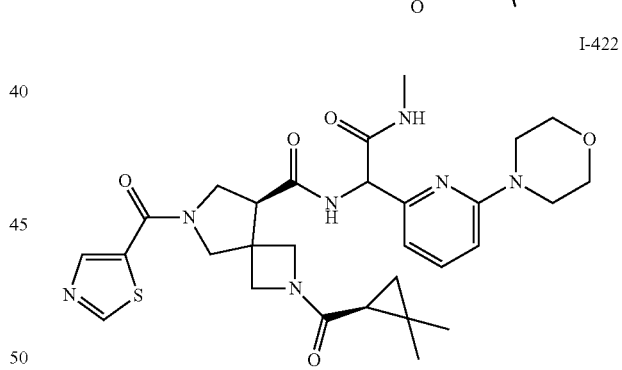
I-423
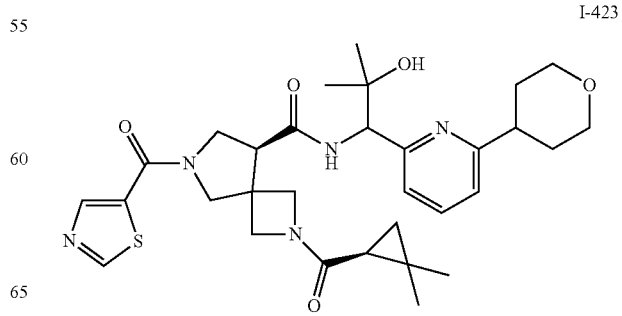

I-424
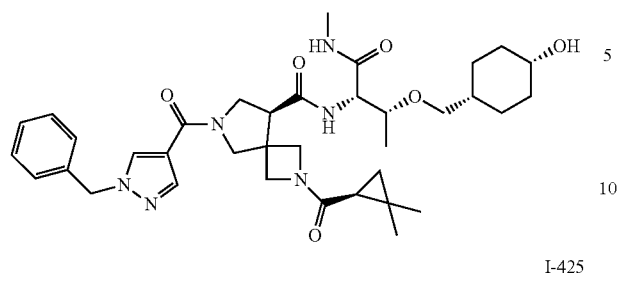
I-425
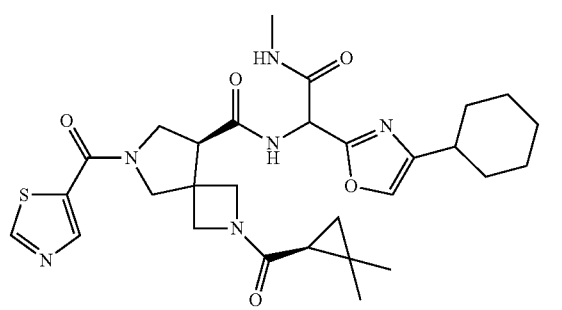
I-426
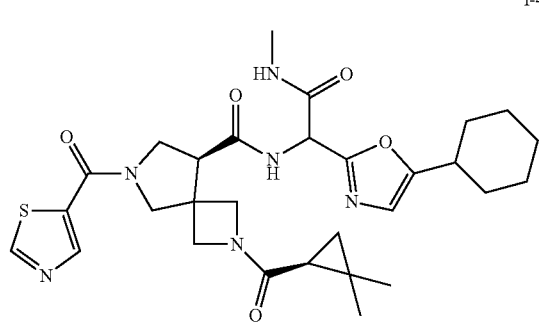
I-427
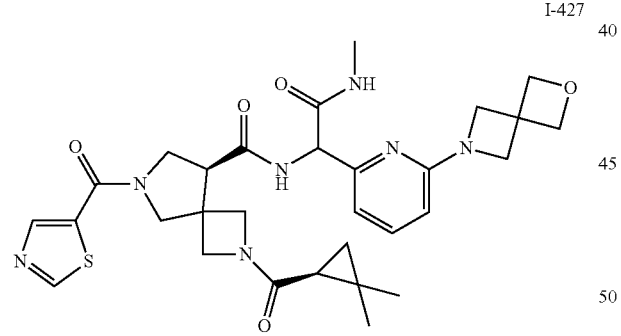
I-428
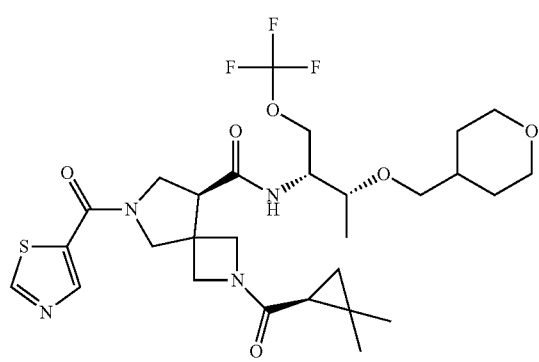
I-429
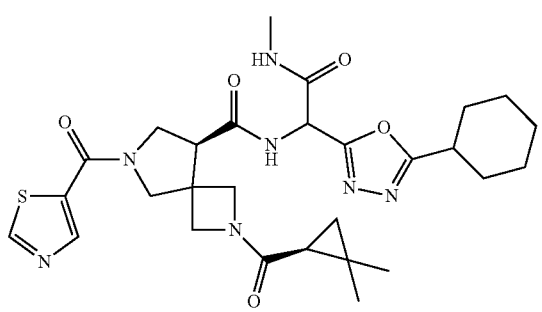
I-430
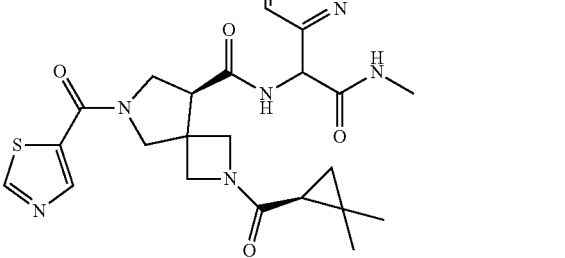
I-431
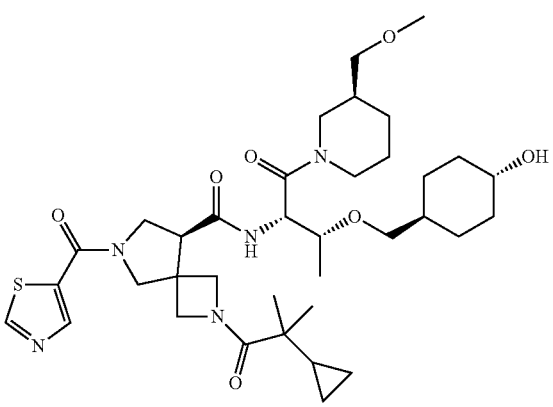
I-432

I-433
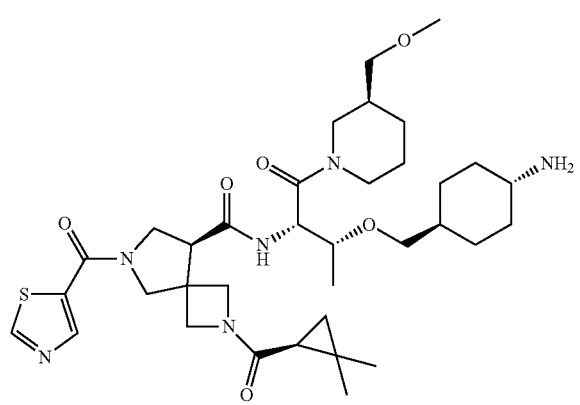
I-434
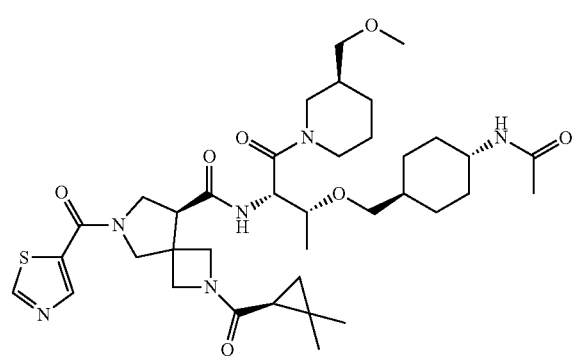
I-435
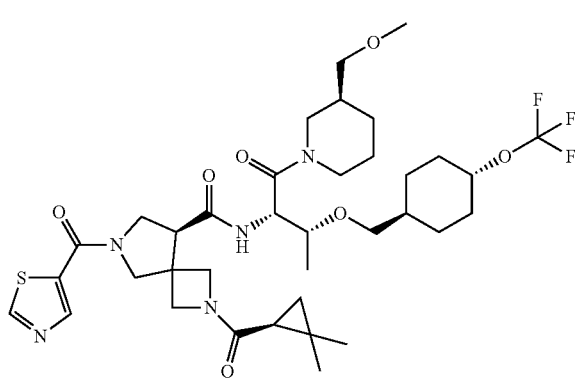
I-436
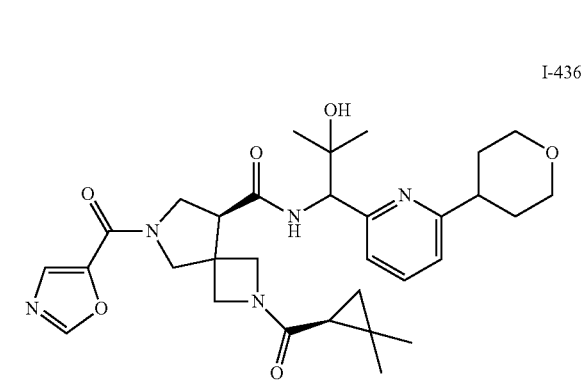
I-437
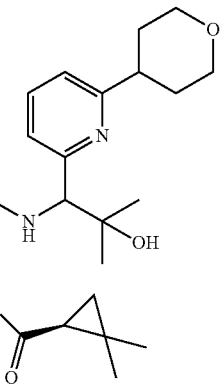
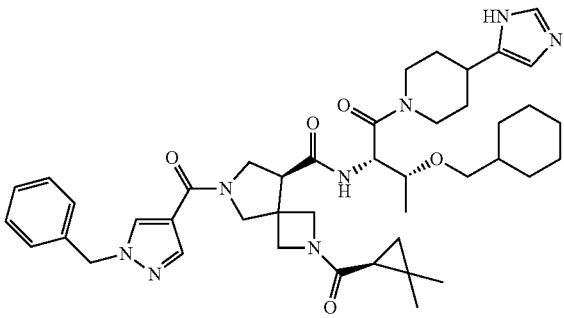
I-438
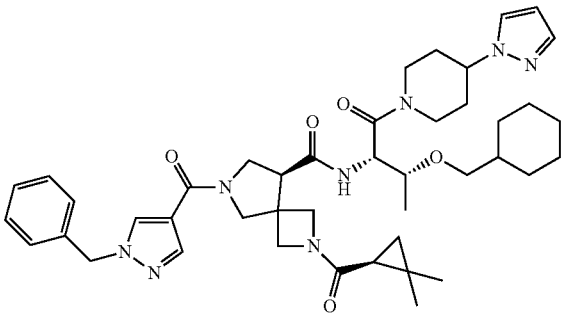
I-439
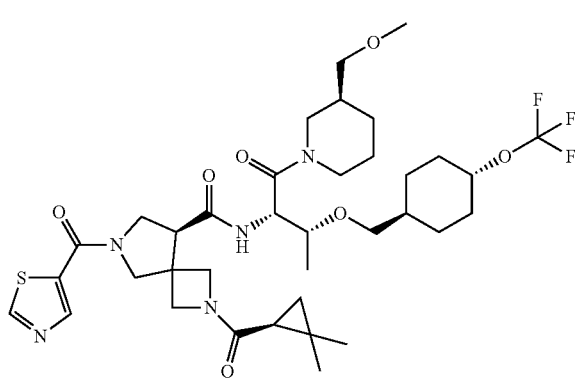
I-440
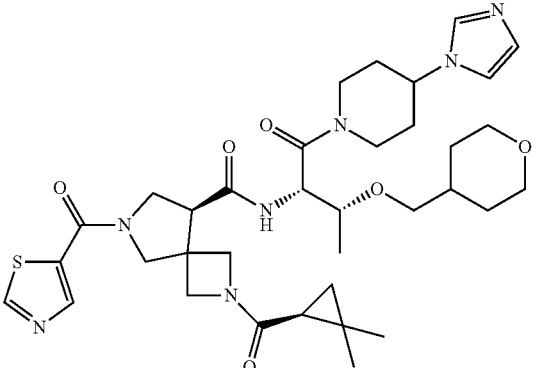

I-441
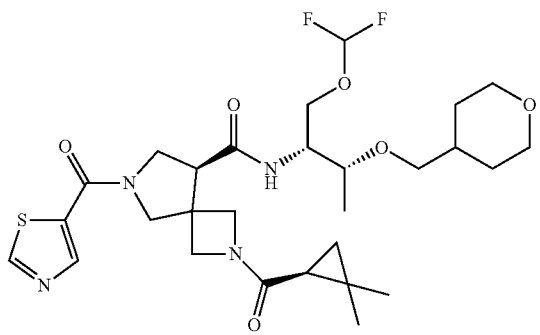
I-445
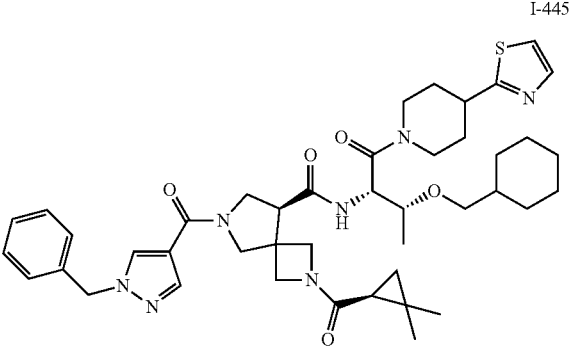
I-442
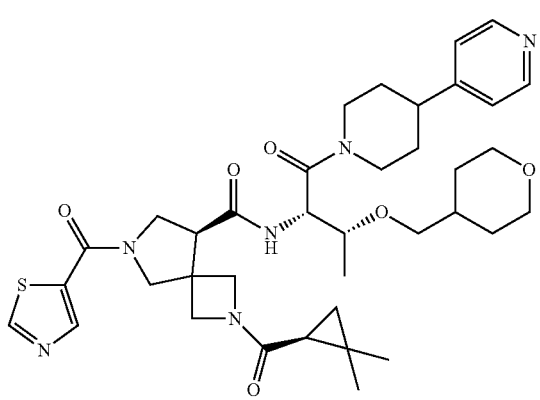
I-446
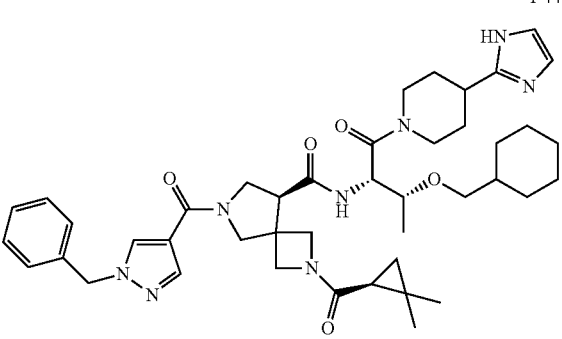
I-447
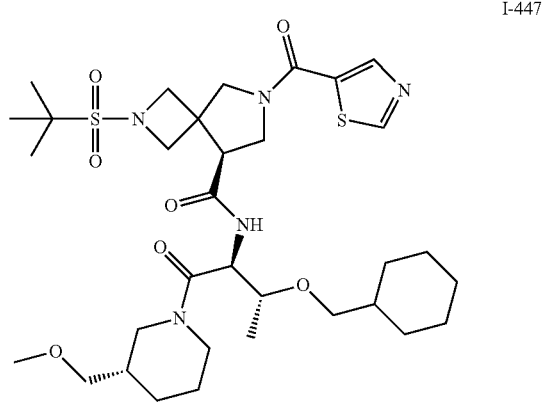
I-443
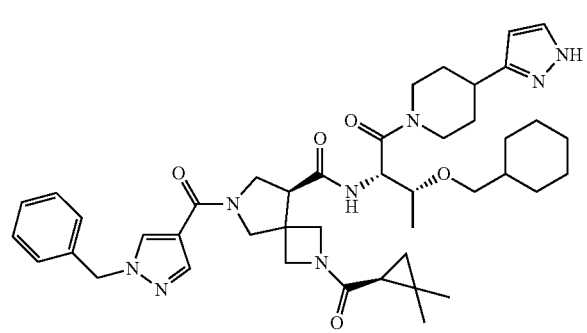
I-444
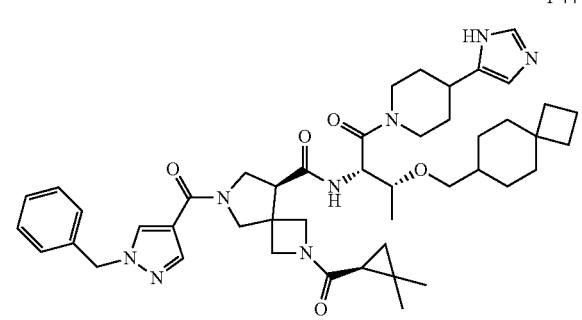
I-448
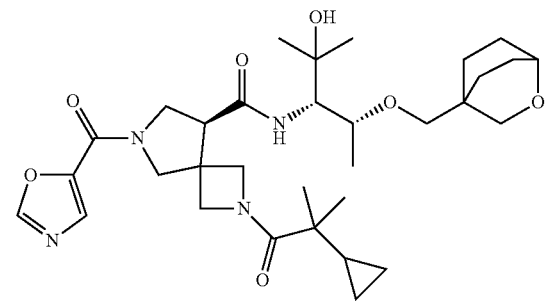

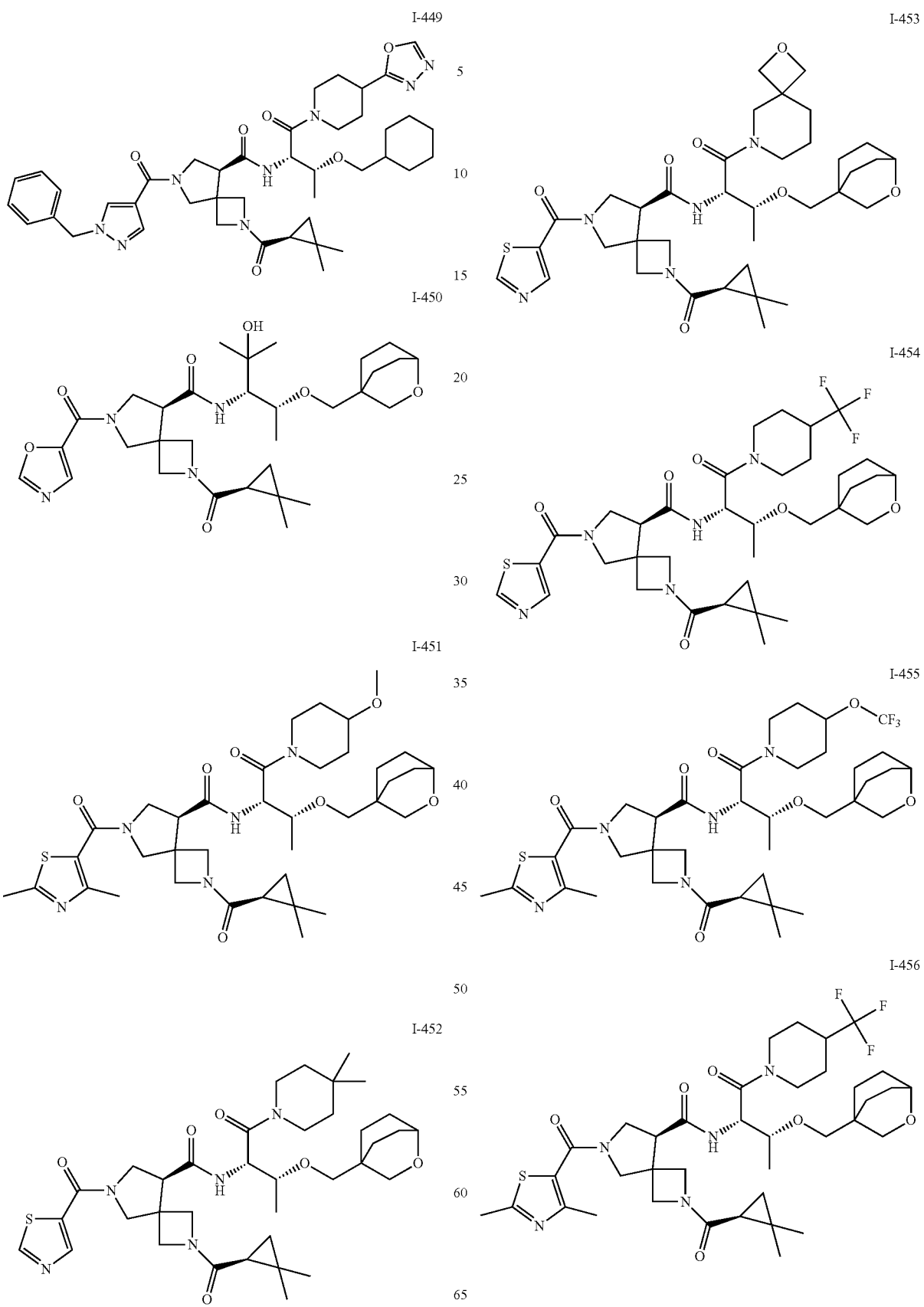

-continued
I-457
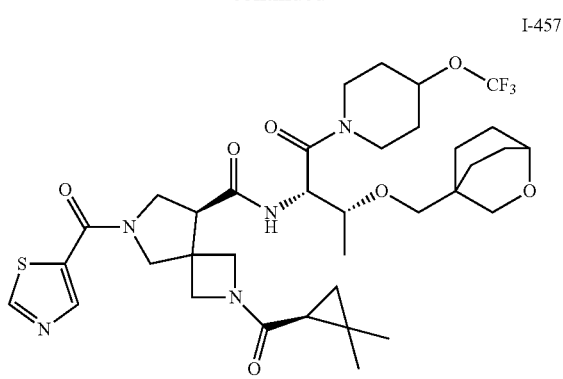
I-458
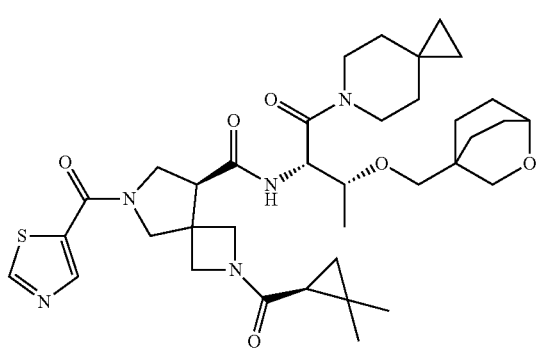
I-459
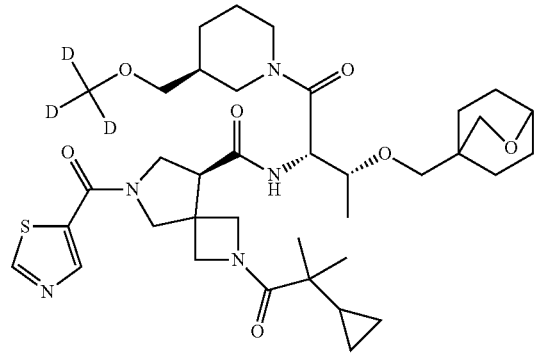
I-460
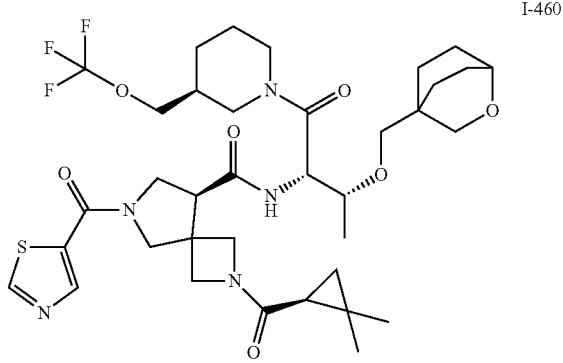
-continued
I-461
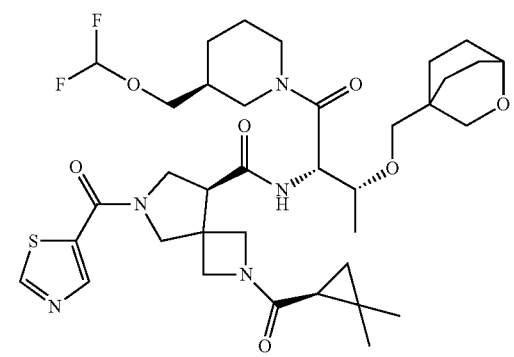
I-462
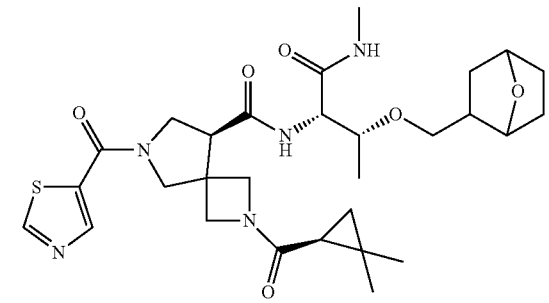
I-463
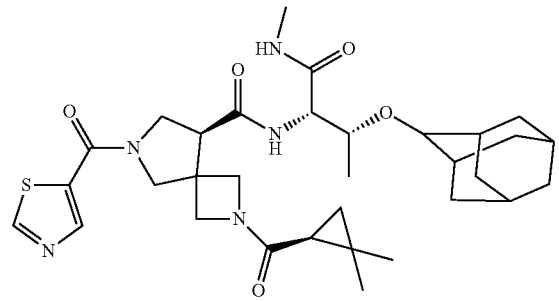
I-464
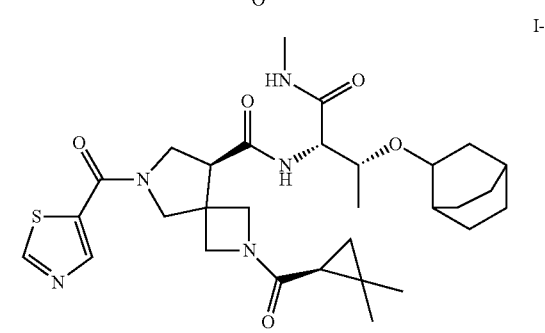
I-465
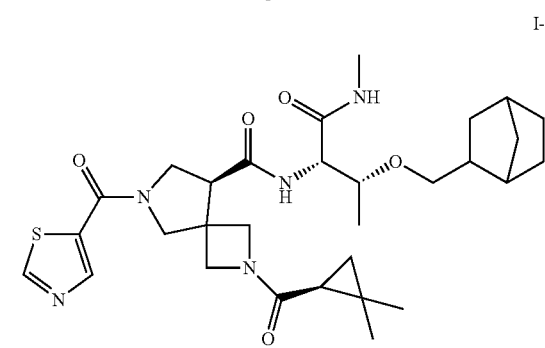

I-466
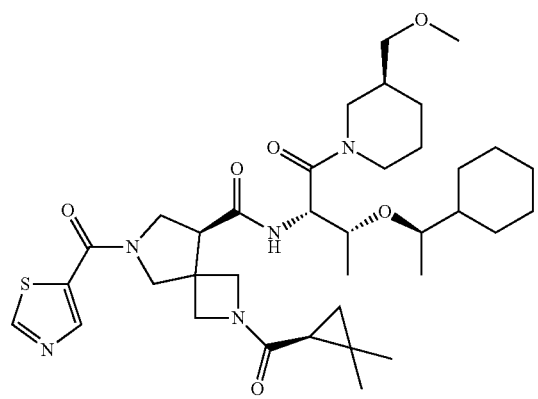
I-467
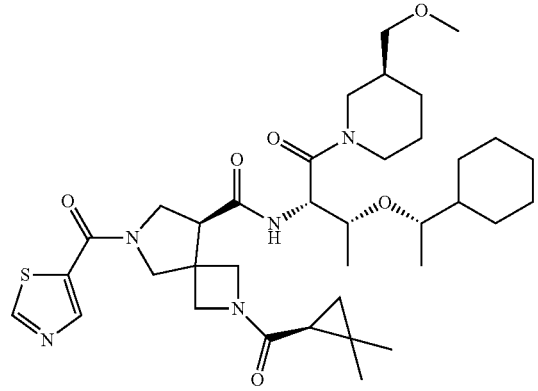
I-468
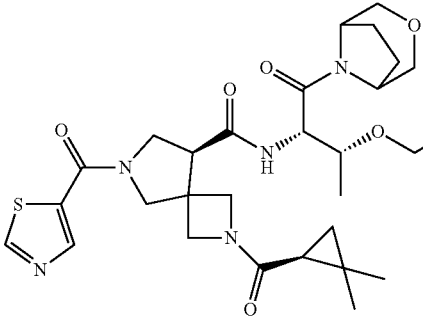
I-469
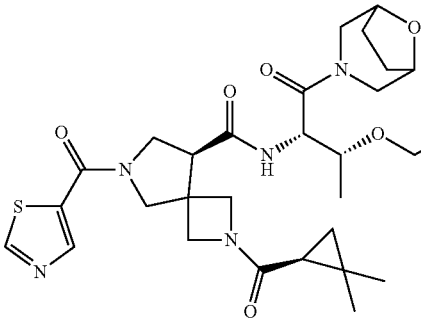
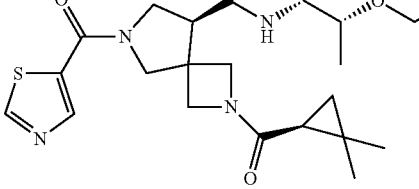
I-470
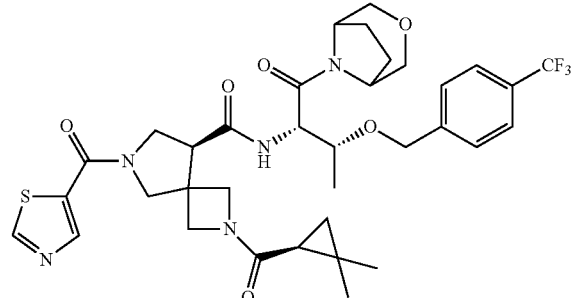
I-471
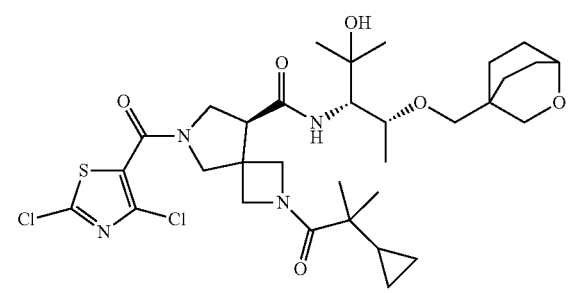
I-472
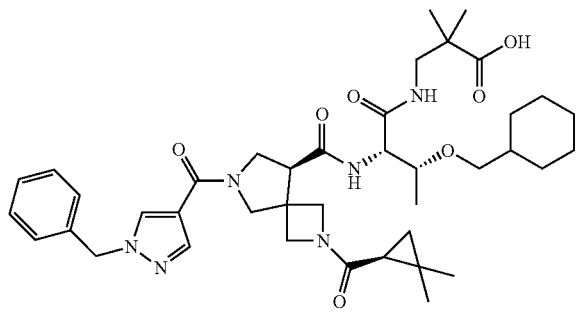
I-473
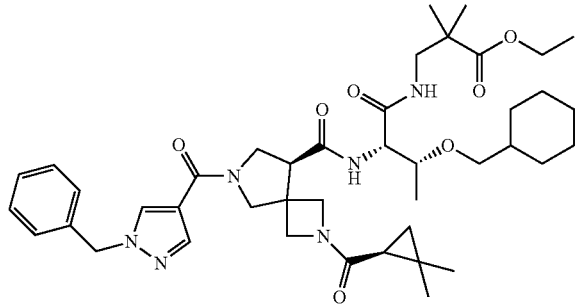
I-474
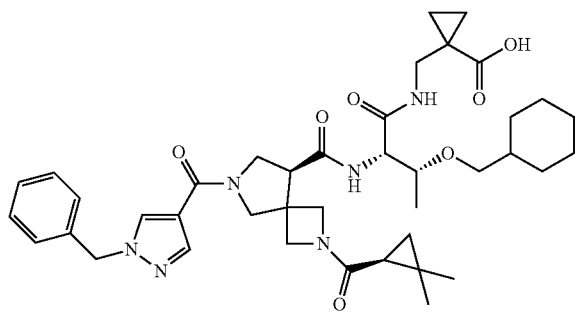

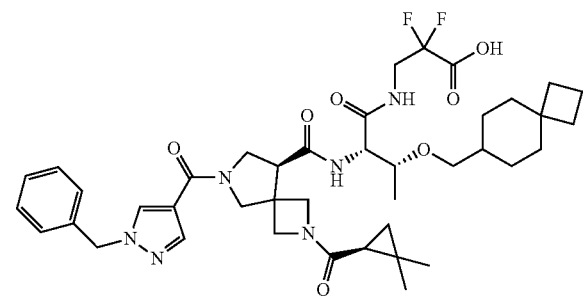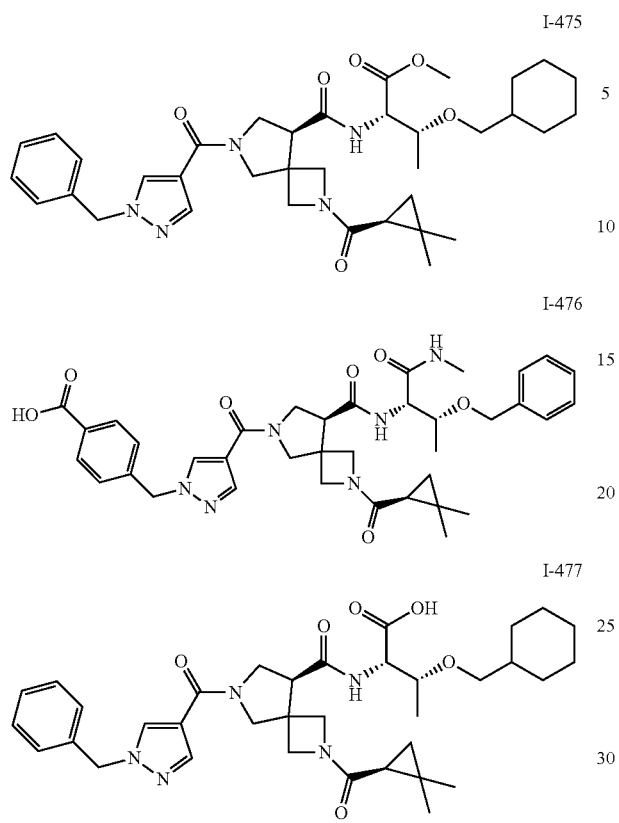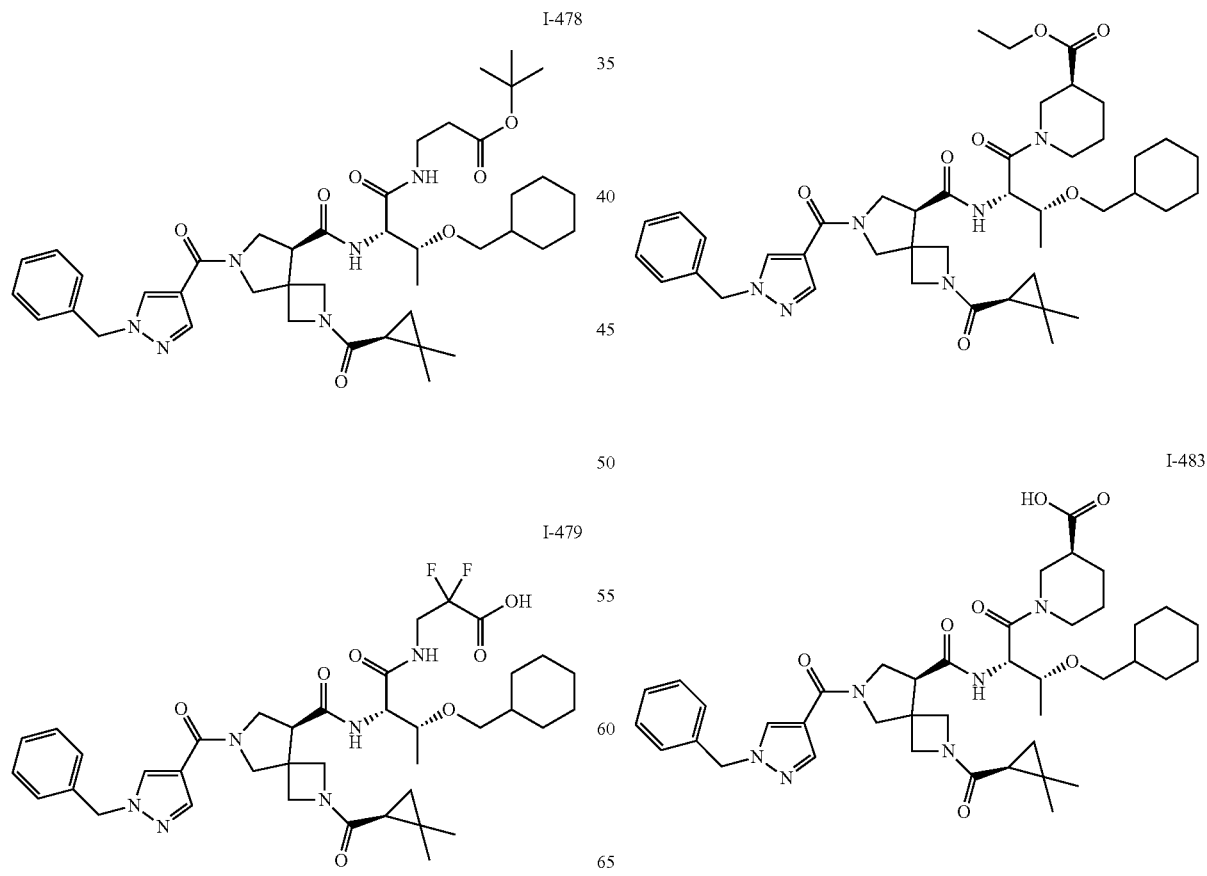

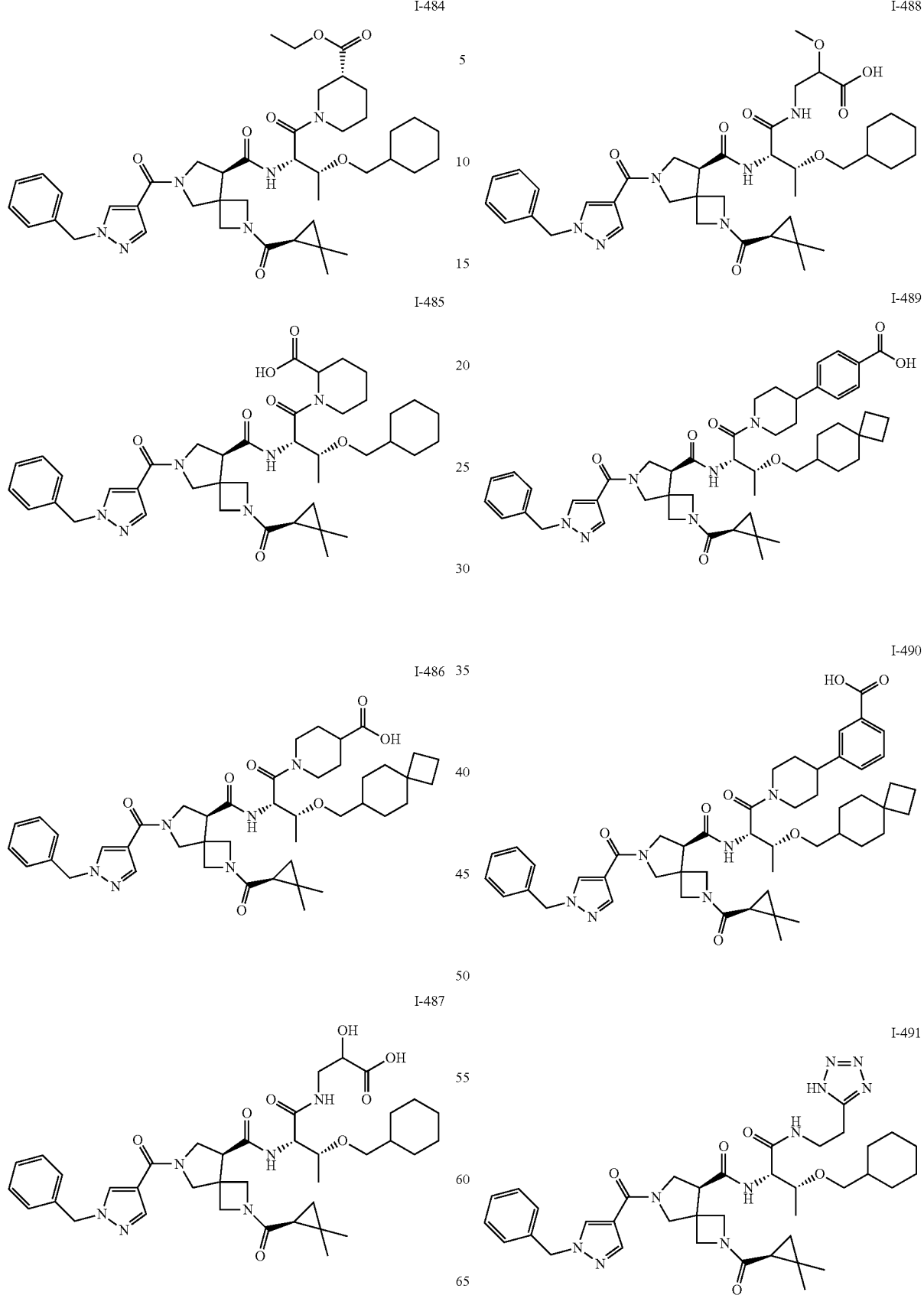

-continued
I-492
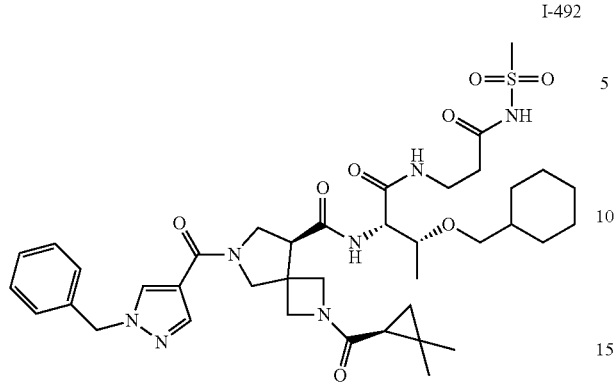
I-493
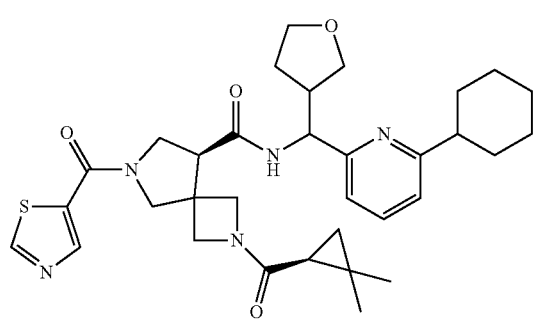
I-495
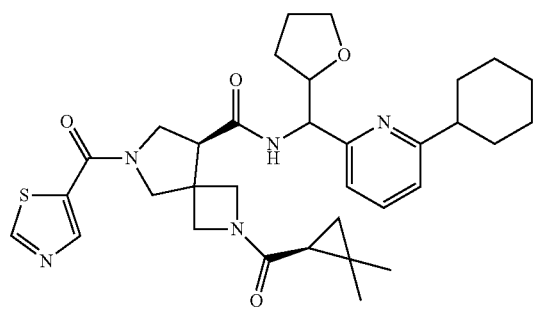
I-496
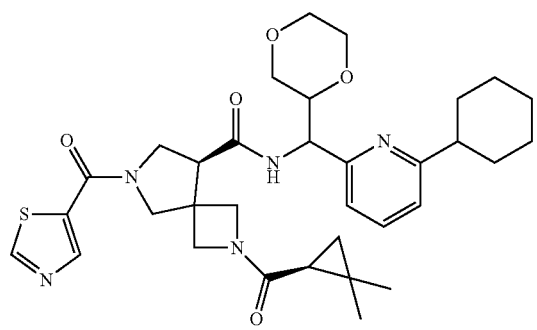
-continued
I-497
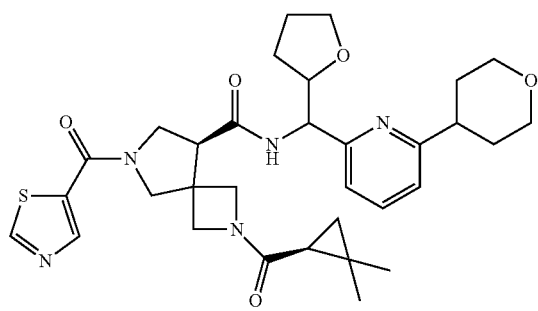
I-498
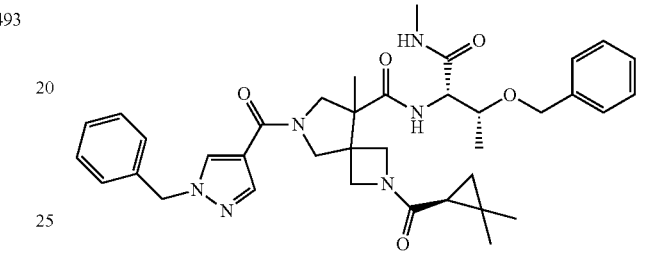
I-499
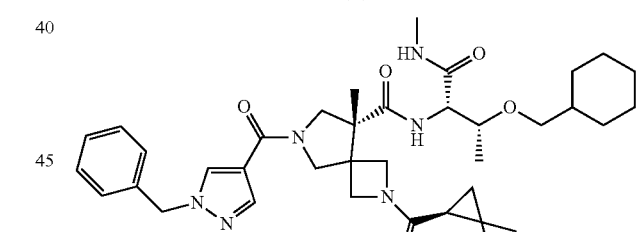
(A)
(B)
I-500
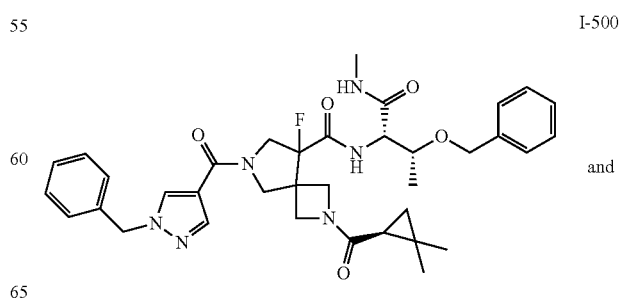
and -continued

I-501

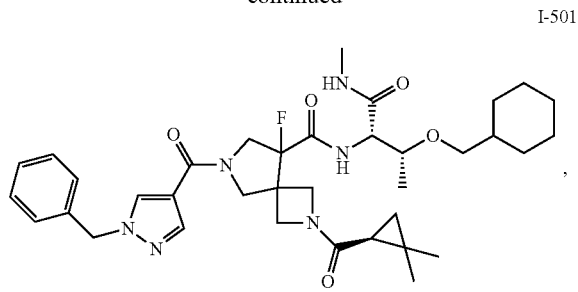

or a pharmaceutically acceptable salt thereof.

17. A pharmaceutically acceptable composition comprising a compound of claim 1, and a pharmaceutically acceptable carrier, excipient, vehicle, adjuvant or diluent; optionally further comprising an additional therapeutic agent.

18. The compound of claim 1, wherein $L^1$ is an optionally substituted straight or branched $C_{1-4}$ alkylene chain, wherein 1-2 methylene units of $L^1$ are independently replaced by —O—, —NR—, —C(O)O—, or —NRC(O)—.

19. The compound of claim 1, wherein $L^1$ is a covalent bond,

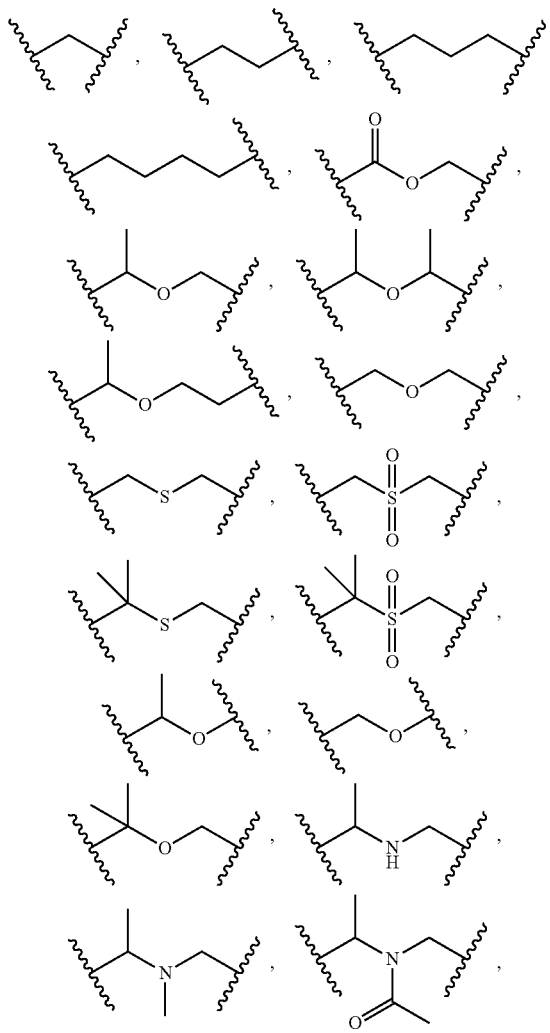

-continued

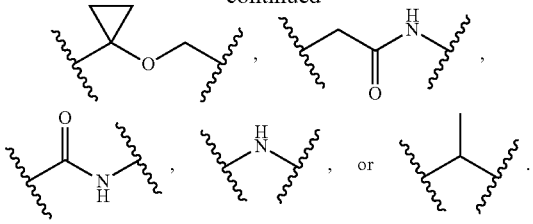

20. The compound of claim 1, wherein $L^1$ is

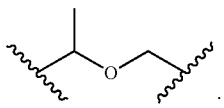

21. The compound of claim 1, wherein $R^1$ is an optionally substituted cyclic group selected from phenyl, cyclohexyl, cyclopentyl, cyclobutyl, cyclopropyl, cycloheptyl, oxazolyl, pyridinyl, pyridazinyl, 1,3,4-oxadiazolyl, 1,2,3-triazolyl, pyrazolyl, and tetrahydropyranyl.

22. The compound of claim 1, wherein $R^1$ is optionally substituted cyclohexyl.

23. The compound of claim 1, wherein $R^1$ is optionally substituted phenyl.

24. The compound of claim 1, wherein $R^2$ is $C(O)NR_2$.

25. The compound of claim 1, wherein $R^2$ is —C(O)NR$_2$, and the two R groups, taken together with the intervening nitrogen atom, form an optionally substituted 4-7 membered saturated ring having 0-3 heteroatoms, in addition to the nitrogen, independently selected from nitrogen, oxygen, and sulfur.

26. The compound of claim 1, wherein $R^2$ is —C(O)NR$_2$, and the two R groups, taken together with the intervening nitrogen atom, form an optionally substituted 4-7 membered saturated ring, selected from a piperidinyl, morpholinyl, piperazinyl, azetindinyl, pyrrolidinyl, azaspiro[3.3]heptanyl, and diazaspiro[3.3]heptanyl.

27. The compound of claim 1, wherein $R^3$ is hydrogen and $R^2$ is

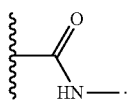

28. The compound of claim 1, wherein $R^4$ is an optionally substituted cyclic group selected from phenyl, piperidinyl, tetrahydropyranyl, 1,4-oxazepanyl, oxazolyl, cyclobutyl, cyclopentyl, or pyrrolidinyl and $R^5$ is hydrogen.

29. The compound of claim 1, wherein $L^2$ is

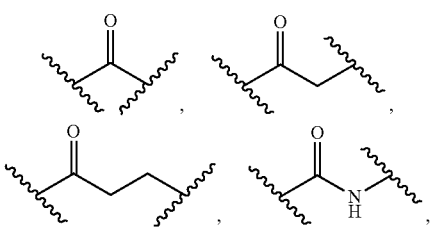

-continued

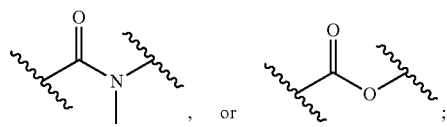

or a pharmaceutically acceptable salt thereof.

30. The compound of claim 1, wherein $L^2$ is

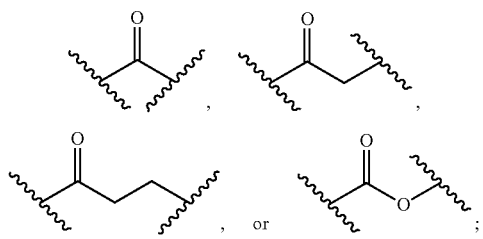

31. The compound of claim 1, wherein $L^2$ is

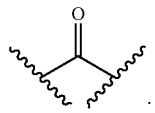 [SMILES: *C(*)=O]

32. The compound of claim 1, wherein $L^3$ is a saturated or unsaturated, straight or branched, optionally substituted bivalent $C_{1-4}$ alkylene chain, wherein 0-2 methylene units of $L^3$ are independently replaced by —C(O)O—, or —C(O)—.

33. The compound of claim 1, wherein $L^3$ is

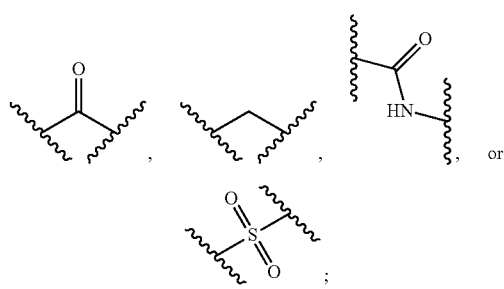

34. The compound of claim 1, wherein $L^3$ is

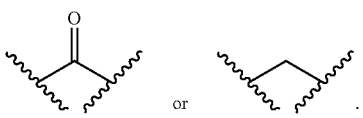

35. The compound of claim 1, wherein $R^6$ is a cyclopropyl group, optionally substituted with one or more instances of $R^7$;
   optionally wherein each instance of $R^7$ is independently —F, methyl, ethyl, isopropyl, isobutyl, —CN, optionally substituted phenyl, optionally substituted benzyl, —CF$_3$, —CH$_2$OH, —CH$_2$OCH$_3$, —CH$_2$CH$_2$OCH$_3$, —CH$_2$CH$_2$F, cyclopropyl or —CH$_2$-(cyclopropyl).

36. The compound of claim 1, wherein $R^8$ is a pyrazolyl or thiazolyl group, optionally substituted with one or more instances of $R^9$.

37. The compound of claim 1, wherein each instance of $R^9$ is an independently an optionally substituted $C_{1-6}$ aliphatic-Cy group, wherein the Cy is an optionally substituted group selected from phenyl, cyclohexyl, pyridinyl, piperidinyl, cyclopropyl, and tetrahydropyranyl.

38. A compound selected from the group consisting of:

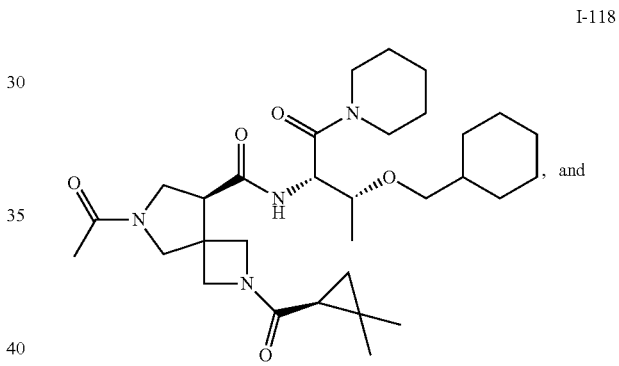

I-118

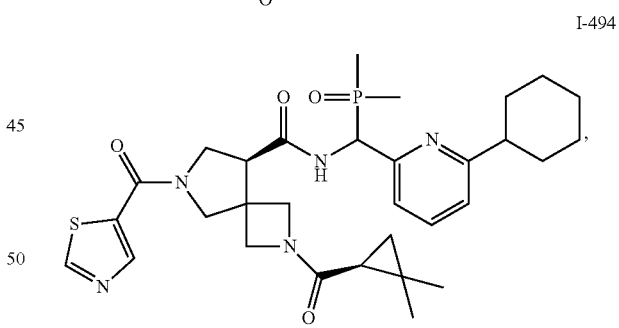

I-494

* * * * *